(12) United States Patent
Meyers et al.

(10) Patent No.: US 7,301,016 B2
(45) Date of Patent: Nov. 27, 2007

(54) HUMAN TRANSFERASE FAMILY MEMBERS AND USES THEREOF

(75) Inventors: Rachel E. Meyers, Newton, MA (US); Mark Williamson, Saugus, MA (US); Kevin R. Leiby, Natick, MA (US); Rosana Kapeller-Libermann, Chestnut Hill, MA (US); Peter J. Olandt, Newton, MA (US); Kyle J. MacBeth, Boston, MA (US); Laura A. Rudolph-Owen, Jamaica Plain, MA (US); Fong-Ying Tsai, Newton, MA (US); John J. Hunter, Somerville, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 576 days.

(21) Appl. No.: 10/184,648

(22) Filed: Jun. 27, 2002

(65) Prior Publication Data

US 2003/0224376 A1    Dec. 4, 2003

Related U.S. Application Data

(63) Continuation-in-part of application No. 10/072,285, filed on Feb. 8, 2002, now abandoned, and a continuation-in-part of application No. 09/973,457, filed on Oct. 9, 2001, now Pat. No. 6,703,230, and a continuation-in-part of application No. 09/962,678, filed on Sep. 25, 2001, now abandoned, and a continuation-in-part of application No. 09/883,060, filed on Jun. 15, 2001, now abandoned, and a continuation-in-part of application No. 09/882,872, filed on Jun. 15, 2001, now abandoned, and a continuation-in-part of application No. 09/882,836, filed on Jun. 15, 2001, now abandoned, and a continuation-in-part of application No. 09/861,164, filed on May 18, 2001, now abandoned, and a continuation-in-part of application No. 09/844,948, filed on Apr. 27, 2001, now abandoned, and a continuation-in-part of application No. 09/842,528, filed on Apr. 25, 2001, now abandoned, and a continuation-in-part of application No. 09/817,910, filed on Mar. 26, 2001, now abandoned, and a continuation-in-part of application No. 09/816,714, filed on Mar. 23, 2001, now abandoned, which is a continuation-in-part of application No. 09/815,028, filed on Mar. 22, 2001, now abandoned, and a continuation-in-part of application No. 09/801,220, filed on Mar. 7, 2001, now abandoned.

(60) Provisional application No. 60/267,494, filed on Feb. 8, 2001, provisional application No. 60/238,849, filed on Oct. 6, 2000, provisional application No. 60/235,044, filed on Sep. 25, 2000, provisional application No. 60/212,079, filed on Jun. 15, 2000, provisional application No. 60/212,077, filed on Jun. 15, 2000, provisional application No. 60/211,730, filed on Jun. 15, 2000, provisional application No. 60/205,408, filed on May 19, 2000, provisional application No. 60/200,604, filed on Apr. 28, 2000, provisional application No. 60/199,500, filed on Apr. 25, 2000, provisional application No. 60/192,092, filed on Mar. 24, 2000, provisional application No. 60/191,964, filed on Mar. 24, 2000, provisional application No. 60/191,865, filed on Mar. 24, 2000, provisional application No. 60/187,456, filed on Mar. 7, 2000.

(30) Foreign Application Priority Data

| Mar. 7, 2001  | (WO) | PCT/US01/07269 |
| Mar. 22, 2001 | (WO) | PCT/US01/09358 |
| Mar. 23, 2001 | (WO) | PCT/US01/09468 |
| Mar. 26, 2001 | (WO) | PCT/US01/09633 |
| Apr. 25, 2001 | (WO) | PCT/US01/40607 |
| Apr. 27, 2001 | (WO) | PCT/US01/13805 |
| May 18, 2001  | (WO) | PCT/US01/16292 |
| Jun. 15, 2001 | (WO) | PCT/US01/19138 |
| Jun. 15, 2001 | (WO) | PCT/US01/19153 |
| Jun. 15, 2001 | (WO) | PCT/US01/19543 |
| Sep. 25, 2001 | (WO) | PCT/US01/29963 |
| Feb. 8, 2002  | (WO) | PCT/US01/03736 |

(51) Int. Cl.

| C07H 1/00   | (2006.01) |
| C07H 5/00   | (2006.01) |
| C07H 19/00  | (2006.01) |
| C07H 21/00  | (2006.01) |
| C07H 21/02  | (2006.01) |
| C08B 37/00  | (2006.01) |
| C12Q 1/68   | (2006.01) |
| C12P 21/06  | (2006.01) |
| C12P 19/34  | (2006.01) |
| C12N 1/12   | (2006.01) |
| C12N 1/20   | (2006.01) |
| C12N 15/00  | (2006.01) |
| C12N 15/06  | (2006.01) |

(52) U.S. Cl. .................. 536/23.2; 536/1.11; 536/18.7; 536/22.1; 536/23.1; 536/23.5; 435/6; 435/69.1; 435/91.1; 435/252.3; 435/320.1

(58) Field of Classification Search ................ 435/6, 435/91.1, 320.1, 252.3, 69.1; 536/23.1, 23.5, 536/1.11, 18.7, 22.1, 23.2

See application file for complete search history.

(56) References Cited

U.S. PATENT DOCUMENTS 6,783,961 B1 *  8/2004  Edwards et al. ........... 435/91.1

FOREIGN PATENT DOCUMENTS

WO    WO 01/70979 A2    9/2001
WO    WO 03/080795 A2   10/2003

OTHER PUBLICATIONS

Lazar et al. (Molecular and Cellular Biology 8(3): 1247-1252, Mar. 1988).*
GenCore sequence alignment between Applicants' sequence and WO2001070979, 5 sheets (filed Mar. 21, 2001).*
GenCore sequence alignment between Applicants' sequence and U.S. Pat. No. 6,783,961 B1, 2 sheets (filed Feb. 24, 2000).*
U.S. Appl. No. 60/200,604, filed Apr. 28, 2000, Rachel E. Meyers.

U.S. Appl. No. 60/191,031, filed Mar. 21, 2000, John Lee et al.
U.S. Appl. No. 60/257,672, filed Dec. 21, 2000, John Lee et al.

* cited by examiner

*Primary Examiner*—Alana M. Harris

(57) ABSTRACT

The invention provides isolated nucleic acids molecules, designated 33877, 47179, 26886, 25552, 32132, 32244, 23680, 32624, 47174, 60491, 46743, 27417, 27960, 32252, and 53320 nucleic acid molecules, which encode novel human transferase family members. The invention also provides antisense nucleic acid molecules, recombinant expression vectors containing 33877, 47179, 26886, 25552, 32132, 32244, 23680, 32624, 47174, 60491, 46743, 27417, 27960, 32252, or 53320 nucleic acid molecules, host cells into which the expression vectors have been introduced, and nonhuman transgenic animals in which a 33877, 47179, 26886, 25552, 32132, 32244, 23680, 32624, 47174, 60491, 46743, 27417, 27960, 32252, or 53320 gene has been introduced or disrupted. The invention still further provides isolated 33877, 47179, 26886, 25552, 32132, 32244, 23680, 32624, 47174, 60491, 46743, 27417, 27960, 32252, or 53320 proteins, fusion proteins, antigenic peptides and anti-33877, 47179, 26886, 25552, 32132, 32244, 23680, 32624, 47174, 60491, 46743, 27417, 27960, 32252, or 53320 antibodies. Diagnostic methods utilizing compositions of the invention are also provided.

10 Claims, 125 Drawing Sheets

|FIG. 1A-1|
|FIG. 1A-2|
|FIG. 1A-3|

FIG. 1A

```
┌─BEGIN SEQ ID NO:1
acgcgtccgg cacagcctcg gattcctccc tctcgctgct cgagtcagtt tccctatcgg     60
cggcagcggg caaggcgggg gcgcgggcgg cggcagccgc ggtggcggcg tggggaacat    120
ctcggcagcc accggcgcttc tcccgctgga gcgggcgtcc agcttggctg ccctcggtcc   180
ttccctgcca cgtttcgggt cgccctgcac ccccaccca ggctcgcttc tcttcgaagc     240
gggaagggcg ccttgcagga tcctgcgcc cctccaaccg gatcctgggt ctagagctcc     300
ccagagcgag gcgctcgca ggactcctgc ccgccaaac ctgaccgccg gggggtgccc      360
ccgggacgta gcgccgcgga gaggaagcgg caaggggac c atg cgg cgc ctg act    416
                                           Met Arg Arg Leu Thr
                                             1               5
                            BEGIN SEQ ID NO:3┘ └BEGIN SEQ ID NO:2
```

FIG. 1A-1

```
cgt cgg ctg gtt ctg cca gtc ttc ggg gtg ctc ttc acg gtg ctg      464
Arg Arg Leu Val Leu Pro Val Phe Gly Val Leu Trp Ile Thr Val Leu
             10                  15                  20 ctg ttc ttc tgg gta acc aag agg aag ttg gag gtg ccg acg gga cct  512
Leu Phe Phe Trp Val Thr Lys Arg Lys Leu Glu Val Pro Thr Gly Pro
         25                  30                  35 gaa gtg cag acc cct aag cct tcg gac gct gac tgg gac gac ctg tgg  560
Glu Val Gln Thr Pro Lys Pro Ser Asp Ala Asp Trp Asp Asp Leu Trp
     40                  45                  50 gac cag ttt gat gag cgg cgg tat ctg aat gcc aaa tgg cgc gtt      608
Asp Gln Phe Asp Glu Arg Arg Tyr Leu Asn Ala Lys Trp Arg Val
 55                  60                  65 ggt gac gac ccc tat aag ctg tat gct ttc aac cag cgg gag agt gag  656
Gly Asp Asp Pro Tyr Lys Leu Tyr Ala Phe Asn Gln Arg Glu Ser Glu
 70                  75                  80                  85 cgg atc tcc agc aat cgg gcc atc ccg gac act cgc cat ctg aga tgc  704
Arg Ile Ser Ser Asn Arg Ala Ile Pro Asp Thr Arg His Leu Arg Cys
             90                  95                 100
```

FIG. 1A-2

```
aca ctg ctg gtg tat tgc acg gac ctt cca ccc act agc atc atc atc    752
Thr Leu Leu Val Tyr Cys Thr Asp Leu Pro Pro Thr Ser Ile Ile Ile
            105                     110                 115 acc ttc cac aac gag gcc cgc tcc acg ctg ctc agg acc atc cgc agt    800
Thr Phe His Asn Glu Ala Arg Ser Thr Leu Leu Arg Thr Ile Arg Ser
            120                     125                 130 gta tta aac cgc acc cct acg cat ctg atc cgg gaa ata tta gtg        848
Val Leu Asn Arg Thr Pro Thr His Leu Ile Arg Glu Ile Leu Val
            135                     140             145 gat gac ttc agc aat gac cct gat gac tgt aaa cag ctc atc aag ttg    896
Asp Asp Phe Ser Asn Asp Pro Asp Asp Cys Lys Gln Leu Ile Lys Leu
            150                     155                 160                 165 ccc aag gtg aaa tgc ttg cgc aat gaa aat gaa cgg caa ggt ctg gtc cgg    944
Pro Lys Val Lys Cys Leu Arg Asn Glu Asn Glu Arg Gln Gly Leu Val Arg
            170                     175                 180 tcc cgg att cgg ggc gct gac atc gcc cag ggc acc act ctg ttc        992
Ser Arg Ile Arg Gly Ala Asp Ile Ala Gln Gly Thr Thr Leu Phe
            185                     190                 195
```

| FIG. 1B-1 |
| FIG. 1B-2 |
| FIG. 1B-3 | ctc gac agc cac tgt gag gtg aac agg gac tgg ctc cag cct ctg ttg    1040
Leu Asp Ser His Cys Glu Val Asn Arg Asp Trp Leu Gln Pro Leu Leu
         200                 205                 210 cac agg gtc aaa gag gac tac acg cgg gtg gtg tgc cct gtg atc gat    1088
His Arg Val Lys Glu Asp Tyr Thr Arg Val Val Cys Pro Val Ile Asp
         215                 220                 225

FIG. 1B-1

```
atc att aac ctg gac acc ttc acc tac atc gag tct gcc tcg gag ctc   1136
Ile Ile Asn Leu Asp Thr Phe Thr Tyr Ile Glu Ser Ala Ser Glu Leu
230                 235                 240                 245 aga ggg ttt gac tgg agc ctc cac ttc cag tgg gag cag ctc tcc       1184
Arg Gly Phe Asp Trp Ser Leu His Phe Gln Trp Glu Gln Leu Ser
    250                 255                 260 cca gag cag aag gct cgg cgc ctg gac ccc acg gag ccc atc agg act   1232
Pro Glu Gln Lys Ala Arg Arg Leu Asp Pro Thr Glu Pro Ile Arg Thr
            265                 270                 275 cct ata gct gga ggg ctc ttc gtg atc gac aaa gct tgg ttt gat       1280
Pro Ile Ala Gly Gly Leu Phe Val Ile Asp Lys Ala Trp Phe Asp
280                 285                 290 tac ctg ggg aaa tat gat atg gac atg gac atc tgg ggt ggg gag aac   1328
Tyr Leu Gly Lys Tyr Asp Met Asp Met Asp Ile Trp Gly Gly Glu Asn
    295                 300                 305 ttt gaa atc tcc ttc cga gtg tgg atg tgc ggg ggc agc cta gag atc   1376
Phe Glu Ile Ser Phe Arg Val Trp Met Cys Gly Gly Ser Leu Glu Ile
310                 315                 320                 325
```

FIG. 1B-2

```
gtc ccc tgc agc cga gtg ggg cac gtc ttc cgg aag aag cac ccc tac   1424
Val Pro Cys Ser Arg Val Gly His Val Phe Arg Lys Lys His Pro Tyr
            330                 335                 340 gtt ttc cct gat gga aat gcc aac acg tat ata aag aac acc aag cgg   1472
Val Phe Pro Asp Gly Asn Ala Asn Thr Tyr Ile Lys Asn Thr Lys Arg
            345                 350                 355 aca gct gaa gtg tgg atg gat gaa tac aag caa tac tat tac gct gcc   1520
Thr Ala Glu Val Trp Met Asp Glu Tyr Lys Gln Tyr Tyr Tyr Ala Ala
            360                 365                 370 cgg cca ttc gcc ctg gag agg ccc ttc ggg aat gtt gag agc aga ttg   1568
Arg Pro Phe Ala Leu Glu Arg Pro Phe Gly Asn Val Glu Ser Arg Leu
            375                 380                 385 gac ctg agg aag aat ctg cgc tgc cag agc ttc aag tgg tac ctg gag   1616
Asp Leu Arg Lys Asn Leu Arg Cys Gln Ser Phe Lys Trp Tyr Leu Glu
            390                 395                 400                 405 aat atc tac cct gaa ctc agc atc ccc aag gag tcc atc cag aag       1664
Asn Ile Tyr Pro Glu Leu Ser Ile Pro Lys Glu Ser Ile Gln Lys
            410                 415                 420
```

FIG. 1B-3

```
ggc aat atc cga cag aga cag aag tgc ctg gaa tct caa agg cag aac    1712
Gly Asn Ile Arg Gln Arg Gln Lys Cys Leu Glu Ser Gln Arg Gln Asn
            425                 430                 435 aac caa gaa acc cca aac cta aag ttg agc ccc tgt gcc aag gtc aaa    1760
Asn Gln Glu Thr Pro Asn Leu Lys Leu Ser Pro Cys Ala Lys Val Lys
        440                 445                 450
```

```
ggc gaa gat gca aag tcc cag gta tgg gcc ttc aca tac acc cag cag    1808
Gly Glu Asp Ala Lys Ser Gln Val Trp Ala Phe Thr Tyr Thr Gln Gln
455                 460                 465 atc ctc cag gag gag ctg tgc ctg tca gtc atc acc ttg ttc cct ggc    1856
Ile Leu Gln Glu Glu Leu Cys Leu Ser Val Ile Thr Leu Phe Pro Gly
        470                 475                 480            485 gcc cca gtg gtt ctt gtc ctt tgc aag aat gga gat gac cga cag caa    1904
Ala Pro Val Val Leu Val Leu Cys Lys Asn Gly Asp Asp Arg Gln Gln
                490                 495                 500 tgg acc aaa act ggt gat tcc cac atc gag cac ata gca tcc cac ctc tgc 1952
Trp Thr Lys Thr Gly Asp Ser His Ile Glu His Ile Ala Ser His Leu Cys
            505                 510                 515 ctc gat aca gat atg ttc ggt gat ggc acc gag aac ggc aag gaa atc    2000
Leu Asp Thr Asp Met Phe Gly Asp Gly Thr Glu Asn Gly Lys Glu Ile
                520                 525                 530
```

FIG. 1C-2

```
gtc gtc aac cca tgt gag tcc tca ctc atg agc cag cac tgg gac atg      2048
Val Val Asn Pro Cys Glu Ser Ser Leu Met Ser Gln His Trp Asp Met
            535                 540                 545 gtg agc tat tga ggaccctgc cagaagcagc aagggccatg gggtggtgct            2100
Val Ser Ser  *  ↳END SEQ ID NO:3
    550      ↳END SEQ ID NO:2 tccctgacc  agaacagact  ggaaactggg  cagcaagcag  caggacagga  cctcagacat  2160
cctgactgg  gaggtggagg  cagagccccc  caggacagga  gcaactgtct  cagggaggac  2220
agaggaaaac atcacaagcc aatggggctc  aaagacaaat  cccacatgtt  ctcaaggccg   2280
ttaagttcca gtcctggcca gtcattccct  gattggtatc  tggagacaga  aacctaatgg   2340
gaagtgttta ttgttccttt tcctacaaag  gaagcagtct  ctggaggcca  gaaagaaaag   2400
ccttctttt  cactaggcca ggactacatt  gagagatgaa  gaatggaggt  tgtttccaaa   2460
agaaataaag agaaacttag aagttgtctc  tgg                                  2493
                                  ↳END SEQ ID NO:1
```

FIG. 1C-3

Glycos_transf_2: domain 1 of 1, from 114 to 292: score 58.8, E = 1.2e-13

```
     SEQ ID NO:7    *->sivIptYNeeadyLeelleSvlaqs.tledieiivvDDgSetDetve
                       si+I +Ne+ ++L+++++Svl+  +t++ eii vDD S   + ++
         33877 114 SIIITFHNEARSTLLRTIRSVLNRTPTHLIREIILVDDFS---NDPD 157 iaedylderikeenpriiivirleensqGpaaArnkgirratGdsdyIlf
                    ++ +     ik    p+ +  +r+ et G ++ r  +g + a+G   ++f
         33877 158 DCKQL----IKL--PK-VKCLRNNERQ-GLVRSRIRGADIAQGT--TLIF 197

LDaDdiftpdkleklidyaeatdaavvlgaida.....yeyaegesnlyr
                    LD+++++  d+l++l+ ++   +     vv++ id   + +++ y e +s l+
         33877 198 LDSHCEVNRDWLQPLLHRVKEDYTRVVCPVIDInldtfTYIESASELRG 247 iaradterslfaglirktgrltggllelsfeigsnaiyrreafeelf<-*
                    ++++ +++++++ +         +r+ ++  ++ + +++ a+ + +++  f
         33877 248 GFDWSLHFQWEQLSPEQKARRLDP-TRPIRTPIIAGGLFVIDKAWF     292
```

FIG. 4

```
                                                                              BEGIN SEQ ID NO:6
                                BEGIN SEQ ID NO:4                             ↓
                                ↓
gtgcggggag cagttcggct ctagggca atg gcg gag gag cag gcc cgg caa                52
                                Met Ala Glu Glu Gln Ala Arg Gln
                                 1               5
                              ↑
                              BEGIN SEQ ID NO:5 cgg gac ctg gtt ccc aag ccg tcg gtg ctg ttc ctg cac cca gac ctc               100
Arg Asp Leu Val Pro Lys Pro Ser Val Leu Phe Leu His Pro Asp Leu
         10                  15                  20
```

```
ggc gta gga ggc gct gag cgt ctg gtg ttg gac gcg gcg ttg ctg           148
Gly Val Gly Gly Ala Glu Arg Leu Val Leu Asp Ala Ala Leu Leu
 25                  30                  35                  40 cag gcg cgc ggg tgt aac gtg aag atc tgg aca cac gcg cac ccg           196
Gln Ala Arg Gly Cys Asn Val Lys Ile Trp Thr Ala His Tyr Asp Pro
                 45                  50                  55 ggc cac tgc ttc gcc gag agc cgc gaa cta ccg gtg cac tgt gcc gga       244
Gly His Cys Phe Ala Glu Ser Arg Glu Leu Pro Val His Cys Ala Gly
         60                  65                  70 gac tgg ctg ccg cgc ggc ctg ggc ctg tgg ggc cac ggc cac gcc gtc       292
Asp Trp Leu Pro Arg Gly Leu Gly Leu Trp Gly His Gly His Ala Val
 75                  80                  85 tgc gcc tac gtg cgc atg gtc cgc ttc ctc tac gcg ctc tac gcc gtc       340
Cys Ala Tyr Val Arg Met Val Arg Phe Leu Tyr Ala Leu Tyr Ala Val
 90                  95                 100 gcc gac gag gag ttc gac gtg gta gtg tgc gac cag gtg tct gcc tgt       388
Ala Asp Glu Glu Phe Asp Val Val Val Cys Asp Gln Val Ser Ala Cys
105                 110                 115                 120
```

FIG. 5A-2

```
att cca gtg ttc agg ctt gct aga cgg aag aag atc ctg ttt tac    436
Ile Pro Val Phe Arg Leu Ala Arg Arg Lys Lys Ile Leu Phe Tyr
            125                 130                 135 tgt cac ttc cca gat ctg ctc acc aag aga gat tct ttt ctt aaa    484
Cys His Phe Pro Asp Leu Leu Thr Lys Arg Asp Ser Phe Leu Lys
            140                 145                 150 cgg tta tac agg gcc ccg att gac tgg ata gag gaa tac aca ggc    532
Arg Leu Tyr Arg Ala Pro Ile Asp Trp Ile Glu Glu Tyr Thr Gly
            155                 160                 165 atg gca gac tgc atc tta gtc aac agc cag ttc act gct gtt ttt    580
Met Ala Asp Cys Ile Leu Val Asn Ser Gln Phe Thr Ala Val Phe
            170                 175                 180 aag aaa aca ttc aag acc ctg tct cac ata gac cct gat gtc ctc tat    628
Lys Lys Thr Phe Lys Thr Leu Ser His Ile Asp Pro Asp Val Leu Tyr
            185                 190                 195                 200 cca tct cta aat gtc acc agc ttt gat tca gtt cct gaa aag ctt    676
Pro Ser Leu Asn Val Thr Ser Phe Asp Ser Val Pro Glu Lys Leu
            205                 210                 215
```

FIG. 5A-3

| FIG. 5B-1 | FIG. 5B-2 | FIG. 5B-3 |

FIG. 5B

```
gat gac cta gtc ccc aag ggg aaa aaa ttc ctg ctc tct atc aac    724
Asp Asp Leu Val Pro Lys Gly Lys Lys Phe Leu Leu Ser Ile Asn
        220                 225                 230 aga tac gaa agg aag aaa aat ctg act ttg gca ttg gaa gcc cta gta    772
Arg Tyr Glu Arg Lys Lys Asn Leu Thr Leu Ala Leu Glu Ala Leu Val
        235                 240                 245 cag ctg cgt gga aga ttg aca tcc caa gat tgg gag agg gtt cat ctg    820
Gln Leu Arg Gly Arg Leu Thr Ser Gln Asp Trp Glu Arg Val His Leu
        250                 255                 260
```

FIG. 5B-1 atc atg gca ggt ggt tat gac gag aga gtc ctg gag aat gtg gaa cat  868
Ile Met Ala Gly Gly Tyr Asp Glu Arg Val Leu Glu Asn Val Glu His
265             270                 275                 280 tac cag gaa ttg aag caa atg gtc caa cag tct gac ctt ggc cag tat  916
Tyr Gln Glu Leu Lys Gln Met Val Gln Gln Ser Asp Leu Gly Gln Tyr
            285                 290                 295 gtg acc ttc ttg agg tct ttc tca gac aaa cag aaa atc tcc ctc ctc  964
Val Thr Phe Leu Arg Ser Phe Ser Asp Lys Gln Lys Ile Ser Leu Leu
300                 305                 310 cac agc tgc acg tgt gtt ctt tac aca cca agc aat gag cac ttt ggc  1012
His Ser Cys Thr Cys Val Leu Tyr Thr Pro Ser Asn Glu His Phe Gly
315                 320                 325 att gtc cct ctg gaa gcc atg tac atg cag tgc cca gtc att gct gtt  1060
Ile Val Pro Leu Glu Ala Met Tyr Met Gln Cys Pro Val Ile Ala Val
330                 335                 340 aat tct ggg gga ccc ttg gag tcc att gac cac agt gtc aca ggg ttt  1108
Asn Ser Gly Gly Pro Leu Glu Ser Ile Asp His Ser Val Thr Gly Phe
345                 350                 355                 360

FIG. 5B-2

```
ctg tgt gag cct gac cca gtg cac ttc tca gaa gca ata gaa aag ttc     1156
Leu Cys Glu Pro Asp Pro Val His Phe Ser Glu Ala Ile Glu Lys Phe
            365                     370                     375 atc cgt gaa cct tcc tta aaa gcc acc atg ggc ctg gct gga aga gcc     1204
Ile Arg Glu Pro Ser Leu Lys Ala Thr Met Gly Leu Ala Gly Arg Ala
            380                     385                     390 aag gtg aag gaa aaa ttt tcc cct gaa gca ttt acg gaa cag ctc tac     1252
Lys Val Lys Glu Lys Phe Ser Pro Glu Ala Phe Thr Glu Gln Leu Tyr
            395                     400                     405 caa tat gtt acc aaa ctg ctg gta taa tcagattcct tttaagatct           1299
Gln Tyr Val Thr Lys Leu Leu Val  *    └ END SEQ ID NO:6
            410             415       └ END SEQ ID NO:5 ttatgctgtg ttcattaatg tcacttttat ggattgtgga cccagtttttg aaaccaaaaa  1359
agaaacctag aatctaatgc agaagagatc ttttaaaaaa taaatttgag tcttgaatct  1419
gagccacttt cctatatacc acacctcctt gtccacttt cagaaaaaca atgtcctta   1479
tgctataatc attccacatt ttgccagtgt taagttacaa atgtataatt ccatgttcag  1539
cagagtattt ttaattatat tttcttggga ttattgctat tctggctata aatttttgaat  1599
gataccgggg ccttaattng g ←                                           1620
└ END SEQ ID NO:4
```

FIG. 5B-3

```
Glycos_transf_1: domain 1 of 1, from 211 to 393: score 131.7, E = 1.4e-36
    SEQ ID NO:8         *->nveekrrklnikenknvllyvgrfvpkKgihllikafkilkeelpav
                           v+ek ++l k++k  ll+++r + kK++ l+++a+ +l+ +l
    47179       211     VVPEKLDDLVPKGKKFLILSINRYERKKNLTLALEALVQLRGRLTSQ 257 klsvllvlvgdgpdkeklenvEylkelvklaeelglnrkIgndniiflgy
                        +    ++++ +g+d++ lenvE++ el++++++ +l+        ++fl +
    47179       258     DWERVHLIMAGGYDERVLENVEHYQELKQMVQQSDLG-----QYVTFLRS 302 vsyedlenllsksdlfllpsqssyEgnGivllEAmaaGvPVIasnsgyGp
                        s++++ +ll+ + ++l+++    s+E+fGiv+lEAm+  +PVIa+nsg Gp
    47179       303     FSDKQKISLLHSCTCVLYTP--SNEHFGIVPLEAMYMQCPVIAVNSG-GP 349 aevivngvnGegvivepndveelaelinkalkdeeelrerikkaarkr<-
                        +e+i + v+G    ++ + d++ + e+i k++ + ++l    + a+r
    47179       350     LESIDHSVTG---FLCEPDPVHFSEAIEKFIRE-PSLKATMGLAGRAK 393

| FIG. 9A-1 |
|---|
| FIG. 9A-2 |
| FIG. 9A-3 |

FIG. 9A

← START SEQ ID NO: 1

GGTTTNTGGTGACGGTGATCTCGGGGTGGGCAGGACTCCAAAGGCCCGTCGACCCGTGTGTGACTCCTTGCACTGGGA

TTGGACATATGCAAGCGGGAGATTTGGGCCCGGCGCTCAAAATCGGGGGGTGGGGGTGACTCGGGTTTGGACCCCAGG

ATCCGATCAGCGGACCCTTGATTCAACGTGAGGTCCCTTCCCTCAAAACCTCCGGTCTACAAACCA

START SEQ ID NO: 2 →  M    A    E    A    H    Q    A    V    G    F    R    11
GGACCCTCAAGACCCTTCAGGGCTCCAGCGTGAC ATG GCT GAA GCG CAC CAG GCC GTG GGC TTC CGA  33
START SEQ ID NO: 3 ↑

FIG. 9A-1

```
        P   S   L   T   S   D   G   A   E   V   E   L   S   A   P   V   L   Q   E   I    31
        CCC TCG CTG ACC TCG GAC GGG GCT GAA GTG GAA CTC AGT GCC CCT GTG CTG CAG GAG ATC    93

Y   L   S   G   L   R   S   W   K   R   H   L   S   R   F   W   N   D   F   L    51
        TAC CTC TCT GGC CTG CGC TCC TGG AAA AGG CAT CTC TCA CGT TTC TGG AAT GAC TTT CTC   153

T   G   V   F   P   A   S   P   L   S   W   L   F   L   F   S   A   I   Q   L    71
        ACC GGT GTG TTT CCT GCC AGC CCC CTC AGT TGG CTT TTC CTC TTC AGT GCC ATC CAG CTT   213

A   W   F   L   Q   L   D   P   S   L   G   L   M   E   K   I   K   E   L   L    91
        GCC TGG TTC CTC CAG CTG GAT CCT TCC TTA GGA CTG ATG GAG AAG ATC AAA GAG TTG CTG   273

P   D   W   G   G   Q   H   H   G   L   R   G   V   L   A   A   A   L   F   A   111
        CCT GAC TGG GGT GGA CAA CAC CAC GGG CTC CGG GGT GTC CTG GCA GCC GCG CTG TTT GCC   333

S   C   W   L   W   G   A   L   I   F   T   L   H   V   A   L   R   L   L   S   131
        TCG TGT TGG CTG TGG GGA GCC CTG ATC TTC ACA CTG CAC GTG GCC CTG AGG CTG CTT CTG TCC   393

Y   H   G   W   L   L   E   P   H   G   A   M   S   P   T   K   T   W   L   151
        TAC CAC GGC TGG CTT CTT GAG CCC CAC GGA GCC ATG TCC CCC ACC AAG ACC TGG CTG   453
```

FIG. 9A-2

```
A   L   V   R   I   F   S   G   R   H   P   M   L   F   S   Y   Q   R   S   L    171
GCC CTG GTC CGC ATC TTC TCT GGC CGC CAC CCG ATG CTG TTC AGT TAC CAG CGC TCC CTG   513

P   R   Q   P   V   P   S   V   Q   D   T   V   R   K   Y   L   E   S   V   R    191
CCA CGC CAG CCC GTG CCC TCT GTG CAG GAC ACC GTG CGC AAG TAC CTG GAG TCG GTC CGG   573

P   I   L   S   D   E   D   F   D   W   T   A   V   L   A   Q   E   F   L   R    211
CCC ATC CTC TCC GAC GAG GAC TTC GAC TGG ACC GCG GTC CTG GCG CAG GAA TTC CTG AGG   633

L   Q   A   S   L   Q   W   Y   L   R   L   K   S   W   A   S   N   Y            231
CTG CAG GCG TCA CTG CAG TAC CTG CGG CTC AAG TCC TGG GCG TCC AAT TAT              693

V   S   D   W   E   E   F   V   Y   L   R   S   R   N   P   V   M   V   N        251
GTC AGT GAC TGG GAG GAA TTT GTG TAC CTG CGC TCC CGA AAT CCG GTG ATG GTG AAC      753

S   N   Y   M   M   D   F   L   Y   V   T   P   T   P   L   Q   A   R            271
AGC AAC TAT ATG ATG GAC TTC CTG TAT GTC ACA CCC ACG CCT CTG CAG GCA CGC          813

A   G   N   A   V   H   A   L   L   Y   R   H   R   L   N   R   Q   E   I        291
GCT GGG AAT GCC GTC CAT GCC CTC CTG TAC CGC CAC CGC CTG AAC CGC CAG GAG ATA      873
```

FIG. 9A-3

| FIG. 9B-1 | FIG. 9B-2 | FIG. 9B-3 |

FIG. 9B

```
     P   P   T   L   L   M   G   M   R   P   L   C   S   A   Q   Y   E   K   I   F    311
    CCC CCG ACT TTG CTG ATG GGA ATG CGC CCC TTA TGC TCT GCC CAG TAC GAG AAG ATC TTC    933

N   T   T   R   I   P   G   V   Q   K   D   Y   I   R   H   L   H   D   S   Q    331
    AAC ACC ACG CGG ATT CCA GGG GTC CAA AAA GAC TAC ATC CGC CAC CTC CAT GAC AGC CAA    993

H   V   A   F   H   R   G   R   F   F   R   M   G   T   H   S   R   N   S        351
    CAC GTG GCT GTC TTC CAC CGG GGC CGA TTC TTC CGC ATG GGG ACC CAC TCC CGA AAC AGC   1053
```

FIG. 9B-1

| | | | | | | | | | | | | | | | | | | | | |
|---|---|---|---|---|---|---|---|---|---|---|---|---|---|---|---|---|---|---|---|---|
| L | L | S | P | R | A | L | E | Q | Q | F | Q | R | I | L | D | D | P | S | P | 371 |
| CTG | CTT | TCC | CCG | AGA | GCC | CTG | GAG | CAG | CAG | TTT | CAG | AGA | ATC | CTG | GAT | GAT | CCC | TCA | CCG | 1113 |
| A | C | P | H | E | E | L | H | A | A | L | T | A | A | P | R | G | T | W | A | 391 |
| GCC | TGC | CCC | CAC | GAG | GAA | CTG | CAT | GCA | GCT | CTG | ACA | GCT | GCT | CCC | AGG | GGC | ACG | TGG | GCC | 1173 |
| Q | V | R | T | S | L | K | T | Q | A | A | E | A | L | E | A | V | E | G | A | 411 |
| CAG | GTG | CGG | ACA | TCC | CTG | AAG | ACC | CAG | GCA | GCA | GAG | GCC | CTG | GAG | GCG | GTG | GAA | GGG | GCC | 1233 |
| A | F | F | V | S | L | D | A | E | P | A | G | L | T | R | E | D | P | A | A | 431 |
| GCT | TTC | TTT | GTG | TCA | CTG | GAT | GCT | GAG | CCC | GCG | GGG | CTC | ACC | AGG | GAG | GAC | CCG | GCA | GCG | 1293 |
| S | L | D | A | Y | A | H | A | L | L | A | G | R | G | H | D | R | W | F | D | 451 |
| TCG | TTG | GAT | GCC | TAC | GCC | CAT | GCT | CTG | CTG | GCC | GGC | CGG | GGC | CAT | GAT | CGC | TGG | TTT | GAC | 1353 |
| K | S | F | T | L | I | V | F | S | N | G | K | L | G | L | S | V | E | H | S | 471 |
| AAA | TCC | TTC | ACC | CTA | ATC | GTC | TTC | TCT | AAC | GGG | AAG | CTC | GGC | CTC | AGC | GTG | GAG | CAC | TCC | 1413 |
| W | A | D | C | P | I | S | G | H | M | W | E | F | T | L | A | T | E | C | F | 491 |
| TGG | GCC | GAC | TGC | CCC | ATC | TCA | GGA | CAC | ATG | TGG | GAG | TTC | ACT | CTG | GCT | ACA | GAA | TGC | TTT | 1473 |
| Q | L | G | Y | S | T | D | G | H | C | K | G | H | P | D | P | T | L | P | Q | 511 |
| CAG | CTG | GGC | TAC | TCA | ACA | GAC | GGC | CAC | TGC | AAG | GGG | CAC | CCG | GAC | CCC | ACA | CTA | CCC | CAG | 1533 |

FIG. 9B-2

```
P    Q    R    L    Q    W    D    L    P    D    Q    I    H    S    I    S    L    A    L    531
CCC  CAG  CGG  CTG  CAA  TGG  GAC  CTT  CCA  GAC  CAG  ATC  CAC  TCC  ATC  TCT  CTA  GCC  CTG  1593

R    G    A    K    I    L    S    E    N    V    D    C    H    V    P    F    S    L    F    551
AGG  GGA  GCC  AAG  ATC  TTG  TCT  GAA  AAT  GTC  GAC  TGC  CAT  GTC  CCA  TTC  TCC  CTA  TTT  1653

G    K    S    F    I    R    R    C    H    L    S    S    D    S    F    I    Q    I    A    L    571
GGC  AAG  AGC  TTC  ATC  CGA  CGC  TGC  CAC  CTC  TCT  TCA  GAC  AGC  TTC  ATC  CAG  ATC  GCC  TTG  1713

Q    L    A    H    F    R    D    R    G    F    Q    C    L    T    Y    E    S    A    M    T    591
CAA  CTG  GCC  CAC  TTC  CGG  GAC  AGG  GGT  CAA  TTC  TGC  CTG  ACT  TAT  GAG  TCG  GCC  ATG  ACT  1773

R    L    F    L    E    G    R    T    E    T    V    R    S    C    T    R    E    A    C    N    611
CGC  TTA  TTC  CTG  GAA  GGC  CGG  ACG  GAG  ACG  GTG  CGG  TCT  TGC  ACG  AGG  GAG  GCC  TGC  AAC  1833

F    V    R    A    M    E    D    K    E    K    T    D    P    Q    C    L    A    L    F    R    631
TTT  GTC  AGG  GCC  ATG  GAG  GAC  AAA  GAG  AAG  ACG  GAC  CCA  CAG  TGC  CTC  GCC  CTG  TTC  CGC  1893

V    A    V    D    K    H    Q    A    L    L    K    A    A    M    S    G    Q    G    V    D    651
GTG  GCA  GTG  GAC  AAG  CAC  CAG  GCT  CTG  CTG  AAG  GCA  GCA  GCC  ATG  AGC  GGG  CAG  GTT  GAC  1953
```

FIG. 9B-3

```
R   H   L   F   A   L   Y   I   V   S   R   F   L   H   L   Q   S   P   F   L    671
CGC CAC CTG TTT GCG CTG TAC ATC GTG TCC CGA TTC CTC CAC CTG CAG TCG CCC TTC CTG  2013

T   Q   V   H   S   E   Q   W   Q   Q   L   S   T   S   Q   I   P   V   Q   M    691
ACC CAG GTC CAT TCG GAG CAG TGG CAG CTG TCC ACC AGC CAG ATC CCT GTT CAG CAA ATG  2073

H   L   F   D   V   H   N   Y   P   D   Y   V   S   G   G   F   Q   P    711
CAT CTG TTT GAC GTC CAC AAT TAC CCG GAC TAT GTT TCC TCA GGC GGT GGA TTC GGG CCT  2133

A   D   H   G   Y   V   S   Y   I   F   M   G   D   G   M   I   T   F    731
GCT GAT GAC CAT GGT TAT GGT GTT TCT TAT ATC TTC ATG GGG GAT GGC ATG ATC ACC TTC  2193

H   I   S   S   K   K   S   T   K   T   D   S   H   R   L   G   Q   H   I    751
CAC ATC TCC AGC AAA AAA TCA AGC ACA AAA ACG GAT TCC CAC AGG CTG GGG CAG CAC ATT  2253

E   D   A   L   L   D   V   A   S   L   F   Q   A   G   Q   H   F   K   R   R    771
GAG GAC GCA CTG CTG GAT GTG GCC TCC CTG TTC CAG GCG GGA CAG CAT TTT AAG CGC CGG  2313

F   R   G   S   G   K   E   N   S   R   H   R   C   G   F   L   S   R   Q   T    791
TTC AGA GGG TCA GGG AAG GAG AAC TCC AGG CAC AGG TGT GGA TTT CTC TCC CGC CAG ACT  2373

G   A   S   K   A   S   M   T   S   T   D   F   *   END SEQ ID NO: 2             804
GGG GCC TCC AAG GCC TCA ATG ACA TCC ACC GAC TTC TGA END SEQ ID NO: 3              2412

CTCCTTCCAGCAGCAGCTGGCCCTCTCCAAGGAATAAGGGTGAAATTGCCACAGCTGGCTGACACAGGACAGGGCAAC
TGGTTTGGCAACCCCACATCCAGGCCAATAAGATGTGTGAGCTGGGAAAAAAAAAAAAAAAAAAAAAAAAAAAAAAA
AAAAAAAAAAAAAAAAAAAAAGGGGCGGCCGCTA END SEQ ID NO: 1

FIG. 9C
```

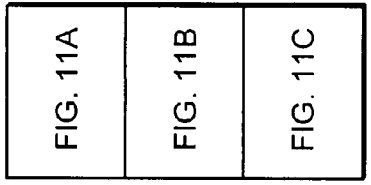

FIG. 11

| FIG. 11A |
| FIG. 11B |
| FIG. 11C |

```
Carn_acyltransf: domain 1 of 1, from 170 to 760: score 710.3, E = 9.1e-210
                 *->sLPkLPVPpLqdTLdrYLealeplvneeGYYqHPLDpEqfrrtqalv
                    sLP+ PVP++qdT+++YLe+++P++++e       +f  t+ l+
         170     SLPRQPVPSVQDTVRKYLESVRPILSDE--------DFDWTAVLA    206
26886 kdFeaggGlgerLQqkLledrankktNwlsewWledaYLryrdeIlplvl
                 ++F    ++ LQ++L   +++++++N++s+wW+e  YLr+r   p+++
26886    207     QEFLRL--QASLLQWYLRL-KSWWASNYVSDWEEFVYLRSR---NPVMV  250

NsNPgvvlpkdpfqdtndqlrrAAnLisgilrfkelldasellPeelakn
                 NsN +++++ + +++t+ q++rA+n +++++L+++  l ++e+ P+ l
26886    251     NSN-YYMMDFLYVTPTPLQAARAGNAVHALLLYRHRLNRQEIPPTLL---  296
```

FIG. 11A

```
       eksSDTaFKRLIRFVPSLSWYGAYLlggqPLCMnQYyrLFsssRiPvGpke
                                                         321
                       +g  PLC++QY+ +F+++RiP G+
26886  297  ----------MGMRPLCSAQYEKIFNTTRIP-GVQR DsivnqtktrkehpepeHvvVlcrGqffvldVldsdNgrllspaEletQL
                                                         362
       D i   + ++      Hv+V +rG+ff  ++     llsp+ le+Q+
26886  322  ---------HVAVFHRGRFFRMGTHSR---NSLLSPRALEQQF eyIlsdssqepeglapiGaLTSeprdnWakaRqyLikdgteNkdsLekIe
                                                         409
       ++Il+d+s++ + + ++aLT+ pR +WA +R+ L +     + Le++e
26886  363  QRILDDDPSPACPHEEHLAALTAAPRGTWAQVRTSLKTQAA---EALEAVE sAlFvvCLDepqpgatnkddDTadlvinRvlserdstataanCkqmlhGg
                                                         439
       A+F+v+LD++++g                + e++    +++  +   ++
26886  410  GAAFFVSLDAEPAG--------------LTREDPA---ASL---DAYAHA GsivQsgnclNRWyDKSlQLivtkdGkaGlvfEHSpaDGivvvrlaeyvy
                                                         486
       ++     g++ +RW+DKS++LiV+++Gk Gl+ EHS+aD ++ +++e +
26886  440  LL---AGRGHDRWFDKSFTLIVFSNGKLGLSVEHSWADCPISGHMWEFTL kksvktlardVakdvvfilsddvtkmdsaekklvradssvdlpkPekLrw
                                                         517
         +   ++              ++++++++++++  lp P++L+w
26886  487  ---------------STDGHCKGHPDPTLPQPQRLQW
```

FIG. 11B

```
26886   518  kispelqndiekAkekldelisdLDivvlkFqsfGKtfiKkeklSPDaFI    567
             +++++++++i A   +++l +++D +v+++F+ fGK+fi ++ lS D+FI
             DLPDQIHSSISLALRGAKILSENVDCHVPFSLFGKSFIRRCHLSSDSFI 26886   568  QLAlQLAyYrlyGrlvaTYESAStRrFkhGRtetIRSatqeslefVqamv    617
             Q AlQLA+++r+ G++++TYEsA+tR+F +GRtet+RS+t e+++fV+am
             QIALQLAHFRDRGQFCLTYESAMTRLFLEGRTETVRSCTREACNFVRAME 26886   618  deeskvskeeKlqLlkdAvkaHsqytkeAitGmGiDRHLlaLkllakfre    662
             d  + +++ + l L++ Av +H+ ++k A++G+G+DRHL+aL+  +++
             D--KEKTDPQCLALFRVAVDKHQALLKAAMSGQGVDRHLFALYIVSR---

26886   663  eeegvelPeLFlDplysesnrfvLSTSPqqqVELFdveqvpsptdcfggf    709
             +  +++P Fl + se +++++S+ P qq  LFdv +  p+++++ggf
             -FLHLQSP--FLTQVHSEQWQLSTSQIPVQQMHLFDVHNYPDYVSSGGGF 26886   710  GPVVpdGYGigYnihdeNqivfnvSSfhscpeTdaaRfakyLekALlDmr    759
             GP+ ++GYG++Y+ +++  i f+++SS+ s   Td++R+++++e+ALlD+
             GPADDHGYGVSYIFMGDGMITFHISSKKSSTKTDSHRLGQHIEDALLDVA 26886   760  d<-*  (SEQ ID NO:4)
             +
         s   760
```

FIG. 11C

| FIG. 16A |
|----------|
| FIG. 16B |
| FIG. 16C |

FIG. 16

Ebh25552FL.seq

START SEQ ID NO:1
```
                                                                          5
CGGCCCCGGGAGCTGTGCTCTATGGAGCTATTGCGGCCCGTGGGTGTGGTCGCGGGCG               15
                              START SEQ ID NO:2
                              M   R   G   C   Q
                              (M)(A)TG CGG GGC TGC CAG
                              START SEQ ID NO:3
 L   L   G   L   R   S   S   W   P   G   D   L   L   S   Q               25
CTC CTC GGG CTT CGT AGC TCT TGG CCC GGG GAC CTA CTA AGT CCT CAA           75

E   K   R   A   A   A   E   T   H   F   G   F   E   T   V   S   E   E   E   K   G      45
GAG AAG CGG GCA GCG GAA ACG CAC TTT GGG TTT GAG ACT GTG TCG GAA GAG GAG AAG GGG         135

G   K   V   Y   Q   V   F   E   S   V   A   K   K   Y   D   V   M   N   D   M          65
GGC AAA GTC TAT CAG GTG TTT GAA AGT GTG GCT AAG AAG TAT GAT GTG ATG AAT GAT ATG        195
```

FIG. 16A

|  |  |  |  |  |  |  |  |  |  |  |
|---|---|---|---|---|---|---|---|---|---|---|
| M | S | L | G | I | H | R | V | W | K | D | L | L | W | K | M | H | P | L | 85 |
| ATG | AGT | CTT | GGT | ATC | CAT | CGT | GTT | TGG | AAG | GAT | TTG | CTC | TGG | AAG | ATG | CAC | CCG | CTT | 255 |
| P | G | T | Q | L | D | V | A | G | T | G | D | I | A | F | R | F | L | 105 |
| CCT | GGG | ACC | CAG | CTG | CTT | GAT | GTT | GCT | GGA | GGC | ACA | GGT | GAC | ATT | GCA | TTC | CGG | TTC | CTT | 315 |
| N | Y | Q | S | Q | H | Q | R | K | A | Q | R | K | A | Q | N | 125 |
| AAT | TAT | CAG | TCC | CAG | CAT | CAG | GTT | GCT | CAG | AGG | AAA | CAG | CAA | AAT | 375 |
| L | S | W | E | E | I | A | K | Y | E | Q | N | L | M | E | D | S | G | G | S | 145 |
| TTA | TCC | TGG | GAA | GAA | ATT | GCC | AAA | TAC | GAG | CAG | AAT | CTA | ATG | GAA | GAT | TCC | GGC | GGG | TCT | 435 |
| R | V | V | C | D | I | N | K | K | V | G | D | A | E | K | Q | L | 165 |
| CGT | GTC | GTG | TGT | GAC | ATC | AAC | AAG | AAG | GTT | GGA | GAT | GCT | GAA | AAG | CAG | TTG | 495 |
| A | Q | G | Y | R | A | G | L | W | V | L | A | F | G | I | K | P | F | 185 |
| GCT | CAA | GGA | TAC | AGA | GCT | GGA | CTT | TGG | GTA | TTA | GCC | TTT | GGG | ATC | AAA | CCA | CCC | TTT | 555 |
| D | D | K | F | D | I | Y | T | I | A | H | R | G | G | N | V | T | H | I | 205 |
| GAT | GAC | AAG | TTT | GAT | ATT | TAC | ACC | ATT | GCC | CAT | CGG | GGA | GGA | AAT | GTC | ACA | CAC | ATT | 615 |
| D | Q | L | A | Q | E | A | G | E | L | V | L | K | P | R | F | L | C | L | 225 |
| GAT | CAG | GCA | CTC | CAG | GAA | GCT | GGT | GAA | CTG | GTG | CTG | AAA | CCA | CGG | TTT | CTC | TGT | CTG | 675 |
| E | F | S | Q | V | N | P | L | I | S | R | L | Y | D | L | Y | S | F | Q | 245 |
| GAA | TTT | AGC | CAA | GTG | AAC | CCC | CTC | ATA | TCC | AGG | CTT | TAT | GAT | CTA | TAT | AGC | TTC | CAG | 735 |

FIG. 16B

```
V   I   P   V   L   G   E   V   I   A   G   D   W   K   S   Y   Q   Y   L   V     265
GTC ATC CCT GTC CTG GGA GAG GTC ATC GCT GGA GAC TGG AAG TCC TAT CAG TAC CTT GTA    795

E   S   I   R   R   F   P   S   Q   E   E   F   K   D   M   I   E   D   A   G     285
GAG AGT ATC CGA AGG TTT CCG TCT CAG GAA GAG TTC AAG GAC ATG ATA GAA GAT GCA GGC    855

F   H   K   V   T   Y   E   S   L   T   S   G   I   V   A   I   H   S   G   F     305
TTT CAC AAG GTG ACT TAC GAA AGT CTA ACA TCA GGC ATT GTG GCC ATT CAT TCT GGC TTC    915

K   *                END SEQ ID NO:2                                                308
AAA CTT TAA END SEQ ID NO:3                                                         924
```

TTCCTTTCCTATCATGGAGCATGAACCAGTCATATCCTGTTGAAAGCCTGAACTGAAGGATAATCTGGCAAATGAGAC

AGCAGCAGAGCATCTCCTCTTAAGGATACGTGCCTTGGACTCATGTTTGAATCGAACAGTCTCRAAGTGGAAGAACAAA

TTCTTGTCACTTTTTTACAGCTTTCTTTGGAGCTGCTTCAGTCCATCTCCCAGAGGCATTGGTCTGTATCTTTGCTCA

ACTGCTAATTTCTCTTGGCTGTAGGGTGTGTGGTTAAGGTACAACCACCCCTAAAGCTCAGTTTGAAGTGAGTGTATT

TATAGCTTCTCTGCTGTGCCTTCTAGAGGGATGATAGATCATTTGAACCCAATGACAATTTTTAACCAGAAAATT

TAATTGTACCTGAATCAACCTTTCAGCCTAGGACGAAGTCTAGGCCCAAGTCAGAGTATTAATGATCATGAGAATTGTG

TGCTGAACCAGTAAACGAGTTTACCTTTTGAAAAAAAAAAAAAAAAAAAAAAAAARNGGCGGCCGCT  END SEQ ID NO:1

FIG. 16C

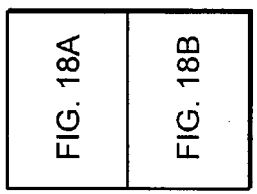

FIG. 18

```
Ubie_methyltran   ubiE/COQ5 methyltransferase family          417.4   1.3e-121

Parsed for domains:
Model              Domain  seq-f  seq-t    hmm-f  hmm-t      score   E-value
--------           ------  -----  -----    -----  -----      -----   -------
Ubie_methyltran     1/1      37    306 ..     1    273 []    417.4   1.3e-121

Alignments of top-scoring domains:
Ubie_methyltran: domain 1 of 1, from 37 to 306: score 417.4, E = 1.3e-121
           *->mtvlkeekeklVhhvFesVAkkyDlMNDvmSfGiHRLwKdhftmklm
              tv++eek  +V  VFesVAkkyD+  MND mS+GiHR wKd     m
    25552  37 ETVSEEEKGGKVYQVFESVAKKYDVMNDMMSLGIHRVWKD-LLLWKM  82
```

FIG. 18A

```
              gpkrGksttPLkfLDvAGGTGDiafrllrsvgesGq..........s
              p++G      LDvAGGTGDiafr+l v + q++++++ + +++ s
25552   83 HPLPGT-----QLLDVAGGTGDIAFRFLNYVQSQHQrkqkrqlraqqnlS 127

FGivPK.......tldeskVvvlDINenMLkvGkkrakeeGkifkdgriE
              + + K+ +++++ l +s Vvv+DIN MLkvGk++a  +G+
25552  128 WEEIAKeyqneedSLGGSRVVVCDINKEMLKVGKQKALAQGYR---AGLA 174 fvqaNAEeLPFeDsdtFDlvTiSFGlRNvtDylKvLrEafRVLKPGGrlv
              +v + AEeLPF+D d FD++Ti FG+RNvt+++ +L Ea RVLKPGGr++
25552  175 WVLGDAEELPFDD-DKFDIYTIAFGIRNVTHIDQALQEAHRVLKPGGRFL 223 cLEFSkpelpllkqAYdlysknVmPvlGkllAndyANmksYryLqeSiRd
              cLEFS++++pl + Ydlys+ V+PvlG+++a d    ksY+yL+eSiR+
25552  224 CLEFSQVNNPLISRLYDLYSFQVIPVLGEVIAGDW---KSYQYLVESIRR 270

FPDqktLksRsATTPmireAGLLFksVeYeslTgGvIAiHKTfGyK<-*
              FP q+++k       mi++AG  F  V  YeslT G++AiH   G K
25552  271 FPSQEEFKD------MIEDAG--FHKVTYESLTSGIVAIH--SGFK    306
```

FIG. 18B

>1416 p99.2 (35) 025366(3) 030511(3) FUT3(2) // TRANSFERASE
GLYCOSYLTRANSFERASE FUCOSYLTRANSFERASE 3-FUCOSYLTRANSFERASE GALACTOSIDE
ALPHA-1 GLYCOPROTEIN TRANSMEMBRANE SIGNAL-ANCHOR GOLGI
     Length = 391

Score = 232 (86.7 bits), Expect = 2.8e-17, P = 2.8e-17
Identities = 91/315 (28%), Positives = 141/315 (44%)

```
Query:   57 GVTRSSGTPRPGREEAGDLPVLLW-WSPGLFPHFPGDSERIECARGACVASRNRRALRDS 115
            G   +S TP P        GL +LLW     P    D  +     C    + +R
Sbjct:   81 GCQSTSATP-PH----GTLTILLWHWPFTNRPTALPDCSEMWPGMADCHITADRSEY--P 133

Query:  116 RTRALLFYGTDFRA---SAAPL---PRLAHQSWALLHEESPLNNFLLSHGPGIRLFNLTS 169
            + A++F+ D A    SA P+   PR     Q W  + ESP N     PG++  N +
Sbjct:  134 KADAVIFHHRDVNANPRSALPMHKSPRPPGQRWVFNMESPSNT-----PGLKALN-KN 186

Query:  170 TFSRHSDYPLSLQWLPGTAYLRRPVPPPMERA-EWRRRGYAPLL-YLQSHCDVPADRDRY 227
            F+    Y           YL     PP E    L+ ++ S+ +  + R RY
Sbjct:  187 YFNWTMSYRTDSDIFVPYGYLTPKSGPPAEVVYPLALSSKTKLVAWVVSNWNEDSARVRY 246

Query:  228 VREL-MRHIPVDSYGKCLQNR--ELPTARLQDTATATTEDPELLAFLSRYKFHLALENAI 284
            +L   +H+ VD YG+C  ++   LP     L+ +T T +     S+YKF+LA EN+
Sbjct:  247 YNQLDQKHLEVDVYGRCYPHKPPNLPADCLMETVLNTLD-----SKYKFYLAFENSK 298

Query:  285 CN-DYMTEKLWRP-MHLGAVPVYRGS--PSVRDWMPNNHSVILIDDFESPQKLAEFIDFL 340
             + DY+TEKLWR  + GAVPV G   +   ++P++ + I  DDF S  L ++  +
Sbjct:  299 DHPDYITEKLWRDAFYAGAVPVVLGPRRANYERFIPDD-AFINYDDFRSNYDLYAYLKHM 357

Query:  341 DKNDEEYMKYLAYKQ 355
            DKN+ +Y+ Y +++
Sbjct:  358 DKNESQYLTYFNWRK 372
```

FIG. 33

| FIG. 34A |
| FIG. 34B |

FIG. 34

```
Alignments of top-scoring domains:
Fucosyl_transf: domain 1 of 1, from 29 to 388: score -24.4, E = 3e-07
        *->lsdaflrllwrekllGllilitvppLllaiaawigleeikewkksplyL
           a+++  w e  G        pp +l           +  + +++ +
  32132   29  EREAGGEAEWAEPWDGAVFR-PPSALG--------AVGVTRSSGTPR-  66

SNDHELdVpillilSqapqGSrfptleenrillwtwp..FndrgaPvpps
           +               +   +   + l   +llw+ p+ F  + +  s
  32132   67  --------PGREEA----GDLP---VLLWWSPglFPHFP----GDS  93 rcslsydntarcrltanRselesAd....avlFNAGHhrDlskgppmdlp
           +   +++        c+ +  nR    + +d++++a+lF    D    +l
  32132   94  ERIECA--RGACVASRNRR--ALRDsrtrALLF---YGTDFRASAA--PL-  134 peftqvrarAedaDavllayednaaaaeaLatdfpRppgQpwVwaSmESP
                       pR       Q w  + ESP
  32132  135  ------------------------PRLAHQSWALLHEESP  150
```

FIG. 34A

```
           snsgRFAVPGFKiNVLNglqilldgy..fNwtlSyradsDafhpYGylep
              n          l++ +g++ fN+t+++ + sD      +l
32132  151 LNN------------------FLLSHGPGIrlFNLTSFSRHSDYPLSLQWLP-   185 ltakarkRGFKVqsqVveaplnlsaKakla..AWVVSNcntrskRerfyk
              ta r+   V+++   a+   + ++ a+   ++ S+c+    R r+++
32132  186 GTAYLRR---PVPPPMERAEW---RRRGYAplLYLQSHCDVPADRDRYVR        229 qLkkHlqVDvyGrv......anplplksgcskGV...elietlsqYkFYLa
           +L  H++VD yG++  +++++ ++ +l  + +     +++el+ +ls+YkF La
32132  230 ELMRHIPVDSYGKClqnreLPTARLQDTATATTedpELLAFLSRYKFHLA        279

FENSqheDYvTEKlwkNAlqagtiPvVLgPsRavyedFvPpk.sFIhVDD
           EN +++DY TEKlW+         g++Pv+ g s++v  d  P ++s I +DD
32132  280 LENAICNDYMTEKLWR-PMHLGAVPVYRG-SPSV-RDWMPNNhSVILIDD        326

FkSakElAdYLlyLdknptAYLDmLYENPLNTLDGKAYFYQDLSFKKILD
           F S+  lA ++ +Ldkn
32132  327 FESPQKLAEFIDFLDKNDEE------------------------------   346

FFKTILENDTIYHKYseYFewRedlrvr.lfswdalrVlEydegfCrvCr
                      Y+ Y + +  ++ f   d l
32132  347 ------------------YMKYLAYKQPGGITnQFLLDSLK---------   370 llqkapdllelSryktipnlakWFg<-*
            + +  d           + pn+  F+
32132  371 REWGVND-------PLLPNYLNGFE                          388
```

FIG. 34B

| FIG. 36A-1 | FIG. 36A-2 |

FIG. 36

AMP-binding: domain 1 of 1, from 67 to 504: score 103.8, E = 3.4e-27

```
Begin SEQ ID NO:4       *->TYrElnerAnrLArhLrsekGvkpgd....lVailmerSpemivaiL
                           TyrEL +r+ rL   + + +G    gd ++++V  l+     +va
32244 (SEQ ID NO:2)  67 TYRELYSRSLRLSQEICRLCGCVGGDlreeRVSFLCANDASYVVAQW 113
                        gilKAGgAYVPIDPgyPaERisyiLedSgAklllTqagfyRaGliklapd
                        + + +Gg+ VP+      +Pa  ++y++ dS+++++L +++     +l+l++
32244              114  ASWMSGGVAVPLYRKHPAAQLEYVICDSQSSVVLASQE-----YLELLSP 158
                        esanGPnvgvvhvllldeeladvveldelaphelvpeqseenlqppvkpe
                        +      ++  v ll         l+++++ +  v+e +e + ++   +
32244              159  VVR-----KL-GVPLLP------LTPAIYTGAVEEPAEVPVPEQGWRN 194
                        dlAYiIYTSGTTGkPKGVmveHrnvvnllqwlkeryglteedddrvlqfa
                        A iIYTSGTTG+PKGV+ +H+n+    ++ l +      t++d  ++l++
32244              195  KGAMIIYTSGTTGRPKGVLSTHQNIRAVVTGLVHKWAWTKDD--VILHVL 242
                        sdayvFDasvwdlFaaLlaGatLvivpketrylDpeaLyqyieke..gvT
                        +    ++ +  v  l  +L +LlaGat Lv  +   + p+    + +++ e+++++
```

FIG. 36A

```
32244  243  P-LHHVHGVVNALLCPLWGATCVMMPEFSP---QQVWEKFLSSEtpRIN  288
             vlslTPsllrmlmpartfan....dkqdl......pSLrtlifgGEalsps
             v   +++P+    lm++  +++++++++++++l+   +  +++r++  +g  al+  +

32244  289  VFMAVPTIYTKLMEYYDRHFtqphAQDFLravceEKIRLMVSGSAALPLP  338
             lvdkwrerfgnekgrliNtyGPTEttvvttvnritpeeirqksvpIGrPl
             +++kw+   +g    +l+   YG+TE  +  ++  ++     t      +      +++  G  Pl 32244  339  VLEKWKNITG---HTLLERYGMTEIGMALSGPLTTAMR---LPGSVGTPL  382
             pntqvyIl..........................Deng.qlvPiGv..aGELyIgGwpg
             p++qv+I+++++++   +  +   ++De+g+++ P   ++++GEL + G p+

32244  383  PGVQVRIVsenpqreacsytihaegDERGtKVTPGFEekEGELLVRG-PS  431
             vARGYLnrPeLTaerFvpnPfqpgeerrgrnrRmYRTGDlaRwlpDGtiE
             v+R Y+n+Pe T  ++F   +++                     +TGD +  +   +  G+++

32244  432  VFREYWNKPEETKSAFTLDGW----------FKTGDTVVFKD-GQYW  467
             ylGRiD.dQVKiRGyRIELGEIEaaLrllqhpgvkeAvV<-* End SEQ ID NO:4
             + GR+    d   +K   +Gy +   E+E  +L+   +hp + + +V 32244  468  IRGRTSvDIIKTGGYKVSALEVEWHLL--AHPSITDVAV  504    SEQ ID NO:2
```

FIG. 36B

```
aminotran_3: domain 1 of 2, from 40 to 141: score 51.7, E = 2.1e-17
          *->GswlyDvdGneqrYlDflSgiavtnlGHcHPkvvqAvkeQadklthl
             ++ D++G +  YlD++  v+ +GHCHP vv+A+ +Q++ l
23680     40   --YMFDENGEQ--YLDCI--NNVAHVGHCHPGVVKAALKQMELLN--   78
          ssgalthppldfdkLaekllkltPgDgldkvffmnSGsEAnEtAlKlAra
          ++   + h+      +++a+ l ++++P  +l +   f+nSGsEAn  Al+lAr+
23680     79   TNSRFLHDNI--VEYAKRLSATLPE-KLSVCYFTNSGSEANDLALRLARQ  125
          yarqkgkvttgktkIIaFsgaFHG<-* (SEQ ID NO:4)
          +          g + +I+ +a+HG
23680    126   F------RGHQDVITLDHAYHG    141
```

FIG. 38A

```
aminotran_3: domain 2 of 2, from 165 to 415: score 210.1, E = 1.6e-
72
          *->pyfppyplpyrlpepkiledGvkenksveaacleeleklikevsgd.
             ++++p+p++yr    +   ed      ++ + a ++e++k+i++++++++
 23680 165   VHVAPTPDTYRGKYR---ED----HADSASAYADEVKKIIEDAHNSg 204

.eiAAvIvEPvIQEGGvippppgfLaglRelCkkhgvLLIaDEVQTGfG
            ++iAA+I E   Q+ GG i+pp+g+++++e    g   +IaDEVQ  GfG
 23680 205 rKIAAFIAES-MQSCGGQIIPPAGYFQKVAEYVHGAGGVFIADEVQVGFG 253

RTGklFA.cehfGELevtPDimtlaKalgGGglPlaAviaraeimqafap
           R Gk F++++ +GE  + +PDi t++K +g+G+ P+a+v+++ei++af +
 23680 254 RVGKHFWsFQMYGE-DFVPDIVTMGKPMGNGH-PVACVVTKEIAEAFSS 301 ggapkaflhgttyggNPLACaaalatLkvleeenllqnaqekgeyllkgL
           g    +  +++tyggNP+ Ca++la+L+++e+e+l+ na+++g yl++ L
 23680 302 SG----MEYFNTYGGNPVSCAVGLAVLDIIENEDLQGNAKRVGNYLTELL 347 lelakkypdvigdvRGrGlmigiElvedrdGpttnrAeeaepddelvaei
           +  + +k++  igd+RG+Gl+igi+lv+d          +r   p+++++ i
 23680 348 KKQKAKHT-LIGDIRGIGLFIGIDLVKD----HLKR----TPATAEAQHI 388 vlkalekGllilpsGdeGnviRflPPL<-*   (SEQ ID NO:5)
           + k++ek +l+  G+  nv+ + PP
 23680 389 IYKMKEKRVLLSADGPHRNVLKIKPPM 415
```

FIG. 38B

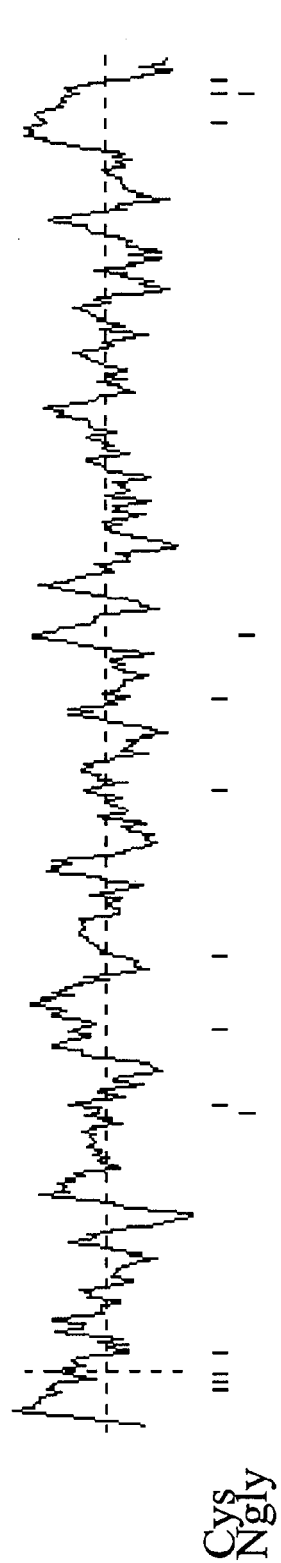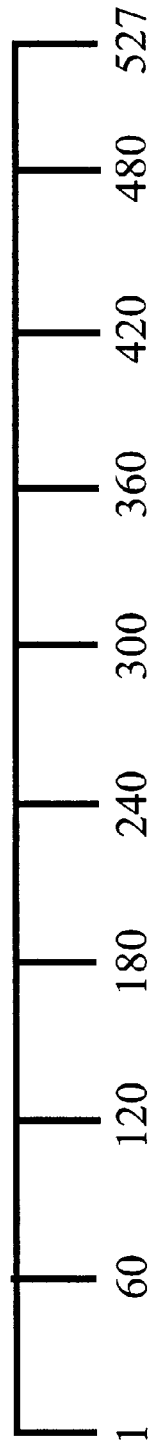
FIG. 39

| FIG. 40A |
|----------|
| FIG. 40B |

UDPGT: domain 1 of 1, from 24 to 525: score 963.2, E = 6.5e-286

```
        *->gkvLvwPmdfShWlnmkgileeLvqrGhevvvLrpsasilikpkkes
           gkvLvwP d ShWln+k ileeL+ rGhev+vL+ s   li+ k+s
32624   24 GKVLVWPCDMSHWLNVKVILEELIVRGHEVTVLTHSKPSLIDYRKPS    70 nlkfetypvsltkeelensflklvkklfeeaselktvwsyfsalqklise
           +lkfe+++++ +++e  + f++l+ ++   +s+   w+ + +l++ + e
32624   71 ALKFEVVHMPQDRTEENEIFVDLALNVLPGLST----WQSVIKLNDFFVE  116 ysdlaessCkevvsnkklmtklqeSsfDvvlaDpvlpcgellAellkiPt
           + + ++   +C++ + n++lm+klqe+    Dv+l Dpv pcg+l +P+
32624  117 IRGTLKMMCESFIYNQTLMKKLQETNYDVMLIDPVIPCGDLMAELLAVPF  166 vyslrfvpgyalekasGgllaPpSYvPvilselsDqmtFieRVkNmlimL
           v   lr  ++g   +e+   G+l+aP+SYvP+   ++++l D+mtF+eRVkN + +
32624  167 VLTLRISVGGNMERSCGKLPAPLSYVPVPMTGLTDRMTFLERVKNSMLSV  216 yfdflfqrfkkkkwdqfaSevlgrpvtlvellskAsvwLlRsywdlefPr
           +f+f+ q  ++    w+++f+S+ lgrp+tl e+++kA+++wL+R+ywd+efP+
32624  217 LFHFWIQDYDYHFWEEFYSKALGRPTTLCETVGKAEIWLIRTYWDFEFPQ  266
```

```
              PllPNvefiGGlnckpakPLpkemEefvqsSGEhGvVVFSLGSmvsnipE
              P  PN+ef+GGl+ckpak+Lpkem E  fvqsSGE G+VVFSLGS  +n++E
32624  267    PYQPNFEFVGGLHCKPAKALPKEMENFVQSSGEDGIVVFSLGSLFQNVTE   316 ekAnaiAsALakiPqkvLWrfdGkkPstLgnNTGrlvkWlPQnDLLGHPk
              ekAn+iAsALa+iPqkvLWr++GkkPstLg NT  rl++W+PQnDLLGHPk
32624  317    EKANIIASALAQIPQKVLWRYKGKKPSTLGANT-RLYDWIPQNDLLGHPK   365 tkAFiTHaGanGvyYEaIyhGvPMvgiPLFGDQmDNakrmeakGAavtlnv
              tkAFiTH+G  nG+yYEaIyhGvPMvg+P FGDQ  DN+++m+akGAav+++n+
32624  366    TKAFITHGGMNGIYEAIYHGVPMVGVPIFGDQLDNIAHMKAKGAAVEINF   415 leMtsedLlnALktVindksYKeNiMrLSsiHkDqPvkPLDrAVFWiEFV
              ++Mtsedll AL tVi  d sYKeN+MrLS+iH+DqPvkPLDrAVFWiEFV
32624  416    KTMTSEDLLRALRTVITDSSYKENAMRLSRIHHDQPVKPLDRAVFWIEFV   465

MRHkGAkHLRpaAhDLtWyQYHSLDVIGFLLavvltvafitfKcclfgyr
              MRHkGAkHLR+aAhDLtW+Q  S  DVIGFLLa+v+t  +f+  +Kc+lf  ++
32624  466    MRHKGAKHLRSAAHDLTWFQHYSIDVIGFLLACVATAIFLFTKCFLFSCQ   515 kfvgkkkrvK<-*  (SEQ ID NO:4)
              kf  ++ k  K
32624  516    KFNKTRKIEK    525
```

```
Glycos_transf_2: domain 1 of 1, from 154 to 336: score 55.7, E = 1e-12
                 *->siviptyNeeadyLeellesvlaqs.tledieiivvDDgSetDetve
                    s+v  + Ne+++ +++ ++Sv +  +    e+i vDD+S + e++
   47174    154  SVVFIFVNEALSVILRSVHSVVNHTpSQLLKEVILVDDNSDNVELKF   200 iaedylderikeenpriiivirleensqGpaaArnkgirratGdsdyIlf
                 ++ y+     ++ +p  + ++r++++  G   +Ar +g ++at      ++ f
   47174    201  NLDQYV----NKRYPGLVKIVRNSRRE-GLIRARLQGWKAATAP--VVGF  243

LDaDdiftpdklekliidyaeatdaavvlgaida......yeyaegesnlyr
                 +Da+++f  ++ e+++++++ +++ +vl+aid    +  +++e +++ ++ ++
   47174    244  FDAHVEFNTGWAEPALSRIREDRRRIVLPAIDNikystFEVQQYANA-AH  292 iaradterslfagllrktgrltgglelsfeigsnaiyrreafeelf<-*
                 ++++ ++    ++   +++  +r g+ ++  +++++ ++  +++e+f
   47174    293  GYNWGLWCMYIIPPQDWLDR--GDESAPIRTPAMIGCSFVVDREYF    336
```

FIG. 42

```
Alignments of top-scoring domains:
ricin_3: domain 1 of 1, from 465 to 595: score 32.5, E = 9.8e-06
                   *->rgyfliiggntglCLdvngnsesksdGnpvqlwdChgggnQlWkltY
                      +g ++ +  ++  CLd  +++++     + +l++Chg ++Ql +++
      47174   465     YGEVRNSK-ASAYCLDQGAEDGD-----RAILYPCHGMSSQLVRYS-   504 nesdgairi.........nsdlCLtvng...tvtlysCdgtdkgndnQk.
                      dg +  ++ +++    + +CL  +g+++  tl++C++   + + Q+
      47174   505  --ADGLLQLgplgstaflPDSKCLVDDGtgrMPTLKKCEDV--ARPTQRl   550

WevnkdgtirnpknskkgvdsglcLdvkdgn......kvqlwtcngsdap
                   W + ++g i+++        +g cL+v  +++ + +  +++  c+g
      47174   551  WDFTQSGPIVSR-------ATGRCLEVEMSKdanfglRLVVQRCSG----   589 nQkWife<-*
                    QkW ++
      47174   590  -QKWMIR    595
```

FIG. 43

>2308 p99.2 (23) PAGT(3)  // N-ACETYLGALACTOSAMINYLTRANSFERASE TRANSFERASE
POLYPEPTIDE ACETYLGALACTOSAMINYLTRANSFERASE UDP-GALNAC:POLYPEPTIDE
GLYCOSYLTRANSFERASE PROTEIN-UDP PROTEIN- UDP N-
Length = 172

Score = 423 (154.0 bits), Expect = 4.7e-40, P = 4.7e-40
Identities = 77/151 (50%), Positives = 104/151 (68%)

```
Query:  312  RGDESAPIRTPAMIGCSFVVDREYFGDIGLLDPGMEVYGGENVELGMRVWQCGGSMEVLP  371
             R D + PIR+P M G  F +++EYF ++G  DPGM+++GGEN+EL RVWQCGG +E++P
Sbjct:   14  RKDPTDPIRSPTMAGGLFAINKEYFEELGTYDPGMDIWGGENLELSFRVWQCGGRLEIVP   73

Query:  372  CSRVAHIERTRKPYNNDIDYYAK-----RNALRAAEVWMDDFKSHVYMAWNIPMSNPGVDF  427
             CS V H+ R R PY          RN +R AEVWMDD+K + Y    + P +   DF
Sbjct:   74  CSHVGHVFRKRSPYTFPGKGSGKDVISRNTVRVAEVWMDDYKEYFYK--HNPQARKVRDF  131

Query:  428  GDVSERLALRQRLKCRSFKWYLENVYPEMRV  458
             GD+SER      LR++L+C+SFKWYLENVYP++ V
Sbjct:  132  GDISERKELREKLQCKSFKWYLENVYPDLYV  162
```

FIG. 44

Acyltransferase: domain 1 of 1, from 190 to 393: score -28.9, E = 2.3

```
                 *->lenlpkkgpaivvsNhrSylDilvlsaalprrgpwlvrrlvfiakke
                    +++ + p ++ s H + 1D+++l + l  +g    +  + +a ++
Fbh60491FL   190    QKAAQAGLPLVLLSTHKTLLDGILLPFMLLSQG----LGVLRVAWDS 232 llkvPllfGwlmrlagaifidRnnra......kdalaaadelvrvlell
                  + P  ++ l+r++g f+  ++  +  +++++   a+a++  ++ ++l+
Fbh60491FL   233 RACSPA-LRALLRKLGGLFLPPEASLsldsseqLLARAVVQAVIEQLL-- 279 rkgrsvliFPEGTRsrsgellppfkKGia........afrlAlkagvpivP
                 g+++liF E   ++       +++   G+a   +    +a+++ +  +vP
Fbh60491FL   280 VSGQPLLIFLEE--PPGALGPRLSALGQAwvgfvvqAVQVGIVPDALLVP 327 vvi.vsgteelepkneagkllrlarkkgpvtvrvlppipld......ped
                 v+++    ++   +   +  +++   +  + +  vl+ +  +++  ++
Fbh60491FL   328 VAVtYDLVPDAPCDI-DHA--SAPLGLWTGALAVLRSLWSRwgcshrICS 374 ikelaerlrdilvqaleel<-* (SEQ ID NO:4)
                 + la++  + + + + +
Fbh60491FL   375 RVHLAQPFSLQEYIVSARS 393
```

FIG. 46 plsc_2: domain 1 of 1, from 199 to 333: score 57.6, E = 2.7e-13

```
              *->alvvaNhqSylDplvlsallprk.rrvrfvakkelfkiPllGwllrl
                 +++++ H + lD+++l  ++l       ++   v   va+++ + +P l+++llr+
Fbh60491FL  199  LVLLSTHKTLLDGILLPFMLLSQgLGVLRVAWDSRACSPALRALLRK  245 agaifidRsng......drkaraalreavrryFEnhellkegewlviFP
                 +g+ f+ ++++ +   +++++ +ara  ++++++         +ll +g++l++iF
Fbh60491FL  246  LGGLFLPPEASlsldsseGLLARAVVQAVIE-----QLLVSGQPLLIFL  289

EG...TrsrdgkldgeeerlklpfKkGafrlAlkag...dvpivPvais
                 E +++        +l++    G++  A++ g    +d+  +vPva++
Fbh60491FL  290  ALGQAWGFVVQAVQVGivpDALLVPVAVT  331 gt<-*    (SEQ ID NO:5)
                 ++
Fbh60491FL  332  YD  333
```

FIG. 47

```
Score = 202 (76.2 bits), Expect = 2.7e-15, P = 2.7e-15
Identities = 38/89 (42%), Positives = 54/89 (60%)

Query:   40 LGKYRPFVGRCCQTCTPKSWESLFHRSITDLGFCNVILVKEENTRFRGWLVRRLCYFLWS 99
            + + RPFVGRCC +CTP+SWE  F+ SI  LG  NVI + E +TR RGWL RRL Y L+
Sbjct:    1 MSRKRPFVGRCCYSCTPQSWERFFNPSIPSLGLRNVIYINETHTRHRGWLARRLSYILFV 60

Query:  100 LEQHIPP---CQDVPQKIMESTGVQNLLS 125
            E+ +        ++ S+ VQ ++
Sbjct:   61 QERDVHKGMFATSITDNVLNSSRVQEAIA 89    (SEQ ID NO:6)
```

FIG. 48A

Score = 272 (100.8 bits), Expect = 1.2e-20, P = 1.2e-20
Identities = 87/300 (29%), Positives = 136/300 (45%)

```
Query:  104  IPPCQ--DVPQKIMESTGVQNLLSGRVPGGTGEGQVPDLVKKEVQRILGHIQAPPRPFLV  161
             I PC+  D+    ++ S   +     +     + Q  D VK+E  +IL  + A  P ++
Sbjct:    6  ITPCKPIDIKCSVLNSEEIHRVIQQQ---SKEKNQSVDKVKEEAAKILDEMSAKLSPGMI   62

Query:  162  RLFSWALLRFLNCLFLNVQLHKGQMKMVQKAAQAGLPLVLLSTHKTLLDGILLPFMLLSQ  221
             RL   W L + N F   +Q+HK Q++M++ A +   LPLV L  H++ +D +LL F+L
Sbjct:   63  RLCGWVLRKLFNRFFWKIQVHKEQLEMLKAATETHLPLVLPCHRSHIDYLLLTFILYHH  122

Query:  222  GLGVLRVAWDSRACS-PALRALLRKLGGLFLPPEASLSLDSSEGLLARAVVQAVIEQLLV  280
             L         +A + + P     LLRK G     F    + D + L RA++  +++LL
Sbjct:  123  NLKPPHIASGMDNLNFPMMGTLLRKTGAFFIRRRFDETPDGGKDKLYRAILHEYVKELLR  182

Query:  281  SGQ-PLLIFLEEPPGALGPRLSALGQAWVGFVVQAVQGIVPDALLVPVAVTYD-LVPDA  338
              G  P+  FLE    G L+        VV+A+Q G VPD  LVPV+++YD ++
Sbjct:  183  KGYAPIEFFLEGTRSRTGKTLTPKF-GLLSVVVEALQHGEVPDIYLVPVSISYDRIIEGT  241

Query:  339  PCDIDHASAPL---GLWTGALAVLRSLWSRWGCSHRICSRVHLAQPFSLQEYIVSARSCW  395
                +     +     +  A   L    ++ L  +C  +   VH  +P SL+EY+  +   W
Sbjct:  242  HYAHELLGAPKKKESLWGVLRGIFKMLSKNYQCGY--VHVHFGEPISLREYLETHTPDW  298
```

(SEQ ID NO:7)

FIG. 48B

```
Score = 113 (44.8 bits), Expect = 0.00038, P = 0.00038
Identities = 45/159 (28%), Positives = 71/159 (44%)

Query:   442 LVRRLSCHVLSASVGSSAVMSTAIMATLLLFKHQKGVFLSQLLGEFSWLTEEILLRGFD- 500
             L+R +   HV+       ++MST ++A LLL + + GV S L + WL E+IL  G D
Sbjct:     5 LIRSIGEHVVFDCSMMCSIMSTHVVACLLLTRWRNGVHRSTLEEDCDWLCEKILAEGGDI 64

Query:   501 VGFSGQLRSLLQHSLSLLRAHVALLRI----RQGDLLVVPQPG-PGLTHLAQLSAELLPV 555
             VGFSG    Q              +++ +  R  + P+ P   LA  S  ++
Sbjct:    65 VGFSGKSTKGSQIVKYACELLGSCVTVTDEDRNDEFYISPKNSVPSFIELAYYSNSVICH 124

Query:   556 FLSEAVGACAVRGLLAGRVPPQGPWELQGI-LLLSQNEL 593
             F +++ AC + L +    G E G+ L+SQ +L
Sbjct:   125 FALKSIIACTIYSL-PNKTKNGG--EAGGLGNLISQEQL 160 (SEQ ID NO:8)
```

FIG. 48C

```
Score = 100 (40.3 bits), Expect = 0.010, P = 0.0099
Identities = 27/86 (31%), Positives = 48/86 (55%)

Query:  690 QGQLPDTELGYTEQLFQFL-QATAQEEGIF-ECADPKLAISAVWTFRDLGVLQQTPSPAG 747
            +G +P++E  Y ++L ++L  T +    ++  E A   L   +AV   F+D+GV  ++T
Sbjct:   94 RGPVPESE--YLQKLHRYLITRTERNVAVYAESATYCLVKNAVKMFKDIGVFKETKQKRA 151

Query:  748 PRLHLSPTFASLDNQEKLEQFIRQFI 773
              L LS TF   N++KL  ++I  F+
Sbjct:  152 SVLELSTTFLPQCNRQKLLEYILSFV 177  (SEQ ID NO:9)
```

| FIG. 49A-1 |
| FIG. 49A-2 |
| FIG. 49A-3 |

FIG. 49A-1

```
ⓒGCGGAATTCCANACAAGAGGATTATGGAGGACCAAAAACCCCTCTTTATAATTAACAAGATCATGAGTAGAGGCCA
START SEQ ID NO:1
TTTCATGCAGACACAGTGATTCACCTCTTTCCACTGCAATTGTTTGTCTCTTACTCTGAAGATGGCTGATGTCA

CCCATTAAACTTATTACTGTTGTGGCATATTAACTTCTACACAGTTAAAGTTGCCCTTTGTCAATTCTTCTGTCG
                                                                START SEQ ID NO:2              4
                                                                 Ⓜ  E  K  G                   12
TATGGCATTTTCTGAGTCCTGATGCTTTCTTTAAGTATTATCAAAGAGAGTCACCC Ⓐ TG GAA AAA GGG
                                                                 START SEQ ID NO:3
  L   S   D   V   F   Y   F   S   K   K                                                       24
  CTG TCT GAC GTG TTT TAT TTC TCC AAG AAG                                                      72

L   S   G   L   R   G   R   D   F   E   L   S   D   V   F   Y   F   S   K   K              44
  CTC TCT GGT CTA CGA GGA AGG GAC TTT GAG CTG TCT GAC GTG TTT TAT TTC TCC AAG AAG              132

```

L   S   G   L   R   G   R   D   F   E   L   S   D   V   F   Y   F   S   K   K         44
CTC TCT GGT CTA CGA GGA AGG GAC TTT GAG CTG TCT GAC GTG TTT TAT TTC TCC AAG AAG        132

G   L   E   A   I   V   E   D   E   V   T   Q   R   F   S   S   E   E   L   V
GGA TTG GAA GCC ATT GAA GAA GAT GAA GTG ACC CAG AGG TTT TCC TCA GAG GAG CTA GTG

```
S    W    N    L    L    T    R    T    N    V    N    F    Q    Y    I    S    L    R    L    T     64
TCA  TGG  AAT  CTC  CTC  ACA  AGA  ACC  AAT  GTA  AAT  TTC  CAG  TAC  ATC  AGT  CTG  CGG  CTC  ACT   192

M    V    W    V    L    G    V    I    V    R    Y    C    V    L    P    L    R    V    T          84
ATG  GTG  TGG  GTG  CTG  GGC  GTC  ATA  GTG  CGC  TAT  TGT  GTC  CTA  CTG  CCT  CTG  AGG  GTT  ACC  252

L    A    F    I    G    I    S    L    L    V    I    G    T    T    L    V    G    Q    L    P    104
TTG  GCT  TTC  ATT  GGG  ATC  AGT  TTG  CTG  GTT  ATA  GGA  ACT  ACA  CTG  GTT  GGG  CAG  CTG  CCA  312

D    S    L    K    N    W    L    S    E    L    V    H    L    T    C    C    R    I    C         124
GAC  AGC  CTC  AAA  AAC  TGG  CTG  AGT  GAA  CTG  GTC  CAT  CTG  ACT  TGC  TGC  CGG  ATC  TGT       372

V    R    A    L    S    G    T    I    H    Y    H    N    K    Q    Y    R    P    Q    K    G    144
GTG  CGA  GCC  CTC  TCT  GGT  ACC  ATT  CAT  TAT  CAT  AAC  AAG  CAG  TAC  AGA  CCC  CAG  AAG  GGA  432

G    I    C    V    A    N    H    T    S    P    I    D    V    L    I    L    T    T    D    G    164
GGC  ATT  TGT  GTT  GCC  AAC  CAT  ACT  TCC  CCC  ATT  GAT  GTT  TTA  ATC  TTG  ACA  ACG  GAT  GGA  492

C    Y    A    M    V    G    Q    V    H    G    G    L    M    G    I    Q    R    A    M         184
TGT  TAT  GCT  ATG  GTT  GGC  CAG  GTT  CAT  GGC  GGC  TTG  ATG  GGA  ATT  CAG  AGA  GCT  ATG       552
```

FIG. 49A-2

```
V   K   A   C   P   H   V   W   F   E   R   S   E   M   K   D   R   H   L   V    204
GTC AAG GCT TGT CCT CAT GTC TGG TTT GAA CGC TCA GAA ATG AAG GAT CGA CAC CTG GTT  612

T   K   R   L   K   E   H   I   A   D   K   K   L   P   I   L   F   P           224
ACT AAG AGA CTA AAA GAA CAT ATT GCT GAT AAG AAG CTA CCC ATA CTA TTT CCT          672

E   G   T   C   I   N   N   T   S   V   M   M   F   K   G   S   F   E   I       244
GAA GGA ACT TGC ATC AAC AAT ACT TCA GTC ATG ATG TTT AAA GGG AGC TTT GAA ATT      732

G   G   T   I   H   P   V   A   I   K   Y   N   P   Q   F   G   D   A   F   W    264
GGA GGA ACC ATA CAT CCA GTT GCA ATT AAG TAT AAC CCT CAG TTC GGT GAT GCA TTT TGG  792

N   S   S   K   Y   N   M   V   S   Y   L   L   R   M   M   T   S   W   A   I    284
AAC AGT AGT AAA TAC AAC ATG GTG AGC TAC CTG CTT CGA ATG ATG ACC AGC TGG GCC ATC  852

V   C   D   V   W   Y   M   P   P   M   P   T   R   E   E   G   E   D   A   V   Q   304
GTC TGT GAC GTG TGG TAC ATG CCC CCC ATG ACC AGA GAG GAA GGA GAA GAT GCA GTC CAG  912

F   A   N   R   V   K   S   A   I   A   I   Q   Q   G   L   T   E   L   P   W    324
TTT GCT AAC AGG GTT AAG TCT GCT ATT GCT ATA CAA CAA GGA GGC CTG ACT GAA CTT CCC TGG  972

```
GAT GGA GGA CTA AAG AGA GCA AAG GTG AAG GAC ATC TTT AAG GAA GAG CAG AAA AAT    1032
 D   G   G   L   K   R   A   K   V   K   D   I   F   K   E   E   Q   K   N     357
                                                           END SEQ ID NO:2
TAC AGC AAG ATG ATT GTG GGC AAT GGA TCT CTC AGC TAA                             1071
 Y   S   K   M   I   V   G   N   G   S   L   Ⓢ   *
                                              END SEQ ID NO:3

GAGGACGGATGACAGCCTTTAGATCTAGAACTAGCCCCTTAGAAATGGAATGGCTTTTTTGTTTTTGTTTTGTTTATTGT

TTTGTTTTTATTATTGTTAATCTTTTCTACAGAATGATTGTCTCTACCTCTTTATGCCAGAGGCAGAACCTACAGGTGC

CCTTTTGGCTTTTGTTTGTTGTTGTTGTAACATTAGCCCCATGGATTGTAAGGTGGTTACTGAGTTMAAACAGAWTYYKSY

TTTKKKWAAAWKRWKGSMWYMMYKKKGRMYKRAWTTKKWWWRRAAAAAGTGCTTGAAAAGTGTGTTGGAACTC

ATCGATAGGGTAATTCTCCAAAAATGCCCAAACTCTCTCTTTCTGTAATTAGCCTTGCCACTTTCTCTTTCAGTCACTTAAAT

ATCGATAGGGTAATTCTCCAAAAATGCCCAAACTCTCTCTTTCTGTAATTAGCCTTGCCACTTTCTCTTTCAGTCACTTAAA(T)
                                                                    END SEQ ID NO:1
```

FIG. 49B

| FIG. 52A |
|----------|
| FIG. 52B |

FIG. 52

>37511 P99.2 (2) O35259(1) Q21812(1) // ACYLTRANSFERASE PUTATIVE
LYSOPHOSPHATIDIC ACID TRANSFERASE RO7E3.5 PROTEIN
Length = 189

Score = 606 (218.4 bits), Expect = 1.9e-59, p = 1.9e-59
Identities = 105/189 (55%), Positives = 136/189 (71%)

```
Query:   26 LEAIVEDEVTQRFSSEELVSWNLLTRTNVNFQYISLRLTMVWVLGVIVRYCVLLPLRVTL 85
            +E  I++D+VT RFS+E+L SWNLL+RTN NF Y + RLT++W  G + RYC LLP R+ L
Sbjct:    1 METIMDDQVTNRFSAEQLPSWNLLSRTNYNFHYFNWRLTILWGAGFMFRYCFLLPCRIAL 60

Query:   86 AFIGISLLVIGTTLVGQLPDSSLKNWLSELVHLTCCRICVRALSGTIHYHNKQYRPQKGG 145
            GI L++GTT++G LP+     + +    HL C RIC RA +  I YHN++ RP  GG
Sbjct:   61 FGTGIGLMIVGTTMIGYLPNGRFREFLNRHCHLMCYRICSRAFTAIIRYHNRRNRPNNGG 120

Query:  146 ICVANHTSPIDVLILTTDGCYAMVGQVHGGLMGIIQRAMVKACPHVWFERSEMKDRHLVT 205
            ICVANHTSPIDV+I       D CYAM+GQ HGG MG IQR M +AC H+WFER E  DRH V
Sbjct:  121 ICVANHTSPIDVMIFACDNCYAMIGQKHGGFMGFIQRTMSRACHHIWFERGEAGDRHKVM 180

Query:  206 KRLKEHIAD 214
            R++EH+ D
Sbjct:  181 DRMREHVND 189
```

QUERY = 46743
SUBJECT = SEQ ID NO:4

FIG. 52A

>21987 P99.2 (3) O35259(1) Q21812(1) Q21598(1) // ACYLTRANSFERASE PROTEIN
PUTATIVE LYSOPHOSPHATIDIC ACID TRANSFERASE RO7E3.5 M79.3
Length = 114

Score = -385 (140.6 bits), Expect = 5.0e 36, p = 5.0e 36
Identities = 73/114 (64%), Positives = 83/114 (72%)

```
Query:  215 KKKLPILIFPEGTCINNTSVMMFKKGSFEIGGTIHPVAIKYNPQFGDAFWNSSKYNMVSY 274
            K K PILIFPEG CINNT VMMFKKGSFE    I+PVAIKY+P+FGD FW   +Y    Y
Sbjct:    1 KSKGPILIFPEGYCINNTKVMMFKKGSFEEGVNIYPVAIKYDPEFGDGFWYEDEYGFFQY 60

Query:  275 LLRMMTSWAIVCDVWYMPPMTREEGEDAVQFANRVKSAIAIQGGLTELPWDGGL 328
            L+RMMT+ WAIVCDVWY+P MTR+E ED     FA RVK AIA    G+    + G L
Sbjct:   61 LVRMMTNWAIVCDVWYLPMMTRKEHEDNSLFAARVKQAIANAAGIPSCEYGGSL 114
```

QUERY = 46743
SUBJECT = SEQ ID NO: 5

| FIG. 56A-1 |
| FIG. 56A-2 |
| FIG. 56A-3 | fbh27417FL.seq
START SEQ ID NO:6
(N)CGGTGTCCGGGCAGGGGGATTGGCGATGGGTGAGGTCATGGGTGAGCATCCCTGAGCCATCGATCCGGGAGGGCC

GCGGGTTCCCCTTGCTTGCCGCCGGAGCAGCCCCGCCACTCGCCTCCGCTACCCGGCCCCCGGCGGCGGCGGCGGC

CCATGCGGCTGGGGGTCTGGGAGCGGAGGCTGAGGGGTTGGGCGCCCGGCGCCCGGGCGGCGGCGTGATTGCCGCTGCT

GGCCGCGACTGAGGCCCGGAGGCGGGGAGCGCCAGGCGGAGCTCGCTGCCGAGCTGAGAAG (A)TG CTG
                                                    START SEQ ID NO:7
                                                          (M)  L     2
                                                          START SEQ ID NO:8     6

L   S   L   V   L   H   T   Y   S   M   R   Y   L   L   P   S   V   L   L       22
CTG TCC CTG GTG CTC CAC ACG TAC TCC ATG CGC TAC CTG CTG CCC AGC GTC CTC CTG      66

G   T   A   P   T   Y   V   L   A   W   G   V   W   R   L   L   S   A   F   L   42
GGC ACG GCG CCC ACC TAC GTG TTG GCC TGG GGG GTC TGG CGG CTG CTG TCC GCC TTC CTG  126

FIG. 56A-1

```
  P   A   R   F   Y   Q   A   L   D   D   R   L   Y   C   V   Y   Q   S   M   V                62
CCC GCC CGC TTC TAC CAA GCG CTG GAC GAC CGG CTC TAC TGC GTC TAC CAG AGC ATG GTG               186

L   F   F   E   N   I   L   V   G   Y   L   L   D   P   K                                    82
CTC TTC TTC GAG AAT ATA TTG GTC TAT CTA TTG GAT TTG CCA AAA                                   246

N   K   E   N   I   A   N   H   Q   V   S   R   V   Y   I   A                               102
AAT AAA GAA AAT ATA TTA GCA AAT CAT CAA AGC CGC TAC GTG ATT GCT                               306

D   I   L   A   I   R   Q   N   A   L   G   H   V   Y   I   G   E   G                       122
GAC ATC TTG GCC ATC AGG CAG AAT GCG CTA GGA CAT GTG TAC GGA AAA GAA GGG                       366

L   W   L   P   Y   L   C   Y   F   A   Q   H   G   I   Y   V   K                           142
TTA TGG CTG CCA TAT TTG TGT TAC TTT GCT CAG CAT GGA ATC TAT GTA AAG                           426

R   S   A   K   F   N   E   M   R   N   K   L   Q   S   Y   V   D   A                       162
CGC AGT GCC AAA TTT AAC GAG ATG CGA AAG TTG CAG AGC TAC GTG GAC GCA                           486

G   T   P   M   Y   L   V   I   F   P   E   G   T   R   Y   N   P   E   Q   T               182
GGA ACT CCA ATG TAT CTT GTG ATT TTT CCA GAA GGT ACA AGG TAT AAT CCA GAG CAA ACA               546
```

FIG. 56A-2

| K | V | L | S | A | Q | A | F | A | A | Q | R | G | L | A | V | L | K | H | 202 |
|---|---|---|---|---|---|---|---|---|---|---|---|---|---|---|---|---|---|---|---|
| AAA | GTC | CTT | TCA | GCT | CAG | GCA | TTT | GCA | GCC | CAA | CGT | GGC | CTT | GCA | GTA | TTA | AAA | CAT | 606 |

| V | L | T | P | R | I | K | A | T | H | V | A | F | D | C | M | K | N | Y | L | 222 |
|---|---|---|---|---|---|---|---|---|---|---|---|---|---|---|---|---|---|---|---|---|
| GTG | CTA | ACA | CCA | CGA | ATA | AAG | GCA | ACT | CAC | GTT | GCT | TTT | GAT | TGC | ATG | AAG | AAT | TAT | TTA | 666 |

| D | A | I | Y | D | V | T | V | V | Y | E | G | K | D | D | G | M | K | R | H | 242 |
|---|---|---|---|---|---|---|---|---|---|---|---|---|---|---|---|---|---|---|---|---|
| GAT | GCA | ATT | TAT | GAT | GTT | ACG | GTT | GTT | TAT | GAA | GGG | AAA | GAC | GAT | GGA | ATG | AAG | CGA | CAG | 726 |

| E | S | P | T | M | T | E | F | L | C | K | E | C | P | K | I | H | I | H | I | 262 |
|---|---|---|---|---|---|---|---|---|---|---|---|---|---|---|---|---|---|---|---|---|
| GAG | TCA | CCG | ACC | ATG | ACG | GAA | TTT | CTC | TGC | AAA | GAA | TGT | CCA | AAA | ATT | CAT | ATT | CAC | ATT | 786 |

| D | R | I | D | K | K | D | V | P | E | E | Q | E | H | M | R | R | W | L | H | 282 |
|---|---|---|---|---|---|---|---|---|---|---|---|---|---|---|---|---|---|---|---|---|
| GAT | CGT | ATC | GAC | AAA | AAA | GAT | GTC | CCA | GAA | GAA | CAA | GAA | CAT | ATG | AGA | AGA | TGG | CTG | CAT | 846 |

| E | R | F | E | I | K | D | K | M | L | I | E | F | Y | E | S | P | D | P | E | 302 |
|---|---|---|---|---|---|---|---|---|---|---|---|---|---|---|---|---|---|---|---|---|
| GAA | CGT | TTC | GAA | ATC | AAA | GAT | AAG | ATG | CTT | ATA | GAA | TTT | TAT | GAG | TCA | CCA | GAT | CCA | GAA | 906 |

| R | R | K | R | F | P | G | K | S | V | N | S | K | L | S | I | K | T | L | 322 |
|---|---|---|---|---|---|---|---|---|---|---|---|---|---|---|---|---|---|---|---|
| AGA | AGA | AAA | AGA | TTT | CCT | GGG | AAA | AGT | GTT | AAT | TCC | AAA | TTA | AGT | ATC | AAG | ACT | TTA | 966 |

FIG. 56A-3

| FIG. 56B-1 |
| FIG. 56B-2 |
| FIG. 56B-3 |

FIG. 56B

```
      P    S    M    L    I    L    S    G    L    T    A    G    M    L    M    T    D    A    G    R      342
     CCA  TCA  ATG  TTG  ATC  TTA  AGT  GGT  TTG  ACT  GCA  GGC  ATG  CTT  ATG  ACC  GAT  GCT  GGA  AGG     1026

K    L    Y    V    N    T    W    I    Y    G    T    L    L    G    C    L    W    V    T    I      362
     AAG  CTG  TAT  GTG  AAC  ACC  TGG  ATA  TAT  GGA  ACC  CTA  CTT  GGC  TGC  CTG  TGG  GTT  ACT  ATT    1086
                                      END SEQ ID NO:7

K    *                                                                                                 365
     AAA  GCA  TAG                                                                                          1095
                    END SEQ ID NO:8

ACAAGTAGCTGTCTCCAGACAGTGGGATGTGCTACATTGTCTATTTTTGGCGGCTGCACATGACATCAAATTGTTTCCT

GAATTTATTAAGGAGTGTAAATAAAGCCTTGTTGATTGAAGATTGGATAATAGAATTTGTGACGAAAGCTGATATGCAA
```

FIG. 56B-1

TGGTCTTGGGCAAACATACCTGTTGTACAACTTTAGCATCGGGGCTGCTGGAAGGGTAAAAGCTAAAATGGAGTTTCTC

CTGCTCTGTCCATTCCTATGAACTAATGACAACTTGAGAAGGCTGGGAGGATTGTGTATTTGCAAGTCAGATGGCTG

CATTTTGAGCATTAATTGCAGCGTATTTCACTTTTTCTGTTATTTCAATTTATTACAACTGACAGCTCCAAGCTC

TTATTACTAAAGTATTTAGTATCTTGCAGCTAGTTAATATATTTCATCTTTTGCTTATTTCTACAAGTCAGTGAAATAAAT

TGTATTTAGGAAGTGTCAGGATGTTCAAAGGAAAGGGTAAAAAGTGTTCATGGGGAAAAAGCTCGTTTAGCACATGAT

TTTATTGTATTGCGTTATTAGCTGATTTTACTCATTTTATATTGCAAAATAAATTTCTAATATTTATTGAAATTGCTT

AATTTGCACACCCTGTACACACAGAAAATGGTATAAAATATGAGAACGAAGTTTAAAATGTGACTCTGATTCATTATA

GCAGAACTTTAAATTCCCAGCTTTTGAAGATTTAAGCTACGCTATTAGTACTTCCCTTGTCTGTGCCATAAGTGCT

TGAAAACGTTAAGGTTTTCTGTTTGTTTGTTTTTTAATATCAAAAGAGTCGGTGTGAACCTTGGTTGGACCCCAAG

TTCACAAGATTTTAAGGTGATGAGAGCCTGCGACATTCTGCCTAGATTACTAGCGTGTGCCTTTGCCTGCTCTCT

TTGATTCACAGAATATTCATTCAGAAGTCGCGTTTCTGAGTGTGGTGGATTCCCACTGGGCTCTGTCCTTCCCTTG

FIG. 56B-2

```
GATCCCGTCAGTGGTGCTGCTCAGCGGCTTGCACGTAGACTTGCTAGGAAGAAATGCAGAGCCAGCCTGTGCTGCCCAC

TTTCAGAGTTGAACTCTTTAAGCCCTTGTGAGTGGGCTTCACCCAGCTACTGCAGAGGCATTTGCATTTGTCTGTGTCA

AGAAGTTCACCTTCTCAAGCCCAGTGAAATACAGACTTAATTCGTCATGACTGAACGAATTGTTTATTTCCCATTAGGT

TTAGTGGAGCTACACATTAATATGTATCGCCTTAGAGAGCAAGAGCTGTGTTCCAGGAACCAGATCACGATTTTAGCCAT

GGAACAATATATCCCATGGGNAGAAGACCCTTTCAGTGTGAACCTGTTCTATTTTGTGTATAATTAAACTTCGATTT

CCTCATAGTCCTTAAGTTGACATTTCTGCNTTACTGCTACTGGATTTTTGCTGCAGAATATATNCAGTGGCCACAT

TAAACATACCAGTGGATCATGATAAGCAAAATGAAAGAAAATAAGTGACTGTGTTACACTG

CTTCTCCCATGCCAGAGAATAAACTCTTTGAAGAGTCGTGTGGTGTGAATTGGTTTNGTGTACAT

TAGAATGTATGCACACATCCATGGACACTCAGGATATANGTTGGCCTAATAATCGGGCATGGGTAAAACTTATGAAAA

TTTCCTCATGCTGAANTTGTAATTTTCTCTTACCTGTAAAGTAAAATTTAGATCAATTCCATGTCTTTGTTAAGTNACA

GGGATTTAATATATTTGAATATAAATGGGTATGTTCTAAATTGAACTTTGNAGAGGCAATACTGTTGAATTATGTGG
```

FIG. 56B-3

ATTCTAACTCATTTTAACAAGGTAGCCTGACCTGCATAAGATCACTTGAATGTNTAGGTTTCATAGAACTATACTAATC

TTCTCACAAAAGGTCTATAAATACAGTCGTTGAAAAAAATTTGTATCAAAAATGTTTGGAAAATTAGAAANGCTTCTCC

TTAACCTGTATTGATACTGACTTGAATTATTTCTAAAATTAAGAGCCGTATACCTACCGTAAGTCTTTTCACATATC

ATTAAACTTTTGTTTGTATTATTACTGATTACAGCTTAGTTATTAATTTTCTTATAAGAATGCCGTCGATGTGCA

TGCTTTTATGTTTTTCAGAAAAGGGTGTGTTTGGATGAAAGTAAAAAAAAAAAAAATAAAATCTTTNCACTGTCTCTAAAAA

AAAAAAAAAAAAAADRMRRMRMWAAAGTCGAGC END SEQ ID NO: 6

FIG. 56C

>4009 p99.2 (14) YBP2(2)   // ACYLTRANSFERASE PROTEIN TRANSFERASE
1-ACYL-GLYCEROL-3-PHOSPHATE 1-ACYL-SN-GLYCEROL-3-PHOSPHATE PUTATIVE
COSMID FIG1-GIP1 INTERGENIC REGION
Length = 172

Score = 183 (69.5 bits), Expect = 3.9e-14, P = 3.9e-14
Identities = 55/170 (32%), Positives = 92/170 (54%)

```
Query:   71 GVQILLYGDLPK--NK----ENIIYLANHQSTVDWIVADILAIRQNALGHVRY----VLKE 121
            GV+  +YGD +  NK      EN I +  NHQS +DWI      LA R  + LG  Y    +LK+
Sbjct:    7 GVKVYMYGDDIETYNKTGKDENAILICNHQSYLDWIPLWWLAYR-SGLGANTYWKIILKK 65

Query:  122 GLKWLPLYGCYFAQHGGIYVKRSAKPNEKEMRNKLQS-----YV--------DAGTPMYLVI 170
            LK++P+ G       HG    I+++R+  + ++       + N L +     Y    ++  P  +L++
Sbjct:   66 SLKYIPVLGWGMRNHGYIFLERNWEKDKDTLLNSLDNCGPNYKKHYKRLNESEDPYWLIL 125

Query:  171 FPEGTRYNPEQTKVLSASQAFAAQRGLAVLKHVLTPRIKATHVAPDCMKN 220
            FPEGT  + ++    +   SQ +A +  GL   L++VL PR    A + M++
Sbjct:  126 FPEGTNLSAKKRE---KSQEYAEKNGLPPLQNVLLPRTGGLKYALEKMRD 172
```

QUERY = 27147
SUBJECT = SEQ ID NO: 9

FIG. 59A

>123477 p99.2 (1) 001783_CAEEL // SIMILAR TO 1-ACYL-GLYCEROL-3-PHOSPHATE
ACYLTRANSFERASES TRANSFERASE ACYLTRANSFERASE
    Length = 160

Score = 97 (39.2 bits), Expect = 0.0030, P = 0.0030
Identities = 44/170 (25%), Positives = 71/170 (41%)

Query:  197  LAVLKHVLTPRIKATHVAFDCMKNYLDAIYDVTVVYEGKDDGGQRRESPTMTEFLC--KE  254
             L+ L +    +       + FD  N L   Y++ ++Y +           +R   +P M +F C  ++
Sbjct:    1  LSTLDAIYDVTVMYGQMRFDLGLN-LTIHYNLIIYRMAE---RRGLAPGMPDFCCGSQQ   56

Query:  255  CPXXXXXXXXXXXVPEEQEHMRWLHERFEIKDKMLIEFYESPDPERRKRFPPGKSVNS   314
                          VP+ +    +R W  ERF    K++++ EFY S  P     P
Sbjct:   57  FKQLHIHLDRIPIDEVPKAKLELRTWTIERFTKKERIIDEFY-SEKPSTGSALPC------  110

Query:  315  KLSIKKTLPSMLILSG-LTAGMLMTDAGRKLYVNTWIYGTLLGCLWVTIK  363
             +   I +TLPS L  S LA      GR +Y+ T    LL    W+ I+
Sbjct:  111  -VPISQTLPSTLFFSAALLAPFFSRTIGR-IYLLTIASSPLL-IAWLHIR  157

QUERY = 27147
SUBJECT = SEQ ID NO: 10

FIG. 59B

```
Acyltransferase: domain 1 of 1, from 77 to 288: score 38.4, E = 1.6e-07
SEQ ID NO: 11    *->lenlpkkg.paivvsNHrSylDilvlsaalprrgpwlvrrlvfiakk
                  + lpk++++ i+ +NH+S +D++v+ ++ r+++ l++ +++++k+
27417      77    YGDLPKNKeNIIYLANHQSTVDWIVADILAIRQNA-LGH-VRYVLKE    121 ellkvPllfGwlmrlagaifidRnnrakdalaaadelvrvlellrkgrsv
                 l+++Pl G + +g l+++R+ +    ++++    ++l +++ +   +
27417     122    GLKWLPL-YGCYFAQHGGIYKRSAKF-NEKEMRNKLQSYVD-AGTPMYL   168 liPPEGTRsrsgellppfKkGlaefrlAlkagvpivPvvl..vsgteele
                 +iPPEGTR   ++ +     + +a   +A++ g+ ++  v+++++ ++++
27417     169    VIFPEGTRYNPEQTKV-LSASQA---FAAQRGLAVLKHVLtpRIKATHVA   214 pkneagkllrlarkkgpvtvrvlppipld..................
                        +   ++ +       +vtv++        ++ ++++++++ ++     ++  ++   +
27417     215    FD----CMKNYLDAIYDVTVVYEGKDDGGqrresptmteflckecpkihi   260

......pedikelaerlrdilvgaleel<-*
                 + ++ ++ d++e +e+++r++l +++e +
27417     261    hidridKKDVPEEQEHMRRWLHERFEIK   288
```

FIG. 60

```
Alignments of top scoring domains:
UQ_con: domain 1 of 1, from 1 to 148: score 138.0, E = 1.6e-37
          *->mSsssaskRlqkElkklqedpppgfsa..gpvddnnifeWnviimGp
             m+s+   kRlqkEl   lq dpppg ++++ V ++ i++W V+  G
   27960   1 MASMQ--KRLQKELLALQNDPPPGMTLneKSVQNS-ITQWIVDMEGA    44 pDTPYEGGVFklejeFPedYPfkPPkvrFtskif..HPNIysntGriCLD
             p+T+YEG+ F+l   +F + YPf +P+v Ft ++++ HP++ysn G+iCL+
   27960  45 PGTLYEGEKFQLLFKFSSRYPFDSPQVMFTGENIpvHPHVYSN-GHICLS    93

ILkdpGDDpngyElaeErWSPaytvesILlsiqSLLs.dPNpdsPanveA
             IL +                WSPa+ v  s++lSi+S+Ls+   ++  +P  ++
   27960  94 ILTE---------------DWSPALSVQSVCLSIISMLSsCKEKRRPPDNSF  130

AklyrkkedreeYekrVkewvek<-*
             ++     +   +  +k++k+w ++
   27960 131 YVRTC-----NKNPKKTKWWYHD    148
```

FIG. 65A

```
Alignments of top scoring domains:
ubc_7: domain 1 of 1, from 6 to 151: score 128.0, E = 1.7e-34
                   *->kRlqkElkelqkdpppgisaipvd...nlleWtvtIvGPpdTpYEgG
                      kRlqkEl   lq dpppg + ++++ ++   ++ W v   G p+T+YEg
            27960   6 KRLQKELLALQNDPPPGMTLNEKSvqnSITQWIVDMEGAPGTLYEGE 52 vfkltieFPedYPfkPPkvkFitk..iyHPNvdsssGeiCLdIlkekWsP
                     +f+l   +F   YPf  P+v F+  + + HP+v+ s+G+iCL+iIL+e+WsP
            27960  53 KFQLLFKFSSRYPFDSPQVMFTGEniPVHPHVY-SNGHICLSILTEDWSP 101 altletvLlsiqsLlnePnpdsPlnvdaaelyrkdreefkkkvrewtkky
                     al++++v+lsi+s+L++   ++++ +       ++++  kk  ++w++
            27960 102 ALSVQSVCLSIISMLSSCKEKRPPDNSFYVRTCNKN--PKKTKWWYHDD 149 ae<-*
            27960 150 TC 151
```

>gi|6996616|dbj|BAA90828| (AB026291) acetoacetyl-CoA synthetase [Rattus norvegicus]
Length = 672

Plus Strand HSPs:

Score = 3210 (1473.7 bits), Expect = 0.0, P = 0.0
Identities = 600/672 (89%), Positives = 638/672 (94%), Frame = +1

```
Query:   136  MSKEERPGREEILECQVMWEPDSKKNTQMDRFRAAVGAACGLALESYDDLYHWSVESYSD    315
              MSK  R  REEI+ECQVMWEPDSKK+TQMDRFRAAVG ACGLAL +YDDLYHWSV SYSD
Sbjct:     1  MSKLARLEREEIMECQVMWEPDSKKDTQMDRFRAAVGTACGLALGNYDDLYHWSVRSYSD     60

Query:   316  FWAEFWKFSGIVFSRVYDEVVDTSKGIADVPEWFKGSRLNYAENLLRHKENDRVALYIAR    495
              FWAEFWKFSGIV  SR+YDEVVDTSKGIADVPEWF+GSRLNYAENLLRHKENDRVALY+AR
Sbjct:    61  FWAEFWKFSGIVCSRMYDEVVDTSKGIADVPEWFRGSRLNYAENLLRHKENDRVALYVAR    120

Query:   496  EGKEEIVKVTFEELRQEVALFAAAMRKMGVKKGDRVVGYLPNSEHAVEAMLAAASIGAIW    675
              EG+EEI KVTFEELRQ+VALFAAAMRKMGVKKGDRVVGYLPNS HAVEAMLAAASIGAIW
Sbjct:   121  EGREEIAKVTFEELRQQVALFAAAMRKMGVKKGDRVVGYLPNSAHAVEAMLAAASIGAIW    180

Query:   676  SSTSPDFGVNGVLDRFSQIQPKLIFSVEAVVYNGKEHNHMEKLQQVVKGLPDLKKVVVIP    855
              SSTSPDFGVNGVLDRFSQIQPKLIFSVEAVVYNGKEH +EKLQ++VVKGLPDL++VV+IP
Sbjct:   181  SSTSPDFGVNGVLDRFSQIQPKLIFSVEAVVYNGKEHGHLEKLQRVVKGLPDLQRVVLIP    240

Query:   856  YVSSRENIDLSKIPNSVFLDDFLATGTSEQAPQLEFEQLPFSHPLFIMFSSGTTGAPKCM   1035
              YV  RE ID+SKIPNS+FLDDFLA+GT  QAPQLEFEQLPFSHPLFIMFSSGTTGAPKCM
Sbjct:   241  YVLPREKIDISKIPNSMFLDDFLASGTGAQAPQLEFEQLPFSHPLFIMFSSGTTGAPKCM    300
```

```
Query: 1036  VHSAGGTLIQHLKEHLLHGNMTSSDILLCYTTVGWMMNWMVSLLATGAAMVLYDGSPLV  1215
              VHSAGGTLIQHLKEH+LHGNMTSSDILL YTTVGWMMNWMVS LATGA++VLYDGSPLV
Sbjct:  301  VHSAGGTLIQHLKEHVLHGNMTSSDILLYYTTVGWMMNWMVSALATGASLVLYDGSPLV   360

Query: 1216  PTPNVLWDLVDRIGITVLVTGAKWLSVLEEKAMKPVETHSLQMLHTILSTGSPLKAQSYE  1395
              PTPNVLWDLVDRIGIT+L TGAKWLSVLEEK MKP+ETH+L  LHTILSTGSPLKAQSYE
Sbjct:  361  PTPNVLWDLVDRIGITILGTGAKWLSVLEEKDMKPMETHNLHTLHTILSTGSPLKAQSYE   420

Query: 1396  YVYRCIKSSILLGSISGGTDIISCFMGHNFSLPVYKGEIQARNLGMAVEAWNEEGKAVWG  1575
              YVYRCIKS++LLGSISGGTDIISCFMG N S+PVYKGEIQARNLGMAVEAW+EEGK VWG
Sbjct:  421  YVYRCIKSTVLLGSISGGTDIISCFMGQNSSIPVYKGEIQARNLGMAVEAWDEEGKTVWG   480

Query: 1576  ESGELVCTKPIPCQPTHFWNDENGNKYRKAYFSKFPGIWAHGDYCRINPKTGGIVMLGRS  1755
              SGELVCTKPIPCQPTHFWNDENG+KYRKAYFSK+PG+WAHGDYCRINPKTGGIVMLGRS
Sbjct:  481  ASGELVCTKPIPCQPTHFWNDENGSKYRKAYFSKYPGVWAHGDYCRINPKTGGIVMLGRS   540

Query: 1756  DGTLNPNGVRFGSSEIYNIVESFEEVEDSLCVPQYNKYREERVILFLKMASGHAFQPDLV  1935
              DGTLNPNGVRFGSSEIYNIVE+F+EVEDSLCVPQYN+  EERV+LFLKMASGH FQPDLV
Sbjct:  541  DGTLNPNGVRFGSSEIYNIVEAFDEVEDSLCVPQYNRDGEERVVLFLKMASGHTFQPDLV   600

Query: 1936  KRIRDAIRMGLSARHVPSLILETKGIPYTLNGKKVEVAVKQIIAGKAVEQGGAFSNPETL  2115
              K IRDAIR+GLSARHVPSLILET+GIPYT+NGKKVEVAVKQ+IAGK VE  GAFSNPE+L
Sbjct:  601  KHIRDAIRLGLSARHVPSLILETQGIPYTINGKKVEVAVKQVIAGKTVEHRGAFSNPESL   660

Query: 2116  DLYRDIPELQGF  2151    (residues 136-2151 of SEQ ID NO:2)
              DLYRDIPELQ F          (SEQ ID NO:5)
Sbjct:  661  DLYRDIPELQDF   672    (SEQ ID NO:4)
```

FIG. 67B

```
>gb|AB026291|AB026291 Rattus norvegicus mRNA for acetoacetyl-CoA synthetase,
   complete cds.
   Length = 3190

Plus Strand HSPs:

Score = 7315 (2023.8 bits), Expect = 0.0, P = 0.0
Identities = 1743/2093 (83%), Positives = 1743/2093 (83%), Strand = Plus / Plus Query:    66 CCCGGCCCTCGCCTCAGCCCCTGTCCCCAGCCCCTCGTCGCAGCCCGGCCGCC 125
             ||| || ||||| ||||   |||  ||||||| || ||| |||   || ||||
Sbjct:    39 CCACGCCTTGCGCTCTCCGACTCTGTCTCCGACCTAAAGCCGGCACCCACGCAG 98

Query:   126 CGCCGCCGCCATGTCCAAGGAGGAGCGCCCGGTCGGGAGGAGATCCTGGAGTGCCAGGT 185
             |  ||||||||||||| ||||||| || ||||| ||||||||||| |||||||||||||
Sbjct:    99 CTCCGCAACCATGTCCAAGCTCCAAGCTGGCACGGCTCGAGGCGCGAGATCATGGAGTGCCAGGT 158

Query:   186 GATGTGGGAGCCTGACAGTAAGAAGAACACGCAGATGGACCGCTTCCGGGGCCGTGTGGG 245
             ||||||||||||||||||| |||||||||||||||||||| ||||||||||||| |||||
Sbjct:   159 GATGTGGGAGCCTGACAGCAAGAAGACACGCAGATGGACCGCTTCCGGGGCCGTGGG 218

Query:   246 CGCCGCCTGGGCGCTGGGCGCTGGGCGCTGGGCGCTTGTACCATTGGTCCGTTGAGTC 305
             | ||| |||||||||||  | ||||||  |||||||||| ||||||||| ||||| ||
Sbjct:   219 TACTGCCTGCGCGCCTGGGCGCTTGGGAATTACGATGACTTATACCACTGGTCTGTCCGGTC 278

Query:   306 ATATTCAGACTTCTGGGCAGAGTTCTGGAAATTGTCTTCTCACGTGTGTA 365
             | ||||||||||||||| ||||||||||| ||||| ||||||||||| ||
Sbjct:   279 GTATTCAGACTTCTGGGCTGAGTTCTGGAAGTTCAGTGGAATTGTCTGCTCTCGCATGTA 338
```

FIG. 68A

```
Query:  366  TGATGAGGTTGTGTGGACACATCGAAAGGAATCGCAGATGTCCCCGAGTGGTTCAAAGGCAG  425
             ||||||||||||||||||||||| ||||||||| ||||||||||||||||||||||||||
Sbjct:  339  TGATGAGGTTGTGTGGACACATCCAAAGGAATTGCAGATGTCCCTGAGTGGTTCAGAGGCAG  398

Query:  426  TCGGCTCAACTATGCAGAAAACCCTCCTGCGGCACAAAGAGAATGACAGAGTTGCCCCTTTA  485
             | ||||||||||||||||      ||||||||||||||||| ||||||| |||||||||
Sbjct:  399  CCGCCTCAACTATGCAGAGAGAACCTTTGCGGCACAAGGAGAACGACAGAGTCGCCCTTTA  458

Query:  486  CATTGCAAGGGAAGGCAAAGAGAGGCAAATTGTGAAGGTGACTTTTGAAGAGCTGAGGCAAGA  545
             |   |||||||||||| ||     ||||||||| ||||||||||||||||||||||||
Sbjct:  459  CGTGGCCCGGGAAGGCAGAGGCAGAGATTGCGAAGGTGACTTTCGAAGAGCTTCGGCAGCA  518

Query:  546  AGTGGCTTTGTTTGCAGCAATGAGCACGCTGTCGAGGCGATGCTGGCTGCGCAAGCATTGG  605
             ||||||||| |  |||||  |||||| |||| |||||| ||||||||||| ||||||||
Sbjct:  519  GGTGGCTCTCGTTTGCAGCCGCATGAGCCGTGAGAGGAAGATGGGGACCCGTGTGTGGT  578

Query:  606  TGGTTATTTACCCAACAGTGAGCACGCTGTCGAGGCGATGCTGGCTGCGCAAGCATTGG  665
             |||||| ||   ||||||||||||||||||| ||||||||||||||| |||| ||||
Sbjct:  579  CGGTTATCTCCCCAACAGTGCCCATGCCGTGGAGGCCATGCTGCTGCCAGTATTGG  638

Query:  666  TGCCATCTGGAGCTCCCACGTCCCCGGACTTCGGTGTGAATGGTGTCTGGACCGGTTTTC  725
             |||||| ||||||||| ||   |||||||| |||||||| |||||||||||||| |||
Sbjct:  639  AGCCATTTGGAGTTCTACCTCACCAGACTTTGGTGTGAATGGTGTCCTGGACCGCTTTTC  698

Query:  726  TCAAATTCAGCCGAAAGCTCATCTCTCTGTGGAGGCTGTGTCTATAATGGCAAAAGAGCA  785
             ||||||||||||||| || |   || || || ||||| ||||||| ||||||||| ||
Sbjct:  699  TCAAATTCAGCCGAAACTTATCTTCTCGGTGGAAGCTGTGGTCTACAACGGCAAGGAACA  758
```

FIG. 68B

```
Query:  786  CAACCACATGGAAAAGCTGCAGCAGGTGGTTAAAGGCCTACCAGACTTGAAGAAAGTGGT  845
             |  ||||||| ||||| ||||||||| ||||||  ||||| ||||||||||||||| ||
Sbjct:  759  CGGCCACCTGGAGAAGCTGCAGCGAGTCGTGAAAGGACTTCCTGACCTTCAGCGAGTGGT  818

Query:  846  GGTGATTCCTTATGTGTCCTCCCAGAGAGAACATAGACCTTTCAAAGATTCCAAACAGTGT  905
             | ||| || ||  |||||    ||| ||||| ||||| |  |||||||||||| ||  |
Sbjct:  819  GCTGATCCCCTATGTCCCTCCCAAGGGAGAAGATAGACATTTCCAAGATCCCCAACAGCAT  878

Query:  906  GTTTCTGGATGACTTTCTTGCCAGTGAGCAGGCCCCGCAGCTGGAGTTCGA  965
             |  |||||||||||| ||||||||| |||||| ||||||||||||||| |
Sbjct:  879  GTTTCTGGATGACTTCCTTGCCAGTGGGCAGGTGCGCAGCTGGAGTTTGA  938

Query:  966  GCAGCTGCCCTTCAGCCACCCACTGTTCATCATGTTCTCATCGGGCACCACGGGGCACC  1025
             |||| ||||||||||||||| |||||||||| ||||||||||||||  |||||||| |
Sbjct:  939  ACAGCTGCCCTTCAGCCACCTACTGTTCATCATGTTCTCCTCGGGCACGACAGGAGCGCC  998

Query:  1026 CAAGTGCATGGTTCCGCTGGCACCCTCATCCAGCATCTGAAGGAGCACCTGCT  1085
             ||||||||||| ||||||||||||||||||||||||||||||||||| ||||
Sbjct:  999  CAAGTGCATGGTGCCGCTGGGACCCTCATCCAGCACCTGAAGGAGCACGTGCT  1058

Query:  1086 GCACGGCAACATGACCAGCAGTGACATCCTCCTGTGCTACACCACGGTTCGGCTGGATGAT  1145
             |||||||||||||||||||||||||||||||||||||||||| |||||||||||||||||
Sbjct:  1059 ACATGGCAACATGACCAGCAGTGACATCCTCTACTACACCACGGTCCGGCTGGATGAT  1118

Query:  1146 GTGGAACTGGATGGTGTCCCTTCTGGCCACAGGAGCGGCCATGGTCTTGTACGATGGCTC  1205
             ||||||||||||||||||||| |||||||||||||||||||||||| |||||||||||||
Sbjct:  1119 GTGGAACTGGATGGTGTCAGCGCTGCCACAGGAGCATCCTTGGTTCTGTACGATGGCTC  1178
```

FIG. 68C

```
Query:  1206  CCCCCTGGTGTGCCCACGCCCCAATGTGTGCTCTGGGACCTGGTTGACAGGATAGGCATCACTGT  1265
              |||| ||||||  ||||||||||| || || |||||||| ||| ||||||||||| ||||| |
Sbjct:  1179  CCCGCTGGTTCCAACACCCCAATGTTGTGTGGGACCTTGTGTGGACAGGATAGGAATCACCAT  1238

Query:  1266  CCTGGTAACTGGGGCCAAGTGGCTGTGTCAGTGCTGGAAGAGAAGGCCATGAAGCCGGTGGA  1325
              |||||  ||||| |||||||||||||||||||||||| |||||||||||||||||||||||
Sbjct:  1239  CCTGGGAACGGGGAGCCAAGTGGCTGTGTCAGTGCTGGAGGAGAAGGACATGAAGCCGATGGA  1298

Query:  1326  AACCCACAGTCTCCAGATGCTCCACACGATCCTGTCCACTGGCTCCCCACTGAAAGCCCA  1385
              |||| ||||| |||||| ||||||| |  ||||||||||||||| || ||||||||||||
Sbjct:  1299  AACTCACAACCTCCACACGCTCCACACGATCCTGTCCACTGGCTCGCCACTGAAAGCCCA  1358

Query:  1386  GAGCTACGAGTATGTCTACAGGTGCATCAAGAGCAGCACCGTGCTCCTCGGCTCCATCTCAGG  1445
              ||||||  |||||||| ||| | |||||||||| |||||||||||||| |||||||||||||
Sbjct:  1359  GAGCTATGAGTATGTGTACAGATGCATCAAGAGCAGCACCGTGCTCCTCGGCTCCATCTCAGG  1418

Query:  1446  AGGCACCGACATCATCTCCCTGCTTCATGGGCCACACAATTTTCTCTTCCTGTGTATAAAGG  1505
              |||||| ||||||||||||| ||| |||||||| ||| ||  ||| ||||||| ||||| ||
Sbjct:  1419  TGGCACTGACATCATCTCCCTGTTTCATGGGCCATGCCAGAACTCATTCCTGTGTACAAGGG  1478

Query:  1506  GGAGATTCAGGCCCGGAACCTGGGCATGGCCGTGAACGAGGAAGGGAAAGGC  1565
              |||| ||||||||| ||||||||| |||||||| ||||| ||| ||||| ||
Sbjct:  1479  TGAGATCCAAGCCCGGAACCTGGGAAGCCGTGGGAGCTGGGAGCGAGGAAGGGAAAAAC  1538

Query:  1566  GGTCTGGGGAGAGCGGCGAGTGGCGAGTCCTGTGTACTAAGCCACACAGCCCTTGCCAGCCCACACA  1625
              | |||||||||||| ||||||||| |||| |||||  ||||||||||||| |||||||||||||||
Sbjct:  1539  CGTCTGGGGAGCGCGGAGTGGCGAGTGGCGAGTTTGCACCAAGCCCATACCCCTGCCAGCCCACGCA  1598
```

FIG. 68D

```
Query:  1626  CTTCTGGAACGATGAGAACGGCAACAAGTACAGGAAGGCGTATTTCTCCAAATTCCCAGG  1685
              ||||||||||||||||| ||||||||||||| ||||||||| ||||| ||||| ||||||
Sbjct:  1599  CTTCTGGAACGACGAGAACGGCAGCAAGTACAGGAAGGCTTACTTCTCCAAATACCCAGG  1658

Query:  1686  TATCTGGGCTCATGGCCGACTACTGCAGAATCAACCCCAAGACCGGGGCATCGTCATGCT  1745
              ||||||||||||||| || ||||||||||||||| |||||||| ||||||| ||| || |
Sbjct:  1659  TGTCTGGGCACACGGCGACTACTGCAGGATCAACCCCAAGACAGGAGTATCGTCATGTT  1718

Query:  1746  TGGCCGAGTGACGGCCACCCTCAACCCCAAACGGGTGCGGTTCGGCAGCTCGGAAATCTA  1805
              |||||||||| |||| |||| |||||||| ||||||| |||||||||||||||| ||||
Sbjct:  1719  GGGCCGAGTGATGGCCACCCTCAACCCCAAATGGCGTACGCTTTGGCAGCTCGGAGATCTA  1778

Query:  1806  TAACATTGTGGAATCCTTCGAGGAGGACAGCCTGTGTCCCCCAGTATAACAA  1865
              ||| ||||||||| ||||||| ||||| ||||| |||||||||||||||| ||
Sbjct:  1779  CAACATTGTGGAAGCCTTCGATGAGGTTGGCCTGTGCCCCCAGTACAACAG  1838

Query:  1866  GTACAGGGAGGAGAGGGTGATCCTCTTCCTGAAGATGGCCTCCGGGCACGCCTTCCAGCC  1925
              | |||||| |||||| ||||||||| ||||| |||||||||  |||||||||||||||||
Sbjct:  1839  GGATGGTGAGGAGCGGGTAGTCCTCGTTTCTGAAGATGGCCTGGGCACACTTTCCAGCC  1898

Query:  1926  TGACTTGGTTAAGAGGATCCGTGACGCCATGGGCTTGTCTGCGGACACGTGCC  1985
              ||| |||| ||| ||| |||||||| ||||||||| |||||||| ||||||||
Sbjct:  1899  CGACCTCGTGAAGCACATCCGTGATGCCATCGGCCTTGGCCTGTCTCGCCACGTGCC  1958

Query:  1986  CAGCCCTCATCCTGGAAAACCAAGGGCATCCCGTATACGCTCAACGGCAAGAAAGTGGAAGT  2045
              ||||||||||||||||| |||||||  ||| |||||||| ||||  ||||||||||||| |
Sbjct:  1959  CAGCCCTCATCCTGGAGACCCAAGGCATTCCATACACAATCAACGGCAAGAAAGTGGAGGT  2018
```

FIG. 68E

```
Query:  2046 TGCCGTCAAACAGATCATCGCTGGAGCAAGCCGTGGAGCAAGGAGGTGCTTTCTCGAACCC 2105
             ||||  ||  |  |  ||    ||  |  |  ||||| | ||||| | |||||  |||||
Sbjct:  2019 GGCCGTGAAGCAGGTGATAGCTGGAAGACTGGGAGCACCGGGGGCCTTCTCCAACCC 2078

Query:  2106 CGAGACCCTGGATCTGTACCGGGACATCCCTGAGCTGCAGGGCTTCTGAGTCA 2158
             |||  ||||||||  |||   ||||||||||||||||||| |||||||  ||
Sbjct:  2079 TGAGTCCCCTGGACCTGTATCGGGACATCCCTGAGCTGCAGGACTTCTGAACCA 2131
(SEQ ID NO:1)
(SEQ ID NO:6)
```

FIG. 68F

Acyltransferase: domain 1 of 1, from 71 to 261: score 72.2, E = 1.1e-17

```
                    *->lenlpkkgpaivvsNHrSylDilvlsaalprrgpwlvrrlvfiakke
START SEQ ID NO:4     +  +p +++ ++++NHr+++D+ +l+++l r+    r  ++++k++
53320      71       DAFVP-GERGVIIMNHRTRMDWTFLWNCLMRYS--YLRLEKICLKAS   114 llkvPllfGwlmrlagaifidRnnrakdalaaadelvrvlellrkgrsvl
                    l+ vP+ fGw+m+ a +ifi R+++ d+   +d +   +++   ++l
53320     115       LKGVPG-FGWAMQAAAYIFIHRKWKD-DKSHFEDMIDYFCD-IHEPLQLL   161 iFPEGTRsrsgellppfkKGiaafrlAlkagvpivPvvivsgteelepkn
                    iFPEGT    ++ ++  +++  ++   +k+ ++++P ++  ++t  +  +
53320     162       IFPEGTDLTENSKSR-SNAFAE-KNGLQKYEYVLHPRTT-GFTFVVDRLR   208 eagklLrlarkkgpvtvrvlppipld.........pedikelaerlrdil
                    e+++    a   +++tv + + ip ++++   +++ p+ i+ + r++  +
53320     209       EGKN--LDAV--HDITVAYPHNIPQSekhllqgdfPREIHFVHRYPVDT   254
                                           End SEQ ID NO:4
                    vqaleel<-*
                    ++ +e
53320     255       LPTSKED   261
```

FIG. 70

HUMAN TRANSFERASE FAMILY MEMBERS AND USES THEREOF

Related Applications

This application is a continuation-in-part and claims priority to U.S. application Ser. No. 09/815,028, filed Mar. 22, 2001, now abandoned and International Application Serial No. PCT/US01/09358, filed Mar. 22, 2001, which claim the benefit of U.S. Provisional Application Ser. No. 60/191,964, filed Mar. 24, 2000; and U.S. application Ser. No. 09/801,220, filed Mar. 7, 2001, now abandoned and International Application Serial No. PCT/US01/07269, filed Mar. 7, 2001, which claim the benefit of U.S. Provisional Application Ser. No. 60/187,456, filed Mar. 7, 2000; and U.S. application Ser. No. 09/816,714, filed Mar. 23, 2001, now abandoned and International Application Serial No. PCT/US01/09468, filed Mar. 23, 2001, which claim the benefit of U.S. Provisional Application Ser. No. 60/191,865, filed Mar. 24, 2000; and U.S. application Ser. No. 09/844,948, filed Apr. 27, 2001, now abandoned and International Application Serial No. PCT/US01/13805, filed Apr. 27, 2001, which claim the benefit of U.S. Provisional Application Ser. No. 60/200,604, filed Apr. 28, 2000; and U.S. application Ser. No. 09/861,164, filed May 18, 2001, now abandoned and International Application Serial No. PCT/US01/16292, filed May 18, 2001, which claim the benefit of U.S. Provisional Application Ser. No. 60/205,408, filed May 19, 2000; and U.S. application Ser. No. 09/883,060, filed Jun. 15, 2001, now abandoned and International Application Serial No. PCT/US01/19138, filed Jun. 15, 2001, which claim the benefit of U.S. Provisional Application Ser. No. 60/212,079, filed Jun. 15, 2000; and U.S. application Ser. No. 09/962,678, filed Sep. 25, 2001, now abandoned and International Application Serial No. PCT/US01/29963, filed Sep. 25, 2001, which claim the benefit of U.S. Provisional Application Ser. No. 60/235,044, filed Sep. 25, 2000; and U.S. application Ser. No. 09/973,457, filed Oct. 9, 2001, now U.S. Pat. No. 6,703,230 which claims the benefit of U.S. Provisional Application Ser. No. 60/238,849, filed Oct. 6, 2000; and U.S. application Ser. No. 10/072,285, filed Feb. 8, 2002, now abandoned and International Application Serial No. PCT/US02/03736, filed Feb. 8, 2002, which claim the benefit of U.S. Provisional Application Ser. No. 60/267,494, filed Feb. 8, 2001; and U.S. application Ser. No. 09/817,910, filed Mar. 26, 2001, now abandoned and International Application Serial No. PCT/US01/09633, filed Mar. 26, 200 1, which claim the benefit of U.S. Provisional Application Ser. No. 60/192,092, filed Mar. 24, 2000; and U.S. application Ser. No. 09/842,528, filed Apr. 25, 2001, now abandoned and International Application Serial No. PCT/US01/40607, filed Apr. 25, 2001, which claim the benefit of U.S. Provisional Application Ser. No. 60/199,500, filed Apr. 25, 2000; and U.S. application Ser. No. 09/882,836, filed Jun. 15, 2001, now abandoned and International Application Serial No. PCT/US01/19543, filed Jun. 15, 2001, which claim the benefit of U.S. Provisional Application Ser. No. 60/211,730, filed Jun. 15, 2000; and U.S. application Ser. No. 09/882,872, filed Jun. 15, 2001, now abandoned and International Application Serial No. PCT/US01/19153, filed Jun. 15, 2001, which claim the benefit of U.S. Provisional Application Ser. No. 60/212,077, filed Jun. 15, 2000, the contents of which are incorporated herein by reference.

Background of the 33877 AND 47179 Invention

A great diversity of oligosaccharide structures and types of glycoconjugates is found in nature, and these are synthesized by a large number of glycosyltransferases. Glycosyltransferases catalyze the synthesis of glycoconjugates, including glycolipids, glycoproteins, and polysaccharides, by transferring an activated mono- or oligosaccharide residue to an existing acceptor molecule for the initiation or elongation of the carbohydrate chain. A catalytic reaction is believed to involve the recognition of both the donor and acceptor by suitable domains, as well as the catalytic site of the enzyme (Amado et al. (1999) *Biochim Biophys Acta* 1473:35-53; Kapitonov et al. (1999) *Glycobiology* 9:961-78).

Because the glycosylation reaction is highly specific with respect to both the configuration of the sugar residue and the site of the addition, it is expected that unique domain structures for substrate recognition and nucleotide-sugar binding are located within the enzyme molecule. Evidence indicates that formation of many glycosidic linkages is covered by large homologous glycosyltransferase gene families, and that the existence of multiple enzyme isoforms provides a degree of redundancy as well as a higher level of regulation of the glycoforms synthesized (Kapitonov et al. (1999) *Glycobiology* 9:961-78).

Glycosylation is the principal chemical modification to proteins as they pass through Golgi vesicles. Glycosyltransferases of the Golgi do not possess an obvious sequence homology which would suggest a common Golgi retention signal. However, they are all membrane proteins and share type II topology, consisting of an amino terminal cytoplasmic tail, a signal anchor transmembrane domain, a stem region, and a large luminal catalyitc domain. The membrane-spanning domain and its flanking regions contain necessary and sufficient information for Golgi retention of these enzymes (Jaskiewicz (1997) *Acta Biochim Pol* 44:173-9). ER localized glycosyltransferases can have either a type II topology, like the Golgi glycosyltransferases, or a type I topolgy, e.g., the N-terminus and catalytic domain inside the ER (Kapitonov et al. (1999) *Glycobiology* 9:961-78). Some glycosyltransferases are present on the cell surface and are thought to function as cell adhesion molecules by binding oligosaccharide substrates on adjacent cell surfaces or in the extracellular matrix. The best studied of these is beta 1,4-galactosyltransferase, which mediates sperm binding to the egg coat and selected cell interactions with the basal lamina (Shur (1993) *Curr Opin Cell Biol* 5:854-63).

Summary of the 33877 and 47179 Invention

The present invention is based, in part, on the discovery of a novel glycosyltransferase family members, referred to herein as "33877 and 47179." The nucleotide sequence of a cDNA encoding 33877 is shown in SEQ ID NO:1, and the amino acid sequence of a 33877 polypeptide is shown in SEQ ID NO:2. In addition, the nucleotide sequences of the coding region are depicted in SEQ ID NO:3. The nucleotide sequence of a cDNA encoding 47179 is shown in SEQ ID NO:4, and the amino acid sequence of a 47179 polypeptide is shown in SEQ ID NO:5. In addition, the nucleotide sequences of the coding region are depicted in SEQ ID NO:6.

Accordingly, in one aspect, the invention features a nucleic acid molecule which encodes a 33877 or 47179 protein or polypeptide, e.g., a biologically active portion of the 33877 or 47179 protein. In a preferred embodiment the isolated nucleic acid molecule encodes a polypeptide having the amino acid sequence of SEQ ID NO:2 or SEQ ID NO:5. In other embodiments, the invention provides isolated 33877 or 47179 nucleic acid molecules having the nucleotide sequence shown in SEQ ID NO:1, SEQ ID NO:3, SEQ ID NO:4, or SEQ ID NO:6. In still other embodiments, the invention provides nucleic acid molecules that are substantially identical (e.g., naturally occurring allelic variants) to the nucleotide sequence shown in SEQ ID NO:1, SEQ ID NO:3, SEQ ID NO:4, or SEQ ID NO:6. In other embodiments, the invention provides a nucleic acid molecule which hybridizes under a stringency condition described herein to a nucleic acid molecule comprising the nucleotide sequence of SEQ ID NO:1, SEQ ID NO:3, SEQ ID NO:4, or SEQ ID NO:6, wherein the nucleic acid encodes a full length 33877 or 47179 protein or an active fragment thereof.

In a related aspect, the invention further provides nucleic acid constructs which include a 33877 or 47179 nucleic acid molecule described herein. In certain embodiments, the nucleic acid molecules of the invention are operatively linked to native or heterologous regulatory sequences. Also included, are vectors and host cells containing the 33877 or 47179 nucleic acid molecules of the invention e.g., vectors and host cells suitable for producing 33877 or 47179 nucleic acid molecules and polypeptides.

In another related aspect, the invention provides nucleic acid fragments suitable as primers or hybridization probes for the detection of 33877 or 47179-encoding nucleic acids.

In still another related aspect, isolated nucleic acid molecules that are antisense to a 33877 or 47179 encoding nucleic acid molecule are provided.

In another aspect, the invention features, 33877 or 47179 polypeptides, and biologically active or antigenic fragments thereof that are useful, e.g., as reagents or targets in assays applicable to treatment and diagnosis of 33877 or 47179-mediated or -related disorders. In another embodiment, the invention provides 33877 or 47179 polypeptides having a 33877 or 47179 activity. Preferred polypeptides are 33877 or 47179 proteins including at least one glycosyltransferase domain, and, preferably, having a 33877 or 47179 activity, e.g., a 33877 or 47179 activity as described herein.

In other embodiments, the invention provides 33877 or 47179 polypeptides, e.g., a 33877 or 47179 polypeptide having the amino acid sequence shown in SEQ ID NO:2, or SEQ ID NO:5; an amino acid sequence that is substantially identical to the amino acid sequence shown in SEQ ID NO:2, or SEQ ID NO:5; or an amino acid sequence encoded by a nucleic acid molecule having a nucleotide sequence which hybridizes under a stringency condition described herein to a nucleic acid molecule comprising the nucleotide sequence of SEQ ID NO:1, SEQ ID NO:3, SEQ ID NO:4, or SEQ ID NO:6, wherein the nucleic acid encodes a full length 33877 or 47179 protein or an active fragment thereof.

In a related aspect, the invention further provides nucleic acid constructs which include a 33877 or 47179 nucleic acid molecule described herein.

In a related aspect, the invention provides 33877 or 47179 polypeptides or fragments operatively linked to non-33877 or 47179 polypeptides to form fusion proteins. In another aspect, the invention features antibodies and antigen-binding fragments thereof, that react with, or more preferably specifically bind 33877 or 47179 polypeptides.

In another aspect, the invention provides methods of screening for compounds that modulate the expression or activity of the 33877 or 47179 polypeptides or nucleic acids.

In still another aspect, the invention provides a process for modulating 33877 or 47179 polypeptide or nucleic acid expression or activity, e.g. using the screened compounds. In certain embodiments, the methods involve treatment of conditions related to aberrant activity or expression of the 33877 or 47179 polypeptides or nucleic acids, such as conditions involving aberrant or deficient cellular proliferation or differentiation, or immune conditions.

In yet another aspect, the invention provides methods for inhibiting the proliferation or inducing the killing, of a 33877 or 47179-expressing cell, e.g., a 33877 or 47179-expressing hyperproliferative or aberrant cell, comprising contacting the cell with a compound (e.g., a compound identified using the methods described herein) that modulates the activity, or expression, of the 33877 or 47179 polypeptide or nucleic acid.

In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol.

In a preferred embodiment, the 33877- or 47179-expressing cell is found in a cancer tissue or cell, e.g., a solid tumor, a soft tissue tumor, or a metastatic lesion. In other embodiments, the 33877 or 47179-expressing cell is an immune cell, e.g., a cell from a myeloid, lymphoid or erythroid lineage, or a precursor cell thereof.

In a preferred embodiment, the compound is an inhibitor of a 33877 or 47179 polypeptide. Preferably, the inhibitor is chosen from a peptide, a phosphopeptide, a peptidomimetic, e.g., a phosphonate analog of a peptide substrate, a small organic molecule, a small inorganic molecule and an antibody (e.g., an antibody conjugated to a therapeutic moiety selected from a cytotoxin, a cytotoxic agent and a radioactive metal ion).

In a preferred embodiment, the compound is an inhibitor of a 33877 or 47179 nucleic acid, e.g., an antisense, a ribozyme, or a triple helix molecule.

In a preferred embodiment, the compound is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

In another aspect, the invention features a method of treating or preventing a disorder characterized by aberrant activity or expression of a 33877 or 47179 nucleic acid or polypeptide in a subject. In one embodiment, the method includes administering to the subject an effective amount of an agent that modulates the activity or expression of a 33877 or 47179 polypeptide or nucleic acid such that the disorder is ameliorated or prevented. In one example, the disorder is a cellular proliferative or differentiative disorder. In another example, the disorder is an immune disorder. In one embodiment, the agent is a peptide, a phosphopeptide, a small molecule, an antibody, or any combination thereof. In another embodiment, the agent is an antisense, a ribozyme, a triple helix molecule, a 33877 or 47179 nucleic acid, or any combination thereof.

The invention also provides assays for determining the activity of or the presence or absence of 33877 or 47179 polypeptides or nucleic acid molecules in a biological sample, including for disease diagnosis. Preferably, the biological sample includes a cancerous or pre-cancerous cell or tissue. For example, the cancerous tissue can be a solid tumor, a soft tissue tumor, or a metastatic lesion. In other embodiments, the biological sample is an immune cell, e.g., a cell from a myeloid, lymphoid or erythroid lineage, or a precursor cell thereof.

In further aspect, the invention provides assays for determining the presence or absence of a genetic alteration in a 33877 or 47179 polypeptide or nucleic acid molecule, including for disease diagnosis. Preferably, the biological sample includes a cancerous or pre-cancerous cell or tissue. For example, the cancerous tissue can be a solid tumor, a soft tissue tumor, or a metastatic lesion. In other embodiments, the biological sample is an immune cell, e.g., a cell from a myeloid, lymphoid or erythroid lineage, or a precursor cell thereof.

In another aspect, the invention features a method of diagnosing, or staging, a 33877 or 47179-mediated disorder, e.g., an immune disorder, or a cancer disorder, in a subject. The method includes evaluating the expression or activity of a 33877 or 47179 nucleic acid or polypeptide, thereby diagnosis or staging the disorder. In a preferred embodiment, the expression or activity is compared with a reference value, e.g., a difference in the expression or activity level of the 33877 or 47179 nucleic or polypeptide relative to a normal subject or a cohort of normal subjects is indicative of the disorder, or a stage in the disorder.

In a preferred embodiment, the subject is a human. For example, the subject is a human suffering from, or at risk of, an immune or a cancer disorder as described herein.

In a preferred embodiment, the evaluating step occurs in vitro or ex vivo. For example, a sample, e.g., a blood or tissue sample, a biopsy, is obtained from the subject. Preferably, the sample contains a cancer or an immune cell.

In a preferred embodiment, the evaluating step occurs in vivo. For example, by administering to the subject a detectably labeled agent that interacts with the 33877 or 47179-associated nucleic acid or polypeptide, such that a signal is generated relative to the level of activity or expression of the 33877 or 47179 nucleic acid or polypeptide.

In preferred embodiments, the method is performed: on a sample from a subject, a sample from a human subject; e.g., a sample of a patient suffering from, or at risk of, an immune or a cancer disorder as described herein; to determine if the individual from which the target nucleic acid or protein is taken should receive a drug or other treatment; to diagnose an individual for a disorder or for predisposition to resistance to treatment, to stage a disease or disorder.

In a still further aspect, the invention provides methods for evaluating the efficacy of a treatment of a disorder, e.g., proliferative disorder, e.g., a cancer, or an immune disorder. The method includes: treating a subject, e.g., a patient or an animal, with a protocol under evaluation (e.g., treating a subject with one or more of: chemotherapy, radiation, and/or a compound identified using the methods described herein); and evaluating the expression of a 33877 or 47179 nucleic acid or polypeptide before and after treatment. A change, e.g., a decrease or increase, in the level of a 33877 or 47179 nucleic acid (e.g., mRNA) or polypeptide after treatment, relative to the level of expression before treatment, is indicative of the efficacy of the treatment of the disorder.

In a preferred embodiment, the evaluating step includes obtaining a sample (e.g., a tissue sample, e.g., a biopsy, or a fluid sample) from the subject, before and after treatment and comparing the level of expressing of a 33877 or 47179 nucleic acid (e.g., mRNA) or polypeptide before and after treatment.

In another aspect, the invention provides methods for evaluating the efficacy of a therapeutic or prophylactic agent (e.g., an anti-neoplastic agent). The method includes: contacting a sample with an agent (e.g., a compound identified using the methods described herein, a cytotoxic agent) and, evaluating the expression or activity of a 33877 or 47179 nucleic acid or polypeptide in the sample before and after the contacting step. A change, e.g., a decrease or increase, in the level of 33877 or 47179 nucleic acid (e.g., mRNA) or polypeptide in the sample obtained after the contacting step, relative to the level of expression in the sample before the contacting step, is indicative of the efficacy of the agent. The level of 33877 or 47179 nucleic acid or polypeptide expression can be detected by any method described herein.

In a preferred embodiment, the sample includes cells obtained from a cancerous or immune tissue where a 33877 or 47179 polypeptide or nucleic acid is obtained.

In a preferred embodiment, the sample is a tissue sample (e.g., a biopsy), a bodily fluid, a cultured cell (e.g., a tumor or immune cell line).

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 33877 or 47179 molecule. In one embodiment, the capture probe is a nucleic acid, e.g., a probe complementary to a 33877 or 47179 nucleic acid sequence. In another embodiment, the capture probe is a polypeptide, e.g., an antibody specific for 33877 or 47179 polypeptides. Also featured is a method of analyzing a sample by contacting the sample to the aforementioned array and detecting binding of the sample to the array.

In another aspect, the invention features a method for identifying an agent that modulates the activity or expression of a 33877 or 47179 polypeptide or nucleic acid. The method includes the steps of: contacting the 33877 or 47179 polypeptide or nucleic acid with an agent; and determining the effect of the agent on the activity or expression of the polypeptide or nucleic acid. In one embodiment, the method includes contacting a 33877 or 47179 polypeptide with the agent and determining the effect of the agent on glycosyltransferase activity of the 33877 or 47179 polypeptide. In another embodiment, the method includes contacting a 33877 or 47179 polypeptide with the agent and determining the effect of the agent on the ability of the 33877 or 47179 polypeptide to modulate protein processing, protein folding, or protein secretion. The agent can be a peptide, a phosphopeptide, a small molecule, an antibody, or any combination thereof. In addition, the agent can be an antisense, a ribozyme, a triple helix molecule, a 33877 or 47179 nucleic acid, or any combination thereof.

Other features and advantages of the invention will be apparent from the following detailed description, and from the claims.

Brief Description of the Drawings

FIGS. 1A-1C depict a cDNA sequence (SEQ ID NO:1) and predicted amino acid sequence (SEQ ID NO:2) of human 33877. The methionine-initiated open reading frame of human 33877 (without the 5' and 3' untranslated regions) extends from nucleotide position 402 to position 2060 of SEQ ID NO:1 (coding sequence shown in SEQ ID NO:3).

FIG. 4 depicts an alignment of the glycosyl transferase group 2 domain of human 33877 with a consensus amino acid sequence derived from a hidden Markov model (HMM) from PFAM. The upper sequence is the consensus amino acid sequence (SEQ ID NO:7), while the lower amino acid sequence corresponds to amino acids 114 to 292 of SEQ ID NO:2.

FIGS. 5A-5B depict a cDNA sequence (SEQ ID NO:4) and predicted amino acid sequence (SEQ ID NO:5) of human 47179. The methionine-initiated open reading frame of human 47179 (without the 5' and 3' untranslated regions) extends from nucleotide position 29 to position 1279 of SEQ ID NO:4 (coding sequence shown in SEQ ID NO:6).

FIG. 8 depicts an alignment of glycosyl transferase group 1 domain of human 47179 with a consensus amino acid sequence derived from a hidden Markov model (HMM) from PFAM. The upper sequence is the consensus amino acid sequence (SEQ ID NO:8), while the lower amino acid sequence corresponds to amino acids 211 to 393 of SEQ ID NO:5.

FIGS. 9A-9C depicts a cDNA sequence (SEQ ID NO:9) and predicted amino acid sequence (SEQ ID NO:10) of human 26886. The methionine-initiated open reading frame of human 26886 (without the 5' and 3' untranslated regions) starts at nucleotide 272 and continues through to nucleotide 2683 of SEQ ID NO:9 (coding sequence also shown in SEQ ID NO:11).

FIG. 11 depicts an alignment of the carnitine acyltransferase domain of human 26886 with a consensus amino acid sequence derived from a hidden Markov model. The upper sequence is the consensus amino acid sequence (SEQ ID NO:12), while the lower amino acid sequence corresponds to amino acids 170 to 760 of SEQ ID NO:10.

FIGS. 16A-16B depicts a cDNA sequence (SEQ ID NO:13) and predicted amino acid sequence (SEQ ID NO:14) of human 25552. The methionine-initiated open reading frame of human 25552 (without the 5' and 3' untranslated regions) starts at nucleotide 57 and ends at nucleotide 980 until the end of SEQ ID NO:13 (shown also as coding sequence (SEQ ID NO:15

FIG. 18 depicts an alignment of the ubiE methyltransferase domain of human 25552 with a consensus amino acid sequence derived from a hidden Markov model. The upper sequence is the consensus amino acid sequence (SEQ ID NO:16), while the lower amino acid sequence corresponds to amino acids 37 to 306 of SEQ ID NO:14.

FIG. 33 depicts a BLAST alignment of the fucosyltransferase domain of human 32132 with a consensus amino acid sequence derived from a ProDomain No. 1416 (Release 1999.2; see also ProDom families PD003529 and PD002778 (ProDomain Release 2001.1). The lower sequence is the consensus amino acid sequence (SEQ ID NO:22), while the upper amino acid sequence corresponds to the fucosyltransferase domain of human 32132, about amino acids 57 to 355 of SEQ ID NO:20.

FIG. 34 depicts an alignment of the fucosyltransferase domain of human 32132 with a consensus amino acid sequence (PFAM identifier PF00852) derived from a hidden Markov model. The upper sequence is the consensus amino acid sequence (SEQ ID NO:23), while the lower amino acid sequence corresponds to amino acids 29 to 388 of SEQ ID NO:20.

FIG. 36 depicts an alignment of the AMP-binding enzyme domain of human 32244 with a consensus amino acid sequence derived from a hidden Markov model (HMM) from PFAM. The upper sequence is the consensus amino acid sequence (SEQ ID NO:28), while the lower amino acid sequence corresponds to amino acids 67 to 504 of SEQ ID NO:26.

FIGS. 38A-38B depicts an alignment of two aminotransferase domains of human 23680 with a consensus amino acid sequence derived from a hidden Markov model. In each of the alignments, the upper sequence is the consensus amino acid sequence (FIG. 38A: SEQ ID NO:35; FIG. 38B: SEQ ID NO:36), while the lower amino acid sequence corresponds to amino acids 40-141 and 165-415 of SEQ ID NO:33.

FIG. 39 depicts a hydropathy plot of human 32624. Relative hydrophobic residues are shown above the dashed horizontal line, and relative hydrophilic residues are below the dashed horizontal line. Numbers corresponding to positions in the amino acid sequence of human 32624 are indicated. Polypeptides of the invention include fragments which include: all or part of a hydrophobic sequence, i.e., a sequence above the dashed line, e.g., the sequence from about amino acid residues 89 to 108, from about 145 to 170, and from about 491 to 507 of SEQ ID NO:39; all or part of a hydrophilic sequence, i.e., a sequence below the dashed line, e.g., the sequence of from about amino acid residues 80 to 88, from about 136 to 144, and from about 433 to 457 of SEQ ID NO:39.

FIGS. 40A-40B depict an alignment of the UDP-glucuronosyl and glycosyl transferase domain of human 32624 with a consensus amino acid sequence derived from a hidden Markov model (HMM) from PFAM. The upper sequence is the consensus amino acid sequence (SEQ ID NO:41), while the lower amino acid sequence corresponds to amino acids 24 to 525 of SEQ ID NO:39.

FIG. 41 depicts a hydropathy plot of human 47174. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human 47174 are indicated. Polypeptides of the invention include fragments that include: all or a part of a hydrophobic sequence (a sequence above the dashed line); or all or part of a hydrophilic fragment (a sequence below the dashed line). Other fragments include a cysteine residue.

FIG. 42 depicts an alignment of the glycosyltransferase group 2 domain of human 47174 with a consensus amino acid sequence derived from a hidden Markov model. The upper sequence is the consensus amino acid sequence (SEQ ID NO:45), while the lower amino acid sequence corresponds to amino acids 154 to 336 of SEQ ID NO:43.

FIG. 43 depicts an alignment of the ricin group 3 domain of human 47174 with a consensus amino acid sequence derived from a hidden Markov model. The upper sequence is the consensus amino acid sequence (SEQ ID NO:46), while the lower amino acid sequence corresponds to amino acids 465 to 595 of SEQ ID NO:43.

FIG. 44 depicts an alignment of the N-acetylgalatosaminyltransferase domain of human 47174 with a consensus amino acid sequence derived from a hidden Markov model. The upper sequence is the consensus amino acid sequence (SEQ ID NO:47), while the lower amino acid sequence corresponds to amino acids 312 to 458 of SEQ ID NO:43.

FIG. 46 depicts an alignment of the acyltransferase domain of human 60491 with a consensus amino acid sequence derived from a hidden Markov model (HMM) from PFAM. The upper sequence is the consensus amino acid sequence (SEQ ID NO:51), while the lower amino acid sequence corresponds to amino acids 190 to 393 of SEQ ID NO:49.

FIG. 47 depicts alignments of the acyltransferase domain of human 60491 with a consensus amino acid sequence derived from SMART. The upper sequence is the consensus amino acid sequence for the phosphate acyltransferase domain (SEQ ID NO:52), while the lower amino acid sequence corresponds to amino acids of about 199 to about 333 of SEQ ID NO:49.

FIGS. 48A-48D depicts a BLAST alignment of the acyltransferase domain of human 60491 with a consensus amino acid sequence derived from a ProDomain Nos. 353751, 7717, 025192, and 042760 (7717 is from the Release 1999.2; 353751, 025192, and 042760 are from the Release 2001.1. The lower sequence is the consensus amino acid sequence (SEQ ID NOs: 53-56, respectively), while the upper amino acid sequence corresponds to the acyltransferase domain of human 60491, about amino acids 40 to 125, 104 to 395, 442 to 593, and 690 to 773 of SEQ ID NO:49, respectively.

FIGS. 49A-49B depict a cDNA sequence (SEQ ID NO:57) and predicted amino acid sequence (SEQ ID NO:58) of human 46743. The coding sequence (without the 5' and 3' untranslated regions), which starts at the methionine-initiated open reading frame of human 46743 and extends until the termination codon, is also indicated (shown as SEQ ID NO:59).

FIGS. 52A-52B depict BLAST alignments of the acyltransferase domain of human 46743 with consensus amino acid sequences derived from ProDomain Nos. 37511 and 21987 (Release 1999.2; see also ProDom families PD036247 and PD022151 (ProDomain Release 2000.1). ProDomain No. 37511 is a consensus amino acid sequence of an N-terminal fragment of a lysophosphatidic acid acyltransferase domain, while ProDomain No. 21987 is a consensus amino acid sequence of a C-terminal fragment of a lysophosphatidic acid acyltransferase domain. In FIG. 52A, the lower sequence is the consensus sequence of ProDomain No. 37511 (SEQ ID NO:60), while the upper amino acid sequence corresponds to an N-terminal fragment of the acyltransferase domain of human 46743, about amino acids 26 to 214 of SEQ ID NO:58. In FIG. 52B, the lower sequence is the amino acid sequence of ProDomain No. 21987 (SEQ ID NO:61), while the upper amino acid sequence corresponds to a C-terminal fragment of the acyltransferase domain of human 46743, about amino acids 215 to 328 of SEQ ID NO:58.

FIG. 54A is a bar graph showing a comparison of 46743 RNA expression in normal and tumorous tissues from the breast, ovary, and lung. The expression of 46743 is reduced in tumors of the ovary relative to normal ovary tissue, and may be elevated in tumors of the lung relative to normal lung tissue. FIG. 54B is a bar graph showing a comparison of 46743 RNA expression in normal and tumorous tissues from the colon, liver, and brain. The expression of 46743 is reduced in tumors of the brain relative to normal brain tissue.

FIGS. 56A-56C depicts a cDNA sequence (SEQ ID NO:62) and predicted amino acid sequence (SEQ ID NO:63) of human 27417. The coding sequence (without the 5' and 3' untranslated regions), which starts at the methionine-initiated open reading frame of human 27147 and extends until the termination codon, is also indicated (shown as SEQ ID NO:64).

FIGS. 59A-59B depict BLAST alignments of the acyltransferase domain of human 27417 with consensus amino acid sequences derived from ProDomain Nos. 4009 and 123477 (Release 1999.2; see also ProDom families PD000989 and PD107727 (ProDomain Release 2000.1). ProDomain No. 4009 is a consensus amino acid sequence of an N-terminal fragment of a lysophosphatidic acid (1-acyl-glycerol-3 phosphate) acyltransferase domain, while Pro-Domain No. 123477 is a consensus amino acid sequence of a C-terminal fragment of a lysophosphatidic acid (1-acyl-3-glycerol phosphate) acyltransferase domain. In FIG. 59A, the lower sequence is the consensus sequence of ProDomain No. 4009 (SEQ ID NO:65), while the upper amino acid sequence corresponds to an N-terminal fragment of the acyltransferase domain of human 27417, about amino acids 71 to 220 of SEQ ID NO:63. In FIG. 59B, the lower sequence is the amino acid sequence of ProDomain No. 123477 (SEQ ID NO:66), while the upper amino acid sequence corresponds to a C-terminal fragment of the acyltransferase domain of human 27147, about amino acids 197 to 363 of SEQ ID NO:63.

FIG. 60 depicts an alignment of the acyltransferase domain of human 27417 with a consensus amino acid sequence derived from a hidden Markov model. The upper sequence is the consensus amino acid sequence (SEQ ID NO:67), while the lower amino acid sequence corresponds to amino acids 77 to 288 of SEQ ID NO:63.

FIGS. 65A-65B depict alignment of the ubiquitin-conjugating enzyme domain of human 27960 with a consensus amino acid sequence derived from hidden Markov models using PFAM (UQ_con) and SMART (ubc_7) programs, respectively. In FIG. 65A, the upper sequence is the consensus amino acid sequence (SEQ ID NO:75), while the lower amino acid sequence corresponds to amino acids 1 to 148 of SEQ ID NO:73. In FIG. 65B, the upper sequence is the consensus amino acid sequence (SEQ ID NO:76), while the lower amino acid sequence corresponds to amino acids 6 to 151 of SEQ ID NO:73.

FIGS. 67A-67B depicts an alignment (BLAST) of amino acids 136 to 2151 of human 32252 (upper sequence; SEQ ID NO:78) with amino acids 1 to 672 of acetoacetyl-CoA synthetase of *Rattus norvegicus* (lower sequence; SEQ ID NO:80). The middle sequence is the consensus sequence (SEQ ID NO:81).

FIGS. 68A-68F depicts an alignment (BLAST) of nucleotides 66 to 2158 of SEQ ID NO:77 (upper sequence) with nucleotides 39 to 2131 of a *Rattus norvegicus* acetoacetyl-CoA synthetase cDNA (lower sequence: SEQ ID NO:82).

FIG. 70 depicts an alignment of the acyltransferase domain of human 53320 with a consensus amino acid sequence derived from a hidden Markov model. The upper sequence is the consensus amino acid sequence (SEQ ID NO:86), while the lower amino acid sequence corresponds to amino acids 71 to 261 of SEQ ID NO:84.

TABLE 1

FIG. 4 data

| Cell | 53320Ave CT | B2m Ave CT | Expression | |
|---|---|---|---|---|
| 1 | 26.23 | 21.23 | 31.3108270 | prolif |
| 2 | 28.32 | 21.87 | 11.4777599 | -GF |
| 3 | 26.095 | 21.52 | 41.9616901 | T5 |
| 4 | 27.95 | 22.335 | 20.4041817 | T25 |
| 5 | 27.22 | 23.035 | 55.1237407 | T2 |
| 6 | 27.145 | 23.21 | 66.4863730 | T6 |
| 7 | 27.31 | 22.46 | 35.2386543 | T16 |
| 8 | 27.765 | 22.47 | 25.5262526 | T6 |
| 9 | 27.245 | 24.035 | 108.160625 | T2 |
| 10 | 26.8 | 22.46 | 49.4962475 | T6 |
| 11 | 27.405 | 23.025 | 49.2892646 | T16 |
| 12 | 28.64 | 23.515 | 28.6606789 | T4 |
| 13 | 29.2 | 26.14 | 125.528039 | T19 |
| 14 | 28.255 | 23.255 | 31.2867919 | T2 |
| 15 | 28.635 | 23.81 | 37.4636912 | T17 |
| 16 | 28.545 | 24.115 | 46.3924760 | T24 |
| 17 | 26.98 | 22.37 | 41.8383390 | T43 |
| 18 | 27.52 | 23.26 | 52.2042797 | C48 |
| 19 | 29 | 22.755 | 13.1853344 | A24 |

TABLE 2

FIG. 5 data

| Cell | 53320 Ave Ct | B2m 5' Ave Ct | Expression | |
|---|---|---|---|---|
| 1 | 27.38 | 21.535 | 17.41487319 | prolif |
| 2 | 28.54 | 20.615 | 4.115902467 | conf |

TABLE 2-continued

FIG. 5 data

| Cell | 53320 Ave Ct | B2m 5' Ave Ct | Expression | |
|---|---|---|---|---|
| 3 | 29.325 | 20.34 | 2.138020854 | GF(-) |
| 4 | 28.005 | 19.765 | 3.379368496 | prolif |
| 5 | 32.975 | 21.165 | 0.286276814 | conf |
| 6 | 29.4 | 22.02 | 6.224113378 | prolif |
| 7 | 30.28 | 21.14 | 1.772881585 | conf |
| 8 | 28.22 | 20.45 | 4.621174573 | prolif |
| 9 | 30.285 | 19.67 | 1.487867597 | conf |
| 10 | 29.255 | 20.235 | 1.946678328 | GT(-) |
| 11 | 30.53 | 22.625 | 4.214321241 | prolif |
| 12 | 31.135 | 21.57 | 1.324421995 | conf |
| 13 | 31.075 | 21.475 | 1.292329333 | GT(-) |
| 14 | 27.06 | 22.24 | 34.95633018 | 293 |

Detailed Description of 33877 and 47179

Human 33877

Figures 1, 1C:
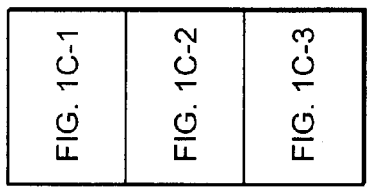
Figure 2:
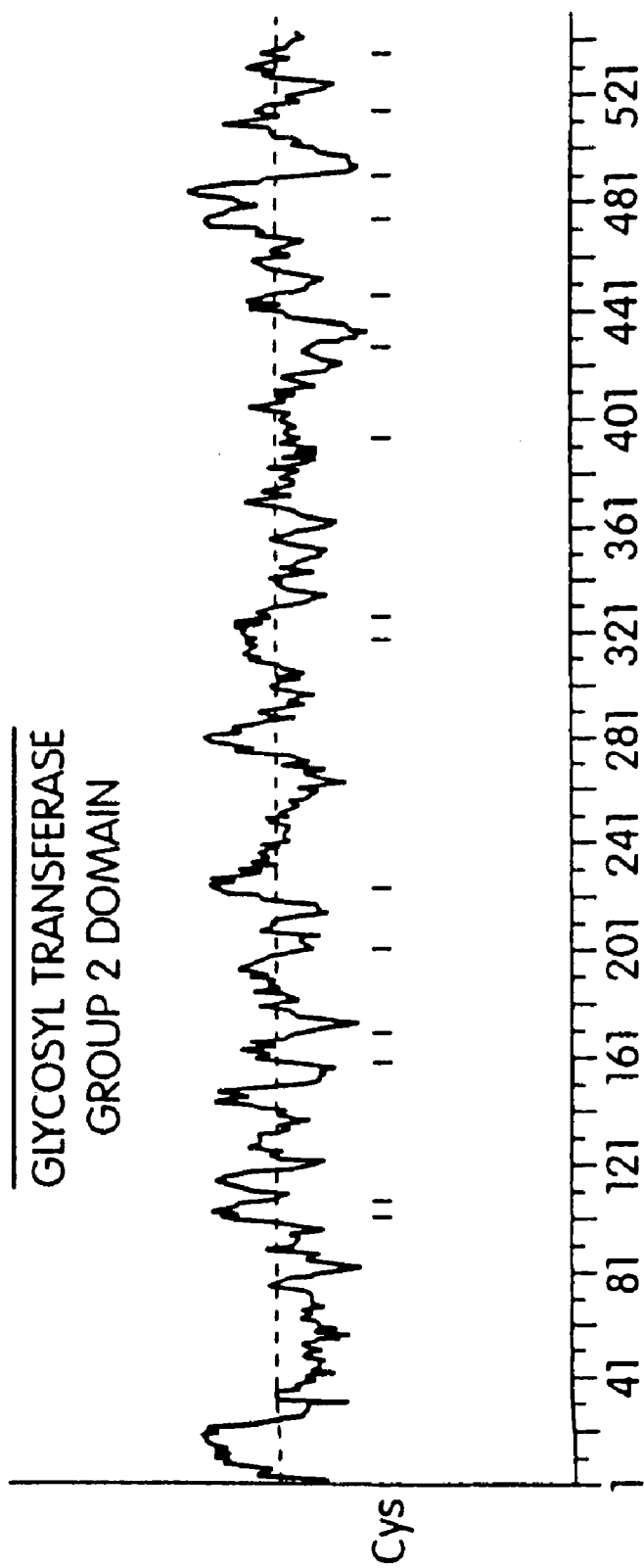
FIG. 2 depicts a hydropathy plot of human 33877. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human 33877 are indicated. Polypeptides of the invention include fragments which include: all or part of a hydrophobic sequence, i.e., a sequence above the dashed line, e.g., the sequence from about amino acid 225 to 235, from about 275 to 285, and from about 310 to 330 of SEQ ID NO:2; all or part of a hydrophilic sequence, i.e., a sequence below the dashed line, e.g., the sequence of from about amino acid 40 to 75, from about 255 to 270, and from about 420 to 440 of SEQ ID NO:2; a sequence which includes a Cys, or a glycosylation site.
Figure 3:
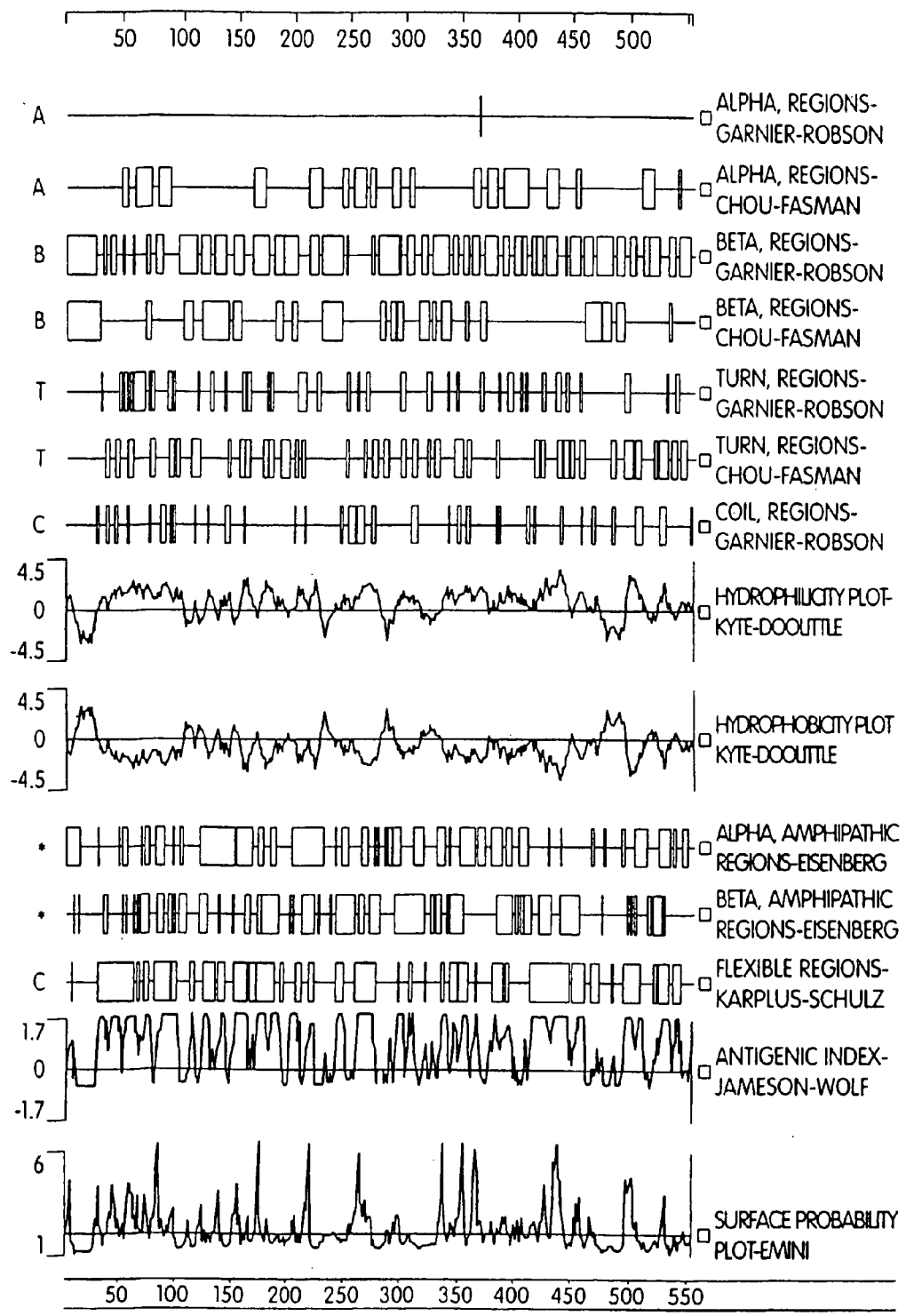
FIG. 3 depicts a series of plots summarizing an analysis of the primary and secondary protein structure of human 33877. The particular algorithm used for each plot is indicated at the right hand side of each plot. The following plots are depicted: Garnier-Robson plots providing the predicted location of alpha, beta, turn, and coil regions (Garnier et al. (1978) *J. Mol Biol.* 120:97); Chou-Fasman plots providing the predicted location of alpha, beta, and turn regions (Chou and Fasman (1978) *Adv. In Enzymol. Mol.* 47:45-148); Kyte-Doolittle hydrophilicity/hydrophobicity plots (Kyte and Doolittle (1982) *J. Mol. Biol.* 157:105-132); Eisenberg plots providing the predicted location of alpha- and beta-amphipathic regions (Eisenberg et al. (1982) *Nature* 299: 371-374); a Karplus-Schulz plot providing the predicted location of flexible regions (Karplus and Schulz (1985) *Naturwissens-Chafen* 72:212-213); a plot of the antigenic index (Jameson-Wolf) (Jameson and Wolf (1988) *CABIOS* 4:121-136); and a surface probability plot (Emini algorithm) (Emini et al. (1985) J. Virol. 55:836-839). The numbers corresponding to the amino acid sequence of human 33877 are indicated. Polypeptide fragments of the invention include polypeptides which have all or part of any of the regions described in this figure. Also included are variants having a mutation in a selected region shown in this figure.

The human 33877 sequence (FIGS. 1A-1C; SEQ ID NO:1), which is approximately 2493 nucleotides long including untranslated regions, contains a predicted methionine-initiated coding sequence of about 1659 nucleotides (nucleotides 402-2060 of SEQ ID NO:1; SEQ ID NO:3). The coding sequence encodes a 552 amino acid protein (SEQ ID NO:2). Human 33877 protein of SEQ ID NO:2 includes an amino-terminal hydrophobic amino acid sequence, consistent with a signal sequence, of about 30 amino acids (from amino acid 1 to about amino acid 30 of SEQ ID NO:2), which upon protease removal results in the production of the mature protein.

This mature protein form is approximately 522 amino acid residues in length (from about amino acid 31 to amino acid 552 of SEQ ID NO:2). Human 33877 contains the following regions or other structural features: a glycosyl transferase group 2 domain (PFAM Accession PF00535) located at about amino acid residues 114 to 292 of SEQ ID NO:2; and a predicted transmembrane domain which extends from about amino acid residue 475 to 492 of SEQ ID NO:2.

The 33877 protein also includes the following domains: one cAMP- and cGMP-dependent protein kinase phophorylation site (PS0004) located at about amino acids 2-5 of SEQ ID NO:2; 10 predicted Protein Kinase C phosphorylation sites (PS00005) located at about amino acids 5-7, 27-29, 41-43, 84-86, 89-91, 130-132, 313-315, 355-357, 399-401, and 433-435 of SEQ ID NO:2; eight predicted Casein Kinase II phosphorylation sites (PS00006) located at about amino 35-38, 45-48, 196-199, 200-203, 237-240, 241-244, 387-390, and 507-510 of SEQ ID NO:2; two predicted tyrosine kinase phosphorylation sites (PS00007) located at about amino acids 68-74 and 401-408 of SEQ ID NO:2; six predicted N-myristoylation sites (PS00008) located at about amino acids 178-183, 186-191, 192-197, 346-351, 383-388, and 526-531 of SEQ ID NO:2; and a predicted vacuolar targeting motif located at about amino acids 164-167 of SEQ ID NO:2.

For general information regarding PFAM identifiers, PS prefix and PF prefix domain identification numbers, refer to Sonnhammer et al. (1997) *Protein* 28:405-420.

Human 47179

Figures 1, 5A:
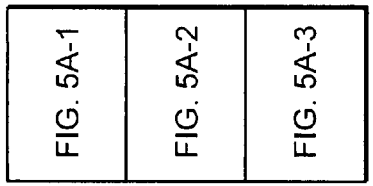
Figure 6:
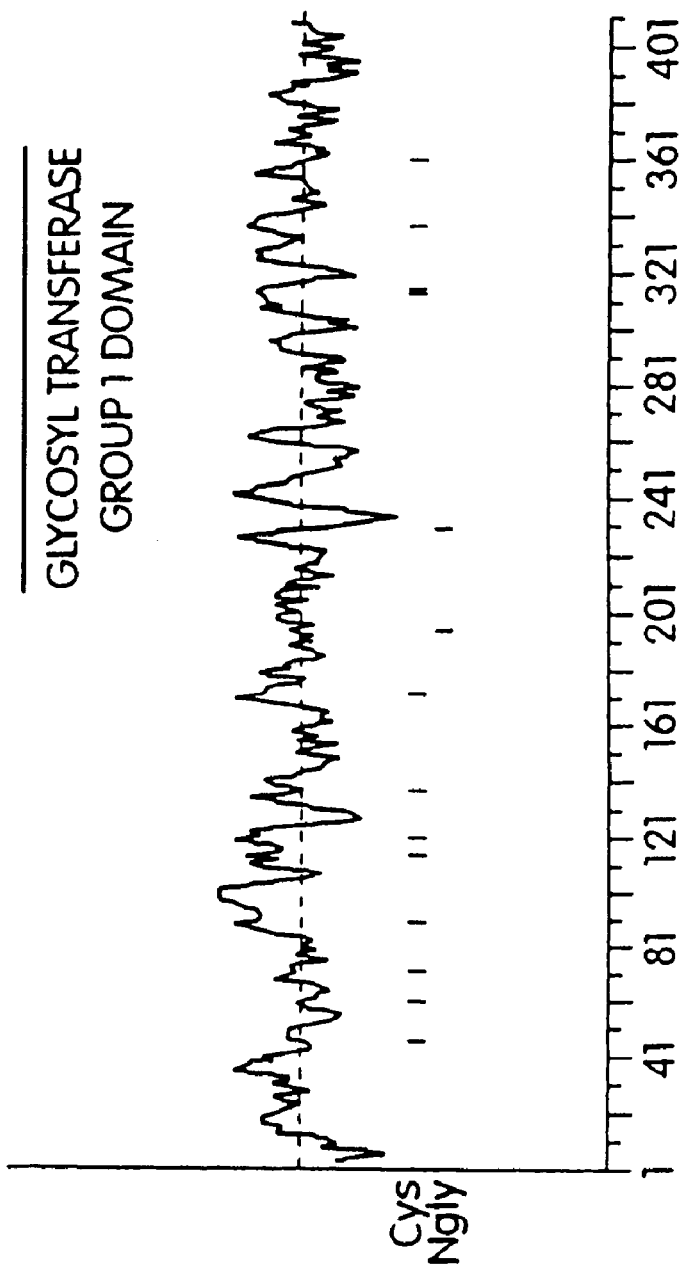
FIG. 6 depicts a hydropathy plot of human 47179. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence of human 47179 are indicated. Polypeptides of the invention include fragments which include: all or part of a hydrophobic sequence, i.e., a sequence above the dashed line, e.g., the sequence from about amino acid 110 to 120, from about 240 to 250, and from about 310 to 320 of SEQ ID NO:5; all or part of a hydrophilic sequence, i.e., a sequence below the dashed line, e.g., the sequence of from about amino acid 230 to 240, from about 270 to 290, and from about 395 to 405 of SEQ ID NO:5; a sequence which includes a Cys, or a glycosylation site.
Figure 7:
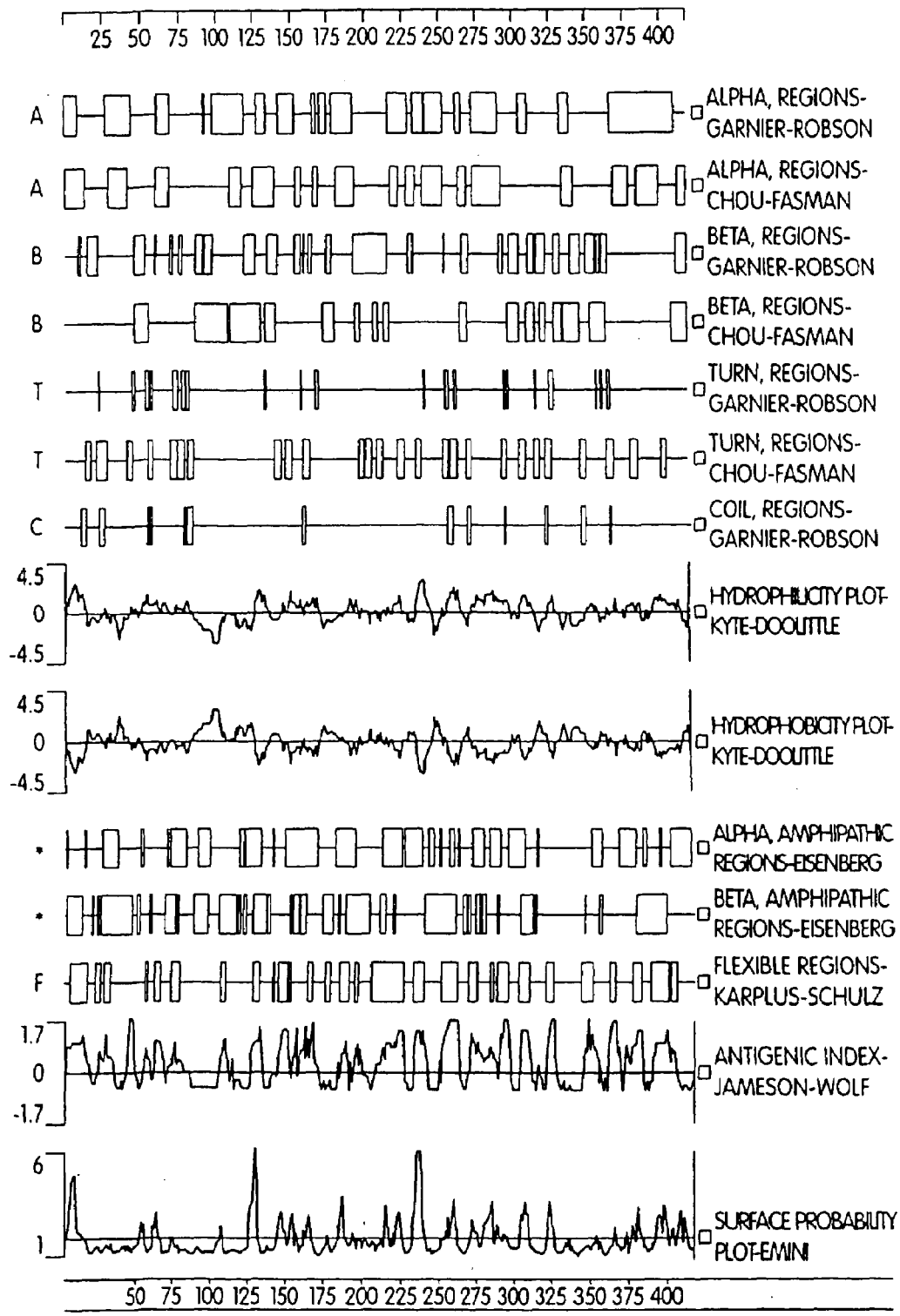
FIG. 7 depicts a series of plots summarizing an analysis of the primary and secondary protein structure of human 47179. The particular algorithm used for each plot is indicated at the right hand side of each plot. The following plots are depicted: Garnier-Robson plots providing the predicted location of alpha, beta, turn, and coil regions (Garnier et al. (1978) *J. Mol. Biol.* 120:97); Chou-Fasman plots providing the predicted location of alpha, beta, and turn regions (Chou and Fasman (1978) *Adv. In Enzymol. Mol.* 47:45-148); Kyte-Doolittle hydrophilicity/hydrophobicity plots (Kyte and Doolittle (1982) *J. Mol. Biol.* 157:105-132); Eisenberg plots providing the predicted location of alpha- and beta-amphipathic regions (Eisenberg et al. (1982) *Nature* 299: 371-374); a Karplus-Schulz plot providing the predicted location of flexible regions (Karplus and Schulz (1985) *Naturwissens-Chafen* 72:212-213); a plot of the antigenic index (Jameson-Wolf) (Jameson and Wolf (1988) *CABIOS* 4:121-136); and a surface probability plot (Emini algorithm) (Emini et al. (1985) J. Virol. 55:836-839). The numbers corresponding to the amino acid sequence of human 47179 are indicated. Polypeptide fragments of the invention include polypeptides which have all or part of any of the regions described in this figure. Also included are variants having a mutation in a selected region shown in this figure.
Figure 10:
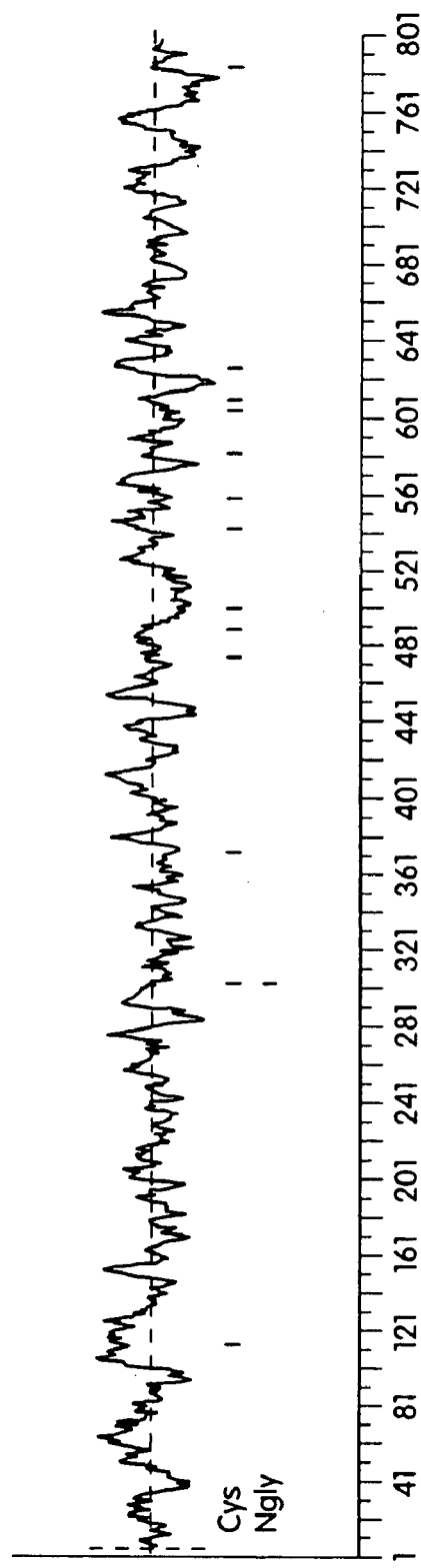
FIG. 10 depicts a hydropathy plot of human 26886. Relative hydrophobic residues are shown above the dashed horizontal line, and relative hydrophilic residues are below the dashed horizontal line. The cysteine residues (Cys) are indicated by short vertical lines just below the hydropathy trace. The numbers corresponding to the amino acid sequence of human 26886 are indicated. Polypeptides of the invention include 26886 fragments which include: all or part of a hydrophobic sequence (a sequence above the dashed line; all or part of a hydrophilic fragment (e.g., a fragment below the dashed line). Other fragments include a cysteine or a glycosylation site.

The human 47179 sequence (FIGS. 5A-5C; SEQ ID NO:4), which is approximately 1620 nucleotides long including untranslated regions, contains a predicted methionine-initiated coding sequence of about 1251 nucleotides (nucleotides 29-1279 of SEQ ID NO:4; SEQ ID NO:6). The coding sequence encodes a 416 amino acid protein (SEQ ID NO:5).

Human 15977 contains the following regions or other structural features: a glycosyl transferase group 1 domain (PFAM Accession PF00534) located at about amino acid residues 211 to 293 of SEQ ID NO:5; and a predicted transmembrane domain which extends from about amino acid residue 81 to 105 of SEQ ID NO:5.

The 47179 protein also includes the following domains: two predicted N-glycosylation sites (PS00001) located at about amino acids 204-207 and 239-242 of SEQ ID NO:5; one cAMP- and cGMP-dependent protein kinase phosphorylation site (PS00004) located at about amino acids 146-149 of SEQ ID NO:5; four predicted Protein Kinase C phosphorylation sites (PS00005) located at about amino acids 145-147, 187-189, 304-306, and 381-383 of SEQ ID NO:5; five predicted Casein Kinase II phosphorylation sites (PS00006) located at about amino acids 145-148, 192-195, 206-209, 255-258, and 302-305 of SEQ ID NO:5; five predicted N-myristoylation sites (PS00008) located at about amino acids 25-30, 78-83, 85-90, 168-173, and 294-299 of SEQ ID NO:5; and one predicted amidation site (PS00009) located at about amino acids 222-225 of SEQ ID NO:5.

TABLE 1

Summary of Sequence Information for 33877 and 47179

| Gene | cDNA | ORF | Polypeptide | Figure | ATCC Accession Number |
|---|---|---|---|---|---|
| 33877 | SEQ ID NO: 1 | SEQ ID NO: 3 | SEQ ID NO: 2 | FIGS. 1A-1C | |
| 47179 | SEQ ID NO: 4 | SEQ ID NO: 6 | SEQ ID NO: 5 | FIGS. 5A-5C | |

TABLE 2

Summary of Selected Domains of 33877 and 47179

| Protein | Glycosyltransferase Domain | Transmembrane Domain |
|---|---|---|
| 33877 | About amino acids 114-292 of SEQ ID NO:2 | About amino acids 475-492 of SEQ ID NO:2 |
| 47179 | About amino acids 211-393 of SEQ ID NO:5 | About amino acids 81-105 of SEQ ID NO:5 |

The 33877 and 47179 proteins contain a significant number of structural characteristics in common with members of the glycosyltransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

Members of the glycosyltransferase family of proteins are characterized by the ability to catalyze the synthesis of glycoconjugates, including glycolipids, glycoproteins, and polysaccharides, by transferring an activated mono- or oligosaccharide residue to an existing acceptor molecule for the initiation or elongation of the carbohydrate chain. The acceptor can be a lipid, a protein, a heterocyclic compound, or another carbohydrate residue. Glycosyltransferases can be divided into numerous subfamilies based upon their specificity for sugar moieties and acceptor molecules. The glycosyltransferase domain of human 33877 bears similarity to a subfamily designated "group 2" glycosyltransferases. These enzymes comprise a diverse subfamily, whose members transfer sugar from UDP-glucose, UDP-N-acetyl-galactosamine, GDP-mannose or CDP-abequose, to a range of substrates including cellulose, dolichol phosphate and teichoic acids. The glycosyltransferase domain of human 47179 bears similarity to a subfamily designated "group 1" glycosyltransferases. Members of this family-transfer activated sugars to a variety of substrates, including glycogen, fructose-6-phosphate and lipopolysaccharides. Members of this family transfer UDP, ADP, GDP or CMP linked sugars. Based on the sequence similarities, the 33877 or 47179 molecules of the present invention are predicted to have similar biological activities as glycosyltransferase family members.

Glycosyltransferases play roles in diverse cellular processes. For example, the major target of the natural IgM and IgG antibodies during hyperacute xenograft rejection is the terminal carbohydrate epitope Gal alpha(1,3)Gal, formed by the alpha 1,3galactosyl transferase, which places a terminal galactose residue in an alpha-linkage to another galactose (Sandrin et al. (1994) *Immunol Rev* 141:169-90). As another example, mutations in the Piga gene, the protein product of which mediates N-acetylglucosamine attachment to phosphatidylinositol, results in the clonal hematologic disorder, paroxysmal nocturnal hemoglobinuria (Ware et al. (1994) *Blood* 83:2418-22). Additionally, UDP-galactose:ceramide galactosyltransferase is the enzyme responsible for the biosynthesis of galactosylceramide, a molecule thought to play a critical role in myelin formation, signal transduction, viral and microbial adhesion, and oligodendrocyte development (Kapitonov et al. (1999) *Glycobiology* 9:961-78).

Glycosylation of glycoproteins and glycolipids is one of many molecular changes that accompany malignant transformation. GlcNAc-branched N-glycans and terminal Lewis antigen sequences have been observed to increase in some cancers, and to correlate with poor prognosis (Dennis et al. (1999) *Biochim Biophys Acta* 1473:21-34). Cellular membrane over-expression and shedding of acidic glycosphingolipids into the interstitial spaces and blood of cancer patients may play a central role in increased tumor cell growth, lack of immune cell recognition and neovascularization and could represent a molecular target for cancer therapy (Fish (1996) *Med Hypotheses* 46:140-44). Thus, the molecules of the present invention may be involved in: 1) the transfer of an activated sugar residue to an acceptor molecule; 2) the processing, folding, and secretion of proteins; 3) the modulation of tumor cell growth and invasion; 4) myelin formation; 5) signal transduction; 6) viral and microbial adhesion; 7) oligodendrocyte development; 8) sperm-egg binding; 9) evasion of immune detection; 10) xenograft rejection; and 11) the ability to antagonize or inhibit, competitively or non-competitively, any of 1-11.

A 33877 or 47179 polypeptide can include a "glycosyltransferase domain" or regions homologous with a "glycosyltransferase domain".

As used herein, the term "glycosyltransferase domain" includes an amino acid sequence of about 100-250 amino acid residues in length and having a bit score for the alignment of the sequence to the glycosyltransferase domain (HMM) of at least 30. Preferably, a glycosyltransferase domain includes at least about 120-220 amino acids, more preferably about 120-200 amino acid residues, or about 130-180 amino acids and has a bit score for the alignment of the sequence to the glycosyltransferase domain (HMM) of at least 50 or greater. Glycosyltransferase domains (HMM) have been assigned numerous PFAM Accession Numbers, including PF00534 (group 1) and PF00535 (group 2). An alignment of the glycosyltransferase domain (amino acids 114 to 292 of SEQ ID NO:2) of human 33877 with a consensus amino acid sequence (group 2 glycosyltransferases) derived from a hidden Markov model is depicted in FIG. 4. An alignment of the glycosyltransferase domain (amino acids 211 to 393 of SEQ ID NO:5) of human 47179 with a consensus amino acid sequence (group 1 glycosyltransferases) derived from a hidden Markov model is depicted in FIG. 8.

In a preferred embodiment 33877 or 47179 polypeptide or protein has a "glycosyltransferase domain" or a region which includes at least about 120-220 more preferably about 120-200 or 130-180 amino acid residues and has at least about 70% 80% 90% 95%, 99%, or 100% homology with a "glycosyltransferase domain," e.g., the glycosyltransferase domain of human 33877 or 47179 (e.g., residues 114 to 292 of SEQ ID NO:2 or residues 211 to 393 of SEQ ID NO:5).

To identify the presence of a "glycosyltransferase" domain in a 33877 or 47179 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3): 405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235: 1501-1531; and Stultz et al. (1993) *Protein Sci.* 2:305-314, the contents of which are incorporated herein by reference.

A 33877 or 47179 molecule can further include a transmembrane domain.

As used herein, the term "transmembrane domain" includes an amino acid sequence of about 15 amino acid residues in length that spans a phospholipid membrane. More preferably, a transmembrane domain includes about at least 18, 20, 22, 24, 25, 30, 35 or 40 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al, (1996) *Annual Rev. Neuronsci.* 19: 235-63, the contents of which are incorporated herein by reference.

In a preferred embodiment, a 33877 or 47179 polypeptide or protein has at least one transmembrane domain or a region which includes at least 18, 20, 22, 24, 25, 30, 35 or 40 amino acid residues and has at least about 60%, 70% 80% 90% 95%, 99%, or 100% homology with a "transmembrane domain," e.g., at least one transmembrane domain of human 33877 (e.g., amino acid residues 475-492 of SEQ ID NO:2) or human 47179 (e.g., amino acid residues 81-105 of SEQ ID NO:5).

In another embodiment, a 33877 or 47179 protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, Golgi, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally-occurring 33877 or 47179, or 33877 or 47179-like protein.

In a preferred embodiment, a 33877 or 47179 polypeptide or protein has a "non-transmembrane domain" or a region which includes at least about 1-500, preferably about 200-450, more preferably about 280-450, and even more preferably about 300-450 amino acid residues, and has at least about 60%, 70% 80% 90% 95%, 99% or 100% homology with a "non-transmembrane domain", e.g., a non-transmembrane domain of human 33877 (e.g., residues 31-474 and 493-552 of SEQ ID NO:2) or human 47179 (e.g., residues 1-80 and 106-416 of SEQ ID NO:5). Preferably, a non-transmembrane domain is capable of catalytic activity (e.g., catalyzing the transfer of a saccharide to an acceptor molecule).

A non-transmembrane domain located at the N-terminus of a 33877 or 47179 protein or polypeptide is referred to herein as an "N-terminal non-transmembrane domain." As used herein, an "N-terminal non-transmembrane domain" includes an amino acid sequence having about 1-500, preferably about 30-470, more preferably about 50-450, or even more preferably about 80-445 amino acid residues in length and is located outside the boundaries of a membrane. For example, an N-terminal non-transmembrane domain is located at about amino acid residues 1-80 of SEQ ID NO:2 and about amino acid residues 31-474 of SEQ ID NO:5.

Similarly, a non-transmembrane domain located at the C-terminus of a 33877 or 47179 protein or polypeptide is referred to herein as a "C-terminal non-transmembrane domain." As used herein, an "C-terminal non-transmembrane domain" includes an amino acid sequence having about 1-400, preferably about 20-350, preferably about 50-320, more preferably about 60-310 amino acid residues in length and is located outside the boundaries of a membrane. For example, an C-terminal non-transmembrane domain is located at about amino acid residues 493-552 of SEQ ID NO:2 and about amino acid residues 106-416 of SEQ ID NO:5.

A 33877 or 47179 family member can include at least one glycosyltransferase domain and at least one transmembrane domain.

A 33877 family member can additionally include: at least one cAMP- and cGMP-dependent protein kinase phophorylation site (PS0004); at least one, two, three, four, five, six, seven, eight, nine, and preferably 10 Protein Kinase C phosphorylation sites (PS00005); at least one, two, three, four, five, six, seven, and preferably eight Casein Kinase II phosphorylation sites (PS00006); at least one and preferably two tyrosine kinase phosphorylation sites (PS00007); at least one, two, three, four, five, and preferably six N-myristoylation sites (PS00008); and at least one vacuolar targeting motif.

A 47179 family member can additionally include: at least one and preferably two N-glycosylation sites (PS00001); at least one cAMP- and cGMP-dependent protein kinase phosphorylation site (PS00004); at least one, two, three, and preferably four Protein Kinase C phosphorylation sites (PS00005); at least one, two, three, four, and preferably five Casein Kinase II phosphorylation sites (PS00006); at least one, two, three, four, and preferably five N-myristoylation sites (PS00008); and at least one amidation site (PS00009).

As the 33877 or 47179 polypeptides of the invention may modulate 33877 or 47179-mediated activities, they may be useful as of for developing novel diagnostic and therapeutic agents for 33877 or 47179-mediated or related disorders, as described below.

As used herein, a "33877 or 47179 activity", "biological activity of 33877 or 47179" or "functional activity of 33877 or 47179", refers to an activity exerted by a 33877 or 47179 protein, polypeptide or nucleic acid molecule. For example, a 33877 or 47179 activity can be an activity exerted by 33877 or 47179 in a physiological milieu on, e.g., a 33877 or 47179-responsive cell or on a 33877 or 47179 substrate, e.g., a lipid, protein, heterocyclic compound, or carbohydrate residue, as determined in vivo or in vitro. A 33877 or 47179 activity can be determined in vivo or in vitro. In one embodiment, a 33877 or 47179 activity is a direct activity, such as an association with a 33877 or 47179 target molecule. A "target molecule" or "binding partner" is a molecule with which a 33877 or 47179 protein binds or interacts in nature, e.g., a lipid, protein, heterocyclic compound, or carbohydrate residue to which the 33877 or 47179 protein attaches a carbohydrate moiety.

A 33877 or 47179 activity can also be an indirect activity, e.g., a cellular signaling activity mediated by interaction of the 33877 or 47179 protein with a 33877 or 47179 ligand. Based on the above-described sequence similarities, the 33877 or 47179 molecules of the present invention are predicted to have similar biological activities as glycosyltransferase family members. For example, the 33877 or 47179 proteins of the present invention can have one or more of the following activities: 1) the ability to transfer an activated sugar residue to an acceptor molecule; 2) the ability to modulate the processing, folding, and secretion of proteins; 3) the ability to modulate tumor cell growth and invasion; 4) the ability to modulate myelin formation; 5) the ability to modulate signal transduction; 6) the ability to modulate viral and microbial adhesion; 7) the ability to modulate oligodendrocyte development; 8) the ability to modulate sperm-egg binding; 9) the ability to promote evasion of immune detection; 10) the ability to modulate xenograft rejection; and 11) the ability to antagonize or inhibit, competitively or non-competitively, any of 1-11.

The 33877 or 47179 molecules can act as novel diagnostic targets and therapeutic agents for controlling cellular proliferative and/or differentiative disorders and/or immune disorders (e.g., inflammatory disorders).

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth. Examples of such cells include cells having an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The 33877 or 47179 nucleic acid and protein of the invention can be used to treat and/or diagnose a variety of immune disorders. Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

The 33877 or 47179 protein, fragments thereof, and derivatives and other variants of the sequence in SEQ ID NO:2 or SEQ ID NO:5 thereof are collectively referred to as "polypeptides or proteins of the invention" or "33877 or 47179 polypeptides or proteins". Nucleic acid molecules encoding such polypeptides or proteins are collectively referred to as "nucleic acids of the invention" or "33877 or 47179 nucleic acids." 33877 or 47179 molecules refer to 33877 or 47179 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:1, SEQ ID NO:3, SEQ ID NO:4, or SEQ ID NO:6, corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a 33877 or 47179 protein. The gene can optionally further include non-coding sequences, e.g., regulatory sequences and introns. Preferably, a gene encodes a mammalian 33877 or 47179 protein or derivative thereof An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of 33877 or 47179 protein is at least 10% pure. In a preferred embodiment, the preparation of 33877 or 47179 protein has less than about 30%, 20%, 10% and more preferably 5% (by dry weight), of non-33877 or 47179 protein (also referred to herein as a "contaminating protein"), or of chemical precursors or non-33877 or 47179 chemicals. When the 33877 or 47179 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 33877 or 47179 without abolishing or substantially altering a 33877 or 47179 activity. Preferably the alteration does not substantially alter the 33877 or 47179 activity, e.g., the activity is at least 20%, 40%, 60%, 70% or 80% of wild-type. An "essential" amino acid residue is a residue that, when altered from the wild-type sequence of 33877 or 47179, results in abolishing a 33877 or 47179 activity such that less than 20% of the wild-type activity is present. For example, conserved amino acid residues in 33877 or 47179 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a 33877 or 47179 protein is preferably replaced with another amino acid residue from the same side chain family. Alternatively, in another embodiment, mutations can be introduced randomly along all or part of a 33877 or 47179 coding sequence, such as by saturation mutagenesis, and the resultant mutants can be screened for 33877 or 47179 biological activity to identify mutants that retain activity. Following mutagenesis of SEQ ID SEQ ID NO:1, SEQ ID NO:3, SEQ ID NO:4, or SEQ ID NO:6, the encoded protein can be expressed recombinantly and the activity of the protein can be determined.

As used herein, a "biologically active portion" of a 33877 or 47179 protein includes a fragment of a 33877 or 47179 protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a 33877 or 47179 molecule and a non-33877 or 47179 molecule or between a first 33877 or 47179 molecule and a second 33877 or 47179 molecule (e.g., a dimerization interaction). Biologically active portions of a 33877 or 47179 protein include peptides comprising amino acid sequences sufficiently homologous to or derived from the amino acid sequence of the 33877 or 47179 protein, e.g., the amino acid sequence shown in SEQ ID NO:2 or SEQ ID NO:5, which include less amino acids than the full length 33877 or 47179 proteins, and exhibit at least one activity of a 33877 or 47179 protein. Typically, biologically active portions comprise a domain or motif with at least one activity of the 33877 or 47179 protein, e.g., glycosyltransferase activity. A biologically active portion of a 33877 or 47179 protein can be a polypeptide which is, for example, 10, 25, 50, 100, 200 or more amino acids in length. Biologically active portions of a 33877 or 47179 protein can be used as targets for developing agents which modulate a 33877 or 47179 mediated activity, e.g., glycosyltransferase activity.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to 33877 or 47179 nucleic acid molecules of the invention. BLAST protein searches can be performed with the XBLAST program, score=50, wordlength=3 to obtain amino acid sequences homologous to 33877 or 47179 protein molecules of the invention. To obtain gapped alignments for comparison purposes, Gapped BLAST can be utilized as described in Altschul et al., (1997) *Nucleic Acids Res.* 25:3389-3402. (e.g., XBLAST and NBLAST) can be used.

Particular 33877 or 47179 polypeptides of the present invention have an amino acid sequence substantially identical to the amino acid sequence of SEQ ID NO:2 or SEQ ID NO:5. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:2 or SEQ ID NO:5 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1, SEQ ID NO:3, SEQ ID NO:4, or SEQ ID NO:6 are termed substantially identical.

"Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules of 33877 and 47179

In one aspect, the invention provides, an isolated or purified, nucleic acid molecule that encodes a 33877 or 47179 polypeptide described herein, e.g., a full-length 33877 or 47179 protein or a fragment thereof, e.g., a biologically active portion of 33877 or 47179 protein. Also included is a nucleic acid fragment suitable for use as a hybridization probe, which can be used, e.g., to identify a nucleic acid molecule encoding a polypeptide of the invention, 33877 or 47179 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1 or SEQ ID NO:4, or a portion of any of these nucleotide sequences. In one embodiment, the nucleic acid molecule includes sequences encoding the human 33877 or 47179 protein (i.e., "the coding region" of SEQ ID NO:1 or SEQ ID NO:4, as shown in SEQ ID NO:3 or SEQ ID NO:6), as well as 5' untranslated sequences. Alternatively, the nucleic acid molecule can include only the coding region of SEQ ID NO:1 or SEQ ID NO:4 (e.g., SEQ ID NO:3 or SEQ ID NO:6) and, e.g., no flanking sequences which normally accompany the subject sequence. In another embodiment, the nucleic acid molecule encodes a sequence corresponding to a fragment of the protein from about amino acids 114-292 of SEQ ID NO:2 or amino acids 211-393 of SEQ ID NO:5.

In another embodiment, an isolated nucleic acid molecule of the invention includes a nucleic acid molecule which is a complement of the nucleotide sequence shown in SEQ ID NO:1, SEQ ID NO:3, SEQ ID NO:4, or SEQ ID NO:6, or a portion of any of these nucleotide sequences. In other embodiments, the nucleic acid molecule of the invention is sufficiently complementary to the nucleotide sequence shown in SEQ ID NO:1, SEQ ID NO:3, SEQ ID NO:4, or SEQ ID NO:6, such that it can hybridize (e.g., under a stringency condition described herein) to the nucleotide sequence shown in SEQ ID NO:1, SEQ ID NO:3, SEQ ID NO:4, or SEQ ID NO:6, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:1, SEQ ID NO:3, SEQ ID NO:4, or SEQ ID NO:6, or a portion, preferably of the same length, of any of these nucleotide sequences.

33877 and 47179 Nucleic Acid Fragments

A nucleic acid molecule of the invention can include only a portion of the nucleic acid sequence of SEQ ID NO:1, SEQ ID NO:3, SEQ ID NO:4, or SEQ ID NO:6. For example, such a nucleic acid molecule can include a fragment which can be used as a probe or primer or a fragment encoding a portion of a 33877 or 47179 protein, e.g., an immunogenic or biologically active portion of a 33877 or 47179 protein. A fragment can comprise those nucleotides of SEQ ID NO:1 or SEQ ID NO:4 which encode a glycosyltransferase domain of human 33877 or 47179. The nucleotide sequence determined from the cloning of the 33877 or 47179 gene allows for the generation of probes and primers designed for use in identifying and/or cloning other 33877 or 47179 family members, or fragments thereof, as well as 33877 or 47179 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 100 amino acids in length, e.g., at least 150, 200, 250, 300, 350, 400, 450, 500, or 550 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 33877 or 47179 nucleic acid fragment can include a sequence corresponding to a glycosyltransferase domain and/or a transmembrane domain.

33877 or 47179 probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:1, SEQ ID NO:3, SEQ ID NO:4, or SEQ ID NO:6, or of a naturally occurring allelic variant or mutant of SEQ ID NO:1, SEQ ID NO:3, SEQ ID NO:4, or SEQ ID NO:6.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes a glycosyltransferase domain (about amino acids 114-292 of SEQ ID NO:2 or 211-393 of SEQ ID NO:5) or a transmembrane domain (about amino acids 475-492 of SEQ ID NO:2 or 81-105 of SEQ ID NO:5).

In another embodiment a set of primers is provided, e.g., primers suitable for use in a PCR, which can be used to amplify a selected region of a 33877 or 47179 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: a glycosyltransferase domain (about amino acids 114-292 of SEQ ID NO:2 or 211-393 of SEQ ID NO:5); or a transmembrane domain (about amino acids 475-492 of SEQ ID NO:2 or 81-105 of SEQ ID NO:5).

A nucleic acid fragment can encode an epitope bearing region of a polypeptide described herein.

A nucleic acid fragment encoding a "biologically active portion of a 33877 or 47179 polypeptide" can be prepared by isolating a portion of the nucleotide sequence of SEQ ID NO:1, SEQ ID NO:3, SEQ ID NO:4, or SEQ ID NO:6, which encodes a polypeptide having a 33877 or 47179 biological activity (e.g., the biological activities of the 33877 or 47179 proteins are described herein), expressing the encoded portion of the 33877 or 47179 protein (e.g., by recombinant expression in vitro) and assessing the activity of the encoded portion of the 33877 or 47179 protein. For example, a nucleic acid fragment encoding a biologically active portion of 33877 or 47179 can include a glycosyltransferase domain, e.g., amino acids 114-292 of SEQ ID NO:2 or amino acids 211-393 of SEQ ID NO:5. A nucleic acid fragment encoding a biologically active portion of a 33877 or 47179 polypeptide, may comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300, 1400, 1500, 1800, 2000, 2200, 2400, or more nucleotides in length and hybridizes under a stringency condition described herein to a nucleic acid molecule of SEQ ID NO:3 or SEQ ID NO:6.

In preferred embodiments, a nucleic acid includes a nucleotide sequence which is about 310, 400, 500, 600, 700, 800, 900, 1000, 1100, 1200, 1300, 1400, 1500, 1800, 2000, 2200, 2400, or more nucleotides in length and hybridizes under a stringency condition described herein to a nucleic acid molecule of SEQ ID NO:1 or SEQ ID NO:4.

33877 and 47179 Nucleic Acid Variants

The invention further encompasses nucleic acid molecules that differ from the nucleotide sequence shown in SEQ ID NO:1, SEQ ID NO:3, SEQ ID NO:4, or SEQ ID NO:6. Such differences can be due to degeneracy of the genetic code (and result in a nucleic acid which encodes the same 33877 or 47179 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2 or SEQ ID NO:5. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1, SEQ ID NO:3, SEQ ID NO:4, or SEQ ID NO:6, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:2 or SEQ ID NO:5 or a fragment of this sequence. Such nucleic acid molecules can readily be identified as being able to hybridize under a stringency condition described herein, to the nucleotide sequence shown in SEQ ID NO 2 or a fragment of the sequence. Nucleic acid molecules corresponding to orthologs, homologs, and allelic variants of the 33877 or 47179 cDNAs of the invention can further be isolated by mapping to the same chromosome or locus as the 33877 or 47179 gene.

Preferred variants include those that are correlated with glycosyltransferase activity.

Allelic variants of 33877 or 47179, e.g., human 33877 or 47179, include both functional and non-functional proteins. Functional allelic variants are naturally occurring amino acid sequence variants of the 33877 or 47179 protein within a population that maintain the ability to catalyze the synthesis of glycoconjugates. Functional allelic variants will typically contain only conservative substitution of one or more amino acids of SEQ ID NO:2 or SEQ ID NO:5, or substitution, deletion or insertion of non-critical residues in non-critical regions of the protein. Non-functional allelic variants are naturally-occurring amino acid sequence variants of the 33877 or 47179, e.g., human 33877 or 47179, protein within a population that do not have the ability to catalyze the synthesis of glycoconjugates. Non-functional allelic variants will typically contain a non-conservative substitution, a deletion, or insertion, or premature truncation of the amino acid sequence of SEQ ID NO:2 or SEQ ID NO:5, or a substitution, insertion, or deletion in critical residues or critical regions of the protein.

Moreover, nucleic acid molecules encoding other 33877 or 47179 family members and, thus, which have a nucleotide sequence which differs from the 33877 or 47179 sequences of SEQ ID NO:1, SEQ ID NO:3, SEQ ID NO:4, or SEQ ID NO:6 are intended to be within the scope of the invention.

Antisense Nucleic Acid Molecules, Ribozymes and Modified 33877 and 47179 Nucleic Acid Molecules In another aspect, the invention features, an isolated nucleic acid molecule which is antisense to 33877 or 47179. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 33877 or 47179 coding strand, or to only a portion thereof (e.g., the coding region of human 33877 or 47179 corresponding to SEQ ID NO:3 or SEQ ID NO:6). In another embodiment, the antisense nucleic acid molecule is antisense to a "noncoding region" of the coding strand of a nucleotide sequence encoding 33877 or 47179 (e.g., the 5' and 3' untranslated regions).

An antisense nucleic acid can be designed such that it is complementary to the entire coding region of 33877 or 47179 mRNA, but more preferably is an oligonucleotide which is antisense to only a portion of the coding or noncoding region of 33877 or 47179 mRNA. For example, the antisense oligonucleotide can be complementary to the region surrounding the translation start site of 33877 or 47179 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 33877 or 47179 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. A ribozyme having specificity for a 33877 or 47179-encoding nucleic acid can include one or more sequences complementary to the nucleotide sequence of a 33877 or 47179 cDNA disclosed herein (i.e., SEQ ID NO:1, SEQ ID NO:3, SEQ ID NO:4, or SEQ ID NO:6), and a sequence having known catalytic sequence responsible for mRNA cleavage (see U.S. Pat. No. 5,093, 246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a 33877 or 47179-encoding mRNA. See, e.g., Cech et al. U.S. Pat. No. 4,987,071; and Cech et al. U.S. Pat. No. 5,116,742. Alternatively, 33877 or 47179 mRNA can be used to select a catalytic RNA having a specific ribonuclease activity from a pool of RNA molecules. See, e.g., Bartel, D. and Szostak, J. W. (1993) *Science* 261:1411-1418.

33877 or 47179 gene expression can be inhibited by targeting nucleotide sequences complementary to the regulatory region of the 33877 or 47179 (e.g., the 33877 or 47179 promoter and/or enhancers) to form triple helical structures that prevent transcription of the 33877 or 47179 gene in target cells. See generally, Helene, C. (1991) *Anticancer Drug Des.* 6:569-84; Helene, C. i (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 33877 or 47179 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19:17 and Faria et al. (2001) *Nature Biotech.* 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675.

PNAs of 33877 or 47179 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 33877 or 47179 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958-976) or intercalating agents. (see, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 33877 or 47179 nucleic acid of the invention, two complementary regions one having a fluorophore and one a quencher such that the molecular beacon is useful for quantitating the presence of the 33877 or 47179 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 33877 and 47179 Polypeptides

In another aspect, the invention features, an isolated 33877 or 47179 protein, or fragment, e.g., a biologically active portion, for use as immunogens or antigens to raise or test (or more generally to bind) anti-33877 or 47179 antibodies. 33877 or 47179 protein can be isolated from cells or tissue sources using standard protein purification techniques. 33877 or 47179 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 33877 or 47179 polypeptide has one or more of the following characteristics:

(i) it has the ability to transfer an activated sugar residue to an acceptor molecule;

(ii) it has a molecular weight, e.g., a deduced molecular weight, preferably ignoring any contribution of post translational modifications, amino acid composition or other physical characteristic of a 33877 or 47179 polypeptide, e.g., a polypeptide of SEQ ID NO:2 or SEQ ID NO:5;

(iii) it has an overall sequence similarity of at least 60%, more preferably at least 70, 80, 90, or 95%, with a polypeptide of SEQ ID NO:2 or SEQ ID NO:5;

(iv) it has a glycosyltransferase domain which preferably has an overall sequence similarity of about 70%, 80%, 90% or 95% with amino acid residues 114-292 of SEQ ID NO:2 or amino acid residues 211-393 of SEQ ID NO:5;

(v) it has a transmembrane domain which preferably has an overall sequence similarity of about 70%, 80%, 90% or 95% with amino acid residues 475-492 of SEQ ID NO:2 or amino acid residues 81-105 of SEQ ID NO:5; or (vi) it has at least 70%, preferably 80%, and most preferably 95% of the cysteines found amino acid sequence of the native protein;

In a preferred embodiment the 33877 or 47179 protein, or fragment thereof, differs from the corresponding sequence in SEQ ID NO:2 or SEQ ID NO:5. In one embodiment it differs by at least one but by less than 15, 10 or 5 amino acid residues. In another it differs from the corresponding sequence in SEQ ID NO:2 or SEQ ID NO:5 by at least one residue but less than 20%, 15%, 10% or 5% of the residues in it differ from the corresponding sequence in SEQ ID NO:2 or SEQ ID NO:5. (If this comparison requires alignment the sequences should be aligned for maximum homology. "Looped" out sequences from deletions or insertions, or mismatches, are considered differences.) The differences are, preferably, differences or changes at a non essential residue or a conservative substitution. In a preferred embodiment the differences are not in the glycosyltransferase domain. In another preferred embodiment one or more differences are in the glycosyltransferase domain.

Other embodiments include a protein that contain one or more changes in amino acid sequence, e.g., a change in an amino acid residue which is not essential for activity. Such 33877 or 47179 proteins differ in amino acid sequence from SEQ ID NO:2 or SEQ ID NO:5, yet retain biological activity.

In one embodiment, the protein includes an amino acid sequence at least about 60%, 65%, 70%, 75%, 80%, 85%, 90%, 95%, 98% or more homologous to SEQ ID NO:2 or SEQ ID NO:5.

A 33877 protein or fragment is provided which varies from the sequence of SEQ ID NO:2 in regions defined by amino acids about 1-113 or 293-552 by at least one but by less than 15, 10 or 5 amino acid residues in the protein or fragment but which does not differ from SEQ ID NO:2 in regions defined by amino acids about 114-292 of SEQ ID NO:2. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

A 47179 protein or fragment is provided which varies from the sequence of SEQ ID NO:5 in regions defined by amino acids about 1-210 or 294-416 by at least one but by less than 15, 10 or 5 amino acid residues in the protein or fragment but which does not differ from SEQ ID NO:5 in regions defined by amino acids about 211-293 of SEQ ID NO:5. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 33877 or 47179 protein includes a glycosyltransferase domain. Moreover, other biologically active portions, in which other regions of the protein are deleted, can be prepared by recombinant techniques and evaluated for one or more of the functional activities of a native 33877 or 47179 protein.

In a preferred embodiment, the 33877 or 47179 protein has an amino acid sequence shown in SEQ ID NO:2 or SEQ ID NO:5. In other embodiments, the 33877 or 47179 protein is substantially identical to SEQ ID NO:2 or SEQ ID NO:5. In yet another embodiment, the 33877 or 47179 protein is substantially identical to SEQ ID NO:2 or SEQ ID NO:5 and retains the functional activity of the protein of SEQ ID NO:2 or SEQ ID NO:5, as described in detail in the subsections above.

33877 or 47179 Chimeric or Fusion Proteins

In another aspect, the invention provides 33877 or 47179 chimeric or fusion proteins. As used herein, a 33877 or 47179 "chimeric protein" or "fusion protein" includes a 33877 or 47179 polypeptide linked to a non-33877 or 47179 polypeptide. A "non-33877 or 47179 polypeptide" refers to a polypeptide having an amino acid sequence corresponding to a protein which is not substantially homologous to the 33877 or 47179 protein, e.g., a protein which is different from the 33877 or 47179 protein and which is derived from the same or a different organism. The 33877 or 47179 polypeptide of the fusion protein can correspond to all or a portion e.g., a fragment described herein of a 33877 or 47179 amino acid sequence. In a preferred embodiment, a 33877 or 47179 fusion protein includes at least one (or two) biologically active portion of a 33877 or 47179 protein. The non-33877 or 47179 polypeptide can be fused to the N-terminus or C-terminus of the 33877 or 47179 polypeptide.

The fusion protein can include a moiety which has a high affinity for a ligand. For example, the fusion protein can be a GST-33877 or 47179 fusion protein in which the 33877 or 47179 sequences are fused to the C-terminus of the GST sequences. Such fusion proteins can facilitate the purification of recombinant 33877 or 47179. Alternatively, the fusion protein can be a 33877 or 47179 protein containing a heterologous signal sequence at its N-terminus. In certain host cells (e.g., mammalian host cells), expression and/or secretion of 33877 or 47179 can be increased through use of a heterologous signal sequence.

Fusion proteins can include all or a part of a serum protein, e.g., an IgG constant region, or human serum albumin.

The 33877 or 47179 fusion proteins of the invention can be incorporated into pharmaceutical compositions and administered to a subject in vivo. The 33877 or 47179 fusion proteins can be used to affect the bioavailability of a 33877 or 47179 substrate. 33877 or 47179 fusion proteins may be useful therapeutically for the treatment of disorders caused by, for example, (i) aberrant modification or mutation of a gene encoding a 33877 or 47179 protein; (ii) mis-regulation of the 33877 or 47179 gene; and (iii) aberrant post-translational modification of a 33877 or 47179 protein.

Moreover, the 33877 or 47179-fusion proteins of the invention can be used as immunogens to produce anti-33877 or 47179 antibodies in a subject, to purify 33877 or 47179 ligands and in screening assays to identify molecules which inhibit the interaction of 33877 or 47179 with a 33877 or 47179 substrate.

Expression vectors are commercially available that already encode a fusion moiety (e.g., a GST polypeptide). A 33877 or 47179-encoding nucleic acid can be cloned into such an expression vector such that the fusion moiety is linked in-frame to the 33877 or 47179 protein.

Variants of 33877 or 47179 Proteins

In another aspect, the invention also features a variant of a 33877 or 47179 polypeptide, e.g., which functions as an agonist (mimetics) or as an antagonist. Variants of the 33877 or 47179 proteins can be generated by mutagenesis, e.g., discrete point mutation, the insertion or deletion of sequences or the truncation of a 33877 or 47179 protein. An agonist of the 33877 or 47179 proteins can retain substantially the same, or a subset, of the biological activities of the naturally occurring form of a 33877 or 47179 protein. An antagonist of a 33877 or 47179 protein can inhibit one or more of the activities of the naturally occurring form of the 33877 or 47179 protein by, for example, competitively modulating a 33877 or 47179-mediated activity of a 33877 or 47179 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 33877 or 47179 protein.

Variants of a 33877 or 47179 protein can be identified by screening combinatorial libraries of mutants, e.g., truncation mutants, of a 33877 or 47179 protein for agonist or antagonist activity.

Libraries of fragments e.g., N terminal, C terminal, or internal fragments, of a 33877 or 47179 protein coding sequence can be used to generate a variegated population of fragments for screening and subsequent selection of variants of a 33877 or 47179 protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of 33877 or 47179 proteins. Recursive ensemble mutagenesis (REM), a new technique which enhances the frequency of functional mutants in the libraries, can be used in combination with the screening assays to identify 33877 or 47179 variants (Arkin and Yourvan (1992) *Proc. Natl. Acad. Sci. USA* 89:7811-7815; Delgrave et al. (1993) *Protein Engineering* 6:327-331).

Cell based assays can be exploited to analyze a variegated 33877 or 47179 library. For example, a library of expression vectors can be transfected into a cell line, e.g., a cell line, which ordinarily responds to 33877 or 47179 in a substrate-dependent manner. The transfected cells are then contacted with 33877 or 47179 and the effect of the expression of the mutant on signaling by the 33877 or 47179 substrate can be detected, e.g., by measuring glycosyltransferase activity. Plasmid DNA can then be recovered from the cells which score for inhibition, or alternatively, potentiation of signaling by the 33877 or 47179 substrate, and the individual clones further characterized.

In another aspect, the invention features a method of making a 33877 or 47179 polypeptide, e.g., a peptide having a non-wild type activity, e.g., an antagonist, agonist, or super agonist of a naturally occurring 33877 or 47179 polypeptide, e.g., a naturally occurring 33877 or 47179 polypeptide. The method includes: altering the sequence of a 33877 or 47179 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 33877 or 47179 polypeptide a biological activity of a naturally occurring 33877 or 47179 polypeptide. The method includes: altering the sequence, e.g., by substitution or deletion of one or more residues, of a 33877 or 47179 polypeptide, e.g., altering the sequence of a non-conserved region, or a domain or residue described herein, and testing the altered polypeptide for the desired activity.

Anti-33877 or 47179 Antibodies

In another aspect, the invention provides an anti-33877 or 47179 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest*, Fifth Edition, U.S. Department of Health and Human Services, NIH Publication No. 91-3242, and Chothia, C. et al. (1987) *J. Mol. Biol.* 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-33877 or 47179 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH—terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 33877 or 47179 polypeptide or fragment thereof. Examples of antigen-binding fragments of the anti-33877 or 47179 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-33877 or 47179 antibody can be a polyclonal or a monoclonal antibody. In other embodiments, the antibody can be recombinantly produced, e.g., produced by phage display or by combinatorial methods.

Phage display and combinatorial methods for generating anti-33877 or 47179 antibodies are known in the art (as described in, e.g., Ladner et al. U.S. Pat. No. 5,223,409; Kang et al. International Publication No. WO 92/18619; Dower et al. International Publication No. WO 91/17271;

Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the anti-33877 or 47179 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An anti-33877 or 47179 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559). antibody may be replaced with at least a portion of a non-human CDR or only some of the CDR's may be replaced with non-human CDR's. It is only necessary to replace the number of CDR's required for binding of the humanized antibody to a 33877 or 47179 or a fragment thereof.

A humanized or CDR-grafted antibody will have at least one or two but generally all three recipient CDR's (of heavy and or light immuoglobulin chains) replaced with a donor CDR. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensusسequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 33877 or 47179 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In preferred embodiments an antibody can be made by immunizing with purified 33877 or 47179 antigen, or a fragment thereof, e.g., a fragment described herein, membrane associated antigen, tissue, e.g., crude tissue preparations, whole cells, preferably living cells, lysed cells, or cell fractions, e.g., membrane fractions.

A full-length 33877 or 47179 protein or, antigenic peptide fragment of 33877 or 47179 can be used as an immunogen or can be used to identify anti-33877 or 47179 antibodies made with other immunogens, e.g., cells, membrane preparations, and the like. The antigenic peptide of 33877 or 47179 should include at least 8 amino acid residues of the amino acid sequence shown in SEQ ID NO:2 or SEQ ID NO:5 and encompasses an epitope of 33877 or 47179. Preferably, the antigenic peptide includes at least 10 amino acid residues, more preferably at least 15 amino acid residues, even more preferably at least 20 amino acid residues, and most preferably at least 30 amino acid residues.

Fragments of 33877 or 47179 which include residues from about amino acid 40 to 75, from about 255 to 270, from about 420 to 440 of SEQ ID NO:2, from about amino acid 230 to 240, from about 270 to 290, or from about 395 to 405 of SEQ ID NO:5 can be used to make, e.g., used as immunogens or used to characterize the specificity of an antibody, antibodies against hydrophilic regions of the 33877 or 47179 protein. Similarly, fragments of 33877 or 47179 which include residues from about amino acid 225 to 235, from about 275 to 285, from about 310 to 330 of SEQ ID NO:2, from about amino acid 110 to 120, from about 240 to 250, or from about 310 to 320 of SEQ ID NO:5 can be used to make an antibody against a hydrophobic region of the 33877 or 47179 protein. Fragments of 33877 or 47179 which include residues about 475-492 of SEQ ID NO:2 or 81-105 of SEQ ID NO:5 can be used to make an antibody against a transmembrane region of the 33877 or 47179 protein. Fragments of 33877 or 47179 which include residues about 114-292 of SEQ ID NO:2 or 211-393 of SEQ ID NO:5 can be used to make an antibody against the glycosyltransferase region of the 33877 or 47179 protein.

Antibodies reactive with, or specific for, any of these regions, or other regions or domains described herein are provided.

Antibodies which bind only native 33877 or 47179 protein, only denatured or otherwise non-native 33877 or 47179 protein, or which bind both, are with in the invention. Antibodies with linear or conformational epitopes are within the invention. Conformational epitopes can sometimes be identified by identifying antibodies which bind to native but not denatured 33877 or 47179 protein.

Preferred epitopes encompassed by the antigenic peptide are regions of 33877 or 47179 are located on the surface of the protein, e.g., hydrophilic regions, as well as regions with high antigenicity. For example, an Emini surface probability analysis of the human 33877 or 47179 protein sequence can be used to indicate the regions that have a particularly high probability of being localized to the surface of the 33877 or 47179 protein and are thus likely to constitute surface residues useful for targeting antibody production.

In a preferred embodiment the antibody can bind to the non-cytoplasmic portion (e.g., extracellular or intra-organelle portion) of the 33877 or 47179 protein, e.g., it can bind to a whole cell which expresses the 33877 or 47179 protein. In another embodiment, the antibody binds an intracellular portion of the 33877 or 47179 protein. In preferred embodiments antibodies can bind one or more of purified antigen, membrane associated antigen, tissue, e.g., tissue sections, whole cells, preferably living cells, lysed cells, cell fractions, e.g., membrane fractions.

The anti-33877 or 47179 antibody can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target 33877 or 47179 protein.

In a preferred embodiment the antibody has: effector function; and can fix complement. In other embodiments the antibody does not; recruit effector cells; or fix complement.

In a preferred embodiment, the antibody has reduced or no ability to bind an Fc receptor. For example., it is a isotype or subtype, fragment or other mutant, which does not support binding to an Fc receptor, e.g., it has a mutagenized or deleted Fc receptor binding region.

In a preferred embodiment, an anti-33877 or 47179 antibody alters (e.g., increases or decreases) the glycosyltransferase activity of a 33877 or 47179 polypeptide.

The antibody can be coupled to a toxin, e.g., a polypeptide toxin, e.g., ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-33877 or 47179 antibody (e.g., monoclonal antibody) can be used to isolate 33877 or 47179 by standard techniques, such as affinity chromatography or immunoprecipitation. Moreover, an anti-33877 or 47179 antibody can be used to detect 33877 or 47179 protein (e.g., in a cellular lysate or cell supernatant) in order to evaluate the abundance and pattern of expression of the protein. Anti-33877 or 47179 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

The invention also includes a nucleic acid which encodes an anti-33877 or 47179 antibody, e.g., an anti-33877 or 47179 antibody described herein. Also included are vectors which include the nucleic acid and cells transformed with the nucleic acid, particularly cells which are useful for producing an antibody, e.g., mammalian cells, e.g. CHO or lymphatic cells.

The invention also includes cell lines, e.g., hybridomas, which make an anti-33877 or 47179 antibody, e.g., and antibody described herein, and method of using said cells to make a 33877 or 47179 antibody.

33877 and 47179 Recombinant Expression Vectors, Host Cells and Genetically Engineered Cells In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 33877 or 47179 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 33877 or 47179 proteins, mutant forms of 33877 or 47179 proteins, fusion proteins, and the like).

The recombinant expression vectors of the invention can be designed for expression of 33877 or 47179 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 33877 or 47179 activity assays, (e.g., direct assays or competitive assays described in detail below), or to generate antibodies specific for 33877 or 47179 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The 33877 or 47179 expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a 33877 or 47179 nucleic acid molecule within a recombinant expression vector or a 33877 or 47179 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 33877 or 47179 protein can be expressed in bacterial cells (such as *E. coli*), insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 33877 or 47179 protein. Accordingly, the invention further provides methods for producing a 33877 or 47179 protein using the host cells of the invention. In one embodiment, the method includes culturing the host cell of the invention (into which a recombinant expression vector encoding a 33877 or 47179 protein has been introduced) in a suitable medium such that a 33877 or 47179 protein is produced. In another embodiment, the method further includes isolating a 33877 or 47179 protein from the medium or the host cell.

In another aspect, the invention features, a cell or purified preparation of cells which include a 33877 or 47179 transgene, or which otherwise misexpress 33877 or 47179. The cell preparation can consist of human or non-human cells, e.g., rodent cells, e.g., mouse or rat cells, rabbit cells, or pig cells. In preferred embodiments, the cell or cells include a 33877 or 47179 transgene, e.g., a heterologous form of a 33877 or 47179, e.g., a gene derived from humans (in the case of a non-human cell). The 33877 or 47179 transgene can be misexpressed, e.g., overexpressed or underexpressed. In other preferred embodiments, the cell or cells include a gene that mis-expresses an endogenous 33877 or 47179, e.g., a gene the expression of which is disrupted, e.g., a knockout. Such cells can serve as a model for studying disorders that are related to mutated or mis-expressed 33877 or 47179 alleles or for use in drug screening.

In another aspect, the invention features, a human cell, e.g., a hematopoietic stem cell, transformed with nucleic acid which encodes a subject 33877 or 47179 polypeptide.

Also provided are cells, preferably human cells, e.g., human hematopoietic or fibroblast cells, in which an endogenous 33877 or 47179 is under the control of a regulatory sequence that does not normally control the expression of the endogenous 33877 or 47179 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 33877 or 47179 gene. For example, an endogenous 33877 or 47179 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 33877 or 47179 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (2001) *Nat. Biotechnol.* 19:35; and U.S. Pat. No. 5,876,742. Production of 33877 or 47179 polypeptide can be regulated in the subject by administering an agent (e.g., a steroid hormone) to the subject. In another preferred embodiment, the implanted recombinant cells express and secrete an antibody specific for a 33877 or 47179 polypeptide. The antibody can be any antibody or any antibody derivative described herein.

33877 and 47179 Transgenic Animals

The invention provides non-human transgenic animals. Such animals are useful for studying the function and/or activity of a 33877 or 47179 protein and for identifying and/or evaluating modulators of 33877 or 47179 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 33877 or 47179 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 33877 or 47179 protein to particular cells. A transgenic founder animal can be identified based upon the presence of a 33877 or 47179 transgene in its genome and/or expression of 33877 or 47179 mRNA in tissues or cells of the animals. A transgenic founder animal can then be used to breed additional animals carrying the transgene. Moreover, transgenic animals carrying a transgene encoding a 33877 or 47179 protein can further be bred to other transgenic animals carrying other transgenes.

33877 or 47179 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses of 33877 and 47179

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 33877 or 47179 protein (e.g., via a recombinant expression vector in a host cell in gene therapy applications), to detect a 33877 or 47179 mRNA (e.g., in a biological sample) or a genetic alteration in a 33877 or 47179 gene, and to modulate 33877 or 47179 activity, as described further below. The 33877 or 47179 proteins can be used to treat disorders characterized by insufficient or excessive production of a 33877 or 47179 substrate or production of 33877 or 47179 inhibitors. In addition, the 33877 or 47179 proteins can be used to screen for naturally occurring 33877 or 47179 substrates, to screen for drugs or compounds which modulate 33877 or 47179 activity, as well as to treat disorders characterized by insufficient or excessive production of 33877 or 47179 protein or production of 33877 or 47179 protein forms which have decreased, aberrant or unwanted activity compared to 33877 or 47179 wild type protein (e.g., cellular proliferative and/or differentiative disorders). Moreover, the anti-33877 or 47179 antibodies of the invention can be used to detect and isolate 33877 or 47179 proteins, regulate the bioavailability of 33877 or 47179 proteins, and modulate 33877 or 47179 activity.

A method of evaluating a compound for the ability to interact with, e.g., bind, a subject 33877 or 47179 polypeptide is provided. The method includes: contacting the compound with the subject 33877 or 47179 polypeptide; and evaluating ability of the compound to interact with, e.g., to bind or form a complex with the subject 33877 or 47179 polypeptide. This method can be performed in vitro, e.g., in a cell free system, or in vivo, e.g., in a two-hybrid interaction trap assay. This method can be used to identify naturally occurring molecules that interact with subject 33877 or 47179 polypeptide. It can also be used to find natural or synthetic inhibitors of subject 33877 or 47179 polypeptide. Screening methods are discussed in more detail below.

33877 and 47179 Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 33877 or 47179 proteins, have a stimulatory or inhibitory effect on, for example, 33877 or 47179 expression or 33877 or 47179 activity, or have a stimulatory or inhibitory effect on, for example, the expression or activity of a 33877 or 47179 substrate. Compounds thus identified can be used to modulate the activity of target gene products (e.g., 33877 or 47179 genes) in a therapeutic protocol, to elaborate the biological function of the target gene product, or to identify compounds that disrupt normal target gene interactions.

In one embodiment, the invention provides assays for screening candidate or test compounds which are substrates of a 33877 or 47179 protein or polypeptide or a biologically active portion thereof. In another embodiment, the invention provides assays for screening candidate or test compounds that bind to or modulate an activity of a 33877 or 47179 protein or polypeptide or a biologically active portion thereof.

In one embodiment, an activity of a 33877 or 47179 protein can be assayed as follows. First a substrate is provided that functions as an acceptor molecule for the initiation or elongation of a carbohydrate chain when acted upon by a 33877 or 47179 protein. The substrate can be, for example, a lipid, a protein, a heterocyclic compound, or a carbohydrate residue. Then a 33877 or 47179 protein is added to the substrate and the synthesis of glycoconjugates, e.g., glycolipids, glycoproteins, or polysaccharides, is measured. The addition of sugar moieties to the substrate can be detected by the labeling of the free sugar moieties, e.g., radiolabeling, and the detection of the labeled moiety attached to the substrate.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869)

or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In one embodiment, an assay is a cell-based assay in which a cell which expresses a 33877 or 47179 protein or biologically active portion thereof is contacted with a test compound, and the ability of the test compound to modulate 33877 or 47179 activity is determined. Determining the ability of the test compound to modulate 33877 or 47179 activity can be accomplished by monitoring, for example, glycosyltransferase activity. The cell, for example, can be of mammalian origin, e.g., human.

The ability of the test compound to modulate 33877 or 47179 binding to a compound, e.g., a 33877 or 47179 substrate, or to bind to 33877 or 47179 can also be evaluated. This can be accomplished, for example, by coupling the compound, e.g., the substrate, with a radioisotope or enzymatic label such that binding of the compound, e.g., the substrate, to 33877 or 47179 can be determined by detecting the labeled compound, e.g., substrate, in a
complex. Alternatively, 33877 or 47179 could be coupled with a radioisotope or enzymatic label to monitor the ability of a test compound to modulate 33877 or 47179 binding to a 33877 or 47179 substrate in a complex. For example, compounds (e.g., 33877 or 47179 substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 33877 or 47179 substrate) to interact with 33877 or 47179 with or without the labeling of any of the interactants can be evaluated. For example, a microphysiometer can be used to detect the interaction of a compound with 33877 or 47179 without the labeling of either the compound or the 33877 or 47179. McConnell, H. M. et al (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 33877 or 47179.

In yet another embodiment, a cell-free assay is provided in which a 33877 or 47179 protein or biologically active portion thereof is contacted with a test compound and the ability of the test compound to bind to the 33877 or 47179 protein or biologically active portion thereof is evaluated. Preferred biologically active portions of the 33877 or 47179 proteins to be used in assays of the present invention include fragments which participate in interactions with non-33877 or 47179 molecules, e.g., fragments with high surface probability scores.

Soluble and/or membrane-bound forms of isolated proteins (e.g., 33877 or 47179 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al, U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 33877 or 47179 protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BLAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 33877 or 47179, an anti-33877 or 47179 antibody or its target molecule to facilitate separation of complexed from uncomplexed forms of one or both of the proteins, as well as to accommodate automation of the assay. Binding of a test compound to a 33877 or 47179 protein, or interaction of a 33877 or 47179 protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/33877 or 47179 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 33877 or 47179 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 33877 or 47179 binding or activity determined using standard techniques.

Other techniques for immobilizing either a 33877 or 47179 protein or a target molecule on matrices include using conjugation of biotin and streptavidin. Biotinylated 33877 or 47179 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 33877 or 47179 protein or target molecules but which do not interfere with binding of the 33877 or 47179 protein to its target molecule. Such antibodies can be derivatized to the wells of the plate, and unbound target or 33877 or 47179 protein trapped in the wells by antibody conjugation. Methods for detecting such complexes, in addition to those described above for the GST-immobilized complexes, include immunodetection of complexes using antibodies reactive with the 33877 or 47179 protein or target molecule, as well as enzyme-linked assays which rely on detecting an enzymatic activity associated with the 33877 or 47179 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141-8; Hage, D. S., and Tweed, S. A. (1997) *J Chromatogr B Biomed Sci Appl.* 699:499-525). Further, fluorescence energy transfer may also be conveniently utilized, as described herein, to detect binding without further purification of the complex from solution.

In a preferred embodiment, the assay includes contacting the 33877 or 47179 protein or biologically active portion thereof with a known compound which binds 33877 or 47179 to form an assay mixture, contacting the assay mixture with a test compound, and determining the ability of the test compound to interact with a 33877 or 47179 protein, wherein determining the ability of the test compound to interact with a 33877 or 47179 protein includes determining the ability of the test compound to preferentially bind to 33877 or 47179 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 33877 or 47179 genes herein identified. In an alternative embodiment, the invention provides methods for determining the ability of the test compound to modulate the activity of a 33877 or 47179 protein through modulation of the activity of a downstream effector of a 33877 or 47179 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 33877 or 47179 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 33877 or 47179 ("33877 or 47179-binding proteins" or "33877 or 47179-bp") and are involved in 33877 or 47179 activity. Such 33877 or 47179-bps can be activators or inhibitors of signals by the 33877 or 47179 proteins or 33877 or 47179 targets as, for example, downstream elements of a 33877 or 47179-mediated signaling pathway.

The two-hybrid system is based on the modular nature of most transcription factors, which consist of separable DNA-binding and activation domains. Briefly, the assay utilizes two different DNA constructs. In one construct, the gene that codes for a 33877 or 47179 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 33877 or 47179 protein can be the fused to the activator domain.) If the "bait" and the "prey" proteins are able to interact, in vivo, forming a 33877 or 47179-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 33877 or 47179 protein.

In another embodiment, modulators of 33877 or 47179 expression are identified. For example, a cell or cell free mixture is contacted with a candidate compound and the expression of 33877 or 47179 mRNA or protein evaluated relative to the level of expression of 33877 or 47179 mRNA or protein in the absence of the candidate compound. When expression of 33877 or 47179 mRNA or protein is greater in the presence of the candidate compound than in its absence, the candidate compound is identified as a stimulator of 33877 or 47179 mRNA or protein expression. Alternatively, when expression of 33877 or 47179 mRNA or protein is less (statistically significantly less) in the presence of the candidate compound than in its absence, the candidate compound is identified as an inhibitor of 33877 or 47179 mRNA or protein expression. The level of 33877 or 47179 mRNA or protein expression can be determined by methods described herein for detecting 33877 or 47179 mRNA or protein.

In another aspect, the invention pertains to a combination of two or more of the assays described herein. For example, a modulating agent can be identified using a cell-based or a cell free assay, and the ability of the agent to modulate the activity of a 33877 or 47179 protein can be confirmed in vivo, e.g., in an animal.

This invention further pertains to novel agents identified by the above-described screening assays. Accordingly, it is within the scope of this invention to further use an agent identified as described herein (e.g., a 33877 or 47179 modulating agent, an antisense 33877 or 47179 nucleic acid molecule, a 33877 or 47179-specific antibody, or a 33877 or 47179-binding partner) in an appropriate animal model to determine the efficacy, toxicity, side effects, or mechanism of action, of treatment with such an agent. Furthermore, novel agents identified by the above-described screening assays can be used for treatments as described herein.

33877 and 47179 Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 33877 or 47179 with a disease; (ii) identify an individual from a minute biological sample (tissue typing); and (iii) aid in forensic identification of a biological sample. These applications are described in the subsections below.

33877 and 47179 Chromosome Mapping

The 33877 or 47179 nucleotide sequences or portions thereof can be used to map the location of the 33877 or 47179 genes on a chromosome. This process is called chromosome mapping. Chromosome mapping is useful in correlating the 33877 or 47179 sequences with genes associated with disease.

Briefly, 33877 or 47179 genes can be mapped to chromosomes by preparing PCR primers (preferably 15-25 bp in length) from the 33877 or 47179 nucleotide sequences. These primers can then be used for PCR screening of somatic cell hybrids containing individual human chromosomes. Only those hybrids containing the human gene corresponding to the 33877 or 47179 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919-924).

Other mapping strategies e.g., in situ hybridization (described in Fan, Y. et al. (1990) *Proc. Natl. Acad. Sci. USA*, 87:6223-27), pre-screening with labeled flow-sorted chromosomes, and pre-selection by hybridization to chromosome specific cDNA libraries can be used to map 33877 or 47179 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783-787.

Moreover, differences in the DNA sequences between individuals affected and unaffected with a disease associated with the 33877 or 47179 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

33877 and 47179 Tissue Typing 33877 or 47179 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 33877 or 47179 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 or SEQ ID NO:4 can provide positive individual identification with a panel of perhaps 10 to 1,000 primers which each yield a noncoding amplified sequence of 100 bases. If predicted coding sequences, such as those in SEQ ID NO:3 or SEQ ID NO:6 are used, a more appropriate number of primers for positive individual identification would be 500-2,000.

If a panel of reagents from 33877 or 47179 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 33877 or 47179 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 or SEQ ID NO:4 (e.g., fragments derived from the noncoding regions of SEQ ID NO:1 or SEQ ID NO:4 having a length of at least 20 bases, preferably at least 30 bases) are particularly appropriate for this use.

The 33877 or 47179 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 33877 or 47179 probes can be used to identify tissue by species and/or by organ type.

In a similar fashion, these reagents, e.g., 33877 or 47179 primers or probes can be used to screen tissue culture for contamination (i.e. screen for the presence of a mixture of different types of cells in a culture).

Predictive Medicine of 33877 and 47179

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 33877 or 47179.

Such disorders include, e.g., a disorder associated with the misexpression of 33877 or 47179 gene; a cellular proliferative or differentiative disorder; or an immune disorder.

The method includes one or more of the following:

detecting, in a tissue of the subject, the presence or absence of a mutation which affects the expression of the 33877 or 47179 gene, or detecting the presence or absence of a mutation in a region which controls the expression of the gene, e.g., a mutation in the 5' control region;

detecting, in a tissue of the subject, the presence or absence of a mutation which alters the structure of the 33877 or 47179 gene;

detecting, in a tissue of the subject, the misexpression of the 33877 or 47179 gene, at the mRNA level, e.g., detecting a non-wild type level of a mRNA;

detecting, in a tissue of the subject, the misexpression of the gene, at the protein level, e.g., detecting a non-wild type level of a 33877 or 47179 polypeptide.

In preferred embodiments the method includes: ascertaining the existence of at least one of: a deletion of one or more nucleotides from the 33877 or 47179 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1 or SEQ ID NO:4, or naturally occurring mutants thereof or 5' or 3' flanking sequences naturally associated with the 33877 or 47179 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 33877 or 47179 gene; the presence of a non-wild type splicing pattern of a messenger RNA transcript of the gene; or a non-wild type level of 33877 or 47179.

Methods of the invention can be used prenatally or to determine if a subject's offspring will be at risk for a disorder.

In preferred embodiments the method includes determining the structure of a 33877 or 47179 gene, an abnormal structure being indicative of risk for the disorder.

In preferred embodiments the method includes contacting a sample from the subject with an antibody to the 33877 or 47179 protein or a nucleic acid, which hybridizes specifically with the gene. These and other embodiments are discussed below.

Diagnostic and Prognostic Assays of 33877 and 47179

Diagnostic and prognostic assays of the invention include method for assessing the expression level of 33877 or 47179 molecules and for identifying variations and mutations in the sequence of 33877 or 47179 molecules.

Expression Monitoring and Profiling:

The presence, level, or absence of 33877 or 47179 protein or nucleic acid in a biological sample can be evaluated by obtaining a biological sample from a test subject and contacting the biological sample with a compound or an agent capable of detecting 33877 or 47179 protein or nucleic acid (e.g., mRNA, genomic DNA) that encodes 33877 or 47179 protein such that the presence of 33877 or 47179 protein or nucleic acid is detected in the biological sample. The term "biological sample" includes tissues, cells and biological fluids isolated from a subject, as well as tissues, cells and fluids present within a subject. A preferred biological sample is serum. The level of expression of the 33877 or 47179 gene can be measured in a number of ways, including, but not limited to: measuring the mRNA encoded by the 33877 or 47179 genes; measuring the amount of protein encoded by the 33877 or 47179 genes; or measuring the activity of the protein encoded by the 33877 or 47179 genes.

The level of mRNA corresponding to the 33877 or 47179 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 33877 or 47179 nucleic acid, such as the nucleic acid of SEQ ID NO:1 or SEQ ID NO:4, or a portion thereof, such as an oligonucleotide of at least 7, 15, 30, 50, 100, 250 or 500 nucleotides in length and sufficient to specifically hybridize under stringent conditions to 33877 or 47179 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 33877 or 47179 genes.

The level of mRNA in a sample that is encoded by one of 33877 or 47179 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 33877 or 47179 gene being analyzed.

In another embodiment, the methods further contacting a control sample with a compound or agent capable of detecting 33877 or 47179 mRNA, or genomic DNA, and comparing the presence of 33877 or 47179 mRNA or genomic DNA in the control sample with the presence of 33877 or 47179 mRNA or genomic DNA in the test sample. In still another embodiment, serial analysis of gene expression, as described in U.S. Pat. No. 5,695,937, is used to detect 33877 or 47179 transcript levels.

A variety of methods can be used to determine the level of protein encoded by 33877 or 47179. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 33877 or 47179 protein in a biological sample in vitro as well as in vivo. In vitro techniques for detection of 33877 or 47179 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 33877 or 47179 protein include introducing into a subject a labeled anti-33877 or 47179 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-33877 or 47179 antibody positioned on an antibody array (as described below). The sample can be detected, e.g., with avidin coupled to a fluorescent label. In another embodiment, the methods further include contacting the control sample with a compound or agent capable of detecting 33877 or 47179 protein, and comparing the presence of 33877 or 47179 protein in the control sample with the presence of 33877 or 47179 protein in the test sample.

The invention also includes kits for detecting the presence of 33877 or 47179 in a biological sample. For example, the kit can include a compound or agent capable of detecting 33877 or 47179 protein or mRNA in a biological sample; and a standard. The compound or agent can be packaged in a suitable container. The kit can further comprise instructions for using the kit to detect 33877 or 47179 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 33877 or 47179 expression or activity. As used herein, the term "unwanted" includes an unwanted phenomenon involved in a biological response such as cancer or deregulated cell proliferation.

In one embodiment, a disease or disorder associated with aberrant or unwanted 33877 or 47179 expression or activity is identified. A test sample is obtained from a subject and 33877 or 47179 protein or nucleic acid (e.g., mRNA or genomic DNA) is evaluated, wherein the level, e.g., the presence or absence, of 33877 or 47179 protein or nucleic acid is diagnostic for a subject having or at risk of developing a disease or disorder associated with aberrant or unwanted 33877 or 47179 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 33877 or 47179 expression or activity. For example, such methods can be used to determine whether a subject can be effectively treated with an agent for a cellular proliferative or differentiative disorder.

In another aspect, the invention features a computer medium having a plurality of digitally encoded data records. Each data record includes a value representing the level of expression of 33877 or 47179 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 33877 or 47179 (e.g., other genes associated with a 33877 or 47179-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 33877 or 47179 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a cellular proliferative or differentiative disorder in a subject. The method can be used to monitor a treatment for a cellular proliferative or differentiative disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 33877 or 47179 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 33877 or 47179 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 33877 or 47179 expression.

33877 and 47179 Arrays and Uses Thereof

In another aspect, the invention features an array that includes a substrate having a plurality of addresses. At least one address of the plurality includes a capture probe that binds specifically to a 33877 or 47179 molecule (e.g., a 33877 or 47179 nucleic acid or a 33877 or 47179 polypeptide). The array can have a density of at least than 10, 50, 100, 200, 500, 1,000, 2,000, or 10,000 or more addresses/ $cm^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 33877 or 47179 nucleic acid, e.g., the sense or anti-sense strand. In one preferred embodiment, a subset of addresses of the plurality of addresses has a nucleic acid capture probe for 33877 or 47179. Each address of the subset can include a capture probe that hybridizes to a different region of a 33877 or 47179 nucleic acid. In another preferred embodiment, addresses of the subset include a capture probe for a 33877 or 47179 nucleic acid. Each address of the subset is unique, overlapping, and complementary to a different variant of 33877 or 47179 (e.g., an allelic variant, or all possible hypothetical variants). The array can be used to sequence 33877 or 47179 by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 33877 or 47179 polypeptide or fragment thereof. The polypeptide can be a naturally-occurring interaction partner of 33877 or 47179 polypeptide. Preferably, the polypeptide is an antibody, e.g., an antibody described herein (see "Anti-33877 or 47179 Antibodies," above), such as a monoclonal antibody or a single-chain antibody.

In another aspect, the invention features a method of analyzing the expression of 33877 or 47179. The method includes providing an array as described above; contacting the array with a sample and detecting binding of a 33877 or 47179-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 33877 or 47179. If a sufficient number of diverse samples is analyzed, clustering (e.g., hierarchical clustering, k-means clustering, Bayesian clustering and the like) can be used to identify other genes which are co-regulated with 33877 or 47179. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 33877 or 47179 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 33877 or 47179-associated disease or disorder; and processes, such as a cellular transformation associated with a 33877 or 47179-associated disease or disorder. The method can also evaluate the treatment and/or progression of a 33877 or 47179-associated disease or disorder The array is also useful for ascertaining differential expression patterns of one or more genes in normal and abnormal cells. This provides a battery of genes (e.g., including 33877 or 47179) that could serve as a molecular target for diagnosis or therapeutic intervention.

In another aspect, the invention features an array having a plurality of addresses. Each address of the plurality includes a unique polypeptide. At least one address of the plurality has disposed thereon a 33877 or 47179 polypeptide or fragment thereof. Methods of producing polypeptide arrays are described in the art, e.g., in De Wildt et al. (2000). *Nature Biotech*. 18, 989-994; Lueking et al. (1999). *Anal. Biochem*. 270, 103-111; Ge, H. (2000). *Nucleic Acids Res*. 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80,85, 90, 95 or 99% identical to a 33877 or 47179 polypeptide or fragment thereof. For example, multiple variants of a 33877 or 47179 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 33877 or 47179 binding compound, e.g., an antibody in a sample from a subject with specificity for a 33877 or 47179 polypeptide or the presence of a 33877 or 47179-binding protein or ligand.

The array is also useful for ascertaining the effect of the expression of a gene on the expression of other genes in the same cell or in different cells (e.g., ascertaining the effect of 33877 or 47179 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 33877 or 47179 or from a cell or subject in which a 33877 or 47179 mediated response has been elicited, e.g., by contact of the cell with 33877 or 47179 nucleic acid or protein, or administration to the cell or subject 33877 or 47179 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 33877 or 47179 (or does not express as highly as in the case of the 33877 or 47179 positive plurality of capture probes) or from a cell or subject which in which a 33877 or 47179 mediated response has not been elicited (or has been elicited to a lesser extent than in the first sample); contacting the array with one or more inquiry probes (which is preferably other than a 33877 or 47179 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 33877 or 47179 or from a cell or subject in which a 33877 or 47179-mediated response has been elicited, e.g., by contact of the cell with 33877 or 47179 nucleic acid or protein, or administration to the cell or subject 33877 or 47179 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 33877 or 47179 (or does not express as highly as in the case of the 33877 or 47179 positive plurality of capture probes) or from a cell or subject which in which a 33877 or 47179 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 33877 or 47179, e.g., analyzing structure, function, or relatedness to other nucleic acid or amino acid sequences. The method includes: providing a 33877 or 47179 nucleic acid or amino acid sequence; comparing the 33877 or 47179 sequence with one or more preferably a plurality of sequences from a collection of sequences, e.g., a nucleic acid or protein sequence database; to thereby analyze 33877 or 47179.

Detection of 33877 and 47179 Variations or Mutations

The methods of the invention can also be used to detect genetic alterations in a 33877 or 47179 gene, thereby determining if a subject with the altered gene is at risk for a disorder characterized by misregulation in 33877 or 47179 protein activity or nucleic acid expression, such as a cellular proliferative or differentiative disorder. In preferred embodiments, the methods include detecting, in a sample from the subject, the presence or absence of a genetic alteration characterized by at least one of an alteration affecting the integrity of a gene encoding a 33877 or 47179-protein, or the mis-expression of the 33877 or 47179 gene. For example, such genetic alterations can be detected by ascertaining the existence of at least one of 1) a deletion of one or more nucleotides from a 33877 or 47179 gene; 2) an addition of one or more nucleotides to a 33877 or 47179 gene; 3) a substitution of one or more nucleotides of a 33877 or 47179 gene, 4) a chromosomal rearrangement of a 33877 or 47179 gene; 5) an alteration in the level of a messenger RNA transcript of a 33877 or 47179 gene, 6) aberrant modification of a 33877 or 47179 gene, such as of the methylation pattern of the genomic DNA, 7) the presence of a non-wild type splicing pattern of a messenger RNA transcript of a 33877 or 47179 gene, 8) a non-wild type level of a 33877 or 47179-protein, 9) allelic loss of a 33877 or 47179 gene, and 10) inappropriate post-translational modification of a 33877 or 47179-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 33877 or 47179-gene. This method can include the steps of collecting a sample of cells from a subject, isolating nucleic acid (e.g., genomic, mRNA or both) from the sample, contacting the nucleic acid sample with one or more primers which specifically hybridize to a 33877 or 47179 gene under conditions such that hybridization and amplification of the 33877 or 47179-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 33877 or 47179 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 33877 or 47179 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 33877 or 47179 nucleic acid or a putative variant (e.g., allelic variant) thereof. A probe can have one or more mismatches to a region of a 33877 or 47179 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in 33877 or 47179 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 33877 or 47179 gene and detect mutations by comparing the sequence of the sample 33877 or 47179 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 33877 or 47179 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 33877 or 47179 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 33877 or 47179 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 33877 or 47179 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 33877 or 47179 nucleic acid.

In a preferred embodiment the set includes a first and a second oligonucleotide. The first and second oligonucleotide can hybridize to the same or to different locations of SEQ ID NO:1 or SEQ ID NO:4 or the complement of SEQ ID NO:1 or SEQ ID NO:4. Different locations can be different but overlapping or nonoverlapping on the same strand. The first and second oligonucleotide can hybridize to sites on the same or on different strands.

The set can be useful, e.g., for identifying SNP's, or identifying specific alleles of 33877 or 47179. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligonucleotides can be used to specifically amplify, e.g., by PCR, or detect, a 33877 or 47179 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 33877 or 47179 gene.

Use of 33877 or 47179 Molecules as Surrogate Markers

The 33877 or 47179 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 33877 or 47179 molecules of the invention may be detected, and may be correlated with one or more biological states in vivo. For example, the 33877 or 47179 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 33877 or 47179 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 33877 or 47179 marker) transcription or expression, the amplified marker may be in a quantity which is more readily detectable than the drug itself. Also, the marker may be more easily detected due to the nature of the marker itself; for example, using the methods described herein, anti-33877 or 47179 antibodies may be employed in an immune-based detection system for a 33877 or 47179 protein marker, or 33877 or 47179-specific radiolabeled probes may be used to detect a 33877 or 47179 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

The 33877 or 47179 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 33877 or 47179 protein or RNA) for specific tumor markers in a subject, a drug or course of treatment may be selected that is optimized for the treatment of the specific tumor likely to be present in the subject. Similarly, the presence or absence of a specific sequence mutation in 33877 or 47179 DNA may correlate 33877 or 47179 drug response. The use of pharmacogenomic markers therefore permits the application of the most appropriate treatment for each subject without having to administer the therapy.

Pharmaceutical Compositions of 33877 and 47179

The nucleic acid and polypeptides, fragments thereof, as well as anti-33877 or 47179 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 33877 and 47179

The present invention provides for both prophylactic and therapeutic methods of treating a subject at risk of (or susceptible to) a disorder or having a disorder associated with aberrant or unwanted 33877 or 47179 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 33877 or 47179 molecules of the present invention or 33877 or 47179 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 33877 or 47179 expression or activity, by administering to the subject a 33877 or 47179 or an agent which modulates 33877 or 47179 expression or at least one 33877 or 47179 activity. Subjects at risk for a disease which is caused or contributed to by aberrant or unwanted 33877 or 47179 expression or activity can be identified by, for example, any or a combination of diagnostic or prognostic assays as described herein. Administration of a prophylactic agent can occur prior to the manifestation of symptoms characteristic of the 33877 or 47179 aberrance, such that a disease or disorder is prevented or, alternatively, delayed in its progression. Depending on the type of 33877 or 47179 aberrance, for example, a 33877 or 47179, 33877 or 47179 agonist or 33877 or 47179 antagonist agent can be used for treating the subject. The appropriate agent can be determined based on screening assays described herein.

It is possible that some 33877 or 47179 disorders can be caused, at least in part, by an abnormal level of gene product, or by the presence of a gene product exhibiting abnormal activity. As such, the reduction in the level and/or activity of such gene products would bring about the amelioration of disorder symptoms.

The 33877 or 47179 molecules can act as novel diagnostic targets and therapeutic agents for controlling one or more of disorders associated with bone metabolism, cardiovascular disorders, liver disorders, viral diseases, pain or metabolic disorders.

Aberrant expression and/or activity of 33877 or 47179 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 33877 or 47179 molecules effects in bone cells, e.g. osteoclasts and osteoblasts, that may in turn result in bone formation and degeneration. For example, 33877 or 47179 molecules may support different activities of bone resorbing osteoclasts such as the stimulation of differentiation of monocytes and mononuclear phagocytes into osteoclasts. Accordingly, 33877 or 47179 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anticonvulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 33877 or 47179 molecules may play an important role in the etiology of certain viral diseases, including but not limited to Hepatitis B, Hepatitis C and Herpes Simplex Virus (HSV). Modulators of 33877 or 47179 activity could be used to control viral diseases. The modulators can be used in the treatment and/or diagnosis of viral infected tissue or virus-associated tissue fibrosis, especially liver and liver fibrosis. Also, 33877 or 47179 modulators can be used in the treatment and/or diagnosis of virus-associated carcinoma, especially hepatocellular cancer.

Additionally, 33877 or 47179 may play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) Pain, New York:McGraw- Hill); pain associated with musculoskeletal disorders, e.g., joint pain; tooth pain; headaches; pain associated with surgery; pain related to irritable bowel syndrome; or chest pain.

As discussed, successful treatment of 33877 or 47179 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 33877 or 47179 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 33877 or 47179 expression is through the use of aptamer molecules specific for 33877 or 47179 protein. Aptamers are nucleic acid molecules having a tertiary structure which permits them to specifically bind to protein ligands (see, e.g., Osborne, et al. (1997) *Curr. Opin. Chem. Biol.* 1: 5-9; and Patel, D. J. (1997) *Curr Opin Chem Biol* 1:32-46). Since nucleic acid molecules may in many cases be more conveniently introduced into target cells than therapeutic protein molecules may be, aptamers offer a method by which 33877 or 47179 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 33877 or 47179 disorders. For a description of antibodies, see the Antibody section above.

In circumstances wherein injection of an animal or a human subject with a 33877 or 47179 protein or epitope for stimulating antibody production is harmful to the subject, it is possible to generate an immune response against 33877 or 47179 through the use of anti-idiotypic antibodies (see, for example, Herlyn, D. (1999) *Ann Med* 31:66-78; and Bhatacharya-Chattedjee, M., and Foon, K. A. (1998) *Cancer Treat Res.* 94:51-68). If an anti-idiotypic antibody is introduced into a mammal or human subject, it should stimulate the production of anti-anti-idiotypic antibodies, which should be specific to the 33877 or 47179 protein. Vaccines directed to a disease characterized by 33877 or 47179 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate 33877 or 47179 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 33877 or 47179 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89-94 and in Shea, K. J. (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645-647. Through the use of isotope-labeling, the "free" concentration of compound which modulates the expression or activity of 33877 or 47179 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142-2144.

Another aspect of the invention pertains to methods of modulating 33877 or 47179 expression or activity for therapeutic purposes. Accordingly, in an exemplary embodiment, the modulatory method of the invention involves contacting a cell with a 33877 or 47179 or agent that modulates one or more of the activities of 33877 or 47179 protein activity associated with the cell. An agent that modulates 33877 or 47179 protein activity can be an agent as described herein, such as a nucleic acid or a protein, a naturally-occurring target molecule of a 33877 or 47179 protein (e.g., a 33877 or 47179 substrate or receptor), a 33877 or 47179 antibody, a 33877 or 47179 agonist or antagonist, a peptidomimetic of a 33877 or 47179 agonist or antagonist, or other small molecule.

In one embodiment, the agent stimulates one or 33877 or 47179 activities. Examples of such stimulatory agents include active 33877 or 47179 protein and a nucleic acid molecule encoding 33877 or 47179. In another embodiment, the agent inhibits one or more 33877 or 47179 activities. Examples of such inhibitory agents include antisense 33877 or 47179 nucleic acid molecules, anti-33877 or 47179 antibodies, and 33877 or 47179 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 33877 or 47179 protein or nucleic acid molecule. In one embodiment, the method involves administering an agent (e.g., an agent identified by a screening assay described herein), or combination of agents that modulates (e.g., up regulates or down regulates) 33877 or 47179 expression or activity. In another embodiment, the method involves administering a 33877 or 47179 protein or nucleic acid molecule as therapy to compensate for reduced, aberrant, or unwanted 33877 or 47179 expression or activity.

Stimulation of 33877 or 47179 activity is desirable in situations in which 33877 or 47179 is abnormally downregulated and/or in which increased 33877 or 47179 activity is likely to have a beneficial effect. For example, stimulation of 33877 or 47179 activity is desirable in situations in which a 33877 or 47179 is downregulated and/or in which increased 33877 or 47179 activity is likely to have a beneficial effect. Likewise, inhibition of 33877 or 47179 activity is desirable in situations in which 33877 or 47179 is abnormally upregulated and/or in which decreased 33877 or 47179 activity is likely to have a beneficial effect.

33877 and 47179 Pharmacogenomics

The 33877 or 47179 molecules of the present invention, as well as agents, or modulators which have a stimulatory or inhibitory effect on 33877 or 47179 activity (e.g., 33877 or 47179 gene expression) as identified by a screening assay described herein can be administered to individuals to treat (prophylactically or therapeutically) 33877- or 47179-disorders associated with aberrant or unwanted 33877 or 47179 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 33877 or 47179 molecule or 33877 or 47179 modulator as well as tailoring the dosage and/or therapeutic regimen of treatment with a 33877 or 47179 molecule or 33877 or 47179 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983-985 and Linder, M. W. et al. (1997) *Clin. Chem.* 43:254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a 33877 or 47179 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a 33877 or 47179 molecule or 33877 or 47179 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 33877 or 47179 molecule or 33877 or 47179 modulator, such as a modulator identified by one of the exemplary screening assays described herein.

The present invention further provides methods for identifying new agents, or combinations, that are based on identifying agents that modulate the activity of one or more of the gene products encoded by one or more of the 33877 or 47179 genes of the present invention, wherein these products may be associated with resistance of the cells to a therapeutic agent. Specifically, the activity of the proteins encoded by the 33877 or 47179 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 33877 or 47179 protein can be applied in clinical trials. For example, the effectiveness of an agent determined by a screening assay as described herein to increase 33877 or 47179 gene expression, protein levels, or upregulate 33877 or 47179 activity, can be monitored in clinical trials of subjects exhibiting decreased 33877 or 47179 gene expression, protein levels, or downregulated 33877 or 47179 activity. Alternatively, the effectiveness of an agent determined by a screening assay to decrease 33877 or 47179 gene expression, protein levels, or downregulate 33877 or 47179 activity, can be monitored in clinical trials of subjects exhibiting increased 33877 or 47179 gene expression, protein levels, or upregulated 33877 or 47179 activity. In such clinical trials, the expression or activity of a 33877 or 47179 gene, and preferably, other genes that have been implicated in, for example, a 33877 or 47179-associated disorder can be used as a "read out" or markers of the phenotype of a particular cell.

33877 or 47179 Informatics

The sequence of a 33877 or 47179 molecule is provided in a variety of media to facilitate use thereof. A sequence can be provided as a manufacture, other than an isolated nucleic acid or amino acid molecule, which contains a 33877 or 47179. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 33877 or 47179 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 33877 or 47179, e.g., analyzing structure, function, or relatedness to one or more other nucleic acid or amino acid sequences. The method includes: providing a 33877 or 47179 nucleic acid or amino acid sequence; comparing the 33877 or 47179 sequence with a second sequence, e.g., one or more preferably a plurality of sequences from a collection of sequences, e.g., a nucleic acid or protein sequence database to thereby analyze 33877 or 47179. The method can be performed in a machine, e.g., a computer, or manually by a skilled artisan.

The method can include evaluating the sequence identity between a 33877 or 47179 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 33877 or 47179 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 33877 or 47179 sequence, or record, in machine-readable form; comparing a second sequence to the 33877 or 47179 sequence; thereby analyzing a sequence. Comparison can include comparing to sequences for sequence identity or determining if one sequence is included within the other, e.g., determining if the 33877 or 47179 sequence includes a sequence being compared. In a preferred embodiment the 33877 or 47179 or second sequence is stored on a first computer, e.g., at a first site and the comparison is performed, read, or recorded on a second computer, e.g., at a second site. E.g., the 33877 or 47179 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 33877 or 47179-associated disease or disorder or a pre-disposition to a 33877 or 47179-associated disease or disorder, wherein the method comprises the steps of determining 33877 or 47179 sequence information associated with the subject and based on the 33877 or 47179 sequence information, determining whether the subject has a 33877 or 47179-associated disease or disorder or a pre-disposition to a 33877 or 47179-associated disease or disorder and/or recommending a particular treatment for the disease, disorder or pre-disease condition.

The invention further provides in an electronic system and/or in a network, a method for determining whether a subject has a 33877 or 47179-associated disease or disorder or a pre-disposition to a disease associated with a 33877 or 47179 wherein the method comprises the steps of determining 33877 or 47179 sequence information associated with the subject, and based on the 33877 or 47179 sequence information, determining whether the subject has a 33877 or 47179-associated disease or disorder or a pre-disposition to a 33877 or 47179-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 33877 or 47179 sequence of the subject to the 33877 or 47179 sequences in the database to thereby determine whether the subject as a 33877 or 47179-associated disease or disorder, or a pre-disposition for such.

The present invention also provides in a network, a method for determining whether a subject has a 33877 or 47179 associated disease or disorder or a pre-disposition to a 33877 or 47179-associated disease or disorder associated with 33877 or 47179, said method comprising the steps of receiving 33877 or 47179 sequence information from the subject and/or information related thereto, receiving phenotypic information associated with the subject, acquiring information from the network corresponding to 33877 or 47179 and/or corresponding to a 33877 or 47179-associated disease or disorder (e.g., a cellular proliferative or differentiative disorder), and based on one or more of the phenotypic information, the 33877 or 47179 information (e.g., sequence information and/or information related thereto), and the acquired information, determining whether the subject has a 33877 or 47179-associated disease or disorder or a pre-disposition to a 33877 or 47179-associated disease or disorder. The method may further comprise the step of recommending a particular treatment for the disease, disorder or pre-disease condition.

The present invention also provides a method for determining whether a subject has a 33877 or 47179-associated disease or disorder or a pre-disposition to a 33877 or 47179-associated disease or disorder, said method comprising the steps of receiving information related to 33877 or 47179 (e.g., sequence information and/or information related thereto), receiving phenotypic information associated with the subject, acquiring information from the network related to 33877 or 47179 and/or related to a 33877 or 47179-associated disease or disorder, and based on one or more of the phenotypic information, the 33877 or 47179 information, and the acquired information, determining whether the subject has a 33877 or 47179-associated disease or disorder or a pre-disposition to a 33877 or 47179-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

Background of the 26886 Invention

Most cell types contain several carnitine acyltransferases. Carnitine acyltransferases are involved in the movement of polar fatty acyl moieties across phospholipid bilayers, which are otherwise impermeable to CoA esters. Carnitine acyltransferases may also regulate numerous aspects of cellular metabolism by virtue of the enzymes' ability to modulate CoA and acyl CoA concentrations in different cellular locations.

Carnitine acyltransferases can be grouped into two families; those that are inhibited by malonyl-CoA and those that are not. Carnitine acyltransferases that have access to the cytosolic compartment of a cell are typically malonyl-CoA sensitive. These carnitine acyltransferases are generally integral membrane proteins and have their catalytic and their malonyl-CoA-binding sites facing the cytosol. The non-malonyl-CoA sensitive carnitine acyltransferases typically occur either as soluble proteins within the lumens of the different membrane systems (e.g., organelles), or are loosely associated with the inner aspect of the respective membrane. Non-malonyl-CoA sensitive carnitine acyltransferases are frequently much more heterogeneous and tend to have a wider range of acyl chain specificities than do malonyl-CoA sensitive carnitine acyltransferases. Most of the non-malonyl-CoA sensitive carnitine acyltransferases are considered to be long- and medium-chain (i.e., $C_8$-$C_{16}$) fatty acyl CoA transferases.

It is believed that the carnitine:acylcarnitine translocation system exists in most cellular membranes (e.g., plasma membranes and membrane-bound organelles, e.g., mitochondria, peroxisomes and microsomes). To date, much of the focus has been on the mitochondrial carnitine:acylcarnitine translocation system, primarily because of the role of mitochondria in fatty acid oxidation. Typically, the carnitine:acylcarnitine translocation system consists of a malonyl-CoA inhibitable long-chain carnitine acyltransferase with access to the cytosolic pool of acyl CoA esters, a non-malonyl-CoA inhibitable transferase, the catalytic site of which faces the lumen of the membrane-bound organelle, and a carnitine:acylcarnitine translocase.

Summary of the 26886 Invention

The present invention is based, in part, on the discovery of a novel carnitine acyltransferase, referred to herein as "26886" nucleic acid and protein molecules. The nucleotide sequence of a cDNA encoding 26886 is shown in SEQ ID NO:9, and the amino acid sequence of a 26886 polypeptide is shown in SEQ ID NO:10. In addition, the nucleotide sequences of the coding region are depicted in SEQ ID NO:11.

Accordingly, in one aspect, the invention features a nucleic acid molecule that encodes a 26886 protein or polypeptide, e.g., a biologically active portion of the 26886 protein. In a preferred embodiment the isolated nucleic acid molecule encodes a polypeptide having the amino acid sequence of SEQ ID NO:10. In other embodiments, the invention provides isolated 26886 nucleic acid molecules having the nucleotide sequence shown in SEQ ID NO:9, or SEQ ID NO:11. In still other embodiments, the invention provides nucleic acid molecules that are substantially identical (e.g., naturally occurring allelic variants) to the nucleotide sequence shown in SEQ ID NO:9, or SEQ ID NO:11. In other embodiments, the invention provides a nucleic acid molecule which hybridizes under stringent hybridization conditions to a nucleic acid molecule comprising the nucleotide sequence of SEQ ID NO:9 or 11, wherein the nucleic acid encodes a full length 26886 protein or a biologically active fragment thereof.

In a related aspect, the invention further provides nucleic acid constructs, which include a 26886 nucleic acid molecule described herein. In certain embodiments, the nucleic acid molecules of the invention are operatively linked to native or heterologous regulatory sequences. Also included, are vectors and host cells containing the 26886 nucleic acid molecules of the invention e.g., vectors and host cells suitable for producing 26886 nucleic acid molecules and polypeptides.

In another related aspect, the invention provides nucleic acid fragments suitable as primers or hybridization probes for the detection of 26886-encoding nucleic acids.

In still another related aspect, isolated nucleic acid molecules that are antisense to a 26886 encoding nucleic acid molecule are provided.

In another aspect, the invention features, 26886 polypeptides, and biologically active or antigenic fragments thereof that are useful, e.g., as reagents or targets in assays applicable to treatment and diagnosis of 26886-mediated or related disorders. In another embodiment, the invention provides 26886 polypeptides having a 26886 activity. Preferred polypeptides are 26886 proteins including at least one carnitine acyltransferase domain, and, preferably, having a 26886 activity, e.g., a 26886 activity as described herein. Other preferred polypeptides are 26886 proteins including at least one carnitine acyltransferase domain and at least one transmembrane domain and, preferably, having a 26886 activity, e.g., a 26886 activity as described herein.

In other embodiments, the invention provides 26886 polypeptides, e.g., a 26886 polypeptide having the amino acid sequence shown in SEQ ID NO:10; an amino acid sequence that is substantially identical to the amino acid sequence shown in SEQ ID NO:10; or an amino acid sequence encoded by a nucleic acid molecule having a nucleotide sequence which hybridizes under stringent hybridization conditions to a nucleic acid molecule comprising the nucleotide sequence of SEQ ID NO:9 or 11, wherein the nucleic acid encodes a full length 26886 protein or an active fragment thereof.

In a related aspect, the invention further provides nucleic acid constructs that include a 26886 nucleic acid molecule described herein.

In a related aspect, the invention provides 26886 polypeptides or fragments operatively linked to non-26886 polypeptides to form fusion proteins.

In another aspect, the invention features antibodies and antigen-binding fragments thereof, that react with, or more preferably, specifically bind 26886 polypeptides.

In another aspect, the invention provides methods of screening for compounds that modulate the expression or activity of the 26886 polypeptides or nucleic acids.

In yet another aspect, the invention features a method of evaluating, or identifying, an agent, e.g., an agent as described herein, e.g., a compound (e.g., a polypeptide, peptide, a peptide fragment, a peptidomimetic, a small molecule), for the ability to modulate, e.g. inhibit, the activity or expression of a 26886 polypeptide. Such agents are useful for treating or preventing cardiovascular disorders (e.g., an endothelial cell disorder) or cancer disorders as described herein. The method includes:

providing a test agent, and a 26886, or a cell expressing an 26886 (e.g., a cancer or endothelial cell or cell line);

contacting said test agent, and said 26886 or said cell expressing said 26886, under conditions that allow an interaction (e.g., activity or expression) between said 26886 and said test agent to occur; and determining whether said test agent modulates, e.g., inhibits, the expression or activity of said 26886 polypeptide, wherein a change, e.g., a decrease, in the level of activity or expression between said 26886 polypeptide in the presence of the test agent relative to the activity or expression in the absence of the test agent, is indicative of modulation, e.g., inhibition, of modulation of 26886 activity or expression.

In a preferred embodiment, the method further comprises the step of evaluating the test agent in the 26886-expressing cell, e.g., an endothelial or a cancer cell, in vitro, or in vivo (e.g., in a subject, e.g., a patient having a cancer or a cardiovascular disorder), to thereby determine the effect of the test agent in the activity or expression of the 26886.

In a preferred embodiment, the contacting step occurs in vitro or ex vivo. For example, a sample, e.g., a blood, biopsy or tissue sample, is obtained from the subject. Preferably, the sample contains a 26886-expressing cell.

In a preferred embodiment, the contacting step occurs in vivo. For example, by administering to the subject a detectably labeled agent that interacts with the 26886 nucleic acid or polypeptide, such that a signal is generated relative to the level of activity or expression of the 26886 nucleic acid or polypeptide.

In a preferred embodiment, the test agent is an inhibitor (partial or complete inhibitor) of the 26886 polypeptide activity or expression.

In preferred embodiments, the test agent is a peptide, a small molecule, e.g., a member of a combinatorial library (e.g., a peptide or organic combinatorial library, or a natural product library), or an antibody, or any combination thereof.

In additional preferred embodiments, the test agent is an antisense, a ribozyme, a triple helix molecule, or any combination thereof.

In a preferred embodiment, a plurality of test agents, e.g., library members, is tested. In a preferred embodiment, the plurality of test agents, e.g., library members, includes at least 10, $10^2$, $10^3$, $10^4$, $10^5$, $10^6$, $10^7$, or $10^8$ compounds. In a preferred embodiment, the plurality of test agents, e.g., library members, share a structural or functional characteristic.

In a preferred embodiment, test agent is a peptide or a small organic molecule.

In a preferred embodiment, the method is performed in cell-free conditions (e.g., a reconstituted system).

In a preferred embodiment, the method further includes: contacting said agent with a test cell, or a test animal, to evaluate the effect of the test agent on the activity or expression of 26886.

In a preferred embodiment, the ability of the agent to modulate the activity or expression of 26886 is evaluated in a second system, e.g., a cell-free, cell-based, or an animal system.

In a preferred embodiment, the ability of the agent to modulate the activity or expression of 26886 is evaluated in a cell based system, e.g., a two-hybrid assay.

In still another aspect, the invention provides a process for modulating 26886 polypeptide or nucleic acid expression or activity, e.g. using the screened compounds. In certain embodiments, the methods involve treatment of conditions related to aberrant activity or expression of the 26886 polypeptides or nucleic acids, such as conditions involving aberrant activity, e.g., proliferation or differentiation, of a 26886-expressing cell, e.g., a 26886-expressing cell (e.g., a hyperproliferative, e.g., a malignant cell) from the colon, lung, ovary; an endothelial cell; a condition involving tumor invasion or metastasis; or a cardiovascular or an endothelial cell condition.

In yet another aspect, the invention provides methods for inhibiting the proliferation or inducing the killing, of a 26886-expressing cell, e.g., a 26886-expressing hyperproliferative cell, comprising contacting the cell with a compound (e.g., a compound identified using the methods described herein) that modulates the activity, or expression, of the 26886 polypeptide or nucleic acid.

In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol.

In a preferred embodiment, the 26886-expressing cell is found in a solid tumor, a soft tissue tumor, or a metastatic lesion. Preferably, the tumor is a sarcoma, a carcinoma, or an adenocarcinoma. Preferably, the cell is found in a cancerous or pre-cancerous tissue, e.g., a cancerous or pre-cancerous tissue where a 26886 polypeptide or nucleic acid is expressed, e.g., breast, ovarian, colon, liver, lung, kidney, or brain cancer. Most preferably, the cell is found in a tumor from the breast, ovary, colon, and lung.

In a preferred embodiment, the 26886-expressing cell is an endothelial cell, e.g., a blood vessel associated cell.

In a preferred embodiment, the compound is an inhibitor of a 26886 polypeptide. Preferably, the inhibitor is chosen from a peptide, a phosphopeptide, a peptidomimetic, e.g., a phosphonate analog of a peptide substrate, a small organic molecule, a small inorganic molecule and an antibody (e.g., an antibody conjugated to a therapeutic moiety selected from a cytotoxin, a cytotoxic agent and a radioactive metal ion).

In a preferred embodiment, the compound is an inhibitor of a 26886 nucleic acid, e.g., an antisense, a ribozyme, or a triple helix molecule.

In a preferred embodiment, the compound is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

In another aspect, the invention features methods for treating or preventing a disorder characterized by aberrant cellular proliferation or differentiation of a 26886-expressing cell, in a subject. Preferably, the method includes comprising administering to the subject (e.g., a mammal, e.g., a human) an effective amount of a compound (e.g., a compound identified using the methods described herein) that modulates the activity, or expression, of the 26886 polypeptide or nucleic acid.

In a preferred embodiment, the disorder is a cancerous or pre-cancerous condition. Most preferably, the disorder is a cancer, e.g., a solid tumor, a soft tissue tumor, or a metastatic lesion. Preferably, the cancer is a sarcoma, a carcinoma, or an adenocarcinoma. Preferably, the cancer is found in a tissue where a 26886 polypeptide or nucleic acid is expressed, e.g., breast, ovarian, colon, liver, lung, kidney, or brain cancer. Most preferably, the cancer is found in the breast, ovary, colon, liver and lung.

In a preferred embodiment, the disorder is an endothelial cell disorder; is a disorder characterized by aberrant, unregulated, or unwanted endothelial cell activity, e.g., proliferation, migration, angiogenesis, or vascularization; or aberrant expression of cell surface adhesion molecules or genes associated with angiogenesis. Examples of endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

In a preferred embodiment, the compound is an inhibitor of a 26886 polypeptide. Preferably, the inhibitor is chosen from a peptide, a phosphopeptide, a small organic molecule, a small inorganic molecule and an antibody (e.g., an antibody conjugated to a therapeutic moiety selected from a cytotoxin, a cytotoxic agent and a radioactive metal ion). The inhibitor can also be a trypsin inhibitor or a derivative thereof, or a peptidomimetic, e.g., a phosphonate analog of a peptide substrate.

In a preferred embodiment, the compound is an inhibitor of a 26886 nucleic acid, e.g., an antisense, a ribozyme, or a triple helix molecule.

In a preferred embodiment, the compound is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

In a preferred embodiment, the subject is a mammal, e.g., a human; a patient, e.g., a patient with a cancer or a cardiovascular condition.

The invention also provides assays for determining the activity of or the presence or absence of 26886 polypeptides or nucleic acid molecules in a biological sample, including for disease diagnosis. Preferably, the biological sample includes a cancerous or pre-cancerous cell or tissue. For example, the cancerous tissue can be a solid tumor, a soft tissue tumor, or a metastatic lesion. Preferably, the cancerous tissue is a sarcoma, a carcinoma, or an adenocarcinoma. Preferably, the cancerous tissue is from the breast, ovarian, colon, lung, liver, kidney, or brain. In other embodiments, the biological sample includes endothelial cells.

In a further aspect the invention provides assays for determining the presence or absence of a genetic alteration in a 26886 polypeptide or nucleic acid molecule in a sample, for, e.g., disease diagnosis. Preferably, the sample includes a cancer cell or tissue, or an endothelial cell or tissue. For example, the cancer can be a solid tumor, a soft tissue tumor, or a metastatic lesion. Preferably, the cancer is a sarcoma, a carcinoma, or an adenocarcinoma. Preferably, the cancer is a breast, ovarian, colon, lung, liver, kidney, or brain cancer.

In another aspect, the invention features a method of diagnosing, or staging, a 26886-mediated disorder, e.g., a cardiovascular disorder (e.g., atherosclerosis), or a cancer disorder, in a subject. The method includes evaluating the expression or activity of a 26886 nucleic acid or polypeptide, thereby diagnosis or staging the disorder. In a preferred embodiment, the expression or activity is compared with a reference value, e.g., a difference in the expression or activity level of the 26886 nucleic or polypeptide relative to a normal subject or a cohort of normal subjects is indicative of the disorder, or a stage in the disorder.

In a preferred embodiment, the subject is a human. For example, the subject is a human suffering from, or at risk of, a cardiovascular or a cancer disorder as described herein.

In a preferred embodiment, the evaluating step occurs in vitro or ex vivo. For example, a sample, e.g., a blood or tissue sample, a biopsy, is obtained from the subject. Preferably, the sample contains a cancer or an endothelial cell.

In a preferred embodiment, the evaluating step occurs in vivo. For example, by administering to the subject a detectably labeled agent that interacts with the 26886-associated nucleic acid or polypeptide, such that a signal is generated relative to the level of activity or expression of the 26886 nucleic acid or polypeptide.

In preferred embodiments, the method is performed: on a sample from a subject, a sample from a human subject; e.g., a sample of a patient suffering from, or at risk of, a cardiovascular or a cancer disorder as described herein; to determine if the individual from which the target nucleic acid or protein is taken should receive a drug or other treatment; to diagnose an individual for a disorder or for predisposition to resistance to treatment, to stage a disease or disorder.

In a still further aspect, the invention provides methods for evaluating the efficacy of a treatment of a disorder, e.g., proliferative disorder, e.g., a cancer (e.g., breast, ovarian, colon, liver or lung cancer); or an endothelial cell disorder. The method includes: treating a subject, e.g., a patient or an animal, with a protocol under evaluation (e.g., treating a subject with one or more of: chemotherapy, radiation, and/or a compound identified using the methods described herein); and evaluating the expression of a 26886 nucleic acid or polypeptide before and after treatment. A change, e.g., a decrease or increase, in the level of a 26886 nucleic acid (e.g., mRNA) or polypeptide after treatment, relative to the level of expression before treatment, is indicative of the efficacy of the treatment of the disorder.

In a preferred embodiment, the disorder is a cancer of the breast, ovary, colon, lung, or liver. In other embodiments, the disorder is an endothelial cell disorder. The level of 26886 nucleic acid or polypeptide expression can be detected by any method described herein.

In a preferred embodiment, the evaluating step includes obtaining a sample (e.g., a tissue sample, e.g., a biopsy, or a fluid sample) from the subject, before and after treatment and comparing the level of expressing of a 26886 nucleic acid (e.g., mRNA) or polypeptide before and after treatment.

In another aspect, the invention provides methods for evaluating the efficacy of a therapeutic or prophylactic agent (e.g., an anti-neoplastic agent). The method includes: contacting a sample with an agent (e.g., a compound identified using the methods described herein, a cytotoxic agent) and, evaluating the expression or activity of a 26886 nucleic acid or polypeptide in the sample before and after the contacting step. A change, e.g., a decrease or increase, in the level of 26886 nucleic acid (e.g., mRNA) or polypeptide in the sample obtained after the contacting step, relative to the level of expression in the sample before the contacting step, is indicative of the efficacy of the agent. The level of 26886 nucleic acid or polypeptide expression can be detected by any method described herein.

In a preferred embodiment, the sample includes cells obtained from a cancerous tissue where a 26886 polypeptide or nucleic acid is obtained, e.g., a cancer of the breast, ovary, colon, lung, or liver.

In a preferred embodiment, the sample is a tissue sample (e.g., a biopsy), a bodily fluid, cultured cells (e.g., a tumor cell line).

In a preferred embodiment, the sample includes endothelial cells.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 26886 molecule. In one embodiment, the capture probe is a nucleic acid, e.g., a probe complementary to a 26886 nucleic acid sequence. In another embodiment, the capture probe is a polypeptide, e.g., an antibody specific for 26886 polypeptides. Also featured is a method of analyzing a sample by contacting the sample to the aforementioned array and detecting binding of the sample to the array.

Other features and advantages of the invention will be apparent from the following detailed description, and from the claims.

Detailed Description of the 26886 Invention

The human 26886 sequence (FIG. 9; SEQ ID NO:9), which is approximately 2875 nucleotides long, including untranslated regions, contains a predicted methionine-initiated coding sequence of about 2412 nucleotides (SEQ ID NO:11, and nucleotides 272-2683 of SEQ ID NO:9). The coding sequence encodes an 804 amino acid protein (SEQ ID NO:10).

Human 26886 contains the following regions or other structural features: a predicted carnitine acyltransferase domain from about amino acids 170 to 760 of SEQ ID NO:10, which includes an acyltransferase family signature 2 region from about amino acids 448-470; and two predicted transmembrane domains from about amino acids 51-75 and 104-126 of SEQ ID NO:10.

The 26886 protein also includes the following domains: a predicted N-glycosylation site (PFAM Accession PS0001) located at about amino acid residues 312-315 of SEQ ID NO:10; two predicted glycosaminoglycan attachment sites (PFAM Accession PS0002) located at about amino acid residues 646-649 and 705-708 of SEQ ID NO:10; a predicted cAMP- and cGMP-dependent protein kinase phosphorylation site (PFAM Accession PS0004) located at about amino acid residues 736-739 of SEQ ID NO:10; twelve predicted Protein Kinase C phosphorylation sites (PS00005) at about amino acids 38-40, 158-160, 182-184, 189-191, 313-315, 354-356, 396-398, 601-603, 734-736, 739-741, 744-746 and 775-777 of SEQ ID NO:10; seven predicted Casein Kinase II phosphorylation sites (PS00006) located at about amino acids 178-181, 195-198, 425-428, 471-474, 740-743, 775-778 and 799-802 of SEQ ID NO:10; and four predicted N-myristoylation sites (PS00008) from about amino acids 53-58, 96-101, 103-108 and 792-797 of SEQ ID NO:10.

For general information regarding PFAM identifiers, PS prefix and PF prefix domain identification numbers, refer to Sonnhammer et al. (1997) *Protein* 28:405-420.

The 26886 protein contains a significant number of structural characteristics in common with members of the carnitine acyltransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

A 26886 polypeptide or a 26886 family member can include a "carnitine acyltransferase domain" or regions homologous with a "carnitine acyltransferase domain".

As used herein, the term "carnitine acyltransferase domain" refers to a protein domain having an amino acid sequence of about 400 to 800 amino acids, preferably about 500 to 700 amino acid residues, more preferably about 550 to 650 amino acids. A carnitine acyltransferase domain typically includes one region of homology with other carnitine acyltransferase enzymes located in the N-terminal section, which is characterized by the presence of three L/I/V/M-P dipeptides. A second region of homology, located in the central portion of the enzyme, is characterized by the conservation of a number of charged residues, including a histidine, which may play a role in the catalytic mechanism. Preferably, a "carnitine acyltransferase domain" includes an amino acid sequence of about 400 to 800 amino acid residues in length and having a bit score for the alignment of the sequence to the carnitine acyltransferase domain (HMM) of at least 300. More preferably, a carnitine acyltransferase domain includes at least about 500 to 700 amino acids, even more preferably about 550 to 650 amino acids, or even most preferably, 590 amino acids, and has a bit score for the alignment of the sequence to the carnitine acyltransferase domain (HMM) of at least 400, 500, 600, 700 or greater. The carnitine acyltransferase domain (HMM) has been assigned the PFAM Accession PF00755. An alignment of the carnitine acyltransferase domain (corresponding to amino acids 170 to 760 of SEQ ID NO:10) of human 26886 with a consensus amino acid sequence derived from a hidden Markov model (SEQ ID NO:12) is depicted in FIG. 11.

In a preferred embodiment, 26886 polypeptide or protein has a "carnitine acyltransferase domain" or a region which includes at least about 300-1000, more preferably about 400-900 or 500-800 amino acid residues, and having at least about 60%, 70% 80% 90% 95%, 99%, or 100% homology with a "carnitine acyltransferase domain," e.g., the carnitine acyltransferase domain of human 26886 (e.g., residues 170-760 of SEQ ID NO:10).

To identify the presence of a "carnitine acyltransferase domain" in a 26886 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonnhammer et al. (1997) *Proteins* 28(3):

405-420 and a detailed description of HMMs can be found, for example, in Gribskov et al.(1990) *Meth. Enzymol.* 183: 146-159; Gribskov et al.(1987) *Proc. Natl. Acad. Sci. USA* 84:4355-4358; Krogh et al.(1994) *J. Mol. Biol.* 235:1501-1531; and Stultz et al. (1993) *Protein Sci.* 2:305-314, the contents of which are incorporated herein by reference. A search was performed against the HMM database resulting in the identification of a "carnitine acyltransferase domain" in the amino acid sequence of human 26886 at about residues 170-760 of SEQ ID NO:10 (see FIG. 11).

In one embodiment, a 26886 protein includes at least one, preferably two, transmembrane domains. As used herein, the term "transmembrane domain" includes an amino acid sequence of about 15 amino acid residues in length that spans a phospholipid membrane. More preferably, a transmembrane domain includes about at least 18, 20, 22, 24, 25, 30, 35 or 40 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al, (1996) *Annual Rev. Neuronsci.* 19: 235-63, the contents of which are incorporated herein by reference.

In a preferred embodiment, a 26886 polypeptide or protein has at least one transmembrane domain or a region which includes at least 18, 20, 22, 24, 25, 30, 35 or 40 amino acid residues and has at least about 60%, 70% 80% 90% 95%, 99%, or 100% homology with a "transmembrane domain," e.g., at least one transmembrane domain of human 26886 (e.g., amino acid residues 51-75 or 104-126 of SEQ ID NO:10).

In another embodiment, a 26886 protein includes at least one "non-transmembrane domain". As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally-occurring 26886, or 26886-like protein.

In a preferred embodiment, a 26886 polypeptide or protein has a "non-transmembrane domain" or a region which includes at least about 1-1000, preferably about 500-900, more preferably about 600-800, and even more preferably about 650-700 amino acid residues, and has at least about 60%, 70% 80% 90% 95%, 99% or 100% homology with a "non-transmembrane domain", e.g., a non-transmembrane domain of human 26886 (e.g., residues 127-804 of SEQ ID NO:10). Preferably, a non-transmembrane domain is capable of catalytic activity (e.g., carnitine and/or fatty acyl CoA binding and acyl group transfer).

In another embodiment, a 26886 protein includes at least one non-transmembrane loop. As defined herein, the term "loop" includes an amino acid sequence having a length of at least about 4, preferably about 5-10, more preferably about 10-20, and even more preferably about 20-30 amino acid residues, and has an amino acid sequence that connects two transmembrane domains within a protein or polypeptide. Accordingly, the N-terminal amino acid of a loop is adjacent to a C-terminal amino acid of a transmembrane domain in a naturally-occurring 26886 or 26886-like molecule, and the C-terminal amino acid of a loop is adjacent to an N-terminal amino acid of a transmembrane domain in a naturally-occurring 26886 or 26886-like molecule. For example, a non-transmembrane loop or a region is located at about amino acid residues 76-103 of SEQ ID NO:10.

In a preferred embodiment, a 26886 polypeptide or protein has at least one non-transmembrane loop or a region which includes at least about 4, preferably about 5-10, preferably about 10-20, and even more preferably about 20-30 amino acid residues, and has at least about 60%, 70% 80% 90% 95%, 99%, or 100% homology with a "non-transmembrane loop," e.g., at least one non-transmembrane loop of human 26886 (e.g., residues 76-103 of SEQ ID NO:10).

A non-transmembrane domain located at the N-terminus of a 26886 protein or polypeptide is referred to herein as an "N-terminal non-transmembrane domain", or an "N-terminal non-transmembrane loop". As used herein, an "N-terminal non-transmembrane domain" includes an amino acid sequence having about 1-300, preferably about 1-200, preferably about 1-100, more preferably about 1-75, or even more preferably about 1-50 amino acid residues in length and is located outside the boundaries of a membrane. For example, an N-terminal non-transmembrane domain is located at about amino acid residues 1-46 of SEQ ID NO:10.

Similarly, a non-transmembrane domain located at the C-terminus of a 26886 protein or polypeptide is referred to herein as a "C-terminal non-transmembrane domain", or a "C-terminal non-transmembrane loop". As used herein, an "C-terminal non-transmembrane domain" includes an amino acid sequence having about 100-800, preferably about 200-750, preferably about 400-700, more preferably about 676 amino acid residues in length and is located outside the boundaries of a membrane. For example, an C-terminal non-transmembrane domain is located at about amino acid residues 127-803 of SEQ ID NO:10.

As the 26886 polypeptides of the invention may modulate 26886-mediated activities, they may be useful as, or for, developing novel diagnostic and therapeutic agents for 26886-mediated or related disorders, as described below.

As used herein, a "26886 activity", "biological activity of 26886" or "functional activity of 26886", refers to an activity exerted by a 26886 protein, polypeptide or nucleic acid molecule on, e.g., a 26886-responsive cell or on a 26886 substrate, e.g., a protein substrate, as determined in vivo or in vitro. In one embodiment, a 26886 activity is a direct activity, such as an association with a 26886 target molecule. A "target molecule" or "binding partner" is a molecule with which a 26886 protein binds or interacts in nature. In an exemplary embodiment, a "target molecule" is, e.g., a fatty acyl CoA complex and/or carnitine. A 26886 activity can also be an indirect activity, e.g., a cellular signaling activity mediated by interaction of the 26886 protein with a 26886 ligand. For example, the 26886 proteins of the present invention can have one or more of the following activities: (1) catalyze fatty acid transfer from a fatty acyl CoA molecule to a carnitine; (2) catalyze the transfer of the fatty acid group from acylcarnitine to CoA; (3) regulate fatty acid transport across phospholipid membranes; or (4) regulate the cellular pool of CoA and acyl CoA.

Based on the above-described sequence similarities, the 26886 molecules of the present invention are predicted to have similar biological activities as carnitine acyltransferase family members. Carnitine acyltransferase enzymes assist in the transport of fatty acids across lipid membranes by catalyzing fatty acid transfer from a fatty acyl CoA molecule to a carnitine, thereby forming an acylcarnitine. Once the acylcarnitine is translocated across the lipid membrane (via a carnitine:acylcarnitine translocase enzyme), another carnitine acyltransferase enzyme catalyzes the transfer of the fatty acid group of acylcarnitine back to a CoA molecule. By performing such a reaction, carnitine acyltransferase enzymes also regulate the amount and location of free CoA and acyl CoA pools. Thus, the 26886 molecules can act as novel diagnostic targets and therapeutic agents for controlling, e.g., metabolic disorders or disorders related to fatty acid oxidation.

Figure 12:
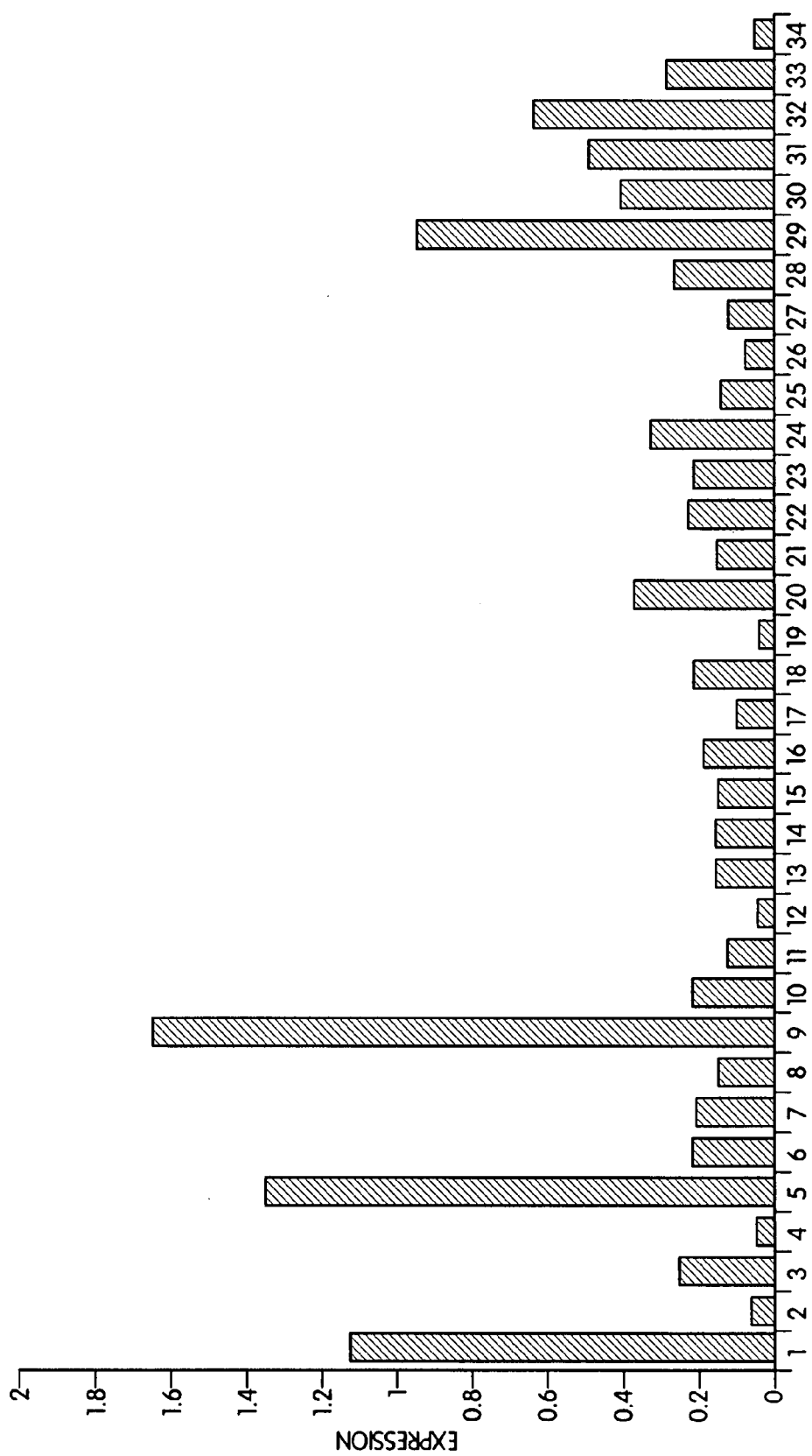
FIG. 12 is a bar graph depicting the expression of 26886 RNA in a panel of normal and tumor human tissues, including colon and liver, detected using TaqMan analysis. The following tissues are shown: normal colon (bars 1-6); adenomas (bars 7-8); colonic adenocarcinomas (bars 9-21); normal liver (bars 22-27); colon-liver metastasis (bars 28-33); and colon abdominal (bar 34). Elevated expression was detected in normal and malignant colon.
Figure 13:
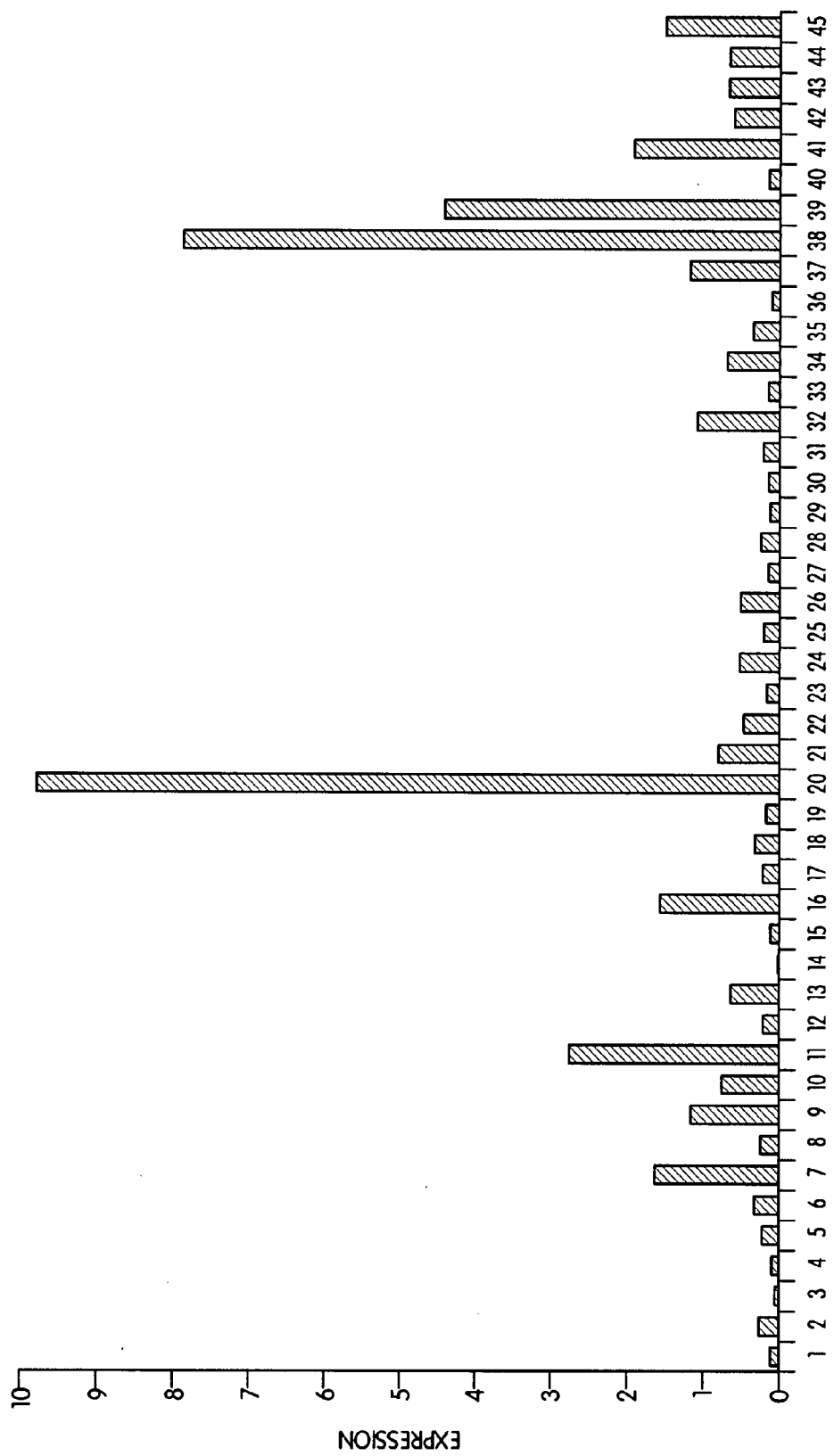
FIG. 13 is a bar graph depicting the expression of 26886 RNA in a panel of normal and tumor human tissues, including breast, colon, liver, and lung, detected using TaqMan analysis. The following tissues are shown: normal breast (bars 1-3); breast tumors, including invasive carcinoma (IDC) (bars 4-9); normal ovary (bars 10-11); ovarian tumor (bars 12-16); normal lung (bars 17-19); lung tumors, including small and non-small cell carcinoma, and adenocarcinomas (bars 20-26); normal colon (bars 27-29); colon tumors (bars 30-33); colon-liver metastasis (bars 34-35); normal liver (36); hemangioma (bar 37); human microvesicular endothelial cells (arrested and proliferating) (bars 38-39, respectively); normal prostate (bars 40-41); prostate tumor (bars 42-44); and prostate liver metastasis (bar 45). Elevated expression of 26886 mRNA was detected in breast tumors, lung small cell carcinomas, and endothelial cells.
Figure 14:
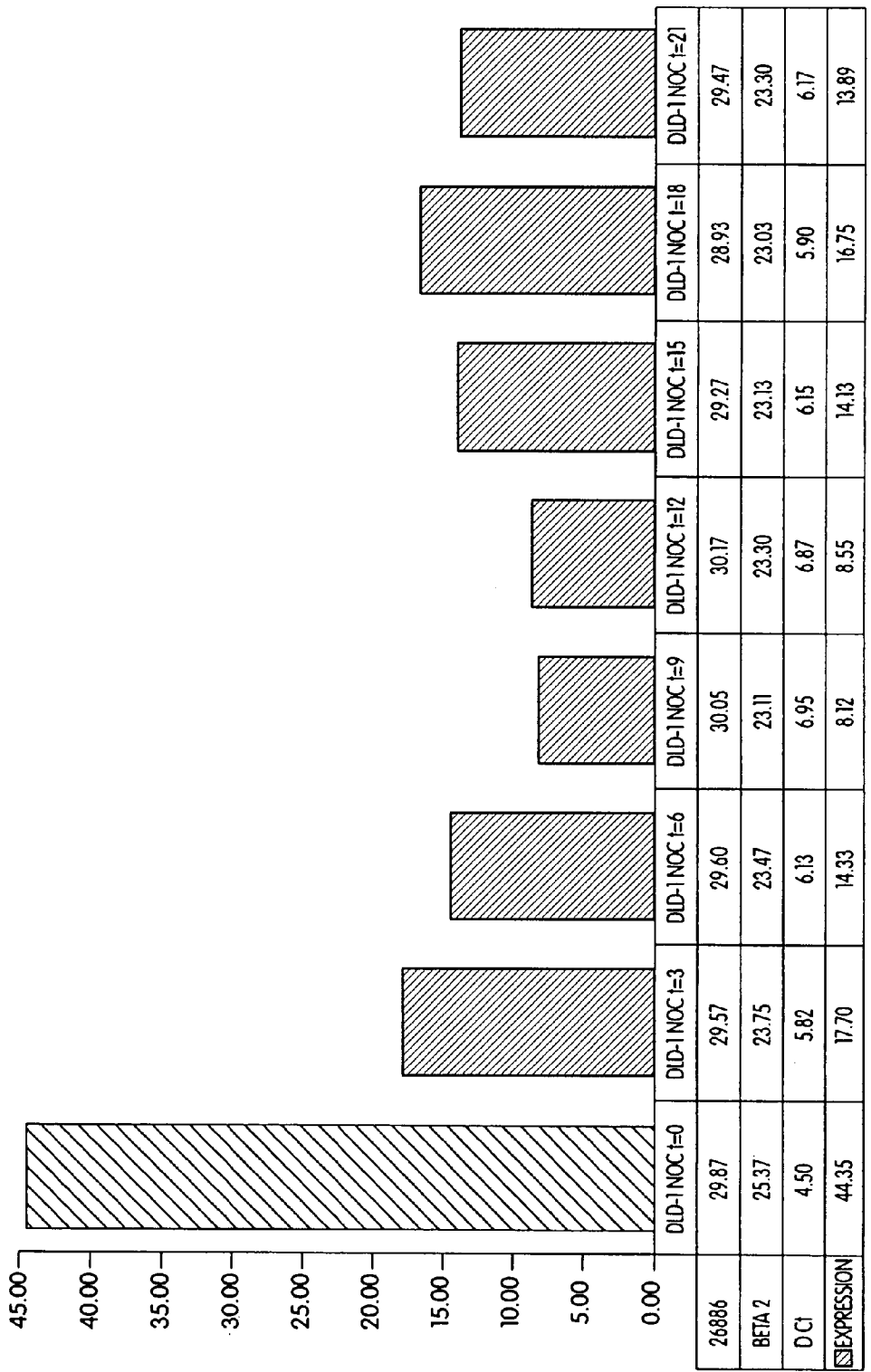
FIG. 14 is a bar graph depicting the changes in 26886 mRNA expression in synchronized colorectal adenocarcinoma DLD-1 cell lines. DLD-1 cells were treated with nocodazole, which induces cell cycle arrest at the G2/M phase of the cell cycle. The profiling and Taqman experiments indicate that 26886 expression is upregulated during the transition from G2/M to G0/G1 phase.

The 26886 protein may be involved in disorders characterized by aberrant activity of the cells in which it is expressed. 26886 is highly expressed in cells and tissues derived from tumors of the breast, ovary, lung (e.g., small lung cell carcinomas), liver, and colon (FIGS. 12-15). Moreover, 26886 mRNA is expressed at high levels on endothelial cells (FIG. 13). 26886 mRNA is also expressed although at lower levels compared to the expression in tumors and endothelial cells, in cells derived from colon, breast, ovary, and liver (FIG. 14). Accordingly, the 26886 molecules can serve as novel diagnostic targets and therapeutic agents for controlling disorders involving the cells or tissues where they are expressed. For example, the 26886 molecules can serve as novel diagnostic targets and therapeutic agents for controlling disorders of cell proliferation, cell differentiation, angiogenesis, organogenesis, and cell signaling.

The polypeptides and nucleic acids of the invention can also be used to treat, prevent, and/or diagnose cancers and neoplastic conditions. As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Examples of cellular proliferative and/or differentiative disorders include cancer, e.g., carcinoma, sarcoma, or metastatic disorders. The 26886 molecules can act as novel diagnostic targets and therapeutic agents for controlling breast cancer, ovarian cancer, colon cancer (e.g., adenocarcinomas), lung cancer (and in particular cancers such as small cell carcinomas), metastasis of such cancers and the like. A metastatic tumor can arise from a multitude of primary tumor types, including but not limited to those of breast, lung, liver, colon and ovarian origin.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Examples of cancers or neoplastic conditions, include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

The 26886 nucleic acid and protein of the invention can be used to treat and/or diagnose a variety of hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol/Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

As the 26886 mRNA is expressed in the normal breast, kidney, liver, and endothelial cells, it is likely that 26886 molecules of the present invention are involved in disorders characterized by aberrant activity of these cells. Thus, the 26886 molecules can act as novel diagnostic targets and therapeutic agents for controlling disorders involving aberrant activity of these cells. For example, modulators of 26886 polypeptide or nucleic acid activity or expression can be used to treat or prevent endothelial cell disorders, and more broadly cardiovascular or blood vessel disorders.

As used herein, an "endothelial cell disorder" refers to a disorder characterized by aberrant, unregulated, or unwanted endothelial cell activity, e.g., proliferation, migration, angiogenesis, or vascularization; or aberrant expression of cell surface adhesion molecules or genes associated with angiogenesis. Examples of endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

Examples of cardiovascular disorders include, but are not limited to, a disease, disorder, or state involving the cardiovascular system, e.g., the heart, and or coronary blood vessels. A cardiovascular disorder can be caused by a malfunction of the heart, an imbalance in arterial pressure or an occlusion of a blood vessel, e.g., by a thrombus. Examples of such disorders include arrhythmias, myocardial infarction, hypertension, atherosclerosis, coronary artery spasm, congestive heart failure, coronary artery disease, valvular disease and cardiomyopathies.

For example, during ischemia (i.e., localized tissue anemia resulting from diminished blood flow) or hypoxia of the heart muscle, oxidation of fatty acids is inhibited by a high mitochondrial redox potential. Such events may result in a build-up of long-chain acylcarnitines in the cytosol. Long-chain acylcarnitines, in turn, have been shown to mediate a number of deleterious events in ischemic tissue. These events include activation of calcium channels and subsequent increases in cytosolic calcium, as well as electrophysiological derangements resulting from incorporation of the long-chain acylcarnitines into the sarcolemma of the cardiac myocyte. Thus, modulators of the carnitine transferase activity of 26886 polypeptides, (for example, carnitine acyltransferase inhibitors) may prevent injury to ischemic tissue, i.e., limit infarct size, improve cardiac function and prevent arrhythmias during and following a myocardial infarction. Additionally, inhibitors of 26886 polypeptides may prevent the onset of ventricular fibrillation and ventricular tachycardia.

Examples of blood vessel disorders include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease--the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Since carnitine acyltransferase enzymes are typically found in one or more organelles of a cell, e.g., a cell in which fatty acid oxidation takes place (e.g., a muscle or a liver cell), it is likely that 26886 proteins may also be expressed in such cells. Therefore, altered expression and/or activity of a 26886 molecule can lead to defects in the metabolism (e.g., due to improper concentrations and/or localization of CoA or acyl CoA pools) or impaired oxidation of fatty acid (e.g., long-chain fatty acids) in cells in which fatty acid oxidation takes place, e.g., muscle or liver cells.

Skeletal muscle cells may be affected by aberrant activity of a 26886 polypeptide. For instance, symptoms of a skeletal muscular disorder may include long-term aching muscles and muscle cramps. In a clinical case of carnitine acyltransferase deficiency, muscle cramping would be precipitated by fasting, exercise or a high-fat diet, since fatty acid oxidation is the major energy-yielding process in all three states. Furthermore, a biopsy of muscle tissue showing that the long-chain acyl CoA synthetase is fully active and a demonstration that medium-chain fatty acids ($C_8$ and $C_{10}$) are metabolized normally (since carnitine, and hence, carnitine acyltransferase, is not required for the permeation of medium-chain acyl CoAs into the mitochondrial matrix) would be indicative of a defect or deficiency in a carnitine acyltransferase enzyme.

Liver metabolic activity (e.g., fat burning, e.g., oxidation) accounts for over 25% of the body's total oxygen consumption in a subject at rest. The substantial energy needs of the liver are met largely by oxidation of fat in the mitochondria. Accordingly, aberrant activity of a 26886 polypeptide may disrupt the production of energy required by the liver, and hence, metabolic function of the liver.

Examples of liver disorders include, but are not limited to, disorders associated with an accumulation of fibrous tissue, such as that resulting from an imbalance between production and degradation of the extracellular matrix accompanied by the collapse and condensation of preexisting fibers; hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic); hepatic injury, such as portal hypertension or hepatic fibrosis; liver fibrosis attributed to inborn errors of metabolism, for example, fibrosis resulting from a storage disorder such as Gaucher's disease (lipid abnormalities) or a glycogen storage disease, e.g., A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome); liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder, such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 26886 may play an important role in overall metabolism. Diseases of metabolic imbalance include, but are not limited to, obesity, anorexia nervosa, cachexia and lipid disorders diabetes.

Moreover, a 26886 protein may regulate cellular pools (e.g., concentration and/or location) of CoA and acyl CoA. A defect or deficiency in a 26886 polypeptide, therefore, may result in inappropriate levels of CoA, thereby causing a variety of disorders, for example, neurological disorders. Examples of neural disorders include, but are not limited to, neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease; psychiatric disorders, e.g., depression, schizophrenic disorders, Korsakoffs psychosis, mania, anxiety disorders, or phobic disorders; learning or memory disorders, e.g., amnesia or age-related memory loss; and neurological disorders, e.g., migraine. The ability to regulate or control the expression of a 26886 protein may result in the ability to likewise regulate or control the cellular pools of CoA, thereby providing a protective and/or therapeutic effect against, e.g., neurological disorders.

Thus, the 26886 molecules can act as novel diagnostic targets and therapeutic agents for controlling defects resulting in metabolic deficiencies and/or impaired fatty acid oxidation.

The presence of 26886 RNA or protein can also be used to identify a cell or tissue, or other biological sample, as being derived from breast, colon, liver, and endothelial cell, or being of human origin. Expression can also be used to diagnose or stage a disorder, e.g., a cancer, a breast, ovarian, or liver disorder, especially a cancer of the breast. Expression can be determined by evaluating RNA, e.g., by hybridization of a 26886 specific probe, or with a 26886 specific antibody.

The 26886 protein, fragments thereof, and derivatives and other variants of the sequence in SEQ ID NO:10 thereof are collectively referred to as "polypeptides or proteins of the invention" or "26886 polypeptides or proteins". Nucleic acid molecules encoding such polypeptides or proteins are collectively referred to as "nucleic acids of the invention" or "26886 nucleic acids." 26886 molecules refer to 26886 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated or purified nucleic acid molecule" includes nucleic acid molecules that are separated from other nucleic acid molecules that are present in the natural source of the nucleic acid. For example, with regards to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under stringent conditions to the sequence of SEQ ID NO:9 or 11, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 26886 protein, preferably a mammalian 26886 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 26886 protein having less than about 30%, 20%, 10% and more preferably 5% (by dry weight), of non-26886 protein (also referred to herein as a "contaminating protein"), or of chemical precursors or non-26886 chemicals. When the 26886 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 26886 (e.g., the nucleotide sequence of SEQ ID NO:9 or 11) without abolishing or more preferably, without substantially altering a biological activity, whereas an "essential" amino acid residue results in such a change. For example, amino acid residues that are conserved among the polypeptides of the present invention, e.g., those present in the carnitine acyltransferase domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a 26886 protein is preferably replaced with another amino acid residue from the same side chain family. Alternatively, in another embodiment, mutations can be introduced randomly along all or part of a 26886 coding sequence, such as by saturation mutagenesis, and the resultant mutants can be screened for 26886 biological activity to identify mutants that retain activity. Following mutagenesis of SEQ ID NO:9 or 11, the encoded protein can be expressed recombinantly and the activity of the protein can be determined.

As used herein, a "biologically active portion" of a 26886 protein includes a fragment of a 26886 protein that participates in an interaction between a 26886 molecule and a non-26886 molecule. Biologically active portions of a 26886 protein include peptides comprising amino acid sequences sufficiently homologous to or derived from the amino acid sequence of the 26886 protein, e.g., the amino acid sequence shown in SEQ ID NO:10, which include less amino acids than the full length 26886 proteins, and exhibit at least one activity of a 26886 protein. Typically, biologically active portions comprise a domain or motif with at least one activity of the 26886 protein, e.g., carnitine acyltransferase. A biologically active portion of a 26886 protein can be a polypeptide that is, for example, 50, 100, 200 or more amino acids in length. Biologically active portions of a 26886 protein can be used as targets for developing agents, which modulate a 26886-mediated activity, e.g., carnitine acyltransferase.

Particular 26886 polypeptides of the present invention have an amino acid sequence substantially identical to the amino acid sequence of SEQ ID NO:10. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:10 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:9 or 11 are termed substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 26886 amino acid sequence of SEQ ID NO:10 having 804 amino acid residues, at least 241, preferably at least 322, more preferably at least 402, even more preferably at least 482, and even more preferably at least 563, 643, 724 or 804 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if the molecule is within the sequence identity limits of a claim) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol Biol.* 215:403-10. BLAST nucleotide searches can be performed with the NBLAST program, score=100, wordlength=12 to obtain nucleotide sequences homologous to 26886 nucleic acid molecules of the invention. BLAST protein searches can be performed with the XBLAST program, score=50, wordlength=3 to obtain amino acid sequences homologous to 26886 protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules of 26886

In one aspect, the invention provides, an isolated or purified, nucleic acid molecule that encodes a 26886 polypeptide described herein, e.g., a full-length 26886 protein or a fragment thereof, e.g., a biologically active portion of 26886 protein. Also included is a nucleic acid fragment suitable for use as a hybridization probe, which can be used, e.g., to a identify nucleic acid molecule encoding a polypeptide of the invention, 26886 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:9, or a portion of any of these nucleotide sequences. In one embodiment, the nucleic acid molecule includes sequences encoding the human 26886 protein (i.e., "the coding region", from nucleotides 272-2683 of SEQ ID NO:9), as well as 5' untranslated sequences (nucleotides 1-271 of SEQ ID NO:9) and 3' untranslated sequences (nucleotides 2684-2875 of SEQ ID NO:9). Alternatively, the nucleic acid molecule can include only the coding region of SEQ ID NO:9 (e.g., nucleotides 272-2683, corresponding to SEQ ID NO:11) and, e.g., no flanking sequences which normally accompany the subject sequence. In another embodiment, the nucleic acid molecule encodes a sequence corresponding to the mature protein from about amino acid 5 to amino acid 804 of SEQ ID NO:10.

In another embodiment, an isolated nucleic acid molecule of the invention includes a nucleic acid molecule which is a complement of the nucleotide sequence shown in SEQ ID NO:9 or 11, or a portion of any of these nucleotide sequences. In other embodiments, the nucleic acid molecule of the invention is sufficiently complementary to the nucleotide sequence shown in SEQ ID NO:9 or 11, such that it can hybridize to the nucleotide sequence shown in SEQ ID NO:9 or 11, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:9 or 11, or a portion, preferably of the same length, of any of these nucleotide sequences.

26886 Nucleic Acid Fragments

A nucleic acid molecule of the invention can include only a portion of the nucleic acid sequence of SEQ ID NO:9 or 11. For example, such a nucleic acid molecule can include a fragment that can be used as a probe or primer or a fragment encoding a portion of a 26886 protein, e.g., an immunogenic or biologically active portion of a 26886 protein. A fragment can comprise nucleotides 448 to 470 of SEQ ID NO:9, which encodes an acyltransferase domain of human 26886. The nucleotide sequence determined from the cloning of the 26886 gene allows for the generation of probes and primers designed for use in identifying and/or cloning other 26886 family members, or fragments thereof, as well as 26886 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment that includes a nucleotide sequence encoding an amino acid fragment described herein. Nucleic acid fragments can encode a specific domain or site described herein or fragments thereof, particulary fragments thereof that are at least 23 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a nucleic acid fragment can include a sequence corresponding to an acyltransferase domain, or more specifically, a carnitine acyltransferase domain.

In a preferred embodiment, the fragment is at least 300, 350, 400, 450, 500, 550, 600, 650, 700, 750, 800, 850, 900, 950, or 1000 nucleotides in length.

26886 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:9 or 11, or of a naturally occurring allelic variant or mutant of SEQ ID NO:9 or 11.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes an acyltransferase domain (corresponding to residues 448-470 of SEQ ID NO:10), or a carnitine acyltransferase domain (corresponding to residues 170-760 of SEQ ID NO:10).

In another embodiment, a set of primers is provided, e.g., primers suitable for use in a PCR, which can be used to amplify a selected region of a 26886 sequence. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying all or a portion of a domain or region described herein, e.g., any of the following regions, are provided: an acyltransferase signature region corresponding to residues 448-470 of SEQ ID NO:10, or a carnitine acyltransferase domain corresponding to residues 170-760 of SEQ ID NO:10.

A nucleic acid fragment can encode an epitope bearing region of a polypeptide described herein.

A nucleic acid fragment encoding a "biologically active portion of a 26886 polypeptide" can be prepared by isolating a portion of the nucleotide sequence of SEQ ID NO:9 or 11, which encodes a polypeptide having a 26886 biological activity (e.g., the biological activities of the 26886 proteins are described herein), expressing the encoded portion of the 26886 protein (e.g., by recombinant expression in vitro) and assessing the activity of the encoded portion of the 26886 protein. For example, a nucleic acid fragment encoding a biologically active portion of 26886 includes a carnitine acyltransferase domain, e.g., amino acid residues 170 to 760 of SEQ ID NO:10. A nucleic acid fragment encoding a biologically active portion of a 26886 polypeptide, may comprise a nucleotide sequence which is greater than 590 residues or more in length.

In a preferred embodiment, the fragment has nucleotide sequence which other than (e.g., differs by at least one nucleotide from) the nucleotide sequence of BF983189, AA614273, AW955734, or BE780927.

In preferred embodiments, nucleic acids include a nucleotide sequence which is about 300, 400, 500, 600, 650, 700, 800, 900, 1000, 1100, 1200, 1300, 1400, 1500, 1600, 1700, 1800, 1900, 2000, 2100, 2200, 2300, 2400, or 2500 nucleotides in length and hybridizes under stringent hybridization conditions to a nucleic acid molecule of SEQ ID NO:9, or SEQ ID NO:11.

26886 Nucleic Acid Variants

The invention further encompasses nucleic acid molecules that differ from the nucleotide sequence shown in SEQ ID NO:9 or 11. Such differences can be due to degeneracy of the genetic code (and result in a nucleic acid that encodes the same 26886 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:10. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one colon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:9 or 11, e.g., as follows: by at least one but less than 10, 20, 30, or 40 nucleotides; at least one but less than 2%, 5%, 10% or 20% of the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the amino acid sequence shown in SEQ ID NO:10 or a fragment of those sequences. Nucleic acid molecules encoding such polypeptides can readily be identified as being able to hybridize under stringent conditions, to the nucleotide sequence shown in SEQ ID NO:9 or 11 or a fragment of the sequence. Nucleic acid molecules corresponding to orthologs, homologs, and allelic variants of the 26886 cDNAs of the invention can further be isolated by mapping to the same chromosome or locus as the 26886 gene.

Preferred variants include those that are correlated with carnitine acyltransferase activity.

Allelic variants of 26886, e.g., human 26886, include both functional and non-functional proteins. Functional allelic variants are naturally occurring amino acid sequence variants of the 26886 protein within a population that maintain the ability to function as an acyltransferase, specifically as a carnitine acyltransferase. Functional allelic variants will typically contain only conservative substitution of one or more amino acids of SEQ ID NO:10, or substitution, deletion or insertion of non-critical residues in non-critical regions of the protein. Non-functional allelic variants are naturally-occurring amino acid sequence variants of the 26886, e.g., human 26886, protein within a population that do not have the ability to function as a carnitine acyltransferase. Non-functional allelic variants will typically contain a non-conservative substitution, a deletion, or insertion, or premature truncation of the amino acid sequence of SEQ ID NO:10, or a substitution, insertion, or deletion in critical residues or critical regions of the protein.

Moreover, nucleic acid molecules encoding other 26886 family members and, thus, which have a nucleotide sequence which differs from the 26886 sequences of SEQ ID NO:9 or 11, are intended to be within the scope of the invention.

Antisense Nucleic Acid Molecules, Ribozymes and Modified 26886 Nucleic Acid Molecules In another aspect, the invention features, an isolated nucleic acid molecule that is antisense to 26886. An "antisense" nucleic acid can include a nucleotide sequence that is complementary to a "sense" nucleic acid encoding a protein, e.g., complementary to the coding strand of a double-stranded cDNA molecule or complementary to an mRNA sequence. The antisense nucleic acid can be complementary to an entire 26886 coding strand, or to only a portion thereof (e.g., the coding region of human 26886 corresponding to SEQ ID NO:11). In another embodiment, the antisense nucleic acid molecule is antisense to a "noncoding region" of the coding strand of a nucleotide sequence encoding 26886 (e.g., the 5' or 3' untranslated regions).

An antisense nucleic acid can be designed such that it is complementary to the entire coding region of 26886 mRNA, but more preferably is an oligonucleotide that is antisense to only a portion of the coding or noncoding region of 26886 mRNA. For example, the antisense oligonucleotide can be complementary to the region surrounding the translation start site of 26886 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 26886 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An (x-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. A ribozyme having specificity for a 26886-encoding nucleic acid can include one or more sequences complementary to the nucleotide sequence of a 26886 cDNA disclosed herein (i.e., SEQ ID NO:9 or 11), and a sequence having known catalytic sequence responsible for mRNA cleavage (see U.S. Pat. No. 5,093,246 or Haselhoff and Gerlach (1988) Nature 334:585-591). For example, a derivative of a Tetrahymena L-19 IVS RNA can be constructed in which the nucleotide sequence of the active site is complementary to the nucleotide sequence to be cleaved in a 26886-encoding mRNA. See, e.g., Cech et al., U.S. Pat. No. 4,987,071; and Cech et al., U.S. Pat. No. 5,116,742. Alternatively, 26886 mRNA can be used to select a catalytic RNA having a specific ribonuclease activity from a pool of RNA molecules. See, e.g., Bartel, D. and Szostak, J. W. (1993) Science 261:1411-1418.

26886 gene expression can be inhibited by targeting nucleotide sequences complementary to the regulatory region of the 26886 (e.g., the 26886 promoter and/or enhancers) to form triple helical structures that prevent transcription of the 26886 gene in target cells. See generally, Helene, C. (1991) Anticancer Drug Des. 6(6):569-84; Helene, C. et al. (1992) Ann. N.Y. Acad. Sci. 660:27-36; and Maher, L. J. (1992) Bioassays 14(12):807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or calorimetric.

A 26886 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) Bioorganic & Medicinal Chemistry 4 (1): 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670-675.

PNAs of 26886 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 26886 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958-976) or intercalating agents. (See, e.g., Zon (1988) Pharm. Res. 5:539-549). To this end, the oligonucleotide may be conjugated to another molecule, (e.g., a peptide, hybridization-triggered cross-linking agent, transport agent, or hybridization-triggered cleavage agent).

The invention also includes molecular beacon oligonucleotide primer and probe molecules having at least one region that is complementary to a 26886 nucleic acid of the invention. One complementary region has a fluorophore, and the other, a quencher, such that the molecular beacon is useful for quantitating the presence of the 26886 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 26886 Polypeptides

In another aspect, the invention features, an isolated 26886 protein, or fragment, e.g., a biologically active portion, for use as immunogens or antigens to raise or test (or more generally to bind) anti-26886 antibodies. 26886 protein can be isolated from cells or tissue sources using standard protein purification techniques. 26886 protein or fragments thereof can be produced by recombinant DNA techniques or synthesized chemically.

Polypeptides of the invention include those that arise as a result of the existence of multiple genes, alternative transcription events, alternative RNA splicing events, and alternative translational and postranslational events. The polypeptide can be expressed in systems, e.g., cultured cells, which result in substantially the same post-translational modifications present when the polypeptide is expressed in a native cell, or in systems which result in the alteration or omission of post-translational modifications when expressed in a native cell, e.g., glycosylation or cleavage.

In a preferred embodiment, a 26886 polypeptide has one or more of the following characteristics:

(i) it has the ability to catalyze fatty acyl group transfer from a fatty acyl CoA molecule to a carnitine, thereby producing an acylcarnitine;

(ii) it has the ability to catalyze the transfer of a fatty acyl group from acylcarnitine to CoA, thereby forming a fatty acyl CoA;

(iii) it has the ability to regulate the concentration and localization of cellular pools of CoA and/or acyl CoA;

(iv) it has a molecular weight (e.g., deduced molecular weight), amino acid composition or other physical characteristic of a 26886 polypeptide, e.g., a 26886 polypeptide having the sequence shown in SEQ ID NO:10;

(v) it has an overall sequence similarity of at least 60%, preferably at least 70%, more preferably at least 80, 90, or 95%, with a polypeptide of SEQ ID NO:10;

(vi) it may be found in one or more organelles of a cell, e.g., a cell in which fatty acid oxidation takes place (e.g., a muscle or a liver cell);

(vii) it has a carnitine acyltransferase domain which is preferably about 60%, 70%, 80%, 90% or 95% homologous to amino acid residues 170-760 of SEQ ID NO:10; or (viii) it has at least 70%, preferably 80%, more preferably 90%, and most preferably 100% of the cysteines found in the amino acid sequence of the native protein.

In a preferred embodiment the 26886 protein, or fragment thereof, differs from the corresponding sequence in SEQ ID NO:10. In one embodiment, it differs by at least one but by less than 15, 10 or 5 amino acid residues. In another, it differs from the corresponding sequence in SEQ ID NO:10 by at least one residue but less than 20%, 15%, 10% or 5% of the residues. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the carnitine acyltransferase domain. In another preferred embodiment one or more differences are in the carnitine acyltransferase domain.

Other embodiments include a protein that contain one or more changes in amino acid sequence, e.g., a change in an amino acid residue which is not essential for activity. Such 26886 proteins differ in amino acid sequence from SEQ ID NO:10, yet retain biological activity.

In one embodiment, the protein includes an amino acid sequence that is at least about 60%, 65%, 70%, 75%, 80%, 85%, 90%, 95%, 98%, 99%, 99.5% or more homologous to SEQ ID NO:10.

A 26886 protein or fragment is provided which varies from the sequence of SEQ ID NO:10 in non-essential regions (e.g., transmembrane domains) by at least one but by less than 15, 10 or 5 amino acid residues in the protein or fragment, but which does not differ from SEQ ID NO:10 in catalytic regions (e.g., the carnitine acyltransferase domain). (If this comparison requires alignment the sequences should be aligned for maximum homology. "Looped" out sequences from deletions or insertions, or mismatches, are considered differences.) In some embodiments, the difference is at a non-essential residue or is a conservative substitution, while in others the difference is at an essential residue or is a non-conservative substitution.

In one embodiment, a biologically active portion of a 26886 protein includes a carnitine acyltransferase domain. Moreover, other biologically active portions, in which other regions of the protein are deleted, can be prepared by recombinant techniques and evaluated for one or more of the functional activities of a native 26886 protein.

In a preferred embodiment, the 26886 protein has an amino acid sequence shown in SEQ ID NO:10. In other embodiments, the 26886 protein is substantially identical to SEQ ID NO:10. In yet another embodiment, the 26886 protein is substantially identical to SEQ ID NO:10 and retains the functional activity of the protein of SEQ ID NO:10, as described in detail in the subsections above. Accordingly, in another embodiment, the 26886 protein is a protein which includes an amino acid sequence at least about 60%, 65%, 70%, 75%, 80%, 85%, 90%, 95%, 98% or more identical to SEQ ID NO:10.

26886 Chimeric or Fusion Proteins

In another aspect, the invention provides 26886 chimeric or fusion proteins. As used herein, a 26886 "chimeric protein" or "fusion protein" includes a 26886 polypeptide linked to a non-26886 polypeptide. A "non-26886 polypeptide" refers to a polypeptide having an amino acid sequence corresponding to a protein which is not substantially homologous to the 26886 protein, e.g., a protein which is different from the 26886 protein and which is derived from the same or a different organism. The 26886 polypeptide of the fusion protein can correspond to all or a portion e.g., a fragment described herein of a 26886 amino acid sequence. In a preferred embodiment, a 26886 fusion protein includes at least one (or two) biologically active portion of a 26886 protein. The non-26886 polypeptide can be fused to the N-terminus or C-terminus of the 26886 polypeptide.

The fusion protein can include a moiety that has a high affinity for a ligand. For example, the fusion protein can be a GST-26886 fusion protein in which the 26886 sequences are fused to the C-terminus of the GST sequences. Such fusion proteins can facilitate the purification of recombinant 26886. Alternatively, the fusion protein can be a 26886 protein containing a heterologous signal sequence at its N-terminus. In certain host cells (e.g., mammalian host cells), expression and/or secretion of 26886 can be increased through use of a heterologous signal sequence.

Fusion proteins can include all or a part of a serum protein, e.g., an IgG constant region, or human serum albumin.

The 26886 fusion proteins of the invention can be incorporated into pharmaceutical compositions and administered to a subject in vivo. The 26886 fusion proteins can be used to affect the bioavailability of a 26886 substrate. 26886 fusion proteins may be useful therapeutically for the treatment of disorders caused by, for example, (i) aberrant modification or mutation of a gene encoding a 26886 protein; (ii) mis-regulation of the 26886 gene; and (iii) aberrant post-translational modification of a 26886 protein.

Moreover, the 26886-fusion proteins of the invention can be used as immunogens to produce anti-26886 antibodies in a subject, to purify 26886 ligands and in screening assays to identify molecules that inhibit the interaction of 26886 with a 26886 substrate.

Expression vectors are commercially available that already encode a fusion moiety (e.g., a GST polypeptide). A 26886-encoding nucleic acid can be cloned into such an expression vector such that the fusion moiety is linked in-frame to the 26886 protein.

Variants of 26886 Proteins

In another aspect, the invention also features a variant of a 26886 polypeptide, e.g., which functions as an agonist (mimetics) or as an antagonist. Variants of the 26886 proteins can be generated by mutagenesis, e.g., discrete point mutation, the insertion or deletion of sequences or the truncation of a 26886 protein. An agonist of the 26886 proteins can retain substantially the same, or a subset, of the biological activities of the naturally occurring form of a 26886 protein. An antagonist of a 26886 protein can inhibit one or more of the activities of the naturally occurring form of the 26886 protein by, for example, competitively modulating a 26886-mediated activity of a 26886 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 26886 protein.

Variants of a 26886 protein can be identified by screening combinatorial libraries of mutants, e.g., truncation mutants, of a 26886 protein for agonist or antagonist activity.

Libraries of fragments e.g., N terminal, C terminal, or internal fragments, of a 26886 protein coding sequence can be used to generate a variegated population of fragments for screening and subsequent selection of variants of a 26886 protein.

Variants in which a cysteine residue is added or deleted or in which a residue which is glycosylated is added or deleted are particularly preferred.

Methods for screening gene products of combinatorial libraries made by point mutations or truncation, and for screening cDNA libraries for gene products having a selected property are known. Recursive ensemble mutagenesis (REM), a new technique which enhances the frequency of functional mutants in the libraries, can be used in combination with the screening assays to identify 26886 variants (Arkin and Yourvan (1992) *Proc. Natl. Acad. Sci. USA* 89:7811-7815; Delgrave et al. (1993) *Protein Engineering* 6(3):327-331).

Cell based assays can be exploited to analyze a variegated 26886 library. For example, a library of expression vectors can be transfected into a cell line, e.g., a cell line, which ordinarily responds to 26886 in a substrate-dependent manner. The transfected cells are then contacted with 26886 and the effect of the expression of the mutant on the 26886 substrate can be detected, e.g., by measuring fatty acid oxidation. Plasmid DNA can then be recovered from the cells that score for inhibition, or alternatively, potentiation of the mutant by the 26886 substrate, and the individual clones further characterized.

In another aspect, the invention features a method of making a 26886 polypeptide, e.g., a peptide having a non-wild type activity, e.g., an antagonist, agonist, or super agonist of a naturally occurring 26886 polypeptide, e.g., a naturally occurring 26886 polypeptide. The method includes: altering the sequence of a 26886 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 26886 polypeptide a biological activity of a naturally occurring 26886 polypeptide. The method includes: altering the sequence, e.g., by substitution or deletion of one or more residues, of a 26886 polypeptide, e.g., altering the sequence of a non-conserved region, or a domain or residue described herein, and testing the altered polypeptide for the desired activity.

Anti-26886 Antibodies

In another aspect, the invention provides an anti-26886 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-26886 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH—terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 26886 polypeptide or fragment thereof. Examples of antigen-binding fragments of the anti-26886 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-26886 antibody can be a polyclonal or a monoclonal antibody. In other embodiments, the antibody can be recombinantly produced, e.g., produced by phage display or by combinatorial methods.

Phage display and combinatorial methods for generating anti-26886 antibodies are known in the art (as described in, e.g., Ladner et al. U.S. Pat. No. 5,223,409; Kang et al.

International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the anti-26886 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An anti-26886 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559). A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 26886 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *Bio Techniques* 4:214, and by Queen et al. U.S. Pat. No. 5,585, 089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 26886 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In preferred embodiments an antibody can be made by immunizing with purified 26886 antigen, or a fragment thereof, e.g., a fragment described herein, membrane associated antigen, tissue, e.g., crude tissue preparations, whole cells, preferably living cells, lysed cells, or cell fractions, e.g., membrane fractions.

A full-length 26886 protein or, antigenic peptide fragment of 26886 can be used as an immunogen or can be used to identify anti-26886 antibodies made with other immunogens, e.g., cells, membrane preparations, and the like. The antigenic peptide of 26886 should include at least 8 amino acid residues of the amino acid sequence shown in SEQ ID NO:10 and encompasses an epitope of 26886. Preferably, the antigenic peptide includes at least 10 amino acid residues, more preferably at least 15 amino acid residues, even more preferably at least 20 amino acid residues, and most preferably at least 30 amino acid residues.

Fragments of 26886 which include, for example, residues 35-50, 85-99, 443-452, 491-523 or 614-622 of SEQ ID NO:10 can be used to make, e.g., antibodies against hydrophilic regions of the 26886 protein or used as immunogens or to characterize the specificity of an antibody. Similarly, a fragment of 26886 which include, for example, residues 51-84, 100-130, 147-155, 402-420 or 542-555 of SEQ ID NO:10 can be used to make an antibody against a hydrophobic region of the 26886 protein; a fragment of 26886 which include residues 51-75, 104-126 or 717-733 of SEQ ID NO:10 can be used to make an antibody against a transmembrane region of the 26886 protein; a fragment of 26886 which include residues 5-51, 76-103, 127-716 or 734-804 of SEQ ID NO:10 can be used to make an antibody against a non-transmembrane (i.e., matrix, cytosolic or lumen) region of the 26886 protein; a fragment of 26886 which include residues 448-470 of SEQ ID NO:10 can be used to make an antibody against the acyltransferase domain of the 26886 protein; and a fragment of 26886 which include residues 170-760 of SEQ ID NO:10 can be used to make an antibody against the carnitine acyltransferase domain of the 26886 protein.

Antibodies reactive with, or specific for, any of these regions, or other regions or domains described herein are provided.

Antibodies which bind only native 26886 protein, only denatured or otherwise non-native 26886 protein, or which bind both, are with in the invention. Antibodies with linear or conformational epitopes are within the invention. Conformational epitopes can sometimes be identified by indentifying antibodies which bind to native but not denatured 26886 protein.

Preferred epitopes encompassed by the antigenic peptide are regions of 26886 are located on the surface of the protein, e.g., hydrophilic regions, as well as regions with high antigenicity. For example, an Emini surface probability analysis of the human 26886 protein sequence can be used to indicate the regions that have a particularly high probability of being localized to the surface of the 26886 protein and are thus likely to constitute surface residues useful for targeting antibody production.

The anti-26886 antibody can be a single chain antibody. A single-chain antibody (scFV) may be engineered (see, for example, Colcher, D. et al. (1999) Ann N Y Acad Sci 880:263-80; and Reiter, Y. (1996) Clin Cancer Res 2:245-52). The single chain antibody can be dimerized or multimerized to generate multivalent antibodies having specificities for different epitopes of the same target 26886 protein.

In a preferred embodiment the antibody has: effector function; and can fix complement. In other embodiments the antibody does not; recruit effector cells; or fix complement.

In a preferred embodiment, the antibody has reduced or no ability to bind an Fc receptor. For example., it is a isotype or subtype, fragment or other mutant, which does not support binding to an Fc receptor, e.g., it has a mutagenized or deleted Fc receptor binding region.

The antibody can be coupled to a toxin, e.g., a polypeptide toxin, e,g, ricin or diptheria toxin or active fragment hereof, or a radionuclide, or imaging agent, e.g. a radioactive, enzymatic, or other, e.g., imaging agent, e.g., a NMR contrast agent. Labels which produce detectable radioactive emissions or fluorescence are preferred.

An anti-26886 antibody (e.g., monoclonal antibody) can be used to isolate 26886 by standard techniques, such as affinity chromatography or immunoprecipitation. Moreover, an anti-26886 antibody can be used to detect 26886 protein (e.g., in a cellular lysate or cell supernatant) in order to evaluate the abundance and pattern of expression of the protein. Anti-26886 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

The invention also includes a nucleic acid which encodes an anti-26886 antibody, e.g., an anti-26886 antibody described herein. Also included are vectors which include the nucleic acid and sells transformed with the nucleic acid, particularly cells which are useful for producing an antibody, e.g., mammalian cells, e.g. CHO or lymphatic cells.

The invention also includes cell lines, e.g., hybridomas, which make an anti-26886 antibody, e.g., and antibody described herein, and method of using said cells to make a 26886 antibody.

26886 Recombinant Expression Vectors, Host Cells and Genetically Engineered Cells In another aspect, the invention includes vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 26886 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 26886 proteins, mutant forms of 26886 proteins, fusion proteins, and the like).

The recombinant expression vectors of the invention can be designed for expression of 26886 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 26886 activity assays, (e.g., direct assays or competitive assays described in detail below), or to generate antibodies specific for 26886 proteins. In a preferred embodiment, a fusion protein expressed in a retroviral expression vector of the present invention can be used to infect bone marrow cells that are subsequently transplanted into irradiated recipients. The pathology of the subject recipient is then examined after sufficient time has passed (e.g., six (6) weeks).

One strategy used to maximize recombinant protein expression in *E. coli* is to express the protein in a host strain with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The 26886 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Baneiji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., Antisense RNA as a molecular tool for genetic analysis, *Reviews—Trends in Genetics, Vol.* 1(1) 1986.

Another aspect the invention provides a host cell which includes a nucleic acid molecule described herein, e.g., a 26886 nucleic acid molecule within a recombinant expression vector or a 26886 nucleic acid molecule containing sequences which allow it to homologously recombine into a specific site of the host cell's genome. The terms "host cell" and "recombinant host cell" are used interchangeably herein. Such terms refer not only to the particular subject cell, but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 26886 protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation A host cell of the invention can be used to produce (i.e., express) a 26886 protein. Accordingly, the invention further provides methods for producing a 26886 protein using the host cells of the invention. In one embodiment, the method includes culturing the host cell of the invention (into which a recombinant expression vector encoding a 26886 protein has been introduced) in a suitable medium such that a 26886 protein is produced. In another embodiment, the method further includes isolating a 26886 protein from the medium or the host cell.

In another aspect, the invention features, a cell or purified preparation of cells which include a 26886 transgene, or which otherwise misexpress 26886. The cell preparation can consist of human or non-human cells, e.g., rodent cells, e.g., mouse or rat cells, rabbit cells, or pig cells. In preferred embodiments, the cell or cells include a 26886 transgene, e.g., a heterologous form of a 26886, e.g., a gene derived from humans (in the case of a non-human cell). The 26886 transgene can be misexpressed, e.g., overexpressed or underexpressed. In other preferred embodiments, the cell or cells include a gene that misexpresses an endogenous 26886, e.g., a gene for which expression is disrupted, e.g., a knockout. Such cells can serve as a model for studying disorders that are related to mutated or misexpressed 26886 alleles or for use in drug screening.

In another aspect, the invention features, a human cell, e.g., a liver or muscle cell, transformed with a nucleic acid that encodes a subject 26886 polypeptide.

Also provided are cells, e.g., human cells, e.g., human hematopoietic or fibroblast cells, in which an endogenous 26886 is under the control of a regulatory sequence that does not normally control the expression of the endogenous 26886 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 26886 gene. For example, an endogenous 26886 gene, e.g., a gene that is "transcriptionally silent", e.g., not normally expressed, or expressed only at very low levels, may be activated by inserting a regulatory element which is capable of promoting the expression of a normally expressed gene product in that cell. Techniques, such as targeted homologous recombination, can be used to insert the heterologous DNA as described in, e.g., Chappel, U.S. Pat. No. 5,272,071; WO 91/06667, published in May 16, 1991.

26886 Transgenic Animals

The invention provides non-human transgenic animals. Such animals are useful for studying the function and/or activity of a 26886 protein and for identifying and/or evaluating modulators of 26886 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 26886 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 26886 protein to particular cells. A transgenic founder animal can be identified based upon the presence of a 26886 transgene in its genome and/or expression of 26886 mRNA in tissues or cells of the animals. A transgenic founder animal can then be used to breed additional animals carrying the transgene. Moreover, transgenic animals carrying a transgene encoding a 26886 protein can further be bred to other transgenic animals carrying other transgenes. 26886 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses of 26886

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 26886 protein (e.g., via a recombinant expression vector in a host cell in gene therapy applications), to detect a 26886 mRNA (e.g., in a biological sample) or a genetic alteration in a 26886 gene, and to modulate 26886 activity, as described further below. The 26886 proteins can be used to treat disorders characterized by insufficient or excessive production of a 26886 substrate or production of 26886 inhibitors. In addition, the 26886 proteins can be used to screen for naturally occurring 26886 substrates, to screen for drugs or compounds which modulate 26886 activity, as well as to treat disorders characterized by insufficient or excessive production of 26886 protein or production of 26886 protein forms which have decreased, aberrant or unwanted activity compared to 26886 wild type protein (e.g., metabolic disorders or defects in fatty acid oxidation). Moreover, the anti-26886 antibodies of the invention can be used to detect and isolate 26886 proteins, regulate the bioavailability of 26886 proteins, and modulate 26886 activity.

A method of evaluating a compound for the ability to interact with, e.g., bind, a subject 26886 polypeptide is provided. The method includes: contacting the compound with the subject 26886 polypeptide; and evaluating ability of the compound to interact with, e.g., to bind or form a complex with the subject 26886 polypeptide. This method can be performed in vitro, e.g., in a cell free system, or in vivo, e.g., in a two-hybrid interaction trap assay. This method can be used to identify naturally occurring molecules that interact with a subject 26886 polypeptide. It can also be used to find natural or synthetic inhibitors of a subject 26886 polypeptide. Screening methods are discussed in more detail below.

26886 Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 26886 proteins, have a stimulatory or inhibitory effect on, for example, 26886 expression or 26886 activity, or have a stimulatory or inhibitory effect on, for example, the expression or activity of a 26886 substrate. Compounds thus identified can be used to modulate the activity of target gene products (e.g., 26886 genes) in a therapeutic protocol, to elaborate the biological function of the target gene product, or to identify compounds that disrupt normal target gene interactions.

In one embodiment, the invention provides assays for screening candidate or test compounds that are substrates of a 26886 protein or polypeptide or a biologically active portion thereof. In another embodiment, the invention provides assays for screening candidate or test compounds that bind to or modulate the activity of a 26886 protein or polypeptide or a biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al. *J. Med. Chem.* 1994, 37: 2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223, 409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell which expresses a 26886 protein or biologically active portion thereof is contacted with a test compound, and the ability of the test compound to modulate 26886 activity is determined. Determining the ability of the test compound to modulate 26886 activity can be accomplished by monitoring, for example, fatty acid oxidation or acyl CoA levels. The cell, for example, can be of mammalian origin, e.g., a liver or muscle cell.

The ability of the test compound to modulate 26886 binding to a compound, e.g., a 26886 substrate, or to bind to 26886 can also be evaluated. This can be accomplished, for example, by coupling the compound, e.g., the substrate, with a radioisotope or enzymatic label such that binding of the compound, e.g., the substrate, to 26886 can be determined by detecting the labeled compound, e.g., substrate, in a complex. Alternatively, 26886 could be coupled with a radioisotope or enzymatic label to monitor the ability of a test compound to modulate 26886 binding to a 26886 substrate in a complex. For example, compounds (e.g., 26886 substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 26886 substrate) to interact with 26886 with or without the labeling of any of the interactants can be evaluated. For example, a microphysiometer can be used to detect the interaction of a compound with 26886 without the labeling of either the compound or the 26886. McConnell, H. M. et al. (1992) *Science* 257: 1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 26886.

In yet another embodiment, a cell-free assay is provided in which a 26886 protein or biologically active portion thereof is contacted with a test compound and the ability of the test compound to bind to the 26886 protein or biologically active portion thereof is evaluated. Preferred biologically active portions of the 26886 proteins to be used in assays of the present invention include fragments that participate in interactions with non-26886 molecules, e.g., fragments with high surface probability scores.

Soluble and/or membrane-bound forms of isolated proteins (e.g., 26886 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl) dimethylamminio]-1-propane sulfonate (CHAPS), 3-[(3- cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

Assay where ability of agent to block binding of the 26886 protein with acyl CoA, carnitine or acylcarnitine is evaluated.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 26886 protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 26886, an anti 26886 antibody or its target molecule to facilitate separation of complexed from uncomplexed forms of one or both of the proteins, as well as to accommodate automation of the assay. Binding of a test compound to a 26886 protein, or interaction of a 26886 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/26886 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 26886 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 26886 binding or activity determined using standard techniques.

Other techniques for immobilizing either a 26886 protein or a target molecule on matrices include using conjugation of biotin and streptavidin. Biotinylated 26886 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 26886 protein or target molecules but which do not interfere with binding of the 26886 protein to its target molecule. Such antibodies can be derivatized to the wells of the plate, and unbound target or 26886 protein trapped in the wells by antibody conjugation. Methods for detecting such complexes, in addition to those described above for the GST-immobilized complexes, include immunodetection of complexes using antibodies reactive with the 26886 protein or target molecule, as well as enzyme-linked assays which rely on detecting an enzymatic activity associated with the 26886 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., *Trends Biochem Sci* 1993 August; 18(8):284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N. H., *J Mol Recognit* 1998 Winter;11 (1-6):141-8; Hage, D. S., and Tweed, S. A. *J Chromatogr B Biomed Sci Appl* 1997 Oct. 10; 699(1-2):499-525). Further, fluorescence energy transfer may also be conveniently utilized, as described herein, to detect binding without further purification of the complex from solution.

In a preferred embodiment, the assay includes contacting the 26886 protein or biologically active portion thereof with a known compound which binds 26886 to form an assay mixture, contacting the assay mixture with a test compound, and determining the ability of the test compound to interact with a 26886 protein, wherein determining the ability of the test compound to interact with a 26886 protein includes determining the ability of the test compound to preferentially bind to 26886 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 26886 genes herein identified. In an alternative embodiment, the invention provides methods for determining the ability of the test compound to modulate the activity of a 26886 protein through modulation of the activity of a downstream effector of a 26886 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 26886 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 26886 ("26886-binding proteins" or "26886-bp") and are involved in 26886 activity. Such 26886-bps can be activators or inhibitors of signals by the 26886 proteins or 26886 targets as, for example, downstream elements of a 26886-mediated signaling pathway.

The two-hybrid system is based on the modular nature of most transcription factors, which consist of separable DNA-binding and activation domains. Briefly, the assay utilizes two different DNA constructs. In one construct, the gene that codes for a 26886 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 26886 protein can be the fused to the activator domain.) If the "bait" and the "prey" proteins are able to interact, in vivo, forming a 26886-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene that encodes the protein which interacts with the 26886 protein.

In another embodiment, modulators of 26886 expression are identified. For example, a cell or cell free mixture is contacted with a candidate compound and the expression of 26886 mRNA or protein evaluated relative to the level of expression of 26886 mRNA or protein in the absence of the candidate compound. When expression of 26886 mRNA or protein is greater in the presence of the candidate compound than in its absence, the candidate compound is identified as a stimulator of 26886 mRNA or protein expression. Alternatively, when expression of 26886 mRNA or protein is less (statistically significantly less) in the presence of the candidate compound than in its absence, the candidate compound is identified as an inhibitor of 26886 mRNA or protein expression. The level of 26886 mRNA or protein expression can be determined by methods described herein for detecting 26886 mRNA or protein.

In another aspect, the invention pertains to a combination of two or more of the assays described herein. For example, a modulating agent can be identified using a cell-based or a cell free assay, and the ability of the agent to modulate the activity of a 26886 protein can be confirmed in vivo, e.g., in an animal such as an animal model for aberrant fatty acid oxidation.

This invention further pertains to novel agents identified by the above-described screening assays. Accordingly, it is within the scope of this invention to further use an agent identified as described herein (e.g., a 26886 modulating agent, an antisense 26886 nucleic acid molecule, a 26886-specific antibody, or a 26886-binding partner) in an appropriate animal model to determine the efficacy, toxicity, side effects, or mechanism of action, of treatment with such an agent. Furthermore, novel agents identified by the above-described screening assays can be used for treatments as described herein.

26886 Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 26886 with a disease; (ii) identify an individual from a minute biological sample (tissue typing); and (iii) aid in forensic identification of a biological sample. These applications are described in the subsections below.

26886 Chromosome Mapping

The 26886 nucleotide sequences or portions thereof can be used to map the location of the 26886 genes on a chromosome. This process is called chromosome mapping. Chromosome mapping is useful in correlating the 26886 sequences with genes associated with disease.

Briefly, 26886 genes can be mapped to chromosomes by preparing PCR primers (preferably 15-25 bp in length) from the 26886 nucleotide sequences. These primers can then be used for PCR screening of somatic cell hybrids containing individual human chromosomes. Only those hybrids containing the human gene corresponding to the 26886 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) Science 220:919-924).

Other mapping strategies e.g., in situ hybridization (described in Fan, Y. et al. (1990) Proc. Natl. Acad. Sci. USA, 87:6223-27), pre-screening with labeled flow-sorted chromosomes, and pre-selection by hybridization to chromosome specific cDNA libraries can be used to map 26886 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783-787.

Moreover, differences in the DNA sequences between individuals affected and unaffected with a disease associated with the 26886 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

26886 Tissue Typing 26886 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 26886 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:9 can provide positive individual identification with a panel of perhaps 10 to 1,000 primers which each yield a noncoding amplified sequence of 100 bases. If predicted coding sequences, such as those in SEQ ID NO:11 are used, a more appropriate number of primers for positive individual identification would be 500-2,000.

If a panel of reagents from 26886 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 26886 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:9 (e.g., fragments derived from the noncoding regions of SEQ ID NO:9 having a length of at least 20 bases, preferably at least 30 bases) are particularly appropriate for this use.

The 26886 nucleotide sequences described herein can further be used to provide polynucleotide reagents, e.g., labeled or labelable probes which can be used in, for example, an in situ hybridization technique, to identify a specific tissue, e.g., a tissue containing organelles having carnitine acyltransferase. This can be very useful in cases where a forensic pathologist is presented with a tissue of unknown origin. Panels of such 26886 probes can be used to identify tissue by species and/or by organ type.

In a similar fashion, these reagents, e.g., 26886 primers or probes can be used to screen tissue culture for contamination (i.e. screen for the presence of a mixture of different types of cells in a culture).

Predictive Medicine of 26886

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes carnitine acyltransferase.

Such disorders include, e.g., a disorder associated with the misexpression of carnitine acyltransferase; or a metabolic disorder, e.g., a disorder involving fatty acid oxidation.

The method includes one or more of the following:

detecting, in a tissue of the subject, the presence or absence of a mutation which affects the expression of the 26886 gene, or detecting the presence or absence of a mutation in a region which controls the expression of the gene, e.g., a mutation in the 5' control region;

detecting, in a tissue of the subject, the presence or absence of a mutation which alters the structure of the 26886 gene;

detecting, in a tissue of the subject, the misexpression of the 26886 gene, at the mRNA level, e.g., detecting a non-wild type level of a mRNA;

detecting, in a tissue of the subject, the misexpression of the gene, at the protein level, e.g., detecting a non-wild type level of a 26886 polypeptide.

In preferred embodiments the method includes: ascertaining the existence of at least one of: a deletion of one or more nucleotides from the 26886 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:9 or 11 or naturally occurring mutants thereof, or 5' or 3' flanking sequences naturally associated with the 26886 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 26886 gene; the presence of a non-wild type splicing pattern of a messenger RNA transcript of the gene; or a non-wild type level of 26886.

Methods of the invention can be used prenatally or to determine if a subject's offspring will be at risk for a disorder.

In preferred embodiments the method includes determining the structure of a 26886 gene, an abnormal structure being indicative of risk for the disorder.

In preferred embodiments the method includes contacting a sample form the subject with an antibody to the 26886 protein or a nucleic acid, which hybridizes specifically with the gene. These and other embodiments are discussed below.

Diagnostic and Prognostic Assays of 26886

Diagnostic and prognostic assays of the invention include method for assessing the expression level of 26886 molecules and for identifying variations and mutations in the sequence of 26886 molecules.

Expression Monitoring and Profiling

The presence, level, or absence of 26886 protein or nucleic acid in a biological sample can be evaluated by obtaining a biological sample from a test subject and contacting the biological sample with a compound or an agent capable of detecting 26886 protein or nucleic acid (e.g., mRNA, genomic DNA) that encodes 26886 protein such that the presence of 26886 protein or nucleic acid is detected in the biological sample. The term "biological sample" includes tissues, cells and biological fluids isolated from a subject, as well as tissues, cells and fluids present within a subject. A preferred biological sample is serum. The level of expression of the 26886 gene can be measured in a number of ways, including, but not limited to: measuring the mRNA encoded by the 26886 genes; measuring the amount of protein encoded by the 26886 genes; or measuring the activity of the protein encoded by the 26886 genes.

The level of mRNA corresponding to the 26886 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 26886 nucleic acid, such as the nucleic acid of SEQ ID NO:9, or a portion thereof, such as an oligonucleotide of at least 7, 15, 30, 50, 100, 250 or 500 nucleotides in length and sufficient to specifically hybridize under stringent conditions to 26886 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 26886 genes.

The level of mRNA in a sample that is encoded by one of 26886 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 26886 gene being analyzed.

In another embodiment, the methods further contacting a control sample with a compound or agent capable of detecting 26886 mRNA, or genomic DNA, and comparing the presence of 26886 mRNA or genomic DNA in the control sample with the presence of 26886 mRNA or genomic DNA in the test sample. In still another embodiment, serial analysis of gene expression, as described in U.S. Pat. No. 5,695,937, is used to detect 26886 transcript levels.

A variety of methods can be used to determine the level of protein encoded by 26886. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 26886 protein in a biological sample in vitro as well as in vivo. In vitro techniques for detection of 26886 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 26886 protein include introducing into a subject a labeled anti-26886 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-26886 antibody positioned on an antibody array (as described below). The sample can be detected, e.g., with avidin coupled to a fluorescent label.

In another embodiment, the methods further include contacting the control sample with a compound or agent capable of detecting 26886 protein, and comparing the presence of 26886 protein in the control sample with the presence of 26886 protein in the test sample.

The invention also includes kits for detecting the presence of 26886 in a biological sample. For example, the kit can include a compound or agent capable of detecting 26886 protein or mRNA in a biological sample; and a standard. The compound or agent can be packaged in a suitable container. The kit can further comprise instructions for using the kit to detect 26886 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 26886 expression or activity. As used herein, the term "unwanted" includes an unwanted phenomenon involved in a biological response such as pain or deregulated cell proliferation.

In one embodiment, a disease or disorder associated with aberrant or unwanted 26886 expression or activity is identified. A test sample is obtained from a subject and 26886 protein or nucleic acid (e.g., mRNA or genomic DNA) is evaluated, wherein the level, e.g., the presence or absence, of 26886 protein or nucleic acid is diagnostic for a subject having or at risk of developing a disease or disorder associated with aberrant or unwanted 26886 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 26886 expression or activity. For example, such methods can be used to determine whether a subject can be effectively treated with an agent for a proliferative or differentiative disorder.

In another aspect, the invention features a computer medium having a plurality of digitally encoded data records. Each data record includes a value representing the level of expression of 26886 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 26886 (e.g., other genes associated with a 26886-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 26886 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a proliferative or differentiative disorder in a subject wherein an increase in 26886 expression is an indication that the subject has or is disposed to having a proliferative or differentiative disorder. The method can be used to monitor a treatment for a proliferative or differentiative disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 26886 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 26886 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 26886 expression.

26886 Arrays and Uses Thereof

In another aspect, the invention features an array that includes a substrate having a plurality of addresses. At least one address of the plurality includes a capture probe that binds specifically to a 26886 molecule (e.g., a 26886 nucleic acid or a 26886 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 26886 nucleic acid, e.g., the sense or anti-sense strand. In one preferred embodiment, a subset of addresses of the plurality of addresses has a nucleic acid capture probe for 26886. Each address of the subset can include a capture probe that hybridizes to a different region of a 26886 nucleic acid. In another preferred embodiment, addresses of the subset include a capture probe for a 26886 nucleic acid. Each address of the subset is unique, overlapping, and complementary to a different variant of 26886 (e.g., an allelic variant, or all possible hypothetical variants). The array can be used to sequence 26886 by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 26886 polypeptide or fragment thereof. The polypeptide can be a naturally-occurring interaction partner of 26886 polypeptide. Preferably, the polypeptide is an antibody, e.g., an antibody described herein (see "Anti-26886 Antibodies," above), such as a monoclonal antibody or a single-chain antibody.

In another aspect, the invention features a method of analyzing the expression of 26886. The method includes providing an array as described above; contacting the array with a sample and detecting binding of a 26886-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 26886. If a sufficient number of diverse samples is analyzed, clustering (e.g., hierarchical clustering, k-means clustering, Bayesian clustering and the like) can be used to identify other genes which are co-regulated with 26886. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 26886 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 26886-associated disease or disorder; and processes, such as a cellular transformation associated with a 26886-associated disease or disorder. The method can also evaluate the treatment and/or progression of a 26886-associated disease or disorder The array is also useful for ascertaining differential expression patterns of one or more genes in normal and abnormal cells. This provides a battery of genes (e.g., including 26886) that could serve as a molecular target for diagnosis or therapeutic intervention.

In another aspect, the invention features an array having a plurality of addresses. Each address of the plurality includes a unique polypeptide. At least one address of the plurality has disposed thereon a 26886 polypeptide or fragment thereof. Methods of producing polypeptide arrays are described in the art, e.g., in De Wildt et al. (2000). *Nature Biotech.* 18, 989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80, 85, 90, 95 or 99% identical to a 26886 polypeptide or fragment thereof. For example, multiple variants of a 26886 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 26886 binding compound, e.g., an antibody in a sample from a subject with specificity for a 26886 polypeptide or the presence of a 26886-binding protein or ligand.

The array is also useful for ascertaining the effect of the expression of a gene on the expression of other genes in the same cell or in different cells (e.g., ascertaining the effect of 26886 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 26886 or from a cell or subject in which a 26886 mediated response has been elicited, e.g., by contact of the cell with 26886 nucleic acid or protein, or administration to the cell or subject 26886 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 26886 (or does not express as highly as in the case of the 26886 positive plurality of capture probes) or from a cell or subject which in which a 26886 mediated response has not been elicited (or has been elicited to a lesser extent than in the first sample); contacting the array with one or more inquiry probes (which is preferably other than a 26886 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 26886 or from a cell or subject in which a 26886-mediated response has been elicited, e.g., by contact of the cell with 26886 nucleic acid or protein, or administration to the cell or subject 26886 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 26886 (or does not express as highly as in the case of the 26886 positive plurality of capture probes) or from a cell or subject which in which a 26886 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 26886, e.g., analyzing structure, function, or relatedness to other nucleic acid or amino acid sequences. The method includes: providing a 26886 nucleic acid or amino acid sequence; comparing the 26886 sequence with one or more preferably a plurality of sequences from a collection of sequences, e.g., a nucleic acid or protein sequence database; to thereby analyze 26886.

Detection of 26886 Variations or Mutations

The methods of the invention can also be used to detect genetic alterations in a 26886 gene, thereby determining if a subject with the altered gene is at risk for a disorder characterized by misregulation in 26886 protein activity or nucleic acid expression, such as a proliferative or differentiative disorder. In preferred embodiments, the methods include detecting, in a sample from the subject, the presence or absence of a genetic alteration characterized by at least one of an alteration affecting the integrity of a gene encoding a 26886-protein, or the mis-expression of the 26886 gene. For example, such genetic alterations can be detected by ascertaining the existence of at least one of 1) a deletion of one or more nucleotides from a 26886 gene; 2) an addition of one or more nucleotides to a 26886 gene; 3) a substitution of one or more nucleotides of a 26886 gene, 4) a chromosomal rearrangement of a 26886 gene; 5) an alteration in the level of a messenger RNA transcript of a 26886 gene, 6) aberrant modification of a 26886 gene, such as of the methylation pattern of the genomic DNA, 7) the presence of a non-wild type splicing pattern of a messenger RNA transcript of a 26886 gene, 8) a non-wild type level of a 26886-protein, 9) allelic loss of a 26886 gene, and 10) inappropriate post-translational modification of a 26886-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 26886-gene. This method can include the steps of collecting a sample of cells from a subject, isolating nucleic acid (e.g., genomic, mRNA or both) from the sample, contacting the nucleic acid sample with one or more primers which specifically hybridize to a 26886 gene under conditions such that hybridization and amplification of the 26886-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 26886 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 26886 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 26886 nucleic acid or a putative variant (e.g., allelic variant) thereof. A probe can have one or more mismatches to a region of a 26886 nucleic acid (e.g., a destabilizing mismatch). The arrays can have a high density of addresses, e.g., can contain hundreds or thousands of oligonucleotides probes (Cronin, M. T. et al. (1996) Human Mutation 7: 244-255; Kozal, M. J. et al. (1996) Nature Medicine 2: 753-759). For example, genetic mutations in 26886 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 26886 gene and detect mutations by comparing the sequence of the sample 26886 with the corresponding wild-type (control) sequence. Automated sequencing procedures can be utilized when performing the diagnostic assays ((1995) Biotechniques 19:448), including sequencing by mass spectrometry.

Other methods for detecting mutations in the 26886 gene include methods in which protection from cleavage agents is used to detect mismatched bases in RNA/RNA or RNA/DNA heteroduplexes (Myers et al. (1985) Science 230:1242; Cotton et al. (1988) Proc. Natl Acad Sci USA 85:4397; Saleeba et al. (1992) Methods Enzymol. 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 26886 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662; U.S. Pat. No. 5,459,039).

In other embodiments, alterations in electrophoretic mobility will be used to identify mutations in 26886 genes. For example, single strand conformation polymorphism (SSCP) may be used to detect differences in electrophoretic mobility between mutant and wild type nucleic acids (Orita et al. (1989) Proc Natl. Acad. Sci USA: 86:2766, see also Cotton (1993) Mutat. Res. 285:125-144; and Hayashi (1992) Genet. Anal. Tech. Appl. 9:73-79). Single-stranded DNA fragments of sample and control 26886 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension (Saiki et al. (1986) Nature 324:163); Saiki et al. (1989) Proc. Natl Acad. Sci USA 86:6230). A further method of detecting point mutations is the chemical ligation of oligonucleotides as described in Xu et al. ((2001) Nature Biotechnol. 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 26886 nucleic acid.

In a preferred embodiment the set includes a first and a second oligonucleotide. The first and second oligonucleotide can hybridize to the same or to different locations of SEQ ID NO:9 or 11 or the complement of SEQ ID NO:9 or 11. Different locations can be different but overlapping or or nonoverlapping on the same strand. The first and second oligonucleotide can hybridize to sites on the same or on different strands.

The set can be useful, e.g., for identifying SNP's, or identifying specific alleles of 26886. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 26886 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 26886 gene.

Use of 26886 Molecules as Surrogate Markers

The 26886 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 26886 molecules of the invention may be detected, and may be correlated with one or more biological states in vivo. For example, the 26886 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 26886 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 26886 marker) transcription or expression, the amplified marker may be in a quantity which is more readily detectable than the drug itself. Also, the marker may be more easily detected due to the nature of the marker itself; for example, using the methods described herein, anti-26886 antibodies may be employed in an immune-based detection system for a 26886 protein marker, or 26886-specific radiolabeled probes may be used to detect a 26886 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

The 26886 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 26886 protein or RNA) for specific tumor markers in a subject, a drug or course of treatment may be selected that is optimized for the treatment of the specific tumor likely to be present in the subject. Similarly, the presence or absence of a specific sequence mutation in 26886 DNA may correlate 26886 drug response. The use of pharmacogenomic markers therefore permits the application of the most appropriate treatment for each subject without having to administer the therapy.

Pharmaceutical Compositions of 26886

The nucleic acid and polypeptides, fragments thereof, as well as anti-26886 antibodies (also referred to herein as "active compounds") of the invention can be incorporated into pharmaceutical compositions. Such compositions typically include the nucleic acid molecule, protein, or antibody and a pharmaceutically acceptable carrier. As used herein, the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including an agent in the composition that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indeces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The present invention encompasses agents that modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate, as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 26886

The present invention provides for both prophylactic and therapeutic methods of treating a subject at risk of (or susceptible to) a disorder or having a disorder associated with aberrant or unwanted 26886 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 26886 molecules of the present invention or 26886 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 26886 expression or activity, by administering to the subject a 26886 or an agent which modulates 26886 expression or at least one 26886 activity. Subjects at risk for a disease which is caused or contributed to by aberrant or unwanted 26886 expression or activity can be identified by, for example, any or a combination of diagnostic or prognostic assays as described herein. Administration of a prophylactic agent can occur prior to the manifestation of symptoms characteristic of the 26886 aberrance, such that a disease or disorder is prevented or, alternatively, delayed in its progression. Depending on the type of 26886 aberrance, for example, a 26886, 26886 agonist or 26886 antagonist agent can be used for treating the subject. The appropriate agent can be determined based on screening assays described herein.

It is possible that some 26886 disorders can be caused, at least in part, by an abnormal level of gene product, or by the presence of a gene product exhibiting abnormal activity. As such, the reduction in the level and/or activity of such gene products would bring about the amelioration of disorder symptoms.

Additional examples of disorders that can be treated, prevented or diagnosed with the methods and compositions of the invention include immune disorders, bone disorders, pain disorders and viral disorders.

Examples of hematopoietic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Aberrant expression and/or activity of 26886 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 26886 molecules effects in bone cells, e.g. osteoclasts and osteoblasts, that may in turn result in bone formation and degeneration. For example, 26886 molecules may support different activities of bone resorbing osteoclasts, such as the stimulation of differentiation of monocytes and mononuclear phagocytes into osteoclasts. Accordingly, 26886 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Additionally, 26886 molecules may play an important role in the etiology of certain viral diseases, including but not limited to Hepatitis B, Heptitis C and Herpes Simplex Virus (HSV). Modulators of 26886 activity could be used to control viral diseases. The modulators can be used in the treatment and/or diagnosis of viral infected tissue or virus-associated tissue fibrosis, especially liver and liver fibrosis.

Also, 26886 modulators can be used in the treatment and/or diagnosis of virus-associated carcinoma, especially hepatocellular cancer.

Additionally, 26886 may play an important role in the regulation of pain disorders. Examples of pain disorders include, but are not limited to, pain response elicited during various forms of tissue injury, e.g., inflammation, infection, and ischemia, usually referred to as hyperalgesia (described in, for example, Fields, H. L. (1987) Pain, New York: McGraw-Hill); pain associated with musculoskeletal disorders, e.g., joint pain; tooth pain; headaches; pain associated with surgery; pain related to irritable bowel syndrome; or chest pain.

As discussed, successful treatment of 26886 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 26886 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 26886 expression is through the use of aptamer molecules specific for 26886 protein. Aptamers are nucleic acid molecules having a tertiary structure which permits them to specifically bind to protein ligands (see, e.g., Osborne, et al. Curr. Opin. Chem Biol. 1997, 1(1): 5-9; and Patel, D. J. Curr Opin Chem Biol June 1997; 1(1):32-46). Since nucleic acid molecules may in many cases be more conveniently introduced into target cells than therapeutic protein molecules may be, aptamers offer a method by which 26886 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 26886 disorders. For a description of antibodies, see the Antibody section above.

In circumstances wherein injection of an animal or a human subject with a 26886 protein or epitope for stimulating antibody production is harmful to the subject, it is possible to generate an immune response against 26886 through the use of anti-idiotypic antibodies (see, for example, Herlyn, D. Ann Med 1999; 31(1):66-78; and Bhattacharya-Chatterjee, M., and Foon, K. A. Cancer Treat Res 1998; 94:51-68). If an anti-idiotypic antibody is introduced into a mammal or human subject, it should stimulate the production of anti-anti-idiotypic antibodies, which should be specific to the 26886 protein. Vaccines directed to a disease characterized by 26886 expression may also be generated in this fashion.

In instances where the target antigen is intracellular and whole antibodies are used, internalizing antibodies may be preferred. Lipofectin or liposomes can be used to deliver the antibody or a fragment of the FAb region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al., 1993, Proc. Natl. Acad. Sci. USA 90:7889-7893).

The identified compounds that inhibit target gene expression, synthesis and/or activity can be administered to a patient at therapeutically effective doses to prevent, treat or ameliorate 26886 disorders. A therapeutically effective dose refers to that amount of the compound sufficient to result in amelioration of symptoms of the disorders.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 26886 activity is used as a template, or "imprinting molecule", to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. A detailed review of this technique can be seen in Ansell, R. J. et al (1996) Current Opinion in Biotechnology 7:89-94 and in Shea, K. J. (1994) Trends in Polymer Science 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) Nature 361:645-647. Through the use of isotope-labeling, the "free" concentration of compound which modulates the expression or activity of 26886 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al (1995) *Analytical Chemistry* 67:2142-2144.

Another aspect of the invention pertains to methods of modulating 26886 expression or activity for therapeutic purposes. Accordingly, in an exemplary embodiment, the modulatory method of the invention involves contacting a cell with a 26886 or agent that modulates one or more of the activities of 26886 protein activity associated with the cell. An agent that modulates 26886 protein activity can be an agent as described herein, such as a nucleic acid or a protein, a naturally-occurring target molecule of a 26886 protein (e.g., a 26886 substrate or receptor), a 26886 antibody, a 26886 agonist or antagonist, a peptidomimetic of a 26886 agonist or antagonist, or other small molecule.

In one embodiment, the agent stimulates one or 26886 activities. Examples of such stimulatory agents include active 26886 protein and a nucleic acid molecule encoding 26886. In another embodiment, the agent inhibits one or more 26886 activities. Examples of such inhibitory agents include antisense 26886 nucleic acid molecules, anti26886 antibodies, and 26886 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 26886 protein or nucleic acid molecule. In one embodiment, the method involves administering an agent (e.g., an agent identified by a screening assay described herein), or combination of agents that modulates (e.g., upregulates or downregulates) 26886 expression or activity. In another embodiment, the method involves administering a 26886 protein or nucleic acid molecule as therapy to compensate for reduced, aberrant, or unwanted 26886 expression or activity.

Stimulation of 26886 activity is desirable in situations in which 26886 is abnormally downregulated and/or in which increased 26886 activity is likely to have a beneficial effect. For example, stimulation of 26886 activity is desirable in situations in which a 26886 is downregulated and/or in which increased 26886 activity is likely to have a beneficial effect. Likewise, inhibition of 26886 activity is desirable in situations in which 26886 is abnormally upregulated and/or in which decreased 26886 activity is likely to have a beneficial effect.

26886 Pharmacogenomics

The 26886 molecules of the present invention, as well as agents, or modulators which have a stimulatory or inhibitory effect on 26886 activity (e.g., 26886 gene expression) as identified by a screening assay described herein can be administered to individuals to treat (prophylactically or therapeutically) 26886 associated disorders (e.g., metabolic disorders or defects associated with fatty acid oxidation) associated with aberrant or unwanted 26886 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 26886 molecule or 26886 modulator as well as tailoring the dosage and/or therapeutic regimen of treatment with a 26886 molecule or 26886 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11):983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 26886 protein of the present invention), all common variants of that gene can be fairly easily identified in the population and it can be determined if having one version of the gene versus another is associated with a particular drug response.

Alternatively, a method termed "gene expression profiling" can be utilized to identify genes that predict drug response. For example, the gene expression of an animal dosed with a drug (e.g., a 26886 molecule or 26886 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 26886 molecule or 26886 modulator, such as a modulator identified by one of the exemplary screening assays described herein.

The present invention further provides methods for identifying new agents, or combinations, that are based on identifying agents that modulate the activity of one or more of the gene products encoded by one or more of the 26886 genes of the present invention, wherein these products may be associated with resistance of the cells to a therapeutic agent. Specifically, the activity of the proteins encoded by the 26886 genes of the present invention can be used as a basis for identifying agents for overcoming agent resistance. By blocking the activity of one or more of the resistance proteins, target cells will become sensitive to treatment with an agent that the unmodified target cells were resistant to.

Monitoring the influence of agents (e.g., drugs) on the expression or activity of a 26886 protein can be applied in clinical trials. For example, the effectiveness of an agent determined by a screening assay as described herein to increase 26886 gene expression, protein levels, or upregulate 26886 activity, can be monitored in clinical trials of subjects exhibiting decreased 26886 gene expression, protein levels, or downregulated 26886 activity. Alternatively, the effectiveness of an agent determined by a screening assay to decrease 26886 gene expression, protein levels, or downregulate 26886 activity, can be monitored in clinical trials of subjects exhibiting increased 26886 gene expression, protein levels, or upregulated 26886 activity. In such clinical trials, the expression or activity of a 26886 gene, and preferably, other genes that have been implicated in, for example, a 26886-associated disorder can be used as a "read out" or markers of the phenotype of a particular cell.

26886 Informatics

The sequence of a 26886 molecule is provided in a variety of media to facilitate use thereof. A sequence can be provided as a manufacture, other than an isolated nucleic acid or amino acid molecule, which contains a 26886. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 26886 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 26886, e.g., analyzing structure, function, or relatedness to one or more other nucleic acid or amino acid sequences. The method includes: providing a 26886 nucleic acid or amino acid sequence; comparing the 26886 sequence with a second sequence, e.g., one or more preferably a plurality of sequences from a collection of sequences, e.g., a nucleic acid or protein sequence database to thereby analyze 26886. The method can be performed in a machine, e.g., a computer, or manually by a skilled artisan.

The method can include evaluating the sequence identity between a 26886 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 26886 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 26886 sequence, or record, in machine-readable form; comparing a second sequence to the 26886 sequence; thereby analyzing a sequence. Comparison can include comparing to sequences for sequence identity or determining if one sequence is included within the other, e.g., determining if the 26886 sequence includes a sequence being compared. In a preferred embodiment the 26886 or second sequence is stored on a first computer, e.g., at a first site and the comparison is performed, read, or recorded on a second computer, e.g., at a second site. E.g., the 26886 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof, the 5' end of the translated region.

In another aspect, the invention provides a machine-readable medium for holding instructions for performing a method for determining whether a subject has a 26886-associated disease or disorder or a pre-disposition to a 26886-associated disease or disorder, wherein the method comprises the steps of determining 26886 sequence information associated with the subject and based on the 26886 sequence information, determining whether the subject has a 26886-associated disease or disorder or a pre-disposition to a 26886-associated disease or disorder and/or recommending a particular treatment for the disease, disorder or pre-disease condition.

The invention further provides in an electronic system and/or in a network, a method for determining whether a subject has a 26886-associated disease or disorder or a pre-disposition to a disease associated with a 26886 wherein the method comprises the steps of determining 26886 sequence information associated with the subject, and based on the 26886 sequence information, determining whether the subject has a 26886-associated disease or disorder or a pre-disposition to a 26886-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 26886 sequence of the subject to the 26886 sequences in the database to thereby determine whether the subject as a 26886-associated disease or disorder, or a pre-disposition for such.

The present invention also provides in a network, a method for determining whether a subject has a 26886 associated disease or disorder or a pre-disposition to a 26886-associated disease or disorder associated with 26886, said method comprising the steps of receiving 26886 sequence information from the subject and/or information related thereto, receiving phenotypic information associated with the subject, acquiring information from the network corresponding to 26886 and/or corresponding to a 26886-associated disease or disorder (e.g., a proliferative or differentiative), and based on one or more of the phenotypic information, the 26886 information (e.g., sequence information and/or information related thereto), and the acquired information, determining whether the subject has a 26886-associated disease or disorder or a pre-disposition to a 26886-associated disease or disorder. The method may further comprise the step of recommending a particular treatment for the disease, disorder or pre-disease condition.

The present invention also provides a method for determining whether a subject has a 26886-associated disease or disorder or a pre-disposition to a 26886-associated disease or disorder, said method comprising the steps of receiving information related to 26886 (e.g., sequence information and/or information related thereto), receiving phenotypic information associated with the subject, acquiring information from the network related to 26886 and/or related to a 26886-associated disease or disorder, and based on one or more of the phenotypic information, the 26886 information, and the acquired information, determining whether the subject has a 26886-associated disease or disorder or a pre-disposition to a 26886-associated disease or disorder. The method may further comprise the step of recommending a particular treatment for the disease, disorder or pre-disease condition.

This invention is further illustrated by the following examples, which should not be construed as limiting. The contents of all references, patents and published patent applications cited throughout this application are incorporated herein by reference.

Background of the 25552 Invention

Numerous methyltransferases catalyze the transfer of a methyl group from the methyl group donor S-adenosyl-L-methionine (AdoMet) to nitrogen, carbon or oxygen atoms in prokaryotic and eukaryotic cells. Methyltransferase substrates methyl group acceptors include DNA, RNA, proteins and small molecules. In prokaryotes, methylation of DNA is involved in restriction systems. In eukaryotes, methylation of DNA is involved gene regulation and cell differentiation. In mammals, DNA methylation is involved in the origins of some types of cancer (Roth et al., 1998, *J. Biol. Chem.* 273:17333-17342). Methylation of RNA is involved in RNA processing and maturation. The function of protein methylation in mammals includes reversible modulation of enzymatic function (Xie et al., 1994, J. Biol. Chem. 269:1981-1984). Biosynthesis of various small molecules involves methyltransferase-catalyzed reaction steps.

Genes for numerous methyltransferases have been cloned, and many of their primary sequences have been characterized (Cheng, *Ann. Rev. Biophys. Biomol. Struct.,* 1995, 24:293-318; Wilson, 1992, Meth. Enzymol. 216:259-279). Comparable protein folding and the existence of equivalent amino acids in similar secondary and tertiary positions indicates that many AdoMet-dependent methyltransferases, including DNA methyltransferases and small molecule methyltransferases, share a common catalytic domain structure (Schluckebier et al., 1995, J. Mol. Biol. 247:16-20; Kagan et al., 1994, *Arch. Biochem Biophys.* 310:417-427). Some small molecule methyltransferases methylate a variety of substrates.

Catechol-O-methyltransferase (COMT) is involved in the metabolism of carcinogenic catechols and catecholamines. COMT exists as two isozymes, a membrane-bound form and a soluble form. The two isozymes play different roles in the metabolism of catecholamines and other catechol compounds (Ellingson et al., 1999, *J. Chromatogr B Biomed Sci. Appl.* 729:347-353). Regulation of COMT gene expression may be important in the pathophysiology of various human disorders including estrogen-induced cancers, Parkinson's disease, depression and hypertension (Xie et al., 1999, Mol. Pharmacol. 56:31-38). In the treatment of Parkinson's disease, COMT inhibitors extend the duration of levodopa action (Lewitt, 2000, Pharmacotherapy 20:26S-32S).

L-isoaspartate (D-aspartate) O-methyltransferase (PCMT1) is involved in repair of age-damaged aspartyl and asparaginyl residues in intracellular proteins (DeVry et al., 1999, *J. Hum. Genet.* 44:275-288).

Figure 31:
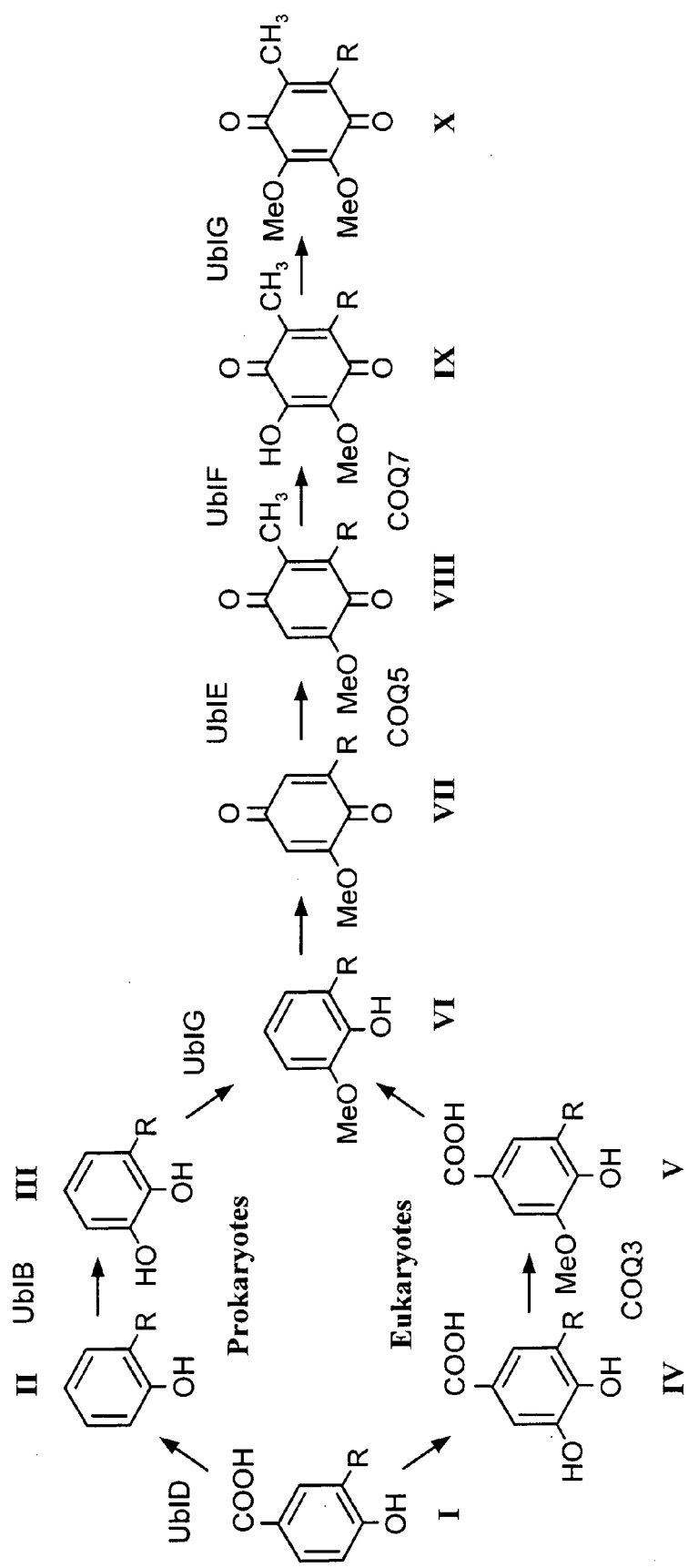
FIG. 31 is a schematic depicting the synthesis of ubiquinone, and indicating the activity of ubiE polypeptides in catalyzing the conversion of (VII) to (VIII).
Figure 32:
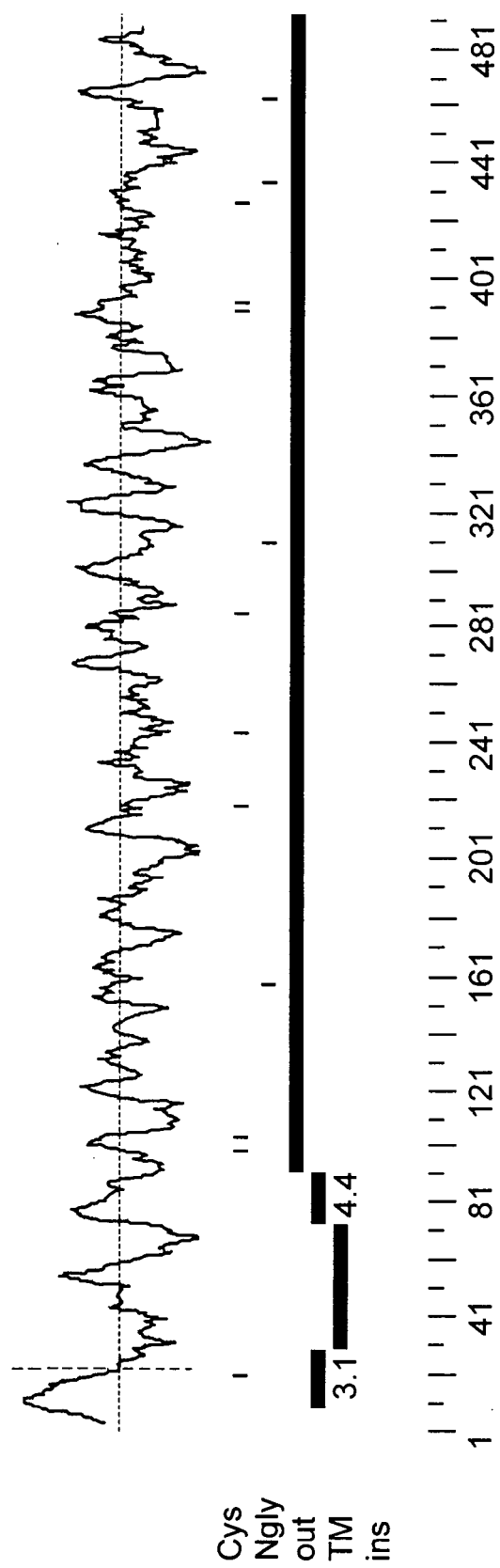
FIG. 32 depicts a hydropathy plot of human 32132. Relative hydrophobic residues are shown above the dashed horizontal line, and relative hydrophilic residues are below the dashed horizontal line. Numbers corresponding to positions in the amino acid sequence of human 32132 are indicated. Polypeptides of the invention include fragments which include: all or part of a hydrophobic sequence, i.e., a sequence above the dashed line, e.g., the sequence from about amino acid 8 to 28, from about 75 to 91, and from about 293 to 305 of SEQ ID NO:20; all or part of a hydrophilic sequence, i.e., a sequence below the dashed line, e.g., the sequence of from about amino acid 60 to 74, from about 190 to 206, and from about 306 to 320 of SEQ ID NO:20.

One type of C-methyltransferase is represented by the ubiE gene of *E. coli* (Lee et al., 1997, *J. Bacteriol.* 179: 1748-1754). The ubiE gene encodes a C-methyltransferase in a biosynthetic pathway leading to ubiquinone (coenzyme Q), which is an essential component in the respiratory electron transport chain in eukaryotes and most prokaryotes. The metaboli step catalyzed by ubiE methyltransferases is depicted in FIG. 31. Ubiquinone transfers electrons to the cytochrome c reductase complex in mitochondrial respiratory chain. A eukaryotic homolog of the ubiE gene has been isolated from yeast and designated COQ5 (Barkovich et al., 1997, *J. Biol. Chem.* 272:9182-9188).

Summary of the 25552 Invention

The present invention is based, in part, on the discovery of a novel ubiE methyltransferase family member, referred to herein as "25552". The nucleotide sequence of a cDNA encoding 25552 is shown in SEQ ID NO:13, and the amino acid sequence of a 25552 polypeptide is shown in SEQ ID NO:14. In addition, the nucleotide sequences of the coding region are depicted in SEQ ID NO:15.

Accordingly, in one aspect, the invention features a nucleic acid molecule that encodes a 25552 protein or polypeptide, e.g., a biologically active portion of the 25552 protein. In a preferred embodiment the isolated nucleic acid molecule encodes a polypeptide having the amino acid sequence of SEQ ID NO:14. In other embodiments, the invention provides isolated 25552 nucleic acid molecules having the nucleotide sequence shown in SEQ ID NO:13, or SEQ ID NO:15. In still other embodiments, the invention provides nucleic acid molecules that are substantially identical (e.g., naturally occurring allelic variants) to the nucleotide sequence shown in SEQ ID NO:13, or SEQ ID NO:15. In other embodiments, the invention provides a nucleic acid molecule which hybridizes under a stringency condition described herein to a nucleic acid molecule comprising the nucleotide sequence of SEQ ID NO:13, or SEQ ID NO:15, wherein the nucleic acid encodes a full length 25552 protein or an active fragment thereof. In some embodiment, the nucleic acid molecule encodes a polypeptide comprising a 25552 polypeptide, e.g., a polypeptide at least 80% identical to SEQ ID NO:15, and optionally having a valine at position 112 of SEQ ID NO:15.

In a related aspect, the invention further provides nucleic acid constructs that include a 25552 nucleic acid molecule described herein. In certain embodiments, the nucleic acid molecules of the invention are operatively linked to native or heterologous regulatory sequences. Also included, are vectors and host cells containing the 25552 nucleic acid molecules of the invention e.g., vectors and host cells suitable for producing 25552 nucleic acid molecules and polypeptides.

In another related aspect, the invention provides nucleic acid fragments suitable as primers or hybridization probes for the detection of 25552-encoding nucleic acids.

In still another related aspect, isolated nucleic acid molecules that are antisense to a 25552 encoding nucleic acid molecule are provided.

In another aspect, the invention features, 25552 polypeptides, and biologically active or antigenic fragments thereof that are useful, e.g., as reagents or targets in assays applicable to treatment and diagnosis of 25552-mediated or -related disorders. In another embodiment, the invention provides 25552 polypeptides having a 25552 activity. Preferred polypeptides are 25552 proteins including at least one ubiE methyltransferase domain, and, preferably, having a 25552 activity, e.g., a 25552 activity as described herein.

In other embodiments, the invention provides 25552 polypeptides, e.g., a 25552 polypeptide having the amino acid sequence shown in SEQ ID NO:14; an amino acid sequence that is substantially identical to the amino acid sequence shown in SEQ ID NO:14; or an amino acid sequence encoded by a nucleic acid molecule having a nucleotide sequence which hybridizes under a stringency condition described herein to a nucleic acid molecule comprising the nucleotide sequence of SEQ ID NO:13, or SEQ ID NO:15, wherein the nucleic acid encodes a full length 25552 protein or an active fragment thereof. Optionally, the amino acid sequence includes a valine at the position corresponding to 112 of SEQ ID NO:14.

In a related aspect, the invention further provides nucleic acid constructs which include a 25552 nucleic acid molecule described herein.

In a related aspect, the invention provides 25552 polypeptides or fragments operatively linked to non-25552 polypeptides to form fusion proteins. In another aspect, the invention features antibodies and antigen-binding fragments thereof, that react with, or more preferably specifically bind 25552 polypeptides.

In another aspect, the invention provides methods of screening for compounds that modulate the expression or activity of the 25552 polypeptides or nucleic acids.

In still another aspect, the invention provides a process for modulating 25552 polypeptide or nucleic acid expression or activity, e.g. using the screened compounds. In certain embodiments, the methods involve treatment of conditions related to aberrant activity or expression of the 25552 polypeptides or nucleic acids, such as conditions involving a neoplastic disorder, e.g., a cancer of the colon or liver.

In still another aspect, the invention provides a process for modulating 25552 polypeptide or nucleic acid expression or activity, e.g. using the screened compounds. In certain embodiments, the methods involve treatment, or prevention, of conditions related to aberrant activity or expression of the 25552 polypeptides or nucleic acids, such as conditions involving aberrant activity of a cell or tissue in which a 25552 polypeptide or nucleic acid is expressed, e.g., a cancer cell or tissue (e.g., a colon, breast, kidney, brain, liver, lung, hematopoietic cancer cell or tissue, preferably a colon or liver cancer cell or tissue); or a cell or tissue from the normal or diseased heart, kidney, skeletal muscle, endothelial cell, adrenal gland, bone, bone marrow, breast, brain (neurons or glia), or liver. Preferably, the methods of the invention treat or prevent conditions involving aberrant or deficient cellular proliferation or differentiation, or tumor invasion or metastasis.

In yet another aspect, the invention provides methods for inhibiting the proliferation, migration, or inducing the killing, of a 25552-expressing cell, e.g., a 25552-expressing hyperproliferative cell, comprising contacting the hyperproliferative cell with a compound (e.g., a compound identified using the methods described herein) that modulates the activity, or expression, of the 25552 polypeptide or nucleic acid.

In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol.

In a preferred embodiment, the 25552-expressing cell is found in a solid tumor, a soft tissue tumor, or a metastatic lesion. Preferably, the cell is found in a cancerous or pre-cancerous tissue, e.g., a cancerous or pre-cancerous tissue where a 25552 polypeptide or nucleic acid is expressed, e.g., a colon or liver cancer. Most preferably, the cell is found in a tumor from the colon or liver.

In other embodiments, the cell is found in the normal or diseased heart, kidney, skeletal muscle, endothelial cell, adrenal gland, bone, bone marrow, breast, brain (neurons or glia), or liver.

In a preferred embodiment, the compound is an inhibitor of a 25552 polypeptide. Preferably, the inhibitor is chosen from a peptide, a phosphopeptide, a small organic molecule, a small inorganic molecule and an antibody (e.g., an antibody conjugated to a therapeutic moiety selected from a cytotoxin, a cytotoxic agent and a radioactive metal ion).

The inhibitor can also be an analog of a ubiquinone or S-adenosyl-L-methionine. In a preferred embodiment, the compound is an inhibitor of a 25552 nucleic acid, e.g., an antisense, a ribozyme, or a triple helix molecule.

In a preferred embodiment, the compound is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

In another aspect, the invention features methods for treating or preventing a disorder characterized by aberrant cellular proliferation or differentiation of a 25552-expressing cell, in a subject. Preferably, the method includes comprising administering to the subject (e.g., a mammal, e.g., a human) an effective amount of a compound (e.g., a compound identified using the methods described herein) that modulates the activity, or expression, of the 25552 polypeptide or nucleic acid.

In a preferred embodiment, the disorder is a cancerous or pre-cancerous condition. Most preferably, the disorder is a cancer, e.g., a solid tumor, a soft tissue tumor, or a metastatic lesion. Preferably, the cancer is found in a tissue where a 25552 polypeptide or nucleic acid is expressed, e.g., colon, liver, kidney, breast, lung, hematopoietic, or brain cancer. Most preferably, the cancer is found in the colon or liver.

In a preferred embodiment, the compound is an inhibitor of a 25552 polypeptide.

Preferably, the inhibitor is chosen from a peptide, a phosphopeptide, a small organic molecule, a small inorganic molecule and an antibody (e.g., an antibody conjugated to a therapeutic moiety selected from a cytotoxin, a cytotoxic agent and a radioactive metal ion).

The inhibitor can also be an analog of a ubiquinone or S-adenosyl-L-methionine. In a preferred embodiment, the compound is an inhibitor of a 25552 nucleic acid, e.g., an antisense, a ribozyme, or a triple helix molecule. In a preferred embodiment, the compound is an inhibitor of a 25552 nucleic acid, e.g., an antisense, a ribozyme, or a triple helix molecule.

In a preferred embodiment, the compound is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

The invention also provides assays for determining the activity of or the presence or absence of 25552 polypeptides or nucleic acid molecules in a biological sample, including for disease diagnosis. Preferably, the biological sample includes a cancerous or pre-cancerous cell or tissue. For example, the cancerous tissue can be a solid tumor, a soft tissue tumor, or a metastatic lesion. Preferably, the cancerous tissue is from the colon or liver.

In a further aspect the invention provides assays for determining the presence or absence of a genetic alteration in a 25552 polypeptide or nucleic acid molecule in a sample, for, e.g., disease diagnosis. Preferably, the sample includes a cancer cell or tissue. For example, the cancer can be a solid tumor, a soft tissue tumor, or a metastatic lesion. Preferably, the cancer is a colon or liver cancer. The assay can include determining the identity of a nucleotide within SEQ ID NO:13, e.g., a nucleotide polymorphism located at about nucleotides 255 to 265, 305 to 320, and/or 325 to 340 of SEQ ID NO:14.

In a still further aspect, the invention provides methods for evaluating the efficacy of a treatment of a disorder, e.g., a disorder as described herein (e.g., a proliferative disorder, e.g., cancer (e.g., breast, lung, or preferably, colon or liver cancer)). The method includes: treating a subject, e.g., a patient or an animal, with a protocol under evaluation (e.g., treating a subject with one or more of: chemotherapy, radiation, and/or a compound identified using the methods described herein); and evaluating the expression of a 25552 nucleic acid or polypeptide before and after treatment. A change, e.g., a decrease or increase, in the level of a 25552 nucleic acid (e.g., mRNA) or polypeptide after treatment, relative to the level of expression before treatment, is indicative of the efficacy of the treatment of the disorder.

In a preferred embodiment, the disorder is a cancer of the breast, ovary, colon, lung, or liver. The level of 25552 nucleic acid or polypeptide expression can be detected by any method described herein.

In a preferred embodiment, the evaluating step includes obtaining a sample (e.g., a tissue sample, e.g., a biopsy, or a fluid sample) from the subject, before and after treatment and comparing the level of expressing of a 25552 nucleic acid (e.g., mRNA) or polypeptide before and after treatment.

In another aspect, the invention provides methods for evaluating the efficacy of a therapeutic or prophylactic agent (e.g., an anti-neoplastic agent). The method includes: contacting a sample with an agent (e.g., a compound identified using the methods described herein, a cytotoxic agent) and, evaluating the expression of 25552 nucleic acid or polypeptide in the sample before and after the contacting step. A change, e.g., a decrease or increase, in the level of 25552 nucleic acid (e.g., mRNA) or polypeptide in the sample obtained after the contacting step, relative to the level of expression in the sample before the contacting step, is indicative of the efficacy of the agent. The level of 25552 nucleic acid or polypeptide expression can be detected by any method described herein.

In a preferred embodiment, the sample includes cells obtained from a cancerous tissue where a 25552 polypeptide or nucleic acid is obtained, e.g., a cancer of the colon or liver. In a preferred embodiment, the sample is a tissue sample (e.g., a biopsy), a bodily fluid, a cultured cell (e.g., a tumor cell line).

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 25552 molecule. In one embodiment, the capture probe is a nucleic acid, e.g., a probe complementary to a 25552 nucleic acid sequence. In another embodiment, the capture probe is a polypeptide, e.g., an antibody specific for 25552 polypeptides. Also featured is a method of analyzing a sample by contacting the sample to the aforementioned array and detecting binding of the sample to the array.

Other features and advantages of the invention will be apparent from the following detailed description, and from the claims.

Detailed Description of 25552

The human 25552 sequence (FIG. 16; SEQ ID NO:13), which is approximately 1529 nucleotides long including untranslated regions, contains a predicted methionine-initiated coding sequence of about 924 nucleotides, including the termination codon (nucleotides indicated as coding of SEQ ID NO:13 in FIG. 16; SEQ ID NO:15). The coding sequence encodes a 307 amino acid protein (SEQ ID NO:14).

Human 25552 contains the following regions or other structural features:

a ubiE methyltransferase domain (PFAM Accession Number PF01209) located at about amino acid residues 37 to 306 of SEQ ID NO:14;

two predicted Protein Kinase C phosphorylation sites (PS00005) at about amino acids 19 to 21, and 267 to 269 of SEQ ID NO:14;

four predicted Casein Kinase II phosphorylation sites (PS00006) located at about amino 38 to 41, 127 to 130, 203 to 206 and 273 to 276 of SEQ ID NO:14; and one predicted N-myristylation sites (PS00008) from about amino 8 to 13 of SEQ ID NO:14.

For general information regarding PFAM identifiers, PS prefix and PF prefix domain identification numbers, refer to Sonnhammer el al. (1997) Protein 28:405-420.

The 25552 protein contains a significant number of structural characteristics in common with members of the ubiE methyltransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

A 25552 polypeptide can include a "ubiE methyltransferase domain" or regions homologous with a "ubiE methyltransferase domain". In a preferred embodiment, a 25552 polypeptide has an identical match to the ubiE methyltransferase signature 1 (Prosite PS01183), Y-D-x-M-N-x(2)-[LIVM]-S-x(3)-H-x(2)-W (SEQ ID NO:17), e.g., at about amino acid 78 to 92 of SEQ ID NO:14, and to the ubiE methyltransferase signature 2 (Prosite PS01184), R-V-[LIVM]-K-[PV]-[GM]-G-x-[LIVMF]-x(2)-[LIVM]-E-x-S (SEQ ID NO:18), e.g., at about amino acid 214 to 228 of SEQ ID NO:14. Such signatures, general hydrophilicity, and a molecular weight on the order of 25 to 40 kDa are indicative of the structural features of a 25552 polypeptide.

As used herein, the term "ubiE methyltransferase domain" includes an amino acid sequence of about 210 to 330 amino acid residues in length and having a bit score for the alignment of the sequence to the ubiE methyltransferase domain profile (Pfam HMM PF 01209) of at least 50. In a preferred embodiment, a human 25552 ubiE methyltransferase domain has a bit score of at least 100, preferably 200, more preferably 300, or even more preferably 400. Preferably, a ubiE methyltransferase domain includes about 240 to 300 amino acids, more preferably about 260 to 280 amino acid, or about 269 amino acid residues. The ubiE methyltransferase domain (HMM) has been assigned the PFAM Accession PF01209. A human 25552 ubiE methyltransferase domain can be located at about amino acids 37 to 306 of SEQ ID NO:14. An alignment of the ubiE niethyltransferase domain (amino acids 37 to 306 of SEQ ID NO:14) of human 25552 with a consensus amino acid sequence derived from a hidden Markov model is depicted in FIG. 18.

To identify the presence of a "ubiE methyltransferase" domain in a 25552 protein sequence, and make the determination that a polypeptide or protein of interest has a particular profile, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28(3): 405-420 and a detailed description of HMMs can be found, for example, in Gribskov et al.(1990) Meth. Enzymol. 183: 146-159; Gribskov et al.(1987) Proc. Natl. Acad. Sci. USA 84:4355-4358; Krogh et al.(1994) J. Mol. Biol. 235:1501-

1531; and Stultz et al.(1993) *Protein Sci.* 2:305-314, the contents of which are incorporated herein by reference. A search was performed against the HMM database resulting in the identification of a "ubiE methyltransferase" domain in the amino acid sequence of human 25552 at about residues 37 to 306 of SEQ ID NO:14 (see FIG. 16).

A 25552 family member can include at least one ubiE methyltransferase domain. Furthermore, a 25552 family member can include at least one, or preferably two protein kinase C phosphorylation sites (PS00005); at least one, two, three, preferably four predicted casein kinase II phosphorylation sites (PS00006); and at least one predicted N-myristylation sites (PS00008).

As the 25552 polypeptides of the invention may modulate 25552-mediated activities, they may be useful as of for developing novel diagnostic and therapeutic agents for 25552-mediated or related disorders, as described below.

As used herein, a "25552 activity", "biological activity of 25552" or "functional activity of 25552", refers to an activity exerted by a 25552 protein, polypeptide or nucleic acid molecule. For example, a 25552 activity can be an activity exerted by 25552 in a physiological milieu on, e.g., a 25552-responsive cell or on a 25552 substrate, e.g., a protein substrate. A 25552 activity can be determined in vivo or in vitro. In one embodiment, a 25552 activity is a direct activity, such as an association with a 25552 target molecule. A "target molecule" or "binding partner" is a molecule with which a 25552 protein binds or interacts in nature. In an exemplary embodiment, 25552 is an enzyme for a ubiquinone precursor, e.g., 25552 is a C-methyltransferase that converts 2-methoxy-6-polyprenyl-1,4-benzoquinone to 2-methodxy-5-methyl-6-polyprenyl-1,4-benzoquinone.

A 25552 activity can also be an indirect activity, e.g., a cellular signaling activity mediated by interaction of the 25552 protein with a 25552 receptor. The 25552 molecules of the present invention can have similar biological activities as ubiE methyltransferase family members. For example, the 25552 proteins of the present invention can have one or more of the following activities: (1) the ability to transfer a methyl group from a donor to an acceptor atom, e.g., a carbon, an oxygen or a nitrogen atom; (2) the ability to regulate a biosynthetic pathway; (3) the ability to methylate a ubiquinone (coenzyme Q) precursor such as 2-methoxy-6-polyprenyl-1,4-benzoquinone or demethylmenaquinol; (4) the ability to bind S-adenosyl-L-methionine, e.g., and transfer a methyl group from S-adenosyl-L-methionine to a substrate; (5) the ability to modulate electron transfer in the mitochondrial respiratory chain; (6) the ability to modulate apoptosis and events related to cell death, e.g., in a colon or liver cell such as a neoplastic colon or liver cell; or (7) the ability to methylate a nucleotide, e.g., a cytosine or an adenine residue in a DNA molecule.

Thus, 25552 proteins are predicted to display enzymatic activity. More particularly, the enzymatic activity is predicted to methylate a carbon atom in a small molecule substrate, e.g., an intermediate compound in a biosynthetic pathway such as 2-methoxy-6-polyprenyl-1,4-benzoquinone or demethylmenaquinol, using S-adenosyl-L-methionine as a methyl group donor. In a preferred embodiment, the product of the biosynthetic pathway is ubiquinone. In other embodiments, the substrate to be methylated is a cytosine or adenine residue in a DNA molecule. In still other embodiments, the 25552 protein functions as an O-methyltransferase or an N-methyltransferase, i.e., adds a methyl group to an oxygen atom or a nitrogen atom (respectively), e.g., in a biosynthetic pathway. The 25552 proteins are predicted to be soluble, non-secreted proteins that reside in the nucleus, cytoplasm or mitochondria when expressed in a eukaryotic cell, e.g., a human cell.

In a preferred embodiment, a 25552 protein modulates synthesis of ubiquinone in the mitochondria. Ubiquinone can function as a selective anti-oxidant, protecting cells from cell death or apoptosis. In cell culture, ubiquinone derivatives can protect cells from lipid peroxidation and from $H_2O_2$-induced apoptosis. Similarly, ubiquinone has been observed to provide some beneficial effects against cancer in animal models. The modulation of ubiquinone biosynthesis by a 25552 polypeptide provides a mechanism for altering (e.g., increasing or decreasing) cell death in a subject.

Thus, the 25552 molecules can act as novel diagnostic targets and therapeutic agents for controlling neoplastic disorders including cancers such as metastatic cancers. For example, as 25552 molecules are highly expressed in colon cancer cells, they can be used as diagnostic markers for a disorder, and compound which alter the activity of 25552 molecules can be used to prevent and/or treat such a disorder. In a preferred embodiment, the disorder is a cancer (e.g., a colon, breast, kidney, brain, liver, lung, hematopoietic cancer); preferably, the cancer is a colon cancer. In situ hybridization results indicate that expression of 25552 mRNA molecules is increased in dysplastic and hyperplastic lesions of the colon relative to normal colon samples.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of colon and liver origin.

As used herein, the terms "cancer", "hyperproliferative" and "neoplastic" refer to cells having the capacity for autonomous growth. Examples of such cells include cells having an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting the colon, as well as adenocarcinomas which include malignancies such as most colon cancers, tumors of the colon, such as non-neoplastic polyps, adenomas, familial syndromes, colorectal carcinogenesis, colorectal carcinoma, and carcinoid tumors.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the colon, and also the cervix, lung, prostate, breast, head and neck, and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cancers or neoplastic conditions, in addition to the ones described above, include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Additional disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis.

Additional examples of proliferative disorders include hematopoietic neoplastic disorders. As used herein, the term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promycloid leukemia (APML), acute myelogenous leukemia (AML) and chronic myelogenous leukemia (CML) (reviewed in Vaickus, L. (1991) *Crit Rev. in Oncol./Hematol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease.

The 25552 protein, fragments thereof, and derivatives and other variants of the sequence in SEQ ID NO:14 thereof are collectively referred to as "polypeptides or proteins of the invention" or "25552 polypeptides or proteins". Nucleic acid molecules encoding such polypeptides or proteins are collectively referred to as "nucleic acids of the invention" or "25552 nucleic acids." 25552 molecules refer to 25552 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:13 or SEQ ID NO:15, corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a 25552 protein. The gene can optionally further include non-coding sequences, e.g., regulatory sequences and introns. Preferably, a gene encodes a mammalian 25552 protein or derivative thereof An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of 25552 protein is at least 10% pure. In a preferred embodiment, the preparation of 25552 protein has less than about 30%, 20%, 10% and more preferably 5% (by dry weight), of non-25552 protein (also referred to herein as a "contaminating protein"), or of chemical precursors or non-25552 chemicals. When the 25552 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 25552 without abolishing or substantially altering a 25552 activity. Preferably the alteration does not substantially alter the 25552 activity, e.g., the activity is at least 20%, 40%, 60%, 70% or 80% of wild-type. An "essential" amino acid residue is a residue that, when altered from the wild-type sequence of 25552, results in abolishing a 25552 activity such that less than 20% of the wild-type activity is present. For example, conserved amino acid residues in 25552 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a 25552 protein is preferably replaced with another amino acid residue from the same side chain family. Alternatively, in another embodiment, mutations can be introduced randomly along all or part of a 25552 coding sequence, such as by saturation mutagenesis, and the resultant mutants can be screened for 25552 biological activity to identify mutants that retain activity. Following mutagenesis of SEQ ID NO:13 or SEQ ID NO:15, the encoded protein can be expressed recombinantly and the activity of the protein can be determined.

As used herein, a "biologically active portion" of a 25552 protein includes a fragment of a 25552 protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a 25552 molecule and a non-25552 molecule or between a first 25552 molecule and a second 25552 molecule (e.g., a dimerization interaction). Biologically active portions of a 25552 protein include peptides comprising amino acid sequences sufficiently homologous to or derived from the amino acid sequence of the 25552 protein, e.g., the amino acid sequence shown in SEQ ID NO:14, which include less amino acids than the full length 25552 proteins, and exhibit at least one activity of a 25552 protein. Typically, biologically active portions comprise a domain or motif with at least one activity of the 25552 protein, e.g., a methyltransferase activity. A biologically active portion of a 25552 protein can be a polypeptide which is, for example, 10, 25, 50, 100, 200 or more amino acids in length. Biologically active portions of a 25552 protein can be used as targets for developing agents which modulate a 25552 mediated activity, e.g., a methyltransferase activity.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, eta al. (1990) *J. Mol. Biol.* 215: 403-10. BLAST nucleotide searches can be performed with the NBLAST program, score=100, wordlength=12 to obtain nucleotide sequences homologous to 25552 nucleic acid molecules of the invention. BLAST protein searches can be performed with the XBLAST program, score=50, wordlength=3 to obtain amino acid sequences homologous to 25552 protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used.

Particular 25552 polypeptides of the present invention have an amino acid sequence substantially identical to the amino acid sequence of SEQ ID NO:14. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:14 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:13 or 15 are termed substantially identical.

"Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules of 25552

In one aspect, the invention provides, an isolated or purified, nucleic acid molecule that encodes a 25552 polypeptide described herein, e.g., a full-length 25552 protein or a fragment thereof, e.g., a biologically active portion of 25552 protein. Also included is a nucleic acid fragment suitable for use as a hybridization probe, which can be used, e.g., to identify a nucleic acid molecule encoding a polypeptide of the invention, 25552 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:13, or a portion of any of these nucleotide sequences. In one embodiment, the nucleic acid molecule includes sequences encoding the human 25552 protein (i.e., "the coding region" of SEQ ID NO:13, as shown in SEQ ID NO:15), as well as 5' untranslated sequences. Alternatively, the nucleic acid molecule can include only the coding region of SEQ ID NO:13 (e.g., SEQ ID NO:15) and, e.g., no flanking sequences which normally accompany the subject sequence. In another embodiment, the nucleic acid molecule encodes a sequence corresponding to a fragment of the protein from about amino acid 37 to 306 of SEQ ID NO:14.

In another embodiment, an isolated nucleic acid molecule of the invention includes a nucleic acid molecule which is a complement of the nucleotide sequence shown in SEQ ID NO:13 or SEQ ID NO:15, or a portion of any of these nucleotide sequences. In other embodiments, the nucleic acid molecule of the invention is sufficiently complementary to the nucleotide sequence shown in SEQ ID NO:13 or SEQ ID NO:15, such that it can hybridize (e.g., under a stringency condition described herein) to the nucleotide sequence shown in SEQ ID NO:13 or 15, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:13 or SEQ ID NO:15, or a portion, preferably of the same length, of any of these nucleotide sequences.

25552 Nucleic Acid Fragments

A nucleic acid molecule of the invention can include only a portion of the nucleic acid sequence of SEQ ID NO:13 or 15. For example, such a nucleic acid molecule can include a fragment which can be used as a probe or primer or a fragment encoding a portion of a 25552 protein, e.g., an immunogenic or biologically active portion of a 25552 protein. A fragment can comprise those nucleotides of SEQ ID NO:13, which encode an ubiE methyltransferase domain of human 25552. The nucleotide sequence determined from the cloning of the 25552 gene allows for the generation of probes and primers designed for use in identifying and/or cloning other 25552 family members, or fragments thereof, as well as 25552 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or polypeptide fragments thereof, particularly polypeptide fragments thereof which are at least 100, 150, 200, 250, 275, or 300 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 25552 nucleic acid fragment can include a sequence corresponding to an ubiE methyltransferase domain.

25552 probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:13 or SEQ ID NO:15, or of a naturally occurring allelic variant or mutant of SEQ ID NO:13 or SEQ ID NO:15.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes a methyltransferase domain.

In another embodiment a set of primers is provided, e.g., primers suitable for use in a PCR, which can be used to amplify a selected region of a 25552 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: an ubiE methyltransferase domain from about amino acid 37 to 306 of SEQ ID NO:14.

A nucleic acid fragment can encode an epitope bearing region of a polypeptide described herein.

A nucleic acid fragment encoding a "biologically active portion of a 25552 polypeptide" can be prepared by isolating a portion of the nucleotide sequence of SEQ ID NO:13 or 15, which encodes a polypeptide having a 25552 biological activity (e.g., the biological activities of the 25552 proteins are described herein), expressing the encoded portion of the 25552 protein (e.g., by recombinant expression in vitro) and assessing the activity of the encoded portion of the 25552 protein. For example, a nucleic acid fragment encoding a biologically active portion of 25552 includes an ubiE methyltransferase domain, e.g., amino acid residues about 37 to 306 of SEQ ID NO:14. A nucleic acid fragment encoding a biologically active portion of a 25552 polypeptide, may comprise a nucleotide sequence which is greater than 300 or more nucleotides in length.

In preferred embodiments, a nucleic acid includes a nucleotide sequence which is about 300, 400, 500, 600, 650, 690, 700, 720, 750, 800, 850, 900, 1000, 1100, 1200, 1300 or more nucleotides in length and hybridizes under a stringency condition described herein to a nucleic acid molecule of SEQ ID NO:13, or SEQ ID NO:15. In a preferred embodiment, a nucleic acid includes an nucleic acid sequence that is identical to SEQ ID NO:13 at least within one of the following regions: regions of about nucleotides 250 to 270, 300 to 320, 320 to 340, 250 to 340, 308 to 340, or 258 to 265 of SEQ ID NO:13. In another embodiment, a nucleic acid includes at least one nucleotide from the region of about nucleotides 1 to 200, 200 to 340, 300 to 500, 400 to 600, 500 to 900, 700 to 1100, 900 to 1300, 1100 to 1529 of SEQ ID NO:13.

25552 Nucleic Acid Variants

The invention further encompasses nucleic acid molecules that differ from the nucleotide sequence shown in SEQ ID NO:13 or SEQ ID NO:15. Such differences can be due to degeneracy of the genetic code (and result in a nucleic acid which encodes the same 25552 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:14. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:13 or 15, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:14 or a fragment of this sequence. Such nucleic acid molecules can readily be identified as being able to hybridize under a stringency condition described herein, to the nucleotide sequence shown in SEQ ID NO:14 or a fragment of the sequence. Nucleic acid molecules corresponding to orthologs, homologs, and allelic variants of the 25552 cDNAs of the invention can further be isolated by mapping to the same chromosome or locus as the 25552 gene.

Preferred variants include those that are correlated with methyltransferase activity.

Allelic variants of 25552, e.g., human 25552, include both functional and non-functional proteins. Functional allelic variants are naturally occurring amino acid sequence variants of the 25552 protein within a population that maintain the ability to bind S-adenosyl-L-methionine or methylate a substrate. Functional allelic variants will typically contain only conservative substitution of one or more amino acids of SEQ ID NO:14, or substitution, deletion or insertion of non-critical residues in non-critical regions of the protein. Non-functional allelic variants are naturally-occurring amino acid sequence variants of the 25552, e.g., human 25552, protein within a population that do not have the ability to bind S-adenosyl-L-methionine or methylate a substrate. Non-functional allelic variants will typically contain a non-conservative substitution, a deletion, or insertion, or premature truncation of the amino acid sequence of SEQ ID NO:14, or a substitution, insertion, or deletion in critical residues or critical regions of the protein.

Moreover, nucleic acid molecules encoding other 25552 family members and, thus, which have a nucleotide sequence which differs from the 25552 sequences of SEQ ID NO:13 or SEQ ID NO:15 are intended to be within the scope of the invention.

Antisense Nucleic Acid Molecules, Ribozymes and Modified 25552 Nucleic Acid Molecules In another aspect, the invention features, an isolated nucleic acid molecule which is antisense to 25552. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 25552 coding strand, or to only a portion thereof (e.g., the coding region of human 25552 corresponding to SEQ ID NO:15). In another embodiment, the antisense nucleic acid molecule is antisense to a "noncoding region" of the coding strand of a nucleotide sequence encoding 25552 (e.g., the 5' and 3' untranslated regions).

An antisense nucleic acid can be designed such that it is complementary to the entire coding region of 25552 mRNA, but more preferably is an oligonucleotide which is antisense to only a portion of the coding or noncoding region of 25552 mRNA. For example, the antisense oligonucleotide can be complementary to the region surrounding the translation start site of 25552 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 25552 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. A ribozyme having specificity for a 25552-encoding nucleic acid can include one or more sequences complementary to the nucleotide sequence of a 25552 cDNA disclosed herein (i.e., SEQ ID NO:13 or SEQ ID NO:15), and a sequence having known catalytic sequence responsible for mRNA cleavage (see U.S. Pat. No. 5,093,246 or Haselhoff and Gerlach (1988) *Nature* 334:585-591). For example, a derivative of a *Tetrahymena* L-19 IVS RNA can be constructed in which the nucleotide sequence of the active site is complementary to the nucleotide sequence to be cleaved in a 25552-encoding mRNA. See, e.g., Cech et al. U.S. Pat. No. 4,987,071; and Cech et al. U.S. Pat. No. 5,116,742. Alternatively, 25552 mRNA can be used to select a catalytic RNA having a specific ribonuclease activity from a pool of RNA molecules. See, e.g., Bartel, D. and Szostak, J. W. (1993) *Science* 261:1411-1418.

25552 gene expression can be inhibited by targeting nucleotide sequences complementary to the regulatory region of the 25552 (e.g., the 25552 promoter and/or enhancers) to form triple helical structures that prevent transcription of the 25552 gene in target cells. See generally, Helene, C. (1991) *Anticancer Drug Des.* 6:569-84; Helene, C. i (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 25552 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19:17 and Faria et al. (2001) *Nature Biotech.* 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675.

PNAs of 25552 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 25552 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. W088/09810) or the blood-brain barrier (see, e.g., PCT Publication No. W089/10134). In addition, oligonucleotides can be modified with hybridization-triggered cleavage agents (see, e.g., Krol et al. (1988) *Bio-Techniques* 6:958-976) or intercalating agents. (see, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 25552 nucleic acid of the invention, two complementary regions one having a fluorophore and one a quencher such that the molecular beacon is useful for quantitating the presence of the 25552 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 25552 Polypeptides

In another aspect, the invention features, an isolated 25552 protein, or fragment, e.g., a biologically active portion, for use as immunogenis or antigens to raise or test (or more generally to bind) anti-25552 antibodies. 25552 protein can be isolated from cells or tissue sources using standard protein purification techniques. 25552 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 25552 polypeptide has one or more of the following characteristics:

(i) it has the ability to transfer a methyl group to a substrate, e.g., from an S-adenosyl-L-methionine substrate;

(ii) it has a molecular weight, e.g., a deduced molecular weight, preferably ignoring any contribution of post translational modifications, amino acid composition or other physical characteristic of a 25552 polypeptide, e.g., a polypeptide of SEQ ID NO:14;

(iii) it has an overall sequence similarity of at least 60%, more preferably at least 70, 80, 90, or 95%, with a polypeptide of SEQ ID NO:14;

(iv) it can be found in a cell of, e.g., the colon, heart, liver, adipose, endothelia, skeletal muscle, brain, or kidney;

(v) it has a ubiE methyltransferase domain which is preferably about 70%, 80%, 90% or 95% with amino acid residues about 37 to 306 of SEQ ID NO:14;

(vi) it has a match or a nearly identical match to the Prosite signatures PS01183, Y-D-x-M-N-x(2)-[LIVM]-S-x (3)-H-x(2)-W (SEQ ID NO:17), e.g., at about amino acid 78 to 92 of SEQ ID NO:14, and to PS01184, R-V-[LIVM]-K-[PV]-[GM]-G-x-[LIVMF]-x(2)-[LIVM]-E-x-S (SEQ ID NO:18), e.g., at about amino acid 214 to 228 of SEQ ID NO:14; or (vii) it can bind to S-adenosyl-L-methionine.

In a preferred embodiment the 25552 protein, or fragment thereof, differs from the corresponding sequence in SEQ ID:2. In one embodiment it differs by at least one but by less than 15, 10 or 5 amino acid residues. In another it differs from the corresponding sequence in SEQ ID NO:14 by at least one residue but less than 20%, 15%, 10% or 5% of the residues in it differ from the corresponding sequence in SEQ ID NO:14. (If this comparison requires aligmnent the sequences should be aligned for maximum homology. "Looped" out sequences from deletions or insertions, or mismatches, are considered differences.) The differences are, preferably, differences or changes at a non essential residue or a conservative substitution. In a preferred embodiment, the differences are not in the ubiE methyltransferase domain. In another preferred embodiment one or more differences are in the ubiE methyltransferase domain.

Other embodiments include a protein that contain one or more changes in amino acid sequence, e.g., a change in an amino acid residue which is not essential for activity. Such 25552 proteins differ in amino acid sequence from SEQ ID NO:14, yet retain biological activity.

In one embodiment, the protein includes an amino acid sequence at least about 60%, 65%, 70%, 75%, 80%, 85%, 90%, 95%, 98% or more homologous to SEQ ID NO:14.

A 25552 protein or fragment is provided which varies from the sequence of SEQ ID NO:14 in regions defined by amino acids about 1 to 111, 113 to 307, or 37 to 306 of SEQ ID NO:14 by at least one but by less than 15, 10 or 5 amino acid residues in the protein or fragment but which does not differ from SEQ ID NO:14 in regions defined by amino acids about 1 to 111, 113 to 307, or 37 to 306 of SEQ ID NO:14. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 25552 protein includes a ubiE methyltransferase domain. Moreover, other biologically active portions, in which other regions of the protein are deleted, can be prepared by recombinant techniques and evaluated for one or more of the functional activities of a native 25552 protein.

In a preferred embodiment, the 25552 protein has an amino acid sequence shown in SEQ ID NO:14. In other embodiments, the 25552 protein is substantially identical to SEQ ID NO:14. In yet another embodiment, the 25552 protein is substantially identical to SEQ ID NO:14 and retains the functional activity of the protein of SEQ ID NO:14, as described in detail in the subsections above.

25552 Chimeric or Fusion Proteins

In another aspect, the invention provides 25552 chimeric or fusion proteins. As used herein, a 25552 "chimeric protein" or "fusion protein" includes a 25552 polypeptide linked to a non-25552 polypeptide. A "non-25552 polypeptide" refers to a polypeptide having an amino acid sequence corresponding to a protein which is not substantially homologous to the 25552 protein, e.g., a protein which is different from the 25552 protein and which is derived from the same or a different organism. The 25552 polypeptide of the fusion protein can correspond to all or a portion e.g., a fragment described herein of a 25552 amino acid sequence. In a preferred embodiment, a 25552 fusion protein includes at least one (or two) biologically active portion of a 25552 protein. The non-25552 polypeptide can be fused to the N-terminus or C-terminus of the 25552 polypeptide.

The fusion protein can include a moiety which has a high affinity for a ligand. For example, the fusion protein can be a GST-25552 fusion protein in which the 25552 sequences are fused to the C-terminus of the GST sequences. Such fusion proteins can facilitate the purification of recombinant 25552. Alternatively, the fusion protein can be a 25552 protein containing a heterologous signal sequence at its N-terminus. In certain host cells (e.g., mammalian host cells), expression and/or secretion of 25552 can be increased through use of a heterologous signal sequence.

Fusion proteins can include all or a part of a serum protein, e.g., an IgG constant region, or human serum albumin.

The 25552 fusion proteins of the invention can be incorporated into pharmaceutical compositions and administered to a subject in vivo. The 25552 fusion proteins can be used to affect the bioavailability of a 25552 substrate. 25552 fusion proteins may be useful therapeutically for the treatment of disorders caused by, for example, (i) aberrant modification or mutation of a gene encoding a 25552 protein; (ii) mis-regulation of the 25552 gene; and (iii) aberrant post-translational modification of a 25552 protein.

Moreover, the 25552-fusion proteins of the invention can be used as immunogens to produce anti-25552 antibodies in a subject, to purify 25552 ligands and in screening assays to identify molecules which inhibit the interaction of 25552 with a 25552 substrate.

Expression vectors are commercially available that already encode a fusion moiety (e.g., a GST polypeptide). A 25552-encoding nucleic acid can be cloned into such an expression vector such that the fusion moiety is linked in-frame to the 25552 protein.

Variants of 25552 Proteins

In another aspect, the invention also features a variant of a 25552 polypeptide, e.g., which functions as an agonist (mimetics) or as an antagonist. Variants of the 25552 proteins can be generated by mutagenesis, e.g., discrete point mutation, the insertion or deletion of sequences or the truncation of a 25552 protein. An agonist of the 25552 proteins can retain substantially the same, or a subset, of the biological activities of the naturally occurring form of a 25552 protein. An antagonist of a 25552 protein can inhibit one or more of the activities of the naturally occurring form of the 25552 protein by, for example, competitively modulating a 25552-mediated activity of a 25552 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 25552 protein.

Variants of a 25552 protein can be identified by screening combinatorial libraries of mutants, e.g., truncation mutants, of a 25552 protein for agonist or antagonist activity.

Libraries of fragments e.g., N terminal, C terminal, or internal fragments, of a 25552 protein coding sequence can be used to generate a variegated population of fragments for screening and subsequent selection of variants of a 25552 protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of 25552 proteins. Recursive ensemble mutagenesis (REM), a new technique which enhances the frequency of functional mutants in the libraries, can be used in combination with the screening assays to identify 25552 variants (Arkin and Yourvan (1992) *Proc. Natl. Acad. Sci. USA* 89:7811-7815; Delgrave et al. (1993) *Protein Engineering* 6:327-331).

Cell based assays can be exploited to analyze a variegated 25552 library. For example, a library of expression vectors can be transfected into a cell line, e.g., a cell line, which ordinarily responds to 25552 in a substrate-dependent manner. The transfected cells are then contacted with 25552 and the effect of the expression of the mutant on signaling by the 25552 substrate can be detected, e.g., by measuring methyltransferase activity. Plasmid DNA can then be recovered from the cells which score for inhibition, or alternatively, potentiation of signaling by the 25552 substrate, and the individual clones further characterized.

In another aspect, the invention features a method of making a 25552 polypeptide, e.g., a peptide having a non-wild type activity, e.g., an antagonist, agonist, or super agonist of a naturally occurring 25552 polypeptide, e.g., a naturally occurring 25552 polypeptide. The method includes: altering the sequence of a 25552 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 25552 polypeptide a biological activity of a naturally occurring 25552 polypeptide. The method includes: altering the sequence, e.g., by substitution or deletion of one or more residues, of a 25552 polypeptide, e.g., altering the sequence of a non-conserved region, or a domain or residue described herein, and testing the altered polypeptide for the desired activity.

Anti-25552 Antibodies

In another aspect, the invention provides an anti-25552 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-25552 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 25552 polypeptide or fragment thereof. Examples of antigen-binding fragments of the anti-25552 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-

5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-25552 antibody can be a polyclonal or a monoclonal antibody. In other embodiments, the antibody can be recombinantly produced, e.g., produced by phage display or by combinatorial methods.

Phage display and combinatorial methods for generating anti-25552 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the anti-25552 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An anti-25552 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., et al., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559). antibody may be replaced with at least a portion of a non-human CDR or only some of the CDR's may be replaced with non-human CDR's. It is only necessary to replace the number of CDR's required for binding of the humanized antibody to a 25552 or a fragment thereof A humanized or CDR-grafted antibody will have at least one or two but generally all three recipient CDR's (of heavy and or light immuoglobulin chains) replaced with a donor CDR. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occuring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 25552 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552-525; Verhoeyan et al. 1988 *Science* 239:1534;

Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

A full-length 25552 protein or, antigenic peptide fragment of 25552 can be used as an immunogen or can be used to identify anti-25552 antibodies made with other immunogens, e.g., cells, membrane preparations, and the like. The antigenic peptide of 25552 should include at least 8 amino acid residues of the amino acid sequence shown in SEQ ID NO:14 and encompasses an epitope of 25552. Preferably, the antigenic peptide includes at least 10 amino acid residues, more preferably at least 15 amino acid residues, even more preferably at least 20 amino acid residues, and most preferably at least 30 amino acid residues.

Fragments of 25552 which include residues about 110 to 125, about 128 to 141, or about 39 to 47 can be used to make, e.g., used as immunogens or used to characterize the specificity of an antibody, antibodies against hydrophilic regions of the 25552 protein. Similarly, fragments of 25552 which include residues about 142 to 150, about 166 to 174, or about 239 to 251 can be used to make an antibody against a hydrophobic region of the 25552 protein; and a fragment of 25552 which include residues about 37 to 306 of SEQ ID NO:14 can be used to make an antibody against the ubiE methyltransferase region of the 25552 protein.

Antibodies reactive with, or specific for, any of these regions, or other regions or domains described herein are provided.

Antibodies which bind only native 25552 protein, only denatured or otherwise non-native 25552 protein, or which bind both, are with in the invention. Antibodies with linear or conformational epitopes are within the invention. Conformational epitopes can sometimes be identified by identifying antibodies which bind to native but not denatured 25552 protein. In a preferred embodiment, an antibody recognizes an epitope of the 25552 protein that includes valine at about amino acid 112 of SEQ ID NO:14.

Preferred epitopes encompassed by the antigenic peptide are regions of 25552 are located on the surface of the protein, e.g., hydrophilic regions, as well as regions with high antigenicity. For example, an Emini surface probability analysis of the human 25552 protein sequence can be used to indicate the regions that have a particularly high probability of being localized to the surface of the 25552 protein and are thus likely to constitute surface residues useful for targeting antibody production.

The anti-25552 antibody can be a single chain antibody. A single-chain antibody (scFV) may be engineered (see, for example, Colcher, D. et al. (1999) *Ann NY Acad Sci* 880: 263-80; and Reiter, Y. (1996) *Clin Cancer Res* 2:245-52). The single chain antibody can be dimerized or multimerized to generate multivalent antibodies having specificities for different epitopes of the same target 25552 protein.

In a preferred embodiment the antibody has: effector function; and can fix complement. In other embodiments the antibody does not; recruit effector cells; or fix complement.

In a preferred embodiment, the antibody has reduced or no ability to bind an Fc receptor. For example., it is a isotype or subtype, fragment or other mutant, which does not support binding to an Fc receptor, e.g., it has a mutagenized or deleted Fc receptor binding region.

In a preferred embodiment, an anti-25552 antibody alters (e.g., increases or decreases) the methyltransferase activity of a 25552 polypeptide. For example, the antibody can bind at or in proximity to the active site, e.g., the S-adenosyl-L-methionine binding site.

The antibody can be coupled to a toxin, e.g., a polypeptide toxin, e.g., ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-25552 antibody (e.g., monoclonal antibody) can be used to isolate 25552 by standard techniques, such as affinity chromatography or immunoprecipitation. Moreover, an anti-25552 antibody can be used to detect 25552 protein (e.g., in a cellular lysate or cell supernatant) in order to evaluate the abundance and pattern of expression of the protein. Anti-25552 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes a nucleic acids which encodes an anti-25552 antibody, e.g., an anti-25552 antibody described herein. Also included are vectors which include the nucleic acid and sells transformed with the nucleic acid, particularly cells which are useful for producing an antibody, e.g., mammalian cells, e.g. CHO or lymphatic cells.

The invention also includes cell lines, e.g., hybridomas, which make an anti-25552 antibody, e.g., and antibody described herein, and method of using said cells to make a 25552 antibody.

25552 Recombinant Expression Vectors, Host Cells and Genetically Engineered Cells In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 25552 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 25552 proteins, mutant forms of 25552 proteins, fusion proteins, and the like).

The recombinant expression vectors of the invention can be designed for expression of 25552 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 25552 activity assays, (e.g., direct assays or competitive assays described in detail below), or to generate antibodies specific for 25552 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The 25552 expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a 25552 nucleic acid molecule within a recombinant expression vector or a 25552 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 25552 protein can be expressed in bacterial cells (such as E. coli), insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 25552 protein. Accordingly, the invention further provides methods for producing a 25552 protein using the host cells of the invention. In one embodiment, the method includes culturing the host cell of the invention (into which a recombinant expression vector encoding a 25552 protein has been introduced) in a suitable medium such that a 25552 protein is produced. In another embodiment, the method further includes isolating a 25552 protein from the medium or the host cell.

In another aspect, the invention features, a cell or purified preparation of cells which include a 25552 transgene, or which otherwise misexpress 25552. The cell preparation can consist of human or non-human cells, e.g., rodent cells, e.g., mouse or rat cells, rabbit cells, or pig cells. In preferred embodiments, the cell or cells include a 25552 transgene, e.g., a heterologous form of a 25552, e.g., a gene derived from humans (in the case of a non-human cell). The 25552 transgene can be misexpressed, e.g., overexpressed or underexpressed. In other preferred embodiments, the cell or cells include a gene that mis-expresses an endogenous 25552, e.g., a gene the expression of which is disrupted, e.g., a knockout. Such cells can serve as a model for studying disorders that are related to mutated or mis-expressed 25552 alleles or for use in drug screening.

In another aspect, the invention features, a human cell, e.g., an endothelial cell or a colonic celll, transformed with nucleic acid which encodes a subject 25552 polypeptide.

Also provided are cells, preferably human cells, e.g., human endothelial cells or fibroblast cells, in which an endogenous 25552 is under the control of a regulatory sequence that does not normally control the expression of the endogenous 25552 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 25552 gene. For example, an endogenous 25552 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 25552 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) Nat. Biotechnol. 14:1107; Joki et al. (2001) Nat. Biotechnol. 19:35; and U.S. Pat. No. 5,876,742. Production of 25552 polypeptide can be regulated in the subject by administering an agent (e.g., a steroid hormone) to the subject. In another preferred embodiment, the implanted recombinant cells express and secrete an antibody specific for a 25552 polypeptide. The antibody can be any antibody or any antibody derivative described herein.

25552 Transgenic Animals

The invention provides non-human transgenic animals. Such animals are useful for studying the function and/or activity of a 25552 protein and for identifying and/or evaluating modulators of 25552 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 25552 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 25552 protein to particular cells. A transgenic founder animal can be identified based upon the presence of a 25552 transgene in its genome and/or expression of 25552 mRNA in tissues or cells of the animals. A transgenic founder animal can then be used to breed additional animals carrying the transgene. Moreover, transgenic animals carrying a transgene encoding a 25552 protein can further be bred to other transgenic animals carrying other transgenes.

25552 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses of 25552

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 25552 protein (e.g., via a recombinant expression vector in a host cell in gene therapy applications), to detect a 25552 mRNA (e.g., in a biological sample) or a genetic alteration in a 25552 gene, and to modulate 25552 activity, as described further below. The 25552 proteins can be used to treat disorders characterized by insufficient or excessive production of a 25552 substrate or production of 25552 inhibitors. In addition, the 25552 proteins can be used to screen for naturally occurring 25552 substrates, to screen for drugs or compounds which modulate 25552 activity, as well as to treat disorders characterized by insufficient or excessive production of 25552 protein or production of 25552 protein forms which have decreased, aberrant or unwanted activity compared to 25552 wild type protein (e.g., a neoplastic disorder, e.g., a cancer of the colon). Moreover, the anti-25552 antibodies of the invention can be used to detect and isolate 25552 proteins, regulate the bioavailability of 25552 proteins, and modulate 25552 activity.

A method of evaluating a compound for the ability to interact with, e.g., bind, a subject 25552 polypeptide is provided. The method includes: contacting the compound with the subject 25552 polypeptide; and evaluating ability of the compound to interact with, e.g., to bind or form a complex with the subject 25552 polypeptide. This method can be performed in vitro, e.g., in a cell free system, or in vivo, e.g., in a two-hybrid interaction trap assay. This method can be used to identify naturally occurring molecules that interact with subject 25552 polypeptide. It can also be used to find natural or synthetic inhibitors of subject 25552 polypeptide. Screening methods are discussed in more detail below.

25552 Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 25552 proteins, have a stimulatory or inhibitory effect on, for example, 25552 expression or 25552 activity, or have a stimulatory or inhibitory effect on, for example, the expression or activity of a 25552 substrate. Compounds thus identified can be used to modulate the activity of target gene products (e.g., 25552 genes) in a therapeutic protocol, to elaborate the biological function of the target gene product, or to identify compounds that disrupt normal target gene interactions.

In one embodiment, the invention provides assays for screening candidate or test compounds which are substrates of a 25552 protein or polypeptide or a biologically active portion thereof. In another embodiment, the invention provides assays for screening candidate or test compounds that bind to or modulate an activity of a 25552 protein or polypeptide or a biologically active portion thereof.

In one embodiment, an activity of a 25552 protein can be assayed for methyltransferase activity following the method of Barkovich et al. (1997) *J Biol Chem* 272:9182. For example, an extract containing a 25552 polypeptide or a purified 25552 polypeptide is incubated in a butter containing 1 mM ZnSO4, 500 µM 2-methoxy-6-farnesyl-1,4-benzoquinone, 50 mM sodium phosphate pH 7.0, and 3.0 mM NADH. The reaction is triggered by the addition of 20 µM labeled S-adenoysl-[methyl-3H]L-methionine. After a set incubation period, the reaction is quenched with acid. Lipids are extracted and analyzed by reverse phase HPLC. Fractions are counted for radioactivity to assess the amount of labeled methyl incorporated into the 2-methoxy-6-farnesyl-1,4-benzoquinone. The desired fraction for identifying the reaction product can be determined by running a standard containing demethyl demthoxy ubiquinone (2-methoxy-6-polyprenyl-1,4-benzoquinone).

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In one embodiment, an assay is a cell-based assay in which a cell which expresses a 25552 protein or biologically active portion thereof is contacted with a test compound, and the ability of the test compound to modulate 25552 activity is determined. Determining the ability of the test compound to modulate 25552 activity can be accomplished by monitoring, for example, methyltransferase activity. The cell, for example, can be of mammalian origin, e.g., human.

The ability of the test compound to modulate 25552 binding to a compound, e.g., a 25552 substrate, or to bind to 25552 can also be evaluated. This can be accomplished, for example, by coupling the compound, e.g., the substrate, with a radioisotope or enzymatic label such that binding of the compound, e.g., the substrate, to 25552 can be determined by detecting the labeled compound, e.g., substrate, in a complex. Alternatively, 25552 could be coupled with a radioisotope or enzymatic label to monitor the ability of a test compound to modulate 25552 binding to a 25552 substrate in a complex. For example, compounds (e.g., 25552 substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 25552 substrate) to interact with 25552 with or without the labeling of any of the interactants can be evaluated. For example, a microphysiometer can be used to detect the interaction of a compound with 25552 without the labeling of either the compound or the 25552. McConnell, H. M. et al. (1992) *Science* 257: 1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 25552.

In yet another embodiment, a cell-free assay is provided in which a 25552 protein or biologically active portion thereof is contacted with a test compound and the ability of the test compound to bind to the 25552 protein or biologically active portion thereof is evaluated. Preferred biologically active portions of the 25552 proteins to be used in assays of the present invention include fragments which participate in interactions with non-25552 molecules, e.g., fragments with high surface probability scores.

Soluble and/or membrane-bound forms of isolated proteins (e.g., 25552 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 25552 protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 25552, an anti-25552 antibody or its target molecule to facilitate separation of complexed from uncomplexed forms of one or both of the proteins, as well as to accommodate automation of the assay. Binding of a test compound to a 25552 protein, or interaction of a 25552 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/25552 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 25552 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 25552 binding or activity determined using standard techniques.

Other techniques for immobilizing either a 25552 protein or a target molecule on matrices include using conjugation of biotin and streptavidin. Biotinylated 25552 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 25552 protein or target molecules but which do not interfere with binding of the 25552 protein to its target molecule. Such antibodies can be derivatized to the wells of the plate, and unbound target or 25552 protein trapped in the wells by antibody conjugation. Methods for detecting such complexes, in addition to those described above for the GST-immobilized complexes, include immunodetection of complexes using antibodies reactive with the 25552 protein or target molecule, as well as enzyme-linked assays which rely on detecting an enzymatic activity associated with the 25552 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141-8; Hage, D. S., and Tweed, S. A. (1997) *J Chromatogr B Biomed Sci Appl.* 699:499-525). Further, fluorescence energy transfer may also be conveniently utilized, as described herein, to detect binding without further purification of the complex from solution.

In a preferred embodiment, the assay includes contacting the 25552 protein or biologically active portion thereof with a known compound which binds 25552 to form an assay mixture, contacting the assay mixture with a test compound, and determining the ability of the test compound to interact with a 25552 protein, wherein determining the ability of the test compound to interact with a 25552 protein includes determining the ability of the test compound to preferentially bind to 25552 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/ products for use in this embodiment are the 25552 genes herein identified. In an alternative embodiment, the invention provides methods for determining the ability of the test compound to modulate the activity of a 25552 protein through modulation of the activity of a downstream effector of a 25552 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 25552 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 25552 ("25552-binding proteins" or "25552-bp") and are involved in 25552 activity. Such 25552-bps can be activators or inhibitors of signals by the 25552 proteins or 25552 targets as, for example, downstream elements of a 25552-mediated signaling pathway.

The two-hybrid system is based on the modular nature of most transcription factors, which consist of separable DNA-binding and activation domains. Briefly, the assay utilizes two different DNA constructs. In one construct, the gene that codes for a 25552 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 25552 protein can be the fused to the activator domain.) If the "bait" and the "prey" proteins are able to interact, in vivo, forming a 25552-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 25552 protein.

In another embodiment, modulators of 25552 expression are identified. For example, a cell or cell free mixture is contacted with a candidate compound and the expression of 25552 mRNA or protein evaluated relative to the level of expression of 25552 mRNA or protein in the absence of the candidate compound. When expression of 25552 mRNA or protein is greater in the presence of the candidate compound than in its absence, the candidate compound is identified as a stimulator of 25552 mRNA or protein expression. Alternatively, when expression of 25552 mRNA or protein is less (statistically significantly less) in the presence of the candidate compound than in its absence, the candidate compound is identified as an inhibitor of 25552 mRNA or protein expression. The level of 25552 mRNA or protein expression can be determined by methods described herein for detecting 25552 mRNA or protein.

In another aspect, the invention pertains to a combination of two or more of the assays described herein. For example, a modulating agent can be identified using a cell-based or a cell free assay, and the ability of the agent to modulate the activity of a 25552 protein can be confirmed in vivo, e.g., in an animal such as an animal model for a neoplastic disorder, e.g., a cancer of the colon.

This invention further pertains to novel agents identified by the above-described screening assays. Accordingly, it is within the scope of this invention to further use an agent identified as described herein (e.g., a 25552 modulating agent, an antisense 25552 nucleic acid molecule, a 25552-specific antibody, or a 25552-binding partner) in an appropriate animal model to determine the efficacy, toxicity, side effects, or mechanism of action, of treatment with such an agent. Furthermore, novel agents identified by the above-described screening assays can be used for treatments as described herein.

25552 Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 25552 with a disease; (ii) identify an individual from a minute biological sample (tissue typing); and (iii) aid in forensic identification of a biological sample. These applications are described in the subsections below.

25552 Chromosome Mapping

The 25552 nucleotide sequences or portions thereof can be used to map the location of the 25552 genes on a chromosome. This process is called chromosome mapping. Chromosome mapping is useful in correlating the 25552 sequences with genes associated with disease.

Briefly, 25552 genes can be mapped to chromosomes by preparing PCR primers (preferably 15-25 bp in length) from the 25552 nucleotide sequences. These primers can then be used for PCR screening of somatic cell hybrids containing individual human chromosomes. Only those hybrids containing the human gene corresponding to the 25552 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919-924).

Other mapping strategies e.g., in situ hybridization (described in Fan, Y. et al. (1990) *Proc. Natl. Acad. Sci. USA,* 87:6223-27), pre-screening with labeled flow-sorted chromosomes, and pre-selection by hybridization to chromosome specific cDNA libraries can be used to map 25552 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783-787.

Moreover, differences in the DNA sequences between individuals affected and unaffected with a disease associated with the 25552 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

25552 Tissue Typing 25552 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 25552 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:13 can provide positive individual identification with a panel of perhaps 10 to 1,000 primers which each yield a noncoding amplified sequence of 100 bases. If predicted coding sequences, such as those in SEQ ID NO:15 are used, a more appropriate number of primers for positive individual identification would be 500-2,000.

If a panel of reagents from 25552 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 25552 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:13 (e.g., fragments derived from the noncoding regions of SEQ ID NO:13 having a length of at least 20 bases, preferably at least 30 bases) are particularly appropriate for this use.

The 25552 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 25552 probes can be used to identify tissue by species and/or by organ type.

In a similar fashion, these reagents, e.g., 25552 primers or probes can be used to screen tissue culture for contamination (i.e. screen for the presence of a mixture of different types of cells in a culture).

Predictive Medicine of 25552

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 25552.

Such disorders include, e.g., a disorder associated with the misexpression of 25552 gene; a disorder of cell proliferation, e.g., a cancer (e.g., a cancer of the colon or liver).

The method includes one or more of the following:

detecting, in a tissue of the subject, the presence or absence of a mutation which affects the expression of the 25552 gene, or detecting the presence or absence of a mutation in a region which controls the expression of the gene, e.g., a mutation in the 5' control region;

detecting, in a tissue of the subject, the presence or absence of a mutation which alters the structure of the 25552 gene;

detecting, in a tissue of the subject, the misexpression of the 25552 gene, at the mRNA level, e.g., detecting a non-wild type level of a mRNA;

detecting, in a tissue of the subject, the misexpression of the gene, at the protein level, e.g., detecting a non-wild type level of a 25552 polypeptide.

In preferred embodiments the method includes: ascertaining the existence of at least one of: a deletion of one or more nucleotides from the 25552 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:13, or naturally occurring mutants thereof or 5' or 3' flanking sequences naturally associated with the 25552 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 25552 gene; the presence of a non-wild type splicing pattern of a messenger RNA transcript of the gene; or a non-wild type level of 25552.

Methods of the invention can be used prenatally or to determine if a subject's offspring will be at risk for a disorder.

In preferred embodiments the method includes determining the structure of a 25552 gene, an abnormal structure being indicative of risk for the disorder.

In preferred embodiments the method includes contacting a sample from the subject with an antibody to the 25552 protein or a nucleic acid, which hybridizes specifically with the gene. These and other embodiments are discussed below.

Diagnostic and Prognostic Assays of 25552

Diagnostic and prognostic assays of the invention include method for assessing the expression level of 25552 molecules and for identifying variations and mutations in the sequence of 25552 molecules.

Expression Monitoring and Profiling

The presence, level, or absence of 25552 protein or nucleic acid in a biological sample can be evaluated by obtaining a biological sample from a test subject and contacting the biological sample with a compound or an agent capable of detecting 25552 protein or nucleic acid (e.g., mRNA, genomic DNA) that encodes 25552 protein such that the presence of 25552 protein or nucleic acid is detected in the biological sample. The term "biological sample" includes tissues, cells and biological fluids isolated from a subject, as well as tissues, cells and fluids present within a subject. A preferred biological sample is serum. The level of expression of the 25552 gene can be measured in a number of ways, including, but not limited to: measuring the mRNA encoded by the 25552 genes; measuring the amount of protein encoded by the 25552 genes; or measuring the activity of the protein encoded by the 25552 genes.

The level of mRNA corresponding to the 25552 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 25552 nucleic acid, such as the nucleic acid of SEQ ID NO:13, or a portion thereof, such as an oligonucleotide of at least 7, 15, 30, 50, 100, 250 or 500 nucleotides in length and sufficient to specifically hybridize under stringent conditions to 25552 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 25552 genes.

The level of mRNA in a sample that is encoded by one of 25552 can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189-193), self sustained sequence replication (Guatelli et al., (1990) Proc. Natl. Acad. Sci. USA 87:1874-1878), transcriptional amplification system (Kwoh et al., (1989), Proc. Natl. Acad. Sci. USA 86:1173-1177), Q-Beta Replicase (Lizardi et al., (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 25552 gene being analyzed.

In another embodiment, the methods further contacting a control sample with a compound or agent capable of detecting 25552 mRNA, or genomic DNA, and comparing the presence of 25552 mRNA or genomic DNA in the control sample with the presence of 25552 mRNA or genomic DNA in the test sample. In still another embodiment, serial analysis of gene expression, as described in U.S. Pat. No. 5,695,937, is used to detect 25552 transcript levels.

A variety of methods can be used to determine the level of protein encoded by 25552. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 25552 protein in a biological sample in vitro as well as in vivo. In vitro techniques for detection of 25552 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 25552 protein include introducing into a subject a labeled anti-25552 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-25552 antibody positioned on an antibody array (as described below). The sample can be detected, e.g., with avidin coupled to a fluorescent label.

In another embodiment, the methods further include contacting the control sample with a compound or agent capable of detecting 25552 protein, and comparing the presence of 25552 protein in the control sample with the presence of 25552 protein in the test sample.

The invention also includes kits for detecting the presence of 25552 in a biological sample. For example, the kit can include a compound or agent capable of detecting 25552 protein or mRNA in a biological sample; and a standard. The compound or agent can be packaged in a suitable container. The kit can further comprise instructions for using the kit to detect 25552 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 25552 expression or activity. As used herein, the term "unwanted" includes an unwanted phenomenon involved in a biological response such as a neoplastic disorder, e.g., a cancer of the colon, liver, or breast.

In one embodiment, a disease or disorder associated with aberrant or unwanted 25552 expression or activity is identified. A test sample is obtained from a subject and 25552 protein or nucleic acid (e.g., mRNA or genomic DNA) is evaluated, wherein the level, e.g., the presence or absence, of 25552 protein or nucleic acid is diagnostic for a subject having or at risk of developing a disease or disorder associated with aberrant or unwanted 25552 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 25552 expression or activity. For example, such methods can be used to determine whether a subject can be effectively treated with an agent for a neoplastic disorder, e.g., a cancer of the colon or the liver.

In another aspect, the invention features a computer medium having a plurality of digitally encoded data records. Each data record includes a value representing the level of expression of 25552 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 25552 (e.g., other genes associated with a 25552-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 25552 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a a neoplastic disorder, e.g., a cancer of the colon or liver, in a subject wherein an increase in 25552 expression is an indication that the subject has or is disposed to having a neoplastic disorder, e.g., a cancer of the colon or liver. The method can be used to monitor a treatment for a neoplastic disorder, e.g., a cancer of the colon or liver, in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 25552 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 25552 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 25552 expression.

25552 Arrays and Uses Thereof

In another aspect, the invention features an array that includes a substrate having a plurality of addresses. At least one address of the plurality includes a capture probe that binds specifically to a 25552 molecule (e.g., a 25552 nucleic acid or a 25552 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 25552 nucleic acid, e.g., the sense or anti-sense strand. In one preferred embodiment, a subset of addresses of the plurality of addresses has a nucleic acid capture probe for 25552. Each address of the subset can include a capture probe that hybridizes to a different region of a 25552 nucleic acid. In another preferred embodiment, addresses of the subset include a capture probe for a 25552 nucleic acid. Each address of the subset is unique, overlapping, and complementary to a different variant of 25552 (e.g., an allelic variant, or all possible hypothetical variants). The array can be used to sequence 25552 by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 25552 polypeptide or fragment thereof. The polypeptide can be a naturally-occurring interaction partner of 25552 polypeptide. Preferably, the polypeptide is an antibody, e.g., an antibody described herein (see "Anti-25552 Antibodies," above), such as a monoclonal antibody or a single-chain antibody.

In another aspect, the invention features a method of analyzing the expression of 25552. The method includes providing an array as described above; contacting the array with a sample and detecting binding of a 25552-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 25552. If a sufficient number of diverse samples is analyzed, clustering (e.g., hierarchical clustering, k-means clustering, Bayesian clustering and the like) can be used to identify other genes which are co-regulated with 25552. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 25552 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 25552-associated disease or disorder; and processes, such as a cellular transformation associated with a 25552-associated disease or disorder. The method can also evaluate the treatment and/or progression of a 25552-associated disease or disorder The array is also useful for ascertaining differential expression patterns of one or more genes in normal and abnormal cells. This provides a battery of genes (e.g., including 25552) that could serve as a molecular target for diagnosis or therapeutic intervention.

In another aspect, the invention features an array having a plurality of addresses. Each address of the plurality includes a unique polypeptide. At least one address of the plurality has disposed thereon a 25552 polypeptide or fragment thereof. Methods of producing polypeptide arrays are described in the art, e.g., in De Wildt et al. (2000). *Nature Biotech.* 18, 989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80,85, 90, 95 or 99% identical to a 25552 polypeptide or fragment thereof. For example, multiple variants of a 25552 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 25552 binding compound, e.g., an antibody in a sample from a subject with specificity for a 25552 polypeptide or the presence of a 25552-binding protein or ligand.

The array is also useful for ascertaining the effect of the expression of a gene on the expression of other genes in the same cell or in different cells (e.g., ascertaining the effect of 25552 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 25552 or from a cell or subject in which a 25552 mediated response has been elicited, e.g., by contact of the cell with 25552 nucleic acid or protein, or administration to the cell or subject 25552 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 25552 (or does not express as highly as in the case of the 25552 positive plurality of capture probes) or from a cell or subject which in which a 25552 mediated response has not been elicited (or has been elicited to a lesser extent than in the first sample); contacting the array with one or more inquiry probes (which is preferably other than a 25552 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 25552 or from a cell or subject in which a 25552-mediated response has been elicited, e.g., by contact of the cell with 25552 nucleic acid or protein, or administration to the cell or subject 25552 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 25552 (or does not express as highly as in the case of the 25552 positive plurality of capture probes) or from a cell or subject which in which a 25552 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 25552, e.g., analyzing structure, function, or relatedness to other nucleic acid or amino acid sequences. The method includes: providing a 25552 nucleic acid or amino acid sequence; comparing the 25552 sequence with one or more preferably a plurality of sequences from a collection of sequences, e.g., a nucleic acid or protein sequence database; to thereby analyze 25552.

Detection of 25552 Variations or Mutations

The methods of the invention can also be used to detect genetic alterations in a 25552 gene, thereby determining if a subject with the altered gene is at risk for a disorder characterized by misregulation in 25552 protein activity or nucleic acid expression, such as a neoplastic disorder, e.g., a cancer of the colon or liver. In a preferred embodiment, the genetic alteration is a nucleotide polymorphism in a region of the 25552 nucleic acid sequence, e.g., located at about nucleotides 255 to 265, 305 to 320, and/or 325 to 340 of SEQ ID NO:14.

In preferred embodiments, the methods include detecting, in a sample from the subject, the presence or absence of a genetic alteration characterized by at least one of an alteration affecting the integrity of a gene encoding a 25552-protein, or the mis-expression of the 25552 gene. For example, such genetic alterations can be detected by ascertaining the existence of at least one of 1) a deletion of one or more nucleotides from a 25552 gene; 2) an addition of one or more nucleotides to a 25552 gene; 3) a substitution of one or more nucleotides of a 25552 gene, 4) a chromosomal rearrangement of a 25552 gene; 5) an alteration in the level of a messenger RNA transcript of a 25552 gene, 6) aberrant modification of a 25552 gene, such as of the methylation pattern of the genomic DNA, 7) the presence of a non-wild type splicing pattern of a messenger RNA transcript of a 25552 gene, 8) a non-wild type level of a 25552-protein, 9) allelic loss of a 25552 gene, and 10) inappropriate post-translational modification of a 25552-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 25552-gene. This method can include the steps of collecting a sample of cells from a subject, isolating nucleic acid (e.g., genomic, mRNA or both) from the sample, contacting the nucleic acid sample with one or more primers which specifically hybridize to a 25552 gene under conditions such that hybridization and amplification of the 25552-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 25552 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 25552 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 25552 nucleic acid or a putative variant (e.g., allelic variant) thereof. A probe can have one or more mismatches to a region of a 25552 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in 25552 can be identified in two-dimensional arrays containing light-generated DNA probes as described in Cronin, M. T. et al supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 25552 gene and detect mutations by comparing the sequence of the sample 25552 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 25552 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 25552 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 25552 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 25552 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 25552 nucleic acid.

In a preferred embodiment the set includes a first and a second oligonucleotide. The first and second oligonucleotide can hybridize to the same or to different locations of SEQ ID NO:13 or the complement of SEQ ID NO:13. Different locations can be different but overlapping, or non-overlapping on the same strand. The first and second oligonucleotide can hybridize to sites on the same or on different strands.

The set can be useful, e.g., for identifying SNP's, or identifying specific alleles of 25552. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 25552 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 25552 gene.

Use of 25552 Molecules as Surrogate Markers

The 25552 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 25552 molecules of the invention may be detected, and may be correlated with one or more biological states in vivo. For example, the 25552 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 25552 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 25552 marker) transcription or expression, the amplified marker may be in a quantity which is more readily detectable than the drug itself. Also, the marker may be more easily detected due to the nature of the marker itself; for example, using the methods described herein, anti-25552 antibodies may be employed in an immune-based detection system for a 25552 protein marker, or 25552-specific radiolabeled probes may be used to detect a 25552 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

The 25552 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 25552 protein or RNA) for specific tumor markers in a subject, a drug or course of treatment may be selected that is optimized for the treatment of the specific tumor likely to be present in the subject. Similarly, the presence or absence of a specific sequence mutation in 25552 DNA may correlate 25552 drug response. The use of pharmacogenomic markers therefore permits the application of the most appropriate treatment for each subject without having to administer the therapy.

Pharmaceutical Compositions of 25552

The nucleic acid and polypeptides, fragments thereof, as well as anti-25552 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, $\alpha$-interferon, $\beta$-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 25552

The present invention provides for both prophylactic and therapeutic methods of treating a subject at risk of (or susceptible to) a disorder or having a disorder associated with aberrant or unwanted 25552 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 25552 molecules of the present invention or 25552 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 25552 expression or activity, by administering to the subject a 25552 or an agent which modulates 25552 expression or at least one 25552 activity. Subjects at risk for a disease which is caused or contributed to by aberrant or unwanted 25552 expression or activity can be identified by, for example, any or a combination of diagnostic or prognostic assays as described herein. Administration of a prophylactic agent can occur prior to the manifestation of symptoms characteristic of the 25552 aberrance, such that a disease or disorder is prevented or, alternatively, delayed in its progression. Depending on the type of 25552 aberrance, for example, a 25552, 25552 agonist or 25552 antagonist agent can be used for treating the subject. The appropriate agent can be determined based on screening assays described herein.

It is possible that some 25552 disorders can be caused, at least in part, by an abnormal level of gene product, or by the presence of a gene product exhibiting abnormal activity. As such, the reduction in the level and/or activity of such gene products would bring about the amelioration of disorder symptoms.

The 25552 molecules can act as novel diagnostic targets and therapeutic agents for controlling one or more of cellular proliferative and/or differentiative disorders and disorders associated with colon as described above, as well as liver, kidney, brain, bone, breast, ovary, endothelia, lung, and/or immune disorders.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, coronary artery disease, valvular disease, arrhythmias, heart failure, including but not limited to, congestive heart failure, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Examples of disorders of the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 25552 molecules may play an important role in the etiology of certain viral diseases, including but not limited to Hepatitis B, Hepatitis C and Herpes Simplex Virus (HSV). Modulators of 25552 activity could be used to control viral diseases. The modulators can be used in the treatment and/or diagnosis of viral infected tissue or virus-associated tissue fibrosis, especially liver and liver fibrosis. Also, 25552 modulators can be used in the treatment and/or diagnosis of virus-associated carcinoma, especially hepatocellular cancer.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephalopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Aberrant expression and/or activity of 25552 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 25552 molecules effects in bone cells, e.g. osteoclasts and osteoblasts, that may in turn result in bone formation and degeneration. For example, 25552 molecules may support different activities of bone resorbing osteoclasts such as the stimulation of differentiation of monocytes and mononuclear phagocytes into osteoclasts. Accordingly, 25552 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

As discussed, successful treatment of 25552 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 25552 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, $F(ab')_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 25552 expression is through the use of aptamer molecules specific for 25552 protein. Aptamers are nucleic acid molecules having a tertiary structure which permits them to specifically bind to protein ligands (see, e.g., Osborne, et al. (1997) *Curr. Opin. Chem Biol.* 1: 5-9; and Patel, D. J. (1997) *Curr Opin Chem Biol* 1:32-46). Since nucleic acid molecules may in many cases be more conveniently introduced into target cells than therapeutic protein molecules may be, aptamers offer a method by which 25552 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 25552 disorders. For a description of antibodies, see the Antibody section above.

In circumstances wherein injection of an animal or a human subject with a 25552 protein or epitope for stimulating antibody production is harmful to the subject, it is possible to generate an immune response against 25552 through the use of anti-idiotypic antibodies (see, for example, Herlyn, D. (1999) *Ann Med* 31:66-78; and Bhattacharya-Chatterjee, M., and Foon, K. A. (1998) *Cancer Treat Res.* 94:51-68). If an anti-idiotypic antibody is introduced into a mammal or human subject, it should stimulate the production of anti-anti-idiotypic antibodies, which should be specific to the 25552 protein. Vaccines directed to a disease characterized by 25552 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate 25552 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 25552 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89-94 and in Shea, K. J. (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645-647. Through the use of isotope-labeling, the "free" concentration of compound which modulates the expression or activity of 25552 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142-2144.

Another aspect of the invention pertains to methods of modulating 25552 expression or activity for therapeutic purposes. Accordingly, in an exemplary embodiment, the modulatory method of the invention involves contacting a cell with a 25552 or agent that modulates one or more of the activities of 25552 protein activity associated with the cell. An agent that modulates 25552 protein activity can be an agent as described herein, such as a nucleic acid or a protein, a naturally-occurring target molecule of a 25552 protein (e.g., a 25552 substrate or receptor), a 25552 antibody, a 25552 agonist or antagonist, a peptidomimetic of a 25552 agonist or antagonist, or other small molecule.

In one embodiment, the agent stimulates one or 25552 activities. Examples of such stimulatory agents include active 25552 protein and a nucleic acid molecule encoding 25552. In another embodiment, the agent inhibits one or more 25552 activities. Examples of such inhibitory agents include antisense 25552 nucleic acid molecules, anti-25552 antibodies, and 25552 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 25552 protein or nucleic acid molecule. In one embodiment, the method involves administering an agent (e.g., an agent identified by a screening assay described herein), or combination of agents that modulates (e.g., up regulates or down regulates) 25552 expression or activity. In another embodiment, the method involves administering a 25552 protein or nucleic acid molecule as therapy to compensate for reduced, aberrant, or unwanted 25552 expression or activity.

Stimulation of 25552 activity is desirable in situations in which 25552 is abnormally downregulated and/or in which increased 25552 activity is likely to have a beneficial effect. For example, stimulation of 25552 activity is desirable in situations in which a 25552 is downregulated and/or in which increased 25552 activity is likely to have a beneficial effect. Likewise, inhibition of 25552 activity is desirable in situations in which 25552 is abnormally upregulated and/or in which decreased 25552 activity is likely to have a beneficial effect.

25552 Pharmacogenomics

The 25552 molecules of the present invention, as well as agents, or modulators which have a stimulatory or inhibitory effect on 25552 activity (e.g., 25552 gene expression) as identified by a screening assay described herein can be administered to individuals to treat (prophylactically or therapeutically) 25552 associated disorders (e.g., a neoplastic disorder, e.g., a cancer of the colon or liver) associated with aberrant or unwanted 25552 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 25552 molecule or 25552 modulator as well as tailoring the dosage and/or therapeutic regimen of treatment with a 25552 molecule or 25552 modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23:983-985 and Linder, M. W. et al. (1997) Clin. Chem. 43:254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a 25552 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a 25552 molecule or 25552 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 25552 molecule or 25552 modulator, such as a modulator identified by one of the exemplary screening assays described herein.

The present invention further provides methods for identifying new agents, or combinations, that are based on identifying agents that modulate the activity of one or more of the gene products encoded by one or more of the 25552 genes of the present invention, wherein these products may be associated with resistance of the cells to a therapeutic agent. Specifically, the activity of the proteins encoded by the 25552 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 25552 protein can be applied in clinical trials. For example, the effectiveness of an agent determined by a screening assay as described herein to increase 25552 gene expression, protein levels, or upregulate 25552 activity, can be monitored in clinical trials of subjects exhibiting decreased 25552 gene expression, protein levels, or downregulated 25552 activity. Alternatively, the effectiveness of an agent determined by a screening assay to decrease 25552 gene expression, protein levels, or downregulate 25552 activity, can be monitored in clinical trials of subjects exhibiting increased 25552 gene expression, protein levels, or upregulated 25552 activity. In such clinical trials, the expression or activity of a 25552 gene, and preferably, other genes that have been implicated in, for example, a 25552-associated disorder can be used as a "read out" or markers of the phenotype of a particular cell.

25552 Informatics

The sequence of a 25552 molecule is provided in a variety of media to facilitate use thereof. A sequence can be provided as a manufacture, other than an isolated nucleic acid or amino acid molecule, which contains a 25552. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 25552 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 25552, e.g., analyzing structure, function, or relatedness to one or more other nucleic acid or amino acid sequences. The method includes: providing a 25552 nucleic acid or amino acid sequence; comparing the 25552 sequence with a second sequence, e.g., one or more preferably a plurality of sequences from a collection of sequences, e.g., a nucleic acid or protein sequence database to thereby analyze 25552. The method can be performed in a machine, e.g., a computer, or manually by a skilled artisan.

The method can include evaluating the sequence identity between a 25552 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 25552 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 25552 sequence, or record, in machine-readable form; comparing a second sequence to the 25552 sequence; thereby analyzing a sequence. Comparison can include comparing to sequences for sequence identity or determining if one sequence is included within the other, e.g., determining if the 25552 sequence includes a sequence being compared. In a preferred embodiment the 25552 or second sequence is stored on a first computer, e.g., at a first site and the comparison is performed, read, or recorded on a second computer, e.g., at a second site. E.g., the 25552 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 25552-associated disease or disorder or a pre-disposition to a 25552-associated disease or disorder, wherein the method comprises the steps of determining 25552 sequence information associated with the subject and based on the 25552 sequence information, determining whether the subject has a 25552-associated disease or disorder or a pre-disposition to a 25552-associated disease or disorder and/or recommending a particular treatment for the disease, disorder or pre-disease condition.

The invention further provides in an electronic system and/or in a network, a method for determining whether a subject has a 25552-associated disease or disorder or a pre-disposition to a disease associated with a 25552 wherein the method comprises the steps of determining 25552 sequence information associated with the subject, and based on the 25552 sequence information, determining whether the subject has a 25552-associated disease or disorder or a pre-disposition to a 25552-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 25552 sequence of the subject to the 25552 sequences in the database to thereby determine whether the subject as a 25552-associated disease or disorder, or a pre-disposition for such.

The present invention also provides in a network, a method for determining whether a subject has a 25552 associated disease or disorder or a pre-disposition to a 25552-associated disease or disorder associated with 25552, said method comprising the steps of receiving 25552 sequence information from the subject and/or information related thereto, receiving phenotypic information associated with the subject, acquiring information from the network corresponding to 25552 and/or corresponding to a 25552-associated disease or disorder (e.g., a neoplastic disorder, e.g., a cancer of the colon or liver), and based on one or more of the phenotypic information, the 25552 information (e.g., sequence information and/or information related thereto), and the acquired information, determining whether the subject has a 25552-associated disease or disorder or a pre-disposition to a 25552-associated disease or disorder. The method may further comprise the step of recommending a particular treatment for the disease, disorder or pre-disease condition.

The present invention also provides a method for determining whether a subject has a 25552-associated disease or disorder or a pre-disposition to a 25552-associated disease or disorder, said method comprising the steps of receiving information related to 25552 (e.g., sequence information and/or information related thereto), receiving phenotypic information associated with the subject, acquiring information from the network related to 25552 and/or related to a 25552-associated disease or disorder, and based on one or more of the phenotypic information, the 25552 information, and the acquired information, determining whether the subject has a 25552-associated disease or disorder or a pre-disposition to a 25552-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

Background of the 32132 Invention

Fucosyltransferases catalyze the transfer of fucose from GDP-Fucose to galactose in an α1,2-linkage and to N-acetylglucosamine (GlcNAc) in an α1,3-, α1,4-, or α1,6-linkage. Since known fucosyltransferases utilize the same nucleotide sugar, it is believed that their specificity resides in the recognition of the acceptor and in the type of linkage formed. On the basis of protein sequence similarities, these enzymes have been classified into four distinct families: (1) alpha-2-fucosyltransferases, (2) alpha-3-fucosyltransferases, (3) mammalian alpha-6-fucosyltransferases, and (4) bacterial alpha-6-fucosyltransferases. Conserved structural features, as well as a consensus peptide motif have been identified in the catalytic domains of all alpha-2 and alpha-6-fucosyltranferases, from both prokaryotes and eukaryotes. Based on these sequence similarities, alpha-2 and alpha-6-fucosyltranferases have been grouped into one superfamily. In addition, a few amino acids were found strictly conserved in this superfamily, and two of these residues have been reported to be essential for enzyme activity for a human alpha-2-fucosyltransferase. The alpha-3-fucosyltransferases constitute a distinct family as they lack the consensus peptide, but some regions display similarities with the alpha-2 and alpha-6-fucosyltranferases. All these observations strongly suggest that the fucosyltransferases share some common structural and/or catalytic features.

Fucosyltransferases are known to be involved in the synthesis of selectin ligands. Selectins are cell surface receptors found on endothelial cells that bind to ligands present on the surface of other cells, especially the cells of the immune system, such as leukocytes and neutrophils. Interactions between selectins and their fucosylated ligands allow leukocytes and neutrophils to attach to the walls of blood vessels and subsequently leave the blood stream and enter into the surrounding tissue. Fucosyltransferase deficiencies in mice can produce defects in the interactions that normally take place between leukocytes and the endothelial wall (see Weninger et al. (2000), *Immunity* 12(6), 665-76), and the loss of cell surface fucosylated glycan epitopes has been correlated with Leukocyte adhesion deficiency type II (LAD II), a disorder characterized by recurrent infections, persistent leukocytosis, and severe mental and growth retardation (see Becker and Lowe (1999), *Biochim Biophys Acta* 1455(2-3), 193-204). Thus, fucosyltransferases appear to play an important role in cellular adhesion and the proper function of the immune system.

Fucosyltransferases have also been implicated in the formation of cancer metastases. For example, increased expression of fucosyltransferases has been observed in some metastatic adenocarcinoma cell lines, as compared to non-metastatic adenocarcinoma cell lines (see Petretti et al. (2000), *Gut* 46(3), 359-66, and Martin-Satue et al. (1999), *Br J Cancer* 80(8), 1169-74). Significantly, overexpression of the fucosyltransferase Fuc-TVII is sufficient to convert a non-metastatic cell line into a metastatic cell line, and anti-sense mediated reduction of FUT3 expression can abrogate the metastatic potential of otherwise metastatic adenocarcinoma cells (see Martin-Satue et al. (1999), *Br J Cancer* 80(8), 1169-74, and Weston et al. (1999), *Cancer Res* 59(9), 2127-35).

Summary of the 32132 Invention

The present invention is based, in part, on the discovery of a novel fucosyltransferase, referred to herein as "32132". The nucleotide sequence of a cDNA encoding 32132 is recited in SEQ ID NO:19, and the amino acid sequence of a 32132 polypeptide is recited in SEQ ID NO:20 (see also Example 15, below). In addition, the nucleotide sequences of the coding region are recited in SEQ ID NO:21.

Accordingly, in one aspect, the invention features a nucleic acid molecule which encodes a 32132 protein or polypeptide, e.g., a biologically active portion of the 32132 protein. In a preferred embodiment the isolated nucleic acid molecule encodes a polypeptide having the amino acid sequence of SEQ ID NO:20. In other embodiments, the invention provides isolated 32132 nucleic acid molecules having the nucleotide sequence shown in SEQ ID NO:19, or SEQ ID NO:21. In still other embodiments, the invention provides nucleic acid molecules that are substantially identical (e.g., naturally occurring allelic variants) to the nucleotide sequence shown in SEQ ID NO:19, or SEQ ID NO:21. In other embodiments, the invention provides a nucleic acid molecule which hybridizes under a stringent hybridization condition described herein to a nucleic acid molecule comprising the nucleotide sequence of SEQ ID NO:19 or 21, where the nucleic acid encodes a full length 32132 protein or an active fragment thereof.

In a related aspect, the invention further provides nucleic acid constructs which include a 32132 nucleic acid molecule described herein. In certain embodiments, the nucleic acid molecules of the invention are operatively linked to native or heterologous regulatory sequences. Also included, are vectors and host cells containing the 32132 nucleic acid molecules of the invention, e.g., vectors and host cells suitable for producing 32132 nucleic acid molecules and polypeptides.

In another related aspect, the invention provides nucleic acid fragments suitable as primers or hybridization probes for the detection of 32132-encoding nucleic acids.

In still another related aspect, isolated nucleic acid molecules that are antisense to a 32132 encoding nucleic acid molecule are provided.

In another aspect, the invention features 32132 polypeptides and biologically active or antigenic fragments thereof that are useful, e.g., as reagents or targets in assays applicable to treatment and diagnosis of 32132 mediated or related disorders. In another embodiment, the invention provides 32132 polypeptides having a 32132 activity. Preferred polypeptides are 32132 proteins including at least one fucosyltransferase domain, and, preferably, having a 32132 activity, e.g., a 32132 activity as described herein.

In other embodiments, the invention provides 32132 polypeptides, e.g., a 32132 polypeptide having the amino acid sequence shown in SEQ ID NO:20; an amino acid sequence that is substantially identical to the amino acid sequence shown in SEQ ID NO:20; or an amino acid sequence encoded by a nucleic acid molecule having a nucleotide sequence which hybridizes under a stringent hybridization condition described herein to a nucleic acid molecule comprising the nucleotide sequence of SEQ ID NO:19 or 21, where the nucleic acid encodes a full length 32132 protein or an active fragment thereof.

In a related aspect, the invention provides 32132 polypeptides or fragments operatively linked to non-32132 polypeptides to form fusion proteins.

In another aspect, the invention features antibodies and antigen-binding fragments thereof, that react with or more preferably specifically bind 32132 polypeptides.

In another aspect, the invention provides methods of screening for compounds that modulate the expression or activity of the 32132 polypeptides or nucleic acids.

In still another aspect, the invention provides a process for modulating 32132 polypeptide or nucleic acid expression or activity, e.g., using the screened compounds. In certain embodiments, the methods involve treatment of conditions related to aberrant activity or expression of the 32132 polypeptides or nucleic acids, such as conditions involving aberrant or deficient cellular proliferation or differentiation. The screened compounds can module the fucosyltransferase activity of a 32132 polypeptide.

The invention also provides assays for determining the activity of or the presence or absence of 32132 polypeptides or nucleic acid molecules in a biological sample, including for disease diagnosis.

In one aspect, the invention provides a method of evaluating a sample. The method includes: providing a sample; detecting a 32132 polypeptide or nucleic acid in the sample; and, optionally, comparing the level of expressed 32132 molecules to a reference sample. In one embodiment, an increased level of 32132 molecules is an indication that the sample includes cells in mitosis. In another embodiment, the level of 32132 molecules is an indication that a sample includes a proliferating cell, e.g., a proliferating colon, liver, lung, breast, or ovary cell, preferably a proliferating colon cell. In still another embodiment, the level of 32132 molecules is indication that a cardiovascular endothelial cell (e.g., a smooth muscle cell (e.g., of the aorta, coronary artery, or heart) or a microvascular endothelial cell) is present in the sample.

In yet another aspect, the invention provides methods for inhibiting the proliferation or migration, or inducing the killing, of a 32132-expressing cell, e.g., a hyper-proliferative 32132-expressing cell. The method includes contacting the cell with a compound (e.g., a compound identified using the methods described herein) that modulates the activity, or expression, of the 32132 polypeptide or nucleic acid. In a preferred embodiment, the contacting step is effected in vitro or ex vivo. In other embodiments, the contacting step is effected in vivo, e.g., in a subject (e.g., a mammal, e.g., a human), as part of a therapeutic or prophylactic protocol. In a preferred embodiment, the cell is a hyperproliferative cell, e.g., a cell found in a solid tumor, a soft tissue tumor, or a metastatic lesion. In a preferred embodiment, the cell is originates from a cardiovascular (e.g., heart, aortic and coronary smooth muscle cells, veins, arteries), kidney, skeletal muscle, colon, liver, or brain tissue.

In a preferred embodiment, the compound is an inhibitor of a 32132 polypeptide. Preferably, the inhibitor is chosen from a peptide, a phosphopeptide, a small organic molecule, a small inorganic molecule and an antibody (e.g., an antibody conjugated to a therapeutic moiety selected from a cytotoxin, a cytotoxic agent and a radioactive metal ion). In another preferred embodiment, the compound is an inhibitor of a 32132 nucleic acid, e.g., an antisense, a ribozyme, or a triple helix molecule.

In a preferred embodiment, the compound is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

In another aspect, the invention features methods for treating or preventing a disorder characterized by aberrant cellular proliferation or differentiation of a 32132-expressing cell, in a subject. Preferably, the method includes comprising administering to the subject (e.g., a mammal, e.g., a human) an effective amount of a compound (e.g., a compound identified using the methods described herein) that modulates the activity, or expression, of the 32132 polypeptide or nucleic acid. In a preferred embodiment, the disorder is a cancerous or pre-cancerous condition.

In a further aspect, the invention provides methods for evaluating the efficacy of a treatment of a disorder, e.g., proliferative disorder. The method includes: treating a subject, e.g., a patient or an animal, with a protocol under evaluation (e.g., treating a subject with one or more of: chemotherapy, radiation, and/or a compound identified using the methods described herein); and evaluating the expression of a 32132 nucleic acid or polypeptide before and after treatment. A change, e.g., a decrease or increase, in the level of a 32132 nucleic acid (e.g., mRNA) or polypeptide after treatment, relative to the level of expression before treatment, is indicative of the efficacy of the treatment of the disorder. The level of 32132 nucleic acid or polypeptide expression can be detected by any method described herein.

In a preferred embodiment, the evaluating step includes obtaining a sample (e.g., a tissue sample, e.g., a biopsy, or a fluid sample) from the subject, before and after treatment and comparing the level of expressing of a 32132 nucleic acid (e.g., mRNA) or polypeptide before and after treatment.

In another aspect, the invention provides methods for evaluating the efficacy of a therapeutic or prophylactic agent (e.g., an anti-neoplastic agent). The method includes: contacting a sample with an agent (e.g., a compound identified using the methods described herein, a cytotoxic agent) and, evaluating the expression of 32132 nucleic acid or polypeptide in the sample before and after the contacting step. A change, e.g., a decrease or increase, in the level of 32132 nucleic acid (e.g., mRNA) or polypeptide in the sample obtained after the contacting step, relative to the level of expression in the sample before the contacting step, is indicative of the efficacy of the agent. The level of 32132 nucleic acid or polypeptide expression can be detected by any method described herein. In a preferred embodiment, the sample includes cells obtained from a cancerous tissue or a cardiovascular (e.g., heart, aortic and coronary smooth muscle cells, veins, arteries), kidney, skeletal muscle, colon, liver, or brain tissue.

In a further aspect the invention provides assays for determining the presence or absence of a genetic alteration in a 32132 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 32132 molecule. In one embodiment, the capture probe is a nucleic acid, e.g., a probe complementary to a 32132 nucleic acid sequence. In another embodiment, the capture probe is a polypeptide, e.g., an antibody specific for 32132 polypeptides. Also featured is a method of analyzing a sample by contacting the sample to the aforementioned array and detecting binding of the sample to the array.

Other features and advantages of the invention will be apparent from the following detailed description, and from the claims.

Detailed Description of 32132

The human 32132 sequence (see SEQ ID NO:19, as recited in Example 15), which is approximately 2557 nucleotides long including untranslated regions, contains a predicted methionine-initiated coding sequence of about 1479 nucleotides, including the termination codon (nucleotides 235-1711 of SEQ ID NO:19; SEQ ID NO:21). The coding sequence encodes a 492 amino acid protein (see SEQ ID NO:20, as recited in Example 15).

Human 32132 contains the following regions or other structural features:

a predicted fucosyltransferase domain, e.g. an alpha-3-fucosyltransferase domain, located at about amino acid residues 57 to 355 of SEQ ID NO:20;

one alpha-3-fucosyltransferase signature motif, located at about amino acids 274 to 304 of SEQ ID NO:20;

one predicted transmembrane domain located at about amino acid residues 8 to 28 of SEQ ID NO:20;

one predicted non-transmembrane domain residing in the cytoplasm located at about amino acid residues 1 to 7;

one predicted non-transmembrane domain residing in the extracellular space, or a topologically equivalent intracellular space, e.g., the lumen of the endoplasmic reticulum or Golgi cisternae, located at about amino acid residues 29 to 492 of SEQ ID NO:20; and four predicted N-glycosylation sites (PS00001) located at about amino acid residues 166 to 169, 318 to 321, 443 to 446, and 471 to 474 of SEQ ID NO:20.

For general information regarding PFAM identifiers, PS prefix, and PF prefix domain identification numbers, refer to Sonnhammer et al. (1997) *Protein* 28:405-420.

The 32132 protein contains a significant number of structural characteristics in common with members of the fucosyltransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

A 32132 polypeptide can include a "fucosyltransferase domain" or regions homologous with a "fucosyltransferase domain."

As used herein, the term "fucosyltransferase domain" includes an amino acid sequence of about 200 to 500 amino acid residues in length and having a bit score for the alignment of the sequence to a fucosyltransferase domain profile (ProDomain No.: 1416, Release 1999.2) of at least 130. Preferably, a fucosyltransferase domain includes at least about 250-450 amino acids, more preferably about 275-425 amino acid residues, or about 300-400 amino acids, and has a bit score for the alignment of the sequence to the fucosyltransferase domain profile (ProDom) of at least 140, 160, 180, 200, 210, 220 or greater. An alignment of the fucosyltransferase domain (amino acids 57 to 355) of human 32132 with a consensus amino acid sequence (SEQ ID NO:22), derived from a recursive PSI-BLAST profile (ProDom), is depicted in FIG. 33. An alternative model for a fucosyltransferase domain (HMM) has been assigned the PFAM Accession PF00852. An alignment of the fucosyltransferase domain (amino acids 29 to 388 of SEQ ID NO:20) of human 32132 with a consensus amino acid sequence derived from a hidden Markov model is depicted in FIG. 34.

In a preferred embodiment a 32132 polypeptide or protein has a "fucosyltransferase domain" or a region which includes at least about 200-500, more preferably about 250-400, or 250-350 amino acid residues and has at least about 50%, 60%, 70% 80% 90% 95%, 99%, or 100% homology with a "fucosyltransferase domain," e.g., the fucosyltransferase domain of human 32132 (e.g., residues 57 to 355 of SEQ ID NO:20).

To identify the presence of a "fucosyltransferase" domain in a 32132 protein sequence, and make the determination that a polypeptide or protein of interest has a particular profile, the amino acid sequence of the protein can be searched against a database of domains, e.g., the ProDom database (Corpet et al. (1999), Nucl. Acids Res. 27:263-267). The ProDom protein domain database consists of an automatic compilation of homologous domains. Current versions of ProDom are built using recursive PSI-BLAST searches (Altschul S F et al. (1997) Nucleic Acids Res. 25:3389-3402; Gouzy et al. (1999) Computers and Chemistry 23:333-340) of the SWISS-PROT 38 and TREMBL protein databases. The database automatically generates a consensus sequence for each domain. A BLAST search was performed against the ProDom database resulting in the identification of a "fucosyltransferase" domain in the amino acid sequences of human 32132 at about residues 57 to 355 of SEQ ID NO:20 (see FIG. 33).

Alternatively, to identify the presence of a "fucosyltransferase" domain in a 32132 protein sequence, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28(3):405-420 and a detailed description of HMMs can be found, for example, in Gribskov et al.(1990) Meth. Enzymol. 183:146-159; Gribskov et al. (1987) Proc. Natl. Acad. Sci. USA 84:4355-4358; Krogh et al.(1994)J. Mol. Biol. 235:1501-1531; and Stultz et al.(1993) Protein Sci. 2:305-314, the contents of which are incorporated herein by reference. A search was performed against the HMM database resulting in the identification of a "fucosyltransferase" domain (PFAM identifier PF00852) in the amino acid sequence of human 32132 at about residues 29 to 388 of SEQ ID NO:20 (see FIG. 34).

In one embodiment, a 32132 protein includes at least one alpha-3-fucosyltrasnferase signature motif, at about amino acid 274 to 304 of SEQ ID NO:20. As used herein, the term "alpha-3-fucosylytransferase signature motif" includes a sequence of at least 22 amino acid residues defined by the sequence: Y-(K/R/H)-F-X-X-X-(F/L/M)-E-N-(A/S)-X-X-X-D-Y-X-T-E-K-(L/F)-W-(R/K)-X-X-X-X-X-X-X-(V/I)-P (SEQ ID NO:24). An alpha-3-fucosyltransferase signature motif, as defined, can be involved in the enzymatic transfer of fucose from GDP-fucose to an appropriate acceptor molecule, e.g., N-acetylglucosamine. More preferably, an alpha-3-fucosyltransferase signature motif includes 25, or even more preferably 31 amino acid residues. Alpha-3-fucosyltransferase signature motifs have been described in, e.g., Breton et al. (1998), *Glycobiology* 8, 87-94, the contents of which are incorporated herein by reference.

In a preferred embodiment, a 32132 polypeptide or protein has at least one alpha-3-fucosyltransferase signature motif, or a region which includes at least 22, 25, or 31 amino acid residues and has at least about 75%, 85%, 90%, 95%, 99%, or 100% homology with an "alpha-3-fucosyltransferase signature motif", e.g., at least one alpha-3-fucosyltransferase signature motif of human 32132 (e.g., amino acid residues 288 to 319 of SEQ ID NO:20).

In one embodiment, a 32132 protein includes at least one transmeinbrane domain. As used herein, the term "transmembrane domain" includes an amino acid sequence of at least about 15 amino acid residues in length that inserts into or spans a phospholipid membrane. A transmembrane domain, as defined, can anchor a polypeptide to a lipid bilayer. More preferably, a transmembrane domain includes about at least 18, 20, 22, 24, 25, 30, 35 or 40 amino acid residues and spans a phospholipid membrane. Transmembrane domains are rich in hydrophobic residues, and typically have an a-helical structure. In a preferred embodiment, at least 50%, 60%, 70%, 80%, 90%, 95% or more of the amino acids of a transmembrane domain are hydrophobic, e.g., leucines, isoleucines, tyrosines, phenylalanine, valine, methionine, or tryptophans. Transmembrane domains are described in, for example, Zagotta W. N. et al, (1996) Annual Rev. Neurosci. 19: 235-63, the contents of which are incorporated herein by reference.

In a preferred embodiment, a 32132 polypeptide or protein has at least one transmembrane domain or a region which includes at least 18, 20, 22, 24, 25, 30, 35 or 40 amino acid residues and has at least about 75%, 85%, 90%, 95%, 99%, or 100% homology with a "transmembrane domain," e.g., at least one transmembrane domain of human 32132 (e.g., amino acid residues 8 to 28 of SEQ ID NO:20).

In one embodiment, a 32132 protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles).

In a preferred embodiment, a 32132 polypeptide or protein has a "non-transmembrane domain" or a region which includes at least about 1 to 500, preferably about 200 to 490, more preferably about 300 to 490, and even more preferably about 410 to 490 amino acid residues, and has at least about 50%, 60%, 70%, 75%, 85%, 90%, 95%, 99% or 100% homology with a "non-transmembrane domain", e.g., a non-transmembrane domain of human 46743 (e.g., residues 29 to 492 of SEQ ID NO:20). Preferably, a non-transmembrane domain is capable of catalytic activity (e.g., catalyzing an fucosyltransferase reaction, e.g., an alpha-3-fucosyltransferase reaction).

A 32132 family member can include at least one fucosyltransferase domain. Furthermore, a 32132 family member can include: at least one alpha-3-fucosyltranferase signature motif; at least one transmembrane domain; at least one non-transmembrane region (e.g., an extracellular region) that can provide fucosyltranferase activity; and at least one, two, three, preferably four predicted N-glycosylation sites (PS00001).

As the 32132 polypeptides of the invention may modulate 32132-mediated activities, they may be useful for developing novel diagnostic and therapeutic agents for 32132-mediated or related disorders, as described below.

As used herein, a "32132 activity", "biological activity of 32132" or "functional activity of 32132", refers to an activity exerted by a 32132 protein, polypeptide or nucleic acid molecule on, e.g., a 32132-responsive cell or a 32132 substrate, e.g., a protein substrate, as determined in vivo or in vitro. In one embodiment, a 32132 activity is a direct activity, such as an association with a 32132 target molecule, "binding molecule" or "substrate". A "target molecule" or "binding partner" or "substrate" is a molecule with which a 32132 protein binds or interacts in nature.

In an exemplary embodiment, 32132 is an enzyme that transfers a fucosyl moiety from GDP-fucose to another molecule, e.g., a molecule that contain N-acetylglucosamine. As used herein, a "fucosyltransferase activity" refers to an activity that catalyzes the transfers a fucosyl moiety from a first compound to a second compound.

A 32132 activity can also be an indirect activity, e.g., a cellular signaling activity mediated by interactions of 32132-modified proteins with their receptors, e.g., an interaction of a selectin ligand with a selectin. The features of the 32132 molecules of the present invention can provide similar biological activities as fucosyltransferase family members, e.g., alpha-3-fucosyltransferase family members. For example, the 32132 proteins of the present invention can have one or more of the following activities: (1) fucosyltransferase activity, e.g., for GDP-fucose to a receiver compound, e.g., N-acetylglucosamine; (2) stimulation of cellular adhesion, e.g., selectin-mediated adhesion; (3) stimulation of cell migration; (4) stimulation of cellular extravasation, e.g., extravasation of leukocytes, neutrophils, or metastatic cells; (5) stimulation of immune function; (6) stimulation of tumor metastasis; (7) stimulation of intracellular signaling, e.g., growth factor- or adhesion-mediated intracellular signaling; (8) synthesis of a selectin ligand, e.g., a sialyl Lewis antigen, e.g., sialyl Lewis x or sialyl Lewis a; or (9) the ability to act as an agonist or antagonist to any of the above activities. Thus, the 32132 molecules can act as novel diagnostic targets and therapeutic agents for controlling (1) cellular proliferative and/or differentiative disorders; (2) cardiovascular disorders; and/or (3) immunological disorders.

The 32132 mRNA is expressed in: cardiovascular tissues such as the heart and blood vessel-associated tissues or cells (e.g., aortic and coronary smooth muscle cells, veins, muscular artery); kidney; normal and malignant tissues from the colon (e.g., adenomas and adenocarcinomas), liver (e.g., colon-liver metastasis); breast; as well as the neural tissues, e.g., brain and glia (see the Examples below). Accordingly, 32132 molecules may act as novel therapeutic and prophylactic agents for controlling disorders or diseases involving aberrant activities of the cells in which these molecules are expressed, and as diagnostic markers useful for indicating the presence or predisposition towards developing such disorders, or monitoring the progression or regression of a disorder. Examples of such disorders include cellular proliferative and/or differentiative disorders, cardiovascular disorders, and neural disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Further examples of cancers or neoplastic conditions, in addition to the ones described above, include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma. Many such neoplastic conditions can progress to a metastatic state, e.g., resulting in tumor cells moving to new locations and forming metastatic tumors. The motility of such cells can depend on extracellular ligands, e.g., a ligand that is synthesized by a 32132 polypeptide.

32132 molecules can also be useful as novel diagnostic targets and therapeutic agents for cardiovascular diseases. Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

32132 molecules can also act as novel diagnostic targets and therapeutic agents for controlling immunological disorders. Examples of hematopoietic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

The 21953 nucleic acid and protein of the invention can be used to treat and/or diagnose a variety of other conditions, in addition to the ones described above (see "Methods of Treatment" for additional examples).

The 32132 protein, fragments thereof, and derivatives and other variants of the sequence in SEQ ID NO:20 thereof are collectively referred to as "polypeptides or proteins of the invention" or "32132 polypeptides or proteins". Nucleic acid molecules encoding such polypeptides or proteins are collectively referred to as "nucleic acids of the invention" or "32132 nucleic acids." 32132 molecules refer to 32132 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 32132 protein, preferably a mammalian 32132 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 32132 protein having less than about 30%, 20%, 10% and more preferably 5% (by dry weight), of non-32132 protein (also referred to herein as a "contaminating protein"), or of chemical precursors or non-32132 chemicals. When the 32132 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 32132 (e.g., the sequence of SEQ ID NO:19 or 21, without abolishing, or more preferably without substantially altering, a biological activity, whereas an "essential" amino acid residue results in such a change. For example, amino acid residues that are conserved among the polypeptides of the present invention, e.g., those present in the fucosyltransferase domain, are predicted to be not particularly amenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 32132 protein is preferably replaced with another amino acid residue from the same side chain family. Alternatively, in another embodiment, mutations can be introduced randomly along all or part of a 32132 coding sequence, such as by saturation mutagenesis, and the resultant mutants can be screened for 32132 biological activity to identify mutants that retain activity. Following mutagenesis of SEQ ID NO:19 or 21, the encoded protein can be expressed recombinantly and the activity of the protein can be determined.

As used herein, a "biologically active portion" of a 32132 protein includes a fragment of a 32132 protein which participates in an interaction between a 32132 molecule and a non-32132 molecule. Biologically active portions of a 32132 protein include peptides comprising amino acid sequences sufficiently homologous to or derived from the amino acid sequence of the 32132 protein, e.g., the amino acid sequence shown in SEQ ID NO:20, which include less amino acids than the full length 32132 proteins, and exhibit at least one activity of a 32132 protein. Typically, biologically active portions comprise a domain or motif with at least one activity of the 32132 protein, e.g., fucosyltransferase activity. A biologically active portion of a 32132 protein can be a polypeptide which is, for example, 10, 25, 50, 100, 200 or more amino acids in length. Biologically active portions of a 32132 protein can be used as targets for developing agents which modulate a 32132 mediated activity, e.g., fucosyltransferase activity.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 32132 amino acid sequence of SEQ ID NO:20 having 360 amino acid residues, at least 50, preferably at least 100, more preferably at least 150, even more preferably at least 200, and even more preferably at least 250, or 370 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to 26886 nucleic acid molecules of the invention. BLAST protein searches can be performed with the XBLAST program, score=50, wordlength=3 to obtain amino acid sequences homologous to 32132 protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

Particular 32132 polypeptides of the present invention have an amino acid sequence substantially identical to the amino acid sequence of SEQ ID NO:20. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:20 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:19 or 21 are termed substantially identical.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 32132 polypeptide described herein, e.g., a full-length 32132 protein or a fragment thereof, e.g., a biologically active portion of 32132 protein. Also included is a nucleic acid fragment suitable for use as a hybridization probe, which can be used, e.g., to a identify nucleic acid molecule encoding a polypeptide of the invention, 32132 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:19, or a portion of any of these nucleotide sequences. In one embodiment, the nucleic acid molecule includes sequences encoding the human 32132 protein (i.e., "the coding region", from nucleotides 236-1711 of SEQ ID NO:19), as well as 5' untranslated sequences (nucleotides 1-235 of SEQ ID NO:19). Alternatively, the nucleic acid molecule can include only the coding region of SEQ ID NO:19(e.g., nucleotides 236-1711, corresponding to SEQ ID NO:21) and, e.g., no flanking sequences which normally accompany the subject sequence. In another embodiment, the nucleic acid molecule encodes a sequence corresponding to the extracellular region of the protein, from about amino acid 29 to amino acid 492 of SEQ ID NO:20.

In another embodiment, an isolated nucleic acid molecule of the invention includes a nucleic acid molecule which is a complement of the nucleotide sequence shown in SEQ ID NO:19 or 21, or a portion of any of these nucleotide sequences. In other embodiments, the nucleic acid molecule of the invention is sufficiently complementary to the nucleotide sequence shown in SEQ ID NO:19 or 21, such that it can hybridize to the nucleotide sequence shown in SEQ ID NO:19 or 21, thereby forming a stable duplex.

In one embodiment, an isolated nucleic acid molecule of the present invention includes a nucleotide sequence which is at least about 60%, 65%, 70%, 75%, 80%, 85%, 86%, 90%, 91%, 92%, 93%, 94%, 95%, 96%, 97%, 98%, 99%, or more homologous to the entire length of the nucleotide sequence shown in SEQ ID NO:19 or 21, or a portion, preferably of the same length, of any of these nucleotide sequences.

32132 Nucleic Acid Fragments

A nucleic acid molecule of the invention can include only a portion of the nucleic acid sequence of SEQ ID NO:19 or 21. For example, such a nucleic acid molecule can include a fragment which can be used as a probe or primer or a fragment encoding a portion of a 32132 protein, e.g., an immunogenic or biologically active portion of a 32132 protein. A fragment can comprise nucleotides 404 to 1300 of SEQ ID NO:19, which encodes a fucosyltransferase domain of human 32132. The nucleotide sequence determined from the cloning of the 32132 gene allows for the generation of probes and primers designed for use in identifying and/or cloning other 32132 family members, or fragments thereof, as well as 32132 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 200 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, sequence, or functional site described herein.

32132 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:19 or 21, or of a naturally occurring allelic variant or mutant of SEQ ID NO:19 or 21.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes the fucosyltransferase domain, e.g., about nucleotides 404 to 1300 of SEQ ID NO:19; the extracellular domain, e.g., about nucleotides 320 to 1711 of SEQ ID NO:19; or any other domain, region, or sequence described herein of human 32132.

In another embodiment a set of primers is provided, e.g., primers suitable for use in a PCR, which can be used to amplify a selected region of a 32132 sequence, e.g., a domain, region, site, or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying the sequence encoding the fucosyltransferase domain of SEQ ID NO:20 are provided.

A nucleic acid fragment can encode an epitope-bearing region of a polypeptide described herein.

A nucleic acid fragment encoding a "biologically active portion of a 32132 polypeptide" can be prepared by isolating a portion of the nucleotide sequence of SEQ ID NO:19 or 21, which encodes a polypeptide having a 32132 biological activity (e.g., the biological activities of the 32132 proteins are described herein), expressing the encoded portion of the 32132 protein (e.g., by recombinant expression in vitro) and assessing the activity of the encoded portion of the 32132 protein. For example, a nucleic acid fragment encoding a biologically active portion of 32132 includes a fucosyltransferase domain, e.g., amino acid residues 29 to 388 of SEQ ID NO:20. A nucleic acid fragment encoding a biologically active portion of a 32132 polypeptide may comprise a nucleotide sequence which is greater than 400 or more nucleotides in length.

In preferred embodiments, a nucleic acid includes a nucleotide sequence which is about 300, 400, 500, 600, 700, 800, 900, 1000, 1100, 1200, 1300, 1500, 1700, 1740, 1900, 2200, 2400 or more nucleotides in length and hybridizes under a stringency condition described herein to a nucleic acid molecule of SEQ ID NO:19, or SEQ ID NO:21. In a preferred embodiment, a nucleic acid includes at least one contiguous nucleotide from the region of about nucleotides 1-200, 100-300, 200-429, 250-429, 450-800, 750-938, 880-938, 880-1100, 1100-1334, 1100-1361, 1300-1550, 1500-1700, 1600-1811, 1760-2000, or 2200-2557.

32132 Nucleic Acid Variants

The invention further encompasses nucleic acid molecules that differ from the nucleotide sequence shown in SEQ ID NO:19 or 21. Such differences can be due to degeneracy of the genetic code (and result in a nucleic acid which encodes the same 32132 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:20. If alignment is needed for this comparison the sequences should be aligned for maximum homology. "Looped" out sequences from deletions or insertions, or mismatches, are considered differences. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one colon, at preferably at least 10%, or 20% of the codons has been altered such that the sequence is optimized for expression in e. coli, yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:19 or 21, e.g., as follows: by at least one but less than 10, 20, 30, or 40 nucleotides; at least one but less than 1%, 5%, 10% or 20% of the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:20 or a fragment of this sequence. Such nucleic acid molecules can readily be identified as being able to hybridize under stringent conditions, to the nucleotide sequence shown in SEQ ID NO:20 or a fragment of the sequence. Nucleic acid molecules corresponding to orthologs, homologs, and allelic variants of the 32132 cDNAs of the invention can further be isolated by mapping to the same chromosome or locus as the 32132 gene.

Preferred variants include those that are correlated with fucosyltransferase activity.

Allelic variants of 32132, e.g., human 32132, include both functional and non-functional proteins. Functional allelic variants are naturally occurring amino acid sequence variants of the 32132 proteins within a population that maintain fucosyltransferase activity. Functional allelic variants will typically contain only conservative substitution of one or more amino acids of SEQ ID NO:20, or substitution, deletion or insertion of non-critical residues in non-critical regions of the protein. Non-functional allelic variants are naturally-occurring amino acid sequence variants of the 32132, e.g., human 32132, proteins within a population that do not have the ability to transfer a fucosyl group to, e.g., N-acetylglucosamine. Non-functional allelic variants will typically contain a non-conservative substitution, a deletion, or insertion, or premature truncation of the amino acid sequence of SEQ ID NO:20, or a substitution, insertion, or deletion in critical residues or critical regions of the protein.

Moreover, nucleic acid molecules encoding other 32132 family members and, thus, which have a nucleotide sequence which differs from the 32132 sequences of SEQ ID NO:19 or 21, are intended to be within the scope of the invention.

Antisense Nucleic Acid Molecules, Ribozymes and Modified 32132 Nucleic Acid Molecules In another aspect, the invention features, an isolated nucleic acid molecule which is antisense to 32132. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 32132 coding strand, or to only a portion thereof (e.g., the coding region of human 32132 corresponding to SEQ ID NO:21). In another embodiment, the antisense nucleic acid molecule is antisense to a "non-coding region" of the coding strand of a nucleotide sequence encoding 32132 (e.g., the 5' and 3' untranslated regions).

An antisense nucleic acid can be designed such that it is complementary to the entire coding region of 32132 mRNA, but more preferably is an oligonucleotide which is antisense to only a portion of the coding or noncoding region of 32132 mRNA. For example, the antisense oligonucleotide can be complementary to the region surrounding the translation start site of 32132 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 32132 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. A ribozyme having specificity for a 32132-encoding nucleic acid can include one or more sequences complementary to the nucleotide sequence of a 32132 cDNA disclosed herein (i.e., SEQ ID NO:19 or 21), and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a 32132-encoding mRNA. See, e.g., Cech et al. U.S. Pat. No. 4,987,071; and Cech et al. U.S. Pat. No. 5,116,742. Alternatively, 32132 mRNA can be used to select a catalytic RNA having a specific ribonuclease activity from a pool of RNA molecules. See, e.g., Bartel, D. and Szostak, J. W. (1993) *Science* 261:1411-1418.

32132 gene expression can be inhibited by targeting nucleotide sequences complementary to the regulatory region of the 32132 (e.g., the 32132 promoter and/or enhancers) to form triple helical structures that prevent transcription of the 32132 gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15. The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 3132 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. (1996) *Proc. Natl. Acad. Sci. USA* 93:14670-14675.

PNAs of 32132 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 32132 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 32132 nucleic acid of the invention, two complementary regions one having a fluorophore and one a quencher such that the molecular beacon is useful for quantitating the presence of the 32132 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 32132 Polypeptides

In another aspect, the invention features, an isolated 32132 protein, or fragment, e.g., a biologically active portion, for use as immunogens or antigens to raise or test (or more generally to bind) anti-32132 antibodies. 32132 protein can be isolated from cells or tissue sources using standard protein purification techniques. 32132 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and posttranslational events. The polypeptide can be expressed in systems, e.g., cultured cells, which result in substantially the same posttranslational modifications present when expressed the polypeptide is expressed in a native cell, or in systems which result in the alteration or omission of posttranslational modifications, e.g., glycosylation or cleavage, present when expressed in a native cell.

In a preferred embodiment, a 32132 polypeptide has one or more of the following characteristics:

(i) the ability to promote transfer of a fucose group from one molecule to another;

(ii) a molecular weight (e.g., a deduced molecular weight, preferably ignoring any contribution of post translational modifications), amino acid composition, or other physical characteristic of a 32132 fucosyltransferase polypeptide, e.g., a polypeptide of SEQ ID NO:20;

(iii) an overall sequence similarity of at least 60%, more preferably at least 70, 80, 90, or 95%, with a polypeptide of SEQ ID NO:20;

(iv) a fucosyltransferase domain which is preferably about 70%, 80%, 90% or 95% identical with amino acid residues 29-388 of SEQ ID NO:20;

(v) a alpha-3-fucosyltransferase signature motif, located at about amino acids 274 to 304 of SEQ ID NO:20;

(vi) a transmembrane domain located at about amino acid residues 8 to 28 of SEQ ID NO:20;

(vii) a non-transmembrane region, e.g., an extracellular region, located at about amino acid residues 29 to 492 of SEQ ID NO:20; or (viii) at least 3, preferably 6, and most preferably 10 of the cysteines found in the amino acid sequence of the native protein.

In a preferred embodiment the 32132 protein, or fragment thereof, differs from the corresponding sequence of SEQ ID NO:20. In one embodiment it differs by at least one but by less than 15, 10 or 5 amino acid residues. In another it differs from the corresponding sequence in SEQ ID NO:20 by at least one residue but less than 20%, 15%, 10% or 5% of the residues in it differ from the corresponding sequence in SEQ ID NO:20. (If this comparison requires alignment, the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the fucosyltransferase domain, e.g., about amino acid residues 57 to 355 of SEQ ID NO:20. In another preferred embodiment one or more differences are in the fucosyltransferase domain.

Other embodiments include a protein that contain one or more changes in amino acid sequence, e.g., a change in an amino acid residue which is not essential for activity. Such 32132 proteins differ in amino acid sequence from SEQ ID NO:20, yet retain biological activity.

In one embodiment, the protein includes an amino acid sequence at least about 60%, 65%, 70%, 75%, 80%, 85%, 90%, 95%, 98%, or more homologous to SEQ ID NO:20.

A 32132 protein or fragment is provided which varies from the sequence of SEQ ID NO:20 by at least one, but less than 15, 10 or 5, amino acid residues defined by the region about amino acid residues 29 to 492 of SEQ ID NO:20, but which does not differ from SEQ ID NO:20 in the region about amino acid residues 160 to 190 and 272 to 307 of SEQ ID NO:20. (If this comparison requires alignment, the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 32132 protein includes the fucosyltransferase domain. Moreover, other biologically active portions, in which other regions of the protein are deleted, can be prepared by recombinant techniques and evaluated for one or more of the functional activities of a native 32132 protein.

In a preferred embodiment, the 32132 protein has an amino acid sequence shown in SEQ ID NO:20. In other embodiments, the 32132 protein is substantially identical to SEQ ID NO:20. In yet another embodiment, the 32132 protein is substantially identical to SEQ ID NO:20 and retains the functional activity of the protein of SEQ ID NO:20, as described in detail herein 32132 Chimeric or Fusion Proteins In another aspect, the invention provides 32132 chimeric or fusion proteins. As used herein, a 32132 "chimeric protein" or "fusion protein" includes a 32132 polypeptide linked to a non-32132 polypeptide. A "non-32132 polypeptide" refers to a polypeptide having an amino acid sequence corresponding to a protein which is not substantially homologous to the 32132 protein, e.g., a protein which is different from the 32132 protein and which is derived from the same or a different organism. The 32132 polypeptide of the fusion protein can correspond to all or a portion, e.g., a fragment described herein of a 32132 amino acid sequence. In a preferred embodiment, a 32132 fusion protein includes at least one (or two) biologically active portion of a 32132 protein. The non-32132 polypeptide can be fused to the N-terminus or C-terminus of the 32132 polypeptide.

The fusion protein can include a moiety which has a high affinity for a ligand. For example, the fusion protein can be a GST-32132 fusion protein in which the 32132 sequences are fused to the C-terminus of the GST sequences. Such fusion proteins can facilitate the purification of recombinant 32132. Alternatively, the fusion protein can be a 32132 protein containing a heterologous signal sequence at its N-terminus. In certain host cells (e.g., mammalian host cells), expression and/or secretion of 32132 can be increased through use of a heterologous signal sequence.

Fusion proteins can include all or a part of a serum protein, e.g., an IgG constant region, or human serum albumin.

The 32132 fusion proteins of the invention can be incorporated into pharmaceutical compositions and administered to a subject in vivo. The 32132 fusion proteins can be used to affect the bioavailability of a 32132 substrate. 32132 fusion proteins may be useful therapeutically for the treatment of disorders caused by, for example, (i) aberrant modification or mutation of a gene encoding a 32132 protein; (ii) mis-regulation of the 32132 gene; and (iii) aberrant post-translational modification of a 32132 protein.

Moreover, the 32132-fusion proteins of the invention can be used as immunogens to produce anti-32132 antibodies in a subject, to purify 32132 ligands and in screening assays to identify molecules which inhibit the interaction of 32132 with a 32132 substrate.

Expression vectors are commercially available that already encode a fusion moiety (e.g., a GST polypeptide). A 32132-encoding nucleic acid can be cloned into such an expression vector such that the fusion moiety is linked in-frame to the 32132 protein.

Variants of 32132 Proteins

In another aspect, the invention also features a variant of a 32132 polypeptide, e.g., which functions as an agonist (mimetics) or as an antagonist. Variants of the 32132 proteins can be generated by mutagenesis, e.g., discrete point mutation, the insertion or deletion of sequences or the truncation of a 32132 protein. An agonist of the 32132 proteins can retain substantially the same, or a subset, of the biological activities of the naturally occurring form of a 32132 protein. An antagonist of a 32132 protein can inhibit one or more of the activities of the naturally occurring form of the 32132 protein by, for example, competitively modulating a 32132-mediated activity of a 32132 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 32132 protein.

Variants of a 32132 protein can be identified by screening combinatorial libraries of mutants, e.g., truncation mutants, of a 32132 protein for agonist or antagonist activity.

Libraries of fragments, e.g., N terminal, C terminal, or internal fragments, of a 32132 protein coding sequence can be used to generate a variegated population of fragments for screening and subsequent selection of variants of a 32132 protein.

Variants in which a cysteine residue is added or deleted or in which a residue which is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify 32132 variants (Arkin and Yourvan (1992) *Proc. Natl. Acad. Sci. USA* 89:7811-7815; Delgrave et al. (1993) *Protein Engineering* 6(3):327-331).

Cell based assays can be exploited to analyze a variegated 32132 library. For example, a library of expression vectors can be transfected into a cell line, e.g., a cell line, which ordinarily responds to 32132 in a substrate-dependent manner. The transfected cells are then contacted with 32132 and the effect of the expression of the mutant on signaling by the 32132 substrate can be detected, e.g., by changes in the glycosylation epitopes, e.g., epitopes including fucose, present on the cell surface. Plasmid DNA can then be recovered from the cells which score for inhibition, or alternatively, potentiation of signaling by the 32132 substrate, and the individual clones further characterized.

In another aspect, the invention features a method of making a 32132 polypeptide, e.g., a peptide having a non-wild type activity, e.g., an antagonist, agonist, or super agonist of a naturally occurring 32132 polypeptide. The method includes: altering the sequence of a 32132 polypeptide, e.g., by substitution or deletion of one or more residues of a non-conserved region, a domain or residue disclosed herein, and testing the altered polypeptide for the desired activity.

In another aspect, the invention features a method of making a fragment or analog of a 32132 polypeptide a biological activity of a naturally occurring 32132 polypeptide. The method includes: altering the sequence, e.g., by substitution or deletion of one or more residues, of a 32132 polypeptide, e.g., altering the sequence of a non-conserved region, or a domain or residue described herein, and testing the altered polypeptide for the desired activity.

Anti-32132 Antibodies

In another aspect, the invention provides an anti-32132 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-32132 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH— terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 32132 polypeptide or fragment thereof Examples of antigen-binding fragments of the anti-32132 antibody include, but are not limited to: (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-32132 antibody can be a polyclonal or a monoclonal antibody. In other embodiments, the antibody can be recombinantly produced, e.g., produced by phage display or by combinatorial methods.

Phage display and combinatorial methods for generating anti-32132 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the anti-32132 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An anti-32132 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559). A humanized or CDR-grafted antibody will have at least one or two but generally all three recipient CDR's (of heavy and or light imnuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 32132 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 32132 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In preferred embodiments an antibody can be made by immunizing with purified 32132 antigen, or a fragment thereof, e.g., a fragment described herein, membrane associated antigen, tissue, e.g., crude tissue preparations, whole cells, preferably living cells, lysed cells, or cell fractions, e.g., membrane fractions.

A full-length 32132 protein or, antigenic peptide fragment of 32132 can be used as an immunogen or can be used to identify anti-32132 antibodies made with other immunogens, e.g., cells, membrane preparations, and the like. The antigenic peptide of 32132 should include at least 8 amino acid residues of the amino acid sequence shown in SEQ ID NO:20 and encompasses an epitope of 32132. Preferably, the antigenic peptide includes at least 10 amino acid residues, more preferably at least 15 amino acid residues, even more preferably at least 20 amino acid residues, and most preferably at least 30 amino acid residues.

Fragments of 32132 which include residues about 8 to 28, about 75 to 91, or about 293 to 305 can be used to make, e.g., used as immunogens or used to characterize the specificity of an antibody, antibodies against hydrophilic regions of the 32132 protein. Similarly, fragments of 32132 which include residues about 60 to 74, about 190 to 206, or about 306 to 320 can be used to make an antibody against a hydrophobic region of the 32132 protein; fragments of 32132 which include residues about 61 to 81, about 230 to 250, or about 325 to 350 can be used to make an antibody against an extracellular region of the 32132 protein; a fragment of 32132 which includes residues about 1 to 8 can be used to make an antibody against an intracellular region of the 32132 protein; fragments of 32132 which include residues about 119 to 136, about 172 to 190, or about 272 to 304 can be used to make an antibody against the fucosyltransferase domain of the 32132 protein.

Antibodies reactive with, or specific for, any of these regions, or other regions or domains described herein are provided.

Antibodies which bind only native 32132 protein, only denatured or otherwise non-native 32132 protein, or which bind both, are with in the invention. Antibodies with linear or conformational epitopes are within the invention. Conformational epitopes can sometimes be identified by identifying antibodies which bind to native but not denatured 32132 protein.

Preferred epitopes encompassed by the antigenic peptide are regions of 32132 are located on the surface of the protein, e.g., hydrophilic regions, as well as regions with high antigenicity. For example, an Emini surface probability analysis of the human 32132 protein sequence can be used to indicate the regions that have a particularly high probability of being localized to the surface of the 32132 protein and are thus likely to constitute surface residues useful for targeting antibody production.

In a preferred embodiment the antibody can bind to the extracellular portion of the 32132 protein, e.g., it can bind to a whole cell which expresses the 32132 protein. In another embodiment, the antibody can bind to an intracellular portion of the 32132 protein. In preferred embodiments antibodies can bind one or more of purified antigen, membrane associated antigen, tissue, e.g., tissue sections, whole cells, preferably living cells, lysed cells, cell fractions, e.g., membrane fractions.

The antibody can bind near a substrate binding region of the 32132 polypeptide, and alter, e.g., enhance or inhibit, the activity of the 32132 polypeptide. In a preferred embodiment, the antibody inhibits the activity of the 32132 polypeptide. The antibody can also binding in a conserved region of the 32132 polypeptide, e.g., in a alpha-3-fucosyl-trasnferase signature motif, at about amino acid 274 to 304 of SEQ ID NO:20.

The anti-32132 antibody can be a single chain antibody. A single-chain antibody (scFV) may be engineered (see, for example, Colcher, D. et al. (1999) *Ann NY Acad Sci* 880: 263-80; and Reiter, Y. (1996) *Clin Cancer Res* 2:245-52). The single chain antibody can be dimerized or multimerized to generate multivalent antibodies having specificities for different epitopes of the same target 32132 protein.

In a preferred embodiment the antibody has: effector function; and can fix complement. In other embodiments the antibody does not; recruit effector cells; or fix complement.

In a preferred embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

The antibody can be coupled to a toxin, e.g., a polypeptide toxin, e.g., ricin or diptheria toxin or active fragment hereof, or a radionuclide, or imaging agent, e.g. a radioactive, enzymatic, or other, e.g., imaging agent, e.g., a NMR contrast agent. Labels which produce detectable radioactive emissions or fluorescence are preferred.

An anti-32132 antibody (e.g., monoclonal antibody) can be used to isolate 32132 by standard techniques, such as affinity chromatography or immunoprecipitation. Moreover, an anti-32132 antibody can be used to detect 32132 protein (e.g., in a cellular lysate or cell supernatant) in order to evaluate the abundance and pattern of expression of the protein. Anti-32132 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes a nucleic acid which encodes an anti-32132 antibody, e.g., an anti-32132 antibody described herenin. Also included are vectors which include the nucleic acid and cells transformed with the nucleic acid, particularly cells which are useful for producing an antibody, e.g., mammalian cells, e.g. CHO or lymphatic cells.

The invention also includes cell lines, e.g., hybridomas, which make an anti-32132 antibody, e.g., and antibody described herein, and method of using said cells to make a 32132 antibody.

32132 Recombinant Expression Vectors, Host Cells, and Genetically Engineered Cells In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 32132 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 32132 proteins, mutant forms of 32132 proteins, fusion proteins, and the like).

The recombinant expression vectors of the invention can be designed for expression of 32132 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 32132 activity assays, (e.g., direct assays or competitive assays described in detail below), or to generate antibodies specific for 32132 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The 32132 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).s In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub et al. (1986) "Antisense RNA as a molecular tool for genetic analysis," *Reviews—Trends in Genetics,* Vol. 1(1).

Another aspect of the invention provides a host cell which includes a nucleic acid molecule described herein, e.g., a 32132 nucleic acid molecule within a recombinant expression vector or a 32132 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 32132 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation A host cell of the invention can be used to produce (i.e., express) a 32132 protein. Accordingly, the invention further provides methods for producing a 32132 protein using the host cells of the invention. In one embodiment, the method includes culturing the host cell of the invention (into which a recombinant expression vector encoding a 32132 protein has been introduced) in a suitable medium such that a 32132 protein is produced. In another embodiment, the method further includes isolating a 32132 protein from the medium or the host cell.

In another aspect, the invention features a cell or purified preparation of cells which include a 32132 transgene, or which otherwise misexpress 32132. The cell preparation can consist of human or non-human cells, e.g., rodent cells, e.g., mouse or rat cells, rabbit cells, or pig cells. In preferred embodiments, the cell or cells include a 32132 transgene, e.g., a heterologous form of a 32132, e.g., a gene derived from humans (in the case of a non-human cell). The 32132 transgene can be misexpressed, e.g., overexpressed or underexpressed. In other preferred embodiments, the cell or cells include a gene which misexpress an endogenous 32132, e.g., a gene the expression of which is disrupted, e.g., a knockout. Such cells can serve as a model for studying disorders which are related to mutated or mis-expressed 32132 alleles or for use in drug screening.

In another aspect, the invention features, a human cell, e.g., a hematopoietic stem cell, transformed with nucleic acid which encodes a subject 32132 polypeptide.

Also provided are cells, preferably human cells, in which an endogenous 32132 is under the control of a regulatory sequence that does not normally control the expression of the endogenous 32132 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 32132 gene. For example, an endogenous 32132 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 32132 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (2001) *Nat. Biotechnol.* 19:35; and U.S. Pat. No. 5,876,742. Production of 32132 polypeptide can be regulated in the subject by administering an agent (e.g., a steroid hormone) to the subject. In another preferred embodiment, the implanted recombinant cells express and secrete an antibody specific for a 32132 polypeptide. The antibody can be any antibody or any antibody derivative described herein.

32132 Transgenic Animals

The invention provides non-human transgenic animals. Such animals are useful for studying the function and/or activity of a 32132 protein and for identifying and/or evaluating modulators of 32132 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 32132 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 32132 protein to particular cells. A transgenic founder animal can be identified based upon the presence of a 32132 transgene in its genome and/or expression of 32132 mRNA in tissues or cells of the animals. A transgenic founder animal can then be used to breed additional animals carrying the transgene. Moreover, transgenic animals carrying a transgene encoding a 32132 protein can further be bred to other transgenic animals carrying other transgenes.

32132 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses of 32132

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); c) methods of treatment (e.g., therapeutic and prophylactic); and d) in vitro modification of compounds.

The isolated nucleic acid molecules of the invention can be used, for example, to express a 32132 protein (e.g., via a recombinant expression vector in a host cell in gene therapy applications), to detect a 32132 mRNA (e.g., in a biological sample) or a genetic alteration in a 32132 gene, and to modulate 32132 activity, as described further below. The 32132 proteins can be used to treat disorders characterized by insufficient or excessive production of a 32132 substrate or production of 32132 inhibitors. In addition, the 32132 proteins can be used to screen for naturally occurring 32132 substrates, to screen for drugs or compounds which modulate 32132 activity, as well as to treat disorders characterized by insufficient or excessive production of 32132 protein or production of 32132 protein forms which have decreased, aberrant or unwanted activity compared to 32132 wild type protein (e.g., 32132 proteins that stimulate aberrant cellular proliferation and/or differentiation). Moreover, the anti-32132 antibodies of the invention can be used to detect and isolate 32132 proteins, regulate the bioavailability of 32132 proteins, and modulate 32132 activity.

The 32132 polypeptide of the invention can also be used in a method of modifying a compound, e.g., a method of synthesizing a fucose linked compound. The method includes: providing a compound of interest, e.g., a sugar or glycoprotein in a solvent, e.g., a reaction-compatible solvent; combining the compound of interest, a 32132 polypeptide described herein, and a fucose compound, e.g., GDP-fucose, in the solvent; and maintaining the solvent mixture under conditions such that the fucose compound is attached to the compound of interest. The method can further include isolating the compound of interest from the solvent. For example, the sugar can be N-acetylglucosamine or galactose. Such a method can be useful for modifying glycoproteins in vitro, e.g., prior to tissue implantation or cell culture, and for synthesizing chemicals, e.g., for laboratory or pharmaceutical use.

A method of evaluating a compound for the ability to interact with, e.g., bind, a subject 32132 polypeptide is provided. The method includes: contacting the compound with the subject 32132 polypeptide; and evaluating ability of the compound to interact with, e.g., to bind or form a complex with the subject 32132 polypeptide. This method can be performed in vitro, e.g., in a cell free system, or in vivo, e.g., in a two-hybrid interaction trap assay. This method can be used to identify naturally occurring molecules which interact with subject 32132 polypeptide. It can also be used to find natural or synthetic inhibitors of a subject 32132 polypeptide. Screening methods are discussed in more detail below.

32132 Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 32132 proteins, have a stimulatory or inhibitory effect on, for example, 32132 expression or 32132 activity, or have a stimulatory or inhibitory effect on, for example, the expression or activity of a 32132 substrate. Compounds thus identified can be used to modulate the activity of target gene products (e.g., 32132 genes) in a therapeutic protocol, to elaborate the biological function of the target gene product, or to identify compounds that disrupt normal target gene interactions.

In one embodiment, the invention provides assays for screening candidate or test compounds which are substrates of a 32132 protein or polypeptide or a biologically active portion thereof. In another embodiment, the invention provides assays for screening candidate or test compounds which bind to or modulate the activity of a 32132 protein or polypeptide or a biologically active portion thereof.

In one embodiment, an activity associated with a 32132 protein, e.g., a fucosyltransferase activity, can be assayed using florescence activated cell sorting (FACS) analysis and an antibody specific to cell surface glycoproteins that contain fucose modifications, e.g., cell surface glycoproteins that contain alpha-(1,3) linked fucose. This fucosyltransferase activity assay, as well as other in vitro and in vivo assays for fucosyltransferase activity, has been well documented in the art (see, e.g., Weston et al. (1999), *Cancer Res* 59(9), 2127-35).

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive. See, e.g., Zuckermann, R. N. et al. *J. Med. Chem.* 1994, 37: 2678-85.); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell which expresses a 32132 protein or biologically active portion thereof is contacted with a test compound, and the ability of the test compound to modulate 32132 activity is determined. Determining the ability of the test compound to modulate 32132 activity can be accomplished by monitoring, for example, the extent of fucose transfer to another molecule, e.g., a molecule containing N-acetylglucosamine. The cell, for example, can be of mammalian origin, e.g., human.

The ability of the test compound to modulate 32132 binding to a compound, e.g., a 32132 substrate, or to bind to 32132 can also be evaluated. This can be accomplished, for example, by coupling the compound, e.g., the substrate, with a radioisotope or enzymatic label such that binding of the compound, e.g., the substrate, to 32132 can be determined by detecting the labeled compound, e.g., substrate, in a complex. Alternatively, 32132 could be coupled with a radioisotope or enzymatic label to monitor the ability of a test compound to modulate 32132 binding to a 32132 substrate in a complex. For example, compounds (e.g., 32132 substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 32132 substrate) to interact with 32132 with or without the labeling of any of the interactants can be evaluated. For example, a microphysiometer can be used to detect the interaction of a compound with 32132 without the labeling of either the compound or the 32132. McConnell et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 32132 protein.

In yet another embodiment, a cell-free assay is provided in which a 32132 protein or biologically active portion thereof is contacted with a test compound and the ability of the test compound to bind to the 32132 protein or biologically active portion thereof is evaluated. Preferred biologically active portions of the 32132 proteins to be used in assays of the present invention include fragments which participate in interactions with non-32132 molecules, e.g., fragments with high surface probability scores.

Soluble and/or membrane-bound forms of isolated proteins (e.g., 32132 proteins engineered to contain a transmembrane domain or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 32132 protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 32132, an anti-32132 antibody, or its target molecule to facilitate separation of complexed from uncomplexed forms of one or both of the proteins, as well as to accommodate automation of the assay. Binding of a test compound to a 32132 protein, or interaction of a 32132 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/32132 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 32132 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 32132 binding or activity determined using standard techniques.

Other techniques for immobilizing either a 32132 protein or a target molecule on matrices include using conjugation of biotin and streptavidin. Biotinylated 32132 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 32132 protein or target molecules but which do not interfere with binding of the 32132 protein to its target molecule. Such antibodies can be derivatized to the wells of the plate, and unbound target or 32132 protein trapped in the wells by antibody conjugation. Methods for detecting such complexes, in addition to those described above for the GST-immobilized complexes, include immunodetection of complexes using antibodies reactive with the 32132 protein or target molecule, as well as enzyme-linked assays which rely on detecting an enzymatic activity associated with the 32132 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., *Trends Biochem Sci August* 1993; 18(8):284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard (1998) *J. Mol. Recognit.* 11:141-148; Hage (1997) *J. Chromatogr. B. Biomed. Sci. Appl.* 699:499-525. Further, fluorescence energy transfer may also be conveniently utilized, as described herein, to detect binding without further purification of the complex from solution.

In a preferred embodiment, the assay includes contacting the 32132 protein or biologically active portion thereof with a known compound which binds 32132 to form an assay mixture, contacting the assay mixture with a test compound, and determining the ability of the test compound to interact with a 32132 protein, wherein determining the ability of the test compound to interact with a 32132 protein includes determining the ability of the test compound to preferentially bind to 32132 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 32132 genes herein identified. In an alternative embodiment, the invention provides methods for determining the ability of the test compound to modulate the activity of a 32132 protein through modulation of the activity of a downstream effector of a 32132 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 32132 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993), *Biotechniques* 14:920-924; Iwabuchi et al. (1993) *Oncogene* 8:1693-1696; and Brent WO94/10300), to identify other proteins, which bind to or interact with 32132 ("32132-binding proteins" or "32132-bp") and are involved in 32132 activity. Such 32132-bps can be activators or inhibitors of signals by the 32132 proteins or 32132 targets as, for example, downstream elements of a 32132-mediated signaling pathway.

The two-hybrid system is based on the modular nature of most transcription factors, which consist of separable DNA-binding and activation domains. Briefly, the assay utilizes two different DNA constructs. In one construct, the gene that codes for a 32132 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 32132 protein can be the fused to the activator domain.) If the "bait" and the "prey" proteins are able to interact, in vivo, forming a 32132-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 32132 protein.

In another embodiment, modulators of 32132 expression are identified. For example, a cell or cell free mixture is contacted with a candidate compound and the expression of 32132 mRNA or protein evaluated relative to the level of expression of 32132 mRNA or protein in the absence of the candidate compound. When expression of 32132 mRNA or protein is greater in the presence of the candidate compound than in its absence, the candidate compound is identified as a stimulator of 32132 mRNA or protein expression. Alternatively, when expression of 32132 mRNA or protein is less (statistically significantly less) in the presence of the candidate compound than in its absence, the candidate compound is identified as an inhibitor of 32132 mRNA or protein expression. The level of 32132 mRNA or protein expression can be determined by methods described herein for detecting 32132 mRNA or protein.

In another aspect, the invention pertains to a combination of two or more of the assays described herein. For example, a modulating agent can be identified using a cell-based or a cell free assay, and the ability of the agent to modulate the activity of a 32132 protein can be confirmed in vivo, e.g., in an animal such as an animal model for a cellular proliferative and/or differentiative disorder or an autoimmunity disease.

This invention further pertains to novel agents identified by the above-described screening assays. Accordingly, it is within the scope of this invention to further use an agent identified as described herein (e.g., a 32132 modulating agent, an antisense 32132 nucleic acid molecule, a 32132-specific antibody, or a 32132-binding partner) in an appropriate animal model to determine the efficacy, toxicity, side effects, or mechanism of action, of treatment with such an agent. Furthermore, novel agents identified by the above-described screening assays can be used for treatments as described herein.

32132 Detection Assays

Portions or fragments of the nucleic acid sequences identified herein can be used as polynucleotide reagents. For example, these sequences can be used to: (i) map their respective genes on a chromosome, e.g., to locate gene regions associated with genetic disease or to associate 32132 with a disease; (ii) identify an individual from a minute biological sample (tissue typing); and (iii) aid in forensic identification of a biological sample. These applications are described in the subsections below.

32132 Chromosome Mapping

The 32132 nucleotide sequences or portions thereof can be used to map the location of the 32132 genes on a chromosome. This process is called chromosome mapping. Chromosome mapping is useful in correlating the 32132 sequences with genes associated with disease.

Briefly, 32132 genes can be mapped to chromosomes by preparing PCR primers (preferably 15-25 bp in length) from the 32132 nucleotide sequences. These primers can then be used for PCR screening of somatic cell hybrids containing individual human chromosomes. Only those hybrids containing the human gene corresponding to the 32132 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) Science 220:919-924).

Other mapping strategies, e.g., in situ hybridization (described in Fan, Y. et al. (1990) Proc. Natl. Acad. Sci. USA, 87:6223-27), pre-screening with labeled flow-sorted chromosomes, and pre-selection by hybridization to chromosome specific cDNA libraries can be used to map 32132 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783-787.

Moreover, differences in the DNA sequences between individuals affected and unaffected with a disease associated with the 32132 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

32132 Tissue Typing 32132 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 32132 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:19 can provide positive individual identification with a panel of perhaps 10 to 1,000 primers which each yield a noncoding amplified sequence of 100 bases. If predicted coding sequences, such as those in SEQ ID NO:21 are used, a more appropriate number of primers for positive individual identification would be 500-2,000.

If a panel of reagents from 32132 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 32132 Sequences in Forensic Biology DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:19 (e.g., fragments derived from the noncoding regions of SEQ ID NO:19 having a length of at least 20 bases, preferably at least 30 bases) are particularly appropriate for this use.

The 32132 nucleotide sequences described herein can further be used to provide polynucleotide reagents, e.g., labeled or labelable probes which can be used in, for example, an in situ hybridization technique, to identify a specific tissue, e.g., a tissue containing a fucosyltransferase. This can be very useful in cases where a forensic pathologist is presented with a tissue of unknown origin. Panels of such 32132 probes can be used to identify tissue by species and/or by organ type.

In a similar fashion, these reagents, e.g., 32132 primers or probes can be used to screen tissue culture for contamination (i.e. screen for the presence of a mixture of different types of cells in a culture).

Predictive Medicine of 32132

The present invention also pertains to the field of predictive medicine in which diagnostic assays, prognostic assays, and monitoring clinical trials are used for prognostic (predictive) purposes to thereby treat an individual.

Generally, the invention provides a method of determining if a subject is at risk for a disorder related to a lesion in or the misexpression of a gene which encodes a fucosyltransferase (e.g., 32132).

Such disorders include, e.g., a disorder, or other unwanted condition, associated with the misexpression of a fucosyltransferase; a cellular proliferative and/or differentiative disorder; or a disorder of the immune system, e.g., autoimmune disease or xeno- or allograft rejection.

The method includes one or more of the following:

detecting, in a tissue of the subject, the presence or absence of a mutation which affects the expression of the 32132 gene, or detecting the presence or absence of a mutation in a region which controls the expression of the gene, e.g., a mutation in the 5' control region;

detecting, in a tissue of the subject, the presence or absence of a mutation which alters the structure of the 32132 gene;

detecting, in a tissue of the subject, the misexpression of the 32132 gene, at the mRNA level, e.g., detecting a non-wild type level of a mRNA; or detecting, in a tissue of the subject, the misexpression of the gene, at the protein level, e.g., detecting a non-wild type level of a 32132 protein.

In preferred embodiments the method includes ascertaining the existence of at least one of: a deletion of one or more nucleotides from the 32132 gene; an insertion of one or more nucleotides into the gene; a point mutation, e.g., a substitution of one or more nucleotides of the gene; or a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:19, a naturally occurring mutants thereof, or 5' or 3' flanking sequences naturally associated with the 32132 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments, detecting the misexpression includes ascertaining the existence of at least one of: an alteration in the level of a messenger RNA transcript of the 32132 gene; the presence of a non-wild type splicing pattern of a messenger RNA transcript of the gene; or a non-wild type level of 32132 protein.

Methods of the invention can be used prenatally or to determine if a subject's offspring will be at risk for a disorder.

In preferred embodiments the method includes determining the structure of a 32132 gene, an abnormal structure being indicative of risk for the disorder.

In preferred embodiments the method includes contacting a sample form the subject with an antibody to the 32132 protein or a nucleic acid which hybridizes specifically with the 32132 gene. Other embodiments are discussed below.

Diagnostic and Prognostic Assays of 32132

Diagnostic and prognostic assays of the invention include method for assessing the expression level of 32132 molecules and for identifying variations and mutations in the sequence of 32132 molecules.

Expression Monitoring and Profiling:

The presence, level, or absence of 32132 protein or nucleic acid in a biological sample can be evaluated by obtaining a biological sample from a test subject and contacting the biological sample with a compound or an agent capable of detecting 32132 protein or nucleic acid (e.g., mRNA, genomic DNA) that encodes 32132 protein such that the presence of 32132 protein or nucleic acid is detected in the biological sample. The term "biological sample" includes tissues, cells and biological fluids isolated from a subject, as well as tissues, cells and fluids present within a subject. A preferred biological sample is serum. The level of expression of the 32132 gene can be measured in a number of ways, including, but not limited to: measuring the mRNA encoded by the 32132 genes; measuring the amount of protein encoded by the 32132 genes; or measuring the activity of the protein encoded by the 32132 genes.

The level of mRNA corresponding to the 32132 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 32132 nucleic acid, such as the nucleic acid of SEQ ID NO:19, or a portion thereof, such as an oligonucleotide of at least 7, 15, 30, 50, 100, 250 or 500 nucleotides in length and sufficient to specifically hybridize under stringent conditions to 32132 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 32132 genes.

The level of mRNA in a sample that is encoded by one of 32132 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 32132 gene being analyzed.

In another embodiment, the methods further contacting a control sample with a compound or agent capable of detecting 32132 mRNA, or genomic DNA, and comparing the presence of 32132 mRNA or genomic DNA in the control sample with the presence of 32132 mRNA or genomic DNA in the test sample. In still another embodiment, serial analysis of gene expression, as described in U.S. Pat. No. 5,695,937, is used to detect 32132 transcript levels.

A variety of methods can be used to determine the level of protein encoded by 32132. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 32132 protein in a biological sample in vitro as well as in vivo. In vitro techniques for detection of 32132 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 32132 protein include introducing into a subject a labeled anti-32132 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-32132 antibody positioned on an antibody array (as described below). The sample can be detected, e.g., with avidin coupled to a fluorescent label.

In another embodiment, the methods further include contacting the control sample with a compound or agent capable of detecting 32132 protein, and comparing the presence of 32132 protein in the control sample with the presence of 32132 protein in the test sample.

The invention also includes kits for detecting the presence of 32132 in a biological sample. For example, the kit can include a compound or agent capable of detecting 32132 protein or mRNA in a biological sample; and a standard. The compound or agent can be packaged in a suitable container. The kit can further comprise instructions for using the kit to detect 32132 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 32132 expression or activity. As used herein, the term "unwanted" includes an unwanted phenomenon involved in a biological response such as pain or deregulated cell proliferation.

In one embodiment, a disease or disorder associated with aberrant or unwanted 32132 expression or activity is identified. A test sample is obtained from a subject and 32132 protein or nucleic acid (e.g., mRNA or genomic DNA) is evaluated, wherein the level, e.g., the presence or absence, of 32132 protein or nucleic acid is diagnostic for a subject having or at risk of developing a disease or disorder associated with aberrant or unwanted 32132 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 32132 expression or activity. For example, such methods can be used to determine whether a subject can be effectively treated with an agent for a cellular hyperproliferative and/or differentiative disorder, or an immunological disorder.

In another aspect, the invention features a computer medium having a plurality of digitally encoded data records. Each data record includes a value representing the level of expression of 32132 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 32132 (e.g., other genes associated with a 32132-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 32132 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a cellular hyperproliferative and/or differentiative disorder in a subject wherein an increase in 32132 expression is an indication that the subject has or is disposed to having a cellular hyperproliferative and/or differentiative disorder. The method can be used to monitor a treatment for a cellular hyperproliferative and/or differentiative disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) Science 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 32132 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 32132 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 32132 expression.

32132 Arrays and Uses Thereof

In another aspect, the invention features an array that includes a substrate having a plurality of addresses. At least one address of the plurality includes a capture probe that binds specifically to a 32132 molecule (e.g., a 32132 nucleic acid or a 32132 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 32132 nucleic acid, e.g., the sense or anti-sense strand. In one preferred embodiment, a subset of addresses of the plurality of addresses has a nucleic acid capture probe for 32132. Each address of the subset can include a capture probe that hybridizes to a different region of a 32132 nucleic acid. In another preferred embodiment, addresses of the subset include a capture probe for a 32132 nucleic acid. Each address of the subset is unique, overlapping, and complementary to a different variant of 32132 (e.g., an allelic variant, or all possible hypothetical variants). The array can be used to sequence 32132 by hybridization (see, e.g., U.S. Pat. No. 5,695,940).

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 32132 polypeptide or fragment thereof. The polypeptide can be a naturally-occurring interaction partner of 32132 polypeptide. Preferably, the polypeptide is an antibody, e.g., an antibody described herein (see "Anti-32132 Antibodies," above), such as a monoclonal antibody or a single-chain antibody.

In another aspect, the invention features a method of analyzing the expression of 32132. The method includes providing an array as described above; contacting the array with a sample and detecting binding of a 32132-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 32132. If a sufficient number of diverse samples is analyzed, clustering (e.g., hierarchical clustering, k-means clustering, Bayesian clustering and the like) can be used to identify other genes which are co-regulated with 32132. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 32132 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 32132-associated disease or disorder; and processes, such as a cellular transformation associated with a 32132-associated disease or disorder. The method can also evaluate the treatment and/or progression of a 32132-associated disease or disorder The array is also useful for ascertaining differential expression patterns of one or more genes in normal and abnormal cells. This provides a battery of genes (e.g., including 32132) that could serve as a molecular target for diagnosis or therapeutic intervention.

In another aspect, the invention features an array having a plurality of addresses. Each address of the plurality includes a unique polypeptide. At least one address of the plurality has disposed thereon a 32132 polypeptide or fragment thereof. Methods of producing polypeptide arrays are described in the art, e.g., in De Wildt et al. (2000). *Nature Biotech.* 18, 989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80,85, 90, 95 or 99% identical to a 32132 polypeptide or fragment thereof. For example, multiple variants of a 32132 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 32132 binding compound, e.g., an antibody in a sample from a subject with specificity for a 32132 polypeptide or the presence of a 32132-binding protein or ligand.

The array is also useful for ascertaining the effect of the expression of a gene on the expression of other genes in the same cell or in different cells (e.g., ascertaining the effect of 32132 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 32132 or from a cell or subject in which a 32132 mediated response has been elicited, e.g., by contact of the cell with 32132 nucleic acid or protein, or administration to the cell or subject 32132 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 32132 (or does not express as highly as in the case of the 32132 positive plurality of capture probes) or from a cell or subject which in which a 32132 mediated response has not been elicited (or has been elicited to a lesser extent than in the first sample); contacting the array with one or more inquiry probes (which is preferably other than a 32132 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 32132 or from a cell or subject in which a 32132-mediated response has been elicited, e.g., by contact of the cell with 32132 nucleic acid or protein, or administration to the cell or subject 32132 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 32132 (or does not express as highly as in the case of the 32132 positive plurality of capture probes) or from a cell or subject which in which a 32132 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 32132, e.g., analyzing structure, function, or relatedness to other nucleic acid or amino acid sequences. The method includes: providing a 32132 nucleic acid or amino acid sequence; comparing the 32132 sequence with one or more preferably a plurality of sequences from a collection of sequences, e.g., a nucleic acid or protein sequence database; to thereby analyze 32132.

Detection of 32132 Variations or Mutations

The methods of the invention can also be used to detect genetic alterations in a 32132 gene, thereby determining if a subject with the altered gene is at risk for a disorder characterized by misregulation in 32132 protein activity or nucleic acid expression, such as a cellular hyperproliferative and/or differentiative disorder. In preferred embodiments, the methods include detecting, in a sample from the subject, the presence or absence of a genetic alteration characterized by at least one of an alteration affecting the integrity of a gene encoding a 32132-protein, or the mis-expression of the 32132 gene. For example, such genetic alterations can be detected by ascertaining the existence of at least one of 1) a deletion of one or more nucleotides from a 32132 gene; 2) an addition of one or more nucleotides to a 32132 gene; 3) a substitution of one or more nucleotides of a 32132 gene, 4) a chromosomal rearrangement of a 32132 gene; 5) an alteration in the level of a messenger RNA transcript of a 32132 gene, 6) aberrant modification of a 32132 gene, such as of the methylation pattern of the genomic DNA, 7) the presence of a non-wild type splicing pattern of a messenger RNA transcript of a 32132 gene, 8) a non-wild type level of a 32132-protein, 9) allelic loss of a 32132 gene, and 10) inappropriate post-translational modification of a 32132-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 32132-gene. This method can include the steps of collecting a sample of cells from a subject, isolating nucleic acid (e.g., genomic, mRNA or both) from the sample, contacting the nucleic acid sample with one or more primers which specifically hybridize to a 32132 gene under conditions such that hybridization and amplification of the 32132-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 32132 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 32132 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 32132 nucleic acid or a putative variant (e.g., allelic variant) thereof. A probe can have one or more mismatches to a region of a 32132 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244-255; Kozal, M. J. et al (1996) *Nature Medicine* 2: 753-759). For example, genetic mutations in 32132 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 32132 gene and detect mutations by comparing the sequence of the sample 32132 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 32132 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 32132 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 32132 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 32132 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 32132 nucleic acid.

In a preferred embodiment the set includes a first and a second oligonucleotide. The first and second oligonucleotide can hybridize to the same or to different locations of SEQ ID NO:19 or the complement of SEQ ID NO:19. Different locations can be different but overlapping or nonoverlapping on the same strand. The first and second oligonucleotide can hybridize to sites on the same or on different strands.

The set can be useful, e.g., for identifying SNP's, or identifying specific alleles of 32132. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligonucleotides can be used to specifically amplify, e.g., by PCR, or detect, a 32132 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 32132 gene.

Use of 32132 Molecules as Surrogate Markers

The 32132 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 32132 molecules of the invention may be detected, and may be correlated with one or more biological states in vivo. For example, the 32132 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 32132 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 32132 marker) transcription or expression, the amplified marker may be in a quantity which is more readily detectable than the drug itself. Also, the marker may be more easily detected due to the nature of the marker itself, for example, using the methods described herein, anti-32132 antibodies may be employed in an immune-based detection system for a 32132 protein marker, or 32132-specific radiolabeled probes may be used to detect a 32132 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am. J. Health-Syst. Pharm.* 56 Suppl. 3: S16-S20.

The 32132 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 32132 protein or RNA) for specific tumor markers in a subject, a drug or course of treatment may be selected that is optimized for the treatment of the specific tumor likely to be present in the subject. Similarly, the presence or absence of a specific sequence mutation in 32132 DNA may correlate 32132 drug response. The use of pharmacogenomic markers therefore permits the application of the most appropriate treatment for each subject without having to administer the therapy.

Pharmaceutical Compositions of 32132

The nucleic acid and polypeptides, fragments thereof, as well as anti-32132 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 32132

The present invention provides for both prophylactic and therapeutic methods of treating a subject at risk of (or susceptible to) a disorder or having a disorder associated with aberrant or unwanted 32132 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 32132 molecules of the present invention or 32132 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 32132 expression or activity, by administering to the subject a 32132 or an agent which modulates 32132 expression or at least one 32132 activity. Subjects at risk for a disease which is caused or contributed to by aberrant or unwanted 32132 expression or activity can be identified by, for example, any or a combination of diagnostic or prognostic assays as described herein. Administration of a prophylactic agent can occur prior to the manifestation of symptoms characteristic of the 32132 aberrance, such that a disease or disorder is prevented or, alternatively, delayed in its progression. Depending on the type of 32132 aberrance, for example, a 32132, a 32132 agonist or, a 32132 antagonist agent can be used for treating the subject. The appropriate agent can be determined based on screening assays described herein.

It is possible that some 32132 disorders can be caused, at least in part, by an abnormal level of gene product, or by the presence of a gene product exhibiting abnormal activity. As such, the reduction in the level and/or activity of such gene products would bring about the amelioration of disorder symptoms.

The 32132 molecules can act as novel diagnostic targets and therapeutic agents for controlling cellular proliferative and/or differentiative disorders and immunological disorders, examples of which have been described above. In addition, 32132 molecules can act as novel diagnostic targets and therapeutic agents for detecting and controlling disorders associated with the cardiovascular system, kidney, skeletal muscle, colon, liver, or brain.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypemephroma, adenocarcinoma of kidney), which includes urothelial carcinomas of renal pelvis.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolsim, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 32132 molecules may play an important role in the etiology of certain viral diseases, including but not limited to Hepatitis B, Hepatitis C and Herpes Simplex Virus (HSV). Modulators of 32132 activity could be used to control viral diseases. The modulators can be used in the treatment and/or diagnosis of viral infected tissue or virus-associated tissue fibrosis, especially liver and liver fibrosis. Also, 32132 modulators can be used in the treatment and/or diagnosis of virus-associated carcinoma, especially hepatocellular cancer.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyclitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Additionally, 32132 may play an important role in the regulation of metabolism or pain disorders. Diseases of metabolic imbalance include, but are not limited to, obesity, anorexia nervosa, cachexia, lipid disorders diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York, McGraw-Hill); pain associated with muscoloskeletal disorders, e.g., joint pain; tooth pain; headaches; pain associated with surgery; pain related to irritable bowel syndrome; or chest pain.

As discussed, successful treatment of 32132 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 32132 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 32132 expression is through the use of aptamer molecules specific for 32132 protein. Aptamers are nucleic acid molecules having a tertiary structure which permits them to specifically bind to protein ligands (see, e.g., Osborne, et al. *Curr. Opin. Chem Biol.* 1997, 1(1): 5-9; and Patel, D. J. *Curr Opin Chem Biol* 1997 June; 1(1):32-46). Since nucleic acid molecules may in many cases be more conveniently introduced into target cells than therapeutic protein molecules may be, aptamers offer a method by which 32132 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 32132 disorders. For a description of antibodies, see the Antibody section above.

In circumstances wherein injection of an animal or a human subject with a 32132 protein or epitope for stimulating antibody production is harmful to the subject, it is possible to generate an immune response against 32132 through the use of anti-idiotypic antibodies (see, for example, Herlyn, D. *Ann Med* 1999; 31(1):66-78; and Bhattacharya-Chatterjee, M., and Foon, K. A. *Cancer Treat Res* 1998; 94:51-68). If an anti-idiotypic antibody is introduced into a mammal or human subject, it should stimulate the production of anti-anti-idiotypic antibodies, which should be specific to the 32132 protein. Vaccines directed to a disease characterized by 32132 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate 32132 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 32132 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell et al. (1996) *Current Opinion in Biotechnology* 7:89-94 and in Shea, K. J. (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645-647. Through the use of isotope-labeling, the "free" concentration of compound which modulates the expression or activity of 32132 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al. (1995) *Analytical Chemistry* 67:2142-2144.

Another aspect of the invention pertains to methods of modulating 32132 expression or activity for therapeutic purposes. Accordingly, in an exemplary embodiment, the modulatory method of the invention involves contacting a cell with a 32132 or agent that modulates one or more of the activities of 32132 protein activity associated with the cell. An agent that modulates 32132 protein activity can be an agent as described herein, such as a nucleic acid or a protein, a naturally-occurring target molecule of a 32132 protein (e.g., a 32132 substrate or receptor), a 32132 antibody, a 32132 agonist or antagonist, a peptidomimetic of a 32132 agonist or antagonist, or other small molecule.

In one embodiment, the agent stimulates one or 32132 activities. Examples of such stimulatory agents include active 32132 protein and a nucleic acid molecule encoding 32132. In another embodiment, the agent inhibits one or more 32132 activities. Examples of such inhibitory agents include antisense 32132 nucleic acid molecules, anti-32132 antibodies, and 32132 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 32132 protein or nucleic acid molecule. In one embodiment, the method involves administering an agent (e.g., an agent identified by a screening assay described herein), or combination of agents that modulates (e.g., upregulates or downregulates) 32132 expression or activity. In another embodiment, the method involves administering a 32132 protein or nucleic acid molecule as therapy to compensate for reduced, aberrant, or unwanted 32132 expression or activity.

Stimulation of 32132 activity is desirable in situations in which 32132 is abnormally downregulated and/or in which increased 32132 activity is likely to have a beneficial effect. For example, stimulation of 32132 activity is desirable in situations in which a 32132 is downregulated and/or in which increased 32132 activity is likely to have a beneficial effect. Likewise, inhibition of 32132 activity is desirable in situations in which 32132 is abnormally upregulated and/or in which decreased 32132 activity is likely to have a beneficial effect.

32132 Pharmacogenomics

The 32132 molecules of the present invention, as well as agents, or modulators which have a stimulatory or inhibitory effect on 32132 activity (e.g., 32132 gene expression) as identified by a screening assay described herein can be administered to individuals to treat (prophylactically or therapeutically) 32132 associated disorders (e.g., cellular hyperproliferative and/or differentiative disorders or immune disorders) associated with aberrant or unwanted 32132 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 32132 molecule or 32132 modulator as well as tailoring the dosage and/or therapeutic regimen of treatment with a 32132 molecule or 32132 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11):983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a 32132 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a 32132 molecule or 32132 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 32132 molecule or 32132 modulator, such as a modulator identified by one of the exemplary screening assays described herein.

The present invention further provides methods for identifying new agents, or combinations, that are based on identifying agents that modulate the activity of one or more of the gene products encoded by one or more of the 32132 genes of the present invention, wherein these products may be associated with resistance of the cells to a therapeutic agent. Specifically, the activity of the proteins encoded by the 32132 genes of the present invention can be used as a basis for identifying agents for overcoming agent resistance. By blocking the activity of one or more of the resistance proteins, target cells will become sensitive to treatment with an agent that the unmodified target cells were resistant to.

Monitoring the influence of agents (e.g., drugs) on the expression or activity of a 32132 protein can be applied in clinical trials. For example, the effectiveness of an agent determined by a screening assay as described herein to increase 32132 gene expression, protein levels, or upregulate 32132 activity, can be monitored in clinical trials of subjects exhibiting decreased 32132 gene expression, protein levels, or downregulated 32132 activity. Alternatively, the effectiveness of an agent determined by a screening assay to decrease 32132 gene expression, protein levels, or downregulate 32132 activity, can be monitored in clinical trials of subjects exhibiting increased 32132 gene expression, protein levels, or upregulated 32132 activity. In such clinical trials, the expression or activity of a 32132 gene, and preferably, other genes that have been implicated in, for example, a 32132-associated disorder can be used as a "read out" or markers of the phenotype of a particular cell.

32132 Informatics

The sequence of a 32132 molecule is provided in a variety of media to facilitate use thereof. A sequence can be provided as a manufacture, other than an isolated nucleic acid or amino acid molecule, which contains a 32132. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 32132 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 32132, e.g., analyzing structure, function, or relatedness to one or more other nucleic acid or amino acid sequences. The method includes: providing a 32132 nucleic acid or amino acid sequence; comparing the 32132 sequence with a second sequence, e.g., one or more preferably a plurality of sequences from a collection of sequences, e.g., a nucleic acid or protein sequence database to thereby analyze 32132. The method can be performed in a machine, e.g., a computer, or manually by a skilled artisan.

The method can include evaluating the sequence identity between a 32132 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 32132 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 32132 sequence, or record, in machine-readable form; comparing a second sequence to the 32132 sequence; thereby analyzing a sequence. Comparison can include comparing to sequences for sequence identity or determining if one sequence is included within the other, e.g., determining if the 32132 sequence includes a sequence being compared. In a preferred embodiment the 32132 or second sequence is stored on a first computer, e.g., at a first site and the comparison is performed, read, or recorded on a second computer, e.g., at a second site. E.g., the 32132 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 32132-associated disease or disorder or a pre-disposition to a 32132-associated disease or disorder, wherein the method comprises the steps of determining 32132 sequence information associated with the subject and based on the 32132 sequence information, determining whether the subject has a 32132-associated disease or disorder or a pre-disposition to a 32132-associated disease or disorder and/or recommending a particular treatment for the disease, disorder or pre-disease condition.

The invention further provides in an electronic system and/or in a network, a method for determining whether a subject has a 32132-associated disease or disorder or a pre-disposition to a disease associated with a 32132 wherein the method comprises the steps of determining 32132 sequence information associated with the subject, and based on the 32132 sequence information, determining whether the subject has a 32132-associated disease or disorder or a pre-disposition to a 32132-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 32132 sequence of the subject to the 32132 sequences in the database to thereby determine whether the subject as a 32132-associated disease or disorder, or a pre-disposition for such.

The present invention also provides in a network, a method for determining whether a subject has a 32132 associated disease or disorder or a pre-disposition to a 32132-associated disease or disorder associated with 32132, said method comprising the steps of receiving 32132 sequence information from the subject and/or information related thereto, receiving phenotypic information associated with the subject, acquiring information from the network corresponding to 32132 and/or corresponding to a 32132-associated disease or disorder (e.g., a cellular hyperproliferative and/or differentiative disorder or an immunological disorder), and based on one or more of the phenotypic information, the 32132 information (e.g., sequence information and/or information related thereto), and the acquired information, determining whether the subject has a 32132-associated disease or disorder or a pre-disposition to a 32132-associated disease or disorder. The method may further comprise the step of recommending a particular treatment for the disease, disorder or pre-disease condition.

The present invention also provides a method for determining whether a subject has a 32132-associated disease or disorder or a pre-disposition to a 32132-associated disease or disorder, said method comprising the steps of receiving information related to 32132 (e.g., sequence information and/or information related thereto), receiving phenotypic information associated with the subject, acquiring information from the network related to 32132 and/or related to a 32132-associated disease or disorder, and based on one or more of the phenotypic information, the 32132 information, and the acquired information, determining whether the subject has a 32132-associated disease or disorder or a pre-disposition to a 32132-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

Background of the 32244 Invention

In addition to luciferase, the AMP-binding enzyme family includes the acyl-CoA ligases (EC 6.2.1.1-6.2.1.3; AMP forming). These enzymes activate various substrates, including acetic acid, aromatic acids and long-chain fatty acids, to the corresponding enzyme-bound acyl-adenylates, which are then transferred to the thiol group of co-enzyme A. Acyl-CoA ligases are classified on the basis of their activity in conjugating saturated fatty acids of differing chain lengths, i.e., short (C2-C4), medium (C4-C12), long (C10-C22), and very long (greater than C22). These enzymes are located in various cell compartments (cytosol, smooth endoplasmic reticulum, mitochondria and peroxisomes). They exhibit wide tissue distribution, but are most abundant in liver and adipose tissue (Knights, 1998, *Clin. Exp. Pharmacol. Physiol.* 25:776-782). In mammals, activation of fatty acids is the first step in fatty acid metabolism. Long-chain fatty acyl-CoA synthetases catalyze esterification of fatty acids into CoA thioesters, which are used either for lipid biosynthesis or oxidized and used as a cellular energy source (Conti et al., 1996, *Structure* 4:287-298). Formation of acyl-CoA occurs with xenobiotic carboxylic acids as well as with endogenous substrates.

Defects in AMP-binding enzymes can give rise to serious disorders. Adrenoleukodystrophy (X-ALD) is a genetic disorder inherited as an X-linked recessive trait. It involves defective peroxisomal oxidation of very long chain fatty acids (VLCFA). The disorder is characterized by demyelination of the central nervous system, and by adrenal insufficiency. Saturated very long chain fatty acids accumulate as a result of impaired activity of VLC acyl-CoA synthetase (VLCAS). The gene that causes X-ALD codes for a peroxisomal integral membrane protein (ALDP). ALDP appears to be involved in stabilizing VLCAS activity, possibly through protein-protein interactions. Loss or impairment of this protein-protein interaction may account for the loss of peroxisomal VLCAS activity in X-ALD (Smith et al., 2000, *Exp. Cell Res.* 254:309-320). This hypothesis is supported by the fact that overexpression of both VLCAS and ALDP in X-ALD fibroblasts synergistically increases very long chain fatty acid β-oxidation, indicating that these proteins interact functionally (Steinberg et al., 1999, *Ann. Neurol.* 46:409-412; Yamada et al., 1999, *Neurology* 52:614-616).

Summary of the 32244 Invention

The present invention is based, in part, on the discovery of a novel AMP-binding enzyme family member, referred to herein as "32244". The nucleotide sequence of a cDNA encoding 32244 is recited in SEQ ID NO:25, and the amino acid sequence of a 32244 polypeptide is recited in SEQ ID NO:26 (see also Example 19, below). In addition, the nucleotide sequences of the coding region are recited in SEQ ID NO:27.

Accordingly, in one aspect, the invention features a nucleic acid molecule that encodes a 32244 protein or polypeptide, e.g., a biologically active portion of the 32244 protein. In a preferred embodiment the isolated nucleic acid molecule encodes a polypeptide having the amino acid sequence of SEQ ID NO:26. In other embodiments, the invention provides isolated 32244 nucleic acid molecules having the nucleotide sequence shown in SEQ ID NO:25, or SEQ ID NO:27. In still other embodiments, the invention provides nucleic acid molecules that are substantially identical (e.g., naturally occurring allelic variants) to the nucleotide sequence shown in SEQ ID NO:25, or SEQ ID NO:27. In other embodiments, the invention provides a nucleic acid molecule which hybridizes under a stringency condition described herein to a nucleic acid molecule comprising the nucleotide sequence of SEQ ID NO:25, or SEQ ID NO:27, wherein the nucleic acid encodes a full length 32244 protein or an active fragment thereof.

In a related aspect, the invention further provides nucleic acid constructs that include a 32244 nucleic acid molecule described herein. In certain embodiments, the nucleic acid molecules of the invention are operatively linked to native or heterologous regulatory sequences. Also included, are vectors and host cells containing the 32244 nucleic acid molecules of the invention e.g., vectors and host cells suitable for producing 32244 nucleic acid molecules and polypeptides.

In another related aspect, the invention provides nucleic acid fragments suitable as primers or hybridization probes for the detection of 32244-encoding nucleic acids.

In still another related aspect, isolated nucleic acid molecules that are antisense to a 32244 encoding nucleic acid molecule are provided.

In another aspect, the invention features, 32244 polypeptides, and biologically active or antigenic fragments thereof that are useful, e.g., as reagents or targets in assays applicable to treatment and diagnosis of 32244-mediated or -related disorders. In another embodiment, the invention provides 32244 polypeptides having a 32244 activity. Preferred polypeptides are 32244 proteins including at least one AMP-binding enzyme domain and, preferably, having a 32244 activity, e.g., a 32244 activity as described herein.

In other embodiments, the invention provides 32244 polypeptides, e.g., a 32244 polypeptide having the amino acid sequence shown in SEQ ID NO:26; an amino acid sequence that is substantially identical to the amino acid sequence shown in SEQ ID NO:26; or an amino acid sequence encoded by a nucleic acid molecule having a nucleotide sequence which hybridizes under a stringency condition described herein to a nucleic acid molecule comprising the nucleotide sequence of SEQ ID NO:25, or SEQ ID NO:27, wherein the nucleic acid encodes a full length 32244 protein or an active fragment thereof.

In a related aspect, the invention provides 32244 polypeptides or fragments operatively linked to non-32244 polypeptides to form fusion proteins.

In another aspect, the invention features antibodies and antigen-binding fragments thereof, that react with, or more preferably specifically bind 32244 polypeptides. In other embodiments, the antibody or antigen-binding fragment thereof reacts with, or more preferably binds specifically to a 32244 polypeptide or a fragment thereof, e.g., an AMP binding domain of a 32244 polypeptide. In one embodiment, the antibody or antigen-binding fragment thereof competitively inhibits the binding of a second antibody to its target epitope.

In another aspect, the invention provides methods of screening for compounds that modulate the expression or activity of the 32244 polypeptides or nucleic acids.

In still another aspect, the invention provides a process for modulating 32244 polypeptide or nucleic acid expression or activity, e.g. using the screened compounds. In certain embodiments, the methods involve treatment of conditions related to aberrant activity or expression of the 32244 polypeptides or nucleic acids, such as conditions involving aberrant or deficient cellular acyl-CoA synthase activity or conditions involving aberrant or deficient cellular proliferation or differentiation.

The invention also provides assays for determining the activity of or the presence or absence of 32244 polypeptides or nucleic acid molecules in a biological sample, including for disease diagnosis.

In yet another aspect, the invention provides methods for inhibiting the proliferation, or inducing the killing, or differentiation, of a 32244-expressing cell, e.g., a hyper-proliferative 32244-expressing cell. The method includes contacting the cell with an agent, e.g., a compound (e.g., a compound identified using the methods described herein) that modulates the activity, or expression, of the 32244 polypeptide or nucleic acid. In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol. In a preferred embodiment, the cell is a hyperproliferative cell, e.g., a cell found in a solid tumor, a soft tissue tumor, or a metastatic lesion. In a preferred embodiment, the hyperproliferative cell originates from the lung, brain, ovary, breast, colon, or liver.

In a preferred embodiment, the agent, e.g., the compound, is an inhibitor of a 32244 polypeptide. Preferably, the inhibitor is chosen from a peptide, a phosphopeptide, a small organic molecule, a small inorganic molecule and an antibody (e.g., an antibody conjugated to a therapeutic moiety selected from a cytotoxin, a cytotoxic agent and a radioactive metal ion). In another preferred embodiment, the agent, e.g., the compound, is an inhibitor of a 32244 nucleic acid, e.g., an antisense, a ribozyme, or a triple helix molecule.

In another embodiment, the agent, e.g., the compound, is an activator of a 32244 polypeptide. Preferably, the activator is chosen from a peptide, a phosphopeptide, a small organic molecule, a small inorganic molecule and an antibody. In another preferred embodiment, the agent, e.g., the compound, stimulates the expression of a 32244 nucleic acid.

In a preferred embodiment, the agent, e.g., the compound, is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

In another aspect, the invention features methods for treating or preventing a disorder characterized by aberrant cellular proliferation or differentiation of a 32244-expressing cell, in a subject. Preferably, the method includes administering to the subject (e.g., a mammal, e.g., a human) an effective amount of an agent, e.g., a compound (e.g., a compound identified using the methods described herein) that modulates the activity, or expression, of the 32244 polypeptide or nucleic acid. In a preferred embodiment, the disorder is a cancerous or pre-cancerous condition.

In a further aspect, the invention provides methods for evaluating the efficacy of a treatment of a disorder, e.g., proliferative disorder or a disorder characterized by aberrant or deficient cellular acyl-CoA synthase activity. The method includes: treating a subject, e.g., a patient or an animal, with a protocol under evaluation (e.g., treating a subject with one or more of: chemotherapy, radiation, and/or a compound identified using the methods described herein); and evaluating the expression of a 32244 nucleic acid or polypeptide before and after treatment. A change, e.g., a decrease or increase, in the level of a 32244 nucleic acid (e.g., mRNA) or polypeptide after treatment, relative to the level of expression before treatment, is indicative of the efficacy of the treatment of the disorder. The level of 32244 nucleic acid or polypeptide expression can be detected by any method described herein.

In a preferred embodiment, the evaluating step includes obtaining a sample (e.g., a tissue sample, e.g., a biopsy, or a fluid sample) from the subject, before and after treatment and comparing the level of expressing of a 32244 nucleic acid (e.g., mRNA) or polypeptide before and after treatment.

In another aspect, the invention provides methods for evaluating the efficacy of a therapeutic or prophylactic agent (e.g., an anti-neoplastic agent). The method includes: contacting a sample with an agent (e.g., a compound identified using the methods described herein, a cytotoxic agent) and, evaluating the expression of 32244 nucleic acid or polypeptide in the sample before and after the contacting step. A change, e.g., a decrease or increase, in the level of 32244 nucleic acid (e.g., mRNA) or polypeptide in the sample obtained after the contacting step, relative to the level of expression in the sample before the contacting step, is indicative of the efficacy of the agent. The level of 32244 nucleic acid or polypeptide expression can be detected by any method described herein. In a preferred embodiment, the sample includes cells obtained from a cancerous tissue or a lung, brain, ovary, breast, colon, or liver tissue.

In further aspect, the invention provides assays for determining the presence or absence of a genetic alteration in a 32244 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 32244 molecule. In one embodiment, the capture probe is a nucleic acid, e.g., a probe complementary to a 32244 nucleic acid sequence. In another embodiment, the capture probe is a polypeptide, e.g., an antibody specific for 32244 polypeptides. Also featured is a method of analyzing a sample by contacting the sample to the aforementioned array and detecting binding of the sample to the array.

Other features and advantages of the invention will be apparent from the following detailed description, and from the claims.

Detailed Description of 32244

The human 32244 sequence (see SEQ ID NO:25, as recited in Example 19), which is approximately 2302 nucleotides long including untranslated regions, contains a predicted methionine-initiated coding sequence of about 1731 nucleotides, including the termination codon. The coding sequence encodes a 576 amino acid protein (see SEQ ID NO:26, as recited in Example 19). The human 32244 protein of SEQ ID NO:26 and FIG. 36 includes an amino-terminal hydrophobic amino acid sequence, consistent with a signal sequence, of about 17 amino acids (from amino acid 1 to about amino acid 17 of SEQ ID NO:26), which upon cleavage results in the production of a mature protein form. The predicted mature protein form is approximately 559 amino acid residues in length (from about amino acid 18 to amino acid 576 of SEQ ID NO:26).

Human 32244 contains the following regions or other structural features:

an AMP-binding domain (PFAM Accession Number PF00501) located at about amino acid residues 67 to 504 of SEQ ID NO:26;

an AMP-binding domain signature motif (PS00455), located at about amino acid residues 199 to 210 of SEQ ID NO:26;

an AMP-binding domain invariant glutamine motif, located at about amino acid residues 355 to 359 of SEQ ID NO:26;

an AMP-binding domain invariant aspartic acid motif, located at about amino acid residues 455 to 457 of SEQ ID NO:26;

nine predicted Protein Kinase C phosphorylation sites (PS00005) located at about amino acid residues 8 to 10, 18 to 20, 40 to 42, 67 to 69, 75 to 77, 206 to 208, 284 to 286, 521 to 523, and 529 to 531 of SEQ ID NO:26;

eight predicted Casein Kinase II phosphorylation sites (PS00006) located at about amino acid residues 67 to 70, 233 to 236, 350 to 353, 472 to 475, 485 to 488, 498 to 501, 521 to 524, and 529 to 532 of SEQ ID NO:26;

one predicted N-glycosylation site (PS00001) from about amino acids 345 to 348 of SEQ ID NO:26: and seven predicted N-myristylation sites (PS00008) from about amino acids 13 to 18, 30 to 35, 87 to 92, 211 to 216, 249 to 254, 361 to 366, and 513 to 518 of SEQ ID NO:26.

For general information regarding PFAM identifiers, PS prefix and PF prefix domain identification numbers, refer to Sonnhammer et al. (1997) *Protein* 28:405-420.

The 32244 protein contains a significant number of structural characteristics in common with members of the AMP-binding family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

The AMP-binding domain family of proteins is characterized by a common fold, the structure of which was solved for firefly luciferase (Conti et al. (1996), *Structure* 4(3):287-298). Based on the luciferase structure, the AMP-binding domain is composed of two subdomains: a compact N-terminal subdomain that contains a distorted antiparallel β-barrel and two β-sheets, which are flanked on either side by α-helices; and a small α+β C-terminal subdomain (Conti et al., supra). The two β-sheets pack together to create a long surface groove, which is closed at one end by the presence of the β-barrel. The packing of the β-barrel against the side of the two β-sheets forms two shallow depressions on the concave surface of the molecule, giving rise to a Y-shaped valley on the surface of the N-terminal subdomain. The C-terminal subdomain is connected to the N-terminal subdomain by a flexible hinge and is positioned above the b-barrel portion of the N-terminal subdomain such that a large cleft is formed between the N-terminal and C-terminal subdomains. In human 32244, the N-terminal subdomain is located at about amino acid residues 67 to 470 of SEQ ID NO:26, while the C-terminal subdomain is located at about amino acid residues 475 to 576 of SEQ ID NO:26.

Several conserved sequence motifs have been identified in the AMP-binding domain family of proteins. The conserved sequence motifs include the "AMP-binding domain signature motif", defined by the sequence [STG]-[STG]-G-[ST]-[TSE]-[GS]-X-[PALIVM]-K (SEQ ID NO:29), as well as an "invariant glutamine motif" defined by the sequences [YFW]-[GASW]-X-[TSA]-E (SEQ ID NO:30), and an "invariant aspartic acid motif" defined by the sequence [STA]-[GRK]-D (SEQ ID NO:31). Due to the conservation these motifs in a family of molecules that have distinct enzymatic activities, the motifs are believed to function in the binding of AMP and in adenylate formation, properties shared by all of the members of the family (Conti et al., supra).

A 32244 polypeptide can include an "AMP-binding domain" or regions homologous with an "AMP-binding domain".

As used herein, the term "AMP-binding domain" includes an amino acid sequence of about 300 to 550 amino acid residues in length and having a bit score for the alignment of the sequence to the AMP-binding domain profile (PFAM HMM) of at least 50. An AMP-binding domain can further include an AMP-binding domain signature sequence motif, aninvariant glutamine motif, and an invariant aspartic acid motif. Preferably, a AMP-binding enzyme domain includes at least about 350 to 550 amino acids, more preferably about 375 to 525 amino acid residues, or about 400 to 525 amino acids, has a bit score for the alignment of the sequence to the AMP-binding domain (HMM) of at least 80, 90, or 100 or greater, and includes an AMP-binding domain signature sequence motif, an invariant glutamine motif, and an invariant aspartic acid motif. The AMP-binding enzyme domain (HMM) has been assigned the PFAM Accession Number PF00501. An alignment of the AMP-binding enzyme domain (amino acids 67 to 504 of SEQ ID NO:26) of human 32244 with a consensus amino acid sequence (SEQ ID NO:28) derived from a hidden Markov model is depicted in FIG. 36.

In a preferred embodiment 32244 polypeptide or protein has a "AMP-binding enzyme domain" or a region which includes at least about 350 to 550, more preferably about 375 to 525, or 400 to 525 amino acid residues and has at least about 50%, 60%, 70% 80% 90% 95%, 99%, or 100% homology with a "AMP-binding enzyme domain," e.g., the AMP-binding enzyme domain of human 32244 (e.g., residues 67 to 504 of SEQ ID NO:26).

To identify the presence of a "AMP-binding enzyme" domain in a 32244 protein sequence, and make the determination that a polypeptide or protein of interest has a particular profile, the amino acid sequence of the protein can be searched against the PFAM database of HMMs (e.g., the PFAM database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the PFAM database can be found in Sonhammer et al. (1997) *Proteins* 28(3): 405-420 and a detailed description of HMMs can be found, for example, in Gribskov et al.(1990) *Meth. Enzymol.* 183: 146-159; Gribskov et al.(1987) *Proc. Natl. Acad. Sci. USA* 84:4355-4358; Krogh et al.(1994) *J. Mol Biol.* 235:1501-1531; and Stultz et al.(1993) *Protein Sci.* 2:305-314, the contents of which are incorporated herein by reference. A search was performed against the HMM database resulting in the identification of a "AMP-binding enzyme" domain in the amino acid sequence of human 32244 at about residues 67 to 504 of SEQ ID NO:26 (see FIG. 36).

A 32244 protein can further include a signal sequence. As used herein, a "signal sequence" refers to a peptide of about 15 to 30, preferably about 17, amino acid residues in length which occurs at the N-terminus of secretory, integral membrane, mitochodrial, and peroxisomal proteins, and which contains a majority of hydrophobic amino acid residues. For example, a signal sequence contains at least about 15 to 25 amino acid residues, preferably about 15 to 20 amino acid residues, more preferably about 18 amino acid residues, and has at least about 40-70%, preferably about 50-65%, and more preferably about 55-60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a 32244 protein contains a signal sequence of about amino acids 1 to 17 of SEQ ID NO:26. The "signal sequence" is cleaved during processing of the mature protein. The predicted mature 32244 protein corresponds to amino acids 18 to 576 of SEQ ID NO:26.

A 32244 family member can include at least one AMP-binding domain. Furthermore, a 32244 family member can include at least one AMP-binding domain signature motif (PS00455); at least one AMP-binding domain invariant glutamine motif; at least one AMP-binding domain invariant aspartic acid motif; at least one predicted signal peptide; at least one, two, three, four, five, six, seven, eight, preferably nine predicted protein kinase C phosphorylation sites (PS00005); at least one, two, three, four, five, six, seven, preferably eight predicted casein kinase II phosphorylation sites (PS00006); at least one, two, three, four, five, six, preferably seven predicted N-myristylation sites (PS00008); and at least one predicted N-glycosylation site (PS00001).

As the 32244 polypeptides of the invention may modulate 32244-mediated activities, they may be useful as of for developing novel diagnostic and therapeutic agents for 32244-mediated or related disorders, as described below.

As used herein, a "32244 activity", "biological activity of 32244" or "functional activity of 32244", refers to an activity exerted by a 32244 protein, polypeptide or nucleic acid molecule. For example, a 32244 activity can be an activity exerted by 32244 in a physiological milieu on, e.g., a 32244-responsive cell or on a 32244 substrate, e.g., a protein substrate. A 32244 activity can be determined in vivo or in vitro. In one embodiment, a 32244 activity is a direct activity, such as an association with a 32244 target molecule. A "target molecule" or "binding partner" is a molecule with which a 32244 protein binds or interacts in nature. In an exemplary embodiment, 32244 is an enzyme for a substrate, e.g., ATP or a carboxyl-containing molecule, e.g., a fatty acid molecule.

A 32244 activity can also be an indirect activity, e.g., a cellular signaling activity mediated by interaction of the 32244 protein with a 32244 receptor. The features of the 32244 molecules of the present invention can provide similar biological activities as AMP-binding family members. For example, the 32244 proteins of the present invention can have one or more of the following activities: (1) ATP-binding activity; (2) substrate adenylation activity; (3) acyl-CoA ligase activity; (4) fatty acid biosynthesis or degradation; (5) xenobiotic carboxylic acid modification or degradation; (6) binding to peroxisomal integral membrane proteins; (7) inhibition of demyelination of the central nervous system; (8) inhibition of adrenal insufficiency; or (9) the ability to act as a agonist or antagonist to any of activities (1)-(8).

The 32244 polypeptide is predicted to be a membrane associated protein that displays enzymatic activity. The 32244 polypeptide is predicted to be localized in various cell compartments, e.g., cytosol, smooth endoplasmic reticulum, mitochondria and peroxisomes. The 32244 enzymatic activity is predicted to include acyl-CoA ligase activity, e.g., esterification of fatty acids (short, medium, long or very long chain) into CoA thioesters, which are used for lipid biosynthesis or oxidized and used as a cellular energy source.

Expression of human 32244 has been detected in a wide range of tissues, including adipose, breast, lung, colon, liver, brain, and ovary tissues (see Example 20, Tables 11-13, below). In many brain and ovary tumor samples, expression of 32244 was reduced as compared to levels in normal brain and ovary tissue (see Example 20, Tables 12 and 13, below). In contrast, expression of human 32244 was increased in many lung tumor samples and some breast tumor sample, relative to its levels in normal lung and breast tissues (see Example 20, Tables 12 and 13, below).

Thus, the 32244 molecules can act as novel diagnostic targets and therapeutic agents for controlling fatty acid and/or xenobiotic metabolism disorders, neural disorders, and cellular proliferative and/or differentiative disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Additional examples of proliferative disorders include hematopoietic neoplastic disorders. As used herein, the term "hematopoictic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease.

Further examples of cancers or neoplastic conditions, in addition to the ones described above, include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma. Many such neoplastic conditions can progress to a metastatic state, e.g., resulting in tumor cells moving to new locations and forming metastatic tumors.

Additionally, 32244 may play an important role in the regulation of metabolism. Diseases of metabolic imbalance include, but are not limited to, obesity, anorexia nervosa, cachexia, lipid and fatty acid metabolism disorders, and diabetes. Examples of fatty acid metabolism disorders include adrenoleukodystrophy.

Neural disorders include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyclitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin B1) deficiency and vitamin B12 deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

The 32244 protein, fragments thereof, and derivatives and other variants of the sequence in SEQ ID NO:26 thereof are collectively referred to as "polypeptides or proteins of the invention" or "32244 polypeptides or proteins". Nucleic acid molecules encoding such polypeptides or proteins are collectively referred to as "nucleic acids of the invention" or "32244 nucleic acids." 32244 molecules refer to 32244 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:25 or SEQ ID NO:27, corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a 32244 protein. The gene can optionally further include non-coding sequences, e.g., regulatory sequences and introns. Preferably, a gene encodes a mammalian 32244 protein or derivative thereof.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of 32244 protein is at least 10% pure. In a preferred embodiment, the preparation of 32244 protein has less than about 30%, 20%, 10% and more preferably 5% (by dry weight), of non-32244 protein (also referred to herein as a "contaminating protein"), or of chemical precursors or non-32244 chemicals. When the 32244 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 32244 without abolishing or substantially altering a 32244 activity. Preferably the alteration does not substantially alter the 32244 activity, e.g., the activity is at least 20%, 40%, 60%, 70% or 80% of wild-type. An "essential" amino acid residue is a residue that, when altered from the wild-type sequence of 32244, results in abolishing a 32244 activity such that less than 20% of the wild-type activity is present. For example, conserved amino acid residues in 32244 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 32244 protein is preferably replaced with another amino acid residue from the same side chain family. Alternatively, in another embodiment, mutations can be introduced randomly along all or part of a 32244 coding sequence, such as by saturation mutagenesis, and the resultant mutants can be screened for 32244 biological activity to identify mutants that retain activity. Following mutagenesis of SEQ ID NO:25 or SEQ ID NO:27, the encoded protein can be expressed recombinantly and the activity of the protein can be determined.

As used herein, a "biologically active portion" of a 32244 protein includes a fragment of a 32244 protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a 32244 molecule and a non-32244 molecule or between a first 32244 molecule and a second 32244 molecule (e.g., a dimerization interaction). Biologically active portions of a 32244 protein include peptides comprising amino acid sequences sufficiently homologous to or derived from the amino acid sequence of the 32244 protein, e.g., the amino acid sequence shown in SEQ ID NO:26, which include less amino acids than the full length 32244 proteins, and exhibit at least one activity of a 32244 protein. Typically, biologically active portions comprise a domain or motif with at least one activity of the 32244 protein, e.g., substrate binding and adenylation and acyl-CoA ligation. A biologically active portion of a 32244 protein can be a polypeptide which is, for example, 10, 25, 50, 100, 200 or more amino acids in length. Biologically active portions of a 32244 protein can be used as targets for developing agents which modulate a 32244 mediated activity, e.g., substrate binding and adenylation and acyl-CoA ligation.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to 32244 nucleic acid molecules of the invention. BLAST protein searches can be performed with the XBLAST program, score=50, wordlength =3 to obtain amino acid sequences homologous to 32244 protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used.

Particularly preferred 32244 polypeptides of the present invention have an amino acid sequence substantially identical to the amino acid sequence of SEQ ID NO:26. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:26 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:25 or 27 are termed substantially identical.

"Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 32244 polypeptide described herein, e.g., a full-length 32244 protein or a fragment thereof, e.g., a biologically active portion of 32244 protein. Also included is a nucleic acid fragment suitable for use as a hybridization probe, which can be used, e.g., to identify a nucleic acid molecule encoding a polypeptide of the invention, 32244 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:25, or a portion of any of these nucleotide sequences. In one embodiment, the nucleic acid molecule includes sequences encoding the human 32244 protein (i.e., "the coding region" of SEQ ID NO:25, as shown in SEQ ID NO:27), as well as 5' untranslated sequences. Alternatively, the nucleic acid molecule can include only the coding region of SEQ ID NO:25 (e.g., SEQ ID NO:27) and, e.g., no flanking sequences which normally accompany the subject sequence. In another embodiment, the nucleic acid molecule encodes a sequence corresponding to a fragment of the protein from about amino acid 67 to 504 of SEQ ID NO:26.

In another embodiment, an isolated nucleic acid molecule of the invention includes a nucleic acid molecule which is a complement of the nucleotide sequence shown in SEQ ID NO:25 or SEQ ID NO:27, or a portion of any of these nucleotide sequences. In other embodiments, the nucleic acid molecule of the invention is sufficiently complementary to the nucleotide sequence shown in SEQ ID NO:25 or SEQ ID NO:27, such that it can hybridize (e.g., under a stringency condition described herein) to the nucleotide sequence shown in SEQ ID NO:25 or 27, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:25 or SEQ ID NO:27, or a portion, preferably of the same length, of any of these nucleotide sequences.

32244 Nucleic Acid Fragments

A nucleic acid molecule of the invention can include only a portion of the nucleic acid sequence of SEQ ID NO:25 or 27. For example, such a nucleic acid molecule can include a fragment which can be used as a probe or primer or a fragment encoding a portion of a 32244 protein, e.g., an immunogenic or biologically active portion of a 32244 protein. A fragment can comprise those nucleotides of SEQ ID NO:25, which encode a AMP-binding domain of human 32244. The nucleotide sequence determined from the cloning of the 32244 gene allows for the generation of probes and primers designed for use in identifying and/or cloning other 32244 family members, or fragments thereof, as well as 32244 homologues, or fragments thereof, from other species.

In another embodiment, a nucleic acid includes a nucleotide sequence that includes part, or all, of the coding region and extends into either (or both) the 5' or 3' non-coding region. Other embodiments include a fragment which includes a nucleotide sequence encoding an amino acid fragment described herein. Nucleic acid fragments can encode a specific domain or site described herein or fragments thereof, particularly fragments thereof which are at least 125 amino acids in length. Fragments also include nucleic acid sequences corresponding to specific amino acid sequences described above or fragments thereof.

A nucleic acid fragment can include a sequence corresponding to a domain, region, or functional site described herein. A nucleic acid fragment can also include one or more domain, region, or functional site described herein. Thus, for example, a 32244 nucleic acid fragment can include a sequence corresponding to an AMP-binding domain.

32244 probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:25 or SEQ ID NO:27, or of a naturally occurring allelic variant or mutant of SEQ ID NO:25 or SEQ ID NO:27.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: an AMP-binding domain, e.g., about nucleotides 374 to 1687 of SEQ ID NO:25; an N-terminal subdomain of an AMP-binding domain, e.g., about nucleotides 374 to 1585 of SEQ ID NO:25; or a C-terminal subdomain of an AMP-binding domain, e.g., about nucleotides 1586 to 1903 of SEQ ID NO:25.

In another embodiment a set of primers is provided, e.g., primers suitable for use in a PCR, which can be used to amplify a selected region of a 32244 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: an AMP-binding domain, e.g., about nucleotides 374 to 1687 of SEQ ID NO:25; an N-terminal subdomain of an AMP-binding domain, e.g., about nucleotides 374 to 1585 of SEQ ID NO:25; or a C-terminal subdomain of an AMP-binding domain, e.g., about nucleotides 1586 to 1903 of SEQ ID NO:25

A nucleic acid fragment can encode an epitope bearing region of a polypeptide described herein.

A nucleic acid fragment encoding a "biologically active portion of a 32244 polypeptide" can be prepared by isolating a portion of the nucleotide sequence of SEQ ID NO:25 or 27, which encodes a polypeptide having a 32244 biological activity (e.g., the biological activities of the 32244 proteins are described herein), expressing the encoded portion of the 32244 protein (e.g., by recombinant expression in vitro) and assessing the activity of the encoded portion of the 32244 protein. For example, a nucleic acid fragment encoding a biologically active portion of 32244 includes: an AMP-binding domain, e.g., about nucleotides 374 to 1687 of SEQ ID NO:25; an N-terminal subdomain of an AMP-binding domain, e.g., about nucleotides 374 to 1585 of SEQ ID NO:25; and a C-terminal subdomain of an AMP-binding domain, e.g., about nucleotides 1586 to 1903 of SEQ ID NO:25. A nucleic acid fragment encoding a biologically active portion of a 32244 polypeptide, may comprise a nucleotide sequence which is greater than 400 or more nucleotides in length.

In preferred embodiments, a nucleic acid includes a nucleotide sequence which is about 300, 400, 500, 600, 700, 800, 900, 1000, 1100, 1200, 1300, 1400, 1500, 1600, 1700, 1800, 1900, 2000, 2100, 2200, 2300 or more nucleotides in length and hybridizes under a stringency condition described herein to a nucleic acid molecule of SEQ ID NO:25, or SEQ ID NO:27. In a preferred embodiment, a nucleic acid includes at least one contiguous nucleotide from the region of about nucleotides 1 to 200, 150 to 375, 175 to 400, 370 to 600, 370 to 810, 600 to 850, 770 to 1000, 770 to 1250, 850 to 1100, 1000 to 1250, 1200 to 1450, 1200 to 1550, 1350 to 1600, 1500 to 1700, 1600 to 1906, 1700 to 2000, 1900 to 2302 of SEQ ID NO:25.

In a preferred embodiment, a nucleic acid fragment differs by at least one, preferably two, three or more nucleotides from the nucleotide sequences of AW008529 and AW025904, or a fragment thereof (e.g., nucleotides 1777-1978 and 1980-2149 of SEQ ID NO:25; or 1901-2288 of SEQ ID NO:25).

32244 Nucleic Acid Variants

The invention further encompasses nucleic acid molecules that differ from the nucleotide sequence shown in SEQ ID NO:25 or SEQ ID NO:27. Such differences can be due to degeneracy of the genetic code (and result in a nucleic acid which encodes the same 32244 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:26. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in $E.$ $coli$, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:25 or 27, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:26 or a fragment of this sequence. Such nucleic acid molecules can readily be identified as being able to hybridize under a stringency condition described herein, to the nucleotide sequence shown in SEQ ID NO:26 or a fragment of the sequence. Nucleic acid molecules corresponding to orthologs, homologs, and allelic variants of the 32244 cDNAs of the invention can further be isolated by mapping to the same chromosome or locus as the 32244 gene.

Preferred variants include those that are correlated with ATP-binding, substrate adenylation, and acyl-CoA ligation activities.

Allelic variants of 32244, e.g., human 32244, include both functional and non-functional proteins. Functional allelic variants are naturally occurring amino acid sequence variants of the 32244 protein within a population that maintain the ability to bind and adenylate a substrate molecule. Functional allelic variants will typically contain only conservative substitution of one or more amino acids of SEQ ID NO:26, or substitution, deletion or insertion of non-critical residues in non-critical regions of the protein. Non-functional allelic variants are naturally-occurring amino acid sequence variants of the 32244, e.g., human 32244, protein within a population that do not have the ability to bind ATP and/or adenylate a substrate molecule. Non-functional allelic variants will typically contain a non-conservative substitution, a deletion, or insertion, or premature truncation of the amino acid sequence of SEQ ID NO:26, or a substitution, insertion, or deletion in critical residues or critical regions of the protein.

Moreover, nucleic acid molecules encoding other 32244 family members and, thus, which have a nucleotide sequence which differs from the 32244 sequences of SEQ ID NO:25 or SEQ ID NO:27 are intended to be within the scope of the invention.

Antisense Nucleic Acid Molecules, Ribozymes and Modified 32244 Nucleic Acid Molecules In another aspect, the invention features, an isolated nucleic acid molecule which is antisense to 32244. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 32244 coding strand, or to only a portion thereof (e.g., the coding region of human 32244 corresponding to SEQ ID NO:27). In another embodiment, the antisense nucleic acid molecule is antisense to a "noncoding region" of the coding strand of a nucleotide sequence encoding 32244 (e.g., the 5' and 3' untranslated regions).

An antisense nucleic acid can be designed such that it is complementary to the entire coding region of 32244 mRNA, but more preferably is an oligonucleotide which is antisense to only a portion of the coding or noncoding region of 32244 mRNA. For example, the antisense oligonucleotide can be complementary to the region surrounding the translation start site of 32244 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 32244 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. A ribozyme having specificity for a 32244-encoding nucleic acid can include one or more sequences complementary to the nucleotide sequence of a 32244 cDNA disclosed herein (i.e., SEQ ID NO:25 or SEQ ID NO:27), and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a 32244-encoding mRNA. See, e.g., Cech et al. U.S. Pat. No. 4,987,071; and Cech et al. U.S. Pat. No. 5,116,742. Alternatively, 32244 mRNA can be used to select a catalytic RNA having a specific ribonuclease activity from a pool of RNA molecules. See, e.g., Bartel, D. and Szostak, J. W. (1993) *Science* 261:1411-1418.

32244 gene expression can be inhibited by targeting nucleotide sequences complementary to the regulatory region of the 32244 (e.g., the 32244 promoter and/or enhancers) to form triple helical structures that prevent transcription of the 32244 gene in target cells. See generally, Helene, C. (1991) *Anticancer Drug Des.* 6:569-84; Helene, C. i (1992) *Ann. N. Y Acad. Sci.* 660:27-36; and Maher, L. J. (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 32244 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19:17 and Faria et al. (2001) *Nature Biotech.* 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675.

PNAs of 32244 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 32244 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958-976) or intercalating agents. (see, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 32244 nucleic acid of the invention, two complementary regions one having a fluorophore and one a quencher such that the molecular beacon is useful for quantitating the presence of the 32244 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 32244 Polypeptides

In another aspect, the invention features, an isolated 32244 protein, or fragment, e.g., a biologically active portion, for use as immunogens or antigens to raise or test (or more generally to bind) anti-32244 antibodies. 32244 protein can be isolated from cells or tissue sources using standard protein purification techniques. 32244 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 32244 polypeptide has one or more of the following characteristics:

(i) it has the ability to bind ATP;
(ii) it has the ability to adenylate a substrate molecule;
(iii) it has a molecular weight, e.g., a deduced molecular weight, preferably ignoring any contribution of post translational modifications, amino acid composition or other physical characteristic of a 32244 polypeptide, e.g., a polypeptide of SEQ ID NO:26;
(iv) it has an overall sequence similarity of at least 60%, more preferably at least 70, 80, 90, or 95%, with a polypeptide a of SEQ ID NO:26;
(v) it can be found within, or associated with the surface of, a subcellular compartment, e.g., the endoplasmic reticulum, a mitochondrium, or a peroxisome;
(vi) it has an AMP-binding domain which is preferably about 70%, 80%, 90% or 95% with amino acid residues about 67 to 504 of SEQ ID NO:26;
(vii) it has an AMP-binding domain signature motif;
(viii) it has an AMP-binding domain invariant glutamine motif;
(ix) it has an AMP-binding domain invariant aspartic acid motif;
(x) it has one, two, three, four, five, six, seven, eight, preferably nine predicted Protein Kinase C phosphorylations sites (PS00005);
(xi) it has one, two, three, four, five, six, seven, preferably eight predicted Casein Kinase II phosphorylation sites;
(xii) it has one, two, three, four, five, six, preferably seven predicted N-myristoylation sites; or
(xiii) it has one predicted N-glycosylation site.

In a preferred embodiment the 32244 protein, or fragment thereof, differs from the corresponding sequence in SEQ ID: 2. In one embodiment it differs by at least one but by less than 15, 10 or 5 amino acid residues. In another it differs from the corresponding sequence in SEQ ID NO:26 by at least one residue but less than 20%, 15%, 10% or 5% of the residues in it differ from the corresponding sequence in SEQ ID NO:26. (If this comparison requires alignment the sequences should be aligned for maximum homology. "Looped" out sequences from deletions or insertions, or mismatches, are considered differences.) The differences are, preferably, differences or changes at a non essential residue or a conservative substitution. In a preferred embodiment the differences are not in the AMP-binding domain, e.g., corresponding to about amino acids 67 to 504 of SEQ ID NO:26. In another preferred embodiment one or more differences are in the AMP-binding domain, e.g., corresponding to about amino acids 67 to 504 of SEQ ID NO:26

Other embodiments include a protein that contain one or more changes in amino acid sequence, e.g., a change in an amino acid residue which is not essential for activity. Such 32244 proteins differ in amino acid sequence from SEQ ID NO:26, yet retain biological activity.

In one embodiment, the protein includes an amino acid sequence at least about 60%, 65%, 70%, 75%, 80%, 85%, 90%, 95%, 98% or more homologous to SEQ ID NO:26.

A 32244 protein or fragment is provided which varies from the sequence of SEQ ID NO:26 in regions defined by amino acids about 1 to 198, 211 to 354, 360 to 454, and 458 to 576 of SEQ ID NO:26 by at least one but by less than 15, 10 or 5 amino acid residues in the protein or fragment but which does not differ from SEQ ID NO:26 in regions defined by amino acids about 199 to 210, 355 to 359, and 455 to 457 of SEQ ID NO:26. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 32244 protein includes a AMP-binding domain. Moreover, other biologically active portions, in which other regions of the protein are deleted, can be prepared by recombinant techniques and evaluated for one or more of the functional activities of a native 32244 protein.

In a preferred embodiment, the 32244 protein has an amino acid sequence shown in SEQ ID NO:26. In other embodiments, the 32244 protein is substantially identical to SEQ ID NO:26. In yet another embodiment, the 32244 protein is substantially identical to SEQ ID NO:26 and retains the functional activity of the protein of SEQ ID NO:26, as described in detail in the subsections above.

32244 Chimeric or Fusion Proteins

In another aspect, the invention provides 32244 chimeric or fusion proteins. As used herein, a 32244 "chimeric protein" or "fusion protein" includes a 32244 polypeptide linked to a non-32244 polypeptide. A "non-32244 polypeptide" refers to a polypeptide having an amino acid sequence corresponding to a protein which is not substantially homologous to the 32244 protein, e.g., a protein which is different from the 32244 protein and which is derived from the same or a different organism. The 32244 polypeptide of the fusion protein can correspond to all or a portion e.g., a fragment described herein of a 32244 amino acid sequence. In a preferred embodiment, a 32244 fusion protein includes at least one (or two) biologically active portion of a 32244 protein. The non-32244 polypeptide can be fused to the N-terminus or C-terminus of the 32244 polypeptide.

The fusion protein can include a moiety which has a high affinity for a ligand. For example, the fusion protein can be a GST-32244 fusion protein in which the 32244 sequences are fused to the C-terminus of the GST sequences. Such fusion proteins can facilitate the purification of recombinant 32244. Alternatively, the fusion protein can be a 32244 protein containing a heterologous signal sequence at its N-terminus. In certain host cells (e.g., mammalian host cells), expression and/or secretion of 32244 can be increased through use of a heterologous signal sequence.

Fusion proteins can include all or a part of a serum protein, e.g., an IgG constant region, or human serum albumin.

The 32244 fusion proteins of the invention can be incorporated into pharmaceutical compositions and administered to a subject in vivo. The 32244 fusion proteins can be used to affect the bioavailability of a 32244 substrate. 32244 fusion proteins may be useful therapeutically for the treatment of disorders caused by, for example, (i) aberrant modification or mutation of a gene encoding a 32244 protein; (ii) mis-regulation of the 32244 gene; and (iii) aberrant post-translational modification of a 32244 protein.

Moreover, the 32244-fusion proteins of the invention can be used as immunogens to produce anti-32244 antibodies in a subject, to purify 32244 ligands and in screening assays to identify molecules which inhibit the interaction of 32244 with a 32244 substrate.

Expression vectors are commercially available that already encode a fusion moiety (e.g., a GST polypeptide). A 32244-encoding nucleic acid can be cloned into such an expression vector such that the fusion moiety is linked in-frame to the 32244 protein.

Variants of 32244 Proteins

In another aspect, the invention also features a variant of a 32244 polypeptide, e.g., which functions as an agonist (mimetics) or as an antagonist. Variants of the 32244 proteins can be generated by mutagenesis, e.g., discrete point mutation, the insertion or deletion of sequences or the truncation of a 32244 protein. An agonist of the 32244 proteins can retain substantially the same, or a subset, of the biological activities of the naturally occurring form of a 32244 protein. An antagonist of a 32244 protein can inhibit one or more of the activities of the naturally occurring form of the 32244 protein by, for example, competitively modulating a 32244-mediated activity of a 32244 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 32244 protein.

Variants of a 32244 protein can be identified by screening combinatorial libraries of mutants, e.g., truncation mutants, of a 32244 protein for agonist or antagonist activity.

Libraries of fragments e.g., N terminal, C terminal, or internal fragments, of a 32244 protein coding sequence can be used to generate a variegated population of fragments for screening and subsequent selection of variants of a 32244 protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of 32244 proteins. Recursive ensemble mutagenesis (REM), a new technique which enhances the frequency of functional mutants in the libraries, can be used in combination with the screening assays to identify 32244 variants (Arkin and Yourvan (1992) Proc. Natl. Acad. Sci. USA 89:7811-7815; Delgrave et al. (1993) Protein Engineering 6:327-331).

Cell based assays can be exploited to analyze a variegated 32244 library. For example, a library of expression vectors can be transfected into a cell line, e.g., a cell line, which ordinarily responds to 32244 in a substrate-dependent manner. The transfected cells are then contacted with 32244 and the effect of the expression of the mutant on signaling by the 32244 substrate can be detected, e.g., by measuring adenylation and/or acyl-CoA ligase activity. Plasmid DNA can then be recovered from the cells which score for inhibition, or alternatively, potentiation of signaling by the 32244 substrate, and the individual clones further characterized.

In another aspect, the invention features a method of making a 32244 polypeptide, e.g., a peptide having a non-wild type activity, e.g., an antagonist, agonist, or super agonist of a naturally occurring 32244 polypeptide, e.g., a naturally occurring 32244 polypeptide. The method includes: altering the sequence of a 32244 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 32244 polypeptide a biological activity of a naturally occurring 32244 polypeptide. The method includes: altering the sequence, e.g., by substitution or deletion of one or more residues, of a 32244 polypeptide, e.g., altering the sequence of a non-conserved region, or a domain or residue described herein, and testing the altered polypeptide for the desired activity.

Anti-32244 Antibodies

In another aspect, the invention provides an anti-32244 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-32244 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH—terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 32244 polypeptide or fragment thereof. Examples of antigen-binding fragments of the anti-32244 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-32244 antibody can be a polyclonal or a monoclonal antibody. In other embodiments, the antibody can be recombinantly produced, e.g., produced by phage display or by combinatorial methods.

Phage display and combinatorial methods for generating anti-32244 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the anti-32244 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An anti-32244 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 32244 or a fragment thereof.

Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 32244 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585, 089, the contents of which are hereby incorporated by reference. Other techniques for humanizing antibodies are described in Padlan et al. EP 519596 A1, published on Dec. 23, 1992.

In preferred embodiments an antibody can be made by immunizing with purified 32244 antigen, or a fragment thereof, e.g., a fragment described herein, tissue, e.g., crude tissue preparations, or cell fractions.

A full-length 32244 protein or, antigenic peptide fragment of 32244 can be used as an immunogen or can be used to identify anti-32244 antibodies made with other immunogens, e.g., cells, membrane preparations, and the like. The antigenic peptide of 32244 should include at least 8 amino acid residues of the amino acid sequence shown in SEQ ID NO:26 and encompasses an epitope of 32244. Preferably, the antigenic peptide includes at least 10 amino acid residues, more preferably at least 15 amino acid residues, even more preferably at least 20 amino acid residues, and most preferably at least 30 amino acid residues.

Fragments of 32244 which include from about amino acid 60 to 80, from about 434 to 446, and from about 523 to 535 of SEQ ID NO:26 can be used to make, e.g., used as immunogens or used to characterize the specificity of an antibody, antibodies against hydrophilic regions of the 32244 protein. Similarly, fragments of 32244 which include from about amino acid 245 to 270, from about 327 to 340, and from about 516 to 522 of SEQ ID NO:26 can be used to make an antibody against a hydrophobic region of the 32244 protein; a fragment of 32244 which include residues about 199 to 210, about 355 to 359, or about 455 to 458 of SEQ ID NO:26 can be used to make an antibody against the AMP-binding region of the 32244 protein.

Antibodies reactive with, or specific for, any of these regions, or other regions or domains described herein are provided.

Antibodies which bind only native 32244 protein, only denatured or otherwise non-native 32244 protein, or which bind both, are with in the invention. Antibodies with linear or conformational epitopes are within the invention. Conformational epitopes can sometimes be identified by identifying antibodies which bind to native but not denatured 32244 protein.

Preferred epitopes encompassed by the antigenic peptide are regions of 32244 are located on the surface of the protein, e.g., hydrophilic regions, as well as regions with high antigenicity. For example, an Emini surface probability analysis of the human 32244 protein sequence can be used to indicate the regions that have a particularly high probability of being localized to the surface of the 32244 protein and are thus likely to constitute surface residues useful for targeting antibody production.

In preferred embodiments antibodies can bind one or more of purified antigen, membrane associated antigen, tissue, e.g., tissue sections, whole cells, preferably living cells, lysed cells, cell fractions, e.g., membrane fractions.

The anti-32244 antibody can be a single chain antibody. A single-chain antibody (scFV) may be engineered (see, for example, Colcher, D. et al. (1999) Ann N Y Acad Sci 880:263-80; and Reiter, Y. (1996) Clin Cancer Res 2:245-52). The single chain antibody can be dimerized or multimerized to generate multivalent antibodies having specificities for different epitopes of the same target 32244 protein.

In a preferred embodiment the antibody has: effector function; and can fix complement. In other embodiments the antibody does not; recruit effector cells; or fix complement.

In a preferred embodiment, the antibody has reduced or no ability to bind an Fc receptor. For example., it is a isotype or subtype, fragment or other mutant, which does not support binding to an Fc receptor, e.g., it has a mutagenized or deleted Fc receptor binding region.

In a preferred embodiment, an anti-32244 antibody alters (e.g., increases or decreases) the ATP-binding, adenylation, or acyl-CoA ligation activity of a 32244 polypeptide. For example, the antibody can bind at or in proximity to the active site, e.g., to an epitope that includes a residue located from about 199 to 210, 355 to 359, or 455 to 458 of SEQ ID NO:26.

The antibody can be coupled to a toxin, e.g., a polypeptide toxin, e.g., ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-32244 antibody (e.g., monoclonal antibody) can be used to isolate 32244 by standard techniques, such as affinity chromatography or immunoprecipitation. Moreover, an anti-32244 antibody can be used to detect 32244 protein (e.g., in a cellular lysate or cell supernatant) in order to evaluate the abundance and pattern of expression of the protein. Anti-32244 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes nucleic acids which encode an anti-32244 antibody, e.g., an anti-32244 antibody described herein. Also included are vectors which include the nucleic acid and sells transformed with the nucleic acid, particularly cells which are useful for producing an antibody, e.g., mammalian cells, e.g. CHO or lymphatic cells.

The invention also includes cell lines, e.g., hybridomas, which make an anti-32244 antibody, e.g., an antibody described herein, and method of using said cells to make a 32244 antibody.

32244 Recombinant Expression Vectors, Host Cells and Genetically Engineered Cells In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 32244 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 32244 proteins, mutant forms of 32244 proteins, fusion proteins, and the like).

The recombinant expression vectors of the invention can be designed for expression of 32244 proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 32244 activity assays, (e.g., direct assays or competitive assays described in detail below), or to generate antibodies specific for 32244 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in E. coli is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in E. coli (Wada et al., (1992) *Nucleic Acids Res.* 20:2111-2118). Such alteration of nucleic acid sequences of the invention can be carried out by standard DNA synthesis techniques.

The 32244 expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a 32244 nucleic acid molecule within a recombinant expression vector or a 32244 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 32244 protein can be expressed in bacterial cells (such as E. coli), insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 32244 protein. Accordingly, the invention further provides methods for producing a 32244 protein using the host cells of the invention. In one embodiment, the method includes culturing the host cell of the invention (into which a recombinant expression vector encoding a 32244 protein has been introduced) in a suitable medium such that a 32244 protein is produced. In another embodiment, the method further includes isolating a 32244 protein from the medium or the host cell.

In another aspect, the invention features, a cell or purified preparation of cells which include a 32244 transgene, or which otherwise misexpress 32244. The cell preparation can consist of human or non-human cells, e.g., rodent cells, e.g., mouse or rat cells, rabbit cells, or pig cells. In preferred embodiments, the cell or cells include a 32244 transgene, e.g., a heterologous form of a 32244, e.g., a gene derived from humans (in the case of a non-human cell). The 32244 transgene can be misexpressed, e.g., overexpressed or underexpressed. In other preferred embodiments, the cell or cells include a gene that mis-expresses an endogenous 32244, e.g., a gene the expression of which is disrupted, e.g., a knockout. Such cells can serve as a model for studying disorders that are related to mutated or mis-expressed 32244 alleles or for use in drug screening.

In another aspect, the invention features, a human cell, e.g., a hematopoictic stem cell, transformed with nucleic acid which encodes a subject 32244 polypeptide.

Also provided are cells, preferably human cells, e.g., human hematopoietic or fibroblast cells, in which an endogenous 32244 is under the control of a regulatory sequence that does not normally control the expression of the endogenous 32244 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 32244 gene. For example, an endogenous 32244 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 32244 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (2001) *Nat. Biotechnol.* 19:35; and U.S. Pat. No. 5,876,742. Production of 32244 polypeptide can be regulated in the subject by administering an agent (e.g., a steroid hormone) to the subject. In another preferred embodiment, the implanted recombinant cells express and secrete an antibody specific for a 32244 polypeptide. The antibody can be any antibody or any antibody derivative described herein.

32244 Transgenic Animals

The invention provides non-human transgenic animals. Such animals are useful for studying the function and/or activity of a 32244 protein and for identifying and/or evaluating modulators of 32244 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 32244 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 32244 protein to particular cells. A transgenic founder animal can be identified based upon the presence of a 32244 transgene in its genome and/or expression of 32244 mRNA in tissues or cells of the animals. A transgenic founder animal can then be used to breed additional animals carrying the transgene. Moreover, transgenic animals carrying a transgene encoding a 32244 protein can further be bred to other transgenic animals carrying other transgenes.

32244 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses of 32244

The nucleic acid molecules, proteins, protein homologues, and antibodies described herein can be used in one or more of the following methods: a) in vitro modification of substrate compounds; b) screening assays; c) predictive medicine (e.g., diagnostic assays, prognostic assays, monitoring clinical trials, and pharmacogenetics); and d) methods of treatment (e.g., therapeutic and prophylactic).

Isolated proteins of the invention can be purified and used in vitro to, for example, modify compounds that contain carboxylic acid moieties, e.g., fatty acid molecules or xenobiotic molecules, thus producing derivative molecules that are ligated to coenzyme A.

The isolated nucleic acid molecules of the invention can be used, for example, to express a 32244 protein (e.g., via a recombinant expression vector in a host cell in gene therapy applications), to detect a 32244 mRNA (e.g., in a biological sample) or a genetic alteration in a 32244 gene, and to modulate 32244 activity, as described further below. The 32244 proteins can be used to treat disorders characterized by insufficient or excessive production of a 32244 substrate or production of 32244 inhibitors. In addition, the 32244 proteins can be used to screen for naturally occurring 32244 substrates, to screen for drugs or compounds which modulate 32244 activity, as well as to treat disorders characterized by insufficient or excessive production of 32244 protein or production of 32244 protein forms which have decreased, aberrant or unwanted activity compared to 32244 wild type protein (e.g., lipid metabolism disorders, neural disorders, and cellular proliferative and/or differentiative disorders). Moreover, the anti-32244 antibodies of the invention can be used to detect and isolate 32244 proteins, regulate the bioavailability of 32244 proteins, and modulate 32244 activity.

A method of evaluating a compound for the ability to interact with, e.g., bind, a subject 32244 polypeptide is provided. The method includes: contacting the compound with the subject 32244 polypeptide; and evaluating ability of the compound to interact with, e.g., to bind or form a complex with the subject 32244 polypeptide. This method can be performed in vitro, e.g., in a cell free system, or in vivo, e.g., in a two-hybrid interaction trap assay. This method can be used to identify naturally occurring molecules that interact with subject 32244 polypeptide. It can also be used to find natural or synthetic inhibitors of subject 32244 polypeptide. Screening methods are discussed in more detail below.

32244 Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 32244 proteins, have a stimulatory or inhibitory effect on, for example, 32244 expression or 32244 activity, or have a stimulatory or inhibitory effect on, for example, the expression or activity of a 32244 substrate. Compounds thus identified can be used to modulate the activity of target gene products (e.g., 32244 genes) in a therapeutic protocol, to elaborate the biological function of the target gene product, or to identify compounds that disrupt normal target gene interactions.

In one embodiment, the invention provides assays for screening candidate or test compounds which are substrates of a 32244 protein or polypeptide or a biologically active portion thereof. In another embodiment, the invention provides assays for screening candidate or test compounds that bind to or modulate an activity of a 32244 protein or polypeptide or a biologically active portion thereof.

In one embodiment, an activity of a 32244 protein can be assayed by, for example, expressing a 32244 nucleic acid in a vertebrate cell, e.g., COS-1 cells, adding an appropriate substrate, e.g., a fatty acid or a xenobiotic carboxylic acid-containing molecule, and detecting substrate molecules that have been modified by the addition of coenzyme A. Alternatively, activity of a 32244 protein can be assayed by expression a 32244 nucleic acid in a vertebrate cell, e.g., COS-1 cells, adding an appropriate substrate, e.g., a fatty acid or a xenobiotic carboxylic acid-containing molecule, and detecting the breakdown of the substrate by a β-oxidation pathway. Examples of these methods are presented in Steinberg et al. (2000), *J Biol Chem* 275(45):35162-9, Watkins et al. (1994), *Biochim Biophys Acta* 1214:288-94, and Watkins et al. (1991), *Arch Biochem Biophys* 289:329-36, the contents of which are incorporated herein by reference.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In one embodiment, an assay is a cell-based assay in which a cell which expresses a 32244 protein or biologically active portion thereof is contacted with a test compound, and the ability of the test compound to modulate 32244 activity is determined. Determining the ability of the test compound to modulate 32244 activity can be accomplished by monitoring, for example, ATP-binding or substrate modification, e.g., by adenylation, coenzyme A addition, or degradation. The cell, for example, can be of mammalian origin, e.g., human.

The ability of the test compound to modulate 32244 binding to a compound, e.g., a 32244 substrate, or to bind to 32244 can also be evaluated. This can be accomplished, for example, by coupling the compound, e.g., the substrate, with a radioisotope or enzymatic label such that binding of the compound, e.g., the substrate, to 32244 can be determined by detecting the labeled compound, e.g., substrate, in a complex. Alternatively, 32244 could be coupled with a radioisotope or enzymatic label to monitor the ability of a test compound to modulate 32244 binding to a 32244 substrate in a complex. For example, compounds (e.g., 32244 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 32244 substrate) to interact with 32244 with or without the labeling of any of the interactants can be evaluated. For example, a microphysiometer can be used to detect the interaction of a compound with 32244 without the labeling of either the compound or the 32244. McConnell, H. M. et al. (1992) *Science* 257: 1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 32244.

In yet another embodiment, a cell-free assay is provided in which a 32244 protein or biologically active portion thereof is contacted with a test compound and the ability of the test compound to bind to the 32244 protein or biologically active portion thereof is evaluated. Preferred biologically active portions of the 32244 proteins to be used in assays of the present invention include fragments which participate in interactions with non-32244 molecules, e.g., fragments with high surface probability scores.

Soluble and/or membrane-bound forms of isolated proteins (e.g., 32244 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 32244 protein to bind to a target molecule can be accomplished using real-time Biomolecular Interaction Analysis (BIA) (see, e.g., Sjolander, S. and Urbaniczky, C. (1991) Anal. Chem. 63:2338-2345 and Szabo et al. (1995) Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 32244, an anti-32244 antibody or its target molecule to facilitate separation of complexed from uncomplexed forms of one or both of the proteins, as well as to accommodate automation of the assay. Binding of a test compound to a 32244 protein, or interaction of a 32244 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/32244 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 32244 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 32244 binding or activity determined using standard techniques.

Other techniques for immobilizing either a 32244 protein or a target molecule on matrices include using conjugation of biotin and streptavidin. Biotinylated 32244 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 32244 protein or target molecules but which do not interfere with binding of the 32244 protein to its target molecule. Such antibodies can be derivatized to the wells of the plate, and unbound target or 32244 protein trapped in the wells by antibody conjugation. Methods for detecting such complexes, in addition to those described above for the GST-immobilized complexes, include immunodetection of complexes using antibodies reactive with the 32244 protein or target molecule, as well as enzyme-linked assays which rely on detecting an enzymatic activity associated with the 32244 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141-8; Hage, D. S., and Tweed, S. A. (1997) *J Chromatogr B Biomed Sci Appl.* 699:499-525). Further, fluorescence energy transfer may also be conveniently utilized, as described herein, to detect binding without further purification of the complex from solution.

In a preferred embodiment, the assay includes contacting the 32244 protein or biologically active portion thereof with a known compound which binds 32244 to form an assay mixture, contacting the assay mixture with a test compound, and determining the ability of the test compound to interact with a 32244 protein, wherein determining the ability of the test compound to interact with a 32244 protein includes determining the ability of the test compound to preferentially bind to 32244 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 32244 genes herein identified. In an alternative embodiment, the invention provides methods for determining the ability of the test compound to modulate the activity of a 32244 protein through modulation of the activity of a downstream effector of a 32244 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular binding partner. Control reaction mixtures are incubated without the test compound or with a placebo. The formation of any complexes between the target gene product and the cellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 32244 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 32244 ("32244-binding proteins" or "32244-bp") and are involved in 32244 activity. Such 32244-bps can be activators or inhibitors of signals by the 32244 proteins or 32244 targets as, for example, downstream elements of a 32244-mediated signaling pathway.

The two-hybrid system is based on the modular nature of most transcription factors, which consist of separable DNA-binding and activation domains. Briefly, the assay utilizes two different DNA constructs. In one construct, the gene that codes for a 32244 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 32244 protein can be the fused to the activator domain.) If the "bait" and the "prey" proteins are able to interact, in vivo, forming a 32244-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 32244 protein.

In another embodiment, modulators of 32244 expression are identified. For example, a cell or cell free mixture is contacted with a candidate compound and the expression of 32244 mRNA or protein evaluated relative to the level of expression of 32244 mRNA or protein in the absence of the candidate compound. When expression of 32244 mRNA or protein is greater in the presence of the candidate compound than in its absence, the candidate compound is identified as a stimulator of 32244 mRNA or protein expression. Alternatively, when expression of 32244 mRNA or protein is less (statistically significantly less) in the presence of the candidate compound than in its absence, the candidate compound is identified as an inhibitor of 32244 mRNA or protein expression. The level of 32244 mRNA or protein expression can be determined by methods described herein for detecting 32244 mRNA or protein.

In another aspect, the invention pertains to a combination of two or more of the assays described herein. For example, a modulating agent can be identified using a cell-based or a cell free assay, and the ability of the agent to modulate the activity of a 32244 protein can be confirmed in vivo, e.g., in an animal such as an animal model for metabolic disorders, e.g., disorders of fatty acid metabolism, neural disorders, or cellular proliferative and/or differentiative disorders.

This invention further pertains to novel agents identified by the above-described screening assays. Accordingly, it is within the scope of this invention to further use an agent identified as described herein (e.g., a 32244 modulating agent, an antisense 32244 nucleic acid molecule, a 32244-specific antibody, or a 32244-binding partner) in an appropriate animal model to determine the efficacy, toxicity, side effects, or mechanism of action, of treatment with such an agent. Furthermore, novel agents identified by the above-described screening assays can be used for treatments as described herein.

32244 Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 32244 with a disease; (ii) identify an individual from a minute biological sample (tissue typing); and (iii) aid in forensic identification of a biological sample. These applications are described in the subsections below.

32244 Chromosome Mapping

The 32244 nucleotide sequences or portions thereof can be used to map the location of the 32244 genes on a chromosome. This process is called chromosome mapping. Chromosome mapping is useful in correlating the 32244 sequences with genes associated with disease.

Briefly, 32244 genes can be mapped to chromosomes by preparing PCR primers (preferably 15-25 bp in length) from the 32244 nucleotide sequences. These primers can then be used for PCR screening of somatic cell hybrids containing individual human chromosomes. Only those hybrids containing the human gene corresponding to the 32244 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919-924).

Other mapping strategies e.g., in situ hybridization (described in Fan, Y. et al. (1990) *Proc. Natl. Acad. Sci. USA,* 87:6223-27), pre-screening with labeled flow-sorted chromosomes, and pre-selection by hybridization to chromosome specific cDNA libraries can be used to map 32244 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783-787.

Moreover, differences in the DNA sequences between individuals affected and unaffected with a disease associated with the 32244 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

32244 Tissue Typing 32244 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 32244 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:25 can provide positive individual identification with a panel of perhaps 10 to 1,000 primers which each yield a noncoding amplified sequence of 100 bases. If predicted coding sequences, such as those in SEQ ID NO:27 are used, a more appropriate number of primers for positive individual identification would be 500-2,000.

If a panel of reagents from 32244 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 32244 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:25 (e.g., fragments derived from the noncoding regions of SEQ ID NO:25 having a length of at least 20 bases, preferably at least 30 bases) are particularly appropriate for this use.

The 32244 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 32244 probes can be used to identify tissue by species and/or by organ type.

In a similar fashion, these reagents, e.g., 32244 primers or probes can be used to screen tissue culture for contamination (i.e. screen for the presence of a mixture of different types of cells in a culture).

Predictive Medicine of 32244

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 32244.

Such disorders include, e.g., a disorder associated with the misexpression of 32244 gene, e.g. misexpression in an adipose, breast, lung, colon, liver, brain, or ovary tissue.

The method includes one or more of the following:

detecting, in a tissue of the subject, the presence or absence of a mutation which affects the expression of the 32244 gene, or detecting the presence or absence of a mutation in a region which controls the expression of the gene, e.g., a mutation in the 5' control region;

detecting, in a tissue of the subject, the presence or absence of a mutation which alters the structure of the 32244 gene;

detecting, in a tissue of the subject, the misexpression of the 32244 gene, at the mRNA level, e.g., detecting a non-wild type level of a mRNA;

detecting, in a tissue of the subject, the misexpression of the gene, at the protein level, e.g., detecting a non-wild type level of a 32244 polypeptide.

In preferred embodiments the method includes: ascertaining the existence of at least one of: a deletion of one or more nucleotides from the 32244 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:25, or naturally occurring mutants thereof or 5' or 3' flanking sequences naturally associated with the 32244 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 32244 gene; the presence of a non-wild type splicing pattern of a messenger RNA transcript of the gene; or a non-wild type level of 32244.

Methods of the invention can be used prenatally or to determine if a subject's offspring will be at risk for a disorder.

In preferred embodiments the method includes determining the structure of a 32244 gene, an abnormal structure being indicative of risk for the disorder.

In preferred embodiments the method includes contacting a sample from the subject with an antibody to the 32244 protein or a nucleic acid, which hybridizes specifically with the gene. These and other embodiments are discussed below.

Diagnostic and Prognostic Assays of 32244

Diagnostic and prognostic assays of the invention include method for assessing the expression level of 32244 molecules and for identifying variations and mutations in the sequence of 32244 molecules.

Expression Monitoring and Profiling:

The presence, level, or absence of 32244 protein or nucleic acid in a biological sample can be evaluated by obtaining a biological sample from a test subject and contacting the biological sample with a compound or an agent capable of detecting 32244 protein or nucleic acid (e.g., mRNA, genomic DNA) that encodes 32244 protein such that the presence of 32244 protein or nucleic acid is detected in the biological sample. The term "biological sample" includes tissues, cells and biological fluids isolated from a subject, as well as tissues, cells and fluids present within a subject. A preferred biological sample is serum. The level of expression of the 32244 gene can be measured in a number of ways, including, but not limited to: measuring the mRNA encoded by the 32244 genes; measuring the amount of protein encoded by the 32244 genes; or measuring the activity of the protein encoded by the 32244 genes.

The level of mRNA corresponding to the 32244 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 32244 nucleic acid, such as the nucleic acid of SEQ ID NO:25, or a portion thereof, such as an oligonucleotide of at least 7, 15, 30, 50, 100, 250 or 500 nucleotides in length and sufficient to specifically hybridize under stringent conditions to 32244 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 32244 genes.

The level of mRNA in a sample that is encoded by one of 32244 can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189-193), self sustained sequence replication (Guatelli et al., (1990) Proc. Natl. Acad. Sci. USA 87:1874-1878), transcriptional amplification system (Kwoh et al., (1989), Proc. Natl. Acad. Sci. USA 86:1173-1177), Q-Beta Replicase (Lizardi et al., (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 32244 gene being analyzed.

In another embodiment, the methods further contacting a control sample with a compound or agent capable of detecting 32244 mRNA, or genomic DNA, and comparing the presence of 32244 mRNA or genomic DNA in the control sample with the presence of 32244 mRNA or genomic DNA in the test sample. In still another embodiment, serial analysis of gene expression, as described in U.S. Pat. No. 5,695,937, is used to detect 32244 transcript levels.

A variety of methods can be used to determine the level of protein encoded by 32244. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 32244 protein in a biological sample in vitro as well as in vivo. In vitro techniques for detection of 32244 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 32244 protein include introducing into a subject a labeled anti-32244 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-32244 antibody positioned on an antibody array (as described below). The sample can be detected, e.g., with avidin coupled to a fluorescent label.

In another embodiment, the methods further include contacting the control sample with a compound or agent capable of detecting 32244 protein, and comparing the presence of 32244 protein in the control sample with the presence of 32244 protein in the test sample.

The invention also includes kits for detecting the presence of 32244 in a biological sample. For example, the kit can include a compound or agent capable of detecting 32244 protein or mRNA in a biological sample; and a standard. The compound or agent can be packaged in a suitable container. The kit can further comprise instructions for using the kit to detect 32244 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 32244 expression or activity. As used herein, the term "unwanted" includes an unwanted phenomenon involved in a biological response such as a metabolic disorder, e.g., a disorder in fatty acid metabolism, a neural disorder, or deregulated cell proliferation.

In one embodiment, a disease or disorder associated with aberrant or unwanted 32244 expression or activity is identified. A test sample is obtained from a subject and 32244 protein or nucleic acid (e.g., mRNA or genomic DNA) is evaluated, wherein the level, e.g., the presence or absence, of 32244 protein or nucleic acid is diagnostic for a subject having or at risk of developing a disease or disorder associated with aberrant or unwanted 32244 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 32244 expression or activity. For example, such methods can be used to determine whether a subject can be effectively treated with an agent for a a metabolic disorder, e.g., a disorder in fatty acid metabolism, a neural disorder, or a cellular proliferative and/or differentiative disorder.

In another aspect, the invention features a computer medium having a plurality of digitally encoded data records. Each data record includes a value representing the level of expression of 32244 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 32244 (e.g., other genes associated with a 32244-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 32244 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a disorder, e.g., a cellular proliferative and/or differentiative disorder, in a subject wherein either an increase or a decrease, depending upon the disorder and the cell type, in 32244 expression is an indication that the subject has or is disposed to having a cellular proliferative and/or differentiative disorder. The method can be used to monitor a treatment for a disorder, e.g., a cellular proliferative and/or differentiative disorder, in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) Science 286:53 1).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 32244 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 32244 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 32244 expression.

32244 Arrays and Uses Thereof

In another aspect, the invention features an array that includes a substrate having a plurality of addresses. At least one address of the plurality includes a capture probe that binds specifically to a 32244 molecule (e.g., a 32244 nucleic acid or a 32244 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 32244 nucleic acid, e.g., the sense or anti-sense strand. In one preferred embodiment, a subset of addresses of the plurality of addresses has a nucleic acid capture probe for 32244. Each address of the subset can include a capture probe that hybridizes to a different region of a 32244 nucleic acid. In another preferred embodiment, addresses of the subset include a capture probe for a 32244 nucleic acid. Each address of the subset is unique, overlapping, and complementary to a different variant of 32244 (e.g., an allelic variant, or all possible hypothetical variants). The array can be used to sequence 32244 by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 32244 polypeptide or fragment thereof. The polypeptide can be a naturally-occurring interaction partner of 32244 polypeptide. Preferably, the polypeptide is an antibody, e.g., an antibody described herein (see "Anti-32244 Antibodies," above), such as a monoclonal antibody or a single-chain antibody.

In another aspect, the invention features a method of analyzing the expression of 32244. The method includes providing an array as described above; contacting the array with a sample and detecting binding of a 32244-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 32244. If a sufficient number of diverse samples is analyzed, clustering (e.g., hierarchical clustering, k-means clustering, Bayesian clustering and the like) can be used to identify other genes which are co-regulated with 32244. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 32244 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 32244-associated disease or disorder; and processes, such as a cellular transformation associated with a 32244-associated disease or disorder. The method can also evaluate the treatment and/or progression of a 32244-associated disease or disorder The array is also useful for ascertaining differential expression patterns of one or more genes in normal and abnormal cells. This provides a battery of genes (e.g., including 32244) that could serve as a molecular target for diagnosis or therapeutic intervention.

In another aspect, the invention features an array having a plurality of addresses. Each address of the plurality includes a unique polypeptide. At least one address of the plurality has disposed thereon a 32244 polypeptide or fragment thereof. Methods of producing polypeptide arrays are described in the art, e.g., in De Wildt et al. (2000). *Nature Biotech.* 18, 989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80, 85, 90, 95 or 99% identical to a 32244 polypeptide or fragment thereof. For example, multiple variants of a 32244 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 32244 binding compound, e.g., an antibody in a sample from a subject with specificity for a 32244 polypeptide or the presence of a 32244-binding protein or ligand.

The array is also useful for ascertaining the effect of the expression of a gene on the expression of other genes in the same cell or in different cells (e.g., ascertaining the effect of 32244 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 32244 or from a cell or subject in which a 32244 mediated response has been elicited, e.g., by contact of the cell with 32244 nucleic acid or protein, or administration to the cell or subject 32244 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 32244 (or does not express as highly as in the case of the 32244 positive plurality of capture probes) or from a cell or subject which in which a 32244 mediated response has not been elicited (or has been elicited to a lesser extent than in the first sample); contacting the array with one or more inquiry probes (which is preferably other than a 32244 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 32244 or from a cell or subject in which a 32244-mediated response has been elicited, e.g., by contact of the cell with 32244 nucleic acid or protein, or administration to the cell or subject 32244 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 32244 (or does not express as highly as in the case of the 32244 positive plurality of capture probes) or from a cell or subject which in which a 32244 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 32244, e.g., analyzing structure, function, or relatedness to other nucleic acid or amino acid sequences. The method includes: providing a 32244 nucleic acid or amino acid sequence; comparing the 32244 sequence with one or more preferably a plurality of sequences from a collection of sequences, e.g., a nucleic acid or protein sequence database; to thereby analyze 32244.

Detection of 32244 Variations or Mutations

The methods of the invention can also be used to detect genetic alterations in a 32244 gene, thereby determining if a subject with the altered gene is at risk for a disorder characterized by misregulation in 32244 protein activity or nucleic acid expression, such as a metabolic disorder, e.g., a disorder in fatty acid metabolism, a neural disorder, or deregulated cell proliferation. In preferred embodiments, the methods include detecting, in a sample from the subject, the presence or absence of a genetic alteration characterized by at least one of an alteration affecting the integrity of a gene encoding a 32244-protein, or the mis-expression of the 32244 gene. For example, such genetic alterations can be detected by ascertaining the existence of at least one of 1) a deletion of one or more nucleotides from a 32244 gene; 2) an addition of one or more nucleotides to a 32244 gene; 3) a substitution of one or more nucleotides of a 32244 gene, 4) a chromosomal rearrangement of a 32244 gene; 5) an alteration in the level of a messenger RNA transcript of a 32244 gene, 6) aberrant modification of a 32244 gene, such as of the methylation pattern of the genomic DNA, 7) the presence of a non-wild type splicing pattern of a messenger RNA transcript of a 32244 gene, 8) a non-wild type level of a 32244-protein, 9) allelic loss of a 32244 gene, and 10) inappropriate post-translational modification of a 32244-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 32244-gene. This method can include the steps of collecting a sample of cells from a subject, isolating nucleic acid (e.g., genomic, mRNA or both) from the sample, contacting the nucleic acid sample with one or more primers which specifically hybridize to a 32244 gene under conditions such that hybridization and amplification of the 32244-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 32244 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 32244 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 32244 nucleic acid or a putative variant (e.g., allelic variant) thereof. A probe can have one or more mismatches to a region of a 32244 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in 32244 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 32244 gene and detect mutations by comparing the sequence of the sample 32244 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 32244 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 32244 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 32244 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 32244 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 32244 nucleic acid.

In a preferred embodiment the set includes a first and a second oligonucleotide. The first and second oligonucleotide can hybridize to the same or to different locations of SEQ ID NO:25 or the complement of SEQ ID NO:25. Different locations can be different but overlapping, or non-overlapping on the same strand. The first and second oligonucleotide can hybridize to sites on the same or on different strands.

The set can be useful, e.g., for identifying SNP's, or identifying specific alleles of 32244. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 32244 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 32244 gene.

Use of 32244 Molecules as Surrogate Markers

The 32244 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 32244 molecules of the invention may be detected, and may be correlated with one or more biological states in vivo. For example, the 32244 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 32244 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 32244 marker) transcription or expression, the amplified marker may be in a quantity which is more readily detectable than the drug itself. Also, the marker may be more easily detected due to the nature of the marker itself; for example, using the methods described herein, anti-32244 antibodies may be employed in an immune-based detection system for a 32244 protein marker, or 32244-specific radiolabeled probes may be used to detect a 32244 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

The 32244 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 32244 protein or RNA) for specific tumor markers in a subject, a drug or course of treatment may be selected that is optimized for the treatment of the specific tumor likely to be present in the subject. Similarly, the presence or absence of a specific sequence mutation in 32244 DNA may correlate 32244 drug response. The use of pharmacogenomic markers therefore permits the application of the most appropriate treatment for each subject without having to administer the therapy.

Pharmaceutical Compositions of 32244

The nucleic acid and polypeptides, fragments thereof, as well as anti-32244 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents that modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 32244

The present invention provides for both prophylactic and therapeutic methods of treating a subject at risk of (or susceptible to) a disorder or having a disorder associated with aberrant or unwanted 32244 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 32244 molecules of the present invention or 32244 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 32244 expression or activity, by administering to the subject a 32244 or an agent which modulates 32244 expression or at least one 32244 activity. Subjects at risk for a disease which is caused or contributed to by aberrant or unwanted 32244 expression or activity can be identified by, for example, any or a combination of diagnostic or prognostic assays as described herein. Administration of a prophylactic agent can occur prior to the manifestation of symptoms characteristic of the 32244 aberrance, such that a disease or disorder is prevented or, alternatively, delayed in its progression. Depending on the type of 32244 aberrance, for example, a 32244, 32244 agonist or 32244 antagonist agent can be used for treating the subject. The appropriate agent can be determined based on screening assays described herein.

It is possible that some 32244 disorders can be caused, at least in part, by an abnormal level of gene product, or by the presence of a gene product exhibiting abnormal activity. As such, the reduction in the level and/or activity of such gene products would bring about the amelioration of disorder symptoms.

The 32244 molecules can act as novel diagnostic targets and therapeutic agents for controlling one or more of metabolic disorders, neural disorders, and cellular proliferative and/or differentiative disorders, which have been described above, as well as disorders associated with bone metabolism, the immune system, the cardiovascular system, the liver, viral diseases, and pain.

Aberrant expression and/or activity of 32244 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 32244 molecules effects in bone cells, e.g. osteoclasts and osteoblasts, that may in turn result in bone formation and degeneration. For example, 32244 molecules may support different activities of bone resorbing osteoclasts such as the stimulation of differentiation of monocytes and mononuclear phagocytes into osteoclasts. Accordingly, 32244 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

The 32244 nucleic acid and protein of the invention can be used to treat and/or diagnose a variety of immune disorders. Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isoniazid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 32244 molecules may play an important role in the etiology of certain viral diseases, including but not limited to Hepatitis B, Hepatitis C and *Herpes Simplex* Virus (HSV). Modulators of 32244 activity could be used to control viral diseases. The modulators can be used in the treatment and/or diagnosis of viral infected tissue or virus-associated tissue fibrosis, especially liver and liver fibrosis. Also, 32244 modulators can be used in the treatment and/or diagnosis of virus-associated carcinoma, especially hepatocellular cancer.

Additionally, 32244 may play an important role in the regulation pain disorders. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York: McGraw-Hill); pain associated with musculoskeletal disorders, e.g., joint pain; tooth pain; headaches; pain associated with surgery; pain related to irritable bowel syndrome; or chest pain.

As discussed, successful treatment of 32244 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 32244 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 32244 expression is through the use of aptamer molecules specific for 32244 protein. Aptamers are nucleic acid molecules having a tertiary structure which permits them to specifically bind to protein ligands (see, e.g., Osborne, et al. (1997) *Curr. Opin. Chem Biol.* 1: 5-9; and Patel, D. J. (1997) *Curr Opin Chem Biol* 1:32-46). Since nucleic acid molecules may in many cases be more conveniently introduced into target cells than therapeutic protein molecules may be, aptamers offer a method by which 32244 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 32244 disorders. For a description of antibodies, see the Antibody section above.

In circumstances wherein injection of an animal or a human subject with a 32244 protein or epitope for stimulating antibody production is harmful to the subject, it is possible to generate an immune response against 32244 through the use of anti-idiotypic antibodies (see, for example, Herlyn, D. (1999) *Ann Med* 31:66-78; and Bhattacharya-Chatterjee, M., and Foon, K. A. (1998) *Cancer Treat Res.* 94:51-68). If an anti-idiotypic antibody is introduced into a mammal or human subject, it should stimulate the production of anti-anti-idiotypic antibodies, which should be specific to the 32244 protein. Vaccines directed to a disease characterized by 32244 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate 32244 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 32244 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89-94 and in Shea, K. J. (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645-647. Through the use of isotope-labeling, the "free" concentration of compound which modulates the expression or activity of 32244 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142-2144.

Another aspect of the invention pertains to methods of modulating 32244 expression or activity for therapeutic purposes. Accordingly, in an exemplary embodiment, the modulatory method of the invention involves contacting a cell with a 32244 or agent that modulates one or more of the activities of 32244 protein activity associated with the cell. An agent that modulates 32244 protein activity can be an agent as described herein, such as a nucleic acid or a protein, a naturally-occurring target molecule of a 32244 protein (e.g., a 32244 substrate or receptor), a 32244 antibody, a 32244 agonist or antagonist, a peptidomimetic of a 32244 agonist or antagonist, or other small molecule.

In one embodiment, the agent stimulates one or 32244 activities. Examples of such stimulatory agents include active 32244 protein and a nucleic acid molecule encoding 32244. In another embodiment, the agent inhibits one or more 32244 activities. Examples of such inhibitory agents include antisense 32244 nucleic acid molecules, anti-32244 antibodies, and 32244 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 32244 protein or nucleic acid molecule. In one embodiment, the method involves administering an agent (e.g., an agent identified by a screening assay described herein), or combination of agents that modulates (e.g., up regulates or down regulates) 32244 expression or activity. In another embodiment, the method involves administering a 32244 protein or nucleic acid molecule as therapy to compensate for reduced, aberrant, or unwanted 32244 expression or activity.

Stimulation of 32244 activity is desirable in situations in which 32244 is abnormally downregulated and/or in which increased 32244 activity is likely to have a beneficial effect. For example, stimulation of 32244 activity is desirable in situations in which a 32244 is downregulated and/or in which increased 32244 activity is likely to have a beneficial effect. Likewise, inhibition of 32244 activity is desirable in situations in which 32244 is abnormally upregulated and/or in which decreased 32244 activity is likely to have a beneficial effect.

32244 Pharmacogenomics

The 32244 molecules of the present invention, as well as agents, or modulators which have a stimulatory or inhibitory effect on 32244 activity (e.g., 32244 gene expression) as identified by a screening assay described herein can be administered to individuals to treat (prophylactically or therapeutically) 32244 associated disorders (e.g., metabolic disorders, e.g., a disorders in fatty acid metabolism, neural disorders, or celluelar proliferative and/or differentiative disorders) associated with aberrant or unwanted 32244 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 32244 molecule or 32244 modulator as well as tailoring the dosage and/or therapeutic regimen of treatment with a 32244 molecule or 32244 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983-985 and Linder, M. W. et al. (1997) Clin. Chem. 43:254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a 32244 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a 32244 molecule or 32244 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 32244 molecule or 32244 modulator, such as a modulator identified by one of the exemplary screening assays described herein.

The present invention further provides methods for identifying new agents, or combinations, that are based on identifying agents that modulate the activity of one or more of the gene products encoded by one or more of the 32244 genes of the present invention, wherein these products may be associated with resistance of the cells to a therapeutic agent. Specifically, the activity of the proteins encoded by the 32244 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 32244 protein can be applied in clinical trials. For example, the effectiveness of an agent determined by a screening assay as described herein to increase 32244 gene expression, protein levels, or upregulate 32244 activity, can be monitored in clinical trials of subjects exhibiting decreased 32244 gene expression, protein levels, or downregulated 32244 activity. Alternatively, the effectiveness of an agent determined by a screening assay to decrease 32244 gene expression, protein levels, or downregulate 32244 activity, can be monitored in clinical trials of subjects exhibiting increased 32244 gene expression, protein levels, or upregulated 32244 activity. In such clinical trials, the expression or activity of a 32244 gene, and preferably, other genes that have been implicated in, for example, a 32244-associated disorder can be used as a "read out" or markers of the phenotype of a particular cell.

32244 Informatics

The sequence of a 32244 molecule is provided in a variety of media to facilitate use thereof. A sequence can be provided as a manufacture, other than an isolated nucleic acid or amino acid molecule, which contains a 32244. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 32244 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 32244, e.g., analyzing structure, function, or relatedness to one or more other nucleic acid or amino acid sequences. The method includes: providing a 32244 nucleic acid or amino acid sequence; comparing the 32244 sequence with a second sequence, e.g., one or more preferably a plurality of sequences from a collection of sequences, e.g., a nucleic acid or protein sequence database to thereby analyze 32244. The method can be performed in a machine, e.g., a computer, or manually by a skilled artisan.

The method can include evaluating the sequence identity between a 32244 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 32244 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features a method of analyzing a sequence. The method includes: providing a 32244 sequence, or record, in machine-readable form; comparing a second sequence to the 32244 sequence; thereby analyzing a sequence. Comparison can include comparing to sequences for sequence identity or determining if one sequence is included within the other, e.g., determining if the 32244 sequence includes a sequence being compared. In a preferred embodiment the 32244 or second sequence is stored on a first computer, e.g., at a first site and the comparison is performed, read, or recorded on a second computer, e.g., at a second site. E.g., the 32244 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 32244-associated disease or disorder or a pre-disposition to a 32244-associated disease or disorder, wherein the method comprises the steps of determining 32244 sequence information associated with the subject and based on the 32244 sequence information, determining whether the subject has a 32244-associated disease or disorder or a pre-disposition to a 32244-associated disease or disorder and/or recommending a particular treatment for the disease, disorder or pre-disease condition.

The invention further provides in an electronic system and/or in a network, a method for determining whether a subject has a 32244-associated disease or disorder or a pre-disposition to a disease associated with a 32244 wherein the method comprises the steps of determining 32244 sequence information associated with the subject, and based on the 32244 sequence information, determining whether the subject has a 32244-associated disease or disorder or a pre-disposition to a 32244-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 32244 sequence of the subject to the 32244 sequences in the database to thereby determine whether the subject as a 32244-associated disease or disorder, or a pre-disposition for such.

The present invention also provides in a network, a method for determining whether a subject has a 32244 associated disease or disorder or a pre-disposition to a 32244-associated disease or disorder associated with 32244, said method comprising the steps of receiving 32244 sequence information from the subject and/or information related thereto, receiving phenotypic information associated with the subject, acquiring information from the network corresponding to 32244 and/or corresponding to a 32244-associated disease or disorder (e.g., a metabolic disorder, e.g., a disorder in fatty acid metabolism, a neural disorder, or cellular proliferative and/or differentiative disorder), and based on one or more of the phenotypic information, the 32244 information (e.g., sequence information and/or information related thereto), and the acquired information, determining whether the subject has a 32244-associated disease or disorder or a pre-disposition to a 32244-associated disease or disorder. The method may further comprise the step of recommending a particular treatment for the disease, disorder or pre-disease condition.

The present invention also provides a method for determining whether a subject has a 32244-associated disease or disorder or a pre-disposition to a 32244-associated disease or disorder, said method comprising the steps of receiving information related to 32244 (e.g., sequence information and/or information related thereto), receiving phenotypic information associated with the subject, acquiring information from the network related to 32244 and/or related to a 32244-associated disease or disorder, and based on one or more of the phenotypic information, the 32244 information, and the acquired information, determining whether the subject has a 32244-associated disease or disorder or a pre-disposition to a 32244-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

Background of the 23680 Invention

Amino acids are deaminated at some point in their catabolism; that is, their α-amino groups is removed. Most amino acids are deaminated by the catalytic action of aminotransferases (i.e., transaminases), enzymes that interconvert α-amino and α-keto acids. The major site of amino acid catabolism in mammals is the liver.

An aminotransferase, or transaminase, transfers the α-amino group from an α-amino acid to an α-keto acid. More than 50 aminotransferases have been identified to date. These enzymes are present in all cells and are typically found in both the cytosol and mitochondria or eukaryotic cells. The α-amino groups of all amino acids except lysine, arginine and threonine can be removed by aminotransferases in one organism or another.

Aminotransferases have two-fold specificity; that is, they are specific for the α-keto acid that serves as the amino-group acceptor, and, to a lesser extent, for the α-amino acid that donates the amino group. Most aminotransferases are specific for α-ketoglutarate as the acceptor α-keto acid. The glutamate produced in these transaminations can either be deaminated to yield α-ketoglutarate and $NH_4^+$, or it can donate amino groups for amino acid biosynthesis. In fact, glutamate is the major amino-group donor in the biosynthesis of amino acids. Thus, the α-ketoglutarate-glutamate pair is centrally involved in amino acid metabolism.

The coenzyme pyridoxal phosphate (PLP) is required for the function of aminotransferases and several other critical enzymes of amino acid catabolism. PLP is derived from the $B_6$ family of water-soluble vitamins, which consists of the closely related molecules, pyridoxine, pyridoxal, and pyridoxamine. Pyridoxal kinase catalyzes phosphoryl-group transfer from ATP to the hydroxymethyl group of pyridoxal, forming PLP.

At pH 7.0, the C-3 hydroxyl group of PLP is ionized and the ring nitrogen is protonated. In most PLP-dependent enzymes, the ε-amino group of an active-site lysine reacts with the carbonyl carbon of PLP to yield an aldimine, or Schiff base. The positive charge of the aldiminium ion is stabilized by the adjacent negatively charged oxygen atom at C-3 of the pyridinium ring. The positively charged pyridinium ion, in conjunction with the positively charged aldiminium ion, is an electrophile in the reaction of PLP with an amino acid.

The transfer of the α-amino group of a donor amino acid to an acceptor α-keto acid by an aminotransferase can be divided into four steps:
    (1) a transimination occurs in which the α-amino group of the donor amino acid displaces the ε-amino group of the active-site lysine and binds to PLP, thereby forming an external aldimine. This external aldimine is held at the catalytic site by hydrogen bonds and other noncovalent interactions;

(2) the α-hydrogen of the donor amino acid is abstracted by a base of the enzyme. In the case of aspartate aminotransferase, this base has been determined to be the same active-site lysine displaced by the donor amino acid. Abstraction of the proton by the base is aided by the positively charged aldiminium and pyridinium ions, which withdraw electrons from the $C_\alpha$—H bond of the donor amino acid. A quinonoid intermediate is formed in this step;

(3) protonation of the quinonoid intermediate occurs at the 4'-carbon of PLP and yields a ketimine. In aspartate aminotransferase, this proton is donated by the active-site lysine; and (4) hydrolysis of the ketimine produces pyridoxamine phosphate and an α-keto acid whose carbon skeleton is derived from the original amino acid.

The aldehyde carbon of the original PLP molecule is reduced by transamination, but the α-carbon of the amino acid also loses two electrons; therefore, no net oxidation has occurred.

Summary of the 23680 Invention

The present invention is based, in part, on the discovery of a novel gene encoding an aminotransferase, referred to herein as "23680". The nucleotide sequence of a cDNA encoding 23680 is shown in SEQ ID NO:32, and the amino acid sequence of a 23680 polypeptide is shown in SEQ ID NO:33. In addition, the nucleotide sequence of the coding region is depicted in SEQ ID NO:34.

Accordingly, in one aspect, the invention features a nucleic acid molecule that encodes a 23680 protein or polypeptide, e.g., a biologically active portion of the 23680 protein. In a preferred embodiment the isolated nucleic acid molecule encodes a polypeptide having the amino acid sequence of SEQ ID NO:33. In other embodiments, the invention provides isolated 23680 nucleic acid molecules having the nucleotide sequence shown in SEQ ID NO:32, or SEQ ID NO:34. In still other embodiments, the invention provides nucleic acid molecules that are substantially identical (e.g., naturally occurring allelic variants) to the nucleotide sequence shown in SEQ ID NO:32, or SEQ ID NO:34. In other embodiments, the invention provides a nucleic acid molecule which hybridizes under a stringent hybridization condition as described herein to a nucleic acid molecule comprising the nucleotide sequence of SEQ ID NO:32, or SEQ ID NO:34 wherein the nucleic acid encodes a full length 23680 protein or an active fragment thereof.

In a related aspect, the invention further provides nucleic acid constructs that include a 23680 nucleic acid molecule described herein. In certain embodiments, the nucleic acid molecules of the invention are operatively linked to native or heterologous regulatory sequences. Also included are vectors and host cells containing the 23680 nucleic acid molecules of the invention, e.g., vectors and host cells suitable for producing 23680 nucleic acid molecules and polypeptides.

In another related aspect, the invention provides nucleic acid fragments suitable as primers or hybridization probes for the detection of 23680-encoding nucleic acids.

In still another related aspect, isolated nucleic acid molecules that are antisense to a 23680 encoding nucleic acid molecule are provided.

In another aspect, the invention features 23680 polypeptides, and biologically active or antigenic fragments thereof that are useful, e.g., as reagents or targets in assays applicable to treatment and diagnosis of 23680-mediated or related disorders. In another embodiment, the invention provides 23680 polypeptides having a 23680 activity, and, preferably, having a 23680 activity, e.g., a 23680 activity as described herein. Preferred polypeptides are 23680 proteins including at least one, preferably two, aminotransferase domains, e.g., class III-aminotransferase domains.

In other embodiments, the invention provides 23680 polypeptides, e.g., a 23680 polypeptide having the amino acid sequence shown in SEQ ID NO:33; an amino acid sequence that is substantially identical to the amino acid sequence shown in SEQ ID NO:33; or an amino acid sequence encoded by a nucleic acid molecule having a nucleotide sequence which hybridizes under a stringent hybridization condition described herein to a nucleic acid molecule comprising the nucleotide sequence of SEQ ID NO:32, or SEQ ID NO:34, wherein the nucleic acid encodes a full length 23680 protein or an active fragment thereof.

In a related aspect, the invention further provides nucleic acid constructs that include a 23680 nucleic acid molecule described herein.

In a related aspect, the invention provides 23680 polypeptides or fragments operatively linked to non-23680 polypeptides to form fusion proteins.

In another aspect, the invention features antibodies and antigen-binding fragments thereof, that react with, or more preferably, specifically bind to, 23680 polypeptides or fragments thereof, e.g., an aminotransferase domain of a 23680 polypeptide. In one embodiment, the antibodies or antigen-binding fragment thereof competitively inhibit the binding of a second antibody to a 23680 polypeptide or a fragment thereof, e.g., an aminotransferase domain of a 23680 polypeptide.

In another aspect, the invention provides methods of screening for compounds that modulate the expression or activity of the 23680 polypeptides or nucleic acids.

In still another aspect, the invention provides a process for modulating 23680 polypeptide or nucleic acid expression or activity, e.g. using the screened compounds. In certain embodiments, the methods involve treatment of conditions related to aberrant activity or expression of the 23680 polypeptides or nucleic acids, such as conditions involving aberrant, e.g., elevated, level or activity of an aminotransferase (e.g., an aspartate or alanine aminotransferase), such as, for example, brain disorders, liver diseases, heart diseases, malignant or pre-malignant disorders (e.g., carcinomas), diseases involving skeletal muscle, periodontal diseases or viral diseases (e.g., Hepatitis C).

In yet another aspect, the invention provides methods for modulating, e.g., increasing or decreasing, the activity (e.g., proliferation, differentiation or survival), or inducing the killing, of a 23680-expressing cell. The method includes contacting the cell with an agent, e.g., a compound (e.g., a compound identified using the methods described herein) that modulates the activity, or expression, of the 23680 polypeptide or nucleic acid.

In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol.

In a preferred embodiment, the cell is a hyperproliferative cell, e.g., a cell found in a solid tumor, a soft tissue tumor, or a metastatic lesion. For example, the hyperproliferative cell is found in a lung, breast, ovarian, or brain or glial tissue tumor.

In other embodiments, the cell has aberrant, e.g., elevated, levels of aminotransferases (e.g., aspartate or alanine aminotransferases). Examples of such cells include brain or glial cells, liver cells, heart cells, malignant or pre-malignant cells (e.g., carcinoma cells), skeletal muscle cells, periodontal cells or viral (e.g., Hepatitis C)-infected cells.

In a preferred embodiment, the agent, e.g., the compound, is an inhibitor of a 23680 polypeptide. Preferably, the inhibitor is chosen from a peptide, a phosphopeptide, a small organic molecule, a small inorganic molecule and an antibody (e.g., an antibody conjugated to a therapeutic moiety selected from a cytotoxin, a cytotoxic agent and a radioactive metal ion). In another preferred embodiment, the agent, e.g., the compound, is an inhibitor of a 23680 nucleic acid, e.g., an antisense, a ribozyme, or a triple helix molecule.

In a preferred embodiment, the agent, e.g., the compound, is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

In another aspect, the invention features methods for treating or preventing a disorder characterized by aberrant, e.g., elevated, level or activity of an aminotransferase (e.g., aspartate or alanine aminotransferase), in a subject. The method includes administering to the subject (e.g., a mammal, e.g., a human) an effective amount of an agent, e.g., a compound (e.g., a compound identified using the methods described herein) that modulates the activity, or expression, of the 23680 polypeptide or nucleic acid.

In a preferred embodiment, the disorder is a cancerous or pre-cancerous condition.

In other embodiments, the disorder is a brain disorder, liver disease, heart disease, malignant or pre-malignant disorder (e.g., carcinoma, glial cell malignancy, e.g., glioma), disease involving skeletal muscle, periodontal disease or viral disease (e.g., Hepatitis C).

In a further aspect, the invention provides methods for evaluating the efficacy of a treatment of a disorder, e.g., proliferative disorder or a disorder characterized by aberrant, e.g., elevated, level or activity of an aminotransferase (e.g., aspartate or alanine aminotransferase). The method includes: treating a subject, e.g., a patient or an animal, with a protocol under evaluation (e.g., treating a subject with one or more of: chemotherapy, radiation, and/or a compound identified using the methods described herein); and evaluating the expression of a 23680 nucleic acid or polypeptide before and after treatment. A change, e.g., a decrease or increase, in the level of a 23680 nucleic acid (e.g., mRNA) or polypeptide after treatment, relative to the level of expression before treatment, is indicative of the efficacy of the treatment of the disorder. The level of 23680 nucleic acid or polypeptide expression can be detected by any method described herein. In a preferred embodiment, the evaluating step includes obtaining a sample (e.g., a tissue sample, e.g., a biopsy, or a fluid sample) from the subject, before and after treatment and comparing the level of expressing of a 23680 nucleic acid (e.g., mRNA) or polypeptide before and after treatment.

In a preferred embodiment, the disorder is a cancerous or pre-cancerous condition.

In other embodiments, the disorder is a brain disorder, liver disease, heart disease, malignant or pre-malignant disorder (e.g., carcinoma), disease involving skeletal muscle, periodontal disease or viral disease (e.g., Hepatitis C).

In another aspect, the invention provides methods for evaluating the efficacy of a therapeutic or prophylactic agent (e.g., an anti-neoplastic agent). The method includes: contacting a sample with an agent (e.g., a compound identified using the methods described herein, a cytotoxic agent) and, evaluating the expression of 23680 nucleic acid or polypeptide in the sample before and after the contacting step. A change, e.g., a decrease or increase, in the level of 23680 nucleic acid (e.g., mRNA) or polypeptide in the sample obtained after the contacting step, relative to the level of expression in the sample before the contacting step, is indicative of the efficacy of the agent. The level of 23680 nucleic acid or polypeptide expression can be detected by any method described herein.

In a preferred embodiment, the sample includes cells obtained from a cancerous or pre-cancerous tissue. In other embodiments, the sample is obtained from the brain, liver, cardiovascular, e.g., heart, tissue, skeletal muscle, periodontal tissue or viral- (e.g., Hepatitis C-) infected tissue.

The invention also provides assays for determining the activity of, or the presence or absence of, 23680 polypeptides or nucleic acid molecules in a biological sample, including for example disease diagnosis.

In further aspect the invention provides assays for determining the presence or absence of a genetic alteration in a 23680 polypeptide or nucleic acid molecule, including for example disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 23680 molecule. In one embodiment, the capture probe is a nucleic acid, e.g., a probe complementary to a 23680 nucleic acid sequence. In another embodiment, the capture probe is a polypeptide, e.g., an antibody specific for 23680 polypeptides. Also featured is a method of analyzing a sample by contacting the sample to the aforementioned array and detecting binding of the sample to the array.

Other features and advantages of the invention will be apparent from the following detailed description, and from the claims.

Detailed Description of 23680

Figure 37:
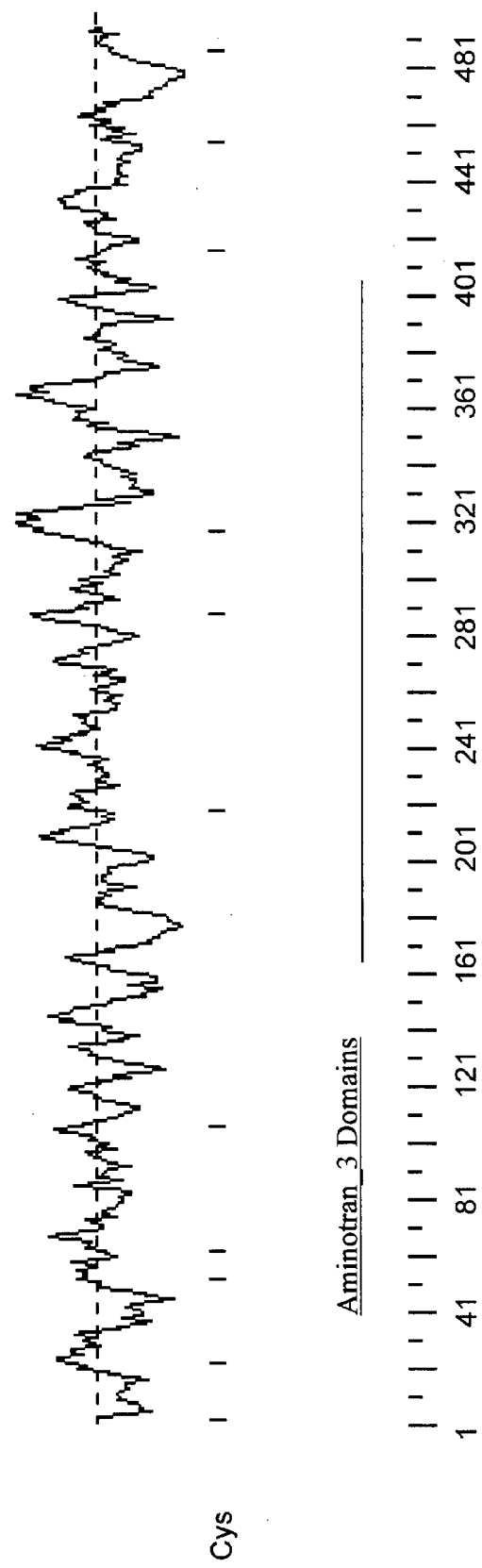
FIG. 37 depicts a hydropathy plot of human 23680. Relative hydrophobic residues are shown above the dashed horizontal line, and relative hydrophilic residues are below the dashed horizontal line. The cysteine residues (cys) are indicated by short vertical lines below the hydropathy trace. The numbers corresponding to the amino acid sequence of human 23680 are indicated. Polypeptides of the invention include fragments which include: all or part of a hydrophobic sequence, i.e., a sequence above the dashed line, e.g., the sequence of residues 310-330 or 355-370 of SEQ ID NO:33; all or part of a hydrophilic sequence, i.e., a sequence below the dashed line, e.g., the sequence of residues 30-50, 170-190 or 460-490 of SEQ ID NO:33; a sequence which includes a Cys; or a glycosylation site.

The human 23680 sequence (FIG. 37; SEQ ID NO:32), which is approximately 2103 nucleotides long including untranslated regions, contains a predicted methionine-initiated coding sequence of about 1500 nucleotides, excluding termination codon (nucleotides 145-1644 of SEQ ID NO:32; also shown in SEQ ID NO:34). The coding sequence encodes a 499 amino acid protein (SEQ ID NO:33).

Human 23680 contains the following regions or other structural features: two predicted aminotransferase class-III domain from about residues 40-141 and 165-415 of SEQ ID NO:33, which includes a predicted aminotransferase class-III pyridoxal-phosphate attachment site (PS00600) from about amino acids 243-283 of SEQ ID NO:33.

The human 23680 additionally contains two predicted cAMP and cGMP-dependent protein kinase phosphorylation site (PS00004) at about amino acids 7-10 and 93-96 of SEQ ID NO:33; seven predicted Protein kinase C phosphorylation sites (PS00005) at about amino acids 6-8, 21-23, 173-175, 203-2-5, 291-293, 479-481 and 494-496; ten predicted Casein kinase II phosphorylation sites (PS00006) located at about amino acids 6-9, 98-101, 111-114, 145-148, 291-294, 302-305, 418-421, 434-437, 442-445 and 470-473 of SEQ ID NO:33; six predicted N-myristoylation sites (PS00008) from about amino acids 65-70, 112-117, 241-246, 312-317, 340-345 and 364-369 of SEQ ID NO:33; one predicted amidation site (PS00009) from about amino acids 203-206.

For general information regarding PFAM identifiers, PS prefix and PF prefix domain identification numbers, refer to Sonnhammer et al. (1997) *Protein* 28:405-420.

The 23680 protein contains a significant number of structural characteristics in common with members of the class-III aminotransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

Aminotransferases are an extensive group of proteins, which catalyze the transfer of an α-amino acid to an α-keto acid. A typical consensus pattern for class-III aminotransferases is as follows: [LIVMFYWC](2)-x-D-E-[IVA]-x(2)-G-[LIVMFAGC]-x(0,1)-[RSACLI]-x-[GSAD]-x(12,16)-D-[LIVMFC]-[LIVMFYSTA]-x(2)-[GSA]-K-x(3)-[GSTADNV]-[GSAC] (SEQ ID NO:37).

A 23680 polypeptide can include an "aminotransferase class-II pyridoxal-phosphate attachment site" or regions homologous with an "aminotransferase class-III pyridoxal-phosphate attachment site". As used herein, the term "aminotransferase class-III pyridoxal-phosphate attachment site" refers to a protein domain having an amino acid sequence of about 10 to 70 amino acid residues in length. Preferably, an aminotransferase class-III pyridoxal-phosphate attachment site includes at least about 20-60 amino acids, more preferably about 30-50 amino acid residues, or even more preferably about 35-45 amino acids, and most preferably, 40 amino acid residues. The aminotransferase class-III pyridoxal-phosphate attachment site has been assigned the ProSite Accession PS00600.

In a preferred embodiment, 23680 polypeptide or protein has an "aminotransferase class-III pyridoxal-phosphate attachment site" or a region which includes at least about 10-70, more preferably about 20-60, even more preferably about 30-50 or 35-45 amino acid residues and has at least about 60%, 70% 80% 90% 95%, 99%, or 100% homology with an "aminotransferase class-III pyridoxal-phosphate attachment site" e.g., the aminotransferase class-III pyridoxal-phosphate attachment site of human 23680 (e.g., residues 243-283 of SEQ ID NO:33).

A 23680 polypeptide can also include one and preferably two aminotransferase class-III pyridoxal-phosphate domain. As used herein, the term "aminotransferase class-III pyridoxal-phosphate domain" refers to a protein domain having an amino acid sequence of about 50-500 amino acid residues in length, preferably, at least about 100-400 amino acids, more preferably about 100-300 amino acid residues, or about 101 or 250 amino acids and has a bit score for the alignment of the sequence to the aminotransferase class-III pyridoxal-phosphate domain (HMM) of at least 50 or greater, preferably 100 or greater, more preferably, 150 or greater, and most preferably, 200 or greater. The aminotransferase class-III pyridoxal-phosphate domain (HMM) has been assigned the PFAM Accession PDOC00519. An alignment of the aminotransferase class-III pyridoxal-phosphate domains (amino acids 40-141 and 165-415 of SEQ ID NO:33) of human 23680 with consensus amino acid sequences derived from a hidden Markov model is depicted in FIG. 38.

To identify the presence of an aminotransferase class-III domain in a 23680 polypeptide, the amino acid sequence of the protein is searched against a database of HMMs (e.g., the Pfam database, release 2.1) using the default parameters. For example, the hmmsf program, which is available as part of the HMMER package of search programs, is a family specific default program for PS00600 and score of 50, preferably 100, even more preferably 200, is the default threshold score for determining a hit.

The 23680 molecules of the present invention can further include at least one, preferably two, cAMP and cGMP-dependent protein kinase phosphorylation sites. The 23680 molecules can also include at least one, two, three, four, five, six or even seven Protein kinase C phosphorylation sites. The 23680 molecules can additionally include at least one, two, three, four, five, six, seven, eight, nine, and preferably ten, Casein kinase II phosphorylation sites. The 23680 molecules can further include at least one, two, three, four, five and preferably six, N-myristoylation sites. The 23680 molecules can additionally include an amidation site and an aminotransferase class-III pyridoxal-phosphate attachment site. A 23680 family member can further include an aminotransferase class-III pyridoxal-phosphate domain.

As the 23680 polypeptides of the invention may modulate 23680-mediated activities, they may be useful as of for developing novel diagnostic and therapeutic agents for 23680-mediated or related disorders, as described below.

As used herein, a "23680 activity", "biological activity of 23680" or "functional activity of 23680", refers to an activity exerted by a 23680 protein, polypeptide or nucleic acid molecule on e.g., a 23680-responsive cell or on a 23680 substrate, e.g., a protein substrate, as determined in vivo or in vitro. In one embodiment, a 23680 activity is a direct activity, such as an association with a 23680 target molecule. A "target molecule" or "binding partner" is a molecule with which a 23680 protein binds or interacts in nature. In an exemplary embodiment, is a 23680 receptor. A 23680 activity can also be an indirect activity.

The 23680 molecules of the present invention are predicted to have similar biological activities as aminotransferase family members. For example, the 23680 proteins of the present invention can have one or more of the following activities: (1) the ability to catalyze the transfer of an α-amino group from an α-amino acid to an α-keto acid; (2) the ability to catalyze the following reaction: amino acid$_1$+aminotransferase-pyridoxal phosphate□α-keto acid$_1$+aminotransferase-pyridoxamine phosphate; (3) the ability to catalyze the following reaction: α-keto acid$_2$+aminotransferase-pyridoxamine phosphate□amino acid$_2$+aminotransferase-pyridoxal phosphate; (4) the ability to catalyze the following reaction: amino acid$_1$+α-keto acid$_2$+amino acid$_2$+α-keto acid$_1$ (i.e., the sum of steps (2) and (3)); (5) the ability to catalyze, via transamination, the conversion of aspartate and α-ketoglutarate to oxaloacetate and glutamate (i.e., aspartate aminotransferase); or (6) the ability to catalyze, via transamination, the conversion of alanine and α-ketoglutarate to pyruvate and glutamate (i.e., alanine aminotransferase). Thus, the 23680 molecules can act as novel diagnostic targets and therapeutic agents for controlling aminotransferase-related disorders.

The response mediated by a 23680 receptor protein depends on the type of cell. For example, in some cells, binding of a ligand to the receptor protein may stimulate an activity, while in other cells, the binding of the ligand will produce a different result. Regardless of the cellular activity/response modulated by the receptor protein, it is universal that the protein is an aminotransferase that catalyzes the transfer of an α-amino group from an α-amino aid to an α-keto acid. Examples of such functions include transamination of aspartate to α-ketoglutarate to produce oxaloacetate and glutamate (via an aspartate aminotransferase), or alternatively, transamination of alanine to α-ketoglutarate to produce pyruvate and glutamate (via an alanine aminotransferase).

Other activities, as described below, include the ability to modulate function, survival, morphology, proliferation and/or differentiation of cells of tissues in which 23680 molecules are expressed, e.g., liver cells, brain cells. For example, the activities of 23680 can include modulation of, e.g., liver or brain cell proliferation, differentiation, survival and/or cell death. 23680 molecules of the present invention may be involved in disorders characterized by elevated levels of aminotransferases, e.g., in disorders of the liver, brain, cardiovascular system, e.g., the heart, skeletal muscle, cancers, e.g., carcinomas, glioblastoma, periodontal diseases and viral diseases (e.g., Hepatitis C). Thus, the 23680 molecules can act as novel diagnostic targets and therapeutic agents for controlling disorders involving elevated levels of aminotransferases.

Examples of liver disorders include, but are not limited to, disorders associated with an accumulation in the liver of fibrous tissue, such as those resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolsim, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome. Examples of liver or hepatic disorders include hepatitis, liver cirrhosis, hepatoma, liver cysts, and hepatic vein thrombosis.

Examples of brain disorders include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

Additionally, skeletal muscle cells may be affected by aberrant activity of a 23680 polypeptide. For instance, symptoms of a skeletal muscular disorder may include aching muscles, muscle cramps or muscle degeneracy.

The 23680 molecules can also act as novel diagnostic targets and therapeutic agents for controlling cellular proliferative and/or differentiative disorders (e.g., neoplastic disorders). Additional examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors. Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Additional examples of proliferative disorders include hematopoietic neoplastic disorders. As used herein, the term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myclogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

23680 polypeptides may also be associated with active periodontal disease. Periodontal diseases are inflammatory conditions of microbial etiology affecting the supporting tissues of the teeth. Typically, periodontal disease encompasses two major subclasses of disease, gingivitis and periodontitis. Gingivitis is characterized by inflammation of the gums in the absence of bone and attachment loss. Periodontitis is generally accepted to be an advanced stage of gingivitis characterized further by formation of periodontal pockets between the gum tissue and tooth. Severe cases of periodontitis are associated with loss of bone from the tooth and weakening of tooth attachment, eventually leading to tooth loss. The most common form of periodontitis among American adults is chronic inflammatory periodontitis (CIPD) and is characterized by loss of attachment of periodontal ligament to cementum, apical migration of junctional epithelium, and loss of alveolar bone. Both gingivitis and periodontitis are further characterized by accumulation of crevicular fluid (a transudate of serum) at the junction of the teeth and gums.

Additionally, 23680 molecules may play an important role in the etiology of certain viral diseases, including, but not limited to, Hepatitis B, Hepatitis C and Herpes Simplex Virus (HSV). Modulators of 23680 activity could be used to control viral diseases. The modulators can be used in the treatment and/or diagnosis of viral infected tissue or virus-associated tissue fibrosis, especially liver and liver fibrosis. Also, 23680 modulators can be used in the treatment and/or diagnosis of virus-associated carcinoma, especially hepatocellular cancer.

The 23680 protein, fragments thereof, and derivatives and other variants of the sequence in SEQ ID NO:33 thereof are collectively referred to as "polypeptides or proteins of the invention" or "23680 polypeptides or proteins". Nucleic acid molecules encoding such polypeptides or proteins are collectively referred to as "nucleic acids of the invention" or "23680 nucleic acids." 23680 molecules refer to 23680 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated" or "purified" nucleic acid molecule includes nucleic acid molecules that are separated from other nucleic acid molecules that are present in the natural source of the nucleic acid. For example, with regards to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and non-aqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 23680 protein, preferably a mammalian 23680 protein, and can further include non-coding regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 23680 protein having less than about 30%, 20%, 10% and more preferably 5% (by dry weight), of non-23680 protein (also referred to herein as a "contaminating protein"), or of chemical precursors or non-23680 chemicals. When the 23680 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 23680 (e.g., the sequence of SEQ ID NO:32, SEQ ID NO:34 without abolishing or more preferably, without substantially altering a biological activity, whereas an "essential" amino acid residue results in such a change. For example, amino acid residues that are conserved among the polypeptides of the present invention, e.g., those present in the aminotransferase domains, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 23680 protein is preferably replaced with another amino acid residue from the same side chain family. Alternatively, in another embodiment, mutations can be introduced randomly along all or part of a 23680 coding sequence, such as by saturation mutagenesis, and the resultant mutants can be screened for 23680 biological activity to identify mutants that retain activity. Following mutagenesis of SEQ ID NO:32, or SEQ ID NO:34 the encoded protein can be expressed recombinantly and the activity of the protein can be determined.

As used herein, a "biologically active portion" of a 23680 protein includes a fragment of a 23680 protein that participates in an interaction between a 23680 molecule and a non-23680 molecule. Biologically active portions of a 23680 protein include peptides comprising amino acid sequences sufficiently homologous to or derived from the amino acid sequence of the 23680 protein, e.g., the amino acid sequence shown in SEQ ID NO:33, which include less amino acids than the full length 23680 proteins, and exhibit at least one activity of a 23680 protein. Typically, biologically active portions comprise a domain or motif with at least one activity of the 23680 protein, e.g., a domain or motif capable of: (1) catalyzing the transfer of an α-amino group from an α-amino acid to an α-keto acid; (2) catalyzing the following reaction: amino acid$_1$+aminotransferase-pyridoxal phosphate☐α-keto acid$_1$+aminotransferase-pyridoxamine phosphate; (3) catalyzing the following reaction: α-keto acid$_2$+aminotransferase-pyridoxamine phosphate☐amino acid$_2$+aminotransferase-pyridoxal phosphate; (4) catalyzing the following reaction: amino acid$_1$+ α-keto acid$_2$☐amino acid$_2$+α-keto acid$_1$ (i.e., the sum of steps (2) and (3)); (5) catalyzing, via transamination, the conversion of aspartate and α-ketoglutarate to oxaloacetate and glutamate (i.e., aspartate aminotransferase); or (6) catalyzing, via transamination, the conversion of alanine and α-ketoglutarate to pyruvate and glutamate (i.e., alanine aminotransferase).

A biologically active portion of a 23680 protein can be a polypeptide that for example, 10, 25, 50, 100, 200 or more amino acids in length. Biologically active portions of a 23680 protein can be used as targets for developing agents that modulate a 23680-mediated activity, e.g., a biological activity described herein.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even preferably at least 60%, and even more preferably at least 70%, 80%, 90%, 100% of the length of the reference sequence (e.g., when aligning a second sequence to the 23680 amino acid sequence of SEQ ID NO:33 having 499 amino acid residues, at least 150, preferably at least 200, more preferably at least 250, even more preferably at least 300, and even more preferably at least 350, 400, 450 or 499 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to 23680 nucleic acid molecules of the invention. BLAST protein searches can be performed with the XBLAST program, score=50, wordlength=3 to obtain amino acid sequences homologous to 23680 protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

"Misexpression or aberrant expression", as used herein, refers to a non-wild-type pattern of gene expression, at the RNA or protein level. It includes: expression at non-wild-type levels, i.e., over- or under-expression; a pattern of expression that differs from wild-type in terms of the time or stage at which the gene is expressed, e.g., increased or decreased expression (as compared with wild-type) at a predetermined developmental period or stage; a pattern of expression that differs from wild-type in terms of decreased expression (as compared with wild-type) in a predetermined cell type or tissue type; a pattern of expression that differs from wild-type in terms of the splicing size, amino acid sequence, post-transitional modification, or biological activity of the expressed polypeptide; a pattern of expression that differs from wild-type in terms of the effect of an environmental stimulus or extracellular stimulus on expression of the gene, e.g., a pattern of increased or decreased expression (as compared with wild-type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10%, and more preferably, 50% of the subject cells.

Various aspects of the invention are described in further detail below.

Isolated Nucleic Acid Molecules of 23680

In one aspect, the invention provides, an isolated or purified, nucleic acid molecule that encodes a 23680 polypeptide described herein, e.g., a full-length 23680 protein or a fragment thereof, e.g., a biologically active portion of 23680 protein. Also included is a nucleic acid fragment suitable for use as a hybridization probe, which can be used, e.g., to a identify nucleic acid molecule encoding a polypeptide of the invention, 23680 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:32, or a portion of any of these nucleotide sequences. In one embodiment, the nucleic acid molecule includes sequences encoding the human 23680 protein (i.e., "the coding region", from nucleotides 145-1644 of SEQ ID NO:32), as well as 5' untranslated sequences (nucleotides 1-144 of SEQ ID NO:32) or 3' untranslated sequences (nucleotides 1645-2103 of SEQ ID NO:32). Alternatively, the nucleic acid molecule can include only the coding region of SEQ ID NO:32 (e.g., nucleotides 145-1644, corresponding to SEQ ID NO:34) and, e.g., no flanking sequences which normally accompany the subject sequence. In another embodiment, the nucleic acid molecule encodes a sequence corresponding to the 499 amino acid protein of SEQ ID NO:33.

In another embodiment, an isolated nucleic acid molecule of the invention includes a nucleic acid molecule which is a complement of the nucleotide sequence shown in SEQ ID NO:32, or SEQ ID NO:34, or a portion of any of these nucleotide sequences. In other embodiments, the nucleic acid molecule of the invention is sufficiently complementary to the nucleotide sequence shown in SEQ ID NO:32, or SEQ ID NO:34 such that it can hybridize to the nucleotide sequence shown in SEQ ID NO:32, or SEQ ID NO:34, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:32, or SEQ ID NO:34, or a portion, preferably of the same length, of any of these nucleotide sequences.

23680 Nucleic Acid Fragments

A nucleic acid molecule of the invention can include only a portion of the nucleic acid sequence of SEQ ID NO:32 or 34. For example, such a nucleic acid molecule can include a fragment that can be used as a probe or primer or a fragment encoding a portion of a 23680 protein, e.g., an immunogenic or biologically active portion of a 23680 protein. A fragment can comprise nucleotides corresponding to residues 40-141, or 165-415 of SEQ ID NO:33, which encodes an aminotransferase class-III pyridoxal-phosphate domain of human 23680. The nucleotide sequence determined from the cloning of the 23680 gene allows for the generation of probes and primers designed for use in identifying and/or cloning other 23680 family members, or fragments thereof, as well as 23680 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment that includes a nucleotide sequence encoding an amino acid described herein. Nucleic acid fragments can encode a specific domain or site described herein or fragments thereof, particularly fragments thereof that are at least about 250 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domains, regions, or functional sites described herein.

23680 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:32, or SEQ ID NO:34, or of a naturally occurring allelic variant or mutant of SEQ ID NO:32, or SEQ ID NO:34.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid that encodes: an aminotransferase class-III pyridoxal-phosphate attachment site which extends from about amino acid 243 to about amino acid 283 of SEQ ID NO:33; an aminotransferase class-III pyridoxal-phosphate domain from about 40-141 or 165-415 of SEQ ID NO:33.

In another embodiment a set of primers is provided, e.g., primers suitable for use in a PCR, which can be used to amplify a selected region of a 23680 sequence. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying all or a portion of any of the following regions are provided: e.g., an aminotransferase class-III pyridoxal-phosphate attachment site or an aminotransferase class-III pyridoxal-phosphate domain as defined above relative to SEQ ID NO:33.

A nucleic acid fragment can encode an epitope bearing region of a polypeptide described herein.

A nucleic acid fragment encoding a "biologically active portion of a 23680 polypeptide" can be prepared by isolating a portion of the nucleotide sequence of SEQ ID NO:32, or SEQ ID NO:34 which encodes a polypeptide having a 23680 biological activity (e.g., the biological activities of the 23680 proteins are described herein), expressing the encoded portion of the 23680 protein (e.g., by recombinant expression in vitro) and assessing the activity of the encoded portion of the 23680 protein. For example, a nucleic acid fragment encoding a biologically active portion of 23680 includes an aminotransferase class-III pyridoxal-phosphate domain, e.g., amino acid residues 40-141 or 165-415 of SEQ ID NO:33. A nucleic acid fragment encoding a biologically active portion of a 23680 polypeptide may comprise a nucleotide sequence that is greater than 25 or more nucleotides in length.

In one embodiment, a nucleic acid includes a nucleotide sequence which is greater than 100, more preferably, 200, 300, 400, 500, 600, 700, 800, 900, 1000, 1100, 1200, 1300, 1400, 1500 or more nucleotides in length and hybridizes under stringent hybridization conditions to a nucleic acid molecule of SEQ ID NO:32, or SEQ ID NO:34.

23680 Nucleic Acid Variants

The invention further encompasses nucleic acid molecules that differ from the nucleotide sequence shown in SEQ ID NO:32, or SEQ ID NO:34. Such differences can be due to degeneracy of the genetic code (and result in a nucleic acid that encodes the same 23680 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:33. If alignment is needed for this comparison the sequences should be aligned for maximum homology. "Looped" out sequences from deletions or insertions, or mismatches, are considered differences.

Nucleic acids of the invention can be chosen for having codons, which are preferred, or non-preferred, for a particular expression system. E.g., the nucleic acid can be one in which at least one colon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:32, or SEQ ID NO:34 e.g., as follows: by at least one but less than 10, 20, 30, or 40 nucleotides; at least one but less than 5%, 10% or 20% of the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:33 or a fragment of this sequence. Such nucleic acid molecules can readily be identified as being able to hybridize under stringent conditions, to the nucleotide sequence shown in SEQ ID NO:33 or a fragment of the sequence. Nucleic acid molecules corresponding to orthologs, homologs, and allelic variants of the 23680 cDNAs of the invention can further be isolated by mapping to the same chromosome or locus as the 23680 gene.

Preferred variants include those that are correlated with any of the 23680 biological activities described herein, e.g., (1) catalyzing the transfer of an α-amino group from an α-amino acid to an α-keto acid; (2) catalyzing the following reaction: amino acid$_1$+aminotransferase-pyridoxal phosphate□α-keto acid$_1$+aminotransferase-pyridoxamine phosphate; (3) catalyzing the following reaction: α-keto acid$_2$+aminotransferase-pyridoxamine phosphate□amino acid$_2$+aminotransferase-pyridoxal phosphate; (4) catalyzing the following reaction: amino acid$_1$+α-keto acid$_2$□amino acid$_2$+α-keto acid$_1$ (i.e., the sum of steps (2) and (3)); (5) catalyzing, via transamination, the conversion of aspartate and α-ketoglutarate to oxaloacetate and glutamate (i.e., via an aspartate aminotransferase); or (6) catalyzing, via transamination, the conversion of alanine and α-ketoglutarate to pyruvate and glutamate (i.e., via an alanine aminotransferase).

Allelic variants of 23680, e.g., human 23680, include both functional and non-functional proteins. Functional allelic variants are naturally occurring amino acid sequence variants of the 23680 protein within a population that maintain the ability to mediate any of the 23680 biological activities described herein, e.g., (1) catalyzing the transfer of an α-amino group from an α-amino acid to an α-keto acid; (2) catalyzing the following reaction: amino acid$_1$+aminotransferase-pyridoxal phosphate□α-keto acid$_1$+aminotransferase-pyridoxamine phosphate; (3) catalyzing the following reaction: α-keto acid$_2$+aminotransferase-pyridoxamine phosphate□amino acid$_2$+aminotransferase-pyridoxal phosphate; (4) catalyzing the following reaction: amino acid$_1$+α-keto acid$_2$□amino acid$_2$+α-keto acid$_1$ (i.e., the sum of steps (2) and (3)); (5) catalyzing, via transamination, the conversion of aspartate and α-ketoglutarate to oxaloacetate and glutamate (i.e., aspartate aminotransferase); or (6) catalyzing, via transamination, the conversion of alanine and α-ketoglutarate to pyruvate and glutamate (i.e., alanine aminotransferase).

Functional allelic variants will typically contain only conservative substitution of one or more amino acids of SEQ ID NO:33, or substitution, deletion or insertion of non-critical residues in non-critical regions of the protein. Non-functional allelic variants are naturally-occurring amino acid sequence variants of the 23680, e.g., human 23680, protein within a population that do not have the ability to mediate any of the 23680 biological activities described herein. Non-functional allelic variants will typically contain a non-conservative substitution, a deletion, or insertion or premature truncation of the amino acid sequence of SEQ ID NO:33, or a substitution, insertion, or deletion in critical residues or critical regions of the protein.

Moreover, nucleic acid molecules encoding other 23680 family members and, thus, which have a nucleotide sequence which differs from the 23680 sequences of SEQ ID NO:32, or SEQ ID NO:34 are intended to be within the scope of the invention.

Antisense Nucleic Acid Molecules, Ribozymes and Modified 23680 Nucleic Acid Molecules In another aspect, the invention features, an isolated nucleic acid molecule that is antisense to 23680. An "antisense" nucleic acid can include a nucleotide sequence that is complementary to a "sense" nucleic acid encoding a protein, e.g., complementary to the coding strand of a double-stranded cDNA molecule or complementary to an mRNA sequence. The antisense nucleic acid can be complementary to an entire 23680 coding strand, or to only a portion thereof (e.g., the coding region of human 23680 corresponding to SEQ ID NO:34). In another embodiment, the antisense nucleic acid molecule is antisense to a "noncoding region" of the coding strand of a nucleotide sequence encoding 23680 (e.g., the 5' and 3' untranslated regions).

An antisense nucleic acid can be designed such that it is complementary to the entire coding region of 23680 mRNA, but more preferably is an oligonucleotide that is antisense to only a portion of the coding or noncoding region of 23680 mRNA. For example, the antisense oligonucleotide can be complementary to the region surrounding the translation start site of 23680 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 23680 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. A ribozyme having specificity for a 23680-encoding nucleic acid can include one or more sequences complementary to the nucleotide sequence of a 23680 cDNA disclosed herein (i.e., SEQ ID NO:32 or SEQ ID NO:34), and a sequence having known catalytic sequence responsible for mRNA cleavage (see, for example, U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a 23680-encoding mRNA (see, e.g., Cech et al. U.S. Pat. No. 4,987,071; and Cech et al. U.S. Pat. No. 5,116,742). Alternatively, 23680 mRNA can be used to select a catalytic RNA having a specific ribonuclease activity from a pool of RNA molecules (see, e.g., Bartel, D. and Szostak, J. W. (1993) *Science* 261:1411-1418).

23680 gene expression can be inhibited by targeting nucleotide sequences complementary to the regulatory region of the 23680 (e.g., the 23680 promoter and/or enhancers) to form triple helical structures that prevent transcription of the 23680 gene in target cells (see generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15). The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 23680 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670-675.

PNAs of 23680 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 23680 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958-976) or intercalating agents. (See, e.g., Zon (1988) Pharm. Res. 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 23680 nucleic acid of the invention, two complementary regions, one having a fluorophore and one a quencher, such that the molecular beacon is useful for quantitating the presence of the 23680 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 23680 Polypeptides

In another aspect, the invention features, an isolated 23680 protein, or fragment, e.g., a biologically active portion, for use as immunogens or antigens to raise or test (or more generally to bind) anti-23680 antibodies. 23680 protein can be isolated from cells or tissue sources using standard protein purification techniques. 23680 protein or fragments thereof can be produced by recombinant DNA techniques or synthesized chemically.

Polypeptides of the invention include those that arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when the polypeptide is expressed in a native cell, or in systems which result in the alteration or omission of post-translational modifications, e.g., glycosylation or cleavage, present when expressed in a native cell.

In a preferred embodiment, a 23680 polypeptide has one or more of the following characteristics:

(i) the ability to catalyze the transfer of an α-amino group from an α-amino acid to an α-keto acid according to the following steps:

(a) transimination, in which the α-amino group of the donor amino acid displaces the ε-amino group of the active-site lysine and binds to pyridoxal phosphate (PLP), thereby forming an external aldimine, which is held at the catalytic site by hydrogen bonds and other noncovalent interactions;

(b) abstraction of the α-hydrogen of the donor amino acid by a base of the enzyme (e.g., the same active-site lysine displaced by the donor amino acid) (abstraction of the proton by the base is aided by the positively charged aldiminium and pyridinium ions, which withdraw electrons from the $C_\alpha$—H bond of the donor amino acid, thereby forming a quinonoid intermediate);

(c) protonation (e.g., donated by the active-site lysine) of the quinonoid intermediate at the 4'-carbon of PLP to yield a ketimine; and (d) hydrolysis of the ketimine to produce pyridoxamine phosphate (PMP) and an α-keto acid, whose carbon skeleton is derived from the original amino acid;

(ii) the ability to catalyze the following reaction: amino acid$_1$+aminotransferase-pyridoxal phosphate☐α-keto acid$_1$+aminotransferase-pyridoxamine phosphate;

(iii) the ability to catalyze the following reaction: α-keto acid$_2$+aminotransferase-pyridoxamine phosphate☐amino acid$_2$+aminotransferase-pyridoxal phosphate;

(iv) the ability to catalyze the following reaction: amino acid$_1$+α-keto acid$_2$☐amino acid$_2$+α-keto acid$_1$ (i.e., the sum of steps (ii) and (iii));

(v) the ability to catalyze, via transamination, the conversion of aspartate and α-ketoglutarate to oxaloacetate and glutamate (i.e., aspartate aminotransferase);

(vi) the ability to catalyze, via transamination, the conversion of alanine and α-ketoglutarate to pyruvate and glutamate (i.e., alanine aminotransferase);

(vii) it has a molecular weight, amino acid composition or other physical characteristic of a 23680 protein, e.g., a protein of SEQ ID NO:33;

(viii) it has an overall sequence similarity (identity) of at least 60-65%, preferably at least 70%, more preferably at least 75, 80, 85, 86, 87, 88, 89, 90, 91, 92, 93, 94, 95, 96, 97, 98, 99% or more, with a polypeptide of SEQ ID NO:33; or (ix) it has an aminotransferase class-III pyridoxal-phosphate domain which is preferably about 70%, 80%, 90%, 95%, 96%, 97%, 98%, 99% or higher, identical with amino acid residues 40-141 or 165-415 of SEQ ID NO:33.

In a preferred embodiment, the 23680 protein or fragment thereof differs from the corresponding sequence in SEQ ID NO:33. In one embodiment, it differs by at least one, but by less than 15, 10 or 5 amino acid residues. In another, it differs from the corresponding sequence in SEQ ID NO:33 by at least one residue but less than 20%, 15%, 10% or 5% of the residues in it differ from the corresponding sequence in SEQ ID NO:33 (if this comparison requires alignment the sequences should be aligned for maximum homology. "Looped" out sequences from deletions or insertions, or mismatches, are considered differences). The differences are, preferably, differences or changes at a non-essential residue or a conservative substitution.

Other embodiments include a protein that contain one or more changes in amino acid sequence, e.g., a change in an amino acid residue which is not essential for activity. Such 23680 proteins differ in amino acid sequence from SEQ ID NO:33, yet retain biological activity.

In one embodiment, the protein includes an amino acid sequence at least about 60%, 65%, 70%, 75%, 80%, 85%, 90%, 95%, 98% or more homologous to SEQ ID NO:33.

In one embodiment, a biologically active portion of a 23680 protein includes an aminotransferase class-III pyridoxal-phosphate attachment site or an aminotransferase class-III pyridoxal-phosphate domain. Moreover, other biologically active portions, in which other regions of the protein are deleted, can be prepared by recombinant techniques and evaluated for one or more of the functional activities of a native 23680 protein.

Particularly preferred 23680 polypeptides of the present invention have an amino acid sequence substantially identical to the amino acid sequence of SEQ ID NO:33. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:33 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:32 or 34 are termed substantially identical.

23680 Chimeric or Fusion Proteins

In another aspect, the invention provides 23680 chimeric or fusion proteins. As used herein, a 23680 "chimeric protein" or "fusion protein" includes a 23680 polypeptide linked to a non-23680 polypeptide. A "non-23680 polypeptide" refers to a polypeptide having an amino acid sequence corresponding to a protein which is not substantially homologous to the 23680 protein, e.g., a protein which is different from the 23680 protein and which is derived from the same or a different organism. The 23680 polypeptide of the fusion protein can correspond to all or a portion e.g., a fragment described herein of a 23680 amino acid sequence. In a preferred embodiment, a 23680 fusion protein includes at least one or more biologically active portions of a 23680 protein. The non-23680 polypeptide can be fused to the N-terminus or C-terminus of the 23680 polypeptide.

The fusion protein can include a moiety that has a high affinity for a ligand. For example, the fusion protein can be a GST-23680 fusion protein in which the 23680 sequences are fused to the C-terminus of the GST sequences. Such fusion proteins can facilitate the purification of recombinant 23680. Alternatively, the fusion protein can be a 23680 protein containing a heterologous signal sequence at its N-terminus. In certain host cells (e.g., mammalian host cells), expression and/or secretion of 23680 can be increased through use of a heterologous signal sequence. Fusion proteins can include all or a part of a serum protein, e.g., an IgG constant region, or human serum albumin.

The 23680 fusion proteins of the invention can be incorporated into pharmaceutical compositions and administered to a subject in vivo. The 23680 fusion proteins can be used to affect the bioavailability of a 23680 substrate. 23680 fusion proteins may be useful therapeutically for the treatment of disorders caused by, for example, (i) aberrant modification or mutation of a gene encoding a 23680 protein; (ii) mis-regulation of the 23680 gene; and (iii) aberrant post-translational modification of a 23680 protein.

Moreover, the 23680-fusion proteins of the invention can be used as immunogens to produce anti-23680 antibodies in a subject, to purify 23680 ligands and in screening assays to identify molecules that inhibit the interaction of 23680 with a 23680 substrate.

Expression vectors are commercially available that already encode a fusion moiety (e.g., a GST polypeptide). A 23680-encoding nucleic acid can be cloned into such an expression vector such that the fusion moiety is linked in-frame to the 23680 protein.

Variants of 23680 Proteins

In another aspect, the invention also features a variant of a 23680 polypeptide, e.g., which functions as an agonist (mimetics) or as an antagonist. Variants of the 23680 proteins can be generated by mutagenesis, e.g., discrete point mutation, the insertion or deletion of sequences or the truncation of a 23680 protein. An agonist of the 23680 proteins can retain substantially the same, or a subset, of the biological activities of the naturally occurring form of a 23680 protein. An antagonist of a 23680 protein can inhibit one or more of the activities of the naturally occurring form of the 23680 protein by, for example, competitively modulating a 23680-mediated activity of a 23680 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 23680 protein.

Variants of a 23680 protein can be identified by screening combinatorial libraries of mutants, e.g., truncation mutants, of a 23680 protein for agonist or antagonist activity.

Libraries of fragments e.g., N-terminal, C-terminal, or internal fragments, of a 23680 protein coding sequence can be used to generate a variegated population of fragments for screening and subsequent selection of variants of a 23680 protein.

Variants in which a cysteine residue is added or deleted or in which a residue that is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify 23680 variants (Arkin and Yourvan (1992) *Proc. Natl. Acad. Sci. USA* 89:7811-7815; Delgrave et al. (1993) *Protein Engineering* 6(3):327-331).

Cell-based assays can be exploited to analyze a variegated 23680 library. For example, a library of expression vectors can be transfected into a cell line, e.g., a cell line, which ordinarily responds to 23680 in a substrate-dependent manner. The transfected cells are then contacted with 23680 and the effect of the expression of the mutant on signaling by the 23680 substrate can be detected, e.g., by measuring changes in cell growth and/or enzymatic activity. Plasmid DNA can then be recovered from the cells that score for inhibition, or alternatively, potentiation of signaling by the 23680 substrate, and the individual clones further characterized.

In another aspect, the invention features a method of making a 23680 polypeptide, e.g., a peptide having a non-wild-type activity, e.g., an antagonist, agonist, or super agonist of a naturally-occurring 23680 polypeptide, e.g., a naturally-occurring 23680 polypeptide. The method includes: altering the sequence of a 23680 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 23680 polypeptide a biological activity of a naturally occurring 23680 polypeptide. The method includes: altering the sequence, e.g., by substitution or deletion of one or more residues, of a 23680 polypeptide, e.g., altering the sequence of a non-conserved region, or a domain or residue described herein, and testing the altered polypeptide for the desired activity.

Anti-23680 Antibodies

In another aspect, the invention provides an anti-23680 antibody. The term "antibody" as used herein refers to an immunoglobulin molecule or immunologically active portion thereof, i.e., an antigen-binding portion. Examples of immunologically active portions of immunoglobulin molecules include F(ab) and F(ab')₂ fragments which can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment, it has effector function and can fix complement. The antibody can be coupled to a toxin or imaging agent.

As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest*, Fifth Edition, U.S. Department of Health and Human Services, NIH Publication No. 91-3242, and Chothia, C. et al. (1987) *J. Mol. Biol.* 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-23680 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH—terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 23680 polypeptide or fragment thereof. Examples of antigen-binding fragments of the anti-23680 antibody include, but are not limited to: (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-23680 antibody can be a polyclonal or a monoclonal antibody. In other embodiments, the antibody can be recombinantly produced, e.g., produced by phage display or by combinatorial methods.

Phage display and combinatorial methods for generating anti-23680 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the anti-23680 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

An anti-23680 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 23680 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, Science 229:1202-1207, by Oi et al., 1986, BioTechniques 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 23680 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 Nature 321:552-525; Verhoeyan et al. 1988 Science 239:1534; Beidler et al. 1988 J. Immunol. 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585, 089, the contents of which are hereby incorporated by reference. Other techniques for humanizing antibodies are described in Padlan et al. EP 519596 A1, published on Dec. 23, 1992.

In preferred embodiments an antibody can be made by immunizing with purified 23680 antigen, or a fragment thereof, e.g., a fragment described herein, e.g., tissue, e.g., crude tissue preparations, lysed cells, or cell fractions, e.g., membrane fractions.

A full-length 23680 protein or, antigenic peptide fragment of 23680 can be used as an immunogen or can be used to identify anti-23680 antibodies made with other immunogens, e.g., cells, membrane preparations, and the like. The antigenic peptide of 23680 should include at least 8 amino acid residues of the amino acid sequence shown in SEQ ID NO:33 and encompasses an epitope of 23680. Preferably, the antigenic peptide includes at least 10 amino acid residues, more preferably at least 15 amino acid residues, even more preferably at least 20 amino acid residues, and most preferably at least 30 amino acid residues.

Fragments of 23680 which include residues from about 310 to about 330 or residues from about 355 to about 370 of SEQ ID NO:33 can be used to make antibodies, e.g., for use as immunogens or to characterize the specificity of an antibody, against hydrophobic regions of the 23680 protein. Similarly, a fragment of 23680 which include residues from about 170 to about 190 or residues from about 460 to about 490 of SEQ ID NO:33 can be used to make an antibody against a hydrophilic region of the 23680 protein. Similarly, a fragment of 23680 which include residues from about 40 to about 141 (or any portion thereof, e.g., amino acids 40-50, 50-60, 60-70, 70-80, 80-90, 90-100, 100-110, 110-120, 120-130, 130-140) or residues from about 165 to about 415 (or any portion thereof) of SEQ ID NO:33 can be used to make an antibody against an aminotransferase domain of the 23680 protein Antibodies reactive with, or specific for, any of these regions, or other regions or domains described herein are provided.

Preferred epitopes encompassed by the antigenic peptide are regions of 23680 are located on the surface of the protein, e.g., hydrophilic regions, as well as regions with high antigenicity. For example, an Emini surface probability analysis of the human 23680 protein sequence can be used to indicate the regions that have a particularly high probability of being localized to the surface of the 23680 protein and are thus likely to constitute surface residues useful for targeting antibody production.

In preferred embodiments an antibody can be made by immunizing with purified 23680 antigen, or a fragment thereof, e.g., a fragment described herein, membrane associated antigen, tissue, e.g., crude tissue preparations, whole cells, preferably living cells, lysed cells, or cell fractions, e.g., membrane fractions.

Antibodies which bind only native 23680 protein, only denatured or otherwise non-native 23680 protein, or which bind both, are with in the invention. Antibodies with linear or conformational epitopes are within the invention. Conformational epitopes can sometimes be identified by indentifying antibodies which bind to native but not denatured 23680 protein.

In a preferred embodiment, the antibody can bind to the extracellular portion of the 23680 protein, e.g., it can bind to a whole cell which expresses the 23680 protein. In another embodiment, the antibody binds an intracellular portion of the 23680 protein.

In a preferred embodiment, the antibody binds an epitope on any domain or region on 23680 proteins described herein.

Chimeric, humanized, but most preferably, completely human antibodies are desirable for applications which include repeated administration, e.g., therapeutic treatment (and some diagnostic applications) of human patients.

The anti-23680 antibody can be a single chain antibody. A single-chain antibody (scFV) may be engineered (see, for example, Colcher, D., et al. Ann NY Acad Sci 1999 June 30; 880:263-80; and Reiter, Y. Clin Cancer Res 1996 February ;2(2):245-52). The single chain antibody can be dimerized or multimerized to generate multivalent antibodies having specificities for different epitopes of the same target 23680 protein.

In a preferred embodiment, the antibody has reduced or no ability to bind an Fc receptor. E.g., it is an isotype, subtype, fragment or other mutant, which does not support binding to an Fc receptor, e.g., it has a mutagenized or deleted Fc receptor binding region.

An anti-23680 antibody (e.g., monoclonal antibody) can be used to isolate 23680 by standard techniques, such as affinity chromatography or immunoprecipitation. Moreover, an anti-23680 antibody can be used to detect 23680 protein (e.g., in a cellular lysate or cell supernatant) in order to evaluate the abundance and pattern of expression of the protein. Anti-23680 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

The invention also includes a nucleic acids which encodes an anti-23680 antibody, e.g., an anti-23680 antibody described herenin. Also included are vectors which include the nucleic acid and sells transformed with the nucleic acid, particularly cells which are useful for producing an antibody, e.g., mammalian cells, e.g. CHO or lymphatic cells.

The invention also includes cell lines, e.g., hybridomas, which make an anti-23680 antibody, e.g., and antibody described herein, and method of using said cells to make a 23680 antibody.

23680 Recombinant Expression Vectors, Host Cells and Genetically Engineered Cells In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 23680 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 23680 proteins, mutant forms of 23680 proteins, fusion proteins, and the like).

The recombinant expression vectors of the invention can be designed for expression of 23680 proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 23680 activity assays, (e.g., direct assays or competitive assays described in detail below), or to generate antibodies specific for 23680 proteins. In a preferred embodiment, a fusion protein expressed in a retroviral expression vector of the present invention can be used to infect bone marrow cells that are subsequently transplanted into irradiated recipients. The pathology of the subject recipient is then examined after sufficient time has passed (e.g., six (6) weeks).

To maximize recombinant protein expression in E. coli, the protein is expressed in a host bacterial strain with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in E. coli (Wada et al., (1992) *Nucleic Acids Res.* 20:2111-2118). Such alteration of nucleic acid sequences of the invention can be carried out by standard DNA synthesis techniques.

The 23680 expression vector can be a yeast expression vector, a vector for expression in insect cells, e.g., a baculovirus expression vector, or a vector suitable for expression in mammalian cells.

When used in mammalian cells, the expression vector's control functions are often provided by viral regulatory elements. For example, commonly used viral promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes, see Weintraub, H. et al., Antisense RNA as a molecular tool for genetic analysis, *Reviews: Trends in Genetics*, Vol. 1(1) 1986.

Another aspect the invention provides a host cell which includes a nucleic acid molecule described herein, e.g., a 23680 nucleic acid molecule within a recombinant expression vector or a 23680 nucleic acid molecule containing sequences which allow it to homologously recombine into a specific site of the host cell's genome. The terms "host cell" and "recombinant host cell" are used interchangeably herein. Such terms refer not only to the particular subject cell, but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 23680 protein can be expressed in bacterial cells such as E. coli, insect cells, yeast or mammalian cells (such as Chinese hamster ovary cells (CHO)) or COS cells. Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 23680 protein. Accordingly, the invention further provides methods for producing a 23680 protein using the host cells of the invention. In one embodiment, the method includes culturing the host cell of the invention (into which a recombinant expression vector encoding a 23680 protein has been introduced) in a suitable medium such that a 23680 protein is produced. In another embodiment, the method further includes isolating a 23680 protein from the medium or the host cell.

In another aspect, the invention features, a cell or purified preparation of cells which include a 23680 transgene, or which otherwise mis-express 23680. The cell preparation can consist of human or non-human cells, e.g., rodent cells, e.g., mouse or rat cells, rabbit cells, or pig cells. In preferred embodiments, the cell or cells include a 23680 transgene, e.g., a heterologous form of a 23680, e.g., a gene derived from humans (in the case of a non-human cell). The 23680 transgene can be mis-expressed, e.g., overexpressed or underexpressed. In other preferred embodiments, the cell or cells include a gene that mis-express an endogenous 23680, e.g., a gene the expression of which is disrupted, e.g., a knockout. Such cells can serve as a model for studying disorders that are related to mutated or mis-expressed 23680 alleles or for use in drug screening.

In another aspect, the invention features, a human cell, e.g., a liver cell, transformed with nucleic acid that encodes a subject 23680 polypeptide.

Also provided are cells, preferably human cells, e.g., human hematopoietic or fibroblast cells, in which an endogenous 23680 is under the control of a regulatory sequence that does not normally control the expression of the endogenous 23680 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 23680 gene. For example, an endogenous 23680 gene that is "transcriptionally silent," e.g., not normally expressed, or expressed only at very low levels, may be activated by inserting a regulatory element that is capable of promoting the expression of a normally expressed gene product in that cell. Techniques such as targeted homologous recombination, can be used to insert the heterologous DNA as described in, e.g., Chappel, U.S. Pat. No. 5,272,071; WO 91/06667, published in May 16, 1991.

23680 Transgenic Animals

The invention provides non-human transgenic animals. Such animals are useful for studying the function and/or activity of a 23680 protein and for identifying and/or evaluating modulators of 23680 activity. As used herein, a "transgenic animal" is a non-human animal, preferably a mammal, more preferably a rodent such as a rat or mouse, in which one or more of the cells of the animal include a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 23680 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 23680 protein to particular cells. A transgenic founder animal can be identified based upon the presence of a 23680 transgene in its genome and/or expression of 23680 mRNA in tissues or cells of the animals. A transgenic founder animal can then be used to breed additional animals carrying the transgene. Moreover, transgenic animals carrying a transgene encoding a 23680 protein can further be bred to other transgenic animals carrying other transgenes.

23680 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk- or egg-specific promoter, and recovered from the milk or eggs produced by the animal. Suitable animals are mice, pigs, cows, goats, and sheep.

The invention also includes a population of cells from a transgenic animal, as discussed, e.g., below.

Uses of 23680

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express a 23680 protein (e.g., via a recombinant expression vector in a host cell in gene therapy applications), to detect a 23680 mRNA (e.g., in a biological sample), to detect a genetic alteration in a 23680 gene and to modulate 23680 activity, as described further below. The 23680 proteins can be used to treat disorders characterized by insufficient or excessive production of a 23680 substrate or production of 23680 inhibitors. In addition, the 23680 proteins can be used to screen for naturally occurring 23680 substrates, to screen for drugs or compounds which modulate 23680 activity, as well as to treat disorders characterized by insufficient or excessive production of 23680 protein or production of 23680 protein forms which have decreased, aberrant or unwanted activity compared to 23680 wild-type protein. Exemplary disorders include: conditions involving elevated levels of aminotransferases, such as liver diseases, heart diseases, skeletal muscle diseases, carcinomas, periodontal disease and viral diseases (e.g., Hepatitis C). Moreover, the anti-23680 antibodies of the invention can be used to detect and isolate 23680 proteins, regulate the bioavailability of 23680 proteins, and modulate 23680 activity.

A method of evaluating a compound for the ability to interact with, e.g., bind to, a subject 23680 polypeptide is provided. The method includes: contacting the compound with the subject 23680 polypeptide; and evaluating the ability of the compound to interact with, e.g., to bind or form a complex with, the subject 23680 polypeptide. This method can be performed in vitro, e.g., in a cell free system, or in vivo, e.g., in a two-hybrid interaction trap assay. This method can be used to identify naturally-occurring molecules that interact with a subject 23680 polypeptide. It can also be used to find natural or synthetic inhibitors of a subject 23680 polypeptide. Screening methods are discussed in more detail below.

23680 Screening Assays

The invention provides screening methods (also referred to herein as "assays") for identifying modulators, i.e., candidate or test compounds or agents (e.g., proteins, peptides, peptidomimetics, peptoids, small molecules or other drugs) which bind to 23680 proteins, have a stimulatory or inhibitory effect on, for example, 23680 expression or 23680 activity, or have a stimulatory or inhibitory effect on, for example, the expression or activity of a 23680 substrate. Compounds thus identified can be used to modulate the activity of target gene products (e.g., 23680 genes) in a therapeutic protocol, to elaborate the biological function of the target gene product, or to identify compounds that disrupt normal target gene interactions.

In one embodiment, the invention provides assays for screening candidate or test compounds that are substrates of a 23680 protein or polypeptide or a biologically active portion thereof. In another embodiment, the invention provides assays for screening candidate or test compounds that bind to or modulate the activity of a 23680 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive) (see, e.g., Zuckermann, R. N. et al. *J. Med. Chem.* 1994, 37: 2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell which expresses a 23680 protein or biologically active portion thereof is contacted with a test compound, and the ability of the test compound to modulate 23680 activity is determined. Determining the ability of the test compound to modulate 23680 activity can be accomplished by monitoring, for example, changes in enzymatic activity. The cell, for example, can be of mammalian origin.

The ability of the test compound to modulate 23680 binding to a compound, e.g., a 23680 substrate, or to bind to 23680 can also be evaluated. This can be accomplished, for example, by coupling the compound, e.g., the substrate, with a radioisotope or enzymatic label such that binding of the compound, e.g., the substrate, to 23680 can be determined by detecting the labeled compound, e.g., substrate, in a complex. Alternatively, 23680 could be coupled with a radioisotope or enzymatic label to monitor the ability of a test compound to modulate 23680 binding to a 23680 substrate in a complex. For example, compounds (e.g., 23680 substrates) can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 23680 substrate) to interact with 23680 with or without the labeling of any of the interactants can be evaluated. For example, a microphysiometer can be used to detect the interaction of a compound with 23680 without the labeling of either the compound or the 23680. McConnell, H. M. et al. (1992) *Science* 257: 1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 23680.

In yet another embodiment, a cell-free assay is provided in which a 23680 protein or biologically active portion thereof is contacted with a test compound and the ability of the test compound to bind to the 23680 protein or biologically active portion thereof is evaluated. Preferred biologically active portions of the 23680 proteins to be used in assays of the present invention include fragments that participate in interactions with non-23680 molecules, e.g., fragments with high surface probability scores.

Soluble and/or membrane-bound forms of isolated proteins (e.g., 23680 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label is selected such that a first donor molecule's emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 23680 protein to bind to a target molecule can be accomplished using real-time Biomolecular Interaction Analysis (BIA) (see, e.g., Sjolander, S. and Urbaniczky, C. (1991) Anal. Chem. 63:2338-2345 and Szabo et al. (1995) Curr. Opin. Struct. Biol. 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 23680, an anti-23680 antibody or its target molecule to facilitate separation of complexed from un-complexed forms of one or both of the proteins, as well as to accommodate automation of the assay. Binding of a test compound to a 23680 protein, or interaction of a 23680 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/23680 fusion proteins or glutathione-S-transferase/target fusion proteins can be adsorbed onto glutathione sepharose beads (Sigma Chemical, St. Louis, Mo.) or glutathione-derivatized microtiter plates, which are then combined with the test compound or the test compound and either the non-adsorbed target protein or 23680 protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 23680 binding or activity determined using standard techniques.

Other techniques for immobilizing either a 23680 protein or a target molecule on matrices include using conjugation of biotin and streptavidin. Biotinylated 23680 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 23680 protein or target molecules but which do not interfere with binding of the 23680 protein to its target molecule. Such antibodies can be derivatized to the wells of the plate, and unbound target or 23680 protein trapped in the wells by antibody conjugation. Methods for detecting such complexes, in addition to those described above for the GST-immobilized complexes, include immunodetection of complexes using antibodies reactive with the 23680 protein or target molecule, as well as enzyme-linked assays which rely on detecting an enzymatic activity associated with the 23680 protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas, G., and Minton, A. P., Trends Biochem Sci 1993 August;18(8):284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N.H., J Mol Recognit 1998 Winter; 11(1-6):141-8; Hage, D. S., and Tweed, S. A. J Chromatogr B Biomed Sci Appl 1997 October 10; 699(1-2):499-525). Further, fluorescence energy transfer may also be conveniently utilized, as described herein, to detect binding without further purification of the complex from solution.

In a preferred embodiment, the assay includes contacting the 23680 protein or biologically active portion thereof with a known compound which binds 23680 to form an assay mixture, contacting the assay mixture with a test compound, and determining the ability of the test compound to interact with a 23680 protein, wherein determining the ability of the test compound to interact with a 23680 protein includes determining the ability of the test compound to preferentially bind to 23680 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 23680 genes herein identified. In an alternative embodiment, the invention provides methods for determining the ability of the test compound to modulate the activity of a 23680 protein through modulation of the activity of a downstream effector of a 23680 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 23680 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 23680 ("23680-binding proteins" or "23680-bp") and are involved in 23680 activity. Such 23680-bps can be activators or inhibitors of signals by the 23680 proteins or 23680 targets as, for example, downstream elements of a 23680-mediated signaling pathway.

The two-hybrid system is based on the modular nature of most transcription factors, which consist of separable DNA-binding and activation domains. Briefly, the assay utilizes two different DNA constructs. In one construct, the gene that codes for a 23680 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively, the 23680 protein can be fused to the activator domain). If the "bait" and the "prey" proteins are able to interact in vivo forming a 23680-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein that interacts with the 23680 protein.

In another embodiment, modulators of 23680 expression are identified. For example, a cell or cell free mixture is contacted with a candidate compound and the expression of 23680 mRNA or protein evaluated relative to the level of expression of 23680 mRNA or protein in the absence of the candidate compound. When expression of 23680 mRNA or protein is greater in the presence of the candidate compound than in its absence, the candidate compound is identified as a stimulator of 23680 mRNA or protein expression. Alternatively, when expression of 23680 mRNA or protein is less (i.e., statistically significantly less) in the presence of the candidate compound than in its absence, the candidate compound is identified as an inhibitor of 23680 mRNA or protein expression. The level of 23680 mRNA or protein expression can be determined by methods described herein for detecting 23680 mRNA or protein.

In another aspect, the invention pertains to a combination of two or more of the assays described herein. For example, a modulating agent can be identified using a cell-based or a cell free assay, and the ability of the agent to modulate the activity of a 23680 protein can be confirmed in vivo, e.g., in an animal such as an animal model for an aminotransferase-related disease.

This invention further pertains to novel agents identified by the above-described screening assays. Accordingly, it is within the scope of this invention to further use an agent identified as described herein (e.g., a 23680 modulating agent, an antisense 23680 nucleic acid molecule, a 23680-specific antibody, or a 23680-binding partner) in an appropriate animal model to determine the efficacy, toxicity, side effects, or mechanism of action, of treatment with such an agent. Furthermore, novel agents identified by the above-described screening assays can be used for treatments as described herein.

23680 Detection Assays

Portions or fragments of the nucleic acid sequences identified herein can be used as polynucleotide reagents. For example, these sequences can be used to: (i) map their respective genes on a chromosome, e.g., to locate gene regions associated with genetic disease or to associate 23680 with a disease; (ii) identify an individual from a minute biological sample (tissue typing); and (iii) aid in forensic identification of a biological sample. These applications are described in the subsections below.

23680 Chromosome Mapping

The 23680 nucleotide sequences or portions thereof can be used to map the location of the 23680 genes on a chromosome. This process is called chromosome mapping. Chromosome mapping is useful in correlating the 23680 sequences with genes associated with disease.

Briefly, 23680 genes can be mapped to chromosomes by preparing PCR primers (preferably 15-25 bp in length) from the 23680 nucleotide sequence (e.g., SEQ ID NO:32 or SEQ ID NO:34). These primers can then be used for PCR screening of somatic cell hybrids containing individual human chromosomes. Only those hybrids containing the human gene corresponding to the 23680 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919-924).

Other mapping strategies e.g., in situ hybridization (described in Fan, Y. et al. (1990) *Proc. Natl. Acad. Sci. USA*, 87:6223-27), pre-screening with labeled flow-sorted chromosomes, and pre-selection by hybridization to chromosome specific cDNA libraries can be used to map 23680 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of FISH, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to non-coding regions of the genes are typically preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783-787.

Moreover, differences in the DNA sequences between individuals affected and unaffected with a disease associated with the 23680 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

23680 Tissue Typing 23680 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 23680 nucleotide sequence described herein can be used to prepare PCR primers homologous to the 5' and 3' ends of the sequence. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the non-coding regions. Each of the sequences described herein can, to some degree, be used as a standard against which DNA from an individual can be compared for identification purposes. Because greater numbers of polymorphisms occur in the non-coding regions, fewer sequences are necessary to differentiate individuals. The non-coding sequences of SEQ ID NO:32 can provide positive individual identification with a panel of perhaps 10 to 1,000 primers which each yield a non-coding amplified sequence of 100 bases. If predicted coding sequences are used, such as those in SEQ ID NO:34, a more appropriate number of primers for positive individual identification would be 500-2,000.

If a panel of reagents from 23680 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 23680 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to non-coding regions of SEQ ID NO:32 (e.g., fragments having a length of at least 20 bases, preferably at least 30 bases) are particularly appropriate for this use.

The 23680 nucleotide sequences described herein can further be used to provide polynucleotide reagents, e.g., labeled or labelable probes which can be used in, for example, an in situ hybridization technique, to identify a specific tissue, e.g., a tissue containing hematopoietic cells. This can be very useful in cases where a forensic pathologist is presented with a tissue of unknown origin. Panels of such 23680 probes can be used to identify tissue by species and/or by organ type.

In a similar fashion, these reagents, e.g., 23680 primers or probes can be used to screen tissue culture for contamination (i.e., to screen for the presence of a mixture of different types of cells in a culture).

Predictive Medicine of 23680

The present invention also pertains to the field of predictive medicine in which diagnostic assays, prognostic assays, and monitoring clinical trials are used for prognostic (predictive) purposes to thereby treat an individual.

Generally, the invention provides a method of determining if a subject is at risk for a disorder related to a lesion in, or the misexpression of, a gene that encodes a 23680 polypeptide.

Such disorders include, e.g., a disorder associated with the misexpression of a 23680 polypeptide, e.g., liver diseases, heart diseases, diseases involving skeletal muscles, carcinomas, periodontal diseases or viral diseases (e.g., Hepatitis C).

The method includes one or more of the following:

detecting, in a tissue of the subject, the presence or absence of a mutation which affects the expression of the 23680 gene, or detecting the presence or absence of a mutation in a region which controls the expression of the gene, e.g., a mutation in the 5' control region;

detecting, in a tissue of the subject, the presence or absence of a mutation which alters the structure of the 23680 gene;

detecting, in a tissue of the subject, the misexpression of the 23680 gene at the mRNA level, e.g., detecting a non-wild-type level of a mRNA;

detecting, in a tissue of the subject, the misexpression of the gene at the protein level, e.g., detecting a non-wild-type level of a 23680 polypeptide.

In preferred embodiments the method includes: ascertaining the existence of at least one of: a deletion of one or more nucleotides from the 23680 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:32, or naturally occurring mutants thereof, or 5' or 3' flanking sequences naturally associated with the 23680 gene; (ii) exposing the probe/primer to nucleic acid of the tissue; and detecting the presence or absence of the genetic lesion by hybridization of the probe/primer to the nucleic acid, e.g., by in situ hybridization.

In preferred embodiments, detecting the misexpression includes ascertaining the existence of at least one of: an alteration in the level of a messenger RNA transcript of the 23680 gene; the presence of a non-wild-type splicing pattern of a messenger RNA transcript of the gene; or a non-wild-type level of 23680 RNA or protein.

Methods of the invention can be used for prenatal screening or to determine if a subject's offspring will be at risk for a disorder.

In preferred embodiments the method includes determining the structure of a 23680 gene, an abnormal structure being indicative of risk for the disorder.

In preferred embodiments the method includes contacting a sample form the subject with an antibody to the 23680 protein or a nucleic acid, which hybridizes specifically with the gene. These and other embodiments are discussed below.

Diagnostic and Prognostic Assays of 23680

Diagnostic and prognostic assays of the invention include method for assessing the expression level of 23680 molecules and for identifying variations and mutations in the sequence of 23680 molecules.

Expression Monitoring and Profiling:

The presence, level, or absence of 23680 protein or nucleic acid in a biological sample can be evaluated by obtaining a biological sample from a test subject and contacting the biological sample with a compound or an agent capable of detecting 23680 protein or nucleic acid (e.g., mRNA, genomic DNA) that encodes 23680 protein such that the presence of 23680 protein or nucleic acid is detected in the biological sample. The term "biological sample" includes tissues, cells and biological fluids isolated from a subject, as well as tissues, cells and fluids present within a subject. A preferred biological sample is serum. The level of expression of the 23680 gene can be measured in a number of ways, including, but not limited to: measuring the mRNA encoded by the 23680 genes; measuring the amount of protein encoded by the 23680 genes; or measuring the activity of the protein encoded by the 23680 genes.

The level of mRNA corresponding to the 23680 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 23680 nucleic acid, such as the nucleic acid of SEQ ID NO:32, or a portion thereof, such as an oligonucleotide of at least 7, 15, 30, 50, 100, 250 or 500 nucleotides in length and sufficient to specifically hybridize under stringent conditions to 23680 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 23680 genes.

The level of mRNA in a sample that is encoded by one of 23680 can be evaluated with nucleic acid amplification, e.g., by RT-PCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 23680 gene being analyzed.

In another embodiment, the methods further contacting a control sample with a compound or agent capable of detecting 23680 mRNA, or genomic DNA, and comparing the presence of 23680 mRNA or genomic DNA in the control sample with the presence of 23680 mRNA or genomic DNA in the test sample. In still another embodiment, serial analysis of gene expression, as described in U.S. Pat. No. 5,695,937, is used to detect 23680 transcript levels.

A variety of methods can be used to determine the level of protein encoded by 23680. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 23680 protein in a biological sample in vitro as well as in vivo. In vitro techniques for detection of 23680 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 23680 protein include introducing into a subject a labeled anti-23680 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-23680 antibody positioned on an antibody array (as described below). The sample can be detected, e.g., with avidin coupled to a fluorescent label.

In another embodiment, the methods further include contacting the control sample with a compound or agent capable of detecting 23680 protein, and comparing the presence of 23680 protein in the control sample with the presence of 23680 protein in the test sample.

The invention also includes kits for detecting the presence of 23680 in a biological sample. For example, the kit can include a compound or agent capable of detecting 23680 protein or mRNA in a biological sample; and a standard. The compound or agent can be packaged in a suitable container. The kit can further comprise instructions for using the kit to detect 23680 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein-stabilizing agent. The kit can also includes components necessary for detecting the detectable agent (e.g., an enzyme or a substrate). The kit can also contain a control sample or a series of control samples that can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 23680 expression or activity. As used herein, the term "unwanted" includes an unwanted phenomenon involved in a biological response such as pain or deregulated cell proliferation.

In one embodiment, a disease or disorder associated with aberrant or unwanted 23680 expression or activity is identified. A test sample is obtained from a subject and 23680 protein or nucleic acid (e.g., mRNA or genomic DNA) is evaluated, wherein the level, e.g., the presence or absence, of 23680 protein or nucleic acid is diagnostic for a subject having or at risk of developing a disease or disorder associated with aberrant or unwanted 23680 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 23680 expression or activity. For example, such methods can be used to determine whether a subject can be effectively treated with an agent for an aminotransferase-related disorder.

In another aspect, the invention features a computer medium having a plurality of digitally encoded data records. Each data record includes a value representing the level of expression of 23680 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 23680 (e.g., other genes associated with a 23680-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 23680 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose an aminotransferase-related disorder in a subject wherein an increase or a decrease in 23680 expression is an indication that the subject has or is disposed to having an aminotransferase-related disorder. The method can be used to monitor a treatment for such aminotransferase-related disorders in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 23680 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 23680 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 23680 expression.

23680 Arrays and Uses Thereof

In another aspect, the invention features an array that includes a substrate having a plurality of addresses. At least one address of the plurality includes a capture probe that binds specifically to a 23680 molecule (e.g., a 23680 nucleic acid or a 23680 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 23680 nucleic acid, e.g., the sense or anti-sense strand. In one preferred embodiment, a subset of addresses of the plurality of addresses has a nucleic acid capture probe for 23680. Each address of the subset can include a capture probe that hybridizes to a different region of a 23680 nucleic acid. In another preferred embodiment, addresses of the subset include a capture probe for a 23680 nucleic acid. Each address of the subset is unique, overlapping, and complementary to a different variant of 23680 (e.g., an allelic variant, or all possible hypothetical variants). The array can be used to sequence 23680 by hybridization (see, e.g., U.S. Pat. No. 5,695,940).

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 23680 polypeptide or fragment thereof. The polypeptide can be a naturally occurring interaction partner of a 23680 polypeptide. Preferably, the polypeptide is an antibody, e.g., an antibody described herein (see "Anti-23680 Antibodies," above), such as a monoclonal antibody or a single-chain antibody.

In another aspect, the invention features a method of analyzing the expression of 23680. The method includes providing an array as described above; contacting the array with a sample and detecting binding of a 23680-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 23680. If a sufficient number of diverse samples is analyzed, clustering (e.g., hierarchical clustering, k-means clustering, Bayesian clustering and the like) can be used to identify other genes which are co-regulated with 23680. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 23680 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 23680-associated disease or disorder; and processes, such as a cellular transformation associated with a 23680-associated disease or disorder. The method can also evaluate the treatment and/or progression of a 23680-associated disease or disorder The array is also useful for ascertaining differential expression patterns of one or more genes in normal and abnormal cells. This provides a battery of genes (e.g., including 23680) that could serve as a molecular target for diagnosis or therapeutic intervention.

In another aspect, the invention features an array having a plurality of addresses. Each address of the plurality includes a unique polypeptide. At least one address of the plurality has disposed thereon a 23680 polypeptide or fragment thereof. Methods of producing polypeptide arrays are described in the art, e.g., in De Wildt et al. (2000). *Nature Biotech.* 18, 989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80,85, 90, 95 or 99% identical to a 23680 polypeptide or fragment thereof. For example, multiple variants of a 23680 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 23680 binding compound, e.g., an antibody in a sample from a subject with specificity for a 23680 polypeptide or the presence of a 23680-binding protein or ligand.

The array is also useful for ascertaining the effect of the expression of a gene on the expression of other genes in the same cell or in different cells (e.g., ascertaining the effect of 23680 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 23680 or from a cell or subject in which a 23680 mediated response has been elicited, e.g., by contact of the cell with 23680 nucleic acid or protein, or administration to the cell or subject 23680 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 23680 (or does not express as highly as in the case of the 23680 positive plurality of capture probes) or from a cell or subject which in which a 23680 mediated response has not been elicited (or has been elicited to a lesser extent than in the first sample); contacting the array with one or more inquiry probes (which is preferably other than a 23680 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 23680 or from a cell or subject in which a 23680-mediated response has been elicited, e.g., by contact of the cell with 23680 nucleic acid or protein, or administration to the cell or subject 23680 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 23680 (or does not express as highly as in the case of the 23680 positive plurality of capture probes) or from a cell or subject which in which a 23680 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 23680, e.g., analyzing structure, function, or relatedness to other nucleic acid or amino acid sequences. The method includes: providing a 23680 nucleic acid or amino acid sequence; comparing the 23680 sequence with one or more preferably a plurality of sequences from a collection of sequences, e.g., a nucleic acid or protein sequence database; to thereby analyze 23680.

Detection of 23680 Variations or Mutations

The methods of the invention can also be used to detect genetic alterations in a 23680 gene, thereby determining if a subject with the altered gene is at risk for a disorder characterized by misregulation in 23680 protein activity or nucleic acid expression, such as an aminotransferase-related disorder. In preferred embodiments, the methods include detecting, in a sample from the subject, the presence or absence of a genetic alteration characterized by at least one of an alteration affecting the integrity of a gene encoding a 23680-protein, or the mis-expression of the 23680 gene. For example, such genetic alterations can be detected by ascertaining the existence of at least one of 1) a deletion of one or more nucleotides from a 23680 gene; 2) an addition of one or more nucleotides to a 23680 gene; 3) a substitution of one or more nucleotides of a 23680 gene, 4) a chromosomal rearrangement of a 23680 gene; 5) an alteration in the level of a messenger RNA transcript of a 23680 gene, 6) aberrant modification of a 23680 gene, such as of the methylation pattern of the genomic DNA, 7) the presence of a non-wild type splicing pattern of a messenger RNA transcript of a 23680 gene, 8) a non-wild type level of a 23680-protein, 9) allelic loss of a 23680 gene, and 10) inappropriate post-translational modification of a 23680-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 23680-gene. This method can include the steps of collecting a sample of cells from a subject, isolating nucleic acid (e.g., genomic, mRNA or both) from the sample, contacting the nucleic acid sample with one or more primers which specifically hybridize to a 23680 gene under conditions such that hybridization and amplification of the 23680-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 23680 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 23680 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 23680 nucleic acid or a putative variant (e.g., allelic variant) thereof. A probe can have one or more mismatches to a region of a 23680 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in 23680 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 23680 gene and detect mutations by comparing the sequence of the sample 23680 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 23680 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 23680 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 23680 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 23680 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 23680 nucleic acid.

In a preferred embodiment the set includes a first and a second oligonucleotide. The first and second oligonucleotide can hybridize to the same or to different locations of SEQ ID NO:32 or the complement of SEQ ID NO:32. Different locations can be different but overlapping or nonoverlapping on the same strand. The first and second oligonucleotide can hybridize to sites on the same or on different strands.

The set can be useful, e.g., for identifying SNP's, or identifying specific alleles of 23680. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 23680 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 23680 gene.

Use of 23680 Molecules as Surrogate Markers

The 23680 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 23680 molecules of the invention may be detected, and may be correlated with one or more biological states in vivo. For example, the 23680 molecules of the invention may serve as surrogate markers for one or more disorders or disease states or for conditions leading up to disease states. As used herein, a "surrogate marker" is an objective biochemical marker that correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 23680 molecules of the invention are also useful as pharmacodynamic markers. As used herein, a "pharmacodynamic marker" is an objective biochemical marker that correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 23680 marker) transcription or expression, the amplified marker may be in a quantity which is more readily detectable than the drug itself. Also, the marker may be more easily detected due to the nature of the marker itself; for example, using the methods described herein, anti-23680 antibodies may be employed in an immune-based detection system for a 23680 protein marker, or 23680-specific radio-labeled probes may be used to detect a 23680 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J Health-Syst. Pharm.* 56 Suppl. 3: S21-S24; and Nicolau (1999) *Am, J. Health-Syst. Pharm.* 56 Suppl. 3: S16-S20.

The 23680 molecules of the invention are also useful as pharmacogenomic markers. As used herein, a "pharmacogenomic marker" is an objective biochemical marker that correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 23680 protein or RNA) for specific tumor markers in a subject, a drug or course of treatment may be selected that is optimized for the treatment of the specific tumor likely to be present in the subject. Similarly, the presence or absence of a specific sequence mutation in 23680 DNA may correlate 23680 drug response. The use of pharmacogenomic markers therefore permits the application of the most appropriate treatment for each subject without having to administer the therapy.

Pharmaceutical Compositions of 23680

The nucleic acid and polypeptides, fragments thereof, as well as anti-23680 antibodies (also referred to herein as "active compounds") of the invention can be incorporated into pharmaceutical compositions. Such compositions typically include the nucleic acid molecule, protein, or antibody and a pharmaceutically acceptable carrier. As used herein, the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including an agent in the composition that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents and/or adjuvant materials can be included as part of the composition. The tablets, pills, capsules, troches and the like can contain any of the following ingredients, or compounds of a similar nature: a binder, such as microcrystalline cellulose, gum tragacanth or gelatin; an excipient, such as starch or lactose; a disintegrating agent, such as alginic acid, Primogel, or corn starch; a lubricant, such as magnesium stearate or Sterotes; a glidant, such as colloidal silicon dioxide; a sweetening agent, such as sucrose or saccharin; or a flavoring agent, such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells using monoclonal antibodies directed towards viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration are often possible. Modifications such as lipidation can be used to stabilize antibodies and to enhance uptake and tissue penetration (e.g., into the brain). A method for the lipidation of antibodies is described by Cruikshank et al. ((1997) *J. Acquired Immune Deficiency Syndromes and Human Retrovirology* 14:193). The present invention encompasses agents that modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including hetero-organic and organo-metallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1 065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, and the drug moiety is not to be construed as limited to classical chemical therapeutic agents. For example, the drug moiety may be a protein or polypeptide possessing a desired biological activity. Such proteins may include, for example, a toxin such as abrin, ricin A, gelonin, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors. Alternatively, an antibody can be conjugated to a second antibody to form an antibody heteroconjugate as described by Segal in U.S. Pat. No. 4,676, 980.

The nucleic acid molecules of the invention can be inserted into vectors and used as gene therapy vectors. Gene therapy vectors can be delivered to a subject by, for example, intravenous injection, local administration (see U.S. Pat. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 23680

The present invention provides for both prophylactic and therapeutic methods of treating a subject at risk of (or susceptible to) a disorder or having a disorder associated with aberrant or unwanted 23680 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 23680 molecules of the present invention or 23680 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing a disease or condition in a subject associated with an aberrant or unwanted 23680 expression or activity, by administering to the subject a 23680 or an agent which modulates 23680 expression, or at least one 23680 activity. Subjects at risk for a disease which is caused or contributed to by aberrant or unwanted 23680 expression or activity can be identified by, for example, any or a combination of diagnostic or prognostic assays as described herein. Administration of a prophylactic agent can occur prior to the manifestation of symptoms characteristic of the 23680 aberrance, such that a disease or disorder is prevented or, alternatively, delayed in its progression. Depending on the type of 23680 aberrance, for example, a 23680, 23680 agonist or 23680 antagonist agent can be used for treating the subject. The appropriate agent can be determined based on screening assays described herein.

It is possible that some 23680 disorders can be caused, at least in part, by an abnormal level of gene product, or by the presence of a gene product exhibiting abnormal activity. As such, the reduction in the level and/or activity of such gene products would bring about the amelioration of disorder symptoms.

The 23680 molecules can act as novel diagnostic targets and therapeutic agents for controlling one or more of the disorders described above, as well as disorders associated with bone metabolism, lung disorders, immune disorders, pain or metabolic disorders.

Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions,leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of disorders of the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of kidney or renal disorders include renal cell carcinoma, nephritis and polycystic kidney disease.

Aberrant expression and/or activity of 23680 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 23680 molecules effects in bone cells, e.g. osteoclasts and osteoblasts, that may in turn result in bone formation and degeneration. For example, 23680 molecules may support different activities of bone resorbing osteoclasts such as the stimulation of differentiation of monocytes and mononuclear phagocytes into osteoclasts. Accordingly, 23680 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Additionally, 23680 may play an important role in the regulation of metabolism or pain disorders. Diseases of metabolic imbalance include, but are not limited to, obesity, anorexia nervosa, cachexia, lipid disorders diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York, McGraw-Hill); pain associated with muscoloskeletal disorders, e.g., joint pain; tooth pain; headaches; pain associated with surgery; pain.

As discussed, successful treatment of 23680 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 23680 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 23680 expression is through the use of aptamer molecules specific for 23680 protein. Aptamers are nucleic acid molecules having a tertiary structure that permits them to specifically bind to protein ligands (see, e.g., Osborne, et al. *Curr. Opin. Chem Biol.* 1997, 1(1): 5-9; and Patel, D. J. *Curr Opin Chem Biol* 1997 June;1(1):32-46). Since nucleic acid molecules may in many cases be more conveniently introduced into target cells than therapeutic protein molecules may be, aptamers offer a method by which 23680 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 23680 disorders. For a description of antibodies, see the Antibody section above.

In circumstances wherein injection of an animal or a human subject with a 23680 protein or epitope for stimulating antibody production is harmful to the subject, it is possible to generate an immune response against 23680 through the use of anti-idiotypic antibodies (see, for example, Herlyn, D. *Ann Med* 1999; 31(1):66-78; and Bhattacharya-Chatterjee, M., and Foon, K. A. *Cancer Treat Res* 1998; 94:51-68). If an anti-idiotypic antibody is introduced into a mammal or human subject, it should stimulate the production of anti-anti-idiotypic antibodies, which should be specific to the 23680 protein. Vaccines directed to a disease characterized by 23680 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993, Proc. Natl. Acad. Sci. USA 90:7889-7893).

The identified compounds that inhibit target gene expression, synthesis and/or activity can be administered to a patient at therapeutically effective doses to prevent, treat or ameliorate 23680 disorders. A therapeutically effective dose refers to that amount of the compound sufficient to result in amelioration of symptoms of the disorders. Toxicity and therapeutic efficacy of such compounds can be determined by standard pharmaceutical procedures in cell cultures or experimental animals, as described above.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 23680 activity is used as a template, or "imprinting molecule", to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. A detailed review of this technique can be found in Ansell, R. J. et al (1996) *Current Opinion in Biotechnology* 7:89-94 and in Shea, K. J. (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be found in Vlatakis, G. et al (1993) *Nature* 361:645-647. Through the use of isotope-labeling, the "free" concentration of compound which modulates the expression or activity of 23680 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al (1995) *Analytical Chemistry* 67:2142-2144.

Another aspect of the invention pertains to methods of modulating 23680 expression or activity for therapeutic purposes. Accordingly, in an exemplary embodiment, the modulatory method of the invention involves contacting a cell with a 23680 or agent that modulates one or more of the activities of 23680 protein activity associated with the cell. An agent that modulates 23680 protein activity can be an agent as described herein, such as a nucleic acid or a protein, a naturally-occurring target molecule of a 23680 protein (e.g., a 23680 substrate or receptor), a 23680 antibody, a 23680 agonist or antagonist, a peptidomimetic of a 23680 agonist or antagonist, or other small molecule.

In one embodiment, the agent stimulates one or 23680 activities. Examples of such stimulatory agents include active 23680 protein and a nucleic acid molecule encoding 23680. In another embodiment, the agent inhibits one or more 23680 activities. Examples of such inhibitory agents include antisense 23680 nucleic acid molecules, anti-23680 antibodies, and 23680 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 23680 protein or nucleic acid molecule. In one embodiment, the method involves administering an agent (e.g., an agent identified by a screening assay described herein), or combination of agents that modulates (e.g., upregulates or downregulates) 23680 expression or activity. In another embodiment, the method involves administering a 23680 protein or nucleic acid molecule as therapy to compensate for reduced, aberrant, or unwanted 23680 expression or activity.

Stimulation of 23680 activity is desirable in situations in which 23680 is abnormally downregulated and/or in which increased 23680 activity is likely to have a beneficial effect. For example, stimulation of 23680 activity is desirable in situations in which a 23680 is downregulated and/or in which increased 23680 activity is likely to have a beneficial effect. Likewise, inhibition of 23680 activity is desirable in situations in which 23680 is abnormally upregulated and/or in which decreased 23680 activity is likely to have a beneficial effect.

23680 Pharmacogenomics

The 23680 molecules of the present invention, as well as agents, or modulators which have a stimulatory or inhibitory effect on 23680 activity (e.g., 23680 gene expression) as identified by a screening assay described herein can be administered to individuals to treat (prophylactically or therapeutically) 23680-associated disorders associated with aberrant or unwanted 23680 activity (e.g., disorders associated with hematopoiesis and immune disorders). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 23680 molecule or 23680 modulator as well as tailoring the dosage and/or therapeutic regimen of treatment with a 23680 molecule or 23680 modulator.

Pharmacogenomics deals with clinically significant hereditary variations in the response to drugs due to altered drug disposition and abnormal action in affected persons (see, for example, Eichelbaum, M. et al. (1996) *Clin. Exp. Pharmacol. Physiol.* 23(10-11):983-985 and Linder, M. W. et al. (1997) *Clin. Chem.* 43(2):254-266). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug's target is known (e.g., a 23680 protein of the present invention), all common variants of that gene can be fairly easily identified in the population and it can be determined if having one version of the gene versus another is associated with a particular drug response.

Alternatively, a method termed "gene expression profiling", can be utilized to identify genes that predict drug response. For example, the gene expression of an animal dosed with a drug (e.g., a 23680 molecule or 23680 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 23680 molecule or 23680 modulator, such as a modulator identified by one of the exemplary screening assays described herein.

The present invention further provides methods for identifying new agents, or combinations, that are based on identifying agents that modulate the activity of one or more of the gene products encoded by one or more of the 23680 genes of the present invention, wherein these products may be associated with resistance of the cells to a therapeutic agent. Specifically, the activity of the proteins encoded by the 23680 genes of the present invention can be used as a basis for identifying agents for overcoming agent resistance. By blocking the activity of one or more of the resistance proteins, target cells, e.g., hematopoietic cells, will become sensitive to treatment with an agent that the unmodified target cells were resistant to.

Monitoring the influence of agents (e.g., drugs) on the expression or activity of a 23680 protein can be applied in clinical trials. For example, the effectiveness of an agent determined by a screening assay as described herein to increase 23680 gene expression, protein levels, or up-regulate 23680 activity, can be monitored in clinical trials of subjects exhibiting decreased 23680 gene expression, protein levels, or down-regulated 23680 activity. Alternatively, the effectiveness of an agent determined by a screening assay to decrease 23680 gene expression, protein levels, or down-regulate 23680 activity, can be monitored in clinical trials of subjects exhibiting increased 23680 gene expression, protein levels, or upregulated 23680 activity. In such clinical trials, the expression or activity of a 23680 gene, and preferably, other genes that have been implicated in, for example, a 23680-associated disorder can be used as a "read out" or markers of the phenotype of a particular cell.

23680 Informatics

The sequence of a 23680 molecule is provided in a variety of media to facilitate use thereof. A sequence can be provided as a manufacture, other than an isolated nucleic acid or amino acid molecule, which contains a 23680. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 23680 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention that match a particular target sequence or target motif. The search can be a BLAST search or other routine sequence comparison, e.g., a search described herein.

Thus, in one aspect, the invention features a method of analyzing 23680, e.g., analyzing structure, function, or relatedness to one or more other nucleic acid or amino acid sequences. The method includes: providing a 23680 nucleic acid or amino acid sequence; comparing the 23680 sequence with a second sequence, e.g., one or more preferably a plurality of sequences from a collection of sequences, e.g., a nucleic acid or protein sequence database to thereby analyze 23680. The method can be performed in a machine, e.g., a computer, or manually by a skilled artisan.

The method can include evaluating the sequence identity between a 23680 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 23680 sequence that includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 23680 sequence, or record, in machine-readable form; comparing a second sequence to the 23680 sequence; thereby analyzing a sequence. Comparison can include comparing to sequences for sequence identity or determining if one sequence is included within the other, e.g., determining if the 23680 sequence includes a sequence being compared. In a preferred embodiment the 23680 or second sequence is stored on a first computer, e.g., at a first site and the comparison is performed, read, or recorded on a second computer, e.g., at a second site. E.g., the 23680 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 23680-associated disease or disorder or a pre-disposition to a 23680-associated disease or disorder, wherein the method comprises the steps of determining 23680] sequence information associated with the subject and based on the 23680 sequence information, determining whether the subject has a 23680-associated disease or disorder or a pre-disposition to a 23680-associated disease or disorder and/or recommending a particular treatment for the disease, disorder or pre-disease condition.

The invention further provides in an electronic system and/or in a network, a method for determining whether a subject has a 23680-associated disease or disorder or a pre-disposition to a disease associated with a 23680 wherein the method comprises the steps of determining 23680 sequence information associated with the subject, and based on the 23680 sequence information, determining whether the subject has a 23680-associated disease or disorder or a pre-disposition to a 23680-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 23680 sequence of the subject to the 23680 sequences in the database to thereby determine whether the subject as a 23680-associated disease or disorder, or a pre-disposition for such.

The present invention also provides in a network, a method for determining whether a subject has a 23680 associated disease or disorder or a pre-disposition to a 23680-associated disease or disorder associated with 23680, said method comprising the steps of receiving 23680 sequence information from the subject and/or information related thereto, receiving phenotypic information associated with the subject, acquiring information from the network corresponding to 23680 and/or corresponding to a 23680-associated disease or disorder (e.g., an aminotransferase-related disorder), and based on one or more of the phenotypic information, the 23680 information (e.g., sequence information and/or information related thereto), and the acquired information, determining whether the subject has a 23680-associated disease or disorder or a pre-disposition to a 23680-associated disease or disorder. The method may further comprise the step of recommending a particular treatment for the disease, disorder or pre-disease condition.

The present invention also provides a method for determining whether a subject has a 23680-associated disease or disorder or a pre-disposition to a 23680-associated disease or disorder, said method comprising the steps of receiving information related to 23680 (e.g., sequence information and/or information related thereto), receiving phenotypic information associated with the subject, acquiring information from the network related to 23680 and/or related to a 23680-associated disease or disorder, and based on one or more of the phenotypic information, the 23680 information, and the acquired information, determining whether the subject has a 23680-associated disease or disorder or a pre-disposition to a 23680-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

Background of the 32624 Invention

A great diversity of oligosaccharide structures and types of glycoconjugates is found in nature, and these molecules are synthesized by a large number of glycosyltransferases (Tukey and Strassburg (2000), *Annu Rev Pharmacol Toxicol* 40:581-616). Glycosyltransferases catalyze the synthesis of glycoconjugates, including glycolipids, glycoproteins, and polysaccharides, as well as glycosylated small molecules, such as steroids, drugs, and toxins, by transferring an activated mono- or oligosaccharide residue to an existing acceptor molecule for the initiation or elongation of the carbohydrate chain. A catalytic reaction is believed to involve the recognition of both the donor and acceptor by suitable domains, as well as the catalytic site of the enzyme (Amado et al. (1999), *Biochim Biophys Acta* 1473:35-53; Kapitonov and Yu (1999), *Glycobiology* 9:961-78).

Because the glycosylation reaction is highly specific with respect to both the configuration of the sugar residue and the site of the addition, it is expected that unique domain structures for substrate recognition and nucleotide-sugar binding are located within the enzyme molecule. Evidence indicates that the formation of many glycosidic linkages is provided by a large homologous glycosyltransferase gene family, and that the existence of multiple enzyme isoforms provides a degree of redundancy as well as a higher level of regulation of the glycoforms synthesized (Tukey and Strassburg (2000), supra; Kapitonov and Yu (1999), supra).

Glycosyltransferases of the Golgi apparatus are all membrane proteins that share type II topology, consisting of an amino terminal cytoplasmic tail, a signal anchor transmembrane domain, a stem region, and a large luminal catalyitc domain. The membrane-spanning domain and its flanking regions contain necessary and sufficient information for Golgi retention of these enzymes (Jaskiewicz (1997), *Acta Biochim Pol* 44:173-9). An important function of the Golgi glycotransferases is the modification of proteins as they are transported through the secretory pathway. ER localized glycosyltransferases can have either a type II topology, like the Golgi glycosyltransferases, or a type I topology, e.g., the N-terminus and catalytic domain inside the ER (Kapitonov et al. (1999), Glycobiology 9:961-78). The glycotransferases of the ER can function to modify proteins, similar to the Golgi glycotransferases, or they can function to glycosylate lipids or small hydrophobic molecules.

Some glycosyltransferases are present on the cell surface and are thought to function as cell adhesion molecules by binding oligosaccharide substrates present on adjacent cell surfaces or in the extracellular matrix. The best studied of these is beta 1,4-galactosyltransferase, which mediates sperm binding to the egg coat and selected cellular interactions with the basal lamina (Shur (1993), *Curr Opin Cell Biol* 5:854-63).

Summary of the 32624 Invention

The present invention is based, in part, on the discovery of a novel UDP-glucuronosyl and glycosyl transferase family member, referred to herein as "32624". The nucleotide sequence of a cDNA encoding 32624 is depicted in SEQ ID NO:38, and the amino acid sequence of a 32624 polypeptide is depicted in SEQ ID NO:39. In addition, the nucleotide sequences of the coding region are depicted in SEQ ID NO:40.

Accordingly, in one aspect, the invention features a nucleic acid molecule that encodes a 32624 protein or polypeptide, e.g., a biologically active portion of the 32624 protein. In a preferred embodiment the isolated nucleic acid molecule encodes a polypeptide having the amino acid sequence of SEQ ID NO:39. In other embodiments, the invention provides isolated 32624 nucleic acid molecules having the nucleotide sequence shown in SEQ ID NO:38, or SEQ ID NO:40. In still other embodiments, the invention provides nucleic acid molecules that are substantially identical (e.g., naturally occurring allelic variants) to the nucleotide sequence shown in SEQ ID NO:38, or SEQ ID NO:40. In other embodiments, the invention provides a nucleic acid molecule which hybridizes under a stringency condition described herein to a nucleic acid molecule comprising the nucleotide sequence of SEQ ID NO:38, or SEQ ID NO:40, wherein the nucleic acid encodes a full length 32624 protein or an active fragment thereof.

In a related aspect, the invention further provides nucleic acid constructs that include a 32624 nucleic acid molecule described herein. In certain embodiments, the nucleic acid molecules of the invention are operatively linked to native or heterologous regulatory sequences. Also included, are vectors and host cells containing the 32624 nucleic acid molecules of the invention e.g., vectors and host cells suitable for producing 32624 nucleic acid molecules and polypeptides.

In another related aspect, the invention provides nucleic acid fragments suitable as primers or hybridization probes for the detection of 32624-encoding nucleic acids.

In still another related aspect, isolated nucleic acid molecules that are antisense to a 32624 encoding nucleic acid molecule are provided.

In another aspect, the invention features, 32624 polypeptides, and biologically active or antigenic fragments thereof that are useful, e.g., as reagents or targets in assays applicable to treatment and diagnosis of 32624-mediated or -related disorders. In another embodiment, the invention provides 32624 polypeptides having a 32624 activity. Preferred polypeptides are 32624 proteins including at least one UDP-glucuronosyl and glycosyl transferase domain and, preferably, having a 32624 activity, e.g., a 32624 activity as described herein.

In other embodiments, the invention provides 32624 polypeptides, e.g., a 32624 polypeptide having the amino acid sequence shown in SEQ ID NO:39; an amino acid sequence that is substantially identical to the amino acid sequence shown in SEQ ID NO:39; or an amino acid sequence encoded by a nucleic acid molecule having a nucleotide sequence which hybridizes under a stringency condition described herein to a nucleic acid molecule comprising the nucleotide sequence of SEQ ID NO:38, or SEQ ID NO:40, wherein the nucleic acid encodes a full length 32624 protein or an active fragment thereof.

In a related aspect, the invention provides 32624 polypeptides or fragments operatively linked to non-32624 polypeptides to form fusion proteins.

In another aspect, the invention features antibodies and antigen-binding fragments thereof, that react with, or more preferably specifically bind 32624 polypeptides or fragments thereof, e.g., an extracellular domain (or a topologically extracellular domain, e.g., an ER luminal domain) or a cytoplasmic domain of an 32624 polypeptide.

In another aspect, the invention provides methods of screening for compounds that modulate the expression or activity of the 32624 polypeptides or nucleic acids.

In still another aspect, the invention provides a process for modulating 32624 polypeptide or nucleic acid expression or activity, e.g. using the screened compounds. In certain embodiments, the methods involve treatment of conditions or disorders related to aberrant activity or expression of the 32624 polypeptides or nucleic acids, such as conditions or disorders involving aberrant or deficient glycosylation of small lipophilic agents (e.g., steroids, bile acids, lipids, drugs and xenobiotics) and related disorders, including metabolic disorders, autoimmune disorders, viral disorders, neural disorders, and cellular proliferation and/or differentiation disorders.

In another aspect, the invention provides methods for modulating the activity of a 32624-expressing cell. The method includes contacting the cell with an agent, e.g., a compound (e.g., a compound identified using the methods described herein) that modulates the activity, or expression, of the 32624 polypeptide or nucleic acid. The contacting step can be effected in vitro or ex vivo. In other embodiments, the contacting step is effected in vivo, e.g., in a subject (e.g., a mammal, e.g., a human), as part of a therapeutic or prophylactic protocol. In one embodiment, the cell is a hyperproliferative cell, e.g., a cell found in a solid tumor, a soft tissue tumor, or a metastatic lesion.

In a preferred embodiment, the agent, e.g., compound, is an inhibitor of a 32624 polypeptide. Preferably, the inhibitor is chosen from a peptide, a phosphopeptide, a small organic molecule, a small inorganic molecule and an antibody (e.g., an antibody conjugated to a therapeutic moiety selected from a cytotoxin, a cytotoxic agent and a radioactive metal ion). In another preferred embodiment, the agent, e.g., compound, is an inhibitor of a 32624 nucleic acid, e.g., an antisense, a ribozyme, or a triple helix molecule.

In a preferred embodiment, the agent, e.g., compound, is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

The invention also provides assays for determining the activity of or the presence or absence of 32624 polypeptides or nucleic acid molecules in a biological sample, including for disease diagnosis.

In further aspect, the invention provides assays for determining the presence or absence of a genetic alteration in a 32624 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 32624 molecule. In one embodiment, the capture probe is a nucleic acid, e.g., a probe complementary to a 32624 nucleic acid sequence. In another embodiment, the capture probe is a polypeptide, e.g., an antibody specific for 32624 polypeptides. Also featured is a method of analyzing a sample by contacting the sample to the aforementioned array and detecting binding of the sample to the array.

Other features and advantages of the invention will be apparent from the following detailed description, and from the claims.

Detailed Description of 32624

The human 32624 sequence (see SEQ ID NO:38, as recited in Example 28), which is approximately 2996 nucleotides long including untranslated regions, contains a predicted methionine-initiated coding sequence of about 1584 nucleotides, including the termination codon. The coding sequence encodes a 527 amino acid protein (see SEQ ID NO:39, as recited in Example 28). The human 32624 protein of SEQ ID NO:39 and FIG. 40 includes an amino-terminal hydrophobic amino acid sequence, consistent with a signal sequence, of about 23 amino acids (from amino acid residue 1 to about amino acid residue 23 of SEQ ID NO:39), which upon cleavage results in the production of a mature protein form. This mature protein form is approximately 504 amino acid residues in length (from about amino acid residue 24 to amino acid residue 527 of SEQ ID NO:39).

Human 32624 contains the following regions or other structural features:

a UDP-glucuronosyl and glycosyl transferase domain (PFAM Accession Number PF00201) located at about amino acid residues 24 to 525 of SEQ ID NO:39;

a UDP-glucuonosyl and glycosyl transferase signature motif (PS00375) located at about amino acid residues 354 to 397 of SEQ ID NO:39;

a signal peptide from about amino acid residues 1 to 23 of SEQ ID NO:39;

one predicted transmembrane domain from about amino acid residues 491 to 507 of SEQ ID NO:39;

one predicted Protein Kinase C phosphorylation sites (PS00005) located at about amino acid residues 520 to 522 of SEQ ID NO:39; and one predicted amidation site (PS0009) from about amino acids 338 to 341 of SEQ ID NO:39.

For general information regarding PFAM identifiers, PS prefix and PF prefix domain identification numbers, refer to Sonnhammer et al (1997) *Protein* 28:405-420.

The 32624 protein contains a significant number of structural characteristics in common with members of the UDP-glucuronosyl and glycosyl transferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

The human UDP-glucuronosyl and UDP-glycosyl transferase family (UGT) includes proteins or polypeptides that are capable of catalyzing the synthesis of glycoconjugates, including glycolipids, glycoproteins, and polysaccharides, by transferring an activated mono- or oligosaccharide residue to an existing acceptor molecule for the initiation or elongation of the carbohydrate chain. The acceptor can be a lipid, a protein, a heterocyclic compound, or another carbohydrate residue. Glycosyltransferases can be divided into numerous subfamilies based upon their specificity for sugar moieties and acceptor molecules. "Group 1" glycosyltransferases transfer activated sugars to a variety of substrates, including glycogen, fructose-6-phosphate and lipopolysaccharides. Members of this family transfer UDP, ADP, GDP or CMP linked sugars. "Group 2" glycosyltransferases transfer sugar from UDP-glucuronic acid, UDP-glucose, UDP-N-acetyl-galactosamine, GDP-mannose or CDP-abequose, to a range of substrates including cellulose, dolichol phosphate and teichoic acids. UDP-glucuronosyl and UDP-glycosyltransferases have been described in Kapitonov and Yu (1999), supra, and Tukey and Strassburg (2000), supra, the contents of which are incorporated herein by reference. Based on sequence similarities, 32624 molecules of the present invention are predicted to have similar biological activities as glycosyltransferase family members, to reside in the endoplasmic reticulum (ER), and to exhibit Type I topology.

A 32624 polypeptide can include a human "UDP-glucuronosyl and UDP-glycosyltransferase domain" or regions homologous with a "human UDPGT domain".

As used herein, the term "UDP-glucuronosyl and UDP-glycosyltransferase domain" includes an amino acid sequence of about 200 to 800 amino acid residues in length and having a bit score for the alignment of the sequence to the UDP-glucuronosyl and UDP-glycosyltransferase domain (HMM) of at least 500. Preferably, a human UDP-glucuronosyl and UDP-glycosyltransferase domain includes at least about 300 to 600 amino acids, more preferably about 400 to 550 amino acid residues, or about 490 to 510 amino acids, and most preferably about 501-502 amino acids and has a bit score for the alignment of the sequence to the UDP-glucuronosyl and UDP-glycosyltransferase domain (HMM) of at least 600, preferably 800, more preferably 900 or greater. The UDP-glucuronosyl and UDP-glycosyltransferase domain (HMM) has been assigned the PFAM Accession Number PF002001. An alignment of the human UDPGT domain (amino acids 24 to 525 of SEQ ID NO:39) of human 32624 with a consensus amino acid sequence derived from a hidden Markov model is depicted in FIGS. 40A-40B.

In a preferred embodiment 32624 polypeptide or protein has a "UDP-glucuronosyl and UDP-glycosyltransferase domain" or a region that includes at least about 300 to 600 amino acids, more preferably about 400 to 550 amino acid residues, or about 490 to 510 amino acids, and most preferably about 501 amino acid residues and has at least about 60%, 70% 80% 90% 95%, 99%, or 100% homology with a "UDP-glucuronosyl and UDP-glycosyltransferase domain", e.g., the UDP-glucuronosyl and UDP-glycosyltransferase domain of human 32624 (e.g., residues 24 to 525 of SEQ ID NO:39).

To identify the presence of a "human UDPGT" domain in a 32624 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28(3):405-420 and a detailed description of HMMs can be found, for example, in Gribskov et al.(1990) Meth. Enzymol. 183:146-159; Gribskov et al.(1987) Proc. Natl. Acad. Sci. USA 84:4355-4358; Krogh et al.(1994) J. Mol. Biol. 235:1501-1531; and Stultz et al.(1993) Protein Sci. 2:305-314, the contents of which are incorporated herein by reference. A search was performed against the HMM database resulting in the identification of a "human UDPGT domain" domain in the amino acid sequence of human 32624 at about residues 24 to 525 of SEQ ID NO:39 (see FIGS. 40A-40B).

In one embodiment, a 32624 protein includes at least one UDP-glucuronosyl and UDP-glycosyltransferase signature motif. As used herein, an "UDP-glucuronosyl and UDP-glycosyltransferase signature motif" includes a sequence of at least 33 amino acid residues defined by the sequence: [FW]-X-X-Q-X-X-[LIVMYA]-[LIMV]-X-X-X-X-X-X-[LVGAC]-[LVFYA]-[LIVMF]-[STAGCM]-[HNQ]-[STAGC]-G-X-X-[STAG]-X-X-X-[STAGL]-[LIVMFA]-X-X-X-X-[PQR]-[LIVMT]-X-X-X-[PA]-X-X-X-[DES]-[QEHN]. A UDP-glucuronosyl and UDP-glycosyltransferase signature motif, as defined, can be involved in the catalytic transfer of a glycosyl group from a UDP-sugar molecule to a small hydrophobic molecule, e.g., a steroid, bile acid, metabolite, drug, toxin, carcinogen, or lipid. More preferably, a UDP-glucuronosyl and UDP-glycosyltransferase signature motif includes 36, 41, or most preferably 44 amino acid residues. Human 32624 contains a UDP-glucuronosyl and UDP-glycosyltransferase signature motif located at about amino acid residues 354 to 397 of SEQ ID NO:39.

In a preferred embodiment, a 32624 polypeptide or protein has at least one UDP-glucuronosyl and UDP-glycosyltransferase signature motif which includes 33, 36, 41, or preferably 44 amino acid residues and has at least 70%, 80%, 90%, 95%, 98%, or 100% homology with a UDP-glucuronosyl and UDP-glycosyltransferase signature motif, e.g., the UDP-glucuronosyl and UDP-glycosyltransferase signature motif of human 32624 (e.g., about amino acid residues 354 to 397 of SEQ ID NO:39).

Human 32624 protein is predicted to have a Type I topology (i.e., an N-terminal and catalytic domain residing in the lumen of an organelle, e.g., the endoplasmic reticulum, located at about amino acid residues 1-490 of SEQ ID NO:39 (including signal sequence), a transmembrane domain located at about amino acid residues 491-507 of SEQ ID NO:39, and a short cytoplasmic tail located at about amino acid residues 508-528 of SEQ ID NO:39.

Accordingly, a 32624 molecule can further include at least one transmembrane domain. As used herein, the term "transmembrane domain" includes an amino acid sequence of about 15 amino acid residues in length that spans a phospholipid membrane. More preferably, a transmembrane domain includes about at least 10, 15, 16, 17, 20, 21, 22 or 25 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al, (1996) *Annual Rev. Neuronsci.* 19: 235-63, the contents of which are incorporated herein by reference.

In a preferred embodiment, a 32624 polypeptide or protein has at least one transmembrane domain or a region which includes at least 10, 15, 16, 17, 20, 21, 22 or 25 amino acid residues and has at least about 60%, 70% 80% 90% 95%, 99%, or 100% homology with a "transmembrane domain," e.g., at least one transmembrane domain of human 32624 (e.g., amino acid residues 491 to 507 of SEQ ID NO:39).

In another embodiment, a 32624 protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, Golgi, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally-occurring 32624, or 32624-like protein.

A non-transmembrane domain located at the N-terminus of a 32624 protein or polypeptide is referred to herein as an "N-terminal non-transmembrane domain." As used herein, an "N-terminal non-transmembrane domain" includes an amino acid sequence having about 1-700, preferably about 200-600, more preferably about 300-550, and even more preferably about 450-500 amino acid residues in length, has at least about 60%, 70% 80% 90% 95%, 99% or 100% homology with an "N-terminal non-transmembrane domain," e.g., a non-transmembrane domain of human 32624 (e.g., residues 24 to 490 of SEQ ID NO:39) and is located outside the boundaries of a membrane. For example, an N-terminal non-transmembrane domain is located at about amino acid residues 24-490 of SEQ ID NO:39. Preferably, the N-terminal non-transmembrane domain is capable of catalytic activity (e.g., catalyzing the transfer of a sugar, e.g., a saccharide, to an acceptor molecule). Preferably, the N-terminal non-transmembrane domain (e.g., amino acids 24-490 of SEQ ID NO:39) is localized in the lumen of an intracellular organelle (e.g., endoplasmic reticulum).

Similarly, a non-transmembrane domain located at the C-terminus of a 32624 protein or polypeptide is referred to herein as a "C-terminal non-transmembrane domain." As used herein, an "C-terminal non-transmembrane domain" includes an amino acid sequence having about 1-30, preferably about 10-25, preferably about 15-22, more preferably about 19-20 amino acid residues in length and is located outside the boundaries of a membrane. For example, a C-terminal non-transmembrane domain is located at about amino acid residues 508 to 527 of SEQ ID NO:39.

A 32624 family member can include at least one UDP-glucuronosyl and glycosyl transferase domain. Furthermore, a 32624 family member can include at least one UDP-glucuronosyl and UDP-glycosyltransferase signature motif (PS00375); at least one signal peptide; at least one transmembrane domain; and at least one predicted amidation site (PS00009).

As the 32624 polypeptides of the invention may modulate 32624-mediated activities, they may be useful as of for developing novel diagnostic and therapeutic agents for 32624-mediated or related disorders, as described below.

As used herein, a "32624 activity", "biological activity of 32624" or "functional activity of 32624", refers to an activity exerted by a 32624 protein, polypeptide or nucleic acid molecule. For example, a 32624 activity can be an activity exerted by 32624 in a physiological milieu on, e.g., a 32624-responsive cell or on a 32624 substrate, e.g., a small hydrophobic molecule, e.g., a steroid, bile acid, metabolite, drug, toxin, carcinogen, or lipid. A 32624 activity can be determined in vivo or in vitro. In one embodiment, a 32624 activity is a direct activity, such as an association with a 32624 target molecule. A "target molecule" or "binding partner" is a molecule with which a 32624 protein binds or interacts in nature. In an exemplary embodiment, 32624 is an enzyme for a small hydrophobic molecule substrate, e.g., a steroid, bile acid, metabolite, drug, toxin, carcinogen, or lipid substrate.

A 32624 activity can also be an indirect activity, e.g., a cellular signaling activity mediated by interaction of the 32624 protein with a 32624 receptor. The features of the 32624 molecules of the present invention can provide similar biological activities as UDP-glucuronosyl and glycosyl transferase family members. For example, the 32624 proteins of the present invention can have one or more of the following activities: 1) catalyzing the transfer of an activated sugar residue (e.g., glucuronic acid) to an acceptor molecule (e.g., a small hydrophobic molecule substrate, e.g., a steroid, bile acid, metabolite, drug, toxin, carcinogen, or lipid substrate); 2) detoxifying and eliminating xenobiotics (e.g., drugs, carcinogens, or toxins); 3) modulation of tumor cell growth and invasion; 4) myelin formation; 5) signal transduction; 6) viral and microbial adhesion; 7) oligodendrocyte development; 8) sperm-egg binding; 9) catalyzing the processing, folding, and secretion of proteins; 10) immune detection; 11) xenograft rejection; and 12) the ability to antagonize or inhibit, competitively or non-competitively, any of 1-11.

Thus, the 32624 molecules can act as novel diagnostic targets and therapeutic agents for controlling proliferation and differentiation disorders, liver disorders, gastrointestinal (biliary and gastric epithelial disorders), kidney disorders, metabolic disorders, immune disorders, viral disorders, as well as neural disorders (e.g., disorders of the brain). For example, the 32624 molecules can act as diagnostic and therapeutic targets for disorders involving aberrant transfer of glucuronic acid to small hydrophobic molecule substrates, e.g., steroid, bile acid, metabolite, drug, toxin, carcinogen, or lipid substrates. Examples of other substrates include, but are not limited to, dietary amines, flavones, phenols, and bilirubin.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth. Examples of such cells include cells having an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Additional examples of proliferative disorders include hematopoietic neoplastic disorders. As used herein, the term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The 32624 nucleic acid and protein of the invention can be used to treat and/or diagnose a variety of immune disorders. Examples of hematopoieitic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

32624 molecules may play an important role in the etiology of certain viral diseases, including but not limited to Hepatitis B, Hepatitis C and Herpes Simplex Virus (HSV). Modulators of 32624 activity could be used to control viral diseases. The modulators can be used in the treatment and/or diagnosis of viral infected tissue or virus-associated tissue fibrosis, especially liver and liver fibrosis. Also, 32624 modulators can be used in the treatment and/or diagnosis of virus-associated carcinoma, especially hepatocellular cancer.

Additionally, 32624 may play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York:McGraw-Hill); pain associated with musculoskeletal disorders, e.g., joint pain; tooth pain; headaches; pain associated with surgery; pain related to irritable bowel syndrome; or chest pain.

Examples of gastrointestinal disorders include, but are not limited to, disorders of the colon such as congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Additional examples of gastrointestinal disorders include, but are not limited to, disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin B1) deficiency and vitamin B12 deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

The 32624 protein, fragments thereof, and derivatives and other variants of the sequence in SEQ ID NO:39 thereof are collectively referred to as "polypeptides or proteins of the invention" or "32624 polypeptides or proteins". Nucleic acid molecules encoding such polypeptides or proteins are collectively referred to as "nucleic acids of the invention" or "32624 nucleic acids." 32624 molecules refer to 32624 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:38 or SEQ ID NO:40, corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a 32624 protein. The gene can optionally further include non-coding sequences, e.g., regulatory sequences and introns. Preferably, a gene encodes a mammalian 32624 protein or derivative thereof.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of 32624 protein is at least 10% pure. In a preferred embodiment, the preparation of 32624 protein has less than about 30%, 20%, 10% and more preferably 5% (by dry weight), of non-32624 protein (also referred to herein as a "contaminating protein"), or of chemical precursors or non-32624 chemicals. When the 32624 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 32624 without abolishing or substantially altering a 32624 activity. Preferably the alteration does not substantially alter the 32624 activity, e.g., the activity is at least 20%, 40%, 60%, 70% or 80% of wild-type. An "essential" amino acid residue is a residue that, when altered from the wild-type sequence of 32624, results in abolishing a 32624 activity such that less than 20% of the wild-type activity is present. For example, conserved amino acid residues in 32624 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a 32624 protein is preferably replaced with another amino acid residue from the same side chain family. Alternatively, in another embodiment, mutations can be introduced randomly along all or part of a 32624 coding sequence, such as by saturation mutagenesis, and the resultant mutants can be screened for 32624 biological activity to identify mutants that retain activity. Following mutagenesis of SEQ ID NO:38 or SEQ ID NO:40, the encoded protein can be expressed recombinantly and the activity of the protein can be determined.

As used herein, a "biologically active portion" of a 32624 protein includes a fragment of a 32624 protein that participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a 32624 molecule and a non-32624 molecule or between a first 32624 molecule and a second 32624 molecule (e.g., a dimerization interaction). Biologically active portions of a 32624 protein include peptides comprising amino acid sequences sufficiently homologous to or derived from the amino acid sequence of the 32624 protein, e.g., the amino acid sequence shown in SEQ ID NO:39, which include less amino acids than the full length 32624 proteins, and exhibit at least one activity of a 32624 protein. Typically, biologically active portions comprise a domain or motif with at least one activity of the 32624 protein, e.g., the catalytic transfer of a glycosyl group (e.g., glucuronic acid) from a UTP-sugar to a small hydrophobic substrate molecule, e.g., a steroid, bile acid, metabolite, drug, toxin, carcinogen, or lipid substrate. A biologically active portion of a 32624 protein can be a polypeptide that is, for example, 10, 25, 50, 100, 200 or more amino acids in length. Biologically active portions of a 32624 protein can be used as targets for developing agents that modulate a 32624 mediated activity, e.g., the catalytic transfer of a glycosyl group (e.g., glucuronic acid) from a UTP-sugar to a small hydrophobic substrate molecule, e.g., a steroid, bile acid, metabolite, drug, toxin, carcinogen, or lipid substrate.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to 32624 nucleic acid molecules of the invention. BLAST protein searches can be performed with the XBLAST program, score=50, wordlength=3 to obtain amino acid sequences homologous to 32624 protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used.

Particularly preferred 32624 polypeptides of the present invention have an amino acid sequence substantially identical to the amino acid sequence of SEQ ID NO:39. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:39 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:38 or 40 are termed substantially identical.

"Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules of 32624

In one aspect, the invention provides, an isolated or purified, nucleic acid molecule that encodes a 32624 polypeptide described herein, e.g., a full-length 32624 protein or a fragment thereof, e.g., a biologically active portion of 32624 protein. Also included is a nucleic acid fragment suitable for use as a hybridization probe, which can be used, e.g., to identify a nucleic acid molecule encoding a polypeptide of the invention, 32624 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:38, or a portion of any of these nucleotide sequences. In one embodiment, the nucleic acid molecule includes sequences encoding the human 32624 protein (i.e., "the coding region" of SEQ ID NO:38, as shown in SEQ ID NO:40), as well as 5' untranslated sequences. Alternatively, the nucleic acid molecule can include only the coding region of SEQ ID NO:38 (e.g., SEQ ID NO:40) and, e.g., no flanking sequences which normally accompany the subject sequence. In another embodiment, the nucleic acid molecule encodes a sequence corresponding to a fragment of the protein from about amino acid 24 to 525.

In another embodiment, an isolated nucleic acid molecule of the invention includes a nucleic acid molecule which is a complement of the nucleotide sequence shown in SEQ ID NO:38 or SEQ ID NO:40, or a portion of any of these nucleotide sequences. In other embodiments, the nucleic acid molecule of the invention is sufficiently complementary to the nucleotide sequence shown in SEQ ID NO:38 or SEQ ID NO:40, such that it can hybridize (e.g., under a stringency condition described herein) to the nucleotide sequence shown in SEQ ID NO:38 or 40, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:38 or SEQ ID NO:40, or a portion, preferably of the same length, of any of these nucleotide sequences.

32624 Nucleic Acid Fragments

A nucleic acid molecule of the invention can include only a portion of the nucleic acid sequence of SEQ ID NO:38 or 40. For example, such a nucleic acid molecule can include a fragment that can be used as a probe or primer or a fragment encoding a portion of a 32624 protein, e.g., an immunogenic or biologically active portion of a 32624 protein. A fragment can comprise those nucleotides of SEQ ID NO:38, which encode a UDP-glucuronosyl and glycosyl transferase domain of human 32624. The nucleotide sequence determined from the cloning of the 32624 gene allows for the generation of probes and primers designed for use in identifying and/or cloning other 32624 family members, or fragments thereof, as well as 32624 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment that includes a nucleotide sequence encoding an amino acid fragment described herein. Nucleic acid fragments can encode a specific domain or site described herein or fragments thereof, particularly fragments thereof which are at least 50, 75, 100, 110, 120, 130, 140, 150, 160, 175, 200, 250, 300, 350, 400, or more amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 32624 nucleic acid fragment can include a sequence corresponding to a UDP-glucuronosyl and glycosyl transferase domain, a UDP-glucuonosyl and glycosyl signature motif, an N-terminal fragment of a UDP-glucuronosyl and glycosyl transferase domain (e.g., about amino acid residues 24 to 353 of SEQ ID NO:39), or a transmembrane domain.

32624 probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:38 or SEQ ID NO:40, or of a naturally occurring allelic variant or mutant of SEQ ID NO:38 or SEQ ID NO:40. Preferably, an oligonucleotide is less than about 200, 150, 120, or 100 nucleotides in length.

In one embodiment, the probe or primer is attached to a solid support, e.g., a solid support described herein.

One exemplary kit of primers includes a forward primer that anneals to the coding strand and a reverse primer that anneals to the non-coding strand. The forward primer can anneal to the start codon, e.g., the nucleic acid sequence encoding amino acid residue 1 of SEQ ID NO:39. The reverse primer can anneal to the ultimate codon, e.g., the codon immediately before the stop codon, e.g., the codon encoding amino acid residue 527 of SEQ ID NO:39. In a preferred embodiment, the annealing temperatures of the forward and reverse primers differ by no more than 5, 4, 3, or 2° C.

In a preferred embodiment, the nucleic acid is a probe which is at least 10, 12, 15, 18, 20 and less than 200, more preferably less than 100, or less than 50, nucleotides in length. It should be identical, or differ by 1, or 2, or less than 5 or 10 nucleotides, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: a UDP-glucuronosyl and glycosyl transferase domain of human 32624, e.g., about amino acid residues 24 to 525 of SEQ ID NO:39; a fragment of the UDP-glucuronosyl and glycosyl transferase domain of human 32624, e.g., an N-terminal fragment, e.g., about amino acid residues 24 to 353 of SEQ ID NO:39; a UDP-glucuronosyl and glycosyl transferase signature motif of human 32624, e.g., about amino acid residues 354 to 397 of SEQ ID NO:39; or a transmembrane domain of human 32624, e.g., about amino acid residues 491 to 507 of SEQ ID NO:39.

In another embodiment, a set of primers is provided, e.g., primers suitable for use in a PCR, which can be used to amplify a selected region of a 32624 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: a UDP-glucuronosyl and glycosyl transferase domain of human 32624, e.g., about amino acid residues 24 to 525 of SEQ ID NO:39; a fragment of the UDP-glucuronosyl and glycosyl transferase domain of human 32624, e.g., an N-terminal fragment, e.g., about amino acid residues 24 to 353 of SEQ ID NO:39; a UDP-glucuronosyl and glycosyl transferase signature motif of human 32624, e.g., about amino acid residues 354 to 397 of SEQ ID NO:39; or a transmembrane domain of human 32624, e.g., about amino acid residues 491 to 507 of SEQ ID NO:39.

A nucleic acid fragment can encode an epitope bearing region of a polypeptide described herein.

A nucleic acid fragment encoding a "biologically active portion of a 32624 polypeptide" can be prepared by isolating a portion of the nucleotide sequence of SEQ ID NO:38 or 40, which encodes a polypeptide having a 32624 biological activity (e.g., the biological activities of the 32624 proteins are described herein), expressing the encoded portion of the 32624 protein (e.g., by recombinant expression in vitro) and assessing the activity of the encoded portion of the 32624 protein. For example, a nucleic acid fragment encoding a biologically active portion of 32624 includes a UDP-glucuronosyl and glycosyl transferase domain, e.g., amino acid residues about 24 to 525 of SEQ ID NO:39. A nucleic acid fragment encoding a biologically active portion of a 32624 polypeptide, may comprise a nucleotide sequence which is greater than 300, 500, 700, 900, 1000, 1100, 1300, 1500, 1600, or more nucleotides in length.

In preferred embodiments, a nucleic acid includes a nucleotide sequence which is about 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or more nucleotides in length and hybridizes under a stringency condition described herein to a nucleic acid molecule of SEQ ID NO:38, or SEQ ID NO:40.

In a preferred embodiment, a nucleic acid fragment differs by at least 1, 2, 3, 10, 20, or more nucleotides from the sequence of Genbank accession number AW972452, AI816782, AW301261, AI766289, AW771510, AI651431, AI670866, or SEQ ID NO:1395 of WO 98/45435, SEQ ID NO:10 of WO 00/63351, or SEQ ID NO:3284 of EP 1 033 401. Differences can include differing in length or sequence identity. For example, a nucleic acid fragment can: include one or more nucleotides from SEQ ID NO:38 or SEQ ID NO:40 located outside the region of nucleotides 22 to 505, 786 to 1135, or 1094 to 1520; not include all of the nucleotides of SEQ ID NO:1395 of WO 98/45435 or SEQ ID NO:3284 of EP 1 033 401, e.g., can be one or more nucleotides shorter (at one or both ends) than the sequence of SEQ ID NO:1395 of WO 98/45435 or SEQ ID NO:3284 of EP 1 033 401; or can differ by one or more nucleotides in the region of overlap.

32624 Nucleic Acid Variants

The invention further encompasses nucleic acid molecules that differ from the nucleotide sequence shown in SEQ ID NO:38 or SEQ ID NO:40. Such differences can be due to degeneracy of the genetic code (and result in a nucleic acid which encodes the same 32624 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:39. If alignment is needed for this comparison the sequences should be aligned for maximum homology. The encoded protein can differ by no more than 5, 4, 3, 2, or 1 amino acid. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:38 or 40, e.g., as follows: by at least one but less than 10, 20, 30, or 40 nucleotides; at least one but less than 1%, 5%, 10% or 20% of the nucleotides in the subject nucleic acid. The nucleic acid can differ by no more than 5, 4, 3, 2, or 1 nucleotide. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:39 or a fragment of this sequence. Such nucleic acid molecules can readily be identified as being able to hybridize under a stringency condition described herein, to the nucleotide sequence shown in SEQ ID NO:39 or a fragment of the sequence. Nucleic acid molecules corresponding to orthologs, homologs, and allelic variants of the 32624 cDNAs of the invention can further be isolated by mapping to the same chromosome or locus as the 32624 gene.

Preferred variants include those that are correlated with the ability to catalytically transfer a glycosyl group (e.g., glucuronic acid) from a UTP-sugar to a small hydrophobic substrate molecule, e.g., a steroid, bile acid, metabolite, drug, toxin, carcinogen, or lipid substrate.

Allelic variants of 32624, e.g., human 32624, include both functional and non-functional proteins. Functional allelic variants are naturally occurring amino acid sequence variants of the 32624 protein within a population that maintain the ability to bind to UTP-sugar molecules, e.g., UTP-glucuronic acid, and small hydrophobic substrate molecules, e.g., steroids, bile acids, metabolites, drugs, toxins, carcinogens, or lipid substrates, and catalyze the transfer of the sugar molecule to the substrate molecule. Functional allelic variants will typically contain only conservative substitution of one or more amino acids of SEQ ID NO:39, or substitution, deletion or insertion of non-critical residues in non-critical regions of the protein. Non-functional allelic variants are naturally-occurring amino acid sequence variants of the 32624, e.g., human 32624, protein within a population that do not have the ability to catalyze the transfer of a glycosyl group (e.g., glucuronic acid) from a UTP-sugar to a small hydrophobic substrate molecule, e.g., a steroid, bile acid, metabolite, drug, toxin, carcinogen, or lipid substrate. For example, non-functional allelic variants may be unable to bind to either the UTP-sugar molecule or the substrate molecule. Non-functional allelic variants will typically contain a non-conservative substitution, a deletion, or insertion, or premature truncation of the amino acid sequence of SEQ ID NO:39, or a substitution, insertion, or deletion in critical residues or critical regions of the protein.

Moreover, nucleic acid molecules encoding other 32624 family members and, thus, which have a nucleotide sequence which differs from the 32624 sequences of SEQ ID NO:38 or SEQ ID NO:40 are intended to be within the scope of the invention.

Antisense Nucleic Acid Molecules, Ribozymes and Modified 32624 Nucleic Acid Molecules In another aspect, the invention features, an isolated nucleic acid molecule which is antisense to 32624. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 32624 coding strand, or to only a portion thereof (e.g., the coding region of human 32624 corresponding to SEQ ID NO:40). In another embodiment, the antisense nucleic acid molecule is antisense to a "noncoding region" of the coding strand of a nucleotide sequence encoding 32624 (e.g., the 5' and 3' untranslated regions).

An antisense nucleic acid can be designed such that it is complementary to the entire coding region of 32624 mRNA, but more preferably is an oligonucleotide which is antisense to only a portion of the coding or noncoding region of 32624 mRNA. For example, the antisense oligonucleotide can be complementary to the region surrounding the translation start site of 32624 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 32624 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. A ribozyme having specificity for a 32624-encoding nucleic acid can include one or more sequences complementary to the nucleotide sequence of a 32624 cDNA disclosed herein (i.e., SEQ ID NO:38 or SEQ ID NO:40), and a sequence having known catalytic sequence responsible for mRNA cleavage (see U.S. Pat. No. 5,093,246 or Haselhoff and Gerlach (1988) *Nature* 334:585-591). For example, a derivative of a *Tetrahymena* L-19 IVS RNA can be constructed in which the nucleotide sequence of the active site is complementary to the nucleotide sequence to be cleaved in a 32624-encoding mRNA. See, e.g., Cech et al. U.S. Pat. No. 4,987,071; and Cech et al. U.S. Pat. No. 5,116,742. Alternatively, 32624 mRNA can be used to select a catalytic RNA having a specific ribonuclease activity from a pool of RNA molecules. See, e.g., Bartel, D. and Szostak, J. W. (1993) *Science* 261:1411-1418.

32624 gene expression can be inhibited by targeting nucleotide sequences complementary to the regulatory region of the 32624 (e.g., the 32624 promoter and/or enhancers) to form triple helical structures that prevent transcription of the 32624 gene in target cells. See generally, Helene, C. (1991) *Anticancer Drug Des.* 6:569-84; Helene, C.i (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 32624 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19:17 and Faria et al. (2001) *Nature Biotech.* 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675.

PNAs of 32624 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 32624 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. W088/09810) or the blood-brain barrier (see, e.g., PCT Publication No. W089/10134). In addition, oligonucleotides can be modified with hybridization-triggered cleavage agents (see, e.g., Krol et al. (1988) *Bio-Techniques* 6:958-976) or intercalating agents. (see, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 32624 nucleic acid of the invention, two complementary regions one having a fluorophore and one a quencher such that the molecular beacon is useful for quantitating the presence of the 32624 nucleic acid of the invention in a sample. Molecular beacon nucleic acids are described, for example, in Lizardi et al, U.S. Pat.

No. 5,854,033; Nazarenko et al., U.S. Pat. No. 5,866,336, and Livak et al., U.S. Pat. No. 5,876,930.

Isolated 32624 Polypeptides

In another aspect, the invention features, an isolated 32624 protein, or fragment, e.g., a biologically active portion, for use as immunogens or antigens to raise or test (or more generally to bind) anti-32624 antibodies. 32624 protein can be isolated from cells or tissue sources using standard protein purification techniques. 32624 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 32624 polypeptide has one or more of the following characteristics:

(i) it has the ability to catalyze the transfer of a glycosyl group (e.g., glucuronic acid) from a UTP-sugar to a small hydrophobic substrate molecule, e.g., a steroid, bile acid, metabolite, drug, toxin, carcinogen, or lipid substrate;

(ii) it has a molecular weight, e.g., a deduced molecular weight, preferably ignoring any contribution of post translational modifications, amino acid composition or other physical characteristic of a 32624 polypeptide, e.g., a polypeptide of SEQ ID NO:39;

(iii) it has an overall sequence similarity of at least 60%, more preferably at least 70, 80, 90, or 95%, with a polypeptide of SEQ ID NO:39;

(iv) it can be found in the liver, intestine, colon, kidney, breast, ovary, or it can be associated with neural support cells, e.g., Schwann cells;

(v) it has a UDP-glucuronosyl and glycosyl transferase domain which is preferably about 70%, 80%, 90% or 95% with amino acid residues about 24 to 525 of SEQ ID NO:39;

(vi) it has a UDP-glucuronosyl and glycosyl transferase signature motif;

(vii) it has a signal peptide;

(viii) it has a transmembrane domain;

(ix) it localizes to cell membranes, e.g., ER or cell surface membranes; or (x) at least one, two, preferably three predicted N-glycosylation sites (PS00001).

In a preferred embodiment the 32624 protein, or fragment thereof, differs from the corresponding sequence in SEQ ID:2. In one embodiment it differs by at least one but by less than 15, 10 or 5 amino acid residues. In another it differs from the corresponding sequence in SEQ ID NO:39 by at least one residue but less than 20%, 15%, 10% or 5% of the residues in it differ from the corresponding sequence in SEQ ID NO:39. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the UDP-glucuronosyl and glycosyl transferase signature motif, e.g., about amino acid residues 354 to 397 of SEQ ID NO:39, or the transmembrane domain, e.g., about amino acid residues 491 to 507 of SEQ ID NO:39. In another preferred embodiment one or more differences are in the UDP-glucuronosyl and glycosyl transferase signature motif, e.g., about amino acid residues 354 to 397 of SEQ ID NO:39, or the transmembrane domain, e.g., about amino acid residues 491 to 507 of SEQ ID NO:39.

Other embodiments include a protein that contain one or more changes in amino acid sequence, e.g., a change in an amino acid residue which is not essential for activity. Such 32624 proteins differ in amino acid sequence from SEQ ID NO:39, yet retain biological activity.

In one embodiment, the protein includes an amino acid sequence at least about 60%, 65%, 70%, 75%, 80%, 85%, 90%, 95%, 98% or more homologous to SEQ ID NO:39.

A 32624 protein or fragment is provided which varies from the sequence of SEQ ID NO:39 in regions defined by amino acid residues about 24 to 353 and/or 398 to 527 by at least one but by less than 15, 10 or 5 amino acid residues in the protein or fragment but which does not differ from SEQ ID NO:39 in regions defined by amino acid residues about 354 to 397. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 32624 protein includes a UDP-glucuronosyl and glycosyl transferase domain. Moreover, other biologically active portions, in which other regions of the protein are deleted, can be prepared by recombinant techniques and evaluated for one or more of the functional activities of a native 32624 protein.

In a preferred embodiment, the 32624 protein has an amino acid sequence shown in SEQ ID NO:39. In other embodiments, the 32624 protein is substantially identical to SEQ ID NO:39. In yet another embodiment, the 32624 protein is substantially identical to SEQ ID NO:39 and retains the functional activity of the protein of SEQ ID NO:39, as described in detail in the subsections above.

In a preferred embodiment, a protein fragment differs by at least 1, 2, 3, 10, 20, or more amino acid residues from the sequence encoded by Genbank accession number AW972452, AI816782, AW301261, AI766289, AW771510, AI651431, AI670866, or SEQ ID NO:1395 of WO 98/45435, SEQ ID NO:10 of WO 00/63351, or SEQ ID NO:3284 of EP 1 033 401. Differences can include differing in length or sequence identity. For example, a protein fragment can: include one or more amino acid residues from SEQ ID NO:39 located outside the region encoded by nucleotides 22 to 505, 786 to 1135, or 1094 to 1520 of SEQ ID NO:38; not include all of the amino acid residues encoded by SEQ ID NO:1395 of WO 98/45435 or SEQ ID NO:3284 of EP 1 033 401, e.g., can be one or more amino acid shorter (at one or both ends) than the sequence encoded by SEQ ID NO:1395 of WO 98/45435 or SEQ ID NO:3284 of EP 1 033 401; or can differ by one or more amino acid residues in the region of overlap.

32624 Chimeric or Fusion Proteins

In another aspect, the invention provides 32624 chimeric or fusion proteins. As used herein, a 32624 "chimeric protein" or "fusion protein" includes a 32624 polypeptide linked to a non-32624 polypeptide. A "non-32624 polypeptide" refers to a polypeptide having an amino acid sequence corresponding to a protein which is not substantially homologous to the 32624 protein, e.g., a protein which is different from the 32624 protein and which is derived from the same or a different organism. The 32624 polypeptide of the fusion protein can correspond to all or a portion e.g., a fragment described herein of a 32624 amino acid sequence. In a preferred embodiment, a 32624 fusion protein includes at least one (or two) biologically active portion of a 32624 protein. The non-32624 polypeptide can be fused to the N-terminus or C-terminus of the 32624 polypeptide.

The fusion protein can include a moiety which has a high affinity for a ligand. For example, the fusion protein can be a GST-32624 fusion protein in which the 32624 sequences are fused to the C-terminus of the GST sequences. Such fusion proteins can facilitate the purification of recombinant 32624. Alternatively, the fusion protein can be a 32624 protein containing a heterologous signal sequence at its N-terminus. In certain host cells (e.g., mammalian host cells), expression and/or secretion of 32624 can be increased through use of a heterologous signal sequence.

Fusion proteins can include all or a part of a serum protein, e.g., an IgG constant region, or human serum albumin.

The 32624 fusion proteins of the invention can be incorporated into pharmaceutical compositions and administered to a subject in vivo. The 32624 fusion proteins can be used to affect the bioavailability of a 32624 substrate. 32624 fusion proteins may be useful therapeutically for the treatment of disorders caused by, for example, (i) aberrant modification or mutation of a gene encoding a 32624 protein; (ii) mis-regulation of the 32624 gene; and (iii) aberrant post-translational modification of a 32624 protein.

Moreover, the 32624-fusion proteins of the invention can be used as immunogens to produce anti-32624 antibodies in a subject, to purify 32624 ligands and in screening assays to identify molecules which inhibit the interaction of 32624 with a 32624 substrate.

Expression vectors are commercially available that already encode a fusion moiety (e.g., a GST polypeptide). A 32624-encoding nucleic acid can be cloned into such an expression vector such that the fusion moiety is linked in-frame to the 32624 protein.

Variants of 32624 Proteins

In another aspect, the invention also features a variant of a 32624 polypeptide, e.g., which functions as an agonist (mimetics) or as an antagonist. Variants of the 32624 proteins can be generated by mutagenesis, e.g., discrete point mutation, the insertion or deletion of sequences or the truncation of a 32624 protein. An agonist of the 32624 proteins can retain substantially the same, or a subset, of the biological activities of the naturally occurring form of a 32624 protein. An antagonist of a 32624 protein can inhibit one or more of the activities of the naturally occurring form of the 32624 protein by, for example, competitively modulating a 32624-mediated activity of a 32624 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 32624 protein.

Variants of a 32624 protein can be identified by screening combinatorial libraries of mutants, e.g., truncation mutants, of a 32624 protein for agonist or antagonist activity.

Libraries of fragments e.g., N terminal, C terminal, or internal fragments, of a 32624 protein coding sequence can be used to generate a variegated population of fragments for screening and subsequent selection of variants of a 32624 protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of 32624 proteins. Recursive ensemble mutagenesis (REM), a new technique which enhances the frequency of functional mutants in the libraries, can be used in combination with the screening assays to identify 32624 variants (Arkin and Yourvan (1992) *Proc. Natl. Acad. Sci. USA* 89:7811-7815; Delgrave et al. (1993) *Protein Engineering* 6:327-331).

Cell based assays can be exploited to analyze a variegated 32624 library. For example, a library of expression vectors can be transfected into a cell line, e.g., a cell line, which ordinarily responds to 32624 in a substrate-dependent manner. The transfected cells are then contacted with the 32624 substrate and the effect of the expression of the mutant on signaling by the 32624 substrate can be detected, e.g., by measuring cell proliferation or migration. Plasmid DNA can then be recovered from the cells which score for inhibition, or alternatively, potentiation of signaling by the 32624 substrate, and the individual clones further characterized.

In another aspect, the invention features a method of making a 32624 polypeptide, e.g., a peptide having a non-wild type activity, e.g., an antagonist, agonist, or super agonist of a 32624 polypeptide, e.g., a naturally occurring 32624 polypeptide. The method includes altering the sequence of the 32624 polypeptide, e.g., altering the sequence by substitution or deletion of one or more residues of a non-conserved region, domain or residue disclosed herein, and testing the altered polypeptide for the desired activity.

In another aspect, the invention features a method of making a fragment or analog of a 32624 polypeptide a biological activity of a naturally occurring 32624 polypeptide. The method includes: altering the sequence, e.g., by substitution or deletion of one or more residues, of a 32624 polypeptide, e.g., altering the sequence of a non-conserved region, or a domain or residue described herein, and testing the altered polypeptide for the desired activity.

Anti-32624 Antibodies

In another aspect, the invention provides an anti-32624 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-32624 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH—terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 32624 polypeptide or fragment thereof. Examples of antigen-binding fragments of the anti-32624 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-32624 antibody can be a polyclonal or a monoclonal antibody. In other embodiments, the antibody can be recombinantly produced, e.g., produced by phage display or by combinatorial methods.

Phage display and combinatorial methods for generating anti-32624 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, the contents of all of which are incorporated by reference herein).

In one embodiment, the anti-32624 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

An anti-32624 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 32624 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region that are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 32624 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method that may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In preferred embodiments an antibody can be made by immunizing with purified 32624 antigen, or a fragment thereof, e.g., a fragment described herein, membrane associated antigen, tissue, e.g., crude tissue preparations, whole cells, preferably living cells, lysed cells, or cell fractions, e.g., membrane fractions.

A full-length 32624 protein or, antigenic peptide fragment of 32624 can be used as an immunogen or can be used to identify anti-32624 antibodies made with other immunogens, e.g., cells, membrane preparations, and the like. The antigenic peptide of 32624 should include at least 8 amino acid residues of the amino acid sequence shown in SEQ ID NO:39 and encompasses an epitope of 32624. Preferably, the antigenic peptide includes at least 10 amino acid residues, more preferably at least 15 amino acid residues, even more preferably at least 20 amino acid residues, and most preferably at least 30 amino acid residues.

Fragments of 32624 can be used as immunogens or used to characterize the specificity of an antibody. For example, fragments of 32624 which include residues about 80 to 88, about 136 to 144, or about 433 to 457 or SEQ ID NO:39 can be used to make antibodies against hydrophilic regions of the 32624 protein. Similarly, fragments of 32624 which include residues about 89 to 108, about 145 to 170, or about 301 to 311 of SEQ ID NO:39 can be used to make an antibody against a hydrophobic region of the 32624 protein; fragments of 32624 which include residues from about 24 to 527 can be used to make an antibody against an extracellular (or topologically equivalent, e.g., ER luminal) region of the 32624 protein; fragments of 32624 which include residues about 508 to 527 can be used to make an antibody against an cytoplasmic region of the 32624 protein; and a fragment of 32624 which include residues about 354 to 397 can be used to make an antibody against the UDP-glucuronosyl and glycosyl transferase signature motif of the 32624 protein.

Antibodies reactive with, or specific for, any of these regions, or other regions or domains described herein are provided.

Antibodies which bind only native 32624 protein, only denatured or otherwise non-native 32624 protein, or which bind both, are with in the invention. Antibodies with linear or conformational epitopes are within the invention. Conformational epitopes can sometimes be identified by identifying antibodies that bind to native but not denatured 32624 protein.

Preferred epitopes encompassed by the antigenic peptide are regions of 32624 are located on the surface of the protein, e.g., hydrophilic regions, as well as regions with high antigenicity. For example, an Emini surface probability analysis of the human 32624 protein sequence can be used to indicate the regions that have a particularly high probability of being localized to the surface of the 32624 protein and are thus likely to constitute surface residues useful for targeting antibody production.

In a preferred embodiment the antibody can bind to the extracellular portion of the 32624 protein, e.g., it can bind to a whole cell which expresses the 32624 protein. In another embodiment, the antibody binds an intracellular portion of the 32624 protein. In preferred embodiments antibodies can bind one or more of purified antigen, membrane associated antigen, tissue, e.g., tissue sections, whole cells, preferably living cells, lysed cells, cell fractions, e.g., membrane fractions.

The anti-32624 antibody can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target 32624 protein.

In a preferred embodiment the antibody has effector function and/or can fix complement. In other embodiments the antibody does not recruit effector cells; or fix complement.

In a preferred embodiment, the antibody has reduced or no ability to bind an Fe receptor. For example, it is a isotype or subtype, fragment or other mutant, which does not support binding to an Fc receptor, e.g., it has a mutagenized or deleted Fc receptor binding region.

In a preferred embodiment, an anti-32624 antibody alters (e.g., increases or decreases) the ability of a 32624 polypeptide to catalytze the transfer of a glycosyl group (e.g., glucuronic acid) from a UTP-sugar to a small hydrophobic substrate molecule, e.g., a steroid, bile acid, metabolite, drug, toxin, carcinogen, or lipid substrate. For example, the antibody can bind at or in proximity to the active site, e.g., to an epitope that includes a residue located from about 354 to 397 of SEQ ID NO:39.

The antibody can be coupled to a toxin, e.g., a polypeptide toxin, e,g, ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-32624 antibody (e.g., monoclonal antibody) can be used to isolate 32624 by standard techniques, such as affinity chromatography or immunoprecipitation. Moreover, an anti-32624 antibody can be used to detect 32624 protein (e.g., in a cellular lysate or cell supernatant) in order to evaluate the abundance and pattern of expression of the protein. Anti-32624 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes a nucleic acid which encodes an anti-32624 antibody, e.g., an anti-32624 antibody described herein. Also included are vectors which include the nucleic acid and cells transformed with the nucleic acid, particularly cells which are useful for producing an antibody, e.g., mammalian cells, e.g. CHO or lymphatic cells.

The invention also includes cell lines, e.g., hybridomas, which make an anti-32624 antibody, e.g., and antibody described herein, and method of using said cells to make a 32624 antibody.

32624 Recombinant Expression Vectors, Host Cells and Genetically Engineered Cells In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 32624 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 32624 proteins, mutant forms of 32624 proteins, fusion proteins, and the like).

The recombinant expression vectors of the invention can be designed for expression of 32624 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 32624 activity assays, (e.g., direct assays or competitive assays described in detail below), or to generate antibodies specific for 32624 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The 32624 expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., C A, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a 32624 nucleic acid molecule within a recombinant expression vector or a 32624 nucleic acid molecule containing sequences which allow it to homologously recombine into a specific site of the host cell's genome. The terms "host cell" and "recombinant host cell" are used interchangeably herein. Such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 32624 protein can be expressed in bacterial cells (such as *E. coli*), insect cells, yeast or mammalian cells (such as Chinese hamster ovary cells (CHO) or COS cells (African green monkey kidney cells CV-1 origin SV40 cells; Gluzman (1981) *Cell*23:175-182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 32624 protein. Accordingly, the invention further provides methods for producing a 32624 protein using the host cells of the invention. In one embodiment, the method includes culturing the host cell of the invention (into which a recombinant expression vector encoding a 32624 protein has been introduced) in a suitable medium such that a 32624 protein is produced. In another embodiment, the method further includes isolating a 32624 protein from the medium or the host cell.

In another aspect, the invention features, a cell or purified preparation of cells which include a 32624 transgene, or which otherwise misexpress 32624. The cell preparation can consist of human or non-human cells, e.g., rodent cells, e.g., mouse or rat cells, rabbit cells, or pig cells. In preferred embodiments, the cell or cells include a 32624 transgene, e.g., a heterologous form of a 32624, e.g., a gene derived from humans (in the case of a non-human cell). The 32624 transgene can be misexpressed, e.g., overexpressed or underexpressed. In other preferred embodiments, the cell or cells include a gene that mis-expresses an endogenous 32624, e.g., a gene the expression of which is disrupted, e.g., a knockout. Such cells can serve as a model for studying disorders that are related to mutated or mis-expressed 32624 alleles or for use in drug screening.

In another aspect, the invention features, a human cell, e.g., a hematopoietic or hepatic stem cell, transformed with nucleic acid which encodes a subject 32624 polypeptide.

Also provided are cells, preferably human cells, e.g., human hematopoietic, hepatic, neural, or fibroblast cells, in which an endogenous 32624 is under the control of a regulatory sequence that does not normally control the expression of the endogenous 32624 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 32624 gene. For example, an endogenous 32624 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 32624 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (2001) *Nat. Biotechnol.* 19:35; and U.S. Pat. No. 5,876,742. Production of 32624 polypeptide can be regulated in the subject by administering an agent (e.g., a steroid hormone) to the subject. In another preferred embodiment, the implanted recombinant cells express and secrete an antibody specific for a 32624 polypeptide. The antibody can be any antibody or any antibody derivative described herein.

32624 Transgenic Animals

The invention provides non-human transgenic animals. Such animals are useful for studying the function and/or activity of a 32624 protein and for identifying and/or evaluating modulators of 32624 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 32624 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 32624 protein to particular cells. A transgenic founder animal can be identified based upon the presence of a 32624 transgene in its genome and/or expression of 32624 mRNA in tissues or cells of the animals. A transgenic founder animal can then be used to breed additional animals carrying the transgene. Moreover, transgenic animals carrying a transgene encoding a 32624 protein can further be bred to other transgenic animals carrying other transgenes.

32624 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses of 32624

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); c) methods of treatment (e.g., therapeutic and prophylactic); and d) synthesis of glycosylated molecules, e.g., glycosylated forms of small hydrophobic substrate molecules, e.g., steroids, bile acids, metabolites, drugs, toxins, carcinogens, or lipid substrates.

The isolated nucleic acid molecules of the invention can be used, for example, to express a 32624 protein (e.g., via a recombinant expression vector in a host cell in gene therapy applications), to detect a 32624 mRNA (e.g., in a biological sample) or a genetic alteration in a 32624 gene, and to modulate 32624 activity, as described further below. The 32624 proteins can be used to treat disorders characterized by insufficient or excessive production of a 32624 substrate or production of 32624 inhibitors. In addition, the 32624 proteins can be used to screen for naturally occurring 32624 substrates, to screen for drugs or compounds which modulate 32624 activity, as well as to treat disorders characterized by insufficient or excessive production of 32624 protein or production of 32624 protein forms which have decreased, aberrant or unwanted activity compared to 32624 wild type protein (e.g., metabolic disorders, liver disorders, gastrointestinal disorders, kidney disorders, immunological disorders, neural disorders, or cellular proliferation or differentiation disorders). Moreover, the anti-32624 antibodies of the invention can be used to detect and isolate 32624 proteins, regulate the bioavailability of 32624 proteins, and modulate 32624 activity.

A method of evaluating a compound for the ability to interact with, e.g., bind, a subject 32624 polypeptide is provided. The method includes: contacting the compound with the subject 32624 polypeptide; and evaluating ability of the compound to interact with, e.g., to bind or form a complex with the subject 32624 polypeptide. This method can be performed in vitro, e.g., in a cell free system, or in vivo, e.g., in a two-hybrid interaction trap assay. This method can be used to identify naturally occurring molecules that interact with subject 32624 polypeptide. It can also be used to find natural or synthetic inhibitors of subject 32624 polypeptide. Screening methods are discussed in more detail below.

32624 Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 32624 proteins, have a stimulatory or inhibitory effect on, for example, 32624 expression or 32624 activity, or have a stimulatory or inhibitory effect on, for example, the expression or activity of a 32624 substrate. Compounds thus identified can be used to modulate the activity of target gene products (e.g., 32624 genes) in a therapeutic protocol, to elaborate the biological function of the target gene product, or to identify compounds that disrupt normal target gene interactions.

In one embodiment, the invention provides assays for screening candidate or test compounds which are substrates of a 32624 protein or polypeptide or a biologically active portion thereof. In another embodiment, the invention provides assays for screening candidate or test compounds that bind to or modulate an activity of a 32624 protein or polypeptide or a biologically active portion thereof.

In one embodiment, an activity of a 32624 protein can be assayed by transforming a cell line, e.g., COS cells, with a vector which expresses a 32624 protein in the cells, allowing the cells to produce protein, and then homogenizing the cells so as to produce microsomes that contain the 32624 protein. The microsomes can then be partially purified and incubated with an appropriate substrate, e.g., a radioactively labeled steroid, e.g., 14C-testosterone. Finally, the activity of the 32624 protein can be determined by measuring the amount of glycosylated substrate present in the reaction. This type of assay has been described in Meech and Mackenzie (1997), *J Biol Chem* 272(43):26913-7, the contents of which are incorporated herein by reference.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In one embodiment, an assay is a cell-based assay in which a cell which expresses a 32624 protein or biologically active portion thereof is contacted with a test compound, and the ability of the test compound to modulate 32624 activity is determined. Determining the ability of the test compound to modulate 32624 activity can be accomplished by monitoring, for example, the catalytic transfer of a glycosyl group (e.g., glucuronic acid) from a UTP-sugar to a small hydrophobic substrate molecule, e.g., a steroid, bile acid, metabolite, drug, toxin, carcinogen, or lipid substrate. The cell, for example, can be of mammalian origin, e.g., human.

The ability of the test compound to modulate 32624 binding to a compound, e.g., a 32624 substrate, or to bind to 32624 can also be evaluated. This can be accomplished, for example, by coupling the compound, e.g., the substrate, with a radioisotope or enzymatic label such that binding of the compound, e.g., the substrate, to 32624 can be determined by detecting the labeled compound, e.g., substrate, in a complex. Alternatively, 32624 could be coupled with a radioisotope or enzymatic label to monitor the ability of a test compound to modulate 32624 binding to a 32624 substrate in a complex. For example, compounds (e.g., 32624 substrates) can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 32624 substrate) to interact with 32624 with or without the labeling of any of the interactants can be evaluated. For example, a microphysiometer can be used to detect the interaction of a compound with 32624 without the labeling of either the compound or the 32624. McConnell, H. M. et al. (1992) *Science* 257: 1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 32624.

In yet another embodiment, a cell-free assay is provided in which a 32624 protein or biologically active portion thereof is contacted with a test compound and the ability of the test compound to bind to the 32624 protein or biologically active portion thereof is evaluated. Preferred biologically active portions of the 32624 proteins to be used in assays of the present invention include fragments which participate in interactions with non-32624 molecules, e.g., fragments with high surface probability scores.

Soluble and/or membrane-bound forms of isolated proteins (e.g., 32624 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 32624 protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 32624, an anti-32624 antibody or its target molecule to facilitate separation of complexed from uncomplexed forms of one or both of the proteins, as well as to accommodate automation of the assay. Binding of a test compound to a 32624 protein, or interaction of a 32624 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/32624 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 32624 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 32624 binding or activity determined using standard techniques.

Other techniques for immobilizing either a 32624 protein or a target molecule on matrices include using conjugation of biotin and streptavidin. Biotinylated 32624 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 32624 protein or target molecules but which do not interfere with binding of the 32624 protein to its target molecule. Such antibodies can be derivatized to the wells of the plate, and unbound target or 32624 protein trapped in the wells by antibody conjugation. Methods for detecting such complexes, in addition to those described above for the GST-immobilized complexes, include immunodetection of complexes using antibodies reactive with the 32624 protein or target molecule, as well as enzyme-linked assays which rely on detecting an enzymatic activity associated with the 32624 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al, eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141-8; Hage, D. S., and Tweed, S. A. (1997) *J Chromatogr B Biomed Sci Appl.* 699:499-525). Further, fluorescence energy transfer may also be conveniently utilized, as described herein, to detect binding without further purification of the complex from solution.

In a preferred embodiment, the assay includes contacting the 32624 protein or biologically active portion thereof with a known compound which binds 32624 to form an assay mixture, contacting the assay mixture with a test compound, and determining the ability of the test compound to interact with a 32624 protein, wherein determining the ability of the test compound to interact with a 32624 protein includes determining the ability of the test compound to preferentially bind to 32624 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 32624 genes herein identified. In an alternative embodiment, the invention provides methods for determining the ability of the test compound to modulate the activity of a 32624 protein through modulation of the activity of a downstream effector of a 32624 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 32624 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 32624 ("32624-binding proteins" or "32624-bp") and are involved in 32624 activity. Such 32624-bps can be activators or inhibitors of signals by the 32624 proteins or 32624 targets as, for example, downstream elements of a 32624-mediated signaling pathway.

The two-hybrid system is based on the modular nature of most transcription factors, which consist of separable DNA-binding and activation domains. Briefly, the assay utilizes two different DNA constructs. In one construct, the gene that codes for a 32624 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 32624 protein can be the fused to the activator domain.) If the "bait" and the "prey" proteins are able to interact, in vivo, forming a 32624-dependent complex, the DNA-binding and activation domains of the transcription factor are brought into close proximity. This proximity allows transcription of a reporter gene (e.g., lacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with the 32624 protein.

In another embodiment, modulators of 32624 expression are identified. For example, a cell or cell free mixture is contacted with a candidate compound and the expression of 32624 mRNA or protein evaluated relative to the level of expression of 32624 mRNA or protein in the absence of the candidate compound. When expression of 32624 mRNA or protein is greater in the presence of the candidate compound than in its absence, the candidate compound is identified as a stimulator of 32624 mRNA or protein expression. Alternatively, when expression of 32624 mRNA or protein is less (statistically significantly less) in the presence of the candidate compound than in its absence, the candidate compound is identified as an inhibitor of 32624 mRNA or protein expression. The level of 32624 mRNA or protein expression can be determined by methods described herein for detecting 32624 mRNA or protein.

In another aspect, the invention pertains to a combination of two or more of the assays described herein. For example, a modulating agent can be identified using a cell-based or a cell free assay, and the ability of the agent to modulate the activity of a 32624 protein can be confirmed in vivo, e.g., in an animal such as an animal model for a metabolic disorder, liver disorder, gastrointestinal disorder, kidney disorder, immunological disorder, neural disorder, or cellular proliferation or differentiation disorder.

This invention further pertains to novel agents identified by the above-described screening assays. Accordingly, it is within the scope of this invention to further use an agent identified as described herein (e.g., a 32624 modulating agent, an antisense 32624 nucleic acid molecule, a 32624-specific antibody, or a 32624-binding partner) in an appropriate animal model to determine the efficacy, toxicity, side effects, or mechanism of action, of treatment with such an agent. Furthermore, novel agents identified by the above-described screening assays can be used for treatments as described herein.

32624 Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 32624 with a disease; (ii) identify an individual from a minute biological sample (tissue typing); and (iii) aid in forensic identification of a biological sample. These applications are described in the subsections below.

32624 Chromosome Mapping

The 32624 nucleotide sequences or portions thereof can be used to map the location of the 32624 genes on a chromosome. This process is called chromosome mapping. Chromosome mapping is useful in correlating the 32624 sequences with genes associated with disease.

Briefly, 32624 genes can be mapped to chromosomes by preparing PCR primers (preferably 15-25 bp in length) from the 32624 nucleotide sequences. These primers can then be used for PCR screening of somatic cell hybrids containing individual human chromosomes. Only those hybrids containing the human gene corresponding to the 32624 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919-924).

Other mapping strategies e.g., in situ hybridization (described in Fan, Y. et al. (1990) *Proc. Natl. Acad. Sci. USA*, 87:6223-27), pre-screening with labeled flow-sorted chromosomes, and pre-selection by hybridization to chromosome specific cDNA libraries can be used to map 32624 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783-787.

Moreover, differences in the DNA sequences between individuals affected and unaffected with a disease associated with the 32624 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

32624 Tissue Typing 32624 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 32624 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:38 can provide positive individual identification with a panel of perhaps 10 to 1,000 primers which each yield a noncoding amplified sequence of 100 bases. If predicted coding sequences, such as those in SEQ ID NO:40 are used, a more appropriate number of primers for positive individual identification would be 500-2,000.

If a panel of reagents from 32624 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 32624 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:38 (e.g., fragments derived from the noncoding regions of SEQ ID NO:38 having a length of at least 20 bases, preferably at least 30 bases) are particularly appropriate for this use.

The 32624 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 32624 probes can be used to identify tissue by species and/or by organ type.

In a similar fashion, these reagents, e.g., 32624 primers or probes can be used to screen tissue culture for contamination (i.e. screen for the presence of a mixture of different types of cells in a culture).

Predictive Medicine of 32624

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 32624.

Such disorders include, e.g., a disorder associated with the misexpression of a 32624 gene, which may include a metabolic disorder, liver disorder, gastrointestinal disorder, kidney disorder, immunological disorder, neural disorder, or cellular proliferation or differentiation disorder.

The method includes one or more of the following:

detecting, in a tissue of the subject, the presence or absence of a mutation which affects the expression of the 32624 gene, or detecting the presence or absence of a mutation in a region which controls the expression of the gene, e.g., a mutation in the 5' control region;

detecting, in a tissue of the subject, the presence or absence of a mutation which alters the structure of the 32624 gene;

detecting, in a tissue of the subject, the misexpression of the 32624 gene, at the mRNA level, e.g., detecting a non-wild type level of a mRNA;

detecting, in a tissue of the subject, the misexpression of the gene, at the protein level, e.g., detecting a non-wild type level of a 32624 polypeptide.

In preferred embodiments the method includes: ascertaining the existence of at least one of: a deletion of one or more nucleotides from the 32624 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:38, or naturally occurring mutants thereof or 5' or 3' flanking sequences naturally associated with the 32624 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 32624 gene; the presence of a non-wild type splicing pattern of a messenger RNA transcript of the gene; or a non-wild type level of 32624.

Methods of the invention can be used prenatally or to determine if a subject's offspring will be at risk for a disorder.

In preferred embodiments the method includes determining the structure of a 32624 gene, an abnormal structure being indicative of risk for the disorder.

In preferred embodiments the method includes contacting a sample from the subject with an antibody to the 32624 protein or a nucleic acid, which hybridizes specifically with the gene. These and other embodiments are discussed below.

Diagnostic and Prognostic Assays of 32624

Diagnostic and prognostic assays of the invention include method for assessing the expression level of 32624 molecules and for identifying variations and mutations in the sequence of 32624 molecules.

Expression Monitoring and Profiling

The presence, level, or absence of 32624 protein or nucleic acid in a biological sample can be evaluated by obtaining a biological sample from a test subject and contacting the biological sample with a compound or an agent capable of detecting 32624 protein or nucleic acid (e.g., mRNA, genomic DNA) that encodes 32624 protein such that the presence of 32624 protein or nucleic acid is detected in the biological sample. The term "biological sample" includes tissues, cells and biological fluids isolated from a subject, as well as tissues, cells and fluids present within a subject. A preferred biological sample is serum. The level of expression of the 32624 gene can be measured in a number of ways, including, but not limited to: measuring the mRNA encoded by the 32624 genes; measuring the amount of protein encoded by the 32624 genes; or measuring the activity of the protein encoded by the 32624 genes.

The level of mRNA corresponding to the 32624 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 32624 nucleic acid, such as the nucleic acid of SEQ ID NO:38, or a portion thereof, such as an oligonucleotide of at least 7, 15, 30, 50, 100, 250 or 500 nucleotides in length and sufficient to specifically hybridize under stringent conditions to 32624 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 32624 genes.

The level of mRNA in a sample that is encoded by one of 32624 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 32624 gene being analyzed.

In another embodiment, the methods further contacting a control sample with a compound or agent capable of detecting 32624 mRNA, or genomic DNA, and comparing the presence of 32624 mRNA or genomic DNA in the control sample with the presence of 32624 mRNA or genomic DNA in the test sample. In still another embodiment, serial analysis of gene expression, as described in U.S. Pat. No. 5,695,937, is used to detect 32624 transcript levels.

A variety of methods can be used to determine the level of protein encoded by 32624. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 32624 protein in a biological sample in vitro as well as in vivo. In vitro techniques for detection of 32624 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 32624 protein include introducing into a subject a labeled anti-32624 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-32624 antibody positioned on an antibody array (as described below). The sample can be detected, e.g., with avidin coupled to a fluorescent label.

In another embodiment, the methods further include contacting the control sample with a compound or agent capable of detecting 32624 protein, and comparing the presence of 32624 protein in the control sample with the presence of 32624 protein in the test sample.

The invention also includes kits for detecting the presence of 32624 in a biological sample. For example, the kit can include a compound or agent capable of detecting 32624 protein or mRNA in a biological sample; and a standard. The compound or agent can be packaged in a suitable container. The kit can further comprise instructions for using the kit to detect 32624 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 32624 expression or activity. As used herein, the term "unwanted" includes an unwanted phenomenon involved in a biological response such as a metabolic disorder, liver disorder, gastrointestinal disorder, kidney disorder, immunological disorder, neural disorder, or cellular proliferation or differentiation disorder.

In one embodiment, a disease or disorder associated with aberrant or unwanted 32624 expression or activity is identified. A test sample is obtained from a subject and 32624 protein or nucleic acid (e.g., mRNA or genomic DNA) is evaluated, wherein the level, e.g., the presence or absence, of 32624 protein or nucleic acid is diagnostic for a subject having or at risk of developing a disease or disorder associated with aberrant or unwanted 32624 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 32624 expression or activity. For example, such methods can be used to determine whether a subject can be effectively treated with an agent for a metabolic disorder, liver disorder, gastrointestinal disorder, kidney disorder, immunological disorder, neural disorder, or cellular proliferation or differentiation disorder.

In another aspect, the invention features a computer medium having a plurality of digitally encoded data records. Each data record includes a value representing the level of expression of 32624 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 32624 (e.g., other genes associated with a 32624-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 32624 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose, e.g., a metabolic disorder or a cellular proliferation or differentiation disorder in a subject, wherein a decrease in 32624 expression is an indication that the subject has or is disposed to having, e.g., a metabolic disorder or a cellular proliferation or differentiation disorder. The method can be used to monitor a treatment for, e.g., a metabolic disorder or a cellular proliferation or differentiation disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 32624 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 32624 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 32624 expression.

32624 Arrays and Uses Thereof

In another aspect, the invention features an array that includes a substrate having a plurality of addresses. At least one address of the plurality includes a capture probe that binds specifically to a 32624 molecule (e.g., a 32624 nucleic acid or a 32624 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 32624 nucleic acid, e.g., the sense or anti-sense strand. In one preferred embodiment, a subset of addresses of the plurality of addresses has a nucleic acid capture probe for 32624. Each address of the subset can include a capture probe that hybridizes to a different region of a 32624 nucleic acid. In another preferred embodiment, addresses of the subset include a capture probe for a 32624 nucleic acid. Each address of the subset is unique, overlapping, and complementary to a different variant of 32624 (e.g., an allelic variant, or all possible hypothetical variants). The array can be used to sequence 32624 by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 32624 polypeptide or fragment thereof. The polypeptide can be a naturally-occurring interaction partner of 32624 polypeptide. Preferably, the polypeptide is an antibody, e.g., an antibody described herein (see "Anti-32624 Antibodies," above), such as a monoclonal antibody or a single-chain antibody.

In another aspect, the invention features a method of analyzing the expression of 32624. The method includes providing an array as described above; contacting the array with a sample and detecting binding of a 32624-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 32624. If a sufficient number of diverse samples is analyzed, clustering (e.g., hierarchical clustering, k-means clustering, Bayesian clustering and the like) can be used to identify other genes which are co-regulated with 32624. For example, the array can be used for the quantitation of the expression of multiple genes. Thus, not only tissue specificity, but also the level of expression of a battery of genes in the tissue is ascertained.

Quantitative data can be used to group (e.g., cluster) genes on the basis of their tissue expression per se and level of expression in that tissue.

For example, array analysis of gene expression can be used to assess the effect of cell-cell interactions on 32624 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 32624-associated disease or disorder; and processes, such as a cellular transformation associated with a 32624-associated disease or disorder. The method can also evaluate the treatment and/or progression of a 32624-associated disease or disorder The array is also useful for ascertaining differential expression patterns of one or more genes in normal and abnormal cells. This provides a battery of genes (e.g., including 32624) that could serve as a molecular target for diagnosis or therapeutic intervention.

In another aspect, the invention features an array having a plurality of addresses. Each address of the plurality includes a unique polypeptide. At least one address of the plurality has disposed thereon a 32624 polypeptide or fragment thereof. Methods of producing polypeptide arrays are described in the art, e.g., in De Wildt et al. (2000). *Nature Biotech.* 18, 989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80,85, 90, 95 or 99% identical to a 32624 polypeptide or fragment thereof. For example, multiple variants of a 32624 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 32624 binding compound, e.g., an antibody in a sample from a subject with specificity for a 32624 polypeptide or the presence of a 32624-binding protein or ligand.

The array is also useful for ascertaining the effect of the expression of a gene on the expression of other genes in the same cell or in different cells (e.g., ascertaining the effect of 32624 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 32624 or from a cell or subject in which a 32624 mediated response has been elicited, e.g., by contact of the cell with 32624 nucleic acid or protein, or administration to the cell or subject 32624 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 32624 (or does not express as highly as in the case of the 32624 positive plurality of capture probes) or from a cell or subject which in which a 32624 mediated response has not been elicited (or has been elicited to a lesser extent than in the first sample); contacting the array with one or more inquiry probes (which is preferably other than a 32624 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 32624 or from a cell or subject in which a 32624-mediated response has been elicited, e.g., by contact of the cell with 32624 nucleic acid or protein, or administration to the cell or subject 32624 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 32624 (or does not express as highly as in the case of the 32624 positive plurality of capture probes) or from a cell or subject which in which a 32624 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 32624, e.g., analyzing structure, function, or relatedness to other nucleic acid or amino acid sequences. The method includes: providing a 32624 nucleic acid or amino acid sequence; comparing the 32624 sequence with one or more preferably a plurality of sequences from a collection of sequences, e.g., a nucleic acid or protein sequence database; to thereby analyze 32624.

Detection of 32624 Variations or Mutations

The methods of the invention can also be used to detect genetic alterations in a 32624 gene, thereby determining if a subject with the altered gene is at risk for a disorder characterized by misregulation in 32624 protein activity or nucleic acid expression, such as a metabolic disorder, liver disorder, gastrointestinal disorder, kidney disorder, immunological disorder, neural disorder, or cellular proliferation or differentiation disorder. In preferred embodiments, the methods include detecting, in a sample from the subject, the presence or absence of a genetic alteration characterized by at least one of an alteration affecting the integrity of a gene encoding a 32624-protein, or the mis-expression of the 32624 gene. For example, such genetic alterations can be detected by ascertaining the existence of at least one of 1) a deletion of one or more nucleotides from a 32624 gene; 2) an addition of one or more nucleotides to a 32624 gene; 3) a substitution of one or more nucleotides of a 32624 gene, 4) a chromosomal rearrangement of a 32624 gene; 5) an alteration in the level of a messenger RNA transcript of a 32624 gene, 6) aberrant modification of a 32624 gene, such as of the methylation pattern of the genomic DNA, 7) the presence of a non-wild type splicing pattern of a messenger RNA transcript of a 32624 gene, 8) a non-wild type level of a 32624-protein, 9) allelic loss of a 32624 gene, and 10) inappropriate post-translational modification of a 32624-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 32624-gene. This method can include the steps of collecting a sample of cells from a subject, isolating nucleic acid (e.g., genomic, mRNA or both) from the sample, contacting the nucleic acid sample with one or more primers which specifically hybridize to a 32624 gene under conditions such that hybridization and amplification of the 32624-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 32624 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 32624 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 32624 nucleic acid or a putative variant (e.g., allelic variant) thereof. A probe can have one or more mismatches to a region of a 32624 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in 32624 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 32624 gene and detect mutations by comparing the sequence of the sample 32624 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 32624 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 32624 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 32624 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 32624 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 32624 nucleic acid.

In a preferred embodiment the set includes a first and a second oligonucleotide. The first and second oligonucleotide can hybridize to the same or to different locations of SEQ ID NO:38 or the complement of SEQ ID NO:38. Different locations can be different but overlapping, or non-overlapping on the same strand. The first and second oligonucleotide can hybridize to sites on the same or on different strands.

The set can be useful, e.g., for identifying SNP's, or identifying specific alleles of 32624. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 32624 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 32624 gene.

Use of 32624 Molecules as Surrogate Markers

The 32624 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 32624 molecules of the invention may be detected, and may be correlated with one or more biological states in vivo. For example, the 32624 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 32624 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 32624 marker) transcription or expression, the amplified marker may be in a quantity which is more readily detectable than the drug itself. Also, the marker may be more easily detected due to the nature of the marker itself; for example, using the methods described herein, anti-32624 antibodies may be employed in an immune-based detection system for a 32624 protein marker, or 32624-specific radiolabeled probes may be used to detect a 32624 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J Health-Syst. Pharm.* 56 Suppl. 3: S16-S20.

The 32624 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 32624 protein or RNA) for specific tumor markers in a subject, a drug or course of treatment may be selected that is optimized for the treatment of the specific tumor likely to be present in the subject. Similarly, the presence or absence of a specific sequence mutation in 32624 DNA may correlate 32624 drug response. The use of pharmacogenomic markers therefore permits the application of the most appropriate treatment for each subject without having to administer the therapy.

Pharmaceutical Compositions of 32624

The nucleic acid and polypeptides, fragments thereof, as well as anti-32624 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 32624

The present invention provides for both prophylactic and therapeutic methods of treating a subject at risk of (or susceptible to) a disorder or having a disorder associated with aberrant or unwanted 32624 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 32624 molecules of the present invention or 32624 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 32624 expression or activity, by administering to the subject a 32624 or an agent which modulates 32624 expression or at least one 32624 activity. Subjects at risk for a disease which is caused or contributed to by aberrant or unwanted 32624 expression or activity can be identified by, for example, any or a combination of diagnostic or prognostic assays as described herein. Administration of a prophylactic agent can occur prior to the manifestation of symptoms characteristic of the 32624 aberrance, such that a disease or disorder is prevented or, alternatively, delayed in its progression. Depending on the type of 32624 aberrance, for example, a 32624, 32624 agonist or 32624 antagonist agent can be used for treating the subject. The appropriate agent can be determined based on screening assays described herein.

It is possible that some 32624 disorders can be caused, at least in part, by an abnormal level of gene product, or by the presence of a gene product exhibiting abnormal activity. As such, the reduction in the level and/or activity of such gene products would bring about the amelioration of disorder symptoms.

The 32624 molecules can act as novel diagnostic targets and therapeutic agents for controlling one or more of proliferation and differentiation disorders, liver disorders, gastrointestinal (biliary and gastric epithelial disorders), kidney disorders, metabolic disorders, immune disorders, viral disorders, and neural disorders (e.g., disorders of the brain), as discussed above, as well as disorders associated with bone metabolism or cardiovascular disorders.

Aberrant expression and/or activity of 32624 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 32624 molecules effects in bone cells, e.g. osteoclasts and osteoblasts, that may in turn result in bone formation and degeneration. For example, 32624 molecules may support different activities of bone resorbing osteoclasts such as the stimulation of differentiation of monocytes and mononuclear phagocytes into osteoclasts. Accordingly, 32624 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

As used herein, disorders involving the heart, or "cardiovascular disease" or a "cardiovascular disorder" includes a disease or disorder which affects the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. A cardiovascular disorder includes, but is not limited to disorders such as arteriosclerosis, atherosclerosis, cardiac hypertrophy, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, valvular disease, including but not limited to, valvular degeneration caused by calcification, rheumatic heart disease, endocarditis, or complications of artificial valves; atrial fibrillation, long-QT syndrome, congestive heart failure, sinus node dysfunction, angina, heart failure, hypertension, atrial fibrillation, atrial flutter, pericardial disease, including but not limited to, pericardial effusion and pericarditis; cardiomyopathies, e.g., dilated cardiomyopathy or idiopathic cardiomyopathy, myocardial infarction, coronary artery disease, coronary artery spasm, ischemic disease, arrhythmia, sudden cardiac death, and cardiovascular developmental disorders (e.g., arteriovenous malformations, arteriovenous fistulae, raynaud's syndrome, neurogenic thoracic outlet syndrome, causalgia/ reflex sympathetic dystrophy, hemangioma, aneurysm, cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistance of the fetal circulation, pulmonary valve stenosis, single ventricle, total anomalous pulmonary venous return, transposition of the great vessels, tricuspid atresia, truncus arteriosus, ventricular septal defects). A cardiovasular disease or disorder also can include an endothelial cell disorder.

As used herein, an "endothelial cell disorder" includes a disorder characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

As discussed, successful treatment of 32624 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 32624 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 32624 expression is through the use of aptamer molecules specific for 32624 protein. Aptamers are nucleic acid molecules having a tertiary structure which permits them to specifically bind to protein ligands (see, e.g., Osborne, et al. (1997) Curr. Opin. Chem Biol. 1: 5-9; and Patel, D. J. (1997) Curr Opin Chem Biol 1:32-46). Since nucleic acid molecules may in many cases be more conveniently introduced into target cells than therapeutic protein molecules may be, aptamers offer a method by which 32624 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 32624 disorders. For a description of antibodies, see the Antibody section above.

In circumstances wherein injection of an animal or a human subject with a 32624 protein or epitope for stimulating antibody production is harmful to the subject, it is possible to generate an immune response against 32624 through the use of anti-idiotypic antibodies (see, for example, Herlyn, D. (1999) Ann Med 31:66-78; and Bhattacharya-Chatterjee, M., and Foon, K. A. (1998) Cancer Treat Res. 94:51-68). If an anti-idiotypic antibody is introduced into a mammal or human subject, it should stimulate the production of anti-anti-idiotypic antibodies, which should be specific to the 32624 protein. Vaccines directed to a disease characterized by 32624 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) Proc. Natl. Acad. Sci. USA 90:7889-7893).

The identified compounds that inhibit target gene expression, synthesis and/or activity can be administered to a patient at therapeutically effective doses to prevent, treat or ameliorate 32624 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography. Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 32624 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89-94 and in Shea, K. J. (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645-647. Through the use of isotope-labeling, the "free" concentration of compound which modulates the expression or activity of 32624 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142-2144.

Another aspect of the invention pertains to methods of modulating 32624 expression or activity for therapeutic purposes. Accordingly, in an exemplary embodiment, the modulatory method of the invention involves contacting a cell with a 32624 or agent that modulates one or more of the activities of 32624 protein activity associated with the cell. An agent that modulates 32624 protein activity can be an agent as described herein, such as a nucleic acid or a protein, a naturally-occurring target molecule of a 32624 protein (e.g., a 32624 substrate or receptor), a 32624 antibody, a 32624 agonist or antagonist, a peptidomimetic of a 32624 agonist or antagonist, or other small molecule.

In one embodiment, the agent stimulates one or 32624 activities. Examples of such stimulatory agents include active 32624 protein and a nucleic acid molecule encoding 32624. In another embodiment, the agent inhibits one or more 32624 activities. Examples of such inhibitory agents include antisense 32624 nucleic acid molecules, anti-32624 antibodies, and 32624 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 32624 protein or nucleic acid molecule. In one embodiment, the method involves administering an agent (e.g., an agent identified by a screening assay described herein), or combination of agents that modulates (e.g., up regulates or down regulates) 32624 expression or activity. In another embodiment, the method involves administering a 32624 protein or nucleic acid molecule as therapy to compensate for reduced, aberrant, or unwanted 32624 expression or activity.

Stimulation of 32624 activity is desirable in situations in which 32624 is abnormally downregulated and/or in which increased 32624 activity is likely to have a beneficial effect. For example, stimulation of 32624 activity is desirable in situations in which a 32624 is downregulated and/or in which increased 32624 activity is likely to have a beneficial effect. Likewise, inhibition of 32624 activity is desirable in situations in which 32624 is abnormally upregulated and/or in which decreased 32624 activity is likely to have a beneficial effect.

32624 Pharmacogenomics

The 32624 molecules of the present invention, as well as agents, or modulators which have a stimulatory or inhibitory effect on 32624 activity (e.g., 32624 gene expression) as identified by a screening assay described herein can be administered to individuals to treat (prophylactically or therapeutically) 32624 associated disorders (e.g., metabolic disorders, liver disorders, gastrointestinal disorders, kidney disorders, immunological disorders, neural disorders, or cellular proliferation or differentiation disorders) associated with aberrant or unwanted 32624 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 32624 molecule or 32624 modulator as well as tailoring the dosage and/or therapeutic regimen of treatment with a 32624 molecule or 32624 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983-985 and Linder, M. W. et al. (1997) *Clin. Chem.* 43:254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a 32624 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a 32624 molecule or 32624 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 32624 molecule or 32624 modulator, such as a modulator identified by one of the exemplary screening assays described herein.

The present invention further provides methods for identifying new agents, or combinations, that are based on identifying agents that modulate the activity of one or more of the gene products encoded by one or more of the 32624 genes of the present invention, wherein these products may be associated with resistance of the cells to a therapeutic agent. Specifically, the activity of the proteins encoded by the 32624 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 32624 protein can be applied in clinical trials. For example, the effectiveness of an agent determined by a screening assay as described herein to increase 32624 gene expression, protein levels, or upregulate 32624 activity, can be monitored in clinical trials of subjects exhibiting decreased 32624 gene expression, protein levels, or downregulated 32624 activity. Alternatively, the effectiveness of an agent determined by a screening assay to decrease 32624 gene expression, protein levels, or downregulate 32624 activity, can be monitored in clinical trials of subjects exhibiting increased 32624 gene expression, protein levels, or upregulated 32624 activity. In such clinical trials, the expression or activity of a 32624 gene, and preferably, other genes that have been implicated in, for example, a 32624-associated disorder can be used as a "read out" or markers of the phenotype of a particular cell.

32624 Informatics

The sequence of a 32624 molecule is provided in a variety of media to facilitate use thereof. A sequence can be provided as a manufacture, other than an isolated nucleic acid or amino acid molecule, which contains a 32624. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 32624 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers.

Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 32624, e.g., analyzing structure, function, or relatedness to one or more other nucleic acid or amino acid sequences. The method includes: providing a 32624 nucleic acid or amino acid sequence; comparing the 32624 sequence with a second sequence, e.g., one or more preferably a plurality of sequences from a collection of sequences, e.g., a nucleic acid or protein sequence database to thereby analyze 32624. The method can be performed in a machine, e.g., a computer, or manually by a skilled artisan.

The method can include evaluating the sequence identity between a 32624 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 32624 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 32624 sequence, or record, in machine-readable form; comparing a second sequence to the 32624 sequence; thereby analyzing a sequence. Comparison can include comparing to sequences for sequence identity or determining if one sequence is included within the other, e.g., determining if the 32624 sequence includes a sequence being compared. In a preferred embodiment the 32624 or second sequence is stored on a first computer, e.g., at a first site and the comparison is performed, read, or recorded on a second computer, e.g., at a second site. E.g., the 32624 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 32624-associated disease or disorder or a pre-disposition to a 32624-associated disease or disorder, wherein the method comprises the steps of determining 32624 sequence information associated with the subject and based on the 32624 sequence information, determining whether the subject has a 32624-associated disease or disorder or a pre-disposition to a 32624-associated disease or disorder and/or recommending a particular treatment for the disease, disorder or pre-disease condition.

The invention further provides in an electronic system and/or in a network, a method for determining whether a subject has a 32624-associated disease or disorder or a pre-disposition to a disease associated with a 32624 wherein the method comprises the steps of determining 32624 sequence information associated with the subject, and based on the 32624 sequence information, determining whether the subject has a 32624-associated disease or disorder or a pre-disposition to a 32624-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 32624 sequence of the subject to the 32624 sequences in the database to thereby determine whether the subject as a 32624-associated disease or disorder, or a pre-disposition for such.

The present invention also provides in a network, a method for determining whether a subject has a 32624 associated disease or disorder or a pre-disposition to a 32624-associated disease or disorder associated with 32624, said method comprising the steps of receiving 32624 sequence information from the subject and/or information related thereto, receiving phenotypic information associated with the subject, acquiring information from the network corresponding to 32624 and/or corresponding to a 32624-associated disease or disorder (e.g., a metabolic disorder, liver disorder, gastrointestinal disorder, kidney disorder, immunological disorder, neural disorder, or cellular proliferation or differentiation disorder), and based on one or more of the phenotypic information, the 32624 information (e.g., sequence information and/or information related thereto), and the acquired information, determining whether the subject has a 32624-associated disease or disorder or a predisposition to a 32624-associated disease or disorder. The method may further comprise the step of recommending a particular treatment for the disease, disorder or pre-disease condition.

The present invention also provides a method for determining whether a subject has a 32624-associated disease or disorder or a pre-disposition to a 32624-associated disease or disorder, said method comprising the steps of receiving information related to 32624 (e.g., sequence information and/or information related thereto), receiving phenotypic information associated with the subject, acquiring information from the network related to 32624 and/or related to a 32624-associated disease or disorder, and based on one or more of the phenotypic information, the 32624 information, and the acquired information, determining whether the subject has a 32624-associated disease or disorder or a pre-disposition to a 32624-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

Background of the 47174 Invention

A great diversity of oligosaccharide structures and types of glycoconjugates is found in nature, and these are synthesized by a large number of glycosyltransferases. Glycosyltransferases catalyze the synthesis of glycoconjugates, including glycolipids, glycoproteins, and polysaccharides, by transferring an activated mono- or oligosaccharide residue to an existing acceptor molecule for the initiation or elongation of the carbohydrate chain. A catalytic reaction is believed to involve the recognition of both the donor and acceptor by suitable domains, as well as the catalytic site of the enzyme (Amado et al. (1999) *Biochim Biophys Acta* 1473:35-53; Kapitonov et al. (1999) *Glycobiology* 9:961-78).

Because the glycosylation reaction is highly specific with respect to both the configuration of the sugar residue and the site of the addition, it is expected that unique domain structures for substrate recognition and nucleotide-sugar binding are located within the enzyme molecule. Evidence indicates that formation of many glycosidic linkages is covered by large homologous glycosyltransferase gene families, and that the existence of multiple enzyme isoforms provides a degree of redundancy as well as a higher level of regulation of the glycoforms synthesized (Kapitonov et al. (1999) *Glycobiology* 9:961-78).

Glycosylation is the principal chemical modification to proteins as they pass through Golgi vesicles. Glycosyltransferases of the Golgi do not possess an obvious sequence homology which would suggest a common Golgi retention signal. However, they are all membrane proteins and share type II topology, consisting of an amino terminal cytoplasmic tail, a signal anchor transmembrane domain, a stem region, and a large luminal catalyitc domain. The membrane-spanning domain and its flanking regions contain necessary and sufficient information for Golgi retention of these enzymes (Jaskiewicz (1997) *Acta Biochim Pol* 44:173-9). ER localized glycosyltransferases can have either a type II topology, like the Golgi glycosyltransferases, or a type I topolgy, e.g., the N-terminus and catalytic domain inside the ER (Kapitonov et al. (1999) *Glycobiology* 9:961-78). Some glycosyltransferases are present on the cell surface and are thought to function as cell adhesion molecules by binding oligosaccharide substrates on adjacent cell surfaces or in the extracellular matrix. The best studied of these is beta 1,4-galactosyltransferase, which mediates sperm binding to the egg coat and selected cell interactions with the basal lamina (Shur (1993) *Curr Opin Cell Biol* 5:854-63).

Summary of the 47174 Invention

The present invention is based, in part, on the discovery of a novel glycosyltransferase family member, referred to herein as "47174." The nucleotide sequence of a cDNA encoding 47174 is shown in SEQ ID NO:42, and the amino acid sequence of a 47174 polypeptide is shown in SEQ ID NO:43. In addition, the nucleotide sequence of the coding region is depicted in SEQ ID NO:44.

Accordingly, in one aspect, the invention features a nucleic acid molecule which encodes a 47174 protein or polypeptide, e.g., a biologically active portion of a 47174 protein. In a preferred embodiment the isolated nucleic acid molecule encodes a polypeptide having the amino acid sequence of SEQ ID NO:43. In other embodiments, the invention provides isolated 47174 nucleic acid molecules having the nucleotide sequence shown in SEQ ID NO:42, or SEQ ID NO:44. In still other embodiments, the invention provides nucleic acid molecules that are substantially identical (e.g., naturally occurring allelic variants) to the nucleotide sequence shown in SEQ ID NO:42, or SEQ ID NO:44. In other embodiments, the invention provides a nucleic acid molecule which hybridizes under a stringent hybridization condition described herein to a nucleic acid molecule comprising the nucleotide sequence of SEQ ID NO:42, or SEQ ID NO:44 wherein the nucleic acid encodes a full length 47174 protein or an active fragment thereof.

In a preferred embodiment, the 47174 nucleic acid has a nucleotide sequence identical to, or substantially identical to, SEQ ID NO:42 or 44. In other embodiments, the 47174 nucleic acid is a fragment of at least 50, 100, 150, 200, 250, 300, 350, 400, 450, 500, 1000, 1500, 2000, 2500, 2550, or more contiguous nucleotides of SEQ ID NO:42 or 44. In another aspect, the invention features antibodies and antigen-binding fragments thereof, that react with, or more preferably specifically bind 47174 polypeptides.

In another embodiment, the invention provides 47174 polypeptides. Preferred polypeptides are 47174 proteins having a 47174-associated activity, e.g., a glycosyltransferase activity as described herein. In another aspect, the invention features, 47174 polypeptides, and biologically active or antigenic fragments thereof that are useful, e.g., as reagents or targets in assays applicable to treatment and diagnosis of 47174 mediated or related disorders.

In other embodiments, the invention provides 47174 polypeptides, e.g., a 47174 polypeptide having the amino acid sequence shown in SEQ ID NO:43; an amino acid sequence that is substantially identical to the amino acid sequence shown in SEQ ID NO:43; or an amino acid sequence encoded by a nucleic acid molecule having a nucleotide sequence which hybridizes under a stringent hybridization condition described herein to a nucleic acid molecule comprising the nucleotide sequence of SEQ ID NO:42 or SEQ ID NO:44, wherein the nucleic acid encodes a full length 47174 protein or an active fragment thereof.

In a preferred embodiment, the 47174 polypeptide has an amino acid sequence identical to, or substantially identical to, SEQ ID NO:43. In other embodiments, the 47174 polypeptide is a fragment of at least 15, 20, 50, 100, 150, 200, 300, 400, 500, 600, or more contiguous amino acids of SEQ ID NO:43.

In a related aspect, the invention provides 47174 polypeptides or fragments operatively linked to non-47174 polypeptides to form fusion proteins.

In another aspect, the invention provides methods of screening for agents, e.g., compounds, that modulate the expression or activity of the 47174 polypeptides or nucleic acids, e.g., compounds that modulate neurological activity or function, e.g., central nervous system (CNS) development or function, or that modulate the normal, or aberrant or altered pain response.

In a preferred embodiment, the effect of an agent, e.g., a compound, on the pain response is evaluated by an analgesic test, e.g., the hot plate test, tail flick test, writhing test, paw pressure test, all electric stimulation test, tail withdrawal test, or formalin test.

In a preferred embodiment, the agent, e.g., compound, inhibits 47174 activity.

In a preferred embodiment, the agent, e.g., compound, increases endogenous levels of a 47174 substrate, e.g., glycoconjugates, including glycolipids, glycoproteins, and polysaccharides.

In still another aspect, the invention provides a process for modulating 47174 polypeptide or nucleic acid expression or activity, e.g. using the screened compounds. In certain embodiments, the methods involve treatment of conditions related to aberrant, e.g., decreased or increased expression of the 47174 polypeptides or nucleic acids, such as conditions involving neurological, e.g., CNS, function, e.g., pain response, aberrant or altered pain response, pain related disorders.

In still another aspect, the invention features a method of modulating (e.g., enhancing or inhibiting) an activity of a 47174-expressing cell (e.g., a neural (e.g., a CNS) cell, or a kidney cell), or a response, e.g., a neurological response (e.g., a pain or nociceptive response) in a subject. The method includes contacting the 47174-expressing cell with, or administered to the subject, an agent, e.g., a compound, that modulates the activity or expression of a 47174 polypeptide or nucleic acid, in an amount effective to modulate the activity or the response.

The agent, e.g., the compound, and the 47174-polypeptide or nucleic acid can be contacted in vitro or ex vivo. In other embodiments, the contacting step is effected in vivo in a subject, e.g., as part of a therapeutic or prophylactic protocol. The contacting or administering step(s) can be repeated.

In a preferred embodiment, the agent modulates (e.g., increases or decreases) glycosyltransferase activity. In other embodiments, the agent modulates (e.g., increases or decreases) expression of the 47174 nucleic acid by, e.g., modulating transcription, mRNA stability, etc.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a growth factor, e.g., a neurotrophic or neurotropic factor (e.g., BDNF, NGF, NT-3), a hormone, etc. In those embodiments where cell killing is desired the therapeutic moiety is selected from a cytotoxin, a cytotoxic agent and a radioactive metal ion.

In additional preferred embodiments, the agent is an antisense molecule, a ribozyme, a triple helix molecule, or a 47174 nucleic acid, or any combination thereof.

In a preferred embodiment, the agent is administered in combination with a growth factor, e.g., a neurotrophic or neurotropic factor (e.g., BDNF, NGF, NT-3), a hormone. In other embodiments, the agent is a cytotoxic agent.

In a preferred embodiment, the cell, e.g., the 47174-expressing cell, is a central or peripheral nervous system cell, e.g., a cortical or a hypothalamic cell; a spinal cord cell (e.g., a cell in the DRG); a cell in an area involved in pain control, e.g., a cell in the substantia gelatinosa of the spinal cord, or a cell in the periaqueductal gray matter.

Preferably, the subject is a human, e.g., a patient with a neurological disorder, e.g., a neurodegenerate disorder, a CNS dysfunction, pain or a pain-associated disorder disclosed herein. For example, the subject can be a patient with pain elicited from tissue injury, e.g., inflammation, infection, ischemia; pain associated with musculoskeletal disorders, e.g., joint pain; tooth pain; headaches, e.g., migrane; pain associated with surgery; pain related to inflammation, e.g., irritable bowel syndrome; or chest pain. The subject can be a patient with complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, Costen's pain-dysfunction, acute chest pain syndrome, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, or pain asymbolia. The subject can be a cancer patient, e.g., a patient with brain cancer, bone cancer, or prostate cancer. In other embodiments, the subject is a non-human animal, e.g., an experimental animal, e.g., an arthritic rat model of chronic pain, a chronic constriction injury (CCI) rat model of neuropathic pain, or a rat model of unilateral inflammatory pain by intraplantar injection of Freund's complete adjuvant (FCA).

In another aspect, the invention features a method of treating or preventing, in a subject, a 47174-associated disorder. The method includes administering to the subject, e.g., a subject at risk of, or afflicted with, a 47174-associated disorder, an agent, e.g., a compound as described herein, that modulates the activity or expression of a 47174 polypeptide or nucleic acid, in an amount effective to treat or prevent the disorder.

In a preferred embodiment, the disorder is neurological, e.g., a neurodegenerative, disorder, a CNS disorder, e.g., a brain or spinal cord related disorder, or a pain or a pain related disorder. In other embodiments, the disorder is a renal disorder.

In a preferred embodiment, the subject is a subject as described herein, e.g., a human, e.g., a patient with a neurological disorder, e.g., a neurodegenerate disorder, or a subject suffering from pain or a pain-associated disorder disclosed herein. In other embodiments, the subject is a patient having a renal disorder.

In still another aspect, the invention features a method for evaluating the efficacy of a treatment of a disorder, e.g., a disorder disclosed herein, in a subject. The method includes treating a subject with a protocol under evaluation; assessing the expression of a 47174 nucleic acid or 47174 polypeptide, such that a change in the level of 47174 nucleic acid or 47174 polypeptide after treatment, relative to the level before treatment, is indicative of the efficacy of the treatment of the disorder.

In a preferred embodiment, the disorder is neurological, e.g., a neurodegenerative, disorder, a CNS disorder, e.g., a brain or spinal cord related disorder, or a pain or a pain related disorder. In other embodiments, the disorder is a renal disorder.

In a preferred embodiment, the subject is a subject as described herein, e.g., a human, e.g., a patient with a neurological disorder, e.g., a neurodegenerate disorder, or a subject suffering from pain or a pain-associated disorder disclosed herein. In other embodiments, the subject is a patient having a renal disorder.

The invention also features a method of diagnosing a disorder, e.g., a disorder disclosed herein, in a subject. The method includes evaluating the expression or activity of a 47174 nucleic acid or a 47174 polypeptide, such that, a difference in the level of 47174 nucleic acid or 47174 polypeptide relative to a normal subject or a cohort of normal subjects is indicative of the disorder.

In a preferred embodiment, the disorder is neurological, e.g., a neurodegenerative, disorder, a CNS disorder, e.g., a brain or spinal cord related disorder, or a pain or a pain related disorder. In other embodiments, the disorder is a renal disorder.

In a preferred embodiment, the subject is a subject as described herein, e.g., a human, e.g., a patient with a neurological disorder, e.g., a neurodegenerate disorder, or a subject suffering from pain or a pain-associated disorder disclosed herein. In other embodiments, the subject is a patient having a renal disorder.

In a preferred embodiment, the evaluating step occurs in vitro or ex vivo. For example, a sample, e.g., a blood sample, is obtained from the subject.

In a preferred embodiment, the evaluating step occurs in vivo. For example, by administering to the subject a detectably labeled agent that interacts with the 47174 nucleic acid or polypeptide, such that a signal is generated relative to the level of activity or expression of the 47174 nucleic acid or polypeptide.

The invention also provides assays for determining the activity of or the presence or absence of 47174 polypeptides or nucleic acid molecules in a biological sample, including for disease diagnosis.

In further aspect, the invention provides assays for determining the presence or absence of a genetic alteration in a 47174 polypeptide or nucleic acid molecule, including for disease diagnosis.

In yet another aspect, the invention features a method for identifying an agent, e.g., a compound, which modulates the activity of a 47174 polypeptide, e.g., a 47174 polypeptide as described herein, or the expression of a 47174 nucleic acid, e.g., a 47174 nucleic acid as described herein, including contacting the 47174 polypeptide or nucleic acid with a test agent (e.g., a test compound); and determining the effect of the test compound on the activity of the 47174 polypeptide or nucleic acid to thereby identify a compound which modulates the activity of the 47174 polypeptide or nucleic acid.

In a preferred embodiment, the activity of the 47174 polypeptide is a glycosyltransferase activity, e.g., the synthesis of a glycoconjugate, e.g., a glycolipid, glycoprotein, orolysaccharides In a preferred embodiment, the activity of the 47174 polypeptide is modulation of a neural response, e.g., a pain response.

In preferred embodiments, the agent is a peptide, a phosphopeptide, a small molecule, e.g., a member of a combinatorial library, or an antibody, or any combination thereof.

In additional preferred embodiments, the agent is an antisense, a ribozyme, or a triple helix molecule, or a 47174 nucleic acid, or any combination thereof.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 47174 molecule. In one embodiment, the capture probe is a nucleic acid, e.g., a probe complementary to a 47174 nucleic acid sequence. In another embodiment, the capture probe is a polypeptide, e.g., an antibody specific for 47174 polypeptides. Also featured is a method of analyzing a sample by contacting the sample to the aforementioned array and detecting binding of the sample to the array.

Other features and advantages of the invention will be apparent from the following detailed description, and from the claims.

Detailed Description of 47174

The human 47174 sequence (Example 33; SEQ ID NO:42), which is approximately 2572 nucleotides long including untranslated regions, contains a predicted methionine-initiated coding sequence of about 1812 nucleotides (nucleotides 325-2136 of SEQ ID NO:42; SEQ ID NO:44). The coding sequence encodes a 603 amino acid protein (SEQ ID NO:43). Human 47174 protein of SEQ ID NO:43 includes an amino-terminal hydrophobic amino acid sequence, consistent with a signal sequence of about 30 amino acids (from amino acid 1 to about amino acid 28 of SEQ ID NO:43), which upon protease removal results in the production of the mature protein.

This mature protein form is approximately 575 amino acid residues in length (from about amino acid 29 to amino acid 603 of SEQ ID NO:43). Human 47174 contains the following regions or other structural features: a glycosyltransferase group 2 domain (PFAM Accession PF00535) located at about amino acid residues 154 to 336 of SEQ ID NO:43; and a ricin domain at about amino acids residues 465-595 of SEQ ID NO:43.

The 47174 protein further includes the following domains: one an asparagine N-glycosylation site (PS00001) located at about amino acids 2-5; 10 predicted Protein Kinase C phosphorylation sites (PS00005) located at about amino acids 102-104, 124-126, 220-222, 381-383, 431-433, 444-446, 531-533, 536-538, 547-549 and 564-566 of SEQ ID NO:43; five predicted Casein Kinase II phosphorylation sites (PS00006) located at about amino 56-59, 102-105, 132-135, 220-223 and 280-283 of SEQ ID NO:43; two predicted tyrosine kinase phosphorylation sites (PS00007) located at about amino acids 113-119 and 446-453 of SEQ ID NO:43; four predicted N-myristoylation sites (PS00008) located at about amino acids 93-98, 224-229, 424-429 and 481-486 of SEQ ID NO:43; one predicted RGD Cell attachment site (PS00016) located at about amino acids 312-314 of SEQ ID NO:43; and a predicted leucine zipper motif located at about amino acids 16-37 of SEQ ID NO:43. For general information regarding PFAM identifiers, PS prefix and PF prefix domain identification numbers, refer to Sonnhammer et al. (1997) *Protein* 28:405-420.

The 47174 protein contains a significant number of structural characteristics in common with members of the glycosyltransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics. A 47174 polypeptide can include a "glycosyltransferase domain" or regions homologous with a "glycosyltransferase domain." A 47174 polypeptide can further include a "ricin domain" or regions homologous with a "ricin domain".

As used herein, the term "glycosyltransferase" includes a protein or polypeptide which is capable of catalyzing the synthesis of glycoconjugates, including glycolipids, glycoproteins, and polysaccharides, by transferring an activated mono- or oligosaccharide residue to an existing acceptor molecule for the initiation or elongation of the carbohydrate chain. The acceptor can be a lipid, a protein, a heterocyclic compound, or another carbohydrate residue. Glycosyltransferases can be divided into numerous subfamilies based upon their specificity for sugar moieties and acceptor molecules. The glycosyltransferase domain of human 47174 bears similarity to a subfamily designated "group 2" glycosyltransferases. These enzymes comprise a diverse subfamily, whose members transfer sugar from UDP-glucose, UDP-N-acetyl-galactosamine, GDP-mannose or CDP-abequose, to a range of substrates including cellulose, dolichol phosphate and teichoic acids. Based on the sequence similarities, the 47174 molecule of the present invention is predicted to have similar biological activities as glycosyltransferase family members.

Glycosyltransferases play roles in diverse cellular processes. For example, the major target of the natural IgM and IgG antibodies during hyperacute xenograft rejection is the terminal carbohydrate epitope Gal alpha(1,3)Gal, formed by the alpha 1,3galactosyl transferase, which places a terminal galactose residue in an alpha-linkage to another galactose (Sandrin et al. (1994) *Immunol Rev* 141:169-90). Additionally, UDP-galactose:ceramide galactosyltransferase is the enzyme responsible for the biosynthesis of galactosylceramide, a molecule thought to play a critical role in myelin formation, signal transduction, viral and microbial adhesion, and oligodendrocyte development (Kapitonov et al. (1999) *Glycobiology* 9:961-78). As 47174 mRNA is highly expressed in brain cortex and hypothalamus, the 47174 molecules of the invention are likely to play a role in the development and/or function of the nervous system, e.g., the brain, e.g., in modulating the pain response.

Glycosylation of glycoproteins and glycolipids is one of many molecular changes that accompany malignant transformation. GlcNAc-branched N-glycans and terminal Lewis antigen sequences have been observed to increase in some cancers, and to correlate with poor prognosis (Dennis et al. (1999) *Biochim Biophys Acta* 1473:21-34). Cellular membrane over-expression and shedding of acidic glycosphingolipids into the interstitial spaces and blood of cancer patients may play a central role in increased tumour cell growth, lack of immune cell recognition and neovascularization and could represent a molecular target for cancer therapy (Fish (1996) *Med Hypotheses* 46:140-44).

Thus, the 47174 molecules of the present invention may be involved in: 1) brain function, e.g., pain response, oligodendrocyte development, or myelin formation; 2) the transfer of an activated sugar residue to an acceptor molecule; 3) the processing, folding, and secretion of proteins; 4) the modulation of tumor cell growth and invasion; 5) signal transduction; 6) viral and microbial adhesion; 7) sperm-egg binding; 8) evasion of immune detection; 9) xenograft rejection; and 10) the ability to antagonize or inhibit, competitively or non-competitively, any of 1-10.

As used herein, the term "glycosyltransferase domain" includes an amino acid sequence of about 100-250 amino acid residues in length and having a bit score for the alignment of the sequence to the glycosyltransferase domain (HMM) of at least 30. Preferably, a glycosyltransferase domain includes at least about 120-220 amino acids, more preferably about 120-200 amino acid residues, or about 130-180 amino acids and has a bit score for the alignment of the sequence to the glycosyltransferase domain (HMM) of at least 50 or greater. Glycosyltransferase domains (HMM) have been assigned numerous PFAM Accession Numbers, including PF00534 (group 1) and PF00535 (group 2). An alignment of the glycosyltransferase domain (amino acids 154 to 336 of SEQ ID NO:43) of human 47174 with a consensus amino acid sequence (group 2 glycosyltransferases) derived from a hidden Markov model is depicted in FIG. 42.

In a preferred embodiment, the 47174 polypeptide or protein has a "glycosyltransferase domain" or a region which includes at least about 120-220 more preferably about 120-200 or 130-180 amino acid residues and has at least about 70% 80% 90% 95%, 99%, or 100% homology with a "glycosyltransferase domain," e.g., the glycosyltransferase domain of human 47174 (e.g., residues 154 to 336 of SEQ ID NO:43).

A 47174 family member can additionally include a ricin domain. Ricin is a heterodimer composed of two subunits, a lectin and a glycosidase, and it binds to terminal galactose residues on the cell surface via the lectin. Following endocytosis of the intact molecule, a disulfide bond linking the two subunits is cleaved, and only the glycosidase subunit enters the cytoplasm, where it inhibits cytoplasmic protein synthesis by catalyzing the cleavage of the 28S rRNA. Ricin B-chain (RTB) is a galactose-specific lectin that folds into two globular domains, each of which binds a single galactoside. The two binding sites are structurally similar and both contain a conserved tripeptide kink and an aromatic residue that comprises a sugar-binding platform. As used herein, the term "ricin" includes a protein or polypeptide which is capable of inhibiting cytoplasmic protein synthesis by catalyzing the cleavage of the 28S rRNA. For example, ricin has been utilized as an anticancer agent.

As used herein, the term "ricin domain" includes an amino acid sequence of about 100-250 amino acid residues in length and having a bit score for the alignment of the sequence to the ricin domain (HMM) of at least 30. Preferably, a ricin domain includes at least about 120-220 amino acids, more preferably about 120-200 amino acid residues, or about 130-180 amino acids and has a bit score for the alignment of the sequence to the ricin domain (HMM) of at least 50 or greater. An alignment of the ricin domain (amino acids 465-595 of SEQ ID NO:43) of human 47174 with a consensus amino acid sequence (Ricin B lectin) derived from a hidden Markov model is depicted in FIG. 43.

In a preferred embodiment, the 47174 polypeptide or protein has a "ricin domain" or a region which includes at least about 120-220 more preferably about 120-200 or 130-180 amino acid residues and has at least about 70% 80% 90% 95%, 99%, or 100% homology with a "ricin domain," e.g., the ricin domain of human 47174 (e.g., residues 465 to 595 of SEQ ID NO:43).

To identify the presence of a "glycosyltransferase" or a "ricin" domain in a 47174 protein sequence, and make the determination that a polypeptide or protein of interest has a particular profile, the amino acid sequence of the protein can be searched against a database of HMMs (e.g., the Pfam database, release 2.1) using the default parameters (online at sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al.(1990) *Meth Enzymol* 183:146-159; Gribskov et al.(1987) *Proc Natl Acad Sci* USA 84:4355-4358; Krogh et al.(1994) *J Mol Biol.* 235:1501-1531; and Stultz et al. (1993) *Protein Sci* 2:305-314, the contents of which are incorporated herein by reference. A search was performed against the HMM database resulting in the identification of a "glycosyltransferase" domain in the amino acid sequence of human 47174 at about residues 154 to 336 of SEQ ID NO:43 and a ricin domain at about residues 465-595 of SEQ ID NO:43.

As the 47174 polypeptides of the invention may modulate 47174-mediated activities, they may be useful as or for developing novel diagnostic and therapeutic agents for 47174-mediated or related disorders, as described below.

As used herein, a "47174 activity", "biological activity of 47174" or "functional activity of 47174", refers to an activity exerted by a 47174 protein, polypeptide or nucleic acid molecule on e.g., a 47174-responsive cell or on a 47174 substrate, e.g., a lipid, protein, heterocyclic compound, or carbohydrate residue, as determined in vivo or in vitro. In one embodiment, a 47174 activity is a direct activity, such as an association with a 47174 target molecule. A "target molecule" or "binding partner" is a molecule with which a 47174 protein binds or interacts in nature, e.g., a lipid, protein, heterocyclic compound, or carbohydrate residue to which the 47174 protein attaches a carbohydrate moiety. A 47174 activity can also be an indirect activity, e.g., a cellular signaling activity mediated by interaction of the 47174 protein with a 47174 ligand.

47174 mRNA is expressed in brain cortex and hypothalamus and in kidney. As other glycosyltransferases are known to be involved in, e.g., oligodendrocyte development and myelin formation, it suggests a role for 47174 in, e.g., CNS function and/or development. Thus, the 47174 molecules can act as novel diagnostic targets and therapeutic agents in conditions related to CNS function, e.g., neurodegenerative disorders, neural development and maintenance, oligodendrocyte development and maintenance, myelin formation and maintenance, or pain response.

Animal models of pain response that may be useful as assays in the methods described herein include, but are not limited to, axotomy, the cutting or severing of an axon; chronic constriction injury (CCI), a model of neuropathic pain which involves ligation of the sciatic nerve in rodents, e.g., rats; or intraplantar Freund's adjuvant injection as a model of arthritic pain. Other animal models of pain response known in the art are described in, e.g., ILAR Journal (1999) Volume 40, Number 3 (entire issue).

As the 47174 polypeptides of the invention may modulate 47174-mediated activities, they may be useful for developing novel diagnostic and therapeutic agents for 47174-mediated or related disorders. For example, the 47174 molecules can act as novel diagnostic targets and therapeutic agents controlling CNS function or related disorders. Examples of glycosyltransferase associated disorders in which the 47174 molecules of the invention may be directly or indirectly involved include CNS related disorders, e.g., aberrant oligodendrocyte development, myelin formation or pain response.

Thus, the 47174 molecules can act as novel diagnostic targets and therapeutic agents for neurological, e.g., brain or glial, disorders. Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, *Herpes simplex* virus Type 1, *Herpes simplex* virus Type 2, *Varicalla-zoster* virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease. Examples of pain conditions include, but are not limited to, pain elicited during various forms of tissue injury, e.g., inflammation, infection, and ischemia; pain associated with musculoskeletal disorders, e.g., joint pain, or arthritis; tooth pain; headaches, e.g., migrane; pain associated with surgery; pain related to inflammation, e.g., irritable bowel syndrome; chest pain; or hyperalgesia, e.g., excessive sensitivity to pain (described in, for example, Fields (1987) *Pain*, New York: McGraw-Hill). Other examples of pain disorders or pain syndromes include, but are not limited to, complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, Costen's pain-dysfunction, acute chest pain syndrome, nonulcer dyspepsia, interstitial cystitis, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, or pain asymbolia (the inability to feel pain). Other examples of pain conditions include pain induced by parturition, or post partum pain.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

The 47174 protein, fragments thereof, and derivatives and other variants of the sequence in SEQ ID NO:43 thereof are collectively referred to as "polypeptides or proteins of the invention" or "47174 polypeptides or proteins." Nucleic acid molecules encoding such polypeptides or proteins are collectively referred to as "nucleic acids of the invention" or "47174 nucleic acids." 47174 molecules refer to 47174 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45□C., followed by two washes in 0.2×SSC, 0.1% SDS at least at 50° C. (the temperature of the washes can be increased to 55° C. for low stringency conditions); 2) medium stringency hybridization conditions in 6×SSC at about 45□C., followed by one or more washes in 0.2×SSC, 0.1% SDS at 60° C.; 3) high stringency hybridization conditions in 6×SSC at about 45□C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:42 or SEQ ID NO:44, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein). As used herein, the terms "gene" and "recombinant gene" refer to nucleic acid molecules which include an open reading frame encoding a 47174 protein, preferably a mammalian 47174 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 47174 protein having less than about 30%, 20%, 10% and more preferably 5% (by dry weight), of non-47174 protein (also referred to herein as a "contaminating protein"), or of chemical precursors or non-47174 chemicals. When the 47174 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 47174 (e.g., the sequence of SEQ ID NO:42 or 44) without abolishing or more preferably, without substantially altering a biological activity, whereas an "essential" amino acid residue results in such a change. For example, amino acid residues that are conserved among the polypeptides of the present invention, e.g., those present in the glycosyltransferase domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 47174 protein is preferably replaced with another amino acid residue from the same side chain family. Alternatively, in another embodiment, mutations can be introduced randomly along all or part of a 47174 coding sequence, such as by saturation mutagenesis, and the resultant mutants can be screened for 47174 biological activity to identify mutants that retain activity. Following mutagenesis of SEQ ID NO:42 or SEQ ID NO:44, the encoded protein can be expressed recombinantly and the activity of the protein can be determined.

As used herein, a "biologically active portion" of a 47174 protein includes a fragment of a 47174 protein that participates in an interaction between a 47174 molecule and a non-47174 molecule. Biologically active portions of a 47174 protein include peptides comprising amino acid sequences sufficiently homologous to or derived from the amino acid sequence of the 47174 protein, e.g., the amino acid sequence shown in SEQ ID NO:43, which include fewer amino acids than the full length 47174 proteins, and exhibit at least one activity of a 47174 protein. Typically, biologically active portions comprise a domain or motif with at least one activity of the 47174 protein, e.g., glycosyltransferase activity. A biologically active portion of a 47174 protein can be a polypeptide which is, for example, 10, 25, 50, 100, 200 or more amino acids in length. Biologically active portions of a 47174 protein can be used as targets for developing agents which modulate a 47174 mediated activity, e.g., a glycosyltransferase activity.

Particularly preferred 47174 polypeptides of the present invention have an amino acid sequence substantially identical to the amino acid sequence of SEQ ID NO:43. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:43 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:42 or 44 are termed substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 20%, 30%, preferably at least 40%, more preferably at least 50%, even more preferably at least 60%, and even more preferably at least 70%, 80%, 90%, 100% of the length of the reference sequence (e.g., when aligning a second sequence to the 47174 amino acid sequence of SEQ ID NO:43 having 206 amino acid residues (the glycosyltransferase domain), at least 40, 60, preferably at least 80, more preferably at least 100, even more preferably at least 120, and even more preferably at least 140, 160, or 180 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J Mol Biol* (48):444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS* 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al. (1990) *J Mol Biol* 215:403-10. BLAST nucleotide searches can be performed with the NBLAST program, score=100, wordlength=12 to obtain nucleotide sequences homologous to 47174 nucleic acid molecules of the invention. BLAST protein searches can be performed with the XBLAST program, score=50, wordlength=3 to obtain amino acid sequences homologous to 47174 protein molecules of the invention. To obtain gapped alignments for comparison purposes, Gapped BLAST can be utilized as described in Altschul et al. (1997) *Nucleic Acids Res* 25(17):3389-3402. When utilizing BLAST and Gapped BLAST programs, the default parameters of the respective programs (e.g., XBLAST and NBLAST) can be used. See, e.g., the NCBI web site at ncbi.nlm.nih.gov.

"Misexpression or aberrant expression," as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus. "Subject," as used herein, can refer to a mammal, e.g., a human, or to an experimental or animal or disease model, e.g., a rodent model of pain, e.g., an arthritic rat, a CCI rodent, or an axotomized rodent. The subject can also be a non-human animal, e.g., a horse, cow, goat, or other domestic animal.

A "purified preparation of cells," as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules of 47174

In one aspect, the invention provides, an isolated or purified, nucleic acid molecule that encodes a 47174 polypeptide described herein, e.g., a full length 47174 protein or a fragment thereof, e.g., a biologically active portion of 47174 protein. Also included is a nucleic acid fragment suitable for use as a hybridization probe, which can be used, e.g., to identify a nucleic acid molecule encoding a polypeptide of the invention, 47174 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:42, or a portion of the nucleotide sequence. In one embodiment, the nucleic acid molecule includes sequences encoding the human 47174 protein (i.e., "the coding region" of SEQ ID NO:42, as shown in SEQ ID NO:44), as well as 5' untranslated sequences. Alternatively, the nucleic acid molecule can include only the coding region of SEQ ID NO:42 (e.g., SEQ ID NO:44) and, e.g., no flanking sequences which normally accompany the subject sequence. In another embodiment, the nucleic acid molecule encodes a sequence corresponding to a fragment of the protein from about amino acid 154 to 336.

In another embodiment, an isolated nucleic acid molecule of the invention includes a nucleic acid molecule which is a complement of the nucleotide sequence shown in SEQ ID NO:42 or SEQ ID NO:44, or a portion of any of these nucleotide sequences. In other embodiments, the nucleic acid molecule of the invention is sufficiently complementary to the nucleotide sequence shown in SEQ ID NO:42 or SEQ ID NO:44, such that it can hybridize to the nucleotide sequence shown in SEQ ID NO:42 or 44, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:42 or SEQ ID NO:44, or a portion, preferably of the same length, of any of these nucleotide sequences.

47174 Nucleic Acid Fragments

A nucleic acid molecule of the invention can include only a portion of the nucleic acid sequence of SEQ ID NO:42 or 44. For example, such a nucleic acid molecule can include a fragment which can be used as a probe or primer or a fragment encoding a portion of a 47174 protein, e.g., an immunogenic or biologically active portion of a 47174 protein. A fragment can comprise those nucleotides of SEQ ID NO:42, which encode a glycosyltransferase domain of human 47174. The nucleotide sequence determined from the cloning of the 47174 gene allows for the generation of probes and primers designed for use in identifying and/or cloning other 47174 family members, or fragments thereof, as well as 47174 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein.

Nucleic acid fragments can encode a specific domain or site described herein or fragments thereof, particularly fragments thereof which are at least 100 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 47174 nucleic acid fragment can include a sequence corresponding to a glycosyltransferase domain.

47174 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:42 or SEQ ID NO:44, or of a naturally occurring allelic variant or mutant of SEQ ID NO:42 or SEQ ID NO:44.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes the glycosyltransferase domain of 47174 (from amino acids 154 to 336 of SEQ ID NO:43).

In another embodiment a set of primers is provided, e.g., primers suitable for use in a PCR, which can be used to amplify a selected region of a 47174 sequence, e.g., a domain, region, site or other sequence described herein. The primers should be at least 5, 10, or 50 base pairs in length and less than 100, or less than 200, base pairs in length. The primers should be identical, or differ by one base from a sequence disclosed herein or from a naturally occurring variant. For example, primers suitable for amplifying all or a portion of any of the following regions are provided: a glycosyltransferase domain from about amino acid 154 to 336 of SEQ ID NO:43; a ricin domain from about residues 465 to 595 of SEQ ID NO:43. A nucleic acid fragment can encode an epitope bearing region of a polypeptide described herein.

A nucleic acid fragment encoding a "biologically active portion of a 47174 polypeptide" can be prepared by isolating a portion of the nucleotide sequence of SEQ ID NO:42 or 44, which encodes a polypeptide having a 47174 biological activity (e.g., the biological activities of the 47174 proteins are described herein), expressing the encoded portion of the 47174 protein (e.g., by recombinant expression in vitro) and assessing the activity of the encoded portion of the 47174 protein. For example, a nucleic acid fragment encoding a biologically active portion of 47174 includes a glycosyltransferase domain, e.g., amino acid residues about 154 to 336 of SEQ ID NO:43. A nucleic acid fragment encoding a biologically active portion of a 47174 polypeptide, may comprise a nucleotide sequence which is greater than 300 or more nucleotides in length.

In a preferred embodiment, a nucleic acid fragment includes a nucleotide sequence comprising nucleotides SEQ ID NO:42 or SEQ ID NO:44, or a portion thereof, wherein each portion is about 50 or longer nucleotides and hybridizes under stringent hybridization conditions to a nucleic acid molecule of SEQ ID NO:42, or SEQ ID NO:44.

In preferred embodiments, a nucleic acid fragment includes a nucleotide sequence which is at least 50, 100, 200, 300, 400, 500, 600, 700, 800, 900, 1000, 1100, 1200, 1208, 1300, 1400, 1500, 1600, 1700, 1800, 1900, 2000, 2100, 2200, 2300, 2400, 2500 or more nucleotides in length and hybridizes under stringent hybridization conditions to a nucleic acid molecule of SEQ ID NO:42, or SEQ ID NO:44.

In one preferred embodiment, the nucleic acid fragment includes at least 2 contiguous nucleotides from the sequence of amino acids 1 to 834 or 1634 to 2572 of SEQ ID NO:43. In a preferred embodiment, a nucleic acid fragment differs by at least 1, 2, 3, 10, 20, or more nucleotides from a sequence described in WO00/58473, WO 01/53312,or WO 01/59063. Differences can include differing in length or sequence identity. For example, a nucleic acid fragment can: include one or more nucleotides from SEQ ID NO:42 or SEQ ID NO:44 located outside the region of nucleotides 835-1633, 1011-2217 or 244-1389 of SEQ ID NO:42; not include all of the nucleotides of a sequence of WO00/58473, WO 01/53312,or WO 01/59063, e.g., can be one or more nucleotides shorter (at one or both ends) than a sequence of WO00/58473, WO 01/53312,or WO 01/59063; or can differ by one or more nucleotides in the region of overlap.

47174 Nucleic Acid Variants

The invention further encompasses nucleic acid molecules that differ from the nucleotide sequence shown in SEQ ID NO:42 or SEQ ID NO:44. Such differences can be due to degeneracy of the genetic code (and result in a nucleic acid which encodes the same 47174 proteins as those encoded by the nucleotide sequence disclosed herein). In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:43. If alignment is needed for this comparison the sequences should be aligned for maximum homology. "Looped" out sequences from deletions or insertions, or mismatches, are considered differences.

Nucleic acids of the invention can be chosen for having codons, which are preferred, or non preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells. Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:42 or 44, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95%, 95-99%, or more identical to the nucleotide sequence shown in SEQ ID NO:43 or a fragment of this sequence. Such nucleic acid molecules can readily be identified as being able to hybridize under stringent conditions, to the nucleotide sequence encoding the amino acid sequence shown in SEQ ID NO:43 or a fragment of the sequence. Nucleic acid molecules corresponding to orthologs, homologs, and allelic variants of the 47174 cDNAs of the invention can further be isolated by mapping to the same chromosome or locus as the 47174 gene.

Preferred variants include those that are correlated with glycosyltransferase activity. Allelic variants of 47174, e.g., human 47174, include both functional and non-functional proteins. Functional allelic variants are naturally occurring amino acid sequence variants of the 47174 protein within a population that maintain the ability to bind substrates and hydrolyze them. Functional allelic variants will typically contain only conservative substitution of one or more amino acids of SEQ ID NO:43, or substitution, deletion or insertion of non-critical residues in non-critical regions of the protein. Non-functional allelic variants are naturally-occurring amino acid sequence variants of the 47174, e.g., human 47174, protein within a population that do not have the ability to bind and/or hydrolyze a substrate. Non-functional allelic variants will typically contain a non-conservative substitution, a deletion, or insertion, or premature truncation of the amino acid sequence of SEQ ID NO:43, or a substitution, insertion, or deletion in critical residues or critical regions of the protein.

Moreover, nucleic acid molecules encoding other 47174 family members and, thus, which have a nucleotide sequence which differs from the 47174 sequences of SEQ ID NO:42 or SEQ ID NO:44 are intended to be within the scope of the invention.

Antisense Nucleic Acid Molecules, Ribozymes and Modified 47174 Nucleic Acid Molecules In another aspect, the invention features, an isolated nucleic acid molecule which is antisense to 47174. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 47174 coding strand, or to only a portion thereof (e.g., the coding region of human 47174 corresponding to SEQ ID NO:44). In another embodiment, the antisense nucleic acid molecule is antisense to a "noncoding region" of the coding strand of a nucleotide sequence encoding 47174 (e.g., the 5' and 3' untranslated regions).

An antisense nucleic acid can be designed such that it is complementary to the entire coding region of 47174 mRNA, but more preferably is an oligonucleotide that is antisense to only a portion of the coding or noncoding region of 47174 mRNA. For example, the antisense oligonucleotide can be complementary to the region surrounding the translation start site of 47174 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 47174 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An alpha-anomeric nucleic acid molecule forms specific double-stranded hybrids with complementary RNA in which, contrary to the usual beta-units, the strands run parallel to each other (Gaultier et al. (1987) *Nucleic Acids Res* 15:6625-6641). The antisense nucleic acid molecule can also comprise a 2'-o-methylribonucleotide (Inoue et al. (1987) *Nucleic Acids Res* 15:6131-6148) or a chimeric RNA-DNA analogue (Inoue et al. (1987) *FEBS Lett* 215: 327-330).

In still another embodiment, an antisense nucleic acid of the invention is a ribozyme. A ribozyme having specificity for a 47174-encoding nucleic acid can include one or more sequences complementary to the nucleotide sequence of a 47174 cDNA disclosed herein (i.e., SEQ ID NO:42 or SEQ ID NO:44), and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a 47174-encoding mRNA. See, e.g., Cech et al. U.S. Pat. No. 4,987,071; and Cech et al. U.S. Pat. No. 5,116,742. Alternatively, 47174 mRNA can be used to select a catalytic RNA having a specific ribonuclease activity from a pool of RNA molecules. See, e.g., Bartel and Szostak (1993) *Science* 261:1411-1418.

47174 gene expression can be inhibited by targeting nucleotide sequences complementary to the regulatory region of the 47174 (e.g., the 47174 promoter and/or enhancers) to form triple helical structures that prevent transcription of the 47174 gene in target cells. See generally, Helene (1991) *Anticancer Drug Des* 6(6):569-84; Helene et al. (1992) *Ann NY Acad Sci* 660:27-36; and Maher (1992) *Bioassays* 14(12):807-15. The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric. A 47174 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup et al. (1996) *Bioorganic & Medicinal Chemistry* 4 (1): 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. *Proc Natl Acad Sci.* 93: 14670-675.

PNAs of 47174 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 47174 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup (1996) supra)); or as probes or primers for DNA sequencing or hybridization (Hyrup et al. (1996) supra; Perry-O'Keefe, supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc Natl Acad Sci USA* 86:6553-6556; Lemaitre et al. (1987) *Proc Natl Acad Sci USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958-976) or intercalating agents (See, e.g., Zon (1988) *Pharm Res* 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 47174 nucleic acid of the invention, two complementary regions one having a fluorophore and one a quencher such that the molecular beacon is useful for quantitating the presence of the 47174 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 47174 Polypeptides

In another aspect, the invention features, an isolated 47174 protein, or fragment, e.g., a biologically active portion, for use as immunogens or antigens to raise or test (or more generally to bind) anti-47174 antibodies. 47174 protein can be isolated from cells or tissue sources using standard protein purification techniques. 47174 protein or fragments thereof can be produced by recombinant DNA techniques or synthesized chemically.

Polypeptides of the invention include those that arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 47174 polypeptide has one or more of the following characteristics:

(i) it has the ability to transfer an activated sugar residue to an acceptor molecule;

(ii) it has a molecular weight, e.g., a deduced molecular weight, amino acid composition or other physical characteristic of a 47174 polypeptide, e.g., the polypeptide of SEQ ID NO:43;

(iii) it has an overall sequence similarity of at least 60%, more preferably at least 70, 80, 90, 95, 98, or 99%, with a polypeptide of SEQ ID NO:43;

(iv) it has a glycosyltransferase domain which preferably has an overall sequence similarity of about 70%, 80%, 90% or 95% with amino acid residues 154-336 of SEQ ID NO:43; or (v) it has at least 70%, preferably 80%, and most preferably 95% of the cysteines found amino acid sequence of the native protein.

In a preferred embodiment, the 47174 protein, or fragment thereof, includes at least two contiguous amino acids from the amino acid sequence of residues 1-170 or 437-603 of SEQ ID NO:43.

In a preferred embodiment the 47174 protein, or fragment thereof, differs from the corresponding sequence in SEQ ID NO:43. In one embodiment it differs by about 1, 2, 3, 4, 5, 6, 7, 8, 9, or more amino acids. In another it differs by at least one but less than 15, 10 or 5 amino acid residues. In another it differs from the corresponding sequence in SEQ ID NO:43 by at least 1%. In another it differs from the corresponding sequence in SEQ ID NO:43 by at least one residue but less than 20%, 15%, 10%, 5%, or 1% of the residues in it differ from the corresponding sequence in SEQ ID NO:43. If this comparison requires alignment the sequences should be aligned for maximum homology. "Looped" out sequences from deletions or insertions, or mismatches, are considered differences. The differences are, preferably, differences or changes at a non essential residue or a conservative substitution. In a preferred embodiment the differences are not in the glycosyltransferase domain (about amino acids 154 to 336 of SEQ ID NO:43). In another preferred embodiment one or more differences are in the glycosyltransferase domain (about amino acids 154 to 336 of SEQ ID NO:43).

Other embodiments include a protein that contains one or more changes in amino acid sequence, e.g., a change in an amino acid residue which is not essential for activity. Such 47174 proteins differ in amino acid sequence from SEQ ID NO:43, yet retain biological activity.

In one embodiment, the protein includes an amino acid sequence at least about 60%, 65%, 70%, 75%, 80%, 85%, 90%, 95%, 98%, 99%, or more homologous to SEQ ID NO:43.

A 47174 protein or fragment is provided which varies from the sequence of SEQ ID NO:43 in regions defined by amino acids about 1-153 or 337-603 by at least one but by less than 15, 10 or 5 amino acid residues in the protein or fragment but which does not differ from SEQ ID NO:43 in regions defined by amino acids about 154 to 336 of SEQ ID NO:43. If this comparison requires alignment the sequences should be aligned for maximum homology. "Looped" out sequences from deletions or insertions, or mismatches, are considered differences. In some embodiments the difference is at a non essential residue or is a conservative substitution, while in others the difference is at an essential residue or is a non conservative substitution.

In a preferred embodiment, a fragment differs by at least 1, 2, 3, 10, 20, or more amino acid residues encoded by a sequence present in WO00/58473, WO 01/53312, or WO 01/59063. Differences can include differing in length or sequence identity. For example, a fragment can: include one or more amino acid residues from SEQ ID NO:43 outside the region encoded by nucleotides 835-1633, 1011-2217, or 244-1389 of SEQ ID NO:42; not include all of the amino acid residues of a sequence present in WO00/58473, WO 01/53312, or WO 01/59063, e.g., can be one or more amino acid residues shorter (at one or both ends) than a sequence present in WO00/58473, WO 01/53312, or WO 01/59063; or can differ by one or more amino acid residues in the region of overlap.

In one embodiment, a biologically active portion of a 47174 protein includes a glycosyltransferase domain. Moreover, other biologically active portions, in which other regions of the protein are deleted, can be prepared by recombinant techniques and evaluated for one or more of the functional activities of a native 47174 protein.

In a preferred embodiment, the 47174 protein has an amino acid sequence shown in SEQ ID NO:43. In other embodiments, the 47174 protein is substantially identical to SEQ ID NO:43. In yet another embodiment, the 47174 protein is substantially identical to SEQ ID NO:43 and retains the functional activity of the protein of SEQ ID NO:43, as described in detail in the subsections above.

47174 Chimeric or Fusion Proteins

In another aspect, the invention provides 47174 chimeric or fusion proteins. As used herein, a 47174 "chimeric protein" or "fusion protein" includes a 47174 polypeptide linked to a non-47174 polypeptide. A "non-47174 polypeptide" refers to a polypeptide having an amino acid sequence corresponding to a protein which is not substantially homologous to the 47174 protein, e.g., a protein which is different from the 47174 protein and which is derived from the same or a different organism. The 47174 polypeptide of the fusion protein can correspond to all or a portion e.g., a fragment described herein of a 47174 amino acid sequence. In a preferred embodiment, a 47174 fusion protein includes at least one (or two) biologically active portion of a 47174 protein. The non-47174 polypeptide can be fused to the N-terminus or C-terminus of the 47174 polypeptide.

The fusion protein can include a moiety that has a high affinity for a ligand. For example, the fusion protein can be a GST-47174 fusion protein in which the 47174 sequences are fused to the C-terminus of the GST sequences. Such fusion proteins can facilitate the purification of recombinant 47174. Alternatively, the fusion protein can be a 47174 protein containing a heterologous signal sequence at its N-terminus. In certain host cells (e.g., mammalian host cells), expression and/or secretion of 47174 can be increased through use of a heterologous signal sequence.

Fusion proteins can include all or a part of a serum protein, e.g., an IgG constant region, or human serum albumin.

The 47174 fusion proteins of the invention can be incorporated into pharmaceutical compositions and administered to a subject in vivo. The 47174 fusion proteins can be used to affect the bioavailability of a 47174 substrate. 47174 fusion proteins may be useful therapeutically for the treatment of disorders caused by, for example, (i) aberrant modification or mutation of a gene encoding a 47174 protein; (ii) mis-regulation of the 47174 gene; and (iii) aberrant post-translational modification of a 47174 protein.

Moreover, the 47174-fusion proteins of the invention can be used as immunogens to produce anti-47174 antibodies in a subject, to purify 47174 ligands and in screening assays to identify molecules that inhibit the interaction of 47174 with a 47174 substrate.

Expression vectors are commercially available that already encode a fusion moiety (e.g., a GST polypeptide). A 47174-encoding nucleic acid can be cloned into such an expression vector such that the fusion moiety is linked in-frame to the 47174 protein.

Variants of 47174 Proteins

In another aspect, the invention also features a variant of a 47174 polypeptide, e.g., which functions as an agonist (mimetics) or as an antagonist. Variants of the 47174 proteins can be generated by mutagenesis, e.g., discrete point mutation, the insertion or deletion of sequences or the truncation of a 47174 protein. An agonist of the 47174 proteins can retain substantially the same, or a subset, of the biological activities of the naturally occurring form of a 47174 protein. An antagonist of a 47174 protein can inhibit one or more of the activities of the naturally occurring form of the 47174 protein by, for example, competitively modulating a 47174-mediated activity of a 47174 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 47174 protein.

Variants of a 47174 protein can be identified by screening combinatorial libraries of mutants, e.g., truncation mutants, of a 47174 protein for agonist or antagonist activity.

Libraries of fragments e.g., N-terminal, C-terminal, or internal fragments, of a 47174 protein coding sequence can be used to generate a variegated population of fragments for screening and subsequent selection of variants of a 47174 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Recursive ensemble mutagenesis (REM), a new technique which enhances the frequency of functional mutants in the libraries, can be used in combination with the screening assays to identify 47174 variants (Arkin and Yourvan (1992) *Proc Natl Acad Sci USA* 89:7811-7815; Delgrave et al. (1993) *Protein Engineering* 6(3):327-331).

Cell based assays can be exploited to analyze a variegated 47174 library. For example, a library of expression vectors can be transfected into a cell line, e.g., a cell line, which ordinarily responds to 47174 in a substrate-dependent manner. The transfected cells are then contacted with 47174 and the effect of the expression of the mutant on signaling by the 47174 substrate can be detected, e.g., by measuring glycosyltransferase peptidase activity. Plasmid DNA can then be recovered from the cells which score for inhibition, or alternatively, potentiation of signaling by the 47174 substrate, and the individual clones further characterized.

In another aspect, the invention features a method of making a 47174 polypeptide, e.g., a peptide having a non-wild type activity, e.g., an antagonist, agonist, or super agonist of a naturally occurring 47174 polypeptide, e.g., a naturally occurring 47174 polypeptide. The method includes: altering the sequence of a 47174 polypeptide, e.g., altering the sequence by substitution or deletion of one or more residues of a non-conserved region, a domain or residue disclosed herein, and testing the altered polypeptide for the desired activity.

In another aspect, the invention features a method of making a fragment or analog of a 47174 polypeptide a biological activity of a naturally occurring 47174 polypeptide. The method includes: altering the sequence, e.g., by substitution or deletion of one or more residues, of a 47174 polypeptide, e.g., altering the sequence of a non-conserved region, or a domain or residue described herein, and testing the altered polypeptide for the desired activity.

Anti-47174 Antibodies

In another aspect, the invention provides an anti-47174 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-47174 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH—terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 47174 polypeptide or fragment thereof. Examples of antigen-binding fragments of the anti-47174 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-47174 antibody can be a polyclonal or a monoclonal antibody. In other embodiments, the antibody can be recombinantly produced, e.g., produced by phage display or by combinatorial methods.

Phage display and combinatorial methods for generating anti-47174 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the anti-47174 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An anti-47174 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 47174 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, Science 229:1202-1207, by Oi et al., 1986, Bio Techniques 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 47174 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 Nature 321:552-525; Verhoeyan et al. 1988 Science 239:1534; Beidler et al. 1988 J. Immunol. 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

A full-length 47174 protein or, antigenic peptide fragment of 47174 can be used as an immunogen or can be used to identify anti-47174 antibodies made with other immunogens, e.g., cells, membrane preparations, and the like. The antigenic peptide of 47174 should include at least 8 amino acid residues of the amino acid sequence shown in SEQ ID NO:43 and encompasses an epitope of 47174. Preferably, the antigenic peptide includes at least 10 amino acid residues, more preferably at least 15 amino acid residues, even more preferably at least 20 amino acid residues, and most preferably at least 30 amino acid residues.

Fragments of 47174 which include residues about 151-175 of SEQ ID NO:43 can be used to make, e.g., used as immunogens or used to characterize the specificity of an antibody, antibodies against hydrophilic regions of the 47174 protein. Similarly, a fragment of 47174 which includes residues about 101-135 of SEQ ID NO:43 can be used to make an antibody against a hydrophobic region of the 47174 protein; a fragment of 47174 which include residues about 154-336 of SEQ ID NO:43, or a portion thereof (e.g., amino acids 154-174, 174-200, 200-220, 220-250, 250-275, 275-300, or 300-336 of SEQ ID NO:43), about can be used to make an antibody against the glycosyltransferase region of the 47174 protein.

Antibodies reactive with, or specific for, any of these regions, or other regions or domains described herein are provided.

Preferred epitopes encompassed by the antigenic peptide are regions of 47174 are located on the surface of the protein, e.g., hydrophilic regions, as well as regions with high antigenicity. For example, an Emini surface probability analysis of the human 47174 protein sequence can be used to indicate the regions that have a particularly high probability of being localized to the surface of the 47174 protein and are thus likely to constitute surface residues useful for targeting antibody production.

In a preferred embodiment the antibody binds an epitope on any domain or region on 47174 proteins described herein.

Chimeric, humanized, but most preferably, completely human antibodies are desirable for applications which include repeated administration, e.g., therapeutic treatment (and some diagnostic applications) of human patients.

The anti-47174 antibody can be a single chain antibody. A single-chain antibody (scFV) may be engineered (see, for example, Colcher et al. (1999) Ann N Y Acad Sci 880:263-80; and (1996) Reiter Clin Cancer Res 2:245-52). The single chain antibody can be dimerized or multimerized to generate multivalent antibodies having specificities for different epitopes of the same target 47174 protein.

In a preferred embodiment the antibody has effector function and/or can fix complement. In other embodiments the antibody does not recruit effector cells; or fix complement.

In a preferred embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

An anti-47174 antibody (e.g., monoclonal antibody) can be used to isolate 47174 by standard techniques, such as affinity chromatography or immunoprecipitation. Moreover, an anti-47174 antibody can be used to detect 47174 protein (e.g., in a cellular lysate or cell supernatant) in order to evaluate the abundance and pattern of expression of the protein. Anti-47174 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, □-galactosidase, or acetylcholinesterase; examples of suitable prosthetic group complexes include streptavidin/ biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

The invention also includes a nucleic acid that encodes an anti-47174 antibody, e.g., an anti-47174 antibody described herein. Also included are vectors which include the nucleic acid and cells transformed with the nucleic acid, particularly cells that are useful for producing an antibody, e.g., mammalian cells, e.g. CHO or lymphatic cells.

The invention also includes cell lines, e.g., hybridomas, which make an anti-47174 antibody, e.g., and antibody described herein, and method of using said cells to make a 47174 antibody.

47174 Recombinant Expression Vectors, Host Cells and Genetically Engineered Cells In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 47174 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 47174 proteins, mutant forms of 47174 proteins, fusion proteins, and the like).

The recombinant expression vectors of the invention can be designed for expression of 47174 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, Gene Expression Technology: *Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 47174 activity assays, (e.g., direct assays or competitive assays described in detail below), or to generate antibodies specific for 47174 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res* 20:2111-2118). Such alteration of nucleic acid sequences of the invention can be carried out by standard DNA synthesis techniques.

The 47174 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev* 1:268-277), lymphoid-specific promoters (Calame and Eaton (1988) *Adv Immunol* 43:235-275), in particular promoters of T cell receptors (Winoto and Baltimore (1989) *EMBO J* 8:729-733) and immunoglobulins (Baneiji et al. (1983) *Cell* 33:729-740; Queen and Baltimore (1983) *Cell* 33:741-748), neuron-specific promoters (e.g., the neurofilament promoter; Byrne and Ruddle (1989) *Proc Natl Acad Sci USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the alpha-fetoprotein promoter (Campes and Tilghman (1989) *Genes Dev* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub et al. (1986) Antisense RNA as a molecular tool for genetic analysis, Reviews—Trends in Genetics, Vol. 1(1).

Another aspect the invention provides a host cell which includes a nucleic acid molecule described herein, e.g., a 47174 nucleic acid molecule within a recombinant expression vector or a 47174 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 47174 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAR-dextran-mediated transfection, lipofection, or electroporation.

A host cell of the invention can be used to produce (i.e., express) a 47174 protein. Accordingly, the invention further provides methods for producing a 47174 protein using the host cells of the invention. In one embodiment, the method includes culturing the host cell of the invention (into which a recombinant expression vector encoding a 47174 protein has been introduced) in a suitable medium such that a 47174 protein is produced. In another embodiment, the method further includes isolating a 47174 protein from the medium or the host cell.

In another aspect, the invention features, a cell or purified preparation of cells which include a 47174 transgene, or which otherwise misexpress 47174. The cell preparation can consist of human or non human cells, e.g., rodent cells, e.g., mouse or rat cells, rabbit cells, or pig cells. In preferred embodiments, the cell or cells include a 47174 transgene, e.g., a heterologous form of a 47174, e.g., a gene derived from humans (in the case of a non-human cell). The 47174 transgene can be misexpressed, e.g., overexpressed or underexpressed. In other preferred embodiments, the cell or cells include a gene which misexpress an endogenous 47174, e.g., a gene the expression of which is disrupted, e.g., a knockout. Such cells can serve as a model for studying disorders which are related to mutated or mis-expressed 47174 alleles or for use in drug screening.

In another aspect, the invention features, a human cell, e.g., a CNS cell or a kidney cell, transformed with nucleic acid that encodes a subject 47174 polypeptide.

Also provided are cells, preferably human cells, e.g., human hematopoietic or fibroblast cells, in which an endogenous 47174 is under the control of a regulatory sequence that does not normally control the expression of the endogenous 47174 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 47174 gene. For example, an endogenous 47174 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published May 16, 1991.

47174 Transgenic Animals

The invention provides non-human transgenic animals. Such animals are useful for studying the function and/or activity of a 47174 protein and for identifying and/or evaluating modulators of 47174 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 47174 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 47174 protein to particular cells. A transgenic founder animal can be identified based upon the presence of a 47174 transgene in its genome and/or expression of 47174 mRNA in tissues or cells of the animals. A transgenic founder animal can then be used to breed additional animals carrying the transgene. Moreover, transgenic animals carrying a transgene encoding a 47174 protein can further be bred to other transgenic animals carrying other transgenes.

47174 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses of 47174

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 47174 protein (e.g., via a recombinant expression vector in a host cell in gene therapy applications), to detect a 47174 mRNA (e.g., in a biological sample) or a genetic alteration in a 47174 gene, and to modulate 47174 activity, as described further below. The 47174 proteins can be used to treat disorders characterized by insufficient or excessive production of a 47174 substrate or production of 47174 inhibitors. In addition, the 47174 proteins can be used to screen for naturally occurring 47174 substrates, to screen for drugs or compounds which modulate 47174 activity, as well as to treat disorders characterized by insufficient or excessive production of 47174 protein or production of 47174 protein forms which have decreased, aberrant or unwanted activity compared to 47174 wild type protein (e.g., pain or pain related disorders). Moreover, the anti-47174 antibodies of the invention can be used to detect and isolate 47174 proteins, regulate the bioavailability of 47174 proteins, and modulate 47174 activity.

A method of evaluating a compound for the ability to interact with, e.g., bind, a subject 47174 polypeptide is provided. The method includes: contacting the compound with the subject 47174 polypeptide; and evaluating ability of the compound to interact with, e.g., to bind, form a complex with, or act as a substrate for, or of, the subject 47174 polypeptide. This method can be performed in vitro, e.g., in a cell free system, or in vivo, e.g., in a two-hybrid interaction trap assay. This method can be used to identify naturally occurring molecules which interact with subject 47174 polypeptide. It can also be used to find natural or synthetic inhibitors of subject 47174 polypeptide. Screening methods are discussed in more detail below.

47174 Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 47174 proteins, have a stimulatory or inhibitory effect on, for example, 47174 expression or 47174 activity, or have a stimulatory or inhibitory effect on, for example, the expression or activity of a 47174 substrate. Compounds thus identified can be used to modulate the activity of target gene products (e.g., 47174 genes) in a therapeutic protocol, to elaborate the biological function of the target gene product, or to identify compounds that disrupt normal target gene interactions.

In one embodiment, the invention provides assays for screening candidate or test compounds that are substrates of a 47174 protein or polypeptide or a biologically active portion thereof. In another embodiment, the invention provides assays for screening candidate or test compounds that bind to or modulate the activity of a 47174 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al. (1994) *J Med Chem* 37: 2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des* 12:145).

Examples of methods for the synthesis of molecular libraries can be found in the art, for example in: DeWitt et al. (1993) *Proc Natl Acad Sci USA* 90:6909; Erb et al. (1994) *Proc Natl Acad Sci USA* 91:11422; Zuckermann et al. (1994). *J. Med. Chem.* 37:2678; Cho et al. (1993) *Science* 261:1303; Carrell et al. (1994) *Angew Chem Int Ed Engl.* 33:2059; Carell et al. (1994) *Angew Chem Int Ed Engl* 33:2061; and in Gallop et al. (1994) *J Med Chem* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc Natl Acad Sci USA* 87:6378-6382; Felici (1991) *J Mol Biol* 222:301-310; Ladner, supra.

In one embodiment, an assay is a cell-based assay in which a cell which expresses a 47174 protein or biologically active portion thereof is contacted with a test compound, and the ability of the test compound to modulate 47174 activity is determined. Determining the ability of the test compound to modulate 47174 activity can be accomplished by monitoring, for example, glycosyltransferase activity, e.g., zinc binding activity or hydrolysis of a peptide substrate, e.g., enkephalin cleavage activity. The cell, for example, can be of mammalian origin, e.g., human.

The ability of the test compound to modulate 47174 binding to a compound, e.g., a 47174 substrate, or to bind to 47174 can also be evaluated. This can be accomplished, for example, by coupling the compound, e.g., the substrate, with a radioisotope or enzymatic label such that binding of the compound, e.g., the substrate, to 47174 can be determined by detecting the labeled compound, e.g., substrate, in a complex. Alternatively, 47174 could be coupled with a radioisotope or enzymatic label to monitor the ability of a test compound to modulate 47174 binding to a 47174 substrate in a complex. For example, compounds (e.g., 47174 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 47174 substrate) to interact with 47174 with or without the labeling of any of the interactants can be evaluated. For example, a microphysiometer can be used to detect the interaction of a compound with 47174 without the labeling of either the compound or the 47174. McConnell et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 47174.

In yet another embodiment, a cell-free assay is provided in which a 47174 protein or biologically active portion thereof is contacted with a test compound and the ability of the test compound to bind to the 47174 protein or biologically active portion thereof is evaluated. Preferred biologically active portions of the 47174 proteins to be used in assays of the present invention include fragments that participate in interactions with non-47174 molecules, e.g., fragments with high surface probability scores.

Soluble and/or membrane-bound forms of isolated proteins (e.g., 47174 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 47174 protein to bind to a target molecule or substrate can be accomplished using real-time Biomolecular Interaction Analysis (BIA) (see, e.g., Sjolander and Urbaniczky (1991) *Anal Chem* 63:2338-2345 and Szabo et al. (1995) *Curr Opin Struct Biol* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 47174, an anti-47174 antibody or its target molecule to facilitate separation of complexed from uncomplexed forms of one or both of the proteins, as well as to accommodate automation of the assay. Binding of a test compound to a 47174 protein, or interaction of a 47174 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/47174 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 47174 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 47174 binding or activity determined using standard techniques.

Other techniques for immobilizing either a 47174 protein or a target molecule on matrices include using conjugation of biotin and streptavidin. Biotinylated 47174 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 47174 protein or target molecules but which do not interfere with binding of the 47174 protein to its target molecule. Such antibodies can be derivatized to the wells of the plate, and unbound target or 47174 protein trapped in the wells by antibody conjugation. Methods for detecting such complexes, in addition to those described above for the GST-immobilized complexes, include immunodetection of complexes using antibodies reactive with the 47174 protein or target molecule, as well as enzyme-linked assays which rely on detecting an enzymatic activity associated with the 47174 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas and Minton (1993) *Trends Biochem Sci* 18(8):284-7); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard (1998) *J Mol Recognit* 11 (1-6):141-8; Hage and Tweed (1997) *J Chromatogr B Biomed Sci Appl* 699(1-2):499-525). Further, fluorescence energy transfer may also be conveniently utilized, as described herein, to detect binding without further purification of the complex from solution.

In a preferred embodiment, the assay includes contacting the 47174 protein or biologically active portion thereof with a known compound which binds 47174 to form an assay mixture, contacting the assay mixture with a test compound, and determining the ability of the test compound to interact with a 47174 protein, wherein determining the ability of the test compound to interact with a 47174 protein includes determining the ability of the test compound to preferentially bind to 47174 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 47174 genes herein identified. In an alternative embodiment, the invention provides methods for determining the ability of the test compound to modulate the activity of a 47174 protein through modulation of the activity of a downstream effector of a 47174 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 47174 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J Biol Chem* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 47174 ("47174-binding proteins" or "47174-bp") and are involved in 47174 activity. Such 47174-bps can be activators or inhibitors of signals by the 47174 proteins or 47174 targets as, for example, downstream elements of a 47174-mediated signaling pathway.

The two-hybrid system is based on the modular nature of most transcription factors, which consist of separable DNA-binding and activation domains. Briefly, the assay utilizes two different DNA constructs. In one construct, the gene that codes for a 47174 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively 47174 protein can be the fused to the activator domain.) If the "bait" and the "prey" proteins are able to interact, in vivo, forming a 47174-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 47174 protein.

In another embodiment, modulators of 47174 expression are identified. For example, a cell or cell free mixture is contacted with a candidate compound and the expression of 47174 mRNA or protein evaluated relative to the level of expression of 47174 mRNA or protein in the absence of the candidate compound. When expression of 47174 mRNA or protein is greater in the presence of the candidate compound than in its absence, the candidate compound is identified as a stimulator of 47174 mRNA or protein expression. Alternatively, when expression of 47174 mRNA or protein is less (statistically significantly less) in the presence of the candidate compound than in its absence, the candidate compound is identified as an inhibitor of 47174 mRNA or protein expression. The level of 47174 mRNA or protein expression can be determined by methods described herein for detecting 47174 mRNA or protein.

In another aspect, the invention pertains to a combination of two or more of the assays described herein. For example, a modulating agent can be identified using a cell-based or a cell free assay, e.g., a peptidase assay, and the ability of the agent to modulate the activity of a 47174 protein can be confirmed in vivo, e.g., in an animal such as an animal model for pain response, e.g., an arthritic rodent, a CCI rodent model for neuropathic pain, or a rodent with induced unilateral inflammatory pain by intraplantar injection of Freund's complete adjuvant.

This invention further pertains to novel agents identified by the above-described screening assays. Accordingly, it is within the scope of this invention to further use an agent identified as described herein (e.g., a 47174 modulating agent, an antisense 47174 nucleic acid molecule, a 47174-specific antibody, or a 47174-binding partner) in an appropriate animal model to determine the efficacy, toxicity, side effects, or mechanism of action, of treatment with such an agent. Furthermore, novel agents identified by the above-described screening assays can be used for treatments as described herein.

47174 Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 47174 with a disease; (ii) identify an individual from a minute biological sample (tissue typing); and (iii) aid in forensic identification of a biological sample. These applications are described in the subsections below.

47174 Chromosome Mapping

The 47174 nucleotide sequences or portions thereof can be used to map the location of the 47174 genes on a chromosome. This process is called chromosome mapping. Chromosome mapping is useful in correlating the 47174 sequences with genes associated with disease.

Briefly, 47174 genes can be mapped to chromosomes by preparing PCR primers (preferably 15-25 bp in length) from the 47174 nucleotide sequences. These primers can then be used for PCR screening of somatic cell hybrids containing individual human chromosomes. Only those hybrids containing the human gene corresponding to the 47174 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio et al. (1983) *Science* 220:919-924).

Other mapping strategies e.g., in situ hybridization (described in Fan et al. (1990) *Proc Natl Acad Sci USA* 87:6223-27), pre-screening with labeled flow-sorted chromosomes, and pre-selection by hybridization to chromosome specific cDNA libraries can be used to map 47174 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland et al. (1987) Nature 325:783-787.

Moreover, differences in the DNA sequences between individuals affected and unaffected with a disease associated with the 47174 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

47174 Tissue Typing 47174 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 47174 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:42 can provide positive individual identification with a panel of perhaps 10 to 1,000 primers which each yield a noncoding amplified sequence of 100 bases. If predicted coding sequences, such as those in SEQ ID NO:44 are used, a more appropriate number of primers for positive individual identification would be 500-2,000.

If a panel of reagents from 47174 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 47174 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:42 (e.g., fragments derived from the noncoding regions of SEQ ID NO:42 having a length of at least 20 bases, preferably at least 30 bases) are particularly appropriate for this use.

The 47174 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 47174 probes can be used to identify tissue by species and/or by organ type.

In a similar fashion, these reagents, e.g., 47174 primers or probes can be used to screen tissue culture for contamination (i.e. screen for the presence of a mixture of different types of cells in a culture).

Predictive Medicine of 47174

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 47174.

Such disorders include, e.g., disorders associated with the misexpression of 47174 gene: pain, pain related disorders.

The method includes one or more of the following:

detecting, in a tissue of the subject, the presence or absence of a mutation which affects the expression of the 47174 gene, or detecting the presence or absence of a mutation in a region which controls the expression of the gene, e.g., a mutation in the 5' control region;

detecting, in a tissue of the subject, the presence or absence of a mutation which alters the structure of the 47174 gene;

detecting, in a tissue of the subject, the misexpression of the 47174 gene, at the mRNA level, e.g., detecting a non-wild type level of a mRNA;

detecting, in a tissue of the subject, the misexpression of the gene, at the protein level, e.g., detecting a non-wild type level of a 47174 polypeptide.

In preferred embodiments the method includes: ascertaining the existence of at least one of: a deletion of one or more nucleotides from the 47174 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:42, or naturally occurring mutants thereof or 5' or 3' flanking sequences naturally associated with the 47174 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 47174 gene; the presence of a non-wild type splicing pattern of a messenger RNA transcript of the gene; or a non-wild type level of 47174.

Methods of the invention can be used prenatally or to determine if a subject's offspring will be at risk for a disorder.

In preferred embodiments the method includes determining the structure of a 47174 gene, an abnormal structure being indicative of risk for the disorder.

In preferred embodiments the method includes contacting a sample form the subject with an antibody to the 47174 protein or a nucleic acid, which hybridizes specifically with the gene. There and other embodiments are discussed below.

Diagnostic and Prognostic Assays of 47174

Diagnostic and prognostic assays of the invention include method for assessing the expression level of 47174 molecules and for identifying variations and mutations in the sequence of 47174 molecules.

Expression Monitoring and Profiling

The presence, level, or absence of 47174 protein or nucleic acid in a biological sample can be evaluated by obtaining a biological sample from a test subject and contacting the biological sample with a compound or an agent capable of detecting 47174 protein or nucleic acid (e.g., mRNA, genomic DNA) that encodes 47174 protein such that the presence of 47174 protein or nucleic acid is detected in the biological sample. The term "biological sample" includes tissues, cells and biological fluids isolated from a subject, as well as tissues, cells and fluids present within a subject. A preferred biological sample is serum. The level of expression of the 47174 gene can be measured in a number of ways, including, but not limited to: measuring the mRNA encoded by the 47174 genes; measuring the amount of protein encoded by the 47174 genes; or measuring the activity of the protein encoded by the 47174 genes.

The level of mRNA corresponding to the 47174 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 47174 nucleic acid, such as the nucleic acid of SEQ ID NO:42, or a portion thereof, such as an oligonucleotide of at least 7, 15, 30, 50, 100, 250 or 500 nucleotides in length and sufficient to specifically hybridize under stringent conditions to 47174 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 47174 genes.

The level of mRNA in a sample that is encoded by one of 47174 can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189-193), self sustained sequence replication (Guatelli et al., (1990) Proc. Natl. Acad. Sci. USA 87:1874-1878), transcriptional amplification system (Kwoh et al., (1989), Proc. Natl. Acad. Sci. USA 86:1173-1177), Q-Beta Replicase (Lizardi et al., (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 47174 gene being analyzed.

In another embodiment, the methods further contacting a control sample with a compound or agent capable of detecting 47174 mRNA, or genomic DNA, and comparing the presence of 47174 mRNA or genomic DNA in the control sample with the presence of 47174 mRNA or genomic DNA in the test sample. In still another embodiment, serial analysis of gene expression, as described in U.S. Pat. No. 5,695,937, is used to detect 47174 transcript levels.

A variety of methods can be used to determine the level of protein encoded by 47174. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 47174 protein in a biological sample in vitro as well as in vivo. In vitro techniques for detection of 47174 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 47174 protein include introducing into a subject a labeled anti-47174 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-47174 antibody positioned on an antibody array (as described below). The sample can be detected, e.g., with avidin coupled to a fluorescent label.

In another embodiment, the methods further include contacting the control sample with a compound or agent capable of detecting 47174 protein, and comparing the presence of 47174 protein in the control sample with the presence of 47174 protein in the test sample.

The invention also includes kits for detecting the presence of 47174 in a biological sample. For example, the kit can include a compound or agent capable of detecting 47174 protein or mRNA in a biological sample; and a standard. The compound or agent can be packaged in a suitable container. The kit can further comprise instructions for using the kit to detect 47174 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 47174 expression or activity. As used herein, the term "unwanted" includes an unwanted phenomenon involved in a biological response such as oligodendrocyte development, myclin formation, pain or deregulated cell proliferation.

In one embodiment, a disease or disorder associated with aberrant or unwanted 47174 expression or activity is identified. A test sample is obtained from a subject and 47174 protein or nucleic acid (e.g., mRNA or genomic DNA) is evaluated, wherein the level, e.g., the presence or absence, of 47174 protein or nucleic acid is diagnostic for a subject having or at risk of developing a disease or disorder associated with aberrant or unwanted 47174 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 47174 expression or activity. For example, such methods can be used to determine whether a subject can be effectively treated with an agent for a disorder as described herein.

In another aspect, the invention features a computer medium having a plurality of digitally encoded data records. Each data record includes a value representing the level of expression of 47174 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 47174 (e.g., other genes associated with a 47174-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 47174 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a DISORDERA disorder in a subject wherein an increase in 47174 expression is an indication that the subject has or is disposed to having a disorder as described herein. The method can be used to monitor a treatment for the disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 47174 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 47174 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 47174 expression.

47174 Arrays and Uses Thereof

In another aspect, the invention features an array that includes a substrate having a plurality of addresses. At least one address of the plurality includes a capture probe that binds specifically to a 47174 molecule (e.g., a 47174 nucleic acid or a 47174 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 47174 nucleic acid, e.g., the sense or anti-sense strand. In one preferred embodiment, a subset of addresses of the plurality of addresses has a nucleic acid capture probe for 47174. Each address of the subset can include a capture probe that hybridizes to a different region of a 47174 nucleic acid. In another preferred embodiment, addresses of the subset include a capture probe for a 47174 nucleic acid. Each address of the subset is unique, overlapping, and complementary to a different variant of 47174 (e.g., an allelic variant, or all possible hypothetical variants). The array can be used to sequence 47174 by hybridization (see, e.g., U.S. Pat. No. 5,695,940).

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 47174 polypeptide or fragment thereof. The polypeptide can be a naturally-occurring interaction partner of 47174 polypeptide. Preferably, the polypeptide is an antibody, e.g., an antibody described herein (see "Anti-47174 Antibodies," above), such as a monoclonal antibody or a single-chain antibody.

In another aspect, the invention features a method of analyzing the expression of 47174. The method includes providing an array as described above; contacting the array with a sample and detecting binding of a 47174-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 47174. If a sufficient number of diverse samples is analyzed, clustering (e.g., hierarchical clustering, k-means clustering, Bayesian clustering and the like) can be used to identify other genes which are co-regulated with 47174. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 47174 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 47174-associated disease or disorder; and processes, such as a cellular transformation associated with a 47174-associated disease or disorder. The method can also evaluate the treatment and/or progression of a 47174-associated disease or disorder The array is also useful for ascertaining differential expression patterns of one or more genes in normal and abnormal cells. This provides a battery of genes (e.g., including 47174) that could serve as a molecular target for diagnosis or therapeutic intervention.

In another aspect, the invention features an array having a plurality of addresses. Each address of the plurality includes a unique polypeptide. At least one address of the plurality has disposed thereon a 47174 polypeptide or fragment thereof. Methods of producing polypeptide arrays are described in the art, e.g., in De Wildt et al. (2000). *Nature Biotech.* 18, 989-994; Lueking et al (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80, 85, 90, 95 or 99% identical to a 47174 polypeptide or fragment thereof. For example, multiple variants of a 47174 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 47174 binding compound, e.g., an antibody in a sample from a subject with specificity for a 47174 polypeptide or the presence of a 47174-binding protein or ligand.

The array is also useful for ascertaining the effect of the expression of a gene on the expression of other genes in the same cell or in different cells (e.g., ascertaining the effect of 47174 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 47174 or from a cell or subject in which a 47174 mediated response has been elicited, e.g., by contact of the cell with 47174 nucleic acid or protein, or administration to the cell or subject 47174 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 47174 (or does not express as highly as in the case of the 47174 positive plurality of capture probes) or from a cell or subject which in which a 47174 mediated response has not been elicited (or has been elicited to a lesser extent than in the first sample); contacting the array with one or more inquiry probes (which is preferably other than a 47174 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 47174 or from a cell or subject in which a 47174-mediated response has been elicited, e.g., by contact of the cell with 47174 nucleic acid or protein, or administration to the cell or subject 47174 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 47174 (or does not express as highly as in the case of the 47174 positive plurality of capture probes) or from a cell or subject which in which a 47174 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 47174, e.g., analyzing structure, function, or relatedness to other nucleic acid or amino acid sequences. The method includes: providing a 47174 nucleic acid or amino acid sequence; comparing the 47174 sequence with one or more preferably a plurality of sequences from a collection of sequences, e.g., a nucleic acid or protein sequence database; to thereby analyze 47174.

Detection of 47174 Variations or Mutations

The methods of the invention can also be used to detect genetic alterations in a 47174 gene, thereby determining if a subject with the altered gene is at risk for a disorder characterized by misregulation in 47174 protein activity or nucleic acid expression, such as a disorder as described herein. In preferred embodiments, the methods include detecting, in a sample from the subject, the presence or absence of a genetic alteration characterized by at least one of an alteration affecting the integrity of a gene encoding a 47174-protein, or the mis-expression of the 47174 gene. For example, such genetic alterations can be detected by ascertaining the existence of at least one of 1) a deletion of one or more nucleotides from a 47174 gene; 2) an addition of one or more nucleotides to a 47174 gene; 3) a substitution of one or more nucleotides of a 47174 gene, 4) a chromosomal rearrangement of a 47174 gene; 5) an alteration in the level of a messenger RNA transcript of a 47174 gene, 6) aberrant modification of a 47174 gene, such as of the methylation pattern of the genomic DNA, 7) the presence of a non-wild type splicing pattern of a messenger RNA transcript of a 47174 gene, 8) a non-wild type level of a 47174-protein, 9) allelic loss of a 47174 gene, and 10) inappropriate post-translational modification of a 47174-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 47174-gene. This method can include the steps of collecting a sample of cells from a subject, isolating nucleic acid (e.g., genomic, mRNA or both) from the sample, contacting the nucleic acid sample with one or more primers which specifically hybridize to a 47174 gene under conditions such that hybridization and amplification of the 47174-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 47174 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 47174 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 47174 nucleic acid or a putative variant (e.g., allelic variant) thereof. A probe can have one or more mismatches to a region of a 47174 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in 47174 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 47174 gene and detect mutations by comparing the sequence of the sample 47174 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 47174 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 47174 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 47174 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 47174 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 47174 nucleic acid.

In a preferred embodiment the set includes a first and a second oligonucleotide. The first and second oligonucleotide can hybridize to the same or to different locations of SEQ ID NO:42 or 44 or the complement of SEQ ID NO:42 or 44. Different locations can be different but overlapping or or nonoverlapping on the same strand. The first and second oligonucleotide can hybridize to sites on the same or on different strands.

The set can be useful, e.g., for identifying SNP's, or identifying specific alleles of 47174. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 47174 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 47174 gene.

Use of 47174 Molecules as Surrogate Markers

The 47174 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 47174 molecules of the invention may be detected, and may be correlated with one or more biological states in vivo. For example, the 47174 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 47174 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 47174 marker) transcription or expression, the amplified marker may be in a quantity which is more readily detectable than the drug itself. Also, the marker may be more easily detected due to the nature of the marker itself; for example, using the methods described herein, anti-47174 antibodies may be employed in an immune-based detection system for a 47174 protein marker, or 47174-specific radiolabeled probes may be used to detect a 47174 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

The 47174 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 47174 protein or RNA) for specific tumor markers in a subject, a drug or course of treatment may be selected that is optimized for the treatment of the specific tumor likely to be present in the subject. Similarly, the presence or absence of a specific sequence mutation in 47174 DNA may correlate 47174 drug response. The use of pharmacogenomic markers therefore permits the application of the most appropriate treatment for each subject without having to administer the therapy.

Pharmaceutical Compositions of 47174

The nucleic acid and polypeptides, fragments thereof, as well as anti-47174 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, □-interferon, □-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors. Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc Natl Acad Sci USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 47174

The present invention provides for both prophylactic and therapeutic methods of treating a subject at risk of (or susceptible to) a disorder or having a disorder associated with aberrant or unwanted 47174 expression or activity. "Treatment" or "treating a subject" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment with either the 47174 molecules of the present invention or 47174 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 47174 expression or activity, by administering to the subject a 47174 or an agent which modulates 47174 expression or at least one 47174 activity. Subjects at risk for a disease which is caused or contributed to by aberrant or unwanted 47174 expression or activity can be identified by, for example, any or a combination of diagnostic or prognostic assays as described herein. Administration of a prophylactic agent can occur prior to the manifestation of symptoms characteristic of the 47174 aberrance, such that a disease or disorder is prevented or, alternatively, delayed in its progression. Depending on the type of 47174 aberrance, for example, a 47174 agonist or 47174 antagonist agent can be used for treating the subject. The appropriate agent can be determined based on screening assays described herein.

As the 47174 mRNA is expressed in brain cortex and hypothalamus, the molecules of the invention can be used to treat, prevent, and/or diagnose disorders involving activities of CNS, as described above.

It is possible that some 47174 disorders can be caused, at least in part, by an abnormal level of gene product, or by the presence of a gene product exhibiting abnormal activity. As such, the reduction in the level and/or activity of such gene products would bring about the amelioration of disorder symptoms, for example, in neurological, e.g., CNS-related or pain-related disorders.

As discussed, successful treatment of 47174 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 47174 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')2 and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 47174 expression is through the use of aptamer molecules specific for 47174 protein. Aptamers are nucleic acid molecules having a tertiary structure which permits them to specifically bind to protein ligands (see, e.g., Osborne et al. (1997) *Curr Opin Chem Biol* 1(1): 5-9; and Patel (1997) *Curr Opin Chem Biol* 1(1):32-46). Since nucleic acid molecules may in many cases be more conveniently introduced into target cells than therapeutic protein molecules may be, aptamers offer a method by which 47174 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 47174 disorders. For a description of antibodies, see the Antibody section above.

In circumstances wherein injection of an animal or a human subject with a 47174 protein or epitope for stimulating antibody production is harmful to the subject, it is possible to generate an immune response against 47174 through the use of anti-idiotypic antibodies (see, for example, Herlyn (1999) *Ann Med* 31(1):66-78; and Bhattacharya-Chatterjee and Foon (1998) *Cancer Treat Res* 94:51-68). If an anti-idiotypic antibody is introduced into a mammal or human subject, it should stimulate the production of anti-anti-idiotypic antibodies, which should be specific to the 47174 protein. Vaccines directed to a disease characterized by 47174 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc Natl Acad Sci USA* 90:7889-7893).

The identified compounds that inhibit target gene expression, synthesis and/or activity can be administered to a patient at therapeutically effective doses to prevent, treat or ameliorate 47174 disorders, e.g., to control CNS disorders, e.g., pain or pain related disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 47174 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell et al (1996) *Current Opinion in Biotechnology* 7:89-94 and in Shea (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis et al (1993) *Nature* 361:645-647. Through the use of isotope-labeling, the "free" concentration of compound which modulates the expression or activity of 47174 can be readily monitored and used in calculations of IC50.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual IC50. An rudimentary example of such a "biosensor" is discussed in Kriz et al. (1995) *Analytical Chemistry* 67:2142-2144.

Another aspect of the invention pertains to methods of modulating 47174 expression or activity for therapeutic purposes. Accordingly, in an exemplary embodiment, the modulatory method of the invention involves contacting a cell with a 47174 or agent that modulates one or more of the activities of 47174 protein activity associated with the cell. An agent that modulates 47174 protein activity can be an agent as described herein, such as a nucleic acid or a protein, a naturally-occurring target molecule of a 47174 protein (e.g., a 47174 substrate or receptor), a 47174 antibody, a 47174 agonist or antagonist, a peptidomimetic of a 47174 agonist or antagonist, or other small molecule.

In one embodiment, the agent stimulates one or 47174 activities. Examples of such stimulatory agents include active 47174 protein and a nucleic acid molecule encoding 47174. In another embodiment, the agent inhibits one or more 47174 activities. Examples of such inhibitory agents include antisense 47174 nucleic acid molecules, anti 47174 antibodies, and 47174 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 47174 protein or nucleic acid molecule. In one embodiment, the method involves administering an agent (e.g., an agent identified by a screening assay described herein), or combination of agents that modulates (e.g., up regulates or down regulates) 47174 expression or activity. In another embodiment, the method involves administering a 47174 protein or nucleic acid molecule as therapy to compensate for reduced, aberrant, or unwanted 47174 expression or activity.

Stimulation of 47174 activity is desirable in situations in which 47174 is abnormally downregulated and/or in which increased 47174 activity is likely to have a beneficial effect. For example, stimulation of 47174 activity is desirable in situations in which a 47174 is downregulated and/or in which increased 47174 activity is likely to have a beneficial effect. Likewise, inhibition of 47174 activity is desirable in situations in which 47174 is abnormally upregulated and/or in which decreased 47174 activity is likely to have a beneficial effect.

47174 Pharmacogenomics

The 47174 molecules of the present invention, as well as agents, or modulators which have a stimulatory or inhibitory effect on 47174 activity (e.g., 47174 gene expression) as identified by a screening assay described herein can be administered to individuals to treat (prophylactically or therapeutically) 47174 associated disorders (e.g., CNS, pain, pain related disorders) associated with aberrant or unwanted 47174 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 47174 molecule or 47174 modulator as well as tailoring the dosage and/or therapeutic regimen of treatment with a 47174 molecule or 47174 modulator.

Pharmacogenomics deals with clinically significant hereditary variations in the response to drugs due to altered drug disposition and abnormal action in affected persons. See, for example, Eichelbaum et al. (1996) *Clin Exp Pharmacol Physiol* 23(10-11):983-985 and Linder et al. (1997) *Clin Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 47174 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 47174 molecule or 47174 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 47174 molecule or 47174 modulator, such as a modulator identified by one of the exemplary screening assays described herein.

The present invention further provides methods for identifying new agents, or combinations, that are based on identifying agents that modulate the activity of one or more of the gene products encoded by one or more of the 47174 genes of the present invention, wherein these products may be associated with resistance of the cells to a therapeutic agent. Specifically, the activity of the proteins encoded by the 47174 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 47174 protein can be applied in clinical trials. For example, the effectiveness of an agent determined by a screening assay as described herein to increase 47174 gene expression, protein levels, or upregulate 47174 activity, can be monitored in clinical trials of subjects exhibiting decreased 47174 gene expression, protein levels, or downregulated 47174 activity. Alternatively, the effectiveness of an agent determined by a screening assay to decrease 47174 gene expression, protein levels, or downregulate 47174 activity, can be monitored in clinical trials of subjects exhibiting increased 47174 gene expression, protein levels, or upregulated 47174 activity. In such clinical trials, the expression or activity of a 47174 gene, and preferably, other genes that have been implicated in, for example, a 47174-associated disorder can be used as a "read out" or markers of the phenotype of a particular cell.

47174 Informatics

The sequence of a 47174 molecule is provided in a variety of media to facilitate use thereof. A sequence can be provided as a manufacture, other than an isolated nucleic acid or amino acid molecule, which contains a 47174. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 47174 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 47174, e.g., analyzing structure, function, or relatedness to one or more other nucleic acid or amino acid sequences. The method includes: providing a 47174 nucleic acid or amino acid sequence; comparing the 47174 sequence with a second sequence, e.g., one or more preferably a plurality of sequences from a collection of sequences, e.g., a nucleic acid or protein sequence database to thereby analyze 47174. The method can be performed in a machine, e.g., a computer, or manually by a skilled artisan.

The method can include evaluating the sequence identity between a 47174 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 47174 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 47174 sequence, or record, in machine-readable form; comparing a second sequence to the 47174 sequence; thereby analyzing a sequence. Comparison can include comparing to sequences for sequence identity or determining if one sequence is included within the other, e.g., determining if the 47174 sequence includes a sequence being compared. In a preferred embodiment the 47174 or second sequence is stored on a first computer, e.g., at a first site and the comparison is performed, read, or recorded on a second computer, e.g., at a second site. E.g., the 47174 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 47174-associated disease or disorder or a pre-disposition to a 47174-associated disease or disorder, wherein the method comprises the steps of determining 47174 sequence information associated with the subject and based on the 47174 sequence information, determining whether the subject has a 47174-associated disease or disorder or a pre-disposition to a 47174-associated disease or disorder and/or recommending a particular treatment for the disease, disorder or pre-disease condition.

The invention further provides in an electronic system and/or in a network, a method for determining whether a subject has a 47174-associated disease or disorder or a pre-disposition to a disease associated with a 47174 wherein the method comprises the steps of determining 47174 sequence information associated with the subject, and based on the 47174 sequence information, determining whether the subject has a 47174-associated disease or disorder or a pre-disposition to a 47174-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 47174 sequence of the subject to the 47174 sequences in the database to thereby determine whether the subject as a 47174-associated disease or disorder, or a pre-disposition for such.

The present invention also provides in a network, a method for determining whether a subject has a 47174 associated disease or disorder or a pre-disposition to a 47174-associated disease or disorder associated with 47174, said method comprising the steps of receiving 47174 sequence information from the subject and/or information related thereto, receiving phenotypic information associated with the subject, acquiring information from the network corresponding to 47174 and/or corresponding to a 47174-associated disease or disorder (e.g., CNS or pain related disorders), and based on one or more of the phenotypic information, the 47174 information (e.g., sequence information and/or information related thereto), and the acquired information, determining whether the subject has a 47174-associated disease or disorder or a pre-disposition to a 47174-associated disease or disorder. The method may further comprise the step of recommending a particular treatment for the disease, disorder or pre-disease condition.

The present invention also provides a method for determining whether a subject has a 47174-associated disease or disorder or a pre-disposition to a 47174-associated disease or disorder, said method comprising the steps of receiving information related to 47174 (e.g., sequence information and/or information related thereto), receiving phenotypic information associated with the subject, acquiring information from the network related to 47174 and/or related to a 47174-associated disease or disorder, and based on one or more of the phenotypic information, the 47174 information, and the acquired information, determining whether the subject has a 47174-associated disease or disorder or a pre-disposition to a 47174-associated disease or disorder. The method may further comprise the step of recommending a particular treatment for the disease, disorder or pre-disease condition.

This invention is further illustrated by the following examples which should not be construed as limiting. The contents of all references, patents and published patent applications cited throughout this application are incorporated herein by reference.

Background of the 60491 Invention

Acyltransferases include a superfamily of enzymes that participate in phospholipid biosynthesis. Acyltransferases catalyze the transfer of an acyl chain to a lipid precursor and have been grouped into several subfamilies based upon their target specificity: lysophosphatidic acid acyltransferase (1-acyl-sn-glycerol-3-phosphate acyltransferase; LPAAT); sn-glycerol-3-phosphate acyltransferase (GPAT); acyl-CoA: dihydroxyacetone-phosphate acyltransferase (DHAPAT); and 2-acylglycerophosphatidylethanolamine acyltransferase (LPEAT). Acyltransferases generally contain four regions of conserved amino acid residues, suggesting that these may be domains relevant to the catalytic activity of the enzymes (Lewin et al. (1999) *Biochemistry* 38: 5764-71).

GPAT catalyzes the initial reaction in the pathway of glycerolipid biosynthesis, the transfer of an activated fatty acyl chain to the sn-1 position of glycerol 3-phosphate. LPAAT converts lysophosphatidic acid (LPA) into phosphatidic acid (PA) in the course of lipid metabolism in the ER (Eberhardt et al. (1997) *J Biol Chem* 272:20299-20305). LPAAT catalyses the transfer of an acyl chain from either acyl-coenzyme A or acyl-acyl carrier protein onto LPA, an intermediate in de novo lipid biosynthesis, to produce PA, the precursor of all glycerolipids. PA can either be hydrolyzed to yield diacylglycerol (DAG) or can be converted to CDP-DAG for the synthesis of more complex phospholipids in the ER. Two human cDNAs have been cloned that encode enzymes having LPAAT activity, LPAAT-α and LPAAT-β

(West et al. (1997) *DNA Cell Biol* 16: 691-701; Eberhardt et al. (1997) *J Biol Chem* 272: 20299-20305; Aguado and Campbell (1998) *J. Biol Chem* 273: 4096-4105). Both human LPAATs localize to the ER. LPAAT-α and LPAAT-β are encoded by genes located on chromosomes 6 and 9, respectively.

Aside from its role in the formation of biological membranes, LPA is produced by activated platelets and functions as a bioactive mediator, stimulating platelet aggregation, cell proliferation, cell migration, and cell proliferation (Lee et al. (2000) *Am J Physiol Cell Physiol* 278: 612-18). LPA generated in the plasma membrane of activated platelets and growth factor-stimulated fibroblasts appears to arise from hydrolysis of PA by a phospholipase A2. One possible means of the attenuation of the bioactive effects of LPA is acylation by LPAAT to yield PA. PA also has been implicated as an intracellular messenger, suggesting that its generation via acylation of LPA by LPAAT at an inflammatory site may lead to further cellular activation (Eberhardt et al. (1999) *Adv Exp Med Biol* 469: 351-356).

Several specific acyltransferases have been found to participate in critical biological functions. Endophilin 1, an SH3 domain-containing LPAAT, mediates the formation of synaptic-like microvesicles (SLMVs) from the plasma membrane via the conversion of LPA to PA (Schmidt et al. (1999) *Nature* 401:133-141). Barth syndrome is associated with mutations in a gene that encodes, by means of alternate splicing, several putative acyltransferases known as tafazzins. Barth syndrome is characterized by short stature, cardioskeletal myopathy, neutropenia, abnormal mitochondria, and respiratory-chain dysfunction (Bione et al. (1996) *Nature Genetics* 12: 385-389).

Summary of the 6091 Invention

The present invention is based, in part, on the discovery of a novel acyltransferase family member, referred to herein as "60491". The nucleotide sequence of a cDNA encoding 60491 is shown in SEQ ID NO:48, and the amino acid sequence of a 60491 polypeptide is shown in SEQ ID NO:49. In addition, the nucleotide sequences of the coding region are depicted in SEQ ID NO:50.

Accordingly, in one aspect, the invention features a nucleic acid molecule that encodes a 60491 protein or polypeptide, e.g., a biologically active portion of the 60491 protein. In a preferred embodiment the isolated nucleic acid molecule encodes a polypeptide having the amino acid sequence of SEQ ID NO:49. In other embodiments, the invention provides isolated 60491 nucleic acid molecules having the nucleotide sequence shown in SEQ ID NO:48, or SEQ ID NO:50. In still other embodiments, the invention provides nucleic acid molecules that are substantially identical (e.g., naturally occurring allelic variants) to the nucleotide sequence shown in SEQ ID NO:48, or SEQ ID NO:50. In other embodiments, the invention provides a nucleic acid molecule which hybridizes under a stringency condition described herein to a nucleic acid molecule comprising the nucleotide sequence of SEQ ID NO:48, or SEQ ID NO:50, wherein the nucleic acid encodes a full length 60491 protein or an active fragment thereof.

In a related aspect, the invention further provides nucleic acid constructs that include a 60491 nucleic acid molecule described herein. In certain embodiments, the nucleic acid molecules of the invention are operatively linked to native or heterologous regulatory sequences. Also included, are vectors and host cells containing the 60491 nucleic acid molecules of the invention e.g., vectors and host cells suitable for producing 60491 nucleic acid molecules and polypeptides.

In another related aspect, the invention provides nucleic acid fragments suitable as primers or hybridization probes for the detection of 60491-encoding nucleic acids.

In still another related aspect, isolated nucleic acid molecules that are antisense to a 60491 encoding nucleic acid molecule are provided.

In another aspect, the invention features, 60491 polypeptides, and biologically active or antigenic fragments thereof that are useful, e.g., as reagents or targets in assays applicable to treatment and diagnosis of 60491-mediated or -related disorders. In another embodiment, the invention provides 60491 polypeptides having a 60491 activity. Preferred polypeptides are 60491 proteins including at least one acyltransferase domain, and, preferably, having a 60491 activity, e.g., a 60491 activity as described herein.

In other embodiments, the invention provides 60491 polypeptides, e.g., a 60491 polypeptide having the amino acid sequence shown in SEQ ID NO:49; an amino acid sequence that is substantially identical to the amino acid sequence shown in SEQ ID NO:49; or an amino acid sequence encoded by a nucleic acid molecule having a nucleotide sequence which hybridizes under a stringency condition described herein to a nucleic acid molecule comprising the nucleotide sequence of SEQ ID NO:48, SEQ ID NO:50, wherein the nucleic acid encodes a full length 60491 protein or an active fragment thereof.

In a related aspect, the invention further provides nucleic acid constructs that include a 60491 nucleic acid molecule described herein.

In a related aspect, the invention provides 60491 polypeptides or fragments operatively linked to non-60491 polypeptides to form fusion proteins.

In another aspect, the invention features antibodies and antigen-binding fragments thereof, that react with, or more preferably specifically bind 60491 polypeptides or fragments thereof, e.g., an acyltransferase domain.

In another aspect, the invention provides methods of screening for compounds that modulate the expression or activity of the 60491 polypeptides or nucleic acids.

In still another aspect, the invention provides a process for modulating 60491 polypeptide or nucleic acid expression or activity, e.g. using the screened compounds. In certain embodiments, the methods involve treatment of conditions related to aberrant activity or expression of the 60491 polypeptides or nucleic acids, such as conditions involving conditions involving brain disorders, pain response, or pain related disorders, as well as cardiovascular disorders.

The invention also provides assays for determining the activity of or the presence or absence of 60491 polypeptides or nucleic acid molecules in a biological sample, including for disease diagnosis.

In still another aspect, the invention features a method of modulating (e.g., enhancing or inhibiting) an activity of a cell, e.g., a 60491-expressing cell (e.g., a brain cell or a neural cell), or a response (e.g., a neurological or pain response) in a subject. The method includes contacting the cell with, or administered to the subject, an agent, e.g., a compound, that modulates the activity or expression of a 60491 polypeptide or nucleic acid, in an amount effective to modulate the activity or the response.

In a preferred embodiment, the agent modulates (e.g., increases or decreases) catalysis of the transfer of an acyl chain to a lipid precursor, or lipid biosynthesis.

In a preferred embodiment, the agent modulates (e.g., increases or decreases) expression of the 60491 nucleic acid by, e.g., modulating transcription, mRNA stability, etc.

In a preferred embodiment, the cell, e.g., the 60491-expressing cell, is a brain cell, e.g., a cortical or a hypothalamic cell; a cell in an area involved in pain control, e.g., a cell in the dorsal root ganglion or the substantia gelatinosa of the spinal cord, or a cell in the periaqueductal gray matter. In other embodiments, the cell is a cardiovascular or a blood vessel cell. Examples of cardiovascular or blood vessel cells include arterial cells, coronary smooth muscle cells, vascular endothelial cells, as well as skeletal muscle cells, skin cells, normal and malignant breast and ovarian cells.

In a preferred embodiment, the agent, e.g., the compound, and the 60491-polypeptide or nucleic acid are contacted in vitro or ex vivo. In a preferred embodiment, the contacting step is effected in vivo in a subject, e.g., as part of a therapeutic or prophylactic protocol. The contacting or administering step(s) can be repeated.

Preferably, the subject is a human, e.g., a patient with a brain disorder, pain-associated disorder, or a cardiovascular or blood vessel disorder disclosed herein.

In preferred embodiments, the agent is a peptide, a phosphopeptide, a small molecule, e.g., a member of a combinatorial library, or an antibody, or any combination thereof. The antibody can be conjugated to a therapeutic moiety selected from the group consisting of a cytotoxin, a cytotoxic agent and a radioactive metal ion.

In additional preferred embodiments, the agent is an antisense molecule, a ribozyme, a triple helix molecule, or a 60491 nucleic acid, or any combination thereof.

In a preferred embodiment, the agent is administered in combination with a cytotoxic agent.

In another aspect, the invention features a method of treating or preventing, in a subject, a 60491-associated disorder. The method includes administering to the subject, e.g., a subject at risk of, or afflicted with, a 60491-associated disorder, an agent, e.g., a compound as described herein, that modulates the activity or expression of a 60491 polypeptide or nucleic acid, in an amount effective to treat or prevent the disorder.

In a preferred embodiment, the disorder is a brain disorder, a pain-associated disorder, or a cardiovascular or blood vessel disorder.

In a preferred embodiment, the subject is a subject as described herein, e.g., a human.

In still another aspect, the invention features a method for evaluating the efficacy of a treatment of a disorder, e.g., a disorder disclosed herein, in a subject. The method includes treating a subject with a protocol under evaluation; assessing the expression of a 60491 nucleic acid or 60491 polypeptide, such that a change in the level of 60491 nucleic acid or 60491 polypeptide after treatment, relative to the level before treatment, is indicative of the efficacy of the treatment of the disorder.

In a preferred embodiment, the disorder is a brain disorder, a pain-associated disorder, or a cardiovascular or blood vessel disorder.

In a preferred embodiment, the subject is a human.

The invention also features a method of diagnosing a disorder, e.g., a disorder disclosed herein, in a subject. The method includes evaluating the expression or activity of a 60491 nucleic acid or a 60491 polypeptide, such that, a difference in the level of 60491 nucleic acid or 60491 polypeptide relative to a normal subject or a cohort of normal subjects is indicative of the disorder.

In a preferred embodiment, the disorder is a brain disorder, a pain-associated disorder, or a cardiovascular or blood vessel disorder.

In a preferred embodiment, the subject is a human.

In a preferred embodiment, the evaluating step occurs in vitro or ex vivo. For example, a sample, e.g., a blood sample, is obtained from the subject.

In a preferred embodiment, the evaluating step occurs in vivo. For example, by administering to the subject a detectably labeled agent that interacts with the 60491 nucleic acid or polypeptide, such that a signal is generated relative to the level of activity or expression of the 60491 nucleic acid or polypeptide.

The invention also provides assays for determining the activity of or the presence or absence of 60491 polypeptides or nucleic acid molecules in a biological sample, including for disease diagnosis.

In further aspect, the invention provides assays for determining the presence or absence of a genetic alteration in a 60491 polypeptide or nucleic acid molecule, including for disease diagnosis.

In yet another aspect, the invention features a method for identifying an agent, e.g., a compound, which modulates the activity of a 60491 polypeptide, e.g., a 60491 polypeptide as described herein, or the expression of a 60491 nucleic acid, e.g., a 60491 nucleic acid as described herein, including contacting the 60491 polypeptide or nucleic acid with a test agent (e.g., a test compound); and determining the effect of the test compound on the activity of the 60491 polypeptide or nucleic acid to thereby identify a compound which modulates the activity of the 60491 polypeptide or nucleic acid.

In a preferred embodiment, the activity of the 60491 polypeptide is an acyltransferase activity, e.g., catalysis of the transfer of an acyl chain to a lipid precursor.

In a preferred embodiment, the activity of the 60491 polypeptide is catalysis of the transfer of an acyl chain to a lipid precursor.

In a preferred embodiment, the activity of the 60491 polypeptide is modulation of brain or cardiovascular disorders, or pain response.

In preferred embodiments, the agent is a peptide, a phosphopeptide, a small molecule, e.g., a member of a combinatorial library, or an antibody, or any combination thereof.

In additional preferred embodiments, the agent is an antisense, a ribozyme, or a triple helix molecule, or a 60491 nucleic acid, or any combination thereof.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 60491 molecule. In one embodiment, the capture probe is a nucleic acid, e.g., a probe complementary to a 60491 nucleic acid sequence. In another embodiment, the capture probe is a polypeptide, e.g., an antibody specific for 60491 polypeptides. Also featured is a method of analyzing a sample by contacting the sample to the aforementioned array and detecting binding of the sample to the array.

Other features and advantages of the invention will be apparent from the following detailed description, and from the claims.

Detailed Description of 60491

The human 60491 sequence (see SEQ ID NO:48, as recited in Example 38), which is approximately 2682 nucleotides long including untranslated regions, contains a predicted methionine-initiated coding sequence of about 2328 nucleotides, including the termination codon. The coding sequence encodes a 775 amino acid protein (see SEQ ID NO:49, as recited in Example 38).

Human 60491 contains the following regions or other structural features:

one acyltransferase domain (SMART Number SM0563) located at about amino acid residues 199 to 333 of SEQ ID NO:49;

one predicted transmembrane domain located at about amino acids 450 to 472 of SEQ ID NO:49;

one predicted N-terminal cytoplasmic domain located at about amino acids 1 to 449 of SEQ ID NO:49;

one predicted C-terminal cytoplasmic domain located at about amino acids 473 to 775 of SEQ ID NO:49;

one predicted glycosaminoglycan attachment site (PS00002) located at about amino acids 27 to 30 of SEQ ID NO:49;

one predicted cAMP- and cGMP-dependent protein kinase phosphorylation site (PS00004) located at about amino acids 444 to 447 of SEQ ID NO:49;

ten predicted Protein Kinase C phosphorylation sites (PS00005) located at about amino acids 18 to 20, 55 to 57, 125 to 127, 204 to 206, 369 to 371, 390 to 392, 419 to 421, 622 to 624, 628 to 630, and 732 to 734 of SEQ ID NO:49;

ten predicted Casein Kinase II phosphorylation sites (PS00006) located at about amino acids 3 to 6, 18 to 21, 66 to 69, 207 to 210, 383 to 386, 419 to 422, 589 to 592, 640 to 643, 711 to 714, and 732 to 735 of SEQ ID NO:49;

nine predicted N-myristoylation sites (PS00008) located at about amino acids 131 to 136, 350 to 355, 396 to 401, 411 to 416, 477 to 482, 505 to 510, 568 to 573, 615 to 620, and 716 to 721 of SEQ ID NO:49;

one predicted leucine zipper site (PS00029) located at about amino acids 511 to 532 of SEQ ID NO:49; and ten predicted dileucine motifs located at about amino acids 123 to 124, 168 to 169, 201 to 202, 208 to 209, 213 to 214, 218 to 219, 242 to 243, 265 to 266, 278 to 279, and 285 to 286 of SEQ ID NO:49.

For general information regarding PFAM identifiers, PS prefix and PF prefix domain identification numbers, refer to Sonnhammer et al. (1997) *Protein* 28:405-420.

The 60491 protein contains a significant number of structural characteristics in common with members of the acyltransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

Acyltransferase family members have a characteristic structure. The three-dimensional structure of recombinant glycerol-3-phosphate-acyltransferase from squash chloroplast has been determined by X-ray crystallography and provides the first representative structure of an enzyme of this class. The tertiary structure comprises two domains, the larger of which, domain II, features an extensive cleft lined by hydrophobic residues and contains at one end a cluster of positively charged residues flanked by a $H(X)_4D$ motif, which is conserved amongst many glycerolipid acyltransferases. These hydrophobic and positively charged residues represent the binding sites for the fatty acyl substrate and the phosphate moiety of the glycerol 3-phosphate, respectively, and that the $H(X)_4D$ motif is a critical component of the enzyme's catalytic machinery. See Turnbull et al. (2001) *Structure* 9(5): 347-53.

Phosphate acyltransferases function in phospholipid biosynthesis and have either glycerolphosphate, 1-acylglycerolphosphate, or 2-acylglycerolphosphoethanolamine acyltransferase activities. Genetic alterations in these acyltransferases have been associated with Barth syndrome (Neuwald, A F. (1997) *Curr Biol* 7: 4656-4656).

A 60491 polypeptide can include an "acyltransferase domain" or regions homologous with an "acyltransferase domain." As used herein, the term "acyltransferase domain" includes an amino acid sequence of about 50 to 400 amino acid residues in length and having a bit score for the alignment of the sequence to the acyltransferase domain (SMART) of at least 20. Preferably, an acyltransferase domain includes at least about 100 to 300 amino acids, more preferably about 120 to 205 amino acid residues, and has a bit score for the alignment of the sequence to the acyltransferase domain (SMART) of at least 30, 40, 50, 57, or greater. The acyltransferase domain (HMM) has been assigned the SMART identifier plsc. An alignment of the acyltransferase domain (amino acids 199 to 333 of SEQ ID NO:49) of human 60491 with a consensus amino acid sequence (SEQ ID NO:52) derived from a hidden Markov model according to SMART is depicted in FIG. 47.

Typically, an acyltransferase domain includes one histidine and one aspartic acid residues located approximately 4 amino acids apart, i.e., $H(X)_4D$. For example, the acyltransferase domain of the 60491 polypeptide HKTLLD which matches this motif at position about 206 to 211 of SEQ ID NO:49.

In a preferred embodiment 60491 polypeptide or protein has an "acyltransferase" or a region which includes at least about 50 to 400, preferably about 120 to 205 amino acid residues and has at least about 60%, 70% 80% 90% 95%, 99%, or 100% homology with a "acyltransferase," e.g., the acyltransferase domains of human 60491 (e.g., residues 199 to 333 of SEQ ID NO:49).

To identify the presence of a "acyltransferase" domain in a 60491 protein sequence, and make the determination that a polypeptide or protein of interest has a particular profile, the amino acid sequence of the protein can be searched against a SMART database (Simple Modular Architecture Research Tool) of HMMs as described in Schultz et al. (1998), *Proc. Natl. Acad. Sci. USA* 95:5857 and Schultz et al. (200) *Nucl. Acids Res* 28:231. The database contains domains identified by profiling with the hidden Markov models of the HMMer2 search program (R. Durbin et al. (1998) *Biological sequence analysis: probabilistic models of proteins and nucleic acids.* Cambridge University Press.; http://hmmer.wustl.edu/). The database also is extensively annotated and monitored by experts to enhance accuracy. A search was performed against the HMM database resulting in the identification of a "acyltransferase" domain in the amino acid sequence of human 60491 at about residues 199 to 333 of SEQ ID NO:50 (see FIG. 46).

An alignment of the acyltransferase domain (amino acids 190 to 393 of SEQ ID NO:49) of human 60491 with a consensus amino acid sequence (SEQ ID NO:51) derived from a hidden Markov model according to PFAM is depicted in FIG. 46. BLAST alignments of the acyltransferase domain of human 60491 with a consensus amino acid sequence derived from a ProDomain Nos. 353751, 7717, 025192, and 042760 (7717 is from the Release 1999.2; 353751, 025192, and 042760 are from the Release 2001.1; are depicted in FIGS. 48A-48D. The lower sequence is the consensus amino acid sequence (SEQ ID NOs:53-56, respectively), while the upper amino acid sequence corresponds to the acyltransferase domain of human 60491, about amino acids 40 to 125, 104 to 395, 442 to 593, and 690 to 773 of SEQ ID NO:49, respectively.

A 60491 family member can include at least one transmembrane domain. As used herein, the term "transmembrane domain" includes an amino acid sequence of about 15 amino acid residues in length that spans a phospholipid membrane. More preferably, a transmembrane domain includes about at least 17, 19, 21 or 23 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al, (1996) *Ann. Rev. Neurosci.* 19: 235-63, the contents of which are incorporated herein by reference.

In a preferred embodiment, a 60491 polypeptide or protein has at least one transmembrane domain or a region which includes at least 17, 19, 21, 22 or 23 amino acid residues and has at least about 60%, 70% 80% 90% 95%, 99%, or 100% homology with a "transmembrane domain," e.g., at least one transmembrane domain of human 60491 (e.g., amino acid residues 450 to 472 of SEQ ID NO:49).

A 60491 protein further includes a predicted N-terminal cytoplasmic domain located at about amino acids 1 to 449 of SEQ ID NO:49. As used herein, a "N-terminal cytoplasmic domain" includes an amino acid sequence having about 1 to 700, preferably about 100 to 500, or even more preferably about 1 to 450 amino acid residues in length and is located inside of a cell or intracellularly. The C-terminal amino acid residue of a "N-terminal cytoplasmic domain" is adjacent to a N-terminal amino acid residue of a transmembrane domain in a 60491 protein. For example, a N-terminal cytoplasmic domain is located at about amino acid residues 1 to 449 of SEQ ID NO:49.

In a preferred embodiment 60491 polypeptide or protein has an "N-terminal cytoplasmic domain" or a region which includes at least about 1 to 700, preferably about 100 to 500, and even more preferably about 449 amino acid residues and has at least about 60%, 70% 80% 90% 95%, 99%, or 100% homology with an "N-terminal cytoplasmic domain," e.g., the N-terminal cytoplasmic domain of human 60491 (e.g., residues 1 to 449 of SEQ ID NO:49).

In another embodiment, a 60491 protein includes a "C-terminal cytoplasmic domain," also referred to herein as a C-terminal cytoplasmic tail, in the sequence of the protein. As used herein, a "C-terminal cytoplasmic domain" includes an amino acid sequence having a length of at least about 100, more preferably 150, 200 or more amino acid residues and is located within a cell or within the cytoplasm of a cell. Accordingly, the N-terminal amino acid residue of a "C-terminal cytoplasmic domain" is adjacent to a C-terminal amino acid residue of a transmembrane domain in a naturally-occurring 60491 protein. For example, a C-terminal cytoplasmic domain is found at about amino acid residues 473 to 775 of SEQ ID NO:49.

In a preferred embodiment, a 60491 polypeptide or protein has a C-terminal cytoplasmic domain or a region which includes at least about 100, more preferably 150, 200 or more amino acid residues and has at least about 60%, 70% 80% 90% 95%, 99%, or 100% homology with an "C-terminal cytoplasmic domain," e.g., the C-terminal cytoplasmic domain of human 60491 (e.g., residues 473 to 775 of SEQ ID NO:49).

As used herein, a "leucine zipper" consists of a periodic repetition of leucine residues at every seventh position over a distance covering helical turns. The segments containing these periodic arrays of leucine residues seem to exist in an alpha-helical conformation. The leucine side chains extending from one alpha-helix interact with those from a similar alpha helix of a second polypeptide, facilitating dimerization; the structure formed by cooperation of these two regions forms a coiled coil. See, e.g., Landschulz et al. (1988) *Science* 240: 1759-1764; and O'Shea et al. (1989) *Science* 243: 538-542. A 60491 polypeptide or protein has at least one leucine zipper or a region which includes at least 15, 17, 19, 20 or 22 amino acid residues and has at least about 60%, 70% 80% 90% 95%, 99%, or 100% homology with a "leucine zipper," e.g., a leucine zipper of human 60491 (e.g., amino acid residues 511 to 532 of SEQ ID NO:49).

A 60491polypeptide can further include at least one, two, three, four, five, six, seven, eight, nine or preferably ten protein kinase C phosphorylation sites (PS00005); at least one, two, three, four, five, six, seven, eight, nine or preferably ten predicted casein kinase II phosphorylation sites (PS00006); at least one, two, three, four, five, six, seven, eight, or preferably nine predicted N-myristylation sites (PS00008); and at least one, two, three, four, five, six, seven, eight, nine, or preferably ten predicted dileucine motifs.

As the 60491 polypeptides of the invention may modulate 60491-mediated activities, they may be useful as of for developing novel diagnostic and therapeutic agents for 60491-mediated or related disorders, as described below.

As used herein, a "60491 activity", "biological activity of 60491" or "functional activity of 60491," refers to an activity exerted by a 60491 protein, polypeptide or nucleic acid molecule. For example, a 60491 activity can be an activity exerted by 60491 in a physiological milieu on, e.g., a 60491-responsive cell or on a 60491 substrate, e.g., a protein substrate. A 60491 activity can be determined in vivo or in vitro. In one embodiment, a 60491 activity is a direct activity, such as an association with a 60491 target molecule. A "target molecule" or "binding partner" is a molecule with which a 60491 protein binds or interacts in nature.

In an exemplary embodiment, 60491 is an enzyme that catalyzes the transfer of an acyl chain to a lipid precursor.

A 60491 activity can also be an indirect activity, e.g., a cellular signaling activity mediated by interaction of the 60491 protein with a 60491 receptor. The features of the 60491 molecules of the present invention can provide similar biological activities as acyltransferase family members. Acyltransferases play a role in diverse cellular processes. For example, the biosynthesis of complex lipids involves specific acylation reactions catalyzed by acyltransferases. These reactions are important for the formation of storage lipids, triacylglycerols, as well as structural lipids such as phospholipids and galactolipids. Acyltransferases also participate in signaling by regulating the levels of lipids that function as signaling molecules in diverse cellular processes. For example, the 60491 proteins of the present invention can have one or more of the following activities: 1) catalysis of the transfer of an acyl chain to a lipid precursor; 2) regulation of lipid biosynthesis; 3) modulation of cellular differentiation; 4) modulation of cellular proliferation; 5) modulation of mitogenesis; 6) modulation of neurite retraction; 7) modulation of pain or inflammation response; 8) modulation of tumor cell growth and invasion; or 9) the ability to antagonize or inhibit, competitively or non-competitively, any of 1-8.

Thus, the 60491 molecules can act as novel diagnostic targets and therapeutic agents for controlling a brain disorder, a pain disorder, or a cardiovascular disorder.

60491 mRNA is expressed in human artery, coronary smooth muscle cells (SMC), human vascular endothelial cells (HUVEC), heart, skeletal muscle, pancreas, brain cortex, brain hypothalamus, nerve, dorsal root ganglion (DRG), and skin decubitus. The highest 60491 mRNA expression was observed in brain cortex, brain hypothalamus, nerve, and dorsal root ganglion (Table 19). It suggests a role for 60491 in modulation of the activity of lipid biosynthesis in brain the nervous system. Thus, the 60491 molecules can act as novel diagnostic targets and therapeutic agents controlling a brain or pain-associated disorder, as well as a cardiovascular disorder.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, *Herpes simplex* virus Type 1, *Herpes simplex* virus Type 2, *Varicalla-zoster* virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinson's, idiopathic Parkinson disease (paralysis agitans), progressive supranuclear palsy, corticobasal degeneration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Examples of pain conditions include, but are not limited to, pain elicited during various forms of tissue injury, e.g., inflammation, infection, and ischemia; pain associated with musculoskeletal disorders, e.g., joint pain, or arthritis; tooth pain; headaches, e.g., migrane; pain associated with surgery; pain related to inflammation, e.g., irritable bowel syndrome; chest pain; or hyperalgesia, e.g., excessive sensitivity to pain (described in, for example, Fields (1987) *Pain*, New York: McGraw-Hill). Other examples of pain disorders or pain syndromes include, but are not limited to, complex regional pain syndrome (CRPS), reflex sympathetic dystrophy (RSD), causalgia, neuralgia, central pain and dysesthesia syndrome, carotidynia, neurogenic pain, refractory cervicobrachial pain syndrome, myofascial pain syndrome, craniomandibular pain dysfunction syndrome, chronic idiopathic pain syndrome, Costen's pain-dysfunction, acute chest pain syndrome, nonulcer dyspepsia, interstitial cystitis, gynecologic pain syndrome, patellofemoral pain syndrome, anterior knee pain syndrome, recurrent abdominal pain in children, colic, low back pain syndrome, neuropathic pain, phantom pain from amputation, phantom tooth pain, or pain asymbolia (the inability to feel pain). Other examples of pain conditions include pain induced by parturition, or post partum pain.

Agents that modulate 60491 polypeptide or nucleic acid activity or expression can be used to treat pain elicited by any medical condition. A subject receiving the treatment can be additionally treated with a second agent, e.g., an anti-inflammatory agent, an antibiotic, or a chemotherapeutic agent, to further ameliorate the condition.

The 60491 molecules can also act as novel diagnostic targets and therapeutic agents controlling pain caused by other disorders, e.g., cancer, e.g., prostate cancer. For example, endothelin, which is inactivated by neprilysin, is associated with the excruciating, debilitating pain that comes when prostate cancer invades the bone (reviewed in Nelson and Carducci (2000) *BJU Int* 85 Suppl 2: 45-8). In addition, a neprolysin family member can be a marker of common acute lymphoblastic leukemia antigen present at the surface of B cells (Roques et al. (1993) *Pharmacol Rev* 45: 87). Accordingly, the 14063 molecules can act as novel diagnostic targets and therapeutic agents for controlling one or more of cellular proliferative and/or differentiative disorders, or pain therefrom.

As the 60491 mRNA is expressed in cardiovascular cells, 60491 agents can be used as diagnostic or therapeutic targets for cardiovascular or blood vessel-associated disorders. As used herein, disorders involving the heart, or "cardiovascular diseases" or a "cardiovascular disorders" include diseases or disorders which affect the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. A cardiovascular disorder includes, but is not limited to disorders such as arteriosclerosis, atherosclerosis, cardiac hypertrophy, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, valvular disease, including but not limited to, valvular degeneration caused by calcification, rheumatic heart disease, endocarditis, or complications of artificial valves; atrial fibrillation, long-QT syndrome, congestive heart failure, sinus node dysfunction, angina, heart failure, hypertension, atrial fibrillation, atrial flutter, pericardial disease, including but not limited to, pericardial effusion and pericarditis; cardiomyopathies, e.g., dilated cardiomyopathy or idiopathic cardiomyopathy, myocardial infarction, coronary artery disease, coronary artery spasm, ischemic disease, arrhythmia, sudden cardiac death, and cardiovascular developmental disorders (e.g., arteriovenous malformations, arteriovenous fistulae, raynaud's syndrome, neurogenic thoracic outlet syndrome, causalgia/reflex sympathetic dystrophy, hemangioma, aneurysm, cavernous angioma, aortic valve stenosis, atrial septal defects, atrioventricular canal, coarctation of the aorta, ebsteins anomaly, hypoplastic left heart syndrome, interruption of the aortic arch, mitral valve prolapse, ductus arteriosus, patent foramen ovale, partial anomalous pulmonary venous return, pulmonary atresia with ventricular septal defect, pulmonary atresia without ventricular septal defect, persistance of the fetal circulation, pulmonary valve stenosis, single ventricle, total anomalous pulmonary venous return, transposition of the great vessels, tricuspid atresia, truncus arteriosus, ventricular septal defects). A cardiovasular disease or disorder can also include an endothelial cell disorder and a hematological disorder.

A hematological disorder can include thrombosis. Thrombosis can result from platelet dysfunction, e.g., seen in myocardial infarction, angina, hypertension, lipid disorders, diabetes mellitus; myelodysplastic syndromes; myeloproliferative syndromes (including polycythemia vera and thombocythemia); thrombotic thrombocytopenic purpuras; HIV-induced platelet disorders (AIDS-Thrombocytopenia); heparin induced thrombocytopenia; mural cell alterations/interactions leading to platelet aggregation/degranulation, vascular endothelial cell activation/injury, monocyte/macrophage extravasation and smooth muscle cell proliferation; autoimmune disorders such as, but not limited to vasculitis, antiphospholipid syndromes, systemic lupus erythromatosis; inflammatory diseases, such as, but not limited to immune activation; graft vs. host disease; radiation induced hypercoagulation; clotting factor dysregulation either hereditary (autosomal dominant or recessive) such as, but not limited to clotting factor pathways including protein C/S, Anti-thrombin III deficiency, and the Factor V Leiden mutation or acquired such as but not limited to autoimmune, cancer-associated and drug-induced dysregulation of clotting factors.

As used herein, an "endothelial cell disorder" includes a disorder characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

As the 60491 mRNA is expressed, albeit at low levels, in the normal and malignant breast and ovaries, 60491 molecules can act as diagnostic and therapeutic targets for cellular proliferative and/or differentiative disorders. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of breast, ovary, prostate, colon, lung, and liver origin.

The 60491 protein, fragments thereof, and derivatives and other variants of the sequence in SEQ ID NO:49 thereof are collectively referred to as "polypeptides or proteins of the invention" or "60491 polypeptides or proteins". Nucleic acid molecules encoding such polypeptides or proteins are collectively referred to as "nucleic acids of the invention" or "60491 nucleic acids." 60491 molecules refer to 60491 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:48 or SEQ ID NO:50, corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a 60491 protein. The gene can optionally further include non-coding sequences, e.g., regulatory sequences and introns. Preferably, a gene encodes a mammalian 60491 protein or derivative thereof.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of 60491 protein is at least 10% pure. In a preferred embodiment, the preparation of 60491 protein has less than about 30%, 20%, 10% and more preferably 5% (by dry weight), of non-60491 protein (also referred to herein as a "contaminating protein"), or of chemical precursors or non-60491 chemicals. When the 60491 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 60491 without abolishing or substantially altering a 60491 activity. Preferably the alteration does not substantially alter the 60491 activity, e.g., the activity is at least 20%, 40%, 60%, 70% or 80% of wild-type. An "essential" amino acid residue is a residue that, when altered from the wild-type sequence of 60491, results in abolishing a 60491 activity such that less than 20% of the wild-type activity is present. For example, conserved amino acid residues in 60491 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 60491 protein is preferably replaced with another amino acid residue from the same side chain family. Alternatively, in another embodiment, mutations can be introduced randomly along all or part of a 60491 coding sequence, such as by saturation mutagenesis, and the resultant mutants can be screened for 60491 biological activity to identify mutants that retain activity. Following mutagenesis of SEQ ID NO:48 or SEQ ID NO:50, the encoded protein can be expressed recombinantly and the activity of the protein can be determined.

As used herein, a "biologically active portion" of a 60491 protein includes a fragment of a 60491 protein that participates in an interaction, e.g., an intramolecular or an intermolecular interaction. An inter-molecular interaction can be a specific binding interaction or an enzymatic interaction (e.g., the interaction can be transient and a covalent bond is formed or broken). An inter-molecular interaction can be between a 60491 molecule and a non-60491 molecule or between a first 60491 molecule and a second 60491 molecule (e.g., a dimerization interaction). Biologically active portions of a 60491 protein include peptides comprising amino acid sequences sufficiently homologous to or derived from the amino acid sequence of the 60491 protein, e.g., the amino acid sequence shown in SEQ ID NO:49, which include less amino acids than the full length 60491 proteins, and exhibit at least one activity of a 60491 protein. Typically, biologically active portions comprise a domain or motif with at least one activity of the 60491 protein, e.g., catalyzation of the transfer of an acyl chain to a lipid precursor. A biologically active portion of a 60491 protein can be a polypeptide which is, for example, 10, 25, 50, 100, 200 or more amino acids in length. Biologically active portions of a 60491 protein can be used as targets for developing agents which modulate a 60491 mediated activity, e.g., catalyzation of the transfer of an acyl chain to a lipid precursor.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to 60491 nucleic acid molecules of the invention. BLAST protein searches can be performed with the XBLAST program, score=50, wordlength=3 to obtain amino acid sequences homologous to 60491 protein molecules of the invention. To obtain gapped alignments for comparison purposes, Gapped BLAST can be utilized as described in Altschul et al., (1997) *Nucleic Acids Res.* 25: 3389-3402. When utilizing BLAST and Gapped BLAST programs, the default parameters of the respective programs (e.g., XBLAST and NBLAST) can be used.

Particularly preferred 60491 polypeptides of the present invention have an amino acid sequence substantially identical to the amino acid sequence of SEQ ID NO:49. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:49 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:48 or 50 are termed substantially identical.

"Misexpression or aberrant expression," as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells," as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules of 60491

In one aspect, the invention provides, an isolated or purified, nucleic acid molecule that encodes a 60491 polypeptide described herein, e.g., a full-length 60491 protein or a fragment thereof, e.g., a biologically active portion of 60491 protein. Also included is a nucleic acid fragment suitable for use as a hybridization probe, which can be used, e.g., to identify a nucleic acid molecule encoding a polypeptide of the invention, 60491 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:48, or a portion of any of these nucleotide sequences. In one embodiment, the nucleic acid molecule includes sequences encoding the human 60491 protein (i.e., "the coding region" of SEQ ID NO:48, as shown in SEQ ID NO:50), as well as 5' untranslated sequences. Alternatively, the nucleic acid molecule can include only the coding region of SEQ ID NO:48 (e.g., SEQ ID NO:50) and, e.g., no flanking sequences which normally accompany the subject sequence. In another embodiment, the nucleic acid molecule encodes a sequence corresponding to a fragment of the protein from about amino acid 199 to 333.

In another embodiment, an isolated nucleic acid molecule of the invention includes a nucleic acid molecule which is a complement of the nucleotide sequence shown in SEQ ID NO:48 or SEQ ID NO:50, or a portion of any of these nucleotide sequences. In other embodiments, the nucleic acid molecule of the invention is sufficiently complementary to the nucleotide sequence shown in SEQ ID NO:48 or SEQ ID NO:50, such that it can hybridize (e.g., under a stringency condition described herein) to the nucleotide sequence shown in SEQ ID NO:48 or 50, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:48 or SEQ ID NO:50, or a portion, preferably of the same length, of any of these nucleotide sequences.

60491 Nucleic Acid Fragments

A nucleic acid molecule of the invention can include only a portion of the nucleic acid sequence of SEQ ID NO:48 or 50. For example, such a nucleic acid molecule can include a fragment which can be used as a probe or primer or a fragment encoding a portion of a 60491 protein, e.g., an immunogenic or biologically active portion of a 60491 protein. A fragment can comprise those nucleotides of SEQ ID NO:48, which encode an acyltransferase domain of human 60491. The nucleotide sequence determined from the cloning of the 60491 gene allows for the generation of probes and primers designed for use in identifying and/or cloning other 60491 family members, or fragments thereof, as well as 60491 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 50 amino acids in length.

Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 60491 nucleic acid fragment can include a sequence corresponding to an acyltransferase domain.

60491 probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:48 or SEQ ID NO:50, or of a naturally occurring allelic variant or mutant of SEQ ID NO:48 or SEQ ID NO:50. Preferably, an oligonucleotide is less than about 200, 150, 120, or 100 nucleotides in length.

In one embodiment, the probe or primer is attached to a solid support, e.g., a solid support described herein.

One exemplary kit of primers includes a forward primer that anneals to the coding strand and a reverse primer that anneals to the non-coding strand. The forward primer can anneal to the start codon, e.g., the nucleic acid sequence encoding amino acid residue 1 of SEQ ID NO:49. The reverse primer can anneal to the ultimate codon, e.g., the codon immediately before the stop codon, e.g., the codon encoding amino acid residue 775 of SEQ ID NO:49. In a preferred embodiment, the annealing temperatures of the forward and reverse primers differ by no more than 5, 4, 3, or 2° C.

In a preferred embodiment the nucleic acid is a probe which is at least 10, 12, 15, 18, 20 and less than 200, more preferably less than 100, or less than 50, nucleotides in length. It should be identical, or differ by 1, or 2, or less than 5 or 10 nucleotides, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: an acyltransferase domain.

In another embodiment a set of primers is provided, e.g., primers suitable for use in a PCR, which can be used to amplify a selected region of a 60491 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: an acyltransferase domain from about amino acid 199 to 333 of SEQ ID NO:49.

A nucleic acid fragment can encode an epitope bearing region of a polypeptide described herein.

A nucleic acid fragment encoding a "biologically active portion of a 60491 polypeptide" can be prepared by isolating a portion of the nucleotide sequence of SEQ ID NO:48 or 50, which encodes a polypeptide having a 60491 biological activity (e.g., the biological activities of the 60491 proteins are described herein), expressing the encoded portion of the 60491 protein (e.g., by recombinant expression in vitro) and assessing the activity of the encoded portion of the 60491 protein. For example, a nucleic acid fragment encoding a biologically active portion of 60491 includes an acyltransferase domain, e.g., amino acid residues about 199 to 333 of SEQ ID NO:49. A nucleic acid fragment encoding a biologically active portion of a 60491 polypeptide, may comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300 or more nucleotides in length and hybridizes under a stringency condition described herein to a nucleic acid molecule of SEQ ID NO:48 or SEQ ID NO:50.

60491 Nucleic Acid Variants

The invention further encompasses nucleic acid molecules that differ from the nucleotide sequence shown in SEQ ID NO:48 or SEQ ID NO:50. Such differences can be due to degeneracy of the genetic code (and result in a nucleic acid that encodes the same 60491 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:49. If alignment is needed for this comparison the sequences should be aligned for maximum homology. The encoded protein can differ by no more than 5, 4, 3, 2, or 1 amino acid. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:48 or 50, e.g., as follows: by at least one but less than 10, 20, 30, or 40 nucleotides; at least one but less than 1%, 5%, 10% or 20% of the nucleotides in the subject nucleic acid. The nucleic acid can differ by no more than 5, 4, 3, 2, or 1 nucleotide. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:49 or a fragment of this sequence. Such nucleic acid molecules can readily be identified as being able to hybridize under a stringency condition described herein, to the nucleotide sequence shown in SEQ ID NO:49 or a fragment of the sequence. Nucleic acid molecules corresponding to orthologs, homologs, and allelic variants of the 60491 cDNAs of the invention can further be isolated by mapping to the same chromosome or locus as the 60491 gene.

Preferred variants include those that are correlated with catalyzing the transfer of an acyl chain to a lipid precursor.

Allelic variants of 60491, e.g., human 60491, include both functional and non-functional proteins. Functional allelic variants are naturally occurring amino acid sequence variants of the 60491 protein within a population that maintain the ability to catalyze the transfer of an acyl chain to a lipid precursor. Functional allelic variants will typically contain only conservative substitution of one or more amino acids of SEQ ID NO:49, or substitution, deletion or insertion of non-critical residues in non-critical regions of the protein. Non-functional allelic variants are naturally-occurring amino acid sequence variants of the 60491, e.g., human 60491, protein within a population that do not have the ability to catalyze the transfer of an acyl chain to a lipid precursor. Non-functional allelic variants will typically contain a non-conservative substitution, a deletion, or insertion, or premature truncation of the amino acid sequence of SEQ ID NO:49, or a substitution, insertion, or deletion in critical residues or critical regions of the protein.

Moreover, nucleic acid molecules encoding other 60491 family members and, thus, which have a nucleotide sequence which differs from the 60491 sequences of SEQ ID NO:48 or SEQ ID NO:50 are intended to be within the scope of the invention.

Antisense Nucleic Acid Molecules, Ribozymes and Modified 60491 Nucleic Acid Molecules In another aspect, the invention features, an isolated nucleic acid molecule which is antisense to 60491. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 60491 coding strand, or to only a portion thereof (e.g., the coding region of human 60491 corresponding to SEQ ID NO:50). In another embodiment, the antisense nucleic acid molecule is antisense to a "non-coding region" of the coding strand of a nucleotide sequence encoding 60491 (e.g., the 5' and 3' untranslated regions).

An antisense nucleic acid can be designed such that it is complementary to the entire coding region of 60491 mRNA, but more preferably is an oligonucleotide which is antisense to only a portion of the coding or noncoding region of 60491 mRNA. For example, the antisense oligonucleotide can be complementary to the region surrounding the translation start site of 60491 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 60491 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an a-anomeric nucleic acid molecule. An a-anomeric nucleic acid molecule forms specific double-stranded hybrids with complementary RNA in which, contrary to the usual b-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. A ribozyme having specificity for a 60491-encoding nucleic acid can include one or more sequences complementary to the nucleotide sequence of a 60491 cDNA disclosed herein (i.e., SEQ ID NO:48 or SEQ ID NO:50), and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a 60491-encoding mRNA. See, e.g., Cech et al. U.S. Pat. No. 4,987,071; and Cech et al. U.S. Pat. No. 5,116,742. Alternatively, 60491 mRNA can be used to select a catalytic RNA having a specific ribonuclease activity from a pool of RNA molecules. See, e.g., Bartel, D. and Szostak, J. W. (1993) *Science* 261:1411-1418.

60491 gene expression can be inhibited by targeting nucleotide sequences complementary to the regulatory region of the 60491 (e.g., the 60491 promoter and/or enhancers) to form triple helical structures that prevent transcription of the 60491 gene in target cells. See generally, Helene, C. (1991) *Anticancer Drug Des.* 6:569-84; Helene, C. i (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or calorimetric.

A 60491 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19: 17 and Faria et al. (2001) *Nature Biotech.* 19: 40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675.

PNAs of 60491 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 60491 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. W088/09810) or the blood-brain barrier (see, e.g., PCT Publication No. W089/10134). In addition, oligonucleotides can be modified with hybridization-triggered cleavage agents (see, e.g., Krol et al. (1988) *Bio-Techniques* 6:

958-976) or intercalating agents. (see, e.g., Zon (1988) *Pharm. Res.* 5: 539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 60491 nucleic acid of the invention, two complementary regions one having a fluorophore and one a quencher such that the molecular beacon is useful for quantitating the presence of the 60491 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 60491 Polypeptides

In another aspect, the invention features, an isolated 60491 protein, or fragment, e.g., a biologically active portion, for use as immunogens or antigens to raise or test (or more generally to bind) anti-60491 antibodies. 60491 protein can be isolated from cells or tissue sources using standard protein purification techniques. 60491 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 60491 polypeptide has one or more of the following characteristics:
 (i) it has the ability to catalyze the transfer of an acyl chain to a lipid precursor;
 (ii) it has the ability to modulate cellular differentiation;
 (iii) it has the ability to modulate cellular proliferation;
 (iv) it has the ability to modulate mitogenesis;
 (v) it has the ability to modulate neurite retraction;
 (vi) it has the ability to modulate pain or inflammation response;
 (vii) it has the ability to modulate tumor cell growth and invasion;
 (viii) it has the ability to antagonize or inhibit, competitively or non-competitively, any of i-vii.
 (ix) it has a molecular weight, e.g., a deduced molecular weight, preferably ignoring any contribution of post translational modifications, amino acid composition or other physical characteristic of a 60491 polypeptide, e.g., a polypeptide of SEQ ID NO:49;
 (x) it has an overall sequence similarity of at least 60%, preferably at least 70, 80, 90, or 95%, with a polypeptide a of SEQ ID NO:49; or
 (xi) it has an acyltransferase domain which is preferably about 70%, 80%, 90% or 95% with amino acid residues about 199 to 333 of SEQ ID NO:49.

In a preferred embodiment the 60491 protein, or fragment thereof, differs from the corresponding sequence in SEQ ID NO:49. In one embodiment it differs by at least one but by less than 15, 10 or 5 amino acid residues. In another it differs from the corresponding sequence in SEQ ID NO:49 by at least one residue but less than 20%, 15%, 10% or 5% of the residues in it differ from the corresponding sequence in SEQ ID NO:49. (If this comparison requires alignment the sequences should be aligned for maximum homology. "Looped" out sequences from deletions or insertions, or mismatches, are considered differences.) The differences are, preferably, differences or changes at a non essential residue or a conservative substitution. In a preferred embodiment the differences are not in the acyltransferase domain located at residues 199 to 333 of SEQ ID NO:49. In another preferred embodiment one or more differences are in the acyltransferase domain located at residues 199 to 333 of SEQ ID NO:49.

Other embodiments include a protein that contain one or more changes in amino acid sequence, e.g., a change in an amino acid residue which is not essential for activity. Such 60491 proteins differ in amino acid sequence from SEQ ID NO:49, yet retain biological activity.

In one embodiment, the protein includes an amino acid sequence at least about 60%, 65%, 70%, 75%, 80%, 85%, 90%, 95%, 98% or more homologous to SEQ ID NO:49.

A 60491 protein or fragment is provided which varies from the sequence of SEQ ID NO:49 in regions defined by amino acids about 1 to 198 by at least one but by less than 15, 10 or 5 amino acid residues in the protein or fragment but which does not differ from SEQ ID NO:49 in regions defined by amino acids about 199 to 333 of SEQ ID NO:49. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 60491 protein includes an acyltransferase domain. Moreover, other biologically active portions, in which other regions of the protein are deleted, can be prepared by recombinant techniques and evaluated for one or more of the functional activities of a native 60491 protein.

In a preferred embodiment, the 60491 protein has an amino acid sequence shown in SEQ ID NO:49. In other embodiments, the 60491 protein is substantially identical to SEQ ID NO:49. In yet another embodiment, the 60491 protein is substantially identical to SEQ ID NO:49 and retains the functional activity of the protein of SEQ ID NO:49, as described in detail in the subsections above.

60491 Chimeric or Fusion Proteins

In another aspect, the invention provides 60491 chimeric or fusion proteins. As used herein, a 60491 "chimeric protein" or "fusion protein" includes a 60491 polypeptide linked to a non-60491 polypeptide. A "non-60491 polypeptide" refers to a polypeptide having an amino acid sequence corresponding to a protein which is not substantially homologous to the 60491 protein, e.g., a protein which is different from the 60491 protein and which is derived from the same or a different organism. The 60491 polypeptide of the fusion protein can correspond to all or a portion e.g., a fragment described herein of a 60491 amino acid sequence. In a preferred embodiment, a 60491 fusion protein includes at least one (or two) biologically active portion of a 60491 protein. The non-60491 polypeptide can be fused to the N-terminus or C-terminus of the 60491 polypeptide.

The fusion protein can include a moiety which has a high affinity for a ligand. For example, the fusion protein can be a GST-60491 fusion protein in which the 60491 sequences are fused to the C-terminus of the GST sequences. Such fusion proteins can facilitate the purification of recombinant 60491. Alternatively, the fusion protein can be a 60491 protein containing a heterologous signal sequence at its N-terminus. In certain host cells (e.g., mammalian host cells), expression and/or secretion of 60491 can be increased through use of a heterologous signal sequence.

Fusion proteins can include all or a part of a serum protein, e.g., an IgG constant region, or human serum albumin.

The 60491 fusion proteins of the invention can be incorporated into pharmaceutical compositions and administered to a subject in vivo. The 60491 fusion proteins can be used to affect the bioavailability of a 60491 substrate. 60491 fusion proteins may be useful therapeutically for the treatment of disorders caused by, for example, (i) aberrant modification or mutation of a gene encoding a 60491 protein; (ii) mis-regulation of the 60491 gene; and (iii) aberrant post-translational modification of a 60491 protein.

Moreover, the 60491-fusion proteins of the invention can be used as immunogens to produce anti-60491 antibodies in a subject, to purify 60491 ligands and in screening assays to identify molecules which inhibit the interaction of 60491 with a 60491 substrate.

Expression vectors are commercially available that already encode a fusion moiety (e.g., a GST polypeptide). A 60491-encoding nucleic acid can be cloned into such an expression vector such that the fusion moiety is linked in-frame to the 60491 protein.

Variants of 60491 Proteins

In another aspect, the invention also features a variant of a 60491 polypeptide, e.g., which functions as an agonist (mimetics) or as an antagonist. Variants of the 60491 proteins can be generated by mutagenesis, e.g., discrete point mutation, the insertion or deletion of sequences or the truncation of a 60491 protein. An agonist of the 60491 proteins can retain substantially the same, or a subset, of the biological activities of the naturally occurring form of a 60491 protein. An antagonist of a 60491 protein can inhibit one or more of the activities of the naturally occurring form of the 60491 protein by, for example, competitively modulating a 60491-mediated activity of a 60491 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 60491 protein.

Variants of a 60491 protein can be identified by screening combinatorial libraries of mutants, e.g., truncation mutants, of a 60491 protein for agonist or antagonist activity.

Libraries of fragments e.g., N terminal, C terminal, or internal fragments, of a 60491 protein coding sequence can be used to generate a variegated population of fragments for screening and subsequent selection of variants of a 60491 protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of 60491 proteins. Recursive ensemble mutagenesis (REM), a new technique which enhances the frequency of functional mutants in the libraries, can be used in combination with the screening assays to identify 60491 variants (Arkin and Yourvan (1992) *Proc. Natl. Acad. Sci. USA* 89:7811-7815; Delgrave et al. (1993) *Protein Engineering* 6:327-331).

Cell based assays can be exploited to analyze a variegated 60491 library. For example, a library of expression vectors can be transfected into a cell line, e.g., a cell line, which ordinarily responds to 60491 in a substrate-dependent manner. The transfected cells are then contacted with 60491 and the effect of the expression of the mutant on signaling by the 60491 substrate can be detected, e.g., by measuring catalyzation of the transfer of an acyl chain to a lipid precursor. Plasmid DNA can then be recovered from the cells which score for inhibition, or alternatively, potentiation of signaling by the 60491 substrate, and the individual clones further characterized.

In another aspect, the invention features a method of making a 60491 polypeptide, e.g., a peptide having a non-wild type activity, e.g., an antagonist, agonist, or super agonist of a naturally occurring 60491 polypeptide, e.g., a naturally occurring 60491 polypeptide. The method includes: altering the sequence of a 60491 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 60491 polypeptide a biological activity of a naturally occurring 60491 polypeptide. The method includes: altering the sequence, e.g., by substitution or deletion of one or more residues, of a 60491 polypeptide, e.g., altering the sequence of a non-conserved region, or a domain or residue described herein, and testing the altered polypeptide for the desired activity.

Anti-60491 Antibodies

In another aspect, the invention provides an anti-60491 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-60491 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH—terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 60491 polypeptide or fragment thereof. Examples of antigen-binding fragments of the anti-60491 antibody include, but are not limited to: (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242: 423-426; and Huston et al. (1988) *Proc. Natl. Acad. Sci. USA* 85: 5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-60491 antibody can be a polyclonal or a monoclonal antibody. In other embodiments, the antibody can be recombinantly produced, e.g., produced by phage display or by combinatorial methods.

Phage display and combinatorial methods for generating anti-60491 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9: 1370-1372; Hay et al. (1992) *Hum Antibod Hybridomas* 3: 81-85; Huse et al. (1989) *Science* 246: 1275-1281; Griffths et al. (1993) *EMBO J* 12: 725-734; Hawkins et al. (1992) *J Mol Biol* 226: 889-896; Clackson et al. (1991) *Nature* 352: 624-628; Gram et al. (1992) *PNAS* 89: 3576-3580; Garrad et al. (1991) *Bio/Technology* 9: 1373-1377; Hoogenboom et al. (1991) *Nuc Acid Res* 19: 4133-4137; and Barbas et al. (1991) *PNAS* 88: 7978-7982, the contents of all of which are incorporated by reference herein).

In one embodiment, the anti-60491 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368: 856-859; Green, L. L. et al. 1994 *Nature Genet.* 7: 13-21; Morrison, S. L. et al. 1994 *Proc. Natl. Acad. Sci. USA* 81: 6851-6855; Bruggeman et al. 1993 *Year Immunol* 7: 33-40; Tuaillon et al. 1993 *PNAS* 90: 3720-3724; Bruggeman et al. 1991 *Eur J Immunol* 21: 1323-1326).

An anti-60491 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240: 1041-1043); Liu et al. (1987) *PNAS* 84: 3439-3443; Liu et al., 1987, *J. Immunol.* 139: 3521-3526; Sun et al. (1987) *PNAS* 84:214-218; Nishimura et al., 1987, *Canc. Res.* 47: 999-1005; Wood et al. (1985) *Nature* 314: 446-449; and Shaw et al., 1988, *J. Natl Cancer Inst.* 80: 1553-1559).

A humanized or CDR-grafted antibody will have at least one or two but generally all three recipient CDR's (of heavy and or light imuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 60491 or a fragment thereof. Preferably, the donor will be a rodent antibody, e.g., a rat or mouse antibody, and the recipient will be a human framework or a human consensus framework. Typically, the immunoglobulin providing the CDR's is called the "donor"

and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 60491 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

A full-length 60491 protein or, antigenic peptide fragment of 60491 can be used as an immunogen or can be used to identify anti-60491 antibodies made with other immunogens, e.g., cells, membrane preparations, and the like. The antigenic peptide of 60491 should include at least 8 amino acid residues of the amino acid sequence shown in SEQ ID NO:49 and encompasses an epitope of 60491. Preferably, the antigenic peptide includes at least 10 amino acid residues, more preferably at least 15 amino acid residues, even more preferably at least 20 amino acid residues, and most preferably at least 30 amino acid residues.

Fragments of 60491 which include residues about 228 to 235, or about 337 to 346, can be used to make, e.g., used as immunogens or used to characterize the specificity of an antibody, antibodies against hydrophilic regions of the 60491 protein. Similarly, fragments of 60491 which include residues about 163 to 176, about 342 to 359, or about 450 to 472 can be used to make an antibody against a hydrophobic region of the 60491 protein; a fragment of 60491 which include residues about 199 to 333, can be used to make an antibody against the acyltransferase region of the 60491 protein.

Antibodies reactive with, or specific for, any of these regions, or other regions or domains described herein are provided.

Antibodies which bind only native 60491 protein, only denatured or otherwise non-native 60491 protein, or which bind both, are with in the invention. Antibodies with linear or conformational epitopes are within the invention. Conformational epitopes can sometimes be identified by identifying antibodies which bind to native but not denatured 60491 protein.

Preferred epitopes encompassed by the antigenic peptide are regions of 60491 are located on the surface of the protein, e.g., hydrophilic regions, as well as regions with high antigenicity. For example, an Emini surface probability analysis of the human 60491 protein sequence can be used to indicate the regions that have a particularly high probability of being localized to the surface of the 60491 protein and are thus likely to constitute surface residues useful for targeting antibody production.

The anti-60491 antibody can be a single chain antibody. A single-chain antibody (scFV) may be engineered (see, for example, Colcher, D. et al. (1999) *Ann NY Acad Sci* 880: 263-80; and Reiter, Y. (1996) *Clin Cancer Res* 2:245-52). The single chain antibody can be dimerized or multimerized to generate multivalent antibodies having specificities for different epitopes of the same target 60491 protein.

In a preferred embodiment the antibody has effector function and/or can fix complement. In other embodiments the antibody does not recruit effector cells; or fix complement.

In a preferred embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

In a preferred embodiment, an anti-60491 antibody alters (e.g., increases or decreases) the catalyzing the transfer of an acyl chain to a lipid precursoractivity of a 60491 polypeptide. For example, the antibody can bind at or in proximity to the active site, e.g., to an epitope that includes a residue located from about 199 to 333 of SEQ ID NO:49.

The antibody can be coupled to a toxin, e.g., a polypeptide toxin, e,g, ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-60491 antibody (e.g., monoclonal antibody) can be used to isolate 60491 by standard techniques, such as affinity chromatography or immunoprecipitation. Moreover, an anti-60491 antibody can be used to detect 60491 protein (e.g., in a cellular lysate or cell supernatant) in order to evaluate the abundance and pattern of expression of the protein. Anti-60491 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

The invention also includes a nucleic acid which encodes an anti-60491 antibody, e.g., an anti-60491 antibody described herein. Also included are vectors which include the nucleic acid and cells transformed with the nucleic acid, particularly cells which are useful for producing an antibody, e.g., mammalian cells, e.g. CHO or lymphatic cells.

The invention also includes cell lines, e.g., hybridomas, which make an anti-60491 antibody, e.g., and antibody described herein, and method of using said cells to make a 60491 antibody.

60491 Recombinant Expression Vectors, Host Cells and Genetically Engineered Cells In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 60491 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 60491 proteins, mutant forms of 60491 proteins, fusion proteins, and the like).

The recombinant expression vectors of the invention can be designed for expression of 60491 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 60491 activity assays, (e.g., direct assays or competitive assays described in detail below), or to generate antibodies specific for 60491 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The 60491 expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., C A, Gossen and Bujard (1992) Proc. Natl. Acad. Sci. USA 89:5547, and Paillard (1989) Human Gene Therapy 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) Science 249:374-379) and the α-fetoprotein promoter (Campes and Tilghman (1989) Genes Dev. 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a 60491 nucleic acid molecule within a recombinant expression vector or a 60491 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 60491 protein can be expressed in bacterial cells (such as E. coli), insect cells, yeast or mammalian cells (such as Chinese hamster ovary cells (CHO) or COS cells (African green monkey kidney cells CV-1 origin SV40 cells; Gluzman (1981) Cell 123:175-182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 60491 protein. Accordingly, the invention further provides methods for producing a 60491 protein using the host cells of the invention. In one embodiment, the method includes culturing the host cell of the invention (into which a recombinant expression vector encoding a 60491 protein has been introduced) in a suitable medium such that a 60491 protein is produced. In another embodiment, the method further includes isolating a 60491 protein from the medium or the host cell.

In another aspect, the invention features, a cell or purified preparation of cells which include a 60491 transgene, or which otherwise misexpress 60491. The cell preparation can consist of human or non-human cells, e.g., rodent cells, e.g., mouse or rat cells, rabbit cells, or pig cells. In preferred embodiments, the cell or cells include a 60491 transgene, e.g., a heterologous form of a 60491, e.g., a gene derived from humans (in the case of a non-human cell). The 60491 transgene can be misexpressed, e.g., overexpressed or underexpressed. In other preferred embodiments, the cell or cells include a gene that mis-expresses an endogenous 60491, e.g., a gene the expression of which is disrupted, e.g., a knockout. Such cells can serve as a model for studying disorders that are related to mutated or mis-expressed 60491 alleles or for use in drug screening.

In another aspect, the invention features, a human cell, transformed with nucleic acid which encodes a subject 60491 polypeptide.

Also provided are cells, preferably human cells, e.g., fibroblast cells, in which an endogenous 60491 is under the control of a regulatory sequence that does not normally control the expression of the endogenous 60491 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 60491 gene. For example, an endogenous 60491 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 60491 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) Nat. Biotechnol. 14:1107; Joki et al. (2001) Nat. Biotechnol 19:35; and U.S. Pat. No. 5,876,742. Production of 60491 polypeptide can be regulated in the subject by administering an agent (e.g., a steroid hormone) to the subject. In another preferred embodiment, the implanted recombinant cells express and secrete an antibody specific for a 60491 polypeptide. The antibody can be any antibody or any antibody derivative described herein.

60491 Transgenic Animals

The invention provides non-human transgenic animals. Such animals are useful for studying the function and/or activity of a 60491 protein and for identifying and/or evaluating modulators of 60491 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 60491 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 60491 protein to particular cells. A transgenic founder animal can be identified based upon the presence of a 60491 transgene in its genome and/or expression of 60491 mRNA in tissues or cells of the animals. A transgenic founder animal can then be used to breed additional animals carrying the transgene. Moreover, transgenic animals carrying a transgene encoding a 60491 protein can further be bred to other transgenic animals carrying other transgenes.

60491 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

60491 Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 60491 protein (e.g., via a recombinant expression vector in a host cell in gene therapy applications), to detect a 60491 mRNA (e.g., in a biological sample) or a genetic alteration in a 60491 gene, and to modulate 60491 activity, as described further below. The 60491 proteins can be used to treat disorders characterized by insufficient or excessive production of a 60491 substrate or production of 60491 inhibitors. In addition, the 60491 proteins can be used to screen for naturally occurring 60491 substrates, to screen for drugs or compounds which modulate 60491 activity, as well as to treat disorders characterized by insufficient or excessive production of 60491 protein or production of 60491 protein forms which have decreased, aberrant or unwanted activity compared to 60491 wild type protein (e.g., a brain or pain-associated disorder). Moreover, the anti-60491 antibodies of the invention can be used to detect and isolate 60491 proteins, regulate the bioavailability of 60491 proteins, and modulate 60491 activity.

A method of evaluating a compound for the ability to interact with, e.g., bind, a subject 60491 polypeptide is provided. The method includes: contacting the compound with the subject 60491 polypeptide; and evaluating ability of the compound to interact with, e.g., to bind or form a complex with the subject 60491 polypeptide. This method can be performed in vitro, e.g., in a cell free system, or in vivo, e.g., in a two-hybrid interaction trap assay. This method can be used to identify naturally occurring molecules that interact with subject 60491 polypeptide. It can also be used to find natural or synthetic inhibitors of subject 60491 polypeptide. Screening methods are discussed in more detail below.

60491 Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 60491 proteins, have a stimulatory or inhibitory effect on, for example, 60491 expression or 60491 activity, or have a stimulatory or inhibitory effect on, for example, the expression or activity of a 60491 substrate. Compounds thus identified can be used to modulate the activity of target gene products (e.g., 60491 genes) in a therapeutic protocol, to elaborate the biological function of the target gene product, or to identify compounds that disrupt normal target gene interactions.

In one embodiment, the invention provides assays for screening candidate or test compounds which are substrates of a 60491 protein or polypeptide or a biologically active portion thereof. In another embodiment, the invention provides assays for screening candidate or test compounds that bind to or modulate an activity of a 60491 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91: 11422; Zuckermann et al. (1994). *J. Med. Chem.* 37: 2678; Cho et al. (1993) *Science* 261: 1303; Carrell et al. (1994) *Angew. Chem. Int. Ed. Engl.* 33:2059; Carell et al. (1994) *Angew. Chem. Int. Ed. Engl.* 33: 2061; and Gallop et al. (1994) *J. Med. Chem.* 37: 1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89: 1865-1869) or on phage (Scott and Smith (1990) *Science* 249: 386-390; Devlin (1990) *Science* 249:404-406; Cwirla et al. (1990) *Proc. Natl. Acad. Sci.* 87: 6378-6382; Felici (1991) *J. Mol. Biol.* 222: 301-310; Ladner supra.).

In one embodiment, an assay is a cell-based assay in which a cell which expresses a 60491 protein or biologically active portion thereof is contacted with a test compound, and the ability of the test compound to modulate 60491 activity is determined. Determining the ability of the test compound to modulate 60491 activity can be accomplished by monitoring, for example, catalyzation of the transfer of an acyl chain to a lipid precusor. The cell, for example, can be of mammalian origin, e.g., human.

The ability of the test compound to modulate 60491 binding to a compound, e.g., a 60491 substrate, or to bind to 60491 can also be evaluated. This can be accomplished, for example, by coupling the compound, e.g., the substrate, with a radioisotope or enzymatic label such that binding of the compound, e.g., the substrate, to 60491 can be determined by detecting the labeled compound, e.g., substrate, in a complex. Alternatively, 60491 could be coupled with a radioisotope or enzymatic label to monitor the ability of a test compound to modulate 60491 binding to a 60491 substrate in a complex. For example, compounds (e.g., 60491 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 60491 substrate) to interact with 60491 with or without the labeling of any of the interactants can be evaluated. For example, a microphysiometer can be used to detect the interaction of a compound with 60491 without the labeling of either the compound or the 60491. McConnell, H. M. et al. (1992) *Science* 257: 1996-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 60491.

In yet another embodiment, a cell-free assay is provided in which a 60491 protein or biologically active portion thereof is contacted with a test compound and the ability of the test compound to bind to the 60491 protein or biologically active portion thereof is evaluated. Preferred biologically active portions of the 60491 proteins to be used in assays of the present invention include fragments which participate in interactions with non-60491 molecules, e.g., fragments with high surface probability scores.

Soluble and/or membrane-bound forms of isolated proteins (e.g., 60491 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 60491 protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 60491, an anti-60491 antibody or its target molecule to facilitate separation of complexed from uncomplexed forms of one or both of the proteins, as well as to accommodate automation of the assay. Binding of a test compound to a 60491 protein, or interaction of a 60491 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/60491 fusion proteins or glutathione-S-transferase/target fusion proteins can be adsorbed onto glutathione sepharose beads (Sigma Chemical, St.

Louis, Mo.) or glutathione derivatized microtiter plates, which are then combined with the test compound or the test compound and either the non-adsorbed target protein or 60491 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 60491 binding or activity determined using standard techniques.

Other techniques for immobilizing either a 60491 protein or a target molecule on matrices include using conjugation of biotin and streptavidin. Biotinylated 60491 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 60491 protein or target molecules but which do not interfere with binding of the 60491 protein to its target molecule. Such antibodies can be derivatized to the wells of the plate, and unbound target or 60491 protein trapped in the wells by antibody conjugation. Methods for detecting such complexes, in addition to those described above for the GST-immobilized complexes, include immunodetection of complexes using antibodies reactive with the 60491 protein or target molecule, as well as enzyme-linked assays which rely on detecting an enzymatic activity associated with the 60491 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141-8; Hage, D. S., and Tweed, S. A. (1997) *J Chromatogr B Biomed Sci Appl.* 699:499-525). Further, fluorescence energy transfer may also be conveniently utilized, as described herein, to detect binding without further purification of the complex from solution.

In a preferred embodiment, the assay includes contacting the 60491 protein or biologically active portion thereof with a known compound which binds 60491 to form an assay mixture, contacting the assay mixture with a test compound, and determining the ability of the test compound to interact with a 60491 protein, wherein determining the ability of the test compound to interact with a 60491 protein includes determining the ability of the test compound to preferentially bind to 60491 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 60491 genes herein identified. In an alternative embodiment, the invention provides methods for determining the ability of the test compound to modulate the activity of a 60491 protein through modulation of the activity of a downstream effector of a 60491 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 60491 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 60491 ("60491-binding proteins" or "60491-bp") and are involved in 60491 activity. Such 60491-bps can be activators or inhibitors of signals by the 60491 proteins or 60491 targets as, for example, downstream elements of a 60491-mediated signaling pathway.

The two-hybrid system is based on the modular nature of most transcription factors, which consist of separable DNA-binding and activation domains. Briefly, the assay utilizes two different DNA constructs. In one construct, the gene that codes for a 60491 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 60491 protein can be the fused to the activator domain.) If the "bait" and the "prey" proteins are able to interact, in vivo, forming a 60491-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 60491 protein.

In another embodiment, modulators of 60491 expression are identified. For example, a cell or cell free mixture is contacted with a candidate compound and the expression of 60491 mRNA or protein evaluated relative to the level of expression of 60491 mRNA or protein in the absence of the candidate compound. When expression of 60491 mRNA or protein is greater in the presence of the candidate compound than in its absence, the candidate compound is identified as a stimulator of 60491 mRNA or protein expression. Alternatively, when expression of 60491 mRNA or protein is less (statistically significantly less) in the presence of the candidate compound than in its absence, the candidate compound is identified as an inhibitor of 60491 mRNA or protein expression. The level of 60491 mRNA or protein expression can be determined by methods described herein for detecting 60491 mRNA or protein.

In another aspect, the invention pertains to a combination of two or more of the assays described herein. For example, a modulating agent can be identified using a cell-based or a cell free assay, and the ability of the agent to modulate the activity of a 60491 protein can be confirmed in vivo, e.g., in an animal such as an animal model for a brain or pain-associated disorder.

This invention further pertains to novel agents identified by the above-described screening assays. Accordingly, it is within the scope of this invention to further use an agent identified as described herein (e.g., a 60491 modulating agent, an antisense 60491 nucleic acid molecule, a 60491-specific antibody, or a 60491-binding partner) in an appropriate animal model to determine the efficacy, toxicity, side effects, or mechanism of action, of treatment with such an agent. Furthermore, novel agents identified by the above-described screening assays can be used for treatments as described herein.

60491 Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 60491 with a disease; (ii) identify an individual from a minute biological sample (tissue typing); and (iii) aid in forensic identification of a biological sample. These applications are described in the subsections below.

60491 Chromosome Mapping

The 60491 nucleotide sequences or portions thereof can be used to map the location of the 60491 genes on a chromosome. This process is called chromosome mapping. Chromosome mapping is useful in correlating the 60491 sequences with genes associated with disease.

Briefly, 60491 genes can be mapped to chromosomes by preparing PCR primers (preferably 15-25 bp in length) from the 60491 nucleotide sequences. These primers can then be used for PCR screening of somatic cell hybrids containing individual human chromosomes. Only those hybrids containing the human gene corresponding to the 60491 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220: 919-924).

Other mapping strategies e.g., in situ hybridization (described in Fan, Y. et al. (1990) *Proc. Natl. Acad. Sci. USA*, 87:6223-27), pre-screening with labeled flow-sorted chromosomes, and pre-selection by hybridization to chromosome specific cDNA libraries can be used to map 60491 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783-787.

Moreover, differences in the DNA sequences between individuals affected and unaffected with a disease associated with the 60491 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

60491 Tissue Typing 60491 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 60491 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:48 can provide positive individual identification with a panel of perhaps 10 to 1,000 primers which each yield a noncoding amplified sequence of 100 bases. If predicted coding sequences, such as those in SEQ ID NO:50 are used, a more appropriate number of primers for positive individual identification would be 500-2,000.

If a panel of reagents from 60491 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 60491 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:48 (e.g., fragments derived from the noncoding regions of SEQ ID NO:48 having a length of at least 20 bases, preferably at least 30 bases) are particularly appropriate for this use.

The 60491 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 60491 probes can be used to identify tissue by species and/or by organ type.

In a similar fashion, these reagents, e.g., 60491 primers or probes can be used to screen tissue culture for contamination (i.e. screen for the presence of a mixture of different types of cells in a culture).

Predictive Medicine of 60491

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 60491.

Such disorders include, e.g., a disorder associated with the misexpression of 60491 gene; a disorder of the nerve system.

The method includes one or more of the following:

detecting, in a tissue of the subject, the presence or absence of a mutation which affects the expression of the 60491 gene, or detecting the presence or absence of a mutation in a region which controls the expression of the gene, e.g., a mutation in the 5' control region;

detecting, in a tissue of the subject, the presence or absence of a mutation which alters the structure of the 60491 gene;

detecting, in a tissue of the subject, the misexpression of the 60491 gene, at the mRNA level, e.g., detecting a non-wild type level of a mRNA;

detecting, in a tissue of the subject, the misexpression of the gene, at the protein level, e.g., detecting a non-wild type level of a 60491 polypeptide.

In preferred embodiments the method includes: ascertaining the existence of at least one of: a deletion of one or more nucleotides from the 60491 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:48, or naturally occurring mutants thereof or 5' or 3' flanking sequences naturally associated with the 60491 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 60491 gene; the presence of a non-wild type splicing pattern of a messenger RNA transcript of the gene; or a non-wild type level of 60491.

Methods of the invention can be used prenatally or to determine if a subject's offspring will be at risk for a disorder.

In preferred embodiments the method includes determining the structure of a 60491 gene, an abnormal structure being indicative of risk for the disorder.

In preferred embodiments the method includes contacting a sample from the subject with an antibody to the 60491 protein or a nucleic acid, which hybridizes specifically with the gene. These and other embodiments are discussed below.

Diagnostic and Prognostic Assays of 60491

Diagnostic and prognostic assays of the invention include method for assessing the expression level of 60491 molecules and for identifying variations and mutations in the sequence of 60491 molecules.

Expression Monitoring and Profiling

The presence, level, or absence of 60491 protein or nucleic acid in a biological sample can be evaluated by obtaining a biological sample from a test subject and contacting the biological sample with a compound or an agent capable of detecting 60491 protein or nucleic acid (e.g., mRNA, genomic DNA) that encodes 60491 protein such that the presence of 60491 protein or nucleic acid is detected in the biological sample. The term "biological sample" includes tissues, cells and biological fluids isolated from a subject, as well as tissues, cells and fluids present within a subject. A preferred biological sample is serum. The level of expression of the 60491 gene can be measured in a number of ways, including, but not limited to: measuring the mRNA encoded by the 60491 genes; measuring the amount of protein encoded by the 60491 genes; or measuring the activity of the protein encoded by the 60491 genes.

The level of mRNA corresponding to the 60491 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 60491 nucleic acid, such as the nucleic acid of SEQ ID NO:48, or a portion thereof, such as an oligonucleotide of at least 7, 15, 30, 50, 100, 250 or 500 nucleotides in length and sufficient to specifically hybridize under stringent conditions to 60491 mRNA or genomic DNA. The probe can be disposed on an address of an array, e.g., an array described below. Other suitable probes for use in the diagnostic assays are described herein.

In one format, mRNA (or CDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 60491 genes.

The level of mRNA in a sample that is encoded by one of 60491 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88: 189-193), self sustained sequence replication (Guatelli et al., (1990) *Proc. Natl. Acad. Sci. USA* 87: 1874-1878), transcriptional amplification system (Kwoh et al., (1989), *Proc. Natl. Acad. Sci. USA* 86: 1173-1177), Q-Beta Replicase (Lizardi et al., (1988) *Bio/Technology* 6: 1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 60491 gene being analyzed.

In another embodiment, the methods further contacting a control sample with a compound or agent capable of detecting 60491 mRNA, or genomic DNA, and comparing the presence of 60491 mRNA or genomic DNA in the control sample with the presence of 60491 mRNA or genomic DNA in the test sample. In still another embodiment, serial analysis of gene expression, as described in U.S. Pat. No. 5,695,937, is used to detect 60491 transcript levels.

A variety of methods can be used to determine the level of protein encoded by 60491. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 60491 protein in a biological sample in vitro as well as in vivo. In vitro techniques for detection of 60491 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 60491 protein include introducing into a subject a labeled anti-60491 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-60491 antibody positioned on an antibody array (as described below). The sample can be detected, e.g., with avidin coupled to a fluorescent label.

In another embodiment, the methods further include contacting the control sample with a compound or agent capable of detecting 60491 protein, and comparing the presence of 60491 protein in the control sample with the presence of 60491 protein in the test sample.

The invention also includes kits for detecting the presence of 60491 in a biological sample. For example, the kit can include a compound or agent capable of detecting 60491 protein or mRNA in a biological sample; and a standard. The compound or agent can be packaged in a suitable container. The kit can further comprise instructions for using the kit to detect 60491 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 60491 expression or activity. As used herein, the term "unwanted" includes an unwanted phenomenon involved in a biological response such as a brain or pain associated disorder or deregulated cell proliferation.

In one embodiment, a disease or disorder associated with aberrant or unwanted 60491 expression or activity is identified. A test sample is obtained from a subject and 60491 protein or nucleic acid (e.g., mRNA or genomic DNA) is evaluated, wherein the level, e.g., the presence or absence, of 60491 protein or nucleic acid is diagnostic for a subject having or at risk of developing a disease or disorder associated with aberrant or unwanted 60491 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 60491 expression or activity. For example, such methods can be used to determine whether a subject can be effectively treated with an agent for a cell a brain or pain-associated disorder.

In another aspect, the invention features a computer medium having a plurality of digitally encoded data records. Each data record includes a value representing the level of expression of 60491 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 60491 (e.g., other genes associated with a 60491-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 60491 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a a brain disorder or paindisorder in a subject wherein an increase in 60491 expression is an indication that the subject has or is disposed to having a brain or pain associated disorder. The method can be used to monitor a treatment for a brain or pain associated disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286: 531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 60491 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 60491 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 60491 expression.

60491 Arrays and Uses Thereof

In another aspect, the invention features an array that includes a substrate having a plurality of addresses. At least one address of the plurality includes a capture probe that binds specifically to a 60491 molecule (e.g., a 60491 nucleic acid or a 60491 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 60491 nucleic acid, e.g., the sense or anti-sense strand. In one preferred embodiment, a subset of addresses of the plurality of addresses has a nucleic acid capture probe for 60491. Each address of the subset can include a capture probe that hybridizes to a different region of a 60491 nucleic acid. In another preferred embodiment, addresses of the subset include a capture probe for a 60491 nucleic acid. Each address of the subset is unique, overlapping, and complementary to a different variant of 60491 (e.g., an allelic variant, or all possible hypothetical variants). The array can be used to sequence 60491 by hybridization (see, e.g., U.S. Pat. No. 5,695,940).

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 60491 polypeptide or fragment thereof. The polypeptide can be a naturally-occurring interaction partner of 60491 polypeptide. Preferably, the polypeptide is an antibody, e.g., an antibody described herein (see "Anti-60491 Antibodies," above), such as a monoclonal antibody or a single-chain antibody.

In another aspect, the invention features a method of analyzing the expression of 60491. The method includes providing an array as described above; contacting the array with a sample and detecting binding of a 60491-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 60491. If a sufficient number of diverse samples is analyzed, clustering (e.g., hierarchical clustering, k-means clustering, Bayesian clustering and the like) can be used to identify other genes which are co-regulated with 60491. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 60491 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 60491-associated disease or disorder; and processes, such as a cellular transformation associated with a 60491-associated disease or disorder. The method can also evaluate the treatment and/or progression of a 60491-associated disease or disorder The array is also useful for ascertaining differential expression patterns of one or more genes in normal and abnormal cells. This provides a battery of genes (e.g., including 60491) that could serve as a molecular target for diagnosis or therapeutic intervention.

In another aspect, the invention features an array having a plurality of addresses. Each address of the plurality includes a unique polypeptide. At least one address of the plurality has disposed thereon a 60491 polypeptide or fragment thereof. Methods of producing polypeptide arrays are described in the art, e.g., in De Wildt et al. (2000). *Nature Biotech.* 18, 989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80, 85, 90, 95 or 99% identical to a 60491 polypeptide or fragment thereof. For example, multiple variants of a 60491 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 60491 binding compound, e.g., an antibody in a sample from a subject with specificity for a 60491 polypeptide or the presence of a 60491-binding protein or ligand.

The array is also useful for ascertaining the effect of the expression of a gene on the expression of other genes in the same cell or in different cells (e.g., ascertaining the effect of 60491 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 60491 or from a cell or subject in which a 60491 mediated response has been elicited, e.g., by contact of the cell with 60491 nucleic acid or protein, or administration to the cell or subject 60491 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 60491 (or does not express as highly as in the case of the 60491 positive plurality of capture probes) or from a cell or subject which in which a 60491 mediated response has not been elicited (or has been elicited to a lesser extent than in the first sample); contacting the array with one or more inquiry probes (which is preferably other than a 60491 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 60491 or from a cell or subject in which a 60491-mediated response has been elicited, e.g., by contact of the cell with 60491 nucleic acid or protein, or administration to the cell or subject 60491 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 60491 (or does not express as highly as in the case of the 60491 positive plurality of capture probes) or from a cell or subject which in which a 60491 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 60491, e.g., analyzing structure, function, or relatedness to other nucleic acid or amino acid sequences. The method includes: providing a 60491 nucleic acid or amino acid sequence; comparing the 60491 sequence with one or more preferably a plurality of sequences from a collection of sequences, e.g., a nucleic acid or protein sequence database; to thereby analyze 60491.

Detection of 60491 Variations or Mutations

The methods of the invention can also be used to detect genetic alterations in a 60491 gene, thereby determining if a subject with the altered gene is at risk for a disorder characterized by misregulation in 60491 protein activity or nucleic acid expression, such as a brain or pain associated disorder. In preferred embodiments, the methods include detecting, in a sample from the subject, the presence or absence of a genetic alteration characterized by at least one of an alteration affecting the integrity of a gene encoding a 60491-protein, or the mis-expression of the 60491 gene. For example, such genetic alterations can be detected by ascertaining the existence of at least one of 1) a deletion of one or more nucleotides from a 60491 gene; 2) an addition of one or more nucleotides to a 60491 gene; 3) a substitution of one or more nucleotides of a 60491 gene, 4) a chromosomal rearrangement of a 60491 gene; 5) an alteration in the level of a messenger RNA transcript of a 60491 gene, 6) aberrant modification of a 60491 gene, such as of the methylation pattern of the genomic DNA, 7) the presence of a non-wild type splicing pattern of a messenger RNA transcript of a 60491 gene, 8) a non-wild type level of a 60491-protein, 9) allelic loss of a 60491 gene, and 10) inappropriate post-translational modification of a 60491-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 60491-gene. This method can include the steps of collecting a sample of cells from a subject, isolating nucleic acid (e.g., genomic, mRNA or both) from the sample, contacting the nucleic acid sample with one or more primers which specifically hybridize to a 60491 gene under conditions such that hybridization and amplification of the 60491-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 60491 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 60491 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 60491 nucleic acid or a putative variant (e.g., allelic variant) thereof. A probe can have one or more mismatches to a region of a 60491 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in 60491 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 60491 gene and detect mutations by comparing the sequence of the sample 60491 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 60491 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 60491 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 60491 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 60491 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 60491 nucleic acid.

In a preferred embodiment the set includes a first and a second oligonucleotide. The first and second oligonucleotide can hybridize to the same or to different locations of SEQ ID NO:48 or the complement of SEQ ID NO:48. Different locations can be different but overlapping, or non-overlapping on the same strand. The first and second oligonucleotide can hybridize to sites on the same or on different strands.

The set can be useful, e.g., for identifying SNP's, or identifying specific alleles of 60491. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 60491 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 60491 gene.

Use of 60491 Molecules as Surrogate Markers

The 60491 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 60491 molecules of the invention may be detected, and may be correlated with one or more biological states in vivo. For example, the 60491 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 60491 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 60491 marker) transcription or expression, the amplified marker may be in a quantity which is more readily detectable than the drug itself. Also, the marker may be more easily detected due to the nature of the marker itself; for example, using the methods described herein, anti-60491 antibodies may be employed in an immune-based detection system for a 60491 protein marker, or 60491-specific radiolabeled probes may be used to detect a 60491 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3; S16-S20.

The 60491 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 60491 protein or RNA) for specific tumor markers in a subject, a drug or course of treatment may be selected that is optimized for the treatment of the specific tumor likely to be present in the subject. Similarly, the presence or absence of a specific sequence mutation in 60491 DNA may correlate 60491 drug response. The use of pharmacogenomic markers therefore permits the application of the most appropriate treatment for each subject without having to administer the therapy.

Pharmaceutical Compositions of 60491

The nucleic acid and polypeptides, fragments thereof, as well as anti-60491 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 60491

The present invention provides for both prophylactic and therapeutic methods of treating a subject at risk of (or susceptible to) a disorder or having a disorder associated with aberrant or unwanted 60491 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 60491 molecules of the present invention or 60491 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 60491 expression or activity, by administering to the subject a 60491 or an agent which modulates 60491 expression or at least one 60491 activity. Subjects at risk for a disease which is caused or contributed to by aberrant or unwanted 60491 expression or activity can be identified by, for example, any or a combination of diagnostic or prognostic assays as described herein. Administration of a prophylactic agent can occur prior to the manifestation of symptoms characteristic of the 60491 aberrance, such that a disease or disorder is prevented or, alternatively, delayed in its progression. Depending on the type of 60491 aberrance, for example, a 60491, 60491 agonist or 60491 antagonist agent can be used for treating the subject. The appropriate agent can be determined based on screening assays described herein.

It is possible that some 60491 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of 60491 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 60491 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 60491 expression is through the use of aptamer molecules specific for 60491 protein. Aptamers are nucleic acid molecules having a tertiary structure which permits them to specifically bind to protein ligands (see, e.g., Osborne, et al. (1997) *Curr. Opin. Chem Biol.* 1: 5-9; and Patel, D. J. (1997) *Curr Opin Chem Biol* 1:32-46). Since nucleic acid molecules may in many cases be more conveniently introduced into target cells than therapeutic protein molecules may be, aptamers offer a method by which 60491 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 60491 disorders. For a description of antibodies, see the Antibody section above.

In circumstances wherein injection of an animal or a human subject with a 60491 protein or epitope for stimulating antibody production is harmful to the subject, it is possible to generate an immune response against 60491 through the use of anti-idiotypic antibodies (see, for example, Herlyn, D. (1999) *Ann Med* 31:66-78; and Bhattacharya-Chatterjee, M., and Foon, K. A. (1998) *Cancer Treat Res.* 94:51-68). If an anti-idiotypic antibody is introduced into a mammal or human subject, it should stimulate the production of anti-anti-idiotypic antibodies, which should be specific to the 60491 protein. Vaccines directed to a disease characterized by 60491 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate 60491 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 60491 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7: 89-94 and in Shea, K. J. (1994) *Trends in Polymer Science* 2: 166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645-647. Through the use of isotope-labeling, the "free" concentration of compound which modulates the expression or activity of 60491 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142-2144.

Another aspect of the invention pertains to methods of modulating 60491 expression or activity for therapeutic purposes. Accordingly, in an exemplary embodiment, the modulatory method of the invention involves contacting a cell with a 60491 or agent that modulates one or more of the activities of 60491 protein activity associated with the cell. An agent that modulates 60491 protein activity can be an agent as described herein, such as a nucleic acid or a protein, a naturally-occurring target molecule of a 60491 protein (e.g., a 60491 substrate or receptor), a 60491 antibody, a 60491 agonist or antagonist, a peptidomimetic of a 60491 agonist or antagonist, or other small molecule.

In one embodiment, the agent stimulates one or 60491 activities. Examples of such stimulatory agents include active 60491 protein and a nucleic acid molecule encoding 60491. In another embodiment, the agent inhibits one or more 60491 activities. Examples of such inhibitory agents include antisense 60491 nucleic acid molecules, anti-60491 antibodies, and 60491 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 60491 protein or nucleic acid molecule. In one embodiment, the method involves administering an agent (e.g., an agent identified by a screening assay described herein), or combination of agents that modulates (e.g., up regulates or down regulates) 60491 expression or activity. In another embodiment, the method involves administering a 60491 protein or nucleic acid molecule as therapy to compensate for reduced, aberrant, or unwanted 60491 expression or activity.

Stimulation of 60491 activity is desirable in situations in which 60491 is abnormally downregulated and/or in which increased 60491 activity is likely to have a beneficial effect. For example, stimulation of 60491 activity is desirable in situations in which a 60491 is downregulated and/or in which increased 60491 activity is likely to have a beneficial effect. Likewise, inhibition of 60491 activity is desirable in situations in which 60491 is abnormally upregulated and/or in which decreased 60491 activity is likely to have a beneficial effect.

60491 Pharmacogenomics

The 60491 molecules of the present invention, as well as agents, or modulators which have a stimulatory or inhibitory effect on 60491 activity (e.g., 60491 gene expression) as identified by a screening assay described herein can be administered to individuals to treat (prophylactically or therapeutically) 60491 associated disorders (e.g., a brain or pain associated disorder) associated with aberrant or unwanted 60491 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 60491 molecule or 60491 modulator as well as tailoring the dosage and/or therapeutic regimen of treatment with a 60491 molecule or 60491 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23: 983-985 and Linder, M. W. et al. (1997) *Clin. Chem.* 43: 254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a 60491 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a 60491 molecule or 60491 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 60491 molecule or 60491 modulator, such as a modulator identified by one of the exemplary screening assays described herein.

The present invention further provides methods for identifying new agents, or combinations, that are based on identifying agents that modulate the activity of one or more of the gene products encoded by one or more of the 60491 genes of the present invention, wherein these products may be associated with resistance of the cells to a therapeutic agent. Specifically, the activity of the proteins encoded by the 60491 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 60491 protein can be applied in clinical trials. For example, the effectiveness of an agent determined by a screening assay as described herein to increase 60491 gene expression, protein levels, or upregulate 60491 activity, can be monitored in clinical trials of subjects exhibiting decreased 60491 gene expression, protein levels, or downregulated 60491 activity. Alternatively, the effectiveness of an agent determined by a screening assay to decrease 60491 gene expression, protein levels, or downregulate 60491 activity, can be monitored in clinical trials of subjects exhibiting increased 60491 gene expression, protein levels, or upregulated 60491 activity. In such clinical trials, the expression or activity of a 60491 gene, and preferably, other genes that have been implicated in, for example, a 60491-associated disorder can be used as a "read out" or markers of the phenotype of a particular cell.

60491 Informatics

The sequence of a 60491 molecule is provided in a variety of media to facilitate use thereof. A sequence can be provided as a manufacture, other than an isolated nucleic acid or amino acid molecule, which contains a 60491. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 60491 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 60491, e.g., analyzing structure, function, or relatedness to one or more other nucleic acid or amino acid sequences. The method includes: providing a 60491 nucleic acid or amino acid sequence; comparing the 60491 sequence with a second sequence, e.g., one or more preferably a plurality of sequences from a collection of sequences, e.g., a nucleic acid or protein sequence database to thereby analyze 60491. The method can be performed in a machine, e.g., a computer, or manually by a skilled artisan.

The method can include evaluating the sequence identity between a 60491 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 60491 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 60491 sequence, or record, in machine-readable form; comparing a second sequence to the 60491 sequence; thereby analyzing a sequence. Comparison can include comparing to sequences for sequence identity or determining if one sequence is included within the other, e.g., determining if the 60491 sequence includes a sequence being compared. In a preferred embodiment the 60491 or second sequence is stored on a first computer, e.g., at a first site and the comparison is performed, read, or recorded on a second computer, e.g., at a second site. E.g., the 60491 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 60491-associated disease or disorder or a pre-disposition to a 60491-associated disease or disorder, wherein the method comprises the steps of determining 60491 sequence information associated with the subject and based on the 60491 sequence information, determining whether the subject has a 60491-associated disease or disorder or a pre-disposition to a 60491-associated disease or disorder and/or recommending a particular treatment for the disease, disorder or pre-disease condition.

The invention further provides in an electronic system and/or in a network, a method for determining whether a subject has a 60491-associated disease or disorder or a pre-disposition to a disease associated with a 60491 wherein the method comprises the steps of determining 60491 sequence information associated with the subject, and based on the 60491 sequence information, determining whether the subject has a 60491-associated disease or disorder or a pre-disposition to a 60491-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 60491 sequence of the subject to the 60491 sequences in the database to thereby determine whether the subject as a 60491-associated disease or disorder, or a pre-disposition for such.

The present invention also provides in a network, a method for determining whether a subject has a 60491 associated disease or disorder or a pre-disposition to a 60491-associated disease or disorder associated with 60491, said method comprising the steps of receiving 60491 sequence information from the subject and/or information related thereto, receiving phenotypic information associated with the subject, acquiring information from the network corresponding to 60491 and/or corresponding to a 60491-associated disease or disorder (e.g., a brain or pain associated disorder), and based on one or more of the phenotypic information, the 60491 information (e.g., sequence information and/or information related thereto), and the acquired information, determining whether the subject has a 60491-associated disease or disorder or a pre-disposition to a 60491-associated disease or disorder. The method may further comprise the step of recommending a particular treatment for the disease, disorder or pre-disease condition.

The present invention also provides a method for determining whether a subject has a 60491-associated disease or disorder or a pre-disposition to a 60491-associated disease or disorder, said method comprising the steps of receiving information related to 60491 (e.g., sequence information and/or information related thereto), receiving phenotypic information associated with the subject, acquiring information from the network related to 60491 and/or related to a 60491-associated disease or disorder, and based on one or more of the phenotypic information, the 60491 information, and the acquired information, determining whether the subject has a 60491-associated disease or disorder or a pre-disposition to a 60491-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

Background of the 46743 and 27417 Invention

Acyltransferases are a superfamily of enzymes that participate in phospholipid biosynthesis. Acyltransferases catalyze the transfer of an acyl chain to a lipid precursor and can be grouped into several subfamilies based upon their target specificity, for example: lysophosphatidic acid acyltransferases (1-acyl-sn-glycerol-3-phosphate acyltransferase; LPAAT); sn-glycerol-3-phosphate acyltransferases (GPAT); acyl-CoA: dihydroxyacetone-phosphate acyltransferases (DHAPAT); and 2-acylglycerophosphatidylethanolamine acyltransferases (LPEAT). Acyltransferases generally contain four regions of conserved amino acid residues, suggesting that these may be domains relevant to the catalytic activity of the enzymes (Lewin et al. (1999) Biochemistry 38:5764-71).

GPAT catalyzes the initial reaction in the pathway of glycerolipid biosynthesis, the transfer of an activated fatty acyl chain to the sn-1 position of glycerol 3-phosphate. LPAAT converts lysophosphatidic acid (LPA) into phosphatidic acid (PA) in the course of lipid metabolism in the endoplasmic reticulum (ER) (Eberhardt et al. (1997) J Biol Chem 272:20299-20305). LPAAT catalyses the transfer of an acyl chain from either acyl-coenzyme A or acyl-acyl carrier protein onto LPA, an intermediate in de novo lipid biosynthesis, to produce PA, the precursor of glycerolipids. PA can either be hydrolyzed to yield diacylglycerol (DAG) or can be converted to CDP-DAG for the synthesis of more complex phospholipids in the ER. Two human cDNAs have been cloned that encode enzymes having LPAAT activity, LPAAT-a and LPAAT-b (West et al. (1997) DNA Cell Biol 16:691-701; Eberhardt et al. (1997) J Biol Chem 272:20299-20305; Aguado and Campbell (1998) J Biol Chem 273:4096-4105). Both human LPAAT-a and LPAAT-b localize to the ER, and are encoded by genes located on chromosomes 6 and 9, respectively.

Aside from its role in the formation of biological membranes, LPA is produced by activated platelets and functions as a bioactive mediator, stimulating platelet aggregation, cell migration, and cell proliferation (Lee et al. (2000) Am J Physiol Cell Physiol 278:612-18). LPA generated in the plasma membrane of activated platelets and growth factor-stimulated fibroblasts appears to arise from hydrolysis of PA by a phospholipase A2. One possible means of the attenuation of the bioactive effects of LPA is acylation by LPAAT to yield PA. PA also has been implicated as an intracellular messenger, suggesting that its generation via acylation of LPA by LPAAT at an inflammatory site may lead to further cellular activation (Eberhardt et al. (1999) Adv Exp Med Biol 469:351-356). Several specific acyltransferases have been found to participate in critical biological functions. Endophilin 1, an SH3 domain-containing LPAAT, mediates the formation of synaptic-like microvesicles (SLMVs) from the plasma membrane via the conversion of LPA to PA (Schmidt et al. (1999) Nature 401:133-141). Mutations in a one type of acyltransferase, the tafazzins, cause a heritable disease, Barth syndrome. Barth syndrome is characterized by short stature, cardioskeletal myopathy, neutropenia, abnormal mitochondria, and respiratory-chain dysfunction (Bione et al. (1996) Nature Genetics 12: 385-389). These examples are indicative of the significant, and diverse regulatory functions that LPAAT acyltransferases can mediate.

Summary of the 46743 and 27417 Invention

The present invention is based, in part, on the discovery of novel human acyltransferases, referred to herein as "46743 and 27417". The nucleotide sequence of a cDNA encoding 46743 is shown in SEQ ID NO:57, and the amino acid sequence of a 46743 polypeptide is shown in SEQ ID NO:58. In addition, the nucleotide sequences of the coding region of 46743 are depicted in SEQ ID NO:59. The nucleotide sequence of a cDNA encoding 27417 is shown in SEQ ID NO:62, and the amino acid sequence of a 27417 polypeptide is shown in SEQ ID NO:63. In addition, the nucleotide sequences of the coding region of 27417 are depicted in SEQ ID NO:64.

Accordingly, in one aspect, the invention features a nucleic acid molecule that encodes a 46743 or 27417 protein or polypeptide, e.g., a biologically active portion of the 46743 or 27417 protein. In a preferred embodiment the isolated nucleic acid molecule encodes a polypeptide having the amino acid sequence of SEQ ID NO:58 or SEQ ID NO:63. In other embodiments, the invention provides isolated 46743 or 27417 nucleic acid molecules having the nucleotide sequence shown in SEQ ID NO:57, SEQ ID NO:59, SEQ ID NO:62, SEQ ID NO:64. In still other embodiments, the invention provides nucleic acid molecules that are substantially identical (e.g., naturally occurring allelic variants) to the nucleotide sequence shown in SEQ ID NO:57, SEQ ID NO:59, SEQ ID NO:62, SEQ ID NO:64. In other embodiments, the invention provides a nucleic acid molecule which hybridizes under stringent hybridization conditions to a nucleic acid molecule comprising the nucleotide sequence of SEQ ID NO:57, SEQ ID NO:59, SEQ ID NO:62, or SEQ ID NO:64, wherein the nucleic acid encodes a full length 46743 or 27417 protein or an active fragment thereof.

In a related aspect, the invention further provides nucleic acid constructs which include a 46743 or 27417 nucleic acid molecule described herein. In certain embodiments, the nucleic acid molecules of the invention are operatively linked to native or heterologous regulatory sequences. Also included are vectors and host cells containing the 46743 or 27417 nucleic acid molecules of the invention, e.g., vectors and host cells suitable for producing 46743 or 27417 nucleic acid molecules and polypeptides.

In another related aspect, the invention provides nucleic acid fragments suitable as primers or hybridization probes for the detection of 46743 or 27417 encoding nucleic acids.

In still another related aspect, isolated nucleic acid molecules that are antisense to a 46743 or 27417 encoding nucleic acid molecule are provided.

In another aspect, the invention features 46743 or 27417 polypeptides, and biologically active or antigenic fragments thereof that are useful, e.g., as reagents or targets in assays applicable to treatment and diagnosis of 46743 or 27417 mediated or related disorders. In another embodiment, the invention provides 46743 or 27417 polypeptides having a 46743 or 27417 activity. Preferred polypeptides are 46743 or 27417 proteins including at least one acyltransferase domain, and, preferably, having a 46743 or 27417 activity, e.g., a 46743 or 27417 activity as described herein.

In other embodiments, the invention provides 46743 or 27417 polypeptides, e.g., a 46743 or 27417 polypeptide having the amino acid sequence shown in SEQ ID NO:58 or SEQ ID NO:63; an amino acid sequence that is substantially identical to the amino acid sequence shown in SEQ ID NO:58 or SEQ ID NO:63; or an amino acid sequence encoded by a nucleic acid molecule having a nucleotide sequence which hybridizes under stringent hybridization conditions to a nucleic acid molecule comprising the nucleotide sequence of SEQ ID NO:57, SEQ ID NO:59, SEQ ID NO:62, or SEQ ID NO:64, wherein the nucleic acid encodes a full length 46743 or 27417 protein or an active fragment thereof.

In a related aspect, the invention provides 46743 or 27417 polypeptides or fragments operatively linked to non-46743 or 27417 polypeptides to form fusion proteins.

In another aspect, the invention features antibodies and antigen-binding fragments thereof that react with or, more preferably, specifically bind 46743 or 27417 polypeptides.

In another aspect, the invention provides methods of screening for compounds that modulate the expression or activity of the 46743 or 27417 polypeptides or nucleic acids.

In still another aspect, the invention provides a process for modulating 46743 or 27417 polypeptide or nucleic acid expression or activity, e.g., using the screened compounds. In certain embodiments, the methods involve treatment of conditions related to aberrant activity or expression of the 46743 or 27417 polypeptides or nucleic acids, such as conditions involving aberrant or deficient cellular proliferation, migration, and/or differentiation.

In yet another aspect, the invention provides methods for inhibiting the proliferation or migration, or inducing the killing, of a 46743- or 27417-expressing cell, e.g., a hyperproliferative and/or metastatic cell. The methods include contacting the cell with a compound (e.g., a compound identified using the methods described herein) that modulates the activity or expression of the 46743 or 27417 polypeptide or nucleic acid.

In a preferred embodiment, the 46743-expressing cell is found in the heart (normal or diseased heart), blood vessels (e.g., artery, vein, vascular smooth muscle, endothelia), kidney, skeletal muscle, brain (nerve or glial cell), or liver. In other embodiments, the 27147-expressing cell is a skeletal muscle or a blood vessel (e.g., arterial, vein, vascular smooth muscle, endothelial) cell.

In a preferred embodiment, the 46743 or 27147 expressing cell is found in a solid tumor, a soft tissue tumor, or a metastatic lesion. Preferably, the 46743 or 27147 expressing cells are hyperproliferative and/or metastatic. Preferably, the tumor is a sarcoma, a carcinoma, or an adenocarcinoma. Preferably, the hyperproliferative and/or metastatic cells are found in a cancerous or pre-cancerous tissue, e.g., a cancerous or pre-cancerous tissue where a 46743 or 27417 polypeptide or nucleic acid is expressed, e.g., heart, kidney, skeletal muscle, brain, glial cells, ovary, liver, artery, vein, vascular smooth muscle cell, bone marrow, skeletal muscle, colon, or lung tissue. More preferably, the hyperproliferative and/or metastatic cells are found in an ovarian, brain, colon, or lung cancer.

In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol.

In a preferred embodiment, the compound is an activator of a 46743 or 27417 polypeptide. Preferably, the activator is chosen from a peptide, a phosphopeptide, a small organic molecule, and an antibody. The activator can also be an allosteric effector that stimulates acyltransferase activity.

In another embodiment, the compound can be an inhibitor of a 46743 or 27417 polypeptide. Preferably, the inhibitor is chosen from a peptide, a phosphopeptide, a small organic molecule, and an antibody (e.g., an antibody conjugated to a therapeutic moiety selected from a cytotoxin, a cytotoxic agent, and a radioactive metal ion). In one preferred embodiment, the inhibitor is an analog or a derivative of lysophosphatidic acid (LPA).

In another embodiment, the compound is an inhibitor of a 46743 or a 27417 nucleic acid, e.g., an antisense, ribozyme, or triple helix molecule.

In another embodiment, the compound is administered in combination with a cytotoxic agent. Examples of cytotoxic agents include an anti-microtubule agent, a topoisomerase I inhibitor, a topoisomerase II inhibitor, an anti-metabolite, a mitotic inhibitor, an alkylating agent, an intercalating agent, and agent capable of interfering with a signal transduction pathway, an agent that promotes apoptosis or necrosis, and radiation.

In one embodiment, the compound is administered in an amount sufficient to alter the lipid metabolism of a cell. For example, the compound may alter the conversion of lysophosphatidic acid (LPA) to phosphatidic acid (PA), thereby mediating signaling between and within cells.

In another aspect, the invention features a method of modulating lipid metabolism in a 46743- or 27147-expressing cell (e.g., a heart, blood vessel (e.g., arterial, vein, vascular smooth muscle, endothelial), kidney, skeletal muscle, brain (nerve or glial cell), liver, or a cancer cell. The method includes, contacting the cell with a compound that modulates the activity or expression of a 46743 or a 27147 polypeptide as described herein, in an amount which is sufficient to alter metabolism of a lipid in the cell.

In a preferred embodiment, the compound is administered in an amount sufficient to alter the conversion of lysophosphatidic acid (LPA) to phosphatidic acid (PA), thereby mediating signaling between and within cells.

In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol.

In a preferred embodiment, the 46743-expressing cell is found in the heart (normal or diseased heart), blood vessels (e.g., artery, vein, vascular smooth muscle, endothelia), kidney, skeletal muscle, brain (nerve or glial cell), or liver. In other embodiments, the 27147-expressing cell is a skeletal muscle or a blood vessel (e.g., arterial, vein, vascular smooth muscle, endothelial) cell.

In a preferred embodiment, the 46743 or 27147 expressing cell is found in a solid tumor, a soft tissue tumor, or a metastatic lesion. Preferably, the 46743 or 27147 expressing cells are hyperproliferative and/or metastatic. Preferably, the tumor is a sarcoma, a carcinoma, or an adenocarcinoma. Preferably, the hyperproliferative and/or metastatic cells are found in a cancerous or pre-cancerous tissue, e.g., a cancerous or pre-cancerous tissue where a 46743 or 27417 polypeptide or nucleic acid is expressed, e.g., heart, kidney, skeletal muscle, brain, glial cells, ovary, liver, artery, vein, vascular smooth muscle cell, bone marrow, skeletal muscle, colon, or lung tissue. More preferably, the hyperproliferative and/or metastatic cells are found in an ovarian, brain, colon, or lung cancer.

In another aspect, the invention features a method for treating or preventing a disorder characterized by aberrant cellular proliferation, migration, or differentiation of a 46743- or a 27417-expressing cell, in a subject. Preferably, the method includes administering to the subject (e.g., a mammal, e.g., a human) an effective amount of a compound (e.g., a compound identified using the methods described herein) that modulates the activity, or expression of the 46743 or 27417 polypeptide or nucleic acid.

In preferred embodiment, the 46743-expressing cell is found in the heart (normal or diseased heart), blood vessels (e.g., artery, vein, vascular smooth muscle, endothelia), kidney, skeletal muscle, brain (nerve or glial cell), or liver.

In other embodiments, the 27147-expressing cell is a skeletal muscle or a blood vessel (e.g., arterial, vein, vascular smooth muscle, endothelial) cell.

In a preferred embodiment, the disorder is a cardiovascular, neurological, hepatic, renal or skeletal muscular disorder.

In a preferred embodiment, the disorder is a cancerous or pre-cancerous condition. Most preferably, the disorder is a cancer, e.g., a solid tumor, a soft tissue tumor, or a metastatic lesion. Preferably, the cancer is a sarcoma, a carcinoma, or an adenocarcinoma. Preferably, the cancer is found in a tissue where a 46743 or 27417 polypeptide or nucleic acid is expressed, e.g., heart, kidney, skeletal muscle, brain, glial cells, ovary, liver, artery, vein, vascular smooth muscle cell, bone marrow, colon, or lung tissue. Most preferably, the cancer is found in the ovary, brain, colon, or lung.

In a preferred embodiment, the compound is an activator of a 46743 or 27417 polypeptide. Preferably, the activator is chosen from a peptide, a phosphopeptide, a small molecule, a small inorganic molecule, and an antibody. The activator can also be an allosteric effector that stimulates acyltransferase activity.

In another embodiment, the compound can be an inhibitor of a 46743 or 27417 polypeptide. Preferably, the inhibitor is chosen from a peptide, a phosphopeptide, a small organic molecule, a small inorganic molecule, and an antibody (e.g., an antibody conjugated to a therapeutic moiety selected from a cytotoxin, a cytotoxic agent, and a radioactive metal ion). In one preferred embodiment, the inhibitor is an analog or derivative of LPA.

In another embodiment, the compound is an inhibitor of a 46743 or a 27417 nucleic acid, e.g., an antisense, ribozyme, or triple helix molecule.

In one embodiment, the compound is administered in an amount sufficient to alter the lipid metabolism of a cell. For example, the compound may alter the conversion of lysophosphatidic acid (LPA) to phosphatidic acid (PA), thereby mediating signaling between and within cells.

In another embodiment, the compound is administered in combination with a cytotoxic agent. Examples of cytotoxic agents include an anti-microtuble agent, a topoisomerase I inhibitor, a topoisomerase II inhibitor, an anti-metabolite, a mitotic inhibitor, an alkylating agent, an intercalating agent, and agent capable of interfering with a signal transduction pathway, an agent that promotes apoptosis or necrosis, and radiation.

The invention also provides assays for determining the activity of, or the presence or absence of, 46743 or 27417 polypeptides or nucleic acid molecules in a biological sample, including for disease diagnosis. Preferably, the biological sample includes a diseased cell or tissue. In one embodiment, the diseased cell or tissue is obtained from a subject having a cardiovascular, neurological, hepatic, renal or skeletal muscular disorder. In other embodiments, the biological sample includes cancerous or pre-cancerous cell or tissue. For example, the cancerous tissue can be a solid tumor, a soft tissue tumor, or a metastatic lesion. Preferably, the cancerous tissue is a sarcoma, a carcinoma, or an adenocarcinoma. Preferably, the cancerous tissue is from the heart, kidney, skeletal muscle, brain, glial cells, ovary, liver, artery, vein, vascular smooth muscle cell, bone marrow, colon, or lung. Most preferably, the cancerous tissue is from the ovary, brain, colon, or lung. The activity of 46743 or 27417 polypeptides or nucleic acid molecules can be determined using a method described herein.

In another aspect the invention provides a method of detecting a polypeptide hormone or activity thereof. The method includes detecting the presence of a 46743 polypeptide or nucleic acid molecule in a sample, e.g., a sample prepared from a biopsy or from cultured cells. An increase in the level of 46743 molecules indicates a polypeptide hormone activity. In a preferred embodiment, the polypeptide hormone is epidermal growth factor (EGF).

In a further aspect the invention provides assays for determining the presence or absence of a genetic alteration in a 46743 or 27417 polypeptide or nucleic acid molecule in a sample, for, e.g., disease diagnosis. Preferably, the biological sample includes a diseased cell or tissue. In one embodiment, the diseased cell or tissue is obtained from a subject having a cardiovascular, neurological, hepatic, renal or skeletal muscular disorder. For example, the cancerous tissue can be a solid tumor, a soft tissue tumor, or a metastatic lesion. Preferably, the cancerous tissue is a sarcoma, a carcinoma, or an adenocarcinoma. Preferably, the cancerous tissue is from the heart, kidney, skeletal muscle, brain, glial cells, ovary, liver, artery, vein, vascular smooth muscle cell, bone marrow, colon, or lung tissue. Most preferably, the cancerous tissue is from the ovary, brain, colon, or lung.

In a still further aspect, the invention provides methods for evaluating the efficacy of a treatment of a disorder, e.g., a cardiovascular, neurological, hepatic, renal or skeletal muscular disorder, or a hyperproliferative and/or metastatic disorder, e.g., cancer (e.g., ovarian, brain, colon, or lung cancer). The method includes: treating the subject, e.g., a patient or an animal, with a protocol under evaluation (e.g., treating a subject with one or more of: chemotherapy, radiation, and/or a compound identified using the methods described herein); and evaluating the activity of a 46743 or 27417 polypeptide, or the expression of a 46743 or 27417 polypeptide or nucleic acid, before and after treatment. A change, e.g., a decrease or increase, in the activity of a 46743 or 27417 polypeptide, or the expression of a 46743 or 27417 polypeptide or nucleic acid, relative to the level of activity or expression before treatment, is indicative of the efficacy of the disorder.

In a preferred embodiment, the disorder is a cardiovascular, neurological, hepatic, renal or skeletal muscular disorder.

In a preferred embodiment, the disorder is a cancer of the heart, kidney, skeletal muscle, brain, glial cells, ovary, liver, artery, vein, vascular smooth muscle cell, bone marrow, colon, or lung tissue. Most preferably, the disorder is a cancer of the ovary, brain, colon, or lung. The activity of a 46743 or 27417 polypeptide, or the expression of a 46743 or 27417 polypeptide or nucleic acid, can be assayed by any method described herein.

In a preferred embodiment, the evaluating step includes obtaining a sample (e.g., a tissue sample, e.g., a biopsy, or a fluid sample) from the subject, before and after treatment and comparing the level of activity and/or expression of a 46743 or 27417 polypeptide or nucleic acid before and after treatment.

In another aspect, the invention provides methods for evaluating the efficacy of a therapeutic or prophylactic agent (e.g., an anti-neoplastic and/or metastatic agent). The method includes: contacting a sample with an agent (e.g., a compound identified using the methods described herein); and evaluating the activity and/or expression of a 46743 or 27417 polypeptide or nucleic acid in the sample, before and after the contacting step. A change, e.g., a decrease or increase in the level of 46743 or 27417 polypeptide or nucleic acid in the sample obtained after the contacting step, relative to the level of activity and/or expression in the sample before the contacting step, is indicative of the efficacy of the agent. The activity or expression level of 46743 or 27417 polypeptide or nucleic acid can be detected by any method described herein.

In a preferred embodiment, the sample includes cells obtained from a cancerous tissue where a 46743 or 27417 polypeptide or nucleic acid is expressed, e.g., a cancer of the ovary, brain, colon, or lung.

In a preferred embodiment, the sample is a tissue sample (e.g., a biopsy), a bodily fluid, or cultured cells (e.g., a tumor cell line).

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 46743 or 27417 molecule. In one embodiment, the capture probe is a nucleic acid, e.g., a probe complementary to a 46743 or 27417 nucleic acid sequence. In another embodiment, the capture probe is a polypeptide, e.g., an antibody specific for 46743 or 27417 polypeptides. Also featured is a method of analyzing a sample by contacting the sample to the aforementioned array and detecting binding of the sample to the array.

Other features and advantages of the invention will be apparent from the following detailed description, and from the claims.

Detailed Description of 46743 and 27417

Human 46743

The human 46743 sequence (FIGS. 49A-49B; SEQ ID NO:57), which is approximately 1766 nucleotides long including untranslated regions, contains a predicted methionine-initiated coding sequence of about 1071 nucleotides, including the termination codon (nucleotides 301-1371 of SEQ ID NO:57; SEQ ID NO:59). The coding sequence encodes a protein about 356 amino acid in length, not including the termination codon (SEQ ID NO:58).

Human 46743 contains the following regions or other structural features:

a predicted lysophosphatidic acid acyltransferase domain located at about amino acid residues 26-328 of SEQ ID NO:58;

one predicted transmembrane region located at about amino acid residues 83 to about 101 of SEQ ID NO:58;

two predicted non-transmembrane regions located at about amino acids 1 to about 82 (N-terminal non-transmembrane domain), and from about amino acids 102 to about 356 (C-terminal non-transmembrane domain) of SEQ ID NO:58;

five predicted N-glycosylation sites (PS00001) located from about amino acids 150 to 153, 230 to 233, 265 to 268, 344 to 347, and 352 to 355 of SEQ ID NO:58;

one cAMP- and cGMP-dependent protein kinase phosphorylation site (PS00004) located at about amino acids 238 to 241 of SEQ ID NO:58;

six predicted Protein Kinase C phosphorylation sites (PS00005) located at about amino acids 22 to 24, 35 to 37, 60 to 62, 107 to 109, 205 to 207, and 266 to 268 of SEQ ID NO:58;

three predicted Casein Kinase II phosphorylation sites (PS00006) located at about amino acids 39 to 42, 153 to 156, and 295 to 298 of SEQ ID NO:58;

four predicted N-myristoylation sites (PS00008) located at about amino acids 145 to 150, 170 to 175, 226 to 231, and 327 to 332 of SEQ ID NO:58;

one predicted leucine zipper pattern (PS00029) located at about amino acids 78 to 99 of SEQ ID NO:58;

and one predicted vacuolar targeting motif located at about amino acids 217 to 220 of SEQ ID NO:58.

For general information regarding PS prefix domain identification numbers, refer to Sonnhammer et al. (1997) Protein 28:405-420.

Human 27417

The human 27417 sequence (FIGS. 56A-56C; SEQ ID NO:62), which is approximately 3725 nucleotides long including untranslated regions, contains a predicted methionine-initiated coding sequence of about 1095 nucleotides (nucleotides 306-1400 of SEQ ID NO:62; SEQ ID NO:64). The coding sequence encodes a 364 amino acid protein, not including the termination codon (SEQ ID NO:63). The human 27147 protein of SEQ ID NO:63 and FIG. 56 includes an amino-terminal hydrophobic amino acid sequence, consistent with a signal sequence, of about 49 amino acids (from about amino acid 1 to 49 of SEQ ID NO:63), which upon cleavage results in the production of a mature protein form. This mature protein form is approximately 315 amino acid residues in length (from about amino acids 50 to 364 of SEQ ID NO:63).

Human 27417 contains the following regions or other structural features:

a predicted acyltransferase domain located at about amino acid residues 71 to 363 of SEQ ID NO:63;

one predicted transmembrane region located at about amino acids 321 to 337 of SEQ ID NO:63;

two predicted non-transmembrane regions located at about amino acids 50 to about 320 (N-terminal non-transmembrane domain), and from about amino acids 338 to 364 (C-terminal non-transmembrane domain) of SEQ ID NO:63;

one predicted N-glycosylation site (PS00001) located at about amino acids 68 to about 71 of SEQ ID NO:63;

one cAMP- and cGMP-dependent protein kinase phosphorylation site (PS00004) located at about amino acids 241 to 244 of SEQ ID NO:63;

five predicted Protein Kinase C phosphorylation sites (PS00005) located at about amino acids 11 to 13, 144 to 146, 205 to 207, 317 to 319, and 361 to 363 of SEQ ID NO:63;

three predicted Casein Kinase II phosphorylation sites (PS00006) located at about amino acids 95 to 98, 158 to 161, and 246 to 249 of SEQ ID NO:63;

two predicted tyrosine kinase phosphorylation sites (PS00007) located at about amino acids 82 to about 89 and about 219 to about 226 of SEQ ID NO:63;

four predicted N-myristoylation sites (PS00008) located at about amino acids 23 to 28, 130 to 135, 330 to 335, and 352 to 357 of SEQ ID NO:63;

one predicted amidation site (PS00009) located at about amino acids 340 to 343 of SEQ ID NO:63;

and one predicted leucine zipper pattern (PS00029) located at about amino acids 105 to 126 of SEQ ID NO:63.

For general information regarding PS prefix domain identification numbers, refer to Sonnhammer et al. (1997) Protein 28:405-420.

TABLE 20

Summary of Sequence Information for 46743 and 27417

| Gene | cDNA | ORF | Polypeptide | Figure | ATCC Accession Number |
|---|---|---|---|---|---|
| 46743 | SEQ ID NO: 57 | SEQ ID NO: 59 | SEQ ID NO: 58 | FIGS. 49A-49B | |
| 27417 | SEQ ID NO: 62 | SEQ ID NO: 63 | SEQ ID NO: 64 | FIGS. 56A-56C | |

TABLE 21

Summary of Domains of 46743 and 27417

| Protein | Acyltransferase | Leucine Zipper | Transmembrane |
|---|---|---|---|
| 46743 | About amino acids 26-328 of SEQ ID NO:58 | About amino acids 78-99 of SEQ ID NO:58 | About amino acids 83-101 of SEQ ID NO:58 |
| 27417 | About amino acids 71-363 of SEQ ID NO:63 | About amino acids 105-126 of SEQ ID NO:63 | About amino acids 321-337 of SEQ ID NO:63 |

The 46743 and 27417 proteins contain a significant number of structural characteristics in common with members of the acyltransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

An "acyltransferase", as defined above, can catalyze an acylation reaction. Typically, acyltransferases have a specificity (e.g., a substrate specificity) for various lipid precursors. Acyltransferases can be divided into several subfamilies based upon their target specificity, e.g.: lysophosphatidic acid acyltransferase (1-acyl-sn-glycerol-3-phosphate acyltransferase; LPAAT); sn-glycerol-3-phosphate acyltransferase (GPAT); acyl-CoA: dihydroxyacetone-phosphate acyltransferase (DHAPAT); and 2-acylglycerophosphatidylethanolamine acyltransferase (LPEAT). Specificity of an acyltransferase for acylation of a particular lipid target can be predicted by the presence of sequences within four highly conserved blocks described below, whereby particular amino acid residues are associated with particular classes of acyltransferases (e.g., as described in Lewin et al. (1999) Biochemistry 38:5764-71, the contents of which are incorporated herein by reference).

A 46743 or 27417 polypeptide can include an "acyltransferase domain" or regions homologous with an "acyltransferase domain".

As used herein, the term "acyltransferase domain" includes an amino acid sequence of about 100 to 310 amino acid residues in length and having a bit score for the alignment of the sequence to an acyltransferase domain profile (ProDom), wherein the domain profile is selected form the group consisting of ProDomain No. 37511, 21987, and 4009 (ProDom Release 1999.2), of at least 150. Preferably, an acyltransferase domain includes at least about 150 to 310 amino acids, more preferably about 150 to 200 amino acid residues, or about 150 to 170 amino acids and has a bit score for the alignment of the sequence to the acyltransferase domain profile (ProDom) of at least 180 or greater. The acyltransferase domain is homologous to several ProDom family entries, e.g., ProDomain Nos. 37511, 21987, and 4009 (ProDomain Release 1999.2; see also respectively ProDomain Nos. PD036247, PD022151, and PD000989, Release 2000.1).

An alignment of the N-terminal portion of the acyltransferase domain (amino acids 26 to 214 of SEQ ID NO:58) of human 46743 with a consensus amino acid sequence (SEQ ID NO:60) derived from a recursive PSI-BLAST profile (ProDom) is depicted in FIG. 52A. An alignment of the C-terminal portion of the acyltransferase domain (amino acids 215 to 328 of SEQ ID NO:58) of human 46743 with a consensus amino acid sequence (SEQ ID NO:61) derived from a recursive PSI-BLAST profile (ProDom) is depicted in FIG. 52B. An alignment of the N-terminal portion of the acyltransferase domain (amino acids 71 to 220 of SEQ ID NO:63) of human 27147 with a consensus amino acid sequence (SEQ ID NO:65) derived from a recursive PSI-BLAST profile (ProDom) is depicted in FIG. 59A. An alignment of the C-terminal portion of the acyltransferase domain (amino acids 197 to 363 of SEQ ID NO:63) of human 27147 with a consensus amino acid sequence (SEQ ID NO:66) derived from a recursive PSI-BLAST profile (ProDom) is depicted in FIG. 59B. The acyltransferase domain (HMM) has also been assigned the PFAM Accession Number PF01553. An alignment of human 27147 with a consensus amino acid sequence derived from a hidden Markov model (Pfam) is depicted in FIG. 60.

In a preferred embodiment a 46743 or 27147 polypeptide or protein has an "acyltransferase domain" or a region which includes at least about 150 to 310, more preferably about 150 to 200, or 150 to 170 amino acid residues and has at least about 75%, 80%, 85%, 90%, 95%, 99%, or 100% homology with an "acyltransferase domain," e.g., the acyltransferase domain of human 46743 or 27147 (e.g., residues 100 to 170 of SEQ ID NO:58, or residues 71 to 220 of SEQ ID NO:63).

To identify the presence of an "acyltransferase" domain in a 46743 or 27147 protein sequence, and make the determination that a polypeptide or protein of interest has a particular profile, the amino acid sequence of the protein can be searched against a database of domains, e.g., the ProDom database (Corpet et al. (1999), Nucl. Acids Res. 27:263-267) The ProDom protein domain database consists of an automatic compilation of homologous domains. Current versions of ProDom are built using recursive PSI-BLAST searches (Altschul S F et al. (1997) Nucleic Acids Res. 25:3389-3402; Gouzy et al. (1999) Computers and Chemistry 23:333-340.) of the SWISS-PROT 38 and TREMBL protein databases. The database automatically generates a consensus sequence for each domain. A BLAST search was performed against the ProDom database resulting in the identification of an "acyltransferase" domain in the amino acid sequences of human 46743 and 27147 at about residues 26 to 328 of SEQ ID NO:58 (see FIG. 49), and about residues 71 to 363 of SEQ ID NO:63 (see FIG. 56).

Alternatively, to identify the presence of an "acyltransferase" domain in a 46743 or 27147 protein sequence, the amino acid sequence of the protein can be searched against the Pfam database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28(3):405-420 and a detailed description of HMMs can be found, for example, in Gribskov et al. (1990) Meth. Enzymol. 183:146-159; Gribskov et al. (1987) Proc. Natl. Acad. Sci. USA 84:4355-4358; Krogh et al. (1994) J. Mol. Biol. 235:1501-1531; and Stultz et al.(1993) Protein Sci. 2:305-314, the contents of which are incorporated herein by reference. A search was performed against the HMM database resulting in the identification of an "acyltransferase" domain in the amino acid sequence of human 27147 at about residues 77 to 288 of SEQ ID NO:63 (see FIG. 59).

Preferably, an acyltransferase domain can also include at least one of four blocks of homology commonly found in members of the acyltransferase family. The four blocks are each characterized by the following peptide motifs: (1) [NX]-H-[RQ]-S-X-[LYIM]-D, SEQ ID NO:68 ; (2) G-X-[IF]-F-I-[RD]-R, SEQ ID NO:69; (3) F-[PLI]-E-G-[TG]-R-[SX]-[RX], SEQ ID NO:70; and (4) [VI]-[PX]-[IVL]-[IV]-P-[VI], SEQ ID NO:71.

Both 46743 and 27417 include many of the residues present in these four acyltransferase motifs that are constant among all specificity classes: motif (1) is located at about amino acids 150 to 156 of SEQ ID NO:58 and about amino acids 192 to 198 of SEQ ID NO:63; motif (2) is located at about amino acids 178 to 183 of SEQ ID NO:58, and about amino acids 137 to 143 of SEQ ID NO:63; motif (3) is located at about amino acids 223 to 230 of SEQ ID NO:58, and about amino acids 171 to 178 of SEQ ID NO:63; and motif (4) is located at about amino acids 246 to 251 if SEQ ID NO:58, and about amino acids 202 to 207 of SEQ ID NO:63. In addition, both 46743 and 27147 include amino acids that are typically found in LPAATs and not typically found in GPATs: first, amino acid residues asparagine and glutamine in motif (1) (e.g., asparagine at amino acid residue 150 of SEQ ID NO:58 and amino acid residue 112 of SEQ ID NO:63, and glutamine at amino acid residue 114 of SEQ ID NO:63); and second, amino acid residue proline in motif (2) (e.g., proline at amino acid residue 224 of SEQ ID NO:58 and amino acid residue 192 of SEQ ID NO:63). Based on these structural properties, the 46743 and 27417 molecules of the present invention can have similar biological activities as acyltransferase family members, e.g., members of the LPAAT sub-family of acyltransferases.

In one embodiment, a 46743 or 27417 protein includes at least one transmembrane domain. As used herein, the term "transmembrane domain" includes an amino acid sequence of at least about 15 amino acid residues in length that inserts into or spans a phospholipid membrane. A transmembrane domain, as defined, can anchor a polypeptide to a lipid bilayer. More preferably, a transmembrane domain includes about at least 18, 20, 22, 24, 25, 30, 35 or 40 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al, (1996) Annual Rev. Neurosci. 19: 235-63, the contents of which are incorporated herein by reference.

In a preferred embodiment, a 46743 or 27417 polypeptide or protein has at least one transmembrane domain or a region which includes at least 18, 20, 22, 24, 25, 30, 35 or 40 amino acid residues and has at least about 75%, 85%, 90%, 95%, 99%, or 100% homology with a "transmembrane domain," e.g., at least one transmembrane domain of human 46743 (e.g., amino acid residues 83 to 101 of SEQ ID NO:58) or human 27417 (e.g., amino acid residues 321 to 337 of SEQ ID NO:63).

In another embodiment, a 46743 or 27417 protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally-occurring 46743 or 27417, or 46743- or 27417-like protein.

In a preferred embodiment, a 46743 or 27417 polypeptide or protein has a "non-transmembrane domain" or a region which includes at least about 1 to 350, preferably about 200 to 320, more preferably about 230 to 300, and even more preferably about 240 to 280 amino acid residues, and has at least about 75%, 85%, 90%, 95%, 99% or 100% homology with a "non-transmembrane domain", e.g., a non-transmembrane domain of human 46743 (e.g., residues 1 to 82 and 102 to 356 of SEQ ID NO:58) or human 27417 (e.g., residues 50 to 320 and 338 to 364 of SEQ ID NO:63). Preferably, a non-transmembrane domain is capable of catalytic activity (e.g., catalyzing an acylation reaction).

A non-transmembrane domain located at the N-terminus of a 46743 or 27417 protein or polypeptide is referred to herein as an "N-terminal non-transmembrane domain." As used herein, an "N-terminal non-transmembrane domain" includes an amino acid sequence having about 1 to 300, preferably about 30 to 290, more preferably about 50 to 280, or even more preferably about 80 to 275 amino acid residues in length and is located outside the boundaries of a membrane. For example, an N-terminal non-transmembrane domain is located at about amino acid residues 1 to 82 of SEQ ID NO:58 and about amino acid residues 50 to 320 of SEQ ID NO:63.

Similarly, a non-transmembrane domain located at the C-terminus of a 46743 or 27417 protein or polypeptide is referred to herein as a "C-terminal non-transmembrane domain." As used herein, an "C-terminal non-transmembrane domain" includes an amino acid sequence having about 1-300, preferably about 15 to 290, preferably about 20 to 270, more preferably about 25 to 255 amino acid residues in length and is located outside the boundaries of a membrane. For example, an C-terminal non-transmembrane domain is located at about amino acid residues 102 to 356 of SEQ ID NO:58 and about amino acid residues 338 to 364 of SEQ ID NO:63.

A 46743 family member can include at least one acyltransferase domain. Furthermore, a 46743 family member can include at least one transmembrane domain; at least one, two, three, four, preferably five predicted N-glycosylation sites (PS00001); at least one predicted cAMP- and cGMP-dependent protein kinase phosphorylation sites (PS00004); at least one, two, three, four, five, preferably six predicted protein kinase C phosphorylation sites (PS00005); at least one, two, preferably three predicted casein kinase II phosphorylation sites (PS00006); at least one, two, three, and preferably four predicted N-myristylation sites (PS00008); at least one predicted leucine zipper pattern (PS00029); and at least one predicted vacuolar targeting motif.

A 27147 family member can include at least one acyltransferase domain. Furthermore, a 27147 family member can include at least one transmembrane domain; at least one predicted N-glycosylation site (PS00001); at least one predicted cAMP- and cGMP-dependent protein kinase phosphorylation sites (PS00004); at least one, two, three, four, preferably five predicted protein kinase C phosphorylation sites (PS00005); at least one, two, preferably three predicted casein kinase II phosphorylation sites (PS00006); at least one, preferably two predicted tyrosine kinase phosphorylation sites(PS00007); at least one, two, three, and preferably four predicted N-myristylation sites (PS00008); at least one predicted amidation site (PS00009); and at least one predicted leucine zipper pattern (PS00029).

As the 46743 and 27147 polypeptides of the invention may modulate 46743- or 27147-mediated activities, they may be useful as of for developing novel diagnostic and therapeutic agents for 46743- or 27147-mediated or related disorders, as described below.

As used herein, a "46743 activity" or "27147 activity", "biological activity of 46743" "biological activity of 27147", "functional activity of 46743", or "functional activity of 27147", refers to an activity exerted by a 46743 or 27147 protein, polypeptide or nucleic acid molecule. For example, a 46743 or 27147 activity can be an activity exerted by 46743 or 27147 in a physiological milieu on, e.g., a 46743- or 27147-responsive cell, or on a 46743 or 27147 substrate, e.g., a protein or a lipid precursor, e.g., lysophosphatidic acid. A 46743 or 27147 activity can be determined in vivo or in vitro, according to standard assay techniques. In one embodiment, a 46743 or 27147 activity is a direct activity, such as an association with a 46743 or 27147 target molecule. A "target molecule" or "binding partner" is a molecule with which a 46743 or 27147 protein binds or interacts in nature, e.g., a lipid to which the 46743 or 27147 protein attaches an acyl chain. In an exemplary embodiment, 46743 and 27147 are acyltransferases, e.g., lysophosphatidic acid acyltransferases (LPAATs).

A 46743 or 27147 activity can also be an indirect activity, e.g., a cellular signaling activity mediated by reduction in the concentration of a 46743 or 27147 substrate or an increase in the concentration of enzymatic product produced by a 46743 or 27147 protein. Based on their sequence features, the 46743 and 27147 molecules of the present invention can have similar biological activities as acyltransferase family members, e.g., LPAATs.

Acyltransferases play a role in diverse cellular processes, e.g., lipid metabolism. The term "lipid metabolism" is defined herein as the synthesis or degradation of a lipid molecule in a cell. The effect in the synthesis or degradation of a lipid molecule can be direct or indirect. For example, acyltransferases typically catalyze the biosynthesis of complex lipids by specific acylation reactions. These reactions are important for the formation of both storage lipids and triacylglycerols, as well as structural lipids such as phospholipids and galactolipids. Acyltransferases also participate in signaling by regulating the levels of lipids that function as signaling molecules in diverse cellular processes. For example, LPAAT converts LPA to phosphatidic acid (PA), both of which have the capacity to mediate signaling between and within cells. Thus, the molecules of the present invention may be involved in one or more of: 1) transfer of an acyl chain to a substrate, e.g., a lipid precursor; 2) regulation of lipid biosynthesis; 3) modulation of mitogenesis; 4) modulation of cellular differentiation; 5) modulation of cell morphology, e.g., actin cytoskleleton remodeling; 6) regulation of cell migration, e.g., chemotaxis, such as chemotaxis of a blood cell (e.g., a monocytes), or neurite tracking (e.g., neurite extension or retraction); 7) modulation of tumor cell growth and invasion; 8) regulation of wound healing; 9) regulation of platelet aggregation; 10) modulation of vasoconstriction; 11) modulation of metabolite uptake, e.g., glutamate and glucose uptake, in a cell such as an astrocytes or 12) formation of vesicles, e.g., synaptic-like microvesicles. The 46743 or 27147 proteins of the present invention can have one or more of activities listed above as well as the ability to antagonize or inhibit, competitively or non-competitively, any of the same activities.

Thus, the 46743 or 27147 molecules can act as novel diagnostic targets and therapeutic agents for controlling one or more of cellular proliferative and/or differentiative disorders, heart disorders, cardiovascular disorders, liver disorders, skeletal muscle disorders, kidney disorders, brain disorders, bone marrow disorders, and metabolic disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast, and liver origin.

As used herein, the terms "cancer", "hyperproliferative" and "neoplastic" refer to cells having the capacity for autonomous growth. Examples of such cells include cells having an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Examples of cellular proliferative and differentiative disorders of the brain and the nervous system include, but are not limited to tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

In ovarian tissues, the proliferative and/or differentiative disorder can include ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cancers or neoplastic conditions, in addition to the ones described above, include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Disorders involving the skeletal muscle include, but are not limited to, tumors such as rhabdomyosarcoma.

The 46743 and 27147 proteins, fragments thereof, and derivatives and other variants of the sequences in SEQ ID NO:58 and SEQ ID NO:63 thereof are collectively referred to as "polypeptides or proteins of the invention" or "46743 polypeptides or proteins" and "27147 polypeptides or proteins". Nucleic acid molecules encoding such polypeptides or proteins are collectively referred to as "nucleic acids of the invention" or "46743 nucleic acids" and "27147 nucleic acids". 46743 or 27147 molecules refer to 46743 or 27147 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:57, SEQ ID NO:59, SEQ ID NO:62, or SEQ ID NO:64 corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a 46743 or 27147 protein. The gene can optionally further include non-coding sequences, e.g., regulatory sequences and introns. Preferably, a gene encodes a mammalian 46743 or 27147 protein or derivative thereof.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of 46743 or 27147 protein is at least 10% pure. In a preferred embodiment, the preparation of 46743 or 27147 protein has less than about 30%, 20%, 10% and more preferably 5% (by dry weight), of non-46743 or 27147 protein (also referred to herein as a "contaminating protein"), or of chemical precursors of non-46743 or 27147 chemicals. When the 46743 or 27147 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 46743 or 27147 without abolishing or substantially altering a 46743 or 27147 activity. Preferably the alteration does not substantially alter the 46743 or 27147 activity, e.g., the activity is at least 20%, 40%, 60%, 70% or 80% of wild-type. An "essential" amino acid residue is a residue that, when altered from the wild-type sequence of 46743 or 27147, results in abolishing a 46743 or 27147 activity such that less than 20% of the wild-type activity is present. For example, conserved amino acid residues in 46743 or 27147 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a 46743 or 27147 protein is preferably replaced with another amino acid residue from the same side chain family. Alternatively, in another embodiment, mutations can be introduced randomly along all or part of a 46743 or 27147 coding sequence, such as by saturation mutagenesis, and the resultant mutants can be screened for 46743 or 27147 biological activity to identify mutants that retain activity. Following mutagenesis of SEQ ID NO:57, SEQ ID NO:59, SEQ ID NO:62, or SEQ ID NO:64, the encoded protein can be expressed recombinantly and the activity of the protein can be determined.

As used herein, a "biologically active portion" of a 46743 or 27147 protein includes a fragment of a 46743 or 27147 protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a 46743 or 27147 molecule and a non-46743 or 27147 molecule, or between a first 46743 or 27147 molecule and a second 46743 or 27147 molecule (e.g., a dimerization interaction). Biologically active portions of a 46743 or 27147 protein include peptides comprising amino acid sequences sufficiently homologous to or derived from the amino acid sequence of the 46743 or 27147 protein, e.g., the amino acid sequence shown in SEQ ID NO:58 or SEQ ID NO:63, which include less amino acids than the full length 46743 or 27147 proteins, and exhibit at least one activity of a 46743 or 27147 protein. Typically, biologically active portions comprise a domain or motif with at least one activity of the 46743 or 27147 protein, e.g., acyltransferase activity. A biologically active portion of a 46743 or 27147 protein can be a polypeptide which is, for example, 10, 25, 50, 100, 200 or more amino acids in length. Biologically active portions of a 46743 or 27147 protein can be used as targets for developing agents which modulate a 46743 or 27147 mediated activity, e.g., an acyltransferase activity.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 46743 amino acid sequence of SEQ ID NO:58 having 106 amino acid residues, at least 142, preferably at least 178, more preferably at least 213, even more preferably at least 249, and even more preferably at least 284, 320 or 356 amino acid residues are aligned; when aligning a second sequence to the 27417 amino acid sequence of SEQ ID NO:61 having 109 amino acid residues, at least 145, preferably at least 182, more preferably at least 218, even more preferably at least 254, and even more preferably at least 291, 327 or 364 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS*, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to 46743 or 27147 nucleic acid molecules of the invention. BLAST protein searches can be performed with the XBLAST program, score=50, wordlength=3 to obtain amino acid sequences homologous to 46743 or 27147 protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used.

Particular 46743 or 27147 polypeptides of the present invention have an amino acid sequence substantially identical to the amino acid sequence of SEQ ID NO:58 or SEQ ID NO:63. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 75%, or 80% identity, likely 85% identity, more likely 90%, 91%, 92%, 93%, 94%, 95%, 96%, 97%, 98%, or 99% identity to SEQ ID NO:58 or SEQ ID NO:63 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 65%, or 70% identity, likely 75% identity, more likely 80%, 85%, 90%, 91%, 92%, 93%, 94%, 95%, 96%, 97%, 98%, or 99% identity to SEQ ID NO:57, SEQ ID NO:59, SEQ ID NO:62, or SEQ ID NO:64 are termed substantially identical.

"Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules of 46743 and 27417

In one aspect, the invention provides, an isolated or purified, nucleic acid molecule that encodes a 46743 or 27417 polypeptide described herein, e.g., a full length 46743 or 27417 protein or a fragment thereof, e.g., a biologically active portion of a 46743 or 27417 protein. Also included is a nucleic acid fragment suitable for use as a hybridization probe, which can be used, e.g., to a identify nucleic acid molecule encoding a polypeptide of the invention, 46743 or 27417 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:57, or SEQ ID NO:62, or a portion of any of these nucleotide sequences. In one embodiment, the nucleic acid molecule includes sequences encoding the human 46743 or 27417 protein (i.e., "the coding region", from nucleotides 301-1371 of SEQ ID NO:57 and nucleotides 306-1400 of SEQ ID NO:62), as well as 3' untranslated sequences (nucleotides 1072-1766 of SEQ ID NO:57 and nucleotides 1401-3725 of SEQ ID NO:62). Alternatively, the nucleic acid molecule can include only the coding region of SEQ ID NO:57 or SEQ ID NO:62 (e.g., nucleotides 301-1371 of SEQ ID NO:57, corresponding to SEQ ID NO:59; and nucleotides 306-1400 of SEQ ID NO:62, corresponding to SEQ ID NO:64) and, e.g., no flanking sequences which normally accompany the subject sequence. In another embodiment, the nucleic acid molecule encodes a sequence corresponding to the mature protein of SEQ ID NO:58 or SEQ ID NO:63.

In another embodiment, an isolated nucleic acid molecule of the invention includes a nucleic acid molecule which is a complement of the nucleotide sequence shown in SEQ ID NO:57, SEQ ID NO:59, SEQ ID NO:62, or SEQ ID NO:64, or a portion of any of these nucleotide sequences. In other embodiments, the nucleic acid molecule of the invention is sufficiently complementary to the nucleotide sequence shown in SEQ ID NO:57, SEQ ID NO:59, SEQ ID NO:62, or SEQ ID NO:64, such that it can hydbridize (e.g., under a stringency condition described herein) to the nucleotide sequence shown in SEQ ID NO:57, SEQ ID NO:59, SEQ ID NO:62, or SEQ ID NO:64, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the nucleotide sequence shown in SEQ ID NO:57, SEQ ID NO:59, SEQ ID NO:62, or SEQ ID NO:64, In the case of an isolated nucleic acid molecule which is longer than or equivalent in length to the reference sequence, e.g., SEQ ID NO:57, SEQ ID NO:59, SEQ ID NO:62, or SEQ ID NO:64, the comparison is made with the full length of the reference sequence. Where the isolated nucleic acid molecule is shorter than the reference sequence, e.g., shorter than SEQ ID NO:57, SEQ ID NO:59, SEQ ID NO:62, or SEQ ID NO:64, the comparison is made to a segment of the reference sequence of the same length (excluding any loop required by the homology calculation).

46743 or 27417 Nucleic Acid Fragments

A nucleic acid molecule of the invention can include only a portion of the nucleic acid sequence of SEQ ID NO:57, SEQ ID NO:59, SEQ ID NO:62, or SEQ ID NO:64. For example, such a nucleic acid molecule can include a fragment which can be used as a probe or primer or a fragment encoding a portion of a 46743 or 27417 protein, e.g., an immunogenic or biologically active portion of a 46743 or 27417 protein. A fragment can comprise: nucleotides 376-1344 of SEQ ID NO:57, which encodes an acyltransferase domain of human 46743; or nucleotides 515-1699 of SEQ ID NO:62, which encodes an acyltransferase domain of human 27417. The nucleotide sequence determined from the cloning of the 46743 or 27417 gene allows for the generation of probes and primers designed for use in identifying and/or cloning other 46743 or 27417 family members, or fragments thereof, as well as 46743 or 27417 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include an acyltransferase domain. In a preferred embodiment the fragment is at least, 50, 100, 200, 300, 400, 500, 600, 700, or 900 base pairs in length.

46743 or 27417 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:57, SEQ ID NO:59, SEQ ID NO:62, or SEQ ID NO:64, or of a naturally occurring allelic variant or mutant of SEQ ID NO:57, SEQ ID NO:59, SEQ ID NO:62, or SEQ ID NO:64.

In a preferred embodiment the nucleic acid is a probe which is at least 5 or 10, and less than 200, more preferably less than 100, or less than 50, base pairs in length. The probe can be identical, or differ by 1 nucleotide, or less than in 3, 4, 5 or 10 nucleotides, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes an acyltransferase domain (e.g., about amino acid residues 26-328 of SEQ ID NO:58; or about amino acid residues 71-263 of SEQ ID NO:63).

In another embodiment a set of primers is provided, e.g., primers suitable for use in a PCR, which can be used to amplify a selected region of a 46743 or 27417 sequence, e.g., a region described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: an acyltransferase domain (e.g., about amino acid residues 26-328 of SEQ ID NO:58; about amino acid residues 71-363 of SEQ ID NO:63).

A nucleic acid fragment can encode an epitope bearing region of a polypeptide described herein.

A nucleic acid fragment encoding a "biologically active portion of a 46743 or 27417 polypeptide" can be prepared by isolating a portion of the nucleotide sequence of SEQ ID NO:57, SEQ ID NO:59, SEQ ID NO:62, or SEQ ID NO:64, which encodes a polypeptide having a 46743 or 27417 biological activity (e.g., the biological activities of the 46743 or 27417 proteins are described herein), expressing the encoded portion of the 46743 or 27417 protein (e.g., by recombinant expression in vitro) and assessing the activity of the encoded portion of the 46743 or 27417 protein. For example, a nucleic acid fragment encoding a biologically active portion of 46743 or 27417 includes an acyltransferase domain (e.g., about amino acid residues 26-328 of SEQ ID NO:58 or about amino acid residues 71-363 of SEQ ID NO:63). A nucleic acid fragment encoding a biologically active portion of a 46743 or 27417 polypeptide, may comprise a nucleotide sequence which is greater than 400 nucleotides in length.

In a preferred embodiment, the fragment includes at least one, preferably at least 5, 10, 15 nucleotides from one of the following regions: about nucleotides 1 to 200, 110 to 310, 300 to 500, 400 to 700, 550 to 850, 700 to 1000, 850 to 1150, 1000 to 1300, 1150 to 1450, 1300 to 1600, 1450 to 1766 of SEQ ID NO:57.

In another preferred embodiment, the fragment includes at least one, preferably at least 5, 10, 15 nucleotides from one of the following regions: about nucleotides 1 to 150, 100 to 300, 200 to 400, 250 to 500, 300 to 550, 375 to 800, 500 to 800, 650 to 900, 700 to 1000, 800 to 1100, 900 to 1110, 1000 to 1400, 1300 to 1600, 1500 to 2000, 1750 to 2250, 2000 to 2500, 2500 to 3000, 3000 to 3500, or 3500 to 3725 of SEQ ID NO:62. In a preferred embodiment, the fragment includes at least one nucleotide from either the region of about nucleotides 1 to 308 or 2325 to 3725 of SEQ ID NO:62.

In preferred embodiments, a nucleic acid includes a nucleotide sequence encoding a 46743 polypeptide which is at least about 400, 500, 600, 650, 675, 700, 800, 850, 900, 950, 1000, 1100, 1200, or 1300 nucleotides in length and hybridizes under a stringency condition described herein to a nucleic acid molecule of SEQ ID NO:57, or SEQ ID NO:62. In one embodiment, a nucleic acid for a 27417 encoding sequence is at least about 500, 600, 650, 675, 700, 800, 850, 900, 950, 1000, 1100, 1200, 1300, 1800, 2100, 2400, 3000, or more nucleotides in length.

46743 or 27417 Nucleic Acid Variants

The invention further encompasses nucleic acid molecules that differ from the nucleotide sequence shown in SEQ ID NO:57, SEQ ID NO:59, SEQ ID NO:62, or SEQ ID NO:64. Such differences can be due to degeneracy of the genetic code (and result in a nucleic acid which encodes the same 46743 or 27417 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:58 or SEQ ID NO:63. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. For example, the nucleic acid can be one in which at least one codon, preferably at least 10% or 20% of the codons, has been altered such that the sequence is optimized for expression in, e.g., E. coli, yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:57, SEQ ID NO:59, SEQ ID NO:62, or SEQ ID NO:64, e.g., as follows: by at least one but less than 10, 20, 30, or 40 nucleotides; at least one but less than 1%, 5%, 10%, or 20% of the in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 75%, at least about 80%, typically at least about 80-55%, more typically at least about 85-90%, and most typically at least about 90-95% or more identical to the amino acid sequence shown in SEQ ID NO:58 or SEQ ID NO:63 or a fragment of one of these sequences. Such nucleic acid molecules can readily be obtained as being able to hybridize under stringent conditions, to the nucleotide sequence shown in SEQ ID NO:59 or SEQ ID NO:64 or a fragment of one of these sequences. Nucleic acid molecules corresponding to orthologs, homologs, and allelic variants of the 46743 or 27417 cDNAs of the invention can further be isolated by mapping to the same chromosome or locus as the 46743 or 27417 gene.

Preferred variants include those that are correlated with acyltransferase activity, e.g., LPAAT activity.

Allelic variants of 46743 or 27417, e.g., human 46743 or 27417, include both functional and non-functional proteins. Functional allelic variants are naturally occurring amino acid sequence variants of the 46743 or 27417 protein within a population that maintain the ability to modulate the phosphorylation state of itself or another protein or polypeptide. Functional allelic variants will typically contain only conservative substitution of one or more amino acids of SEQ ID NO:58 or SEQ ID NO:63, or substitution, deletion or insertion of non-critical residues in non-critical regions of the protein. Non-functional allelic variants are naturally-occurring amino acid sequence variants of 46743 or 27417, e.g., human 46743 or 27417, within a population that do not have the ability to attach an acyl chain to a lipid precursor. Non-functional allelic variants will typically contain a non-conservative substitution, a deletion, or insertion, or premature truncation of the amino acid sequence of SEQ ID NO:58 or SEQ ID NO:63, or a substitution, insertion, or deletion in critical residues or critical regions of the protein.

Moreover, nucleic acid molecules encoding other 46743 or 27417 family members and, thus, which have a nucleotide sequence which differs from the 46743 or 27417 sequences of SEQ ID NO:57, SEQ ID NO:59, SEQ ID NO:62, or SEQ ID NO:64 are intended to be within the scope of the invention.

Antisense Nucleic Acid Molecules, Ribozymes and Modified 46743 or 27417 Nucleic Acid Molecules In another aspect, the invention features, an isolated nucleic acid molecule which is antisense to 46743 or 27417. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 46743 or 27417 coding strand, or to only a portion thereof (e.g., the coding region of human 46743 or 27417 corresponding to SEQ ID NO:59 or SEQ ID NO:64). In another embodiment, the antisense nucleic acid molecule is antisense to a "noncoding region" of the coding strand of a nucleotide sequence encoding 46743 or 27417 (e.g., the 5' and 3' untranslated regions).

An antisense nucleic acid can be designed such that it is complementary to the entire coding region of 46743 or 27417 mRNA, but more preferably is an oligonucleotide which is antisense to only a portion of the coding or noncoding region of 46743 or 27417 mRNA. For example, the antisense oligonucleotide can be complementary to the region surrounding the translation start site of 46743 or 27417 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 46743 or 27417 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215: 327-330).

In still another embodiment, an antisense nucleic acid of the invention is a ribozyme. A ribozyme having specificity for a 46743 or 27417-encoding nucleic acid can include one or more sequences complementary to the nucleotide sequence of a 46743 or 27417 cDNA disclosed herein (i.e., SEQ ID NO:57, SEQ ID NO:59, SEQ ID NO:62, or SEQ ID NO:64), and a sequence having known catalytic sequence responsible for mRNA cleavage (see U.S. Pat. No. 5,093, 246 or Haselhoff and Gerlach (1988) Nature 334:585-591). For example, a derivative of a Tetrahymena L-19 IVS RNA can be constructed in which the nucleotide sequence of the active site is complementary to the nucleotide sequence to be cleaved in a 46743 or 27417-encoding mRNA. See, e.g., Cech et al. U.S. Pat. No. 4,987,071; and Cech et al. U.S. Pat. No. 5,116,742. Alternatively, 46743 or 27417 mRNA can be used to select a catalytic RNA having a specific ribonuclease activity from a pool of RNA molecules. See, e.g., Bartel, D. and Szostak, J. W. (1993) Science 261:1411-1418.

46743 or 27417 gene expression can be inhibited by targeting nucleotide sequences complementary to the regulatory region of the 46743 or 27417 (e.g., the 46743 or 27417 promoter and/or enhancers) to form triple helical structures that prevent transcription of the 46743 or 27417 gene in target cells. See generally, Helene, C. (1991) Anticancer Drug Des. 6(6):569-84; Helene, C. et al. (1992) Ann. N.Y. Acad. Sci. 660:27-36; and Maher, L. J. (1992) Bioassays 14(12):807-15. The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 46743 or 27417 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) Nature Biotech. 19:17 and Faria et al. (2001) Nature Biotech. 19:40-44. Such phosphoramidite oligonucleotides can be effective antisense agents. For example, the deoxyribose phosphate backbone of the nucleic acid molecules can be modified to generate peptide nucleic acids (see Hyrup B. et al. (1996) Bioorganic & Medicinal Chemistry 4 (1): 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670-675.

PNAs of 46743 or 27417 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 46743 or 27417 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958-976) or intercalating agents. (See, e.g., Zon (1988) Pharm. Res. 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 46743 or 27417 nucleic acid of the invention, two complementary regions one having a fluorophore and one a quencher such that the molecular beacon is useful for quantitating the presence of the 46743 or 27417 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. 5,876,930.

Isolated 46743 or 27417 Polypeptides

In another aspect, the invention features, an isolated 46743 or 27417 protein, or fragment, e.g., a biologically active portion, for use as immunogens or antigens to raise or test (or more generally to bind) anti-46743 or 27417 antibodies. 46743 or 27417 protein can be isolated from cells or tissue sources using standard protein purification techniques. 46743 or 27417 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 46743 or 27417 polypeptide has one or more of the following characteristics:

(i) it has the ability to catalyze the transfer of an acyl chain to a lipid precursor;

(ii) it has a molecular weight, e.g., a deduced molecular weight (preferably ignoring any contribution arising from post-translational modifications, e.g., phosphorylation or glycosylation), an amino acid composition, or other physical characteristics of the polypeptide of SEQ ID NO:58 or SEQ ID NO:63;

(iii) it has an overall sequence similarity of at least 75%, preferably at least 80%, more preferably at least 85%, 90%, or 95%, with a polypeptide of SEQ ID NO:58 or SEQ ID NO:63;

(iv) it has an acyltransferase domain which preferably has an overall sequence similarity of about 75%, 80%, 85%, 90% or 95% with amino acid residues 26-328 of SEQ ID NO:58 or amino acid residues 71-363 of SEQ ID NO:63;

(v) it has at least 70%, preferably 80%, and most preferably 95% of the cysteines found amino acid sequence of the native protein; and/or (vi) it is associated with a cellular membrane.

In a preferred embodiment the 46743 or 27417 protein, or fragment thereof, differs from the corresponding sequence in SEQ ID NO:58 or SEQ ID NO:63. In one embodiment it differs by at least one but by less than 15, 10, or 5 amino acid residues. In another it differs from the corresponding sequence in SEQ ID NO:58 or SEQ ID NO:63 by at least one residue but less than 20%, 15%, 10% or 5% of the residues in it differ from the corresponding sequence in SEQ ID NO:58 or SEQ ID NO:63. (If this comparison requires alignment the sequences should be aligned for maximum homology. "Looped" out sequences from deletions or insertions, or mismatches, are considered differences.) The differences are, preferably, differences or changes at a non-essential residue, or constitute a conservative substitution. In a preferred embodiment the differences are not in the acyltransferase domain, e.g., amino acids 26-328 or SEQ ID NO:58 or amino acids 71-363 of SEQ ID NO:63. In another preferred embodiment one or more differences are in the acyltransferase domain, e.g., amino acids 26-328 or SEQ ID NO:58 or amino acids 71-363 of SEQ ID NO:63.

Other embodiments include a protein that contain one or more changes in amino acid sequence, e.g., a change in an amino acid residue which is not essential for activity. Such 46743 or 27417 proteins differ in amino acid sequence from SEQ ID NO:58 or SEQ ID NO:63, yet retain biological activity.

In one embodiment, a biologically active portion of a 46743 or 27417 protein includes an acyltransferase domain. In another embodiment, a biologically active portion of a 46743 or 27417 protein includes a leucine zipper domain. Moreover, other biologically active portions, in which other regions of the protein are deleted, can be prepared by recombinant techniques and evaluated for one or more of the functional activities of a native 46743 or 27417 protein.

In a preferred embodiment, the 46743 or 27417 protein has an amino acid sequence shown in SEQ ID NO:58 or SEQ ID NO:63. In other embodiments, the 46743 or 27417 protein is substantially identical to SEQ ID NO:58 or SEQ ID NO:63. In yet another embodiment, the 46743 or 27417 protein is substantially identical to SEQ ID NO:58 or SEQ ID NO:63 and retains the functional activity of the protein of SEQ ID NO:58 or SEQ ID NO:63, as described in detail above.

46743 or 27417 Chimeric or Fusion Proteins

In another aspect, the invention provides 46743 or 27417 chimeric or fusion proteins. As used herein, a 46743 or 27417 "chimeric protein" or "fusion protein" includes a 46743 or 27417 polypeptide linked to a non-46743 or 27417 polypeptide. A "non-46743 or 27417 polypeptide" refers to a polypeptide having an amino acid sequence corresponding to a protein which is not substantially homologous to the 46743 or 27417 protein, e.g., a protein which is different from the 46743 or 27417 protein and which is derived from the same or a different organism. The 46743 or 27417 polypeptide of the fusion protein can correspond to all or a portion e.g., a fragment described herein of a 46743 or 27417 amino acid sequence. In a preferred embodiment, a 46743 or 27417 fusion protein includes at least one (or two) biologically active portion of a 46743 or 27417 protein. The non-46743 or 27417 polypeptide can be fused to the N-terminus or C-terminus of the 46743 or 27417 polypeptide.

The fusion protein can include a moiety which has a high affinity for a ligand. For example, the fusion protein can be a GST-46743 or GST-27417 fusion protein in which the 46743 or 27417 sequences are fused to the C-terminus of the GST sequences. Such fusion proteins can facilitate the purification of recombinant 46743 or 27417. Alternatively, the fusion protein can be a 46743 or 27417 protein containing a heterologous signal sequence at its N-terminus. In certain host cells (e.g., mammalian host cells), expression and/or secretion of 46743 or 27417 can be increased through use of a heterologous signal sequence.

Fusion proteins can include all or a part of a serum protein, e.g., an IgG constant region, or human serum albumin.

The 46743 or 27417 fusion proteins of the invention can be incorporated into pharmaceutical compositions and administered to a subject in vivo. The 46743 or 27417 fusion proteins can be used to affect the bioavailability of a 46743 or 27417 substrate. 46743 or 27417 fusion proteins may be useful therapeutically for the treatment of disorders caused by, for example, (i) aberrant modification or mutation of a gene encoding a 46743 or 27417 protein; (ii) mis-regulation of the 46743 or 27417 gene; and (iii) aberrant post-translational modification of a 46743 or 27417 protein.

Moreover, the 46743 or 27417-fusion proteins of the invention can be used as immunogens to produce anti-46743 or 27417 antibodies in a subject, to purify 46743 or 27417 ligands and in screening assays to identify molecules which inhibit the interaction of 46743 or 27417 with a 46743 or 27417 substrate.

Expression vectors are commercially available that already encode a fusion moiety (e.g., a GST polypeptide). A 46743 or 27417-encoding nucleic acid can be cloned into such an expression vector such that the fusion moiety is linked in-frame to the 46743 or 27417 protein.

Variants of 46743 or 27417 Proteins

In another aspect, the invention also features a variant of a 46743 or 27417 polypeptide, e.g., which functions as an agonist (mimetics) or as an antagonist. Variants of the 46743 or 27417 proteins can be generated by mutagenesis, e.g., discrete point mutation, the insertion or deletion of sequences or the truncation of a 46743 or 27417 protein. An agonist of the 46743 or 27417 proteins can retain substantially the same, or a subset, of the biological activities of the naturally occurring form of a 46743 or 27417 protein. An antagonist of a 46743 or 27417 protein can inhibit one or more of the activities of the naturally occurring form of the 46743 or 27417 protein by, for example, competitively modulating a 46743 or 27417-mediated activity of a 46743 or 27417 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 46743 or 27417 protein.

Variants of a 46743 or 27417 protein can be identified by screening combinatorial libraries of mutants, e.g., truncation mutants, of a 46743 or 27417 protein for agonist or antagonist activity.

Libraries of fragments e.g., N terminal, C terminal, or internal fragments, of a 46743 or 27417 protein coding sequence can be used to generate a variegated population of fragments for screening and subsequent selection of variants of a 46743 or 27417 protein. Variants in which a cysteine residue is added or deleted, or in which a residue that can be glycosylated is added or deleted, are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify 46743 or 27417 variants (Arkin and Yourvan (1992) Proc. Natl. Acad. Sci. USA 89:7811-7815; Delgrave et al. (1993) Protein Engineering 6(3):327-331).

Cell based assays can be exploited to analyze a variegated 46743 or 27417 library. For example, a library of expression vectors can be transfected into a cell line, e.g., a cell line, which ordinarily responds to 46743 or 27417 in a substrate-dependent manner. The transfected cells are then contacted with 46743 or 27417 and the effect of the expression of the mutant on signaling by the 46743 or 27417 substrate can be detected, e.g., by measuring acyltransferase activity. Plasmid DNA can then be recovered from the cells which score for inhibition, or alternatively, potentiation of signaling by the 46743 or 27417 substrate, and the individual clones further characterized.

In another aspect, the invention features a method of making a 46743 or 27417 polypeptide, e.g., a peptide having a non-wild type activity, e.g., an antagonist, agonist, or super agonist of a naturally occurring 46743 or 27417 polypeptide, e.g., a naturally occurring 46743 or 27417 polypeptide. The method includes: altering the sequence of a 46743 or 27417 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 46743 or 27417 polypeptide a biological activity of a naturally occurring 46743 or 27417 polypeptide. The method includes: altering the sequence, e.g., by substitution or deletion of one or more residues, of a 46743 or 27417 polypeptide, e.g., altering the sequence of a non-conserved region, or a domain or residue described herein, and testing the altered polypeptide for the desired activity.

Anti-46743 or 27147 Antibodies

In another aspect, the invention provides an anti-46743 or 27147 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-46743 or 27147 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., a 46743 or 27147 polypeptide, or fragment thereof. Examples of antigen-binding fragments of the anti-46743 or 27147 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-46743 or 27147 antibody can be a polyclonal or a monoclonal antibody. In other embodiments, the antibody can be recombinantly produced, e.g., produced by phage display or by combinatorial methods.

Phage display and combinatorial methods for generating anti-46743 or 27147 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the anti-46743 or 27147 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An anti-46743 or 27147 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc constant region, and the equivalent portion of a gene encoding a human Fc constant region is substituted (see Robinson et al., International Patent Publication PCT/US86/02269; Akira, et al., European Patent Application 184,187; Taniguchi, M., European Patent Application 171, 496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

A humanized or CDR-grafted antibody may be replaced with at least a portion of a non-human CDR or only some of the CDR's may be replaced with non-human CDR's. It is only necessary to replace the number of CDR's required for binding of the humanized antibody to a 46743 or 27147molecule, or a fragment thereof.

A humanized or CDR-grafted antibody will have at least one or two but generally all three recipient CDR's (of heavy and or light immuoglobulin chains) replaced with a donor CDR. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, Science 229:1202-1207, by Oi et al., 1986, BioTechniques 4:214, and by Queen et al. U.S. Pat. No. 5,585,089, U.S. Pat. No. 5,693,761 and U.S. Pat No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 46743 or 27147 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 Nature 321:552-525; Verhoeyan et al. 1988 Science 239:1534; Beidler et al. 1988 J. Immunol. 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In preferred embodiments an antibody can be made by immunizing with purified 46743 or 27147 antigen, or a fragment thereof, e.g., a fragment described herein, a membrane associated antigen, or a tissue, e.g., a crude tissue preparation, whole cells (preferably living), lysed cells, or cell fractions, e.g., membrane fractions.

A full-length 46743 or 27147 protein, or an antigenic peptide fragment of 46743 or 27147, can be used as an immunogen, or can be used to identify anti-46743 or anti-27147 antibodies made with other immunogens, e.g., cells, membrane preparations, and the like. The antigenic peptide of 46743 or 27147 should include at least 8 amino acid residues of the amino acid sequence shown in SEQ ID NO:58 or SEQ ID NO:63 and encompasses an epitope of 46743 or 27147. Preferably, the antigenic peptide includes at least 10 amino acid residues, more preferably at least 15 amino acid residues, even more preferably at least 20 amino acid residues, and most preferably at least 30 amino acid residues.

Fragments of 46743 or 27417 which include, e.g., residues 195 to 220 of SEQ ID NO:58 or residues 270 to 290 of SEQ ID NO:63 can be used, e.g., used as immunogens, or used to characterize the specificity of an antibody or antibodies against what are believed to be hydrophilic regions of the 46743 or 27417 protein. Similarly, fragments of 46743 or 27417 which include, e.g., residues 70 to 105 or 160 to 190 of SEQ ID NO:58 or residues 321 to 337 of SEQ ID NO:63 can be used to make an antibody against what is believed to be a hydrophobic region of the 46743 or 27417 protein; and fragment of 46743 or 27417 which includes residues 26 to 328 of SEQ ID NO:58 or residues 71 to 363 of SEQ ID NO:63 can be used to make an antibody against the acyltransferase region of the 46743 or 27147 protein.

Antibodies reactive with, or specific for, any of these regions, or other regions or domains described herein are provided.

Antibodies which bind only native 46743 or 27147 protein, only denatured or otherwise non-native 46743 or 27147 protein, or which bind both, are with in the invention. Antibodies with linear or conformational epitopes are within the invention. Conformational epitopes can sometimes be identified by identifying antibodies which bind to native but not denatured 46743 or 27147 protein.

Preferred epitopes encompassed by the antigenic peptide are regions of 46743 or 27147 are located on the surface of the protein, e.g., hydrophilic regions, as well as regions with high antigenicity. For example, an Emini surface probability analysis of the human 46743 or 27147 protein sequence can be used to indicate the regions that have a particularly high probability of being localized to the surface of the 46743 or 27147 protein and are thus likely to constitute surface residues useful for targeting antibody production.

In a preferred embodiment the antibody can bind to the extracellular portion of the 46743 or 27147 protein, e.g., it can bind to a whole cell which expresses a 46743 or 27147 protein. In another embodiment, the antibody can bind to an intracellular portion of a 46743 or 27147 protein. In preferred embodiments antibodies can bind one or more of the following: purified antigen, membrane associated antigen, tissue, e.g., tissue sections, whole cells, preferably living cells, lysed cells, or cell fractions, e.g., membrane fractions.

The anti-46743 or 27147 antibody can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target 46743 or 27147 protein.

In a preferred embodiment the antibody has effector function and can fix complement. In other embodiments the antibody does not recruit effector cells or fix complement.

In a preferred embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

In a preferred embodiment, an anti-46743 or 27147 antibody alters (e.g., increases or decreases) the acyltransferase activity of a 46743 or 27147 polypeptide. For example, the antibody can bind at or in proximity to the active site, e.g., to an epitope that includes a residue located from about amino acid 140 to 270 of SEQ ID NO:58 or about amino acid 80 to 220 or SEQ ID NO:63.

The antibody can be coupled to a toxin, e.g., a polypeptide toxin, e,g, ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-46743 or 27147 antibody (e.g., monoclonal antibody) can be used to isolate 46743 or 27147 protein by standard techniques, such as affinity chromatography or immunoprecipitation. Moreover, an anti-46743 or 27147 antibody can be used to detect 46743 or 27147 protein (e.g., in a cellular lysate or cell supernatant) in order to evaluate the abundance and pattern of expression of the protein. Anti-46743 or 27147 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes a nucleic acids which encodes an anti-46743 or 27147 antibody, e.g., an anti-46743 or 27147 antibody described herein. Also included are vectors which include the nucleic acid and cells transformed with the nucleic acid, particularly cells which are useful for producing an antibody, e.g., mammalian cells, e.g., CHO or lymphatic cells.

The invention also includes cell lines, e.g., hybridomas, which make an anti-46743 or 27147 antibody, e.g., and antibody described herein, and method of using said cells to make a 46743 or 27147 antibody.

46743 and 27417 Recombinant Expression Vectors, Host Cells and Genetically Engineered Cells In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 46743 or 27417 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 46743 or 27417 proteins, mutant forms of 46743 or 27417 proteins, fusion proteins, and the like).

The recombinant expression vectors of the invention can be designed for expression of 46743 or 27417 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 46743 or 27417 activity assays, (e.g., direct assays or competitive assays described in detail below), or to generate antibodies specific for 46743 or 27417 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six (6) weeks).

To maximize recombinant protein expression in E. coli is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111-2118). Such alteration of nucleic acid sequences of the invention can be carried out by standard DNA synthesis techniques.

The 46743 or 27417 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., C A, Gossen and Bujard (1992) Proc. Natl. Acad. Sci. USA 89:5547, and Paillard (1989) Human Gene Therapy 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) Science 249:374-379) and the α-fetoprotein promoter (Campes and Tilghman (1989) Genes Dev. 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., Antisense RNA as a molecular tool for genetic analysis, Reviews-Trends in Genetics, Vol. 1(1) 1986.

Another aspect the invention provides a host cell which includes a nucleic acid molecule described herein, e.g., a 46743 or 27417 nucleic acid molecule within a recombinant expression vector or a 46743 or 27417 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 46743 or 27417 protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation A host cell of the invention can be used to produce (i.e., express) a 46743 or 27417 protein. Accordingly, the invention further provides methods for producing a 46743 or 27417 protein using the host cells of the invention. In one embodiment, the method includes culturing the host cell of the invention (into which a recombinant expression vector encoding a 46743 or 27417 protein has been introduced) in a suitable medium such that a 46743 or 27417 protein is produced. In another embodiment, the method further includes isolating a 46743 or 27417 protein from the medium or the host cell.

In another aspect, the invention features, a cell or purified preparation of cells which include a 46743 or 27417 transgene, or which otherwise misexpress 46743 or 27417. The cell preparation can consist of human or non human cells, e.g., rodent cells, e.g., mouse or rat cells, rabbit cells, or pig cells. In preferred embodiments, the cell or cells include a 46743 or 27417 transgene, e.g., a heterologous form of a 46743 or 27417, e.g., a gene derived from humans (in the case of a non-human cell). The 46743 or 27417 transgene can be misexpressed, e.g., overexpressed or underexpressed. In other preferred embodiments, the cell or cells include a gene which misexpress an endogenous 46743 or 27417, e.g., a gene the expression of which is disrupted, e.g., a knockout. Such cells can serve as a model for studying disorders which are related to mutated or mis-expressed 46743 or 27417 alleles or for use in drug screening.

In another aspect, the invention features, a human cell, e.g., a hematopoietic stem cell, transformed with nucleic acid which encodes a subject 46743 or 27417 polypeptide.

Also provided are cells, preferably human cells, e.g., human hematopoietic or fibroblast cells, in which an endogenous 46743 or 27417 is under the control of a regulatory sequence that does not normally control the expression of the endogenous 46743 or 27417 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 46743 or 27417 gene. For example, an endogenous 46743 or 27417 gene, e.g., a gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 46743 or 27147 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (2001) *Nat. Biotechnol.* 19:35; and U.S. Pat. No. 5,876,742. Production of 46743 or 27147 polypeptide can be regulated in the subject by administering an agent (e.g., a steroid hormone) to the subject. In another preferred embodiment, the implanted recombinant cells express and secrete an antibody specific for a 46743 or 27147 polypeptide. The antibody can be any antibody or any antibody derivative described herein.

46743 and 27417 Transgenic Animals

The invention provides non-human transgenic animals. Such animals are useful for studying the function and/or activity of a 46743 or 27417 protein and for identifying and/or evaluating modulators of 46743 or 27417 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 46743 or 27417 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 46743 or 27417 protein to particular cells. A transgenic founder animal can be identified based upon the presence of a 46743 or 27417 transgene in its genome and/or expression of 46743 or 27417 mRNA in tissues or cells of the animals. A transgenic founder animal can then be used to breed additional animals carrying the transgene. Moreover, transgenic animals carrying a transgene encoding a 46743 or 27417 protein can further be bred to other transgenic animals carrying other transgenes.

46743 or 27417 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses of 46743 and 27417

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 46743 or 27417 protein (e.g., via a recombinant expression vector in a host cell in gene therapy applications), to detect a 46743 or 27417 mRNA (e.g., in a biological sample) or a genetic alteration in a 46743 or 27417 gene, and to modulate 46743 or 27417 activity, as described further below. The 46743 or 27417 proteins can be used to treat disorders characterized by insufficient or excessive production of a 46743 or 27417 substrate or production of 46743 or 27417 inhibitors. In addition, the 46743 or 27417 proteins can be used to screen for naturally occurring 46743 or 27417 substrates, to screen for drugs or compounds which modulate 46743 or 27417 activity, as well as to treat disorders characterized by insufficient or excessive production of 46743 or 27417 protein or production of 46743 or 27417 protein forms which have decreased, aberrant or unwanted activity compared to 46743 or 27417 wild type protein. Such disorders include those characterized by aberrant signaling or aberrant, e.g., hyperproliferative, cell growth. Moreover, the anti-46743 or 27417 antibodies of the invention can be used to detect and isolate 46743 or 27417 proteins, regulate the bioavailability of 46743 or 27417 proteins, and modulate 46743 or 27417 activity.

A method of evaluating a compound for the ability to interact with, e.g., bind, a subject 46743 or 27417 polypeptide is provided. The method includes: contacting the compound with the subject 46743 or 27417 polypeptide; and evaluating ability of the compound to interact with, e.g., to bind or form a complex with the subject 46743 or 27417 polypeptide. This method can be performed in vitro, e.g., in a cell free system, or in vivo, e.g., in a two-hybrid interaction trap assay. This method can be used to identify naturally occurring molecules which interact with subject 46743 or 27417 polypeptide. It can also be used to find natural or synthetic inhibitors of subject 46743 or 27417 polypeptide. Screening methods are discussed in more detail below.

46743 and 27417 Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 46743 or 27417 proteins, have a stimulatory or inhibitory effect on, for example, 46743 or 27417 expression or 46743 or 27417 activity, or have a stimulatory or inhibitory effect on, for example, the expression or activity of a 46743 or 27417 substrate. Compounds thus identified can be used to modulate the activity of target gene products (e.g., 46743 or 27417 genes) in a therapeutic protocol, to elaborate the biological function of the target gene product, or to identify compounds that disrupt normal target gene interactions.

In one embodiment, the invention provides assays for screening candidate or test compounds which are substrates of a 46743 or 27417 protein or polypeptide or a biologically active portion thereof. In another embodiment, the invention provides assays for screening candidate or test compounds which bind to or modulate the activity of a 46743 or 27417 protein or polypeptide or a biologically active portion thereof.

In one embodiment, an activity associated with a 46743 or 27147 protein, in particular an acyltransferase activity, can be assayed as follows: 10 µl of a cell lysate, e.g., a lysate from a cell expressing 46743 or 27147, or of a purified or partially purified 46743 or 27147 protein, diluted 10-fold, is added to 240 µl of assay buffer and substrate. Final concentrations of assay components are as follows: 100 mM HEPES-NaOH (pH 7.5), 200 mM NaCl, 5% (w/v) glycerol, 10 mM EDTA, and 5 mM β-mercaptoethanol. Acyl acceptor species, e.g., 1-palmitoyl-2-hydroxy-sn-glycero-3-phosphate, 1-myristoyl-2-hydroxy-sn-glycero-3-phosphocholine, 1-palmitoyl-2-hydroxy-sn-glycero-3-phosphocholine, or 1-alkyl-2-hydroxy-sn-glycero-3-phosphocholine (all from Avanti Polar Lipids, Alabaster, Ala.), are added to a final concentration of 20 µM. Also included are 1.3 µM 14C-radiolabeled acyl-CoA donor substrate (American Radiolabeled Chemicals, St. Louis, Mo.) and 40 µM of the corresponding non-labeled acyl-CoA, e.g., myristoyl coenzyme A, palmitoyl coenzyme A, stearoyl coenzyme A, and arachidonyl coenzyme A (all from Sigma, Mo.). After a 5-min incubation at 37° C., reactions are terminated by the addition of 250 µl of 1 M KCl, 0.2 M $H_3PO_4$, and 40 µl of 1 mg/ml BSA. Next, lipids are extracted by the addition of 0.75 ml of chloroform:methanol (2:1). The resulting organic phase is recovered, and 400 µl is dried to 30 µl and applied to a silica gel thin layer chromatography plate (TLC; 0.25-mm layer). Ascending TLC is performed in chloroform: pyridine: formic acid (50:30:7). Radioactive spots resolved by TLC are quantitated using a Phospholmager, and the resulting quantitation is uses as a measure of acyltransferase activity. Additional details for determination of the activity of an LPAAT is described in Eberhardt et al. (1997) J. Biol. Chem. 272(32): 20299-305, for example, the contents of which are incorporated herein by reference.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al. J. Med. Chem. 1994, 37: 2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233. Additional chemical libraries can be designed based on the structure of known substrates and products of acyltransferases. For example, a combinatorial library of derivatives of LPA can be screened to identify an acyltransferase inhibitor.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat No, '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); (Ladner supra.).

In one embodiment, an assay is a cell-based assay in which a cell which expresses a 46743 or 27417 protein or biologically active portion thereof is contacted with a test compound, and the ability of the test compound to modulate 46743 or 27417 activity is determined. Determining the ability of the test compound to modulate 46743 or 27417 activity can be accomplished by monitoring, for example, acyltransferase activity. The cell, for example, can be of mammalian origin, e.g., human. Cell homogenates, or fractions, preferably membrane containing fractions, can also be tested.

The ability of the test compound to modulate 46743 or 27417 binding to a compound, e.g., a 46743 or 27417 substrate, or to bind to 46743 or 27417 can also be evaluated. This can be accomplished, for example, by coupling the compound, e.g., the substrate, with a radioisotope or enzymatic label such that binding of the compound, e.g., the substrate, to 46743 or 27417 can be determined by detecting the labeled compound, e.g., substrate, in a complex. Alternatively, 46743 or 27417 could be coupled with a radioisotope or enzymatic label to monitor the ability of a test compound to modulate 46743 or 27417 binding to a 46743 or 27417 substrate in a complex. For example, compounds (e.g., 46743 or 27417 substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 46743 or 27417 substrate) to interact with 46743 or 27417 with or without the labeling of any of the interactants can be evaluated. For example, a microphysiometer can be used to detect the interaction of a compound with 46743 or 27417 without the labeling of either the compound or the 46743 or 27417. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 46743 or 27417.

In yet another embodiment, a cell-free assay is provided in which a 46743 or 27417 protein or biologically active portion thereof is contacted with a test compound and the ability of the test compound to bind to the 46743 or 27417 protein or biologically active portion thereof is evaluated. Preferred biologically active portions of the 46743 or 27417 proteins to be used in assays of the present invention include fragments which participate in interactions with non-46743 or 27417 molecules, e.g., fragments with high surface probability scores.

Soluble and/or membrane-bound forms of isolated proteins (e.g., 46743 or 27417 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

In one embodiment, assays are performed where the ability of an agent to block acyltransferase activity within a cell is evaluated.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 46743 or 27417 protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIA-core). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 46743 or 27417, an anti 46743 or 27417 antibody or its target molecule to facilitate separation of complexed from uncomplexed forms of one or both of the proteins, as well as to accommodate automation of the assay. Binding of a test compound to a 46743 or 27417 protein, or interaction of a 46743 or 27417 protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/46743 or 27417 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 46743 or 27417 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 46743 or 27417 binding or activity determined using standard techniques.

Other techniques for immobilizing either a 46743 or 27417 protein or a target molecule on matrices include using conjugation of biotin and streptavidin. Biotinylated 46743 or 27417 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 46743 or 27417 protein or target molecules but which do not interfere with binding of the 46743 or 27417 protein to its target molecule. Such antibodies can be derivatized to the wells of the plate, and unbound target or 46743 or 27417 protein trapped in the wells by antibody conjugation. Methods for detecting such complexes, in addition to those described above for the GST-immobilized complexes, include immunodetection of complexes using antibodies reactive with the 46743 or 27417 protein or target molecule, as well as enzyme-linked assays which rely on detecting an enzymatic activity associated with the 46743 or 27417 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., *Trends Biochem Sci* Aug. 18, 1993 (8):284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N. H., *J Mol Recognit* 1998 Winter; 11(1-6):141-8; Hage, D. S., and Tweed, S. A. *J Chromatogr B Biomed Sci Appl* Oct. 10, 1997; 699(1-2):499-525). Further, fluorescence energy transfer may also be conveniently utilized, as described herein, to detect binding without further purification of the complex from solution.

In a preferred embodiment, the assay includes contacting the 46743 or 27417 protein or biologically active portion thereof with a known compound which binds 46743 or 27417 to form an assay mixture, contacting the assay mixture with a test compound, and determining the ability of the test compound to interact with a 46743 or 27417 protein, wherein determining the ability of the test compound to interact with a 46743 or 27417 protein includes determining the ability of the test compound to preferentially bind to 46743 or 27417 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 46743 or 27417 genes herein identified. In an alternative embodiment, the invention provides methods for determining the ability of the test compound to modulate the activity of a 46743 or 27417 protein through modulation of the activity of a downstream effector of a 46743 or 27417 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), e.g., a substrate, a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 46743 or 27417 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268: 12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 46743 or 27417 ("46743 or 27417-binding proteins" or "46743 or 27417-bp") and are involved in 46743 or 27417 activity. Such 46743 or 27417-bps can be activators or inhibitors of signals by the 46743 or 27417 proteins or 46743 or 27417 targets as, for example, downstream elements of a 46743 or 27417-mediated signaling pathway.

The two-hybrid system is based on the modular nature of most transcription factors, which consist of separable DNA-binding and activation domains. Briefly, the assay utilizes two different DNA constructs. In one construct, the gene that codes for a 46743 or 27417 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 46743 or 27417 protein can be the fused to the activator domain.) If the "bait" and the "prey" proteins are able to interact, in vivo, forming a 46743 or 27417-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 46743 or 27417 protein.

In another embodiment, modulators of 46743 or 27417 expression are identified. For example, a cell or cell free mixture is contacted with a candidate compound and the expression of 46743 or 27417 mRNA or protein evaluated relative to the level of expression of 46743 or 27417 mRNA or protein in the absence of the candidate compound. When expression of 46743 or 27417 mRNA or protein is greater in the presence of the candidate compound than in its absence, the candidate compound is identified as a stimulator of 46743 or 27417 mRNA or protein expression. Alternatively, when expression of 46743 or 27417 mRNA or protein is less (statistically significantly less) in the presence of the candidate compound than in its absence, the candidate compound is identified as an inhibitor of 46743 or 27417 mRNA or protein expression. The level of 46743 or 27417 mRNA or protein expression can be determined by methods described herein for detecting 46743 or 27417 mRNA or protein.

In another aspect, the invention pertains to a combination of two or more of the assays described herein. For example, a modulating agent can be identified using a cell-based or a cell free assay, and the ability of the agent to modulate the activity of a 46743 or 27417 protein can be confirmed in vivo, e.g., in an animal, such as an animal model for cancer.

This invention further pertains to novel agents identified by the above-described screening assays. Accordingly, it is within the scope of this invention to further use an agent identified as described herein (e.g., a 46743 or 27417 modulating agent, an antisense 46743 or 27417 nucleic acid molecule, a 46743 or 27417-specific antibody, or a 46743 or 27417-binding partner) in an appropriate animal model to determine the efficacy, toxicity, side effects, or mechanism of action, of treatment with such an agent. Furthermore, novel agents identified by the above-described screening assays can be used for treatments as described herein.

46743 and 27417 Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 46743 or 27417 with a disease; (ii) identify an individual from a minute biological sample (tissue typing); and (iii) aid in forensic identification of a biological sample. These applications are described in the subsections below.

46743 and 27417 Chromosome Mapping

The 46743 or 27417 nucleotide sequences or portions thereof can be used to map the location of the 46743 or 27417 genes on a chromosome. This process is called chromosome mapping. Chromosome mapping is useful in correlating the 46743 or 27417 sequences with genes associated with disease.

Briefly, 46743 or 27417 genes can be mapped to chromosomes by preparing PCR primers (preferably 15-25 bp in length) from the 46743 or 27417 nucleotide sequences. These primers can then be used for PCR screening of somatic cell hybrids containing individual human chromosomes. Only those hybrids containing the human gene corresponding to the 46743 or 27417 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) *Science* 220:919-924).

Other mapping strategies e.g., in situ hybridization (described in Fan, Y. et al. (1990) *Proc. Natl. Acad. Sci. USA*, 87:6223-27), pre-screening with labeled flow-sorted chromosomes, and pre-selection by hybridization to chromosome specific cDNA libraries can be used to map 46743 or 27417 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783-787.

Moreover, differences in the DNA sequences between individuals affected and unaffected with a disease associated with the 46743 or 27417 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

46743 and 27417 Tissue Typing 46743 or 27417 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 46743 or 27417 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:57 or SEQ ID NO:62 can provide positive individual identification with a panel of perhaps 10 to 1,000 primers which each yield a noncoding amplified sequence of 100 bases. If predicted coding sequences, such as those in SEQ ID NO:59 or SEQ ID NO:64 are used, a more appropriate number of primers for positive individual identification would be 500-2,000.

If a panel of reagents from 46743 or 27417 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 46743 or 27417 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:57 or SEQ ID NO:62 (e.g., fragments derived from the noncoding regions of SEQ ID NO:57 or SEQ ID NO:62 having a length of at least 20 bases, preferably at least 30 bases) are particularly appropriate for this use.

The 46743 or 27417 nucleotide sequences described herein can further be used to provide polynucleotide reagents, e.g., labeled or labelable probes which can be used in, for example, an in situ hybridization technique, to identify a specific tissue, e.g., a tissue containing acyltransferase activity. This can be very useful in cases where a forensic pathologist is presented with a tissue of unknown origin. Panels of such 46743 or 27417 probes can be used to identify tissue by species and/or by organ type.

In a similar fashion, these reagents, e.g., 46743 or 27417 primers or probes can be used to screen tissue culture for contamination (i.e. screen for the presence of a mixture of different types of cells in a culture).

Predictive Medicine of 46743 and 27417

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 46743 or 27417.

Such disorders include, e.g., a disorder associated with the misexpression of 46743 or 27417, e.g., a hyperproliferative and/or migratory cell disorder, e.g., a cancer, or lipid metabolism related disorder.

The method includes one or more of the following:

detecting, in a tissue of the subject, the presence or absence of a mutation which affects the expression of the 46743 or 27417 gene, or detecting the presence or absence of a mutation in a region which controls the expression of the gene, e.g., a mutation in the 5' control region;

detecting, in a tissue of the subject, the presence or absence of a mutation which alters the structure of the 46743 or 27417 gene;

detecting, in a tissue of the subject, the misexpression of the 46743 or 27417 gene, at the mRNA level, e.g., detecting a non-wild type level of a mRNA;

detecting, in a tissue of the subject, the misexpression of the gene, at the protein level, e.g., detecting a non-wild type level of a 46743 or 27417 polypeptide.

In preferred embodiments the method includes: ascertaining the existence of at least one of: a deletion of one or more nucleotides from the 46743 or 27417 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:57 or SEQ ID NO:62 naturally occurring mutants thereof or 5' or 3' flanking sequences naturally associated with the 46743 or 27417 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 46743 or 27417 gene; the presence of a non-wild type splicing pattern of a messenger RNA transcript of the gene; or a non-wild type level of 46743 or 27417.

Methods of the invention can be used prenatally or to determine if a subject's offspring will be at risk for a disorder.

In preferred embodiments the method includes determining the structure of a 46743 or 27417 gene, an abnormal structure being indicative of risk for the disorder.

In preferred embodiments the method includes contacting a sample form the subject with an antibody to the 46743 or 27417 protein or a nucleic acid, which hybridizes specifically with the gene. There and other embodiments are discussed below.

Diagnostic and Prognostic Assays of 46743 and 27417

Diagnostic and prognostic assays of the invention include method for assessing the expression level of 46743 or 27147 molecules and for identifying variations and mutations in the sequence of 46743 or 27147 molecules.

Expression Monitoring and Profiling

The presence, level, or absence of 46743 or 27417 protein or nucleic acid in a biological sample can be evaluated by obtaining a biological sample from a test subject and contacting the biological sample with a compound or an agent capable of detecting 46743 or 27417 protein or nucleic acid (e.g., mRNA, genomic DNA) that encodes 46743 or 27417 protein such that the presence of 46743 or 27417 protein or nucleic acid is detected in the biological sample. The term "biological sample" includes tissues, cells and biological fluids isolated from a subject, as well as tissues, cells and fluids present within a subject. A preferred biological sample is serum. The level of expression of the 46743 or 27417 gene can be measured in a number of ways, including, but not limited to: measuring the mRNA encoded by the 46743 or 27417 genes; measuring the amount of protein encoded by the 46743 or 27417 genes; or measuring the activity of the protein encoded by the 46743 or 27417 genes.

The level of mRNA corresponding to the 46743 or 27417 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 46743 or 27417 nucleic acid, such as the nucleic acid of SEQ ID NO:57, SEQ ID NO:62, or a portion thereof, such as an oligonucleotide of at least 7, 15, 30, 50, 100, 250 or 500 nucleotides in length and sufficient to specifically hybridize under stringent conditions to 46743 or 27417 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 46743 or 27417 genes.

The level of mRNA in a sample that is encoded by one of 46743 or 27417 can be evaluated with nucleic acid amplification, e.g., by rtPCR (Mullis, 1987, U.S. Pat. No. 4,683, 202), ligase chain reaction (Barany, 1991, Proc. Natl. Acad. Sci. USA 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854, 033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 46743 or 27417 gene being analyzed.

In another embodiment, the methods further contacting a control sample with a compound or agent capable of detecting 46743 or 27417 mRNA, or genomic DNA, and comparing the presence of 46743 or 27417 mRNA or genomic DNA in the control sample with the presence of 46743 or 27417 mRNA or genomic DNA in the test sample.

In still another embodiment, serial analysis of gene expression, as described in U.S. Pat. No. 5,695,937, is used to detect 46743 or 27147 transcript levels.

A variety of methods can be used to determine the level of protein encoded by 46743 or 27417. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 46743 or 27417 protein in a biological sample in vitro as well as in vivo. In vitro techniques for detection of 46743 or 27417 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 46743 or 27417 protein include introducing into a subject a labeled anti-46743 or 27417 antibody. For example, the antibody can be labeled with a radioactive marker whose presence and location in a subject can be detected by standard imaging techniques.

In another embodiment, the sample is labeled, e.g., biotinylated and then contacted to the antibody, e.g., an anti-46743 or 27147 antibody positioned on an antibody array (as described below). The sample can be detected, e.g., with avidin coupled to a fluorescent label.

In another embodiment, the methods further include contacting the control sample with a compound or agent capable of detecting 46743 or 27417 protein, and comparing the presence of 46743 or 27417 protein in the control sample with the presence of 46743 or 27417 protein in the test sample.

The invention also includes kits for detecting the presence of 46743 or 27417 in a biological sample. For example, the kit can include a compound or agent capable of detecting 46743 or 27417 protein or mRNA in a biological sample; and a standard. The compound or agent can be packaged in a suitable container. The kit can further comprise instructions for using the kit to detect 46743 or 27417 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 46743 or 27417 expression or activity. As used herein, the term "unwanted" includes an unwanted phenomenon involved in a biological response such as deregulated cell proliferation and/or migration or pain.

In one embodiment, a disease or disorder associated with aberrant or unwanted 46743 or 27417 expression or activity is identified. A test sample is obtained from a subject and 46743 or 27417 protein or nucleic acid (e.g., mRNA or genomic DNA) is evaluated, wherein the level, e.g., the presence or absence, of 46743 or 27417 protein or nucleic acid is diagnostic for a subject having or at risk of developing a disease or disorder associated with aberrant or unwanted 46743 or 27417 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 46743 or 27417 expression or activity. For example, such methods can be used to determine whether a subject can be effectively treated with an agent for a cellular proliferation and/or migration-related disorder.

In another aspect, the invention features a computer medium having a plurality of digitally encoded data records. Each data record includes a value representing the level of expression of 46743 or 27147 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 46743 or 27147 (e.g., other genes associated with a 46743 or 27147 disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 46743 or 27147 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a cellular proliferation and/or migration disorder in a subject wherein a decrease in 46743 or 27147 expression is an indication that the subject has or is disposed to having a cellular proliferation and/or migration disorder. The method can be used to monitor a treatment for cellular proliferation and/or migration disorder in a subject. For example, the gene expression profile can be determined for a sample from a subject undergoing treatment. Further, the method can be used to monitor a cellular response to a polypeptide hormone, e.g., to EGF. The profile can be compared to a reference profile or to a profile obtained from the subject prior to treatment or prior to onset of the disorder (see, e.g., Golub et al. (1999) *Science* 286: 531).

In yet another aspect, the invention features a method of evaluating a test compound (see also, "Screening Assays", above). The method includes: providing a cell and a test compound; contacting the test compound to the cell; obtaining a subject expression profile for the contacted cell; and comparing the subject expression profile to one or more reference profiles. The profiles include a value representing the level of 46743 or 27147 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 46743 or 27147 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 46743 or 27147 expression.

46743 and 27417 Arrays and Uses Thereof

In another aspect, the invention features an array that includes a substrate having a plurality of addresses. At least one address of the plurality includes a capture probe that binds specifically to a 46743 or 27147 molecule (e.g., 46743 or 27147 nucleic acid, or a 46743 or 27147 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 46743 or 27147 nucleic acid, e.g., the sense or anti-sense strand. In one preferred embodiment, a subset of addresses of the plurality of addresses has a nucleic acid capture probe for 46743 or 27147. Each address of the subset can include a capture probe that hybridizes to a different region of a 46743 or 27147 nucleic acid. In another preferred embodiment, addresses of the subset include a capture probe for a 46743 or 27147 nucleic acid. Each address of the subset is unique, overlapping, and complementary to a different variant of 46743 or 27147 (e.g., an allelic variant, or all possible hypothetical variants). The array can be used to sequence 46743 or 27147 by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 46743 or 27147 polypeptide or fragment thereof. The polypeptide can be a naturally-occurring interaction partner of 46743 or 27147 polypeptide. Preferably, the polypeptide is an antibody, e.g., an antibody described herein (see "Anti-46743 or 27147 Antibodies," above), such as a monoclonal antibody or a single-chain antibody.

In another aspect, the invention features a method of analyzing the expression of 46743 or 27147. The method includes providing an array as described above; contacting the array with a sample and detecting binding of a 46743 or 27147-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 46743 or 27147. If a sufficient number of diverse samples is analyzed, clustering (e.g., hierarchical clustering, k-means clustering, Bayesian clustering and the like) can be used to identify other genes which are co-regulated with 46743 or 27147. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 46743 or 27147 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 46743 or 27147-associated disease or disorder; and processes, such as a cellular transformation associated with a 46743 or 27147-associated disease or disorder. The method can also evaluate the treatment and/or progression of a 46743 or 27147-associated disease or disorder The array is also useful for ascertaining differential expression patterns of one or more genes in normal and abnormal cells, e.g., a cell having a neoplastic disorder such as a cancerous cell from the ovary, brain, colon, or lung, or a cell responding to EGF. This provides a battery of genes (e.g., including 46743 or 27147) that could serve as a molecular target for diagnosis or therapeutic intervention.

In another aspect, the invention features an array having a plurality of addresses. Each address of the plurality includes a unique polypeptide. At least one address of the plurality has disposed thereon a 46743 or 27147 polypeptide or fragment thereof. Methods of producing polypeptide arrays are described in the art, e.g., in De Wildt et al. (2000). *Nature Biotech.* 18, 989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80, 85, 90, 95 or 99% identical to a 46743 or 27147 polypeptide or fragment thereof. For example, multiple variants of a 46743 or 27147 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 46743 or 27147 binding compound, e.g., an antibody in a sample from a subject with specificity for a 46743 or 27147 polypeptide or the presence of a 46743 or 27147-binding protein or ligand.

The array is also useful for ascertaining the effect of the expression of a gene on the expression of other genes in the same cell or in different cells (e.g., ascertaining the effect of 46743 or 27147 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 46743 or 27147 or from a cell or subject in which a 46743 or 27147-mediated response has been elicited, e.g., by contact of the cell with 46743 or 27147 nucleic acid or protein, or administration to the cell or subject 46743 or 27147 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 46743 or 27147 (or does not express as highly as in the case of the 46743 or 27147 positive plurality of capture probes) or from a cell or subject which in which a 46743 or 27147 mediated response has not been elicited (or has been elicited to a lesser extent than in the first sample); contacting the array with one or more inquiry probes (which is preferably other than a 46743 or 27147 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 46743 or 27147 or from a cell or subject in which a 46743 or 27147-mediated response has been elicited, e.g., by contact of the cell with 46743 or 27147 nucleic acid or protein, or administration to the cell or subject 46743 or 27147 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 46743 or 27147 (or does not express as highly as in the case of the 46743 or 27147 positive plurality of capture probes) or from a cell or subject which in which a 46743 or 27147-mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 46743 or 27147, e.g., analyzing structure, function, or relatedness to other nucleic acid or amino acid sequences. The method includes: providing a 46743 or 27147 nucleic acid or amino acid sequence; comparing the 46743 or 27147 sequence with one or more preferably a plurality of sequences from a collection of sequences, e.g., a nucleic acid or protein sequence database; to thereby analyze 46743 or 27147.

Detection of 46743 and 27417 Variations or Mutations

The methods of the invention can also be used to detect genetic alterations in a 46743 or 27417 gene, thereby determining if a subject with the altered gene is at risk for a disorder characterized by misregulation in 46743 or 27417 protein activity or nucleic acid expression, such as a cellular growth related disorder. In preferred embodiments, the methods include detecting, in a sample from the subject, the presence or absence of a genetic alteration characterized by at least one of an alteration affecting the integrity of a gene encoding a 46743 or 27417-protein, or the mis-expression of the 46743 or 27417 gene. For example, such genetic alterations can be detected by ascertaining the existence of at least one of 1) a deletion of one or more nucleotides from a 46743 or 27417 gene; 2) an addition of one or more nucleotides to a 46743 or 27417 gene; 3) a substitution of one or more nucleotides of a 46743 or 27417 gene, 4) a chromosomal rearrangement of a 46743 or 27417 gene; 5) an alteration in the level of a messenger RNA transcript of a 46743 or 27417 gene, 6) aberrant modification of a 46743 or 27417 gene, such as of the methylation pattern of the genomic DNA, 7) the presence of a non-wild type splicing pattern of a messenger RNA transcript of a 46743 or 27417 gene, 8) a non-wild type level of a 46743 or 27417-protein, 9) allelic loss of a 46743 or 27417 gene, and 10) inappropriate post-translational modification of a 46743 or 27417-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 46743 or 27417-gene. This method can include the steps of collecting a sample of cells from a subject, isolating nucleic acid (e.g., genomic, mRNA or both) from the sample, contacting the nucleic acid sample with one or more primers which specifically hybridize to a 46743 or 27417 gene under conditions such that hybridization and amplification of the 46743 or 27417 gene (if present) occurs, and detecting the presence or absence of an amplification product, or detecting the size of the amplification product and comparing the length to a control sample.

It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) Proc. Natl. Acad. Sci. USA 87:1874-1878), transcriptional amplification system (Kwoh, D. Y. et al., (1989) Proc. Natl. Acad. Sci. USA 86:1173-1177), Q-Beta Replicase (Lizardi, P. M. et al. (1988) Bio-Technology 6:1197), or other nucleic acid amplification methods, followed by the detection of the amplified molecules using techniques known to those of skill in the art.

In another embodiment, mutations in a 46743 or 27417 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 46743 or 27417 can be identified by hybridizing a sample and control nucleic acids, e.g., DNA or RNA, to two dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al. (1996) Human Mutation 7: 244-255; Kozal, M. J. et al. (1996) Nature Medicine 2: 753-759). For example, genetic mutations in 46743 or 27417 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 46743 or 27417 gene and detect mutations by comparing the sequence of the sample 46743 or 27417 with the corresponding wild-type (control) sequence. Automated sequencing procedures can be utilized when performing the diagnostic assays ((1995) Biotechniques 19:448), including sequencing by mass spectrometry.

Other methods for detecting mutations in the 46743 or 27417 gene include methods in which protection from cleavage agents is used to detect mismatched bases in RNA/RNA or RNA/DNA heteroduplexes (Myers et al. (1985) Science 230:1242; Cotton et al. (1988) Proc. Natl Acad Sci USA 85:4397; Saleeba et al. (1992) Methods Enzymol. 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 46743 or 27417 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662; U.S. Pat. No. 5,459,039).

In other embodiments, alterations in electrophoretic mobility will be used to identify mutations in 46743 or 27417 genes. For example, single strand conformation polymorphism (SSCP) may be used to detect differences in electrophoretic mobility between mutant and wild type nucleic acids (Orita et al. (1989) Proc Natl. Acad. Sci USA: 86: 2766, see also Cotton (1993) Mutat. Res. 285: 125-144; and Hayashi (1992) Genet. Anal. Tech. Appl. 9: 73-79). Single-stranded DNA fragments of sample and control 46743 or 27417 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension (Saiki et al. (1986) Nature 324:163); Saiki et al. (1989) Proc. Natl Acad. Sci USA 86:6230). ). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 65%, 75%, 85%, 90%, 92%, 95%, 97%, 98%, or 99% complementary) to a 46743 or 27147 nucleic acid.

In a preferred embodiment the set includes a first and a second oligonucleotide. The first and second oligonucleotide can hybridize to the same or to different locations of SEQ ID NO:57 or SEQ ID NO:62, or the complement of SEQ ID NO:57 or SEQ ID NO:62. Different locations can be different and non-overlapping or different but overlapping on the same strand. The first and second oligonucleotide can hybridize to sites on the same or on different strands.

The set can be useful, e.g., for identifying SNP's, or identifying specific alleles of 46743 or 27147. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligonucleotides can be used to specifically amplify, e.g., by PCR, or detect, a 46743 or 27147 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 46743 or 27417 gene.

Use of 46743 or 27147 Molecules as Surrogate Markers

The 46743 or 27147 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 46743 or 27147 molecules of the invention may be detected, and may be correlated with one or more biological states in vivo. For example, the 46743 or 27147 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 46743 or 27147 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 46743 or 27147 marker) transcription or expression, the amplified marker may be in a quantity which is more readily detectable than the drug itself. Also, the marker may be more easily detected due to the nature of the marker itself; for example, using the methods described herein, anti-46743 or 27147 antibodies may be employed in an immune-based detection system for a 46743 or 27147 protein marker, or 46743 or 27147-specific radiolabeled probes may be used to detect a 46743 or 27147 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

The 46743 or 27147 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 46743 or 27147 protein or RNA) for specific tumor markers in a subject, a drug or course of treatment may be selected that is optimized for the treatment of the specific tumor likely to be present in the subject. Similarly, the presence or absence of a specific sequence mutation in 46743 or 27147 DNA may correlate with a 46743 or 27147-related drug response. The use of pharmacogenomic markers therefore permits the application of the most appropriate treatment for each subject without having to administer the therapy.

Pharmaceutical Compositions of 46743 and 27417

The nucleic acid and polypeptides, fragments thereof, as well as anti-46743 or 27147 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, $\alpha$-interferon, $\beta$-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 46743 and 27417

The present invention provides for both prophylactic and therapeutic methods of treating a subject at risk of (or susceptible to) a disorder or having a disorder associated with aberrant or unwanted 46743 or 27147 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 46743 or 27147 molecules of the present invention or 46743 or 27147 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 46743 or 27417 expression or activity, by administering to the subject a 46743 or 27417 or an agent which modulates 46743 or 27417 expression or at least one 46743 or 27417 activity. Subjects at risk for a disease which is caused or contributed to by aberrant or unwanted 46743 or 27417 expression or activity can be identified by, for example, any or a combination of diagnostic or prognostic assays as described herein. Administration of a prophylactic agent can occur prior to the manifestation of symptoms characteristic of the 46743 or 27417 aberrance, such that a disease or disorder is prevented or, alternatively, delayed in its progression. Depending on the type of 46743 or 27417 aberrance, for example, a 46743 or 27417, 46743 or 27417 agonist or 46743 or 27417 antagonist agent can be used for treating the subject. The appropriate agent can be determined based on screening assays described herein.

It is possible that some 46743 or 27417 disorders can be caused, at least in part, by an abnormal level of gene product, or by the presence of a gene product exhibiting abnormal activity. As such, the reduction in the level and/or activity of such gene products would bring about the amelioration of disorder symptoms.

Thus, the 46743 or 27147 molecules can act as novel diagnostic targets and therapeutic agents for controlling one or more disorders associated with cardiovascular disease, neoplastic disorders (e.g., leukemias), bone metabolism, reproductive (e.g., ovarian) disorders, brain disorders, kidney disorders, immune disorders, viral diseases, or pain.

Examples of proliferative disorders in addition to those described above include hematopoietic neoplastic disorders. As used herein, the term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Aberrant expression and/or activity of 46743 or 27147 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 46743 or 27147 molecules effects in bone cells, e.g. osteoclasts and osteoblasts, that may in turn result in bone formation and degeneration. For example, 46743 or 27147 molecules may support different activities of bone resorbing osteoclasts such as the stimulation of differentiation of monocytes and mononuclear phagocytes into osteoclasts. Accordingly, 46743 or 27147 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

The 46743 or 27147 nucleic acid and protein of the invention can be used to treat and/or diagnose a variety of immune disorders. Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 46743 or 27147 molecules may play an important role in the etiology of certain viral diseases, including but not limited to Hepatitis B, Hepatitis C and Herpes Simplex Virus (HSV). Modulators of 46743 or 27147 activity could be used to control viral diseases. The modulators can be used in the treatment and/or diagnosis of viral infected tissue or virus-associated tissue fibrosis, especially liver and liver fibrosis. Also, 46743 or 27147 modulators can be used in the treatment and/or diagnosis of virus-associated carcinoma, especially hepatocellular cancer.

Additionally, 46743 or 27147 may play an important role in the regulation of pain disorders. Examples of pain disorders include, but are not limited to, pain response elicited during various forms of tissue injury, e.g., inflammation, infection, and ischemia, usually referred to as hyperalgesia (described in, for example, Fields, H. L. (1987) Pain, New York:McGraw-Hill); pain associated with musculoskeletal disorders, e.g., joint pain; tooth pain; headaches; pain associated with surgery; pain related to irritable bowel syndrome; or chest pain.

As discussed, successful treatment of 46743 or 27417 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 46743 or 27417 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 46743 or 27417 expression is through the use of aptamer molecules specific for 46743 or 27417 protein. Aptamers are nucleic acid molecules having a tertiary structure which permits them to specifically bind to protein ligands (see, e.g., Osborne, et al. Curr. Opin. Chem Biol. 1997, 1(1): 5-9; and Patel, D. J. Curr Opin Chem Biol 1997 June; 1(1):32-46). Since nucleic acid molecules may in many cases be more conveniently introduced into target cells than therapeutic protein molecules may be, aptamers offer a method by which 46743 or 27417 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 46743 or 27417 disorders. For a description of antibodies, see the Antibody section above.

In circumstances wherein injection of an animal or a human subject with a 46743 or 27417 protein or epitope for stimulating antibody production is harmful to the subject, it is possible to generate an immune response against 46743 or 27417 through the use of anti-idiotypic antibodies (see, for example, Herlyn, D. Ann Med 1999; 31(1):66-78; and Bhattacharya-Chatterjee, M., and Foon, K. A. Cancer Treat Res 1998; 94:51-68). If an anti-idiotypic antibody is introduced into a mammal or human subject, it should stimulate the production of anti-anti-idiotypic antibodies, which should be specific to the 46743 or 27417 protein. Vaccines directed to a disease characterized by 46743 or 27417 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993, Proc. Natl. Acad. Sci. USA 90:7889-7893).

The identified compounds that inhibit target gene expression, synthesis and/or activity can be administered to a patient at therapeutically effective doses to prevent, treat or ameliorate 46743 or 27417 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 46743 or 27417 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89-94 and in Shea, K. J. (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645-647. Through the use of isotope-labeling, the "free" concentration of compound which modulates the expression or activity of 46743 or 27417 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142-2144.

Another aspect of the invention pertains to methods of modulating 46743 or 27417 expression or activity for therapeutic purposes. Accordingly, in an exemplary embodiment, the modulatory method of the invention involves contacting a cell with a 46743 or 27417 or agent that modulates one or more of the activities of 46743 or 27417 protein activity associated with the cell. An agent that modulates 46743 or 27417 protein activity can be an agent as described herein, such as a nucleic acid or a protein, a naturally-occurring target molecule of a 46743 or 27417 protein (e.g., a 46743 or 27417 substrate or receptor), a 46743 or 27417 antibody, a 46743 or 27417 agonist or antagonist, a peptidomimetic of a 46743 or 27417 agonist or antagonist, or other small molecule.

In one embodiment, the agent stimulates one or 46743 or 27417 activities. Examples of such stimulatory agents include active 46743 or 27417 protein and a nucleic acid molecule encoding 46743 or 27417. In another embodiment, the agent inhibits one or more 46743 or 27417 activities. Examples of such inhibitory agents include antisense 46743 or 27417 nucleic acid molecules, anti46743 or 27417 antibodies, and 46743 or 27417 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 46743 or 27417 protein or nucleic acid molecule. In one embodiment, the method involves administering an agent (e.g., an agent identified by a screening assay described herein), or combination of agents that modulates (e.g., upregulates or downregulates) 46743 or 27417 expression or activity. In another embodiment, the method involves administering a 46743 or 27417 protein or nucleic acid molecule as therapy to compensate for reduced, aberrant, or unwanted 46743 or 27417 expression or activity.

Stimulation of 46743 or 27417 activity is desirable in situations in which 46743 or 27417 is abnormally downregulated and/or in which increased 46743 or 27417 activity is likely to have a beneficial effect. For example, stimulation of 46743 or 27417 activity is desirable in situations in which a 46743 or 27417 is downregulated and/or in which increased 46743 or 27417 activity is likely to have a beneficial effect. Likewise, inhibition of 46743 or 27417 activity is desirable in situations in which 46743 or 27417 is abnormally upregulated and/or in which decreased 46743 or 27417 activity is likely to have a beneficial effect.

46743 and 27417 Pharmacogenomics

The 46743 or 27417 molecules of the present invention, as well as agents, or modulators which have a stimulatory or inhibitory effect on 46743 or 27417 activity (e.g., 46743 or 27417 gene expression) as identified by a screening assay described herein can be administered to individuals to treat (prophylactically or therapeutically) 46743 or 27417 associated disorders (e.g., cellular growth related disorders) associated with aberrant or unwanted 46743 or 27417 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 46743 or 27417 molecule or 46743 or 27417 modulator as well as tailoring the dosage and/or therapeutic regimen of treatment with a 46743 or 27417 molecule or 46743 or 27417 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11):983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 46743 or 27417 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 46743 or 27417 molecule or 46743 or 27417 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 46743 or 27417 molecule or 46743 or 27417 modulator, such as a modulator identified by one of the exemplary screening assays described herein.

The present invention further provides methods for identifying new agents, or combinations, that are based on identifying agents that modulate the activity of one or more of the gene products encoded by one or more of the 46743 or 27417 genes of the present invention, wherein these products may be associated with resistance of the cells to a therapeutic agent. Specifically, the activity of the proteins encoded by the 46743 or 27417 genes of the present invention can be used as a basis for identifying agents for overcoming agent resistance. By blocking the activity of one or more of the resistance proteins, target cells, e.g., cancer cells, will become sensitive to treatment with an agent that the unmodified target cells were resistant to.

Monitoring the influence of agents (e.g., drugs) on the expression or activity of a 46743 or 27417 protein can be applied in clinical trials. For example, the effectiveness of an agent determined by a screening assay as described herein to increase 46743 or 27417 gene expression, protein levels, or upregulate 46743 or 27417 activity, can be monitored in clinical trials of subjects exhibiting decreased 46743 or 27417 gene expression, protein levels, or downregulated 46743 or 27417 activity. Alternatively, the effectiveness of an agent determined by a screening assay to decrease 46743 or 27417 gene expression, protein levels, or downregulate 46743 or 27417 activity, can be monitored in clinical trials of subjects exhibiting increased 46743 or 27417 gene expression, protein levels, or upregulated 46743 or 27417 activity. In such clinical trials, the expression or activity of a 46743 or 27417 gene, and preferably, other genes that have been implicated in, for example, a 46743 or 27417-associated disorder can be used as a "read out" or markers of the phenotype of a particular cell.

46743 or 27147 Informatics

The sequence of a 46743 or 27147 molecule is provided in a variety of media to facilitate use thereof. A sequence can be provided as a manufacture, other than an isolated nucleic acid or amino acid molecule, which contains a 46743 or 27147. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 46743 or 27147 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 46743 or 27147, e.g., analyzing structure, function, or relatedness to one or more other nucleic acid or amino acid sequences. The method includes: providing a 46743 or 27147 nucleic acid or amino acid sequence; comparing the 46743 or 27147 sequence with a second sequence, e.g., one or more preferably a plurality of sequences from a collection of sequences, e.g., a nucleic acid or protein sequence database to thereby analyze 46743 or 27147. The method can be performed in a machine, e.g., a computer, or manually by a skilled artisan.

The method can include evaluating the sequence identity between a 46743 or 27147 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 46743 or 27147 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 46743 or 27147 sequence, or record, in machine-readable form; comparing a second sequence to the 46743 or 27147 sequence; thereby analyzing a sequence. Comparison can include comparing to sequences for sequence identity or determining if one sequence is included within the other, e.g., determining if the 46743 or 27147 sequence includes a sequence being compared. In a preferred embodiment the 46743 or 27147 sequence or a second sequence is stored on a first computer, e.g., at a first site and the comparison is performed, read, or recorded on a second computer, e.g., at a second site. For example, the 46743 or 27147 sequence or the second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 46743 or 27147-associated disease or disorder or a pre-disposition to a 46743 or 27147-associated disease or disorder, wherein the method comprises the steps of determining 46743 or 27147 sequence information associated with the subject and based on the 46743 or 27147 sequence information, determining whether the subject has a 46743 or 27147-associated disease or disorder, or a pre-disposition to a 46743 or 27147-associated disease or disorder, and/or recommending a particular treatment for the disease, disorder, or pre-disease condition.

The invention further provides in an electronic system and/or in a network, a method for determining whether a subject has a 46743 or 27147-associated disease or disorder or a pre-disposition to a disease associated with a 46743 or 27147 wherein the method comprises the steps of determining 46743 or 27147 sequence information associated with the subject, and based on the 46743 or 27147 sequence information, determining whether the subject has a 46743 or 27147-associated disease or disorder, or a pre-disposition to a 46743 or 27147-associated disease or disorder, and/or recommending a particular treatment for the disease, disorder, or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 46743 or 27147 sequence of the subject to the 46743 or 27147 sequences in the database to thereby determine whether the subject as a 46743 or 27147-associated disease or disorder, or a pre-disposition for such.

The present invention also provides in a network, a method for determining whether a subject has a 46743 or 27147-associated disease or disorder, or a pre-disposition to a 46743 or 27147-associated disease or disorder, associated with 46743 or 27147, said method comprising the steps of receiving 46743 or 27147 sequence information from the subject and/or information related thereto, receiving phenotypic information associated with the subject, acquiring information from the network corresponding to 46743 or 27147 and/or corresponding to a 46743 or 27147-associated disease or disorder (e.g., an abnormal hyperproliferative and/or migratory cell disorder, e.g., a cancer) and based on one or more of the phenotypic information, the 46743 or 27147 information (e.g., sequence information and/or information related thereto), and the acquired information, determining whether the subject has a 46743 or 27147-associated disease or disorder or a pre-disposition to a 46743 or 27147-associated disease or disorder. The method may further comprise the step of recommending a particular treatment for the disease, disorder or pre-disease condition.

The present invention also provides a method for determining whether a subject has a 46743 or 27147-associated disease or disorder, or a pre-disposition to a 46743 or 27147-associated disease or disorder, said method comprising the steps of receiving information related to 46743 or 27147 (e.g., sequence information and/or information related thereto), receiving phenotypic information associated with the subject, acquiring information from the network related to 46743 or 27147 and/or related to a 46743 or 27147-associated disease or disorder, and based on one or more of the phenotypic information, the 46743 or 27147 information, and the acquired information, determining whether the subject has a 46743 or 27147-associated disease or disorder, or a pre-disposition to a 46743 or 27147-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

Background of the 27960 Invention

Living cells are capable of modulating the levels of proteins that they express. A variety of different mechanisms exist through which protein levels can be modulated. The ubiquitin pathway is one example of a post-translational mechanism used to regulate protein levels. Ubiquitin is a highly conserved polypeptide expressed in all eukaryotic cells that marks proteins for degradation. An activated ubiquitin moiety is transferred from a ubiquitin-activating enzyme (E1) to a ubiquitin-conjugating enzyme (E2), which ligates ubiquitin directly to substrate proteins with or without the assistance of 'N-end' recognizing proteins. Ubiquitin is attached as a single molecule or in a conjugated form to lysine residue(s) of proteins via formation of an isopeptide bond at the C-terminal glycine residue. Most ubiquitinated proteins are subsequently targeted to the 26S proteasome, a multicatalytic protease, which cleaves the marked protein into peptide fragments.

Ubiquitination has been implicated in regulating numerous cellular processes including, for example, proliferation, differentiation, apoptosis, transcription, signal-transduction, cell-cycle progression, receptor-mediated endocytosis, antigen presentation, organelle biogenesis, and others. The presence of abnormal amounts of ubiquitinated proteins in neuropathological conditions such as Alzheimer's and Pick's disease, and the association of ubiquitin-dependent proteolysis with cachexia, indicates that ubiquitination plays a role in various physiological disorders. See, for example, Gregori et al. (1994) *Biochem. Biophys. Res. Commun.*, 203:1731-1738; and Llovera et al. (1995) *Int. J. Cancer*, 61:138-141. Oncogenes (e.g., v-jun and v-fos) are often found to be resistant to ubiquitination in comparison with their normal cell counterparts, suggesting that a failure to degrade oncogene protein products accounts for some of their cell transformation capability. Ubiquitin-dependent proteolysis also is associated with degradation of the tumor suppressor protein p53. Ciechanover (1994) *Cell*, 79:13-21.

In sum, ubiquitination and de-ubiquitination are important processes through which protein levels and function are modulated in cells. The identification of genes and polypeptides that participate in ubiquitination and de-ubiquitination would provide a greater understanding of their role in cellular function and associated abnormalities.

Summary of the 27960 Invention

The present invention is based, in part, on the discovery of a novel human ubiquitin conjugating enzyme, referred to herein as "27960". The nucleotide sequence of a cDNA encoding 27960 is shown in SEQ ID NO:72, and the amino acid sequence of a 27960 polypeptide is shown in SEQ ID NO:73. In addition, the nucleotide sequences of the coding region are depicted in SEQ ID NO:74.

Accordingly, in one aspect, the invention features a nucleic acid molecule that encodes a 27960 protein or polypeptide, e.g., a biologically active portion of the 27960 protein. In a preferred embodiment, the isolated nucleic acid molecule encodes a polypeptide having the amino acid sequence of SEQ ID NO:73. In other embodiments, the invention provides isolated 27960 nucleic acid molecules having the nucleotide sequence shown in SEQ ID NO:72, or SEQ ID NO:74. In still other embodiments, the invention provides nucleic acid molecules that are substantially identical (e.g., naturally occurring allelic variants) to the nucleotide sequence shown in SEQ ID NO:72, or SEQ ID NO:74. In other embodiments, the invention provides a nucleic acid molecule that hybridizes under a stringent hybridization condition described herein to a nucleic acid molecule comprising the nucleotide sequence of SEQ ID NO:72 or 74, wherein the nucleic acid encodes a full length 27960 protein or an active fragment thereof.

In a related aspect, the invention further provides nucleic acid constructs that include a 27960 nucleic acid molecule described herein. In certain embodiments, the nucleic acid molecules of the invention are operatively linked to native or heterologous regulatory sequences. Also included are vectors and host cells containing the 27960 nucleic acid molecules of the invention e.g., vectors and host cells suitable for producing 27960 nucleic acid molecules and polypeptides.

In another related aspect, the invention provides nucleic acid fragments suitable as primers or hybridization probes for the detection of 27960-encoding nucleic acids.

In still another related aspect, isolated nucleic acid molecules that are antisense to a 27960 encoding nucleic acid molecule are provided.

In another aspect, the invention features 27960 polypeptides and biologically active or antigenic fragments thereof that are useful, e.g., as reagents or targets in assays applicable to treatment and diagnosis of 27960-mediated or -related disorders. In another embodiment, the invention provides 27960 polypeptides having a 27960 activity. Preferred polypeptides are 27960 proteins including at least one ubiquitin-conjugating enzyme domain, and, preferably, having a 27960 activity, e.g., a 27960 activity described herein.

In other embodiments, the invention provides 27960 polypeptides, e.g., a 27960 polypeptide having the amino acid sequence shown in SEQ ID NO:73; an amino acid sequence that is substantially identical to the amino acid sequence shown in SEQ ID NO:73; or an amino acid sequence encoded by a nucleic acid molecule having a nucleotide sequence that hybridizes under a stringent hybridization condition described herein to a nucleic acid molecule comprising the nucleotide sequence of SEQ ID NO:72 or 74, wherein the nucleic acid encodes a full length 27960 protein or an active fragment thereof.

In a related aspect, the invention provides 27960 polypeptides or fragments operatively linked to non-27960 polypeptides to form fusion proteins.

In another aspect, the invention features antibodies and antigen-binding fragments thereof, that react with, or more preferably, specifically bind 27960 polypeptides.

In another aspect, the invention provides methods of screening for compounds that modulate the expression or activity of the 27960 polypeptides or nucleic acids.

In still another aspect, the invention provides a process for modulating 27960 polypeptide or nucleic acid expression or activity, e.g., using the screened compounds. In certain embodiments, the methods involve treatment of disorders or diseases related to aberrant activity or expression of the 27960 polypeptides or nucleic acids, such as disorders or diseases involving aberrant accumulation of ubiquitinated proteins; aberrant or deficient angiogenesis; aberrant or deficient cellular proliferation or differentiation, e.g., cancers of the lung, breast, ovaries, neural organs (e.g., neuroblastoma or glioblastoma), colon, or a hemangioma or a Wilm's tumor; neuropathological disorders; renal disorders; reproductive disorders, e.g., prostatic disorders, or cardiovascular disorders, e.g., blood vessel disorders.

The invention also provides assays for determining the activity of or the presence or absence of 27960 polypeptides or nucleic acid molecules in a biological sample, including for disease diagnosis.

In yet another aspect, the invention provides methods for inhibiting or reducing the proliferation, or inducing the killing, of a 27960-expressing cell, e.g., a hyperproliferative 27960-expressing cell. The method includes contacting the cell with a compound (e.g., a compound identified using the methods described herein) that modulates the activity, or expression, of the 27960 polypeptide or nucleic acid. In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol.

In a preferred embodiment, the cell is a hyperproliferative cell, e.g., a cell found in a solid tumor such as a breast, ovarian, colon, or prostate tumor, a neural tumor (e.g., a neuroblastoma or a glioblastoma); a hemangioma; a Wilm's tumor; a soft tissue tumor, or a metastatic lesion.

In other preferred embodiments, the cell is a brain cell (e.g., a cortical, spinal cord or hypothalamic cell); a kidney cell; a blood vessel-associated cell (e.g., a smooth muscle cell, an endothelial cell, an arterial cell); or an epithelial cell (e.g., a prostate epithelial cell).

In a preferred embodiment, the compound is an inhibitor of a 27960 polypeptide. Preferably, the inhibitor is chosen from a peptide, a phosphopeptide, a small organic molecule, a small inorganic molecule, and an antibody (e.g., an antibody conjugated to a therapeutic moiety selected from a cytotoxin, a cytotoxic agent, and a radioactive metal ion). In another preferred embodiment, the compound is an inhibitor of a 27960 nucleic acid, e.g., an antisense, a ribozyme, or a triple helix molecule.

In a preferred embodiment, the compound is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

In another aspect, the invention features methods for treating or preventing, in a subject, a disorder characterized by aberrant activity of a 27960-expressing cell. Preferably, the method includes administering to the subject (e.g., a mammal, e.g., a human) an effective amount of an agent, e.g., a compound (e.g., a compound identified using the methods described herein) that modulates the activity, or expression, of the 27960 polypeptide or nucleic acid, such that the disorder is treated or prevented.

In a preferred embodiment, the disorder is a cancerous or pre-cancerous condition. For example, the disorder is a cancer of the lung, breast, ovaries, neural organs (e.g., neuroblastoma or glioblastoma), colon, or a hemangioma or a Wilm's tumor.

In other embodiments, the disorder involves aberrant accumulation of ubiquitinated proteins, or aberrant or deficient angiogenesis. In other embodiments, the disorder is a neuropathological disorder; a reproductive disorder, e.g., a prostatic disorder; a renal disorder; or a cardiovascular disorder, e.g., a blood vessel disorder.

In a further aspect, the invention provides methods for evaluating the efficacy of a treatment of a disorder, e.g., proliferative disorder. The method includes: treating a subject, e.g., a patient or an animal, with a protocol under evaluation (e.g., treating a subject with one or more of: chemotherapy, radiation, and/or a compound identified using the methods described herein); and evaluating the expression of a 27960 nucleic acid or polypeptide before and after treatment. A change, e.g., a decrease or increase, in the level of a 27960 nucleic acid (e.g., mRNA) or polypeptide after treatment, relative to the level of expression before treatment, is indicative of the efficacy of the treatment of the disorder. The level of 27960 nucleic acid or polypeptide expression can be detected by any method described herein.

In a preferred embodiment, the evaluating step includes obtaining a sample (e.g., a tissue sample, e.g., a biopsy, or a fluid sample) from the subject, before and after treatment and comparing the level of expressing of a 27960 nucleic acid (e.g., mRNA) or polypeptide before and after treatment.

In another aspect, the invention provides methods for evaluating the efficacy of a therapeutic or prophylactic agent (e.g., an anti-neoplastic agent). The method includes: contacting a sample with an agent (e.g., a compound identified using the methods described herein, a cytotoxic agent) and, evaluating the expression of 27960 nucleic acid or polypeptide in the sample before and after the contacting step. A change, e.g., a decrease or increase, in the level of 27960 nucleic acid (e.g., mRNA) or polypeptide in the sample obtained after the contacting step, relative to the level of expression in the sample before the contacting step, is indicative of the efficacy of the agent. The level of 27960 nucleic acid or polypeptide expression can be detected by any method described herein. In a preferred embodiment, the sample includes cells obtained from a tissue in which a 27960 polypeptide or nucleic acid is expressed, e.g., a cancerous tissue of the breast, ovarian, lung, colon, liver, hemangioma, neuroblastoma, glioblastoma, Wilm's tumor; a blood vessel-associated cell, e.g., an artery, vein, heart, smooth muscle cell, endothelial cell; kidney; skeletal muscle, adipose; skin, brain, e.g., nerve cell (e.g., cortical, hypothalamic cells).

In a further aspect, the invention provides assays for determining the presence or absence of a genetic alteration in a 27960 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 27960 molecule. In one embodiment, the capture probe is a nucleic acid, e.g., a probe complementary to a 27960 nucleic acid sequence. In another embodiment, the capture probe is a polypeptide, e.g., an antibody specific for 27960 polypeptides. Also featured is a method of analyzing a sample by contacting the sample to the aforementioned array and detecting binding of the sample to the array.

Other features and advantages of the invention will be apparent from the following detailed description, and from the claims.

Detailed Description of 27960

The human 27960 sequence (SEQ ID NO:72, see Example 47), which is approximately 859 nucleotides long including untranslated regions, contains a predicted methionine-initiated coding sequence of about 456 nucleotides (nucleotides 41 to 496 of SEQ ID NO:72; SEQ ID NO:74). The coding sequence encodes a 151 amino acid protein (SEQ ID NO:73).

Human 27960 contains the following regions or other structural features: a ubiquitin-conjugating enzyme domain (PFAM Accession PF00179) located at about amino acid residues 1 to 148 of SEQ ID NO:73; two predicted Protein Kinase C sites (PS00005) at about amino acids 61 to 63 and 118 to 120 of SEQ ID NO:73; three predicted Casein Kinase II sites (PS00006) located at about amino acids 24 to 27, 47 to 50, and 118 to 121 of SEQ ID NO:73; one tyrosine kinase phosphorylation site (PS00007) at amino acids 123 to 131 of SEQ ID NO:73, and two predicted N-myristylation sites (PS00008) from about amino acids 22 to 27 and 43 to 48 of SEQ ID NO:73.

For general information regarding PFAM identifiers, PS prefix and PF prefix domain identification numbers, refer to Sonnhammer et al. (1997) *Protein* 28:405-420.

The 27960 protein contains a significant number of structural characteristics in common with members of the ubiquitin-conjugating enzyme family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

Ubiquitin-conjugating enzymes (also referred to as UBC or E2 enzymes) are a family of related proteins that catalyze the covalent attachment of ubiquitin to target proteins. Typically, an activated ubiquitin moiety is transferred from an ubiquitin-activating enzyme (E1) to E2, which subsequently ligates ubiquitin directly to substrate proteins with or without the assistance of 'N-end' recognizing proteins (E3). Typically, ubiquitin is attached as a single molecule or in a conjugated form to lysine residue(s) of proteins via formation of an isopeptide bond at the C-terminal glycine residue. Most ubiquitinated proteins are subsequently targeted to the 26S proteasome, a multicatalytic protease, which cleaves the marked protein into peptide fragments. Ubiquitin-conjugating enzymes have been implicated in regulating numerous cellular processes including, for example, proliferation, differentiation, apoptosis, transcription, signal-transduction, cell-cycle progression, receptor-mediated endocytosis, antigen presentation, organelle biogenesis, and others.

A 27960 polypeptide can include a "ubiquitin-conjugating enzyme domain" or regions homologous with a "ubiquitin-conjugating enzyme domain". As used herein, the term "ubiquitin-conjugating enzyme domain" refers to a protein domain having an amino acid sequence of 100 to 200 amino acids, preferably 130 to 160, more preferably about 145 to 148 amino acid residues. Preferably, the "ubiquitin-conjugating enzyme domain" catalyzes the covalent attachment of ubiquitin to a target protein. The ubiquitin-conjugating enzyme domain can include an active site that contains at least one cysteine residue that is required for ubiquitin-thiolester formation. The ubiquitin-conjugating enzyme domain can also include a proline-rich region located N-terminal to the active cysteine residue.

Preferably, the ubiquitin-conjugating enzyme domain includes an amino acid sequence of about 100 to 200 amino acids, preferably 130 to 160, more preferably about 145 to 148 amino acid residues in length and having a bit score for the alignment of the sequence to the ubiquitin-conjugating enzyme domain (HMM) of at least 100, more preferably 120, and most preferably 125 to 140. The ubiquitin-conjugating enzyme domain (HMM) has been assigned the PFAM Accession No. PF00179 An alignment of the ubiquitin-conjugating enzyme domain (amino acids 1 to 148 of SEQ ID NO:73) of human 27960 with a consensus amino acid sequence derived from hidden Markov models are depicted in FIGS. 65A and 65B.

In a preferred embodiment, 27960 polypeptide or protein has a "ubiquitin-conjugating enzyme domain" or a region that includes at least about 100 to 200 amino acids, preferably 130 to 160, more preferably about 145 to 148 amino acid residues and has at least about 60%, 70% 80% 90% 95%, 99%, or 100% homology with a "ubiquitin-conjugating enzyme domain," e.g., the ubiquitin-conjugating enzyme domain of human 27960 (e.g., residues 1-148 of SEQ ID NO:73).

To identify the presence of a "ubiquitin-conjugating enzyme" domain in a 27960 protein sequence, and to make the determination that a polypeptide or protein of interest has a particular profile, the amino acid sequence of the protein can be searched against a database of HMMs (e.g., the Pfam database, release 2.1) using the default parameters For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3): 405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al.(1994) *J. Mol. Biol.* 235: 1501-1531; and Stultz et al.(1993) *Protein Sci.* 2:305-314, the contents of which are incorporated herein by reference. A search was performed against the HMM database resulting in the identification of a "ubiquitin-conjugating enzyme" domain in the amino acid sequence of human 27960 at about residues 1-148 of SEQ ID NO:73.

A 27960 family member can include a ubiquitin conjugating enzyme domain, protein kinase C phosphorylation sites, casein kinase II phosphorylation sites, tyrosine kinase phosphorylation sites, and/or N-myristylation sites.

As the 27960 polypeptides of the invention may modulate 27960-mediated activities, they may be useful as of for developing novel diagnostic and therapeutic agents for 27960-mediated or related disorders, as described below.

As used herein, a "27960 activity", "biological activity of 27960", or "functional activity of 27960", refers to an activity exerted by a 27960 protein, polypeptide, or nucleic acid molecule on e.g., a 27960-responsive cell or on a 27960 substrate, e.g., a protein substrate, as determined in vivo or in vitro. In one embodiment, a 27960 activity is a direct activity, such as an association with a 27960 target molecule. A "target molecule" or "binding partner" is a molecule with which a 27960 protein binds or interacts in nature. In an exemplary embodiment, a substrate ubiquitinated by 27960 is a target molecule, e.g., a cell cycle regulator (e.g., p53). A 27960 activity can also be an indirect activity, e.g., increased degradation or increased stability of a protein due to 27960-mediated ubiquitination, or a cellular signaling activity (e.g., proliferation, differentiation, apoptosis, etc.) that results from or is mediated by the 27960 protein, or a protein ubiquitinated by 27960. For example, the 27960 proteins of the invention may modulate, directly or indirectly, one or more of the following activities: proliferation (e.g., through regulation of oncoprotein/tumor suppressor/transcription factor activity), differentiation, apoptosis (programmed cell death), transcription, signal transduction, antigen processing, cell-cycle progression (e.g., through regulation of cyclins), cell-cell adhesion, receptor-mediated endocytosis, organelle biogenesis and development (e.g., Angelman syndrome).

Based on the above-described sequence similarities, the 27960 molecules of the present invention are predicted to have similar biological activities as ubiquitin conjugating enzyme family members. Ubiquitin-conjugating enzymes are known to catalyze the addition of a ubiquitin moiety to a substrate (e.g., a target protein), thereby modulating (e.g., accelerating or inhibiting) the proteolysis of such target protein. Therefore, ubiquitin-conjugating enzymes are modulators of protein degradation and the recycling of ubiquitin, as well as participants in cell signaling pathways in which ubiquitination of a protein can alter or modify the activity of the protein. For example, TSG101 proteins, which are subjected to somatic mutations in breast cancer, contain an amino terminal domain that is homologous to ubiquitin conjugating enzymes (Ponting, C P et al. (1997) *J Mol Med* 75(7):467-9). Therefore, ubiquitin conjugating enzymes have been implicated in cellular proliferative and/or differentiative disorders, such as breast cancer. Accordingly, 27960 molecules may act as novel therapeutic agents for controlling disorders associated with excessive or insufficient ubiquitination (e.g., protein degradation), and as diagnostic markers useful for indicating the presence or predisposition towards developing such disorders, or monitoring the progression or regression of a disorder. Such disorders that can be controlled, detected or monitored using the 27960 molecules of the invention include cellular proliferative, differentiative or degenerative disorders, neural (brain) disorders, and weight disorders (e.g., cachexia).

Moreover, 27960 mRNA is expressed in several solid and metastatic tumors, including breast tumors, ovarian and uterine tumors (e.g., uterine adenocarcinomas), lung tumors (e.g., adenocarcinomas, small cell and non small cell carcinomas); colon-liver metastasis; neural malignancies, e.g. neuroblastoma and glioblastoma; Wilm's tumors; and angiogenic malignancies such as hemangiomas (see the Examples below). Accordingly, 27960 molecules may act as novel therapeutic agents for controlling cancerous conditions or disorders, and as diagnostic markers useful for indicating the presence or predisposition towards developing such disorders, or monitoring the progression or regression of a disorder.

27960 mRNA is also expressed in the in normal and fetal kidney, fetal adrenal, normal and fetal heart, endothelial cells, blood vessel cells, and neural tissues (e.g., brain cortex and hypothalamus). Accordingly, the molecules of the invention may act as novel therapeutic and diagnostic agents for treating, preventing and/or diagnosing disorders involving aberrant activities of these cells.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast, and liver origin. Particularly preferred cancers are those involving pathological angiogenesis or abnormal neovascularization, including solid tumor growth and metastasis.

As used herein, the terms "cancer," "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

Examples of cellular proliferative and/or differentiative disorders of the lung include, but are not limited to, squamous cell lung carcinomas, small cell lung carcinoma, lung adenocarcinomas, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Another preferred cancer that can be treated, prevented and/or diagnosed with the molecules and methods of the invention is Wilm's tumor. Wilm's tumor (WT) is an embryonal malignacy of the kidney which affects approximately 1 in 10,000 infants and young children (A. J. Buckler et al. U.S. Pat. No. 5,350,840; and Matsunaga, *Human Genetics*, 57: 231-246 (1981)). A subset of Wilms' tumor cases (approximately 2%) occur in association with aniridia (AN2), a defect in the development of the iris, as well as urogenital abnormalities and mental retardation (Miller et al., New Engl. J. Med., 227:922-927 (1964)). These disorders form the WAGR syndrome, and can be attributed to constitutional deletions of DNA in band 11p13 on human chromosome 11 in a group of genes known as the WAGR complex (Riccardi et al., Pediatrics, 61:604-610 (1978); Francke, et al., Cytogenet. Cell Genet., 24:185-192 (1979)). In these cases, bilateral Wilms' tumors are frequently observed, as are dysplastic changes in surrounding renal tissue (nephroblastomatosis) which are thought to precede malignant transformation (Bove and McAdams, Perspectives on Pediatric Pathol., 3:185-223 (1976)). As a recessive oncogene or anti-oncogene, the Wilms' tumor locus curtails the growth of undifferentiated nephretic cells. Heterozygosity at polymorphic loci supports the localization of Wilms' tumor gene to 11p13 (Koufos et al., Nature, 309:170-172 (1984); Orkin et al., Nature, 309:172-174 (1984); Reeve et al., Nature, 309:174-176 (1984); Fearon et al., Nature, 309:176-178 (1984)).

The 27960 nucleic acid and protein of the invention can be used to treat and/or diagnose a variety of other proliferative disorders, e.g., hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of neural disorders that can be treated with the 27960 molecules include disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington's disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; Creutzfeld-Jakob, Machado-Joseph and other polyglutamine associated neural disorders and ataxias; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Examples of cardiovascular disorders include but are not limited to, diseases or disorders involving the cardiovascular system, e.g., the heart, the blood vessels, and/or the blood. Such disorders include but are not limited to heart failure, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

As used herein, "a prostate disorder" refers to an abnormal condition occurring in the male pelvic region characterized by, e.g., male sexual dysfunction and/or urinary symptoms. This disorder may be manifested in the form of genitourinary inflammation (e.g., inflammation of smooth muscle cells) as in several common diseases of the prostate including prostatitis, benign prostatic hyperplasia and cancer, e.g. adenocarcinoma or carcinoma, of the prostate.

Examples of weight disorders (or disorders of metabolic imbalance) include, but are not limited to, obesity, anorexia nervosa, cachexia, lipid disorders, and diabetes.

The 27960 protein, fragments thereof, and derivatives and other variants of the sequence in SEQ ID NO:73 thereof are collectively referred to as "polypeptides or proteins of the invention" or "27960 polypeptides or proteins." Nucleic acid molecules encoding such polypeptides or proteins are collectively referred to as "nucleic acids of the invention" or "27960 nucleic acids." 27960 molecules refer to 27960 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules that are separated from other nucleic acid molecules that are present in the natural source of the nucleic acid. For example, with respect to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5' and/or 3' ends of the nucleic acid) in the genomic DNA of the organism from that the nucleic acid is derived. For example, in various embodiments, the isolated nucleic acid molecule can contain less than about 5 kb, 4 kb, 3 kb, 2 kb, 1 kb, 0.5 kb, or 0.1 kb of 5' and/or 3' nucleotide sequences that naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows:

1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules that include an open reading frame encoding a 27960 protein, preferably a mammalian 27960 protein, and can further include non-coding regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 27960 protein having less than about 30%, 20%, 10%, and more preferably, 5% (by dry weight) of non-27960 protein (also referred to herein as a "contaminating protein"), or of chemical precursors or non-27960 chemicals. When the 27960 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 27960 (e.g., the sequence of SEQ ID NO:72 or 74, without abolishing or more preferably, without substantially altering a biological activity, whereas an "essential" amino acid residue results in such a change. For example, amino acid residues that are conserved among the polypeptides of the present invention, e.g.,those present in the active site of the ubiquitin-conjugating enzyme domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in a 27960 protein is preferably replaced with another amino acid residue from the same side chain family. Alternatively, in another embodiment, mutations can be introduced randomly along all or part of a 27960 coding sequence, such as by saturation mutagenesis, and the resultant mutants can be screened for 27960 biological activity to identify mutants that retain activity. Following mutagenesis of SEQ ID NO:72 or 74 the encoded protein can be expressed recombinantly and the activity of the protein can be determined.

As used herein, a "biologically active portion" of a 27960 protein includes a fragment of a 27960 protein that participates in an interaction between a 27960 molecule and a non-27960 molecule. Biologically active portions of a 27960 protein include peptides comprising amino acid sequences sufficiently homologous to or derived from the amino acid sequence of the 27960 protein, e.g., the amino acid sequence shown in SEQ ID NO:73, which includes less amino acids than the full length 27960 proteins, and exhibit at least one activity of a 27960 protein. Typically, biologically active portions comprise a domain or motif with at least one activity of the 27960 protein, e.g., conjugation of ubiquitin to a target protein. A biologically active portion of a 27960 protein can be a polypeptide that is, for example, 10, 25, 50, 100, 200 or more amino acids in length. Biologically active portions of a 27960 protein can be used as targets for developing agents that modulate a 27960 mediated activity, e.g., conjugation of ubiquitin to a target protein.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 27960 amino acid sequence of SEQ ID NO:73 having 46 amino acid residues, at least 61, preferably at least 76, more preferably at least 91, even more preferably at least 106, and even more preferably at least 122 or 137 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444-453 (1970)) algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS* 4:11-17) that has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to 27960 nucleic acid molecules of the invention. BLAST protein searches can be performed with the XBLAST program, score=50, wordlength=3 to obtain amino acid sequences homologous to 27960 protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

Particularly preferred 27960 polypeptides of the present invention have an amino acid sequence substantially identical to the amino acid sequence of SEQ ID NO:73. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:73 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:72 or 74 are termed substantially identical.

"Misexpression or aberrant expression", as used herein, refers to a non-wild type pattern of gene expression at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably, 50% of the subject cells.

Various aspects of the invention are described in further detail below.

Isolated Nucleic Acid Molecules of 27960

In one aspect, the invention provides an isolated or purified nucleic acid molecule that encodes a 27960 polypeptide described herein, e.g., a full length 27960 protein or a fragment thereof, e.g., a biologically active portion of 27960 protein. Also included is a nucleic acid fragment suitable for use as a hybridization probe, which can be used, e.g., to identify a nucleic acid molecule encoding a polypeptide of the invention, 27960 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:72, or a portion of any of these nucleotide sequences. In one embodiment, the nucleic acid molecule includes sequences encoding the human 27960 protein (i.e., "the coding region", from nucleotides 41-496 of SEQ ID NO:72), as well as 5' untranslated sequences (nucleotides 1-40 of SEQ ID NO:72). Alternatively, the nucleic acid molecule can include only the coding region of SEQ ID NO:72 (e.g., nucleotides 41-456, corresponding to SEQ ID NO:74) and, e.g., no flanking sequences that normally accompany the subject sequence. In another embodiment, the nucleic acid molecule encodes a sequence corresponding to the mature protein from about amino acid 1 to amino acid 151 of SEQ ID NO:73.

In another embodiment, an isolated nucleic acid molecule of the invention includes a nucleic acid molecule that is a complement of the nucleotide sequence shown in SEQ ID NO:72 or 74, or a portion of any of these nucleotide sequences. In other embodiments, the nucleic acid molecule of the invention is sufficiently complementary to the nucleotide sequence shown in SEQ ID NO:72 or 74 such that it can hybridize to the nucleotide sequence shown in SEQ ID NO:72 or 74, thereby forming a stable duplex.

In one embodiment, an isolated nucleic acid molecule of the present invention includes a nucleotide sequence that is at least about 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:72 or 74, or a portion, preferably of the same length, of any of these nucleotide sequences.

27960 Nucleic Acid Fragments

A nucleic acid molecule of the invention can include only a portion of the nucleic acid sequence of SEQ ID NO:72 or 74. For example, such a nucleic acid molecule can include a fragment that can be used as a probe or primer or a fragment encoding a portion of a 27960 protein, e.g., an immunogenic or biologically active portion of a 27960 protein. A fragment can comprise nucleotides 41 to 484 of SEQ ID NO:72, which encodes a ubiquitin-conjugating enzyme domain of human 27960. The nucleotide sequence determined from the cloning of the 27960 gene allows for the generation of probes and primers designed for use in identifying and/or cloning other 27960 family members, or fragments thereof, as well as 27960 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment that includes a nucleotide sequence encoding an amino acid fragment described herein. Nucleic acid fragments can encode a specific domain or site described herein or fragments thereof, particularly fragments thereof that are at least 148 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domains, regions, or functional sites described herein. Thus, for example, the nucleic acid fragment can encode a ubiquitin-conjugating enzyme domain and a protein kinase C phosphorylation site.

27960 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:72 or 74, or of a naturally occurring allelic variant or mutant of SEQ ID NO:72 or 74.

In a preferred embodiment the nucleic acid is a probe that is at least 5 or 10, and less than 200, more preferably less than 100, or less than 50 base pairs in length. It should be identical, or differ by 1, or less than 5 or 10 base pairs from a sequence disclosed herein. If alignment is needed for this comparison, the sequences should be aligned for maximum homology. "Looped" out sequences from deletions, insertions, or mismatches are considered differences.

A probe or primer can be derived from the sense or anti-sense strand of a nucleic acid that encodes a ubiquitin-conjugating enzyme domain (e.g., residues 1-148 of SEQ ID NO:73).

In another embodiment a set of primers is provided, e.g., primers suitable for use in a PCR, which can be used to amplify a selected region of a 27960 sequence, e.g., a domain, region, site or other sequence described herein. The primers should be at least 5, 10, or 50 base pairs in length and less than 100, or less than 200 base pairs in length. The primers should be identical, or differs by one base from a sequence disclosed herein or from a naturally occurring variant. E.g., primers suitable for amplifying all or a portion of any of the following regions are provided: a ubiquitin-conjugating enzyme domain (e.g., residues 1-148 of SEQ ID NO:73).

A nucleic acid fragment can encode an epitope bearing region of a polypeptide described herein.

A nucleic acid fragment encoding a "biologically active portion of a 27960 polypeptide" can be prepared by isolating a portion of the nucleotide sequence of SEQ ID NO:72 or 74, which encodes a polypeptide having a 27960 biological activity (e.g., the biological activities of the 27960 proteins are described herein), expressing the encoded portion of the 27960 protein (e.g., by recombinant expression in vitro) and assessing the activity of the encoded portion of the 27960 protein. For example, a nucleic acid fragment encoding a biologically active portion of 27960 includes a ubiquitin-conjugating enzyme domain, e.g., amino acid residues 1 to 148 of SEQ ID NO:73. A nucleic acid fragment encoding a biologically active portion of a 27960 polypeptide may comprise a nucleotide sequence that is greater than 440 or more nucleotides in length.

In preferred embodiments the nucleic acid fragment is 300, 400, 500, 600, 700, 800 or more nucleotides in length and hybridizes under a stringency condition described herein to a nucleic acid molecule of SEQ ID NO:72, or SEQ ID NO:74. In other embodiment the nucleic acid includes a contiguous sequence that includes about nucleotides 1 to 25, 1 to 27, 1 to 100, 100 to 300, 200 to 400, 300 to 500, 400 to 600, 500 to 700, 600 to 800, or 800 to 859 of SEQ ID NO:72.

27960 Nucleic Acid Variants

The invention further encompasses nucleic acid molecules that differ from the nucleotide sequence shown in SEQ ID NO:72 or 74. Such differences can be due to degeneracy of the genetic code and result in a nucleic acid that encodes the same 27960 proteins as those encoded by the nucleotide sequence disclosed herein. In another embodiment, an isolated nucleic acid molecule of the invention has a nucleotide sequence encoding a protein having an amino acid sequence that differs, by at least 1, but less than 5, 10, 20, 50, or 100 amino acid residues than shown in SEQ ID NO:73. If alignment is needed for this comparison, the sequences should be aligned for maximum homology. "Looped" out sequences from deletions, insertions, or mismatches are considered differences.

Nucleic acids of the invention can be chosen for having codons, which are preferred, or non-preferred, for a particular expression system. E.g., the nucleic acid can be one in which at least one codon, and preferably at least 10% or 20% of the codons, have been altered such that the sequence is optimized for expression in E. coli, yeast, human, insect, or Chinese hamster ovary (CHO) cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions, and insertions. Variation can occur in either or both of the coding and non-coding regions. The variations can produce both conservative and non-conservative amino acid substitutions (as compared in the encoded product).

In a preferred embodiment, the nucleic acid differs from that of SEQ ID NO:72 or 74, e.g., as follows: by at least one, but less than 10, 20, 30, or 40 nucleotides; at least one, but less than 1%, 5%, 10% or 20% of the nucleotides in the subject nucleic acid. If necessary for this analysis the sequences should be aligned for maximum homology. "Looped" out sequences from deletions, insertions, or mismatches are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the amino acid sequence shown in SEQ ID NO:73 or a fragment of this sequence. Such nucleic acid molecules can readily be identified as being able to hybridize under stringent conditions to the nucleotide sequence shown in SEQ ID NO:72 or a fragment of the sequence. Nucleic acid molecules corresponding to orthologs, homologs, and allelic variants of the 27960 cDNAs of the invention can further be isolated by mapping to the same chromosome or locus as the 27960 gene. Preferred variants include those that are correlated with conjugation of ubiquitin to a target protein.

Allelic variants of 27960, e.g., human 27960, include both functional and non-functional proteins. Functional allelic variants are naturally occurring amino acid sequence variants of the 27960 protein within a population that maintain the ability to conjugate ubiquitin to a target protein. Functional allelic variants will typically contain only conservative substitution of one or more amino acids of SEQ ID NO:73, or substitution, deletion or insertion of non-critical residues in non-critical regions of the protein. Non-functional allelic variants are naturally-occurring amino acid sequence variants of the 27960, e.g., human 27960, protein within a population that do not have the ability to conjugate ubiquitin to a target protein. Non-functional allelic variants will typically contain a non-conservative substitution, a deletion, or insertion, or premature truncation of the amino acid sequence of SEQ ID NO:73, or a substitution, insertion, or deletion in critical residues or critical regions of the protein.

Moreover, nucleic acid molecules encoding other 27960 family members and, thus, which have a nucleotide sequence that differs from the 27960 sequences of SEQ ID NO:72 or 74 are intended to be within the scope of the invention.

Antisense Nucleic Acid Molecules, Ribozymes and Modified 27960 Nucleic Acid Molecules In another aspect, the invention features an isolated nucleic acid molecule that is antisense to 27960. An "antisense" nucleic acid can include a nucleotide sequence that is complementary to a "sense" nucleic acid encoding a protein, e.g., complementary to the coding strand of a double-stranded cDNA molecule or complementary to an mRNA sequence. The antisense nucleic acid can be complementary to an entire 27960 coding strand, or to only a portion thereof (e.g., the coding region of human 27960 corresponding to SEQ ID NO:74). In another embodiment, the antisense nucleic acid molecule is antisense to a "noncoding region" of the coding strand of a nucleotide sequence encoding 27960 (e.g., the 5' and 3' untranslated regions).

An antisense nucleic acid can be designed such that it is complementary to the entire coding region of 27960 mRNA, but more preferably, is an oligonucleotide that is antisense to only a portion of the coding or noncoding region of 27960 mRNA. For example, the antisense oligonucleotide can be complementary to the region surrounding the translation start site of 27960 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, and is described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 27960 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. A ribozyme having specificity for a 27960-encoding nucleic acid can include one or more sequences complementary to the nucleotide sequence of a 27960 cDNA disclosed herein (i.e., SEQ ID NO:72 or 74), and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a 27960-encoding mRNA. See, e.g., Cech et al. U.S. Pat. No. 4,987,071; and Cech et al. U.S. Pat. No. 5,116,742. Alternatively, 27960 mRNA can be used to select a catalytic RNA having a specific ribonuclease activity from a pool of RNA molecules. See, e.g., Bartel, D. and Szostak, J. W. (1993) *Science* 261:1411-1418.

27960 gene expression can be inhibited by targeting nucleotide sequences complementary to the regulatory region of the 27960 (e.g., the 27960 promoter and/or enhancers) to form triple helical structures that prevent transcription of the 27960 gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15. The potential sequences that can be targeted for triple helix formation can be increased by creating a "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 27960 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1):5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. (1996) *Proc. Natl. Acad. Sci. USA* 93: 14670-675.

PNAs of 27960 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 27960 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe (1996) supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; and PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *BioTechniques* 6:958-976) or intercalating agents (see, e.g., Zon (1988) Pharm. Res. 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region that is complementary to a 27960 nucleic acid of the invention, two complementary regions one having a fluorophore and one a quencher such that the molecular beacon is useful for quantitating the presence of the 27960 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 27960 Polypeptides

In another aspect, the invention features an isolated 27960 protein or fragment, e.g., a biologically active portion, for use as immunogens or antigens to raise or test (or more generally to bind) anti-27960 antibodies. 27960 protein can be isolated from cells or tissue sources using standard protein purification techniques. 27960 protein or fragments thereof can be produced by recombinant DNA techniques or synthesized chemically.

Polypeptides of the invention include those that arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems that result in the alteration or omission of postranslational modifications, e.g., glycosylation or cleavage, present when expressed in a native cell.

In a preferred embodiment, a 27960 polypeptide has one or more of the following characteristics:

(i) it has the ability to conjugate ubiquitin to a target protein;

(ii) it has the ability to modulate protein degradation;

(iii) it has a molecular weight, e.g., a deduced molecular weight, preferably ignoring any contribution of post translational modifications, of a 27960 polypeptide, e.g., a polypeptide encoded by SEQ ID NO:73;

(iv) it has an amino acid composition or other physical characteristic of a 27960 polypeptide, e.g., a polypeptide encoded by SEQ ID NO:73;

(v) it has an overall sequence similarity of at least 60%, more preferably at least 70, 80, 90, or 95%, with a polypeptide of SEQ ID NO:73;

(vi) it has a ubiquitin-conjugating enzyme domain that has an overall sequence similarity of preferably about 70%, 80%, 90% or 95% with amino acid residues 1-148 of SEQ ID NO:73; or (vii) it has at least 50%, preferably 80%, and most preferably 90% of the cysteines found in the amino acid sequence of the native protein.

In a preferred embodiment the 27960 protein or fragment thereof differs from the corresponding sequence in SEQ ID NO:73. In one embodiment, it differs by at least one, but by less than 15, 10 or 5 amino acid residues. In another it differs from the corresponding sequence in SEQ ID NO:73 by at least one residue, but less than 20%, 15%, 10% or 5% of the residues in it differ from the corresponding sequence in SEQ ID NO:73. (If this comparison requires alignment the sequences should be aligned for maximum homology. "Looped" out sequences from deletions, insertions, or mismatches, are considered differences.) The differences are, preferably, differences or changes at a non-essential residue or a conservative substitution. In a preferred embodiment, the differences are not in a ubiquitin conjugating enzyme domain. In another preferred embodiment, one or more differences are in non-active site residues.

Other embodiments include a protein that contains one or more changes in amino acid sequence, e.g., a change in an amino acid residue that is not essential for activity. Such 27960 proteins differ in amino acid sequence from SEQ ID NO:73, yet retain biological activity.

In one embodiment, the protein includes an amino acid sequence at least about 60%, 65%, 70%, 75%, 80%, 85%, 90%, 95%, 98% or more homologous to SEQ ID NO:73.

A 27960 protein or fragment is provided that varies from the sequence of SEQ ID NO:73 in non-active site regions by at least one, but by less than 15, 10 or 5 amino acid residues in the protein or fragment, but that does not differ from SEQ ID NO:73 in the active site. (If this comparison requires alignment the sequences should be aligned for maximum homology. "Looped" out sequences from deletions, insertions, or mismatches, are considered differences.) In some embodiments the difference is at a non-essential residue or is a conservative substitution, while in others, the difference is at an essential residue or is a non conservative substitution.

In one embodiment, a biologically active portion of a 27960 protein includes a ubiquitin conjugating-enzyme domain. Moreover, other biologically active portions, in which other regions of the protein are deleted, can be prepared by recombinant techniques and evaluated for one or more of the functional activities of a native 27960 protein.

In a preferred embodiment, the 27960 protein has an amino acid sequence shown in SEQ ID NO:73. In other embodiments, the 27960 protein is substantially identical to SEQ ID NO:73. In yet another embodiment, the 27960 protein is substantially identical to SEQ ID NO:73 and retains the functional activity of the protein of SEQ ID NO:73, as described in detail in subsection I above.

27960 Chimeric or Fusion Proteins

In another aspect, the invention provides 27960 chimeric or fusion proteins. As used herein, a 27960 "chimeric protein" or "fusion protein" includes a 27960 polypeptide linked to a non-27960 polypeptide. A "non-27960 polypeptide" refers to a polypeptide having an amino acid sequence corresponding to a protein that is not substantially homologous to the 27960 protein, e.g., a protein that is different from the 27960 protein and that is derived from the same or a different organism. The 27960 polypeptide of the fusion protein can correspond to all or a portion e.g., a fragment described herein of a 27960 amino acid sequence. In a preferred embodiment, a 27960 fusion protein includes at least one (e.g., two) biologically active portion of a 27960 protein. The non-27960 polypeptide can be fused to the N-terminus or C-terminus of the 27960 polypeptide.

The fusion protein can include a moiety that has a high affinity for a ligand. For example, the fusion protein can be a glutathione-S-transferase (GST)-27960 fusion protein in which the 27960 sequences are fused to the C-terminus of the GST sequences. Such fusion proteins can facilitate the purification of recombinant 27960. Alternatively, the fusion protein can be a 27960 protein containing a heterologous signal sequence at its N-terminus. In certain host cells (e.g., mammalian host cells), expression and/or secretion of 27960 can be increased through use of a heterologous signal sequence.

Fusion proteins can include all or a part of a serum protein, e.g., an IgG constant region, or human serum albumin.

The 27960 fusion proteins of the invention can be incorporated into pharmaceutical compositions and administered to a subject in vivo. The 27960 fusion proteins can be used to affect the bioavailability of a 27960 substrate. 27960 fusion proteins may be useful therapeutically for the treatment of disorders caused by, for example, (i) aberrant modification or mutation of a gene encoding a 27960 protein; (ii) mis-regulation of the 27960 gene; and (iii) aberrant post-translational modification of a 27960 protein.

Moreover, the 27960-fusion proteins of the invention can be used as immunogens to produce anti-27960 antibodies in a subject, to purify 27960 ligands and in screening assays to identify molecules that inhibit the interaction of 27960 with a 27960 substrate.

Expression vectors are commercially available that already encode a fusion moiety (e.g., a GST polypeptide). A 27960-encoding nucleic acid can be cloned into such an expression vector such that the fusion moiety is linked in-frame to the 27960 protein.

Variants of 27960 Proteins

In another aspect, the invention also features a variant of a 27960 polypeptide, e.g., that functions as an agonist (mimetics) or as an antagonist. Variants of the 27960 proteins can be generated by mutagenesis, e.g., discrete point mutations, insertion or deletion of sequences, or the truncation of a 27960 protein. An agonist of the 27960 proteins can retain substantially the same, or a subset, of the biological activities of the naturally occurring form of a 27960 protein. An antagonist of a 27960 protein can inhibit one or more of the activities of the naturally occurring form of the 27960 protein by, for example, competitively modulating a 27960-mediated activity of a 27960 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 27960 protein.

Variants of a 27960 protein can be identified by screening combinatorial libraries of mutants, e.g., truncation mutants, of a 27960 protein for agonist or antagonist activity.

Libraries of fragments e.g., N terminal, C terminal, or internal fragments, of a 27960 protein coding sequence can be used to generate a variegated population of fragments for screening and subsequent selection of variants of a 27960 protein.

Variants in which one or more cysteine residues are added or deleted or in which a residue that is glycosylated is added or deleted are particularly preferred.

Methods for screening gene products of combinatorial libraries made by point mutations or truncation, and for screening cDNA libraries for gene products having a selected property are known. Recursive ensemble mutagenesis (REM), a new technique that enhances the frequency of functional mutants in the libraries, can be used in combination with the screening assays to identify 27960 variants (Arkin and Yourvan (1992) *Proc. Natl. Acad. Sci. USA* 89:7811-7815; Delgrave et al. (1993) Protein Engineering 6(3):327-331).

Cell based assays can be exploited to analyze a variegated 27960 library. For example, a library of expression vectors can be transfected into a cell line, e.g., a cell line, that ordinarily responds to 27960 in a substrate-dependent manner. The transfected cells are then contacted with 27960 and the effect of the expression of the mutant on signaling by the 27960 substrate can be detected, e.g., by monitoring proteolysis of a target protein. Plasmid DNA can then be recovered from the cells that score for inhibition, or alternatively, potentiation of signaling by the 27960 substrate, and the individual clones further characterized.

In another aspect, the invention features a method of making a 27960 polypeptide, e.g., a peptide having a non-wild type activity, an antagonist, agonist, or super agonist of a naturally occurring 27960 polypeptide, or a naturally occurring 27960 polypeptide. The method includes: altering the sequence of a 27960 polypeptide, e.g., by substitution or deletion of one or more residues of a non-conserved region, a domain or residue disclosed herein, and testing the altered polypeptide for the desired activity.

In another aspect, the invention features a method of making a fragment or analog of a 27960 polypeptide having a biological activity of a naturally occurring 27960 polypeptide. The method includes: altering the sequence, e.g., by substitution or deletion of one or more residues, of a 27960 polypeptide, e.g., altering the sequence of a non-conserved region, or a domain or residue described herein, and testing the altered polypeptide for the desired activity.

Anti-27960 Antibodies

In another aspect, the invention provides an anti-27960 antibody. The term "antibody" as used herein refers to an immunoglobulin molecule or immunologically active portion thereof, i.e., an antigen-binding portion. Antibodies are proteins that include at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4. Examples of immunologically active portions of immunoglobulin molecules include F(ab) and F(ab')$_2$ fragments that can be generated by treating the antibody with an enzyme such as pepsin.

The anti-27960 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 27960 polypeptide or fragment thereof. Examples of antigen-binding fragments of the anti-27960 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The antibody can be a polyclonal, monoclonal, recombinant, e.g., a chimeric or humanized, fully human, non-human, e.g., murine, or a single chain antibody. In a preferred embodiment it has effector function and can fix complement. The antibody can be coupled to a toxin or imaging agent. In other embodiments, the antibody can be recombinantly produced, e.g., produced by phage display or by combinatorial methods.

Phage display and combinatorial methods for generating anti-27960 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the anti27960 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An anti-27960 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559). antibody may be replaced with at least a portion of a non-human CDR or only some of the CDR's may be replaced with non-human CDR's. It is only necessary to replace the number of CDR's required for binding of the humanized antibody to a 27960 molecule or a fragment thereof.

A humanized or CDR-grafted antibody will have at least one or two but generally all three recipient CDR's (of heavy and or light immuoglobulin chains) replaced with a donor CDR. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto. As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, Science 229:1202-1207, by Oi et al., 1986, BioTechniques 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 27960 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 Nature 321:552-525; Verhoeyan et al. 1988 Science 239:1534; Beidler et al. 1988 J. Immunol. 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In preferred embodiments, an antibody can be made by immunizing with purified 27960 antigen or a fragment thereof, e.g., a fragment described herein or tissue, e.g., crude tissue preparations, whole cells, preferably living cells, lysed cells, or cell fractions.

A full-length 27960 protein or antigenic peptide fragment of 27960 can be used as an immunogen or can be used to identify anti-27960 antibodies made with other immunogens, e.g., cells, membrane preparations, and the like. The antigenic peptide of 27960 should include at least 8 amino acid residues of the amino acid sequence shown in SEQ ID NO:73 and encompasses an epitope of 27960. Preferably, the antigenic peptide includes at least 10 amino acid residues, more preferably at least 15 amino acid residues, even more preferably at least 20 amino acid residues, and most preferably at least 30 amino acid residues.

Fragments of 27960 that include residues 15-20, 21-31, 46-53, 58-71, or 116-131 can be used to make, e.g., used as immunogens or used to characterize the specificity of an antibody, antibodies against hydrophilic regions of the 27960 protein. Similarly, a fragment of 27960 that includes residues 53-58, 85-95, or 101-118 can be used to make an antibody against a hydrophobic region of the 27960 protein; a fragment of 27960 that include residues all or portion of amino acids 1-148 of SEQ ID NO:73 (e.g., 11-31, 51-71, 91-111, or 121-141) can be used to make an antibody against the ubiquitin-conjugating enzyme region of the 27960 protein.

Antibodies reactive with, or specific for, any of these regions, or other regions or domains described herein are provided.

Antibodies that bind only native 27960 protein, only denatured or otherwise non-native 27960 protein, or which bind both, are with in the invention. Antibodies with linear or conformational epitopes are within the invention. Conformational epitopes can sometimes be identified by identifying antibodies that bind to native but not denatured 27960 protein.

Preferred epitopes encompassed by the antigenic peptide are regions of 27960 are located on the surface of the protein, e.g., hydrophilic regions, as well as regions with high antigenicity. For example, an Emini surface probability analysis of the human 27960 protein sequence can be used to indicate the regions that have a particularly high probability of being localized to the surface of the 27960 protein and are thus likely to constitute surface residues useful for targeting antibody production.

In a preferred embodiment the antibody binds an epitope on any domain or region on 27960 proteins described herein.

Chimeric, humanized, but most preferably, completely human antibodies are desirable for applications that include repeated administration, e.g., therapeutic treatment (and some diagnostic applications) of human patients.

The anti-27960 antibody can be a single chain antibody. A single-chain antibody (scFV) may be engineered (see, for example, Colcher, D., et al. (1999) Ann N Y Acad Sci; 880:263-80; and Reiter, Y. (1996) Clin Cancer Res; 2(2): 245-52). The single chain antibody can be dimerized or multimerized to generate multivalent antibodies having specificities for different epitopes of the same target 27960 protein.

In a preferred embodiment the antibody has effector function and can fix complement. In other embodiments, the antibody does not recruit effector cells or fix complement.

In a preferred embodiment, the antibody has reduced or no ability to bind an Fc receptor. E.g., it is an isotype or subtype, fragment or other mutant, that does not support binding to an Fc receptor, e.g., it has a mutagenized or deleted Fc receptor binding region.

The antibody can be coupled to a toxin, e.g., a polypeptide toxin such as ricin or diphtheria toxin or active fragment thereof, or a radioactive nucleus, or imaging agent, e.g. a radioactive, enzymatic, or other, e.g., imaging agent, e.g., a NMR contrast agent. Labels that produce detectable radioactive emissions or fluorescence are preferred.

An anti-27960 antibody (e.g., monoclonal antibody) can be used to isolate 27960 by standard techniques, such as affinity chromatography or immunoprecipitation. Moreover, an anti-27960 antibody can be used to detect 27960 protein (e.g., in a cellular lysate or cell supernatant) in order to evaluate the abundance and pattern of expression of the protein. Anti-27960 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes a nucleic acids which encodes an anti-27960 antibody, e.g., an anti-27960 antibody described herein. Also included are vectors which include the nucleic acid and sells transformed with the nucleic acid, particularly cells which are useful for producing an antibody, e.g., mammalian cells, e.g. CHO or lymphatic cells.

The invention also includes cell lines, e.g., hybridomas, which make an anti-27960 antibody, e.g., an antibody described herein, and method of using said cells to make a 27960 antibody.

27960 Recombinant Expression Vectors, Host Cells and Genetically Engineered Cells In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 27960 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 27960 proteins, mutant forms of 27960 proteins, fusion proteins, and the like).

The recombinant expression vectors of the invention can be designed for expression of 27960 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes:1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) that fuse GST, maltose E binding protein, or protein A, respectively, to the target recombinant protein.

Purified fusion proteins can be used in 27960 activity assays, (e.g., direct assays or competitive assays described in detail below), or to generate antibodies specific for 27960 proteins. In a preferred embodiment, a fusion protein expressed in a retroviral expression vector of the present invention can be used to infect bone marrow cells that are subsequently transplanted into irradiated recipients. The pathology of the subject recipient is then examined after sufficient time has passed (e.g., six (6) weeks).

To maximize recombinant protein expression in *E. coli*, the protein can be expressed in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The 27960 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen that direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al. (1986) *Reviews—Trends in Genetics*, Vol. 1(1).

Another aspect the invention provides a host cell that includes a nucleic acid molecule described herein, e.g., a 27960 nucleic acid molecule within a recombinant expression vector or a 27960 nucleic acid molecule containing sequences that allow it to homologously recombine into a specific site of the host cell's genome. The terms "host cell" and "recombinant host cell" are used interchangeably herein. Such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 27960 protein can be expressed in bacterial cells such as *E. Coli*, insect cells, yeast or mammalian cells (such as CHO or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation A host cell of the invention can be used to produce (i.e., express) a 27960 protein. Accordingly, the invention further provides methods for producing a 27960 protein using the host cells of the invention. In one embodiment, the method includes culturing the host cell of the invention (into which a recombinant expression vector encoding a 27960 protein has been introduced) in a suitable medium such that a 27960 protein is produced. In another embodiment, the method further includes isolating a 27960 protein from the medium or the host cell.

In another aspect, the invention features a cell or purified preparation of cells that include a 27960 transgene, or that otherwise misexpress 27960. The cell preparation can consist of human or non-human cells, e.g., rodent cells such as mouse or rat cells, rabbit cells, or pig cells. In preferred embodiments, the cell or cells include a 27960 transgene, e.g., a heterologous form of a 27960, such as a gene derived from humans (in the case of a non-human cell). The 27960 transgene can be misexpressed, e.g., overexpressed or underexpressed. In other preferred embodiments, the cell or cells include a gene that misexpress an endogenous 27960, e.g., a gene the expression of which is disrupted, e.g., a knockout. Such cells can serve as a model for studying disorders that are related to mutated or mis-expressed 27960 alleles or for use in drug screening.

In another aspect, the invention features a human cell, e.g., a hematopoietic stem cell, transformed with a nucleic acid that encodes a subject 27960 polypeptide.

Also provided are cells, preferably human cells, e.g., human hematopoietic or fibroblast cells, in which endogenous 27960 is under the control of a regulatory sequence that does not normally control the expression of the endogenous 27960 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 27960 gene. For example, an endogenous 27960 gene that is "transcriptionally silent," e.g., not normally expressed, or expressed only at very low levels, may be activated by inserting a regulatory element that is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 27960 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (2001) *Nat. Biotechnol.* 19:35; and U.S. Pat. No. 5,876,742. Production of 27960 polypeptide can be regulated in the subject by administering an agent (e.g., a steroid hormone) to the subject. In another preferred embodiment, the implanted recombinant cells express and secrete an antibody specific for a 27960 polypeptide. The antibody can be any antibody or any antibody derivative described herein.

27960 Transgenic Animals

The invention provides non-human transgenic animals. Such animals are useful for studying the function and/or activity of a 27960 protein and for identifying and/or evaluating modulators of 27960 activity. As used herein, a "transgenic animal" is a non-human animal, preferably a mammal, more preferably a rodent such as a rat or mouse, in which one or more of the cells of the animal include a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 27960 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 27960 protein to particular cells. A transgenic founder animal can be identified based upon the presence of a 27960 transgene in its genome and/or expression of 27960 mRNA in tissues or cells of the animals. A transgenic founder animal can then be used to breed additional animals carrying the transgene. Moreover, transgenic animals carrying a transgene encoding a 27960 protein can further be bred to other transgenic animals carrying other transgenes.

27960 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed herein.

Uses of 27960

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 27960 protein (e.g., via a recombinant expression vector in a host cell in gene therapy applications), to detect a 27960 mRNA (e.g., in a biological sample) or a genetic alteration in a 27960 gene, and to modulate 27960 activity, as described further below. The 27960 proteins can be used to treat disorders characterized by insufficient or excessive production of a 27960 substrate or production of 27960 inhibitors. In addition, the 27960 proteins can be used to screen for naturally occurring 27960 substrates, to screen for drugs or compounds that modulate 27960 activity, as well as to treat disorders characterized by insufficient or excessive production of 27960 protein or production of 27960 protein forms that have decreased, aberrant or unwanted activity compared to 27960 wild type protein (e.g., Alzheimer's disease, Pick's disease, cachexia, or cancer). Moreover, the anti-27960 antibodies of the invention can be used to detect and isolate 27960 proteins, regulate the bioavailability of 27960 proteins, and modulate 27960 activity.

A method of evaluating a compound for the ability to interact with, e.g., bind, a subject 27960 polypeptide is provided. The method includes: contacting the compound with the subject 27960 polypeptide; and evaluating ability of the compound to interact with, e.g., to bind or form a complex with the subject 27960 polypeptide. This method can be performed in vitro, e.g., in a cell free system, or in vivo, e.g., in a two-hybrid interaction trap assay. This method can be used to identify naturally occurring molecules that interact with subject 27960 polypeptide. It can also be used to find natural or synthetic inhibitors of subject 27960 polypeptide. Screening methods are discussed in more detail below.

27960 Screening Assays

The invention provides methods (also referred to herein as "screening assays") for identifying modulators, i.e., candidate or test compounds or agents (e.g., proteins, peptides, peptidomimetics, peptoids, small molecules or other drugs) that bind to 27960 proteins, have a stimulatory or inhibitory effect on, for example, 27960 expression or 27960 activity, or have a stimulatory or inhibitory effect on, for example, the expression or activity of a 27960 substrate. Compounds thus identified can be used to modulate the activity of target gene products (e.g., 27960 genes) in a therapeutic protocol, to elaborate the biological function of the target gene product, or to identify compounds that disrupt normal target gene interactions.

In one embodiment, the invention provides assays for screening candidate or test compounds that are substrates of a 27960 protein or polypeptide or a biologically active portion thereof. In another embodiment, the invention provides assays for screening candidate or test compounds that bind to or modulate the activity of a 27960 protein or polypeptide or a biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone that are resistant to enzymatic degradation but that nevertheless remain bioactive] (see, e.g., Zuckermann, R. N. et al. (1994) *J. Med. Chem.*, 37: 2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer, or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria or spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) Science 249:404-406; Cwirla et al. (1990) *Proc. Natl. Acad. Sci.* 87:6378-6382; Felici (1991) *J. Mol. Biol.* 222:301-310; and Ladner supra.).

In one embodiment, an assay is a cell-based assay in which a cell that expresses a 27960 protein or biologically active portion thereof is contacted with a test compound, and the ability of the test compound to modulate 27960 activity is determined. Determining the ability of the test compound to modulate 27960 activity can be accomplished by monitoring, for example, degradation of a target protein. The cell, for example, can be of mammalian origin, e.g., a COS cell.

The ability of the test compound to modulate 27960 binding to a compound, e.g., a 27960 substrate, or to bind to 27960 can also be evaluated. This can be accomplished, for example, by coupling the compound, e.g., the substrate, with a radioisotope or enzymatic label such that binding of the compound, e.g., the substrate, to 27960 can be determined by detecting the labeled compound, e.g., substrate, in a complex. Alternatively, 27960 can be coupled with a radio-isotope or enzymatic label to monitor the ability of a test compound to modulate 27960 binding to a 27960 substrate in a complex. For example, compounds (e.g., 27960 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 27960 substrate) to interact with 27960 with or without the labeling of any of the interactants can be evaluated. For example, a microphysiometer can be used to detect the interaction of a compound with 27960 without the labeling of either the compound or the 27960. McConnell, H. M. et al. (1992) *Science* 257: 1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 27960.

In yet another embodiment, a cell-free assay is provided in which a 27960 protein or biologically active portion thereof is contacted with a test compound and the ability of the test compound to bind to the 27960 protein or biologically active portion thereof is evaluated. Preferred biologically active portions of the 27960 proteins to be used in assays of the present invention include fragments that participate in interactions with non-27960 molecules, e.g., fragments with high surface probability scores.

Soluble and/or membrane-bound forms of isolated proteins (e.g., 27960 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first 'donor' molecule is selected such that its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, the ability of the 27960 protein to bind to a target molecule can be assessed using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled either directly or indirectly, with detectable labels discussed herein.

It may be desirable to immobilize either 27960, an anti 27960 antibody or its target molecule to facilitate separation of complexed from uncomplexed forms of one or both of the proteins, as well as to accommodate automation of the assay. Binding of a test compound to a 27960 protein, or interaction of a 27960 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST/27960 fusion proteins or GST/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 27960 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 27960 binding or activity can be determined using standard techniques.

Other techniques for immobilizing either a 27960 protein or a target molecule on matrices include using conjugation of biotin and streptavidin. Biotinylated 27960 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 27960 protein or target molecules but that do not interfere with binding of the 27960 protein to its target molecule. Such antibodies can be derivatized to the wells of the plate, and unbound target or 27960 protein trapped in the wells by antibody conjugation. Methods for detecting such complexes, in addition to those described above for the GST-immobilized complexes, include immunodetection of complexes using antibodies reactive with the 27960 protein or target molecule, as well as enzyme-linked assays that rely on detecting an enzymatic activity associated with the 27960 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci;* 18(8):284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N. H., (1998) *J Mol Recognit;*11(1-6): 141-8; Hage, D. S., and Tweed, S. A. (1997) *J Chromatogr B Biomed Sci Appl;* 699(1-2):499-525). Further, fluorescence energy transfer may also be conveniently utilized, as described herein, to detect binding without further purification of the complex from solution.

In a preferred embodiment, the assay includes contacting the 27960 protein or biologically active portion thereof with a known compound that binds 27960 to form an assay mixture, contacting the assay mixture with a test compound, and determining the ability of the test compound to interact with a 27960 protein, wherein determining the ability of the test compound to interact with a 27960 protein includes determining the ability of the test compound to preferentially bind to 27960 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to, molecules such as antibodies, peptides, and small molecules. The preferred target genes/products for use in this embodiment are the 27960 genes herein identified. In an alternative embodiment, the invention provides methods for determining the ability of the test compound to modulate the activity of a 27960 protein through modulation of the activity of a downstream effector of a 27960 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 27960 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 27960 ("27960-binding proteins" or "27960-bp") and are involved in 27960 activity. Such 27960-bps can be activators or inhibitors of signals by the 27960 proteins or 27960 targets as, for example, downstream elements of a 27960-mediated signaling pathway.

The two-hybrid system is based on the modular nature of most transcription factors, which consist of separable DNA-binding and activation domains. Briefly, the assay utilizes two different DNA constructs. In one construct, the gene that codes for a 27960 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the 27960 protein can be the fused to the activator domain.) If the "bait" and the "prey" proteins are able to interact, in vivo, forming a 27960-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein that interacts with the 27960 protein.

In another embodiment, modulators of 27960 expression are identified. For example, a cell or cell free mixture is contacted with a candidate compound and the expression of 27960 mRNA or protein evaluated relative to the level of expression of 27960 mRNA or protein in the absence of the candidate compound. When expression of 27960 mRNA or protein is greater in the presence of the candidate compound than in its absence, the candidate compound is identified as a stimulator of 27960 mRNA or protein expression. Alternatively, when expression of 27960 mRNA or protein is less (statistically significantly less) in the presence of the candidate compound than in its absence, the candidate compound is identified as an inhibitor of 27960 mRNA or protein expression. The level of 27960 mRNA or protein expression can be determined by methods described herein for detecting 27960 mRNA or protein.

In another aspect, the invention pertains to a combination of two or more of the assays described herein. For example, a modulating agent can be identified using a cell-based or a cell free assay, and the ability of the agent to modulate the activity of a 27960 protein can be confirmed in vivo, e.g., in an animal such as an animal model for Alzheimer's disease.

This invention further pertains to novel agents identified by the above-described screening assays. Accordingly, it is within the scope of this invention to further use an agent identified as described herein (e.g., a 27960 modulating agent, an antisense 27960 nucleic acid molecule, a 27960-specific antibody, or a 27960-binding partner) in an appropriate animal model to determine the efficacy, toxicity, side effects, or mechanism of action, of treatment with such an agent. Furthermore, novel agents identified by the above-described screening assays can be used for treatments as described herein.

27960 Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 27960 with a disease; (ii) identify an individual from a minute biological sample (tissue typing); and (iii) aid in forensic identification of a biological sample. These applications are described in the subsections below.

27960 Chromosome Mapping

The 27960 nucleotide sequences or portions thereof can be used to map the location of the 27960 genes on a chromosome. This process is called chromosome mapping. Chromosome mapping is useful in correlating the 27960 sequences with genes associated with disease.

Briefly, 27960 genes can be mapped to chromosomes by preparing PCR primers (preferably 15-25 bp in length) from the 27960 nucleotide sequences. These primers can then be used for PCR screening of somatic cell hybrids containing individual human chromosomes. Only those hybrids containing the human gene corresponding to the 27960 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) Science 220:919-924).

Other mapping strategies e.g., in situ hybridization (described in Fan, Y. et al. (1990) Proc. Natl. Acad. Sci. USA, 87:6223-27), pre-screening with labeled flow-sorted chromosomes, and pre-selection by hybridization to chromosome specific cDNA libraries can be used to map 27960 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783-787.

Moreover, differences in the DNA sequences between individuals affected and unaffected with a disease associated with the 27960 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

27960 Tissue Typing 27960 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 27960 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:72 can provide positive individual identification with a panel of perhaps 10 to 1,000 primers that each yield a noncoding amplified sequence of 100 bases. If predicted coding sequences, such as those in SEQ ID NO:74 are used, a more appropriate number of primers for positive individual identification would be 500-2,000.

If a panel of reagents from 27960 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 27960 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:72 (e.g., fragments derived from the noncoding regions of SEQ ID NO:72 having a length of at least 20 bases, preferably at least 30 bases) are particularly appropriate for this use.

The 27960 nucleotide sequences described herein can further be used to provide polynucleotide reagents, e.g., labeled or labelable probes that can be used in, for example, an in situ hybridization technique, to identify a specific tissue, e.g., a tissue containing 27960. This can be very useful in cases where a forensic pathologist is presented with a tissue of unknown origin. Panels of such 27960 probes can be used to identify tissue by species and/or by organ type.

In a similar fashion, these reagents, e.g., 27960 primers or probes can be used to screen tissue culture for contamination (i.e. screen for the presence of a mixture of different types of cells in a culture).

Predictive Medicine of 27960

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene that encodes a ubiquitin-conjugating enzyme. Such disorders include, e.g., a disorder associated with the misexpression of 27960; a disorder of the neurological system, muscles, or immune system.

The method includes one or more of the following:

detecting, in a tissue of the subject, the presence or absence of a mutation that affects the expression of the 27960 gene, or detecting the presence or absence of a mutation in a region that controls the expression of the gene, e.g., a mutation in the 5' control region;

detecting, in a tissue of the subject, the presence or absence of a mutation that alters the structure of the 27960 gene;

detecting, in a tissue of the subject, the misexpression of the 27960 gene, at the mRNA level, e.g., detecting a non-wild type level of a mRNA; and detecting, in a tissue of the subject, the misexpression of the gene, at the protein level, e.g., detecting a non-wild type level of a 27960 polypeptide.

In preferred embodiments the method includes: ascertaining the existence of at least one of: a deletion of one or more nucleotides from the 27960 gene; an insertion of one or more nucleotides into the gene, a point mutation, e.g., a substitution of one or more nucleotides of the gene, and a gross chromosomal rearrangement of the gene, e.g., a translocation, inversion, or deletion.

For example, detecting the genetic lesion can include: (i) providing a probe/primer including an oligonucleotide containing a region of nucleotide sequence that hybridizes to a sense or antisense sequence from SEQ ID NO:72 or 74, or naturally occurring mutants thereof or 5' or 3' flanking sequences naturally associated with the 27960 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a mRNA transcript of the 27960 gene; the presence of a non-wild type splicing pattern of a mRNA transcript of the gene; or a non-wild type level of 27960.

Methods of the invention can be used prenatally or to determine if a subject's offspring will be at risk for a disorder.

In preferred embodiments the method includes determining the structure of a 27960 gene, an abnormal structure being indicative of risk for the disorder.

In preferred embodiments the method includes contacting a sample from the subject with an antibody to the 27960 protein or a nucleic acid that hybridizes specifically with the gene. These and other embodiments are discussed below.

Diagnostic and Prognostic Assays of 27960

Diagnostic and prognostic assays of the invention include method for assessing the expression level of 27960 molecules and for identifying variations and mutations in the sequence of 27960 molecules.

Expression Monitoring and Profiling. The presence, level, or absence of 27960 protein or nucleic acid in a biological sample can be evaluated by obtaining a biological sample from a test subject and contacting the biological sample with a compound or an agent capable of detecting 27960 protein or nucleic acid (e.g., mRNA, genomic DNA) that encodes 27960 protein such that the presence of 27960 protein or nucleic acid is detected in the biological sample. The term "biological sample" includes tissues, cells and biological fluids isolated from a subject, as well as tissues, cells and fluids present within a subject. A preferred biological sample is serum. The level of expression of the 27960 gene can be measured in a number of ways, including, but not limited to: measuring the mRNA encoded by the 27960 genes; measuring the amount of protein encoded by the 27960 genes; or measuring the activity of the protein encoded by the 27960 genes.

The level of mRNA corresponding to the 27960 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 27960 nucleic acid, such as the nucleic acid of SEQ ID NO:72, or a portion thereof, such as an oligonucleotide of at least 7, 15, 30, 50, 100, 250 or 500 nucleotides in length and sufficient to specifically hybridize under stringent conditions to 27960 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 27960 genes.

The level of mRNA in a sample that is encoded by one of 27960 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 27960 gene being analyzed.

In another embodiment, the methods further contacting a control sample with a compound or agent capable of detecting 27960 mRNA, or genomic DNA, and comparing the presence of 27960 mRNA or genomic DNA in the control sample with the presence of 27960 mRNA or genomic DNA in the test sample. In still another embodiment, serial analysis of gene expression, as described in U.S. Pat. No. 5,695,937, is used to detect 27960 transcript levels.

A variety of methods can be used to determine the level of protein encoded by 27960. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 27960 protein in a biological sample in vitro as well as in vivo. In vitro techniques for detection of 27960 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 27960 protein include introducing into a subject a labeled anti-27960 antibody. For example, the antibody can be labeled with a radioactive marker whose presence and location in a subject can be detected by standard imaging techniques. In another embodiment, the sample is labeled, e.g., biotinylated, and then contacted with the antibody, e.g., an anti-27960 antibody positioned on an antibody array (as described below). The sample can be detected, e.g., with avidin coupled to a fluorescent label.

In another embodiment, the method further includes contacting the control sample with a compound or agent capable of detecting 27960 protein, and comparing the presence of 27960 protein in the control sample with the presence of 27960 protein in the test sample.

The invention also includes kits for detecting the presence of 27960 in a biological sample. For example, the kit can include a compound or agent capable of detecting 27960 protein or mRNA in a biological sample; and a standard. The compound or agent can be packaged in a suitable container. The kit can further comprise instructions for using the kit to detect 27960 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples that can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 27960 expression or activity. As used herein, the term "unwanted" includes an unwanted phenomenon involved in a biological response such as pain or deregulated cell proliferation.

In one embodiment, a disease or disorder associated with aberrant or unwanted 27960 expression or activity is identified. A test sample is obtained from a subject and 27960 protein or nucleic acid (e.g., mRNA or genomic DNA) is evaluated, wherein the level, e.g., the presence or absence, of 27960 protein or nucleic acid is diagnostic for a subject having or at risk of developing a disease or disorder associated with aberrant or unwanted 27960 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 27960 expression or activity. For example, such methods can be used to determine whether a subject can be effectively treated with an agent for a cell proliferation disorder.

In another aspect, the invention features a computer medium having a plurality of digitally encoded data records. Each data record includes a value representing the level of expression of 27960 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 27960 (e.g., other genes associated with a 27960-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 27960 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a cell proliferation disorder in a subject wherein an increase in 27960 expression is an indication that the subject has or is disposed to having breast cancer, prostate cancer, or lung cancer. The method can be used to monitor a treatment for a cell proliferation disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 27960 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 27960 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 27960 expression.

27960 Arrays and Uses Thereof

In another aspect, the invention features an array that includes a substrate having a plurality of addresses. At least one address of the plurality includes a capture probe that binds specifically to a 27960 molecule (e.g., a 27960 nucleic acid or a 27960 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 27960 nucleic acid, e.g., the sense or anti-sense strand. In one preferred embodiment, a subset of addresses of the plurality of addresses has a nucleic acid capture probe for 27960. Each address of the subset can include a capture probe that hybridizes to a different region of a 27960 nucleic acid. In another preferred embodiment, addresses of the subset include a capture probe for a 27960 nucleic acid. Each address of the subset is unique, overlapping, and complementary to a different variant of 27960 (e.g., an allelic variant, or all possible hypothetical variants). The array can be used to sequence 27960 by hybridization (see, e.g., U.S. Pat. No. 5,695,940).

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 27960 polypeptide or fragment thereof. The polypeptide can be a naturally-occurring interaction partner of 27960 polypeptide. Preferably, the polypeptide is an antibody, e.g., an antibody described herein (see "Anti-27960 Antibodies," above), such as a monoclonal antibody or a single-chain antibody.

In another aspect, the invention features a method of analyzing the expression of 27960. The method includes providing an array as described above; contacting the array with a sample and detecting binding of a 27960-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 27960. If a sufficient number of diverse samples is analyzed, clustering (e.g., hierarchical clustering, k-means clustering, Bayesian clustering and the like) can be used to identify other genes which are co-regulated with 27960. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 27960 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 27960-associated disease or disorder; and processes, such as a cellular transformation associated with a 27960-associated disease or disorder. The method can also evaluate the treatment and/or progression of a 27960-associated disease or disorder The array is also useful for ascertaining differential expression patterns of one or more genes in normal and abnormal cells. This provides a battery of genes (e.g., including 27960) that could serve as a molecular target for diagnosis or therapeutic intervention.

In another aspect, the invention features an array having a plurality of addresses. Each address of the plurality includes a unique polypeptide. At least one address of the plurality has disposed thereon a 27960 polypeptide or fragment thereof. Methods of producing polypeptide arrays are described in the art, e.g., in De Wildt et al. (2000). *Nature Biotech.* 18, 989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80, 85, 90, 95 or 99% identical to a 27960 polypeptide or fragment thereof. For example, multiple variants of a 27960 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 27960 binding compound, e.g., an antibody in a sample from a subject with specificity for a 27960 polypeptide or the presence of a 27960-binding protein or ligand.

The array is also useful for ascertaining the effect of the expression of a gene on the expression of other genes in the same cell or in different cells (e.g., ascertaining the effect of 27960 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 27960 or from a cell or subject in which a 27960 mediated response has been elicited, e.g., by contact of the cell with 27960 nucleic acid or protein, or administration to the cell or subject 27960 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 27960 (or does not express as highly as in the case of the 27960 positive plurality of capture probes) or from a cell or subject which in which a 27960 mediated response has not been elicited (or has been elicited to a lesser extent than in the first sample); contacting the array with one or more inquiry probes (which is preferably other than a 27960 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 27960 or from a cell or subject in which a 27960-mediated response has been elicited, e.g., by contact of the cell with 27960 nucleic acid or protein, or administration to the cell or subject 27960 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 27960 (or does not express as highly as in the case of the 27960 positive plurality of capture probes) or from a cell or subject which in which a 27960 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 27960, e.g., analyzing structure, function, or relatedness to other nucleic acid or amino acid sequences. The method includes: providing a 27960 nucleic acid or amino acid sequence; comparing the 27960 sequence with one or more preferably a plurality of sequences from a collection of sequences, e.g., a nucleic acid or protein sequence database; to thereby analyze 27960.

Detection of 27960 Variations or Mutations

The methods of the invention can also be used to detect genetic alterations in a 27960 gene, thereby determining if a subject with the altered gene is at risk for a disorder characterized by misregulation in 27960 protein activity or nucleic acid expression, such as a cell proliferation disorder. In preferred embodiments, the methods include detecting, in a sample from the subject, the presence or absence of a genetic alteration characterized by at least one of an alteration affecting the integrity of a gene encoding a 27960-protein, or the mis-expression of the 27960 gene. For example, such genetic alterations can be detected by ascertaining the existence of at least one of 1) a deletion of one or more nucleotides from a 27960 gene; 2) an addition of one or more nucleotides to a 27960 gene; 3) a substitution of one or more nucleotides of a 27960 gene, 4) a chromosomal rearrangement of a 27960 gene; 5) an alteration in the level of a messenger RNA transcript of a 27960 gene, 6) aberrant modification of a 27960 gene, such as of the methylation pattern of the genomic DNA, 7) the presence of a non-wild type splicing pattern of a messenger RNA transcript of a 27960 gene, 8) a non-wild type level of a 27960-protein, 9) allelic loss of a 27960 gene, and 10) inappropriate post-translational modification of a 27960-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 27960-gene. This method can include the steps of collecting a sample of cells from a subject, isolating nucleic acid (e.g., genomic, mRNA or both) from the sample, contacting the nucleic acid sample with one or more primers which specifically hybridize to a 27960 gene under conditions such that hybridization and amplification of the 27960-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 27960 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 27960 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 27960 nucleic acid or a putative variant (e.g., allelic variant) thereof. A probe can have one or more mismatches to a region of a 27960 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in 27960 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 27960 gene and detect mutations by comparing the sequence of the sample 27960 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 27960 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 27960 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 27960 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 27960 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 27960 nucleic acid.

In a preferred embodiment the set includes a first and a second oligonucleotide. The first and second oligonucleotide can hybridize to the same or to different locations of SEQ ID NO:72 or the complement of SEQ ID NO:72. Different locations can be different but overlapping or or nonoverlapping on the same strand. The first and second oligonucleotide can hybridize to sites on the same or on different strands.

The set can be useful, e.g., for identifying SNP's, or identifying specific alleles of 27960. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 27960 nucleic acid.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 27960 gene.

Use of 27960 Molecules as Surrogate Markers

The 27960 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 27960 molecules of the invention may be detected, and may be correlated with one or more biological states in vivo. For example, the 27960 molecules of the invention may serve as surrogate markers for one or more disorders or disease states or for conditions leading up to disease states. As used herein, a "surrogate marker" is an objective biochemical marker that correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 27960 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 27960 marker) transcription or expression, the amplified marker may be in a quantity that is more readily detectable than the drug itself. Also, the marker may be more easily detected due to the nature of the marker itself; for example, using the methods described herein, anti-27960 antibodies may be employed in an immune-based detection system for a 27960 protein marker, or 27960-specific radiolabeled probes may be used to detect a 27960 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

The 27960 molecules of the invention are also useful as pharmacogenomic markers. As used herein, a "pharmacogenomic marker" is an objective biochemical marker that correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 27960 protein or RNA) for specific tumor markers in a subject, a drug or course of treatment may be selected that is optimized for the treatment of the specific tumor likely to be present in the subject. Similarly, the presence or absence of a specific sequence mutation in 27960 DNA may correlate with a 27960 drug response. The use of pharmacogenomic markers therefore permits the application of the most appropriate treatment for each subject without having to administer the therapy.

Pharmaceutical Compositions of 27960

The nucleic acid and polypeptides, fragments thereof, as well as anti-27960 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents that modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 µg/kg to about 500 mg/kg, about 100 µg/kg to about 5 mg/kg, or about 1 µg/kg to about 50 µg/kg. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, $\alpha$-interferon, $\beta$-interferon, nerve growth factor, platelet derived growth factor, or tissue plasminogen activator; or, biological response modifiers such as lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Methods of Treatment for 27960

The present invention provides for both prophylactic and therapeutic methods of treating a subject at risk of (or susceptible to) a disorder or having a disorder associated with aberrant or unwanted 27960 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 27960 molecules of the present invention or 27960 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 27960 expression or activity, by administering to the subject a 27960 or an agent that modulates 27960 expression or at least one 27960 activity. Subjects at risk for a disease that is caused or contributed to by aberrant or unwanted 27960 expression or activity can be identified by, for example, any or a combination of diagnostic or prognostic assays as described herein. Administration of a prophylactic agent can occur prior to the manifestation of symptoms characteristic of the 27960 aberrance, such that a disease or disorder is prevented or, alternatively, delayed in its progression. Depending on the type of 27960 aberrance, for example, a 27960, 27960 agonist or 27960 antagonist agent can be used for treating the subject. The appropriate agent can be determined based on screening assays described herein.

It is possible that some 27960 disorders can be caused, at least in part, by an abnormal level of gene product, or by the presence of a gene product exhibiting abnormal activity. As such, the reduction in the level and/or activity of such gene products would bring about the amelioration of disorder symptoms.

The 27960 molecules can act as novel diagnostic targets and therapeutic agents for controlling one or more of cellular proliferative and/or differentiative disorders, neurological disorders, prostatic disorders as described above, as well as disorders associated with bone metabolism, hematopoietic disorders, kidney disorders, liver disorders, viral diseases, pain or metabolic disorders.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypemephroma, adenocarcinoma of kidney), which includes urothelial carcinomas of renal pelvis.

Aberrant expression and/or activity of 27960 molecules may mediate disorders associated with bone metabolism. "Bone metabolism" refers to direct or indirect effects in the formation or degeneration of bone structures, e.g., bone formation, bone resorption, etc., that may ultimately affect the concentrations in serum of calcium and phosphate. This term also includes activities mediated by 27960 molecules effects in bone cells, e.g. osteoclasts and osteoblasts, that may in turn result in bone formation and degeneration. For example, 27960 molecules may support different activities of bone resorbing osteoclasts such as the stimulation of differentiation of monocytes and mononuclear phagocytes into osteoclasts. Accordingly, 27960 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

The 27960 nucleic acid and protein of the invention can be used to treat and/or diagnose a variety of hematopoieitic disorders. Examples of hematopoieitic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Disorders that may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes that disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 27960 molecules may play an important role in the etiology of certain viral diseases, inducing but not limited to Hepatitis B, Heptitis C and *Herpes Simplex* Virus (HSV). Modulators of 27960 activity could be used to control viral diseases. The modulators can be used in the treatment and/or diagnosis of viral infected tissue or virus-associated tissue fibrosis, especially liver and liver fibrosis. Also, 27960 modulators can be used in the treatment and/or diagnosis of virus-associated carcinoma, especially hepatocellular cancer.

27960 also may play an important role in the regulation of metabolism or pain disorders. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York: McGraw-Hill); pain associated with muscoloskeletal disorders, e.g., joint pain; tooth pain; headaches; pain associated with surgery;

pain related to irritable bowel syndrome; or chest pain.

As discussed herein, successful treatment of 27960 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 27960 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 27960 expression is through the use of aptamer molecules specific for 27960 protein. Aptamers are nucleic acid molecules having a tertiary structure that permits them to specifically bind to protein ligands (see, e.g., Osborne, et al. (1997) *Curr. Opin. Chem Biol.*, 1(1): 5-9; and Patel, D. J. (1997) *Curr Opin Chem Biol;* 1(1):32-46). Since nucleic acid molecules may in many cases be more conveniently introduced into target cells than therapeutic protein molecules may be, aptamers offer a method by which 27960 protein activity may be specifically decreased without the introduction of drugs or other molecules that may have pluripotent effects.

Antibodies can be generated that are both specific for target gene product and that reduce target gene product activity. Such antibodies may, therefore, by administered in instances whereby negative modulatory techniques are appropriate for the treatment of 27960 disorders. For a description of antibodies, see the Antibody section above.

In circumstances wherein injection of an animal or a human subject with a 27960 protein or epitope for stimulating antibody production is harmful to the subject, it is possible to generate an immune response against 27960 through the use of anti-idiotypic antibodies (see, for example, Herlyn, D. *Ann Med* 1999; 31(1):66-78; and Bhattacharya-Chatterjee, M., and Foon, K. A. *Cancer Treat Res* 1998; 94:51-68). If an anti-idiotypic antibody is introduced into a mammal or human subject, it should stimulate the production of anti-anti-idiotypic antibodies, which should be specific to the 27960 protein. Vaccines directed to a disease characterized by 27960 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate 27960 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ and the $ED_{50}$, as described above in the Pharmaceutical Composition section.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound that is able to modulate 27960 activity is used as a template, or "imprinting molecule", to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. A detailed review of this technique can be seen in Ansell, R. J. et al (1996) *Current Opinion in Biotechnology* 7:89-94 and in Shea, K. J. (1994) *Trends in*

*Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645-647. Through the use of isotope-labeling, the "free" concentration of compound that modulates the expression or activity of 27960 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al (1995) *Analytical Chemistry* 67:2142-2144.

Another aspect of the invention pertains to methods of modulating 27960 expression or activity for therapeutic purposes. Accordingly, in an exemplary embodiment, the modulatory method of the invention involves contacting a cell with a 27960 or agent that modulates one or more of the activities of 27960 protein activity associated with the cell. An agent that modulates 27960 protein activity can be an agent as described herein, such as a nucleic acid or a protein, a naturally-occurring target molecule of a 27960 protein (e.g., a 27960 substrate or receptor), a 27960 antibody, a 27960 agonist or antagonist, a peptidomimetic of a 27960 agonist or antagonist, or other small molecule.

In one embodiment, the agent stimulates one or more 27960 activities. Examples of such stimulatory agents include active 27960 proteins and a nucleic acid molecule encoding such active 27960 proteins. In another embodiment, the agent inhibits one or more 27960 activities. Examples of such inhibitory agents include antisense 27960 nucleic acid molecules, anti-27960 antibodies, and 27960 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 27960 protein or nucleic acid molecule. In one embodiment, the method involves administering an agent (e.g., an agent identified by a screening assay described herein), or combination of agents that modulates (e.g., upregulates or downregulates) 27960 expression or activity. In another embodiment, the method involves administering a 27960 protein or nucleic acid molecule as therapy to compensate for reduced, aberrant, or unwanted 27960 expression or activity.

Stimulation of 27960 activity is desirable in situations in which 27960 is abnormally downregulated and/or in which increased 27960 activity is likely to have a beneficial effect. For example, stimulation of 27960 activity is desirable in situations in which a 27960 protein is downregulated and/or in which increased 27960 activity is likely to have a beneficial effect. Likewise, inhibition of 27960 activity is desirable in situations in which 27960 is abnormally upregulated and/or in which decreased 27960 activity is likely to have a beneficial effect.

27960 Pharmacogenomics

The 27960 molecules of the present invention, as well as agents, or modulators that have a stimulatory or inhibitory effect on 27960 activity (e.g., 27960 gene expression) as identified by a screening assay described herein can be administered to individuals to treat (prophylactically or therapeutically) 27960 associated disorders (e.g., cachexia) associated with aberrant or unwanted 27960 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 27960 molecule or 27960 modulator as well as tailoring the dosage and/or therapeutic regimen of treatment with a 27960 molecule or 27960 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11):983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map that consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 27960 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 27960 molecule or 27960 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 27960 molecule or 27960 modulator, such as a modulator identified by one of the exemplary screening assays described herein.

The present invention further provides methods for identifying new agents, or combinations, that are based on identifying agents that modulate the activity of one or more of the gene products encoded by one or more of the 27960 genes of the present invention, wherein these products may be associated with resistance of the cells to a therapeutic agent. Specifically, the activity of the proteins encoded by the 27960 genes of the present invention can be used as a basis for identifying agents for overcoming agent resistance. By blocking the activity of one or more of the resistance proteins, target cells will become sensitive to treatment with an agent that the unmodified target cells were resistant to.

Monitoring the influence of agents (e.g., drugs) on the expression or activity of a 27960 protein can be applied in clinical trials. For example, the effectiveness of an agent determined by a screening assay as described herein to increase 27960 gene expression, protein levels, or upregulate 27960 activity, can be monitored in clinical trials of subjects exhibiting decreased 27960 gene expression, protein levels, or downregulated 27960 activity. Alternatively, the effectiveness of an agent determined by a screening assay to decrease 27960 gene expression, protein levels, or downregulate 27960 activity, can be monitored in clinical trials of subjects exhibiting increased 27960 gene expression, protein levels, or upregulated 27960 activity. In such clinical trials, the expression or activity of a 27960 gene, and preferably, other genes that have been implicated in, for example, a 27960-associated disorder can be used as a "read out" or markers of the phenotype of a particular cell.

27960 Informatics

The sequence of a 27960 molecule is provided in a variety of media to facilitate use thereof. A sequence can be provided as an article of manufacture, other than an isolated nucleic acid or amino acid molecule, which contains a 27960 molecule. Such a manufacture can provide a nucleotide or amino acid sequence, e.g., an open reading frame, in a form that allows examination of the manufacture using means not directly applicable to examining the nucleotide or amino acid sequences, or a subset thereof, as they exists in nature or in purified form. The sequence information can include, but is not limited to, 27960 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention that match a particular target sequence or target motif. The search can be a BLAST search or other routine sequence comparison, e.g., a search described herein.

Thus, in one aspect, the invention features a method of analyzing 27960, e.g., analyzing structure, function, or relatedness to one or more other nucleic acid or amino acid sequences. The method includes: providing a 27960 nucleic acid or amino acid sequence; comparing the 27960 sequence with a second sequence, e.g., one or more preferably a plurality of sequences from a collection of sequences, e.g., a nucleic acid or protein sequence database to thereby analyze 27960. The method can be performed in a machine, e.g., a computer, or manually by a skilled artisan.

The method can include evaluating the sequence identity between a 27960 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 27960 sequence that includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 27960 sequence or record in machine-readable form; comparing a second sequence to the 27960 sequence; thereby analyzing a sequence. Comparison can include comparing to sequences for sequence identity or determining if one sequence is included within the other, e.g., determining if the 27960 sequence includes a sequence being compared. In a preferred embodiment, the 27960 or second sequence is stored on a first computer, e.g., at a first site and the comparison is performed, read, or recorded on a second computer, e.g., at a second site. E.g., the 27960 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 27960-associated disease or disorder or a pre-disposition to a 27960-associated disease or disorder, wherein the method comprises the steps of determining 27960 sequence information associated with the subject and based on the 27960 sequence information, determining whether the subject has a 27960-associated disease or disorder or a pre-disposition to a 27960-associated disease or disorder and/or recommending a particular treatment for the disease, disorder or pre-disease condition.

The invention further provides in an electronic system and/or in a network, a method for determining whether a subject has a 27960-associated disease or disorder or a pre-disposition to a disease associated with a 27960 wherein the method comprises the steps of determining 27960 sequence information associated with the subject, and based on the 27960 sequence information, determining whether the subject has a 27960-associated disease or disorder or a pre-disposition to a 27960-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 27960 sequence of the subject to the 27960 sequences in the database to thereby determine whether the subject as a 27960-associated disease or disorder, or a pre-disposition for such.

The present invention also provides in a network, a method for determining whether a subject has a 27960 associated disease or disorder or a pre-disposition to a 27960-associated disease or disorder associated with 27960, said method comprising the steps of receiving 27960 sequence information from the subject and/or information related thereto, receiving phenotypic information associated with the subject, acquiring information from the network corresponding to 27960 and/or corresponding to a 27960-associated disease or disorder (e.g., a cell proliferation disorder), and based on one or more of the phenotypic information, the 27960 information (e.g., sequence information and/or information related thereto), and the acquired information, determining whether the subject has a 27960-associated disease or disorder or a pre-disposition to a 27960-associated disease or disorder. The method may further comprise the step of recommending a particular treatment for the disease, disorder or pre-disease condition.

The present invention also provides a method for determining whether a subject has a 27960-associated disease or disorder or a pre-disposition to a 27960-associated disease or disorder, said method comprising the steps of receiving information related to 27960 (e.g., sequence information and/or information related thereto), receiving phenotypic information associated with the subject, acquiring information from the network related to 27960 and/or related to a 27960-associated disease or disorder, and based on one or more of the phenotypic information, the 27960 information, and the acquired information, determining whether the subject has a 27960-associated disease or disorder or a pre-disposition to a 27960-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

Background of the 32252 Invention

Acyl-CoA synthases are classified on the basis of their activity in conjugating saturated fatty acids of differing chain lengths, i.e., short (C2-C4), medium (C4-C12), long (C10-C22), and very long (greater than C22). These enzymes are located in various cell compartments (e.g., cytosol, smooth endoplasmic reticulum, mitochondria and peroxisomes). They exhibit wide tissue distribution, but are most abundant in liver and adipose tissue (Knights, 1998, *Clin. Exp. Pharmacol. Physiol.* 25:776-782). In mammals, activation of fatty acids is the first step in fatty acid metabolism. Long-chain fatty acyl-CoA synthetases catalyze esterification of fatty acids into CoA thioesters, which are used either for lipid biosynthesis or oxidized and used as a cellular energy source (Conti et al., 1996, *Structure* 4:287-298). Formation of acyl-CoA occurs with xenobiotic carboxylic acids as well as with endogenous substrates.

Defects in AMP-binding enzymes can give rise to serious disorders. Adrenoleukodystrophy (X-ALD) is a genetic disorder inherited as an X-linked recessive trait. It involves defective peroxisomal oxidation of very long chain fatty acids (VLCFA). The disorder is characterized by demyelination of the central nervous system, and by adrenal insufficiency. Saturated very long chain fatty acids accumulate as a result of impaired activity of VLC acyl-CoA synthetase (VLCAS). The gene that causes X-ALD codes for a peroxisomal integral membrane protein (ALDP). ALDP appears to be involved in stabilizing VLCAS activity, possibly through protein-protein interactions. Loss or impairment of this protein-protein interaction may account for the loss of peroxisomal VLCAS activity in X-ALD (Smith et al., 2000, *Exp. Cell Res.* 254:309-320). Overexpression of both VLCAS and ALDP in X-ALD fibroblasts synergistically increases very long chain fatty acid β-oxidation, indicating that these proteins interact functionally (Steinberg et al., 1999, *Ann. Neurol.* 46:409-412; Yamada et al., 1999, *Neurology* 52:614-616).

Acetoacetyl-CoA synthetase has been purified from rat liver (Ito et al., 1984, *Biochim. Biophys. Acta* 794:183-193). A cDNA encoding this enzyme has been cloned from a rat liver cDNA library and sequenced (Iwahori et al., 2000, *FEBS Lett.* 466:239-243). Acetoacetyl-CoA synthetase catalyzes the following reaction:

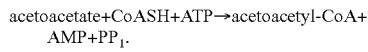

acetoacetate+CoASH+ATP→acetoacetyl-CoA+ AMP+PP$_i$.

In mammals, acetoacetyl-CoA synthetase is a cytosolic enzyme found in various tissues and is most abundant in lipogenic tissues (Bergstrom et al., 1984, *J. Biol. Chem.* 259:14548-14553; Ito et al., 1986, *Biochim. Biophys Acta* 876:280-287; Yeh, 1982, *Int. J. Biochem.* 14:81-86; Bunckley et al., 1975, *FEBS Lett.* 60:7-10). This enzyme is found, e.g., in liver, infant brain, lactating mammary gland, and adipose tissue. Acetoacetate is used preferentially for cholesterol biosynthesis. In rats, acetoacetate synthetase activity is depressed by cholesterol feeding or mevalonate administration, and activity is increased by feeding mevinolin or cholestyramine (Bergstrom et al., supra).

Summary of the 32252 Invention

The present invention is based, in part, on the discovery of a novel AMP-binding enzyme family member, referred to herein as "32252". The nucleotide sequence of a cDNA encoding 32252 is shown in SEQ ID NO:77, and the amino acid sequence of a 32252 polypeptide is shown in SEQ ID NO:78. In addition, the nucleotide sequences of the coding region are depicted in SEQ ID NO:79.

Accordingly, in one aspect, the invention features a nucleic acid molecule that encodes a 32252 protein or polypeptide, e.g., a biologically active portion of the 32252 protein. In a preferred embodiment the isolated nucleic acid molecule encodes a polypeptide having the amino acid sequence of SEQ ID NO:78. In other embodiments, the invention provides isolated 32252 nucleic acid molecules having the nucleotide sequence shown in SEQ ID NO:77, or SEQ ID NO:79. In still other embodiments, the invention provides nucleic acid molecules that are substantially identical (e.g., naturally occurring allelic variants) to the nucleotide sequence shown in SEQ ID NO:77, or SEQ ID NO:79. In other embodiments, the invention provides a nucleic acid molecule which hybridizes under a stringency condition described herein to a nucleic acid molecule comprising the nucleotide sequence of SEQ ID NO:77, or SEQ ID NO:79, wherein the nucleic acid encodes a full length 32252 protein or an active fragment thereof.

In a related aspect, the invention further provides nucleic acid constructs that include a 32252 nucleic acid molecule described herein. In certain embodiments, the nucleic acid molecules of the invention are operatively linked to native or heterologous regulatory sequences. Also included, are vectors and host cells containing the 32252 nucleic acid molecules of the invention e.g., vectors and host cells suitable for producing 32252 nucleic acid molecules and polypeptides.

In another related aspect, the invention provides nucleic acid fragments suitable as primers or hybridization probes for the detection of 32252-encoding nucleic acids.

In still another related aspect, isolated nucleic acid molecules that are antisense to a 32252 encoding nucleic acid molecule are provided.

In another aspect, the invention features, 32252 polypeptides, and biologically active or antigenic fragments thereof that are useful, e.g., as reagents or targets in assays applicable to treatment and diagnosis of 32252-mediated or -related disorders. In another embodiment, the invention provides 32252 polypeptides having a 32252 activity. Preferred polypeptides are 32252 proteins including at least one AMP-binding domain, and, preferably, having a 32252 activity, e.g., a 32252 activity as described herein.

In other embodiments, the invention provides 32252 polypeptides, e.g., a 32252 polypeptide having the amino acid sequence shown in SEQ ID NO:78; an amino acid sequence that is substantially identical to the amino acid sequence shown in SEQ ID NO:78; or an amino acid sequence encoded by a nucleic acid molecule having a nucleotide sequence which hybridizes under a stringency condition described herein to a nucleic acid molecule comprising the nucleotide sequence of SEQ ID NO:77, or SEQ ID NO:79, wherein the nucleic acid encodes a full length 32252 protein or an active fragment thereof.

In a related aspect, the invention further provides nucleic acid constructs which include a 32252 nucleic acid molecule described herein.

In a related aspect, the invention provides 32252 polypeptides or fragments operatively linked to non-32252 polypeptides to form fusion proteins.

In another aspect, the invention features antibodies and antigen-binding fragments thereof, that react with, or more preferably specifically bind 32252 polypeptides or fragments thereof, e.g., an AMP-binding domain. In one embodiment, the antibodies or antigen-binding fragment thereof competitively inhibit the binding of a second antibody to a 32252 polypeptide or a fragment thereof, e.g., an AMP-binding domain.

In another aspect, the invention provides methods of screening for compounds that modulate the expression or activity of the 32252 polypeptides or nucleic acids.

In still another aspect, the invention provides a method for modulating 32252 polypeptide or nucleic acid expression or activity, e.g. using the screened compounds. The method includes contacting a cell, e.g., a 32252-expressing cell, with an agent, e.g., a compound identified using the methods described herein, such that the expression or activity of a 32252 polypeptide or nucleic acid is modulated. Preferably, the cell, e.g., the 32252-expressing cell, is a neural cell, a cardiovascular cell (e.g., an endothelial cell), a malignant cell.

In certain embodiments, the methods involve treatment or prevention of conditions related to aberrant activity or expression of the 32252 polypeptides or nucleic acids, such as conditions involving aberrant or deficient acyl-CoA synthetase activity, cholesterol or fatty acid biosynthesis, cellular proliferation or differentiation, or neural (e.g., brain disorders). For example, the invention features a method of modulating cholesterol and/or fatty acid biosynthesis in a cell. The method includes contacting the cell, e.g., the 32252-expressing cell, with an effective amount of an agonist or antagonist of 32252 activity.

In yet another aspect, the invention provides methods for retarding cell growth, inhibiting the proliferation or inducing the killing, of a 32252-expressing cell, e.g., a hyper-proliferative 32252-expressing cell. The method includes contacting the cell with a compound (e.g., a compound identified using the methods described herein) that modulates the activity, or expression, of the 32252 polypeptide or nucleic acid. In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol. In a preferred embodiment, the cell is a hyperproliferative cell, e.g., a cell found in a solid tumor, a soft tissue tumor, or a metastatic lesion (e.g., breast, ovary, lung, and colon tissue).

In a preferred embodiment, the agent, e.g., the compound, is an inhibitor of a 32252 polypeptide. Preferably, the inhibitor is chosen from a peptide, a phosphopeptide, a small organic molecule, a small inorganic molecule and an antibody (e.g., an antibody conjugated to a therapeutic moiety selected from a cytotoxin, a cytotoxic agent and a radioactive metal ion). In another preferred embodiment, the agent, e.g., the compound, is an inhibitor of a 32252 nucleic acid, e.g., an antisense, a ribozyme, or a triple helix molecule. A small molecule inhibitor can be a mimic of a steroid or fatty acid.

In a preferred embodiment, the agent, e.g., the compound, is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

In another aspect, the invention features methods for treating or preventing a disorder characterized by aberrant activity (e.g., cellular proliferation or differentiation, fatty acid metabolism) of a 32252-expressing cell, in a subject. Preferably, the method includes comprising administering to the subject (e.g., a mammal, e.g., a human) an effective amount of a compound (e.g., a compound identified using the methods described herein) that modulates the activity, or expression, of the 32252 polypeptide or nucleic acid.

In a preferred embodiment, the disorder is a cancerous or pre-cancerous condition. In other embodiments, the disorder is a cardiovascular disorder, or a neural disorder.

In a further aspect, the invention provides methods for evaluating the efficacy of a treatment of a disorder, e.g., proliferative disorder or metabolic disorder. The method includes: treating a subject, e.g., a patient or an animal, with a protocol under evaluation (e.g., treating a subject with one or more of: chemotherapy, radiation, and/or a compound identified using the methods described herein); and evaluating the expression of a 32252 nucleic acid or polypeptide before and after treatment. A change, e.g., a decrease or increase, in the level of a 32252 nucleic acid (e.g., mRNA) or polypeptide after treatment, relative to the level of expression before treatment, is indicative of the efficacy of the treatment of the disorder. The level of 32252 nucleic acid or polypeptide expression can be detected by any method described herein.

In a preferred embodiment, the evaluating step includes obtaining a sample (e.g., a tissue sample, e.g., a biopsy, or a fluid sample) from the subject, before and after treatment and comparing the level of expressing of a 32252 nucleic acid (e.g., mRNA) or polypeptide before and after treatment.

In another aspect, the invention provides methods for evaluating the efficacy of a therapeutic or prophylactic agent (e.g., an anti-neoplastic agent, a cholesterol-lowering agent). The method includes: contacting a sample with an agent (e.g., a compound identified using the methods described herein, a cytotoxic agent) and, evaluating the expression of 32252 nucleic acid or polypeptide in the sample before and after the contacting step. A change, e.g., a decrease or increase, in the level of 32252 nucleic acid (e.g., mRNA) or polypeptide in the sample obtained after the contacting step, relative to the level of expression in the sample before the contacting step, is indicative of the efficacy of the agent. The level of 32252 nucleic acid or polypeptide expression can be detected by any method described herein. In a preferred embodiment, the sample includes cells obtained from a cancerous tissue or a breast, ovary, lung, colon, or brain tissue.

In another aspect, the invention features a method of detecting a disorder, e.g., a neoplastic, cardiovascular or neural disorder. The method includes detecting a 32252 nucleic acid or polypeptide and determining if the abundance of such molecules differs from a reference or control value.

In further aspect, the invention provides assays for determining the presence or absence of a genetic alteration in a 32252 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 32252 molecule. In one embodiment, the capture probe is a nucleic acid, e.g., a probe complementary to a 32252 nucleic acid sequence. In another embodiment, the capture probe is a polypeptide, e.g., an antibody specific for 32252 polypeptides. Also featured is a method of analyzing a sample by contacting the sample to the aforementioned array and detecting binding of the sample to the array.

Other features and advantages of the invention will be apparent from the following detailed description, and from the claims.

Detailed Description of 32252

The human 32252 sequence (see SEQ ID NO:77, as recited in Example 52), which is approximately 2625 nucleotides long including untranslated regions, contains a predicted methionine-initiated coding sequence of about 2019 nucleotides, including the termination codon (nucleotides 136 to 2019 of SEQ ID NO:77; SEQ ID NO:79). The coding sequence encodes a 672 amino acid protein (see SEQ ID NO:78, as recited in Example 52).

Human 32252 has the structural features of an acetoacetyl-CoA enzyme. Amino acid residues 1 to 672 of SEQ ID NO:78 align with amino acid residues 1-672 of rat acetoacetyl-CoA synthetase (SEQ ID NO:80) with 89% sequence identity (600/672) (FIG. 67). The BLAST score for this alignment is 3210 (1473.7 bits). Human 32252 contains the following structural features:

one acetyl-CoA synthetase ACS-1 domain (Prodom 101494) located at about amino acid residues 13-122 of SEQ ID NO:78;

one ligase synthetase protein enzyme biosynthesis antibiotic phosphopantetheine multifunctional repeat acyl-CoA domain (Prodom 43) located at about amino acid residues 130-420 of SEQ ID NO:78, which includes an AMP binding domain signature at about amino acid residues 287-298;

one acetyl-CoA synthetase ACS-1 domain (Prodom 100407) located at about amino acid residues 555-660 of SEQ ID NO:78; and one acetyl-coenzyme A synthetase (NCB1 G1:1118129) domain (Prodom 91186) located at about amino acid residues 580-661 of SEQ ID NO:78.

The 32252 protein additionally includes:

two N-glycosylation sites (PS00001) located at about amino acids 320 to 323 and 449 to 452 of SEQ ID NO:78;

one cAMP- and cGMP-dependent protein kinase phosphorylation site located at about amino acids 24 to 27 of SEQ ID NO:78;

four Protein Kinase C sites (PS00005) at about amino acids 23 to 25, 83 to 85, 243 to 245, and 612 to 614 of SEQ ID NO:78;

eleven Casein Kinase II sites (PS00006) located at about amino acids 2 to 5, 27 to 30, 46 to 49, 57 to 60, 130 to 133, 183 to 186, 243 to 246, 322 to 325, 386 to 389, 562 to 565, and 655 to 658 of SEQ ID NO:78;

eleven N-myristoylation sites (PS00008) from about amino acids 37 to 42, 70 to 75, 96to 101, 149 to 154, 177 to 182,295 to 300,319 to 324,433 to 438,548 to 553,625 to 630, and 651 to 656 of SEQ ID NO:78; and one amidation site (PS00455) located at about amino acids 631 to 634 of SEQ ID NO:78.

For general information regarding PFAM identifiers, PS prefix and PF prefix domain identification numbers, refer to Sonnhammer et al. (1997) Protein 28:405-420.

The 32252 protein contains a significant number of structural characteristics in common with members of the AMP-binding enzyme family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

The AMP-binding domain family of proteins is characterized by a common fold, the structure of which was solved for firefly luciferase (Conti et al. (1996), *Structure* 4(3):287-298). Based on the luciferase structure, the AMP-binding domain is composed of two subdomains: a compact N-terminal subdomain that contains a distorted antiparallel β-barrel and two β-sheets, which are flanked on either side by α-helices; and a small α+β C-terminal subdomain (Conti et al., supra). The two β-sheets pack together to create a long surface groove, which is closed at one end by the presence of the β-barrel. The packing of the β-barrel against the side of the two β-sheets forms two shallow depressions on the concave surface of the molecule, giving rise to a Y-shaped valley on the surface of the N-terminal subdomain. The C-terminal subdomain is connected to the N-terminal subdomain by a flexible hinge and is positioned above the b-barrel portion of the N-terminal subdomain such that a large cleft is formed between the N-terminal and C-terminal subdomains.

Several conserved sequence motifs have been identified in the AMP-binding domain family of proteins. The conserved sequence motifs include the "AMP-binding domain signature motif", defined by the sequence [STG]-[STG]-G-[ST]-[TSE]-[GS]-X-[PALIVM]-K, as well as an "invariant glutamine motif" defined by the sequences [YFW]-[GASW]-X-[TSA]-E, and an "invariant aspartic acid motif" defined by the sequence [STA]-[GRK]-D. Due to the conservation these motifs in a family of molecules that have distinct enzymatic activities, the motifs are believed to function in the binding of AMP and in adenylate formation, properties shared by all of the members of the family (Conti et al., supra).

A 32252 polypeptide can include a "AMP-binding domain" or regions homologous with a "AMP-binding domain".

As used herein, the term "AMP-binding domain" includes an amino acid sequence of about 70 to 300 amino acid residues in length and having a score for the alignment of the sequence to the AMP-binding domain (Prodom) of at least 50, more preferably at least 75, 100, or 200. In some embodiments, an AMP-binding domain includes about 70 to 90 amino acids, and has a score for the alignment of the sequence to the AMP-binding domain (Prodom) of 150 or greater. In other embodiments, the AMP-binding domain includes about 100 to 120 amino acids and has a score for the alignment of the sequence to the AMP-binding domain (Prodom) of 150 or greater. In still other embodiments, the AMP-binding domain includes about 280 to 300 amino acids and has a score for the alignment of the sequence to the AMP-binding domain (Prodom) of 150 or greater.

In a preferred embodiment 32252 polypeptide or protein has a "AMP-binding domain" or a region which includes about 70 to 300, and preferably about 70 to 90, 100 to 120, or 280 to 300 amino acid residues and has at least about 50%, 60%, 70% 80% 90% 95%, 99%, or 100% homology with an "AMP-binding domain," e.g., one of the AMP-binding domains of human 32252 (e.g., residues 67 to 504 of SEQ ID NO:78).

To identify the presence of a "AMP binding" domain in a 32252 protein sequence, and make the determination that a polypeptide or protein of interest has a particular profile, the amino acid sequence of the protein can be searched against a database of domains, e.g., the ProDom database (Corpet et al. (1999), *Nucl. Acids Res.* 27:263-267) The ProDom protein domain database consists of an automatic compilation of homologous domains. Current versions of ProDom are built using recursive PSI-BLAST searches (Altschul S F et al. (1997) *Nucleic Acids Res.* 25:3389-3402; Gouzy et al. (1999) *Computers and Chemistry* 23:333-340.) of the SWISS-PROT 38 and TREMBL protein databases. The database automatically generates a consensus sequence for each domain. A BLAST search was performed against the ProDom database resulting in the identification of an "AMP binding" domain in the amino acid sequence of human 32252 at about residues 67 to 504 of SEQ ID NO:78.

A 32252 family member can include at least one predicted acetyl-CoA synthetase ACS-1 domain (Prodom 101494). Furthermore a 32252 family member can include at least one AMP-binding domain (PS00455); at least one, preferably two predicted N-glycosylation sites (PS00001); at least one predicted cAMP- and cGMP-dependent protein kinase phosphorylation site (PS00004); at least one, two, three, preferably four predicted Protein Kinase C sites (PS00005); at least one, two, three, four, five, six, seven, eight, nine, ten, preferably eleven predicted Casein Kinase II sites (PS00006); at least one, two, three, four, five, six, seven, eight, nine, ten, preferably eleven predicted N-myristoylation sites (PS00008); and at least one amidation site (PS00009).

As the 32252 polypeptides of the invention may modulate 32252-mediated activities, they may be useful as of for developing novel diagnostic and therapeutic agents for 32252-mediated or related disorders, as described below.

As used herein, a "32252 activity", "biological activity of 32252" or "functional activity of 32252", refers to an activity exerted by a 32252 protein, polypeptide or nucleic acid molecule on e.g., a 32252-responsive cell or on a 32252 substrate, e.g., a protein substrate, as determined in vivo or in vitro. In one embodiment, a 32252 activity is a direct activity, such as acyl-CoA ligase activity, e.g., acetoacetyl-CoA synthetase. A "target molecule" or "binding partner" is a molecule with which a 32252 protein binds or interacts in nature, e.g., a peroxisomal integral membrane protein (ALDP). For example, the 32252 proteins of the present invention can have one or more of the following activities: (1) acyl-CoA ligase activity; (2) promotion of fatty acid metabolism and/or cholesterol metabolism; (3) recycling of acetoacetate; (4) promotion of xenobiotic carboxylic acid metabolism; (5) regulation and/or mediation of cellular growth, particularly of tumor cells; and/or (6) a agonizing or antagonizing (1)-(5).

The 32252 polypeptide is predicted to be a membrane associated protein that displays enzymatic activity. The 32252 polypeptide is predicted to be localized in various cell compartments, e.g., cytosol, smooth endoplasmic reticulum, mitochondria and peroxisomes. The 32252 enzymatic activity is predicted to include acyl-CoA ligase activity, e.g., esterification of fatty acids (short, medium, long or very long chain) into CoA thioesters, which are used for lipid biosynthesis or oxidized and used as a cellular energy source.

As shown in the Examples below, expression of human 32252 has been detected in a wide range of tissues, including brain, cardiovascular tissues (e.g., human vascular endothelial cells), ovary, lung, breast, and colon tissues (see Example 53, Tables 25-27, below). Expression of human 32252 was increased in many breast tumor, ovary tumor, lung tumor, and colon tumor samples, relative to its levels in normal breast, ovary, lung, and colon tissues (see Example 53, Tables 26 and 27, below).

Notably, human 32252 mRNA is overexpressed in lung tumor cells grown in soft agar relative to the same cells grown on plastic. Soft agar simulates the milieu of a tumor cell.

Thus, the 32252 molecules can act as novel diagnostic targets and therapeutic agents for controlling lipid metabolic disorders, cellular proliferative and/or differentiative disorders, and neural disorders.

The 32252 molecules can act as novel diagnostic targets and therapeutic agents for controlling one or more of cellular proliferative and/or differentiative disorders, or metabolic disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of colon, lung, breast and ovarian origin.

As used herein, the terms "cancer", "hyperproliferative" and "neoplastic" refer to cells having the capacity for autonomous growth. Examples of such cells include cells having an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometeriod tumors, clear cell adenocarcinoma, adenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Examples of cancers or neoplastic conditions, in addition to the ones described above, include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

The term "cardiovascular disorders" or "disease" includes heart disorders, as well as disorders of the blood vessels of the circulation system caused by, e.g., abnormally high concentrations of lipids in the blood vessels.

Examples of disorders involving aberrant lipid (e.g., fatty acid) metabolism that can be treated, prevented or diagnosed with the methods of the invention include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices. Preferred examples of lipid metabolic disorders include atherosclerosis, myocardial infarction, aneurism, and stroke.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, aneurism, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, asthma, emphysema and chronic pulmonary disease and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyartenrtis, hypersensitivity or leukocytoclastic anglitis), Wegener granulomatosis, thromboanglitis obliterans (Buerger disease), vasculitis associated with other disorders, and infectious arteritis; Raynaud disease; aneunsms and dissection, such as abdominal aortic aneurisms, syphilitic (luetic) aneun'sms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

"Procedural vascular trauma" includes the effects of surgical/medical-mechanical interventions into mammalian vasculature, but does not include vascular trauma due to the organic vascular pathologies listed hereinabove, or to unintended traumas, such as due to an accident. Thus, procedural vascular traumas within the scope of the present treatment method include (1) organ grafting or transplantation, such as transplantation and grafting of heart, kidney, liver and the like, e.g., involving vessel anastomosis; (2) vascular surgery, such as coronary bypass surgery, biopsy, heart valve replacement, atheroectomy, thrombectomy, and the like; (3) transcatheter vascular therapies (TVT) including angioplasty, e.g., laser angioplasty and PTCA procedures discussed hereinbelow, employing balloon catheters, or indwelling catheters; (4) vascular grafting using natural or synthetic materials, such as in saphenous vein coronary bypass grafts, dacron and venous grafts used for peripheral arterial reconstruction, etc.; (5) placement of a mechanical shunt, such as a PTFE hemodialysis shunt used for arteriovenous communications; and (6) placement of an intravascular stent, which may be metallic, plastic or a biodegradable polymer. See U.S. patent application Ser. No. 08/389,712, filed Feb. 15, 1995, which is incorporated by reference herein. For a general discussion of implantable devices and biomaterials from which they can be formed, see H. Kambic et al., "Biomaterials in Artificial Organs", Chem. Eng. News, 30 (Apr. 14, 1986), the disclosure of which is incorporated by reference herein. Small vessel disease includes, but is not limited to, vascular insufficiency in the limbs, peripheral neuropathy and retinopathy, e.g., diabetic retinopathy.

As used herein, an "endothelial cell disorder" includes a disorder characterized by aberrant, unregulated, or unwanted endothelial cell activity, e.g., proliferation, migration, angiogenesis, or vascularization; or aberrant expression of cell surface adhesion molecules or genes associated with angiogenesis, e.g., TIE-2, FLT and FLK. Endothelial cell disorders include tumorigenesis, tumor metastasis, psoriasis, diabetic retinopathy, endometriosis, Grave's disease, ischemic disease (e.g., atherosclerosis), and chronic inflammatory diseases (e.g., rheumatoid arthritis).

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-bome (Arbo) viral encephalitis, *Herpes simplex* virus Type 1, *Herpes simplex* virus Type 2, *Varicalla-zoster* virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

The 32252 protein, fragments thereof, and derivatives and other variants of the sequence in SEQ ID NO:78 thereof are collectively referred to as "polypeptides or proteins of the invention" or "32252 polypeptides or proteins". Nucleic acid molecules encoding such polypeptides or proteins are collectively referred to as "nucleic acids of the invention" or "32252 nucleic acids." 32252 molecules refer to 32252 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:77 or SEQ ID NO:79, corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein. As used herein, the terms "gene" and "recombinant gene" refer to nucleic acid molecules which include at least an open reading frame encoding a 32252 protein. The gene can optionally further include non-coding sequences, e.g., regulatory sequences and introns. Preferably, a gene encodes a mammalian 32252 protein or derivative thereof.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of 32252 protein is at least 10% pure. In a preferred embodiment, the preparation of 32252 protein has less than about 30%, 20%, 10% and more preferably 5% (by dry weight), of non-32252 protein (also referred to herein as a "contaminating protein"), or of chemical precursors or non-32252 chemicals. When the 32252 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 32252 without abolishing or substantially altering a 32252 activity. Preferably the alteration does not substantially alter the 32252 activity, e.g., the activity is at least 20%, 40%, 60%, 70% or 80% of wild-type. An "essential" amino acid residue is a residue that, when altered from the wild-type sequence of 32252, results in abolishing a 32252 activity such that less than 20% of the wild-type activity is present. For example, conserved amino acid residues in 32252 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a 32252 protein is preferably replaced with another amino acid residue from the same side chain family. Alternatively, in another embodiment, mutations can be introduced randomly along all or part of a 32252 coding sequence, such as by saturation mutagenesis, and the resultant mutants can be screened for 32252 biological activity to identify mutants that retain activity. Following mutagenesis of SEQ ID NO:77 or SEQ ID NO:79, the encoded protein can be expressed recombinantly and the activity of the protein can be determined.

As used herein, a "biologically active portion" of a 32252 protein includes a fragment of a 32252 protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a 32252 molecule and a non-32252 molecule or between a first 32252 molecule and a second 32252 molecule (e.g., a dimerization interaction). Biologically active portions of a 32252 protein include peptides comprising amino acid sequences sufficiently homologous to or derived from the amino acid sequence of the 32252 protein, e.g., the amino acid sequence shown in SEQ ID NO:78, which include less amino acids than the full length 32252 proteins, and exhibit at least one activity of a 32252 protein. Typically, biologically active portions comprise a domain or motif with at least one activity of the 32252 protein, e.g., substrate binding (such as AMP binding), adenylation, and acyl-CoA ligation. A biologically active portion of a 32252 protein can be a polypeptide which is, for example, 10, 25, 50, 100, 200 or more amino acids in length. Biologically active portions of a 32252 protein can be used as targets for developing agents which modulate a 32252 mediated activity, e.g., substrate binding, adenylation and acyl-CoA ligation.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453 ) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to 32252 nucleic acid molecules of the invention. BLAST protein searches can be performed with the XBLAST program, score=50, wordlength=3 to obtain amino acid sequences homologous to 32252 protein molecules of the invention. To obtain gapped alignments for comparison purposes, Gapped BLAST can be utilized as described in Altschul et al, (1997) *Nucleic Acids Res.* 25:3389-3402. When utilizing BLAST and Gapped BLAST programs, the default parameters of the respective programs (e.g., XBLAST and NBLAST) can be used.

Particularly preferred 32252 polypeptides of the present invention have an amino acid sequence substantially identical to the amino acid sequence of SEQ ID NO:78. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:78 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:77 or 79 are termed substantially identical.

"Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules of 32252

In one aspect, the invention provides, an isolated or purified, nucleic acid molecule that encodes a 32252 polypeptide described herein, e.g., a full-length 32252 protein or a fragment thereof, e.g., a biologically active portion of 32252 protein. Also included is a nucleic acid fragment suitable for use as a hybridization probe, which can be used, e.g., to identify a nucleic acid molecule encoding a polypeptide of the invention, 32252 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:77, or a portion of any of these nucleotide sequences. In one embodiment, the nucleic acid molecule includes sequences encoding the human 32252 protein (i.e., "the coding region", from nucleotides 136 to 2154 of SEQ ID NO:77), as well as 5' untranslated sequences (nucleotides 1 to 135 of SEQ ID NO:77). Alternatively, the nucleic acid molecule can include only the coding region of SEQ ID NO:77 (e.g., nucleotides 136 to 2154, corresponding to SEQ ID NO:79) and, e.g., no flanking sequences which normally accompany the subject sequence.

In another embodiment, an isolated nucleic acid molecule of the invention includes a nucleic acid molecule which is a complement of the nucleotide sequence shown in SEQ ID NO:77 or SEQ ID NO:79, or a portion of any of these nucleotide sequences. In other embodiments, the nucleic acid molecule of the invention is sufficiently complementary to the nucleotide sequence shown in SEQ ID NO:77 or SEQ ID NO:79, such that it can hybridize (e.g., under a stringency condition described herein) to the nucleotide sequence shown in SEQ ID NO:77 or 79, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:77 or SEQ ID NO:79, or a portion, preferably of the same length, of any of these nucleotide sequences.

Further the nucleic acid fragments can include at least one contiguous nucleotide from one or more of the following regions: about nucleotides 1-135, 136-300, 136-600, 400-700, 700-1300, 1100-1600, 1300-1800, or 1700-2151 of SEQ ID NO:77.

32252 Nucleic Acid Fragments

A nucleic acid molecule of the invention can include only a portion of the nucleic acid sequence of SEQ ID NO:77 or 79. For example, such a nucleic acid molecule can include a fragment which can be used as a probe or primer or a fragment encoding a portion of a 32252 protein, e.g., an immunogenic or biologically active portion of a 32252 protein. A fragment can comprise those nucleotides of SEQ ID NO:77, which encode a AMP-binding domain of human 32252. The nucleotide sequence determined from the cloning of the 32252 gene allows for the generation of probes and primers designed for use in identifying and/or cloning other 32252 family members, or fragments thereof, as well as 32252 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 24, 50, 75, 100, 200, 250, 300, 500, or so amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 32252 nucleic acid fragment can include a sequence corresponding to a AMP-binding domain.

32252 probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:77 or SEQ ID NO:79, or of a naturally occurring allelic variant or mutant of SEQ ID NO:77 or SEQ ID NO:79.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: an AMP binding region.

In another embodiment a set of primers is provided, e.g., primers suitable for use in a PCR, which can be used to amplify a selected region of a 32252 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the AMP-binding enzyme domain are provided.

A nucleic acid fragment can encode an epitope bearing region of a polypeptide described herein.

A nucleic acid fragment encoding a "biologically active portion of a 32252 polypeptide" can be prepared by isolating a portion of the nucleotide sequence of SEQ ID NO:77 or 79, which encodes a polypeptide having a 32252 biological activity (e.g., the biological activities of the 32252 proteins are described herein), expressing the encoded portion of the 32252 protein (e.g., by recombinant expression in vitro) and assessing the activity of the encoded portion of the 32252 protein. For example, a nucleic acid fragment encoding a biologically active portion of 32252 includes a AMP-binding domain, e.g., about amino acid residues 13 to 660, 13 to 122, 555 to 660, or 580 to 661 of SEQ ID NO:78. A nucleic acid fragment encoding a biologically active portion of 3252 polypeptide, may comprise a nucleotide sequence which is greater than 300, 500, 800, 1200, 1600, 2000 or more nucleotides in length.

In preferred embodiments, a nucleic acid includes a nucleotide sequence which is about 300, 400, 500, 600, 700, 800, 900, 1000, 1100, 1200, 1300 or more nucleotides in length and hybridizes under a stringency condition described herein to a nucleic acid molecule of SEQ ID NO:77, or SEQ ID NO:79.

32252 Nucleic Acid Variants

The invention further encompasses nucleic acid molecules that differ from the nucleotide sequence shown in SEQ ID NO:77 or SEQ ID NO:79. Such differences can be due to degeneracy of the genetic code (and result in a nucleic acid which encodes the same 32252 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:78. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:77 or 79, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:78 or a fragment of this sequence. Such nucleic acid molecules can readily be identified as being able to hybridize under a stringency condition described herein, to the nucleotide sequence shown in SEQ ID NO:78 or a fragment of the sequence. Nucleic acid molecules corresponding to orthologs, homologs, and allelic variants of the 32252 cDNAs of the invention can further be isolated by mapping to the same chromosome or locus as the 32252 gene.

Preferred variants include those that are correlated with ATP-binding, substrate adenylation, and acyl-CoA ligation activities.

Allelic variants of 32252, e.g., human 32252, include both functional and non-functional proteins. Functional allelic variants are naturally occurring amino acid sequence variants of the 32252 protein within a population that maintain the ability to bind and adenylate a substrate molecule. Functional allelic variants will typically contain only conservative substitution of one or more amino acids of SEQ ID NO:78, or substitution, deletion or insertion of non-critical residues in non-critical regions of the protein. Non-functional allelic variants are naturally-occurring amino acid sequence variants of the 32252, e.g., human 32252, protein within a population that do not have the ability to bind ATP and/or adenylate a substrate molecule. Non-functional allelic variants will typically contain a non-conservative substitution, a deletion, or insertion, or premature truncation of the amino acid sequence of SEQ ID NO:78, or a substitution, insertion, or deletion in critical residues or critical regions of the protein.

Moreover, nucleic acid molecules encoding other 32252 family members and, thus, which have a nucleotide sequence which differs from the 32252 sequences of SEQ ID NO:77 or SEQ ID NO:79 are intended to be within the scope of the invention.

Antisense Nucleic Acid Molecules, Ribosomes and Modified 32252 Nucleic Acid Molecules In another aspect, the invention features, an isolated nucleic acid molecule which is antisense to 32252. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 32252 coding strand, or to only a portion thereof (e.g., the coding region of human 32252 corresponding to SEQ ID NO:79). In another embodiment, the antisense nucleic acid molecule is antisense to a "noncoding region" of the coding strand of a nucleotide sequence encoding 32252 (e.g., the 5' and 3' untranslated regions).

An antisense nucleic acid can be designed such that it is complementary to the entire coding region of 32252 mRNA, but more preferably is an oligonucleotide which is antisense to only a portion of the coding or noncoding region of 32252 mRNA. For example, the antisense oligonucleotide can be complementary to the region surrounding the translation start site of 32252 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 32252 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

In still another embodiment, an antisense nucleic acid of the invention is a ribozyme. A ribozyme having specificity for a 32252-encoding nucleic acid can include one or more sequences complementary to the nucleotide sequence of a 32252 cDNA disclosed herein (i.e., SEQ ID NO:77 or SEQ ID NO:79), and a sequence having known catalytic sequence responsible for mRNA cleavage (see U.S. Pat. No. 5,093,246 or Haseloff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a 32252-encoding mRNA. See, e.g., Cech et al. U.S. Pat. No. 4,987,071; and Cech et al. U.S. Pat. No. 5,116,742. Alternatively, 32252 mRNA can be used to select a catalytic RNA having a specific ribonuclease activity from a pool of RNA molecules. See, e.g., Bartel, D. and Szostak, J. W. (1993) *Science* 261:1411-1418.

32252 gene expression can be inhibited by targeting nucleotide sequences complementary to the regulatory region of the 32252 (e.g., the 32252 promoter and/or enhancers) to form triple helical structures that prevent transcription of the 32252 gene in target cells. See generally, Helene, C. (1991) *Anticancer Drug Des.* 6:569-84; Helene, C. i (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5'manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 32252 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19:17 and Faria et al. (2001) *Nature Biotech.* 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675.

PNAs of 32252 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 32252 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al (1988) *Bio-Techniques* 6:958-976) or intercalating agents. (see, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 32252 nucleic acid of the invention, two complementary regions one having a fluorophore and one a quencher such that the molecular beacon is useful for quantitating the presence of the 32252 nucleic acid of the invention in a sample. Molecular beacon nucleic acids are described, for example, in Lizardi et al, U.S. Pat. No. 5,854,033; Nazarenko et al., U.S. Pat. No. 5,866,336, and Livak et al., U.S. Pat. No. 5,876,930.

Isolated 32252 Polypeptides

In another aspect, the invention features, an isolated 32252 protein, or fragment, e.g., a biologically active portion, for use as immunogens or antigens to raise or test (or more generally to bind) anti-32252 antibodies. 32252 protein can be isolated from cells or tissue sources using standard protein purification techniques. 32252 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 32252 polypeptide has one or more of the following characteristics:

(i) it has the ability to catalyze an acyl-CoA ligase or acetoacetyl-CoA synthetase reaction;

(ii) it has a molecular weight, e.g., a molecular weight deduced from a 32252 polypeptide, e.g., a polypeptide of SEQ ID NO:78, ignoring any contribution of post-translational modification;

(iii) it has an overall sequence similarity of at least 60%, preferably at least 70, 80, 90, or 95%, with a polypeptide of SEQ ID NO:78;

(iv) it can be found in brain, breast, lung, colon, and ovary tissue;

(v) it has an AMP-binding enzyme domain which is preferably about 70%, 80%, 90% or 95% with amino acid residues 13 to 122, 130 to 420, 519 to 630, 555 to 660, or 580 to 661 of SEQ ID NO:78;

(vii) it has at least 6, preferably 8, and most preferably 10 of the cysteines found in the amino acid sequence of the native protein;

(viii) it has at least one predicted acetyl-CoA synthetase ACS-1 domain (Prodom 101494);

(ix) it has at least one AMP-binding domain (PS00455); at least one, preferably two predicted N-glycosylation sites (PS00001);

(x) it has at least one predicted cAMP- and cGMP-dependent protein kinase phosphorylation site (PS00004);

(xi) it has at least one, two, three, preferably four predicted Protein Kinase C sites (PS00005);

(xii) it has at least one, two, three, four, five, six, seven, eight, nine, ten, preferably eleven predicted Casein Kinase II sites (PS00006);

(xiii) it has at least one, two, three, four, five, six, seven, eight, nine, ten, preferably eleven predicted N-myristoylation sites (PS00008); or (xiv) it has at least one amidation site (PS00009).

In a preferred embodiment the 32252 protein, or fragment thereof, differs from the corresponding sequence in SEQ ID:2. In one embodiment it differs by at least one but by less than 15, 10 or 5 amino acid residues. In another it differs from the corresponding sequence in SEQ ID NO:78 by at least one residue but less than 20%, 15%, 10% or 5% of the residues in it differ from the corresponding sequence in SEQ ID NO:78. (If this comparison requires alignment the sequences should be aligned for maximum homology. "Looped" out sequences from deletions or insertions, or mismatches, are considered differences.) The differences are, preferably, differences or changes at a non essential residue or a conservative substitution. In a preferred embodiment the differences are not in the AMP-binding domain. In another preferred embodiment one or more differences are in the AMP-binding domain.

Other embodiments include a protein that contain one or more changes in amino acid sequence, e.g., a change in an amino acid residue which is not essential for activity. Such 32252 proteins differ in amino acid sequence from SEQ ID NO:78, yet retain biological activity.

In one embodiment, the protein includes an amino acid sequence at least about 60%, 65%, 70%, 75%, 80%, 85%, 90%, 95%, 98% or more homologous to SEQ ID NO:78.

A 32252 protein or fragment is provided which varies from the sequence of SEQ ID NO:78 in regions from amino acids 1 to 12, 123 to 554, 661 to 579, or 662 to 672 by at least one but by less than 15, 10 or 5 amino acid residues in the protein or fragment but which does not differ from SEQ ID NO:78 in the regions from amino acids 13 to 122, 555 to 660, or 580 to 661. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 32252 protein includes a AMP-binding domain. Moreover, other biologically active portions, in which other regions of the protein are deleted, can be prepared by recombinant techniques and evaluated for one or more of the functional activities of a native 32252 protein.

In a preferred embodiment, the 32252 protein has an amino acid sequence shown in SEQ ID NO:78. In other embodiments, the 32252 protein is substantially identical to SEQ ID NO:78. In yet another embodiment, the 32252 protein is substantially identical to SEQ ID NO:78 and retains the functional activity of the protein of SEQ ID NO:78, as described in detail in the subsections above.

32252 Chimeric or Fusion Proteins

In another aspect, the invention provides 32252 chimeric or fusion proteins. As used herein, a 32252 "chimeric protein" or "fusion protein" includes a 32252 polypeptide linked to a non-32252 polypeptide. A "non-32252 polypeptide" refers to a polypeptide having an amino acid sequence corresponding to a protein which is not substantially homologous to the 32252 protein, e.g., a protein which is different from the 32252 protein and which is derived from the same or a different organism. The 32252 polypeptide of the fusion protein can correspond to all or a portion e.g., a fragment described herein of a 32252 amino acid sequence. In a preferred embodiment, a 32252 fusion protein includes at least one (or two) biologically active portion of a 32252 protein. The non-32252 polypeptide can be fused to the N-terminus or C-terminus of the 32252 polypeptide.

The fusion protein can include a moiety which has a high affinity for a ligand. For example, the fusion protein can be a GST-32252 fusion protein in which the 32252 sequences are fused to the C-terminus of the GST sequences. Such fusion proteins can facilitate the purification of recombinant 32252. Alternatively, the fusion protein can be a 32252 protein containing a heterologous signal sequence at its N-terminus. In certain host cells (e.g., mammalian host cells), expression and/or secretion of 32252 can be increased through use of a heterologous signal sequence.

Fusion proteins can include all or a part of a serum protein, e.g., an IgG constant region, or human serum albumin.

The 32252 fusion proteins of the invention can be incorporated into pharmaceutical compositions and administered to a subject in vivo. The 32252 fusion proteins can be used to affect the bioavailability of a 32252 substrate. 32252 fusion proteins may be useful therapeutically for the treatment of disorders caused by, for example, (i) aberrant modification or mutation of a gene encoding a 32252 protein; (ii) mis-regulation of the 32252 gene; and (iii) aberrant post-translational modification of a 32252 protein.

Moreover, the 32252-fusion proteins of the invention can be used as immunogens to produce anti-32252 antibodies in a subject, to purify 32252 ligands and in screening assays to identify molecules which inhibit the interaction of 32252 with a 32252 substrate.

Expression vectors are commercially available that already encode a fusion moiety (e.g., a GST polypeptide). A 32252-encoding nucleic acid can be cloned into such an expression vector such that the fusion moiety is linked in-frame to the 32252 protein.

Variants of 32252 Proteins

In another aspect, the invention also features a variant of a 32252 polypeptide, e.g., which functions as an agonist (mimetics) or as an antagonist. Variants of the 32252 proteins can be generated by mutagenesis, e.g., discrete point mutation, the insertion or deletion of sequences or the truncation of a 32252 protein. An agonist of the 32252 proteins can retain substantially the same, or a subset, of the biological activities of the naturally occurring form of a 32252 protein. An antagonist of a 32252 protein can inhibit one or more of the activities of the naturally occurring form of the 32252 protein by, for example, competitively modulating a 32252-mediated activity of a 32252 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 32252 protein.

Variants of a 32252 protein can be identified by screening combinatorial libraries of mutants, e.g., truncation mutants, of a 32252 protein for agonist or antagonist activity.

Libraries of fragments e.g., N terminal, C terminal, or internal fragments, of a 32252 protein coding sequence can be used to generate a variegated population of fragments for screening and subsequent selection of variants of a 32252 protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of 32252 proteins. Recursive ensemble mutagenesis (REM), a new technique which enhances the frequency of functional mutants in the libraries, can be used in combination with the screening assays to identify 32252 variants (Arkin and Yourvan (1992) *Proc. Natl. Acad. Sci. USA* 89:7811-7815; Delgrave et al. (1993) *Protein Engineering* 6:327-331).

Cell based assays can be exploited to analyze a variegated 32252 library. For example, a library of expression vectors can be transfected into a cell line, e.g., a cell line, which ordinarily responds to 32252 in a substrate-dependent manner. The transfected cells are then contacted with 32252 and the effect of the expression of the mutant on signaling by the 32252 substrate can be detected, e.g., by measuring adenylation and/or acyl-CoA ligase activity. Plasmid DNA can then be recovered from the cells which score for inhibition, or alternatively, potentiation of signaling by the 32252 substrate, and the individual clones further characterized.

In another aspect, the invention features a method of making a 32252 polypeptide, e.g., a peptide having a non-wild type activity, e.g., an antagonist, agonist, or super agonist of a naturally occurring 32252 polypeptide, e.g., a naturally occurring 32252 polypeptide. The method includes: altering the sequence of a 32252 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 32252 polypeptide a biological activity of a naturally occurring 32252 polypeptide. The method includes: altering the sequence, e.g., by substitution or deletion of one or more residues, of a 32252 polypeptide, e.g., altering the sequence of a non-conserved region, or a domain or residue described herein, and testing the altered polypeptide for the desired activity.

Anti-32252 Antibodies

In another aspect, the invention provides an anti-32252 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-32252 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 32252 polypeptide or fragment thereof. Examples of antigen-binding fragments of the anti-32252 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al, (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al (1988) *Science* 242:423-426; and Huston et al. (1988) *Proc. Natl. Acad. Sci. USA* 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-32252 antibody can be a polyclonal or a monoclonal antibody. In other embodiments, the antibody can be recombinantly produced, e.g., produced by phage display or by combinatorial methods.

Phage display and combinatorial methods for generating anti-32252 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the anti-32252 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An anti-32252 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDR's (of heavy and or light immunoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 32252 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 32252 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In preferred embodiments an antibody can be made by immunizing with purified 32252 antigen, or a fragment thereof, e.g., a fragment described herein, tissue, e.g., crude tissue preparations, or cell fractions.

A full-length 32252 protein or, antigenic peptide fragment of 32252 can be used as an immunogen or can be used to identify anti-32252 antibodies made with other immunogens, e.g., cells, membrane preparations, and the like. The antigenic peptide of 32252 should include at least 8 amino acid residues of the amino acid sequence shown in SEQ ID NO:78 and encompasses an epitope of 32252. Preferably, the antigenic peptide includes at least 10 amino acid residues, more preferably at least 15 amino acid residues, even more preferably at least 20 amino acid residues, and most preferably at least 30 amino acid residues.

Fragments of 32252 which include residues about 210 to 225, or 490 to 520 can be used to make, e.g., used as immunogens or used to characterize the specificity of an antibody, antibodies against hydrophilic regions of the 32252 protein. Similarly, fragments of 32252 which include residues about 190 to 210 or 335 to 354 of SEQ ID NO:78 can be used to make an antibody against a hydrophobic region of the 32252 protein.

Antibodies reactive with, or specific for, any of these regions, or other regions or domains described herein are provided.

Antibodies which bind only native 32252 protein, only denatured or otherwise non-native 32252 protein, or which bind both, are with in the invention. Antibodies with linear or conformational epitopes are within the invention. Conformational epitopes can sometimes be identified by identifying antibodies which bind to native but not denatured 32252 protein.

Preferred epitopes encompassed by the antigenic peptide are regions of 32252 are located on the surface of the protein, e.g., hydrophilic regions, as well as regions with high antigenicity. For example, an Emini surface probability analysis of the human 32252 protein sequence can be used to indicate the regions that have a particularly high probability of being localized to the surface of the 32252 protein and are thus likely to constitute surface residues useful for targeting antibody production.

In preferred embodiments antibodies can bind one or more of purified antigen, tissue, e.g., tissue sections, whole cells, preferably living cells, lysed cells, cell fractions.

The anti-32252 antibody can be a single chain antibody. A single-chain antibody (scFV) may be engineered (see, for example, Colcher, D. et al. (1999) *Ann NY Acad Sci* 880: 263-80; and Reiter, Y. (1996) *Clin Cancer Res* 2:245-52). The single chain antibody can be dimerized or multimerized to generate multivalent antibodies having specificities for different epitopes of the same target 32252 protein.

In a preferred embodiment the antibody has: effector function; and can fix complement. In other embodiments the antibody does not; recruit effector cells; or fix complement.

In a preferred embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

In a preferred embodiment, an anti-32252 antibody alters (e.g., increases or decreases) the ATP-binding, adenylation, or acyl-CoA ligation activity of a 32252 polypeptide.

The antibody can be coupled to a toxin, e.g., a polypeptide toxin, e,g, ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-32252 antibody (e.g., monoclonal antibody) can be used to isolate 32252 by standard techniques, such as affinity chromatography or immunoprecipitation. Moreover, an anti-32252 antibody can be used to detect 32252 protein (e.g., in a cellular lysate or cell supernatant) in order to evaluate the abundance and pattern of expression of the protein. Anti-32252 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes a nucleic acid which encodes an anti-32252 antibody, e.g., an anti-32252 antibody described herein. Also included are vectors which include the nucleic acid and cells transformed with the nucleic acid, particularly cells which are useful for producing an antibody, e.g., mammalian cells, e.g. CHO or lymphatic cells.

The invention also includes cell lines, e.g., hybridomas, which make an anti-32252 antibody, e.g., and antibody described herein, and method of using said cells to make a 32252 antibody.

32252 Recombinant Expression Vectors, Host Cells and Genetically Engineered Cells In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 32252 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 32252 proteins, mutant forms of 32252 proteins, fusion proteins, and the like).

The recombinant expression vectors of the invention can be designed for expression of 32252 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 32252 activity assays, (e.g., direct assays or competitive assays described in detail below), or to generate antibodies specific for 32252 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The 32252 expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a 32252 nucleic acid molecule within a recombinant expression vector or a 32252 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 32252 protein can be expressed in bacterial cells (such as *E. coli*), insect cells, yeast or mammalian cells (such as Chinese hamster ovary cells (CHO) or COS cells (African green monkey kidney cells CV-1 origin SV40 cells; Gluzman (1981) *Cell* 23:175-182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 32252 protein. Accordingly, the invention further provides methods for producing a 32252 protein using the host cells of the invention. In one embodiment, the method includes culturing the host cell of the invention (into which a recombinant expression vector encoding a 32252 protein has been introduced) in a suitable medium such that a 32252 protein is produced. In another embodiment, the method further includes isolating a 32252 protein from the medium or the host cell.

In another aspect, the invention features, a cell or purified preparation of cells which include a 32252 transgene, or which otherwise misexpress 32252. The cell preparation can consist of human or non-human cells, e.g., rodent cells, e.g., mouse or rat cells, rabbit cells, or pig cells. In preferred embodiments, the cell or cells include a 32252 transgene, e.g., a heterologous form of a 32252, e.g., a gene derived from humans (in the case of a non-human cell). The 32252 transgene can be misexpressed, e.g., overexpressed or underexpressed. In other preferred embodiments, the cell or cells include a gene that mis-expresses an endogenous 32252, e.g., a gene the expression of which is disrupted, e.g., a knockout. Such cells can serve as a model for studying disorders that are related to mutated or mis-expressed 32252 alleles or for use in drug screening.

In another aspect, the invention features, a human cell, e.g., a hematopoietic stem cell, transformed with nucleic acid which encodes a subject 32252 polypeptide.

Also provided are cells, preferably human cells, e.g., human hematopoietic or fibroblast cells, in which an endogenous 32252 is under the control of a regulatory sequence that does not normally control the expression of the endogenous 32252 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 32252 gene. For example, an endogenous 32252 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 32252 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (2001) *Nat. Biotechnol.* 19:35; and U.S. Pat. No. 5,876,742. Production of 32252 polypeptide can be regulated in the subject by administering an agent (e.g., a steroid hormone) to the subject. In another preferred embodiment, the implanted recombinant cells express and secrete an antibody specific for a 32252 polypeptide. The antibody can be any antibody or any antibody derivative described herein.

32252 Transgenic Animals

The invention provides non-human transgenic animals. Such animals are useful for studying the function and/or activity of a 32252 protein and for identifying and/or evaluating modulators of 32252 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 32252 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 32252 protein to particular cells. A transgenic founder animal can be identified based upon the presence of a 32252 transgene in its genome and/or expression of 32252 mRNA in tissues or cells of the animals. A transgenic founder animal can then be used to breed additional animals carrying the transgene. Moreover, transgenic animals carrying a transgene encoding a 32252 protein can further be bred to other transgenic animals carrying other transgenes.

32252 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses of 32252

The nucleic acid molecules, proteins, protein homologues, and antibodies described herein can be used in one or more of the following methods: a) in vitro modification of substrate compounds, e.g., lipids such as cholesterols and/or fatty acids; b) screening assays; c) predictive medicine (e.g., diagnostic assays, prognostic assays, monitoring clinical trials, and pharmacogenetics); and d) methods of treatment (e.g., therapeutic and prophylactic).

Isolated proteins of the invention can be purified and used in vitro to, for example, modify compounds that contain carboxylic acid moieties, e.g., fatty acid molecules or xenobiotic molecules, thus producing derivative molecules that are ligated to coenzyme A.

The isolated nucleic acid molecules of the invention can be used, for example, to express a 32252 protein (e.g., via a recombinant expression vector in a host cell in gene therapy applications), to detect a 32252 mRNA (e.g., in a biological sample) or a genetic alteration in a 32252 gene, and to modulate 32252 activity, as described further below. The 32252 proteins can be used to treat disorders characterized by insufficient or excessive production of a 32252 substrate or production of 32252 inhibitors. In addition, the 32252 proteins can be used to screen for naturally occurring 32252 substrates, to screen for drugs or compounds which modulate 32252 activity, as well as to treat disorders characterized by insufficient or excessive production of 32252 protein or production of 32252 protein forms which have decreased, aberrant or unwanted activity compared to 32252 wild type protein (e.g., lipid metabolism disorders, neural disorders, and cellular proliferative and/or differentiative disorders). Moreover, the anti-32252 antibodies of the invention can be used to detect and isolate 32252 proteins, regulate the bioavailability of 32252 proteins, and modulate 32252 activity.

A method of evaluating a compound for the ability to interact with, e.g., bind, a subject 32252 polypeptide is provided. The method includes: contacting the compound with the subject 32252 polypeptide; and evaluating ability of the compound to interact with, e.g., to bind or form a complex with the subject 32252 polypeptide. This method can be performed in vitro, e.g., in a cell free system, or in vivo, e.g., in a two-hybrid interaction trap assay. This method can be used to identify naturally occurring molecules that interact with subject 32252 polypeptide. It can also be used to find natural or synthetic inhibitors of subject 32252 polypeptide. Screening methods are discussed in more detail below.

32252 Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 32252 proteins, have a stimulatory or inhibitory effect on, for example, 32252 expression or 32252 activity, or have a stimulatory or inhibitory effect on, for example, the expression or activity of a 32252 substrate. Compounds thus identified can be used to modulate the activity of target gene products (e.g., 32252 genes) in a therapeutic protocol, to elaborate the biological function of the target gene product, or to identify compounds that disrupt normal target gene interactions.

In one embodiment, the invention provides assays for screening candidate or test compounds which are substrates of a 32252 protein or polypeptide or a biologically active portion thereof. In another embodiment, the invention provides assays for screening candidate or test compounds that bind to or modulate an activity of a 32252 protein or polypeptide or a biologically active portion thereof.

In one embodiment, an activity of a 32252 protein can be assayed by, for example, expressing a 32252 nucleic acid in a vertebrate cell, e.g., COS-1 cells, adding an appropriate substrate, e.g., a fatty acid or a xenobiotic carboxylic acid-containing molecule, and detecting substrate molecules that have been modified by the addition of coenzyme A. Alternatively, activity of a 32252 protein can be assayed by expression a 32252 nucleic acid in a vertebrate cell, e.g., COS-1 cells, adding an appropriate substrate, e.g., a fatty acid or a xenobiotic carboxylic acid-containing molecule, and detecting the breakdown of the substrate by a oxidation pathway. Examples of these methods are presented in Steinberg et al. (2000), *J Biol Chem* 275(45):35162-9, Watkins et al. (1994), *Biochim Biophys Acta* 1214:288-94, and Watkins et al. (1991), *Arch Biochem Biophys* 289:329-36, the contents of which are incorporated herein by reference.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Libraries can be designed based on steroid and fatty acid compounds and/or on known drugs (e.g., lovastatin).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In one embodiment, an assay is a cell-based assay in which a cell which expresses a 32252 protein or biologically active portion thereof is contacted with a test compound, and the ability of the test compound to modulate 32252 activity is determined. Determining the ability of the test compound to modulate 32252 activity can be accomplished by monitoring, for example, ATP-binding or substrate modification, e.g., by adenylation, coenzyme A addition, or degradation. The cell, for example, can be of mammalian origin, e.g., human.

The ability of the test compound to modulate 32252 binding to a compound, e.g., a 32252 substrate, or to bind to 32252 can also be evaluated. This can be accomplished, for example, by coupling the compound, e.g., the substrate, with a radioisotope or enzymatic label such that binding of the compound, e.g., the substrate, to 32252 can be determined by detecting the labeled compound, e.g., substrate, in a complex. Alternatively, 32252 could be coupled with a radioisotope or enzymatic label to monitor the ability of a test compound to modulate 32252 binding to a 32252 substrate in a complex. For example, compounds (e.g., 32252 substrates) can be labeled with 125I, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 32252 substrate) to interact with 32252 with or without the labeling of any of the interactants can be evaluated. For example, a microphysiometer can be used to detect the interaction of a compound with 32252 without the labeling of either the compound or the 32252. McConnell, H. M. et al. (1992) *Science* 257: 1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 32252.

In yet another embodiment, a cell-free assay is provided in which a 32252 protein or biologically active portion thereof is contacted with a test compound and the ability of the test compound to bind to the 32252 protein or biologically active portion thereof is evaluated. Preferred biologically active portions of the 32252 proteins to be used in assays of the present invention include fragments which participate in interactions with non-32252 molecules, e.g., fragments with high surface probability scores.

Soluble and/or membrane-bound forms of isolated proteins (e.g., 32252 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 32252 protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 32252, an anti-32252 antibody or its target molecule to facilitate separation of complexed from uncomplexed forms of one or both of the proteins, as well as to accommodate automation of the assay. Binding of a test compound to a 32252 protein, or interaction of a 32252 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/32252 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 32252 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 32252 binding or activity determined using standard techniques.

Other techniques for immobilizing either a 32252 protein or a target molecule on matrices include using conjugation of biotin and streptavidin. Biotinylated 32252 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 32252 protein or target molecules but which do not interfere with binding of the 32252 protein to its target molecule. Such antibodies can be derivatized to the wells of the plate, and unbound target or 32252 protein trapped in the wells by antibody conjugation. Methods for detecting such complexes, in addition to those described above for the GST-immobilized complexes, include immunodetection of complexes using antibodies reactive with the 32252 protein or target molecule, as well as enzyme-linked assays which rely on detecting an enzymatic activity associated with the 32252 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141-8; Hage, D. S., and Tweed, S. A. (1997) *J Chromatogr B Biomed Sci Appl.* 699:499-525). Further, fluorescence energy transfer may also be conveniently utilized, as described herein, to detect binding without further purification of the complex from solution.

In a preferred embodiment, the assay includes contacting the 32252 protein or biologically active portion thereof with a known compound which binds 32252 to form an assay mixture, contacting the assay mixture with a test compound, and determining the ability of the test compound to interact with a 32252 protein, wherein determining the ability of the test compound to interact with a 32252 protein includes determining the ability of the test compound to preferentially bind to 32252 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 32252 genes herein identified. In an alternative embodiment, the invention provides methods for determining the ability of the test compound to modulate the activity of a 32252 protein through modulation of the activity of a downstream effector of a 32252 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 32252 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 32252 ("32252-binding proteins" or "32252-bp") and are involved in 32252 activity. Such 32252-bps can be activators or inhibitors of signals by the 32252 proteins or 32252 targets as, for example, downstream elements of a 32252-mediated signaling pathway.

The two-hybrid system is based on the modular nature of most transcription factors, which consist of separable DNA-binding and activation domains. Briefly, the assay utilizes two different DNA constructs. In one construct, the gene that codes for a 32252 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 32252 protein can be the fused to the activator domain.) If the "bait" and the "prey" proteins are able to interact, in vivo, forming a 32252-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 32252 protein.

In another embodiment, modulators of 32252 expression are identified. For example, a cell or cell free mixture is contacted with a candidate compound and the expression of 32252 mRNA or protein evaluated relative to the level of expression of 32252 mRNA or protein in the absence of the candidate compound. When expression of 32252 mRNA or protein is greater in the presence of the candidate compound than in its absence, the candidate compound is identified as a stimulator of 32252 mRNA or protein expression. Alternatively, when expression of 32252 mRNA or protein is less (statistically significantly less) in the presence of the candidate compound than in its absence, the candidate compound is identified as an inhibitor of 32252 mRNA or protein expression. The level of 32252 mRNA or protein expression can be determined by methods described herein for detecting 32252 mRNA or protein.

In another aspect, the invention pertains to a combination of two or more of the assays described herein. For example, a modulating agent can be identified using a cell-based or a cell free assay, and the ability of the agent to modulate the activity of a 32252 protein can be confirmed in vivo, e.g., in an animal such as an animal model for cellular proliferative and/or differentiative disorders or an animal model for metabolic disorders.

This invention further pertains to novel agents identified by the above-described screening assays. Accordingly, it is within the scope of this invention to further use an agent identified as described herein (e.g., a 32252 modulating agent, an antisense 32252 nucleic acid molecule, a 32252-specific antibody, or a 32252-binding partner) in an appropriate animal model to determine the efficacy, toxicity, side effects, or mechanism of action, of treatment with such an agent. Furthermore, novel agents identified by the above-described screening assays can be used for treatments as described herein.

32252 Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 32252 with a disease; (ii) identify an individual from a minute biological sample (tissue typing); and (iii) aid in forensic identification of a biological sample. These applications are described in the subsections below.

32252 Chromosome Mapping

The 32252 nucleotide sequences or portions thereof can be used to map the location of the 32252 genes on a chromosome. This process is called chromosome mapping. Chromosome mapping is useful in correlating the 32252 sequences with genes associated with disease.

Briefly, 32252 genes can be mapped to chromosomes by preparing PCR primers (preferably 15-25 bp in length) from the 32252 nucleotide sequences. These primers can then be used for PCR screening of somatic cell hybrids containing individual human chromosomes. Only those hybrids containing the human gene corresponding to the 32252 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al (1983) *Science* 220:919-924).

Other mapping strategies e.g., in situ hybridization (described in Fan, Y. et al. (1990) *Proc. Natl. Acad. Sci. USA*, 87:6223-27), pre-screening with labeled flow-sorted chromosomes, and pre-selection by hybridization to chromosome specific cDNA libraries can be used to map 32252 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783-787.

Moreover, differences in the DNA sequences between individuals affected and unaffected with a disease associated with the 32252 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

32252 Tissue Typing 32252 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 32252 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:77 can provide positive individual identification with a panel of perhaps 10 to 1,000 primers which each yield a noncoding amplified sequence of 100 bases. If predicted coding sequences, such as those in SEQ ID NO:79 are used, a more appropriate number of primers for positive individual identification would be 500-2,000.

If a panel of reagents from 32252 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 32252 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:77 (e.g., fragments derived from the noncoding regions of SEQ ID NO:77 having a length of at least 20 bases, preferably at least 30 bases) are particularly appropriate for this use.

The 32252 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 32252 probes can be used to identify tissue by species and/or by organ type.

In a similar fashion, these reagents, e.g., 32252 primers or probes can be used to screen tissue culture for contamination (i.e. screen for the presence of a mixture of different types of cells in a culture).

Predictive Medicine of 32252

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 32252.

Such disorders include, e.g., a disorder associated with the misexpression of 32252 gene, e.g. misexpression in brain, breast, ovary, lung, and colon tissue.

The method includes one or more of the following:

detecting, in a tissue of the subject, the presence or absence of a mutation which affects the expression of the 32252 gene, or detecting the presence or absence of a mutation in a region which controls the expression of the gene, e.g., a mutation in the 5' control region;

detecting, in a tissue of the subject, the presence or absence of a mutation which alters the structure of the 32252 gene;

detecting, in a tissue of the subject, the misexpression of the 32252 gene, at the mRNA level, e.g., detecting a non-wild type level of a mRNA;

detecting, in a tissue of the subject, the misexpression of the gene, at the protein level, e.g., detecting a non-wild type level of a 32252 polypeptide.

In preferred embodiments the method includes: ascertaining the existence of at least one of: a deletion of one or more nucleotides from the 32252 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:77, or naturally occurring mutants thereof or 5' or 3' flanking sequences naturally associated with the 32252 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 32252 gene; the presence of a non-wild type splicing pattern of a messenger RNA transcript of the gene; or a non-wild type level of 32252.

Methods of the invention can be used prenatally or to determine if a subject's offspring will be at risk for a disorder.

In preferred embodiments the method includes determining the structure of a 32252 gene, an abnormal structure being indicative of risk for the disorder.

In preferred embodiments the method includes contacting a sample from the subject with an antibody to the 32252 protein or a nucleic acid, which hybridizes specifically with the gene. These and other embodiments are discussed below.

Diagnostic and Prognostic Assays of 32252

Diagnostic and prognostic assays of the invention include method for assessing the expression level of 32252 molecules and for identifying variations and mutations in the sequence of 32252 molecules.

Expression Monitoring and Profiling

The presence, level, or absence of 32252 protein or nucleic acid in a biological sample can be evaluated by obtaining a biological sample from a test subject and contacting the biological sample with a compound or an agent capable of detecting 32252 protein or nucleic acid (e.g., mRNA, genomic DNA) that encodes 32252 protein such that the presence of 32252 protein or nucleic acid is detected in the biological sample. The term "biological sample" includes tissues, cells and biological fluids isolated from a subject, as well as tissues, cells and fluids present within a subject. A preferred biological sample is serum. The level of expression of the 32252 gene can be measured in a number of ways, including, but not limited to: measuring the mRNA encoded by the 32252 genes; measuring the amount of protein encoded by the 32252 genes; or measuring the activity of the protein encoded by the 32252 genes.

The level of mRNA corresponding to the 32252 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 32252 nucleic acid, such as the nucleic acid of SEQ ID NO:77, or a portion thereof, such as an oligonucleotide of at least 7, 15, 30, 50, 100, 250 or 500 nucleotides in length and sufficient to specifically hybridize under stringent conditions to 32252 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 32252 genes.

The level of mRNA in a sample that is encoded by one of 32252 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 32252 gene being analyzed.

In another embodiment, the methods further contacting a control sample with a compound or agent capable of detecting 32252 mRNA, or genomic DNA, and comparing the presence of 32252 mRNA or genomic DNA in the control sample with the presence of 32252 mRNA or genomic DNA in the test sample. In still another embodiment, serial analysis of gene expression, as described in U.S. Pat. No. 5,695,937, is used to detect 32252 transcript levels.

A variety of methods can be used to determine the level of protein encoded by 32252.

In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 32252 protein in a biological sample in vitro as well as in vivo. In vitro techniques for detection of 32252 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 32252 protein include introducing into a subject a labeled anti-32252 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-32252 antibody positioned on an antibody array (as described below). The sample can be detected, e.g., with avidin coupled to a fluorescent label.

In another embodiment, the methods further include contacting the control sample with a compound or agent capable of detecting 32252 protein, and comparing the presence of 32252 protein in the control sample with the presence of 32252 protein in the test sample.

The invention also includes kits for detecting the presence of 32252 in a biological sample. For example, the kit can include a compound or agent capable of detecting 32252 protein or mRNA in a biological sample; and a standard. The compound or agent can be packaged in a suitable container. The kit can further comprise instructions for using the kit to detect 32252 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 32252 expression or activity. As used herein, the term "unwanted" includes an unwanted phenomenon involved in a biological response such as a metabolic disorder, e.g., a disorder in fatty acid metabolism, or deregulated cell proliferation.

In one embodiment, a disease or disorder associated with aberrant or unwanted 32252 expression or activity is identified. A test sample is obtained from a subject and 32252 protein or nucleic acid (e.g., mRNA or genomic DNA) is evaluated, wherein the level, e.g., the presence or absence, of 32252 protein or nucleic acid is diagnostic for a subject having or at risk of developing a disease or disorder associated with aberrant or unwanted 32252 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 32252 expression or activity. For example, such methods can be used to determine whether a subject can be effectively treated with an agent for a cell displaying a neoplastic disorder or a metabolic disorder, e.g., a disorder in fatty acid metabolism.

In another aspect, the invention features a computer medium having a plurality of digitally encoded data records. Each data record includes a value representing the level of expression of 32252 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 32252 (e.g., other genes associated with a 32252-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 32252 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a disorder, e.g., a cellular proliferative and/or differentiative disorder, in a subject wherein either an increase or a decrease, depending upon the disorder and the cell type, in 32252 expression is an indication that the subject has or is disposed to having a cellular proliferative and/or differentiative disorder. The method can be used to monitor a treatment for a disorder, e.g., a cellular proliferative and/or differentiative disorder, in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 32252 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 32252 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 32252 expression.

32252 Arrays and Uses Thereof

In another aspect, the invention features an array that includes a substrate having a plurality of addresses. At least one address of the plurality includes a capture probe that binds specifically to a 32252 molecule (e.g., a 32252 nucleic acid or a 32252 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 32252 nucleic acid, e.g., the sense or anti-sense strand. In one preferred embodiment, a subset of addresses of the plurality of addresses has a nucleic acid capture probe for 32252. Each address of the subset can include a capture probe that hybridizes to a different region of a 32252 nucleic acid. In another preferred embodiment, addresses of the subset include a capture probe for a 32252 nucleic acid. Each address of the subset is unique, overlapping, and complementary to a different variant of 32252 (e.g., an allelic variant, or all possible hypothetical variants).

The array can be used to sequence 32252 by hybridization (see, e.g., U.S. Pat. No. 5,695,940).

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 32252 polypeptide or fragment thereof. The polypeptide can be a naturally-occurring interaction partner of 32252 polypeptide. Preferably, the polypeptide is an antibody, e.g., an antibody described herein (see "Anti-32252 Antibodies," above), such as a monoclonal antibody or a single-chain antibody.

In another aspect, the invention features a method of analyzing the expression of 32252. The method includes providing an array as described above; contacting the array with a sample and detecting binding of a 32252-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 32252. If a sufficient number of diverse samples is analyzed, clustering (e.g., hierarchical clustering, k-means clustering, Bayesian clustering and the like) can be used to identify other genes which are co-regulated with 32252. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 32252 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 32252-associated disease or disorder; and processes, such as a cellular transformation associated with a 32252-associated disease or disorder. The method can also evaluate the treatment and/or progression of a 32252-associated disease or disorder The array is also useful for ascertaining differential expression patterns of one or more genes in normal and abnormal cells. This provides a battery of genes (e.g., including 32252) that could serve as a molecular target for diagnosis or therapeutic intervention.

In another aspect, the invention features an array having a plurality of addresses. Each address of the plurality includes a unique polypeptide. At least one address of the plurality has disposed thereon a 32252 polypeptide or fragment thereof. Methods of producing polypeptide arrays are described in the art, e.g., in De Wildt et al. (2000). *Nature Biotech.* 18,989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80, 85, 90, 95 or 99% identical to a 32252 polypeptide or fragment thereof. For example, multiple variants of a 32252 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 32252 binding compound, e.g., an antibody in a sample from a subject with specificity for a 32252 polypeptide or the presence of a 32252-binding protein or ligand.

The array is also useful for ascertaining the effect of the expression of a gene on the expression of other genes in the same cell or in different cells (e.g., ascertaining the effect of 32252 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 32252 or from a cell or subject in which a 32252 mediated response has been elicited, e.g., by contact of the cell with 32252 nucleic acid or protein, or administration to the cell or subject 32252 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 32252 (or does not express as highly as in the case of the 32252 positive plurality of capture probes) or from a cell or subject which in which a 32252 mediated response has not been elicited (or has been elicited to a lesser extent than in the first sample); contacting the array with one or more inquiry probes (which is preferably other than a 32252 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 32252 or from a cell or subject in which a 32252-mediated response has been elicited, e.g., by contact of the cell with 32252 nucleic acid or protein, or administration to the cell or subject 32252 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 32252 (or does not express as highly as in the case of the 32252 positive plurality of capture probes) or from a cell or subject which in which a 32252 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 32252, e.g., analyzing structure, function, or relatedness to other nucleic acid or amino acid sequences. The method includes: providing a 32252 nucleic acid or amino acid sequence; comparing the 32252 sequence with one or more preferably a plurality of sequences from a collection of sequences, e.g., a nucleic acid or protein sequence database; to thereby analyze 32252.

Detection of 32252 Variations or Mutations

The methods of the invention can also be used to detect genetic alterations in a 32252 gene, thereby determining if a subject with the altered gene is at risk for a disorder characterized by misregulation in 32252 protein activity or nucleic acid expression, such as a metabolic disorder, e.g., a disorder in fatty acid metabolism, a neural disorder, or deregulated cell proliferation. In preferred embodiments, the methods include detecting, in a sample from the subject, the presence or absence of a genetic alteration characterized by at least one of an alteration affecting the integrity of a gene encoding a 32252-protein, or the misexpression of the 32252 gene. For example, such genetic alterations can be detected by ascertaining the existence of at least one of 1) a deletion of one or more nucleotides from a 32252 gene; 2) an addition of one or more nucleotides to a 32252 gene; 3) a substitution of one or more nucleotides of a 32252 gene, 4) a chromosomal rearrangement of a 32252 gene; 5) an alteration in the level of a messenger RNA transcript of a 32252 gene, 6) aberrant modification of a 32252 gene, such as of the methylation pattern of the genomic DNA, 7) the presence of a non-wild type splicing pattern of a messenger RNA transcript of a 32252 gene, 8) a non-wild type level of a 32252-protein, 9) allelic loss of a 32252 gene, and 10) inappropriate post-translational modification of a 32252-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 32252-gene. This method can include the steps of collecting a sample of cells from a subject, isolating nucleic acid (e.g., genomic, mRNA or both) from the sample, contacting the nucleic acid sample with one or more primers which specifically hybridize to a 32252 gene under conditions such that hybridization and amplification of the 32252-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 32252 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 32252 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 32252 nucleic acid or a putative variant (e.g., allelic variant) thereof. A probe can have one or more mismatches to a region of a 32252 nucleic acid (e.g., a destabilizing mismatch). The arrays can have a high density of addresses, e.g., can contain hundreds or thousands of oligonucleotides probes (Cronin, M. T. et al. (1996) *Human Mutation* 7:244-255; Kozal, M. J. et al (1996) *Nature Medicine* 2:753-759). For example, genetic mutations in 32252 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 32252 gene and detect mutations by comparing the sequence of the sample 32252 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 32252 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 32252 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 32252 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 32252 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 32252 nucleic acid.

In a preferred embodiment the set includes a first and a second oligonucleotide. The first and second oligonucleotide can hybridize to the same or to different locations of SEQ ID NO:77 or the complement of SEQ ID NO:77. Different locations can be different but overlapping, or non-overlapping on the same strand. The first and second oligonucleotide can hybridize to sites on the same or on different strands.

The set can be useful, e.g., for identifying SNP's, or identifying specific alleles of 32252. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 32252 nucleic acid.

The methods described herein may be performed, for example, by utilizing prepackaged diagnostic kits comprising at least one probe nucleic acid or antibody reagent described herein, which may be conveniently used, e.g., in clinical settings to diagnose patients exhibiting symptoms or family history of a disease or illness involving a 32252 gene.

Use of 32252 Molecules as Surrogate Markers

The 32252 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 32252 molecules of the invention may be detected, and may be correlated with one or more biological states in vivo. For example, the 32252 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35:258-264; and James (1994) *AIDS Treatment News Archive* 209.

The 32252 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 32252 marker) transcription or expression, the amplified marker may be in a quantity which is more readily detectable than the drug itself. Also, the marker may be more easily detected due to the nature of the marker itself; for example, using the methods described herein, anti-32252 antibodies may be employed in an immune-based detection system for a 32252 protein marker, or 32252-specific radio-labeled probes may be used to detect a 32252 mRNA marker. Furthermore, the use of a pharmacodynamic marker may offer mechanism-based prediction of risk due to drug treatment beyond the range of possible direct observations.

Examples of the use of pharmacodynamic markers in the art include: Matsuda et al. U.S. Pat. No. 6,033,862; Hattis et al. (1991) *Env. Health Perspect.* 90:229-238; Schentag (1999) *Am. J. Health-Syst. Pharm.* 56 Suppl. 3:S21-S24; and Nicolau (1999) *Am, J. Health-Syst. Pharm.* 56 Suppl. 3:S16-S20.

The 32252 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 32252 protein or RNA) for specific tumor markers in a subject, a drug or course of treatment may be selected that is optimized for the treatment of the specific tumor likely to be present in the subject. Similarly, the presence or absence of a specific sequence mutation in 32252 DNA may correlate 32252 drug response. The use of pharmacogenomic markers therefore permits the application of the most appropriate treatment for each subject without having to administer the therapy.

Pharmaceutical Compositions of 32252

The nucleic acid and polypeptides, fragments thereof, as well as anti-32252 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors. Alternatively, an antibody can be conjugated to a second antibody to form an antibody heteroconjugate as described by Segal in U.S. Pat. No. 4,676,980.

In yet other embodiments, the agents of the invention can be administered alone or in combination with a cholesterol lowering agent. Examples of cholesterol lowering agents include bile acid sequestering resins (e.g. colestipol hydrochloride or cholestyramine), fibric acid derivatives (e.g. clofibrate, fenofibrate, or gemfibrozil), thiazolidenediones (e.g., troglitazone, pioglitazone, ciglitazone, englitazone, rosiglitazone), or hydroxymethylglutaryl coenzyme A reductase (HMG-CoA reductase) inhibitors (e.g. statins, such as fluvastatin sodium, lovastatin, pravastatin sodium, simvastatin, atorvastatin calcium, cerivastatin), an ApoAII-lowering agent, a VLDL lowering agent, an ApoAI-stimulating agent, as well as inhibitors of, nicotinic acid, niacin, or probucol. Preferred cholesterol lowering agents include inhibitors of HMG-CoA reductase (e.g., statins), nicotinic acid, and niacin. Preferably, the cholesterol lowering agent results in a favorable plasma lipid profile (e.g., increased HDL and/or reduced LDL).

In other embodiments, the agent(s) of the invention is administered in combination with an interventional procedure ("procedural vascular trauma"). Examples of interventional procedures, include but are not limited to, angioplasty, placement of a shunt, stent, synthetic or natural excision grafts, indwelling catheter, valve and other implantable devices.

The second agent or procedure can be administered or effected prior to, at the same time, or after administration of the agent(s) of the invention, in single or multiple administration schedules. For example, the second agent and the agents of the invention can be administered continually over a preselected period of time, or administered in a series of spaced doses, i.e., intermittently, for a period of time.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 32252

The present invention provides for both prophylactic and therapeutic methods of treating a subject at risk of (or susceptible to) a disorder or having a disorder associated with aberrant or unwanted 32252 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Phannacogenomics", as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 32252 molecules of the present invention or 32252 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 32252 expression or activity, by administering to the subject a 32252 or an agent which modulates 32252 expression or at least one 32252 activity. Subjects at risk for a disease which is caused or contributed to by aberrant or unwanted 32252 expression or activity can be identified by, for example, any or a combination of diagnostic or prognostic assays as described herein. Administration of a prophylactic agent can occur prior to the manifestation of symptoms characteristic of the 32252 aberrance, such that a disease or disorder is prevented or, alternatively, delayed in its progression. Depending on the type of 32252 aberrance, for example, a 32252, 32252 agonist or 32252 antagonist agent can be used for treating the subject. The appropriate agent can be determined based on screening assays described herein.

It is possible that some 32252 disorders can be caused, at least in part, by an abnormal level of gene product, or by the presence of a gene product exhibiting abnormal activity. As such, the reduction in the level and/or activity of such gene products would bring about the amelioration of disorder symptoms.

The 32252 molecules can act as novel diagnostic targets and therapeutic agents for controlling the disorders described above, as well as, disorders associated with bone metabolism, immune disorders, cardiovascular disorders, liver disorders, viral diseases, pain or metabolic disorders, in addition to disorders described above.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promycloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Aberrant expression and/or activity of 32252 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 32252 molecules effects in bone cells, e.g. osteoclasts and osteoblasts, that may in turn result in bone formation and degeneration. For example, 32252 molecules may support different activities of bone resorbing osteoclasts such as the stimulation of differentiation of monocytes and mononuclear phagocytes into osteoclasts. Accordingly, 32252 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

The 32252 nucleic acid and protein of the invention can be used to treat and/or diagnose a variety of immune disorders. Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isoniazid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 32252 molecules may play an important role in the etiology of certain viral diseases, including but not limited to Hepatitis B, Hepatitis C and Herpes Simplex Virus (HSV). Modulators of 32252 activity could be used to control viral diseases. The modulators can be used in the treatment and/or diagnosis of viral infected tissue or virus-associated tissue fibrosis, especially liver and liver fibrosis.

Also, 32252 modulators can be used in the treatment and/or diagnosis of virus-associated carcinoma, especially hepatocellular cancer.

Additionally, 32252 may play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York:McGraw-Hill); pain associated with musculoskeletal disorders, e.g., joint pain; tooth pain; headaches; pain associated with surgery; pain related to irritable bowel syndrome; or chest pain.

As discussed, successful treatment of 32252 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 32252 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 32252 expression is through the use of aptamer molecules specific for 32252 protein. Aptamers are nucleic acid molecules having a tertiary structure which permits them to specifically bind to protein ligands (see, e.g., Osborne, et al. (1997) *Curr. Opin. Chem Biol.* 1: 5-9; and Patel, D. J. (1997) *Curr Opin Chem Biol* 1:32-46). Since nucleic acid molecules may in many cases be more conveniently introduced into target cells than therapeutic protein molecules may be, aptamers offer a method by which 32252 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 32252 disorders. For a description of antibodies, see the Antibody section above.

In circumstances wherein injection of an animal or a human subject with a 32252 protein or epitope for stimulating antibody production is harmful to the subject, it is possible to generate an immune response against 32252 through the use of anti-idiotypic antibodies (see, for example, Herlyn, D. (1999) *Ann Med* 31:66-78; and Bhattacharya-Chatterjee, M., and Foon, K. A. (1998) *Cancer Treat Res.* 94:51-68). If an anti-idiotypic antibody is introduced into a mammal or human subject, it should stimulate the production of anti-anti-idiotypic antibodies, which should be specific to the 32252 protein. Vaccines directed to a disease characterized by 32252 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate 32252 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography. Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 32252 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions.

A detailed review of this technique can be seen in Ansell, R. J. et al (1996) *Current Opinion in Biotechnology* 7:89-94 and in Shea, K. J. (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645-647. Through the use of isotope-labeling, the "free" concentration of compound which modulates the expression or activity of 32252 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142-2144.

Another aspect of the invention pertains to methods of modulating 32252 expression or activity for therapeutic purposes. Accordingly, in an exemplary embodiment, the modulatory method of the invention involves contacting a cell with a 32252 or agent that modulates one or more of the activities of 32252 protein activity associated with the cell. An agent that modulates 32252 protein activity can be an agent as described herein, such as a nucleic acid or a protein, a naturally-occurring target molecule of a 32252 protein (e.g., a 32252 substrate or receptor), a 32252 antibody, a 32252 agonist or antagonist, a peptidomimetic of a 32252 agonist or antagonist, or other small molecule.

In one embodiment, the agent stimulates one or 32252 activities. Examples of such stimulatory agents include active 32252 protein and a nucleic acid molecule encoding 32252. In another embodiment, the agent inhibits one or more 32252 activities. Examples of such inhibitory agents include antisense 32252 nucleic acid molecules, anti-32252 antibodies, and 32252 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 32252 protein or nucleic acid molecule. In one embodiment, the method involves administering an agent (e.g., an agent identified by a screening assay described herein), or combination of agents that modulates (e.g., up regulates or down regulates) 32252 expression or activity. In another embodiment, the method involves administering a 32252 protein or nucleic acid molecule as therapy to compensate for reduced, aberrant, or unwanted 32252 expression or activity.

Stimulation of 32252 activity is desirable in situations in which 32252 is abnormally downregulated and/or in which increased 32252 activity is likely to have a beneficial effect. For example, stimulation of 32252 activity is desirable in situations in which a 32252 is downregulated and/or in which increased 32252 activity is likely to have a beneficial effect. Likewise, inhibition of 32252 activity is desirable in situations in which 32252 is abnormally upregulated and/or in which decreased 32252 activity is likely to have a beneficial effect.

32252 Pharmacogenomics

The 32252 molecules of the present invention, as well as agents, or modulators which have a stimulatory or inhibitory effect on 32252 activity (e.g., 32252 gene expression) as identified by a screening assay described herein can be administered to individuals to treat (prophylactically or therapeutically) 32252 associated disorders (e.g., metabolic disorders, e.g., a disorders in fatty acid metabolism, neural disorders, or cellular proliferative and/or differentiative disorders) associated with aberrant or unwanted 32252 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 32252 molecule or 32252 modulator as well as tailoring the dosage and/or therapeutic regimen of treatment with a 32252 molecule or 32252 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983-985 and Linder, M. W. et al. (1997) *Clin. Chem.* 43:254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a 32252 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a 32252 molecule or 32252 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 32252 molecule or 32252 modulator, such as a modulator identified by one of the exemplary screening assays described herein.

The present invention further provides methods for identifying new agents, or combinations, that are based on identifying agents that modulate the activity of one or more of the gene products encoded by one or more of the 32252 genes of the present invention, wherein these products may be associated with resistance of the cells to a therapeutic agent. Specifically, the activity of the proteins encoded by the 32252 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 32252 protein can be applied in clinical trials. For example, the effectiveness of an agent determined by a screening assay as described herein to increase 32252 gene expression, protein levels, or upregulate 32252 activity, can be monitored in clinical trials of subjects exhibiting decreased 32252 gene expression, protein levels, or downregulated 32252 activity. Alternatively, the effectiveness of an agent determined by a screening assay to decrease 32252 gene expression, protein levels, or downregulate 32252 activity, can be monitored in clinical trials of subjects exhibiting increased 32252 gene expression, protein levels, or upregulated 32252 activity. In such clinical trials, the expression or activity of a 32252 gene, and preferably, other genes that have been implicated in, for example, a 32252-associated disorder can be used as a "read out" or markers of the phenotype of a particular cell.

32252 Informatics

The sequence of a 32252 molecule is provided in a variety of media to facilitate use thereof. A sequence can be provided as a manufacture, other than an isolated nucleic acid or amino acid molecule, which contains a 32252. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 32252 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 32252, e.g., analyzing structure, function, or relatedness to one or more other nucleic acid or amino acid sequences. The method includes: providing a 32252 nucleic acid or amino acid sequence; comparing the 32252 sequence with a second sequence, e.g., one or more preferably a plurality of sequences from a collection of sequences, e.g., a nucleic acid or protein sequence database to thereby analyze 32252. The method can be performed in a machine, e.g., a computer, or manually by a skilled artisan.

The method can include evaluating the sequence identity between a 32252 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 32252 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 32252 sequence, or record, in machine-readable form; comparing a second sequence to the 32252 sequence; thereby analyzing a sequence. Comparison can include comparing to sequences for sequence identity or determining if one sequence is included within the other, e.g., determining if the 32252 sequence includes a sequence being compared. In a preferred embodiment the 32252 or second sequence is stored on a first computer, e.g., at a first site and the comparison is performed, read, or recorded on a second computer, e.g., at a second site. E.g., the 32252 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 32252-associated disease or disorder or a pre-disposition to a 32252-associated disease or disorder, wherein the method comprises the steps of determining 32252 sequence information associated with the subject and based on the 32252 sequence information, determining whether the subject has a 32252-associated disease or disorder or a pre-disposition to a 32252-associated disease or disorder and/or recommending a particular treatment for the disease, disorder or pre-disease condition.

The invention further provides in an electronic system and/or in a network, a method for determining whether a subject has a 32252-associated disease or disorder or a pre-disposition to a disease associated with a 32252 wherein the method comprises the steps of determining 32252 sequence information associated with the subject, and based on the 32252 sequence information, determining whether the subject has a 32252-associated disease or disorder or a pre-disposition to a 32252-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 32252 sequence of the subject to the 32252 sequences in the database to thereby determine whether the subject as a 32252-associated disease or disorder, or a pre-disposition for such.

The present invention also provides in a network, a method for determining whether a subject has a 32252 associated disease or disorder or a pre-disposition to a 32252-associated disease or disorder associated with 32252, said method comprising the steps of receiving 32252 sequence information from the subject and/or information related thereto, receiving phenotypic information associated with the subject, acquiring information from the network corresponding to 32252 and/or corresponding to a 32252-associated disease or disorder (e.g., a metabolic disorder, e.g., a disorder in fatty acid metabolism, a neural disorder, or cellular proliferative and/or differentiative disorder), and based on one or more of the phenotypic information, the 32252 information (e.g., sequence information and/or information related thereto), and the acquired information, determining whether the subject has a 32252-associated disease or disorder or a pre-disposition to a 32252-associated disease or disorder. The method may further comprise the step of recommending a particular treatment for the disease, disorder or pre-disease condition.

The present invention also provides a method for determining whether a subject has a 32252-associated disease or disorder or a pre-disposition to a 32252-associated disease or disorder, said method comprising the steps of receiving information related to 32252 (e.g., sequence information and/or information related thereto), receiving phenotypic information associated with the subject, acquiring information from the network related to 32252 and/or related to a 32252-associated disease or disorder, and based on one or more of the phenotypic information, the 32252 information, and the acquired information, determining whether the subject has a 32252-associated disease or disorder or a pre-disposition to a 32252-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

Background of the 53320 Invention

Acyltransferases comprise a superfamily of enzymes that participate in phospholipid biosynthesis. Acyltransferases catalyze the transfer of an acyl chain to a lipid precursor and have been grouped into several subfamilies based upon their target specificity: lysophosphatidic acid acyltransferase (1-acyl-sn-glycerol-3-phosphate acyltransferase; LPAAT); sn-glycerol-3-phosphate acyltransferase (GPAT); acyl-CoA: dihydroxyacetone-phosphate acyltransferase (DHAPAT); and 2-acylglycerophosphatidylethanolamine acyltransferase (LPEAT). Acyltransferases generally contain four regions of conserved amino acid residues, suggesting that these may be domains relevant to the catalytic activity of the enzymes (Lewin et al., (1999) *Biochemistry* 38:5764-71).

GPAT catalyzes the initial reaction in the pathway of glycerolipid biosynthesis, the transfer of an activated fatty acyl chain to the sn-1 position of glycerol 3-phosphate. LPAAT converts lysophosphatidic acid (LPA) into phosphatidic acid (PA) in the course of lipid metabolism in the ER (Eberhardt et al., (1997) *J. Bio.l Chem.* 272:20299-20305). LPAAT catalyses the transfer of an acyl chain from either acyl-coenzyme A or acyl-acyl carrier protein onto LPA, an intermediate in de novo lipid biosynthesis, to produce PA, the precursor of all glycerolipids. PA can either be hydrolyzed to yield diacylglycerol (DAG) or can be converted to CDP-DAG for the synthesis of more complex phospholipids in the ER. Two human cDNAs have been cloned that encode enzymes having LPAAT activity, LPAAT-$\alpha$ and LPAAT-$\beta$ (West et al., (1997) *DNA Cell. Biol.* 16:691-701; Eberhardt et al., (1997) *J. Biol. Chem.* 272:20299-20305; Aguado and Campbell, (1998) *J. Biol. Chem.* 273:4096-4105). Both human LPAATs localize to the ER. LPAAT-$\alpha$ and LPAAT-$\beta$ are encoded by genes located on chromosomes 6 and 9, respectively.

Aside from its role in the formation of biological membranes, LPA is produced by activated platelets and functions as a bioactive mediator, stimulating platelet aggregation, cell proliferation, cell migration, and cell proliferation (Lee et al., (2000) *Am. J. Physiol. Cell. Physiol.* 278:612-18). LPA generated in the plasma membrane of activated platelets and growth factor-stimulated fibroblasts appears to arise from hydrolysis of PA by a phospholipase A2. One possible means of the attenuation of the bioactive effects of LPA is acylation by LPAAT to yield PA. PA also has been implicated as an intracellular messenger, suggesting that its generation via acylation of LPA by LPAAT at an inflammatory site may lead to further cellular activation (Eberhardt et al., (1999) *Adv. Exp. Med. Biol.* 469:351-356).

Several specific acyltransferases have been found to participate in critical biological functions. Endophilin 1, an SH3 domain-containing LPAAT, mediates the formation of synaptic-like microvesicles (SLMVs) from the plasma membrane via the conversion of LPA to PA (Schmidt et al., (1999) *Nature* 401:133-141). Barth syndrome is associated with mutations in a gene that encodes, by means of alternate splicing, several putative acyltransferases known as tafazzins. Barth syndrome is characterized by short stature, cardioskeletal myopathy, neutropenia, abnormal mitochondria, and respiratory-chain dysfunction (Bione et al., (1996) *Nature Genetics* 12:385-389).

Summary of the 53320 Invention

The present invention is based, in part, on the discovery of a novel acyltransferase family member, referred to herein as "53320". The nucleotide sequence of a cDNA encoding 53320 is shown in SEQ ID NO:83, and the amino acid sequence of a 53320 polypeptide is shown in SEQ ID NO:84. In addition, the nucleotide sequences of the coding region are depicted in SEQ ID NO:85.

Accordingly, in one aspect, the invention features a nucleic acid molecule that encodes a 53320 protein or polypeptide, e.g., a biologically active portion of the 53320 protein. In a preferred embodiment the isolated nucleic acid molecule encodes a polypeptide having the amino acid sequence of SEQ ID NO:84. In other embodiments, the invention provides isolated 53320 nucleic acid molecules having the nucleotide sequence shown in SEQ ID NO:83, or SEQ ID NO:85. In still other embodiments, the invention provides nucleic acid molecules that are substantially identical (e.g., naturally occurring allelic variants) to the nucleotide sequence shown in SEQ ID NO:83, or SEQ ID NO:85. In other embodiments, the invention provides a nucleic acid molecule which hybridizes under a stringency condition described herein to a nucleic acid molecule comprising the nucleotide sequence of SEQ ID NO:83, or SEQ ID NO:85, wherein the nucleic acid encodes a full length 53320 protein or an active fragment thereof.

In a related aspect, the invention further provides nucleic acid constructs that include a 53320 nucleic acid molecule described herein. In certain embodiments, the nucleic acid molecules of the invention are operatively linked to native or heterologous regulatory sequences. Also included, are vectors and host cells containing the 53320 nucleic acid molecules of the invention e.g., vectors and host cells suitable for producing 53320 nucleic acid molecules and polypeptides.

In another related aspect, the invention provides nucleic acid fragments suitable as primers or hybridization probes for the detection of 53320-encoding nucleic acids.

In still another related aspect, isolated nucleic acid molecules that are antisense to a 53320 encoding nucleic acid molecule are provided.

In another aspect, the invention features, 53320 polypeptides, and biologically active or antigenic fragments thereof that are useful, e.g., as reagents or targets in assays applicable to treatment and diagnosis of 53320-mediated or -related disorders. In another embodiment, the invention provides 53320 polypeptides having a 53320 activity. Preferred polypeptides are 53320 proteins including at least one acyltransferase domain, and, preferably, having a 53320 activity, e.g., a 53320 activity as described herein.

In other embodiments, the invention provides 53320 polypeptides, e.g., a 53320 polypeptide having the amino acid sequence shown in SEQ ID NO:84; an amino acid sequence that is substantially identical to the amino acid sequence shown in SEQ ID NO:84; or an amino acid sequence encoded by a nucleic acid molecule having a nucleotide sequence which hybridizes under a stringency condition described herein to a nucleic acid molecule comprising the nucleotide sequence of SEQ ID NO:83, or SEQ ID NO:85, wherein the nucleic acid encodes a full length 53320 protein or an active fragment thereof.

In a related aspect, the invention further provides nucleic acid constructs which include a 53320 nucleic acid molecule described herein.

In a related aspect, the invention provides 53320 polypeptides or fragments operatively linked to non-53320 polypeptides to form fusion proteins.

In another aspect, the invention features antibodies and antigen-binding fragments thereof, that react with, or more preferably specifically bind 53320 polypeptides or fragments thereof.

In another aspect, the invention provides methods of screening for compounds that modulate the expression or activity of the 53320 polypeptides or nucleic acids.

In still another aspect, the invention provides a process for modulating 53320 polypeptide or nucleic acid expression or activity, e.g. using the screened compounds. In certain embodiments, the methods involve treatment of conditions related to aberrant activity or expression of the 53320 polypeptides or nucleic acids, such as conditions involving aberrant or deficient cellular proliferation or differentiation.

The invention also provides assays for determining the activity of or the presence or absence of 53320 polypeptides or nucleic acid molecules in a biological sample, including for disease diagnosis.

In further aspect the invention provides assays for determining the presence or absence of a genetic alteration in a 53320 polypeptide or nucleic acid molecule, including for disease diagnosis.

In another aspect, the invention provides a method for inhibiting angiogenesis. The method includes contacting a cell with a compound (e.g., a compound identified using the methods described herein) that modulates the activity, or expression, of the 53320 polypeptide or nucleic acid. In a preferred embodiment, the contacting step is effected in vitro or ex vivo. In other embodiments, the contacting step is effected in vivo, e.g., in a subject (e.g., a mammal, e.g., a human), as part of a therapeutic or prophylactic protocol. In a preferred embodiment, the cell is an endothelial cell, e.g., an endothelial cell found in proximity or within a solid tumor, a soft tissue tumor, or a metastatic lesion. A cell in proximity to a tumor can be within 1 cm, 1 mm, or 0.5 mm of a tumor. In a much preferred embodiment, the tumor is a lung, breast, ovarian, or colon tumor. The method can include targeting the compound to a tumor (e.g., using an antibody against a tumor associated antigen) or to a zone in proximity to the tumor.

In a preferred embodiment, the compound is an inhibitor of a 53320 polypeptide. Preferably, the inhibitor is chosen from a peptide, a phosphopeptide, a small organic molecule, a small inorganic molecule and an antibody (e.g., an antibody conjugated to a therapeutic moiety selected from a cytotoxin, a cytotoxic agent and a radioactive metal ion). In another preferred embodiment, the compound is an inhibitor of a 53320 nucleic acid, e.g., an antisense, a ribozyme, or a triple helix molecule.

In still another aspect, the invention provides a method of altering wound healing, e.g., stimulating wound healing. The method includes contacting a cell with a compound (e.g., a compound identified using the methods described herein) that modulates the activity, or expression, of the 53320 polypeptide or nucleic acid. In a preferred embodiment, the contacting step is effected with respect to a wound of a subject, e.g., a human or other mammal, e.g., as part of a therapeutic or prophylactic protocol.

In a preferred embodiment, the compound stimulates 53320 activity.

In another aspect, the invention provides a method of altering (e.g., stimulating or inhibiting) cytokine production and/or ras signaling in a cell, e.g., an endothelial cell. The method includes contacting the cell with a compound (e.g., a compound identified using the methods described herein) that modulates the activity, or expression, of the 53320 polypeptide or nucleic acid.

In yet another aspect, the invention provides methods for inhibiting the proliferation or inducing the killing, of a 53320-expressing cell, e.g., a hyper-proliferative 53320-expressing cell. The method includes contacting the cell with a compound (e.g., a compound identified using the methods described herein) that modulates the activity, or expression, of the 53320 polypeptide or nucleic acid. In a preferred embodiment, the contacting step is effective in vitro or ex vivo. In other embodiments, the contacting step is effected in vivo, e.g., in a subject (e.g., a mammal, e.g., a human), as part of a therapeutic or prophylactic protocol. In a preferred embodiment, the cell is a hyperproliferative cell, e.g., a cell found in a solid tumor, a soft tissue tumor, or a metastatic lesion. In a much preferred embodiment, the tumor is a lung, breast, ovarian, or colon tumor.

In a preferred embodiment, the compound is an inhibitor of a 53320 polypeptide. Preferably, the inhibitor is chosen from a peptide, a phosphopeptide, a small organic molecule, a small inorganic molecule and an antibody (e.g., an antibody conjugated to a therapeutic moiety selected from a cytotoxin, a cytotoxic agent and a radioactive metal ion). In another preferred embodiment, the compound is an inhibitor of a 53320 nucleic acid, e.g., an antisense, a ribozyme, or a triple helix molecule.

In a preferred embodiment, the compound is administered in combination with a cytotoxic agent. Examples of cytotoxic agents include anti-microtubule agent, a topoisomerase I inhibitor, a topoisomerase II inhibitor, an anti-metabolite, a mitotic inhibitor, an alkylating agent, an intercalating agent, an agent capable of interfering with a signal transduction pathway, an agent that promotes apoptosis or necrosis, and radiation.

In another aspect, the invention features methods for treating or preventing a disorder characterized by aberrant cellular proliferation or differentiation of a 53320-expressing cell, in a subject. Preferably, the method includes comprising administering to the subject (e.g., a mammal, e.g., a human) an effective amount of a compound (e.g., a compound identified using the methods described herein) that modulates the activity, or expression, of the 53320 polypeptide or nucleic acid. In a preferred embodiment, the disorder is a cancerous or pre-cancerous condition.

In a further aspect, the invention provides methods for evaluating the efficacy of a treatment of a disorder, e.g., proliferative disorder or associated disorder (e.g., tumor formation). The method includes: treating a subject, e.g., a patient or an animal, with a protocol under evaluation (e.g., treating a subject with one or more of: chemotherapy, radiation, and/or a compound identified using the methods described herein); and evaluating the expression of a 53320 nucleic acid or polypeptide before and after treatment. A change, e.g., a decrease or increase, in the level of a 53320 nucleic acid (e.g., mRNA) or polypeptide after treatment, relative to the level of expression before treatment, is indicative of the efficacy of the treatment of the disorder. The level of 53320 nucleic acid or polypeptide expression can be detected by any method described herein.

In a preferred embodiment, the evaluating step includes obtaining a sample (e.g., a tissue sample, e.g., a biopsy, or a fluid sample) from the subject, before and after treatment and comparing the level of expressing of a 53320 nucleic acid (e.g., mRNA) or polypeptide before and after treatment.

In another aspect, the invention provides methods for evaluating the efficacy of a therapeutic or prophylactic agent (e.g., an anti-neoplastic agent). The method includes: contacting a sample with an agent (e.g., a compound identified using the methods described herein, a cytotoxic agent) and, evaluating the expression of 53320 nucleic acid or polypeptide in the sample before and after the contacting step. A change, e.g., a decrease or increase, in the level of 53320 nucleic acid (e.g., mRNA) or polypeptide in the sample obtained after the contacting step, relative to the level of expression in the sample before the contacting step, is indicative of the efficacy of the agent. The level of 53320 nucleic acid or polypeptide expression can be detected by any method described herein. In a preferred embodiment, the sample includes cells obtained from a cancerous tissue such as a lung, breast, colon, or ovarian tumor.

In further aspect, the invention provides assays for determining the presence or absence of a genetic alteration in a 53320 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 53320 molecule. In one embodiment, the capture probe is a nucleic acid, e.g., a probe complementary to a 53320 nucleic acid sequence. In another embodiment, the capture probe is a polypeptide, e.g., an antibody specific for 53320 polypeptides. Also featured is a method of analyzing a sample by contacting the sample to the aforementioned array and detecting binding of the sample to the array.

Other features and advantages of the invention will be apparent from the following detailed description, and from the claims.

Detailed Description of 53320

The human 53320 sequence (SEQ ID NO:83), which is approximately 1475 nucleotides long including untranslated regions, contains a predicted methionine-initiated coding sequence of about 1131 nucleotides (nucleotides 81-1211 of SEQ ID NO:83; SEQ ID NO:85), including the terminal codon. The coding sequence encodes a 376 amino acid protein (SEQ ID NO:84).

This mature protein form is approximately 313 amino acid residues in length (from about amino acid 64 to amino acid 376 or about amino acid 41 to amino acid 376 of SEQ ID NO:84). Human 53320 contains the following regions or other structural features: a predicted acyltransferase domain (PFAM Accession PF01553) located at about amino acid residues 71-261 of SEQ ID NO:84; a predicted extracellular domain from about amino acid residue 64 to 303; a predicted intracellular domain from about amino acid residue 329 to 376; and a predicted transmembrane domain which extends from about amino acid residue 304-328 of SEQ ID NO:84.

The 53320 protein also includes the following domains: one predicted Protein Kinase C phosphorylation sites (PS00005) located at about amino acids 372-374 of SEQ ID NO:84; two predicted N-myristoylation sites (PS00008)

located at about amino acids 16-21, and 166-171 of SEQ ID NO:84; a predicted $2^{nd}$ peroxisomal targeting signal located at about amino acids 362-370 of SEQ ID NO:84; and one predicted leucine zipper pattern (PS00029) located at about amino acids 310-331 of SEQ ID NO:84.

For general information regarding PFAM identifiers, PS prefix and PF prefix domain identification numbers, refer to Sonnhammer et al. (1997) Protein 28:405-420.

TABLE 28

Summary of Domains of 53320

| Protein | Acyltransferase | Leucine Zipper | Transmembrane |
|---|---|---|---|
| 53320 | About amino acids 71-261 of SEQ ID NO:84 | About amino acids 310-331 of SEQ ID NO:84 | About amino acids 304-328 of SEQ ID NO:84 |

The 53320 protein contains a significant number of structural characteristics in common with members of the acyltransferase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, the term "acyltransferase" refers to a protein or polypeptide which is capable of catalyzing an acylation reaction. Acyltransferases can have a specificity for (i.e., a specificity to attach an acyl chain) various lipid precursors. Acyltransferases can be divided into several subfamilies based upon their target specificity, e.g.: lysophosphatidic acid acyltransferase (1-acyl-sn-glycerol-3-phosphate acyltransferase; LPAAT or AGPAT); sn-glycerol-3-phosphate acyltransferase (GPAT); acyl-CoA: dihydroxyacetone-phosphate acyltransferase (DHAPAT); and 2-acylglycerophosphatidylethanolamine acyltransferase (LPEAT). As referred to herein, acyltransferases preferably include a catalytic domain of about 100-250 amino acid residues in length, preferably about 130-200 amino acid residues in length, or more preferably about 160-200 amino acid residues in length. An acyltransferase domain typically includes at least one of four blocks of homology commonly found in members of the acyltransferase family. The four blocks are each characterized by the following motifs: (1) [NX]-H-[RQ]-S-X-[LYIM]-D, SEQ ID NO:87; (2) G-X-[IF]-F-I-[RD]-R, SEQ ID NO:88; (3) F-[PLI]-E-G-[TG]-R-[SX]-[RX], SEQ ID NO:89; and (4) [VI]-[PX]-[IVL]-[IV]-P-[VI], SEQ ID NO:90. Specificity of an acyltransferase for acylation of a particular lipid target can be predicted by the presence of sequences within the four blocks, whereby particular amino acid residues are associated with particular classes of acyltransferases (as described in Lewin et al., (1999) *Biochemistry* 38:5764-71, for example, the contents of which are incorporated herein by reference). For example, 53320 contains some residues in these blocks of homology that are typically found in LPAATs and not typically found in GPATs: (1) amino acid residues N in block 1 (e.g., N at amino acid residue 84 of SEQ ID NO:84; and (2) amino acid residue P in block 3 (e.g., P at amino acid residue 164 of SEQ ID NO:84). Based on these sequence similarities, the 53320 molecules of the present invention are predicted to have similar biological activities as acyltransferase family members.

Typically, acyltransferases play a role in diverse cellular processes. For example, the biosynthesis of complex lipids involves specific acylation reactions catalyzed by acyltransferases. These reactions are important for the formation of both storage lipids, triacylglycerols, as well as structural lipids such as phospholipids and galactolipids. Acyltransferases also participate in signaling by regulating the levels of lipids that function as signaling molecules in diverse cellular processes.

In a preferred embodiment, 53320 polypeptides function as LPA acyltransferases (also "LPAAT" and "AGPAT") that converts LPA to PA, both of which have the capacity to mediate signaling between and within cells. LPA and PA are potent mitogens that signal through the EDG family and ras pathways. These pathways can, directly or indirectly, induce chemotactic migration of endothelial cells and induce cytokine expression.

The molecules of the present invention can be involved in one or more of: 1) the transfer of an acyl chain to a lipid precursor; 2) the conversion of LPA to PA; 3) the regulation of lipid biosynthesis; 4) the regulation of chemotactic migration of endothelial cells; 5) the regulation of proliferation of endothelial cells; 6) the regulation of cytokine expression; 7) the regulation of wound healing; 8) the regulation of angiogenesis, e.g., near or within a tumor or near or within a wound; 9) the regulation of platelet aggregation; 10) the modulation of vasoconstriction; 11) the modulation of mitogenesis; 12) the modulation of cellular differentiation; 13) the modulation of tumor cell growth and invasion; 14) the modulation of actin cytoskleleton remodeling; 15) the regulation of monocyte chemotaxis; or 16) the modulation of neurite retraction.

A 53320 polypeptide can include a "acyltransferase domain" or regions homologous with an "acyltransferase domain".

Figure 71:
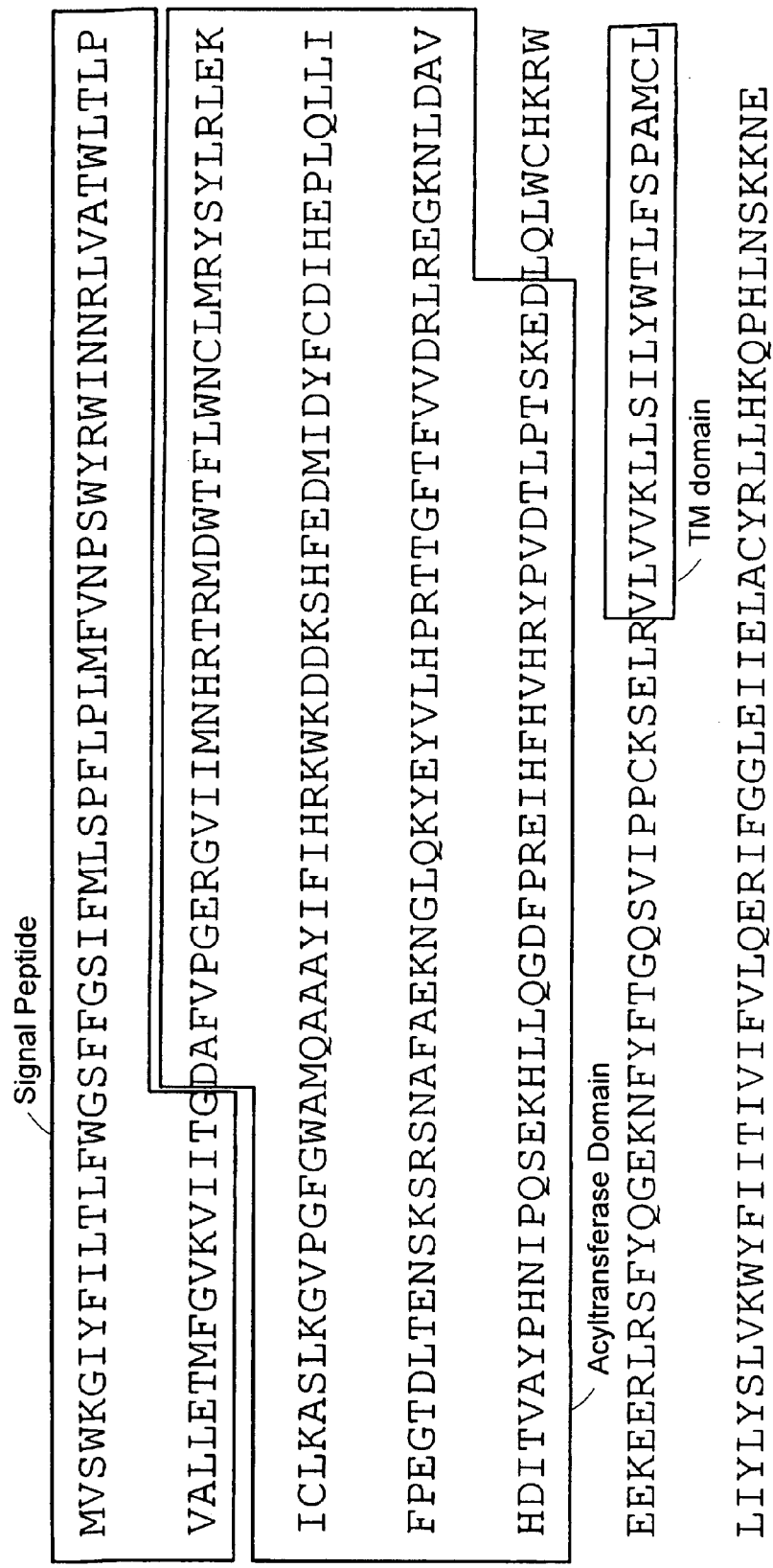
FIG. 71 depicts structural features of one embodiment of the 53320 polypeptide.

As used herein, the term "acyltransferase domain" includes an amino acid sequence of about 80-300 amino acid residues in length and having a bit score for the alignment of the sequence to the acyltransferase domain (HMM) of at least 8. Preferably, an acyltransferase domain includes at least about 100-250 amino acids, more preferably about 130-200 amino acid residues, or about 160-200 amino acids and has a bit score for the alignment of the sequence to the acyltransferase domain (HMM) of at least 16 or greater. The acyltransferase domain (HMM) has been assigned the PFAM Accession PF01553. An alignment of the acyltransferase domain (amino acids 71 to 261 of SEQ ID NO:84) of human 53320 with a consensus amino acid sequence derived from a hidden Markov model is depicted in FIG. 71.

In a preferred embodiment 53320 polypeptide or protein has a "acyltransferase domain" or a region which includes at least about 100-250 more preferably about 130-200 or 160-200 amino acid residues and has at least about 60%, 70%, 80%, 90%, 95%, 99%, or 100% homology with an "acyltransferase domain," e.g., the acyltransferase domain of human 53320 (e.g., amino acid residues 71-261 of SEQ ID NO:84).

To identify the presence of an "acyltransferase" domain in a 53320 protein sequence, and make the determination that a polypeptide or protein of interest has a particular profile, the amino acid sequence of the protein can be searched against a database of HMMs (e.g., the Pfam database, release 2.1) using the default parameters. For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al., (1997) *Proteins* 28(3):405-420 and a detailed description of HMMs can be found, for example, in Gribskov et al., (1990) *Meth. Enzymol.* 183:146-159; Gribskov et al., (1987) *Proc. Natl. Acad. Sci. USA* 84:4355-4358; Krogh et al., (1994) *J. Mol. Biol.* 235:1501-1531; and Stultz et al., (1993) *Protein Sci.* 2:305-314, the contents of which are incorporated herein by reference.

In one embodiment, a 53320 protein includes at least one transmembrane domain. As used herein, the term "transmembrane domain" includes an amino acid sequence of about 15 amino acid residues in length that spans a phospholipid membrane. More preferably, a transmembrane domain includes about at least 18, 20, 22, 24, 25, 30, 35 or 40 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta W. N. et al., (1996) *Annual Rev. Neuro. sci.* 19:235-63, the contents of which are incorporated herein by reference.

In a preferred embodiment, a 53320 polypeptide or protein has at least one transmembrane domain or a region which includes at least 18, 20, 22, 24, 25, 30, 35 or 40 amino acid residues and has at least about 60%, 70% 80% 90% 95%, 99%, or 100% homology with a "transmembrane domain," e.g., at least one transmembrane domain of human 53320 (e.g., about amino acid residues 304-328 of SEQ ID NO:84).

In another embodiment, a 53320 protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally-occurring 53320, or 53320-like protein.

In a preferred embodiment, a 53320 polypeptide or protein has a "non-transmembrane domain" or a region which includes at least about 1-350, preferably about 200-320, more preferably about 230-300, and even more preferably about 240-280 amino acid residues, and has at least about 60%, 70% 80% 90% 95%, 99% or 100% homology with a "non-transmembrane domain", e.g., a non-transmembrane domain of human 53320 (e.g., residues 64-303 and/or 329-376 of SEQ ID NO:84). Preferably, a non-transmembrane domain, e.g., residues 64-303 of SEQ ID NO:84, is capable of catalytic activity (e.g., catalyzing an acylation reaction).

A non-transmembrane domain located at the N-terminus of a 53320 protein or polypeptide is referred to herein as an "N-terminal non-transmembrane domain." As used herein, an "N-terminal non-transmembrane domain" includes an amino acid sequence having about 1-350, preferably about 30-325, more preferably about 50-320, or even more preferably about 80-310 amino acid residues in length and is located outside the boundaries of a membrane. For example, an N-terminal non-transmembrane domain is located at about amino acid residues 1-303 of SEQ ID NO:84.

Similarly, a non-transmembrane domain located at the C-terminus of a 53320 protein or polypeptide is referred to herein as a "C-terminal non-transmembrane domain." As used herein, an "C-terminal non-transmembrane domain" includes an amino acid sequence having about 1-300, preferably about 15-290, preferably about 20-270, more preferably about 25-255 amino acid residues in length and is located outside the boundaries of a membrane. For example, an C-terminal non-transmembrane domain is located at about amino acid residues 329-376 of SEQ ID NO:84.

A 53320 molecule can further include a signal sequence. As used herein, a "signal sequence" refers to a peptide of about 20-80 amino acid residues in length which occurs at the N-terminus of secretory and integral membrane proteins and which contains a majority of hydrophobic amino acid residues. For example, a signal sequence contains at least about 12-25 amino acid residues, preferably about 30-70 amino acid residues, more preferably about 61 amino acid residues, and has at least about 40-70%, preferably about 50-65%, and more preferably about 55-60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, a 53320 protein contains a signal sequence of about amino acids 1-6 of SEQ ID NO:84. The "signal sequence" is cleaved during processing of the mature protein. The mature 53320 protein corresponds to amino acids 17 to 782 of SEQ ID NO:84.

As the 53320 polypeptides of the invention may modulate 53320-mediated activities, they may be useful as of for developing novel diagnostic and therapeutic agents for 53320-mediated or related disorders, as described below.

As used herein, a "53320 activity", "biological activity of 53320" or "functional activity of 53320", refers to an activity exerted by a 53320 protein, polypeptide or nucleic acid molecule on e.g., a 53320-responsive cell or on a 53320 substrate, e.g., a lipid or protein substrate, as determined in vivo or in vitro. In one embodiment, a 53320 activity is a direct activity, such as an association with a 53320 target molecule. A "target molecule" or "binding partner" is a molecule with which a 53320 protein binds or interacts in nature, e.g., a lipid to which the 53320 protein attaches an acyl chain. A 53320 activity can also be an indirect activity, e.g., a cellular signaling activity mediated by interaction of the 53320 protein with a 53320 ligand. For example, the 53320 proteins of the present invention can have one or more of the following activities: 1) catalysis of the transfer of an acyl chain to a lipid precursor (e.g., a 1-acyl-sn-glycerol-3-phosphate acyltransferase ),e.g., conversion of LPA to PA, or an analogous reaction; 2) regulation of lipid biosynthesis; 3) regulation of endothelial cell behavior; 4) regulation of platelet aggregation; 5) modulation of mitogenesis; 6) modulation of cellular differentiation; 7) modulation of actin cytoskleleton remodeling; 8) regulation of monocyte chemotaxis; 9) regulation of angiogenesis; 10) modulation of vasoconstriction; 11) modulation of glutamate and glucose uptake by astrocytes; 12) modulation of tumor cell growth and invasion; 13) formation of synaptic-like microvesicles; and 14) the ability to antagonize or inhibit, competitively or non-competitively, any of 1-13.

The 53320 molecules can act as novel diagnostic targets and therapeutic agents for controlling one or more of cellular proliferative and/or differentiative disorders, e.g., a neoplasia, e.g., carcinoma, sarcoma, or metastatic disorders. The 53320 molecules can act as novel diagnostic targets and therapeutic agents for controlling breast cancer, colon cancer, lung cancer, ovarian cancer, metastasis of such cancers and the like. A metastatic tumor can arise from a multitude of primary tumor types, including but not limited to those of breast, lung, liver, colon and ovarian origin. The 53320 molecules are associated with angiogenesis by endothelial cells, e.g., in proximity to a tumor.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometeriod tumors, clear cell adenocarcinoma, adenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Examples of cancers or neoplastic conditions, in addition to the ones described above, include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

As explicated in the Examples, below, 53320 mRNA is expressed under a variety of conditions, which are summarized as follows:

Endothelial phase 1 panel: 53320 is up-regulated in proliferating endothelial cells as compared to arrested endothelial cells in 5/5 independent experiments.

Endothelial tube panel: 53320 is up-regulated in endothelial tube formation in 4/4 matrigel experiments and 2/2 collagen gel experiments.

Oncology panel: 53320 is up-regulated in 4/8 breast tumors, 8/8 lung tumors, 3/5 colon tumors and 4/4 liver metastasis of colon tumors as compared to normal controls.

Angiogenesis panel: 53320 is expressed at relatively high levels in some angiogenic tissues including fetal liver, Wilm's tumors and endometrial adenocarcinoma.

Angiogenic tissues: 3/10 tissues are positive, including fetal adrenal, neuroblastoma, and Wilm's tumor.

Lung samples: 6/6 tumors are positive, often upregulated in comparison to normal bronchial epithelium.

Breast samples: 2/2 tumors and 0/1 normal are positive.

As the 53320 mRNA is expressed in endothelial cells undergoing proliferation and endothelial tube formation, it is likely that 14094 molecules of the present invention are involved in angiogenic activity. Thus, the 14094 molecules can act as novel diagnostic targets and therapeutic agents for controlling disorders involving angiogenesis.

As the 53320 mRNA is expressed in the tumors of the breast, lung, colon, and liver, 53320 molecules of the present invention are involved in disorders characterized by aberrant activity of these cells. For example, 53320 polypeptide in endothelial cells near and within this tumors can direct blood vessel formation therein. Thus, the 53320 molecules can act as novel diagnostic targets and therapeutic agents for controlling disorders involving aberrant activity of these cells.

The presence of 53320 RNA or protein can also be used to identify a tumor derived from breast, lung, colon, or liver, or an endothelial cell, e.g., associated with angiogenic activity. Expression can also be used to diagnose or stage a disorder, e.g., a cancer, a breast, lung, colon, or liver disorder. Expression can be determined by evaluating RNA, e.g., by hybridization of a 53320 specific probe, or with a 53320 specific antibody.

The 53320 protein, fragments thereof, and derivatives and other variants of the sequence in SEQ ID NO:84 thereof are collectively referred to as "polypeptides or proteins of the invention" or "53320 polypeptides or proteins". Nucleic acid molecules encoding such polypeptides or proteins are collectively referred to as "nucleic acids of the invention" or "53320 nucleic acids." 53320 molecules refer to 53320 nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:83 or SEQ ID NO:85, corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a 53320 protein. The gene can optionally further include non-coding sequences, e.g., regulatory sequences and introns. Preferably, a gene encodes a mammalian 53320 protein or derivative thereof.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of 53320 protein is at least 10% pure. In a preferred embodiment, the preparation of 53320 protein has less than about 30%, 20%, 10% and more preferably 5% (by dry weight), of non-53320 protein (also referred to herein as a "contaminating protein"), or of chemical precursors or non-53320 chemicals. When the 53320 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 53320 without abolishing or substantially altering a 53320 activity. Preferably the alteration does not substantially alter the 53320 activity, e.g., the activity is at least 20%, 40%, 60%, 70% or 80% of wild-type. An "essential" amino acid residue is a residue that, when altered from the wild-type sequence of 53320, results in abolishing a 53320 activity such that less than 20% of the wild-type activity is present. For example, conserved amino acid residues in 53320 are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a 53320 protein is preferably replaced with another amino acid residue from the same side chain family. Alternatively, in another embodiment, mutations can be introduced randomly along all or part of a 53320 coding sequence, such as by saturation mutagenesis, and the resultant mutants can be screened for 53320 biological activity to identify mutants that retain activity. Following mutagenesis of SEQ ID NO:83 or SEQ ID NO:85, the encoded protein can be expressed recombinantly and the activity of the protein can be determined.

As used herein, a "biologically active portion" of a 53320 protein includes a fragment of a 53320 protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a 53320 molecule and a non-53320 molecule or between a first 53320 molecule and a second 53320 molecule (e.g., a dimerization interaction). Biologically active portions of a 53320 protein include peptides comprising amino acid sequences sufficiently homologous to or derived from the amino acid sequence of the 53320 protein, e.g., the amino acid sequence shown in SEQ ID NO:84, which include less amino acids than the full length 53320 proteins, and exhibit at least one activity of a 53320 protein.

Typically, biologically active portions comprise a domain or motif with at least one activity of the 53320 protein, e.g., catalysis of the transfer of an acyl chain. A biologically active portion of a 53320 protein can be a polypeptide which is, for example, 10, 25, 50, 100, 200 or more amino acids in length. Biologically active portions of a 53320 protein can be used as targets for developing agents which modulate a 53320 mediated activity, e.g., catalysis of the transfer of an acyl chain.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J Mol. Biol.* 48:444-453 ) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to 53320 nucleic acid molecules of the invention. BLAST protein searches can be performed with the XBLAST program, score=50, wordlength=3 to obtain amino acid sequences homologous to 53320 protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used.

Particular 53320 polypeptides of the present invention have an amino acid sequence substantially identical to the amino acid sequence of SEQ ID NO:84. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%. 91%, 92%, 93%, 94%, 95%, 96%, 97%, 98% or 99% identity to SEQ ID NO:84 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:83 or 85 are termed substantially identical.

"Misexpression or aberrant expression", as used herein, refers to a non-wildtype pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

Various aspects of the invention are described in further detail below.

Isolated Nucleic Acid Molecules of 53320

In one aspect, the invention provides, an isolated or purified, nucleic acid molecule that encodes a 53320 polypeptide described herein, e.g., a full-length 53320 protein or a fragment thereof, e.g., a biologically active portion of 53320 protein. Also included is a nucleic acid fragment suitable for use as a hybridization probe, which can be used, e.g., to identify a nucleic acid molecule encoding a polypeptide of the invention, 53320 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:83, or a portion of any of these nucleotide sequences. In one embodiment, the nucleic acid molecule includes sequences encoding the human 53320 protein (i.e., "the coding region" of SEQ ID NO:83, as shown in SEQ ID NO:85), as well as 5' untranslated sequences. Alternatively, the nucleic acid molecule can include only the coding region of SEQ ID NO:83 (e.g., SEQ ID NO:85) and, e.g., no flanking sequences which normally accompany the subject sequence. In another embodiment, the nucleic acid molecule encodes a sequence corresponding to a fragment of the protein from about amino acid 71 to 261.

In another embodiment, an isolated nucleic acid molecule of the invention includes a nucleic acid molecule which is a complement of the nucleotide sequence shown in SEQ ID NO:83 or SEQ ID NO:85, or a portion of any of these nucleotide sequences. In other embodiments, the nucleic acid molecule of the invention is sufficiently complementary to the nucleotide sequence shown in SEQ ID NO:83 or SEQ ID NO:85, such that it can hybridize (e.g., under a stringency condition described herein) to the nucleotide sequence shown in SEQ ID NO:83 or 85, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO:83 or SEQ ID NO:85, or a portion, preferably of the same length, of any of these nucleotide sequences.

53320 Nucleic Acid Fragments

A nucleic acid molecule of the invention can include only a portion of the nucleic acid sequence of SEQ ID NO:83 or 85. For example, such a nucleic acid molecule can include a fragment which can be used as a probe or primer or a fragment encoding a portion of a 53320 protein, e.g., an immunogenic or biologically active portion of a 53320 protein. A fragment can comprise those nucleotides of SEQ ID NO:83, which encode an acyltransferase domain of human 53320. The nucleotide sequence determined from the cloning of the 53320 gene allows for the generation of probes and primers designed for use in identifying and/or cloning other 53320 family members, or fragments thereof, as well as 53320 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 15, 24, 70, 100, 150, or 200 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 53320 nucleic acid fragment can include a sequence corresponding to an acyltransferase domain.

53320 probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:83 or SEQ ID NO:85, or of a naturally occurring allelic variant or mutant of SEQ ID NO:83 or SEQ ID NO:85.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: an acyltransferase domain (e.g., about amino acid residues 71-261 of SEQ ID NO:84).

In another embodiment a set of primers is provided, e.g., primers suitable for use in a PCR, which can be used to amplify a selected region of a 53320 sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: an acyltransferase domain (e.g., about amino acid residues 71-261 of SEQ ID NO:84)

A nucleic acid fragment can encode an epitope bearing region of a polypeptide described herein.

A nucleic acid fragment encoding a "biologically active portion of a 53320 polypeptide" can be prepared by isolating a portion of the nucleotide sequence of SEQ ID NO:83 or 85, which encodes a polypeptide having a 53320 biological activity (e.g., the biological activities of the 53320 proteins are described herein), expressing the encoded portion of the 53320 protein (e.g., by recombinant expression in vitro) and assessing the activity of the encoded portion of the 53320 protein. For example, a nucleic acid fragment encoding a biologically active portion of 53320 includes an acyltransferase domain, e.g., amino acid residues about 71 to 261 of SEQ ID NO:84. A nucleic acid fragment encoding a biologically active portion of a 53320 polypeptide, may comprise a nucleotide sequence which is greater than 300, 400, or 500 nucleotides in length.

In preferred embodiments, a nucleic acid includes a nucleotide sequence which is about 300, 400, 500, 600, 700, 800, 900, 1000, 1100, 1200, 1300 or more nucleotides in length and hybridizes under a stringency condition described herein to a nucleic acid molecule of SEQ ID NO:83, or SEQ ID NO:85. In some embodiment, the fragment includes at least one contiguous amino acid from the region of about nucleotides 1-80, 81-300, 200-500, 400-800, 600-1000, or 800-1200 of SEQ ID NO:83.

53320 Nucleic Acid Variants

The invention further encompasses nucleic acid molecules that differ from the nucleotide sequence shown in SEQ ID NO:83 or SEQ ID NO:85. Such differences can be due to degeneracy of the genetic code (and result in a nucleic acid which encodes the same 53320 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:84. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:83 or 85, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the nucleotide sequence shown in SEQ ID NO:84 or a fragment of this sequence. Such nucleic acid molecules can readily be identified as being able to hybridize under a stringency condition described herein, to the nucleotide sequence shown in SEQ ID NO:84 or a fragment of the sequence. Nucleic acid molecules corresponding to orthologs, homologs, and allelic variants of the 53320 cDNAs of the invention can further be isolated by mapping to the same chromosome or locus as the 53320 gene.

Preferred variants include those that are correlated with acyltransferase activity.

Allelic variants of 53320, e.g., human 53320, include both functional and non-functional proteins. Functional allelic variants are naturally occurring amino acid sequence variants of the 53320 protein within a population that maintain the ability to modulate the phosphorylation state of itself or another protein or polypeptide. Functional allelic variants will typically contain only conservative substitution of one or more amino acids of SEQ ID NO:84, or substitution, deletion or insertion of non-critical residues in non-critical regions of the protein. Non-functional allelic variants are naturally-occurring amino acid sequence variants of the 53320, e.g., human 53320, protein within a population that do not have the ability to attach an acyl chain to a lipid precursor. Non-functional allelic variants will typically contain a non-conservative substitution, a deletion, or insertion, or premature truncation of the amino acid sequence of SEQ ID NO:84, or a substitution, insertion, or deletion in critical residues or critical regions of the protein.

Moreover, nucleic acid molecules encoding other 53320 family members and, thus, which have a nucleotide sequence which differs from the 53320 sequences of SEQ ID NO:83 or SEQ ID NO:85 are intended to be within the scope of the invention.

Antisense Nucleic Acid Molecules, Ribozymes and Modified 53320 Nucleic Acid Molecules In another aspect, the invention features, an isolated nucleic acid molecule which is antisense to 53320. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 53320 coding strand, or to only a portion thereof (e.g., the coding region of human 53320 corresponding to SEQ ID NO:85). In another embodiment, the antisense nucleic acid molecule is antisense to a "non-coding region" of the coding strand of a nucleotide sequence encoding 53320 (e.g., the 5' and 3' untranslated regions).

An antisense nucleic acid can be designed such that it is complementary to the entire coding region of 53320 mRNA, but more preferably is an oligonucleotide which is antisense to only a portion of the coding or noncoding region of 53320 mRNA. For example, the antisense oligonucleotide can be complementary to the region surrounding the translation start site of 53320 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 53320 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215: 327-330).

In still another embodiment, an antisense nucleic acid of the invention is a ribozyme. A ribozyme having specificity for a 53320-encoding nucleic acid can include one or more sequences complementary to the nucleotide sequence of a 53320 cDNA disclosed herein (i.e., SEQ ID NO:83 or SEQ ID NO:85), and a sequence having known catalytic sequence responsible for mRNA cleavage (see U.S. Pat. No. 5,093,246 or Haselhoff and Gerlach (1988) Nature 334:585-591). For example, a derivative of a Tetrahymena L-19 IVS RNA can be constructed in which the nucleotide sequence of the active site is complementary to the nucleotide sequence to be cleaved in a 53320-encoding mRNA. See, e.g., Cech et al. U.S. Pat. No. 4,987,071; and Cech et al. U.S. Pat. No. 5,116,742. Alternatively, 53320 mRNA can be used to select a catalytic RNA having a specific ribonuclease activity from a pool of RNA molecules. See, e.g., Bartel, D. and Szostak, J. W. (1993) Science 261:1411-1418.

53320 gene expression can be inhibited by targeting nucleotide sequences complementary to the regulatory region of the 53320 (e.g., the 53320 promoter and/or enhancers) to form triple helical structures that prevent transcription of the 53320 gene in target cells. See generally, Helene, C. (1991) Anticancer Drug Des. 6:569-84; Helene, C. i (1992) Ann. N. Y. Acad. Sci. 660:27-36; and Maher, L. J. (1992) Bioassays 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 53320 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) Nature Biotech. 19:17 and Faria et al. (2001) Nature Biotech. 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) Bioorganic & Medicinal Chemistry 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. Proc. Natl. Acad. Sci. 93: 14670-675.

PNAs of 53320 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 53320 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553-6556; Lemaitre et al. (1987) Proc. Natl. Acad. Sci. USA 84:648-652; PCT Publication No. W088/09810) or the blood-brain barrier (see, e.g., PCT Publication No. W089/10134). In addition, oligonucleotides can be modified with hybridization-triggered cleavage agents (see, e.g., Krol et al. (1988) Bio-Techniques 6:958-976) or intercalating agents. (see, e.g., Zon (1988) Pharm. Res. 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 53320 nucleic acid of the invention, two complementary regions one having a fluorophore and one a quencher such that the molecular beacon is useful for quantitating the presence of the 53320 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 53320 Polypeptides

In another aspect, the invention features, an isolated 53320 protein, or fragment, e.g., a biologically active portion, for use as immunogens or antigens to raise or test (or more generally to bind) anti-53320 antibodies. 53320 protein can be isolated from cells or tissue sources using standard protein purification techniques. 53320 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a 53320 polypeptide has one or more of the following characteristics:

(i) it has the ability to catalyze the transfer of an acyl chain to a lipid precursor;

(ii) it has a molecular weight, e.g., a deduced molecular weight, preferably ignoring any contribution of post translational modifications, amino acid composition or other physical characteristic of SEQ ID NO:84;

(iii) it has an overall sequence similarity of at least 50%, preferably at least 60%, more preferably at least 70, 80, 90, or 95%, with a polypeptide a of SEQ ID NO:84;

(iv) it can be found in endothelial cells, e.g., within a tumor such as a lung, breast, colon, or ovarian tumor;

(v) it has an acyltransferase domain which is preferably about 70%, 80%, 90% or 95% with amino acid residues 71-261 of SEQ ID NO:84;

(vi) it includes N at amino acid residue 84 and P at amino acid residue 164 of SEQ ID NO:84;

(vii) it has a signal sequence which is excised; and (viii) it has at least 70%, preferably 80%, and most preferably 95% of the cysteines found amino acid sequence of the native protein.

In a preferred embodiment the 53320 protein, or fragment thereof, differs from the corresponding sequence in SEQ ID NO:2. In one embodiment it differs by at least one but by less than 15, 10 or 5 amino acid residues. In another it differs from the corresponding sequence in SEQ ID NO:84 by at least one residue but less than 20%, 15%, 10% or 5% of the residues in it differ from the corresponding sequence in SEQ ID NO:84. (If this comparison requires alignment the sequences should be aligned for maximum homology. "Looped" out sequences from deletions or insertions, or mismatches, are considered differences.) The differences are, preferably, differences or changes at a non essential residue or a conservative substitution. In one embodiment, a biologically active portion of a 53320 protein includes an acyltransferase domain. In another embodiment, a biologically active portion of a 53320 protein includes a leucine zipper domain. Moreover, other biologically active portions, in which other regions of the protein are deleted, can be prepared by recombinant techniques and evaluated for one or more of the functional activities of a native 53320 protein.

Other embodiments include a protein that contain one or more changes in amino acid sequence, e.g., a change in an amino acid residue which is not essential for activity. Such 53320 proteins differ in amino acid sequence from SEQ ID NO:84, yet retain biological activity.

In one embodiment, the protein includes an amino acid sequence at least about 50%, 55%, 60%, 65%, 70%, 75%, 80%, 85%, 90%, 95%, 98% or more homologous to SEQ ID NO:84.

A 53320 protein or fragment is provided which varies from the sequence of SEQ ID NO:84 in regions defined by amino acids about 71 to 261 by at least one but by less than 15, 10 or 5 amino acid residues in the protein or fragment but which does not differ from SEQ ID NO:84 in regions defined by amino acids about 71 to 261. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 53320 protein includes an acyltransferase domain. Moreover, other biologically active portions, in which other regions of the protein are deleted, can be prepared by recombinant techniques and evaluated for one or more of the functional activities of a native 53320 protein.

In a preferred embodiment, the 53320 protein has an amino acid sequence shown in SEQ ID NO:84. In other embodiments, the 53320 protein is substantially identical to SEQ ID NO:84. In yet another embodiment, the 53320 protein is substantially identical to SEQ ID NO:84 and retains the functional activity of the protein of SEQ ID NO:84, as described in detail in the subsections above.

53320 Chimeric or Fusion Proteins

In another aspect, the invention provides 53320 chimeric or fusion proteins. As used herein, a 53320 "chimeric protein" or "fusion protein" includes a 53320 polypeptide linked to a non-53320 polypeptide. A "non-53320 polypeptide" refers to a polypeptide having an amino acid sequence corresponding to a protein which is not substantially homologous to the 53320 protein, e.g., a protein which is different from the 53320 protein and which is derived from the same or a different organism. The 53320 polypeptide of the fusion protein can correspond to all or a portion e.g., a fragment described herein of a 53320 amino acid sequence. In a preferred embodiment, a 53320 fusion protein includes at least one (or two) biologically active portion of a 53320 protein. The non-53320 polypeptide can be fused to the N-terminus or C-terminus of the 53320 polypeptide.

The fusion protein can include a moiety which has a high affinity for a ligand. For example, the fusion protein can be a GST-53320 fusion protein in which the 53320 sequences are fused to the C-terminus of the GST sequences. Such fusion proteins can facilitate the purification of recombinant 53320. Alternatively, the fusion protein can be a 53320 protein containing a heterologous signal sequence at its N-terminus. In certain host cells (e.g., mammalian host cells), expression and/or secretion of 53320 can be increased through use of a heterologous signal sequence.

Fusion proteins can include all or a part of a serum protein, e.g., an IgG constant region, or human serum albumin.

The 53320 fusion proteins of the invention can be incorporated into pharmaceutical compositions and administered to a subject in vivo. The 53320 fusion proteins can be used to affect the bioavailability of a 53320 substrate. 53320 fusion proteins may be useful therapeutically for the treatment of disorders caused by, for example, (i) aberrant modification or mutation of a gene encoding a 53320 protein; (ii) mis-regulation of the 53320 gene; and (iii) aberrant post-translational modification of a 53320 protein.

Moreover, the 53320-fusion proteins of the invention can be used as immunogens to produce anti-53320 antibodies in a subject, to purify 53320 ligands and in screening assays to identify molecules which inhibit the interaction of 53320 with a 53320 substrate.

Expression vectors are commercially available that already encode a fusion moiety (e.g., a GST polypeptide). A 53320-encoding nucleic acid can be cloned into such an expression vector such that the fusion moiety is linked in-frame to the 53320 protein.

Variants of 53320 Proteins

In another aspect, the invention also features a variant of a 53320 polypeptide, e.g., which functions as an agonist (mimetics) or as an antagonist. Variants of the 53320 proteins can be generated by mutagenesis, e.g., discrete point mutation, the insertion or deletion of sequences or the truncation of a 53320 protein. An agonist of the 53320 proteins can retain substantially the same, or a subset, of the biological activities of the naturally occurring form of a 53320 protein. An antagonist of a 53320 protein can inhibit one or more of the activities of the naturally occurring form of the 53320 protein by, for example, competitively modulating a 53320-mediated activity of a 53320 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 53320 protein.

Variants of a 53320 protein can be identified by screening combinatorial libraries of mutants, e.g., truncation mutants, of a 53320 protein for agonist or antagonist activity.

Libraries of fragments e.g., N terminal, C terminal, or internal fragments, of a 53320 protein coding sequence can be used to generate a variegated population of fragments for screening and subsequent selection of variants of a 53320 protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of 53320 proteins. Recursive ensemble mutagenesis (REM), a new technique which enhances the frequency of functional mutants in the libraries, can be used in combination with the screening assays to identify 53320 variants (Arkin and Yourvan (1992) *Proc. Natl. Acad. Sci. USA* 89:7811-7815; Delgrave et al. (1993) *Protein Engineering* 6:327-331).

Cell based assays can be exploited to analyze a variegated 53320 library. For example, a library of expression vectors can be transfected into a cell line, e.g., a cell line, which ordinarily responds to 53320 in a substrate-dependent manner. The transfected cells are then contacted with 53320 and the effect of the expression of the mutant on signaling by the 53320 substrate can be detected, e.g., by measuring acyltransferase activity. Plasmid DNA can then be recovered from the cells which score for inhibition, or alternatively, potentiation of signaling by the 53320 substrate, and the individual clones further characterized.

In another aspect, the invention features a method of making a 53320 polypeptide, e.g., a peptide having a non-wild type activity, e.g., an antagonist, agonist, or super agonist of a naturally occurring 53320 polypeptide, e.g., a naturally occurring 53320 polypeptide. The method includes: altering the sequence of a 53320 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 53320 polypeptide a biological activity of a naturally occurring 53320 polypeptide. The method includes: altering the sequence, e.g., by substitution or deletion of one or more residues, of a 53320 polypeptide, e.g., altering the sequence of a non-conserved region, or a domain or residue described herein, and testing the altered polypeptide for the desired activity.

Anti-53320 Antibodies

In another aspect, the invention provides an anti-53320 antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-53320 antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., 53320 polypeptide or fragment thereof. Examples of antigen-binding fragments of the anti-53320 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-53320 antibody can be a polyclonal or a monoclonal antibody. In other embodiments, the antibody can be recombinantly produced, e.g., produced by phage display or by combinatorial methods.

Phage display and combinatorial methods for generating anti-53320 antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffiths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, the contents of all of which are incorporated by reference herein).

In one embodiment, the anti-53320 antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art. Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

An anti-53320 antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559). antibody may be replaced with at least a portion of a non-human CDR or only some of the CDR's may be replaced with non-human CDR's. It is only necessary to replace the number of CDR's required for binding of the humanized antibody to a 53320 or a fragment thereof. A humanized or CDR-grafted antibody will have at least one or two but generally all three recipient CDR's (of heavy and or light immuoglobulin chains) replaced with a donor CDR. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 53320 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

A full-length 53320 protein or, antigenic peptide fragment of 53320 can be used as an immunogen or can be used to identify anti-53320 antibodies made with other immunogens, e.g., cells, membrane preparations, and the like. The antigenic peptide of 53320 should include at least 8 amino acid residues of the amino acid sequence shown in SEQ ID NO:84 and encompasses an epitope of 53320. Preferably, the antigenic peptide includes at least 10 amino acid residues, more preferably at least 15 amino acid residues, even more preferably at least 20 amino acid residues, and most preferably at least 30 amino acid residues.

Fragments of 53320 which include, e.g., residues 130-150 of SEQ ID NO:84 of SEQ ID NO:87 can be used to make, e.g., used as immunogens, or used to characterize the specificity of an antibody or antibodies against what are believed to be hydrophilic regions of the 53320 protein. Similarly, a fragment of 53320 which includes, e.g., residues 300-350 of SEQ ID NO:84 can be used to make an antibody against what is believed to be a hydrophobic region of the 53320 protein; a fragment of 53320 which includes residues 71-261 of SEQ ID NO:84 can be used to make an antibody against the acyltransferase region of the 53320 protein. Antibodies reactive with, or specific for, any of these regions, or other regions or domains described herein are provided.

Antibodies which bind only native 53320 protein, only denatured or otherwise non-native 53320 protein, or which bind both, are with in the invention. Antibodies with linear or conformational epitopes are within the invention. Conformational epitopes can sometimes be identified by identifying antibodies which bind to native but not denatured 53320 protein.

Preferred epitopes encompassed by the antigenic peptide are regions of 53320 are located on the surface of the protein, e.g., hydrophilic regions, as well as regions with high antigenicity. For example, an Emini surface probability analysis of the human 53320 protein sequence can be used to indicate the regions that have a particularly high probability of being localized to the surface of the 53320 protein and are thus likely to constitute surface residues useful for targeting antibody production.

In a preferred embodiment the antibody can bind to the extracellular portion of the 53320 protein, e.g., it can bind to a whole cell which expresses the 53320 protein. In another embodiment, the antibody binds an intracellular portion of the 53320 protein. In preferred embodiments antibodies can bind one or more of purified antigen, membrane associated antigen, tissue, e.g., tissue sections, whole cells, preferably living cells, lysed cells, cell fractions, e.g., membrane fractions.

The anti-53320 antibody can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target 53320 protein.

In a preferred embodiment the antibody has: effector function; and can fix complement. In other embodiments the antibody does not; recruit effector cells; or fix complement.

In a preferred embodiment, the antibody has reduced or no ability to bind an Fe receptor. For example., it is a isotype or subtype, fragment or other mutant, which does not support binding to an Fc receptor, e.g., it has a mutagenized or deleted Fc receptor binding region.

In a preferred embodiment, an anti-53320 antibody alters (e.g., increases or decreases) the catalysis of the transfer of an acyl chain activity of a 53320 polypeptide. For example, the antibody can bind at or in proximity to the active site, e.g., to an epitope that includes a residue within five amino acids of N at amino acid residue 84 of SEQ ID NO:84 or P at amino acid residue 164 of SEQ ID NO:84.

The antibody can be coupled to a toxin, e.g., a polypeptide toxin, e,g, ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-53320 antibody (e.g., monoclonal antibody) can be used to isolate 53320 by standard techniques, such as affinity chromatography or immunoprecipitation. Moreover, an anti-53320 antibody can be used to detect 53320 protein (e.g., in a cellular lysate or cell supernatant) in order to evaluate the abundance and pattern of expression of the protein. Anti-53320 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes a nucleic acids which encodes an anti-53320 antibody, e.g., an anti-53320 antibody described herein. Also included are vectors which include the nucleic acid and sells transformed with the nucleic acid, particularly cells which are useful for producing an antibody, e.g., mammalian cells, e.g. CHO or lymphatic cells.

The invention also includes cell lines, e.g., hybridomas, which make an anti-53320 antibody, e.g., and antibody described herein, and method of using said cells to make a 53320 antibody.

53320 Recombinant Expression Vectors, Host Cells and Genetically Engineered Cells In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 53320 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 53320 proteins, mutant forms of 53320 proteins, fusion proteins, and the like).

The recombinant expression vectors of the invention can be designed for expression of 53320 proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 53320 activity assays, (e.g., direct assays or competitive assays described in detail below), or to generate antibodies specific for 53320 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in E. coli is to express the protein in a host bacteria with an impaired capacity to proteolytically cleave the recombinant protein (Gottesman, S., (1990) Gene Expression Technology: Methods in Enzymology 185, Academic Press, San Diego, Calif. 119-128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111-2118). Such alteration of nucleic acid sequences of the invention can be carried out by standard DNA synthesis techniques.

The 53320 expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) Proc. Natl. Acad. Sci. USA 89:5547, and Paillard (1989) Human Gene Therapy 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al (1985) *Science* 230:912-916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a 53320 nucleic acid molecule within a recombinant expression vector or a 53320 nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 53320 protein can be expressed in bacterial cells (such as *E. coli*), insect cells, yeast or mammalian cells (such as Chinese hamster ovary cells (CHO) or COS cells (African green monkey kidney cells CV-1 origin SV40 cells; Gluzman (1981) *Cell*23:175-182)). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 53320 protein. Accordingly, the invention further provides methods for producing a 53320 protein using the host cells of the invention. In one embodiment, the method includes culturing the host cell of the invention (into which a recombinant expression vector encoding a 53320 protein has been introduced) in a suitable medium such that a 53320 protein is produced. In another embodiment, the method further includes isolating a 53320 protein from the medium or the host cell.

In another aspect, the invention features, a cell or purified preparation of cells which include a 53320 transgene, or which otherwise misexpress 53320. The cell preparation can consist of human or non-human cells, e.g., rodent cells, e.g., mouse or rat cells, rabbit cells, or pig cells. In preferred embodiments, the cell or cells include a 53320 transgene, e.g., a heterologous form of a 53320, e.g., a gene derived from humans (in the case of a non-human cell). The 53320 transgene can be misexpressed, e.g., overexpressed or underexpressed. In other preferred embodiments, the cell or cells include a gene that mis-expresses an endogenous 53320, e.g., a gene the expression of which is disrupted, e.g., a knockout. Such cells can serve as a model for studying disorders that are related to mutated or mis-expressed 53320 alleles or for use in drug screening.

In another aspect, the invention features, a human cell, e.g., a hematopoietic stem cell or an endothelial cell, transformed with nucleic acid which encodes a subject 53320 polypeptide.

Also provided are cells, preferably human cells, e.g., human hematopoietic or fibroblast or endothelial cells, in which an endogenous 53320 is under the control of a regulatory sequence that does not normally control the expression of the endogenous 53320 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 53320 gene. For example, an endogenous 53320 gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a 53320 polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (2001) *Nat. Biotechnol.* 19:35; and U.S. Pat. No. 5,876,742. Production of 53320 polypeptide can be regulated in the subject by administering an agent (e.g., a steroid hormone) to the subject. In another preferred embodiment, the implanted recombinant cells express and secrete an antibody specific for a 53320 polypeptide. The antibody can be any antibody or any antibody derivative described herein.

53320 Transgenic Animals

The invention provides non-human transgenic animals. Such animals are useful for studying the function and/or activity of a 53320 protein and for identifying and/or evaluating modulators of 53320 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 53320 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 53320 protein to particular cells. A transgenic founder animal can be identified based upon the presence of a 53320 transgene in its genome and/or expression of 53320 mRNA in tissues or cells of the animals. A transgenic founder animal can then be used to breed additional animals carrying the transgene. Moreover, transgenic animals carrying a transgene encoding a 53320 protein can further be bred to other transgenic animals carrying other transgenes.

53320 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses of 53320

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); c) methods of treatment (e.g., therapeutic and prophylactic); and d) in vitro modification of a lipid, e.g., for chemical production.

The isolated nucleic acid molecules of the invention can be used, for example, to express a 53320 protein (e.g., via a recombinant expression vector in a host cell in gene therapy applications), to detect a 53320 mRNA (e.g., in a biological sample) or a genetic alteration in a 53320 gene, and to modulate 53320 activity, as described further below. The 53320 proteins can be used to treat disorders characterized by insufficient or excessive production of a 53320 substrate or production of 53320 inhibitors. In addition, the 53320 proteins can be used to screen for naturally occurring 53320 substrates, to screen for drugs or compounds which modulate 53320 activity, as well as to treat disorders characterized by insufficient or excessive production of 53320 protein or production of 53320 protein forms which have decreased, aberrant or unwanted activity compared to 53320 wild type protein (e.g., tumor formation or tumor-associated angiogenesis). Moreover, the anti-53320 antibodies of the invention can be used to detect and isolate 53320 proteins, regulate the bioavailability of 53320 proteins, and modulate 53320 activity.

A method of evaluating a compound for the ability to interact with, e.g., bind, a subject 53320 polypeptide is provided. The method includes: contacting the compound with the subject 53320 polypeptide; and evaluating ability of the compound to interact with, e.g., to bind or form a complex with the subject 53320 polypeptide. This method can be performed in vitro, e.g., in a cell free system, or in vivo, e.g., in a two-hybrid interaction trap assay. This method can be used to identify naturally occurring molecules that interact with subject 53320 polypeptide. It can also be used to find natural or synthetic inhibitors of subject 53320 polypeptide. Screening methods are discussed in more detail below.

53320 Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 53320 proteins, have a stimulatory or inhibitory effect on, for example, 53320 expression or 53320 activity, or have a stimulatory or inhibitory effect on, for example, the expression or activity of a 53320 substrate. Compounds thus identified can be used to modulate the activity of target gene products (e.g., 53320 genes) in a therapeutic protocol, to elaborate the biological function of the target gene product, or to identify compounds that disrupt normal target gene interactions.

In one embodiment, the invention provides assays for screening candidate or test compounds which are substrates of a 53320 protein or polypeptide or a biologically active portion thereof. In another embodiment, the invention provides assays for screening candidate or test compounds that bind to or modulate an activity of a 53320 protein or polypeptide or a biologically active portion thereof.

An activity of a 53320 protein can be assayed following the methods described in Kume and Shimizu (1997) *Biochem Biophys Res Commun* 237:663-666.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In one embodiment, an assay is a cell-based assay in which a cell which expresses a 53320 protein or biologically active portion thereof is contacted with a test compound, and the ability of the test compound to modulate 53320 activity is determined. Determining the ability of the test compound to modulate 53320 activity can be accomplished by monitoring, for example, catalysis of the transfer of an acyl chain. The cell, for example, can be of mammalian origin, e.g., human.

The ability of the test compound to modulate 53320 binding to a compound, e.g., a 53320 substrate, or to bind to 53320 can also be evaluated. This can be accomplished, for example, by coupling the compound, e.g., the substrate, with a radioisotope or enzymatic label such that binding of the compound, e.g., the substrate, to 53320 can be determined by detecting the labeled compound, e.g., substrate, in a complex. Alternatively, 53320 could be coupled with a radioisotope or enzymatic label to monitor the ability of a test compound to modulate 53320 binding to a 53320 substrate in a complex. For example, compounds (e.g., 53320 substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 53320 substrate) to interact with 53320 with or without the labeling of any of the interactants can be evaluated. For example, a microphysiometer can be used to detect the interaction of a compound with 53320 without the labeling of either the compound or the 53320. McConnell, H. M. et al. (1992) *Science* 257: 1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 53320.

In yet another embodiment, a cell-free assay is provided in which a 53320 protein or biologically active portion thereof is contacted with a test compound and the ability of the test compound to bind to the 53320 protein or biologically active portion thereof is evaluated. Preferred biologically active portions of the 53320 proteins to be used in assays of the present invention include fragments which participate in interactions with non-53320 molecules, e.g., fragments with high surface probability scores.

Soluble and/or membrane-bound forms of isolated proteins (e.g., 53320 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 53320 protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 53320, an anti-53320 antibody or its target molecule to facilitate separation of complexed from uncomplexed forms of one or both of the proteins, as well as to accommodate automation of the assay. Binding of a test compound to a 53320 protein, or interaction of a 53320 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/53320 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 53320 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 53320 binding or activity determined using standard techniques.

Other techniques for immobilizing either a 53320 protein or a target molecule on matrices include using conjugation of biotin and streptavidin. Biotinylated 53320 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 53320 protein or target molecules but which do not interfere with binding of the 53320 protein to its target molecule. Such antibodies can be derivatized to the wells of the plate, and unbound target or 53320 protein trapped in the wells by antibody conjugation. Methods for detecting such complexes, in addition to those described above for the GST-immobilized complexes, include immunodetection of complexes using antibodies reactive with the 53320 protein or target molecule, as well as enzyme-linked assays which rely on detecting an enzymatic activity associated with the 53320 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141-8; Hage, D. S., and Tweed, S. A. (1997) *J Chromatogr B Biomed Sci Appl.* 699:499-525). Further, fluorescence energy transfer may also be conveniently utilized, as described herein, to detect binding without further purification of the complex from solution.

In a preferred embodiment, the assay includes contacting the 53320 protein or biologically active portion thereof with a known compound which binds 53320 to form an assay mixture, contacting the assay mixture with a test compound, and determining the ability of the test compound to interact with a 53320 protein, wherein determining the ability of the test compound to interact with a 53320 protein includes determining the ability of the test compound to preferentially bind to 53320 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 53320 genes herein identified. In an alternative embodiment, the invention provides methods for determining the ability of the test compound to modulate the activity of a 53320 protein through modulation of the activity of a downstream effector of a 53320 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 53320 proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with 53320 ("53320-binding proteins" or "53320-bp") and are involved in 53320 activity. Such 53320-bps can be activators or inhibitors of signals by the 53320 proteins or 53320 targets as, for example, downstream elements of a 53320-mediated signaling pathway.

The two-hybrid system is based on the modular nature of most transcription factors, which consist of separable DNA-binding and activation domains. Briefly, the assay utilizes two different DNA constructs. In one construct, the gene that codes for a 53320 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 53320 protein can be the fused to the activator domain.) If the "bait" and the "prey" proteins are able to interact, in vivo, forming a 53320-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 53320 protein.

In another embodiment, modulators of 53320 expression are identified. For example, a cell or cell free mixture is contacted with a candidate compound and the expression of 53320 mRNA or protein evaluated relative to the level of expression of 53320 mRNA or protein in the absence of the candidate compound. When expression of 53320 mRNA or protein is greater in the presence of the candidate compound than in its absence, the candidate compound is identified as a stimulator of 53320 mRNA or protein expression. Alternatively, when expression of 53320 mRNA or protein is less (statistically significantly less) in the presence of the candidate compound than in its absence, the candidate compound is identified as an inhibitor of 53320 mRNA or protein expression. The level of 53320 mRNA or protein expression can be determined by methods described herein for detecting 53320 mRNA or protein.

In another aspect, the invention pertains to a combination of two or more of the assays described herein. For example, a modulating agent can be identified using a cell-based or a cell free assay, and the ability of the agent to modulate the activity of a 53320 protein can be confirmed in vivo, e.g., in an animal such as an animal model for tumor formation or tumor-associated angiogenesis.

This invention further pertains to novel agents identified by the above-described screening assays. Accordingly, it is within the scope of this invention to further use an agent identified as described herein (e.g., a 53320 modulating agent, an antisense 53320 nucleic acid molecule, a 53320-specific antibody, or a 53320-binding partner) in an appropriate animal model to determine the efficacy, toxicity, side effects, or mechanism of action, of treatment with such an agent. Furthermore, novel agents identified by the above-described screening assays can be used for treatments as described herein.

53320 Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 53320 with a disease; (ii) identify an individual from a minute biological sample (tissue typing); and (iii) aid in forensic identification of a biological sample. These applications are described in the subsections below.

53320 Chromosome Mapping

The 53320 nucleotide sequences or portions thereof can be used to map the location of the 53320 genes on a chromosome. This process is called chromosome mapping. Chromosome mapping is useful in correlating the 53320 sequences with genes associated with disease.

Briefly, 53320 genes can be mapped to chromosomes by preparing PCR primers (preferably 15-25 bp in length) from the 53320 nucleotide sequences. These primers can then be used for PCR screening of somatic cell hybrids containing individual human chromosomes. Only those hybrids containing the human gene corresponding to the 53320 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) Science 220:919-924).

Other mapping strategies e.g., in situ hybridization (described in Fan, Y. et al. (1990) Proc. Natl. Acad. Sci. USA, 87:6223-27), pre-screening with labeled flow-sorted chromosomes, and pre-selection by hybridization to chromosome specific cDNA libraries can be used to map 53320 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques ((1988) Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783-787.

Moreover, differences in the DNA sequences between individuals affected and unaffected with a disease associated with the 53320 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

53320 Tissue Typing 53320 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 53320 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:83 can provide positive individual identification with a panel of perhaps 10 to 1,000 primers which each yield a noncoding amplified sequence of 100 bases. If predicted coding sequences, such as those in SEQ ID NO:85 are used, a more appropriate number of primers for positive individual identification would be 500-2,000.

If a panel of reagents from 53320 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 53320 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:83 (e.g., fragments derived from the noncoding regions of SEQ ID NO:83 having a length of at least 20 bases, preferably at least 30 bases) are particularly appropriate for this use.

The 53320 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 53320 probes can be used to identify tissue by species and/or by organ type.

In a similar fashion, these reagents, e.g., 53320 primers or probes can be used to screen tissue culture for contamination (i.e. screen for the presence of a mixture of different types of cells in a culture).

Predictive Medicine of 53320

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 53320.

Such disorders include, e.g., a disorder associated with the misexpression of 53320 gene; a disorder of endothelial cells, e.g., angiogenesis associated with tumor formation.

The method includes one or more of the following:

detecting, in a tissue of the subject, the presence or absence of a mutation which affects the expression of the 53320 gene, or detecting the presence or absence of a mutation in a region which controls the expression of the gene, e.g., a mutation in the 5' control region;

detecting, in a tissue of the subject, the presence or absence of a mutation which alters the structure of the 53320 gene;

detecting, in a tissue of the subject, the misexpression of the 53320 gene, at the mRNA level, e.g., detecting a non-wild type level of a mRNA;

detecting, in a tissue of the subject, the misexpression of the gene, at the protein level, e.g., detecting a non-wild type level of a 53320 polypeptide.

In preferred embodiments the method includes: ascertaining the existence of at least one of: a deletion of one or more nucleotides from the 53320 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:83, or naturally occurring mutants thereof or 5' or 3' flanking sequences naturally associated with the 53320 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 53320 gene; the presence of a non-wild type splicing pattern of a messenger RNA transcript of the gene; or a non-wild type level of 53320.

Methods of the invention can be used prenatally or to determine if a subject's offspring will be at risk for a disorder.

In preferred embodiments the method includes determining the structure of a 53320 gene, an abnormal structure being indicative of risk for the disorder.

In preferred embodiments the method includes contacting a sample from the subject with an antibody to the 53320 protein or a nucleic acid, which hybridizes specifically with the gene. These and other embodiments are discussed below.

Diagnostic and Prognostic Assays of 53320

Diagnostic and prognostic assays of the invention include method for assessing the expression level of 53320 molecules and for identifying variations and mutations in the sequence of 53320 molecules.

Expression Monitoring and Profiling:

The presence, level, or absence of 53320 protein or nucleic acid in a biological sample can be evaluated by obtaining a biological sample from a test subject and contacting the biological sample with a compound or an agent capable of detecting 53320 protein or nucleic acid (e.g., mRNA, genomic DNA) that encodes 53320 protein such that the presence of 53320 protein or nucleic acid is detected in the biological sample. The term "biological sample" includes tissues, cells and biological fluids isolated from a subject, as well as tissues, cells and fluids present within a subject. A preferred biological sample is serum. The level of expression of the 53320 gene can be measured in a number of ways, including, but not limited to: measuring the mRNA encoded by the 53320 genes; measuring the amount of protein encoded by the 53320 genes; or measuring the activity of the protein encoded by the 53320 genes.

The level of mRNA corresponding to the 53320 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 53320 nucleic acid, such as the nucleic acid of SEQ ID NO:83, or a portion thereof, such as an oligonucleotide of at least 7, 15, 30, 50, 100, 250 or 500 nucleotides in length and sufficient to specifically hybridize under stringent conditions to 53320 mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the 53320 genes.

The level of mRNA in a sample that is encoded by one of 53320 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 53320 gene being analyzed.

In another embodiment, the methods further contacting a control sample with a compound or agent capable of detecting 53320 mRNA, or genomic DNA, and comparing the presence of 53320 mRNA or genomic DNA in the control sample with the presence of 53320 mRNA or genomic DNA in the test sample. In still another embodiment, serial analysis of gene expression, as described in U.S. Pat. No. 5,695,937, is used to detect 53320 transcript levels.

A variety of methods can be used to determine the level of protein encoded by 53320. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 53320 protein in a biological sample in vitro as well as in vivo. In vitro techniques for detection of 53320 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 53320 protein include introducing into a subject a labeled anti-53320 antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-53320 antibody positioned on an antibody array (as described below). The sample can be detected, e.g., with avidin coupled to a fluorescent label.

In another embodiment, the methods further include contacting the control sample with a compound or agent capable of detecting 53320 protein, and comparing the presence of 53320 protein in the control sample with the presence of 53320 protein in the test sample.

The invention also includes kits for detecting the presence of 53320 in a biological sample. For example, the kit can include a compound or agent capable of detecting 53320 protein or mRNA in a biological sample; and a standard. The compound or agent can be packaged in a suitable container. The kit can further comprise instructions for using the kit to detect 53320 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 53320 expression or activity. As used herein, the term "unwanted" includes an unwanted phenomenon involved in a biological response such as tumor formation or tumor-associated angiogenesis or deregulated cell proliferation.

In one embodiment, a disease or disorder associated with aberrant or unwanted 53320 expression or activity is identified. A test sample is obtained from a subject and 53320 protein or nucleic acid (e.g., mRNA or genomic DNA) is evaluated, wherein the level, e.g., the presence or absence, of 53320 protein or nucleic acid is diagnostic for a subject having or at risk of developing a disease or disorder associated with aberrant or unwanted 53320 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 53320 expression or activity. For example, such methods can be used to determine whether a subject can be effectively treated with an agent for a cell tumor formation or tumor-associated angiogenesis disorder.

In another aspect, the invention features a computer medium having a plurality of digitally encoded data records. Each data record includes a value representing the level of expression of 53320 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than 53320 (e.g., other genes associated with a 53320-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of 53320 expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a tumor formation or tumor-associated angiogenesis disorder in a subject wherein an increase in 53320 expression is an indication that the subject has or is disposed to having a tumor formation or tumor-associated angiogenesis. The method can be used to monitor a treatment for tumor formation or tumor-associated angiogenesis in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) Science 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of 53320 expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of 53320 expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of 53320 expression.

53320 Arrays and Uses Thereof

In another aspect, the invention features an array that includes a substrate having a plurality of addresses. At least one address of the plurality includes a capture probe that binds specifically to a 53320 molecule (e.g., a 53320 nucleic acid or a 53320 polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a 53320 nucleic acid, e.g., the sense or anti-sense strand. In one preferred embodiment, a subset of addresses of the plurality of addresses has a nucleic acid capture probe for 53320. Each address of the subset can include a capture probe that hybridizes to a different region of a 53320 nucleic acid. In another preferred embodiment, addresses of the subset include a capture probe for a 53320 nucleic acid. Each address of the subset is unique, overlapping, and complementary to a different variant of 53320 (e.g., an allelic variant, or all possible hypothetical variants). The array can be used to sequence 53320 by hybridization (see, e.g., U.S. Pat. No. 5,695,940).

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a 53320 polypeptide or fragment thereof. The polypeptide can be a naturally-occurring interaction partner of 53320 polypeptide. Preferably, the polypeptide is an antibody, e.g., an antibody described herein (see "Anti-53320 Antibodies," above), such as a monoclonal antibody or a single-chain antibody.

In another aspect, the invention features a method of analyzing the expression of 53320. The method includes providing an array as described above; contacting the array with a sample and detecting binding of a 53320-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of 53320. If a sufficient number of diverse samples is analyzed, clustering (e.g., hierarchical clustering, k-means clustering, Bayesian clustering and the like) can be used to identify other genes which are co-regulated with 53320. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on 53320 expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a 53320-associated disease or disorder; and processes, such as a cellular transformation associated with a 53320-associated disease or disorder. The method can also evaluate the treatment and/or progression of a 53320-associated disease or disorder The array is also useful for ascertaining differential expression patterns of one or more genes in normal and abnormal cells. This provides a battery of genes (e.g., including 53320) that could serve as a molecular target for diagnosis or therapeutic intervention.

In another aspect, the invention features an array having a plurality of addresses. Each address of the plurality includes a unique polypeptide. At least one address of the plurality has disposed thereon a 53320 polypeptide or fragment thereof. Methods of producing polypeptide arrays are described in the art, e.g., in De Wildt et al. (2000). *Nature Biotech.* 18, 989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80, 85, 90, 95 or 99% identical to a 53320 polypeptide or fragment thereof. For example, multiple variants of a 53320 polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a 53320 binding compound, e.g., an antibody in a sample from a subject with specificity for a 53320 polypeptide or the presence of a 53320-binding protein or ligand.

The array is also useful for ascertaining the effect of the expression of a gene on the expression of other genes in the same cell or in different cells (e.g., ascertaining the effect of 53320 expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express 53320 or from a cell or subject in which a 53320 mediated response has been elicited, e.g., by contact of the cell with 53320 nucleic acid or protein, or administration to the cell or subject 53320 nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express 53320 (or does not express as highly as in the case of the 53320 positive plurality of capture probes) or from a cell or subject which in which a 53320 mediated response has not been elicited (or has been elicited to a lesser extent than in the first sample); contacting the array with one or more inquiry probes (which is preferably other than a 53320 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express 53320 or from a cell or subject in which a 53320-mediated response has been elicited, e.g., by contact of the cell with 53320 nucleic acid or protein, or administration to the cell or subject 53320 nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express 53320 (or does not express as highly as in the case of the 53320 positive plurality of capture probes) or from a cell or subject which in which a 53320 mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing 53320, e.g., analyzing structure, function, or relatedness to other nucleic acid or amino acid sequences. The method includes: providing a 53320 nucleic acid or amino acid sequence; comparing the 53320 sequence with one or more preferably a plurality of sequences from a collection of sequences, e.g., a nucleic acid or protein sequence database; to thereby analyze 53320.

Detection of 53320 Variations or Mutations

The methods of the invention can also be used to detect genetic alterations in a 53320 gene, thereby determining if a subject with the altered gene is at risk for a disorder characterized by misregulation in 53320 protein activity or nucleic acid expression, such as a tumor formation or tumor-associated angiogenesis disorder. In preferred embodiments, the methods include detecting, in a sample from the subject, the presence or absence of a genetic alteration characterized by at least one of an alteration affecting the integrity of a gene encoding a 53320-protein, or the mis-expression of the 53320 gene. For example, such genetic alterations can be detected by ascertaining the existence of at least one of 1) a deletion of one or more nucleotides from a 53320 gene; 2) an addition of one or more nucleotides to a 53320 gene; 3) a substitution of one or more nucleotides of a 53320 gene, 4) a chromosomal rearrangement of a 53320 gene; 5) an alteration in the level of a messenger RNA transcript of a 53320 gene, 6) aberrant modification of a 53320 gene, such as of the methylation pattern of the genomic DNA, 7) the presence of a non-wild type splicing pattern of a messenger RNA transcript of a 53320 gene, 8) a non-wild type level of a 53320-protein, 9) allelic loss of a 53320 gene, and 10) inappropriate post-translational modification of a 53320-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 53320-gene. This method can include the steps of collecting a sample of cells from a subject, isolating nucleic acid (e.g., genomic, mRNA or both) from the sample, contacting the nucleic acid sample with one or more primers which specifically hybridize to a 53320 gene under conditions such that hybridization and amplification of the 53320-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 53320 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 53320 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a 53320 nucleic acid or a putative variant (e.g., allelic variant) thereof. A probe can have one or more mismatches to a region of a 53320 nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in 53320 can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 53320 gene and detect mutations by comparing the sequence of the sample 53320 with the corresponding wild-type (control) sequence. Automated sequencing procedures can be utilized when performing the diagnostic assays ((1995) *Biotechniques* 19:448), including sequencing by mass spectrometry.

Other methods for detecting mutations in the 53320 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 53320 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in 53320 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control 53320 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230). A further method of detecting point mutations is the chemical ligation of oligonucleotides as described in Xu et al. ((2001) *Nature Biotechnol.* 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a 53320 nucleic acid.

In a preferred embodiment the set includes a first and a second oligonucleotide. The first and second oligonucleotide can hybridize to the same or to different locations of SEQ ID NO:83 or the complement of SEQ ID NO:83. Different locations can be different but overlapping, or non-overlapping on the same strand. The first and second oligonucleotide can hybridize to sites on the same or on different strands.

The set can be useful, e.g., for identifying SNP's, or identifying specific alleles of 53320. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a 53320 nucleic acid.

The methods described herein may be performed, for example, by utilizing prepackaged diagnostic kits comprising at least one probe nucleic acid or antibody reagent described herein, which may be conveniently used, e.g., in clinical settings to diagnose patients exhibiting symptoms or family history of a disease or illness involving a 53320 gene.

Use of 53320 Molecules as Surrogate Markers

The 53320 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 53320 molecules of the invention may be detected, and may be correlated with one or more biological states in vivo. For example, the 53320 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The 53320 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 53320 marker) transcription or expression, the amplified marker may be in a quantity which is more readily detectable than the drug itself. Also, the marker may be more easily detected due to the nature of the marker itself; for example, using the methods described herein, anti-53320 antibodies may be employed in an immune-based detection system for a 53320 protein marker, or 53320-specific radiolabeled probes may be used to detect a 53320 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

The 53320 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 53320 protein or RNA) for specific tumor markers in a subject, a drug or course of treatment may be selected that is optimized for the treatment of the specific tumor likely to be present in the subject. Similarly, the presence or absence of a specific sequence mutation in 53320 DNA may correlate 53320 drug response. The use of pharmacogenomic markers therefore permits the application of the most appropriate treatment for each subject without having to administer the therapy.

Pharmaceutical Compositions of 53320

The nucleic acid and polypeptides, fragments thereof, as well as anti-53320 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment for 53320

The present invention provides for both prophylactic and therapeutic methods of treating a subject at risk of (or susceptible to) a disorder or having a disorder associated with aberrant or unwanted 53320 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 53320 molecules of the present invention or 53320 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 53320 expression or activity, by administering to the subject a 53320 or an agent which modulates 53320 expression or at least one 53320 activity. Subjects at risk for a disease which is caused or contributed to by aberrant or unwanted 53320 expression or activity can be identified by, for example, any or a combination of diagnostic or prognostic assays as described herein. Administration of a prophylactic agent can occur prior to the manifestation of symptoms characteristic of the 53320 aberrance, such that a disease or disorder is prevented or, alternatively, delayed in its progression. Depending on the type of 53320 aberrance, for example, a 53320, 53320 agonist or 53320 antagonist agent can be used for treating the subject. The appropriate agent can be determined based on screening assays described herein.

It is possible that some 53320 disorders can be caused, at least in part, by an abnormal level of gene product, or by the presence of a gene product exhibiting abnormal activity. As such, the reduction in the level and/or activity of such gene products would bring about the amelioration of disorder symptoms.

The 53320 molecules can act as novel diagnostic targets and therapeutic agents for controlling one or more of cellular proliferative and/or differentiative disorders (and also as described above), disorders associated with lung, colon, breast, kidney, or brain, immune disorders, cardiovascular disorders, and pain or metabolic disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genitourinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The 53320 nucleic acid and protein of the invention can be used to treat and/or diagnose a variety of immune disorders. Examples of immune disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degenration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (1) and TYPE 2 neurofibromatosis (NF2), tuberous sclerosis, and Von Hippel-Lindau disease.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Examples of disorders of the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Additionally, 53320 may play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York:McGraw-Hill); pain associated with musculoskeletal disorders, e.g., joint pain; tooth pain; headaches; pain associated with surgery; pain related to irritable bowel syndrome; or chest pain.

As discussed, successful treatment of 53320 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 53320 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, F(ab')$_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 53320 expression is through the use of aptamer molecules specific for 53320 protein. Aptamers are nucleic acid molecules having a tertiary structure which permits them to specifically bind to protein ligands (see, e.g., Osborne, et al. (1997) *Curr. Opin. Chem Biol.* 1: 5-9; and Patel, D. J. (1997) *Curr Opin Chem Biol* 1:32-46). Since nucleic acid molecules may in many cases be more conveniently introduced into target cells than therapeutic protein molecules may be, aptamers offer a method by which 53320 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 53320 disorders. For a description of antibodies, see the Antibody section above.

In circumstances wherein injection of an animal or a human subject with a 53320 protein or epitope for stimulating antibody production is harmful to the subject, it is possible to generate an immune response against 53320 through the use of anti-idiotypic antibodies (see, for example, Herlyn, D. (1999) *Ann Med* 31:66-78; and Bhattacharya-Chatterjee, M., and Foon, K. A. (1998) *Cancer Treat Res.* 94:51-68). If an anti-idiotypic antibody is introduced into a mammal or human subject, it should stimulate the production of anti-anti-idiotypic antibodies, which should be specific to the 53320 protein. Vaccines directed to a disease characterized by 53320 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate 53320 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography. Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 53320 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89-94 and in Shea, K. J. (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645-647. Through the use of isotope-labeling, the "free" concentration of compound which modulates the expression or activity of 53320 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142-2144.

Another aspect of the invention pertains to methods of modulating 53320 expression or activity for therapeutic purposes. Accordingly, in an exemplary embodiment, the modulatory method of the invention involves contacting a cell with a 53320 or agent that modulates one or more of the activities of 53320 protein activity associated with the cell. An agent that modulates 53320 protein activity can be an agent as described herein, such as a nucleic acid or a protein, a naturally-occurring target molecule of a 53320 protein (e.g., a 53320 substrate or receptor), a 53320 antibody, a 53320 agonist or antagonist, a peptidomimetic of a 53320 agonist or antagonist, or other small molecule.

In one embodiment, the agent stimulates one or 53320 activities. Examples of such stimulatory agents include active 53320 protein and a nucleic acid molecule encoding 53320. In another embodiment, the agent inhibits one or more 53320 activities. Examples of such inhibitory agents include antisense 53320 nucleic acid molecules, anti-53320 antibodies, and 53320 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 53320 protein or nucleic acid molecule. In one embodiment, the method involves administering an agent (e.g., an agent identified by a screening assay described herein), or combination of agents that modulates (e.g., up regulates or down regulates) 53320 expression or activity. In another embodiment, the method involves administering a 53320 protein or nucleic acid molecule as therapy to compensate for reduced, aberrant, or unwanted 53320 expression or activity.

Stimulation of 53320 activity is desirable in situations in which 53320 is abnormally downregulated and/or in which increased 53320 activity is likely to have a beneficial effect. For example, stimulation of 53320 activity is desirable in situations in which a 53320 is downregulated and/or in which increased 53320 activity is likely to have a beneficial effect. Likewise, inhibition of 53320 activity is desirable in situations in which 53320 is abnormally upregulated and/or in which decreased 53320 activity is likely to have a beneficial effect.

53320 Pharmacogenomics

The 53320 molecules of the present invention, as well as agents, or modulators which have a stimulatory or inhibitory effect on 53320 activity (e.g., 53320 gene expression) as identified by a screening assay described herein can be administered to individuals to treat (prophylactically or therapeutically) 53320 associated disorders (e.g., tumor formation or tumor-associated angiogenesis) associated with aberrant or unwanted 53320 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 53320 molecule or 53320 modulator as well as tailoring the dosage and/or therapeutic regimen of treatment with a 53320 molecule or 53320 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983-985 and Linder, M. W. et al. (1997) *Clin. Chem.* 43:254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a 53320 protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a 53320 molecule or 53320 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 53320 molecule or 53320 modulator, such as a modulator identified by one of the exemplary screening assays described herein.

The present invention further provides methods for identifying new agents, or combinations, that are based on identifying agents that modulate the activity of one or more of the gene products encoded by one or more of the 53320 genes of the present invention, wherein these products may be associated with resistance of the cells to a therapeutic agent. Specifically, the activity of the proteins encoded by the 53320 genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a 53320 protein can be applied in clinical trials. For example, the effectiveness of an agent determined by a screening assay as described herein to increase 53320 gene expression, protein levels, or upregulate 53320 activity, can be monitored in clinical trials of subjects exhibiting decreased 53320 gene expression, protein levels, or downregulated 53320 activity. Alternatively, the effectiveness of an agent determined by a screening assay to decrease 53320 gene expression, protein levels, or downregulate 53320 activity, can be monitored in clinical trials of subjects exhibiting increased 53320 gene expression, protein levels, or upregulated 53320 activity. In such clinical trials, the expression or activity of a 53320 gene, and preferably, other genes that have been implicated in, for example, a 53320-associated disorder can be used as a "read out" or markers of the phenotype of a particular cell.

53320 Informatics

The sequence of a 53320 molecule is provided in a variety of media to facilitate use thereof. A sequence can be provided as a manufacture, other than an isolated nucleic acid or amino acid molecule, which contains a 53320. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, 53320 full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing 53320, e.g., analyzing structure, function, or relatedness to one or more other nucleic acid or amino acid sequences. The method includes: providing a 53320 nucleic acid or amino acid sequence; comparing the 53320 sequence with a second sequence, e.g., one or more preferably a plurality of sequences from a collection of sequences, e.g., a nucleic acid or protein sequence database to thereby analyze 53320. The method can be performed in a machine, e.g., a computer, or manually by a skilled artisan.

The method can include evaluating the sequence identity between a 53320 sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 53320 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a 53320 sequence, or record, in machine-readable form; comparing a second sequence to the 53320 sequence; thereby analyzing a sequence. Comparison can include comparing to sequences for sequence identity or determining if one sequence is included within the other, e.g., determining if the 53320 sequence includes a sequence being compared. In a preferred embodiment the 53320 or second sequence is stored on a first computer, e.g., at a first site and the comparison is performed, read, or recorded on a second computer, e.g., at a second site. E.g., the 53320 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a 53320-associated disease or disorder or a pre-disposition to a 53320-associated disease or disorder, wherein the method comprises the steps of determining 53320 sequence information associated with the subject and based on the 53320 sequence information, determining whether the subject has a 53320-associated disease or disorder or a pre-disposition to a 53320-associated disease or disorder and/or recommending a particular treatment for the disease, disorder or pre-disease condition.

The invention further provides in an electronic system and/or in a network, a method for determining whether a subject has a 53320-associated disease or disorder or a pre-disposition to a disease associated with a 53320 wherein the method comprises the steps of determining 53320 sequence information associated with the subject, and based on the 53320 sequence information, determining whether the subject has a 53320-associated disease or disorder or a pre-disposition to a 53320-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the 53320 sequence of the subject to the 53320 sequences in the database to thereby determine whether the subject as a 53320-associated disease or disorder, or a pre-disposition for such.

The present invention also provides in a network, a method for determining whether a subject has a 53320 associated disease or disorder or a pre-disposition to a 53320-associated disease or disorder associated with 53320, said method comprising the steps of receiving 53320 sequence information from the subject and/or information related thereto, receiving phenotypic information associated with the subject, acquiring information from the network corresponding to 53320 and/or corresponding to a 53320-associated disease or disorder (e.g., tumor formation or tumor-associated angiogenesis), and based on one or more of the phenotypic information, the 53320 information (e.g., sequence information and/or information related thereto), and the acquired information, determining whether the subject has a 53320-associated disease or disorder or a pre-disposition to a 53320-associated disease or disorder. The method may further comprise the step of recommending a particular treatment for the disease, disorder or pre-disease condition.

The present invention also provides a method for determining whether a subject has a 53320-associated disease or disorder or a pre-disposition to a 53320-associated disease or disorder, said method comprising the steps of receiving information related to 53320 (e.g., sequence information and/or information related thereto), receiving phenotypic information associated with the subject, acquiring information from the network related to 53320 and/or related to a 53320-associated disease or disorder, and based on one or more of the phenotypic information, the 53320 information, and the acquired information, determining whether the subject has a 53320-associated disease or disorder or a pre-disposition to a 53320-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

EXAMPLES

Examples for 33877 and 47179

Example 1

Identification and Characterization of Human 33877 and 47179 cDNAs

The human 33877 sequence (FIGS. 1A-1C; SEQ ID NO:1), which is approximately 2493 nucleotides long, including untranslated regions, contains a predicted methionine-initiated coding sequence of about 1659 nucleotides, including the termination codon (nucleotides indicated as "coding" of SEQ ID NO:1 in FIGS. 1A-1C; SEQ ID NO:3). The coding sequence encodes a 552 amino acid protein (SEQ ID NO:2).

The human 47179 sequence (FIGS. 5A-5C; SEQ ID NO:4), which is approximately 1620 nucleotides long, including untranslated regions, contains a predicted methionine-initiated coding sequence of about 1251 nucleotides, including the termination codon (nucleotides indicated as "coding" of SEQ ID NO:4 in FIGS. 5A-5C; SEQ ID NO:6). The coding sequence encodes a 416 amino acid protein (SEQ ID NO:5).

Example 2

Tissue Distribution of 33877 and 47179 mRNAs

Northern blot hybridizations with various RNA samples can be performed under standard conditions and washed under stringent conditions, i.e., 0.2×SSC at 65° C. A DNA probe corresponding to all or a portion of the 33877 or 47179 cDNA (SEQ ID NO:1 or SEQ ID NO:4) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 3

Recombinant Expression of 33877 and 47179 in Bacterial Cells

In this example, 33877 or 47179 is expressed as a recombinant glutathione-S-transferase (GST) fusion polypeptide in E. coli and the fusion polypeptide is isolated and characterized. Specifically, 33877 or 47179 is fused to GST and this fusion polypeptide is expressed in E. coli, e.g., strain PEB199. Expression of the GST-33877 or 47179 fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 33877 or 47179 Protein in COS Cells

To express the 33877 or 47179 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire 33877 or 47179 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 33877 or 47179 DNA sequence is amplified by PCR using two primers. The 5' primer contains the restriction site of interest followed by approximately twenty nucleotides of the 33877 or 47179 coding sequence starting from the initiation codon; the 3' end sequence contains complementary sequences to the other restriction site of interest, a translation stop codon, the HA tag or FLAG tag and the last 20 nucleotides of the 33877 or 47179 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 33877 or 47179 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 33877 or 47179-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual. 2nd, ed., Cold Spring Harbor Laboratory*, Cold Spring Harbor Laboratory Press, Cold Spring Harbor, N.Y. The expression of the 33877 or 47179 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual*, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 33877 or 47179 coding sequence is cloned directly into the polylinker of the pCDNA/Amp vector using the appropriate restriction sites. The resulting plasmid is transfected into COS cells in the manner described above, and the expression of the 33877 or 47179 polypeptide is detected by radiolabeling and immunoprecipitation using a 33877 or 47179 specific monoclonal antibody.

Examples for 26886

Example 5

Identification and Characterization of Human 26886 cDNA and Genomic Sequence

The human 26886 sequence (FIG. 9; SEQ ID NO:9), which is approximately 2875 nucleotides long, including 5' and 3' untranslated regions, contains a predicted methionine-initiated coding sequence of about 2875 nucleotides (SEQ ID NO:11 and nucleotides 272 to 2412 of SEQ ID NO:9). The coding sequence encodes an 804 amino acid protein (SEQ ID NO:10).

Example 6

Tissue Distribution of 26886 mRNA by Large-Scale Tissue-Specific Library Sequencing and by Northern Blot Hybridization Endogenous human 26886 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a way of quantitating the initial template concentration. Samples can be internally controlled by the addition of a second set of primers/probe specific for a housekeeping gene such as GAPDH which has been labeled with a different fluorophore on the 5' end (typically VIC).

To determine the level of 26886 in various human tissues a primer/probe set was designed using Primer Express (Perkin-Elmer) software and primary cDNA sequence information. Total RNA was prepared from a series of human tissues using an RNeasy kit from Qiagen. First strand cDNA was prepared from one µg total RNA using an oligo-dT primer and Superscript II reverse transcriptase (Gibco/BRL). cDNA obtained from approximately 50 ng total RNA was used per TaqMan reaction.

Figure 15:
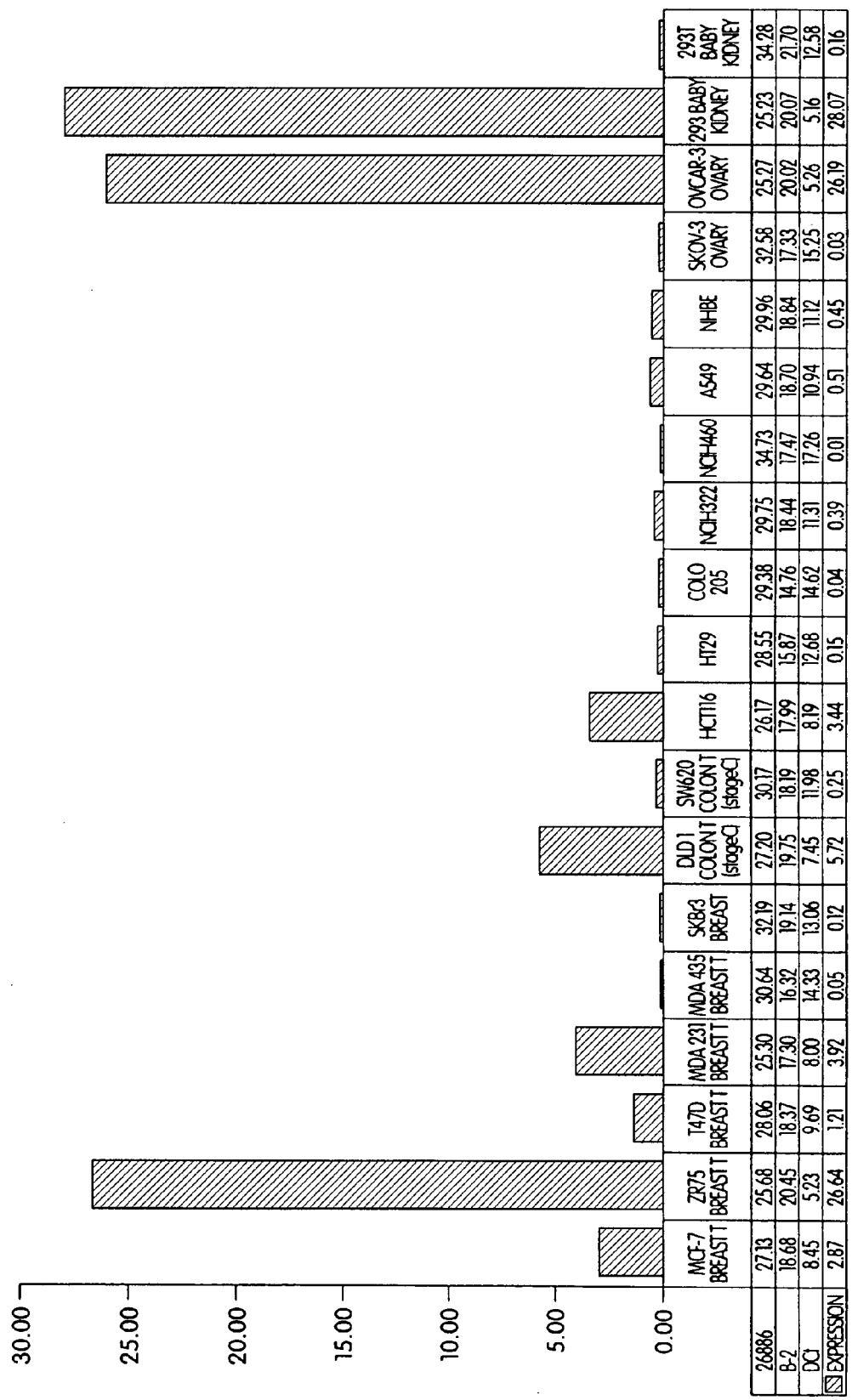
FIG. 15 is a bar graph depicting the expression of 26886 RNA in a panel of tumor cell lines after transplantion in mice. Elevated expression of 26886 mRNA was detected in breast, ovarian, and baby kidney cell lines after transplant.
Figure 17:
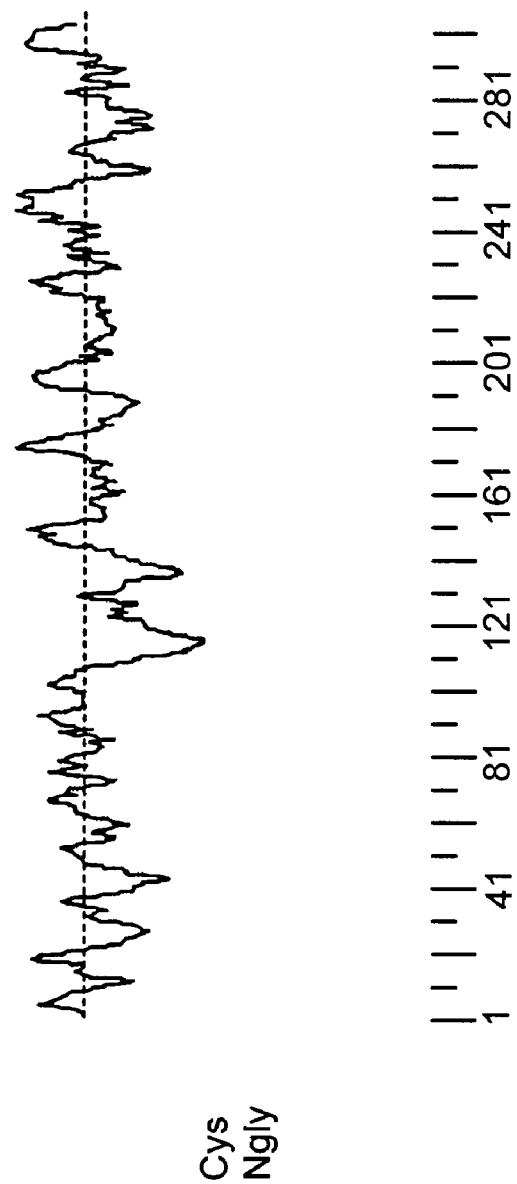
FIG. 17 depicts a hydropathy plot of human 25552. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human 25552 are indicated. Polypeptides of the invention include fragments which include: all or part of a hydrophobic sequence, i.e., a sequence above the dashed line, e.g., the sequence of 220-260; all or part of a hydrophilic sequence, i.e., a sequence below the dashed line, e.g., the sequence of 105-140; a sequence which includes a Cys, or a glycosylation site.
Figure 19:
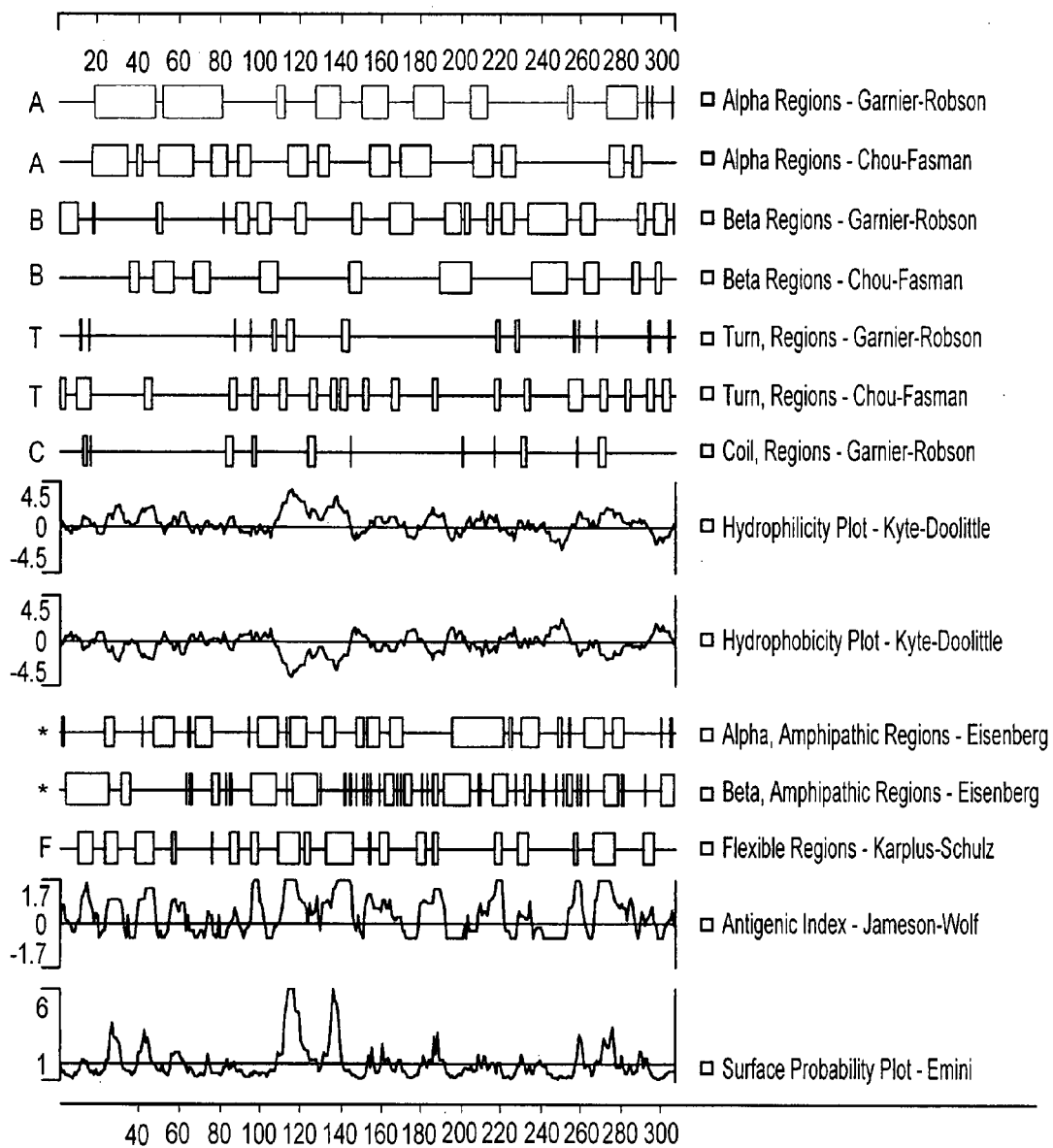
FIG. 19 depicts a series of plots summarizing an analysis of the primary and secondary protein structure of human 33395. The particular algorithm used for each plot is indicated at the right hand side of each plot. The following plots are depicted: Gamier-Robson plots providing the predicted location of alpha-, beta-, turn and coil regions (Gamier et al. (1978) *J. Mol. Biol.* 120:97); Chou-Fasman plots providing the predicted location of alpha-, beta-, turn and coil regions (Chou and Fasman (1978) *Adv. In Enzymol. Mol.* 47:45-148); Kyte-Doolittle hydrophilicity/hydrophobicity plots (Kyte and Doolittle (1982) *J. Mol. Biol.* 157:105-132); Eisenberg plots providing the predicted location of alpha- and beta-amphipathic regions (Eisenberg et al. (1982) *Nature* 299:371-374); a Karplus-Schultz plot providing the predicted location of flexible regions (Karplus and Schulz (1985) *Naturwissens-Chafen* 72:212-213); a plot of the antigenic index (Jameson-Wolf) (Jameson and Wolf (1988) *CABIOS* 4:121-136); and a surface probability plot (Emini algorithm) (Emini et al. (1985) J. Virol. 55:836-839). The numbers corresponding to the amino acid sequence of human 33395 are indicated. Polypeptide fragments of the invention include polypeptides which have all or part of any of the regions described in this figure. Also included are variants having a mutation in a selected region shown in this figure.
Figure 20:
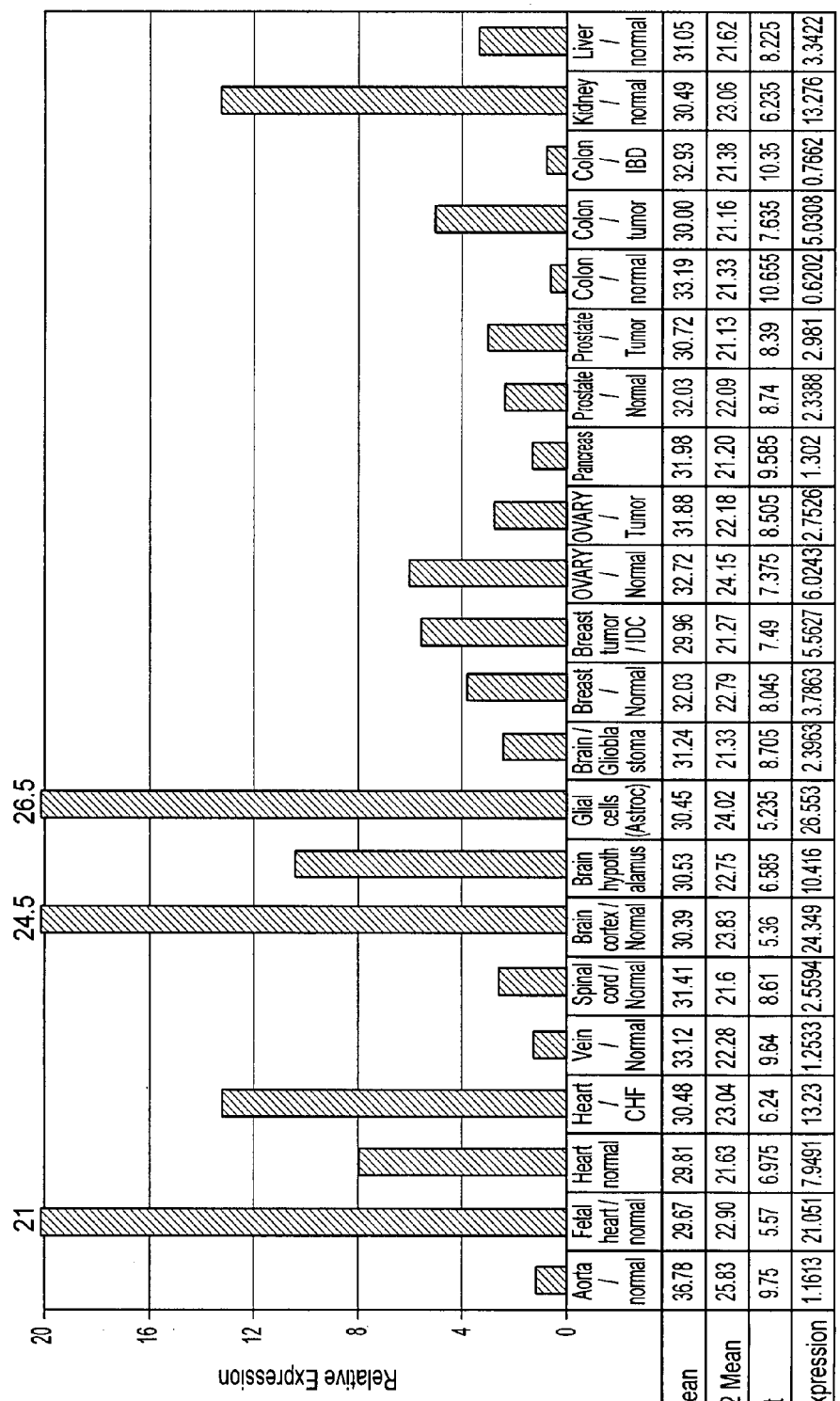
FIG. 20 is a bar graph depicting 25552 mRNA expression levels in various human tissues as detected by TaqMan analysis. As shown, 25552 mRNA is particularly prevalent in fetal heart, heart, brain cortex, glial cells, kidney, fetal liver, epithelial cells (from prostate), skeletal muscle, undifferentiated osteoblasts, and human umbilical vein endothelial cells (HUMVEC).
Figure 20B:
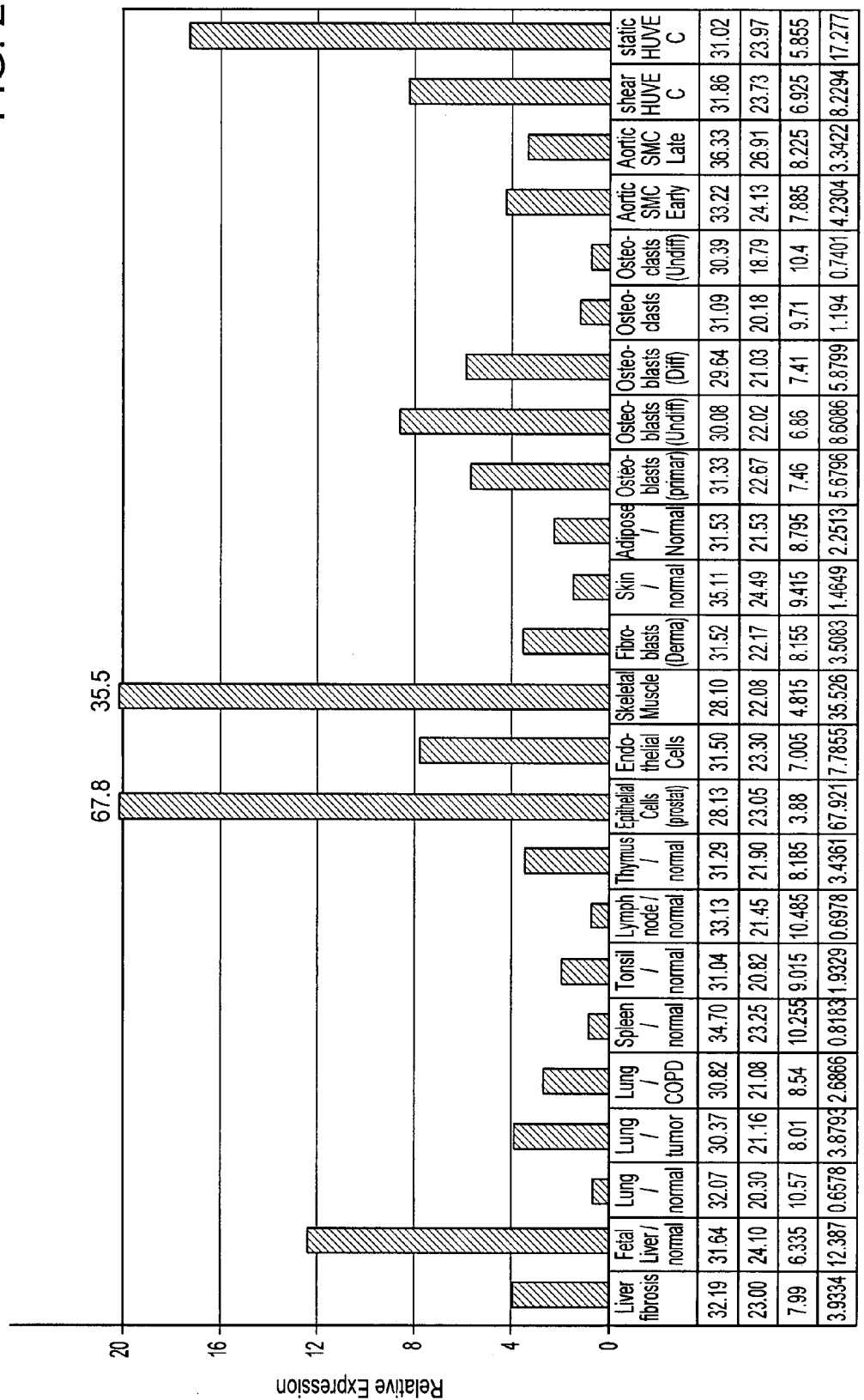
Figure 21:
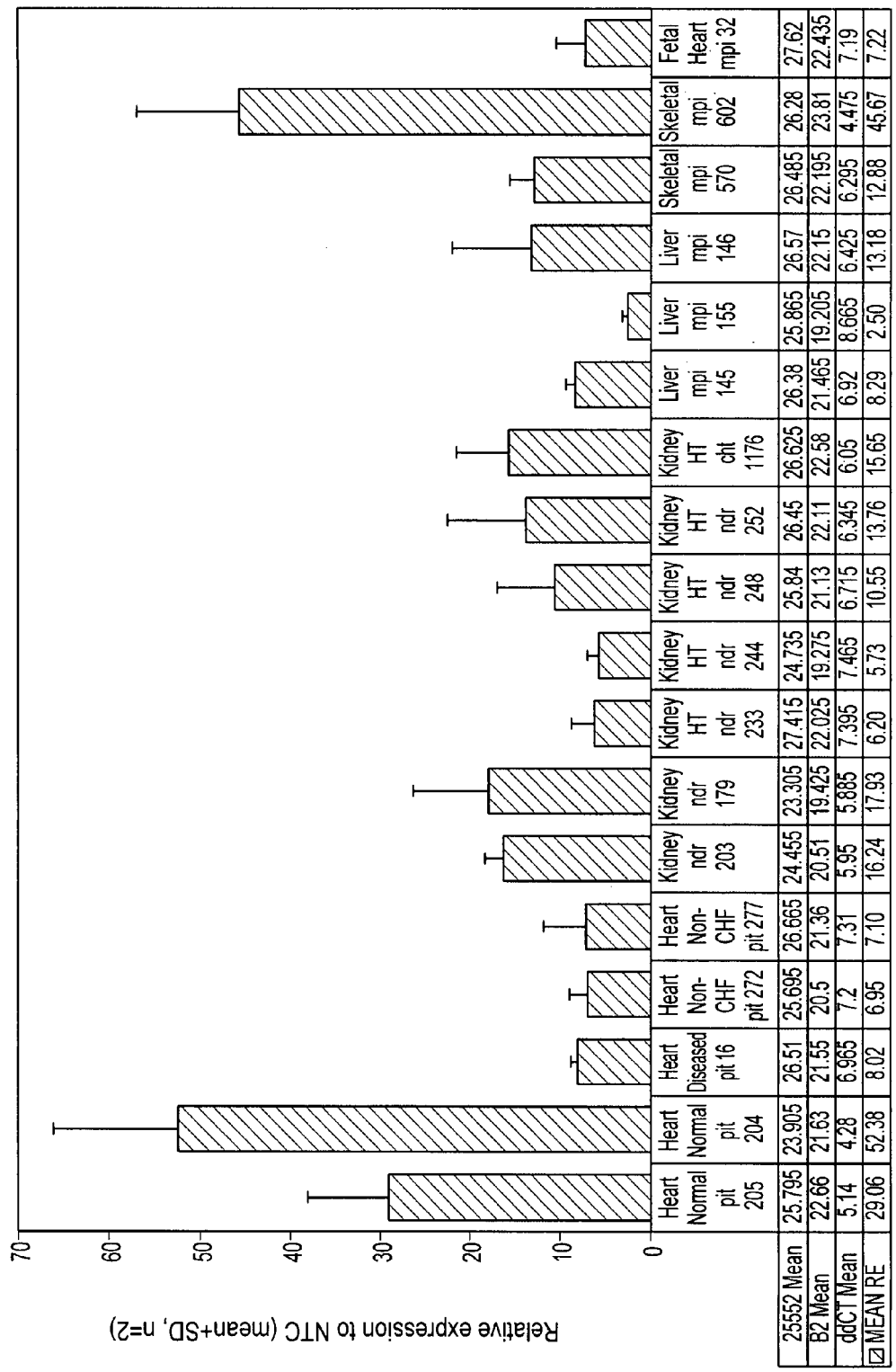
FIG. 21 is a bar graph depicting 25552 mRNA expression levels in various human tissues as detected by TaqMan analysis. As shown, 25552 mRNA is particularly prevalent in heart, kidney, and skeletal tissue.
Figure 22:
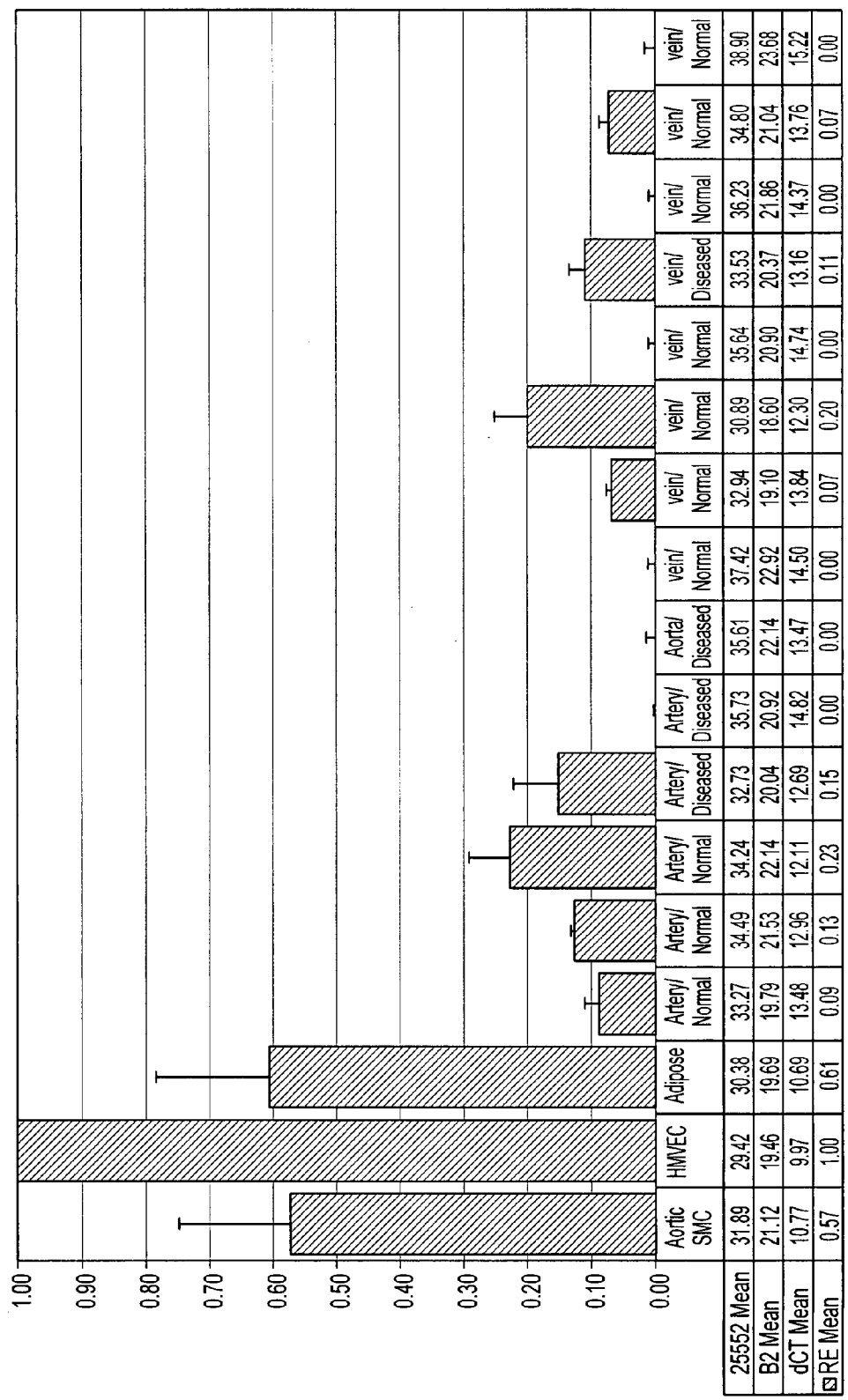
FIG. 22 is a bar graph depicting 25552 mRNA expression levels in various human tissues as detected by TaqMan analysis. As shown, 25552 mRNA is particularly prevalent in aortic smooth muscle cells, human microvascular endothelial cells, and adipose tissue.
Figure 23:
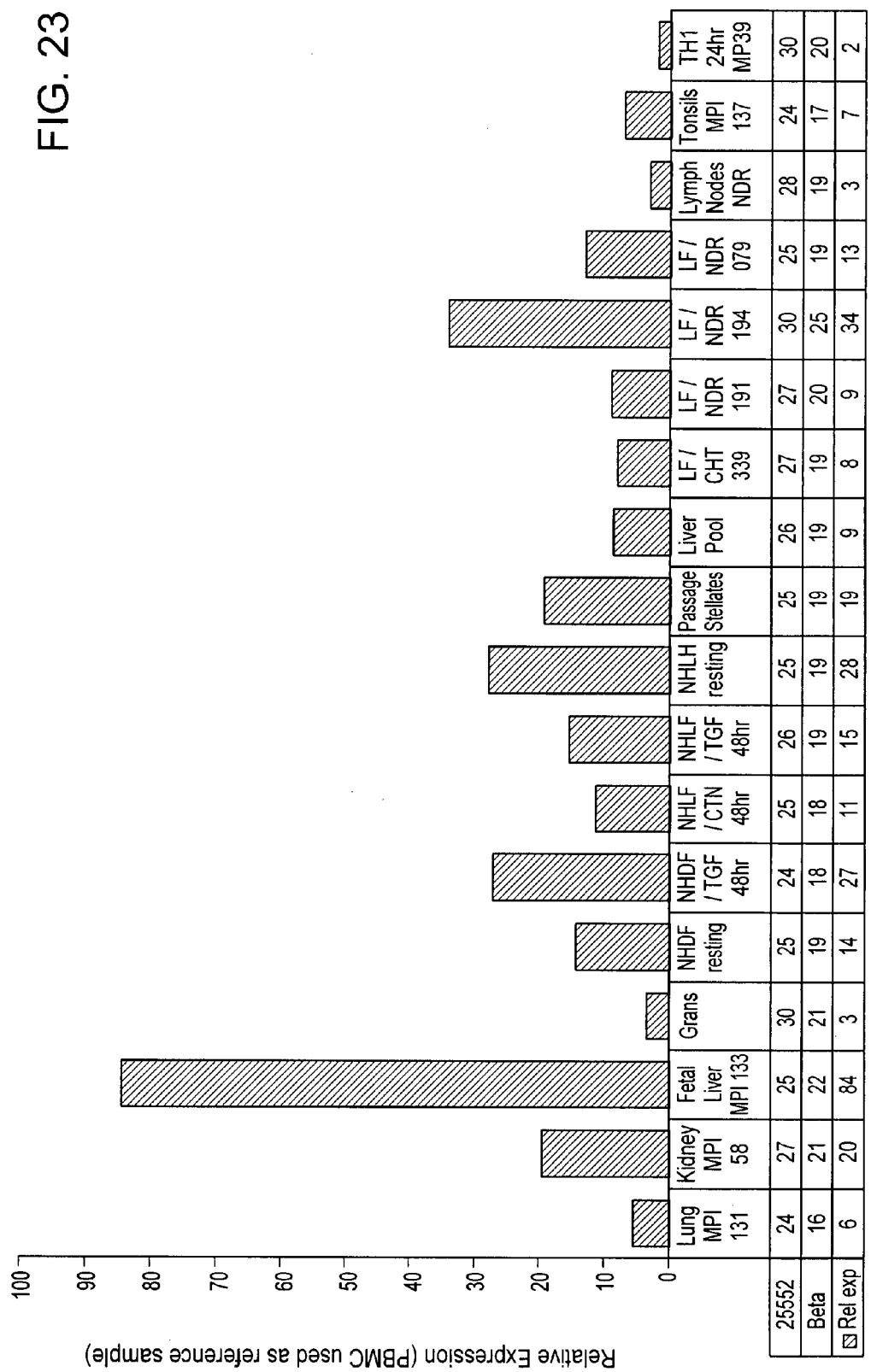
FIG. 23 is a bar graph depicting 25552 mRNA expression levels in various human tissues and cell lines as detected by TaqMan analysis. As shown, 25552 mRNA is particularly prevalent in fetal liver.

Normal tissues tested included the human tissues provided in FIGS. 12 and 13, including ovary, colon, lung, liver, and colon, among others. Expression was also found primarily in ovary, breast, and colon tumors (FIGS. 12, 13, and 15).

FIG. 14 is a bar graph depicting the changes in 26886 mRNA expression in synchronized colorectal adenocarcinoma DLD-1 cell lines. DLD-1 cells were treated with nocodazole, which induces cell cycle arrest at the G2/M phase of the cell cycle. Therefore, DLD-1 cells were reversibly blocked at the G2/M border with nocodazole. Cells were treated with Nocodazole for about 18 hours and then the drug was removed. After removal of the drug, cells moving throughout the various phases of the cell cycle were isolated by collecting cells at various time points after the release, making RNA and profiling the cell populations to determine the gene expression during each phase. The profiling and Taqman experiments indicate that 26886 expression is upregulated during the transition from G2/M to G0/G1 phase.

Northern blot hybridizations with various RNA samples can be performed under standard conditions and washed under stringent conditions, i.e., 0.2×SSC at 65° C. A DNA probe corresponding to all or a portion of the 26886 cDNA (SEQ ID NO:9) can be used. The DNA was radioactively labeled with $^{32}$P-dCTP using the Prime-It Kit (Stratagene, La Jolla, Calif.) according to the instructions of the supplier. Filters containing mRNA from mouse liver, hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 7

Recombinant Expression of 26886 in Bacterial Cells

In this example, 26886 is expressed as a recombinant glutathione-S-transferase (GST) fusion polypeptide in *E. coli* and the fusion polypeptide is isolated and characterized. Specifically, 26886 is fused to GST and this fusion polypeptide is expressed in *E. coli*, e.g., strain PEB199. Expression of the GST-26886 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 8

Expression of Recombinant 26886 Protein in COS Cells

To express the 26886 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 26886 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 26886 DNA sequence is amplified by PCR using two primers. The 5' primer contains the restriction site of interest followed by approximately twenty nucleotides of the 26886 coding sequence starting from the initiation codon; the 3' end sequence contains complementary sequences to the other restriction site of interest, a translation stop codon, the HA tag or FLAG tag and the last 20 nucleotides of the 26886 coding sequence.

The PCR amplified fragment and the pcDNA/Amp vector are digested with the appropriate restriction enzymes and the vector is dephosphorylated using the CIAP enzyme (New England Biolabs, Beverly, Mass.). Preferably, the two restriction sites chosen are different so that the 26886 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 26886-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the 26886 polypeptide is detected by radiolabeling ($^{35}$S-methionine or $^{35}$S-cysteine, available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 26886 coding sequence is cloned directly into the polylinker of the pcDNA/Amp vector using the appropriate restriction sites. The resulting plasmid is transfected into COS cells in the manner described above, and the expression of the 26886 polypeptide is detected by radiolabeling and immunoprecipitation using a 26886 specific monoclonal antibody.

Examples for 25552

Example 9

Identification and Characterization of Human 25552 cDNA

The human 25552 sequence (FIG. 16; SEQ ID NO:13), which is approximately 1529 nucleotides long, including untranslated regions, contains a predicted methionine-initiated coding sequence of about 924 nucleotides, including the termination codon (nucleotides indicated as "coding" of SEQ ID NO:13 in FIG. 16; SEQ ID NO:15). The coding sequence encodes a 307 amino acid protein (SEQ ID NO:14).

Example 10

Tissue Distribution of 25552 mRNA by TaqMan Analysis

Endogenous human 25552 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligo-nucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

To determine the level of 25552 in various human tissues a primer/probe set was designed. Total RNA was prepared from a series of human tissues using an RNeasy kit from Qiagen. First strand cDNA was prepared from 1 μg total RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in FIGS. 20 to 24.

Figure 24:
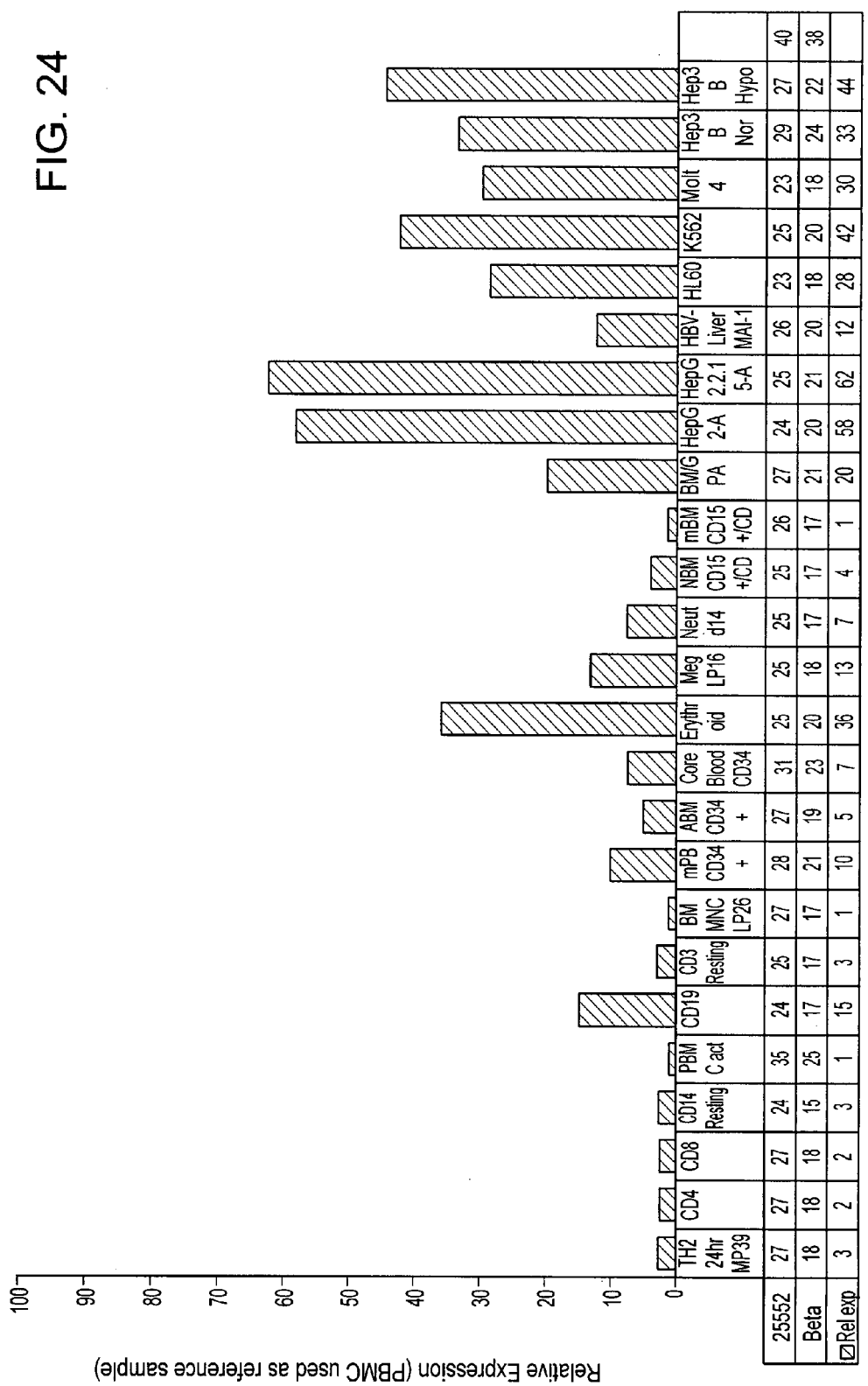
FIG. 24 is a bar graph depicting 25552 mRNA expression levels in various human cells as detected by TaqMan analysis. As shown, 25552 mRNA is particularly prevalent in erythroid cells and hepatic cells such as HepG2 and Hep3B cell lines.

25552 mRNA was detected in fetal heart, heart, brain cortex, glial cells, kidney, fetal liver, epithelial cells, skeletal muscle, undifferentiated osteoblasts, human umbilical vein endothelial cells, kidney, aortic smooth muscle cells, human microvascular endothelial cells, and adipose tissue (FIGS. 20-23). 25552 expression was also detected in erythroid cells and transformed hepatic cells such as HepG2 and Hep3B (FIG. 24).

Figure 25:
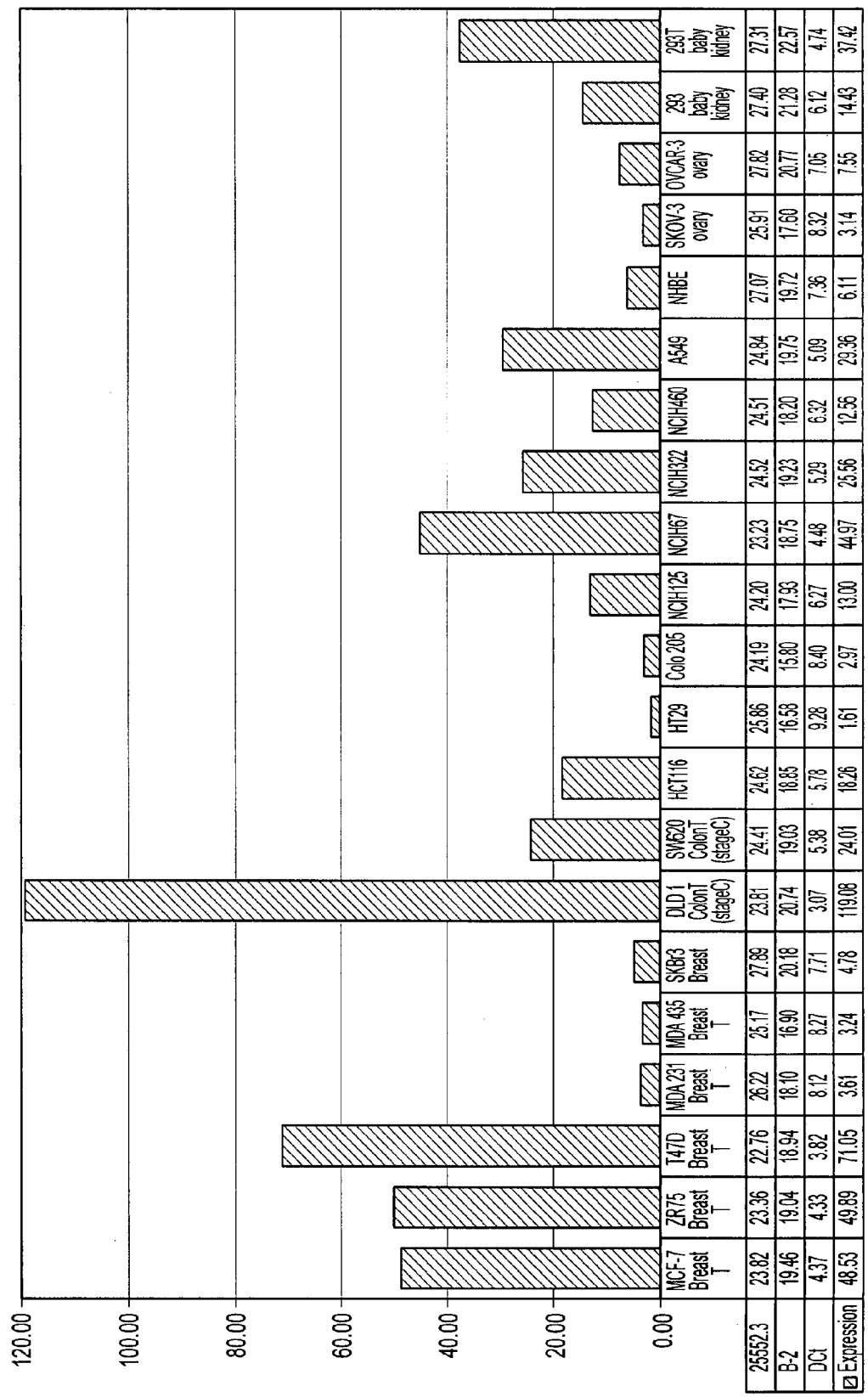
FIG. 25 is a bar graph depicting 25552 mRNA expression levels in various xenotransplanted human tumors as detected by TaqMan analysis. As shown, 25552 mRNA is particularly prevalent in xenotransplanted tumors from breast tumors and colon tumors.
Figure 26:
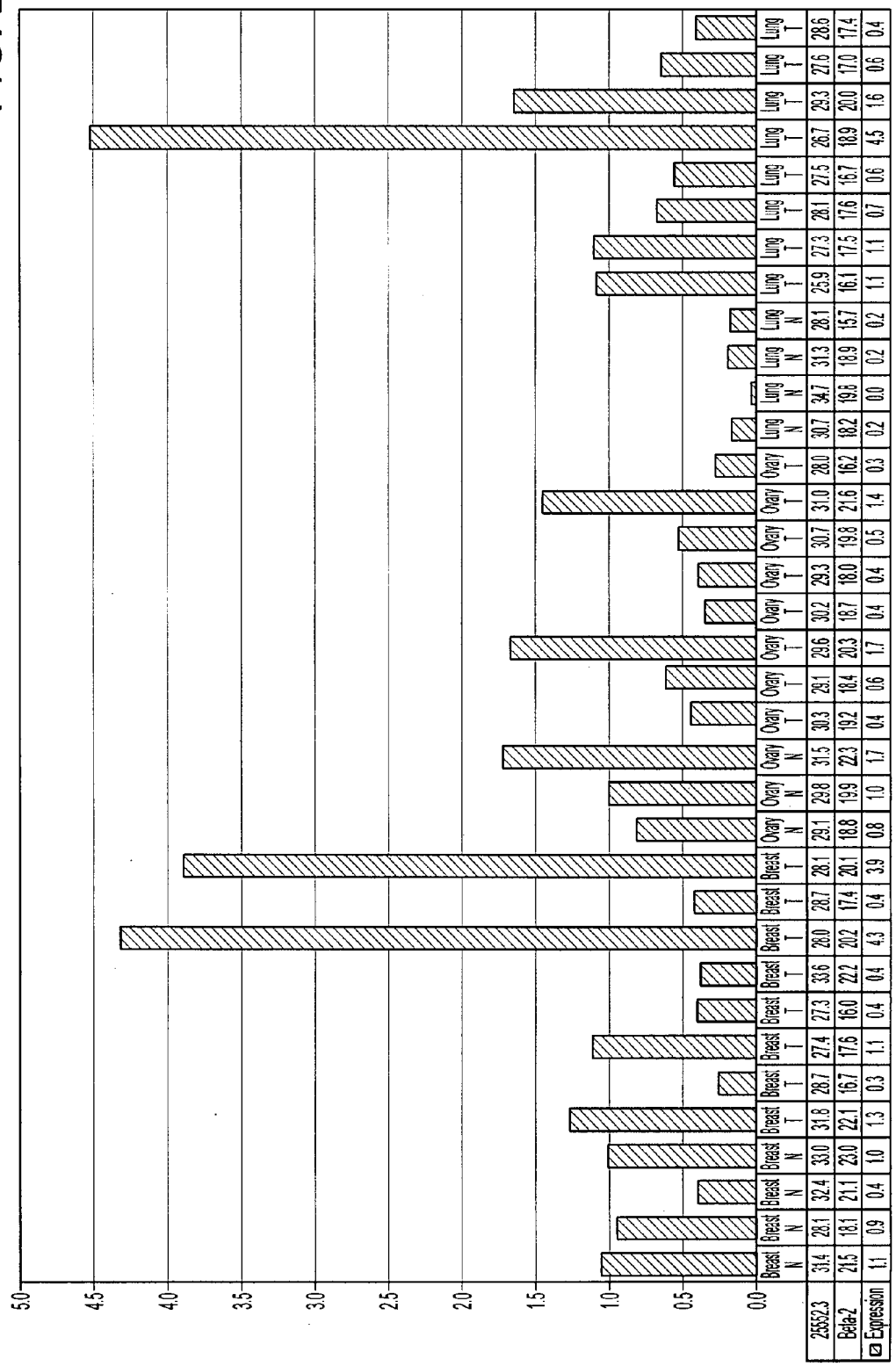
FIG. 26 is a bar graph depicting 25552 mRNA expression levels in various human tumors as detected by TaqMan analysis. As shown, 25552 mRNA expression is elevated in a number of breast, ovarian, and lung tumors.
Figure 27:
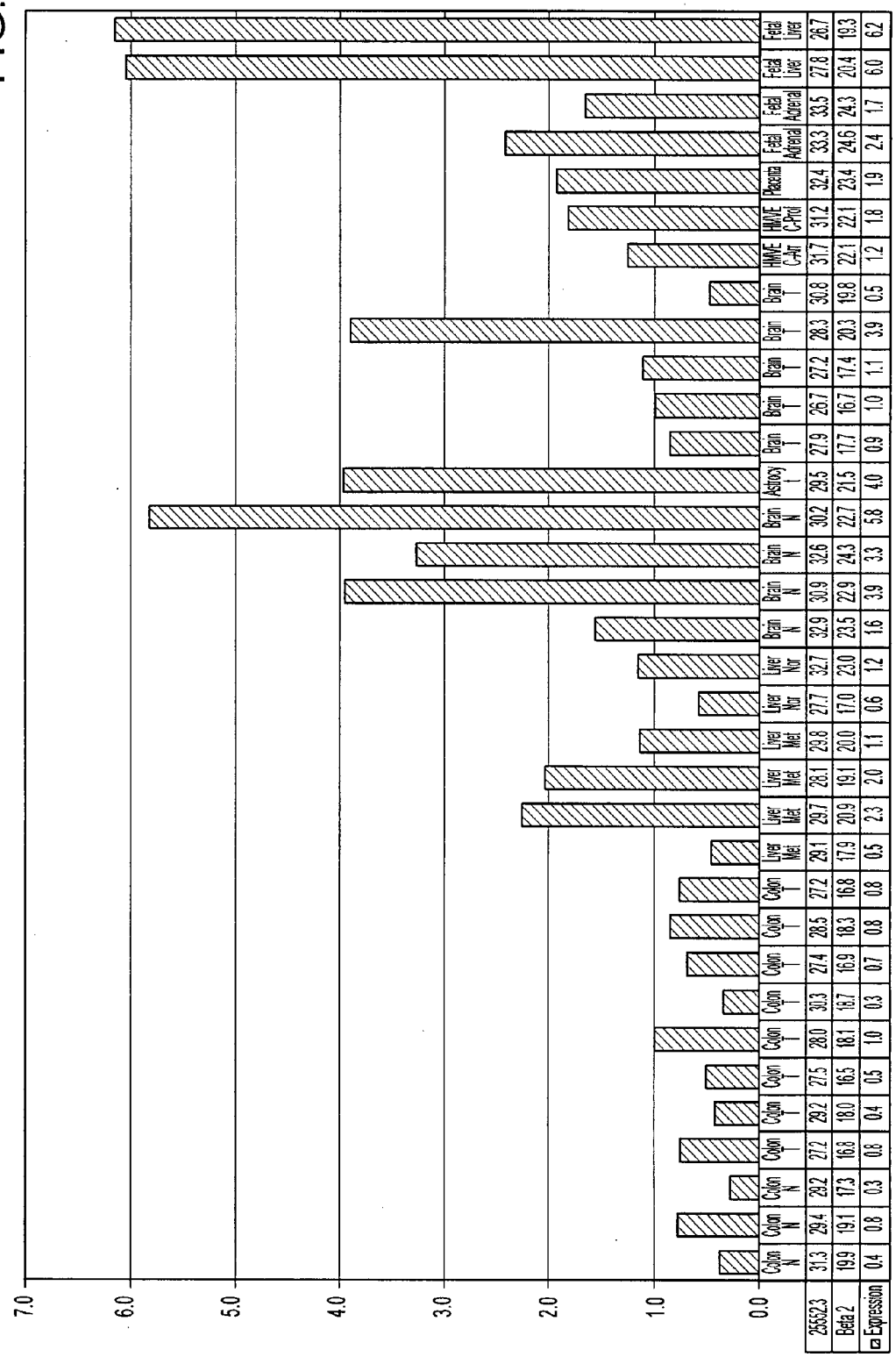
FIG. 27 is a bar graph depicting 25552 mRNA expression levels in various normal and cancerous human tissues as detected by TaqMan analysis. As shown, 25552 mRNA is elevated in some metastatic liver tissues, in normal brain, a brain tumor, and fetal adrenal and liver tissue.
Figure 28:
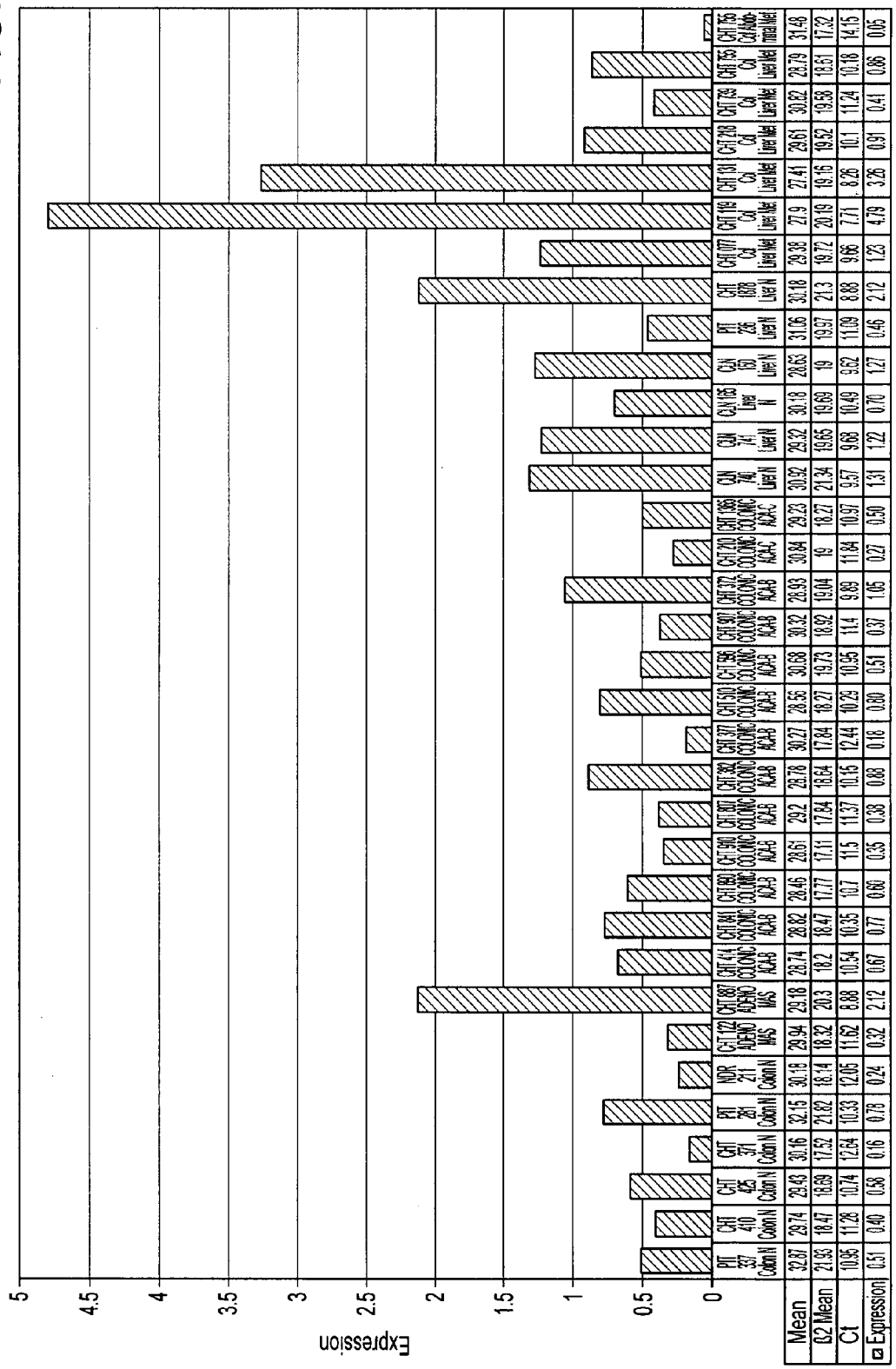
FIG. 28 is a bar graph depicting 25552 mRNA expression levels in various normal and cancerous human tissues as detected by TaqMan analysis. As shown, 25552 mRNA is particularly prevalent in liver metastases.
Figure 29:
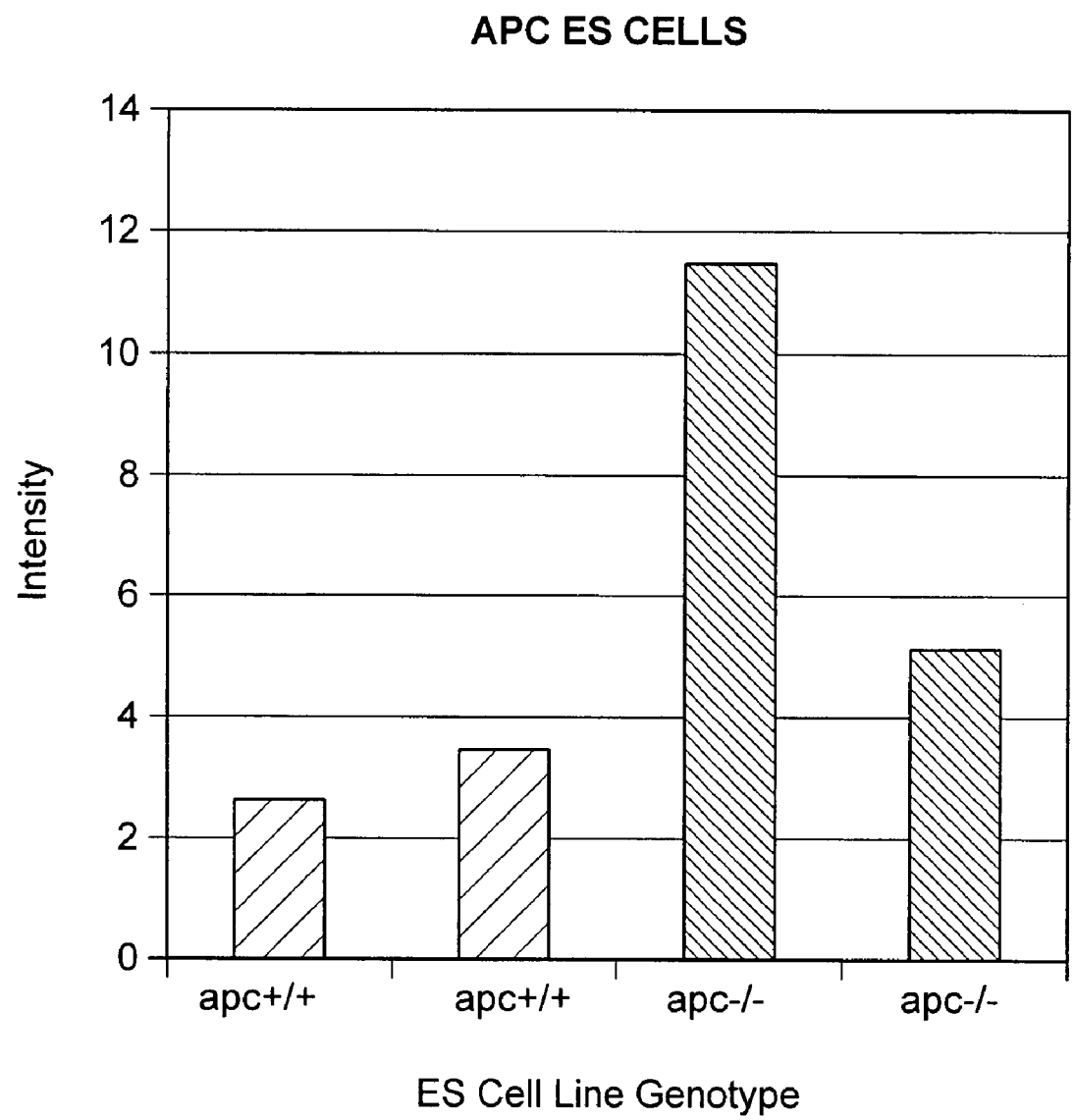
FIG. 29 is a bar graph depicting 25552 mRNA expression levels in a genetically modified ES cell line relative to its wild-type counterpart. 25552 mRNA mRNA expression is increased in ES cells that have a non-functional APC the adenomatous polyposis coli (APC) tumor suppressor gene.
Figure 30A:
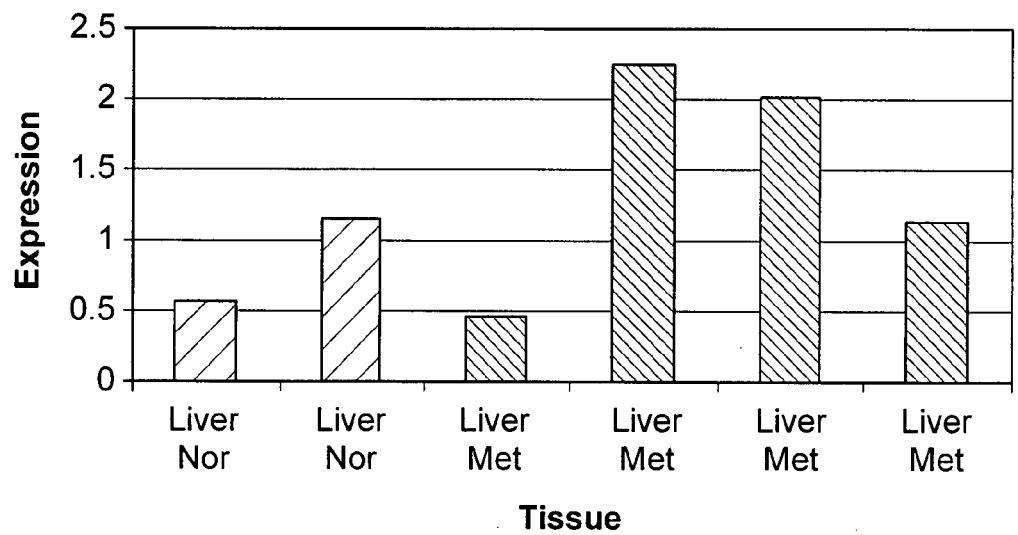
FIG. 30A is a bar graph depicting increased 25552 mRNA expression in metastatic liver samples.
Figure 30B:
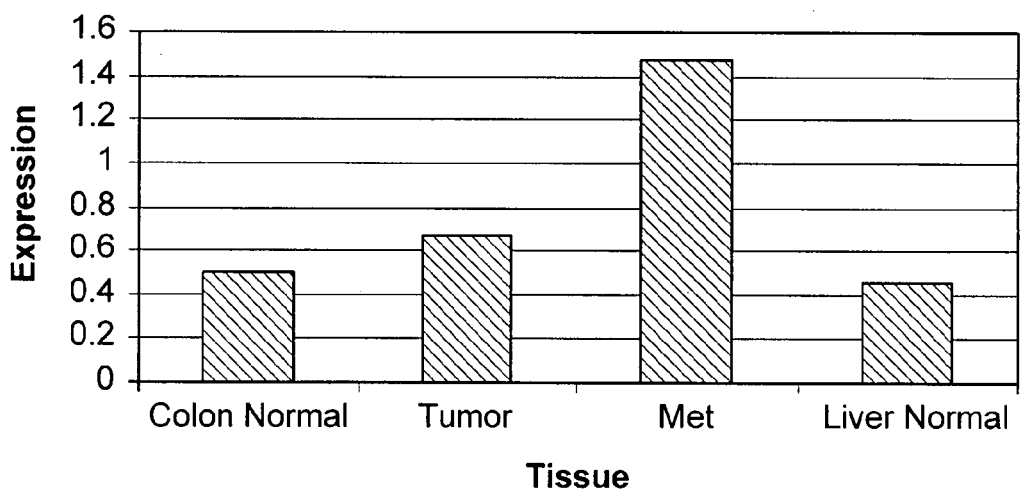
FIG. 30B is a bar graph depicted averaged 25552 mRNA expression for normal colon, colon tumors, metastatic tumors, and normal liver. 25552 mRNA expression is increased in colon tumors, and even more so in metastatic tumors relative to normal tissues.

Human tumor cells were xeno-transplanted into animals including nude mice. Tumors recovered from the animals were analyzed for 25552 mRNA expression. Xeno-transplanted breast and colon tumors had elevated 25552 mRNA expression levels (FIG. 25).

25552 mRNA expression levels were also measured in numerous cancerous and tumor samples. Elevated expression was detected in metastatic liver tumors, in colon tumors, and in tumors of the breast, ovary, lung, and brain (FIGS. 26-28, 30A, and 30B).

25552 mRNA levels were regulated by the APC, the adenomatous polyposis coli (APC) tumor suppressor gene. Embryonic stem cells having a mutated APC gene expressed 25552 mRNA to a greater extent that wild-type embryonic stem cells, indicating that the APC gene product negatively regulates 25552 mRNA production.

Example 11

In situ Hybridization Analysis

Probes to 25552 nucleic acids were used to detect 25552 mRNA molecules in tissue sections using standard in situ hybridization techniques. Results indicated that expression of 25552 mRNA molecules was increased in dysplastic and hyperplastic lesions of the colon relative to normal colon samples.

TABLE 3

In situ Hybridization Results

| Sample | Positives | Tested |
|---|---|---|
| Normal | 0 | 3 |
| In situ dysplasia/hyperplasias | 1 | 2 |

TABLE 3-continued

In situ Hybridization Results

| Sample | Positives | Tested |
|---|---|---|
| Primary Tumors | 3 | 6 |
| Metastases | 3 | 3 |

In addition 25552 mRNA was detected in a lung tumor sample by in situ hybridization analysis.

Example 12

Tissue Distribution of 25552 mRNA by Northern Analysis

Northern blot hybridizations with various RNA samples can be performed under standard conditions and washed under stringent conditions, i.e., 0.2×SSC at 65° C. A DNA probe corresponding to all or a portion of the 25552 cDNA (SEQ ID NO:13) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 13

Recombinant Expression of 25552 in Bacterial Cells

In this example, 25552 is expressed as a recombinant glutathione-S-transferase (GST) fusion polypeptide in *E. coli* and the fusion polypeptide is isolated and characterized. Specifically, 25552 is fused to GST and this fusion polypeptide is expressed in *E. coli*, e.g., strain PEB199. Expression of the GST-25552 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 14

Expression of Recombinant 25552 Protein in COS Cells

To express the 25552 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 25552 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 25552 DNA sequence is amplified by PCR using two primers. The 5' primer contains the restriction site of interest followed by approximately twenty nucleotides of the 25552 coding sequence starting from the initiation codon; the 3' end sequence contains complementary sequences to the other restriction site of interest, a translation stop codon, the HA tag or FLAG tag and the last 20 nucleotides of the 25552 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 25552_gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 25552-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual. 2nd, ed., Cold Spring Harbor Laboratory*, Cold Spring Harbor Laboratory Press, Cold Spring Harbor, N.Y. The expression of the 25552 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual*, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 25552 coding sequence is cloned directly into the polylinker of the pCDNA/Amp vector using the appropriate restriction sites. The resulting plasmid is transfected into COS cells in the manner described above, and the expression of the 25552 polypeptide is detected by radiolabelling and immunoprecipitation using a 25552 specific monoclonal antibody.

Examples for 32132

Example 15

Identification and Characterization of Human 32132 cDNA

The human 32132 nucleic acid sequence is recited as follows:

```
TTTTTTTTTTTATTTTTCAATGCATCTTTAATTTGTAAAGAAATAAAATAAATTAA    (SEQ ID NO:19)

GATGTAACCATTAGCCTCATCTTTACTCCCGAAAGCTCACTTTGCTTTTAGTCCTG

GCCGTCGGCTGAGCGAGCTGCGCATGCGCCACGTGCCCCCGTGGCGTAGGGCCT

CGTCCGGTCACGACTATCCGCTGGGCGGGGTCGGTGCTGGCCGAGGGGGCGCCG

GCTGCCGGAGTGGACATGGCGGCCGGCCCCATTAGGGTGGTGTTGGTCCTTCTAG

GGGTGCTCAGTGTCTGTGCAGCCAGCGGCCATGGGTCCGTAGCGGAGAGGGAGG

CCGGCGGGGAGGCGGAGTGGGCGGAACCGTGGGATGGCGCGGTTTTCCGGCCGC

CCTCGGCGCTGGGCGCAGTGGGGGTGACGCGCAGCTCTGGGACGCCGCGGCCAG

GGAGGGAGGAGGCGGGGGACTTGCCGGTACTGCTGTGGTGGAGCCCAGGGCTAT

TCCCCCACTTCCCGGGAGACTCGGAGCGCATCGAGTGTGCGCGCGGCGCGTGCG

TGGCGTCCCGGAACCGCCGAGCGCTGAGGGACTCGCGGACGCGCGCGCTGCTCT

TCTACGGCACAGACTTCCGCGCGTCGGCCGCCCCGCTGCCGCGCCTGGCGCACC

AGAGCTGGGCGCTCCTCCACGAGGAGTCGCCCCTCAACAACTTCTTGCTGAGCC

ACGGCCCGGGCATCCGCCTCTTCAATCTTACCTCCACCTTCAGTCGCCACTCGGA

TTACCCGCTGTCGCTGCAGTGGCTGCCCGGACCGCCTATCTGCGCCGCCCGGTG

CCTCCGCCCATGGAACGCGCGGAGTGGCGCCGCCGCGGCTACGCGCCGCTGCTC

TATCTGCAGTCACACTGCGACGTGCCAGCGGACCGGGACCGCTACGTGCGCGAG

CTCATGCGCCACATCCCGGTAGACTCCTACGGGAAATGCCTGCAGAATCGGGAG

CTGCCTACCGCGCGGCTACAGGACACAGCCACGGCCACCACCGAGGATCCAGAG

CTCTTGGCTTTCTTGTCCCGCTATAAGTTCCACTTGGCCCTGGAAAATGCCATCTG

TAACGACTACATGACAGAAAAACTGTGGCGTCCCATGCACCTGGGCGCTGTGCC

CGTGTACCGCGGTTCTCCCTCTGTGAGGGACTGGATGCCGAACAATCACTCCGTC
```

-continued
```
ATCCTGATTGATGATTTTGAGTCTCCTCAGAAGCTGGCAGAGTTTATTGACTTTCT

GGACAAGAATGATGAGGAGTATATGAAATACCTGGCATACAAGCAACCTGGGG

GCATCACCAACCAATTTCTTCTGGATAGTCTGAAGCATCGGGAGTGGGGAGTGA

ATGATCCTTTGCTGCCTAACTACCTCAACGGCTTCGAGTGTTTCGTCTGTGACTAC

GAACTGGCTCGGCTGGATGCCGAGAAAGCCCACGCGGCCTCTCCCGGGACAGC

CCCGTCTTTGAGCCCCACATTGCCCAGCCCTCACACATGGACTGCCCAGTGCCCA

CACCTGGCTTTGGCAATGTGGAAGAGATTCCTGAGAATGACAGTTGGAAAGAGA

TGTGGCTGCAAGATTATTGGCAAGGTCTGGACCAGGGGGAAGCTCTCACTGCCA

TGATCCACAACAATGAAACAGAGCAGACGAAATTTTGGGATTACCTACATGAAA

TCTTCATGAAGAGGCAACATCTCTAAGTGCCCTTGCAAGAGCCTTTAACTTGGCG

GAGCTAAGGAGATCTTATTCTACCATGGGACATAAGGAGCATCCACTGCACAAA

CCCTTAATGAACACTGTCTTTTCATGGATTCAAGGAATTCCAGTTTTATCTATTAA

GATTTTATCTTAATGATGAGTAGCCAAGGTCTAACATAGGGCCTCTCCTCAAGGA

GAGATGGAGGGATACAATTCTTGGTTCAGTGGGAAACAGAACCCTAAAACATCC

ATTTGATTCAAGGTGCTGGTCCAACAGAGTTTTTAAACTACTCACTTCTTTATTTC

ATCCTTTCGACTGTACTTGATTACCAGTGAAGTAAGATGGGTCAGGTTACGACTT

ACAACTTTTGTTCTATTCCCCAGACTCCTCATTATTCAGTACATTTCCCAATAATC

TCTTTTTCTCATCTCTTGCTTTATAAATTGTTACGTTGGTGGAGAAGCAAAACATT

TGGTGAGTTGTATTCTGGTTTTCCGGAGTTGGATTTTTTATATTATATACTTTCA

TGTCAAACTTCWAWTTTACTTATTTATTTATTTTTTTAAAATATTTTTTGTAGAGA

TGAGGTTTTGCCACATTGCCCAGGTTGGTCTCCAACTCCTGGATCAAGCAATCCA

TCCGCCTTGACCTCCCAGAGTGCTGGGTTTACAGGCATCAGCCACCTCACCCAGC

CCTAATTTTTTTTTTTTTTGGCTTTTTCTGGCCAGGCGTAGTGGCTTATGCCTGT

AATCCCAACACTTTGGGAGGCCGAGGAGAGGCGACTGCTTGAAGCCAGGAGTTT

GAGACCATCCTAGCAAGACCTTGTCTCTAAAAAATAAAA.
```

The human 32132 nucleic acid sequence (SEQ ID NO:19) is approximately 2557 nucleotides long. The nucleic acid sequence includes an initiation codon (ATG) and a termination codon (TAA) which are underlined above. The region between and inclusive of the initiation codon and the termination codon is a methionine-initiated coding sequence of about 1479 nucleotides (nucleotides 236-1714 of SEQ ID NO:19, designated as SEQ ID NO:21). The coding sequence encodes a 492 amino acid protein, the sequence of which is recited as follows:

```
                                              (SEQ ID NO:20)
MAAGPIRVVLVLLGVLSVCAASGHGSVAEREAGGEAEWAEPWDGAVFRPP

SALGAVGVTRSSGTPRPGREEAGDLPVLLWWSPGLFPHFPGDSERIECAR

GACVASRNRRALRDSRTRALLFYGTDFRASAAPLPRLAHQSWALLHEESP

LNNFLLSHGPGIRLFNLTSTFSRHSDYPLSLQWLPGTAYLRRPVPPPMER

AEWRRRGYAPLLYLQSHCDVPADRDRYVRELMRHIPVDSYGKCLQNRELP

TARLQDTATATTEDPELLAFLSRYKFHLALENAICNDYMTEKLWRPMHLG

AVPVYRGSPSVRDWMPNNHSVILIDDFESPQKLAEFIDFLDKNDEEYMKY
```
-continued
```
LAYKQPGGITNQFLLDSLKHREWGVNDPLLPNYLNGFECFVCDYELARLD

AEKAHAASPGDSPVFEPHIAQPSHMDCPVPTPGFGNVEEIPENDSWKEMW

LQDYWQGLDQGEALTAMIHNNETEQTKFWDYLHEIFMKRQHL.
```

Example 16

Tissue Distribution of 32132 mRNA

Endogenous human 21953 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples were internally controlled by the addition of a second set of primers/probe specific for a reference gene such as β2-macroglobulin, GAPDH which has been labeled with a different fluorophore on the 5' end (typically VIC).

To determine the level of 32132 in various human tissues a primer/probe set was designed. Total RNA was prepared from a series of human tissues using an RNeasy kit from Qiagen. First strand cDNA was prepared from 1 µg total RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in the left column of the tables below.

32132 mRNA expression was detected in several tissues, including cardiovascular (e.g., heart, aortic and coronary smooth muscle cells, veins, and arteries), kidney, skeletal muscle, colon, liver, and brain tissues (see, e.g., Tables 1-2 below). In addition, 32132 mRNA expression was elevated in some adenocarcinomas (ACAs) and most tested liver metastases of colorectal origin (see, e.g., Table 6).

TABLE 4

| Sample | Relative Expression |
| --- | --- |
| Fetal Heart/Normal | 40.52 |
| Heart/Normal/Atrium | 9.82 |
| Heart/Normal/Atrium | 6.75 |
| Heart/Normal/Ventricle | 5.76 |
| Heart/Normal/Ventricle | 19.57 |
| Heart/Normal/Ventricle | 6.13 |
| Heart/Normal/Ventricle | 26.83 |
| Heart/Normal/Ventricle | 14.78 |
| Heart/Diseased/Ventricle | 9.75 |
| Heart/Diseased/Ventricle | 6.17 |
| Kidney/Normal | 23.52 |
| Kidney/Normal | 16.86 |
| Kidney/Normal | 44.81 |
| Kidney/Normal | 8.73 |
| Kidney/Normal | 2.60 |
| Kidney/HT | 3.84 |
| Kidney/HT | 7.02 |
| Kidney/HT | 12.91 |
| Skeletal Muscle/Normal | 13.56 |
| Skeletal Muscle/Normal | 2.65 |
| Liver/Normal | 0.04 |
| Liver/Normal | 1.80 |

The mRNA expression data for 32132 mRNA tabulated in Table 4 indicate that 32132 is expressed in fetal heart, adult heart (atrioles and ventricles), kidney, skeletal muscle, and liver tissues. Relative expression in Table 4 is relative to expression of β2-macroglobulin.

TABLE 5

| Sample | Relative Expression |
| --- | --- |
| Aortic Smooth Muscle Cells | 49.72 |
| Coronary Smooth Muscle Cells | 58.92 |
| HUVEC Static | 231.65 |
| HUVEC Low Shear Stress | 62.50 |
| Adipose | 0.40 |
| Artery/Normal/Carotid | 4.40 |
| Artery/Normal/Carotid | 0.82 |
| Artery/normal | 3.67 |
| IM Artery/Normal | 3.18 |
| Muscular Artery/Normal | 72.04 |

TABLE 5-continued

| Sample | Relative Expression |
| --- | --- |
| Muscular Artery/Normal | 2.43 |
| Muscular Artery/Normal | 10.93 |
| Muscular Artery/Normal | 25.47 |
| Muscular Artery/Normal | 11.92 |
| Muscular Artery/Normal | 38.74 |
| Aorta/Diseased | 3.93 |
| Aorta/Diseased | 38.08 |
| Aorta/Diseased | 24.01 |
| Aorta/Diseased | 29.46 |
| Artery/Diseased/Iliac | 5.66 |
| Artery/Diseased/Tibial | 0.58 |
| Vein/Normal/Saphenous | 0.14 |
| Vein/Normal | 0.00 |
| Vein/Normal/Saphenous | 0.84 |
| Vein/Normal | 27.78 |
| Vein/Normal | 22.33 |
| Vein/Normal | 27.97 |
| Vein/Normal | 26.92 |

The mRNA expression data for 32132 mRNA tabulated in Table 5 indicate that 32132 is expressed in aortic and coronary smooth muscle cells, human umbilical vein endothelial cells (HUVECs), arteries (muscular and aorta), and veins. Relative expression in Table 5 is relative to expression of β2-macroglobulin.

TABLE 6

| Sample | Relative Expression |
| --- | --- |
| Colon Normal | 5.21 |
| Colon Normal | 1.02 |
| Colon Normal | 1.87 |
| Colon Normal | 0.19 |
| Colon Normal | 4.33 |
| Colon Normal | 1.85 |
| Adenomas | 4.47 |
| Adenomas | 10.90 |
| Colonic Adenocarcinoma-B | 5.78 |
| Colonic Adenocarcinoma-B | 8.14 |
| Colonic Adenocarcinoma-B | 0.39 |
| Colonic Adenocarcinoma-B | 0.45 |
| Colonic Adenocarcinoma-B | 1.69 |
| Colonic Adenocarcinoma-B | 2.72 |
| Colonic Adenocarcinoma-B | 1.05 |
| Colonic Adenocarcinoma-C | 2.21 |
| Colonic Adenocarcinoma-C | 0.36 |
| Colonic Adenocarcinoma-C | 1.99 |
| Colonic Adenocarcinoma-C | 1.42 |
| Colonic Adenocarcinoma-C | 1.60 |
| Colonic Adenocarcinoma-C | 0.21 |
| Liver Normal | 1.01 |
| Liver Normal | 0.75 |
| Liver Normal | 1.51 |
| Liver Normal | 1.51 |
| Liver Normal | 1.00 |
| Liver Normal | 1.72 |
| Colonic Liver Metastasis | 1.04 |
| Colonic Liver Metastasis | 7.44 |
| Colonic Liver Metastasis | 4.35 |
| Colonic 1 Liver Metastasis | 5.66 |
| Colonic Liver Metastasis | 7.98 |
| Colonic Liver Metastasis | 3.35 |
| Colonic Abdominal Metastasis | 0.60 |

The mRNA expression data for 32132 mRNA tabulated in Table 6 indicate that 32132 expression is upregulated in some adenomas and adenocarcinomas, and in most colonic liver metastases (see "Relative Expression" values). Relative expression in Table 6 is relative to expression of β2-macroglobulin.

TABLE 7

| Sample | Relative Expression |
| --- | --- |
| PIT 400 Breast Normal | 0.000 |
| PIT 372 Breast Normal | 0.000 |
| CHT 558 Breast Normal | 0.000 |
| CLN 168 Breast Tumor: Invasive Ductal Carcinoma (IDC) | 0.185 |
| MDA 304 Breast Tumor: MD-IDC | 0.000 |
| NDR 57 Breast Tumor: IDC-PD | 0.017 |
| NDR 132 Breast Tumor: IDC/invasive lobular carcinoma | 0.000 |
| CHT 562 Breast Tumor: IDC | 0.035 |
| NDR 12 Breast Tumor | 0.000 |
| PIT 208 Ovary Normal | 0.016 |
| CHT 620 Ovary Normal | 0.000 |
| CLN 03 Ovary Tumor | 0.000 |
| CLN 17 Ovary Tumor | 0.046 |
| MDA 25 Ovary Tumor | 0.000 |
| MDA 216 Ovary Tumor | 0.000 |
| CLN 012 Ovary Tumor | 0.000 |
| MDA 185 Lung Normal | 0.000 |
| CLN 930 Lung Normal | 0.012 |
| MDA 183 Lung Normal | 0.000 |
| MPI 215 Lung Tumor-SmallCell | 0.033 |
| MDA 259 Lung Tumor-PDNSCCL | 0.034 |
| CHT 832 Lung Tumor-PDNSCCL | 0.030 |
| CHT 911 Lung Tumor-Small Cell Carcinoma | 0.041 |
| MDA 262 Lung Tumor-Small Cell Carcinoma | 0.000 |
| CHT 211 Lung Tumor-Adenocarcima | 0.000 |
| MDA 253 Lung Tumor-PDNSCCL | 0.007 |
| NHBE | 1.186 |
| CHT 396 Colon Normal | 0.000 |
| CHT 523 Colon Normal | 0.000 |
| CHT 452 Colon Normal | 0.000 |
| CHT 382 Colon Tumor: MD | 0.014 |
| CHT 528 Colon Tumor: MD | 0.008 |
| CLN 609 Colon Tumor | 0.033 |
| CHT 372 Colon Tumor: MD-PD | 0.000 |
| NDR 217 Colon-Liver Metastasis | 0.000 |
| NDR 100 Colon-Liver Metastasis | 0.044 |
| PIT 260 Liver Normal (female) | 0.004 |
| ONC 102 Hemangioma | 0.093 |
| A24 HMVEC-Arr | 3.206 |
| C48 HMVEC-Prol | 2.347 |

32132 mRNA was analyzed by TaqMan in a number of cell lines derived from normal and tumor cells (Table 7). Relative expression in Table 7 is relative to expression of β2-macroglobulin. Elevated 32132 mRNA expression levels were detected in some breast tumor cell lines, e.g., invasive ductal carcinoma cells (IDC); an ovarian tumor cell line; some lung tumor cell lines, e.g., small cell carcinomas (SCC); some colon tumor cell lines; a colon liver metastasis, a hemangioma cell lines; and human microvascular endothelial cells (HMVEC).

TABLE 8

| Sample | Relative Expression |
| --- | --- |
| Artery normal | 0.000 |
| Vein normal | 0.000 |
| Aortic Smooth Muscle Cells EARLY | 0.193 |
| Coronary Smooth Muscle Cells | 1.059 |
| Static HUVEC | 0.734 |
| Shear HUVEC | 1.151 |
| Heart normal | 0.034 |
| Heart CHF | 0.000 |
| Kidney | 0.149 |
| Skeletal Muscle | 0.000 |
| Adipose normal | 0.000 |
| Pancreas | 0.000 |
| primary osteoblasts | 0.030 |
| Osteoclasts (diff) | 0.000 |
| Skin normal | 0.000 |

TABLE 8-continued

| Sample | Relative Expression |
| --- | --- |
| Spinal cord normal | 0.000 |
| Brain Cortex normal | 0.704 |
| Brain Hypothalamus normal | 0.000 |
| Nerve | 0.000 |
| Dorsal Root Ganglion | 0.000 |
| Glial Cells (Astrocytes) | 1.611 |
| Glioblastoma | 0.000 |

32132 mRNA was detected by TaqMan analysis in a number of tissues, e.g., including cardiovascular endothelial cells such as aortic smooth muscle cells, coronary smooth muscle, static human umbilical vein endothelial cells (HUVEC), shear HUVEC, and heart cells; kidney cells; brain cortex; and glial cells (Table 8). Relative expression in Table 8 is relative to expression of β2-macroglobulin.

TABLE 9

| Sample | Relative Expression |
| --- | --- |
| Breast normal | 0.000 |
| Breast tumor | 0.000 |
| Ovary normal | 0.034 |
| Ovary Tumor | 0.000 |
| Prostate Normal | 0.000 |
| Prostate Tumor | 0.000 |
| Epithelial Cells (Prostate) | 0.261 |
| Colon normal | 0.000 |
| Colon Tumor | 0.016 |
| Lung normal | 0.000 |
| Lung tumor | 0.000 |
| Lung COPD | 0.000 |
| Colon IBD | 0.000 |
| Liver normal | 0.000 |
| Liver fibrosis | 0.000 |
| Dermal Cells-fibroblasts | 0.031 |
| Spleen normal | 0.000 |
| Tonsil normal | 0.000 |
| Lymph node | 0.000 |
| Small Intestine | 0.000 |
| Skin-Decubitus | 0.000 |
| Synovium | 0.000 |
| BM-MNC (Bone marrow mononuclear cells) | 0.000 |
| Activated PBMC | 0.000 |

32132 mRNA was detected by TaqMan analysis in a number of tissues, e.g., including normal ovary, epithelial cells (from prostate), colon tumor, and dermal fibroblasts (Table 9). Relative expression in Table 9 is relative to expression of β2-macroglobulin.

TABLE 10

| Sample | Relative Expression |
| --- | --- |
| HCT 116 NOC t = 0 | 11.36 |
| HCT 116 NOC t = 3 | 11.92 |
| HCT 116 NOC t = 6 | 12.43 |
| HCT 116 NOC t = 9 | 10.20 |
| HCT 116 NOC t = 15 | 11.13 |
| HCT 116 NOC t = 18 | 8.70 |
| HCT 116 NOC t = 21 | 8.03 |
| HCT 116 NOC t = 24 | 6.92 |

32132 mRNA expression is regulated during the cell cycle of HCT 116 cells (Table 10; Relative expression is relative to expression of β2-macroglobulin.). Cells were arrested in mitosis in nocodazole, then released by removal of the agent. 32132 mRNA was monitored at regular intervals after release. 32132 expression peaked during mitosis and G1 phase of the cell cycle, and then decreased.

Example 17

Recombinant Expression of 32132 in Bacterial Cells

In this example, 32132 is expressed as a recombinant glutathione-S-transferase (GST) fusion polypeptide in *E. coli*, and the fusion polypeptide is isolated and characterized. Specifically, 32132 is fused to GST, and this fusion polypeptide is expressed in *E. coli*, e.g., strain PEB199. Expression of the GST-32132 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 18

Expression of Recombinant 32132 Protein in COS Cells

To express the 32132 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 32132 protein and an HA tag (Wilson et al. (1984) *Cell* 37:767) or a FLAG tag fused in-frame to the 3' end of the fragment is cloned into the polylinker region of the vector, thereby placing the expression of the recombinant protein under the control of the CMV promoter.

To construct the plasmid, the 32132 DNA sequence is amplified by PCR using two primers. The 5' primer contains the restriction site of interest followed by approximately twenty nucleotides of the 32132 coding sequence, starting from the initiation codon. The 3' end sequence contains sequences complementary to the other restriction site of interest, a translation stop codon, the HA tag or FLAG tag, and the last 20 nucleotides of the 32132 coding sequence. The PCR amplified fragment and the pCDNA/Amp vector are digested with the appropriate restriction enzymes, and the vector is dephosphorylated using the CIAP enzyme (New England Biolabs, Beverly, Mass.). Preferably, the two restriction sites chosen are different so that the 32132_gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 32132-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the 32132 polypeptide is detected by radiolabeling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected, and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 32132 coding sequence is cloned directly into the polylinker of the pCDNA/Amp vector using the appropriate restriction sites. The resulting plasmid is transfected into COS cells in the manner described above, and the expression of the 32132 polypeptide is detected by radiolabeling and immunoprecipitation using a 32132 specific monoclonal antibody.

Example for 32244

Example 19

Identification and Characterization of Human 32244 cDNA

The human 32244 nucleic acid sequence is recited as follows:

```
CGGAACTGGTCCGGCCCGACTCACGACCCCGCGGGACCCGGCCGGAACCCGGCC    (SEQ ID NO:25)

CGACCCCGGCGCGCGCGGCGGAGGACGAGGAAGAGTTGTGGCGAGGCAGAT

CCTGCCCCGTGGCCGCGGCCGTCTCGTAGCTCGGCCCCAGGAGGCTCCCGGGAG

CGCCTGTCAGTGCAATGCCGCCCCATGTGGTGCTCACCTTCCGGCGCCTGGGCTG

CGCCTTGGCCTCCTGCCGGCTGGCGCCTGCGAGACACAGAGGAAGTGGTCTTCT

GCACACAGCCCCAGTGGCCCGCTCGGACAGGAGCGCCCCGGTGTTCACCCGTGC

CCTGGCCTTTGGGGACAGAATCGCCCTGGTTGACCAGCACGGCCGCCACACGTA

CAGGGAGCTTTATTCCCGCAGCCTTCGCCTGTCCCAGGAGATCTGCAGGCTCTGC

GGGTGTGTCGGCGGGGACCTCCGGGAGGAGAGGGTCTCCTTCCTATGTGCTAAC

GACGCCTCCTACGTCGTGGCCCAGTGGGCCTCATGGATGAGCGGCGGTGTGGCA
```

-continued

```
GTACCCCTCTACAGGAAGCATCCCGCGGCCCAGCTGGAGTATGTCATCTGCGACT

CCCAGAGCTCTGTGGTCCTTGCCAGCCAGGAGTACCTGGAGCTCCTGAGCCCGGT

GGTCAGGAAGCTGGGGGTCCCGCTGCTGCCGCTCACACCAGCCATCTACACTGG

AGCAGTAGAGGAACCGGCAGAGGTCCCGGTCCCAGAGCAGGGATGGAGGAACA

AGGGCGCCATGATCATCTACACCAGTGGGACCACGGGGAGGCCCAAGGGCGTGC

TGAGCACGCACCAAAACATCAGGGCTGTGGTGACCGGGCTGGTCCACAAGTGGG

CATGGACCAAAGACGACGTGATCCTCCACGTGCTCCCGCTGCACCACGTCCATG

GTGTGGTCAACGCGCTGCTCTGTCCTCTCTGGGTGGGAGCCACCTGTGTGATGAT

GCCTGAGTTCAGCCCTCAGCAGGTTTGGGAAAAGTTCTTAAGTTCTGAAACGCCG

CGGATCAATGTCTTTATGGCAGTGCCTACAATATACACCAAGCTGATGGAGTACT

ACGACAGGCATTTTACCCAGCCGCACGCCCAGGATTTCTTGCGTGCAGTTTGTGA

AGAAAAAATTAGGCTGATGGTCTCAGGCTCAGCTGCCCTGCCCCTCCCAGTGCTG

GAGAAGTGGAAGAACATCACGGGCCACACCCTGCTGGAGCGGTATGGCATGACC

GAGATCGGCATGGCTCTGTCCGGGCCCCTGACCACTGCCATGCGCCTGCCAGGTT

CCGTGGGGACCCCACTGCCTGGAGTACAGGTGCGCATTGTCTCAGAAAACCCAC

AGAGGGAAGCCTGCTCCTACACCATCCACGCAGAGGGAGACGAGAGGGGGACC

AAGGTGACCCCAGGGTTTGAAGAAAAGGAGGGGGAGCTGCTGGTGAGGGACC

CTCCGTGTTTCGAGAATACTGGAATAAACCAGAAGAAACTAAGAGTGCATTCAC

CCTGGATGGCTGGTTTAAGACAGGGGACACCGTGGTGTTTAAGGATGGCCAGTA

CTGGATCCGAGGCCGGACCTCAGTGGACATCATCAAGACTGGAGGCTACAAGGT

CAGCGCCCTGGAGGTGGAGTGGCACCTGCTGGCCCACCCCAGCATCACAGATGT

GGCTGTGATTGGAGTTCCGGATATGACATGGGGCCAGCGGGTCACTGCTGTGGT

GACCCTCCGAGAAGGACACTCACTGTCCCACAGGGAGCTCAAAGAGTGGGCCAG

AAATGTCCTGGCCCCGTACGCGGTGCCCTCGGAGCTGGTGCTGGTGGAGGAGAT

CCCGCGGAACCAGATGGGCAAGATTGACAAGAAGGCGCTCATCAGGCACTTCCA

CCCCTCATGACCCGGCAGACTGGGACTGCGGGTCTGGTGGGGAGCAGCAGACGT

CCCCTTCACACCGAGAACCACGGGGCCCGTCCAAGACCTGGCCTCCCTTAAAC

CTGAACCCCCCAAATCAGGTCACGTAGAATCAAGAACTGTTTGGGATGAAATCA

CCATGTGGGGTCCCCAGCCTCGGGCCAGTTGTTGCAGCTCAAGGAGACCGTCCCT

GGTGTCACCTCTGCCTGGTCACCGCCGACCTCATCTGTGCAGCGCGGTGCAGCCA

GCCCCTGGCCCCACGTGCTGAGGCACCTCCCGCCCCACAGTGCCCTGCAGTTGCC

AGGCTCTCCAGGGCAGGTCCCAGAGGTTTCCCACAAAAAACAAATAAAGACTCC

ACTGGAGGAAACAAAAAAAAAAAAA.
```

Figure 35:
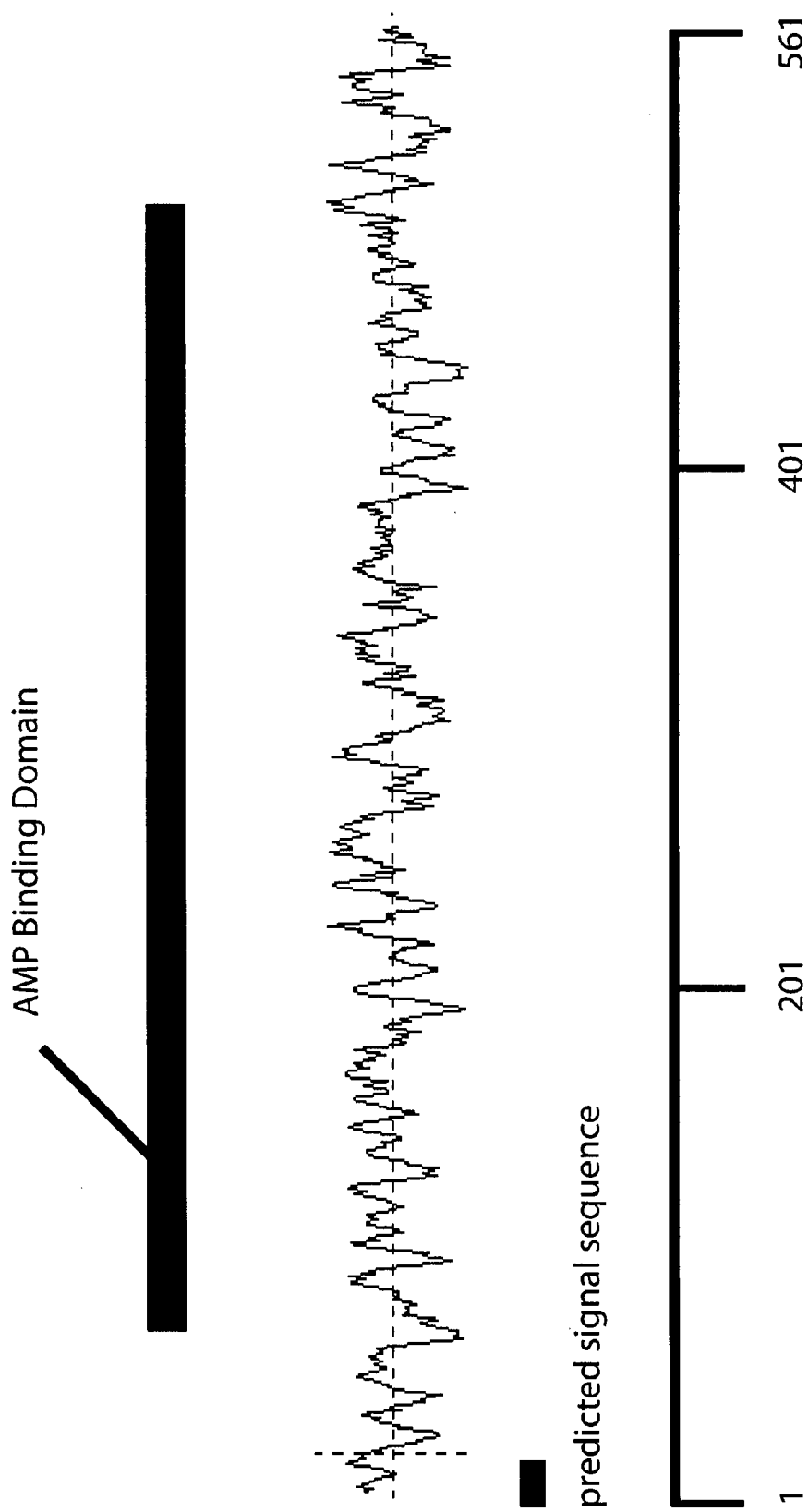
FIG. 35 depicts a hydropathy plot of human 32244. Relative hydrophobic residues are shown above the dashed horizontal line, and relative hydrophilic residues are below the dashed horizontal line. Numbers corresponding to positions in the amino acid sequence of human 32244 are indicated. Polypeptides of the invention include fragments which include: all or part of a hydrophobic sequence, i.e., a sequence above the dashed line, e.g., the sequence from about amino acid 245 to 270, from about 327 to 340, and from about 516 to 522 of SEQ ID NO:26; and all or part of a hydrophilic sequence, i.e., a sequence below the dashed line, e.g., the sequence of from about amino acid 60 to 80, from about 434 to 446, and from about 523 to 535 of SEQ ID NO:26.

The human 32244 sequence (FIG. 35; SEQ ID NO:25), which is approximately 2302 nucleotides long. The nucleic acid sequence includes an initiation codon (ATG) and a termination codon (TGA) which are underscored above. The region between and inclusive of the initiation codon and the termination codon is a methionine-initiated coding sequence of about 1731 nucleotides, including the termination codon (nucleotides indicated as "coding" of SEQ ID NO:25; SEQ ID NO:27). The coding sequence encodes a 576 amino acid protein (SEQ ID NO:26), which is recited as follows:

(SEQ ID NO:26)
MPPHVVLTFRRLGCALASCRLAPARHRGSGLLHTAPVARSDRSAPVFTRA

LAFGDRIALVDQHGRHTYRELYSRSLRLSQEICRLCGCVGGDLREERVSF

LCANDASYVVAQWASWMSGGVAVPLYRKHPAAQLEYVICDSQSSVVLASQ

EYLELLSPVVRKLGVPLLPLTPAIYTGAVEEPAEVPVPEQGWRNKGAMII

YTSGTTGRPKGVLSTHQNIRAVVTGLVHKWAWTKDDVILHVLPLHHVHGV

VNALLCPLWVGATCVMMPEFSPQQVWEKFLSSETPRINVFMAVPTIYTKL

MEYYDRHFTQPHAQDFLRAVCEEKIRLMVSGSAALPLPVLEKWKNITGHT

LLERYGMTEIGMALSGPLTTAMRLPGSVGTPLPGVQVRIVSENPQREACS

YTIHAEGDERGTKVTPGFEEKEGELLVRGPSVFREYWNKPEETKSAFTLD

GWFKTGDTVVFKDGQYWIRGRTSVDIIKTGGYKVSALEVEWHLLAHPSIT

DVAVIGVPDMTWGQRVTAVVTLREGHSLSHRELKEWARNVLAPYAVPSEL

VLVEEIPRNQMGKIDKKALIRHFHPS.

Example 20

Tissue Distribution of 32244 mRNA by TaqMan Analysis

Endogenous human 32244 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

To determine the level of 32244 in various human tissues a primer/probe set was designed. Total RNA was prepared from a series of human tissues using an RNeasy kit from Qiagen. First strand cDNA was prepared from 1 μg total RNA using an oligo-dT primer and Superscript II reverse transcriptase (Gibco/BRL). cDNA obtained from approximately 50 ng total RNA was used per TaqMan reaction. Tissues tested include the human tissues and cell lines shown in Tables 11-15. 32244 mRNA was detected in a wide range of tissues, including adipose, breast, lung, colon, liver, brain, and ovary tissues (Tables 11-13). 32244 expression was also found in several cell lines, including cell lines derived from breast and colon tumors (Tables 14 and 15).

TABLE 11

| Tissue | Relative Expression |
| --- | --- |
| Aorta Normal | 0.26 |
| Fetal heart Normal | 0.53 |

TABLE 11-continued

| Tissue | Relative Expression |
| --- | --- |
| Heart Normal | 0.60 |
| Heart (Congestive Heart Failure) | 0.76 |
| Vein Normal | 3.88 |
| Aortic Smooth Muscle Cells | 0.84 |
| Spinal cord Normal | 0.26 |
| Brain cortex Normal | 0.28 |
| Brain hypothalamus Normal | 0.13 |
| Glial cells (Astrocytes) | 0.27 |
| Brain Glioblastoma | 0.38 |
| Breast Normal | 11.94 |
| Breast tumor (IDC) IDC = invasive ductal carcinoma | 0.53 |
| Ovary Normal | 0.18 |
| Ovary Tumor | 0.19 |
| Pancreas Normal | 0.45 |
| Prostate Normal | 0.67 |
| Prostate Tumor | 1.02 |
| Colon Tumor | 0.44 |
| Colon (Intestinal Bowel Disease) | 0.41 |
| Kidney Normal | 0.18 |
| Liver Normal | 0.20 |
| Liver Fibrosis | 0.33 |
| Fetal Liver Normal | 0.35 |
| Lung Normal | 0.91 |
| Lung Tumor | 0.29 |
| Lung COPD | 3.93 |
| Spleen Normal | 0.27 |
| Tonsil Normal | 2.55 |
| Lymph node Normal | 0.37 |
| Thymus Normal | 0.98 |
| Epithelial Cells (Prostate) | 0.44 |
| Endothelial Cells (Aortic) | 0.24 |
| Skeletal Muscle Normal | 0.97 |
| Fibroblasts (Dermal) | 0.12 |
| Skin/Normal | 0.44 |
| Adipose/Normal | 8.04 |
| Osteoblasts (primary) | 0.17 |
| Osteoblasts (Undifferentiated) | 0.67 |
| Osteoblasts (Differentiated) | 1.38 |
| Osteoclasts | 0.26 |
| Aortic Smooth Muscle Cells Early | 0.07 |
| Aortic Smooth Muscle Cells Late | 0.04 |
| Osteoclasts (Undifferentiated) | 0.00 |
| shear HUVEC | 5.31 |

The mRNA expression data for 32244 mRNA tabulated in Table 11 indicated widespread expression. Tissues in which 32244 mRNA was detected include cardiovascular (human umbilical vein endothelial cells (HUVECs), vein, aortic smooth muscle cell, heart, aorta), brain, glial, breast, ovary, pancreas, prostate, colon, kidney, adult and fetal liver, lung, spleen, tonsil, lymph node, thymus, epithelial and endothelial cell, skeletal muscle, dermal fibroblast, skin, adipose, osteoblast, and osteoclast tissues. Expression was particularly prominent in the breast, adipose, HUVEC, vein, lung, and tonsil tissue samples.

TABLE 12

| Tissue | Relative Expression |
| --- | --- |
| Colon Normal | 145.6 |
| Colon Normal | 35.4 |
| Colon Normal | 76.9 |
| Colon Normal | 31.0 |
| Colon Tumor | 78.6 |
| Colon Tumor | 40.0 |
| Colon Tumor | 74.6 |
| Colon Tumor | 80.8 |
| Colon Tumor | 83.9 |
| Colon Tumor | 128.5 |

TABLE 12-continued

| Tissue | Relative Expression |
|---|---|
| Liver Metastasis | 92.1 |
| Liver Metastasis | 83.3 |
| Liver Metastasis | 85.7 |
| Liver Metastasis | 56.7 |
| Liver Normal | 13.4 |
| Liver Normal | 95.1 |
| Brain Normal | 234.1 |
| Brain Normal | 304.6 |
| Astrocyte | 144.6 |
| Brain Tumor | 22.4 |
| Brain Tumor | 48.0 |
| Brain Tumor | 42.4 |
| Brain Tumor | 25.6 |
| Brain Tumor | 18.6 |
| HMVEC-Arrested | 77.5 |
| HMVEC-Proliferating | 138.7 |
| Placenta | 46.2 |
| Fetal Adrenal Gland | 160.4 |
| Fetal Liver | 464.9 |
| Fetal Liver | 94.4 |

The mRNA expression data for 32244 mRNA tabulated in Table 12 indicated that 32244 mRNA was well-expressed in both colon tumors and liver metastases, but that 32244 mRNA expression was reduced in brain tumors (5/5) compared to the level of 32244 mRNA expression observed in normal brain tissue and astrocytes. The results also indicated high levels of 32244 mRNA expression in fetal liver and HMVEC cells.

TABLE 13

| Tissue | Relative Expression |
|---|---|
| Breast Normal | 0.71 |
| Breast Normal | 0.32 |
| Breast Normal | 0.90 |
| Breast Normal | 1.46 |
| Breast Tumor | 1.41 |
| Breast Tumor | 1.30 |
| Breast Tumor | 0.84 |
| Breast Tumor | 0.53 |
| Breast Tumor | 1.01 |
| Breast Tumor | 3.30 |
| Ovary Normal | 2.52 |
| Ovary Normal | 1.88 |
| Ovary Normal | 2.62 |
| Ovary Tumor | 0.23 |
| Ovary Tumor | 0.98 |
| Ovary Tumor | 0.63 |
| Ovary Tumor | 0.23 |
| Ovary Tumor | 0.24 |
| Ovary Tumor | 0.34 |
| Ovary Tumor | 2.00 |
| Ovary Tumor | 0.26 |
| Lung Normal | 0.27 |
| Lung Normal | 0.12 |
| Lung Normal | 0.53 |
| Lung Normal | 0.20 |
| Lung Tumor | 3.08 |
| Lung Tumor | 2.03 |
| Lung Tumor | 1.78 |
| Lung Tumor | 1.30 |
| Lung Tumor | 3.25 |
| Lung Tumor | 2.53 |
| Lung Tumor | 0.84 |
| MCF10A-B Non-tumorigenic | 10.71 |
| MCF10A-D Non-tumorigenic | 6.19 |
| MCF10A-E Non-tumorigenic | 9.07 |
| MCF10A-G Non-tumorigenic | 6.35 |
| MCF10A-A Tumorigenic | 5.37 |

TABLE 13-continued

| Tissue | Relative Expression |
|---|---|
| MCF10A-C Tumorigenic | 10.75 |
| MCF10A-F Tumorigenic | 10.49 |

The mRNA expression data for 32244 mRNA tabulated in Table 13 indicated that 32244 mRNA was elevated in all lung tumor samples tested (7/7), as compared to the levels of 32244 mRNA expression observed in normal lung tissue, and that some breast tumors exhibit elevated expression of 32244 mRNA (1/6) relative to the levels of 32244 mRNA expression observed in normal breast tissue. In contrast, the level of 32244 mRNA was reduced in most of the ovary tumor samples analyzed (7/8), as compared to the levels of 32244 mRNA observed in normal ovary tissue. 32244 mRNA was well-expressed in both tumorigenic and non-tumorigenic MCF10A human mammary epithelial cells.

TABLE 14

| Cell Line | Relative Expression |
|---|---|
| MCF10A Non-tumor | 12.5 |
| MCF10AT.c11 Non-tumor | 7.2 |
| MCF10AT.c13 Non-tumor | 8.9 |
| MCF10MS Non-tumor | 6.6 |
| MCF10CA1a.c11 Tumor | 4.4 |
| MCF10AT1 Tumor | 7.9 |
| MCF10AT3B Tumor | 8.9 |
| MCF10AT3B Agar | 11.8 |
| MCF10CA1a.c11 Agar | 9.7 |
| MCF10A-m25 Plastic | 22.6 |

The mRNA expression of human 32244 in both tumorigenic and non-tumorigenic MCF10 human mammary epithelial cells is shown in Table 14. 32244 mRNA was well-expressed in both tumorigenic and non-tumorigenic MCF10 cells. In addition, plating tumorigenic MCF10 cells on plastic resulted in an increase in 32244 mRNA expression, as compared to tumorigenic MCF10 cells plated on agar, indicating that a decrease in 32244 mRNA expression correlates with a more transformed phenotype in tumorigenic MCF10 cells. The lower levels of 32244 mRNA expression in the MCF10 cells plated on agar is consistent with the decrease in 32244 mRNA expression observed in brain tumors (as shown in Table 12, above) and most ovarian tumors (as shown in Table 13, above).

TABLE 15

| Cell Line | Relative Expression |
|---|---|
| MCF-7 Breast Tumor | 11.2 |
| ZR75 Breast Tumor | 9.1 |
| T47D Breast Tumor | 7.0 |
| MDA 231 Breast Tumor | 1.9 |
| MDA 435 Breast Tumor | 1.4 |
| DLD-1 Colon Tumor | 32.2 |
| SW 480 Colon Tumor | 0.9 |
| SW 620 Colon Tumor | 4.8 |
| HCT 116 | 15.3 |
| HT 29 | 1.2 |
| Colo 205 | 6.8 |
| NCIH 125 | 8.0 |
| NCIH 67 | 7.0 |
| NCIH 322 | 14.9 |
| NCIH 460 | 3.0 |
| A549 | 13.0 |

TABLE 15-continued

| Cell Line | Relative Expression |
|---|---|
| NHBE | 4.4 |
| H460 −p16 24 hr | 1.2 |
| H460 −p16 48 hr | 1.7 |
| H460 −p16 72 hr | 2.1 |
| H460 −p16 96 hr | 2.3 |
| H460 +p16 48 hr | 1.6 |
| H460 +p16 72 hr | 1.7 |
| H460 +p16 96 hr | 1.4 |

Tumor cell lines were xenografted into nude mice. Expression of human 32244 mRNA in tumors harvested from the mice was analyzed using TaqMan. Results are tabulated in Table 15 (excepting the final seven rows, see below). The results indicated that, for example, 32244 mRNA is highly expressed in some xenografted breast tumor samples, some xenografted breast tumor samples, and some xenografted ovarian cell lines.

The final seven rows of Table 14 tabulate the relative 32244 mRNA expression in NCI-H460 large cell lung carcinoma cells that either express or do not express the p16 tumor suppressor gene. The absence of p16 correlated with a gradual increase in human 32244 mRNA expression in the NCI-H460 cells over the course of 96 hours, while the presence of p16 correlated with stable expression of 32244 mRNA during the same period of time. The increase in 32244 mRNA expression in NCI-H460 cells in the absence of the p16 tumor suppressor gene is consistent with the increase in 32244 mRNA expression observed in lung tumors and some breast tumors (as shown in Table 13, above).

Example 21

Tissue Distribution of 32244 mRNA by Northern Analysis

Northern blot hybridizations with various RNA samples can be performed under standard conditions and washed under stringent conditions, i.e., 0.2×SSC at 65° C. A DNA probe corresponding to all or a portion of the 32244 cDNA (SEQ ID NO:25) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 22

Recombinant Expression of 32244 in Bacterial Cells

In this example, 32244 is expressed as a recombinant glutathione-S-transferase (GST) fusion polypeptide in *E. coli* and the fusion polypeptide is isolated and characterized. Specifically, 32244 is fused to GST and this fusion polypeptide is expressed in *E. coli*, e.g., strain PEB199. Expression of the GST-32244 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 23

Expression of Recombinant 32244 Protein in COS Cells

To express the 32244 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 32244 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 32244 DNA sequence is amplified by PCR using two primers. The 5' primer contains the restriction site of interest followed by approximately twenty nucleotides of the 32244 coding sequence starting from the initiation codon; the 3' end sequence contains complementary sequences to the other restriction site of interest, a translation stop codon, the HA tag or FLAG tag and the last 20 nucleotides of the 32244 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 32244_gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 32244-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual*. 2nd, ed., Cold Spring Harbor Laboratory, Cold Spring Harbor Laboratory Press, Cold Spring Harbor, N.Y. The expression of the 32244 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual*, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 32244 coding sequence is cloned directly into the polylinker of the pCDNA/Amp vector using the appropriate restriction sites. The resulting plasmid is transfected into COS cells in the manner described above, and the expression of the 32244 polypeptide is detected by radiolabelling and immunoprecipitation using a 32244 specific monoclonal antibody.

Examples for 23680

Example 24

Identification and Characterization of Human 23680 cDNA

The human 23680 nucleotide sequence (FIG. 37; SEQ ID NO:32), which is approximately 2103 nucleotides in length including untranslated regions, contains a predicted methionine-initiated coding sequence of about 1500 nucleotides (nucleotides 145-1644 of SEQ ID NO:32; coding sequence also shown as SEQ ID NO:34). The location of the initiation and termination codons is indicated by the underline. The human 23680 nucleic acid sequence is recited as follows:

```
ATTTGGCCCTCGAGGCCAAGAATTCGGCACGAGGGGGATAACGGGAGGAAGGC    (SEQ ID NO:32)
CGGCCGGGGCCGCCAAGGCAGTCCCAGGCTCGCGTAGGAGGCGCGCAGACCTTG
CACCTTGCACCTTCGCAGCGCCCTGCACCCCGCCACCATGTGCGAGCTGTACAGT
AAGCGGGACACTCTGGGGCTGAGGAAGAAGCACATCGGGCCCTCATGCAAAGTT
TTCTTTGCATCGGATCCCATCAAAATAGTGAGAGCCCAGAGGCAGTACATGTTTG
ATGAGAACGGTGAACAGTACTTGGACTGCATCAACAATGTTGCCCATGTGGGAC
ACTGTCACCCAGGAGTGGTCAAAGCTGCCCTGAAACAGATGGAACTGCTAAATA
CAAATTCTCGATTCCTCCACGACAACATTGTTGAGTATGCCAAACGCCTTTCAGC
AACTCTGCCGGAGAAACTCTCTGTTTGTTATTTTACAAATTCAGGATCCGAAGCC
AACGACTTAGCCTTACGCCTGGCTCGGCAGTTCAGAGGCCACCAGGATGTGATC
ACTCTTGACCATGCTTACCATGGTTACCTATCATCCTTAATTGAGATTAGCCCATA
TAAGTTTCAGAAAGGAAAAGATGTCAAAAAAGAATTTGTACATGTGGCACCAAC
TCCAGATACTTACAGAGGAAAATATAGAGAAGACCATGCAGACTCAGCCAGTGC
TTATGCAGATGAAGTGAAGAAAATCATTGAAGATGCTCATAACAGTGGAAGGAA
GATTGCTGCCTTTATTGCTGAATCCATGCAGAGTTGTGGCGGACAAATAATTCCT
CCAGCAGGCTACTTCCAGAAAGTGGCAGAATATGTACACGGTGCAGGGGGTGTG
TTTATAGCTGATGAAGTTCAAGTGGGCTTTGGCAGAGTTGGGAAACATTTCTGGA
GCTTCCAGATGTATGGTGAAGACTTTGTTCCAGACATCGTCACAATGGGAAAACC
GATGGGCAACGGCCACCCGGTGGCATGTGTGGTAACAACCAAAGAAATTGCAGA
AGCCTTCAGCAGCTCTGGGATGGAATATTTTAATACGTATGGAGGAAATCCAGT
ATCTTGTGCTGTTGGTTTGGCTGTCCTGGATATAATTGAAAATGAAGACCTTCAA
GGAAATGCCAAGAGAGTAGGGAATTATCTCACTGAGTTACTGAAAAAACAGAAG
GCTAAACACACTTTGATAGGAGATATTAGGGGCATTGGCCTTTTTATTGGAATTG
ATTTAGTGAAGGACCATCTGAAAAGGACCCCTGCCACAGCTGAAGCTCAGCACA
TCATCTACAAGATGAAAGAAAAACGAGTGCTTCTCAGTGCCGATGGACCTCATA
GAAATGTACTTAAAATAAAACCACCTATGTGCTTCACTGAAGAAGATGCAAAGT
TCATGGTGGACCAACTTGATAGGATTCTAACAGTTTTAGAAGAAGCTATGGGAA
CCAAAACCGAAAGTGTGACCTCTGAGAATACTCCATGCAAAACAAAGATGCTGA
AGAAGCCCACATAGAACTGCTTAGGGACAGCACCACTGACTCCAAAGAAAATC
CCAGCAGAAAGAGAAATGGAATGTGCACGGATACACATTCACTGCTCAGTAAGA
GGCTCAAGACATGACTGATTTGCATTTTAAAGCAAGATGCGATGTCCAGAGTTAC
AGAGAATGAGTAGATGTGTCTCATCGGTTAATAGCTCTATTATACCTCTAAAGGT
GGAATTGTCAGTTTAGATTCATAAATGAAAAGGTAAATGAGTAATCAGAATAAA
CCAAGTGATAATCAAACCATGTCAAGATTATTAGTTCAGACTCTAGCCTGTTAAT
TTTCTTAGTTGATTTCTGAAGCTACCTGATTTATTCTATTAAATTGTAAGCTTGCA
```

-continued
```
AACTCAAAATAAATTGGCAGATTTACCTCTCATGTTTTAATGTGTCAAATTAGAG

AGCAAAGTATAACAGGTGCCTTCACTTTTGAGACTTAGTGCCTTAAAATATGTAT

TCTATAATGATTTCATATATAAAAGTATATTTATTGACTGTAATAAAATAAAATA

TGATGTAAACAAAAAAAAAAAAAAAAAAAAAAAA
```

The coding sequence encodes a 499 amino acid protein (SEQ ID NO:33) and has the following amino acid sequence:

```
                                            (SEQ ID NO:33)
MCELYSKRDTLGLRKKHIGPSCKVFFASDPIKIVRAQRQYMFDENGEQYL

DCINNVAHVGHCHPGVVKAALKQMELLNTNSRFLHDNIVEYAKRLSATLP

EKLSVCYFTNSGSEANDLALRLARQFRGHQDVITLDHAYHGYLSSLIEIS

PYKFQKGKDVKKEFVHVAPTPDTYRGKYREDHADSASAYADEVKKIIEDA

HNSGRKIAAFIAESMQSCGGQIIPPAGYFQKVAEYVHGAGGVFIADEVQV

GFGRVGKHFWSFQMYGEDFVPDIVTMGKPMGNGHPVACVVTTKEIAEAFS

SSGMEYFNTYGGNPVSCAVGLAVLDIIENEDLQGNAKRVGNYLTELLKKQ

KAKHTLIGDIRGIGLFIGIDLVKDHLKRTPATAEAQHIIYKMKEKRVLLS

ADGPHRNVLKIKPPMCFTEEDAKFMVDQLDRILTVLEEAMGTKTESVTSE

NTPCKTKMLKEAHIELLRDSTTDSKENPSRKRNGMCTDTHSLLSKRLKT
```

Example 25

Tissue Distribution of 23680 mRNA

Endogenous human 23680 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) that has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH that has been labeled with a different fluorophore on the 5' end (typically VIC).

To determine the level of 23680 in various human tissues a primer/probe set was designed. Total RNA was prepared from a series of human tissues using an RNeasy kit from Qiagen. First strand cDNA was prepared from 1 μg total RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in the left column of Tables 16-17. The expression is relative to beta 2 mRNA expression.

The mRNA expression data for 23680 mRNA is tabulated in Table 16 and indicates that 23680 mRNA is expressed, for example, in tumor samples, e.g., lung and breast tumor samples.

TABLE 16

| Tissue Type | Relative Expression |
|---|---|
| Breast Normal | 0.00 |
| Breast Normal | 0.00 |
| Breast Normal | 0.00 |
| Breast Normal NTC | 0.00 |
| Breast Tumor | 0.01 |
| Breast Tumor NTC | 0.01 |
| Breast Tumor | 0.00 |
| Breast Tumor | 0.01 |
| Breast Tumor | 0.03 |
| Breast Tumor | 0.05 |
| Ovary Normal NTC | 0.09 |
| Ovary Normal | 0.00 |
| Ovary Normal | 0.00 |
| Ovary Tumor | 0.00 |
| Ovary Tumor | 0.03 |
| Ovary Tumor | 0.01 |
| Ovary Tumor | 0.02 |
| Ovary Tumor | 0.02 |
| Ovary Tumor | 0.00 |
| Ovary Tumor | 0.02 |
| Ovary Tumor | 0.00 |
| Lung Normal | 0.00 |
| Lung Normal | 0.00 |
| Lung Normal | 0.00 |
| Lung Normal | 0.00 |
| Lung Tumor | 0.00 |
| Lung Tumor | 0.00 |
| Lung Tumor | 0.01 |
| Lung Tumor | 0.00 |
| Lung Tumor | 0.09 |
| Lung Tumor | 0.77 |
| Lung Tumor | 0.00 |
| Lung Tumor | 0.00 |

The mRNA expression data for 23680 mRNA tabulated in Table 17 (below) indicated that 23680 mRNA is highly expressed, for example, in liver metastasis, normal liver, normal brain, glioblastoma, fetal adrenal, and fetal liver. 23680 mRNA expression is decreased in brain tumors relative to the normal brain.

TABLE 17

| Tissue Type | Relative Expression |
|---|---|
| Colon Normal | 0.0 |
| Colon Normal | 0.0 |
| Colon Normal | 0.0 |
| Colon Normal | 0.0 |
| Colon Tumor | 0.0 |
| Colon Tumor | 0.0 |
| Colon Tumor | 0.0 |
| Colon Tumor | 0.0 |
| Colon Tumor | 0.0 |
| Colon Tumor | 0.0 |
| Colon Tumor | 0.0 |
| Colon Tumor | 0.0 |

TABLE 17-continued

| Tissue Type | Relative Expression |
| --- | --- |
| Liver Met | 0.0 |
| Liver Met | 0.9 |
| Liver Met | 0.0 |
| Liver Met | 2.9 |
| Liver Normal | 6.4 |
| Liver Normal | 39.4 |
| Brain Normal | 264.3 |
| Brain Normal | 155.5 |
| Brain Normal | 212.4 |
| Brain Normal NTC | 104.4 |
| Glioblastoma | 1.3 |
| Glioblastoma | 7.2 |
| Glioblastoma | 0.0 |
| Glioblastoma | 659.8 |
| Glioblastoma | 2.9 |
| HMVEC-Arr | 0.0 |
| HMVEC-Prol | 0.0 |
| Placenta | 0.1 |
| Fetal Adrenal | 0.0 |
| Fetal Adrenal | 2.7 |
| Fetal Liver | 0.1 |
| Fetal Liver | 4.9 |

Example 26

Recombinant Expression of 23680 in Bacterial Cells

In this example, 23680 is expressed as a recombinant glutathione-S-transferase (GST) fusion polypeptide in *E. coli* and the fusion polypeptide is isolated and characterized. Specifically, 23680 nucleic acid sequences are fused to GST nucleic acid sequences and this fusion construct is expressed in *E. coli*, e.g., strain PEB199. Expression of the GST-23680 fusion construct in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 27

Expression of Recombinant 23680 Protein in COS Cells

To express the 23680 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 23680 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 23680 DNA sequence is amplified by PCR using two primers. The 5' primer contains the restriction site of interest followed by approximately 20 nucleotides of the 23680 coding sequence starting from the initiation codon; the 3' end sequence contains complementary sequences to the other restriction site of interest, a translation stop codon, the HA tag or FLAG tag and the last 20 nucleotides of the 23680 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 23680 gene is inserted in the desired orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 23680-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the 23680 polypeptide is detected by radiolabeling ($^{35}$S-methionine or $^{35}$S-cysteine, available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA-specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA-specific monoclonal antibody. Precipitated polypeptides are then analyzed by SDS-PAGE.

Alternatively, DNA containing the 23680 coding sequence is cloned directly into the polylinker of the pcDNA/Amp vector using the appropriate restriction sites. The resulting plasmid is transfected into COS cells in the manner described above, and the expression of the 23680 polypeptide is detected by radiolabeling and immunoprecipitation using a 23680-specific monoclonal antibody.

Examples for 32624

Example 28

Identification and Characterization of Human 32624 cDNA

The human 32624 nucleic acid sequence is recited as follows:

```
GTCGACCCACGCGTCCGGAGGGAACTGCCATCATGAGGTCTGACAAGTCAGCTT    (SEQ ID NO:38)
TGGTATTTCTGCTCCTGCAGCTCTTCTGTGTTGGCTGTGGATTCTGTGGGAAAGTC
```

-continued

CTGGTGTGGCCCTGTGACATGAGCCATTGGCTTAATGTCAAGGTCATTCTAGAAG

AGCTCATAGTGAGAGGCCATGAGGTAACAGTATTGACTCACTCAAAGCCTTCGTT

AATTGACTACAGGAAGCCTTCTGCATTGAAATTTGAGGTGGTCCATATGCCACAG

GACAGAACAGAAGAAAATGAAATATTTGTTGACCTAGCTCTGAATGTCTTGCCA

GGCTTATCAACCTGGCAATCAGTTATAAAATTAAATGATTTTTTTGTTGAAATAA

GAGGAACTTTAAAAATGATGTGTGAGAGCTTTATCTACAATCAGACGCTTATGA

AGAAGCTACAGGAAACCAACTACGATGTAATGCTTATAGACCCTGTGATTCCCT

GTGGAGACCTGATGGCTGAGTTGCTTGCAGTCCCTTTTGTGCTCACACTTAGAAT

TTCTGTAGGAGGCAATATGGAGCGAAGCTGTGGGAAACTTCCAGCTCCACTTTCC

TATGTACCTGTGCCTATGACAGGACTAACAGACAGAATGACCTTTCTGGAAAGA

GTAAAAAATTCAATGCTTTCAGTTTTGTTCCACTTCTGGATTCAGGATTACGACT

ATCATTTTTGGGAAGAGTTTTATAGTAAGGCATTAGGAAGGCCCACTACATTATG

TGAGACTGTGGGAAAAGCTGAGATATGGCTAATACGAACATATTGGGATTTTGA

ATTTCCTCAACCATACCAACCTAACTTTGAGTTTGTTGGAGGATTGCACTGTAAA

CCTGCCAAAGCTTTGCCTAAGGAAATGGAAAATTTTGTCCAGAGTTCAGGGGAA

GATGGTATTGTGGTGTTTTCTCTGGGGTCACTGTTTCAAAATGTTACAGAAGAAA

AGGCTAATATCATTGCTTCAGCCCTTGCCCAGATCCCACAGAAGGTGTTATGGAG

GTACAAAGGAAAAAAACCATCCACATTAGGAGCCAATACTCGGCTGTATGATTG

GATACCCCAGAATGATCTTCTTGGTCATCCCAAAACCAAAGCTTTTATCACTCAT

GGTGGAATGAATGGGATCTATGAAGCTATTTACCATGGGGTCCCTATGGTGGGA

GTTCCCATATTTGGTGATCAGCTTGATAACATAGCTCACATGAAGGCCAAAGGA

GCAGCTGTAGAAATAAACTTCAAAACTATGACAAGCGAAGATTTACTGAGGGCT

TTGAGAACAGTCATTACCGATTCCTCTTATAAAGAGAATGCTATGAGATTATCAA

GAATTCACCATGATCAACCTGTAAAGCCCCTAGATCGAGCAGTCTTCTGGATCGA

GTTTGTCATGCGCCACAAAGGAGCCAAGCACCTGCGATCAGCTGCCCATGACCT

CACCTGGTTCCAGCACTACTCTATAGATGTGATTGGGTTCCTGCTGGCCTGTGTG

GCAACTGCTATATTCTTGTTCACAAAATGTTTTTTATTTTCCTGTCAAAAATTTAA

TAAAACTAGAAAGATAGAAAAGAGGGAA<u>TAG</u>ATCTTTCCAAATTCAAGAAAGA

CCTGATGGGTAATCCTGTTAATTCCAGCCACATAGAATTTGGTGAAAACCTTGC

TATTTTCATATTATCTATTCTGTTATTTTATCTTAGCTATATAGCCTAGAATTCCAC

GATCATGAGGTTGTGAGTATATCTCATTCTTTCGTTGTATTTTCCTAGGTGTCTTT

ACTCTCTTCTCTCACTTTGTGACACAAGGACATGAATACATCTAAATTTTCCTATT

TCTGATATGACTGTTTTGATGATGTCATTACTTCTATAACCTTAAGTGATAGGGTG

ACATGCAATATGATTATTCCTGGTGTGCGCCCAAACACATGGATATAAAGAGGT

AAAAAACTTAAAATTCACAAAATTCAGTAAACCACACAAATCAGGTAAGTGTTC

TATGAGATTAGCTGGCTATGAGAAACATAATGATGTTTCTTTTTCAATTTAAATA

AGCCCTTCTACATAGCCAGCATCAGTGATCTCAGAAAATAAATTGCTAATAATGA

TGACATGGCATTATGCTTAGAAAAGTTTGCTGTATTTCCATAGACCTCATCTAGA

TGTCATGGCCTACATTTCTGCCATCACTCAACCAATACTTTTTTCTGTTTTCTTGA

TGATAAAAGACCTTTCTCATGATTGCCATCAAATAACAAAAGAAACTATTTTTT

-continued

```
TTCTCACATAGAGAACATGTCAGTAAGATATTCAAGGTGAACAGATTATTTTTGG

GATTAGTAACTATTTGAAATATGTGGTGATAATTACTGAGTTTATAAAATTTATT

TGATAGTACACTTAAAGAAGATTTATATGTTTATTCTTTAAAAATGATGAATACT

CATAATTCTTATCTCTATAATCAAAAGTATAATTTACTGTAGAAAAATAAAGAGA

TGCTTGTTCTGAAAGTAAGATCAGTGAACTGCTTTTCAGTCTCAATCTTTGAGAA

TTGTAAATTCATCAAATAATTGCTTACATAGTAAAAATTTAAGGTATTAGAAAAC

CTGCATAACAAATAGTATTATATATTAAATATTTTGATATGTAAAGCTCTACACA

AAGCTAAATATAGTGTAATAATGTTTACACTAATAAGCAAATATGTTAATCTTCT

CATTTTTTTACTGTCATATAATCTTAGTGATATGCCTATTAATAGTTTTAAATAAA

TAAATTGGCTCATCTGGCCTTTTGAAAATTTTGAAATTCTTACAGATGTTGATTAG

GTATATCTACAAATTAATTTCAATTTTAAAATGATGATATAAAAATAAATATAAG

TATTTTTCTTGTGTATGTATACAATAAATATAAATAAAATTGTAAAAAAAAAAAA

AAAAAAAAAAAAAAAAAAAAAAAAAAAAAAAA.
```

The human 32624 sequence (FIG. 39; SEQ ID NO:38), which is approximately 2996 nucleotides long. The nucleic acid sequence includes an initiation codon (ATG) and a termination codon (TAG) that are underscored above. The region between and inclusive of the initiation codon and the termination codon is a methionine-initiated coding sequence of about 1584 nucleotides, including the termination codon (nucleotides indicated as "coding" of SEQ ID NO:38; SEQ ID NO:40). The coding sequence encodes a 527 amino acid protein (SEQ ID NO:39), which is recited as follows:

```
                                            (SEQ ID NO:39)
MRSDKSALVFLLLQLFCVGCGFCGKVLVWPCDMSHWLNVKVILEELIVRG

HEVTVLTHSKPSLIDYRKPSALKFEVVHMPQDRTEENEIFVDLALNVLPG

LSTWQSVIKLNDFFVEIRGTLKMMCESFIYNQTLMKKLQETNYDVMLIDP

VIPCGDLMAELLAVPFVLTLRISVGGNMERSCGKLPAPLSYVPVPMTGLT

DRMTFLERVKNSMLSVLFHFWIQDYDYHFWEEFYSKALGRPTTLCETVGK

AEIWLIRTYWDFEFPQPYQPNFEFVGGLHCKPAKALPKEMENFVQSSGED

GIVVFSLGSLFQNVTEEKANIIASALAQIPQKVLWRYKGKKPSTLGANTR

LYDWIPQNDLLGHPKTKAFITHGGMNGIYEAIYHGVPMVGVPIFGDQLDN

IAHMKAKGAAVEINFKTMTSEDLLRALRTVITDSSYKENAMRLSRIHHDQ

PVKPLDRAVFWIEFVMRHKGAKHLRSAAHDLTWFQHYSIDVIGFLLACVA

TAIFLFTKCFLFSCQKFNKTRKIEKRE.
```

Example 29

Tissue Distribution of 32624 mRNA by TaqMan Analysis

Endogenous human 32624 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

To determine the level of 32624 in various human tissues a primer/probe set can be designed. Total RNA can be prepared from a series of human tissues using an RNeasy kit from Qiagen. First strand cDNA can be prepared from 1 µg total RNA using an oligo-dT primer and Superscript II reverse transcriptase (Gibco/BRL). cDNA obtained from approximately 50 ng total RNA is used per TaqMan reaction. Tissues tested can include various human tissues, e.g., liver, kidney, intestinal epithelial, colon, breast, ovary, brain, hematopoetic cells, veins and arteries, as well as human cell lines.

Example 30

Tissue Distribution of 32624 mRNA by Northern Analysis

Northern blot hybridizations with various RNA samples can be performed under standard conditions and washed under stringent conditions, i.e., 0.2×SSC at 65° C. A DNA probe corresponding to all or a portion of the 32624 cDNA (SEQ ID NO:38) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 31

Recombinant Expression of 32624 in Bacterial Cells

In this example, 32624 is expressed as a recombinant glutathione-S-transferase (GST) fusion polypeptide in *E. coli* and the fusion polypeptide is isolated and characterized. Specifically, 32624 is fused to GST and this fusion polypeptide is expressed in *E. coli*, e.g., strain PEB199. Expression of the GST-32624 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 32

Expression of Recombinant 32624 Protein in COS Cells

To express the 32624 gene in COS cells (e.g., COS-7 cells, CV-1 origin SV40 cells; Gluzman (1981) *Cell*23:175-182), the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 32624 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 32624 DNA sequence is amplified by PCR using two primers. The 5' primer contains the restriction site of interest followed by approximately twenty nucleotides of the 32624 coding sequence starting from the initiation codon; the 3' end sequence contains complementary sequences to the other restriction site of interest, a translation stop codon, the HA tag or FLAG tag and the last 20 nucleotides of the 32624 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 32624_gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 32624-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual. 2nd, ed., Cold Spring Harbor Laboratory*, Cold Spring Harbor Laboratory Press, Cold Spring Harbor, N.Y. The expression of the 32624 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual*, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 32624 coding sequence is cloned directly into the polylinker of the pCDNA/Amp vector using the appropriate restriction sites. The resulting plasmid is transfected into COS cells in the manner described above, and the expression of the 32624 polypeptide is detected by radiolabelling and immunoprecipitation using a 32624 specific monoclonal antibody.

Examples for 47174

Example 33

Identification and Characterization of Human 47174 cDNA

The human 47174 nucleic acid sequence is recited as follows:

```
GCGCCGCCCGCCCGCGCCTTCCCCGCCGCCCCCGGCGCCCCGGCCCCCTCAC  (SEQ ID NO:42)

CGCTCCCCGGGGCGGGCCGCGCCCTCTGAGCGGGGATGCCGGCCGCGCCCCG

CGACCCCAGCCCCGGGCAGCCCTCTGCGCTCTGGGGACCCCCGGCGGCCGTGG

CCCGGCGCGCTGAGCTGGTGCTGAAGGGACAGCTCCGGCCGAGCCCCGCAGCCC

CCGCAGCCCCGGGCGGCTCATGGTCCCCGAAGCCGAAGCTGAAGCCCAGGCCCG

GGCGGGATGCTGGGGATGCCCCGCGGGTGAGGCCCCGCTGCAGCCGTGTTCA

TGGCGGTGGCCAGGAAGATCCGAACTTTGCTGACGGTGAACATCCTGGTGTTCG

TGGGCATCGTCCTGTTCTCCGTGTACTGCCGCCTGCAGGGCCGCTCCCAGGAGCT

CGTGCGCATCGTGAGCGGCGACCGCCGGGTGCGCAGCCGACACGCCAAGGTGGG

CACGCTGGGGGACCGTGAGGCCATCCTGCAGCGCCTGGACCACCTGGAGGAGGT
```

-continued

```
GGTCTACAACCAGCTCAACGGCCTTGCCAAGCCCATCGGCCTGGTGGAGGGGCC

AGGAGGCCTGGGCCAGGGTGGCTTGGCGGCCACCCTGCGTGATGACGGCCAGGA

GGCGGAAGGCAAGTATGAGGAGTACGGCTACAACGCTCAGCTCAGCGACCGCAT

CTCCCTCGATCGGAGCATCCCCGACTACCGGCCCAGAAAGTGCAGACAGATGAG

CTACGCCCAGGACCTGCCCCAGGTCTCCGTGGTCTTCATCTTCGTCAATGAGGCG

CTGTCGGTCATCCTGCGCTCCGTGCACAGCGTGGTCAACCACACGCCCTCCCAGC

TCCTCAAGGAGGTCATCCTGGTGGACGACAACAGTGACAACGTGGAACTCAAGT

TCAATCTGGACCAGTACGTCAACAAGCGGTACCCAGGCCTCGTGAAGATTGTCC

GCAACAGCCGGCGGGAAGGACTGATCCGCGCGCGGCTGCAGGGCTGGAAGGCG

GCCACCGCCCCAGTCGTCGGCTTCTTTGATGCCCACGTCGAGTTCAACACGGGCT

GGGCCGAGCCCGCACTGTCGCGGATCCGAGAGGACCGGCGTCGCATCGTGCTGC

CAGCCATCGACAACATCAAGTACAGCACGTTTGAGGTGCAGCAGTATGCGAACG

CCGCCCATGGCTACAACTGGGGCCTCTGGTGCATGTACATCATCCCCCCGCAGGA

CTGGCTGGACCGCGGCGACGAGTCAGCACCCATCAGGACCCCAGCCATGATCGG

CTGCTCCTTCGTAGTGGACCGCGAGTACTTCGGAGACATTGGGCTGCTGGACCCC

GGCATGGAGGTGTATGGCGGCGAGAACGTAGAACTGGGCATGAGGGTGTGGCA

GTGTGGCGGCAGCATGGAGGTGCTGCCCTGCTCCCGCGTGGCCCACATCGAGCG

CACCAGGAAGCCCTACAACAACGACATTGACTACTACGCCAAGCGCAACGCCCT

GCGCGCCGCCGAGGTGTGGATGGATGACTTCAAGTCCCACGTGTACATGGCCTG

GAACATCCCCATGTCGAACCCAGGGGTGGACTTCGGGGACGTGTCTGAGAGGCT

GGCCCTGCGTCAGAGGCTGAAGTGTCGCAGCTTCAAGTGGTACCTGGAGAACGT

GTACCCGGAGATGAGGGTCTACAACAACACCCTCACGTACGGAGAGGTGAGAA

ACAGCAAAGCCAGTGCCTACTGTCTGGACCAGGGAGCGGAGGACGGCGACCGG

GCGATCCTCTACCCCTGCCACGGGATGTCCTCCCAGCTGGTGCGGTACAGCGCTG

ACGGCCTGCTGCAGCTGGGGCCTCTGGGCTCCACAGCCTTCTTGCCTGACTCCAA

GTGTCTGGTGGATGACGGCACGGGCCGCATGCCCACCCTGAAGAAGTGTGAGGA

TGTGGCGCGGCCAACACAGCGGCTGTGGGACTTCACCCAGAGTGGCCCCATTGT

GAGCCGGGCCACGGGCCGCTGCCTGGAGGTGGAGATGTCCAAAGATGCCAACTT

TGGGCTCCGGCTGGTGGTACAGAGGTGCTCGGGGCAGAAGTGGATGATCAGAAA

CTGGATCAAACACGCACGGCACTGACCCCACCTCCGCCCGGACCCCCACAGACC

TCGGGAAGGCGCTGGGCCGAGCCAGTGTGGCTGAGTGACCGGGGTGTGCCCGGC

AGACACAGCAGGACAGGGCTCTATGTGCGGCCAGGACAGCAGAGGCTGAGGGG

CCGGGGTGTGGCTGAGTGACCAGGGTGTCACCCACTGCATCTGGAGTACAGCTT

CTCCTAGGACAGGCGGCTCTACCCGAGGGAGGGCGTCTGGGGACAGTGATGCCA

ACTCAAACACGTGCCTTCTCCACGGTATCTCCTGGCCAGGCTGCTGGGACAGCCG

CCGCCTCTGCATGTACCACAGCCCCCCACGCCCCATAGGGAGGCCAAGCCCCGG

ACCATGCACCAGGCTGCACCCTGGTGTCTTCCACCCGCAGGCCTCCCATGCTCCA

AGCAGCCTCCCCCAGCACTTGCGGCCGC.
```

Figure 41:
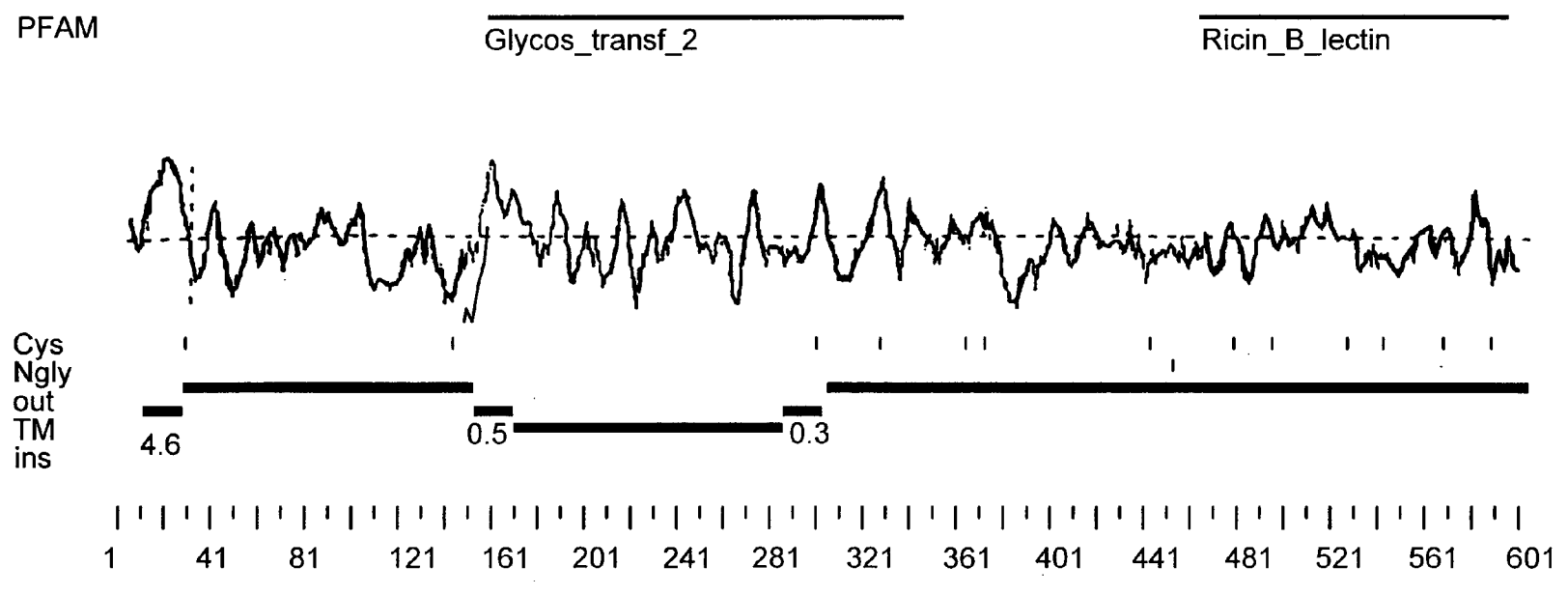

The human 47174 sequence (FIG. 41; SEQ ID NO:42) is approximately 2572 nucleotides long. The nucleic acid sequence includes an initiation codon (ATG) and a termination codon (TGA) which are bolded and underscored above. The region between and inclusive of the initiation codon and the termination codon is a methionine-initiated coding sequence of about 1812 nucleotides, including the termination codon (nucleotides indicated as "coding" of SEQ ID NO:42; SEQ ID NO:44). The coding sequence encodes a 603 amino acid protein (SEQ ID NO:43), which is recited as follows:

obtained from approximately 50 ng total RNA was used per TaqMan reaction. 47174 mRNA levels were analyzed in a variety of samples of human tissues. Table 18 below shows the relative level of expression in a number of tissues. The highest level of relative expression is found in normal brain cortex and hypothalamus. 47174 mRNA expression was also detected in normal kidney.

```
MAVARKIRTLLTVNILVFVGIVLFSVYCRLQGRSQELVRIVSGDRRVRSRHAKVGTL    (SEQ ID NO:43)

GDREAILQRLDHLEEVVYNQLNGLAKPIGLVEGPGGLGQGGLAATLRDDGQEAEGK

YEEYGYNAQLSDRISLDRSIPDYRPRKCRQMSYAQDLPQVSVVFIFVNEALSVILRSV

HSVVNHTPSQLLKEVILVDDNSDNVELKFNLDQYVNKRYPGLVKIVRNSRREGLIRA

RLQGWKAATAPVVGFFDAHVEFNTGWAEPALSRIREDRRRIVLPAIDNIKYSTFEVQ

QYANAAHGYNWGLWCMYIIPPQDWLDRGDESAPIRTPAMIGCSFVVDREYFGDIGL

LDPGMEVYGGENVELGMRVWQCGGSMEVLPCSRVAHIERTRKPYNNDIDYYAKRN

ALRAAEVWMDDFKSHVYMAWNIPMSNPGVDFGDVSERLALRQRLKCRSFKWYLE

NVYPEMRVYNNTLTYGEVRNSKASAYCLDQGAEDGDRAILYPCHGMSSQLVRYSA

DGLLQLGPLGSTAFLPDSKCLVDDGTGRMPTLKKCEDVARPTQRLWDFTQSGPIVSR

ATGRCLEVEMSKDANFGLRLVVQRCSGQKWMIRNWIKHARH.
```

Example 34

Tissue Distribution of 47174 mRNA

Endogenous human 47174 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a way of quantitating the initial template concentration. Samples can be internally controlled by the addition of a second set of primers/probe specific for a housekeeping gene such as GAPDH which has been labeled with a different fluorophore on the 5' end (typically VIC).

To determine the level of 47174 in various human tissues a primer/probe set was designed using Primer Express (Perkin-Elmer) software and primary cDNA sequence information. Total RNA was prepared from a series of human tissues using an RNeasy kit from Qiagen. First strand cDNA was prepared from 1 μg total RNA using an oligo-dT primer and Superscript II reverse transcriptase (Gibco/BRL). cDNA

TABLE 18

| SAMPLE | RELATIVE EXPRESSION |
|---|---|
| Aorta/normal | 0.00 |
| Fetal heart/normal | 0.00 |
| Heart normal | 0.00 |
| Heart/CHF | 0.00 |
| Vein/Normal | 0.00 |
| Spinal cord/Normal | 0.00 |
| Brain cortex/Normal | 33.96 |
| Brain hypothalamus/Normal | 10.13 |
| Glial cells (Astrocytes) | 0.00 |
| Brain/Glioblastoma | 0.00 |
| Breast/Normal | 0.00 |
| Breast tumor/IDC | 0.00 |
| OVARY/Normal | 0.00 |
| OVARY/Tumor | 0.00 |
| Pancreas | 0.00 |
| Prostate/Normal | 0.00 |
| Prostate/Tumor | 0.00 |
| Colon/normal | 0.00 |
| Colon/tumor | 0.00 |
| Colon/IBD | 0.00 |
| Kidney/normal | 0.66 |
| Liver/normal | 0.00 |
| Liver fibrosis | 0.00 |
| Fetal Liver/normal | 0.00 |
| Lung/normal | 0.00 |
| Lung/tumor | 0.00 |
| Lung/COPD | 0.00 |
| Spleen/normal | 0.00 |
| Tonsil/normal | 0.00 |
| Lymph node/normal | 0.00 |
| Thymus/normal | 0.00 |
| Epithelial Cells (prostate) | 0.00 |

TABLE 18-continued

| SAMPLE | RELATIVE EXPRESSION |
|---|---|
| Endothelial Cells (aortic) | 0.00 |
| Skeletal Muscle/Normal | 0.00 |
| Fibroblasts (Dermal) | 0.00 |
| Skin/normal | 0.00 |
| Adipose/Normal | 0.00 |
| Osteoblasts (primary) | 0.00 |
| Osteoblasts (Undiff) | 0.00 |
| Osteoblasts (Diff) | 0.00 |
| Osteoclasts | 0.00 |
| Aortic SMC Early | 0.00 |
| Aortic SMC Late | 0.00 |
| shear HUVEC | 0.00 |
| static HUVEC | 0.00 |
| Osteoclasts (Undiff) | 0.00 |

Example 35

Northern Blot Hybridizations

Northern blot hybridizations with various RNA samples can also be performed under standard conditions and washed under stringent conditions, i.e., 0.2×SSC at 65° C. A DNA probe corresponding to all or a portion of the 47174 cDNA (SEQ ID NO:42) can be used. The DNA can be radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 36

Recombinant Expression of 47174 in Bacterial Cells

In this example, 47174 is expressed as a recombinant glutathione-S-transferase (GST) fusion polypeptide in *E. coli* and the fusion polypeptide is isolated and characterized. Specifically, 47174 is fused to GST and this fusion polypeptide is expressed in *E. coli*, e.g., strain PEB199. Expression of the GST-47174 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 37

Expression of Recombinant 47174 Protein in COS Cells

To express the 47174 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 47174 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 47174 DNA sequence is amplified by PCR using two primers. The 5' primer contains the restriction site of interest followed by approximately twenty nucleotides of the 47174 coding sequence starting from the initiation codon; the 3' end sequence contains complementary sequences to the other restriction site of interest, a translation stop codon, the HA tag or FLAG tag and the last 20 nucleotides of the 47174 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 47174 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 47174-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the 47174 polypeptide is detected by radiolabelling (35S-methionine or 35S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labeled for 8 hours with 35S-methionine (or 35S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 47174 coding sequence is cloned directly into the polylinker of the pCDNA/Amp vector using the appropriate restriction sites. The resulting plasmid is transfected into COS cells in the manner described above, and the expression of the 47174 polypeptide is detected by radiolabelling and immunoprecipitation using a 47174 specific monoclonal antibody.

Examples for 60491

Example 38

Identification and Characterization of Human 60491 cDNA

The human 60491 nucleic acid sequence is recited as follows:

```
CACGCCTTGTGGCGGCTTTGCGGAGCTGCTGCTTTGGCGGGAGTTGGAAGCTGGT      (SEQ ID NO:48)
GTGAGGTTTCTGTGGGAGAAGGAGAGTGCCAGAGGTGACTGGTTCATGGTTCT
TCTAGGCTCTCATGGCCACCATGTTGGAAGGCAGATGCCAAACTCAGCCAAGGA
GCAGCCCCAGTGGCCGAGAGGCTAGCCTGTGGTCGTCAGGCTTTGGGATGAAGC
TGGAGGCTGTCACTCCATTCCTGGGGAAGTATCGCCCCTTTGTGGGTCGCTGTTG
CCAGACCTGCACCCCCAAGAGCTGGGAGTCCCTCTTCCACAGAAGCATAACGGA
CCTAGGCTTCTGCAATGTGATCCTGGTGAAGGAGGAGAACACAAGGTTTCGGGG
CTGGCTGGTTCGGAGGCTCTGCTATTTCCTGTGGTCCCTGGAGCAGCACATCCCC
CCCTGCCAGGATGTCCCACAGAAGATCATGGAAAGCACCGGGGTGCAGAACCTC
CTCTCAGGGAGGGTCCCAGGAGGCACTGGGGAAGGCCAGGTGCCTGACCTTGTG
AAGAAGGAGGTACAGCGCATCCTGGGTCACATCCAGGCCCCACCCCGTCCCTTC
CTGGTCAGGCTGTTCAGCTGGGCGCTGCTGAGGTTCCTGAACTGCCTGTTCCTGA
ATGTGCAGCTCCACAAGGGTCAGATGAAGATGGTCCAGAAGGCCGCCCAGGCAG
GCTTGCCGCTTGTCCTCCTCTCTACTCACAAAACCCTCCTGGATGGGATCCTGCT
GCCCTTTATGCTGCTCTCCCAGGGCCTGGGTGTGCTTCGTGTGGCCTGGGACTCC
CGCGCCTGCTCCCCTGCCCTCAGAGCTCTGCTGAGGAAGCTTGGGGGGCTTTTCC
TGCCCCCAGAGGCCAGCCTCTCCCTGGACAGCTCTGAGGGGCTCCTTGCCAGGG
CTGTGGTCCAGGCGGTCATAGAGCAGCTGCTGGTTAGTGGGCAGCCCCTGCTCAT
CTTCCTGGAGGAACCTCCTGGGGCTCTGGGCCACGGCTGTCAGCCCTGGGCCA
GGCTTGGGTGGGGTTTGTGGTGCAGGCAGTCCAGGTGGGCATCGTCCCAGATGC
TCTGCTGGTACCAGTGGCCGTCACCTATGACCTGGTTCCGGATGCACCGTGTGAC
ATAGACCATGCCTCGGCCCCCCTGGGGCTGTGGACAGGAGCTCTGGCTGTCCTAC
GTAGCTTGTGGAGCCGCTGGGGCTGCAGCCACCGGATCTGCTCCCGGGTGCACC
TAGCTCAGCCCTTTTCCCTGCAGGAATACATCGTCAGTGCCAGAAGCTGCTGGGG
CGGCAGACAGACCCTGGAGCAGCTACTGCAGCCCATCGTGCTGGGCCAATGTAC
TGCTGTCCCAGACACTGAGAAGGAGCAGGAGTGGACCCCCATAACTGGGCCTCT
CCTGGCCCTCAAGGAAGAGGACCAGCTCCTGGTCAGGAGACTGAGCTGTCATGT
CCTGAGTGCCAGTGTAGGGAGCTCTGCGGTGATGAGCACGGCCATTATGGCAAC
GCTGCTGCTCTTCAAGCATCAGAAGGGTGTGTTCCTGTCGCAGCTCCTGGGGGAG
TTCTCCTGGCTGACGGAGGAGATACTGTTGCGTGGCTTTGATGTAGGCTTCTCTG
GGCAGCTGCGGAGCCTGCTGCAGCACTCACTGAGCCTGCTGCGGGCGCACGTGG
CCCTGCTGCGCATCCGTCAGGGTGACTTGCTGGTGGTGCCGCAGCCTGGCCCAGG
CCTCACACACCTGGCACAACTGAGTGCTGAGCTGCTGCCCGTCTTCCTGAGCGAG
GCTGTGGGCGCCTGTGCAGTGCGGGGCTGCTGGCAGGCAGAGTGCCGCCCCAG
GGGCCCTGGGAGCTGCAGGGCATATTGCTGCTGAGCCAGAATGAGCTGTACCGC
CAGATCCTGCTGCTGATGCACCTGCTGCCGCAAGACCTGCTGCTGCTAAAGACCC
CAGGCTCCCGGCCAGCCTGTGACACAGGGCGACAGCGATTGAGCAGAAAGCTGC
TGTGGAAACCGAGTGGGACTTTACTGATAGTGACAGTGATGACTTCGGAGAGG
CTGACGGCCGGTACTTCAGGCTCAGCCAGCAGTCACACTGCCCAGATTTCTTTCT
TTTCCTCTGCCGCCTGCTCAGCCCGCTGCTCAAGGCCTTTGCACAGGCTGCCGCC
```

-continued
```
TTCCTCCGCCAGGGCCAGCTGCCCGATACTGAGTTGGGCTACACAGAGCAGCTG

TTCCAGTTCCTGCAGGCCACCGCCCAGGAAGAAGGGATCTTCGAGTGTGCGGAC

CCAAAGCTCGCCATCAGTGCTGTCTGGACCTTCAGAGACCTAGGGGTTCTGCAGC

AGACGCCGAGCCCTGCAGGCCCCAGGCTCCACCTGTCCCCTACTTTTGCCAGCCT

GGACAATCAGGAAAAACTAGAACAGTTCATCCGGCAGTTCATTTGTAGCTAGAA

CTGTGAGGAGGAGCCTGTGCTGAGACTTCTCAGCCCCAGAACACAGCTGTGTCC

TAGAGCCAGAAGATGGAGAGGAGGCTGCAAACCCTTAGCTGCTCTATAAATATA

ATCATTGAGGCTTGATTGTCCCTTGCCATCTCTTGCTTTTTCCCTTCTTTGATGTGA

TAAACAAGGGGACGAGACGAGTTGTCTTTTCCCCAGCCCAGCAGCAAAAAAAAA

AAAAAAAAAAAAA.
```

Figure 45:
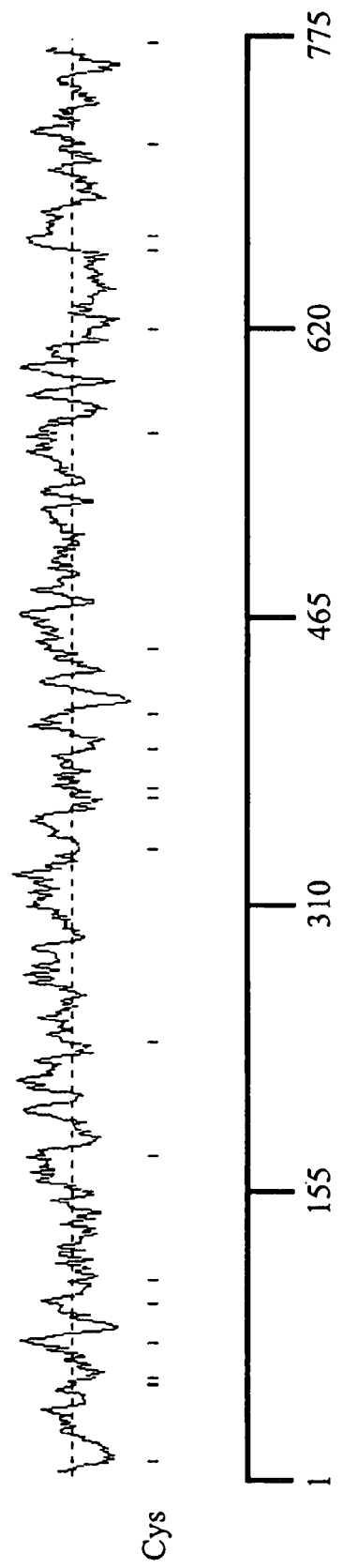
FIG. 45 depicts a hydropathy plot of human 60491. Relative hydrophobic residues are shown above the dashed horizontal line, and relative hydrophilic residues are below the dashed horizontal line. The cysteine residues (Cys) are indicated by short vertical lines just below the hydropathy trace. Numbers corresponding to positions in the amino acid sequence of human 60491 are indicated. Polypeptides of the invention include fragments which include: all or part of a hydrophobic sequence, i.e., a sequence above the dashed line, e.g., the sequence from about amino acid 163 to 179, from about 342 to 359, and from about 450 to 472 of SEQ ID NO:49; all or part of a hydrophilic sequence, i.e., a sequence below the dashed line, e.g., the sequence of from about amino acid 228 to 235 and from about 337 to 346 of SEQ ID NO:49; a sequence which includes a Cys, or a glycosylation site.
Figure 50:
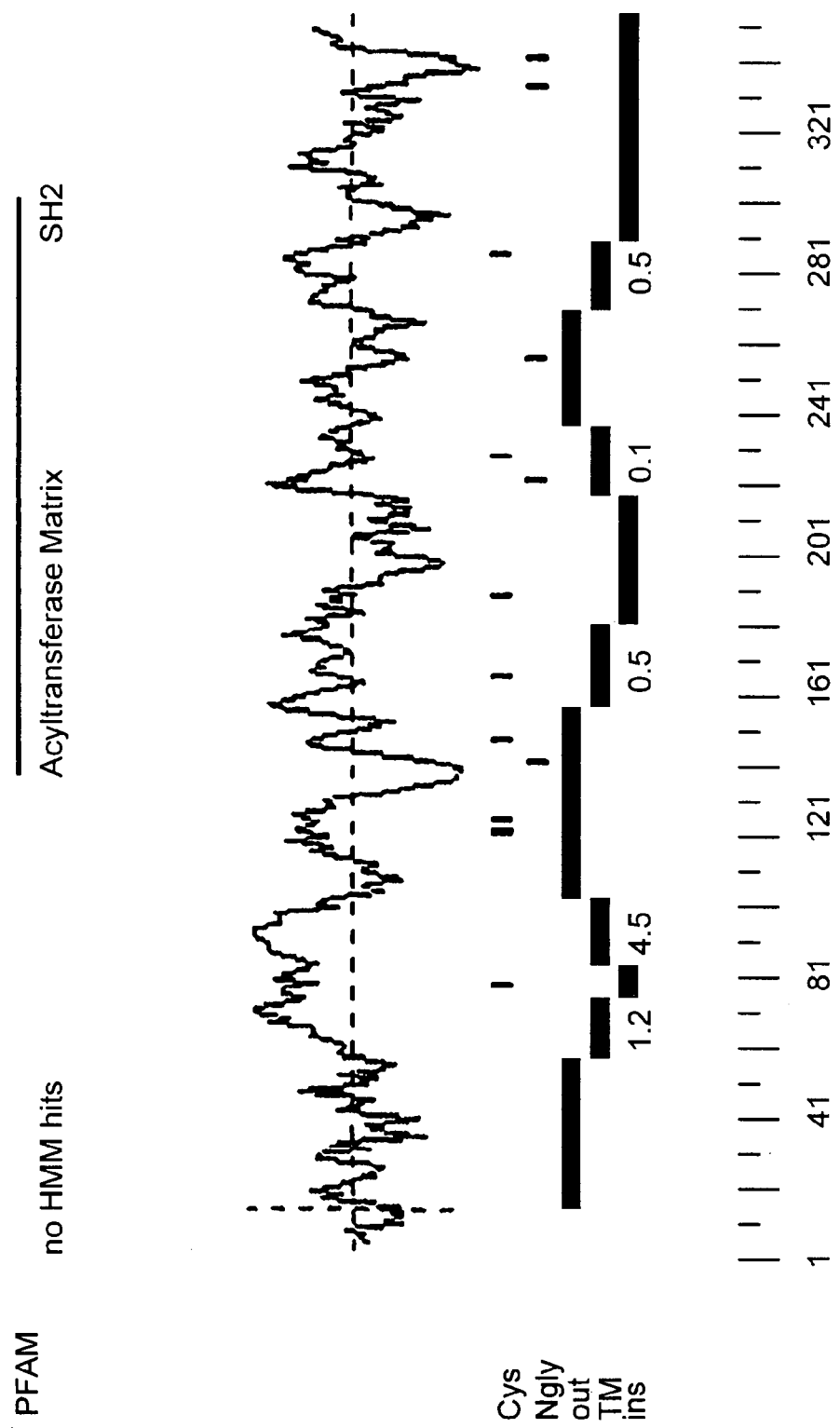
FIG. 50 depicts a hydropathy plot of human 46743. Relative hydrophobic residues are shown above the dashed horizontal line, and relative hydrophilic residues are below the dashed horizontal line. The cysteine residues (cys) and N-glycosylation sites (Ngly) are indicated by short vertical lines just below the hydropathy trace. The numbers corresponding to the amino acid sequence of human 46743 are indicated. Polypeptides of the invention include fragments comprising: all or part of a hydrophobic sequence (a sequence above the dashed line); or all or part of a hydrophilic fragment (a sequence below the dashed line). Other fragments include a cysteine residue or an N-glycosylation site.
Figure 51:
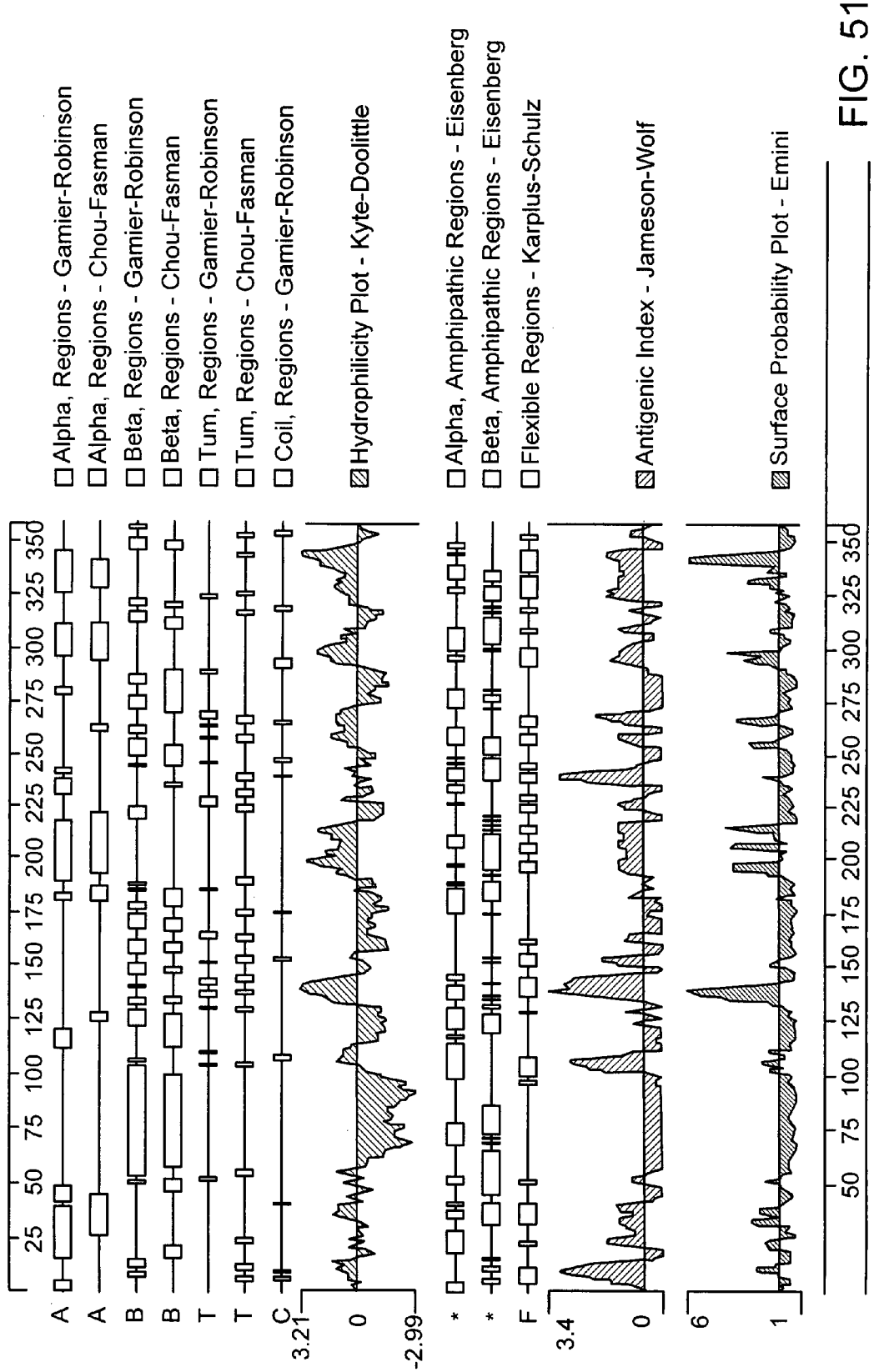
FIG. 51 depicts a series of plots summarizing an analysis of the primary and secondary protein structure of human 46743. The particular algorithm used for each plot is indicated at the right hand side of each plot. The following plots are depicted: Garnier-Robson plots providing the predicted location of alpha, beta, turn, and coil regions (Garnier et al. (1978) *J. Mol. Biol.* 120:97); Chou-Fasman plots providing the predicted location of alpha, beta, and turn regions (Chou and Fasman (1978) *Adv. In Enzymol. Mol.* 47:45-148); Kyte-Doolittle hydrophilicity/hydrophobicity plots (Kyte and Doolittle (1982) *J. Mol. Biol.* 157:105-132); Eisenberg plots providing the predicted location of alpha- and beta-amphipathic regions (Eisenberg et al. (1982) *Nature* 299: 371-374); a Karplus-Schulz plot providing the predicted location of flexible regions (Karplus and Schulz (1985) *Naturwissens-Chafen* 72:212-213); a plot of the antigenic index (Jameson-Wolf) (Jameson and Wolf (1988) *CABIOS* 4:121-136); and a surface probability plot (Emini algorithm) (Emini et al. (1985) *J. Virol.* 55:836-839). The numbers corresponding to the amino acid sequence of human 46743 are indicated.

The human 60491 sequence (FIG. 45; SEQ ID NO:48), which is approximately 2682 nucleotides long. The nucleic acid sequence includes an initiation codon (ATG) and a termination codon (TAG) which are bolded and underscored above. The region between and inclusive of the initiation codon and the termination codon is a methionine-initiated coding sequence of about 2328 nucleotides, including the termination codon (nucleotides indicated as "coding" of SEQ ID NO:48; SEQ ID NO:50). The coding sequence encodes a 775 amino acid protein (SEQ ID NO:49), which is recited as follows:

as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template

```
MATMLEGRCQTQPRSSPSGREASLWSSGFGMKLEAVTPFLGKYRPFVGRCCQTCTP      (SEQ ID NO:49)

KSWESLFHRSITDLGFCNVILVKEENTRFRGWLVRRLCYFLWSLEQHIPPCQDVPQKI

MESTGVQNLLSGRVPGGTGEGQVPDLVKKEVQRILGHIQAPPRPFLVRLFSWALLRF

LNCLFLNVQLHKGQMKMVQKAAQAGLPLVLLSTHKTLLDGILLPFMLLSQGLGVLR

VAWDSRACSPALRALLRKLGGLFLPPEASLSLDSSEGLLARAVVQAVIEQLLVSGQP

LLIFLEEPPGALGPRLSALGQAWVGFVVQAVQVGIVPDALLVPVAVTYDLVPDAPC

DIDHASAPLGLWTGALAVLRSLWSRWGCSHRICSRVHLAQPFSLQEYIVSARSCWG

GRQTLEQLLQPIVLGQCTAVPDTEKEQEWTPITGPLLALKEEDQLLVRRLSCHVLSAS

VGSSAVMSTAIMATLLLFKHQKGVFLSQLLGEFSWLTEEILLRGFDVGFSGQLRSLL

QHSLSLLRAHVALLRIRQGDLLVVPQPGPGLTHLAQLSAELLPVFLSEAVGACAVRG

LLAGRVPPQGPWELQGILLLSQNELYRQILLLMHLLPQDLLLLKTPGSRPACDTGRQ

RLSRKLLWRPSGDFTDSDSDDFGEADGRYFRLSQQSHCPDFFLFLCRLLSPLLKAFA

QAAAFLRQGQLPDTELGYTEQLFQFLQATAQEEGIFECADPKLAISAVWTFRDLGVL

QQTPSPAGPRLHLSPTFASLDNQEKLEQFIRQFICS.
```

Example 39

Tissue Distribution of 60491 mRNA by TaqMan Analysis

Endogenous human 60491 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to concentration. Samples can be internally controlled by the addition of a second set of primers/probe specific for a housekeeping gene such as GAPDH which has been labeled with a different fluorophore on the 5' end (typically VIC).

To determine the level of 60491 in various human tissues a primer/probe set was designed. Total RNA was prepared from a series of human tissues using an RNeasy kit from Qiagen. First strand cDNA was prepared from 1 µg total RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in Table 19.

TABLE 19

| Tissue Type | Mean | β 2 Mean | ∂∂ Ct | Relative Expression |
|---|---|---|---|---|
| Artery normal | 29.42 | 22.84 | 6.59 | 10.4164 |
| Aorta diseased | 30.15 | 22.48 | 7.67 | 4.9102 |
| Vein normal | 28.35 | 20.81 | 7.54 | 5.3732 |
| Coronary SMC | 29.34 | 23.02 | 6.33 | 12.4734 |
| HUVEC | 27.97 | 21.4 | 6.57 | 10.5253 |
| Hemangioma | 28.47 | 20.08 | 8.39 | 2.981 |
| Heart normal | 29.55 | 20.6 | 8.96 | 2.015 |
| Heart CHF | 26.67 | 20.07 | 6.6 | 10.3444 |
| Kidney | 30.36 | 20.27 | 10.1 | 0.9143 |
| Skeletal Muscle | 28.31 | 22.04 | 6.27 | 12.9581 |
| Adipose normal | 28.21 | 20.91 | 7.31 | 6.3238 |
| Pancreas | 28.32 | 21.99 | 6.34 | 12.3873 |
| Primary osteoblasts | 31.83 | 20.79 | 11.04 | 0.4766 |
| Osteoclasts (diff) | 26.11 | 17.82 | 8.29 | 3.1949 |
| Skin normal | 30 | 22.18 | 7.82 | 4.4407 |
| Spinal cord normal | 29.17 | 21.01 | 8.16 | 3.4962 |
| Brain Cortex normal | 27.82 | 23.02 | 4.8 | 35.8968 |
| Brain Hypothalamus normal | 27.03 | 21.9 | 5.13 | 28.5572 |
| Nerve | 27.04 | 22.11 | 4.93 | 32.9175 |
| DRG (Dorsal Root Ganglion) | 27.76 | 22.12 | 5.65 | 19.9841 |
| Breast normal | 28.02 | 21.12 | 6.91 | 8.3443 |
| Breast tumor | 27.71 | 20.88 | 6.83 | 8.7895 |
| Ovary normal | 27.81 | 20.44 | 7.38 | 6.0243 |
| Ovary Tumor | 27.23 | 20.54 | 6.69 | 9.6852 |
| Prostate Normal | 28.69 | 20.04 | 8.65 | 2.498 |
| Prostate Tumor | 31.23 | 20.53 | 10.71 | 0.5991 |
| Salivary glands | 30.14 | 19.93 | 10.21 | 0.8472 |
| Colon normal | 27.82 | 18.63 | 9.19 | 1.7121 |
| Colon Tumor | 28.51 | 19.27 | 9.25 | 1.6481 |
| Lung normal | 30.32 | 18.33 | 11.99 | 0.2467 |
| Lung tumor | 28.78 | 20.36 | 8.42 | 2.9196 |
| Lung COPD | 28.99 | 18.74 | 10.25 | 0.8212 |
| Colon IBD | 28.02 | 18 | 10.02 | 0.9665 |
| Liver normal | 30 | 20.35 | 9.65 | 1.2447 |
| Liver fibrosis | 29.7 | 21.87 | 7.83 | 4.3948 |
| Spleen normal | 28.51 | 20.01 | 8.5 | 2.7621 |
| Tonsil normal | 27.74 | 17.58 | 10.16 | 0.874 |
| Lymph node normal | 27.58 | 19.03 | 8.56 | 2.6588 |
| Small intestine normal | 30.05 | 20.51 | 9.54 | 1.3433 |
| Skin-Decubitus | 27.19 | 21.09 | 6.1 | 14.5786 |
| Synovium | 30.44 | 19.91 | 10.53 | 0.6763 |
| BM-MNC | 31.76 | 19.09 | 12.68 | 0.1529 |
| Activated PBMC | 29.46 | 18.23 | 11.23 | 0.4163 |
| Neutrophils | 27.64 | 19.28 | 8.36 | 3.0436 |
| Megakaryocytes | 29.18 | 19 | 10.18 | 0.862 |
| Erythroid | 30.68 | 21.89 | 8.79 | 2.2592 |

Example 40

Tissue Distribution of 60491 mRNA by Northern Analysis

Northern blot hybridizations with various RNA samples can be performed under standard conditions and washed under stringent conditions, i.e., 0.2×SSC at 65° C. A DNA probe corresponding to all or a portion of the 60491 cDNA (SEQ ID NO:48) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 41

Recombinant Expression of 60491 in Bacterial Cells

In this example, 60491 is expressed as a recombinant glutathione-S-transferase (GST) fusion polypeptide in *E. coli* and the fusion polypeptide is isolated and characterized. Specifically, 60491 is fused to GST and this fusion polypeptide is expressed in *E. coli*, e.g., strain PEB199. Expression of the GST-60491 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 42

Expression of Recombinant 60491 Protein in COS Cells

To express the 60491 gene in COS cells (e.g., COS-7 cells, CV-1 origin SV40 cells; Gluzman (1981) *Cell* 23(1): 175-182), the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 60491 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 60491 DNA sequence is amplified by PCR using two primers. The 5' primer contains the restriction site of interest followed by approximately twenty nucleotides of the 60491 coding sequence starting from the initiation codon; the 3' end sequence contains complementary sequences to the other restriction site of interest, a translation stop codon, the HA tag or FLAG tag and the last 20 nucleotides of the 60491 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 60491 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 60491-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual. 2nd, ed., Cold Spring Harbor Laboratory*, Cold Spring Harbor Laboratory Press, Cold Spring Harbor, N.Y. The expression of the 60491 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual*, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 60491 coding sequence is cloned directly into the polylinker of the pCDNA/Amp vector using the appropriate restriction sites. The resulting plasmid is transfected into COS cells in the manner described above, and the expression of the 60491 polypeptide is detected by radiolabelling and immunoprecipitation using a 60491 specific monoclonal antibody.

Examples for 46743 and 27417

Example 43

Identification and Characterization of Human 46743 or 27417 cDNAs

The human 46743 sequence (FIGS. 49A-49B; SEQ ID NO:57), which is approximately 1766 nucleotides long including untranslated regions, contains a predicted methionine-initiated coding sequence of about 1071 nucleotides (nucleotides 301-1371 of SEQ ID NO:57; SEQ ID NO:59). The coding sequence encodes a 356 amino acid protein (SEQ ID NO:58).

The human 27417 sequence (FIGS. 56A-56C; SEQ ID NO:62), which is approximately 3725 nucleotides long including untranslated regions, contains a predicted methionine-initiated coding sequence of about 1095 nucleotides (nucleotides 306-1400 of SEQ ID NO:62; SEQ ID NO:64). The coding sequence encodes a 364 amino acid protein (SEQ ID NO:63). Human 27417 has a predicted signal peptide that extends from about amino acids 1-49 of SEQ ID NO:63.

Example 44

Tissue Distribution of 46743 or 27417 mRNA

Expression of the endogenous human genes 46743 and 27147 was determined using the Perkin-Elmer/ABI 7700 Sequence Detection System which employs TaqMan Technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is then detected as a fluorescent signal. The PCR cycle where fluorescence is first released and detected is directly proportional to the starting amount of the gene of interest in the test sample, thus providing a way of quantifying the initial template concentration. Samples can be internally controlled by the addition of a second set of primers/probe specific for a housekeeping gene such as GAPDH which has been labeled with a different fluorophore on the 5' end (typically VIC).

To determine the level of 46743 and 27147 in various human tissues primer/probe sets were designed using the Primer Express (Perkin-Elmer) software and the 56743 and 27147 primary cDNA sequence information. Total RNA was prepared form a series of human tissues using an RNeasy kit from Qiagen. First strand cDNA was prepared form one µg of total RNA using an oligo-dT primer and Superscript II reverse transcriptase (Gibco/BRL). cDNA obtained from approximately 50 ng of total RNA was used per TaqMan reaction.

Figure 53:
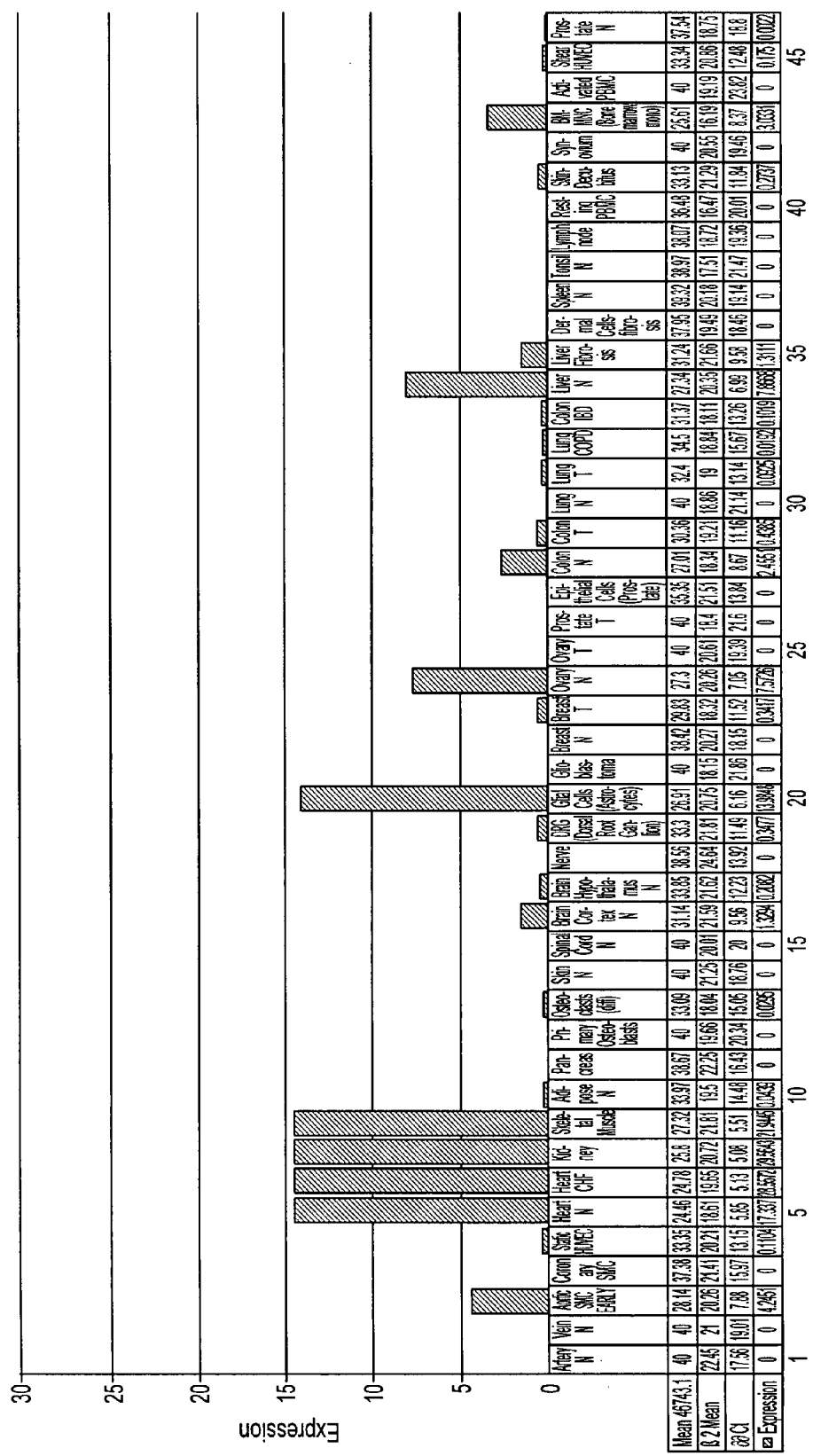
FIG. 53 is a bar graph depicting the expression of 46743 RNA in a panel of normal human normal and tumor tissues detected using Taqman analysis, including blood vessels (arteries, veins, smooth muscle cells, human umbilical vascular endothelial cells (HUVECs) (columns 1-6)), heart, normal and diseased (CHF) (columns 7-8), kidney (column 9), skeletal muscle (column 10), adipose tissue (column 11), pancreas (column 12), bone cells (column 13-14), skin (column 15), brain tissues, including spinal cord, cortex, hypothalamus, nerve cell, dorsal root ganglia, glial cells (columns 16-21, respectively), glioblastoma (column 22), normal and tumor breast (columns 23-24, respectively), normal and tumor ovary (columns 25-26, respectively), normal and tumor prostate (columns 27-28, respectively), epithelial cells (column 29), colon (columns 30-31, respectively and 35), normal, tumor and COPD lung (columns 32-34, respectively), normal and metastatic liver (columns 36-37, respectively), spleen and hematopoietic tissues (columns 39-46, respectively). Expression of 46743 RNA was detected in the kidney, skeletal muscle, heart, glial cells, liver, ovary, aortic smooth muscle cells (SMCs), bone marrow, colon, and brain. Reduced expression of 46743 was observed in tumor tissue from the ovary and the colon.

The expression of 46743 RNA in a panel of normal human tissues, including blood vessels (arteries, veins), heart, kidney, skeletal muscle, skin, brain, glial cells, breast, ovary, prostate, colon, lung, liver, spleen, and bone marrow, as well as some tumor tissues, including breast, ovary, prostate, and colon tumors, was tested (FIG. 53). Expression of 46743 RNA was detected in the kidney, skeletal muscle, heart, glial cells, liver, ovary, aortic smooth muscle cells (SMCs), bone marrow, colon, and brain. In addition, reduced expression of 46743 was observed in tumor tissue from the ovary and the colon.

Figure 54A:
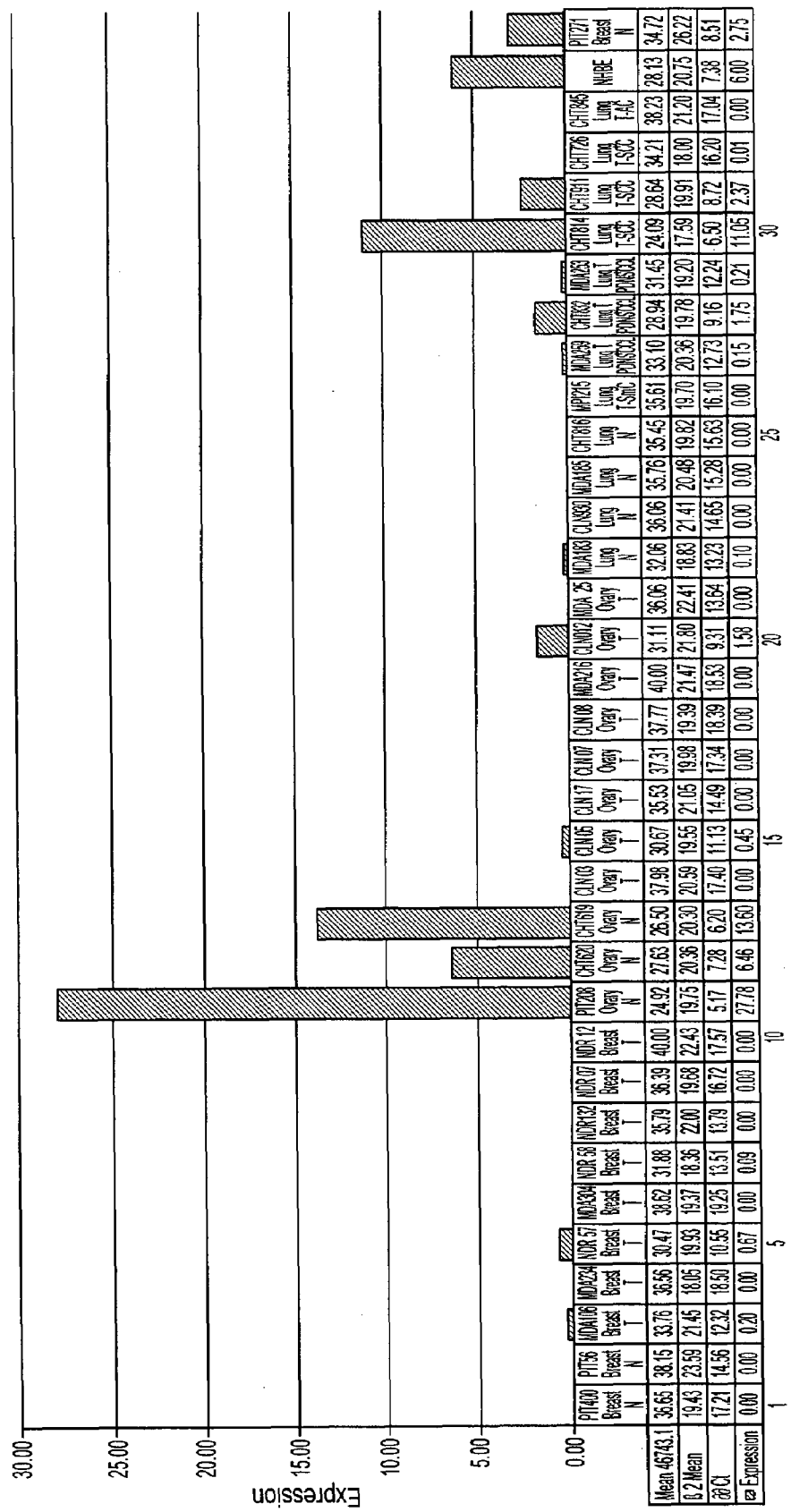
FIGS. 54A-54B are bar graphs depicting the expression of 46743 RNA in a panel of normal and human tumor tissues, including breast (columns 1-10 of FIG. 54A), normal ovary (columns 11-13 of FIG. 54A), tumor ovary (columns 14-21 of FIG. 54A), normal lung (column 22-25 of FIG. 54A), tumor lung (columns 26-33 of FIG. 54A), normal colon (columns 1-4 of FIG. 54B), tumor colon (columns 5-9 of FIG. 54B), metastatic liver (columns 10-13), normal liver (columns 14-15), normal brain (columns 16-19), astrocytes (column 20), brain tumor (columns 21-24), HUVEC (columns 25-26), placenta (column 27), fetal liver (columns 28-29) Wilm's tumor (column 30), and renal and endometrial tumors (columns 31-32).
Figure 54B:
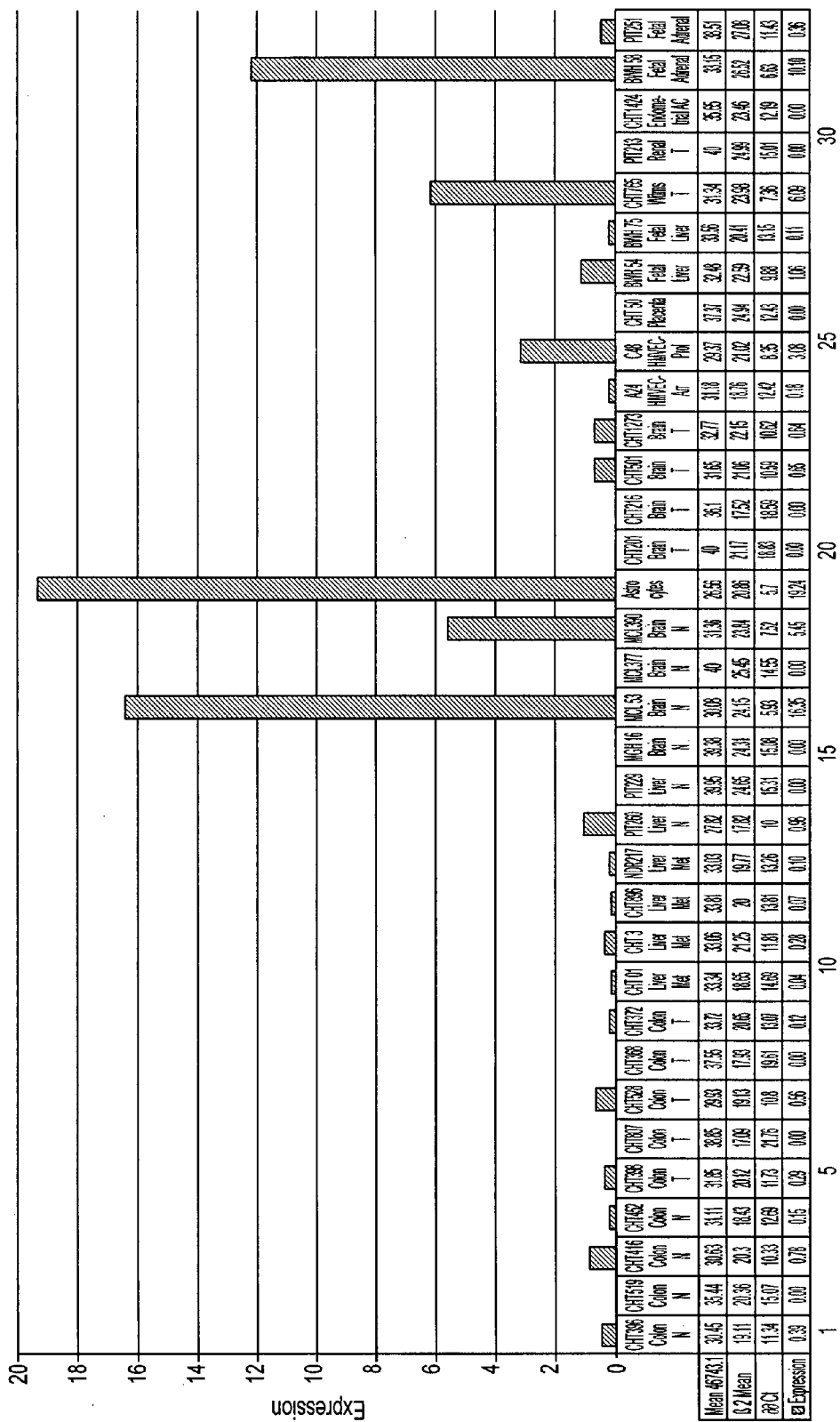

In addition, a comparison of the expression of 46743 RNA was performed for breast, ovary, lung, colon, liver, and brain tissues (FIG. 54). The expression of 46743 is reduced in tumors of the ovary relative to normal ovary tissue, and may be elevated in tumors of the lung relative to normal lung tissue (FIG. 54A). It was also observed that the expression of 46743 is reduced in tumors of the brain relative to normal brain tissue (FIG. 54B).

Figure 55:
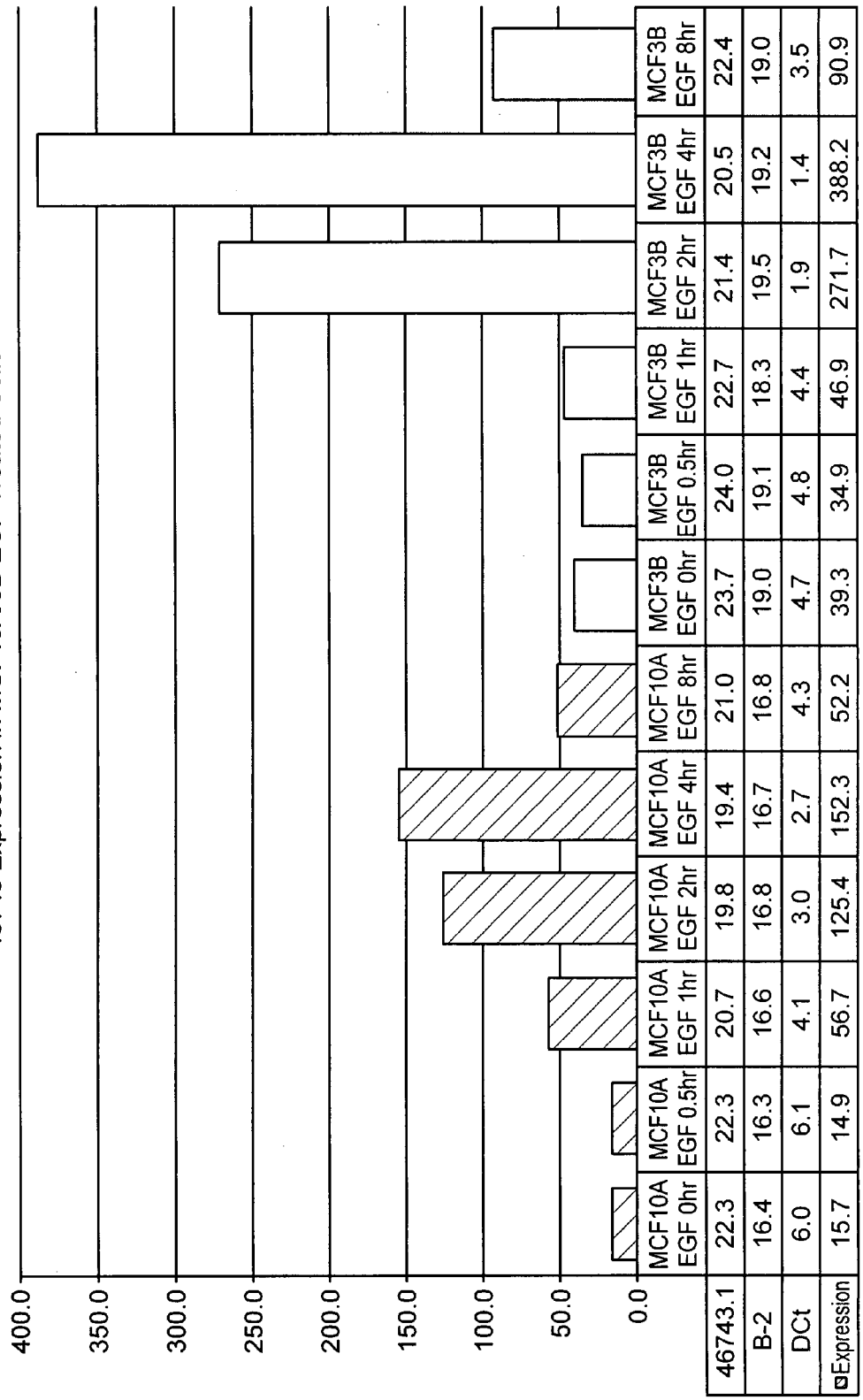
FIG. 55 is a bar graph depicting the temporal expression levels of 46743 RNA in two distinct isolates of human breast cancer (MCF) cell lines that have been stimulated with epidermal growth factor (EGF). In both cell lines, expression of 46743 RNA begins to increase about one hour after the cells have been exposed to EGF, continues to increase until about the 4$^{th}$ hour of EGF exposure, and has started to return to basal levels by the 8$^{th}$ hour of EGF exposure.
Figure 57:
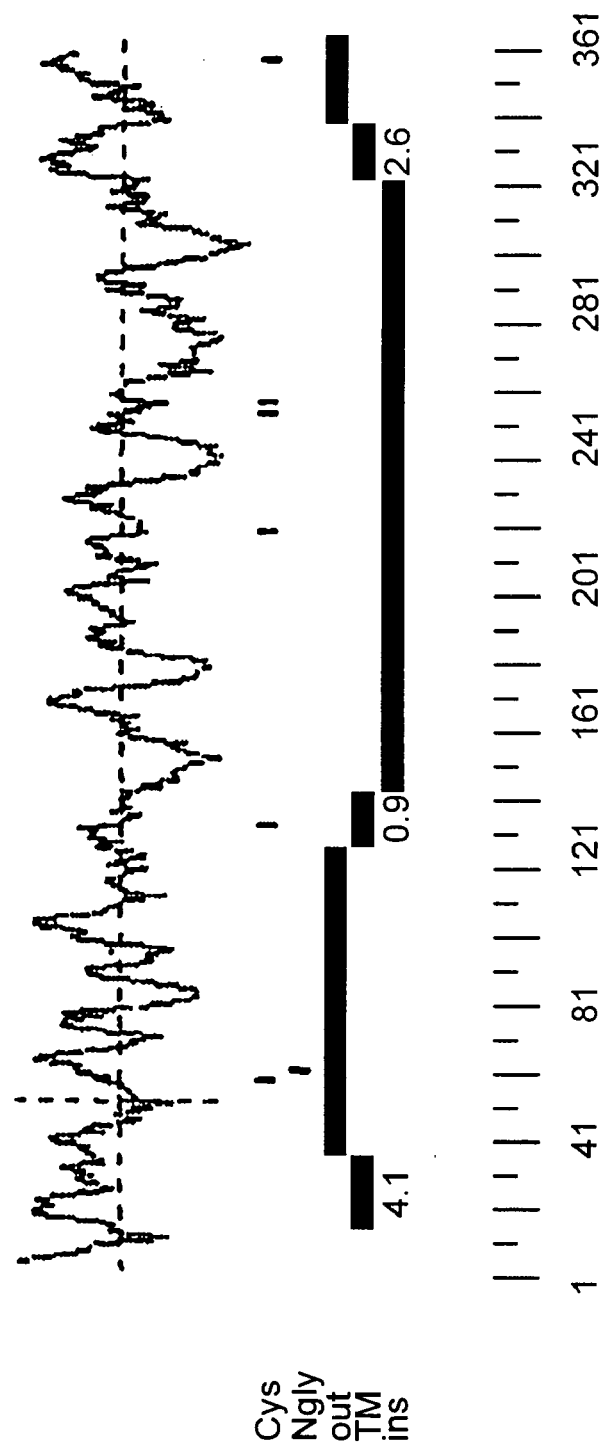
FIG. 57 depicts a hydropathy plot of human 27417. Relative hydrophobic residues are shown above the dashed horizontal line, and relative hydrophilic residues are below the dashed horizontal line. The cysteine residues (cys) and N-glycosylation sites (Ngly) are indicated by short vertical lines just below the hydropathy trace. The numbers corresponding to the amino acid sequence of human 27417 are indicated. Polypeptides of the invention include fragments comprising: all or part of a hydrophobic sequence (a sequence above the dashed line); or all or part of a hydrophilic fragment (a sequence below the dashed line). Other fragments include a cysteine residue or an N-glycosylation site.
Figure 58A:
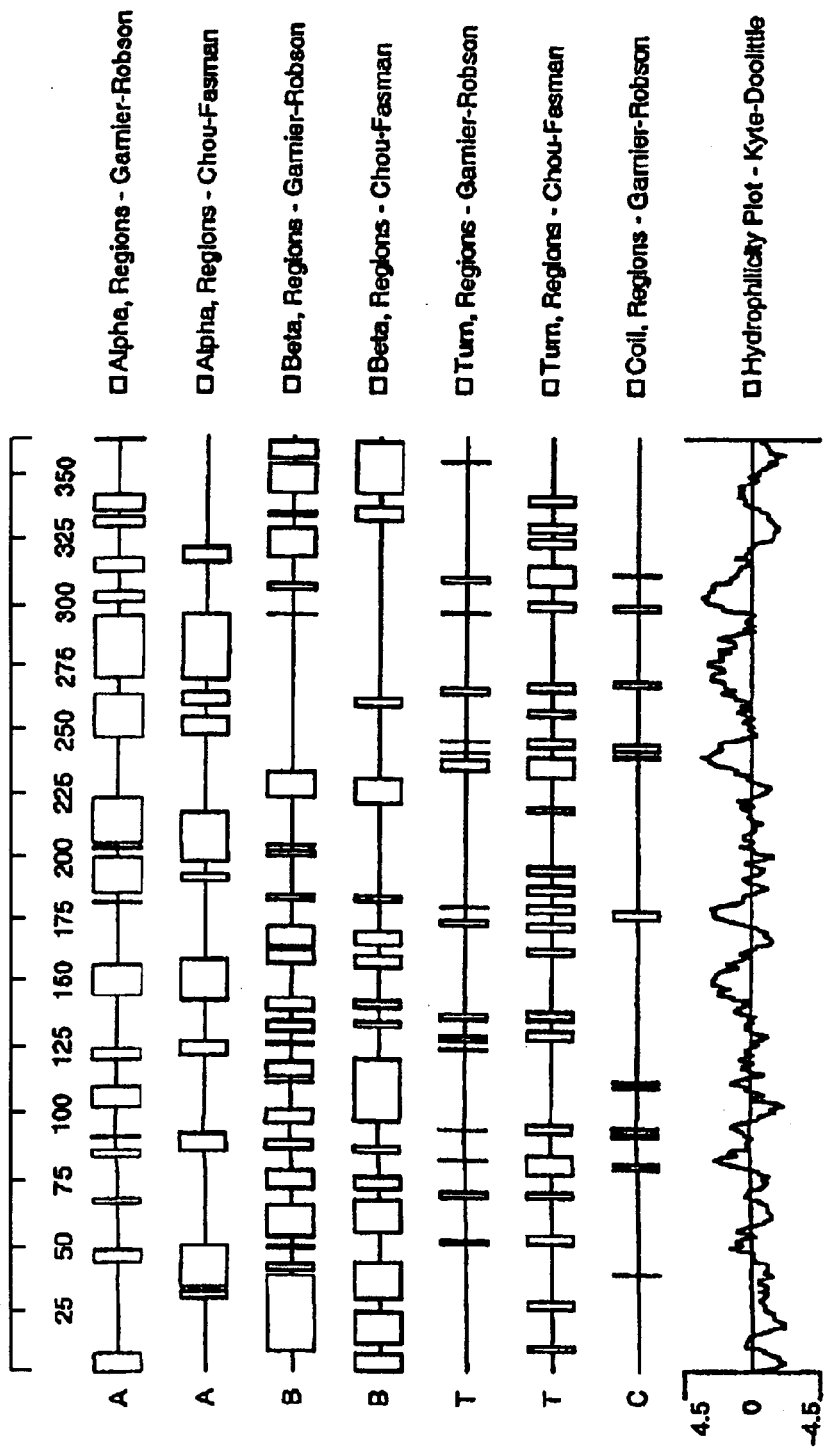
FIG. 58 depicts a series of plots summarizing an analysis of the primary and secondary protein structure of human 27417. The particular algorithm used for each plot is indicated at the right hand side of each plot. The following plots are depicted: Garnier-Robson plots providing the predicted location of alpha, beta, turn, and coil regions (Garnier et al. (1978) J. Mol. Biol. 120:97); Chou-Fasman plots providing the predicted location of alpha, beta, and turn regions (Chou and Fasman (1978) Adv. In Enzymol. Mol. 47:45-148); Kyte-Doolittle hydrophilicity/hydrophobicity plots (Kyte and Doolittle (1982) J. Mol. Biol. 157:105-132); Eisenberg plots providing the predicted location of alpha- and beta-amphipathic regions (Eisenberg et al. (1982) Nature 299: 371-374); a Karplus-Schulz plot providing the predicted location of flexible regions (Karplus and Schulz (1985) Naturwissens-Chafen 72:212-213); a plot of the antigenic index (Jameson-Wolf) (Jameson and Wolf (1988) CABIOS 4:121-136); and a surface probability plot (Emini algorithm) (Emini et al. (1985) J. Virol. 55:836-839). The numbers corresponding to the amino acid sequence of human 27417 are indicated.
Figure 58B:
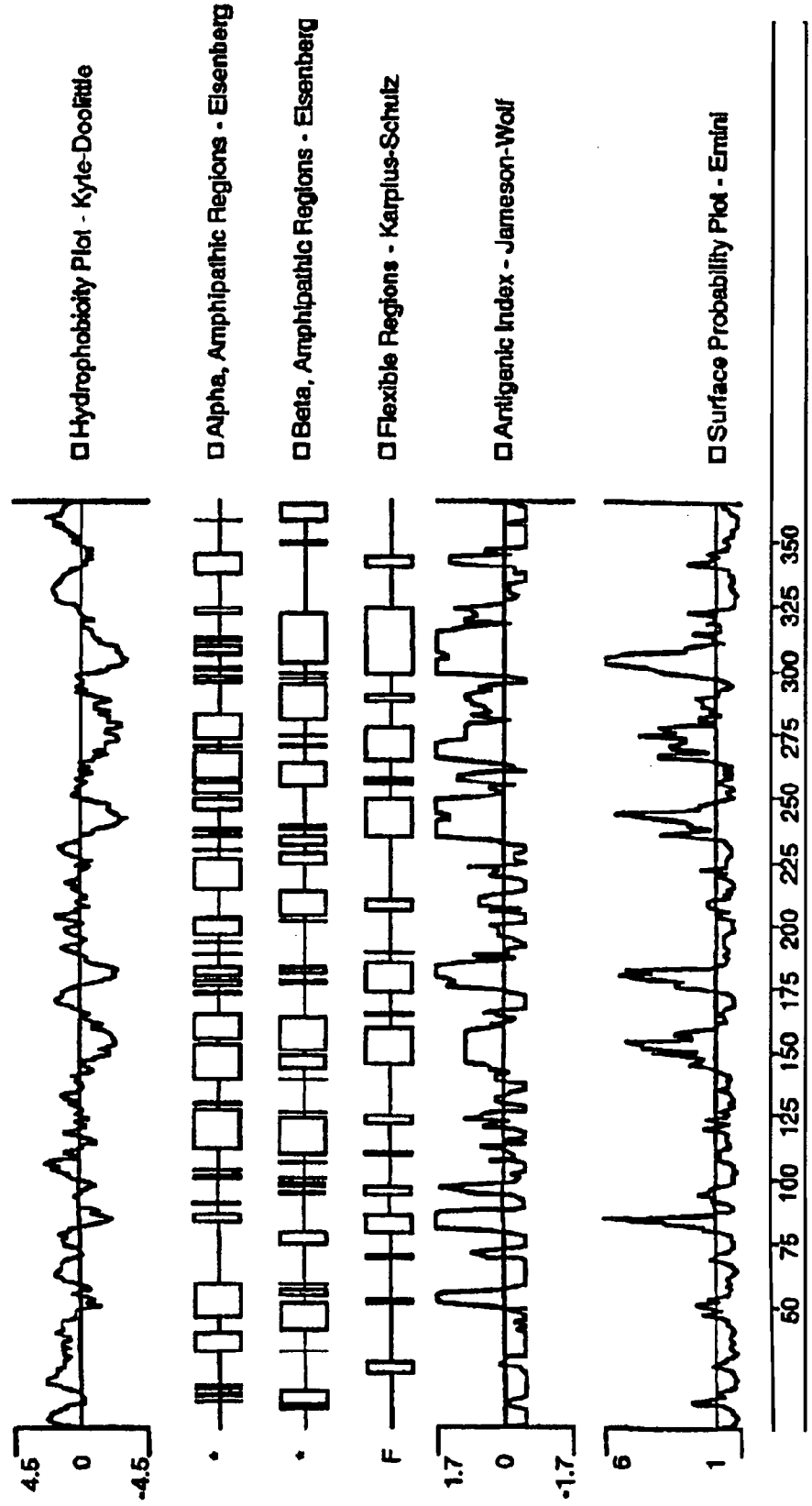

The relationship between 46743 RNA expression levels and cellular exposure to epidermal growth factor (EGF) was also tested (FIG. 55). In two separate lines of MCF cells, the expression levels of 46743 RNA increased after the cells had been exposed to EGF for about one hour. The increased expression level lasted for several hours before returning to near-normal levels.

Figure 61:
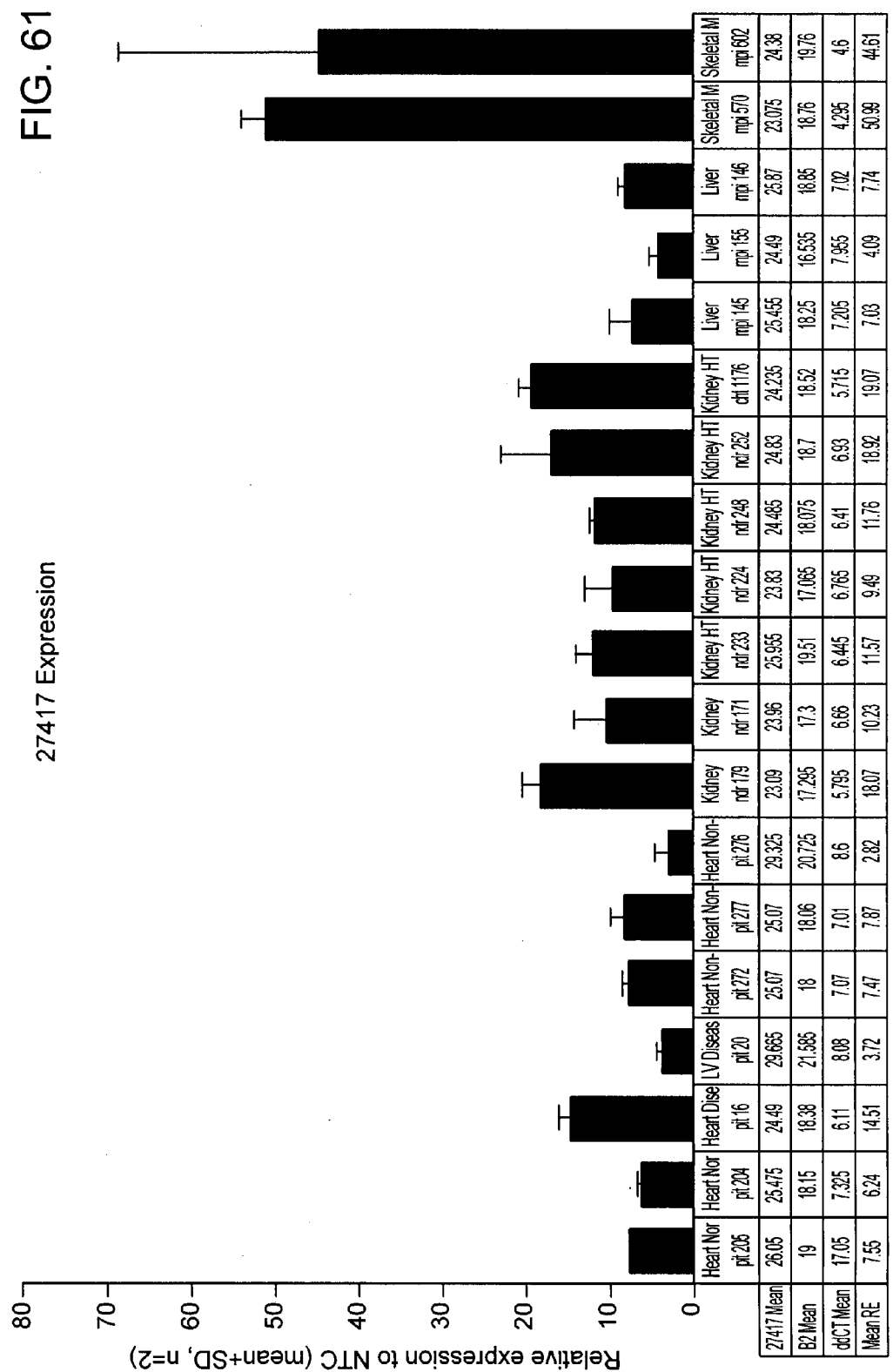
FIG. 61 is a bar graph depicting the expression of 27147 RNA in a panel of normal human tissues, including heart, kidney, liver, and skeletal muscle, as well as some diseased tissues, detected using Taqman analysis. Expression of 27147 RNA is highest in skeletal muscle, but is present in all of the tissues analyzed. Elevated expression of 27147 RNA is present in diseased heart tissue, as compared to normal heart tissue.
Figure 62:
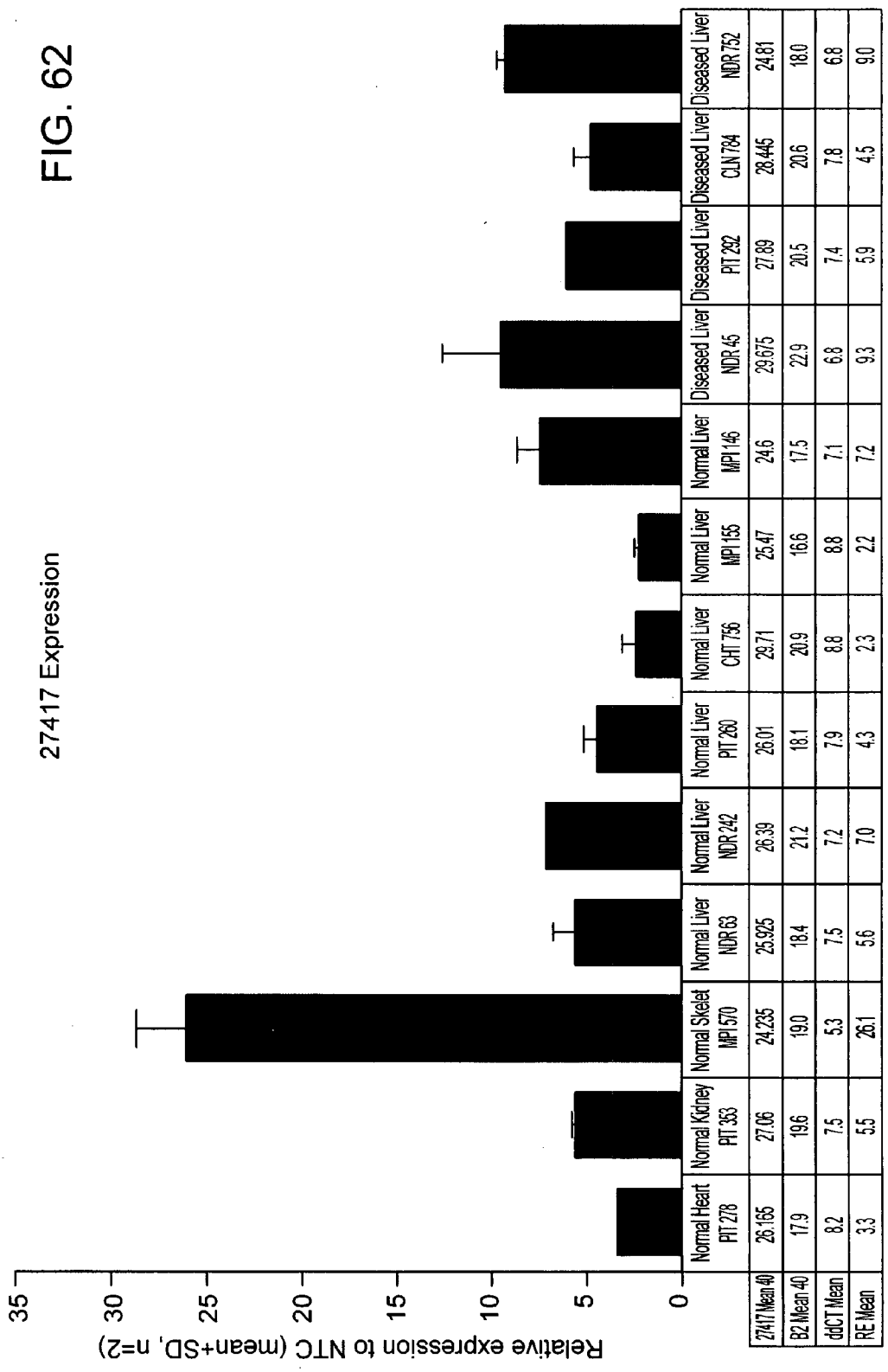
FIG. 62 is a bar graph depicting the expression of 27417 RNA in a panel of normal tissues, including heart, kidney, skeletal muscle, and liver, and several diseased human liver tissue samples. Expression of 27417 is elevated in at least some diseased liver samples, as compared to normal liver samples.
Figure 63:
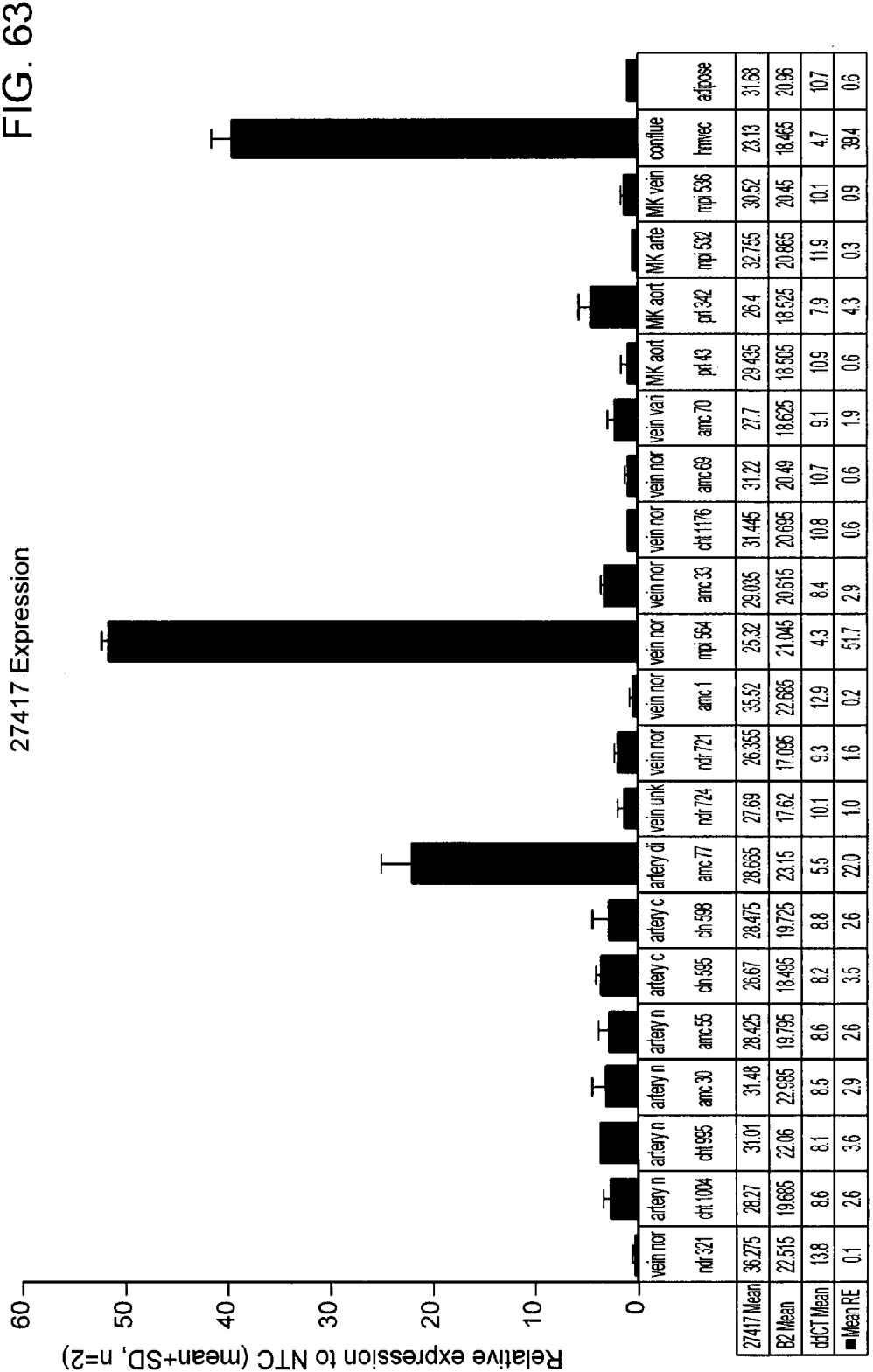
FIG. 63 is a bar graph depicting the expression of 27417 RNA in a panel of normal human artery and vein tissue samples, as well as a couple of diseased human artery and vein tissue samples. Elevated expression of 27147 can be observed in a few of the tissue samples, including samples of a normal vein and endothelial cells isolated from human microvesicular endothelial cells (hmvec's). Elevated expression of 27147 can also be observed in the diseased artery sample.
Figure 64:
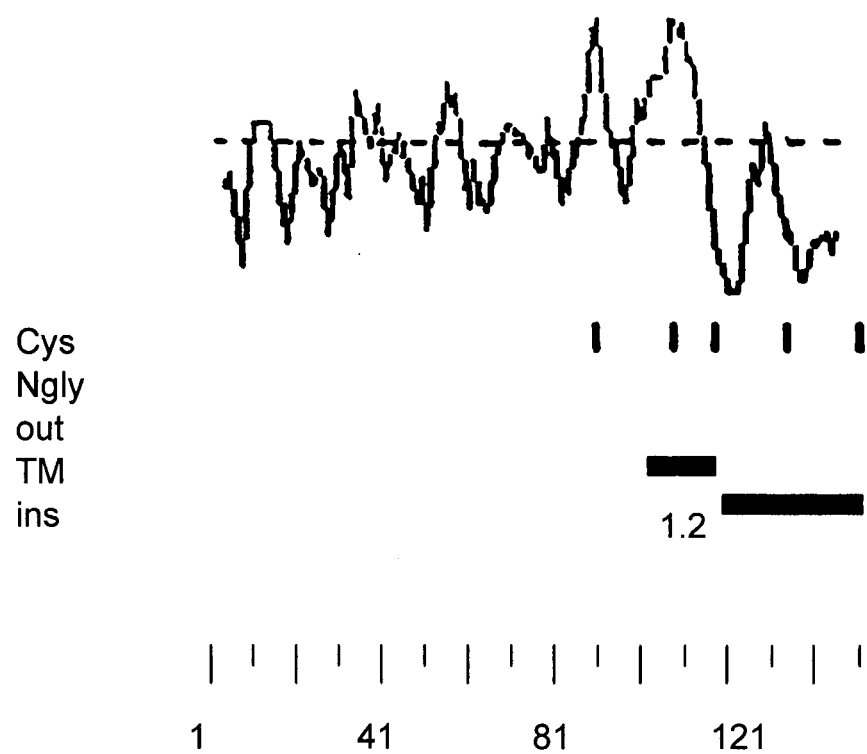
FIG. 64 depicts a hydropathy plot of human 27960. Relative hydrophobic residues are shown above the dashed horizontal line, and relative hydrophilic residues are below the dashed horizontal line. The cysteine residues (cys) are indicated by short vertical lines just below the hydropathy trace. The numbers corresponding to the amino acid sequence of human 27960 are indicated. Polypeptides of the invention include fragments that include: all or part of a hydrophobic sequence, i.e., a sequence above the dashed line, e.g., the sequence of residues 100-119 of SEQ ID NO:73; all or part of a hydrophilic sequence, i.e., a sequence below the dashed line, e.g., the sequence of residues 15-20; a sequence that includes a Cys, e.g., the sequence of residues 118-120 of SEQ ID NO:73.

The expression of 27147 RNA in a panel of normal human tissues, including heart, kidney, liver, skeletal muscle, arteries and veins, was tested (FIGS. 61-63). Expression of 27147 RNA was highest in skeletal muscle, but was present in all of the tissues listed. In addition, there was elevated expression of 27147 RNA in several diseased tissues, as compared to the appropriate normal tissue samples, including diseased heart tissue (FIG. 61), diseased liver tissue (FIG. 62), and diseased artery tissue (FIG. 63).

Example 45

Recombinant Expression of 46743 or 27417 in Bacterial Cells

In this example, 46743 or 27417 is expressed as a recombinant glutathione-S-transferase (GST) fusion polypeptide in *E. coli* and the fusion polypeptide is isolated and characterized. Specifically, 46743 or 27417 is fused to GST and this fusion polypeptide is expressed in *E. coli*, e.g., strain PEB199. Expression of the GST-46743 or GST-27417 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 46

Expression of Recombinant 46743 or 27417 Protein in COS Cells

To express the 46743 or 27417 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire 46743 or 27417 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 46743 or 27417 DNA sequence is amplified by PCR using two primers. The 5' primer contains the restriction site of interest followed by approximately twenty nucleotides of the 46743 or 27417 coding sequence starting from the initiation codon; the 3' end sequence contains complementary sequences to the other restriction site of interest, a translation stop codon, the HA tag or FLAG tag and the last 20 nucleotides of the 46743 or 27417 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 46743 or 27417 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 46743- or 27417-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the 46743 or 27417 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 46743 or 27417 coding sequence is cloned directly into the polylinker of the pCDNA/Amp vector using the appropriate restriction sites. The resulting plasmid is transfected into COS cells in the manner described above, and the expression of the 46743 or 27417 polypeptide is detected by radiolabelling and immunoprecipitation using a 46743 or 27417 specific monoclonal antibody.

Examples for 27960

Example 47

Identification and Characterization of Human 27960 cDNA

The human 27960 nucleic acid sequence is recited as follows:

```
CACTATAGGGAGTCGACCCACGCGTCCGGATGGTTCCATCATGGCGTCAATGCA    (SEQ ID NO:72)

GAAACGACTACAGAAAGAACTGTTGGCTTTGCAAAATGACCCACCTCCTGGAAT

GACCTTAAATGAGAAGAGTGTTCAAAATTCAATTACACAGTGGATTGTAGACAT

GGAAGGTGCACCAGGTACCTTATATGAAGGGGAAAAATTTCAACTTCTATTTAA

ATTTAGTAGTCGATATCCTTTTGACTCTCCTCAGGTCATGTTTACTGGTGAAAATA

TTCCTGTTCATCCTCATGTTTATAGCAATGGTCATATCTGTTTATCCATTCTAACA

GAAGACTGGTCCCCAGCGCTCTCAGTCCAATCAGTTTGTCTTAGCATTATTAGCA

TGCTTTCCAGCTGCAAGGAAAAGAGACGACCACCGGATAATTCTTTTTATGTGCG

AACATGTAACAAGAATCCAAAGAAAACAAAATGGTGGTATCATGATGATACTTG

TTGATGCCACTGTTATCATCCTCCTAGCAGAAGATAGTCCTACTGAGAAAATGAG

CACTTTGATCATTCAGTCTTTGAACTTTAACCTTTGACTGGAAGTGACCTATAGG
```

-continued

```
CAATGAAGACTACTTCCTTTTACTGCATTTTTACTCGTGTGCATTCTGGGCGCATG

TTGATCGCTGGTTCAGTCCAGGCAACTGACATGCTTTTATTAGTCATACAGTATT

AATGCAGGTGTCAGGAAATGTCAAATATAATTCCATTTTTTATTTTTATTTTTTA

AGCTTTTGGAAAAGCTCCAGGTCCTCATGTATTGTGCAATAACAATGACTTCCTT

GGCGGTTTTGGTACCTGCCCGGGCGGCCGCTCNAA
```

The human 27960 sequence (SEQ ID NO:72) is approximately 859 nucleotides long. The nucleic acid sequence includes an initiation codon (ATG) and a termination codon (TGA), which are underscored above. The region between and inclusive of the initiation codon and the termination codon is a methionine-initiated coding sequence of about 456 nucleotides, including the termination codon (nucleotides indicated as "coding" of SEQ ID NO:72; SEQ ID NO:74). The coding sequence encodes a 151 amino acid protein (SEQ ID NO:73), which is recited as follows:

The mRNA expression data for 27960 mRNA is tabulated in Table 22 and indicates that 27960 mRNA is highly expressed, for example, in aortic smooth muscle cells, coronary smooth muscle cells, both static and shear human vascular endothelial cells (HUVEC) cells, normal heart, congestive failure heart, kidney, skeletal muscle, pancreas, primary osteoblasts, brain cortex and hypothalamus, nerve, dorsal root ganglia, breast, ovary, prostate epithelial cells, colon tumor, lung tumor, and liver fibrosis tissue samples.

```
MASMQKRLQKELLALQNDPPPGMTLNEKSVQNSITQWIVDMEGAPGTLYEGEKFQL    (SEQ ID NO:73)

LFKFSSRYPFDSPQVMFTGENIPVHPHVYSNGHICLSILTEDWSPALSVQSVCLSIISM

LSSCKEKRRPPDNSFYVRTCNKNPKKTKWWYHDDTC
```

Example 48

Tissue Distribution of 27960 mRNA by TaqMan Analysis

Endogenous human 27960 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) that has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH that has been labeled with a different fluorophore on the 5' end (typically VIC).

To determine the level of 27960 in various human tissues a primer/probe set was designed. Total RNA was prepared from a series of human tissues using an RNeasy kit from Qiagen. First strand cDNA was prepared from 1 µg total RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in the left column of Tables 1-3.

TABLE 22

| Tissue Type | Expression |
| --- | --- |
| Artery normal | 8.0044 |
| Vein normal | 1.0394 |
| Aortic SMC EARLY | 9.4204 |
| Coronary SMC | 22.0206 |
| Static HUVEC | 11.2807 |
| Shear HUVEC | 11.2417 |
| Heart normal | 8.1443 |
| Heart CHF | 7.2893 |
| Kidney | 12.4303 |
| Skeletal Muscle | 15.1977 |
| Adipose normal | 3.1509 |
| Pancreas | 9.0054 |
| primary osteoblasts | 5.8595 |
| Osteoclasts (diff) | 0.9049 |
| Skin normal | 3.8927 |
| Spinal cord normal | 4.1721 |
| Brain Cortex normal | 50.0669 |
| Brain Hypothalamus normal | 14.8335 |
| Nerve | 7.7049 |
| DRG (Dorsal Root Ganglion) | 12.1744 |
| Resting PBMC | 1.1063 |
| Glioblastoma | 3.6447 |
| Breast normal | 6.6612 |
| Breast tumor | 9.9921 |
| Ovary normal | 10.5985 |
| Ovary Tumor | 3.5697 |
| Prostate Normal | 3.5697 |
| Prostate Tumor | 7.2139 |
| Epithelial Cells (Prostate) | 31.1419 |
| Colon normal | 1.2621 |
| Colon Tumor | 13.7445 |
| Lung normal | 1.1613 |
| Lung tumor | 9.7188 |
| Lung COPD | 1.736 |
| Colon IBD | 0.667 |
| Liver normal | 2.5594 |

TABLE 22-continued

| Tissue Type | Expression |
|---|---|
| Liver fibrosis | 6.4343 |
| Dermal Cells- fibroblasts | 2.7526 |
| Spleen normal | 2.5682 |
| Tonsil normal | 2.0717 |
| Lymph node | 2.4046 |
| small Intestine | 1.4548 |
| Skin-Decubitus | 4.2157 |
| Synovium | 1.6254 |
| BM-MNC (Bone marrow mononuclear cells) | 2.3963 |
| Activated PBMC | 0.4092 |

The mRNA expression data for 27960 mRNA tabulated in Table 23 (below) indicated that 27960 mRNA is highly expressed, for example, hemangiomas, in normal and fetal kidney, Wilm's tumor, uterine adenocarcinoma, neuroblastoma, fetal adrenal, normal and fetal heart, and glioblastoma (2 of 3 samples tested).

TABLE 23

| Tissue Type | Expression |
|---|---|
| Hemangioma | 10.75 |
| Hemangioma | 7.04 |
| Hemangioma | 6.35 |
| Normal Kidney | 21.20 |
| Renal Cell Carcinoma | 1.28 |
| Wilms Tumor | 60.79 |
| Wilms Tumor | 87.47 |
| Skin | 3.38 |
| Uterine Adenocarcinoma | 17.64 |
| Neuroblastoma | 27.30 |
| Fetal Adrenal | 22.17 |
| Fetal Kidney | 37.68 |
| Fetal Heart | 23.68 |
| Normal Heart | 20.69 |
| Spinal cord | 11.09 |
| Glioblastoma | 52.92 |
| Glioblastoma | 5.82 |
| Glioblastoma | 18.14 |

Table 24 below indicates the expression of 27690 RNA in a panel of normal and tumor human tissues, including breast, colon, liver, and lung, detected using TaqMan analysis. The following tissues are indicated: normal (N) breast; breast tumors (T), including invasive carcinoma (IDC); normal (N) ovary; ovarian tumors (T); normal lung; lung tumors (T), including small and non-small cell carcinoma (SmC and PDNSCCL, respectively), and adenocarcinomas; normal colon; colon tumors (T); colon-liver metastasis; normal liver; hemangioma; human microvesicular endothelial cells (HMVEC) (arrested and proliferating). Elevated expression of 26886 mRNA was detected in breast and ovarian tumors, lung tumors, and colon-liver metastasis.

TABLE 24

| Tissue Type | Expression |
|---|---|
| Breast N | 4.11 |
| Breast N | 5.08 |
| Breast N | 4.98 |
| Breast Tumor (T): IDC | 7.60 |
| Breast T: MD-IDC | 8.40 |
| Breast T: IDC | 16.18 |
| Breast T: IDC | 27.97 |
| Breast T: IDC | 9.23 |
| Breast T | 48.19 |

TABLE 24-continued

| Tissue Type | Expression |
|---|---|
| Ovary N | 19.17 |
| Ovary N | 11.76 |
| Ovary T | 7.09 |
| Ovary T | 11.36 |
| Ovary T | 27.30 |
| Ovary T | 8.32 |
| Ovary T | 15.36 |
| Lung N | 2.39 |
| Lung N | 2.95 |
| Lung N | 2.26 |
| Lung T-SmC | 26.37 |
| Lung T-PDNSCCL | 26.64 |
| Lung T-PDNSCCL | 20.19 |
| Lung T-PDNSCCL | 4.71 |
| Lung T-SCC | 47.20 |
| Lung T-AC | 7.21 |
| Lung T-ACA | 10.27 |
| Colon N | 1.39 |
| Colon N | 2.32 |
| Colon N | 1.42 |
| Colon T: MD | 11.40 |
| Colon T: MD | 9.82 |
| Colon T | 7.49 |
| Colon T: MD-PD | 7.60 |
| Colon-Liver Met | 20.76 |
| Colon-Liver Met | 25.03 |
| Liver N (female) | 5.51 |
| Hemangioma | 5.32 |
| HMVEC-Arr | 11.28 |
| HMVEC-Prol | 17.95 |
| NHBE | 44.04 |

Example 49

Tissue Distribution of 27960 mRNA

Northern blot hybridizations with various RNA samples can be performed under standard conditions and washed under stringent conditions, i.e., 0.2×SSC at 65° C. A DNA probe corresponding to all or a portion of the 27960 cDNA (SEQ ID NO:72) can be used. The DNA can be radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 50

Recombinant Expression of 27960 in Bacterial Cells

In this example, 27960 is expressed as a recombinant glutathione-S-transferase (GST) fusion polypeptide in *E. coli* and the fusion polypeptide is isolated and characterized. Specifically, 27960 is fused to GST and this fusion polypeptide is expressed in *E. coli*, e.g., strain PEB199. Expression of the GST-27960 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 51

Expression of Recombinant 27960 Protein in COS Cells

To express the 27960 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 27960 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 27960 DNA sequence is amplified by PCR using two primers. The 5' primer contains the restriction site of interest followed by approximately twenty nucleotides of the 27960 coding sequence starting from the initiation codon; the 3' end sequence contains complementary sequences to the other restriction site of interest, a translation stop codon, the HA tag or FLAG tag and the last 20 nucleotides of the 27960 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably, the two restriction sites chosen are different so that the 27960 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 27960-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989. The expression of the 27960 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual,* Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 27960 coding sequence is cloned directly into the polylinker of the pCDNA/Amp vector using the appropriate restriction sites. The resulting plasmid is transfected into COS cells in the manner described above, and the expression of the 27960 polypeptide is detected by radiolabelling and immunoprecipitation using a 27960 specific monoclonal antibody.

Examples for 32252

Example 52

Identification and Characterization of Human 32252 cDNA

The human 32252 nucleic acid sequence is recited as follows:

```
GCCGCCGCCGTCGCTGACCCAGCCCGCCAGGCGCTCCTGACCGTCGCTTCCTCCG  (SEQ ID NO:77)

GTCCCAGGTCCCCGGCCCTCGCCTCAGCCCCGGCCCCTGGTCCCCAGCCCTCGTC

GCAGCCCCGGCCGCCCGCCGCCGCCATGTCCAAGGAGGAGCGCCCCGGTCGGGA

GGAGATCCTGGAGTGCCAGGTGATGTGGGAGCCTGACAGTAAGAAGAACACGC

AGATGGACCGCTTCCGGGCGGCTGTGGGCGCCGCCTGCGGCCTGGCGCTGGAGA

GTTATGATGACTTGTACCATTGGTCCGTTGAGTCATATTCAGACTTCTGGGCAGA

GTTCTGGAAATTCAGTGGAATTGTCTTCTCACGTGTGTATGATGAGGTTGTGGAC

ACATCGAAAGGAATCGCAGATGTCCCCGAGTGGTTCAAAGGCAGTCGGCTCAAC

TATGCAGAAAACCTCCTGCGGCACAAAGAGAATGACAGAGTTGCCCTTTACATT

GCAAGGGAAGGCAAAGAGGAAATTGTGAAGGTGACTTTTGAAGAGCTGAGGCA

AGAAGTGGCTTTGTTTGCAGCAGCAATGAGGAAAATGGGTGTGAAGAAAGGAG

ATCGGGTTGTTGGTTATTTACCCAACAGTGAGCACGCTGTCGAGGCGATGCTGGC

TGCGGCAAGCATTGGTGCCATCTGGAGCTCCACGTCCCCGGACTTCGGTGTGAAT

GGTGTGCTGGACCGGTTTTCTCAAATTCAGCCAAAGCTCATCTTCTCTGTGGAGG

CTGTTGTCTATAATGGCAAAGAGCACAACCACATGGAAAAGCTGCAGCAGGTGG

TTAAAGGCCTACCAGACTTGAAGAAAGTGGTGGTGATTCCTTATGTGTCCTCCAG
```

-continued

```
AGAGAACATAGACCTTTCAAAGATTCCAAACAGTGTGTTTCTGGATGACTTTCTT

GCCACCGGCACCAGTGAGCAGGCCCCGCAGCTGGAGTTCGAGCAGCTGCCCTTC

AGCCACCCACTGTTCATCATGTTCTCATCGGGCACCACGGGCGCACCCAAGTGCA

TGGTGCATTCCGCTGGGGGCACCCTCATCCAGCATCTGAAGGAGCACCTGCTGC

ACGGCAACATGACCAGCAGTGACATCCTCCTGTGCTACACCACGGTCGGCTGGA

TGATGTGGAACTGGATGGTGTCCCTTCTGGCCACAGGAGCGGCCATGGTCTTGTA

CGATGGCTCCCCCCTGGTGCCCACGCCCAATGTGCTCTGGGACCTGGTTGACAGG

ATAGGCATCACTGTCCTGGTAACTGGGGCCAAGTGGCTGTCAGTGCTGGAAGAG

AAGGCCATGAAGCCGGTGGAAACCCACAGTCTCCAGATGCTCCACACGATCCTG

TCCACTGGCTCCCCACTGAAAGCCCAGAGCTACGAGTATGTCTACAGGTGCATC

AAGAGCAGCATCCTCCTGGGCTCCATCTCAGGAGGCACCGACATCATCTCCTGCT

TCATGGGCCACAATTTTTCTCTTCCTGTGTATAAAGGGGAGATTCAGGCCCGGAA

CCTGGGCATGGCCGTGGAAGCGTGGAACGAGGAAGGAAAGGCGGTCTGGGGAG

AGAGCGGCGAGCTGGTGTGTACTAAGCCGATCCCTTGCCAGCCCACACACTTCT

GGAACGATGAGAACGGCAACAAGTACAGGAAGGCGTATTTCTCCAAATTCCCAG

GTATCTGGGCTCATGGCGACTACTGCAGAATCAACCCCAAGACCGGGGGCATCG

TCATGCTTGGCCGGAGTGACGGCACCCTCAACCCCAACGGGGTGCGGTTCGGCA

GCTCGGAAATCTATAACATTGTGGAATCCTTCGAGGAGGTGGAGGACAGCCTGT

GTGTCCCCAGTATAACAAGTACAGGGAGGAGAGGGTGATCCTCTTCCTGAAGA

TGGCCTCCGGGCACGCCTTCCAGCCTGACTTGGTTAAGAGGATCCGTGACGCCAT

CCGCATGGGCTTGTCTGCGCGACACGTGCCCAGCCTCATCCTGGAAACCAAGGG

CATCCCGTATACGCTCAACGGCAAGAAAGTGGAAGTTGCCGTCAAACAGATCAT

CGCTGGAAAAGCCGTGGAGCAAGGAGGTGCTTTCTCGAACCCCGAGACCCTGGA

TCTGTACCGGGACATCCCTGAGCTGCAGGGCTTCTGAGTCAGACTGGCTGGCGT

GTCACTCAGCCGCACCCGTGTGCACTGTAACTTTTGTGTGCTCAAGAAATTATAC

AGAAACCTACAGCTGTTGTAAAAGGATGCTCGCACCAAGTGTTCTGTAGGCTTG

GGGAGGGATCGTTTCTCTGTTTTGTTAAATCTGGTGGGTACCTGGATCTTCCACA

CGAGTGGGATTCTGGCCTTCAGAGACCAGGAGGGAGTGTCTGGGCCGCAGGTGT

GGCACTGTGGTGAGAGTGTGTGTCTTTGCACACACAGTGCAGCGGGAACGGTGG

GGCTGGCTGGTGCTGAAGACAGACACACTCCTGAGCCAAGGTCTTGTCTTCAAC

CTCCCCGTCCCGTTGTCCCATTTTGCTCTGTGAAGGTGCAAATCCCTTTCTTCCCT

TCCCATCTCAGGCTCTCCTGTTTTCCCTCAGGGTCCAGTATGCCCTTTGAGCTTTA

GCTGTTAGAAAGGAAC.
```

Figure 66:
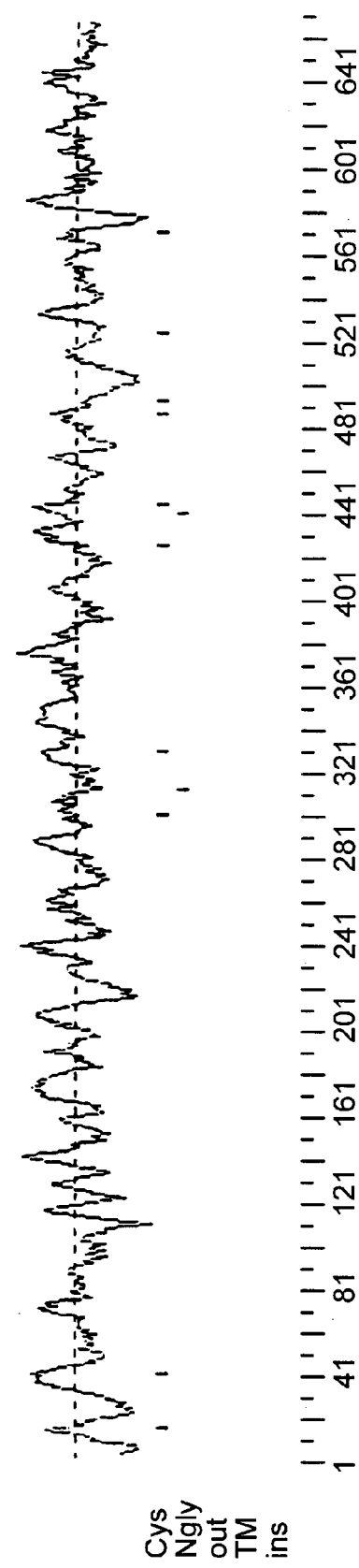
FIG. 66 depicts a hydropathy plot of human 32252. Relative hydrophobic residues are shown above the dashed horizontal line, and relative hydrophilic residues are below the dashed horizontal line. The cysteine residues (cys) are indicated by short vertical lines just below the hydropathy trace. Two glycosylation sites are also indicated. The numbers corresponding to the amino acid sequence of human 32252 are indicated. Polypeptides of the invention include fragments which include: all or part of a hydrophobic sequence, i.e., a sequence above the dashed line, e.g., the sequence from about amino acid 170 to 180, from about 335 to 355, and from about 430 to 450 of SEQ ID NO:78; all or part of a hydrophilic sequence, i.e., a sequence below the dashed line, e.g., the sequence of from about amino acid 210 to 225, and from about 495 to 510 of SEQ ID NO:78.

The human 32252 sequence (FIG. 66; SEQ ID NO:77), which is approximately 2625 nucleotides long. The nucleic acid sequence includes an initiation codon (ATG) and a termination codon (TAA) which are underscored and bolded above. The region between and inclusive of the initiation codon and the termination codon is a methionine-initiated coding sequence of about 2019 nucleotides, including the termination codon (nucleotides indicated as "coding" of SEQ ID NO:77; SEQ ID NO:79). The coding sequence encodes a 672 amino acid protein (SEQ ID NO:78), which is recited as follows:

MSKEERPGREEILECQVMWEPDSKKNTQMDRFRAAVGAACGLALESYDDLYHWSVES  (SEQ ID NO:78)

YSDFWAEFWKFSGIVFSRVYDEVVDTSKGIADVPEWFKGSRLNYAENLLRHKENDRV

ALYIAREGKEEIVKVTFEELRQEVALFAAAMRKMGVKKGDRVVGYLPNSEHAVEAML

AAASIGAIWSSTSPDFGVNGVLDRFSQIQPKLIFSVEAVVYNGKEHNHMEKLQQVVK

GLPDLKKVVVIPYVSSRENIDLSKIPNSVFLDDFLATGTSEQAPQLEFEQLPFSHPL

FIMFSSGTTGAPKCMVHSAGGTLIQHLKEHLLHGNMTSSDILLCYTTVGWMMWNWMV

SLLATGAAMVLYDGSPLVPTPNVLWDLVDRIGITVLVTGAKWLSVLEEKAMKPVETH

SLQMLHTILSTGSPLKAQSYEYVYRCIKSSILLGSISGGTDIISCFMGHNFSLPVYK

GEIQARNLGMAVEAWNEEGKAVWGESGELVCTKPIPCQPTHFWNDENGNKYRKAYFS

KFPGIWAHGDYCRINPKTGGIVMLGRSDGTLNPNGVRFGSSEIYNIVESFEEVEDSL

CVPQYNKYREERVILFLKMASGHAFQPDLVKRIRDAIRMGLSARHVPSLILETKGIP

YTLNGKKVEVAVKQIIAGKAVEQGGAFSNPETLDLYRDIPELQGF.

Example 53

Tissue Distribution of 32252 mRNA by TaqMan Analysis

Endogenous human 32252 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

To determine the level of 32252 in various human tissues a primer/probe set was designed. Total RNA was prepared from a series of human tissues using an RNeasy kit from Qiagen. First strand cDNA was prepared from 1 μg total RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in Tables 25-27. 32252 mRNA was detected include artery, coronary smooth muscle cells (SMC), heart, human umbilical vein endothelial cells (HUVECs), kidney, pancreas, adipose, epithelial, brain and other nerve tissue of the central nervous system, breast, prostate, colon, lung, and megakaryocyte, and erythroid tissues (Table 25). 32252 expression was also found in breast tumors, lung tumors, ovary tumors, and colon tumors (Tables 26 and 27).

TABLE 25

Expression of 32252 with β2

| Tissue Type | Relative Expression |
| --- | --- |
| Artery Normal | 1.6142 |
| Aorta Diseased | 0.4106 |
| Vein Normal | 0 |
| Coronary SMC (Smooth Muscle Cells) | 8.4901 |
| HUVEC (Human Umbilical Vein Endothelial Cells) | 10.3444 |
| Hemangioma | 0.206 |
| Heart Normal | 1.7121 |
| Heart CHF (Congestive Heart Failure) | 1.8542 |
| Kidney | 2.1671 |
| Skeletal Muscle | 0.7689 |
| Adipose Normal | 1.4649 |
| Pancreas | 3.8259 |
| Primary Osteoblasts | 0.4149 |
| Osteoclasts (differentiated) | 0.0135 |
| Skin Normal | 1.1735 |
| Spinal Cord Normal | 0.321 |
| Brain Cortex Normal | 51.8325 |
| Brain Hypothalamus Normal | 3.9334 |
| Nerve | 0.6223 |
| DRG (Dorsal Root Ganglion) | 4.3948 |
| Breast Normal | 4.4871 |
| Breast Tumor | 1.4397 |
| Ovary Normal | 1.5809 |
| Ovary Tumor | 0.1668 |
| Prostate Normal | 1.5271 |
| Prostate Tumor | 2.8007 |
| Salivary Glands | 1.835 |
| Colon Normal | 0.1936 |
| Colon Tumor | 3.4124 |
| Lung Normal | 0.0519 |
| Lung Tumor | 19.0377 |
| Lung COPD (Pulmonary Disease) | 0.2814 |
| Colon IBD (Intestinal Bowel Disease) | 0.1041 |
| Liver Normal | 0.0723 |
| Liver Fibrosis | 0.231 |
| Spleen Normal | 0 |
| Tonsil Normal | 0.7174 |
| Lymph Node Normal | 0.1393 |
| Small Intestine Normal | 0.1345 |
| Skin-Decubitus | 0.1308 |
| Synovium | 0 |

TABLE 25-continued

Expression of 32252 with β2

| Tissue Type | Relative Expression |
|---|---|
| BM-MNC | 0 |
| Activated PBMC | 0.1175 |
| Neutrophils | 0.6354 |
| Megakaryocytes | 7.3146 |
| Erythroid | 16.0643 |

The mRNA expression data for 32252 mRNA tabulated in Table 25 indicated expression in a number of particular tissues. Tissues in which 32252 mRNA was detected include artery, coronary smooth muscle cells (SMC), heart, human umbilical vein endothelial cells (HUVECs), kidney, pancreas, adipose, epithelial, brain and other nerve tissue of the central nervous system, breast, prostate, colon, lung, and megakaryocyte, and erythroid tissues. Expression was particularly prominent in the brain, lung tumor, and erythroid tissue samples, and slightly less in coronary SMC, HUVEC, and megakaryocyte tissue samples. Expression is relative to β-macroglobulin.

TABLE 26

Expression of 32252 in Oncology

| Tissue Type | Relative Expression |
|---|---|
| PIT 400 Breast Normal | 20.33 |
| PIT 372 Breast Normal | 10.64 |
| CHT 558 Breast Normal | 6.00 |
| CLN 168 Breast Tumor: Invasive Ductal Carcinoma (IDC) | 8.23 |
| MDA 304 Breast Tumor: MD-Invasive Ductal Carcinoma | 6.37 |
| NDR 58 Breast Tumor: Invasive Ductal Carcinoma (IDC) | 4.60 |
| NDR 05 Breast Tumor: Invasive Ductal Carcinoma (IDC) | 152.83 |
| MCF-7 Breast Tumor | 86.87 |
| ZR75 Breast Tumor | 110.72 |
| T47D Breast Tumor | 70.32 |
| MDA 231 Breast Tumor | 14.33 |
| MDA 435 Breast Tumor | 9.75 |
| SKBr3 Breast | 35.65 |
| DLD 1 Colon Tumor (stage C) | 173.14 |
| SW480 Colon Tumor (stage B) | 60.58 |
| SW620 Colon Tumor (stage C) | 85.08 |
| HCT116 | 20.69 |
| HT29 | 14.63 |
| Colo 205 | 10.64 |
| NCIH125 | 59.54 |
| NCIH67 | 102.24 |
| NCIH322 | 27.30 |
| NCIH460 | 18.65 |
| A549 | 53.66 |
| NHBE | 38.21 |
| SKOV-3 Ovary | 5.90 |
| OVCAR-3 Ovary | 46.71 |
| 293 Baby Kidney | 88.08 |
| 293T Baby Kidney | 72.04 |

Tumor cell lines were xenografted into nude mice. Expression of human 32252 mRNA in tumors harvested from the mice was analyzed using TaqMan. Results are tabulated in Table 27. The results indicated that, for example, 32252 mRNA is highly expressed in some xenografted colon tumor samples, some xenografted breast tumor samples, some xenografted lung tumor samples, and some xenografted ovary cell lines.

TABLE 27

Expression of 32252 in Lung Xenografts

| Xenografted Cell Line | Relative Expression |
|---|---|
| NHBE | 0.1 |
| A549 (BA) | 0.0 |
| H460 (LCLC) | 0.1 |
| H23 (adenocarcinoma) | 0.2 |
| H522 (adenocarcinoma) | 0.1 |
| H125 (adenocarcinoma/small cell carcinoma) | 0.4 |
| H520 (small cell carcinoma) | 0.1 |
| H69 (SCLC) | 0.1 |
| H324 (SCLC) | 0.3 |

32252 mRNA was expressed in a number of lung tumor cell lines when grown as xenografts in mice.

In situ hybridization procedures detected 32252 mRNA in a number of tissue samples:

Lung: No (1 of 2 samples) or weak (1 of 2 samples) expression was found in normal bronchiolar epithelium, but striking up regulation was detected in all histological subtypes of tumors (6 of 6 tumor samples).

Breast: 32252 mRNA was detected in normal breast tissue (3 of 3 samples) and breast tumors (2 of 2 samples).

Colon: 32252 mRNA was upregulated in primary tumors (2 of 2 samples) and liver metastases (4 of 4 samples) relative to normal.

Ovary: Ovarian tissues were positive for 32252 expression (3 of 3 samples) relative normal ovarian tissue.

32252 mRNA was also highly over expressed in lung tumor cells (for example, NCI-460 lung tumor cells) that are grown in soft agar (0.2 units) relative to the same cells grown on plastic (<0.05 units). This finding is indicative of association of 32252 overexpression with the metastatic state.

Example 54

Tissue Distribution of 32252 mRNA by Northern Analysis

Northern blot hybridizations with various RNA samples can be performed under standard conditions and washed under stringent conditions, i.e., 0.2×SSC at 65° C. A DNA probe corresponding to all or a portion of the 32252 cDNA (SEQ ID NO:77) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 55

Recombinant Expression of 32252 in Bacterial Cells

In this example, 32252 is expressed as a recombinant glutathione-S-transferase (GST) fusion polypeptide in *E. coli* and the fusion polypeptide is isolated and characterized. Specifically, 32252 is fused to GST and this fusion polypeptide is expressed in *E. coli*, e.g., strain PEB199. Expression of the GST-32252 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 56

Expression of Recombinant 32252 Protein in COS Cells

To express the 32252 gene in COS cells (e.g., COS-7 cells, CV-1 origin SV40 cells; Gluzman (1981) CellI23:175-182), the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire 32252 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 32252 DNA sequence is amplified by PCR using two primers. The 5' primer contains the restriction site of interest followed by approximately twenty nucleotides of the 32252 coding sequence starting from the initiation codon; the 3' end sequence contains complementary sequences to the other restriction site of interest, a translation stop codon, the HA tag or FLAG tag and the last 20 nucleotides of the 32252 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 32252_gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 32252-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual. 2nd, ed., Cold Spring Harbor Laboratory*, Cold Spring Harbor Laboratory Press, Cold Spring Harbor, N.Y. The expression of the 32252 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual*, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 32252 coding sequence is cloned directly into the polylinker of the pCDNA/Amp vector using the appropriate restriction sites. The resulting plasmid is transfected into COS cells in the manner described above, and the expression of the 32252 polypeptide is detected by radiolabelling and immunoprecipitation using a 32252 specific monoclonal antibody.

Examples for 53320

Example 57

Identification and Characterization of Human 53320 cDNA

The human 53320 nucleic acid sequence is recited as follows:

```
CCAGCTTGCCCACGCACCCCACTCGGCGTCGCGCGGCGTGCCCTGCTTGTCACAG    (SEQ ID NO:83)

GTGGGAGGCTGGAACTATCAGAATCATGGTGTCATGGAAAGGGATTTACTTTAT

ACTGACTCTGTTTTGGGGAAGCTTCTTTGGAAGCATTTTCATGCTGAGTCCCTTTT

TACCTTTGATGTTTGTAAACCCATCTTGGTATCGCTGGATCAACAACCGCCTTGT

GGCAACATGGCTCACCCTACCTGTGGCATTACTGGAGACCATGTTTGGTGTAAAA

GTGATTATAACTGGGGATGCATTTGTTCCTGGAGAAAGAGGTGTCATTATCATGA

ACCATCGGACAAGAATGGACTGGACGTTCCTGTGGAATTGCCTGATGCGATATA

GCTACCTCAGATTGGAGAAAATTTGCCTCAAAGCGAGTCTCAAAGGTGTTCCTGG

ATTTGGTTGGGCCATGCAGGCTGCTGCCTATATCTTCATTCATAGGAAATGGAAG

GATGACAAGAGCCATTTCGAAGACATGATTGATTACTTTTGTGATATTCACGAAC

CACTTCAACTCCTCATATTCCCAGAAGGGACTGATCTCACAGAAAACAGCAAGT

CTCGAAGTAATGCATTTGCTGAAAAAAATGGACTTCAGAAATATGAATATGTTTT

ACATCCAAGAACTACAGGCTTTACTTTTGTGGTAGACCGTCTAAGAGAAGGTAA

GAACCTTGATGCTGTCCATGATATCACTGTGGCGTATCCTCACAACATTCCTCAA
```

-continued

```
TCAGAGAAGCACCTCCTCCAAGGAGACTTTCCCAGGGAAATCCACTTTCATGTCC

ACCGGTATCCAGTAGACACCCTCCCCACATCCAAGGAGGACCTTCAACTCTGGT

GCCACAAACGGTGGGAAGAGAAAGAAGAGAGGCTGCGTTCCTTCTATCAAGGG

GAGAAGAATTTTTATTTTACCGGACAGAGTGTCATTCCACCTTGCAAGTCTGAAC

TCAGGGTCCTTGTGGTCAAATTGCTCTCTATACTGTATTGGACCCTGTTCAGCCCT

GCAATGTGCCTACTCATATATTTGTACAGTCTTGTTAAGTGGTATTTTATAATCAC

CATTGTAATCTTTGTGCTGCAAGAGAGAATATTTGGTGGACTGGAGATCATAGAA

CTTGCATGTTACCGACTTTTACACAAACAGCCACATTTAAATTCAAAGAAAAATG

AGTAAGATTATAAGGTTTGCCATGTGAAAACCTAGAGCATATTTTGGAAATGTTC

TAAACCTTTCTAAGCTCAGATGCATTTTTGCATGACTATGTCGAATATTTCTTACT

GCCATCATTATTTGTTAAARATATTTTGCACTTAATTTTGTGGGAAAAAWANTTG

CTACAATTTTTTTTAATCTCTKRWRTRWWWTYKMKAYWSTGTRYAYAKMRSRG

RGWGWKMKMSGRKGWARWAAYWWSKKSSRGMMWRWWWWTWAWYAAWCAAT.
```

Figure 69:
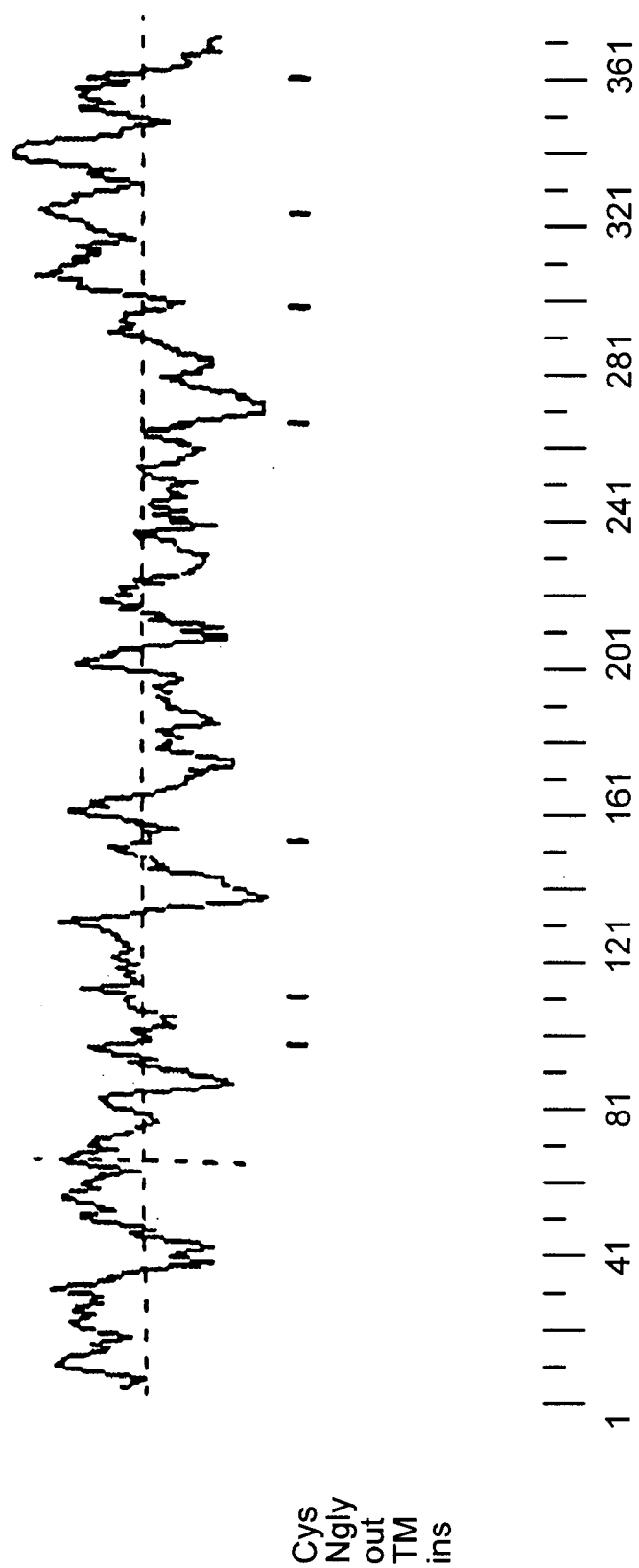
FIG. 69 depicts a hydropathy plot of human 53320. Relative hydrophobic residues are shown above the dashed horizontal line, and relative hydrophilic residues are below the dashed horizontal line. Numbers corresponding to positions in the amino acid sequence of human 53320 are indicated. Polypeptides of the invention include fragments which include: all or a part of a hydrophobic sequence (a sequence above the dashed line); or all or part of a hydrophilic fragment (a sequence below the dashed line).

The human 53320 sequence (FIG. 69; SEQ ID NO:83), which is approximately 1475 nucleotides long. The nucleic acid sequence includes an initiation codon (ATG) and a termination codon (TAA) which are underscored above. The region between and inclusive of the initiation codon and the termination codon is a methionine-initiated coding sequence of about 1131 nucleotides, including the termination codon (nucleotides indicated as "coding" of SEQ ID NO:83; SEQ ID NO:85). The coding sequence encodes a 376 amino acid protein (SEQ ID NO:84), which is recited as follows:

```
MVSWKGIYFILTLFWGSFFGSIFMLSPFLPLMFVNPSWYRWINNRLVATWLTLPVAL    (SEQ ID NO:84)

LETMFGVKVIITGDAFVPGERGVIIMNHRTRMDWTFLWNCLMRYSYLRLEKICLKAS

LKGVPGFGWAMQAAAYIFIHRKWKDDKSHFEDMIDYFCDIHEPLQLLIFPEGTDLTE

NSKSRSNAFAEKNGLQKYEYVLHPRTTGFTFVVDRLREGKNLDAVHDITVAYPHNIP

QSEKHLLQGDFPREIHFHVHRYPVDTLPTSKEDLQLWCHKRWEEKEERLRSFYQGEK

NFYFTGQSVIPPCKSELRVLVVKLLSILYWTLFSPAMCLLIYLYSLVKWYFIITIVI

FVLQERIFGGLEIIELACYRLLHKQPHLNSKKNE.
```

Example 58

Tissue Distribution of 53320 mRNA by TagMan Analysis

Endogenous human 53320 gene expression was determined using the Perkin-Elmer/ABI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of Taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a quantitative measure of the initial template concentration. Samples can be internally controlled by the addition of a second set of primers/probe specific for a housekeeping gene such as GAPDH which has been labeled with a different fluorophore on the 5' end (typically VIC).

To determine the level of 53320 in various human tissues a primer/probe set was designed. Total RNA was prepared from a series of human tissues using an RNeasy kit from Qiagen. First strand cDNA was prepared from 1 μg total RNA using an oligo-dT primer and Superscript II reverse transcriptase (Gibco/BRL). cDNA obtained from approximately 50 ng total RNA was used per TaqMan reaction. Tissues tested include the human tissues and several cell lines shown in Tables 1 to 7.

Figure 72:
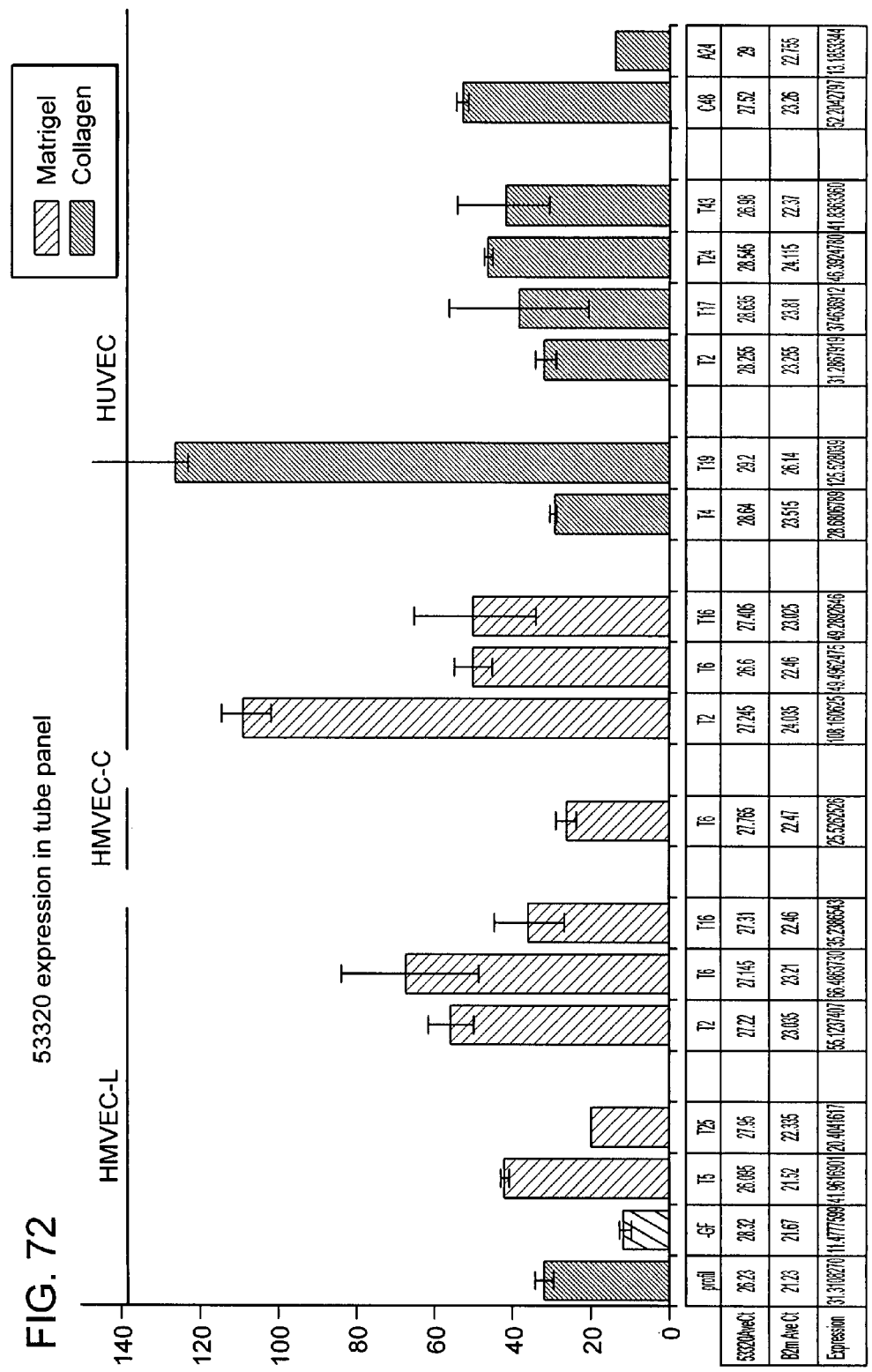
FIGS. 72 and 73 depict bar graphs of 53320 expression in endothelial cells.
Figure 73:
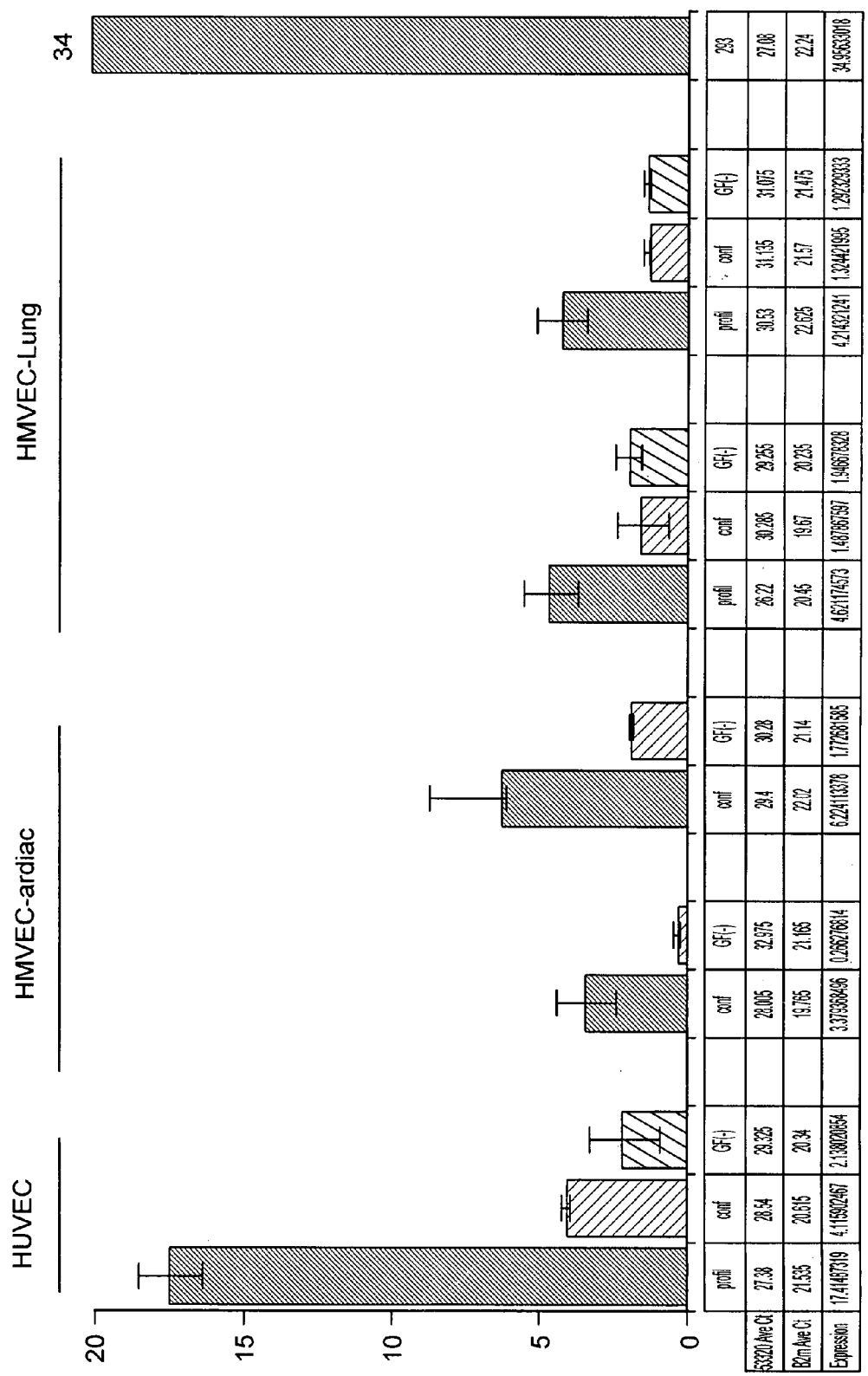

In addition, results depicted in FIGS. 72 and 73 indicated that 53320 was highly expressed in a number of endothelial cells including HMVEC-L, HMVEC-C, and HUVEC cells cultivated in matrigel and collagen

TABLE 29

| Tissue Type | Relative Expression |
|---|---|
| Artery Normal | 44.04 |
| Vein Normal | 51.29 |

TABLE 29-continued

| Tissue Type | Relative Expression |
|---|---|
| Aortic SMC (Smooth Muscle Cells) EARLY | 400.53 |
| Coronary SMC (Smooth Muscle Cells) | 284.20 |
| Static HUVEC (Human Umbilical Vein Endothelial Cells) | 381.56 |
| Shear HUVEC (Human Umbilical Vein Endothelial Cells) | 151.24 |
| Heart Normal | 20.61 |
| Heart CHF (Congestive Heart Failure) | 35.52 |
| Kidney | 17.27 |
| Skeletal Muscle | 106.21 |
| Adipose Normal | 30.39 |
| Pancreas | 8.7288 |
| Primary Osteoblasts | 184.28 |
| Osteoclasts (differentiated) | 38.34 |
| Skin Normal | 123.70 |
| Spinal Cord Normal | 17.15 |
| Brain Cortex Normal | 101.53 |
| Brain Hypothalamus Normal | 13.93 |
| Nerve | 31.68 |
| DRG (Dorsal Root Ganglion) | 95.72 |
| Glial Cells (Astrocytes) | 466.51 |
| Glioblastoma | 47.86 |
| Breast Normal | 54.40 |
| Breast Tumor | 49.721 |
| Ovary Normal | 89.00 |
| Ovary Tumor | 21.49 |
| Prostate Normal | 66.98 |
| Prostate Tumor | 18.07 |
| Epithelial Cells (Prostate) | 278.35 |
| Colon Normal | 1.6653 |
| Colon Tumor | 81.89 |
| Lung Normal | 16.00 |
| Lung Tumor | 66.75 |
| Lung COPD | 14.57 |
| Colon IBD | 5.10 |
| Liver Normal | 10.74 |
| Liver Fibrosis | 52.73 |
| Dermal Cells-fibroblasts | 418.99 |
| Spleen Normal | 5.04 |
| Tonsil Normal | 0.91 |
| Lymph Node | 0.73 |
| Small Intestine | 0.83 |
| Skin-Decubitus | 29.46 |
| Synovium | 19.10 |
| BM-MNC (Bone marrow mononuclear cells) | 0 |
| Activated PBMC | 0.0109 |

Table 29 recites results that indicated that notable high levels of 53320 expression in Aortic SMC (Smooth Muscle Cells), coronary SMC (Smooth Muscle Cells), static HUVEC (Human Umbilical Vein Endothelial Cells) and shear HUVEC (Human Umbilical Vein Endothelial Cells) relative to other tissues. 53320 was also highly expressed in brain, epithelial cells, fibroblasts, glial cells, and skeletal cells. (N.B. relative values are only applicable within a given table).

TABLE 30

Expression in Oncology

| Tissue Type | Relative Expression |
|---|---|
| PIT 400 Breast Normal | 0.38 |
| PIT 56 Breast Normal | 0.90 |
| MDA 106 Breast Tumor | 1.99 |
| MDA 234 Breast Tumor | 0.04 |
| NDR 57 Breast Tumor | 0.54 |
| MDA 304 Breast Tumor | 0.12 |
| NDR 58 Breast Tumor | 3.53 |
| NDR 132 Breast Tumor | 2.31 |

TABLE 30-continued

Expression in Oncology

| Tissue Type | Relative Expression |
|---|---|
| NDR 07 Breast Tumor | 0.50 |
| NDR 12 Breast Tumor | 16.40 |
| PIT 208 Ovary Normal | 1.63 |
| CHT 620 Ovary Normal | 0.88 |
| CHT 619 Ovary Normal | 4.63 |
| CLN 03 Ovary Tumor | 1.42 |
| CLN 05 Ovary Tumor | 1.21 |
| CLN 17 Ovary Tumor | 3.52 |
| CLN 07 Ovary Tumor | 0.21 |
| CLN 08 Ovary Tumor | 0.29 |
| MDA 216 Ovary Tumor | 1.67 |
| CLN 012 Ovary Tumor | 4.07 |
| MDA 25 Ovary Tumor | 1.49 |
| MDA 183 Lung Normal | 0.00 |
| CLN 930 Lung Normal | 0.07 |
| MDA 185 Lung Normal | 0.00 |
| CHT 816 Lung Normal | 0.00 |
| MPI 215 Lung Tumor-SmC (Small Cell Carcinoma) | 20.62 |
| MDA 259 Lung Tumor-PDNSCCL | 7.39 |
| CHT 832 Lung Tumor-PDNSCCL | 2.41 |
| MDA 253 Lung Tumor-PDNSCCL | 0.49 |
| CHT 814 Lung Tumor-SCC (Small Cell Carcinoma) | 3.87 |
| CHT 911 Lung Tumor-SCC (Small Cell Carcinoma) | 34.20 |
| CHT 726 Lung Tumor-SCC (Small Cell Carcinoma) | 1.20 |
| CHT 845 Lung Tumor-AC | 13.65 |
| NHBE | 55.36 |

Table 30 recites results indicating that 53320 mRNA is highly expressed in lung tumors relative to normal lung tissue and to a lesser extent in some breast and ovarian tumors.

TABLE 31

Expression in Oncology

| Tissue Type | Relative Expression |
|---|---|
| CHT 396 Colon Normal | 0.00 |
| CHT 519 Colon Normal | 0.00 |
| CHT 416 Colon Normal | 0.05 |
| CHT 452 Colon Normal | 0.00 |
| CHT 398 Colon Tumor | 9.59 |
| CHT 807 Colon Tumor | 0.10 |
| CHT 528 Colon Tumor | 0.52 |
| CHT 368 Colon Tumor | 0.00 |
| CHT 372 Colon Tumor | 0.16 |
| CHT 01 Liver Metastasis | 1.67 |
| CHT 3 Liver Metastasis | 3.09 |
| CHT 896 Liver Metastasis | 3.89 |
| NDR 217 Liver Metastasis | 0.53 |
| PIT 260 Liver Normal | 0.02 |
| PIT 229 Liver Normal | 0.00 |
| MGH 16 Brain Normal | 8.26 |
| MCL 53 Brain Normal | 22.25 |
| MCL 377 Brain Normal | 5.74 |
| MCL 390 Brain Normal | 20.12 |
| Astrocytes | 10.10 |
| CHT 201 Brain Tumor | 0.00 |
| CHT 216 Brain Tumor | 0.11 |
| CHT 501 Brain Tumor | 1.50 |
| CHT 1273 Brain Tumor | 23.85 |
| A24 HMVEC-Arr | 1.59 |
| C48 HMVEC-Prol | 17.70 |
| CHT 50 Placenta | 0.00 |
| BWH 54 Fetal Liver | 5.05 |
| BWH 75 Fetal Liver | 0.10 |
| CHT 765 Wilms Tumor | 19.10 |
| PIT 213 Renal Tumor | 0.00 |
| CHT 1424 Endometrial AC | 3.32 |

TABLE 31-continued

Expression in Oncology

| Tissue Type | Relative Expression |
|---|---|
| BWH 58 Fetal Adrenal | 1.60 |
| PIT 251 Fetal Adrenal | 1.74 |

Table 31 recites results indicating that 53320 mRNA is highly expressed in human microvascular endothelial cells (HMVEC), Wilms Tumor samples, some colon tumor samples, and some liver metastasis of colon tumors.

TABLE 32

Expression of 53320 w/β2 in Angiogenesis

| Tissue Type | Relative Expression |
|---|---|
| ONC 101 Hemangioma | 0.6905 |
| ONC 102 Hemangioma | 4.7429 |
| ONC 103 Hemangioma | 4.7429 |
| CHT 1273 Glioblastoma | 14.3779 |
| CHT 216 Glioblastoma | 3.472 |
| CHT 501 Glioblastoma | 6.1508 |
| NDR 203 Normal Kidney | 6.8961 |
| PIT 213 Renal Cell Carcinoma | 0.9207 |
| CHT 732 Wilms Tumor | 30.9268 |
| CHT 765 Wilms Tumor | 34.0784 |
| NDR 295 Skin | 2.8398 |
| CHT 1424 Uterine Adenocarcinoma | 6.1084 |
| CHT 1238 Neuroblastoma | 12.9133 |
| BWH 78 Fetal Adrenal | 3.1729 |
| BWH 74 Fetal Kidney | 15.3566 |
| BWH 4 Fetal Heart | 18.453 |
| MPI 849 Normal Heart | 8.9122 |
| NDR 764 Cartilage | 1.7972 |
| CLN 746 Spinal cord | 2.3797 |
| CHT 1753 lymphangiona | 0.3818 |
| CLN 944 Endometrial polyps | 0 |
| NEB 3 Synovium (RA) | 0 |
| CLN 1221 Hyperkeratotic skin | 1.791 |

Table 32 recites results indicating that 53320 mRNA was highly expressed in Wilms Tumors.

TABLE 33

Expression in Lung Model

| Tissue Type | Relative Expression |
|---|---|
| NHBE | 67.92 |
| A549 (BA) | 197.51 |
| H460 (LCLC) | 83.04 |
| H23 (adenocarcinoma) | 258.82 |
| H522 (adenocarcinoma) | 284.20 |
| H125 (adenocarcinoma/small cell carcinoma) | 105.48 |
| H520 (small cell carcinoma) | 138.22 |
| H69 (SCLC) | 141.12 |
| H345 (SCLC) | 218.39 |
| H460 INCX 24 hr | 47.37 |
| H460 p16 24 hr | 50.77 |
| H460 INCX 48 hr | 53.11 |
| H460 p16 48 hr | 54.79 |
| H460 INCX Stable Plas | 94.73 |
| H460 p16 Stable Plas | 127.19 |
| H460 NA-Agar | 26.92 |
| H460 Incx stable Agar | 10.60 |
| H460 p16 stable Agar | 24.10 |
| H125 Incx 96 hr | 159.87 |

TABLE 33-continued

Expression in Lung Model

| Tissue Type | Relative Expression |
|---|---|
| H125 p53 96 hr | 100.13 |
| H345 Mock 144 hr | 267.02 |
| H345 Glue 144 hr | 219.91 |
| H345 VIP 144 hr | 301.45 |

Table 33 recites results indicating that 53320 mRNA is highly expressed in a number of lung adenocarcinoma and small cell carcinoma samples.

TABLE 34

Expression in Xenograft Panel

| Tissue Type | Relative Expression |
|---|---|
| MCF-7 Breast Tumor | 16.5 |
| ZR75 Breast Tumor | 80.5 |
| T47D Breast Tumor | 16.7 |
| MDA 231 Breast Tumor | 26.2 |
| MDA 435 Breast Tumor | 2.8 |
| SKBr3 Breast | 39.6 |
| DLD 1 ColonTumor (stageC) | 79.4 |
| SW620 ColonTumor (stageC) | 38.3 |
| HT29 | 4.7 |
| Colo 205 | 8.6 |
| NCIH125 | 49.9 |
| NCIH322 | 183.6 |
| NCIH460 | 54.8 |
| A549 (Lung adenocarcinoma cell line) | 205.9 |
| NHBE | 32.0 |
| SKOV-3 Ovary | 14.8 |
| OVCAR-3 Ovary | 75.4 |
| 293 Baby Kidney | 178.0 |
| 293T Baby Kidney | 267.0 |

Table 34 recites results indicating that 53320 mRNA is overexpressed in a number of breast and colon tumors, when xenografted into nude mice, as well as in infant kidney.

TABLE 35

Expression in Clinical Ovary Samples and Xenograft Cells

| Tissue Type | | Relative Expression |
|---|---|---|
| PIT 208 | Ovary Normal | 1.20 |
| CHT 620 | Ovary Normal | 0.39 |
| CHT 619 | Ovary Normal | 1.71 |
| CLN 355 | Ovary Normal | 0.12 |
| CLN 03 | Ovary Tumor | 0.35 |
| CLN 15 | Ovary Tumor | 0.07 |
| CLN 07 | Ovary Tumor | 0.13 |
| CLN 08 | Ovary Tumor | 0.04 |
| MDA 216 | Ovary Tumor | 0.15 |
| CLN 012 | Ovary Tumor | 0.90 |
| MDA 25 | Ovary Tumor | 0.31 |
| CLN 17 | Ovary Tumor | 0.38 |
| MDA 127 | Normal Ovarian Epithelial Cells | 1.75 |
| MDA 224 | Normal Ovarian Epithelial Cells | 0.70 |
| MDA 124 | Ovarian Ascites Tumor | 0.12 |
| MDA 126 | Ovarian Ascites Tumor | 1.50 |
| SKOV-3 | | 5.66 |
| OVCAR-3 | | 38.47 |

53320 mRNA was also detected by in situ hybridization. The following results were obtained:

Angiogenic Tissues. Expression was identified in fetal adrenal tissue (+), neuroblastoma (++), and Wilm's tumor (++).

Lung. Expression was identified in 6 of 6 lung tumors (including 2 adenocarcinomas, one squamous cell carcinoma; two poorly differentiated non-small cell carcinomas, and one small cell carcinoma. Expression was consistently up-regulated relative to sporadic weak labeling detecting in normal bronchial epithelium.

Breast. Expression was detected in two breast tumors, and not in normal breast tissue.

Example 59

Tissue Distribution of 53320 mRNA by Northern Analysis

Northern blot hybridizations with various RNA samples can be performed under standard conditions and washed under stringent conditions, i.e., 0.2×SSC at 65° C. A DNA probe corresponding to all or a portion of the 53320 cDNA (SEQ ID NO:83) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 60

Recombinant Expression of 53320 in Bacterial Cells

In this example, 53320 is expressed as a recombinant glutathione-S-transferase (GST) fusion polypeptide in *E. coli* and the fusion polypeptide is isolated and characterized. Specifically, 53320 is fused to GST and this fusion polypeptide is expressed in *E. coli*, e.g., strain PEB199. Expression of the GST-53320 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 61

Expression of Recombinant 53320 Protein in COS Cells

To express the 53320 gene in COS cells (e.g., COS-7 cells, CV-1 origin SV40 cells; Gluzman (1981) *Cell*23:175-182), the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 53320 protein and an HA tag (Wilson et al (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 53320 DNA sequence is amplified by PCR using two primers. The 5' primer contains the restriction site of interest followed by approximately twenty nucleotides of the 53320 coding sequence starting from the initiation codon; the 3' end sequence contains complementary sequences to the other restriction site of interest, a translation stop codon, the HA tag or FLAG tag and the last 20 nucleotides of the 53320 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 53320_gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 53320-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. (1989) *Molecular Cloning: A Laboratory Manual. 2nd, ed.*, Cold Spring Harbor Laboratory, Cold Spring Harbor Laboratory Press, Cold Spring Harbor, N.Y. The expression of the 53320 polypeptide is detected by radiolabelling ($^{35}$S-methionine or $^{35}$S-cysteine available from NEN, Boston, Mass., can be used) and immunoprecipitation (Harlow, E. and Lane, D. (1988) *Antibodies: A Laboratory Manual*, Cold Spring Harbor Laboratory Press, Cold Spring Harbor, N.Y.) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 53320 coding sequence is cloned directly into the polylinker of the pCDNA/Amp vector using the appropriate restriction sites. The resulting plasmid is transfected into COS cells in the manner described above, and the expression of the 53320 polypeptide is detected by radiolabelling and immunoprecipitation using a 53320 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule selected from the group consisting of:
   a) a nucleic acid molecule comprising the nucleotide sequence of SEQ ID NO:19, or SEQ ID NO:21;
   b) a nucleic acid molecule which encodes a polypeptide comprising the amino acid sequence of SEQ ID NO:2;
   c) a nucleic acid molecule comprising a nucleotide sequence which is at least 95% identical to the nucleotide sequence of SEQ ID NO:19 or SEQ ID NO:21, wherein the nucleotide sequence encodes a polypeptide with fucosyltransferase activity; and
   d) a nucleic acid molecule which encodes a polypeptide comprising an amino acid sequence which is at least 95% identical to the amino acid sequence of SEQ ID NO:20, wherein the polypeptide has fucosyltransferase activity.

2. The nucleic acid molecule of claim 1, further comprising vector nucleic acid sequences.

3. The nucleic acid molecule of claim 1, further comprising nucleic acid sequences encoding a heterologous polypeptide.

4. A host cell which contains the nucleic acid molecule of claim 1.

5. A method for producing a polypeptide selected from the group consisting of:
   a) a polypeptide comprising the amino acid sequence of SEQ ID NO:20;
   b) a polypeptide encoded by a nucleic acid molecule comprising the nucleotide sequence of SEQ ID NO:19 or SEQ ID NO:21;
   c) a polypeptide comprising an amino acid sequence which is at least 95% identical to the amino acid sequence of SEQ ID NO:20, wherein the polypeptide has fucosyltransferase activity; and
   d) a polypeptide encoded by a nucleic acid molecule comprising a nucleotide sequence which is at least 95% identical to the nucleotide sequence of SEQ ID NO:19 or SEQ ID NO:21, wherein the polypeptide has fucosyltransferase activity;
   the method comprising culturing the host cell of claim 4 under conditions in which the nucleic acid molecule is expressed.

6. A kit comprising a compound which selectively hybridizes to a nucleic acid molecule of claim 1 and instructions for use.

7. The isolated nucleic acid molecule of claim 1, comprising a nucleotide sequence which is at least 95% identical to the nucleotide sequence of SEQ ID NO:19 or SEQ ID NO:21, wherein the nucleotide sequence encodes a polypeptide with fucosyltransferase activity.

8. The isolated nucleic acid molecule of claim 1, comprising the nucleotide sequence of SEQ ID NO:19 or SEQ ID NO:21.

9. The method of claim 5, wherein the polypeptide comprises an amino acid sequence which is at least 95% identical to the amino acid sequence of SEQ ID NO:20, and wherein the polypeptide has fucosyltransferase activity.

10. The method of claim 5, wherein the polypeptide comprises the amino acid sequence of SEQ ID NO:20.

* * * * *

UNITED STATES PATENT AND TRADEMARK OFFICE
CERTIFICATE OF CORRECTION

PATENT NO. : 7,301,016 B2  
APPLICATION NO. : 10/184648  
DATED : November 27, 2007  
INVENTOR(S) : Rachel E. Meyers et al.

Page 1 of 1

It is certified that error appears in the above-identified patent and that said Letters Patent is hereby corrected as shown below:

INVENTORS: Please make the following corrections to the inventors as per the Amendment and Processing Fee Deleting Correctly Named Person(s) Who are Not Inventor(s) of Invention Now Being Claimed, which was filed on April 11, 2007, a copy of which is attached:

Rachel E. Meyers, Newton, MA (US); Mark J. Williamson, Saugus, MA (US); ~~Kevin R. Leiby, Natick, MA (US);~~ Rosana Kapeller-Libermann, ~~Chestnut Hill, MA (US);~~ Peter J. Olandt, ~~Newton, MA (US);~~ Kyle J. MacBeth, ~~Boston, MA (US);~~ Laura A. Rudolph-Owen, ~~Jamaica Plain, MA (US);~~ ~~Fong-Ying Tsai, Newton, MA (US);~~ John J. Hunter, ~~Somerville, MA (US)~~

CLAIMS:

Please make the following corrections to the claims:

In Claim 1, Column 1221, Line 22, please change "SEQ ID NO:2" to "SEQ ID NO:20".

Signed and Sealed this  
Fifth Day of July, 2011

David J. Kappos  
*Director of the United States Patent and Trademark Office*

SEQUENCE LISTING

<160> NUMBER OF SEQ ID NOS: 90

<210> SEQ ID NO 1
<211> LENGTH: 2493
<212> TYPE: DNA
<213> ORGANISM: Homo sapiens
<220> FEATURE:
<221> NAME/KEY: CDS
<222> LOCATION: (402)...(2057)

<400> SEQUENCE: 1

```
acgcgtccgg cacagcctcg gattcctccc tctcgctgct cgagtcagtt tccctatcgg      60
cggcagcggg caaggcggcg gcggcggcgg cggcagccgc ggtggcggcg tggggaacat     120
ctcggcagcc accgcgcttc tcccgctgga gcgggcgtcc agcttggctg ccctcggtcc     180
ttccctgcca cgtttcgggt cgccctgcac ccccacccca ggctcgcttc tcttcgaagc     240
gggaagggcg ccttgcagga tcctgccgcc cctccaaccg gatcctgggt ctagagctcc     300
ccagagcgag gcgctcgcca ggactcctgc cccgccaacc ctgaccgccg ggggtgccc      360 ccgggacgta gcgccgcgga gaggaagcgg caaagggac atg cgg cgc ctg act        416
                                            Met Arg Arg Leu Thr
                                             1               5
```

```
cgt cgg ctg gtt ctg cca gtc ttc ggg gtg ctc tgg atc acg gtg ctg      464
Arg Arg Leu Val Leu Pro Val Phe Gly Val Leu Trp Ile Thr Val Leu
             10                  15                  20
```

```
ctg ttc ttc tgg gta acc aag agg aag ttg gag gtg ccg acg gga cct      512
Leu Phe Phe Trp Val Thr Lys Arg Lys Leu Glu Val Pro Thr Gly Pro
         25                  30                  35
```

```
gaa gtg cag acc cct aag cct tcg gac gct gac tgg gac gac ctg tgg      560
Glu Val Gln Thr Pro Lys Pro Ser Asp Ala Asp Trp Asp Asp Leu Trp
     40                  45                  50
```

```
gac cag ttt gat gag cgg cgg tat ctg aat gcc aaa aag tgg cgc gtt      608
Asp Gln Phe Asp Glu Arg Arg Tyr Leu Asn Ala Lys Lys Trp Arg Val
 55                  60                  65
```

```
ggt gac gac ccc tat aag ctg tat gct ttc aac cag cgg gag agt gag      656
Gly Asp Asp Pro Tyr Lys Leu Tyr Ala Phe Asn Gln Arg Glu Ser Glu
 70                  75                  80                  85
```

```
cgg atc tcc agc aat cgg gcc atc ccg gac act cgc cat ctg aga tgc      704
Arg Ile Ser Ser Asn Arg Ala Ile Pro Asp Thr Arg His Leu Arg Cys
                 90                  95                 100
```

```
aca ctg ctg gtg tat tgc acg gac ctt cca ccc act agc atc atc atc      752
Thr Leu Leu Val Tyr Cys Thr Asp Leu Pro Pro Thr Ser Ile Ile Ile
            105                 110                 115
```

```
acc ttc cac aac gag gcc cgc tcc acg ctg ctc agg acc atc cgc agt      800
Thr Phe His Asn Glu Ala Arg Ser Thr Leu Leu Arg Thr Ile Arg Ser
        120                 125                 130
```

```
gta tta aac cgc acc cct acg cat ctg atc cgg gaa atc ata tta gtg      848
Val Leu Asn Arg Thr Pro Thr His Leu Ile Arg Glu Ile Ile Leu Val
    135                 140                 145
```

```
gat gac ttc agc aat gac cct gat gac tgt aaa cag ctc atc aag ttg      896
Asp Asp Phe Ser Asn Asp Pro Asp Asp Cys Lys Gln Leu Ile Lys Leu
150                 155                 160                 165
```

```
ccc aag gtg aaa tgc ttg cgc aat aat gaa cgg caa ggt ctg gtc cgg      944
Pro Lys Val Lys Cys Leu Arg Asn Asn Glu Arg Gln Gly Leu Val Arg
                170                 175                 180
```

```
tcc cgg att cgg ggc gct gac atc gcc cag ggc acc act ctg act ttc      992
Ser Arg Ile Arg Gly Ala Asp Ile Ala Gln Gly Thr Thr Leu Thr Phe
            185                 190                 195
```

-continued

| | | |
|---|---|---|
| ctc gac agc cac tgt gag gtg aac agg gac tgg ctc cag cct ctg ttg<br>Leu Asp Ser His Cys Glu Val Asn Arg Asp Trp Leu Gln Pro Leu Leu<br>200 205 210 | 1040 | |
| cac agg gtc aaa gag gac tac acg cgg gtg gtg tgc cct gtg atc gat<br>His Arg Val Lys Glu Asp Tyr Thr Arg Val Val Cys Pro Val Ile Asp<br>215 220 225 | 1088 | |
| atc att aac ctg gac acc ttc acc tac atc gag tct gcc tcg gag ctc<br>Ile Ile Asn Leu Asp Thr Phe Thr Tyr Ile Glu Ser Ala Ser Glu Leu<br>230 235 240 245 | 1136 | |
| aga ggg ggg ttt gac tgg agc ctc cac ttc cag tgg gag cag ctc tcc<br>Arg Gly Gly Phe Asp Trp Ser Leu His Phe Gln Trp Glu Gln Leu Ser<br>250 255 260 | 1184 | |
| cca gag cag aag gct cgg cgc ctg gac ccc acg gag ccc atc agg act<br>Pro Glu Gln Lys Ala Arg Arg Leu Asp Pro Thr Glu Pro Ile Arg Thr<br>265 270 275 | 1232 | |
| cct atc ata gct gga ggg ctc ttc gtg atc gac aaa gct tgg ttt gat<br>Pro Ile Ile Ala Gly Gly Leu Phe Val Ile Asp Lys Ala Trp Phe Asp<br>280 285 290 | 1280 | |
| tac ctg ggg aaa tat gat atg gac atg gac atc tgg ggt ggg gag aac<br>Tyr Leu Gly Lys Tyr Asp Met Asp Met Asp Ile Trp Gly Gly Glu Asn<br>295 300 305 | 1328 | |
| ttt gaa atc tcc ttc cga gtg tgg atg tgc ggg ggc agc cta gag atc<br>Phe Glu Ile Ser Phe Arg Val Trp Met Cys Gly Gly Ser Leu Glu Ile<br>310 315 320 325 | 1376 | |
| gtc ccc tgc agc cga gtg ggg cac gtc ttc cgg aag aag cac ccc tac<br>Val Pro Cys Ser Arg Val Gly His Val Phe Arg Lys Lys His Pro Tyr<br>330 335 340 | 1424 | |
| gtt ttc cct gat gga aat gcc aac acg tat ata aag aac acc aag cgg<br>Val Phe Pro Asp Gly Asn Ala Asn Thr Tyr Ile Lys Asn Thr Lys Arg<br>345 350 355 | 1472 | |
| aca gct gaa gtg tgg atg gat gaa tac aag caa tac tat tac gct gcc<br>Thr Ala Glu Val Trp Met Asp Glu Tyr Lys Gln Tyr Tyr Tyr Ala Ala<br>360 365 370 | 1520 | |
| cgg cca ttc gcc ctg gag agg ccc ttc ggg aat gtt gag agc aga ttg<br>Arg Pro Phe Ala Leu Glu Arg Pro Phe Gly Asn Val Glu Ser Arg Leu<br>375 380 385 | 1568 | |
| gac ctg agg aag aat ctg cgc tgc cag agc ttc aag tgg tac ctg gag<br>Asp Leu Arg Lys Asn Leu Arg Cys Gln Ser Phe Lys Trp Tyr Leu Glu<br>390 395 400 405 | 1616 | |
| aat atc tac cct gaa ctc agc atc ccc aag gag tcc tcc atc cag aag<br>Asn Ile Tyr Pro Glu Leu Ser Ile Pro Lys Glu Ser Ser Ile Gln Lys<br>410 415 420 | 1664 | |
| ggc aat atc cga cag aga cag aag tgc ctg gaa tct caa agg cag aac<br>Gly Asn Ile Arg Gln Arg Gln Lys Cys Leu Glu Ser Gln Arg Gln Asn<br>425 430 435 | 1712 | |
| aac caa gaa acc cca aac cta aag ttg agc ccc tgt gcc aag gtc aaa<br>Asn Gln Glu Thr Pro Asn Leu Lys Leu Ser Pro Cys Ala Lys Val Lys<br>440 445 450 | 1760 | |
| ggc gaa gat gca aag tcc cag gta tgg gcc ttc aca tac acc cag cag<br>Gly Glu Asp Ala Lys Ser Gln Val Trp Ala Phe Thr Tyr Thr Gln Gln<br>455 460 465 | 1808 | |
| atc ctc cag gag gag ctg tgc ctg tca gtc atc acc ttg ttc cct ggc<br>Ile Leu Gln Glu Glu Leu Cys Leu Ser Val Ile Thr Leu Phe Pro Gly<br>470 475 480 485 | 1856 | |
| gcc cca gtg gtt ctt gtc ctt tgc aag aat gga gat gac cga cag caa<br>Ala Pro Val Val Leu Val Leu Cys Lys Asn Gly Asp Asp Arg Gln Gln<br>490 495 500 | 1904 | |
| tgg acc aaa act ggt tcc cac atc gag cac ata gca tcc cac ctc tgc<br>Trp Thr Lys Thr Gly Ser His Ile Glu His Ile Ala Ser His Leu Cys<br>505 510 515 | 1952 | |

-continued

```
ctc gat aca gat atg ttc ggt gat ggc acc gag aac ggc aag gaa atc    2000
Leu Asp Thr Asp Met Phe Gly Asp Gly Thr Glu Asn Gly Lys Glu Ile
        520                 525                 530 gtc gtc aac cca tgt gag tcc tca ctc atg agc cag cac tgg gac atg    2048
Val Val Asn Pro Cys Glu Ser Ser Leu Met Ser Gln His Trp Asp Met
    535                 540                 545 gtg agc tct tgaggacccc tgccagaagc agcaagggcc atgggtggt             2097
Val Ser Ser
550 gcttccctgg accagaacag actggaaact gggcagcaag cagcctgcaa ccacctcaga   2157 catcctggac tgggaggtgg aggcagagcc ccccaggaca ggagcaactg tctcagggag   2217 gacagaggaa aacatcacaa gccaatgggg ctcaaagaca aatcccacat gttctcaagg   2277 ccgttaagtt ccagtcctgg ccagtcattc cctgattggt atctggagac agaaacctaa   2337 tgggaagtgt ttattgttcc ttttcctaca aaggaagcag tctctggagg ccagaaagaa   2397 aagccttctt tttcactagg ccaggactac attgagagat gaagaatgga ggttgtttcc   2457 aaaagaaata aagagaaact tagaagttgt ctctgg                             2493
```

<210> SEQ ID NO 2
<211> LENGTH: 552
<212> TYPE: PRT
<213> ORGANISM: Homo sapiens

<400> SEQUENCE: 2

```
Met Arg Arg Leu Thr Arg Arg Leu Val Leu Pro Val Phe Gly Val Leu
  1               5                  10                  15

Trp Ile Thr Val Leu Leu Phe Phe Trp Val Thr Lys Arg Lys Leu Glu
             20                  25                  30

Val Pro Thr Gly Pro Glu Val Gln Thr Pro Lys Pro Ser Asp Ala Asp
         35                  40                  45

Trp Asp Asp Leu Trp Asp Gln Phe Asp Glu Arg Arg Tyr Leu Asn Ala
     50                  55                  60

Lys Lys Trp Arg Val Gly Asp Asp Pro Tyr Lys Leu Tyr Ala Phe Asn
 65                  70                  75                  80

Gln Arg Glu Ser Glu Arg Ile Ser Ser Asn Arg Ala Ile Pro Asp Thr
                 85                  90                  95

Arg His Leu Arg Cys Thr Leu Leu Val Tyr Cys Thr Asp Leu Pro Pro
            100                 105                 110

Thr Ser Ile Ile Ile Thr Phe His Asn Glu Ala Arg Ser Thr Leu Leu
        115                 120                 125

Arg Thr Ile Arg Ser Val Leu Asn Arg Thr Pro Thr His Leu Ile Arg
    130                 135                 140

Glu Ile Ile Leu Val Asp Asp Phe Ser Asn Asp Pro Asp Asp Cys Lys
145                 150                 155                 160

Gln Leu Ile Lys Leu Pro Lys Val Lys Cys Leu Arg Asn Asn Glu Arg
                165                 170                 175

Gln Gly Leu Val Arg Ser Arg Ile Arg Gly Ala Asp Ile Ala Gln Gly
            180                 185                 190

Thr Thr Leu Thr Phe Leu Asp Ser His Cys Glu Val Asn Arg Asp Trp
        195                 200                 205

Leu Gln Pro Leu Leu His Arg Val Lys Glu Asp Tyr Thr Arg Val Val
    210                 215                 220

Cys Pro Val Ile Asp Ile Ile Asn Leu Asp Thr Phe Thr Tyr Ile Glu
225                 230                 235                 240
```

```
Ser Ala Ser Glu Leu Arg Gly Gly Phe Asp Trp Ser Leu His Phe Gln
                245                 250                 255

Trp Glu Gln Leu Ser Glu Gln Lys Ala Arg Arg Leu Asp Pro Thr
            260                 265                 270

Glu Pro Ile Arg Thr Pro Ile Ala Gly Gly Leu Phe Val Ile Asp
        275                 280                 285

Lys Ala Trp Phe Asp Tyr Leu Gly Lys Tyr Asp Met Asp Met Asp Ile
290                 295                 300

Trp Gly Gly Glu Asn Phe Glu Ile Ser Phe Arg Val Trp Met Cys Gly
305                 310                 315                 320

Gly Ser Leu Glu Ile Val Pro Cys Ser Arg Val Gly His Val Phe Arg
                325                 330                 335

Lys Lys His Pro Tyr Val Phe Pro Asp Gly Asn Ala Asn Thr Tyr Ile
                340                 345                 350

Lys Asn Thr Lys Arg Thr Ala Glu Val Trp Met Asp Glu Tyr Lys Gln
                355                 360                 365

Tyr Tyr Tyr Ala Ala Arg Pro Phe Ala Leu Glu Arg Pro Phe Gly Asn
    370                 375                 380

Val Glu Ser Arg Leu Asp Leu Arg Lys Asn Leu Arg Cys Gln Ser Phe
385                 390                 395                 400

Lys Trp Tyr Leu Glu Asn Ile Tyr Pro Glu Leu Ser Ile Pro Lys Glu
                405                 410                 415

Ser Ser Ile Gln Lys Gly Asn Ile Arg Gln Arg Gln Lys Cys Leu Glu
                420                 425                 430

Ser Gln Arg Gln Asn Asn Gln Glu Thr Pro Asn Leu Lys Leu Ser Pro
            435                 440                 445

Cys Ala Lys Val Lys Gly Glu Asp Ala Lys Ser Gln Val Trp Ala Phe
    450                 455                 460

Thr Tyr Thr Gln Gln Ile Leu Gln Glu Glu Leu Cys Leu Ser Val Ile
465                 470                 475                 480

Thr Leu Phe Pro Gly Ala Pro Val Val Leu Val Leu Cys Lys Asn Gly
                485                 490                 495

Asp Asp Arg Gln Gln Trp Thr Lys Thr Gly Ser His Ile Glu His Ile
                500                 505                 510

Ala Ser His Leu Cys Leu Asp Thr Asp Met Phe Gly Asp Gly Thr Glu
            515                 520                 525

Asn Gly Lys Glu Ile Val Val Asn Pro Cys Glu Ser Ser Leu Met Ser
            530                 535                 540

Gln His Trp Asp Met Val Ser Ser
545                 550
```

<210> SEQ ID NO 3
<211> LENGTH: 1659
<212> TYPE: DNA
<213> ORGANISM: Homo sapiens

<400> SEQUENCE: 3

```
atgcggcgcc tgactcgtcg gctggttctg ccagtcttcg gggtgctctg gatcacggtg      60
ctgctgttct tctgggtaac caagaggaag ttggaggtgc cgacgggacc tgaagtgcag     120 accccctaagc cttcggacgc tgactgggac gacctgtggg accagtttga tgagcggcgg     180
tatctgaatg ccaaaaagtg gcgcgttggt gacgaccct ataagctgta tgctttcaac      240
cagcgggaga gtgagcggat ctccagcaat cgggccatcc cggacactcg ccatctgaga     300
```

```
tgcacactgc tggtgtattg cacggacctt ccacccacta gcatcatcat caccttccac      360
aacgaggccc gctccacgct gctcaggacc atccgcagtg tattaaaccg caccccctacg     420 catctgatcc gggaaatcat attagtggat gacttcagca atgaccctga tgactgtaaa     480
cagctcatca agttgcccaa ggtgaaatgc ttgcgcaata atgaacggca aggtctggtc     540
cggtcccgga ttcggggcgc tgacatcgcc cagggcacca ctctgacttt cctcgacagc     600
cactgtgagg tgaacaggga ctggctccag cctctgttgc acagggtcaa agaggactac     660
acgcgggtgg tgtgccctgt gatcgatatc attaacctgg acaccttcac ctacatcgag     720
tctgcctcgg agctcagagg ggggtttgac tggagcctcc acttccagtg ggagcagctc     780
tccccagagc agaaggctcg gcgcctggac cccacggagc ccatcaggac tcctatcata     840
gctggagggc tcttcgtgat cgacaaagct tggtttgatt acctgggaa atatgatatg     900 gacatggaca tctggggtgg ggagaacttt gaaatctcct tccgagtgtg gatgtgcggg     960
ggcagcctag agatcgtccc ctgcagccga gtggggcacg tcttccggaa gaagcacccc    1020
tacgttttcc ctgatggaaa tgccaacacg tatataaaga acaccaagcg gacagctgaa    1080
gtgtggatgg atgaatacaa gcaatactat tacgctgccc ggccattcgc cctggagagg    1140
cccttcggga atgttgagag cagattggac ctgaggaaga atctgcgctg ccagagcttc    1200
aagtggtacc tggagaatat ctaccctgaa ctcagcatcc caaggagtc ctccatccag    1260 aagggcaata tccgacagag acagaagtgc ctggaatctc aaaggcagaa caaccaagaa    1320 accccaaaccc taaagttgag cccctgtgcc aaggtcaaag cgaagatgc aaagtcccag    1380 gtatgggcct tcacatacac ccagcagatc ctccaggagg agctgtgcct gtcagtcatc    1440
accttgttcc ctggcgcccc agtggttctt gtcctttgca agaatggaga tgaccgacag    1500
caatggacca aaactggttc ccacatcgag cacatagcat cccacctctg cctcgataca    1560
gatatgttcg gtgatggcac cgagaacggc aaggaaatcg tcgtcaaccc atgtgagtcc    1620
tcactcatga gccagcactg ggacatggtg agctcttga                            1659
```

<210> SEQ ID NO 4
<211> LENGTH: 1620
<212> TYPE: DNA
<213> ORGANISM: Homo sapiens
<220> FEATURE:
<221> NAME/KEY: CDS
<222> LOCATION: (29)...(1276)
<220> FEATURE:
<221> NAME/KEY: misc_feature
<222> LOCATION: (1)...(1620)
<223> OTHER INFORMATION: n = A,T,C or G

<400> SEQUENCE: 4

```
gtgcggggag cagttcggct ctagggca atg gcg gag gag cag gcc cgg caa       52
                                Met Ala Glu Glu Gln Ala Arg Gln
                                 1               5 cgg gac ctg gtt ccc aag ccg tcg gtg ctg ttc ctg cac cca gac ctc     100
Arg Asp Leu Val Pro Lys Pro Ser Val Leu Phe Leu His Pro Asp Leu
         10                  15                  20 ggc gta gga ggc gct gag cgt ctg gtg ttg gac gcg gcg ttg gcg ctg     148
Gly Val Gly Gly Ala Glu Arg Leu Val Leu Asp Ala Ala Leu Ala Leu
 25                  30                  35                  40 cag gcg cgc ggg tgt aac gtg aag atc tgg aca gcg cac tac gac ccg     196
Gln Ala Arg Gly Cys Asn Val Lys Ile Trp Thr Ala His Tyr Asp Pro
             45                  50                  55 ggc cac tgc ttc gcc gag agc cgc gaa cta ccg gtg cac tgt gcc gga     244
Gly His Cys Phe Ala Glu Ser Arg Glu Leu Pro Val His Cys Ala Gly
```

-continued

```
                   60                  65                  70
gac tgg ctg ccg cgc ggc ctg ggc tgg ggc ggc cac ggc gcc gcc gtc      292
Asp Trp Leu Pro Arg Gly Leu Gly Trp Gly Gly His Gly Ala Ala Val
         75                  80                  85 tgc gcc tac gtg cgc atg gtc ttc ctg gcg ctc tac gtg ctg ttc ctc      340
Cys Ala Tyr Val Arg Met Val Phe Leu Ala Leu Tyr Val Leu Phe Leu
     90                  95                 100 gcc gac gag gag ttc gac gtg gta gtg tgc gac cag gtg tct gcc tgt      388
Ala Asp Glu Glu Phe Asp Val Val Val Cys Asp Gln Val Ser Ala Cys
105                 110                 115                 120 att cca gtg ttc agg ctt gct aga cgg cgg aag aag atc ctg ttt tac      436
Ile Pro Val Phe Arg Leu Ala Arg Arg Arg Lys Lys Ile Leu Phe Tyr
                125                 130                 135 tgt cac ttc cca gat ctg ctt ctc acc aag aga gat tct ttt ctt aaa      484
Cys His Phe Pro Asp Leu Leu Leu Thr Lys Arg Asp Ser Phe Leu Lys
                140                 145                 150 cgg tta tac agg gcc ccg att gac tgg ata gag gaa tac acc aca ggc      532
Arg Leu Tyr Arg Ala Pro Ile Asp Trp Ile Glu Glu Tyr Thr Thr Gly
            155                 160                 165 atg gca gac tgc atc tta gtc aac agc cag ttc act gct gct gtt ttt      580
Met Ala Asp Cys Ile Leu Val Asn Ser Gln Phe Thr Ala Ala Val Phe
    170                 175                 180 aag aaa aca ttc aag acc ctg tct cac ata gac cct gat gtc ctc tat      628
Lys Lys Thr Phe Lys Thr Leu Ser His Ile Asp Pro Asp Val Leu Tyr
185                 190                 195                 200 cca tct cta aat gtc acc agc ttt gat tca gtt gtt cct gaa aag ctt      676
Pro Ser Leu Asn Val Thr Ser Phe Asp Ser Val Val Pro Glu Lys Leu
                205                 210                 215 gat gac cta gtc ccc aag ggg aaa aaa ttc ctg ctc ctc tct atc aac      724
Asp Asp Leu Val Pro Lys Gly Lys Lys Phe Leu Leu Leu Ser Ile Asn
                220                 225                 230 aga tac gaa agg aag aaa aat ctg act ttg gca ttg gaa gcc cta gta      772
Arg Tyr Glu Arg Lys Lys Asn Leu Thr Leu Ala Leu Glu Ala Leu Val
            235                 240                 245 cag ctg cgt gga aga ttg aca tcc caa gat tgg gag agg gtt cat ctg      820
Gln Leu Arg Gly Arg Leu Thr Ser Gln Asp Trp Glu Arg Val His Leu
    250                 255                 260 atc atg gca ggt ggt tat gac gag aga gtc ctg gag aat gtg gaa cat      868
Ile Met Ala Gly Gly Tyr Asp Glu Arg Val Leu Glu Asn Val Glu His
265                 270                 275                 280 tac cag gaa ttg aag caa atg gtc caa cag tct gac ctt ggc cag tat      916
Tyr Gln Glu Leu Lys Gln Met Val Gln Gln Ser Asp Leu Gly Gln Tyr
                285                 290                 295 gtg acc ttc ttg agg tct ttc tca gac aaa cag aaa atc tcc ctc ctc      964
Val Thr Phe Leu Arg Ser Phe Ser Asp Lys Gln Lys Ile Ser Leu Leu
                300                 305                 310 cac agc tgc acg tgt gtg ctt tac aca cca agc aat gag cac ttt ggc     1012
His Ser Cys Thr Cys Val Leu Tyr Thr Pro Ser Asn Glu His Phe Gly
            315                 320                 325 att gtc cct ctg gaa gcc atg tac atg cag tgc cca gtc att gct gtt     1060
Ile Val Pro Leu Glu Ala Met Tyr Met Gln Cys Pro Val Ile Ala Val
    330                 335                 340 aat tct ggg gga ccc ttg gag tcc att gac cac agt gtc aca ggg ttt     1108
Asn Ser Gly Gly Pro Leu Glu Ser Ile Asp His Ser Val Thr Gly Phe
345                 350                 355                 360 ctg tgt gag cct gac cca gtg cac ttc tca gaa gca ata gaa aag ttc     1156
Leu Cys Glu Pro Asp Pro Val His Phe Ser Glu Ala Ile Glu Lys Phe
                365                 370                 375 atc cgt gaa cct tcc tta aaa gcc acc atg ggc ctg gct gga aga gcc     1204
```

-continued

```
Ile Arg Glu Pro Ser Leu Lys Ala Thr Met Gly Leu Ala Gly Arg Ala
            380                 385                 390 aag gtg aag gaa aaa ttt tcc cct gaa gca ttt acg gaa cag ctc tac      1252
Lys Val Lys Glu Lys Phe Ser Pro Glu Ala Phe Thr Glu Gln Leu Tyr
        395                 400                 405 caa tat gtt acc aaa ctg ctg gta taatcagatt cttttaaga tctttatgct     1306
Gln Tyr Val Thr Lys Leu Leu Val
    410                 415 gtgttcatta atgtcacttt tatggattgt ggacccagtt ttgaaaccaa aaaagaaacc    1366
tagaatctaa tgcagaagag atcttttaaa aaataaattt gagtcttgaa tctgagccac    1426
tttcctatat accacacctc cttgtccact tttcagaaaa acaatgtctc ttatgctata    1486
atcattccac attttgccag tgttaagtta caaatgtata attccatgtt cagcagagta    1546
tttttaatta tattttcttg ggattattgc tattctggct ataaattttg aatgataccg    1606
gggccttaat tngg                                                      1620
```

<210> SEQ ID NO 5
<211> LENGTH: 416
<212> TYPE: PRT
<213> ORGANISM: Homo sapiens

<400> SEQUENCE: 5

```
Met Ala Glu Glu Gln Ala Arg Gln Arg Asp Leu Val Pro Lys Pro Ser
 1               5                  10                  15

Val Leu Phe Leu His Pro Asp Leu Gly Val Gly Gly Ala Glu Arg Leu
            20                  25                  30

Val Leu Asp Ala Ala Leu Ala Leu Gln Ala Arg Gly Cys Asn Val Lys
        35                  40                  45

Ile Trp Thr Ala His Tyr Asp Pro Gly His Cys Phe Ala Glu Ser Arg
    50                  55                  60

Glu Leu Pro Val His Cys Ala Gly Asp Trp Leu Pro Arg Gly Leu Gly
65                  70                  75                  80

Trp Gly Gly His Gly Ala Ala Val Cys Ala Tyr Val Arg Met Val Phe
                85                  90                  95

Leu Ala Leu Tyr Val Leu Phe Leu Ala Asp Glu Glu Phe Asp Val Val
            100                 105                 110

Val Cys Asp Gln Val Ser Ala Cys Ile Pro Val Phe Arg Leu Ala Arg
        115                 120                 125

Arg Arg Lys Lys Ile Leu Phe Tyr Cys His Phe Pro Asp Leu Leu Leu
    130                 135                 140

Thr Lys Arg Asp Ser Phe Leu Lys Arg Leu Tyr Arg Ala Pro Ile Asp
145                 150                 155                 160

Trp Ile Glu Glu Tyr Thr Thr Gly Met Ala Asp Cys Ile Leu Val Asn
                165                 170                 175

Ser Gln Phe Thr Ala Ala Val Phe Lys Lys Thr Phe Lys Thr Leu Ser
            180                 185                 190

His Ile Asp Pro Asp Val Leu Tyr Pro Ser Leu Asn Val Thr Ser Phe
        195                 200                 205

Asp Ser Val Val Pro Glu Lys Leu Asp Asp Leu Val Pro Lys Gly Lys
    210                 215                 220

Lys Phe Leu Leu Leu Ser Ile Asn Arg Tyr Glu Arg Lys Lys Asn Leu
225                 230                 235                 240

Thr Leu Ala Leu Glu Ala Leu Val Gln Leu Arg Gly Arg Leu Thr Ser
                245                 250                 255
```

```
Gln Asp Trp Glu Arg Val His Leu Ile Met Ala Gly Gly Tyr Asp Glu
                260                 265                 270

Arg Val Leu Glu Asn Val Glu His Tyr Gln Glu Leu Lys Gln Met Val
            275                 280                 285

Gln Gln Ser Asp Leu Gly Gln Tyr Val Thr Phe Leu Arg Ser Phe Ser
        290                 295                 300

Asp Lys Gln Lys Ile Ser Leu Leu His Ser Cys Thr Cys Val Leu Tyr
305                 310                 315                 320

Thr Pro Ser Asn Glu His Phe Gly Ile Val Pro Leu Glu Ala Met Tyr
                325                 330                 335

Met Gln Cys Pro Val Ile Ala Val Asn Ser Gly Gly Pro Leu Glu Ser
            340                 345                 350

Ile Asp His Ser Val Thr Gly Phe Leu Cys Glu Pro Asp Pro Val His
        355                 360                 365

Phe Ser Glu Ala Ile Glu Lys Phe Ile Arg Glu Pro Ser Leu Lys Ala
    370                 375                 380

Thr Met Gly Leu Ala Gly Arg Ala Lys Val Lys Glu Lys Phe Ser Pro
385                 390                 395                 400

Glu Ala Phe Thr Glu Gln Leu Tyr Gln Tyr Val Thr Lys Leu Leu Val
                405                 410                 415

<210> SEQ ID NO 6
<211> LENGTH: 1251
<212> TYPE: DNA
<213> ORGANISM: Homo sapiens

<400> SEQUENCE: 6
atggcggagg agcaggcccg gcaacgggac ctggttccca agccgtcggt gctgttcctg      60
cacccagacc tcggcgtagg aggcgctgag cgtctggtgt tggacgcggc gttggcgctg     120
caggcgcgcg ggtgtaacgt gaagatctgg acagcgcact acgacccggg ccactgcttc     180
gccgagagcc gcgaactacc ggtgcactgt gccggagact ggctgccgcg cggcctgggc     240
tggggcggcc acggcgccgc cgtctgcgcc tacgtgcgca tggtcttcct ggcgctctac     300
gtgctgttcc tcgccgacga ggagttcgac gtggtagtgt gcgaccaggt gtctgcctgt     360
attccagtgt tcaggcttgc tagacggcgg aagaagatcc tgttttactg tcacttccca     420
gatctgcttc tcaccaagag agattctttt cttaaacggt tatacagggc cccgattgac     480
tggatagagg aatacaccac aggcatggca gactgcatct tagtcaacag ccagttcact     540
gctgctgttt ttaagaaaac attcaagacc ctgtctcaca tagaccctga tgtcctctat     600
ccatctctaa atgtcaccag ctttgattca gttgttcctg aaaagcttga tgacctagtc     660
cccaagggga aaaaattcct gctgctctct atcaacagat acgaaggaa gaaaaatctg     720 actttggcat ggaagccct agtacagctg cgtggaagat tgacatccca agattgggag     780
agggttcatc tgatcatggc aggtggttat gacgagagag tcctggagaa tgtggaacat     840
taccaggaat tgaagcaaat ggtccaacag tctgaccttg gccagtatgt gaccttcttg     900
aggtctttct cagacaaaca gaaaatctcc ctcctccaca gctgcacgtg tgtgctttac     960
acaccaagca atgagcactt tggcattgtc cctctggaag ccatgtacat gcagtgccca    1020
gtcattgctg ttaattctgg ggacccttg agtccattg accacagtgt cacagggttt     1080
ctgtgtgagc ctgacccagt gcacttctca gaagcaatag aaaagttcat ccgtgaacct    1140 tcctttaaaag ccaccatggg cctggctgga gagccaaggt gaaggaaaa atttccccct    1200 gaagcattta cggaacagct ctaccaatat gttaccaaac tgctggtata a             1251
```

-continued

<210> SEQ ID NO 7
<211> LENGTH: 187
<212> TYPE: PRT
<213> ORGANISM: Artificial Sequence
<220> FEATURE:
<223> OTHER INFORMATION: consensus sequence

<400> SEQUENCE: 7

```
Ser Ile Val Ile Pro Thr Tyr Asn Glu Glu Ala Asp Tyr Leu Glu Glu
1               5                   10                  15

Leu Leu Glu Ser Val Leu Ala Gln Ser Thr Leu Glu Asp Ile Glu Ile
            20                  25                  30

Ile Val Val Asp Asp Gly Ser Glu Thr Asp Glu Thr Val Glu Ile Ala
        35                  40                  45

Glu Asp Tyr Leu Asp Glu Arg Ile Lys Glu Glu Asn Pro Arg Ile Ile
    50                  55                  60

Ile Val Ile Arg Leu Glu Asn Ser Gln Gly Pro Ala Ala Ala Arg
65                  70                  75                  80

Asn Lys Gly Ile Arg Arg Ala Thr Gly Asp Ser Asp Tyr Ile Leu Phe
                85                  90                  95

Leu Asp Ala Asp Asp Ile Phe Thr Pro Asp Lys Leu Glu Lys Leu Ile
            100                 105                 110

Asp Tyr Ala Glu Ala Thr Asp Ala Ala Val Val Leu Gly Ala Ile Asp
        115                 120                 125

Ala Tyr Glu Tyr Ala Glu Gly Glu Ser Asn Leu Tyr Arg Ile Ala Arg
    130                 135                 140

Ala Asp Thr Glu Arg Ser Leu Phe Ala Gly Leu Leu Arg Lys Thr Gly
145                 150                 155                 160

Arg Leu Thr Gly Gly Leu Glu Leu Ser Phe Glu Ile Gly Ser Asn Ala
                165                 170                 175

Ile Tyr Arg Arg Glu Ala Phe Glu Glu Leu Phe
            180                 185
```

<210> SEQ ID NO 8
<211> LENGTH: 195
<212> TYPE: PRT
<213> ORGANISM: Artificial Sequence
<220> FEATURE:
<223> OTHER INFORMATION: consensus sequence

<400> SEQUENCE: 8

```
Asn Val Glu Glu Lys Arg Arg Lys Leu Asn Ile Lys Glu Asn Lys Asn
1               5                   10                  15

Val Leu Leu Tyr Val Gly Arg Phe Val Pro Lys Gly Ile His Leu
            20                  25                  30

Leu Ile Lys Ala Phe Lys Ile Leu Lys Glu Glu Leu Pro Ala Val Lys
        35                  40                  45

Leu Ser Val Leu Leu Val Leu Val Gly Asp Gly Pro Asp Lys Glu Lys
    50                  55                  60

Leu Glu Asn Val Glu Tyr Leu Lys Glu Leu Val Lys Leu Ala Glu Glu
65                  70                  75                  80

Leu Gly Leu Asn Arg Lys Ile Gly Asn Asp Asn Ile Ile Phe Leu Gly
                85                  90                  95

Tyr Val Ser Tyr Glu Asp Leu Glu Asn Leu Leu Ser Lys Ser Asp Leu
            100                 105                 110

Phe Leu Leu Pro Ser Gln Ser Ser Tyr Glu Gly Phe Gly Ile Val Leu
```

-continued

```
                115                 120                 125
Leu Glu Ala Met Ala Ala Gly Val Pro Val Ile Ala Ser Asn Ser Gly
        130                 135                 140

Tyr Gly Pro Ala Glu Val Ile Val Asn Gly Val Asn Gly Glu Gly Val
145                 150                 155                 160

Ile Val Glu Pro Asn Asp Val Glu Glu Leu Ala Glu Leu Ile Asn Lys
                165                 170                 175

Ala Leu Lys Asp Glu Glu Leu Arg Glu Arg Ile Lys Lys Ala Ala
                180                 185                 190

Arg Lys Arg
        195

<210> SEQ ID NO 9
<211> LENGTH: 2875
<212> TYPE: DNA
<213> ORGANISM: Homo sapiens
<220> FEATURE:
<221> NAME/KEY: CDS
<222> LOCATION: (272)...(2680)
<220> FEATURE:
<221> NAME/KEY: misc_feature
<222> LOCATION: (1)...(2875)
<223> OTHER INFORMATION: n = A,T,C or G

<400> SEQUENCE: 9
ggtttntggt gacggtgatc tcggggtggg caggactcca aaggcccgtc gacccggtgg      60
tggactcctt gcactgggat tggacatatg caagcgggag atttggggcc ggcgctcaaa     120
atcggggggc gggggtggac tcgggtttgg accccaggat ccgatcagcg gacccttgat     180
tcaacgtgag gtcccgaatt gacgtccttc cctcaaaacc tccgggtcta caaaccagga     240
ccctcaagac ccttcagggc tccagcgtga c atg gct gaa gcg cac cag gcc        292
                                   Met Ala Glu Ala His Gln Ala
                                     1               5 gtg ggc ttc cga ccc tcg ctg acc tcg gac ggg gct gaa gtg gaa ctc       340
Val Gly Phe Arg Pro Ser Leu Thr Ser Asp Gly Ala Glu Val Glu Leu
         10                  15                  20 agt gcc cct gtg ctg cag gag atc tac ctc tct ggc ctg cgc tcc tgg       388
Ser Ala Pro Val Leu Gln Glu Ile Tyr Leu Ser Gly Leu Arg Ser Trp
 25                  30                  35 aaa agg cat ctc tca cgt ttc tgg aat gac ttt ctc acc ggt gtg ttt       436
Lys Arg His Leu Ser Arg Phe Trp Asn Asp Phe Leu Thr Gly Val Phe
 40                  45                  50                  55 cct gcc agc ccc ctc agt tgg ctt ttc ctc ttc agt gcc atc cag ctt       484
Pro Ala Ser Pro Leu Ser Trp Leu Phe Leu Phe Ser Ala Ile Gln Leu
                 60                  65                  70 gcc tgg ttc ctc cag ctg gat cct tcc tta gga ctg atg gag aag atc       532
Ala Trp Phe Leu Gln Leu Asp Pro Ser Leu Gly Leu Met Glu Lys Ile
         75                  80                  85 aaa gag ttg ctg cct gac tgg ggt gga caa cac cac ggg ctc cgg ggg       580
Lys Glu Leu Leu Pro Asp Trp Gly Gly Gln His His Gly Leu Arg Gly
 90                  95                 100 gtc ctg gca gcc gcg ctg ttt gcc tcg tgt ttg tgg gga gcc ctg atc       628
Val Leu Ala Ala Ala Leu Phe Ala Ser Cys Leu Trp Gly Ala Leu Ile
105                 110                 115 ttc aca ctg cac gtg gcc ctg agg ctg ctt ctg tcc tac cac ggc tgg       676
Phe Thr Leu His Val Ala Leu Arg Leu Leu Leu Ser Tyr His Gly Trp
120                 125                 130                 135 ctt ctt gag ccc cac gga gcc atg tcc tcc ccc acc aag acc tgg ctg       724
Leu Leu Glu Pro His Gly Ala Met Ser Ser Pro Thr Lys Thr Trp Leu
                140                 145                 150
```

-continued

| | |
|---|---|
| gcc ctg gtc cgc atc ttc tct ggc cgc cac ccg atg ctg ttc agt tac<br>Ala Leu Val Arg Ile Phe Ser Gly Arg His Pro Met Leu Phe Ser Tyr<br>155 160 165 | 772 |
| cag cgc tcc ctg cca cgc cag ccc gtg ccc tct gtg cag gac acc gtg<br>Gln Arg Ser Leu Pro Arg Gln Pro Val Pro Ser Val Gln Asp Thr Val<br>170 175 180 | 820 |
| cgc aag tac ctg gag tcg gtc cgg ccc atc ctc tcc gac gag gac ttc<br>Arg Lys Tyr Leu Glu Ser Val Arg Pro Ile Leu Ser Asp Glu Asp Phe<br>185 190 195 | 868 |
| gac tgg acc gcg gtc ctg gcg cag gaa ttc ctg agg ctg cag gcg tca<br>Asp Trp Thr Ala Val Leu Ala Gln Glu Phe Leu Arg Leu Gln Ala Ser<br>200 205 210 215 | 916 |
| ctg ctg cag tgg tac ctg cgg ctc aag tcc tgg tgg gcg tcc aat tat<br>Leu Leu Gln Trp Tyr Leu Arg Leu Lys Ser Trp Trp Ala Ser Asn Tyr<br>220 225 230 | 964 |
| gtc agt gac tgg tgg gag gaa ttt gtg tac ctg cgc tcc cga aat ccg<br>Val Ser Asp Trp Trp Glu Glu Phe Val Tyr Leu Arg Ser Arg Asn Pro<br>235 240 245 | 1012 |
| gtg atg gtg aac agc aac tat tac atg atg gac ttc ctg tat gtc aca<br>Val Met Val Asn Ser Asn Tyr Tyr Met Met Asp Phe Leu Tyr Val Thr<br>250 255 260 | 1060 |
| ccc acg cct ctg cag gca gct cgc gct ggg aat gcc gtc cat gcc ctc<br>Pro Thr Pro Leu Gln Ala Ala Arg Ala Gly Asn Ala Val His Ala Leu<br>265 270 275 | 1108 |
| ctc ctg tac cgc cac cgc ctg aac cgc cag gag ata ccc ccg act ttg<br>Leu Leu Tyr Arg His Arg Leu Asn Arg Gln Glu Ile Pro Pro Thr Leu<br>280 285 290 295 | 1156 |
| ctg atg gga atg cgc ccc tta tgc tct gcc cag tac gag aag atc ttc<br>Leu Met Gly Met Arg Pro Leu Cys Ser Ala Gln Tyr Glu Lys Ile Phe<br>300 305 310 | 1204 |
| aac acc acg cgg att cca ggg gtc caa aaa gac tac atc cgc cac ctc<br>Asn Thr Thr Arg Ile Pro Gly Val Gln Lys Asp Tyr Ile Arg His Leu<br>315 320 325 | 1252 |
| cat gac agc caa cac gtg gct gtc ttc cac cgg ggc cga ttc ttc cgc<br>His Asp Ser Gln His Val Ala Val Phe His Arg Gly Arg Phe Phe Arg<br>330 335 340 | 1300 |
| atg ggg acc cac tcc cga aac agc ctg ctt tcc ccg aga gcc ctg gag<br>Met Gly Thr His Ser Arg Asn Ser Leu Leu Ser Pro Arg Ala Leu Glu<br>345 350 355 | 1348 |
| cag cag ttt cag aga atc ctg gat gat ccc tca ccg gcc tgc ccc cac<br>Gln Gln Phe Gln Arg Ile Leu Asp Asp Pro Ser Pro Ala Cys Pro His<br>360 365 370 375 | 1396 |
| gag gaa cat ctg gca gct ctg aca gct gct ccc agg ggc acg tgg gcc<br>Glu Glu His Leu Ala Ala Leu Thr Ala Ala Pro Arg Gly Thr Trp Ala<br>380 385 390 | 1444 |
| cag gtg cgg aca tcc ctg aag acc cag gca gcg gag gcc ctg gag gcg<br>Gln Val Arg Thr Ser Leu Lys Thr Gln Ala Ala Glu Ala Leu Glu Ala<br>395 400 405 | 1492 |
| gtg gaa ggg gcc gct ttc ttt gtg tca ctg gat gct gag ccc gcg ggg<br>Val Glu Gly Ala Ala Phe Phe Val Ser Leu Asp Ala Glu Pro Ala Gly<br>410 415 420 | 1540 |
| ctc acc agg gag gac ccg gca gcg tcg ttg gat gcc tac gcc cat gct<br>Leu Thr Arg Glu Asp Pro Ala Ala Ser Leu Asp Ala Tyr Ala His Ala<br>425 430 435 | 1588 |
| ctg ctg gcc ggc cgg ggc cat gat cgc tgg ttt gac aaa tcc ttc acc<br>Leu Leu Ala Gly Arg Gly His Asp Arg Trp Phe Asp Lys Ser Phe Thr<br>440 445 450 455 | 1636 |
| cta atc gtc ttc tct aac ggg aag ctg ggc ctc agc gtg gag cac tcc<br>Leu Ile Val Phe Ser Asn Gly Lys Leu Gly Leu Ser Val Glu His Ser | 1684 |

-continued

| | | | | | | | | | | | | | | | |
|---|---|---|---|---|---|---|---|---|---|---|---|---|---|---|---|
| | | | | 460 | | | | | 465 | | | | | 470 | |
| tgg | gcc | gac | tgc | ccc | atc | tca | gga | cac | atg | tgg | gag | ttc | act | ctg | gct | 1732
| Trp | Ala | Asp | Cys | Pro | Ile | Ser | Gly | His | Met | Trp | Glu | Phe | Thr | Leu | Ala |
| | | | 475 | | | | | 480 | | | | | 485 | | |
| aca | gaa | tgc | ttt | cag | ctg | ggc | tac | tca | aca | gac | ggc | cac | tgc | aag | ggg | 1780
| Thr | Glu | Cys | Phe | Gln | Leu | Gly | Tyr | Ser | Thr | Asp | Gly | His | Cys | Lys | Gly |
| | | | | 490 | | | | | 495 | | | | | 500 | |
| cac | ccg | gac | ccc | aca | cta | ccc | cag | ccc | cag | cgg | ctg | caa | tgg | gac | ctt | 1828
| His | Pro | Asp | Pro | Thr | Leu | Pro | Gln | Pro | Gln | Arg | Leu | Gln | Trp | Asp | Leu |
| | 505 | | | | | 510 | | | | | 515 | | | | |
| cca | gac | cag | atc | cac | tcc | tcc | atc | tct | cta | gcc | ctg | agg | gga | gcc | aag | 1876
| Pro | Asp | Gln | Ile | His | Ser | Ser | Ile | Ser | Leu | Ala | Leu | Arg | Gly | Ala | Lys |
| 520 | | | | | 525 | | | | | 530 | | | | | 535 |
| atc | ttg | tct | gaa | aat | gtc | gac | tgc | cat | gtc | gtt | cca | ttc | tcc | cta | ttt | 1924
| Ile | Leu | Ser | Glu | Asn | Val | Asp | Cys | His | Val | Val | Pro | Phe | Ser | Leu | Phe |
| | | | | 540 | | | | | 545 | | | | | 550 | |
| ggc | aag | agc | ttc | atc | cga | cgc | tgc | cac | ctc | tct | tca | gac | agc | ttc | atc | 1972
| Gly | Lys | Ser | Phe | Ile | Arg | Arg | Cys | His | Leu | Ser | Ser | Asp | Ser | Phe | Ile |
| | | | 555 | | | | | 560 | | | | | 565 | | |
| cag | atc | gcc | ttg | caa | ctg | gcc | cac | ttc | cgg | gac | agg | ggt | caa | ttc | tgc | 2020
| Gln | Ile | Ala | Leu | Gln | Leu | Ala | His | Phe | Arg | Asp | Arg | Gly | Gln | Phe | Cys |
| | | 570 | | | | | 575 | | | | | 580 | | | |
| ctg | act | tat | gag | tcg | gcc | atg | act | cgc | tta | ttc | ctg | gaa | ggc | cgg | acg | 2068
| Leu | Thr | Tyr | Glu | Ser | Ala | Met | Thr | Arg | Leu | Phe | Leu | Glu | Gly | Arg | Thr |
| | 585 | | | | | 590 | | | | | 595 | | | | |
| gag | acg | gtg | cgg | tct | tgc | acg | agg | gag | gcc | tgc | aac | ttt | gtc | agg | gcc | 2116
| Glu | Thr | Val | Arg | Ser | Cys | Thr | Arg | Glu | Ala | Cys | Asn | Phe | Val | Arg | Ala |
| 600 | | | | | 605 | | | | | 610 | | | | | 615 |
| atg | gag | gac | aaa | gag | aag | acg | gac | cca | cag | tgc | ctc | gcc | ctg | ttc | cgc | 2164
| Met | Glu | Asp | Lys | Glu | Lys | Thr | Asp | Pro | Gln | Cys | Leu | Ala | Leu | Phe | Arg |
| | | | | 620 | | | | | 625 | | | | | 630 | |
| gtg | gca | gtg | gac | aag | cac | cag | gct | ctg | ctg | aag | gca | gcc | atg | agc | ggg | 2212
| Val | Ala | Val | Asp | Lys | His | Gln | Ala | Leu | Leu | Lys | Ala | Ala | Met | Ser | Gly |
| | | | 635 | | | | | 640 | | | | | 645 | | |
| cag | gga | gtt | gac | cgc | cac | ctg | ttt | gcg | ctg | tac | atc | gtg | tcc | cga | ttc | 2260
| Gln | Gly | Val | Asp | Arg | His | Leu | Phe | Ala | Leu | Tyr | Ile | Val | Ser | Arg | Phe |
| | | 650 | | | | | 655 | | | | | 660 | | | |
| ctc | cac | ctg | cag | tcg | ccc | ttc | ctg | acc | cag | gtc | cat | tcg | gag | cag | tgg | 2308
| Leu | His | Leu | Gln | Ser | Pro | Phe | Leu | Thr | Gln | Val | His | Ser | Glu | Gln | Trp |
| | 665 | | | | | 670 | | | | | 675 | | | | |
| cag | ctg | tcc | acc | agc | cag | atc | cct | gtt | cag | caa | atg | cat | ctg | ttt | gac | 2356
| Gln | Leu | Ser | Thr | Ser | Gln | Ile | Pro | Val | Gln | Gln | Met | His | Leu | Phe | Asp |
| 680 | | | | | 685 | | | | | 690 | | | | | 695 |
| gtc | cac | aat | tac | ccg | gac | tat | gtt | tcc | tca | ggc | ggt | gga | ttc | ggg | cct | 2404
| Val | His | Asn | Tyr | Pro | Asp | Tyr | Val | Ser | Ser | Gly | Gly | Gly | Phe | Gly | Pro |
| | | | | 700 | | | | | 705 | | | | | 710 | |
| gct | gat | gac | cat | ggt | tat | ggt | gtt | tct | tat | atc | ttc | atg | ggg | gat | ggc | 2452
| Ala | Asp | Asp | His | Gly | Tyr | Gly | Val | Ser | Tyr | Ile | Phe | Met | Gly | Asp | Gly |
| | | | 715 | | | | | 720 | | | | | 725 | | |
| atg | atc | acc | ttc | cac | atc | tcc | agc | aaa | aaa | tca | agc | aca | aaa | acg | gat | 2500
| Met | Ile | Thr | Phe | His | Ile | Ser | Ser | Lys | Lys | Ser | Ser | Thr | Lys | Thr | Asp |
| | | 730 | | | | | 735 | | | | | 740 | | | |
| tcc | cac | agg | ctg | ggg | cag | cac | att | gag | gac | gca | ctg | ctg | gat | gtg | gcc | 2548
| Ser | His | Arg | Leu | Gly | Gln | His | Ile | Glu | Asp | Ala | Leu | Leu | Asp | Val | Ala |
| | 745 | | | | | 750 | | | | | 755 | | | | |
| tcc | ctg | ttc | cag | gcg | gga | cag | cat | ttt | aag | cgc | cgg | ttc | aga | ggg | tca | 2596
| Ser | Leu | Phe | Gln | Ala | Gly | Gln | His | Phe | Lys | Arg | Arg | Phe | Arg | Gly | Ser |
| 760 | | | | | 765 | | | | | 770 | | | | | 775 |
| ggg | aag | gag | aac | tcc | agg | cac | agg | tgt | gga | ttt | ctc | tcc | cgc | cag | act | 2644

```
Gly Lys Glu Asn Ser Arg His Arg Cys Gly Phe Leu Ser Arg Gln Thr
            780                 785                 790 ggg gcc tcc aag gcc tca atg aca tcc acc gac ttc tgactccttc          2690
Gly Ala Ser Lys Ala Ser Met Thr Ser Thr Asp Phe
            795                 800 cagcaggcag ctggcctctc caaggaataa gggtgaaatt gccacagctg gctgacacag   2750
gacaggggca actggtttgg caaccccaca tccaggccaa taaagatgtg tgagctggga   2810
aaaaaaaaaa aaaaaaaaaa aaaaaaaaaa aaaaaaaaa aaaaaaaaaa aaagggcggc   2870
cgcta                                                               2875

<210> SEQ ID NO 10
<211> LENGTH: 803
<212> TYPE: PRT
<213> ORGANISM: Homo sapiens

<400> SEQUENCE: 10

Met Ala Glu Ala His Gln Ala Val Gly Phe Arg Pro Ser Leu Thr Ser
 1               5                  10                  15

Asp Gly Ala Glu Val Glu Leu Ser Ala Pro Val Leu Gln Glu Ile Tyr
            20                  25                  30

Leu Ser Gly Leu Arg Ser Trp Lys Arg His Leu Ser Arg Phe Trp Asn
        35                  40                  45

Asp Phe Leu Thr Gly Val Phe Pro Ala Ser Pro Leu Ser Trp Leu Phe
    50                  55                  60

Leu Phe Ser Ala Ile Gln Leu Ala Trp Phe Leu Gln Leu Asp Pro Ser
65                  70                  75                  80

Leu Gly Leu Met Glu Lys Ile Lys Glu Leu Leu Pro Asp Trp Gly Gly
                85                  90                  95

Gln His His Gly Leu Arg Gly Val Leu Ala Ala Leu Phe Ala Ser
            100                 105                 110

Cys Leu Trp Gly Ala Leu Ile Phe Thr Leu His Val Ala Leu Arg Leu
        115                 120                 125

Leu Leu Ser Tyr His Gly Trp Leu Leu Glu Pro His Gly Ala Met Ser
    130                 135                 140

Ser Pro Thr Lys Thr Trp Leu Ala Leu Val Arg Ile Phe Ser Gly Arg
145                 150                 155                 160

His Pro Met Leu Phe Ser Tyr Gln Arg Ser Leu Pro Arg Gln Pro Val
                165                 170                 175

Pro Ser Val Gln Asp Thr Val Arg Lys Tyr Leu Glu Ser Val Arg Pro
            180                 185                 190

Ile Leu Ser Asp Glu Asp Phe Asp Trp Thr Ala Val Leu Ala Gln Glu
        195                 200                 205

Phe Leu Arg Leu Gln Ala Ser Leu Leu Gln Trp Tyr Leu Arg Leu Lys
    210                 215                 220

Ser Trp Trp Ala Ser Asn Tyr Val Ser Asp Trp Glu Glu Phe Val
225                 230                 235                 240

Tyr Leu Arg Ser Arg Asn Pro Val Met Val Asn Ser Asn Tyr Tyr Met
                245                 250                 255

Met Asp Phe Leu Tyr Val Thr Pro Thr Pro Leu Gln Ala Ala Arg Ala
            260                 265                 270

Gly Asn Ala Val His Ala Leu Leu Leu Tyr Arg His Arg Leu Asn Arg
        275                 280                 285

Gln Glu Ile Pro Pro Thr Leu Leu Met Gly Met Arg Pro Leu Cys Ser
    290                 295                 300
```

-continued

```
Ala Gln Tyr Glu Lys Ile Phe Asn Thr Thr Arg Ile Pro Gly Val Gln
305                 310                 315                 320

Lys Asp Tyr Ile Arg His Leu His Asp Ser Gln His Val Ala Val Phe
                325                 330                 335

His Arg Gly Arg Phe Phe Arg Met Gly Thr His Ser Arg Asn Ser Leu
            340                 345                 350

Leu Ser Pro Arg Ala Leu Glu Gln Gln Phe Gln Arg Ile Leu Asp Asp
            355                 360                 365

Pro Ser Pro Ala Cys Pro His Glu Glu His Leu Ala Ala Leu Thr Ala
        370                 375                 380

Ala Pro Arg Gly Thr Trp Ala Gln Val Arg Thr Ser Leu Lys Thr Gln
385                 390                 395                 400

Ala Ala Glu Ala Leu Glu Ala Val Glu Gly Ala Ala Phe Phe Val Ser
                405                 410                 415

Leu Asp Ala Glu Pro Ala Gly Leu Thr Arg Glu Asp Pro Ala Ala Ser
            420                 425                 430

Leu Asp Ala Tyr Ala His Ala Leu Leu Ala Gly Arg Gly His Asp Arg
        435                 440                 445

Trp Phe Asp Lys Ser Phe Thr Leu Ile Val Phe Ser Asn Gly Lys Leu
    450                 455                 460

Gly Leu Ser Val Glu His Ser Trp Ala Asp Cys Pro Ile Ser Gly His
465                 470                 475                 480

Met Trp Glu Phe Thr Leu Ala Thr Glu Cys Phe Gln Leu Gly Tyr Ser
                485                 490                 495

Thr Asp Gly His Cys Lys Gly His Pro Asp Pro Thr Leu Pro Gln Pro
            500                 505                 510

Gln Arg Leu Gln Trp Asp Leu Pro Asp Gln Ile His Ser Ser Ile Ser
        515                 520                 525

Leu Ala Leu Arg Gly Ala Lys Ile Leu Ser Glu Asn Val Asp Cys His
    530                 535                 540

Val Val Pro Phe Ser Leu Phe Gly Lys Ser Phe Ile Arg Arg Cys His
545                 550                 555                 560

Leu Ser Ser Asp Ser Phe Ile Gln Ile Ala Leu Gln Leu Ala His Phe
                565                 570                 575

Arg Asp Arg Gly Gln Phe Cys Leu Thr Tyr Glu Ser Ala Met Thr Arg
            580                 585                 590

Leu Phe Leu Glu Gly Arg Thr Glu Thr Val Arg Ser Cys Thr Arg Glu
        595                 600                 605

Ala Cys Asn Phe Val Arg Ala Met Glu Asp Lys Glu Lys Thr Asp Pro
    610                 615                 620

Gln Cys Leu Ala Leu Phe Arg Val Ala Val Asp Lys His Gln Ala Leu
625                 630                 635                 640

Leu Lys Ala Ala Met Ser Gly Gln Gly Val Asp Arg His Leu Phe Ala
                645                 650                 655

Leu Tyr Ile Val Ser Arg Phe Leu His Leu Gln Ser Pro Phe Leu Thr
            660                 665                 670

Gln Val His Ser Glu Gln Trp Gln Leu Ser Thr Ser Gln Ile Pro Val
        675                 680                 685

Gln Gln Met His Leu Phe Asp Val His Asn Tyr Pro Asp Tyr Val Ser
    690                 695                 700

Ser Gly Gly Gly Phe Gly Pro Ala Asp Asp His Gly Tyr Gly Val Ser
705                 710                 715                 720
```

```
Tyr Ile Phe Met Gly Asp Gly Met Ile Thr Phe His Ile Ser Ser Lys
                725                 730                 735
Lys Ser Ser Thr Lys Thr Asp Ser His Arg Leu Gly Gln His Ile Glu
            740                 745                 750
Asp Ala Leu Leu Asp Val Ala Ser Leu Phe Gln Ala Gly Gln His Phe
        755                 760                 765
Lys Arg Arg Phe Arg Gly Ser Gly Lys Glu Asn Ser Arg His Arg Cys
    770                 775                 780
Gly Phe Leu Ser Arg Gln Thr Gly Ala Ser Lys Ala Ser Met Thr Ser
785                 790                 795                 800
Thr Asp Phe

<210> SEQ ID NO 11
<211> LENGTH: 2412
<212> TYPE: DNA
<213> ORGANISM: Homo sapiens

<400> SEQUENCE: 11
atggctgaag cgcaccaggc cgtgggcttc cgaccctcgc tgacctcgga cggggctgaa      60
gtggaactca gtgcccctgt gctgcaggag atctacctct ctggcctgcg ctcctggaaa     120
aggcatctct cacgtttctg gaatgacttt ctcaccggtg tgtttcctgc cagcccctc     180
agttggcttt tcctcttcag tgccatccag cttgcctggt tcctcagct ggatccttcc     240
ttaggactga tggagaagat caaagagttg ctgcctgact ggggtggaca acaccacggg     300
ctccgggggg tcctggcagc cgcgctgttt gcctcgtgtt tgtggggagc cctgatcttc     360
acactgcacg tggccctgag gctgcttctg tcctaccacg gctggcttct tgagccccac     420
ggagccatgt cctcccccac caagacctgg ctggccctgg tccgcatctt ctctggccgc     480
cacccgatgc tgttcagtta ccagcgctcc ctgccacgcc agcccgtgcc ctctgtgcag     540
gacaccgtgc gcaagtacct ggagtcggtc cggcccatcc tctccgacga ggacttcgac     600
tggaccgcgg tcctggcgca ggaattcctg aggctgcagg cgtcactgct gcagtggtac     660
ctgcggctca gtcctggtg gcgtccaat tatgtcagtg actggtggga ggaatttgtg     720
tacctgcgct cccgaaatcc ggtgatggtg aacagcaact attacatgat ggacttcctg     780
tatgtcacac ccacgcctct gcaggcagct cgcgctggga atgccgtcca tgccctcctc     840
ctgtaccgcc accgcctgaa ccgccaggag ataccccga ctttgctgat gggaatgcgc     900
cccttatgct ctgcccagta cgagaagatc ttcaacacca gcggattcc agggggtccaa     960
aaagactaca tccgccacct ccatgacagc caaacgtgg ctgtcttcca ccggggccga    1020
ttcttccgca tggggaccca ctcccgaaac agcctgcttt ccccgagagc cctggagcag    1080
cagtttcaga gaatcctgga tgatccctca ccggcctgcc ccacgaggg acatctggca    1140
gctctgacag ctgctcccag ggcacgtgg gcccaggtgc ggacatccct gaagacccag    1200
gcagcggagg ccctggaggc ggtggaaggg gccgctttct ttgtgtcact ggatgctgag    1260
cccgcggggc tcaccaggga ggacccggca gcgtcgttgg atgcctacgc ccatgctctg    1320
ctggccggcc ggggccatga tcgctggttt gacaaatcct tcacccctaa cgtcttctct    1380
aacgggaagc tgggcctcag cgtggagcac tcctgggccg actgccccat ctcaggacac    1440
atgtgggagt tcactctggc tacagaatgc tttcagctgg ctactcaac agacggccac    1500
tgcaaggggc acccggaccc cacactaccc cagcccagc ggctgcaatg ggaccttcca    1560
gaccagatcc actcctccat ctctctagcc ctgagggga ccaagatctt gtctgaaaat    1620
```

-continued

```
gtcgactgcc atgtcgttcc attctcccta tttggcaaga gcttcatccg acgctgccac    1680
ctctcttcag acagcttcat ccagatcgcc ttgcaactgg cccacttccg ggacagggt     1740 caattctgcc tgacttatga gtcggccatg actcgcttat tcctggaagg ccggacggag    1800
acggtgcggt cttgcacgag ggaggcctgc aactttgtca gggccatgga ggacaaagag    1860
aagacggacc cacagtgcct cgccctgttc cgcgtggcag tggacaagca ccaggctctg    1920
ctgaaggcag ccatgagcgg gcaggagtt gaccgccacc tgtttgcgct gtacatcgtg     1980
tcccgattcc tccacctgca gtcgcccttc ctgacccagg tccattcgga gcagtggcag    2040
ctgtccacca gccagatccc tgttcagcaa atgcatctgt tgacgtcca caattacccg     2100 gactatgttt cctcaggcgg tggattcggg cctgctgatg accatggtta tggtgtttct    2160
tatatcttca tgggggatgg catgatcacc ttccacatct ccagcaaaaa atcaagcaca    2220
aaaacggatt cccacaggct ggggcagcac attgaggacg cactgctgga tgtggcctcc    2280
ctgttccagg cgggacagca ttttaagcgc cggttcagag ggtcagggaa ggagaactcc    2340
aggcacaggt gtggatttct ctcccgccag actggggcct ccaaggcctc aatgacatcc    2400
accgacttct ga                                                       2412
```

<210> SEQ ID NO 12
<211> LENGTH: 698
<212> TYPE: PRT
<213> ORGANISM: Artificial Sequence
<220> FEATURE:
<223> OTHER INFORMATION: consensus sequence

<400> SEQUENCE: 12

```
Ser Leu Pro Lys Leu Pro Val Pro Pro Leu Gln Asp Thr Leu Asp Arg
 1               5                  10                  15

Tyr Leu Glu Ala Leu Glu Pro Leu Val Asn Glu Glu Gly Tyr Tyr Gln
                20                  25                  30

His Pro Leu Asp Pro Glu Gln Phe Arg Arg Thr Gln Ala Leu Val Lys
            35                  40                  45

Asp Phe Glu Ala Gly Gly Gly Leu Gly Glu Arg Leu Gln Gln Lys Leu
        50                  55                  60

Leu Glu Asp Arg Ala Asn Lys Lys Thr Asn Trp Leu Ser Glu Trp Trp
 65                  70                  75                  80

Leu Glu Asp Ala Tyr Leu Arg Tyr Arg Asp Glu Ile Leu Pro Leu Val
                85                  90                  95

Leu Asn Ser Asn Pro Gly Val Val Leu Pro Lys Asp Pro Phe Gln Asp
            100                 105                 110

Thr Asn Asp Gln Leu Arg Arg Ala Ala Asn Leu Ile Ser Gly Ile Leu
        115                 120                 125

Arg Phe Lys Glu Leu Leu Asp Ala Ser Glu Leu Leu Pro Glu Glu Leu
    130                 135                 140

Ala Lys Asn Glu Lys Ser Asp Thr Ala Phe Lys Arg Leu Ile Arg Phe
145                 150                 155                 160

Val Pro Ser Leu Ser Trp Tyr Gly Ala Tyr Leu Leu Gly Gly Gln Pro
                165                 170                 175

Leu Cys Met Asn Gln Tyr Tyr Arg Leu Phe Ser Ser Arg Ile Pro
            180                 185                 190

Val Gly Pro Lys Glu Asp Ser Ile Val Asn Gln Thr Lys Thr Arg Lys
        195                 200                 205

Glu His Pro Glu Pro Glu His Val Val Leu Cys Arg Gly Gln Phe
    210                 215                 220
```

```
Phe Val Leu Asp Val Leu Asp Ser Asp Asn Gly Arg Leu Leu Ser Pro
225                 230                 235                 240

Ala Glu Leu Glu Thr Gln Leu Glu Tyr Ile Leu Ser Asp Ser Ser Gln
                245                 250                 255

Glu Pro Glu Gly Leu Ala Pro Ile Gly Ala Leu Thr Ser Glu Pro Arg
                260                 265                 270

Asp Asn Trp Ala Lys Ala Arg Gln Tyr Leu Ile Lys Asp Gly Thr Glu
                275                 280                 285

Asn Lys Asp Ser Leu Glu Lys Ile Glu Ser Ala Leu Phe Val Val Cys
290                 295                 300

Leu Asp Glu Pro Gln Pro Gly Ala Thr Asn Lys Asp Asp Thr Ala
305                 310                 315                 320

Asp Leu Val Ile Asn Arg Val Leu Ser Glu Arg Asp Ser Thr Ala Thr
                325                 330                 335

Ala Ala Asn Cys Lys Gln Met Leu His Gly Gly Ser Ile Val Gln
                340                 345                 350

Ser Gly Asn Cys Leu Asn Arg Trp Tyr Asp Lys Ser Leu Gln Leu Ile
                355                 360                 365

Val Thr Lys Asp Gly Lys Ala Gly Leu Val Phe Glu His Ser Pro Ala
                370                 375                 380

Asp Gly Ile Val Val Arg Leu Ala Glu Tyr Val Tyr Lys Lys Ser
385                 390                 395                 400

Val Lys Thr Leu Ala Arg Asp Val Ala Lys Asp Val Phe Ile Leu
                405                 410                 415

Ser Asp Asp Val Thr Lys Met Asp Ser Ala Glu Lys Lys Leu Val Arg
                420                 425                 430

Ala Asp Ser Ser Val Asp Leu Pro Lys Pro Glu Lys Leu Arg Trp Lys
                435                 440                 445

Ile Ser Pro Glu Leu Gln Asn Asp Ile Glu Lys Ala Lys Glu Lys Leu
                450                 455                 460

Asp Glu Leu Ile Ser Asp Leu Asp Ile Val Leu Lys Phe Gln Ser
465                 470                 475                 480

Phe Gly Lys Thr Phe Ile Lys Lys Glu Lys Leu Ser Pro Asp Ala Phe
                485                 490                 495

Ile Gln Leu Ala Leu Gln Leu Ala Tyr Tyr Arg Leu Tyr Gly Arg Leu
                500                 505                 510

Val Ala Thr Tyr Glu Ser Ala Ser Thr Arg Arg Phe Lys His Gly Arg
                515                 520                 525

Thr Glu Thr Ile Arg Ser Ala Thr Gln Glu Ser Leu Glu Phe Val Gln
530                 535                 540

Ala Met Val Asp Glu Glu Ser Lys Val Ser Lys Glu Lys Leu Gln
545                 550                 555                 560

Leu Leu Lys Asp Ala Val Lys Ala His Ser Gln Tyr Thr Lys Glu Ala
                565                 570                 575

Ile Thr Gly Met Gly Ile Asp Arg His Leu Leu Ala Leu Lys Leu Leu
                580                 585                 590

Ala Lys Phe Arg Glu Glu Glu Gly Val Glu Leu Pro Glu Leu Phe
                595                 600                 605

Leu Asp Pro Leu Tyr Ser Glu Ser Asn Arg Phe Val Leu Ser Thr Ser
                610                 615                 620

Pro Gln Gln Gln Val Glu Leu Phe Asp Val Glu Gln Val Pro Ser Pro
625                 630                 635                 640
```

```
Thr Asp Cys Phe Gly Gly Phe Gly Pro Val Pro Asp Gly Tyr Gly
            645                 650                 655
Ile Gly Tyr Asn Ile His Asp Glu Asn Gln Ile Val Phe Asn Val Ser
        660                 665                 670
Ser Phe His Ser Cys Pro Glu Thr Asp Ala Ala Arg Phe Ala Lys Tyr
        675                 680                 685
Leu Glu Lys Ala Leu Leu Asp Met Arg Asp
    690                 695
```

<210> SEQ ID NO 13
<211> LENGTH: 1529
<212> TYPE: DNA
<213> ORGANISM: Homo sapiens
<220> FEATURE:
<221> NAME/KEY: CDS
<222> LOCATION: (57)...(977)
<220> FEATURE:
<221> NAME/KEY: misc_feature
<222> LOCATION: (1)...(1529)
<223> OTHER INFORMATION: n = A,T,C or G

<400> SEQUENCE: 13

```
cggcccccgg gagctgtgct ctatggagct attgcggccg tgggtggtcg cgggcg atg      59
                                                               Met
                                                                 1 cgg ggc tgc cag ctc ctc ggg ctt cgt agc tct tgg ccc ggg gac cta       107
Arg Gly Cys Gln Leu Leu Gly Leu Arg Ser Ser Trp Pro Gly Asp Leu
        5                   10                  15 cta agt gct cgg ctc ttg tcc caa gag aag cgg gca gcg gaa acg cac       155
Leu Ser Ala Arg Leu Leu Ser Gln Glu Lys Arg Ala Ala Glu Thr His
    20                  25                  30 ttt ggg ttt gag act gtg tcg gaa gag gag aag ggg ggc aaa gtc tat       203
Phe Gly Phe Glu Thr Val Ser Glu Glu Glu Lys Gly Gly Lys Val Tyr
35                  40                  45 cag gtg ttt gaa agt gtg gct aag aag tat gat gtg atg aat gat atg       251
Gln Val Phe Glu Ser Val Ala Lys Lys Tyr Asp Val Met Asn Asp Met
 50                  55                  60                  65 atg agt ctt ggt atc cat cgt gtt tgg aag gat ttg ctg ctc tgg aag       299
Met Ser Leu Gly Ile His Arg Val Trp Lys Asp Leu Leu Leu Trp Lys
                70                  75                  80 atg cac ccg ctt cct ggg acc cag ctg ctt gat gtt gct gga ggc aca       347
Met His Pro Leu Pro Gly Thr Gln Leu Leu Asp Val Ala Gly Gly Thr
            85                  90                  95 ggt gac att gca ttc cgg ttc ctt aat tat gtt cag tcc cag cat cag       395
Gly Asp Ile Ala Phe Arg Phe Leu Asn Tyr Val Gln Ser Gln His Gln
        100                 105                 110 aga aaa cag aag agg cag tta agg gcc caa caa aat tta tcc tgg gaa       443
Arg Lys Gln Lys Arg Gln Leu Arg Ala Gln Gln Asn Leu Ser Trp Glu
    115                 120                 125 gaa att gcc aaa gag tac cag aat gaa gaa gat tcc ttg ggc ggg tct       491
Glu Ile Ala Lys Glu Tyr Gln Asn Glu Glu Asp Ser Leu Gly Gly Ser
130                 135                 140                 145 cgt gtc gtg gtg tgt gac atc aac aag gag atg cta aag gtt gga aag       539
Arg Val Val Val Cys Asp Ile Asn Lys Glu Met Leu Lys Val Gly Lys
                150                 155                 160 cag aaa gcc ttg gct caa gga tac aga gct gga ctt gca tgg gta tta       587
Gln Lys Ala Leu Ala Gln Gly Tyr Arg Ala Gly Leu Ala Trp Val Leu
            165                 170                 175 gga gat gct gaa gaa ctg ccc ttt gat gat gac aag ttt gat att tac       635
Gly Asp Ala Glu Glu Leu Pro Phe Asp Asp Asp Lys Phe Asp Ile Tyr
        180                 185                 190
```

-continued

```
acc att gcc ttt ggg atc cgg aat gtc aca cac att gat cag gca ctc        683
Thr Ile Ala Phe Gly Ile Arg Asn Val Thr His Ile Asp Gln Ala Leu
    195                 200                 205 cag gaa gct cat cgg gtg ctg aaa cca gga gga cgg ttt ctc tgt ctg        731
Gln Glu Ala His Arg Val Leu Lys Pro Gly Gly Arg Phe Leu Cys Leu
210                 215                 220                 225 gaa ttt agc caa gtg aac aat ccc ctc ata tcc agg ctt tat gat cta        779
Glu Phe Ser Gln Val Asn Asn Pro Leu Ile Ser Arg Leu Tyr Asp Leu
                230                 235                 240 tat agc ttc cag gtc atc cct gtc ctg gga gag gtc atc gct gga gac        827
Tyr Ser Phe Gln Val Ile Pro Val Leu Gly Glu Val Ile Ala Gly Asp
            245                 250                 255 tgg aag tcc tat cag tac ctt gta gag agt atc cga agg ttt ccg tct        875
Trp Lys Ser Tyr Gln Tyr Leu Val Glu Ser Ile Arg Arg Phe Pro Ser
        260                 265                 270 cag gaa gag ttc aag gac atg ata gaa gat gca ggc ttt cac aag gtg        923
Gln Glu Glu Phe Lys Asp Met Ile Glu Asp Ala Gly Phe His Lys Val
    275                 280                 285 act tac gaa agt cta aca tca ggc att gtg gcc att cat tct ggc ttc        971
Thr Tyr Glu Ser Leu Thr Ser Gly Ile Val Ala Ile His Ser Gly Phe
290                 295                 300                 305 aaa ctt taattccttt cctatcatgg agcatgaacc agtcatatcc tgttgaaagc       1027
Lys Leu
ctggaactga aggataatct ggcaaatgag acagcagcag agcatctcct cttaaggata    1087
cgtgccttgg actcatgttt gaatcgaaca gtctcraagt ggaagaacaa attcttgtca    1147
cttttttaca gctttctttg gagctgcttc agtccatctc ccagaggcat ttggtctgta    1207
tctttgctca actgctaatt tctcttggct gtagggtgtg tggttaaggt acaaccaccc    1267
ctaaagctca gttttgaagt gagtgtattt atagcttctc tgctggtgct gccttctaga    1327
gggatgatag atcatttgaa cccaatgaca attttttaacc agaaaattta attgtacctg   1387
aatcaacctt tcagcctagg acgaagtcta ggcccaagtc agagtattaa tgatcatgag    1447
aattgtgtgc tgaaccagta aacgagttta ccttttgaaa aaaaaaaaaa aaaaaaaaa     1507 aaaaaaaaaa rnggcggccg ct                                             1529
```

<210> SEQ ID NO 14
<211> LENGTH: 307
<212> TYPE: PRT
<213> ORGANISM: Homo sapiens

<400> SEQUENCE: 14

```
Met Arg Gly Cys Gln Leu Leu Gly Leu Arg Ser Ser Trp Pro Gly Asp
1               5                   10                  15

Leu Leu Ser Ala Arg Leu Leu Ser Gln Glu Lys Arg Ala Ala Glu Thr
            20                  25                  30

His Phe Gly Phe Glu Thr Val Ser Glu Glu Lys Gly Gly Lys Val
        35                  40                  45

Tyr Gln Val Phe Glu Ser Val Ala Lys Lys Tyr Asp Val Met Asn Asp
    50                  55                  60

Met Met Ser Leu Gly Ile His Arg Val Trp Lys Asp Leu Leu Leu Trp
65                  70                  75                  80

Lys Met His Pro Leu Pro Gly Thr Gln Leu Leu Asp Val Ala Gly Gly
                85                  90                  95

Thr Gly Asp Ile Ala Phe Arg Phe Leu Asn Tyr Val Gln Ser Gln His
            100                 105                 110

Gln Arg Lys Gln Lys Arg Gln Leu Arg Ala Gln Asn Leu Ser Trp
        115                 120                 125
```

```
Glu Glu Ile Ala Lys Glu Tyr Gln Asn Glu Glu Asp Ser Leu Gly Gly
    130                 135                 140
Ser Arg Val Val Cys Asp Ile Asn Lys Glu Met Leu Lys Val Gly
145                 150                 155                 160
Lys Gln Lys Ala Leu Ala Gln Gly Tyr Arg Ala Gly Leu Ala Trp Val
                165                 170                 175
Leu Gly Asp Ala Glu Leu Pro Phe Asp Asp Lys Phe Asp Ile
            180                 185                 190
Tyr Thr Ile Ala Phe Gly Ile Arg Asn Val Thr His Ile Asp Gln Ala
        195                 200                 205
Leu Gln Glu Ala His Arg Val Leu Lys Pro Gly Gly Arg Phe Leu Cys
    210                 215                 220
Leu Glu Phe Ser Gln Val Asn Asn Pro Leu Ile Ser Arg Leu Tyr Asp
225                 230                 235                 240
Leu Tyr Ser Phe Gln Val Ile Pro Val Leu Gly Glu Val Ile Ala Gly
                245                 250                 255
Asp Trp Lys Ser Tyr Gln Tyr Leu Val Glu Ser Ile Arg Arg Phe Pro
            260                 265                 270
Ser Gln Glu Glu Phe Lys Asp Met Ile Glu Asp Ala Gly Phe His Lys
        275                 280                 285
Val Thr Tyr Glu Ser Leu Thr Ser Gly Ile Val Ala Ile His Ser Gly
    290                 295                 300
Phe Lys Leu
305

<210> SEQ ID NO 15
<211> LENGTH: 924
<212> TYPE: DNA
<213> ORGANISM: Homo sapiens

<400> SEQUENCE: 15
atgcggggct gccagctcct cgggcttcgt agctcttggc ccggggaccct actaagtgct    60
cggctcttgt cccaagagaa gcgggcagcg gaaacgcact ttgggtttga gactgtgtcg   120
gaagaggaga aggggggcaa agtctatcag gtgtttgaaa gtgtggctaa aagtatgat    180
gtgatgaatg atatgatgag tcttggtatc atcgtgtttt ggaaggattt gctgctctgg   240
aagatgcacc cgcttcctgg gacccagctg cttgatgttg ctggaggcac aggtgacatt   300
gcattccggt tccttaatta tgttcagtcc cagcatcaga gaaaacagaa gaggcagtta   360
agggcccaac aaaatttatc ctgggaagaa attgccaaag agtaccagaa tgaagaagat   420
tccttgggcg gtctcgtgt cgtggtgtgt gacatcaaca aggagatgct aaaggttgga   480
aagcagaaag ccttggctca aggatacaga gctggacttg catgggtatt aggagatgct   540
gaagaactgc cctttgatga tgacaagttt gatatttaca ccattgcctt tgggatccgg   600
aatgtcacac acattgatca ggcactccag gaagctcatc gggtgctgaa accaggagga   660
cggtttctct gtctggaatt tagccaagtg aacaatcccc tcatatccag gctttatgat   720
ctatatagct tccaggtcat ccctgtcctg ggagaggtca tcgctggaga ctggaagtcc   780
tatcagtacc ttgtagagag tatccgaagg tttccgtctc aggaagagtt caaggacatg   840
atagaagatg caggctttca caaggtgact tacgaaagtc taacatcagg cattgtggcc   900
attcattctg gcttcaaact ttaa                                           924

<210> SEQ ID NO 16
```

<211> LENGTH: 273
<212> TYPE: PRT
<213> ORGANISM: Artificial Sequence
<220> FEATURE:
<223> OTHER INFORMATION: consensus sequence

<400> SEQUENCE: 16

```
Met Thr Val Leu Lys Glu Lys Glu Lys Leu Val His His Val Phe
 1               5                  10                  15

Glu Ser Val Ala Lys Lys Tyr Asp Leu Met Asn Asp Val Met Ser Phe
                20                  25                  30

Gly Ile His Arg Leu Trp Lys Asp His Phe Thr Met Lys Leu Met Gly
                35                  40                  45

Pro Lys Arg Gly Lys Ser Thr Thr Pro Leu Lys Phe Leu Asp Val Ala
 50                  55                  60

Gly Gly Thr Gly Asp Ile Ala Phe Arg Leu Leu Arg Ser Val Gly Glu
 65                  70                  75                  80

Ser Gly Gln Ser Phe Gly Ile Val Pro Lys Thr Leu Asp Glu Ser Lys
                85                  90                  95

Val Val Val Leu Asp Ile Asn Glu Asn Met Leu Lys Val Gly Lys Lys
                100                 105                 110

Arg Ala Lys Glu Glu Gly Lys Ile Phe Lys Asp Gly Arg Ile Glu Phe
                115                 120                 125

Val Gln Ala Asn Ala Glu Glu Leu Pro Phe Glu Asp Ser Asp Thr Phe
                130                 135                 140

Asp Leu Val Thr Ile Ser Phe Gly Leu Arg Asn Val Thr Asp Tyr Leu
145                 150                 155                 160

Lys Val Leu Arg Glu Ala Phe Arg Val Leu Lys Pro Gly Gly Arg Leu
                165                 170                 175

Val Cys Leu Glu Phe Ser Lys Pro Glu Leu Pro Leu Leu Lys Gln Ala
                180                 185                 190

Tyr Asp Leu Tyr Ser Lys Asn Val Met Pro Val Leu Gly Lys Leu Leu
                195                 200                 205

Ala Asn Asp Tyr Ala Asn Met Lys Ser Tyr Arg Tyr Leu Gln Glu Ser
                210                 215                 220

Ile Arg Asp Phe Pro Asp Gln Lys Thr Leu Lys Ser Arg Ser Ala Thr
225                 230                 235                 240

Thr Pro Met Ile Arg Glu Ala Gly Leu Leu Phe Lys Ser Val Glu Tyr
                245                 250                 255

Glu Ser Leu Thr Gly Gly Val Ile Ala Ile His Lys Thr Phe Gly Tyr
                260                 265                 270

Lys
```

<210> SEQ ID NO 17
<211> LENGTH: 16
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 3, 6-7, 10-12, 14-15
<223> OTHER INFORMATION: Xaa = any amino acid
<220> FEATURE:
<221> NAME/KEY: VARIANT
<222> LOCATION: 8
<223> OTHER INFORMATION: Xaa = Leu, Ile, Val, or Met

<400> SEQUENCE: 17

-continued

```
Tyr Asp Xaa Met Asn Xaa Xaa Xaa Ser Xaa Xaa Xaa His Xaa Xaa Trp
 1               5                  10                  15
```

<210> SEQ ID NO 18
<211> LENGTH: 15
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 3, 12
<223> OTHER INFORMATION: Xaa = Leu, Ile, Val, or Met
<220> FEATURE:
<221> NAME/KEY: VARIANT
<222> LOCATION: 5
<223> OTHER INFORMATION: Xaa = Pro or Val
<220> FEATURE:
<221> NAME/KEY: VARIANT
<222> LOCATION: 6
<223> OTHER INFORMATION: Xaa = Gly or Met
<220> FEATURE:
<221> NAME/KEY: VARIANT
<222> LOCATION: 8, 10-11, 14
<223> OTHER INFORMATION: Xaa = any amino acid
<220> FEATURE:
<221> NAME/KEY: VARIANT
<222> LOCATION: 9
<223> OTHER INFORMATION: Xaa = Leu, Ile, Val, Met, or Phe

<400> SEQUENCE: 18

```
Arg Val Xaa Lys Xaa Xaa Gly Xaa Xaa Xaa Xaa Xaa Glu Xaa Ser
 1               5                  10                  15
```

<210> SEQ ID NO 19
<211> LENGTH: 2557
<212> TYPE: DNA
<213> ORGANISM: Homo sapiens
<220> FEATURE:
<221> NAME/KEY: CDS
<222> LOCATION: (236)...(1711)

<400> SEQUENCE: 19

```
tttttttttt tatttttcaa tgcatcttta atttgtaaag aaataaaata aattaagatg      60
taaccattag cctcatcttt actcccgaaa gctcactttg cttttagtcc tggccgtcgg     120
ctgagcgagc tgcgcatgcg ccacgtgccc ccgtggcgta gggcctcgtc cggtcacgac     180
tatccgctgg gcggggtcgg tgctggccga gggggcgccg gctgccggag tggac atg     238
                                                              Met
                                                               1 gcg gcc ggc ccc att agg gtg gtg ttg gtc ctt cta ggg gtg ctc agt     286
Ala Ala Gly Pro Ile Arg Val Val Leu Val Leu Leu Gly Val Leu Ser
         5                  10                  15 gtc tgt gca gcc agc ggc cat ggg tcc gta gcg gag agg gag gcc ggc     334
Val Cys Ala Ala Ser Gly His Gly Ser Val Ala Glu Arg Glu Ala Gly
     20                  25                  30 ggg gag gcg gag tgg gcg gaa ccg tgg gat ggc gcg gtt ttc cgg ccg     382
Gly Glu Ala Glu Trp Ala Glu Pro Trp Asp Gly Ala Val Phe Arg Pro
 35                  40                  45 ccc tcg gcg ctg ggc gca gtg ggg gtg acg cgc agc tct ggg acg ccg     430
Pro Ser Ala Leu Gly Ala Val Gly Val Thr Arg Ser Ser Gly Thr Pro
 50                  55                  60                  65 cgg cca ggg agg gag gag gcg ggg gac ttg ccg gta ctg ctg tgg tgg     478
Arg Pro Gly Arg Glu Glu Ala Gly Asp Leu Pro Val Leu Leu Trp Trp
             70                  75                  80 agc cca ggg cta ttc ccc cac ttc ccg gga gac tcg gag cgc atc gag     526
Ser Pro Gly Leu Phe Pro His Phe Pro Gly Asp Ser Glu Arg Ile Glu
```

-continued

```
                     85                      90                       95
tgt gcg cgc ggc gcg tgc gtg gcg tcc cgg aac cgc cga gcg ctg agg        574
Cys Ala Arg Gly Ala Cys Val Ala Ser Arg Asn Arg Arg Ala Leu Arg
        100                     105                     110 gac tcg cgg acg cgc gcg ctg ctc ttc tac ggc aca gac ttc cgc gcg        622
Asp Ser Arg Thr Arg Ala Leu Leu Phe Tyr Gly Thr Asp Phe Arg Ala
    115                     120                     125 tcg gcc gcc ccg ctg ccg cgc ctg gcg cac cag agc tgg gcg ctc ctc        670
Ser Ala Ala Pro Leu Pro Arg Leu Ala His Gln Ser Trp Ala Leu Leu
130                     135                     140                 145 cac gag gag tcg ccc ctc aac aac ttc ttg ctg agc cac ggc ccg ggc        718
His Glu Glu Ser Pro Leu Asn Asn Phe Leu Leu Ser His Gly Pro Gly
                    150                     155                     160 atc cgc ctc ttc aat ctt acc tcc acc ttc agt cgc cac tcg gat tac        766
Ile Arg Leu Phe Asn Leu Thr Ser Thr Phe Ser Arg His Ser Asp Tyr
                165                     170                     175 ccg ctg tcg ctg cag tgg ctg ccc ggg acc gcc tat ctg cgc cgc ccg        814
Pro Leu Ser Leu Gln Trp Leu Pro Gly Thr Ala Tyr Leu Arg Arg Pro
            180                     185                     190 gtg cct ccg ccc atg gaa cgc gcg gag tgg cgc cgc cgc ggc tac gcg        862
Val Pro Pro Pro Met Glu Arg Ala Glu Trp Arg Arg Arg Gly Tyr Ala
        195                     200                     205 ccg ctg ctc tat ctg cag tca cac tgc gac gtg cca gcg gac cgg gac        910
Pro Leu Leu Tyr Leu Gln Ser His Cys Asp Val Pro Ala Asp Arg Asp
210                     215                     220                 225 cgc tac gtg cgc gag ctc atg cgc cac atc ccg gta gac tcc tac ggg        958
Arg Tyr Val Arg Glu Leu Met Arg His Ile Pro Val Asp Ser Tyr Gly
                    230                     235                     240 aaa tgc ctg cag aat cgg gag ctg cct acc gcg cgg cta cag gac aca       1006
Lys Cys Leu Gln Asn Arg Glu Leu Pro Thr Ala Arg Leu Gln Asp Thr
                245                     250                     255 gcc acg gcc acc acc gag gat cca gag ctc ttg gct ttc ttg tcc cgc       1054
Ala Thr Ala Thr Thr Glu Asp Pro Glu Leu Leu Ala Phe Leu Ser Arg
            260                     265                     270 tat aag ttc cac ttg gcc ctg gaa aat gcc atc tgt aac gac tac atg       1102
Tyr Lys Phe His Leu Ala Leu Glu Asn Ala Ile Cys Asn Asp Tyr Met
        275                     280                     285 aca gaa aaa ctg tgg cgt ccc atg cac ctg ggc gct gtg ccc gtg tac       1150
Thr Glu Lys Leu Trp Arg Pro Met His Leu Gly Ala Val Pro Val Tyr
290                     295                     300                 305 cgc ggt tct ccc tct gtg agg gac tgg atg ccg aac aat cac tcc gtc       1198
Arg Gly Ser Pro Ser Val Arg Asp Trp Met Pro Asn Asn His Ser Val
                    310                     315                     320 atc ctg att gat gat ttt gag tct cct cag aag ctg gca gag ttt att       1246
Ile Leu Ile Asp Asp Phe Glu Ser Pro Gln Lys Leu Ala Glu Phe Ile
                325                     330                     335 gac ttt ctg gac aag aat gat gag gag tat atg aaa tac ctg gca tac       1294
Asp Phe Leu Asp Lys Asn Asp Glu Glu Tyr Met Lys Tyr Leu Ala Tyr
            340                     345                     350 aag caa cct ggg ggc atc acc aac caa ttt ctt ctg gat agt ctg aag       1342
Lys Gln Pro Gly Gly Ile Thr Asn Gln Phe Leu Leu Asp Ser Leu Lys
        355                     360                     365 cat cgg gag tgg gga gtg aat gat cct ttg ctg cct aac tac ctc aac       1390
His Arg Glu Trp Gly Val Asn Asp Pro Leu Leu Pro Asn Tyr Leu Asn
370                     375                     380                 385 ggc ttc gag tgt ttc gtc tgt gac tac gaa ctg gct cgg ctg gat gcc       1438
Gly Phe Glu Cys Phe Val Cys Asp Tyr Glu Leu Ala Arg Leu Asp Ala
                    390                     395                     400 gag aaa gcc cac gcg gcc tct ccc ggg gac agc ccc gtc ttt gag ccc       1486
```

-continued

```
Glu Lys Ala His Ala Ala Ser Pro Gly Asp Ser Pro Val Phe Glu Pro
            405                 410                 415 cac att gcc cag ccc tca cac atg gac tgc cca gtg ccc aca cct ggc    1534
His Ile Ala Gln Pro Ser His Met Asp Cys Pro Val Pro Thr Pro Gly
        420                 425                 430 ttt ggc aat gtg gaa gag att cct gag aat gac agt tgg aaa gag atg    1582
Phe Gly Asn Val Glu Glu Ile Pro Glu Asn Asp Ser Trp Lys Glu Met
    435                 440                 445 tgg ctg caa gat tat tgg caa ggt ctg gac cag ggg gaa gct ctc act    1630
Trp Leu Gln Asp Tyr Trp Gln Gly Leu Asp Gln Gly Glu Ala Leu Thr
450                 455                 460                 465 gcc atg atc cac aac aat gaa aca gag cag acg aaa ttt tgg gat tac    1678
Ala Met Ile His Asn Asn Glu Thr Glu Gln Thr Lys Phe Trp Asp Tyr
                470                 475                 480 cta cat gaa atc ttc atg aag agg caa cat ctc taagtgccct tgcaagagcc  1731
Leu His Glu Ile Phe Met Lys Arg Gln His Leu
                485                 490 tttaacttgg cggagctaag gagatcttat tctaccatgg acataagga gcatccactg   1791 cacaaaccct taatgaacac tgtcttttca tggattcaag gaattccagt tttatctatt   1851 aagatttat cttaatgatg agtagccaag gtctaacata gggcctctcc tcaaggagag   1911
atggagggat acaattcttg gttcagtggg aaacagaacc ctaaaacatc catttgattc   1971
aaggtgctgg tccaacagag tttttaaact actcacttct ttatttcatc ctttcgactg   2031
tacttgatta ccagtgaagt aagatgggtc aggttacgac ttacaacttt tgttctattc   2091
cccagactcc tcattattca gtacatttcc caataatctc ttttttctcat ctcttgcttt   2151 ataaattgtt acgttggtgg agaagcaaaa catttggtga gttgtattct ggttttccgg   2211
agttggattt ttttatatta tatactttca tgtcaaactt cwawtttact tatttattta   2271 ttttttttaaa atattttttg tagagatgag gttttgccac attgcccagg ttggtctcca   2331
actcctggat caagcaatcc atccgccttg acctcccaga gtgctgggtt tacaggcatc   2391
agccacctca cccagcccta atttttttt tttttttggc ttttttctggc caggcgtagt   2451 ggcttatgcc tgtaatccca acactttggg aggccgagga gaggcgactg cttgaagcca   2511
ggagtttgag accatcctag caagaccttg tctctaaaaa ataaaa                2557
```

```
<210> SEQ ID NO 20
<211> LENGTH: 492
<212> TYPE: PRT
<213> ORGANISM: Homo sapiens

<400> SEQUENCE: 20

Met Ala Ala Gly Pro Ile Arg Val Val Leu Val Leu Leu Gly Val Leu
1               5                   10                  15

Ser Val Cys Ala Ala Ser Gly His Gly Ser Val Ala Glu Arg Glu Ala
            20                  25                  30

Gly Gly Glu Ala Glu Trp Ala Glu Pro Trp Asp Gly Ala Val Phe Arg
        35                  40                  45

Pro Pro Ser Ala Leu Gly Ala Val Gly Val Thr Arg Ser Ser Gly Thr
    50                  55                  60

Pro Arg Pro Gly Arg Glu Glu Ala Gly Asp Leu Pro Val Leu Leu Trp
65                  70                  75                  80

Trp Ser Pro Gly Leu Phe Pro His Phe Pro Gly Asp Ser Glu Arg Ile
                85                  90                  95

Glu Cys Ala Arg Gly Ala Cys Val Ala Ser Arg Asn Arg Arg Ala Leu
            100                 105                 110
```

```
-continued

Arg Asp Ser Arg Thr Arg Ala Leu Leu Phe Tyr Gly Thr Asp Phe Arg
            115                 120                 125

Ala Ser Ala Ala Pro Leu Pro Arg Leu Ala His Gln Ser Trp Ala Leu
    130                 135                 140

Leu His Glu Glu Ser Pro Leu Asn Asn Phe Leu Leu Ser His Gly Pro
145                 150                 155                 160

Gly Ile Arg Leu Phe Asn Leu Thr Ser Thr Phe Ser Arg His Ser Asp
                165                 170                 175

Tyr Pro Leu Ser Leu Gln Trp Leu Pro Gly Thr Ala Tyr Leu Arg Arg
            180                 185                 190

Pro Val Pro Pro Met Glu Arg Ala Glu Trp Arg Arg Gly Tyr
    195                 200                 205

Ala Pro Leu Leu Tyr Leu Gln Ser His Cys Asp Val Pro Ala Asp Arg
    210                 215                 220

Asp Arg Tyr Val Arg Glu Leu Met Arg His Ile Pro Val Asp Ser Tyr
225                 230                 235                 240

Gly Lys Cys Leu Gln Asn Arg Glu Leu Pro Thr Ala Arg Leu Gln Asp
                245                 250                 255

Thr Ala Thr Ala Thr Thr Glu Asp Pro Glu Leu Leu Ala Phe Leu Ser
            260                 265                 270

Arg Tyr Lys Phe His Leu Ala Leu Glu Asn Ala Ile Cys Asn Asp Tyr
            275                 280                 285

Met Thr Glu Lys Leu Trp Arg Pro Met His Leu Gly Ala Val Pro Val
    290                 295                 300

Tyr Arg Gly Ser Pro Ser Val Arg Asp Trp Met Pro Asn Asn His Ser
305                 310                 315                 320

Val Ile Leu Ile Asp Asp Phe Glu Ser Pro Gln Lys Leu Ala Glu Phe
                325                 330                 335

Ile Asp Phe Leu Asp Lys Asn Asp Glu Glu Tyr Met Lys Tyr Leu Ala
                340                 345                 350

Tyr Lys Gln Pro Gly Gly Ile Thr Asn Gln Phe Leu Leu Asp Ser Leu
            355                 360                 365

Lys His Arg Glu Trp Gly Val Asn Asp Pro Leu Leu Pro Asn Tyr Leu
370                 375                 380

Asn Gly Phe Glu Cys Phe Val Cys Asp Tyr Glu Leu Ala Arg Leu Asp
385                 390                 395                 400

Ala Glu Lys Ala His Ala Ala Ser Pro Gly Asp Ser Pro Val Phe Glu
                405                 410                 415

Pro His Ile Ala Gln Pro Ser His Met Asp Cys Pro Val Pro Thr Pro
            420                 425                 430

Gly Phe Gly Asn Val Glu Glu Ile Pro Glu Asn Asp Ser Trp Lys Glu
        435                 440                 445

Met Trp Leu Gln Asp Tyr Trp Gln Gly Leu Asp Gln Gly Glu Ala Leu
    450                 455                 460

Thr Ala Met Ile His Asn Asn Glu Thr Glu Gln Thr Lys Phe Trp Asp
465                 470                 475                 480

Tyr Leu His Glu Ile Phe Met Lys Arg Gln His Leu
                485                 490

<210> SEQ ID NO 21
<211> LENGTH: 1479
<212> TYPE: DNA
<213> ORGANISM: Homo sapiens
```

-continued

```
<400> SEQUENCE: 21
atggcggccg gccccattag ggtggtgttg gtccttctag gggtgctcag tgtctgtgca      60
gccagcggcc atgggtccgt agcggagagg gaggccggcg gggaggcgga gtgggcggaa     120
ccgtgggatg gcgcggtttt ccggccgccc tcggcgctgg gcgcagtggg ggtgacgcgc     180
agctctggga cgccgcggcc agggaggag gaggcggggg acttgccggt actgctgtgg      240
tggagcccag ggctattccc ccacttcccg ggagactcgg agcgcatcga gtgtgcgcgc     300
ggcgcgtgcg tggcgtcccg gaaccgccga gcgctgaggg actcgcggac gcgcgcgctg     360
ctcttctacg gcacagactt ccgcgcgtcg gccgccccgc tgccgcgcct ggcgcaccag     420
agctgggcgc tcctccacga ggagtcgccc ctcaacaact tcttgctgag ccacggcccg     480
ggcatccgcc tcttcaatct tacctccacc ttcagtcgcc actcggatta cccgctgtcg     540
ctgcagtggc tgcccgggac cgcctatctg cgccgcccgg tgcctccgcc catggaacgc     600
gcggagtggc gccgccgcgg ctacgcgccg ctgctctatc tgcagtcaca ctgcgacgtg     660
ccagcggacc gggaccgcta cgtgcgcgag ctcatgcgcc acatcccggt agactcctac     720
gggaaatgcc tgcagaatcg ggagctgcct accgcgcggc tacaggacac agccacggcc     780
accaccgagg atccagagct cttggctttc ttgtcccgct ataagttcca cttggccctg     840
gaaaatgcca tctgtaacga ctacatgaca gaaaaactgt ggcgtcccat gcacctgggc     900
gctgtgcccg tgtaccgcgg ttctccctct gtgagggact ggatgccgaa caatcactcc     960
gtcatcctga ttgatgattt tgagtctcct cagaagctgg cagagtttat tgactttctg    1020
gacaagaatg atgaggagta tgaaaatac ctggcataca agcaacctgg gggcatcacc     1080
aaccaatttc ttctggatag tctgaagcat cgggagtggg gagtgaatga tcctttgctg    1140
cctaactacc tcaacggctt cgagtgtttc gtctgtgact acgaactggc tcggctggat    1200
gccgagaaag cccacgcggc ctctcccggg gacagccccg tctttgagcc ccacattgcc    1260
cagccctcac acatggactg cccagtgccc acacctggct ttggcaatgt ggaagagatt    1320
cctgagaatg acagttggaa agagatgtgg ctgcaagatt attggcaagg tctggaccag    1380
gggaagctc tcactgccat gatccacaac aatgaaacag agcagacgaa atttgggat      1440
tacctacatg aaatcttcat gaagaggcaa catctctaa                           1479
```

<210> SEQ ID NO 22
<211> LENGTH: 292
<212> TYPE: PRT
<213> ORGANISM: Artificial Sequence
<220> FEATURE:
<223> OTHER INFORMATION: consensus sequence

<400> SEQUENCE: 22

```
Gly Cys Gln Ser Thr Ser Ala Thr Pro Pro His Gly Thr Leu Thr Ile
 1               5                  10                  15

Leu Leu Trp His Trp Pro Phe Thr Asn Arg Pro Thr Ala Leu Pro Asp
            20                  25                  30

Cys Ser Glu Met Trp Pro Gly Met Ala Asp Cys His Ile Thr Ala Asp
        35                  40                  45

Arg Ser Glu Tyr Pro Lys Ala Asp Ala Val Ile Phe His His Arg Asp
    50                  55                  60

Val Asn Ala Asn Pro Arg Ser Ala Leu Pro Met His Lys Ser Pro Arg
65                  70                  75                  80

Pro Pro Gly Gln Arg Trp Val Trp Phe Asn Met Glu Ser Pro Ser Asn
                85                  90                  95
```

```
Thr Pro Gly Leu Lys Ala Leu Asn Lys Asn Tyr Phe Asn Trp Thr Met
                100                 105                 110

Ser Tyr Arg Thr Asp Ser Asp Ile Phe Val Pro Tyr Gly Tyr Leu Thr
            115                 120                 125

Pro Lys Ser Gly Pro Pro Ala Glu Val Val Tyr Pro Leu Ala Leu Ser
        130                 135                 140

Ser Lys Thr Lys Leu Val Ala Trp Val Val Ser Asn Trp Asn Glu Asp
145                 150                 155                 160

Ser Ala Arg Val Arg Tyr Tyr Asn Gln Leu Asp Gln Lys His Leu Glu
                165                 170                 175

Val Asp Val Tyr Gly Arg Cys Tyr Pro His Lys Pro Pro Asn Leu Pro
            180                 185                 190

Ala Asp Cys Leu Met Glu Thr Val Leu Asn Thr Leu Asp Ser Lys Tyr
        195                 200                 205

Lys Phe Tyr Leu Ala Phe Glu Asn Ser Lys Asp His Pro Asp Tyr Ile
    210                 215                 220

Thr Glu Lys Leu Trp Arg Asp Ala Phe Tyr Ala Gly Ala Val Pro Val
225                 230                 235                 240

Val Leu Gly Pro Arg Arg Ala Asn Tyr Glu Arg Phe Ile Pro Asp Asp
                245                 250                 255

Ala Phe Ile Asn Tyr Asp Asp Phe Arg Ser Asn Tyr Asp Leu Tyr Ala
            260                 265                 270

Tyr Leu Lys His Met Asp Lys Asn Glu Ser Gln Tyr Leu Thr Tyr Phe
        275                 280                 285

Asn Trp Arg Lys
    290

<210> SEQ ID NO 23
<211> LENGTH: 502
<212> TYPE: PRT
<213> ORGANISM: Artificial Sequence
<220> FEATURE:
<223> OTHER INFORMATION: consensus sequence

<400> SEQUENCE: 23

Leu Ser Asp Ala Phe Leu Arg Leu Leu Trp Arg Glu Lys Leu Leu Gly
1               5                   10                  15

Leu Leu Ile Thr Val Pro Pro Leu Leu Leu Ala Ile Ala Ala Trp Ile
            20                  25                  30

Gly Leu Glu Glu Ile Lys Glu Trp Lys Lys Ser Pro Leu Tyr Leu Ser
        35                  40                  45

Asn Asp His Glu Leu Asp Val Pro Ile Leu Ile Leu Ser Gln Ala
    50                  55                  60

Pro Gln Gly Ser Arg Phe Pro Thr Leu Glu Glu Asn Arg Ile Leu Leu
65                  70                  75                  80

Trp Thr Trp Pro Phe Asn Asp Arg Gly Ala Pro Val Pro Pro Ser Arg
                85                  90                  95

Cys Ser Leu Ser Tyr Asp Asn Thr Ala Arg Cys Arg Leu Thr Ala Asn
            100                 105                 110

Arg Ser Glu Leu Glu Ser Ala Asp Ala Val Leu Phe Asn Ala Gly His
        115                 120                 125

His Arg Asp Leu Ser Lys Gly Pro Pro Met Asp Leu Pro Pro Glu Phe
    130                 135                 140

Thr Gln Val Arg Ala Arg Ala Glu Asp Ala Asp Ala Val Leu Leu Ala
145                 150                 155                 160
```

```
Tyr Glu Asp Asn Ala Ala Ala Glu Ala Leu Ala Thr Asp Phe Pro
                165                 170                 175

Arg Pro Pro Gly Gln Pro Trp Val Trp Ala Ser Met Glu Ser Pro Ser
            180                 185                 190

Asn Ser Gly Arg Phe Ala Val Pro Gly Phe Lys Ile Asn Val Leu Asn
        195                 200                 205

Gly Leu Gln Ile Leu Leu Asp Gly Tyr Phe Asn Trp Thr Leu Ser Tyr
    210                 215                 220

Arg Ala Asp Ser Asp Ala Phe His Pro Tyr Gly Tyr Leu Glu Pro Leu
225                 230                 235                 240

Thr Ala Lys Ala Arg Lys Arg Gly Phe Lys Val Gln Ser Gln Val Val
                245                 250                 255

Glu Ala Pro Leu Asn Leu Ser Ala Lys Ala Lys Leu Ala Ala Trp Val
            260                 265                 270

Val Ser Asn Cys Asn Thr Arg Ser Lys Arg Glu Arg Phe Tyr Lys Gln
        275                 280                 285

Leu Lys Lys His Leu Gln Val Asp Val Tyr Gly Arg Val Ala Asn Pro
    290                 295                 300

Leu Pro Leu Lys Ser Gly Cys Ser Lys Gly Val Glu Leu Ile Glu Thr
305                 310                 315                 320

Leu Ser Gln Tyr Lys Phe Tyr Leu Ala Phe Glu Asn Ser Gln His Glu
                325                 330                 335

Asp Tyr Val Thr Glu Lys Leu Trp Lys Asn Ala Leu Gln Ala Gly Thr
            340                 345                 350

Ile Pro Val Val Leu Gly Pro Ser Arg Ala Val Tyr Glu Asp Phe Val
        355                 360                 365

Pro Pro Lys Ser Phe Ile His Val Asp Asp Phe Lys Ser Ala Lys Glu
    370                 375                 380

Leu Ala Asp Tyr Leu Leu Tyr Leu Asp Lys Asn Pro Thr Ala Tyr Leu
385                 390                 395                 400

Asp Met Leu Tyr Glu Asn Pro Leu Asn Thr Leu Asp Gly Lys Ala Tyr
                405                 410                 415

Phe Tyr Gln Asp Leu Ser Phe Lys Lys Ile Leu Asp Phe Phe Lys Thr
            420                 425                 430

Ile Leu Glu Asn Asp Thr Ile Tyr His Lys Tyr Ser Glu Tyr Phe Glu
        435                 440                 445

Trp Arg Glu Asp Leu Arg Val Arg Leu Phe Ser Trp Asp Ala Leu Arg
    450                 455                 460

Val Leu Glu Tyr Asp Glu Gly Phe Cys Arg Val Cys Arg Leu Leu Gln
465                 470                 475                 480

Lys Ala Pro Asp Leu Leu Glu Leu Ser Arg Tyr Lys Thr Ile Pro Asn
                485                 490                 495

Leu Ala Lys Trp Phe Gln
            500

<210> SEQ ID NO 24
<211> LENGTH: 31
<212> TYPE: PRT
<213> ORGANISM: Artificial Sequence
<220> FEATURE:
<223> OTHER INFORMATION: signature motif
<220> FEATURE:
<221> NAME/KEY: VARIANT
<222> LOCATION: 2
<223> OTHER INFORMATION: Xaa = Lys, Arg, or His
<220> FEATURE:
```

```
<221> NAME/KEY: VARIANT
<222> LOCATION: 4-6, 11-13, 16, 23-29
<223> OTHER INFORMATION: Xaa = any amino acid
<220> FEATURE:
<221> NAME/KEY: VARIANT
<222> LOCATION: 7
<223> OTHER INFORMATION: Xaa = Phe, Leu, or Met
<220> FEATURE:
<221> NAME/KEY: VARIANT
<222> LOCATION: 10
<223> OTHER INFORMATION: Xaa = Ala or Ser
<220> FEATURE:
<221> NAME/KEY: VARIANT
<222> LOCATION: 20
<223> OTHER INFORMATION: Xaa = Leu or Phe
<220> FEATURE:
<221> NAME/KEY: VARIANT
<222> LOCATION: 22
<223> OTHER INFORMATION: Xaa = Arg or Lys
<220> FEATURE:
<221> NAME/KEY: VARIANT
<222> LOCATION: 30
<223> OTHER INFORMATION: Xaa = Val or Ile

<400> SEQUENCE: 24

Tyr Xaa Phe Xaa Xaa Xaa Xaa Glu Asn Xaa Xaa Xaa Xaa Asp Tyr Xaa
 1               5                  10                  15

Thr Glu Lys Xaa Trp Xaa Xaa Xaa Xaa Xaa Xaa Xaa Xaa Pro
         20                  25                  30

<210> SEQ ID NO 25
<211> LENGTH: 2302
<212> TYPE: DNA
<213> ORGANISM: Homo sapiens
<220> FEATURE:
<221> NAME/KEY: CDS
<222> LOCATION: (176)...(1903)

<400> SEQUENCE: 25
cggaactggt ccggcccgac tcacgacccc gcgggacccg ccggaaccc  ggcccgaccc      60 cggcgcgcgc gcggcggagg acgaggaaga gttgtggcga ggcagatcct gccccgtggc     120
cgcggccgtc tcgtagctcg gccccaggag gctcccggga gcgcctgtca gtgca atg     178
                                                             Met
                                                              1 ccg ccc cat gtg gtg ctc acc ttc cgg cgc ctg ggc tgc gcc ttg gcc      226
Pro Pro His Val Val Leu Thr Phe Arg Arg Leu Gly Cys Ala Leu Ala
           5                  10                  15 tcc tgc cgg ctg gcg cct gcg aga cac aga gga agt ggt ctt ctg cac      274
Ser Cys Arg Leu Ala Pro Ala Arg His Arg Gly Ser Gly Leu Leu His
         20                  25                  30 aca gcc cca gtg gcc cgc tcg gac agg agc gcc ccg gtg ttc acc cgt      322
Thr Ala Pro Val Ala Arg Ser Asp Arg Ser Ala Pro Val Phe Thr Arg
     35                  40                  45 gcc ctg gcc ttt ggg gac aga atc gcc ctg gtt gac cag cac ggc cgc      370
Ala Leu Ala Phe Gly Asp Arg Ile Ala Leu Val Asp Gln His Gly Arg
 50                  55                  60                  65 cac acg tac agg gag ctt tat tcc cgc agc ctt cgc ctg tcc cag gag      418
His Thr Tyr Arg Glu Leu Tyr Ser Arg Ser Leu Arg Leu Ser Gln Glu
             70                  75                  80 atc tgc agg ctc tgc ggg tgt gtc ggc ggg gac ctc cgg gag gag agg      466
Ile Cys Arg Leu Cys Gly Cys Val Gly Gly Asp Leu Arg Glu Glu Arg
         85                  90                  95 gtc tcc ttc cta tgt gct aac gac gcc tcc tac gtc gtg gcc cag tgg      514
Val Ser Phe Leu Cys Ala Asn Asp Ala Ser Tyr Val Val Ala Gln Trp
        100                 105                 110
```

-continued

| | |
|---|---|
| gcc tca tgg atg agc ggc ggt gtg gca gta ccc ctc tac agg aag cat<br>Ala Ser Trp Met Ser Gly Gly Val Ala Val Pro Leu Tyr Arg Lys His<br>115                           120                        125 | 562 |
| ccc gcg gcc cag ctg gag tat gtc atc tgc gac tcc cag agc tct gtg<br>Pro Ala Ala Gln Leu Glu Tyr Val Ile Cys Asp Ser Gln Ser Ser Val<br>130                         135                     140                     145 | 610 |
| gtc ctt gcc agc cag gag tac ctg gag ctc ctg agc ccg gtg gtc agg<br>Val Leu Ala Ser Gln Glu Tyr Leu Glu Leu Leu Ser Pro Val Val Arg<br>              150                     155                     160 | 658 |
| aag ctg ggg gtc ccg ctg ctg ccg ctc aca cca gcc atc tac act gga<br>Lys Leu Gly Val Pro Leu Leu Pro Leu Thr Pro Ala Ile Tyr Thr Gly<br>        165                     170                     175 | 706 |
| gca gta gag gaa ccg gca gag gtc ccg gtc cca gag cag gga tgg agg<br>Ala Val Glu Glu Pro Ala Glu Val Pro Val Pro Glu Gln Gly Trp Arg<br>180                         185                     190 | 754 |
| aac aag ggc gcc atg atc atc tac acc agt ggg acc acg ggg agg ccc<br>Asn Lys Gly Ala Met Ile Ile Tyr Thr Ser Gly Thr Thr Gly Arg Pro<br>        195                     200                     205 | 802 |
| aag ggc gtg ctg agc acg cac caa aac atc agg gct gtg gtg acc ggg<br>Lys Gly Val Leu Ser Thr His Gln Asn Ile Arg Ala Val Val Thr Gly<br>210                         215                     220                     225 | 850 |
| ctg gtc cac aag tgg gca tgg acc aaa gac gac gtg atc ctc cac gtg<br>Leu Val His Lys Trp Ala Trp Thr Lys Asp Asp Val Ile Leu His Val<br>                  230                     235                     240 | 898 |
| ctc ccg ctg cac cac gtc cat ggt gtg gtc aac gcg ctg ctc tgt cct<br>Leu Pro Leu His His Val His Gly Val Val Asn Ala Leu Leu Cys Pro<br>              245                     250                     255 | 946 |
| ctc tgg gtg gga gcc acc tgt gtg atg atg cct gag ttc agc cct cag<br>Leu Trp Val Gly Ala Thr Cys Val Met Met Pro Glu Phe Ser Pro Gln<br>260                         265                     270 | 994 |
| cag gtt tgg gaa aag ttc tta agt tct gaa acg ccg cgg atc aat gtc<br>Gln Val Trp Glu Lys Phe Leu Ser Ser Glu Thr Pro Arg Ile Asn Val<br>       275                     280                     285 | 1042 |
| ttt atg gca gtg cct aca ata tac acc aag ctg atg gag tac tac gac<br>Phe Met Ala Val Pro Thr Ile Tyr Thr Lys Leu Met Glu Tyr Tyr Asp<br>290                         295                     300                     305 | 1090 |
| agg cat ttt acc cag ccg cac gcc cag gat ttc ttg cgt gca gtt tgt<br>Arg His Phe Thr Gln Pro His Ala Gln Asp Phe Leu Arg Ala Val Cys<br>              310                     315                     320 | 1138 |
| gaa gaa aaa att agg ctg atg gtc tca ggc tca gct gcc ctg ccc ctc<br>Glu Glu Lys Ile Arg Leu Met Val Ser Gly Ser Ala Ala Leu Pro Leu<br>325                         330                     335 | 1186 |
| cca gtg ctg gag aag tgg aag aac atc acg ggc cac acc ctg ctg gag<br>Pro Val Leu Glu Lys Trp Lys Asn Ile Thr Gly His Thr Leu Leu Glu<br>       340                     345                     350 | 1234 |
| cgg tat ggc atg acc gag atc ggc atg gct ctg tcc ggg ccc ctg acc<br>Arg Tyr Gly Met Thr Glu Ile Gly Met Ala Leu Ser Gly Pro Leu Thr<br>355                         360                     365 | 1282 |
| act gcc atg cgc ctg cca ggt tcc gtg ggg acc cca ctg cct gga gta<br>Thr Ala Met Arg Leu Pro Gly Ser Val Gly Thr Pro Leu Pro Gly Val<br>370                         375                     380                     385 | 1330 |
| cag gtg cgc att gtc tca gaa aac cca cag agg gaa gcc tgc tcc tac<br>Gln Val Arg Ile Val Ser Glu Asn Pro Gln Arg Glu Ala Cys Ser Tyr<br>              390                     395                     400 | 1378 |
| acc atc cac gca gag gga gac gag agg ggg acc aag gtg acc cca ggg<br>Thr Ile His Ala Glu Gly Asp Glu Arg Gly Thr Lys Val Thr Pro Gly<br>              405                     410                     415 | 1426 |
| ttt gaa gaa aag gag ggg gag ctg ctg gtg agg gga ccc tcc gtg ttt<br>Phe Glu Glu Lys Glu Gly Glu Leu Leu Val Arg Gly Pro Ser Val Phe<br>420                         425                     430 | 1474 |

-continued

```
cga gaa tac tgg aat aaa cca gaa gaa act aag agt gca ttc acc ctg      1522
Arg Glu Tyr Trp Asn Lys Pro Glu Glu Thr Lys Ser Ala Phe Thr Leu
    435                 440                 445 gat ggc tgg ttt aag aca ggg gac acc gtg gtg ttt aag gat ggc cag      1570
Asp Gly Trp Phe Lys Thr Gly Asp Thr Val Val Phe Lys Asp Gly Gln
450                 455                 460                 465 tac tgg atc cga ggc cgg acc tca gtg gac atc atc aag act gga ggc      1618
Tyr Trp Ile Arg Gly Arg Thr Ser Val Asp Ile Ile Lys Thr Gly Gly
                470                 475                 480 tac aag gtc agc gcc ctg gag gtg gag tgg cac ctg ctg gcc cac ccc      1666
Tyr Lys Val Ser Ala Leu Glu Val Glu Trp His Leu Leu Ala His Pro
485                 490                 495 agc atc aca gat gtg gct gtg att gga gtt ccg gat atg aca tgg ggc      1714
Ser Ile Thr Asp Val Ala Val Ile Gly Val Pro Asp Met Thr Trp Gly
        500                 505                 510 cag cgg gtc act gct gtg gtg acc ctc cga gaa gga cac tca ctg tcc      1762
Gln Arg Val Thr Ala Val Val Thr Leu Arg Glu Gly His Ser Leu Ser
    515                 520                 525 cac agg gag ctc aaa gag tgg gcc aga aat gtc ctg gcc ccg tac gcg      1810
His Arg Glu Leu Lys Glu Trp Ala Arg Asn Val Leu Ala Pro Tyr Ala
530                 535                 540                 545 gtg ccc tcg gag ctg gtg ctg gtg gag gag atc ccg cgg aac cag atg      1858
Val Pro Ser Glu Leu Val Leu Val Glu Glu Ile Pro Arg Asn Gln Met
                550                 555                 560 ggc aag att gac aag aag gcg ctc atc agg cac ttc cac ccc tca           1903
Gly Lys Ile Asp Lys Lys Ala Leu Ile Arg His Phe His Pro Ser
                565                 570                 575 tgacccggca gactgggact gcgggtctgg tggggagcag cagacgtccc cttcacaccg      1963
agaaccacgg gggcccgtcc aagacctggc ctcccttaaa cctgaacccc ccaaatcagg      2023
tcacgtagaa tcaagaactg tttgggatga atcaccatg tggggtcccc agcctcgggc       2083
cagttgttgc agctcaagga gaccgtccct ggtgtcacct ctgcctggtc accgccgacc      2143
tcatctgtgc agcgcggtgc agccagcccc tggccccacg tgctgaggca cctcccgccc      2203
cacagtgccc tgcagttgcc aggctctcca gggcaggtcc cagaggtttc ccacaaaaaa      2263
caaataaaga ctccactgga ggaaacaaaa aaaaaaaaa                             2302
```

<210> SEQ ID NO 26
<211> LENGTH: 576
<212> TYPE: PRT
<213> ORGANISM: Homo sapiens

<400> SEQUENCE: 26

```
Met Pro Pro His Val Val Leu Thr Phe Arg Arg Leu Gly Cys Ala Leu
1               5                   10                  15

Ala Ser Cys Arg Leu Ala Pro Ala Arg His Arg Gly Ser Gly Leu Leu
            20                  25                  30

His Thr Ala Pro Val Ala Arg Ser Asp Arg Ser Ala Pro Val Phe Thr
        35                  40                  45

Arg Ala Leu Ala Phe Gly Asp Arg Ile Ala Leu Val Asp Gln His Gly
    50                  55                  60

Arg His Thr Tyr Arg Glu Leu Tyr Ser Arg Ser Leu Arg Leu Ser Gln
65                  70                  75                  80

Glu Ile Cys Arg Leu Cys Gly Cys Val Gly Gly Asp Leu Arg Glu Glu
                85                  90                  95

Arg Val Ser Phe Leu Cys Ala Asn Asp Ala Ser Tyr Val Val Ala Gln
            100                 105                 110
```

-continued

```
Trp Ala Ser Trp Met Ser Gly Gly Val Ala Val Pro Leu Tyr Arg Lys
        115                 120                 125

His Pro Ala Ala Gln Leu Glu Tyr Val Ile Cys Asp Ser Gln Ser Ser
    130                 135                 140

Val Val Leu Ala Ser Gln Glu Tyr Leu Glu Leu Ser Pro Val Val
145                 150                 155                 160

Arg Lys Leu Gly Val Pro Leu Pro Leu Thr Pro Ala Ile Tyr Thr
                165                 170                 175

Gly Ala Val Glu Glu Pro Ala Glu Val Pro Val Pro Glu Gln Gly Trp
                180                 185                 190

Arg Asn Lys Gly Ala Met Ile Ile Tyr Thr Ser Gly Thr Thr Gly Arg
        195                 200                 205

Pro Lys Gly Val Leu Ser Thr His Gln Asn Ile Arg Ala Val Val Thr
    210                 215                 220

Gly Leu Val His Lys Trp Ala Trp Thr Lys Asp Asp Val Ile Leu His
225                 230                 235                 240

Val Leu Pro Leu His His Val His Gly Val Val Asn Ala Leu Leu Cys
                245                 250                 255

Pro Leu Trp Val Gly Ala Thr Cys Val Met Met Pro Glu Phe Ser Pro
                260                 265                 270

Gln Gln Val Trp Glu Lys Phe Leu Ser Glu Thr Pro Arg Ile Asn
        275                 280                 285

Val Phe Met Ala Val Pro Thr Ile Tyr Thr Lys Leu Met Glu Tyr Tyr
    290                 295                 300

Asp Arg His Phe Thr Gln Pro His Ala Gln Asp Phe Leu Arg Ala Val
305                 310                 315                 320

Cys Glu Glu Lys Ile Arg Leu Met Val Ser Gly Ser Ala Ala Leu Pro
                325                 330                 335

Leu Pro Val Leu Glu Lys Trp Lys Asn Ile Thr Gly His Thr Leu Leu
                340                 345                 350

Glu Arg Tyr Gly Met Thr Glu Ile Gly Met Ala Leu Ser Gly Pro Leu
        355                 360                 365

Thr Thr Ala Met Arg Leu Pro Gly Ser Val Gly Thr Pro Leu Pro Gly
    370                 375                 380

Val Gln Val Arg Ile Val Ser Glu Asn Pro Gln Arg Glu Ala Cys Ser
385                 390                 395                 400

Tyr Thr Ile His Ala Glu Gly Asp Glu Arg Gly Thr Lys Val Thr Pro
                405                 410                 415

Gly Phe Glu Glu Lys Glu Gly Glu Leu Leu Val Arg Gly Pro Ser Val
                420                 425                 430

Phe Arg Glu Tyr Trp Asn Lys Pro Glu Glu Thr Lys Ser Ala Phe Thr
        435                 440                 445

Leu Asp Gly Trp Phe Lys Thr Gly Asp Thr Val Phe Lys Asp Gly
    450                 455                 460

Gln Tyr Trp Ile Arg Gly Arg Thr Ser Val Asp Ile Ile Lys Thr Gly
465                 470                 475                 480

Gly Tyr Lys Val Ser Ala Leu Glu Val Glu Trp His Leu Leu Ala His
                485                 490                 495

Pro Ser Ile Thr Asp Val Ala Val Ile Gly Val Pro Asp Met Thr Trp
                500                 505                 510

Gly Gln Arg Val Thr Ala Val Val Thr Leu Arg Glu Gly His Ser Leu
        515                 520                 525
```

Ser His Arg Glu Leu Lys Glu Trp Ala Arg Asn Val Leu Ala Pro Tyr
    530                 535                 540

Ala Val Pro Ser Glu Leu Val Leu Val Glu Glu Ile Pro Arg Asn Gln
545                 550                 555                 560

Met Gly Lys Ile Asp Lys Lys Ala Leu Ile Arg His Phe His Pro Ser
                565                 570                 575

<210> SEQ ID NO 27
<211> LENGTH: 1731
<212> TYPE: DNA
<213> ORGANISM: Homo sapiens

<400> SEQUENCE: 27

```
atgccgcccc atgtggtgct caccttccgg cgcctgggct gcgccttggc ctcctgccgg      60
ctggcgcctg cgagacacag aggaagtggt cttctgcaca cagccccagt ggcccgctcg     120
gacaggagcg ccccggtgtt cacccgtgcc ctggcctttg ggacagaat cgccctggtt      180
gaccagcacg gccgccacac gtacagggag ctttattccc gcagccttcg cctgtcccag     240
gagatctgca ggctctgcgg gtgtgtcggc ggggaccctcc ggaggagag gtctccttc      300
ctatgtgcta cgacgcctc ctacgtcgtg gcccagtggg cctcatggat gagcggcggt      360
gtggcagtac ccctctacag gaagcatccc gcggcccagc tggagtatgt catctgcgac     420
tcccagagct ctgtggtcct tgccagccag gagtacctgg agctcctgag cccggtggtc     480
aggaagctgg gggtcccgct gctgccgctc acaccagcca tctacactgg agcagtagag     540
gaaccggcag aggtccgggt cccagagcag ggatggagga caagggcgc catgatcatc     600
tacaccagtg ggaccacggg gaggcccaag ggcgtgctga gcacgcacca aaacatcagg     660
gctgtggtga ccgggctggt ccacaagtgg gcatggacca agacgacgt gatcctccac     720
gtgctcccgc tgcaccacgt ccatggtgtg gtcaacgcgc tgctctgtcc tctctgggtg     780
ggagccacct gtgtgatgat gcctgagttc agccctcagc aggtttggga aaagttctta     840
agttctgaaa cgccgcggat caatgtcttt atggcagtgc ctacaatata caccaagctg     900
atggagtact acgacaggca ttttacccag ccgcacgccc aggatttctt gcgtgcagtt     960
tgtgaagaaa aaattaggct gatggtctca ggctcagctg ccctgccct cccagtgctg    1020
gagaagtgga gaacatcac gggccacacc tgctggagc ggtatggcat gaccgagatc     1080
ggcatggctc tgtccgggcc cctgaccact gccatgcgcc tgccaggttc cgtggggacc    1140
ccactgcctg gagtacaggt gcgcattgtc tcagaaaacc cacagagga gcctgctcc     1200
tacaccatcc acgcagaggg agacgagagg gggaccaagg tgaccccagg gtttgaagaa    1260
aaggaggggg agctgctggt gaggggaccc tccgtgtttc gagaatactg gaataaacca    1320
gaagaaacta agagtgcatt caccctggat ggctggttta agacagggga caccgtggtg    1380
tttaaggatg ccagtactg gatccgaggc cggacctcag tggacatcat caagactgga    1440
ggctacaagg tcagcgccct ggaggtggag tggcacctgc tgcccacccc agcatcaca     1500
gatgtggctg tgattggagt tccggatatg catggggcc agcgggtcac tgctgtggtg    1560
accctccgag aaggacactc actgtcccac agggagctca agagtgggc cagaaatgtc    1620
ctggccccgt acgcggtgcc ctcggagctg gtgctggtgg aggagatccc gcggaaccag    1680
atgggcaaga ttgacaagaa ggcgctcatc aggcacttcc accctcatg a              1731
```

<210> SEQ ID NO 28
<211> LENGTH: 450
<212> TYPE: PRT

-continued

<213> ORGANISM: Artificial Sequence
<220> FEATURE:
<223> OTHER INFORMATION: consensus sequence

<400> SEQUENCE: 28

```
Thr Tyr Arg Glu Leu Asn Glu Arg Ala Asn Arg Leu Ala Arg His Leu
 1               5                  10                  15

Arg Ser Glu Lys Gly Val Lys Pro Gly Asp Leu Val Ala Ile Leu Met
             20                  25                  30

Glu Arg Ser Pro Glu Met Ile Val Ala Ile Leu Gly Ile Leu Lys Ala
         35                  40                  45

Gly Gly Ala Tyr Val Pro Ile Asp Pro Gly Tyr Pro Ala Glu Arg Ile
     50                  55                  60

Ser Tyr Ile Leu Glu Asp Ser Gly Ala Lys Leu Leu Thr Gln Ala
 65                  70                  75                  80

Gly Phe Tyr Arg Ala Gly Leu Leu Lys Leu Ala Pro Asp Glu Ser Ala
             85                  90                  95

Asn Gly Pro Asn Val Gly Val His Val Leu Leu Asp Glu Glu
            100                 105                 110

Leu Ala Asp Val Val Glu Leu Asp Glu Leu Ala Pro His Glu Leu Val
            115                 120                 125

Pro Glu Gln Ser Glu Glu Asn Leu Gln Pro Pro Val Lys Pro Glu Asp
        130                 135                 140

Leu Ala Tyr Ile Ile Tyr Thr Ser Gly Thr Thr Gly Lys Pro Lys Gly
145                 150                 155                 160

Val Met Val Glu His Arg Asn Val Val Asn Leu Leu Gln Trp Leu Lys
                165                 170                 175

Glu Arg Tyr Gly Leu Thr Glu Glu Asp Asp Arg Val Leu Gln Phe
            180                 185                 190

Ala Ser Asp Ala Tyr Val Phe Asp Ala Ser Val Trp Asp Leu Phe Ala
        195                 200                 205

Ala Leu Leu Ala Gly Ala Thr Leu Val Ile Val Pro Lys Glu Thr Arg
    210                 215                 220

Tyr Leu Asp Pro Glu Ala Leu Tyr Gln Tyr Ile Glu Lys Glu Gly Val
225                 230                 235                 240

Thr Val Leu Ser Leu Thr Pro Ser Leu Leu Arg Met Leu Met Pro Ala
                245                 250                 255

Arg Thr Phe Ala Asn Asp Lys Gln Asp Leu Pro Ser Leu Arg Thr Leu
            260                 265                 270

Ile Phe Gly Gly Glu Ala Leu Ser Pro Ser Leu Val Asp Lys Trp Arg
        275                 280                 285

Glu Arg Phe Gly Asn Glu Lys Gly Arg Leu Ile Asn Thr Tyr Gly Pro
    290                 295                 300

Thr Glu Thr Thr Val Val Thr Thr Val Asn Arg Ile Thr Pro Glu Glu
305                 310                 315                 320

Ile Arg Gln Lys Ser Val Pro Ile Gly Arg Pro Leu Pro Asn Thr Gln
                325                 330                 335

Val Tyr Ile Leu Asp Glu Asn Gly Gln Leu Val Pro Ile Gly Val Ala
            340                 345                 350

Gly Glu Leu Tyr Ile Gly Gly Trp Pro Gly Val Ala Arg Gly Tyr Leu
        355                 360                 365

Asn Arg Pro Glu Leu Thr Ala Glu Arg Phe Val Pro Asn Pro Phe Gln
    370                 375                 380

Pro Gly Glu Glu Arg Arg Gly Arg Asn Arg Arg Met Tyr Arg Thr Gly
```

```
                385                 390                 395                 400
Asp Leu Ala Arg Trp Leu Pro Asp Gly Thr Ile Glu Tyr Leu Gly Arg
                    405                 410                 415

Ile Asp Asp Gln Val Lys Ile Arg Gly Tyr Arg Ile Glu Leu Gly Glu
            420                 425                 430

Ile Glu Ala Ala Leu Arg Leu Leu Gln His Pro Gly Val Lys Glu Ala
        435                 440                 445

Val Val
    450

<210> SEQ ID NO 29
<211> LENGTH: 9
<212> TYPE: PRT
<213> ORGANISM: Artificial Sequence
<220> FEATURE:
<223> OTHER INFORMATION: conserved sequence motif
<220> FEATURE:
<221> NAME/KEY: VARIANT
<222> LOCATION: 1, 2
<223> OTHER INFORMATION: Xaa = Ser, Thr, or Gly
<220> FEATURE:
<221> NAME/KEY: VARIANT
<222> LOCATION: 4
<223> OTHER INFORMATION: Xaa = Ser or Thr
<220> FEATURE:
<221> NAME/KEY: VARIANT
<222> LOCATION: 5
<223> OTHER INFORMATION: Xaa = Thr, Ser, or Glu
<220> FEATURE:
<221> NAME/KEY: VARIANT
<222> LOCATION: 6
<223> OTHER INFORMATION: Xaa = Gly or Ser
<220> FEATURE:
<221> NAME/KEY: VARIANT
<222> LOCATION: 7
<223> OTHER INFORMATION: Xaa = any amino acid
<220> FEATURE:
<221> NAME/KEY: VARIANT
<222> LOCATION: 8
<223> OTHER INFORMATION: Xaa = Pro, Ala, Leu, Ile, Val, or Met

<400> SEQUENCE: 29

Xaa Xaa Gly Xaa Xaa Xaa Xaa Xaa Lys
 1               5

<210> SEQ ID NO 30
<211> LENGTH: 5
<212> TYPE: PRT
<213> ORGANISM: Artificial Sequence
<220> FEATURE:
<223> OTHER INFORMATION: conserved sequence motif
<220> FEATURE:
<221> NAME/KEY: VARIANT
<222> LOCATION: 1
<223> OTHER INFORMATION: Xaa = Tyr, Phe, or Trp
<220> FEATURE:
<221> NAME/KEY: VARIANT
<222> LOCATION: 2
<223> OTHER INFORMATION: Xaa = Gly, Ala, Ser, or Trp
<220> FEATURE:
<221> NAME/KEY: VARIANT
<222> LOCATION: 3
<223> OTHER INFORMATION: Xaa = any amino acid
<220> FEATURE:
<221> NAME/KEY: VARIANT
<222> LOCATION: 4
<223> OTHER INFORMATION: Xaa = Thr, Ser, or Ala

<400> SEQUENCE: 30

Xaa Xaa Xaa Xaa Glu
 1               5
```

-continued

<210> SEQ ID NO 31
<211> LENGTH: 3
<212> TYPE: PRT
<213> ORGANISM: Artificial Sequence
<220> FEATURE:
<223> OTHER INFORMATION: conserved sequence motif
<220> FEATURE:
<221> NAME/KEY: VARIANT
<222> LOCATION: 1
<223> OTHER INFORMATION: Xaa = Ser, Thr, or Ala
<220> FEATURE:
<221> NAME/KEY: VARIANT
<222> LOCATION: 2
<223> OTHER INFORMATION: Xaa = Gly, Arg, or Lys

<400> SEQUENCE: 31

Xaa Xaa Asp
 1

<210> SEQ ID NO 32
<211> LENGTH: 2103
<212> TYPE: DNA
<213> ORGANISM: Homo sapiens
<220> FEATURE:
<221> NAME/KEY: CDS
<222> LOCATION: (145)...(1641)

<400> SEQUENCE: 32

```
atttggccct cgaggccaag aattcggcac gaggggata acgggaggaa ggccggccgg      60
ggccgccaag gcagtcccag gctcgcgtag gaggcgcgca gaccttgcac cttgcacctt     120
cgcagcgccc tgcaccccgc cacc atg tgc gag ctg tac agt aag cgg gac       171
                           Met Cys Glu Leu Tyr Ser Lys Arg Asp
                             1               5 act ctg ggg ctg agg aag aag cac atc ggg ccc tca tgc aaa gtt ttc      219
Thr Leu Gly Leu Arg Lys Lys His Ile Gly Pro Ser Cys Lys Val Phe
 10                  15                  20                  25 ttt gca tcg gat ccc atc aaa ata gtg aga gcc cag agg cag tac atg      267
Phe Ala Ser Asp Pro Ile Lys Ile Val Arg Ala Gln Arg Gln Tyr Met
                 30                  35                  40 ttt gat gag aac ggt gaa cag tac ttg gac tgc atc aac aat gtt gcc      315
Phe Asp Glu Asn Gly Glu Gln Tyr Leu Asp Cys Ile Asn Asn Val Ala
             45                  50                  55 cat gtg gga cac tgt cac cca gga gtg gtc aaa gct gcc ctg aaa cag      363
His Val Gly His Cys His Pro Gly Val Val Lys Ala Ala Leu Lys Gln
         60                  65                  70 atg gaa ctg cta aat aca aat tct cga ttc ctc cac gac aac att gtt      411
Met Glu Leu Leu Asn Thr Asn Ser Arg Phe Leu His Asp Asn Ile Val
     75                  80                  85 gag tat gcc aaa cgc ctt tca gca act ctg ccg gag aaa ctc tct gtt      459
Glu Tyr Ala Lys Arg Leu Ser Ala Thr Leu Pro Glu Lys Leu Ser Val
 90                  95                 100                 105 tgt tat ttt aca aat tca gga tcc gaa gcc aac gac tta gcc tta cgc      507
Cys Tyr Phe Thr Asn Ser Gly Ser Glu Ala Asn Asp Leu Ala Leu Arg
                110                 115                 120 ctg gct cgg cag ttc aga ggc cac cag gat gtg atc act ctt gac cat      555
Leu Ala Arg Gln Phe Arg Gly His Gln Asp Val Ile Thr Leu Asp His
                125                 130                 135 gct tac cat ggt tac cta tca tcc tta att gag att agc cca tat aag      603
Ala Tyr His Gly Tyr Leu Ser Ser Leu Ile Glu Ile Ser Pro Tyr Lys
            140                 145                 150 ttt cag aaa gga aaa gat gtc aaa aaa gaa ttt gta cat gtg gca cca      651
Phe Gln Lys Gly Lys Asp Val Lys Lys Glu Phe Val His Val Ala Pro
```

-continued

| | | | | | | | | | | | | | | | | |
|---|---|---|---|---|---|---|---|---|---|---|---|---|---|---|---|---|
| | | 155 | | | | 160 | | | | | 165 | | | | | |
| act | cca | gat | act | tac | aga | gga | aaa | tat | aga | gaa | gac | cat | gca | gac | tca | 699 |
| Thr | Pro | Asp | Thr | Tyr | Arg | Gly | Lys | Tyr | Arg | Glu | Asp | His | Ala | Asp | Ser | |
| 170 | | | | | 175 | | | | | 180 | | | | | 185 | |
| gcc | agt | gct | tat | gca | gat | gaa | gtg | aag | aaa | atc | att | gaa | gat | gct | cat | 747 |
| Ala | Ser | Ala | Tyr | Ala | Asp | Glu | Val | Lys | Lys | Ile | Ile | Glu | Asp | Ala | His | |
| | | | | 190 | | | | | 195 | | | | | 200 | | |
| aac | agt | gga | agg | aag | att | gct | gcc | ttt | att | gct | gaa | tcc | atg | cag | agt | 795 |
| Asn | Ser | Gly | Arg | Lys | Ile | Ala | Ala | Phe | Ile | Ala | Glu | Ser | Met | Gln | Ser | |
| | | | | 205 | | | | | 210 | | | | | 215 | | |
| tgt | ggc | gga | caa | ata | att | cct | cca | gca | ggc | tac | ttc | cag | aaa | gtg | gca | 843 |
| Cys | Gly | Gly | Gln | Ile | Ile | Pro | Pro | Ala | Gly | Tyr | Phe | Gln | Lys | Val | Ala | |
| | | | 220 | | | | | 225 | | | | | 230 | | | |
| gaa | tat | gta | cac | ggt | gca | ggg | ggt | gtg | ttt | ata | gct | gat | gaa | gtt | caa | 891 |
| Glu | Tyr | Val | His | Gly | Ala | Gly | Gly | Val | Phe | Ile | Ala | Asp | Glu | Val | Gln | |
| | | 235 | | | | | 240 | | | | | 245 | | | | |
| gtg | ggc | ttt | ggc | aga | gtt | ggg | aaa | cat | ttc | tgg | agc | ttc | cag | atg | tat | 939 |
| Val | Gly | Phe | Gly | Arg | Val | Gly | Lys | His | Phe | Trp | Ser | Phe | Gln | Met | Tyr | |
| 250 | | | | | 255 | | | | | 260 | | | | | 265 | |
| ggt | gaa | gac | ttt | gtt | cca | gac | atc | gtc | aca | atg | gga | aaa | ccg | atg | ggc | 987 |
| Gly | Glu | Asp | Phe | Val | Pro | Asp | Ile | Val | Thr | Met | Gly | Lys | Pro | Met | Gly | |
| | | | | 270 | | | | | 275 | | | | | 280 | | |
| aac | ggc | cac | ccg | gtg | gca | tgt | gtg | gta | aca | acc | aaa | gaa | att | gca | gaa | 1035 |
| Asn | Gly | His | Pro | Val | Ala | Cys | Val | Val | Thr | Thr | Lys | Glu | Ile | Ala | Glu | |
| | | | 285 | | | | | 290 | | | | | 295 | | | |
| gcc | ttc | agc | agc | tct | ggg | atg | gaa | tat | ttt | aat | acg | tat | gga | gga | aat | 1083 |
| Ala | Phe | Ser | Ser | Ser | Gly | Met | Glu | Tyr | Phe | Asn | Thr | Tyr | Gly | Gly | Asn | |
| | | | 300 | | | | | 305 | | | | | 310 | | | |
| cca | gta | tct | tgt | gct | gtt | ggt | ttg | gct | gtc | ctg | gat | ata | att | gaa | aat | 1131 |
| Pro | Val | Ser | Cys | Ala | Val | Gly | Leu | Ala | Val | Leu | Asp | Ile | Ile | Glu | Asn | |
| | 315 | | | | | 320 | | | | | 325 | | | | | |
| gaa | gac | ctt | caa | gga | aat | gcc | aag | aga | gta | ggg | aat | tat | ctc | act | gag | 1179 |
| Glu | Asp | Leu | Gln | Gly | Asn | Ala | Lys | Arg | Val | Gly | Asn | Tyr | Leu | Thr | Glu | |
| 330 | | | | | 335 | | | | | 340 | | | | | 345 | |
| tta | ctg | aaa | aaa | cag | aag | gct | aaa | cac | act | ttg | ata | gga | gat | att | agg | 1227 |
| Leu | Leu | Lys | Lys | Gln | Lys | Ala | Lys | His | Thr | Leu | Ile | Gly | Asp | Ile | Arg | |
| | | | | 350 | | | | | 355 | | | | | 360 | | |
| ggc | att | ggc | ctt | ttt | att | gga | att | gat | tta | gtg | aag | gac | cat | ctg | aaa | 1275 |
| Gly | Ile | Gly | Leu | Phe | Ile | Gly | Ile | Asp | Leu | Val | Lys | Asp | His | Leu | Lys | |
| | | | 365 | | | | | 370 | | | | | 375 | | | |
| agg | acc | cct | gcc | aca | gct | gaa | gct | cag | cac | atc | atc | tac | aag | atg | aaa | 1323 |
| Arg | Thr | Pro | Ala | Thr | Ala | Glu | Ala | Gln | His | Ile | Ile | Tyr | Lys | Met | Lys | |
| | | 380 | | | | | 385 | | | | | 390 | | | | |
| gaa | aaa | cga | gtg | ctt | ctc | agt | gcc | gat | gga | cct | cat | aga | aat | gta | ctt | 1371 |
| Glu | Lys | Arg | Val | Leu | Leu | Ser | Ala | Asp | Gly | Pro | His | Arg | Asn | Val | Leu | |
| 395 | | | | | 400 | | | | | 405 | | | | | | |
| aaa | ata | aaa | cca | cct | atg | tgc | ttc | act | gaa | gaa | gat | gca | aag | ttc | atg | 1419 |
| Lys | Ile | Lys | Pro | Pro | Met | Cys | Phe | Thr | Glu | Glu | Asp | Ala | Lys | Phe | Met | |
| 410 | | | | | 415 | | | | | 420 | | | | | 425 | |
| gtg | gac | caa | ctt | gat | agg | att | cta | aca | gtt | tta | gaa | gaa | gct | atg | gga | 1467 |
| Val | Asp | Gln | Leu | Asp | Arg | Ile | Leu | Thr | Val | Leu | Glu | Glu | Ala | Met | Gly | |
| | | | | 430 | | | | | 435 | | | | | 440 | | |
| acc | aaa | acc | gaa | agt | gtg | acc | tct | gag | aat | act | cca | tgc | aaa | aca | aag | 1515 |
| Thr | Lys | Thr | Glu | Ser | Val | Thr | Ser | Glu | Asn | Thr | Pro | Cys | Lys | Thr | Lys | |
| | | | | 445 | | | | | 450 | | | | | 455 | | |
| atg | ctg | aaa | gaa | gcc | cac | ata | gaa | ctg | ctt | agg | gac | agc | acc | act | gac | 1563 |
| Met | Leu | Lys | Glu | Ala | His | Ile | Glu | Leu | Leu | Arg | Asp | Ser | Thr | Thr | Asp | |
| | | | 460 | | | | | 465 | | | | | 470 | | | |
| tcc | aaa | gaa | aat | ccc | agc | aga | aag | aga | aat | gga | atg | tgc | acg | gat | aca | 1611 |

```
Ser Lys Glu Asn Pro Ser Arg Lys Arg Asn Gly Met Cys Thr Asp Thr
    475                 480                 485
```

| | | |
|---|---|---|
| cat tca ctg ctc agt aag agg ctc aag aca tgactgattt gcattttaaa<br>His Ser Leu Leu Ser Lys Arg Leu Lys Thr<br>490             495 | | 1661 |
| gcaagatgcg atgtccagag ttacagagaa tgagtagatg tgtctcatcg gttaatagct | | 1721 |
| ctattatacc tctaaaggtg gaattgtcag tttagattca taaatgaaaa ggtaaatgag | | 1781 |
| taatcagaat aaaccaagtg ataatcaaac catgtcaaga ttattagttc agactctagc | | 1841 |
| ctgttaattt tcttagttga tttctgaagc tacctgattt attctattaa attgtaagct | | 1901 |
| tgcaaactca aaataaattg gcagatttac ctctcatgtt ttaatgtgtc aaattagaga | | 1961 |
| gcaaagtata acaggtgcct tcacttttga gacttagtgc cttaaaatat gtattctata | | 2021 |
| atgatttcat atataaaagt atatttattg actgtaataa aataaaatat gatgtaaaca | | 2081 |
| aaaaaaaaaa aaaaaaaaaa aa | | 2103 |

```
<210> SEQ ID NO 33
<211> LENGTH: 499
<212> TYPE: PRT
<213> ORGANISM: Homo sapiens

<400> SEQUENCE: 33

Met Cys Glu Leu Tyr Ser Lys Arg Asp Thr Leu Gly Leu Arg Lys Lys
1               5                   10                  15

His Ile Gly Pro Ser Cys Lys Val Phe Phe Ala Ser Asp Pro Ile Lys
            20                  25                  30

Ile Val Arg Ala Gln Arg Gln Tyr Met Phe Asp Glu Asn Gly Glu Gln
        35                  40                  45

Tyr Leu Asp Cys Ile Asn Asn Val Ala His Val Gly His Cys His Pro
    50                  55                  60

Gly Val Val Lys Ala Ala Leu Lys Gln Met Glu Leu Leu Asn Thr Asn
65                  70                  75                  80

Ser Arg Phe Leu His Asp Asn Ile Val Glu Tyr Ala Lys Arg Leu Ser
                85                  90                  95

Ala Thr Leu Pro Glu Lys Leu Ser Val Cys Tyr Phe Thr Asn Ser Gly
            100                 105                 110

Ser Glu Ala Asn Asp Leu Ala Leu Arg Leu Ala Arg Gln Phe Arg Gly
        115                 120                 125

His Gln Asp Val Ile Thr Leu Asp His Ala Tyr His Gly Tyr Leu Ser
    130                 135                 140

Ser Leu Ile Glu Ile Ser Pro Tyr Lys Phe Gln Lys Gly Lys Asp Val
145                 150                 155                 160

Lys Lys Glu Phe Val His Val Ala Pro Thr Pro Asp Thr Tyr Arg Gly
                165                 170                 175

Lys Tyr Arg Glu Asp His Ala Asp Ser Ala Ser Ala Tyr Ala Asp Glu
            180                 185                 190

Val Lys Lys Ile Ile Glu Asp Ala His Asn Ser Gly Arg Lys Ile Ala
        195                 200                 205

Ala Phe Ile Ala Glu Ser Met Gln Ser Cys Gly Gly Gln Ile Ile Pro
    210                 215                 220

Pro Ala Gly Tyr Phe Gln Lys Val Ala Glu Tyr Val His Gly Ala Gly
225                 230                 235                 240

Gly Val Phe Ile Ala Asp Glu Val Gln Val Gly Phe Gly Arg Val Gly
                245                 250                 255
```

| Lys | His | Phe | Trp | Ser | Phe | Gln | Met | Tyr | Gly | Glu | Asp | Phe | Val | Pro | Asp |
| | | | 260 | | | | | 265 | | | | | 270 | | |

| Ile | Val | Thr | Met | Gly | Lys | Pro | Met | Gly | Asn | Gly | His | Pro | Val | Ala | Cys |
| | | 275 | | | | | 280 | | | | | 285 | | | |

| Val | Val | Thr | Thr | Lys | Glu | Ile | Ala | Glu | Ala | Phe | Ser | Ser | Gly | Met |
| | 290 | | | | | 295 | | | | | 300 | | | |

| Glu | Tyr | Phe | Asn | Thr | Tyr | Gly | Gly | Asn | Pro | Val | Ser | Cys | Ala | Val | Gly |
| 305 | | | | | 310 | | | | | 315 | | | | | 320 |

| Leu | Ala | Val | Leu | Asp | Ile | Ile | Glu | Asn | Glu | Asp | Leu | Gln | Gly | Asn | Ala |
| | | | | 325 | | | | | 330 | | | | | 335 | |

| Lys | Arg | Val | Gly | Asn | Tyr | Leu | Thr | Glu | Leu | Leu | Lys | Lys | Gln | Lys | Ala |
| | | | | 340 | | | | | 345 | | | | | 350 | |

| Lys | His | Thr | Leu | Ile | Gly | Asp | Ile | Arg | Gly | Ile | Gly | Leu | Phe | Ile | Gly |
| | | | 355 | | | | | 360 | | | | | 365 | | |

| Ile | Asp | Leu | Val | Lys | Asp | His | Leu | Lys | Arg | Thr | Pro | Ala | Thr | Ala | Glu |
| | 370 | | | | | 375 | | | | | 380 | | | | |

| Ala | Gln | His | Ile | Ile | Tyr | Lys | Met | Lys | Glu | Lys | Arg | Val | Leu | Leu | Ser |
| 385 | | | | | 390 | | | | | 395 | | | | | 400 |

| Ala | Asp | Gly | Pro | His | Arg | Asn | Val | Leu | Lys | Ile | Lys | Pro | Pro | Met | Cys |
| | | | | 405 | | | | | 410 | | | | | 415 | |

| Phe | Thr | Glu | Glu | Asp | Ala | Lys | Phe | Met | Val | Asp | Gln | Leu | Asp | Arg | Ile |
| | | | 420 | | | | | 425 | | | | | 430 | | |

| Leu | Thr | Val | Leu | Glu | Glu | Ala | Met | Gly | Thr | Lys | Thr | Glu | Ser | Val | Thr |
| | | 435 | | | | | 440 | | | | | 445 | | | |

| Ser | Glu | Asn | Thr | Pro | Cys | Lys | Thr | Lys | Met | Leu | Lys | Glu | Ala | His | Ile |
| | 450 | | | | | 455 | | | | | 460 | | | | |

| Glu | Leu | Leu | Arg | Asp | Ser | Thr | Thr | Asp | Ser | Lys | Glu | Asn | Pro | Ser | Arg |
| 465 | | | | | 470 | | | | | 475 | | | | | 480 |

| Lys | Arg | Asn | Gly | Met | Cys | Thr | Asp | Thr | His | Ser | Leu | Leu | Ser | Lys | Arg |
| | | | | 485 | | | | | 490 | | | | | 495 | |

Leu Lys Thr

<210> SEQ ID NO 34
<211> LENGTH: 1500
<212> TYPE: DNA
<213> ORGANISM: Homo sapiens

<400> SEQUENCE: 34

| atgtgcgagc | tgtacagtaa | gcgggacact | ctggggctga | ggaagaagca | catcgggccc | 60 |
| tcatgcaaag | ttttctttgc | atcggatccc | atcaaaatag | tgagagccca | gaggcagtac | 120 |
| atgtttgatg | agaacggtga | acagtacttg | gactgcatca | acaatgttgc | ccatgtggga | 180 |
| cactgtcacc | caggagtggt | caaagctgcc | ctgaaacaga | tggaactgct | aaatacaaat | 240 |
| tctcgattcc | tccacgacaa | cattgttgag | tatgccaaac | gcctttcagc | aactctgccg | 300 |
| gagaaactct | ctgtttgtta | ttttacaaat | tcaggatccg | aagccaacga | cttagcctta | 360 |
| cgcctggctc | ggcagttcag | aggccaccag | gatgtgatca | ctcttgacca | tgcttaccat | 420 |
| ggttacctat | catccttaat | tgagattagc | ccatataagt | ttcagaaagg | aaaagatgtc | 480 |
| aaaaagaat | ttgtacatgt | ggcaccaact | ccagatactt | acagaggaaa | atatagagaa | 540 |
| gaccatgcag | actcagccag | tgcttatgca | gatgaagtga | agaaaatcat | tgaagatgct | 600 |
| cataacagtg | gaaggaagat | tgctgccttt | attgctgaat | ccatgcagag | ttgtggcgga | 660 |
| caaataattc | ctccagcagg | ctacttccag | aaagtggcag | aatatgtaca | cggtgcaggg | 720 |

-continued

```
ggtgtgttta tagctgatga agttcaagtg ggctttggca gagttgggaa acatttctgg    780
agcttccaga tgtatggtga agactttgtt ccagacatcg tcacaatggg aaaaccgatg    840
ggcaacggcc acccggtggc atgtgtggta caaccaaag aaattgcaga agccttcagc     900
agctctggga tggaatattt taatacgtat ggaggaaatc cagtatcttg tgctgttggt    960
ttggctgtcc tggatataat tgaaaatgaa gaccttcaag gaaatgccaa gagagtaggg   1020
aattatctca ctgagttact gaaaaaacag aaggctaaac acactttgat aggagatatt   1080 agggcattg gcctttttat tggaattgat ttagtgaagg accatctgaa aaggacccct    1140
gccacagctg aagctcagca catcatctac aagatgaaaa aaaacgagt gcttctcagt   1200 gccgatggac ctcatagaaa tgtacttaaa ataaaaccac ctatgtgctt cactgaagaa   1260
gatgcaaagt tcatggtgga ccaacttgat aggattctaa cagttttaga agaagctatg   1320
ggaaccaaaa ccgaaagtgt gacctctgag aatactccat gcaaaacaaa gatgctgaaa   1380
gaagcccaca tagaactgct tagggacagc accactgact ccaaagaaaa tcccagcaga   1440
aagagaaatg gaatgtgcac ggatacacat tcactgctca gtaagaggct caagacatga   1500
```

<210> SEQ ID NO 35
<211> LENGTH: 121
<212> TYPE: PRT
<213> ORGANISM: Artificial Sequence
<220> FEATURE:
<223> OTHER INFORMATION: consensus sequence

<400> SEQUENCE: 35

```
Gly Ser Trp Leu Tyr Asp Val Asp Gly Asn Glu Gln Arg Tyr Leu Asp
  1               5                  10                  15

Phe Leu Ser Gly Ile Ala Val Thr Asn Leu Gly His Cys His Pro Lys
             20                  25                  30

Val Val Gln Ala Val Lys Glu Gln Ala Asp Lys Leu Thr His Leu Ser
         35                  40                  45

Ser Gly Ala Leu Thr His Pro Pro Leu Asp Phe Asp Lys Leu Ala Glu
     50                  55                  60

Lys Leu Leu Lys Leu Thr Pro Gly Asp Gly Leu Asp Lys Val Phe Phe
 65                  70                  75                  80

Met Asn Ser Gly Ser Glu Ala Asn Glu Thr Ala Leu Lys Leu Ala Arg
                 85                  90                  95

Ala Tyr Ala Arg Gln Lys Gly Lys Val Thr Thr Gly Lys Thr Lys Ile
            100                 105                 110

Leu Ala Phe Ser Gly Ala Phe His Gly
        115                 120
```

<210> SEQ ID NO 36
<211> LENGTH: 271
<212> TYPE: PRT
<213> ORGANISM: Artificial Sequence
<220> FEATURE:
<223> OTHER INFORMATION: consensus sequence

<400> SEQUENCE: 36

```
Pro Tyr Phe Pro Pro Tyr Pro Leu Pro Tyr Arg Leu Pro Glu Pro Lys
  1               5                  10                  15

Ile Leu Glu Asp Gly Val Lys Glu Asn Lys Ser Val Glu Ala Ala Cys
             20                  25                  30

Leu Glu Glu Leu Glu Lys Leu Ile Lys Glu Val Ser Gly Asp Glu Ile
         35                  40                  45
```

```
Ala Ala Val Ile Val Glu Pro Val Ile Gln Gly Glu Gly Gly Val Ile
         50                  55                  60

Pro Pro Pro Gly Phe Leu Ala Gly Leu Arg Glu Leu Cys Lys Lys
 65              70                  75                  80

His Gly Val Leu Leu Ile Ala Asp Glu Val Gln Thr Gly Phe Gly Arg
                 85                  90                  95

Thr Gly Lys Leu Phe Ala Cys Glu His Phe Gly Glu Leu Glu Val Thr
                100                 105                 110

Pro Asp Ile Met Thr Leu Ala Lys Ala Leu Gly Gly Gly Leu Pro
            115                 120                 125

Leu Ala Ala Val Ile Ala Arg Ala Glu Ile Met Gln Ala Phe Ala Pro
    130                 135                 140

Gly Gly Ala Pro Lys Ala Phe Leu His Gly Thr Thr Tyr Gly Gly Asn
145                 150                 155                 160

Pro Leu Ala Cys Ala Ala Ala Leu Ala Thr Leu Lys Val Leu Glu Glu
                165                 170                 175

Glu Asn Leu Leu Gln Asn Ala Gln Glu Lys Gly Glu Tyr Leu Leu Lys
                180                 185                 190

Gly Leu Leu Glu Leu Ala Lys Lys Tyr Pro Asp Val Ile Gly Asp Val
            195                 200                 205

Arg Gly Arg Gly Leu Met Ile Gly Ile Glu Leu Val Glu Asp Arg Asp
    210                 215                 220

Gly Pro Thr Thr Asn Arg Ala Glu Glu Ala Glu Pro Asp Asp Glu Leu
225                 230                 235                 240

Val Ala Glu Ile Val Leu Lys Ala Leu Glu Lys Gly Leu Leu Ile Leu
                245                 250                 255

Pro Ser Gly Asp Glu Gly Asn Val Ile Arg Phe Leu Pro Pro Leu
            260                 265                 270

<210> SEQ ID NO 37
<211> LENGTH: 42
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 1-2
<223> OTHER INFORMATION: Xaa = Leu, Ile, Val, Met, Phe, Tyr, Trp, or Cys
<220> FEATURE:
<221> NAME/KEY: VARIANT
<222> LOCATION: 3, 7-8, 11, 13, 15-30, 34-35, 38-40
<223> OTHER INFORMATION: Xaa = any amino acid
<220> FEATURE:
<221> NAME/KEY: VARIANT
<222> LOCATION: 6
<223> OTHER INFORMATION: Xaa = Ile, Val, or Ala
<220> FEATURE:
<221> NAME/KEY: VARIANT
<222> LOCATION: 10
<223> OTHER INFORMATION: Xaa = Leu, Ile, Val, Met, Phe, Ala, Gly, or Cys
<220> FEATURE:
<221> NAME/KEY: VARIANT
<222> LOCATION: 12
<223> OTHER INFORMATION: Xaa = Arg, Ser, Ala, Cys, Leu, or Ile
<220> FEATURE:
<221> NAME/KEY: VARIANT
<222> LOCATION: 14
<223> OTHER INFORMATION: Xaa = Gly, Ser, Ala, or Asp
<220> FEATURE:
<221> NAME/KEY: VARIANT
<222> LOCATION: 32
<223> OTHER INFORMATION: Xaa = Leu, Ile, Val, Met, Phe, or Cys
<220> FEATURE:
<221> NAME/KEY: VARIANT
```

```
<222> LOCATION: 33
<223> OTHER INFORMATION: Xaa = Leu, Ile, Val, Met, Phe, Tyr, Ser, Thr,
      or Ala
<220> FEATURE:
<221> NAME/KEY: VARIANT
<222> LOCATION: 36
<223> OTHER INFORMATION: Xaa = Gly, Ser, or Ala
<220> FEATURE:
<221> NAME/KEY: VARIANT
<222> LOCATION: 41
<223> OTHER INFORMATION: Xaa = Gly, Ser, Thr, Ala, Asp, Asn, or Val
<220> FEATURE:
<221> NAME/KEY: VARIANT
<222> LOCATION: 42
<223> OTHER INFORMATION: Xaa = Gly, Ser, Ala, or Cys

<400> SEQUENCE: 37

Xaa Xaa Xaa Asp Glu Xaa Xaa Xaa Gly Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Asp
             20                  25                  30

Xaa Xaa Xaa Xaa Lys Xaa Xaa Xaa Xaa Xaa
             35                  40

<210> SEQ ID NO 38
<211> LENGTH: 3006
<212> TYPE: DNA
<213> ORGANISM: Homo sapiens
<220> FEATURE:
<221> NAME/KEY: CDS
<222> LOCATION: (33)...(1613)

<400> SEQUENCE: 38
gtcgacccac gcgtccggag ggaactgcca tc atg agg tct gac aag tca gct        53
                                    Met Arg Ser Asp Lys Ser Ala
                                     1               5 ttg gta ttt ctg ctc ctg cag ctc ttc tgt gtt ggc tgt gga ttc tgt      101
Leu Val Phe Leu Leu Leu Gln Leu Phe Cys Val Gly Cys Gly Phe Cys
            10                  15                  20 ggg aaa gtc ctg gtg tgg ccc tgt gac atg agc cat tgg ctt aat gtc      149
Gly Lys Val Leu Val Trp Pro Cys Asp Met Ser His Trp Leu Asn Val
    25                  30                  35 aag gtc att cta gaa gag ctc ata gtg aga ggc cat gag gta aca gta      197
Lys Val Ile Leu Glu Glu Leu Ile Val Arg Gly His Glu Val Thr Val
40                  45                  50                  55 ttg act cac tca aag cct tcg tta att gac tac agg aag cct tct gca      245
Leu Thr His Ser Lys Pro Ser Leu Ile Asp Tyr Arg Lys Pro Ser Ala
                60                  65                  70 ttg aaa ttt gag gtg gtc cat atg cca cag gac aga aca gaa gaa aat      293
Leu Lys Phe Glu Val Val His Met Pro Gln Asp Arg Thr Glu Glu Asn
            75                  80                  85 gaa ata ttt gtt gac cta gct ctg aat gtc ttg cca ggc tta tca acc      341
Glu Ile Phe Val Asp Leu Ala Leu Asn Val Leu Pro Gly Leu Ser Thr
        90                  95                 100 tgg caa tca gtt ata aaa tta aat gat ttt ttt gtt gaa ata aga gga      389
Trp Gln Ser Val Ile Lys Leu Asn Asp Phe Phe Val Glu Ile Arg Gly
    105                 110                 115 act tta aaa atg atg tgt gag agc ttt atc tac aat cag acg ctt atg      437
Thr Leu Lys Met Met Cys Glu Ser Phe Ile Tyr Asn Gln Thr Leu Met
120                 125                 130                 135 aag aag cta cag gaa acc aac tac gat gta atg ctt ata gac cct gtg      485
Lys Lys Leu Gln Glu Thr Asn Tyr Asp Val Met Leu Ile Asp Pro Val
                140                 145                 150 att ccc tgt gga gac ctg atg gct gag ttg ctt gca gtc cct ttt gtg      533
```

|     |     |     |
| --- | --- | --- |
| Ile Pro Cys Gly Asp Leu Met Ala Glu Leu Leu Ala Val Pro Phe Val<br>155                160                165 | | |
| ctc aca ctt aga att tct gta gga ggc aat atg gag cga agc tgt ggg<br>Leu Thr Leu Arg Ile Ser Val Gly Gly Asn Met Glu Arg Ser Cys Gly<br>170                175                180 | | 581 |
| aaa ctt cca gct cca ctt tcc tat gta cct gtg cct atg aca gga cta<br>Lys Leu Pro Ala Pro Leu Ser Tyr Val Pro Val Pro Met Thr Gly Leu<br>185                190                195 | | 629 |
| aca gac aga atg acc ttt ctg gaa aga gta aaa aat tca atg ctt tca<br>Thr Asp Arg Met Thr Phe Leu Glu Arg Val Lys Asn Ser Met Leu Ser<br>200                205                210                215 | | 677 |
| gtt ttg ttc cac ttc tgg att cag gat tac gac tat cat ttt tgg gaa<br>Val Leu Phe His Phe Trp Ile Gln Asp Tyr Asp Tyr His Phe Trp Glu<br>220                225                230 | | 725 |
| gag ttt tat agt aag gca tta gga agg ccc act aca tta tgt gag act<br>Glu Phe Tyr Ser Lys Ala Leu Gly Arg Pro Thr Thr Leu Cys Glu Thr<br>235                240                245 | | 773 |
| gtg gga aaa gct gag ata tgg cta ata cga aca tat tgg gat ttt gaa<br>Val Gly Lys Ala Glu Ile Trp Leu Ile Arg Thr Tyr Trp Asp Phe Glu<br>250                255                260 | | 821 |
| ttt cct caa cca tac caa cct aac ttt gag ttt gtt gga gga ttg cac<br>Phe Pro Gln Pro Tyr Gln Pro Asn Phe Glu Phe Val Gly Gly Leu His<br>265                270                275 | | 869 |
| tgt aaa cct gcc aaa gct ttg cct aag gaa atg gaa aat ttt gtc cag<br>Cys Lys Pro Ala Lys Ala Leu Pro Lys Glu Met Glu Asn Phe Val Gln<br>280                285                290                295 | | 917 |
| agt tca ggg gaa gat ggt att gtg gtg ttt tct ctg ggg tca ctg ttt<br>Ser Ser Gly Glu Asp Gly Ile Val Val Phe Ser Leu Gly Ser Leu Phe<br>300                305                310 | | 965 |
| caa aat gtt aca gaa gaa aag gct aat atc att gct tca gcc ctt gcc<br>Gln Asn Val Thr Glu Glu Lys Ala Asn Ile Ile Ala Ser Ala Leu Ala<br>315                320                325 | | 1013 |
| cag atc cca cag aag gtg tta tgg agg tac aaa gga aaa aaa cca tcc<br>Gln Ile Pro Gln Lys Val Leu Trp Arg Tyr Lys Gly Lys Lys Pro Ser<br>330                335                340 | | 1061 |
| aca tta gga gcc aat act cgg ctg tat gat tgg ata ccc cag aat gat<br>Thr Leu Gly Ala Asn Thr Arg Leu Tyr Asp Trp Ile Pro Gln Asn Asp<br>345                350                355 | | 1109 |
| ctt ctt ggt cat ccc aaa acc aaa gct ttt atc act cat ggt gga atg<br>Leu Leu Gly His Pro Lys Thr Lys Ala Phe Ile Thr His Gly Gly Met<br>360                365                370                375 | | 1157 |
| aat ggg atc tat gaa gct att tac cat ggg gtc cct atg gtg gga gtt<br>Asn Gly Ile Tyr Glu Ala Ile Tyr His Gly Val Pro Met Val Gly Val<br>380                385                390 | | 1205 |
| ccc ata ttt ggt gat cag ctt gat aac ata gct cac atg aag gcc aaa<br>Pro Ile Phe Gly Asp Gln Leu Asp Asn Ile Ala His Met Lys Ala Lys<br>395                400                405 | | 1253 |
| gga gca gct gta gaa ata aac ttc aaa act atg aca agc gaa gat tta<br>Gly Ala Ala Val Glu Ile Asn Phe Lys Thr Met Thr Ser Glu Asp Leu<br>410                415                420 | | 1301 |
| ctg agg gct ttg aga aca gtc att acc gat tcc tct tat aaa gag aat<br>Leu Arg Ala Leu Arg Thr Val Ile Thr Asp Ser Ser Tyr Lys Glu Asn<br>425                430                435 | | 1349 |
| gct atg aga tta tca aga att cac cat gat caa cct gta aag ccc cta<br>Ala Met Arg Leu Ser Arg Ile His His Asp Gln Pro Val Lys Pro Leu<br>440                445                450                455 | | 1397 |
| gat cga gca gtc ttc tgg atc gag ttt gtc atg cgc cac aaa gga gcc<br>Asp Arg Ala Val Phe Trp Ile Glu Phe Val Met Arg His Lys Gly Ala<br>460                465                470 | | 1445 |

| | | | | | | | | | | | | | | | |
|---|---|---|---|---|---|---|---|---|---|---|---|---|---|---|---|
| aag | cac | ctg | cga | tca | gct | gcc | cat | gac | ctc | acc | tgg | ttc | cag | cac | tac | 1493
| Lys | His | Leu | Arg | Ser | Ala | Ala | His | Asp | Leu | Thr | Trp | Phe | Gln | His | Tyr |
| | | | 475 | | | | | 480 | | | | | 485 | | |

| | | | | | | | | | | | | | | | |
|---|---|---|---|---|---|---|---|---|---|---|---|---|---|---|---|
| tct | ata | gat | gtg | att | ggg | ttc | ctg | ctg | gcc | tgt | gtg | gca | act | gct | ata | 1541
| Ser | Ile | Asp | Val | Ile | Gly | Phe | Leu | Leu | Ala | Cys | Val | Ala | Thr | Ala | Ile |
| | | | 490 | | | | | 495 | | | | | 500 | | |

| | | | | | | | | | | | | | | | |
|---|---|---|---|---|---|---|---|---|---|---|---|---|---|---|---|
| ttc | ttg | ttc | aca | aaa | tgt | ttt | tta | ttt | tcc | tgt | caa | aaa | ttt | aat | aaa | 1589
| Phe | Leu | Phe | Thr | Lys | Cys | Phe | Leu | Phe | Ser | Cys | Gln | Lys | Phe | Asn | Lys |
| | | | 505 | | | | | 510 | | | | | 515 | | |

| | | | | | | | |
|---|---|---|---|---|---|---|---|
| act | aga | aag | ata | gaa | aag | agg | gaa | tagatctttc caaattcaag aaagacctga | 1643
| Thr | Arg | Lys | Ile | Glu | Lys | Arg | Glu | |
| 520 | | | | 525 | | | | | tggggtaatc ctgttaattc cagccacata gaatttggtg aaaaccttgc tattttcata 1703
ttatctattc tgttatttta tcttagctat atagcctaga attccacgat catgaggttg 1763
tgagtatatc tcattctttc gttgtatttt cctaggtgtc tttactctct tctctcactt 1823
tgtgacacaa ggacatgaat acatctaaat tttcctattt ctgatatgac tgttttgatg 1883
atgtcattac ttctataacc ttaagtgata gggtgacatg caatatgatt attcctggtg 1943
tgcgcccaaa cacatggata taaagaggta aaaacttaa aattcacaaa attcagtaaa 2003
ccacacaaat caggtaagtg ttctatgaga ttagctggct atgagaaaca taatgatgtt 2063
tcttttcaa tttaaataag cccttctaca tagccagcat cagtgatctc agaaaataaa 2123
ttgctaataa tgatgacatg gcattatgct tagaaaagtt tgctgtattt ccatagacct 2183
catctagatg tcatggccta catttctgcc atcactcaac caatacttt ttctgttttc 2243
ttgatgataa aaagaccttt ctcatgattg ccatcaaata acaaagaaa ctattttttt 2303
tctcacatag agaacatgtc agtaagatat tcaaggtgaa cagattattt ttgggattag 2363
taactatttg aaatatgtgg tgataattac tgagtttata aaatttattt gatagtacac 2423
ttaaagaaga tttatatgtt tattctttaa aaatgatgaa tactcataat tcttatctct 2483
ataatcaaaa gtataattta ctgtagaaaa ataaagagat gcttgttctg aaagtaagat 2543
cagtgaactg cttttcagtc tcaatctttg agaattgtaa attcatcaaa taattgctta 2603
catagtaaaa atttaaggta ttagaaaacc tgcataacaa atagtattat atattaaata 2663
ttttgatatg taaagctcta cacaaagcta aatatagtgt aataatgttt acactaataa 2723
gcaaatatgt taatcttctc attttttac tgtcatataa tcttagtgat atgcctatta 2783
atagttttaa ataaataaat tggctcatct ggccttttga aaattttgaa attcttacag 2843
atgttgatta ggtatatcta caaattaatt tcaattttaa aatgatgata taaaaataaa 2903
tataagtatt tttcttgtgt atgtatacaa taaatataaa taaaattgta aaaaaaaaa 2963
aaaaaaaaaa aaaaaaaaaa aaaaaaaaaa aaagggcggc cgc 3006

<210> SEQ ID NO 39
<211> LENGTH: 527
<212> TYPE: PRT
<213> ORGANISM: Homo sapiens

<400> SEQUENCE: 39

Met Arg Ser Asp Lys Ser Ala Leu Val Phe Leu Leu Gln Leu Phe
1               5                   10                  15

Cys Val Gly Cys Gly Phe Cys Gly Lys Val Leu Val Trp Pro Cys Asp
                20                  25                  30

Met Ser His Trp Leu Asn Val Lys Val Ile Leu Glu Glu Leu Ile Val
            35                  40                      45

```
Arg Gly His Glu Val Thr Val Leu Thr His Ser Lys Pro Ser Leu Ile
     50                  55                  60

Asp Tyr Arg Lys Pro Ser Ala Leu Lys Phe Glu Val Val His Met Pro
 65                  70                  75                  80

Gln Asp Arg Thr Glu Glu Asn Glu Ile Phe Val Asp Leu Ala Leu Asn
                 85                  90                  95

Val Leu Pro Gly Leu Ser Thr Trp Gln Ser Val Ile Lys Leu Asn Asp
            100                 105                 110

Phe Phe Val Glu Ile Arg Gly Thr Leu Lys Met Met Cys Glu Ser Phe
        115                 120                 125

Ile Tyr Asn Gln Thr Leu Met Lys Lys Leu Gln Glu Thr Asn Tyr Asp
    130                 135                 140

Val Met Leu Ile Asp Pro Val Ile Pro Cys Gly Asp Leu Met Ala Glu
145                 150                 155                 160

Leu Leu Ala Val Pro Phe Val Leu Thr Leu Arg Ile Ser Val Gly Gly
                165                 170                 175

Asn Met Glu Arg Ser Cys Gly Lys Leu Pro Ala Pro Leu Ser Tyr Val
            180                 185                 190

Pro Val Pro Met Thr Gly Leu Thr Asp Arg Met Thr Phe Leu Glu Arg
        195                 200                 205

Val Lys Asn Ser Met Leu Ser Val Leu Phe His Phe Trp Ile Gln Asp
    210                 215                 220

Tyr Asp Tyr His Phe Trp Glu Glu Phe Tyr Ser Lys Ala Leu Gly Arg
225                 230                 235                 240

Pro Thr Thr Leu Cys Glu Thr Val Gly Lys Ala Glu Ile Trp Leu Ile
                245                 250                 255

Arg Thr Tyr Trp Asp Phe Glu Phe Pro Gln Pro Tyr Gln Pro Asn Phe
            260                 265                 270

Glu Phe Val Gly Gly Leu His Cys Lys Pro Ala Lys Ala Leu Pro Lys
        275                 280                 285

Glu Met Glu Asn Phe Val Gln Ser Ser Gly Glu Asp Gly Ile Val Val
    290                 295                 300

Phe Ser Leu Gly Ser Leu Phe Gln Asn Val Thr Glu Glu Lys Ala Asn
305                 310                 315                 320

Ile Ile Ala Ser Ala Leu Ala Gln Ile Pro Gln Lys Val Leu Trp Arg
                325                 330                 335

Tyr Lys Gly Lys Lys Pro Ser Thr Leu Gly Ala Asn Thr Arg Leu Tyr
            340                 345                 350

Asp Trp Ile Pro Gln Asn Asp Leu Leu Gly His Pro Lys Thr Lys Ala
        355                 360                 365

Phe Ile Thr His Gly Gly Met Asn Gly Ile Tyr Glu Ala Ile Tyr His
    370                 375                 380

Gly Val Pro Met Val Gly Val Pro Ile Phe Gly Asp Gln Leu Asp Asn
385                 390                 395                 400

Ile Ala His Met Lys Ala Lys Gly Ala Ala Val Glu Ile Asn Phe Lys
                405                 410                 415

Thr Met Thr Ser Glu Asp Leu Leu Arg Ala Leu Arg Thr Val Ile Thr
            420                 425                 430

Asp Ser Ser Tyr Lys Glu Asn Ala Met Arg Leu Ser Arg Ile His His
        435                 440                 445

Asp Gln Pro Val Lys Pro Leu Asp Arg Ala Val Phe Trp Ile Glu Phe
    450                 455                 460

Val Met Arg His Lys Gly Ala Lys His Leu Arg Ser Ala Ala His Asp
```

```
                465                 470                 475                 480
Leu Thr Trp Phe Gln His Tyr Ser Ile Asp Val Ile Gly Phe Leu Leu
                    485                 490                 495

Ala Cys Val Ala Thr Ala Ile Phe Leu Phe Thr Lys Cys Phe Leu Phe
                500                 505                 510

Ser Cys Gln Lys Phe Asn Lys Thr Arg Lys Ile Glu Lys Arg Glu
            515                 520                 525

<210> SEQ ID NO 40
<211> LENGTH: 1584
<212> TYPE: DNA
<213> ORGANISM: Homo sapiens

<400> SEQUENCE: 40
atgaggtctg acaagtcagc tttggtattt ctgctcctgc agctcttctg tgttggctgt      60
ggattctgtg ggaaagtcct ggtgtggccc tgtgacatga gccattggct taatgtcaag     120
gtcattctag aagagctcat agtgagaggc catgaggtaa cagtattgac tcactcaaag     180
ccttcgttaa ttgactacag gaagccttct gcattgaaat tgaggtggt ccatatgcca      240
caggacagaa cagaagaaaa tgaaatattt gttgacctag ctctgaatgt cttgccaggc     300
ttatcaacct ggcaatcagt tataaaatta atgatttttt tgttgaaat aagaggaact      360
ttaaaaatga tgtgtgagag ctttatctac aatcagacgc ttatgaagaa gctacaggaa     420
accaactacg atgtaatgct tatagaccct gtgattccct gtggagacct gatggctgag     480
ttgcttgcag tcccttttgt gctcacactt agaatttctg taggaggcaa tatggagcga     540
agctgtggga aacttccagc tccactttcc tatgtacctg tgcctatgac aggactaaca     600
gacagaatga ccttttctgga aagagtaaaa aattcaatgc tttcagtttt gttccacttc     660
tggattcagg attacgacta tcattttggg gaagagtttt atagtaaggc attaggaagg     720
cccactacat tatgtgagac tgtgggaaaa gctgagatat ggctaatacg aacatattgg     780
gatttttgaat tcctcaacc ataccaacct aactttgagt ttgttggagg attgcactgt     840
aaacctgcca agctttgcc taaggaaatg gaaaattttg tccagagttc aggggaagat      900
ggtattgtgg tgtttttctct ggggtcactg tttcaaaatg ttacagaaga aaaggctaat     960
atcattgctt cagcccttgc ccagatccca cagaaggtgt tatggaggta caaaggaaaa    1020
aaaccatcca cattaggagc caatactcgg ctgtatgatt ggatacccca gaatgatctt    1080
cttggtcatc ccaaaaccaa agcttttatc actcatggtg aatgaatgg gatctatgaa    1140
gctatttacc atgggtccc tatggtggga ttcccatat ttggtgatca gcttgataac     1200
atagctcaca tgaaggccaa aggagcagct gtagaaataa acttcaaaac tatgacaagc    1260
gaagatttac tgagggcttt gagaacagtc attaccgatt cctcttataa agagaatgct    1320
atgagattat caagaattca ccatgatcaa cctgtaaagc ccctagatcg agcagtcttc    1380
tggatcgagt ttgtcatgcg ccacaaagga gccaagcacc tgcgatcagc tgcccatgac    1440
ctcacctggt tccagcacta ctctatagat gtgattgggt tcctgctggc ctgtgtggca    1500
actgctatat tcttgttcac aaaatgttttt ttattttcct gtcaaaaatt taataaaact    1560
agaaagatag aaaagaggga atag                                            1584

<210> SEQ ID NO 41
<211> LENGTH: 507
<212> TYPE: PRT
<213> ORGANISM: Artificial Sequence
<220> FEATURE:
```

<223> OTHER INFORMATION: consensus sequence

<400> SEQUENCE: 41

```
Gly Lys Val Leu Val Trp Pro Met Asp Phe Ser His Trp Leu Asn Met
  1               5                  10                  15

Lys Gly Ile Leu Glu Glu Leu Val Gln Arg Gly His Glu Val Val Val
             20                  25                  30

Leu Arg Pro Ser Ala Ser Ile Leu Ile Lys Pro Lys Lys Glu Ser Asn
         35                  40                  45

Leu Lys Phe Glu Thr Tyr Pro Val Ser Leu Thr Lys Glu Glu Leu Glu
     50                  55                  60

Asn Ser Phe Leu Lys Leu Val Lys Lys Leu Phe Glu Glu Ala Ser Glu
 65                  70                  75                  80

Leu Lys Thr Val Trp Ser Tyr Phe Ser Ala Leu Gln Lys Leu Ile Ser
                 85                  90                  95

Glu Tyr Ser Asp Leu Ala Glu Ser Ser Cys Lys Glu Val Val Ser Asn
                100                 105                 110

Lys Lys Leu Met Thr Lys Leu Gln Glu Ser Ser Phe Asp Val Val Leu
            115                 120                 125

Ala Asp Pro Val Leu Pro Cys Gly Glu Leu Leu Ala Glu Leu Leu Lys
        130                 135                 140

Ile Pro Thr Val Tyr Ser Leu Arg Phe Val Pro Gly Tyr Ala Leu Glu
145                 150                 155                 160

Lys Ala Ser Gly Gly Leu Leu Ala Pro Pro Ser Tyr Val Pro Val Ile
                165                 170                 175

Leu Ser Glu Leu Ser Asp Gln Met Thr Phe Ile Glu Arg Val Lys Asn
                180                 185                 190

Met Leu Ile Met Leu Tyr Phe Asp Phe Leu Phe Gln Arg Phe Lys Lys
            195                 200                 205

Lys Lys Trp Asp Gln Phe Ala Ser Glu Val Leu Gly Arg Pro Val Thr
        210                 215                 220

Leu Val Glu Leu Leu Ser Lys Ala Ser Val Trp Leu Leu Arg Ser Tyr
225                 230                 235                 240

Trp Asp Leu Glu Phe Pro Arg Pro Leu Leu Pro Asn Val Glu Phe Ile
                245                 250                 255

Gly Gly Leu Asn Cys Lys Pro Ala Lys Pro Leu Pro Lys Glu Met Glu
                260                 265                 270

Glu Phe Val Gln Ser Ser Gly Glu His Gly Val Val Phe Ser Leu
            275                 280                 285

Gly Ser Met Val Ser Asn Ile Pro Glu Glu Lys Ala Asn Ala Ile Ala
        290                 295                 300

Ser Ala Leu Ala Lys Ile Pro Gln Lys Val Leu Trp Arg Phe Asp Gly
305                 310                 315                 320

Lys Lys Pro Ser Thr Leu Gly Asn Asn Thr Gly Arg Leu Val Lys Trp
                325                 330                 335

Leu Pro Gln Asn Asp Leu Leu Gly His Pro Lys Thr Lys Ala Phe Ile
            340                 345                 350

Thr His Ala Gly Ala Asn Gly Val Tyr Glu Ala Ile Tyr His Gly Val
        355                 360                 365

Pro Met Val Gly Ile Pro Leu Phe Gly Asp Gln Met Asp Asn Ala Lys
    370                 375                 380

Arg Met Glu Ala Lys Gly Ala Ala Val Thr Leu Asn Val Leu Glu Met
385                 390                 395                 400
```

```
Thr Ser Glu Asp Leu Leu Asn Ala Leu Lys Thr Val Ile Asn Asp Lys
            405                 410                 415

Ser Tyr Lys Glu Asn Ile Met Arg Leu Ser Ser Ile His Lys Asp Gln
            420                 425                 430

Pro Val Lys Pro Leu Asp Arg Ala Val Phe Trp Ile Glu Phe Val Met
            435                 440                 445

Arg His Lys Gly Ala Lys His Leu Arg Pro Ala Ala His Asp Leu Thr
450                 455                 460

Trp Tyr Gln Tyr His Ser Leu Asp Val Ile Gly Phe Leu Leu Ala Val
465                 470                 475                 480

Val Leu Thr Val Ala Phe Ile Thr Phe Lys Cys Cys Leu Phe Gly Tyr
                485                 490                 495

Arg Lys Phe Val Gly Lys Lys Arg Val Lys
            500                 505

<210> SEQ ID NO 42
<211> LENGTH: 2572
<212> TYPE: DNA
<213> ORGANISM: Homo sapiens
<220> FEATURE:
<221> NAME/KEY: CDS
<222> LOCATION: (325)...(2133)

<400> SEQUENCE: 42
gcgccgcccg cccgcgcctt cccgccgcc ccccggcgcc cccggccccc ctcaccgctc      60
cccggggcgg ggccgcgccc tctgagcggg ggatgccggc cgcgccccgc gaccccagcc    120
ccgggcagcc ctctgcgctc tgggggaccc ccggcggccg tgcccggcg cgctgagctg    180 gtgctgaagg acagctccg gccgagcccc gcagcccccg cagcccgggg cggctcatgg    240
tccccgaagc cgaagctgaa gcccaggccc gggcgggat gctggggatg ccccgcgggt    300 gaggccccg ctgcagccgt gttc atg gcg gtg gcc agg aag atc cga act      351
                         Met Ala Val Ala Arg Lys Ile Arg Thr
                          1               5 ttg ctg acg gtg aac atc ctg gtg ttc gtg ggc atc gtc ctg ttc tcc    399
Leu Leu Thr Val Asn Ile Leu Val Phe Val Gly Ile Val Leu Phe Ser
 10                  15                  20                  25 gtg tac tgc cgc ctg cag ggc cgc tcc cag gag ctc gtg cgc atc gtg    447
Val Tyr Cys Arg Leu Gln Gly Arg Ser Gln Glu Leu Val Arg Ile Val
                 30                  35                  40 agc ggc gac cgc cgg gtg cgc agc cga cac gcc aag gtg ggc acg ctg    495
Ser Gly Asp Arg Arg Val Arg Ser Arg His Ala Lys Val Gly Thr Leu
             45                  50                  55 ggg gac cgt gag gcc atc ctg cag cgc ctg gac cac ctg gag gag gtg    543
Gly Asp Arg Glu Ala Ile Leu Gln Arg Leu Asp His Leu Glu Glu Val
         60                  65                  70 gtc tac aac cag ctc aac ggc ctt gcc aag ccc atc ggc ctg gtg gag    591
Val Tyr Asn Gln Leu Asn Gly Leu Ala Lys Pro Ile Gly Leu Val Glu
     75                  80                  85 ggg cca gga ggc ctg ggc cag ggt ggc ttg gcg gcc acc ctg cgt gat    639
Gly Pro Gly Gly Leu Gly Gln Gly Gly Leu Ala Ala Thr Leu Arg Asp
 90                  95                 100                 105 gac ggc cag gag gcg gaa ggc aag tat gag gag tac ggc tac aac gct    687
Asp Gly Gln Glu Ala Glu Gly Lys Tyr Glu Glu Tyr Gly Tyr Asn Ala
                110                 115                 120 cag ctc agc gac cgc atc tcc ctc gat cgg agc atc ccc gac tac cgg    735
Gln Leu Ser Asp Arg Ile Ser Leu Asp Arg Ser Ile Pro Asp Tyr Arg
            125                 130                 135 ccc aga aag tgc aga cag atg agc tac gcc cag gac ctg ccc cag gtc    783
```

```
                Pro Arg Lys Cys Arg Gln Met Ser Tyr Ala Gln Asp Leu Pro Gln Val
                    140                 145                 150 tcc gtg gtc ttc atc ttc gtc aat gag gcg ctg tcg gtc atc ctg cgc              831
Ser Val Val Phe Ile Phe Val Asn Glu Ala Leu Ser Val Ile Leu Arg
    155                 160                 165 tcc gtg cac agc gtg gtc aac cac acg ccc tcc cag ctc ctc aag gag              879
Ser Val His Ser Val Val Asn His Thr Pro Ser Gln Leu Leu Lys Glu
170                 175                 180                 185 gtc atc ctg gtg gac gac aac agt gac aac gtg gaa ctc aag ttc aat              927
Val Ile Leu Val Asp Asp Asn Ser Asp Asn Val Glu Leu Lys Phe Asn
                190                 195                 200 ctg gac cag tac gtc aac aag cgg tac cca ggc ctc gtg aag att gtc              975
Leu Asp Gln Tyr Val Asn Lys Arg Tyr Pro Gly Leu Val Lys Ile Val
            205                 210                 215 cgc aac agc cgg cgg gaa gga ctg atc cgc gcg cgg ctg cag ggc tgg             1023
Arg Asn Ser Arg Arg Glu Gly Leu Ile Arg Ala Arg Leu Gln Gly Trp
        220                 225                 230 aag gcg gcc acc gcc cca gtc gtc ggc ttc ttt gat gcc cac gtc gag             1071
Lys Ala Ala Thr Ala Pro Val Val Gly Phe Phe Asp Ala His Val Glu
    235                 240                 245 ttc aac acg ggc tgg gcc gag ccc gca ctg tcg cgg atc cga gag gac             1119
Phe Asn Thr Gly Trp Ala Glu Pro Ala Leu Ser Arg Ile Arg Glu Asp
250                 255                 260                 265 cgg cgt cgc atc gtg ctg cca gcc atc gac aac atc aag tac agc acg             1167
Arg Arg Arg Ile Val Leu Pro Ala Ile Asp Asn Ile Lys Tyr Ser Thr
                270                 275                 280 ttt gag gtg cag cag tat gcg aac gcc gcc cat ggc tac aac tgg ggc             1215
Phe Glu Val Gln Gln Tyr Ala Asn Ala Ala His Gly Tyr Asn Trp Gly
            285                 290                 295 ctc tgg tgc atg tac atc atc ccc ccg cag gac tgg ctg gac cgc ggc             1263
Leu Trp Cys Met Tyr Ile Ile Pro Pro Gln Asp Trp Leu Asp Arg Gly
        300                 305                 310 gac gag tca gca ccc atc agg acc cca gcc atg atc ggc tgc tcc ttc             1311
Asp Glu Ser Ala Pro Ile Arg Thr Pro Ala Met Ile Gly Cys Ser Phe
    315                 320                 325 gta gtg gac cgc gag tac ttc gga gac att ggg ctg ctg gac ccc ggc             1359
Val Val Asp Arg Glu Tyr Phe Gly Asp Ile Gly Leu Leu Asp Pro Gly
330                 335                 340                 345 atg gag gtg tat ggc ggc gag aac gta gaa ctg ggc atg agg gtg tgg             1407
Met Glu Val Tyr Gly Gly Glu Asn Val Glu Leu Gly Met Arg Val Trp
                350                 355                 360 cag tgt ggc ggc agc atg gag gtg ctg ccc tgc tcc cgc gtg gcc cac             1455
Gln Cys Gly Gly Ser Met Glu Val Leu Pro Cys Ser Arg Val Ala His
            365                 370                 375 atc gag cgc acc agg aag ccc tac aac aac gac att gac tac tac gcc             1503
Ile Glu Arg Thr Arg Lys Pro Tyr Asn Asn Asp Ile Asp Tyr Tyr Ala
        380                 385                 390 aag cgc aac gcc ctg cgc gcc gcc gag gtg tgg atg gat gac ttc aag             1551
Lys Arg Asn Ala Leu Arg Ala Ala Glu Val Trp Met Asp Asp Phe Lys
    395                 400                 405 tcc cac gtg tac atg gcc tgg aac atc ccc atg tcg aac cca ggg gtg             1599
Ser His Val Tyr Met Ala Trp Asn Ile Pro Met Ser Asn Pro Gly Val
410                 415                 420                 425 gac ttc ggg gac gtg tct gag agg ctg gcc ctg cgt cag agg ctg aag             1647
Asp Phe Gly Asp Val Ser Glu Arg Leu Ala Leu Arg Gln Arg Leu Lys
                430                 435                 440 tgt cgc agc ttc aag tgg tac ctg gag aac gtg tac ccg gag atg agg             1695
Cys Arg Ser Phe Lys Trp Tyr Leu Glu Asn Val Tyr Pro Glu Met Arg
            445                 450                 455
```

| | | | | | | | | | | | | | | | |
|---|---|---|---|---|---|---|---|---|---|---|---|---|---|---|---|
| gtc | tac | aac | aac | acc | ctc | acg | tac | gga | gag | gtg | aga | aac | agc | aaa | gcc |
| Val | Tyr | Asn | Asn | Thr | Leu | Thr | Tyr | Gly | Glu | Val | Arg | Asn | Ser | Lys | Ala |
| | | | 460 | | | | 465 | | | | 470 | | | | |

```
gtc tac aac aac acc ctc acg tac gga gag gtg aga aac agc aaa gcc      1743
Val Tyr Asn Asn Thr Leu Thr Tyr Gly Glu Val Arg Asn Ser Lys Ala
            460                 465                 470 agt gcc tac tgt ctg gac cag gga gcg gag gac ggc gac cgg gcg atc      1791
Ser Ala Tyr Cys Leu Asp Gln Gly Ala Glu Asp Gly Asp Arg Ala Ile
475                 480                 485 ctc tac ccc tgc cac ggg atg tcc tcc cag ctg gtg cgg tac agc gct      1839
Leu Tyr Pro Cys His Gly Met Ser Ser Gln Leu Val Arg Tyr Ser Ala
490                 495                 500                 505 gac ggc ctg ctg cag ctg ggg cct ctg ggc tcc aca gcc ttc ttg cct      1887
Asp Gly Leu Leu Gln Leu Gly Pro Leu Gly Ser Thr Ala Phe Leu Pro
            510                 515                 520 gac tcc aag tgt ctg gtg gat gac ggc acg ggc cgc atg ccc acc ctg      1935
Asp Ser Lys Cys Leu Val Asp Asp Gly Thr Gly Arg Met Pro Thr Leu
            525                 530                 535 aag aag tgt gag gat gtg gcg cgg cca aca cag cgg ctg tgg gac ttc      1983
Lys Lys Cys Glu Asp Val Ala Arg Pro Thr Gln Arg Leu Trp Asp Phe
            540                 545                 550 acc cag agt ggc ccc att gtg agc cgg gcc acg ggc cgc tgc ctg gag      2031
Thr Gln Ser Gly Pro Ile Val Ser Arg Ala Thr Gly Arg Cys Leu Glu
555                 560                 565 gtg gag atg tcc aaa gat gcc aac ttt ggg ctc cgg ctg gtg gta cag      2079
Val Glu Met Ser Lys Asp Ala Asn Phe Gly Leu Arg Leu Val Val Gln
570                 575                 580                 585 agg tgc tcg ggg cag aag tgg atg atc aga aac tgg atc aaa cac gca      2127
Arg Cys Ser Gly Gln Lys Trp Met Ile Arg Asn Trp Ile Lys His Ala
            590                 595                 600 cgg cac tgacccacc tccgcccgga cccccacaga cctcgggaag gcgctgggcc        2183
Arg His gagccagtgt ggctgagtga ccggggtgtg cccggcagac acagcaggac agggctctat    2243
gtgcggccag gacagcagag gctgaggggc cggggtgtgg ctgagtgacc agggtgtcac    2303
ccactgcatc tggagtacag cttctcctag gacaggcggc tctacccgag ggagggcgtc    2363
tggggacagt gatgccaact caaacacgtg ccttctccac ggtatctcct ggccaggctg    2423
ctgggacagc cgccgcctct gcatgtacca cagcccccca cgcccatag  ggaggccaag    2483 ccccggacca tgcaccaggc tgcaccctgg tgtcttccac ccgcaggcct cccatgctcc    2543
aagcagcctc ccccagcact tgcggccgc                                      2572
```

<210> SEQ ID NO 43
<211> LENGTH: 603
<212> TYPE: PRT
<213> ORGANISM: Homo sapiens

<400> SEQUENCE: 43

```
Met Ala Val Ala Arg Lys Ile Arg Thr Leu Leu Thr Val Asn Ile Leu
1               5                   10                  15

Val Phe Val Gly Ile Val Leu Phe Ser Val Tyr Cys Arg Leu Gln Gly
                20                  25                  30

Arg Ser Gln Glu Leu Val Arg Ile Val Ser Gly Asp Arg Arg Val Arg
            35                  40                  45

Ser Arg His Ala Lys Val Gly Thr Leu Gly Asp Arg Glu Ala Ile Leu
        50                  55                  60

Gln Arg Leu Asp His Leu Glu Glu Val Val Tyr Asn Gln Leu Asn Gly
65                  70                  75                  80

Leu Ala Lys Pro Ile Gly Leu Val Glu Gly Pro Gly Leu Gly Gln
                85                  90                  95
```

-continued

```
Gly Gly Leu Ala Ala Thr Leu Arg Asp Asp Gly Gln Glu Ala Glu Gly
            100                 105                 110

Lys Tyr Glu Glu Tyr Gly Tyr Asn Ala Gln Leu Ser Asp Arg Ile Ser
        115                 120                 125

Leu Asp Arg Ser Ile Pro Asp Tyr Arg Pro Arg Lys Cys Arg Gln Met
    130                 135                 140

Ser Tyr Ala Gln Asp Leu Pro Gln Val Ser Val Phe Ile Phe Val
145                 150                 155                 160

Asn Glu Ala Leu Ser Val Ile Leu Arg Ser Val His Ser Val Val Asn
                165                 170                 175

His Thr Pro Ser Gln Leu Leu Lys Glu Val Ile Leu Val Asp Asp Asn
            180                 185                 190

Ser Asp Asn Val Glu Leu Lys Phe Asn Leu Asp Gln Tyr Val Asn Lys
        195                 200                 205

Arg Tyr Pro Gly Leu Val Lys Ile Val Arg Asn Ser Arg Arg Glu Gly
    210                 215                 220

Leu Ile Arg Ala Arg Leu Gln Gly Trp Lys Ala Thr Ala Pro Val
225                 230                 235                 240

Val Gly Phe Phe Asp Ala His Val Glu Phe Asn Thr Gly Trp Ala Glu
                245                 250                 255

Pro Ala Leu Ser Arg Ile Arg Glu Asp Arg Arg Ile Val Leu Pro
            260                 265                 270

Ala Ile Asp Asn Ile Lys Tyr Ser Thr Phe Glu Val Gln Gln Tyr Ala
        275                 280                 285

Asn Ala His Gly Tyr Asn Trp Gly Leu Trp Cys Met Tyr Ile Ile
    290                 295                 300

Pro Pro Gln Asp Trp Leu Asp Arg Gly Asp Glu Ser Ala Pro Ile Arg
305                 310                 315                 320

Thr Pro Ala Met Ile Gly Cys Ser Phe Val Val Asp Arg Glu Tyr Phe
                325                 330                 335

Gly Asp Ile Gly Leu Leu Asp Pro Gly Met Glu Val Tyr Gly Gly Glu
            340                 345                 350

Asn Val Glu Leu Gly Met Arg Val Trp Gln Cys Gly Gly Ser Met Glu
        355                 360                 365

Val Leu Pro Cys Ser Arg Val Ala His Ile Glu Arg Thr Arg Lys Pro
    370                 375                 380

Tyr Asn Asn Asp Ile Asp Tyr Tyr Ala Lys Arg Asn Ala Leu Arg Ala
385                 390                 395                 400

Ala Glu Val Trp Met Asp Asp Phe Lys Ser His Val Tyr Met Ala Trp
                405                 410                 415

Asn Ile Pro Met Ser Asn Pro Gly Val Asp Phe Gly Asp Val Ser Glu
            420                 425                 430

Arg Leu Ala Leu Arg Gln Arg Leu Lys Cys Arg Ser Phe Lys Trp Tyr
        435                 440                 445

Leu Glu Asn Val Tyr Pro Glu Met Arg Val Tyr Asn Asn Thr Leu Thr
    450                 455                 460

Tyr Gly Glu Val Arg Asn Ser Lys Ala Ser Tyr Cys Leu Asp Gln
465                 470                 475                 480

Gly Ala Glu Asp Gly Asp Arg Ala Ile Leu Tyr Pro Cys His Gly Met
                485                 490                 495

Ser Ser Gln Leu Val Arg Tyr Ser Ala Asp Gly Leu Leu Gln Leu Gly
            500                 505                 510

Pro Leu Gly Ser Thr Ala Phe Leu Pro Asp Ser Lys Cys Leu Val Asp
```

515                 520                 525
Asp Gly Thr Gly Arg Met Pro Thr Leu Lys Lys Cys Glu Asp Val Ala
            530                 535                 540

Arg Pro Thr Gln Arg Leu Trp Asp Phe Thr Gln Ser Gly Pro Ile Val
545                 550                 555                 560

Ser Arg Ala Thr Gly Arg Cys Leu Glu Val Glu Met Ser Lys Asp Ala
                565                 570                 575

Asn Phe Gly Leu Arg Leu Val Val Gln Arg Cys Ser Gly Gln Lys Trp
            580                 585                 590

Met Ile Arg Asn Trp Ile Lys His Ala Arg His
            595                 600

<210> SEQ ID NO 44
<211> LENGTH: 1812
<212> TYPE: DNA
<213> ORGANISM: Homo sapiens

<400> SEQUENCE: 44

| | | | | | |
|---|---|---|---|---|---|
| atggcggtgg | ccaggaagat | ccgaactttg | ctgacggtga | acatcctggt | gttcgtgggc | 60 |
| atcgtcctgt | tctccgtgta | ctgccgcctg | cagggccgct | cccaggagct | cgtgcgcatc | 120 |
| gtgagcggcg | accgcgggt | cgcagccga | cacgccaagg | tgggcacgct | ggggaccgt | 180 |
| gaggccatcc | tgcagcgcct | ggaccacctg | aggaggtgg | tctacaacca | gctcaacggc | 240 |
| cttgccaagc | ccatcggcct | ggtggagggg | ccaggaggcc | tgggccaggg | tggcttggcg | 300 |
| gccaccctgc | gtgatgacgg | ccaggaggcg | gaaggcaagt | atgaggagta | cggctacaac | 360 |
| gctcagctca | gcgaccgcat | ctccctcgat | cggagcatcc | ccgactaccg | gcccagaaag | 420 |
| tgcagacaga | tgagctacgc | ccaggacctg | ccccaggtct | ccgtggtctt | catcttcgtc | 480 |
| aatgaggcgc | tgtcggtcat | cctgcgctcc | gtgcacagcg | tggtcaacca | cacgccctcc | 540 |
| cagctcctca | aggaggtcat | cctggtggac | gacaacagtg | acaacgtgga | actcaagttc | 600 |
| aatctggacc | agtacgtcaa | caagcggtac | ccaggcctcg | tgaagattgt | ccgcaacagc | 660 |
| cggcgggaag | gactgatccg | cgcgcggctg | cagggctgga | aggcggccac | cgccccagtc | 720 |
| gtcggcttct | tgatgcccca | cgtcgagttc | aacacgggct | gggccgagcc | cgcactgtcg | 780 |
| cggatccgag | aggaccggcg | tcgcatcgtg | ctgccagcca | tcgacaacat | caagtacagc | 840 |
| acgtttgagg | tgcagcagta | tgcgaacgcc | gcccatggct | acaactgggg | cctctggtgc | 900 |
| atgtacatca | tccccccgca | ggactggctg | gaccgcggcg | acgagtcagc | acccatcagg | 960 |
| accccagcca | tgatcggctg | ctccttcgta | gtggaccgcg | agtacttcgg | agacattggg | 1020 |
| ctgctggacc | ccggcatgga | ggtgtatggc | ggcgagaacg | tagaactggg | catgagggtg | 1080 |
| tggcagtgtg | gcggcagcat | ggaggtgctg | ccctgctccc | gcgtggccca | catcgagcgc | 1140 |
| accaggaagc | cctacaacaa | cgacattgac | tactacgcca | gcgcaacgc | cctgcgcgcc | 1200 |
| gccgaggtgt | ggatggatga | cttcaagtcc | cacgtgtaca | tggcctggaa | catccccatg | 1260 |
| tcgaacccag | ggtggactt | cggggacgtg | tctgagaggc | tggccctgcg | tcagaggctg | 1320 |
| aagtgtcgca | gcttcaagtg | gtacctggag | aacgtgtacc | cggagatgag | ggtctacaac | 1380 |
| aacaccctca | cgtacggaga | ggtgagaaac | agcaaagcca | gtgcctactg | tctggaccag | 1440 |
| ggagcggagg | acggcgaccg | ggcgatcctc | tacccctgcc | acgggatgtc | ctcccagctg | 1500 |
| gtgcggtaca | cgctgacgg | cctgctgcag | ctgggcctc | tgggctccac | agccttcttg | 1560 |
| cctgactcca | agtgtctggt | ggatgacggc | acgggccgca | tgcccaccct | gaagaagtgt | 1620 |

-continued

```
gaggatgtgg cgcggccaac acagcggctg tgggacttca cccagagtgg ccccattgtg    1680
agccgggcca cgggccgctg cctggaggtg gagatgtcca agatgccaa ctttgggctc    1740 cggctggtgg tacagaggtg ctcggggcag aagtggatga tcagaaactg gatcaaacac    1800
gcacggcact ga                                                        1812
```

<210> SEQ ID NO 45
<211> LENGTH: 187
<212> TYPE: PRT
<213> ORGANISM: Artificial Sequence
<220> FEATURE:
<223> OTHER INFORMATION: consensus sequence

<400> SEQUENCE: 45

```
Ser Ile Val Ile Pro Thr Tyr Asn Glu Glu Ala Asp Tyr Leu Glu Glu
  1               5                  10                  15

Leu Leu Glu Ser Val Leu Ala Gln Ser Thr Leu Glu Asp Ile Glu Ile
             20                  25                  30

Ile Val Val Asp Asp Gly Ser Glu Thr Asp Glu Thr Val Glu Ile Ala
         35                  40                  45

Glu Asp Tyr Leu Asp Glu Arg Ile Lys Glu Glu Asn Pro Arg Ile Ile
     50                  55                  60

Ile Val Ile Arg Leu Glu Glu Asn Ser Gln Gly Pro Ala Ala Ala Arg
 65                  70                  75                  80

Asn Lys Gly Ile Arg Arg Ala Thr Gly Asp Ser Asp Tyr Ile Leu Phe
                 85                  90                  95

Leu Asp Ala Asp Asp Ile Phe Thr Pro Asp Lys Leu Glu Lys Leu Ile
            100                 105                 110

Asp Tyr Ala Glu Ala Thr Asp Ala Ala Val Val Leu Gly Ala Ile Asp
        115                 120                 125

Ala Tyr Glu Tyr Ala Glu Gly Glu Ser Asn Leu Tyr Arg Ile Ala Arg
    130                 135                 140

Ala Asp Thr Glu Arg Ser Leu Phe Ala Gly Leu Leu Arg Lys Thr Gly
145                 150                 155                 160

Arg Leu Thr Gly Gly Leu Glu Leu Ser Phe Glu Ile Gly Ser Asn Ala
                165                 170                 175

Ile Tyr Arg Arg Glu Ala Phe Glu Glu Leu Phe
            180                 185
```

<210> SEQ ID NO 46
<211> LENGTH: 135
<212> TYPE: PRT
<213> ORGANISM: Artificial Sequence
<220> FEATURE:
<223> OTHER INFORMATION: consensus sequence

<400> SEQUENCE: 46

```
Arg Gly Tyr Phe Leu Ile Ile Gly Gly Asn Thr Gly Leu Cys Leu Asp
  1               5                  10                  15

Val Asn Gly Asn Ser Glu Ser Lys Ser Asp Gly Asn Pro Val Gln Leu
             20                  25                  30

Trp Asp Cys His Gly Gly Asn Gln Leu Trp Lys Leu Thr Tyr Asn
         35                  40                  45

Glu Ser Asp Gly Ala Ile Arg Ile Asn Ser Asp Leu Cys Leu Thr Val
     50                  55                  60

Asn Gly Thr Val Thr Leu Tyr Ser Cys Asp Gly Thr Asp Lys Gly Asn
 65                  70                  75                  80
```

```
Asp Asn Gln Lys Trp Glu Val Asn Lys Asp Gly Thr Ile Arg Asn Pro
                85                  90                  95
Lys Asn Ser Lys Lys Gly Val Asp Ser Gly Leu Cys Leu Asp Val Lys
            100                 105                 110
Asp Gly Asn Lys Val Gln Leu Trp Thr Cys Asn Gly Ser Asp Ala Pro
        115                 120                 125
Asn Gln Lys Trp Ile Phe Glu
    130                 135

<210> SEQ ID NO 47
<211> LENGTH: 149
<212> TYPE: PRT
<213> ORGANISM: Artificial Sequence
<220> FEATURE:
<223> OTHER INFORMATION: consensus sequence

<400> SEQUENCE: 47

Arg Lys Asp Pro Thr Asp Pro Ile Arg Ser Pro Thr Met Ala Gly Gly
  1               5                  10                  15
Leu Phe Ala Ile Asn Lys Glu Tyr Phe Glu Leu Gly Thr Tyr Asp
             20                  25                  30       Asp
Pro Gly Met Asp Ile Trp Gly Gly Glu Asn Leu Glu Leu Ser Phe Arg
         35                  40                  45
Val Trp Gln Cys Gly Gly Arg Leu Glu Ile Val Pro Cys Ser His Val
 50                  55                  60
Gly His Val Phe Arg Lys Arg Ser Pro Tyr Thr Phe Pro Gly Lys Gly
 65                  70                  75                  80
Ser Gly Lys Asp Val Ile Ser Arg Asn Thr Val Arg Val Ala Glu Val
             85                  90                  95
Trp Met Asp Asp Tyr Lys Glu Tyr Phe Tyr Lys His Asn Pro Gln Ala
            100                 105                 110
Arg Lys Val Arg Asp Phe Gly Asp Ile Ser Glu Arg Lys Glu Leu Arg
        115                 120                 125
Glu Lys Leu Gln Cys Lys Ser Phe Lys Trp Tyr Leu Glu Asn Val Tyr
    130                 135                 140
Pro Asp Leu Tyr Val
145

<210> SEQ ID NO 48
<211> LENGTH: 2682
<212> TYPE: DNA
<213> ORGANISM: Homo sapiens
<220> FEATURE:
<221> NAME/KEY: CDS
<222> LOCATION: (121)...(2445)

<400> SEQUENCE: 48
cacgccttgt ggcggctttg cggagctgct gctttggcgg gagttggaag ctggtgtgag      60
gtttctgtgg ggagaaggag agtgccagag gtgactggtt catggttctt ctaggctctc     120 atg gcc acc atg ttg gaa ggc aga tgc caa act cag cca agg agc agc      168
Met Ala Thr Met Leu Glu Gly Arg Cys Gln Thr Gln Pro Arg Ser Ser
  1               5                  10                  15 ccc agt ggc cga gag gct agc ctg tgg tcg tca ggc ttt ggg atg aag      216
Pro Ser Gly Arg Glu Ala Ser Leu Trp Ser Ser Gly Phe Gly Met Lys
             20                  25                  30 ctg gag gct gtc act cca ttc ctg ggg aag tat cgc ccc ttt gtg ggt      264
Leu Glu Ala Val Thr Pro Phe Leu Gly Lys Tyr Arg Pro Phe Val Gly
         35                  40                  45
```

-continued

| | | |
|---|---|---|
| cgc tgt tgc cag acc tgc acc ccc aag agc tgg gag tcc ctc ttc cac<br>Arg Cys Cys Gln Thr Cys Thr Pro Lys Ser Trp Glu Ser Leu Phe His<br>50              55                      60 | 312 |
| aga agc ata acg gac cta ggc ttc tgc aat gtg atc ctg gtg aag gag<br>Arg Ser Ile Thr Asp Leu Gly Phe Cys Asn Val Ile Leu Val Lys Glu<br>65              70                      75                      80 | 360 |
| gag aac aca agg ttt cgg ggc tgg ctg gtt cgg agg ctc tgc tat ttc<br>Glu Asn Thr Arg Phe Arg Gly Trp Leu Val Arg Arg Leu Cys Tyr Phe<br>                    85                      90                      95 | 408 |
| ctg tgg tcc ctg gag cag cac atc ccc ccc tgc cag gat gtc cca cag<br>Leu Trp Ser Leu Glu Gln His Ile Pro Pro Cys Gln Asp Val Pro Gln<br>            100                     105                     110 | 456 |
| aag atc atg gaa agc acc ggg gtg cag aac ctc ctc tca ggg agg gtc<br>Lys Ile Met Glu Ser Thr Gly Val Gln Asn Leu Leu Ser Gly Arg Val<br>      115                     120                     125 | 504 |
| cca gga ggc act ggg gaa ggc cag gtg cct gac ctt gtg aag aag gag<br>Pro Gly Gly Thr Gly Glu Gly Gln Val Pro Asp Leu Val Lys Lys Glu<br>130                     135                     140 | 552 |
| gta cag cgc atc ctg ggt cac atc cag gcc cca ccc cgt ccc ttc ctg<br>Val Gln Arg Ile Leu Gly His Ile Gln Ala Pro Pro Arg Pro Phe Leu<br>145                     150                     155                     160 | 600 |
| gtc agg ctg ttc agc tgg gcg ctg ctg agg ttc ctg aac tgc ctg ttc<br>Val Arg Leu Phe Ser Trp Ala Leu Leu Arg Phe Leu Asn Cys Leu Phe<br>                    165                     170                     175 | 648 |
| ctg aat gtg cag ctc cac aag ggt cag atg aag atg gtc cag aag gcc<br>Leu Asn Val Gln Leu His Lys Gly Gln Met Lys Met Val Gln Lys Ala<br>            180                     185                     190 | 696 |
| gcc cag gca ggc ttg ccg ctt gtc ctc ctc tct act cac aaa acc ctc<br>Ala Gln Ala Gly Leu Pro Leu Val Leu Leu Ser Thr His Lys Thr Leu<br>      195                     200                     205 | 744 |
| ctg gat ggg atc ctg ctg ccc ttt atg ctg ctc tcc cag ggc ctg ggt<br>Leu Asp Gly Ile Leu Leu Pro Phe Met Leu Leu Ser Gln Gly Leu Gly<br>210                     215                     220 | 792 |
| gtg ctt cgt gtg gcc tgg gac tcc cgc gcc tgc tcc cct gcc ctc aga<br>Val Leu Arg Val Ala Trp Asp Ser Arg Ala Cys Ser Pro Ala Leu Arg<br>225                     230                     235                     240 | 840 |
| gct ctg ctg agg aag ctt ggg ggg ctt ttc ctg ccc cca gag gcc agc<br>Ala Leu Leu Arg Lys Leu Gly Gly Leu Phe Leu Pro Pro Glu Ala Ser<br>                    245                     250                     255 | 888 |
| ctc tcc ctg gac agc tct gag ggg ctc ctt gcc agg gct gtg gtc cag<br>Leu Ser Leu Asp Ser Ser Glu Gly Leu Leu Ala Arg Ala Val Val Gln<br>            260                     265                     270 | 936 |
| gcg gtc ata gag cag ctg ctg gtt agt ggg cag ccc ctg ctc atc ttc<br>Ala Val Ile Glu Gln Leu Leu Val Ser Gly Gln Pro Leu Leu Ile Phe<br>      275                     280                     285 | 984 |
| ctg gag gaa cct cct ggg gct ctg ggg cca cgg ctg tca gcc ctg ggc<br>Leu Glu Glu Pro Pro Gly Ala Leu Gly Pro Arg Leu Ser Ala Leu Gly<br>290                     295                     300 | 1032 |
| cag gct tgg gtg ggg ttt gtg gtg cag gca gtc cag gtg ggc atc gtc<br>Gln Ala Trp Val Gly Phe Val Val Gln Ala Val Gln Val Gly Ile Val<br>305                     310                     315                     320 | 1080 |
| cca gat gct ctg ctg gta cca gtg gcc gtc acc tat gac ctg gtt ccg<br>Pro Asp Ala Leu Leu Val Pro Val Ala Val Thr Tyr Asp Leu Val Pro<br>                    325                     330                     335 | 1128 |
| gat gca ccg tgt gac ata gac cat gcc tcg gcc ccc ctg ggg ctg tgg<br>Asp Ala Pro Cys Asp Ile Asp His Ala Ser Ala Pro Leu Gly Leu Trp<br>            340                     345                     350 | 1176 |
| aca gga gct ctg gct gtc cta cgt agc ttg tgg agc cgc tgg ggc tgc<br>Thr Gly Ala Leu Ala Val Leu Arg Ser Leu Trp Ser Arg Trp Gly Cys<br>      355                     360                     365 | 1224 |

-continued

| | | |
|---|---|---|
| agc cac cgg atc tgc tcc cgg gtg cac cta gct cag ccc ttt tcc ctg<br>Ser His Arg Ile Cys Ser Arg Val His Leu Ala Gln Pro Phe Ser Leu<br>370               375                 380 | 1272 |
| cag gaa tac atc gtc agt gcc aga agc tgc tgg ggc ggc aga cag acc<br>Gln Glu Tyr Ile Val Ser Ala Arg Ser Cys Trp Gly Gly Arg Gln Thr<br>385               390              395             400 | 1320 |
| ctg gag cag cta ctg cag ccc atc gtg ctg ggc caa tgt act gct gtc<br>Leu Glu Gln Leu Leu Gln Pro Ile Val Leu Gly Gln Cys Thr Ala Val<br>                     405                 410             415 | 1368 |
| cca gac act gag aag gag cag gag tgg acc ccc ata act ggg cct ctc<br>Pro Asp Thr Glu Lys Glu Gln Glu Trp Thr Pro Ile Thr Gly Pro Leu<br>420               425                 430 | 1416 |
| ctg gcc ctc aag gaa gag gac cag ctc ctg gtc agg aga ctg agc tgt<br>Leu Ala Leu Lys Glu Glu Asp Gln Leu Leu Val Arg Arg Leu Ser Cys<br>435               440                 445 | 1464 |
| cat gtc ctg agt gcc agt gta ggg agc tct gcg gtg atg agc acg gcc<br>His Val Leu Ser Ala Ser Val Gly Ser Ser Ala Val Met Ser Thr Ala<br>450               455                 460 | 1512 |
| att atg gca acg ctg ctc ttc aag cat cag aag ggt gtg ttc ctg<br>Ile Met Ala Thr Leu Leu Leu Phe Lys His Gln Lys Gly Val Phe Leu<br>465               470              475             480 | 1560 |
| tcg cag ctc ctg ggg gag ttc tcc tgg ctg acg gag gag ata ctg ttg<br>Ser Gln Leu Leu Gly Glu Phe Ser Trp Leu Thr Glu Glu Ile Leu Leu<br>                     485                 490             495 | 1608 |
| cgt ggc ttt gat gta ggc ttc tct ggg cag ctg cgg agc ctg ctg cag<br>Arg Gly Phe Asp Val Gly Phe Ser Gly Gln Leu Arg Ser Leu Leu Gln<br>500               505                 510 | 1656 |
| cac tca ctg agc ctg ctg cgg gcg cac gtg gcc ctg ctg cgc atc cgt<br>His Ser Leu Ser Leu Leu Arg Ala His Val Ala Leu Leu Arg Ile Arg<br>515               520                 525 | 1704 |
| cag ggt gac ttg ctg gtg gtg ccg cag cct ggc cca ggc ctc aca cac<br>Gln Gly Asp Leu Leu Val Val Pro Gln Pro Gly Pro Gly Leu Thr His<br>530               535                 540 | 1752 |
| ctg gca caa ctg agt gct gag ctg ctg ccc gtc ttc ctg agc gag gct<br>Leu Ala Gln Leu Ser Ala Glu Leu Leu Pro Val Phe Leu Ser Glu Ala<br>545               550              555             560 | 1800 |
| gtg ggc gcc tgt gca gtg cgg ggg ctg ctg gca ggc aga gtg ccg ccc<br>Val Gly Ala Cys Ala Val Arg Gly Leu Leu Ala Gly Arg Val Pro Pro<br>                     565                 570             575 | 1848 |
| cag ggg ccc tgg gag ctg cag ggc ata ttg ctg ctg agc cag aat gag<br>Gln Gly Pro Trp Glu Leu Gln Gly Ile Leu Leu Leu Ser Gln Asn Glu<br>580               585                 590 | 1896 |
| ctg tac cgc cag atc ctg ctg ctg atg cac ctg ctg ccg caa gac ctg<br>Leu Tyr Arg Gln Ile Leu Leu Leu Met His Leu Leu Pro Gln Asp Leu<br>595               600                 605 | 1944 |
| ctg ctg cta aag acc cca ggc tcc cgg cca gcc tgt gac aca ggg cga<br>Leu Leu Leu Lys Thr Pro Gly Ser Arg Pro Ala Cys Asp Thr Gly Arg<br>610               615                 620 | 1992 |
| cag cga ttg agc aga aag ctg ctg tgg aaa ccg agt ggg gac ttt act<br>Gln Arg Leu Ser Arg Lys Leu Leu Trp Lys Pro Ser Gly Asp Phe Thr<br>625               630              635             640 | 2040 |
| gat agt gac agt gat gac ttc gga gag gct gac ggc cgg tac ttc agg<br>Asp Ser Asp Ser Asp Asp Phe Gly Glu Ala Asp Gly Arg Tyr Phe Arg<br>                     645                 650             655 | 2088 |
| ctc agc cag cag tca cac tgc cca gat ttc ttt ctt ttc ctg tgc cgc<br>Leu Ser Gln Gln Ser His Cys Pro Asp Phe Phe Leu Phe Leu Cys Arg<br>660               665                 670 | 2136 |
| ctg ctc agc ccg ctg ctc aag gcc ttt gca cag gct gcc gcc ttc ctc<br>Leu Leu Ser Pro Leu Leu Lys Ala Phe Ala Gln Ala Ala Ala Phe Leu | 2184 |

-continued

```
              675                 680                 685
cgc cag ggc cag ctg ccc gat act gag ttg ggc tac aca gag cag ctg       2232
Arg Gln Gly Gln Leu Pro Asp Thr Glu Leu Gly Tyr Thr Glu Gln Leu
            690                 695                 700 ttc cag ttc ctg cag gcc acc gcc cag gaa gaa ggg atc ttc gag tgt       2280
Phe Gln Phe Leu Gln Ala Thr Ala Gln Glu Glu Gly Ile Phe Glu Cys
705                 710                 715                 720 gcg gac cca aag ctc gcc atc agt gct gtc tgg acc ttc aga gac cta       2328
Ala Asp Pro Lys Leu Ala Ile Ser Ala Val Trp Thr Phe Arg Asp Leu
                725                 730                 735 ggg gtt ctg cag cag acg ccg agc cct gca ggc ccc agg ctc cac ctg       2376
Gly Val Leu Gln Gln Thr Pro Ser Pro Ala Gly Pro Arg Leu His Leu
            740                 745                 750 tcc cct act ttt gcc agc ctg gac aat cag gaa aaa cta gaa cag ttc       2424
Ser Pro Thr Phe Ala Ser Leu Asp Asn Gln Glu Lys Leu Glu Gln Phe
        755                 760                 765 atc cgg cag ttc att tgt agc tagaactgtg aggaggagcc tgtgctgaga           2475
Ile Arg Gln Phe Ile Cys Ser
    770                 775 cttctcagcc ccagaacaca gctgtgtcct agagccagaa gatggagagg aggctgcaaa    2535
cccttagctg ctctataaat ataatcattg aggcttgatt gtcccttgcc atctcttgct    2595
ttttcccttc tttgatgtga taaacaaggg gacgagacga gttgtctttt ccccagccca    2655
gcagcaaaaa aaaaaaaaaa aaaaaaa                                         2682

<210> SEQ ID NO 49
<211> LENGTH: 775
<212> TYPE: PRT
<213> ORGANISM: Homo sapiens

<400> SEQUENCE: 49

Met Ala Thr Met Leu Glu Gly Arg Cys Gln Thr Gln Pro Arg Ser Ser
1               5                   10                  15

Pro Ser Gly Arg Glu Ala Ser Leu Trp Ser Ser Gly Phe Gly Met Lys
            20                  25                  30

Leu Glu Ala Val Thr Pro Phe Leu Gly Lys Tyr Arg Pro Phe Val Gly
        35                  40                  45

Arg Cys Cys Gln Thr Cys Thr Pro Lys Ser Trp Glu Ser Leu Phe His
    50                  55                  60

Arg Ser Ile Thr Asp Leu Gly Phe Cys Asn Val Ile Leu Val Lys Glu
65                  70                  75                  80

Glu Asn Thr Arg Phe Arg Gly Trp Leu Val Arg Arg Leu Cys Tyr Phe
                85                  90                  95

Leu Trp Ser Leu Glu Gln His Ile Pro Pro Cys Gln Asp Val Pro Gln
            100                 105                 110

Lys Ile Met Glu Ser Thr Gly Val Gln Asn Leu Leu Ser Gly Arg Val
        115                 120                 125

Pro Gly Gly Thr Gly Glu Gly Gln Val Pro Asp Leu Val Lys Lys Glu
    130                 135                 140

Val Gln Arg Ile Leu Gly His Ile Gln Ala Pro Arg Pro Phe Leu
145                 150                 155                 160

Val Arg Leu Phe Ser Trp Ala Leu Leu Arg Phe Leu Asn Cys Leu Phe
                165                 170                 175

Leu Asn Val Gln Leu His Lys Gly Gln Met Lys Met Val Gln Lys Ala
            180                 185                 190

Ala Gln Ala Gly Leu Pro Leu Val Leu Leu Ser Thr His Lys Thr Leu
```

-continued

```
            195                 200                 205
Leu Asp Gly Ile Leu Leu Pro Phe Met Leu Ser Gln Gly Leu Gly
    210                 215                 220
Val Leu Arg Val Ala Trp Asp Ser Arg Ala Cys Ser Pro Ala Leu Arg
225                 230                 235                 240
Ala Leu Arg Lys Leu Gly Gly Leu Phe Leu Pro Pro Glu Ala Ser
                245                 250                 255
Leu Ser Leu Asp Ser Ser Glu Gly Leu Leu Ala Arg Ala Val Val Gln
                260                 265                 270
Ala Val Ile Glu Gln Leu Leu Val Ser Gly Gln Pro Leu Leu Ile Phe
            275                 280                 285
Leu Glu Glu Pro Pro Gly Ala Leu Gly Pro Arg Leu Ser Ala Leu Gly
        290                 295                 300
Gln Ala Trp Val Gly Phe Val Val Gln Ala Val Gln Val Gly Ile Val
305                 310                 315                 320
Pro Asp Ala Leu Leu Val Pro Val Ala Val Thr Tyr Asp Leu Val Pro
                325                 330                 335
Asp Ala Pro Cys Asp Ile Asp His Ala Ser Ala Pro Leu Gly Leu Trp
                340                 345                 350
Thr Gly Ala Leu Ala Val Leu Arg Ser Leu Trp Ser Arg Trp Gly Cys
            355                 360                 365
Ser His Arg Ile Cys Ser Arg Val His Leu Ala Gln Pro Phe Ser Leu
        370                 375                 380
Gln Glu Tyr Ile Val Ser Ala Arg Ser Cys Trp Gly Gly Arg Gln Thr
385                 390                 395                 400
Leu Glu Gln Leu Leu Gln Pro Ile Val Leu Gly Gln Cys Thr Ala Val
                405                 410                 415
Pro Asp Thr Glu Lys Glu Gln Glu Trp Thr Pro Ile Thr Gly Pro Leu
                420                 425                 430
Leu Ala Leu Lys Glu Glu Asp Gln Leu Leu Val Arg Arg Leu Ser Cys
            435                 440                 445
His Val Leu Ser Ala Ser Val Gly Ser Ser Ala Val Met Ser Thr Ala
        450                 455                 460
Ile Met Ala Thr Leu Leu Phe Lys His Gln Lys Gly Val Phe Leu
465                 470                 475                 480
Ser Gln Leu Leu Gly Glu Phe Ser Trp Leu Thr Glu Glu Ile Leu Leu
                485                 490                 495
Arg Gly Phe Asp Val Gly Phe Ser Gly Gln Leu Arg Ser Leu Leu Gln
                500                 505                 510
His Ser Leu Ser Leu Leu Arg Ala His Val Ala Leu Leu Arg Ile Arg
            515                 520                 525
Gln Gly Asp Leu Leu Val Val Pro Gln Pro Gly Pro Gly Leu Thr His
        530                 535                 540
Leu Ala Gln Leu Ser Ala Glu Leu Leu Pro Val Phe Leu Ser Glu Ala
545                 550                 555                 560
Val Gly Ala Cys Ala Val Arg Gly Leu Leu Ala Gly Arg Val Pro Pro
                565                 570                 575
Gln Gly Pro Trp Glu Leu Gln Gly Ile Leu Leu Ser Gln Asn Glu
                580                 585                 590
Leu Tyr Arg Gln Ile Leu Leu Leu Met His Leu Leu Pro Gln Asp Leu
            595                 600                 605
Leu Leu Leu Lys Thr Pro Gly Ser Arg Pro Ala Cys Asp Thr Gly Arg
        610                 615                 620
```

-continued

```
Gln Arg Leu Ser Arg Lys Leu Leu Trp Lys Pro Ser Gly Asp Phe Thr
625                 630                 635                 640

Asp Ser Asp Ser Asp Asp Phe Gly Glu Ala Asp Gly Arg Tyr Phe Arg
            645                 650                 655

Leu Ser Gln Gln Ser His Cys Pro Asp Phe Leu Phe Leu Cys Arg
        660                 665                 670

Leu Leu Ser Pro Leu Leu Lys Ala Phe Ala Gln Ala Ala Phe Leu
            675                 680                 685

Arg Gln Gly Gln Leu Pro Asp Thr Glu Leu Gly Tyr Thr Glu Gln Leu
690                 695                 700

Phe Gln Phe Leu Gln Ala Thr Ala Gln Glu Glu Gly Ile Phe Glu Cys
705                 710                 715                 720

Ala Asp Pro Lys Leu Ala Ile Ser Ala Val Trp Thr Phe Arg Asp Leu
                725                 730                 735

Gly Val Leu Gln Gln Thr Pro Ser Pro Ala Gly Pro Arg Leu His Leu
            740                 745                 750

Ser Pro Thr Phe Ala Ser Leu Asp Asn Gln Glu Lys Leu Glu Gln Phe
        755                 760                 765

Ile Arg Gln Phe Ile Cys Ser
770                 775
```

```
<210> SEQ ID NO 50
<211> LENGTH: 2328
<212> TYPE: DNA
<213> ORGANISM: Homo sapiens

<400> SEQUENCE: 50
atggccacca tgttggaagg cagatgccaa actcagccaa ggagcagccc cagtggccga      60
gaggctagcc tgtggtcgtc aggctttggg atgaagctgg aggctgtcac tccattcctg     120
gggaagtatc gccctttgt gggtcgctgt tgccagacct gcaccccaa gagctgggag       180 tccctcttcc acagaagcat aacggaccta ggcttctgca atgtgatcct ggtgaaggag     240
gagaacacaa ggtttcgggg ctggctggtt cggaggctct gctatttcct gtggtccctg    300
gagcagcaca tccccccctg ccaggatgtc ccacagaaga tcatggaaag caccggggtg    360 cagaaccctcc tctcagggag ggtcccagga ggcactgggg aaggccaggt gcctgacctt   420
gtgaagaagg aggtacagcg catcctgggt cacatccagg ccccacccg tcccttcctg    480 gtcaggctgt tcagctgggc gctgctgagg ttcctgaact gcctgttcct gaatgtgcag   540
ctccacaagg gtcagatgaa gatggtccag aaggccgccc aggcaggctt gccgcttgtc   600
ctcctctcta tcacaaaac cctcctggat gggatcctgc tgccctttat gctgctctcc   660
cagggcctgg gtgtgcttcg tgtggcctgg gactcccgcg cctgctcccc tgccctcaga  720
gctctgctga ggaagcttgg gggcttttc ctgcccccag aggccagcct ctccctggac   780
agctctgagg ggctccttgc cagggctgtg gtccaggcgg tcatagagca gctgctggtt  840
agtgggcagc ccctgctcat cttcctggag aacctcctg gggctctggg gccacggctg  900
tcagccctgg gccaggcttg ggtgggttt gtggtgcagg cagtccaggt gggcatcgtc   960
ccagatgctc tgctggtacc agtggccgtc acctatgacc tggttccgga tgcaccgtgt  1020
gacatagacc atgcctcggc ccccctgggg ctgtggacag agctctggc tgtcctacgt  1080 agcttgtgga gccgctgggg ctgcagccac cggatctgct cccgggtgca cctagctcag  1140
cccttttccc tgcaggaata catcgtcagt gccagaagct gctggggcgg cagacagacc  1200
```

-continued

```
ctggagcagc tactgcagcc catcgtgctg ggccaatgta ctgctgtccc agacactgag    1260
aaggagcagg agtggacccc cataactggg cctctcctgg ccctcaagga agaggaccag    1320
ctcctggtca ggagactgag ctgtcatgtc ctgagtgcca gtgtagggag ctctgcggtg    1380
atgagcacgg ccattatggc aacgctgctg ctcttcaagc atcagaaggg tgtgttcctg    1440
tcgcagctcc tgggggagtt ctcctggctg acggaggaga tactgttgcg tggctttgat    1500
gtaggcttct ctgggcagct gcggagcctg ctgcagcact cactgagcct gctgcgggcg    1560
cacgtggccc tgctgcgcat ccgtcagggt gacttgctgg tggtgccgca gcctggccca    1620
ggcctcacac acctggcaca actgagtgct gagctgctgc ccgtcttcct gagcgaggct    1680
gtgggcgcct gtgcagtgcg ggggctgctg gcaggcagag tgccgcccca ggggccctgg    1740
gagctgcagg gcatattgct gctgagccag aatgagctgt accgccagat cctgctgctg    1800
atgcacctgc tgccgcaaga cctgctgctg ctaaagaccc caggctcccg gccagcctgt    1860
gacacagggc gacagcgatt gagcagaaag ctgctgtgga aaccgagtgg ggactttact    1920
gatagtgaca gtgatgactt cggagaggct gacggccggt acttcaggct cagccagcag    1980
tcacactgcc cagatttctt tcttttcctc tgccgcctgc tcagcccgct gctcaaggcc    2040
tttgcacagg ctgccgcctt cctccgccag ggccagctgc ccgatactga gttgggctac    2100
acagagcagc tgttccagtt cctgcaggcc accgccagg aagaagggat cttcgagtgt    2160
gcggacccaa agctcgccat cagtgctgtc tggaccttca gagacctagg ggttctgcag    2220
cagacgccga gccctgcagg ccccaggctc cacctgtccc ctactttgc cagcctggac    2280 aatcaggaaa aactagaaca gttcatccgg cagttcattt gtagctag                2328
```

<210> SEQ ID NO 51
<211> LENGTH: 195
<212> TYPE: PRT
<213> ORGANISM: Artificial Sequence
<220> FEATURE:
<223> OTHER INFORMATION: consensus sequence

<400> SEQUENCE: 51

```
Leu Glu Asn Leu Pro Lys Lys Gly Pro Ala Ile Val Ser Asn His
  1               5                  10                  15

Arg Ser Tyr Leu Asp Ile Leu Val Leu Ser Ala Ala Leu Pro Arg Arg
             20                  25                  30

Gly Pro Trp Leu Val Arg Arg Leu Val Phe Ile Ala Lys Lys Glu Leu
         35                  40                  45

Leu Lys Val Pro Leu Leu Phe Gly Trp Leu Met Arg Leu Ala Gly Ala
     50                  55                  60

Ile Phe Ile Asp Arg Asn Asn Arg Ala Lys Asp Ala Leu Ala Ala Ala
 65                  70                  75                  80

Asp Glu Leu Val Arg Val Leu Glu Leu Leu Arg Lys Gly Arg Ser Val
                 85                  90                  95

Leu Ile Phe Pro Glu Gly Thr Arg Ser Arg Ser Gly Glu Leu Leu Pro
            100                 105                 110

Pro Phe Lys Lys Gly Ile Ala Ala Phe Arg Leu Ala Leu Lys Ala Gly
        115                 120                 125

Val Pro Ile Val Pro Val Ile Val Ser Gly Thr Glu Glu Leu Glu
    130                 135                 140

Pro Lys Asn Glu Ala Gly Lys Leu Leu Arg Leu Ala Arg Lys Lys Gly
145                 150                 155                 160

Pro Val Thr Val Arg Val Leu Pro Pro Ile Pro Leu Asp Pro Glu Asp
```

-continued

```
                165                 170                 175
Ile Lys Glu Leu Ala Glu Arg Leu Arg Asp Ile Leu Val Gln Ala Leu
            180                 185                 190

Glu Glu Leu
        195

<210> SEQ ID NO 52
<211> LENGTH: 135
<212> TYPE: PRT
<213> ORGANISM: Artificial Sequence
<220> FEATURE:
<223> OTHER INFORMATION: consensus sequence

<400> SEQUENCE: 52

Ala Leu Val Val Ala Asn His Gln Ser Tyr Leu Asp Pro Leu Val Leu
  1               5                  10                  15

Ser Ala Leu Leu Pro Arg Lys Arg Arg Val Arg Phe Val Ala Lys Lys
            20                  25                  30

Glu Leu Phe Lys Ile Pro Leu Leu Gly Trp Leu Leu Arg Leu Ala Gly
        35                  40                  45

Ala Ile Phe Ile Asp Arg Ser Asn Gly Asp Arg Lys Ala Arg Ala Ala
    50                  55                  60

Leu Arg Glu Ala Val Arg Arg Tyr Phe Glu Asn His Glu Leu Leu Lys
65                  70                  75                  80

Glu Gly Glu Trp Leu Val Ile Phe Pro Glu Gly Thr Arg Ser Arg Asp
                85                  90                  95

Gly Lys Leu Asp Gly Glu Glu Glu Arg Leu Lys Leu Leu Pro Phe Lys
            100                 105                 110

Lys Gly Ala Phe Arg Leu Ala Leu Lys Ala Gly Asp Val Pro Ile Val
        115                 120                 125

Pro Val Ala Ile Ser Gly Thr
    130                 135

<210> SEQ ID NO 53
<211> LENGTH: 89
<212> TYPE: PRT
<213> ORGANISM: Artificial Sequence
<220> FEATURE:
<223> OTHER INFORMATION: consensus sequence

<400> SEQUENCE: 53

Met Ser Arg Lys Arg Pro Phe Val Gly Arg Cys Cys Tyr Ser Cys Thr
  1               5                  10                  15

Pro Gln Ser Trp Glu Arg Phe Phe Asn Pro Ser Ile Pro Ser Leu Gly
            20                  25                  30

Leu Arg Asn Val Ile Tyr Ile Asn Glu Thr His Thr Arg His Arg Gly
        35                  40                  45

Trp Leu Ala Arg Arg Leu Ser Tyr Ile Leu Phe Val Gln Glu Arg Asp
    50                  55                  60

Val His Lys Gly Met Phe Ala Thr Ser Ile Thr Asp Asn Val Leu Asn
65                  70                  75                  80

Ser Ser Arg Val Gln Glu Ala Ile Ala
                85

<210> SEQ ID NO 54
<211> LENGTH: 293
<212> TYPE: PRT
<213> ORGANISM: Artificial Sequence
<220> FEATURE:
```

<223> OTHER INFORMATION: consensus sequence

<400> SEQUENCE: 54

Ile Thr Pro Cys Lys Pro Ile Asp Ile Lys Cys Ser Val Leu Asn Ser
1               5                   10                  15

Glu Glu Ile His Arg Val Ile Gln Gln Ser Lys Glu Lys Asn Gln
            20                  25                  30

Ser Val Asp Lys Val Lys Glu Glu Ala Ala Lys Ile Leu Asp Glu Met
        35                  40                  45

Ser Ala Lys Leu Ser Pro Gly Met Ile Arg Leu Cys Gly Trp Val Leu
50                  55                  60

Arg Lys Leu Phe Asn Arg Phe Phe Trp Lys Ile Gln Val His Lys Glu
65                  70              75                  80

Gln Leu Glu Met Leu Lys Ala Ala Thr Glu Thr His Leu Pro Leu Val
                85                  90                  95

Tyr Leu Pro Cys His Arg Ser His Ile Asp Tyr Leu Leu Thr Phe
            100                 105                 110

Ile Leu Tyr His His Asn Leu Lys Pro Pro His Ile Ala Ser Gly Met
            115                 120                 125

Asp Asn Leu Asn Phe Pro Met Met Gly Thr Leu Leu Arg Lys Thr Gly
    130                 135                 140

Ala Phe Phe Ile Arg Arg Arg Phe Asp Glu Thr Pro Asp Gly Lys
145                 150                 155                 160

Asp Lys Leu Tyr Arg Ala Ile Leu His Glu Tyr Val Lys Glu Leu Leu
                165                 170                 175

Arg Lys Gly Tyr Ala Pro Ile Glu Phe Phe Leu Glu Gly Thr Arg Ser
            180                 185                 190

Arg Thr Gly Lys Thr Leu Thr Pro Lys Phe Gly Leu Leu Ser Val Val
        195                 200                 205

Val Glu Ala Leu Gln His Gly Glu Val Pro Asp Ile Tyr Leu Val Pro
210                 215                 220

Val Ser Ile Ser Tyr Asp Arg Ile Ile Glu Gly Thr His Tyr Ala His
225                 230                 235                 240

Glu Leu Leu Gly Ala Pro Lys Lys Glu Ser Leu Trp Gly Val Leu
                245                 250                 255

Arg Gly Ile Phe Lys Met Leu Ser Lys Asn Tyr Gln Cys Gly Tyr Val
            260                 265                 270

His Val His Phe Gly Glu Pro Ile Ser Leu Arg Glu Tyr Leu Glu Thr
        275                 280                 285

His Thr Pro Asp Trp
    290

<210> SEQ ID NO 55
<211> LENGTH: 156
<212> TYPE: PRT
<213> ORGANISM: Artificial Sequence
<220> FEATURE:
<223> OTHER INFORMATION: consensus sequence

<400> SEQUENCE: 55

Leu Ile Arg Ser Ile Gly Glu His Val Val Phe Asp Cys Ser Met Met
1               5                   10                  15

Cys Ser Ile Met Ser Thr His Val Val Ala Cys Leu Leu Leu Thr Arg
            20                  25                  30

Trp Arg Asn Gly Val His Arg Ser Thr Leu Glu Glu Asp Cys Asp Trp
        35                  40                  45

```
Leu Cys Glu Lys Ile Leu Ala Glu Gly Gly Asp Ile Val Gly Phe Ser
     50                  55                  60
Gly Lys Ser Thr Lys Gly Ser Gln Ile Val Lys Tyr Ala Cys Glu Leu
 65                  70                  75                  80
Leu Gly Ser Cys Val Thr Val Thr Asp Glu Asp Arg Asn Asp Glu Phe
                 85                  90                  95
Tyr Ile Ser Pro Lys Asn Ser Val Pro Ser Phe Ile Glu Leu Ala Tyr
            100                 105                 110
Tyr Ser Asn Ser Val Ile Cys His Phe Ala Leu Lys Ser Ile Ile Ala
        115                 120                 125
Cys Thr Ile Tyr Ser Leu Pro Asn Lys Thr Lys Asn Gly Gly Glu Ala
    130                 135                 140
Gly Gly Leu Gly Asn Leu Ile Ser Gln Glu Gln Leu
145                 150                 155
```

<210> SEQ ID NO 56
<211> LENGTH: 84
<212> TYPE: PRT
<213> ORGANISM: Artificial Sequence
<220> FEATURE:
<223> OTHER INFORMATION: consensus sequence

<400> SEQUENCE: 56

```
Arg Gly Pro Val Pro Glu Ser Glu Tyr Leu Gln Lys Leu His Arg Tyr
 1               5                  10                  15
Leu Ile Thr Arg Thr Glu Arg Asn Val Ala Val Tyr Ala Glu Ser Ala
            20                  25                  30
Thr Tyr Cys Leu Val Lys Asn Ala Val Lys Met Phe Lys Asp Ile Gly
        35                  40                  45
Val Phe Lys Glu Thr Lys Gln Lys Arg Ala Ser Val Leu Glu Leu Ser
    50                  55                  60
Thr Thr Phe Leu Pro Gln Cys Asn Arg Gln Lys Leu Leu Glu Tyr Ile
 65                  70                  75                  80
Leu Ser Phe Val
```

<210> SEQ ID NO 57
<211> LENGTH: 1766
<212> TYPE: DNA
<213> ORGANISM: Homo sapiens
<220> FEATURE:
<221> NAME/KEY: CDS
<222> LOCATION: (301)...(1368)
<220> FEATURE:
<221> NAME/KEY: misc_feature
<222> LOCATION: (1)...(1766)
<223> OTHER INFORMATION: n = A,T,C or G

<400> SEQUENCE: 57

| | |
|---|---|
| cgcggaattc cawacaagag gattatggag gaccaaaaac ccctctttat aattaacaaa | 60 |
| gatcatgagg tagwggccat ttcatgcaga cacagtgatt tcacctcttt tcccactgca | 120 |
| attgnttttgt ctcttacttc tgaagatggc tgatgtcacc cattaaactt atttacttgt | 180 |
| ttggcatatt taacttctac acagttaaag ttgcccttt ggtcaattct tctgtcgtat | 240 |
| ggcattttct catgtcctga tgctttcttt taaggtatta tccaaagaga tgagtcaccc | 300 |

```
atg gaa aaa ggg ctc tct ggt cta cga gga agg gac ttt gag ctg tct      348
Met Glu Lys Gly Leu Ser Gly Leu Arg Gly Arg Asp Phe Glu Leu Ser
 1               5                  10                  15 gac gtg ttt tat ttc tcc aag aag gga ttg gaa gcc att gta gaa gat      396
Asp Val Phe Tyr Phe Ser Lys Lys Gly Leu Glu Ala Ile Val Glu Asp
```

```
                Asp Val Phe Tyr Phe Ser Lys Lys Gly Leu Glu Ala Ile Val Glu Asp
                                20                  25                  30 gaa gtg acc cag agg ttt tcc tca gag gag cta gtg tca tgg aat ctc        444
Glu Val Thr Gln Arg Phe Ser Ser Glu Glu Leu Val Ser Trp Asn Leu
         35                  40                  45 ctc aca aga acc aat gta aat ttc cag tac atc agt ctg cgg ctc act        492
Leu Thr Arg Thr Asn Val Asn Phe Gln Tyr Ile Ser Leu Arg Leu Thr
 50                  55                  60 atg gtg tgg gtg ctg ggc gtc ata gtg cgc tat tgt gtc cta ctg cct        540
Met Val Trp Val Leu Gly Val Ile Val Arg Tyr Cys Val Leu Leu Pro
 65                  70                  75                  80 ctg agg gtt acc ttg gct ttc att ggg atc agt ttg ctg gtt ata gga        588
Leu Arg Val Thr Leu Ala Phe Ile Gly Ile Ser Leu Leu Val Ile Gly
                 85                  90                  95 act aca ctg gtt ggg cag ctg cca gac agc agc ctc aaa aac tgg ctg        636
Thr Thr Leu Val Gly Gln Leu Pro Asp Ser Ser Leu Lys Asn Trp Leu
            100                 105                 110 agt gaa ctg gtc cat ctg act tgc tgc cgg atc tgt gtg cga gcc ctc        684
Ser Glu Leu Val His Leu Thr Cys Cys Arg Ile Cys Val Arg Ala Leu
        115                 120                 125 tct ggt acc att cat tat cat aac aag cag tac aga ccc cag aag gga        732
Ser Gly Thr Ile His Tyr His Asn Lys Gln Tyr Arg Pro Gln Lys Gly
130                 135                 140 ggc att tgt gtt gcc aac cat act tcc ccc att gat gtt tta atc ttg        780
Gly Ile Cys Val Ala Asn His Thr Ser Pro Ile Asp Val Leu Ile Leu
145                 150                 155                 160 aca acg gat gga tgt tat gct atg gtt ggc cag gtt cat ggc ggc ttg        828
Thr Thr Asp Gly Cys Tyr Ala Met Val Gly Gln Val His Gly Gly Leu
                165                 170                 175 atg gga att att cag aga gct atg gtc aag gct tgt cct cat gtc tgg        876
Met Gly Ile Ile Gln Arg Ala Met Val Lys Ala Cys Pro His Val Trp
            180                 185                 190 ttt gaa cgc tca gaa atg aag gat cga cac ctg gtt act aag aga cta        924
Phe Glu Arg Ser Glu Met Lys Asp Arg His Leu Val Thr Lys Arg Leu
        195                 200                 205 aaa gaa cat att gct gat aag aag aaa cta ccc ata cta att ttt cct        972
Lys Glu His Ile Ala Asp Lys Lys Lys Leu Pro Ile Leu Ile Phe Pro
210                 215                 220 gaa gga act tgc atc aac aat act tca gtc atg atg ttt aaa aag ggg       1020
Glu Gly Thr Cys Ile Asn Asn Thr Ser Val Met Met Phe Lys Lys Gly
225                 230                 235                 240 agc ttt gaa att gga gga acc ata cat cca gtt gca att aag tat aac       1068
Ser Phe Glu Ile Gly Gly Thr Ile His Pro Val Ala Ile Lys Tyr Asn
                245                 250                 255 cct cag ttc ggt gat gca ttt tgg aac agt agt aaa tac aac atg gtg       1116
Pro Gln Phe Gly Asp Ala Phe Trp Asn Ser Ser Lys Tyr Asn Met Val
            260                 265                 270 agc tac ctg ctt cga atg atg acc agc tgg gcc atc gtc tgt gac gtg       1164
Ser Tyr Leu Leu Arg Met Met Thr Ser Trp Ala Ile Val Cys Asp Val
        275                 280                 285 tgg tac atg ccc ccc atg acc aga gag gaa gga gaa gat gca gtc cag       1212
Trp Tyr Met Pro Pro Met Thr Arg Glu Glu Gly Glu Asp Ala Val Gln
290                 295                 300 ttt gct aac agg gtt aag tct gct att gct ata caa gga ggc ctg act       1260
Phe Ala Asn Arg Val Lys Ser Ala Ile Ala Ile Gln Gly Gly Leu Thr
305                 310                 315                 320 gaa ctt ccc tgg gat gga gga cta aag aga gca aag gtg aag gac atc       1308
Glu Leu Pro Trp Asp Gly Gly Leu Lys Arg Ala Lys Val Lys Asp Ile
                325                 330                 335
```

-continued

```
ttt aag gaa gag cag cag aaa aat tac agc aag atg att gtg ggc aat    1356
Phe Lys Glu Glu Gln Gln Lys Asn Tyr Ser Lys Met Ile Val Gly Asn
        340                 345                 350 gga tct ctc agc taagaggacg gatgacagcc tttagatcta gaactagccc         1408
Gly Ser Leu Ser
        355 ttagaaatgg aatggctttt ttgttttgtt ttgttttatt gttttgtttt tattattgtt   1468 aatcttttct acagaatgat tgtctctacc tctttatgcc agaggcagaa cctacaggtg   1528 cccttttttgg cttttgttgt tgttgtaaca ttagccccat ggattgtaag gtggtttact 1588 gagttmaaac agawtyyksy tttkkwaaaw krwkgsmwym mykkkgrmyk rawkraawtt   1648 kkwwwrraaa aaagtgcttg aaaagtgtgt ttggaactca tcgatagggt aattctccaa   1708 aaatgcccaa actctctttc tgtaattagc cttgccactt tctttcagtc acttaaat    1766
```

<210> SEQ ID NO 58
<211> LENGTH: 356
<212> TYPE: PRT
<213> ORGANISM: Homo sapiens

<400> SEQUENCE: 58

```
Met Glu Lys Gly Leu Ser Gly Leu Arg Gly Arg Asp Phe Glu Leu Ser
  1               5                  10                  15

Asp Val Phe Tyr Phe Ser Lys Lys Gly Leu Glu Ala Ile Val Glu Asp
                 20                  25                  30

Glu Val Thr Gln Arg Phe Ser Glu Glu Leu Val Ser Trp Asn Leu
             35                  40                  45

Leu Thr Arg Thr Asn Val Asn Phe Gln Tyr Ile Ser Leu Arg Leu Thr
         50                  55                  60

Met Val Trp Val Leu Gly Val Ile Val Arg Tyr Cys Val Leu Leu Pro
 65                  70                  75                  80

Leu Arg Val Thr Leu Ala Phe Ile Gly Ile Ser Leu Leu Val Ile Gly
                 85                  90                  95

Thr Thr Leu Val Gly Gln Leu Pro Asp Ser Ser Leu Lys Asn Trp Leu
            100                 105                 110

Ser Glu Leu Val His Leu Thr Cys Cys Arg Ile Cys Val Arg Ala Leu
        115                 120                 125

Ser Gly Thr Ile His Tyr His Asn Lys Gln Tyr Arg Pro Gln Lys Gly
    130                 135                 140

Gly Ile Cys Val Ala Asn His Thr Ser Pro Ile Asp Val Leu Ile Leu
145                 150                 155                 160

Thr Thr Asp Gly Cys Tyr Ala Met Val Gly Gln Val His Gly Leu
                165                 170                 175

Met Gly Ile Ile Gln Arg Ala Met Val Lys Ala Cys Pro His Val Trp
            180                 185                 190

Phe Glu Arg Ser Glu Met Lys Asp Arg His Leu Val Thr Lys Arg Leu
        195                 200                 205

Lys Glu His Ile Ala Asp Lys Lys Leu Pro Ile Leu Ile Phe Pro
    210                 215                 220

Glu Gly Thr Cys Ile Asn Asn Thr Ser Val Met Met Phe Lys Lys Gly
225                 230                 235                 240

Ser Phe Glu Ile Gly Gly Thr Ile His Pro Val Ala Ile Lys Tyr Asn
                245                 250                 255

Pro Gln Phe Gly Asp Ala Phe Trp Asn Ser Ser Lys Tyr Asn Met Val
            260                 265                 270
```

```
Ser Tyr Leu Leu Arg Met Met Thr Ser Trp Ala Ile Val Cys Asp Val
        275                 280                 285

Trp Tyr Met Pro Pro Met Thr Arg Glu Glu Gly Glu Asp Ala Val Gln
        290                 295                 300

Phe Ala Asn Arg Val Lys Ser Ala Ile Ala Ile Gln Gly Gly Leu Thr
305                 310                 315                 320

Glu Leu Pro Trp Asp Gly Gly Leu Lys Arg Ala Lys Val Lys Asp Ile
                325                 330                 335

Phe Lys Glu Glu Gln Gln Lys Asn Tyr Ser Lys Met Ile Val Gly Asn
                340                 345                 350

Gly Ser Leu Ser
        355
```

<210> SEQ ID NO 59
<211> LENGTH: 1071
<212> TYPE: DNA
<213> ORGANISM: Homo sapiens

<400> SEQUENCE: 59

| | | |
|---|---|---|
| atggaaaaag ggctctctgg tctacgagga agggactttg agctgtctga cgtgttttat | 60 |
| ttctccaaga agggattgga agccattgta gaagatgaag tgacccagag gttttcctca | 120 |
| gaggagctag tgtcatggaa tctcctcaca agaaccaatg taaatttcca gtacatcagt | 180 |
| ctgcggctca ctatggtgtg ggtgctgggc gtcatagtgc gctattgtgt cctactgcct | 240 |
| ctgagggtta ccttggcttt cattgggatc agtttgctgg ttataggaac tacactggtt | 300 |
| gggcagctgc cagacagcag cctcaaaaac tggctgagtg aactggtcca tctgacttgc | 360 |
| tgccggatct gtgtgcgagc cctctctggt accattcatt atcataacaa gcagtacaga | 420 |
| ccccagaagg gaggcatttg tgttgccaac catacttccc ccattgatgt tttaatcttg | 480 |
| acaacggatg gatgttatgc tatggttggc caggttcatg gcggcttgat gggaattatt | 540 |
| cagagagcta tggtcaaggc ttgtcctcat gtctggtttg aacgctcaga atgaaggat | 600 |
| cgacacctgg ttactaagag actaaaagaa catattgctg ataagaagaa actacccata | 660 |
| ctaatttttc ctgaaggaac ttgcatcaac aatacttcag tcatgatgtt taaaaagggg | 720 |
| agctttgaaa ttggaggaac catacatcca gttgcaatta gtataacccc tcagttcgt | 780 |
| gatgcatttt ggaacagtag taaatacaac atggtgagct acctgcttcg aatgatgacc | 840 |
| agctgggcca tcgtctgtga cgtgtggtac atgccccca tgaccagaga ggaaggagaa | 900 |
| gatgcagtcc agtttgctaa cagggttaag tctgctattg ctatacaagg aggcctgact | 960 |
| gaacttccct gggatggagg actaaagaga gcaaaggtga aggacatctt taaggaagag | 1020 |
| cagcagaaaa attacagcaa gatgattgtg ggcaatggat ctctcagcta a | 1071 |

<210> SEQ ID NO 60
<211> LENGTH: 189
<212> TYPE: PRT
<213> ORGANISM: Artificial Sequence
<220> FEATURE:
<223> OTHER INFORMATION: consensus sequence

<400> SEQUENCE: 60

```
Met Glu Thr Ile Met Asp Asp Gln Val Thr Asn Arg Phe Ser Ala Glu
1               5                   10                  15

Gln Leu Pro Ser Trp Asn Leu Leu Ser Arg Thr Asn Tyr Asn Phe His
            20                  25                  30

Tyr Phe Asn Trp Arg Leu Thr Ile Leu Trp Gly Ala Gly Phe Met Phe
```

-continued

```
                    35                  40                  45
Arg Tyr Cys Phe Leu Leu Pro Cys Arg Ile Ala Leu Phe Gly Thr Gly
         50                  55                  60

Ile Gly Leu Met Ile Val Gly Thr Thr Met Ile Gly Tyr Leu Pro Asn
 65                  70                  75                  80

Gly Arg Phe Arg Ile Phe Leu Asn Arg His Cys His Leu Met Cys Tyr
                 85                  90                  95

Arg Ile Cys Ser Arg Ala Phe Thr Ala Ile Ile Arg Tyr His Asn Arg
            100                 105                 110

Glu Asn Arg Pro Asn Asn Gly Gly Ile Cys Val Ala Asn His Thr Ser
        115                 120                 125

Pro Ile Asp Val Met Ile Phe Ala Cys Asp Asn Cys Tyr Ala Met Ile
130                 135                 140

Gly Gln Lys His Gly Gly Phe Met Gly Phe Ile Gln Arg Thr Met Ser
145                 150                 155                 160

Arg Ala Cys His His Ile Trp Phe Glu Arg Gly Glu Ala Gly Asp Arg
                165                 170                 175

His Lys Val Met Asp Arg Met Arg Glu His Val Asn Asp
            180                 185
```

<210> SEQ ID NO 61
<211> LENGTH: 114
<212> TYPE: PRT
<213> ORGANISM: Artificial Sequence
<220> FEATURE:
<223> OTHER INFORMATION: consensus sequence

<400> SEQUENCE: 61

```
Lys Ser Lys Gly Pro Ile Leu Ile Phe Pro Glu Gly Tyr Cys Ile Asn
 1               5                  10                  15

Asn Thr Lys Val Met Met Phe Lys Lys Gly Ser Phe Glu Glu Gly Val
             20                  25                  30

Asn Ile Tyr Pro Val Ala Ile Lys Tyr Asp Pro Glu Phe Gly Asp Gly
         35                  40                  45

Phe Trp Tyr Glu Asp Glu Tyr Gly Phe Phe Gln Tyr Leu Val Arg Met
     50                  55                  60

Met Thr Asn Trp Ala Ile Val Cys Asp Val Trp Tyr Leu Pro Met Met
 65                  70                  75                  80

Thr Arg Lys Glu His Glu Asp Asn Ser Leu Phe Ala Ala Arg Val Lys
                 85                  90                  95

Gln Ala Ile Ala Asn Ala Ala Gly Ile Pro Ser Cys Glu Tyr Gly Gly
            100                 105                 110

Ser Leu
```

<210> SEQ ID NO 62
<211> LENGTH: 3725
<212> TYPE: DNA
<213> ORGANISM: Homo sapiens
<220> FEATURE:
<221> NAME/KEY: CDS
<222> LOCATION: (306)...(1397)
<220> FEATURE:
<221> NAME/KEY: misc_feature
<222> LOCATION: (1)...(3725)
<223> OTHER INFORMATION: n = A,T,C or G

<400> SEQUENCE: 62
ncgcgtccgg gcagggggat tggcgatggg tgagggtcat ggggtgtgag catccctgag      60

-continued

```
ccatcgatcc gggagggccg cgggttccct tgctttgccg ccgggagcgg cgcacgcagc       120
cccgcactcg cctacccggc cccggcggc ggcgcggccg atgcggctgg gggcggaggc       180
tgggagcggg tggctgggcg cggaggcccg ggcccgggcg gtgattggcc gcctgctggc       240
cgcgactgag gcccgggagg cgggcgggga gcgcaggcgg agctcgctgc cgccgagctg       300 agaag atg ctg ctg tcc ctg gtg ctc cac acg tac tcc atg cgc tac ctg      350
      Met Leu Leu Ser Leu Val Leu His Thr Tyr Ser Met Arg Tyr Leu
       1               5                   10                  15 ctg ccc agc gtc gtg ctc ctg ggc acg gcg ccc acc tac gtg ttg gcc        398
Leu Pro Ser Val Val Leu Leu Gly Thr Ala Pro Thr Tyr Val Leu Ala
             20                  25                  30 tgg ggg gtc tgg cgg ctg ctc tcc gcc ttc ctg ccc gcc cgc ttc tac        446
Trp Gly Val Trp Arg Leu Leu Ser Ala Phe Leu Pro Ala Arg Phe Tyr
         35                  40                  45 caa gcg ctg gac gac cgg ctc tac tgc gtc tac cag agc atg gtg ctc        494
Gln Ala Leu Asp Asp Arg Leu Tyr Cys Val Tyr Gln Ser Met Val Leu
     50                  55                  60 ttc ttc ttc gag aat tac acc ggg gtc cag ata ttg cta tat gga gat        542
Phe Phe Phe Glu Asn Tyr Thr Gly Val Gln Ile Leu Leu Tyr Gly Asp
 65                  70                  75 ttg cca aaa aat aaa gaa aat ata ata tat tta gca aat cat caa agc        590
Leu Pro Lys Asn Lys Glu Asn Ile Ile Tyr Leu Ala Asn His Gln Ser
 80                  85                  90                  95 aca gtt gac tgg att gtt gct gac atc ttg gcc atc agg cag aat gcg        638
Thr Val Asp Trp Ile Val Ala Asp Ile Leu Ala Ile Arg Gln Asn Ala
                 100                 105                 110 cta gga cat gtg cgc tac gtg ctg aaa gaa ggg tta aaa tgg ctg cca        686
Leu Gly His Val Arg Tyr Val Leu Lys Glu Gly Leu Lys Trp Leu Pro
             115                 120                 125 ttg tat ggg tgt tac ttt gct cag cat gga gga atc tat gta aag cgc        734
Leu Tyr Gly Cys Tyr Phe Ala Gln His Gly Gly Ile Tyr Val Lys Arg
         130                 135                 140 agt gcc aaa ttt aac gag aaa gag atg cga aac aag ttg cag agc tac        782
Ser Ala Lys Phe Asn Glu Lys Glu Met Arg Asn Lys Leu Gln Ser Tyr
145                 150                 155 gtg gac gca gga act cca atg tat ctt gtg att ttt cca gaa ggt aca        830
Val Asp Ala Gly Thr Pro Met Tyr Leu Val Ile Phe Pro Glu Gly Thr
160                 165                 170                 175 agg tat aat cca gag caa aca aaa gtc ctt tca gct agt cag gca ttt        878
Arg Tyr Asn Pro Glu Gln Thr Lys Val Leu Ser Ala Ser Gln Ala Phe
                 180                 185                 190 gct gcc caa cgt ggc ctt gca gta tta aaa cat gtg cta aca cca cga        926
Ala Ala Gln Arg Gly Leu Ala Val Leu Lys His Val Leu Thr Pro Arg
             195                 200                 205 ata aag gca act cac gtt gct ttt gat tgc atg aag aat tat tta gat        974
Ile Lys Ala Thr His Val Ala Phe Asp Cys Met Lys Asn Tyr Leu Asp
         210                 215                 220 gca att tat gat gtt acg gtg gtt tat gaa ggg aaa gac gat gga ggg       1022
Ala Ile Tyr Asp Val Thr Val Val Tyr Glu Gly Lys Asp Asp Gly Gly
     225                 230                 235 cag cga aga gag tca ccg acc atg acg gaa ttt ctc tgc aaa gaa tgt       1070
Gln Arg Arg Glu Ser Pro Thr Met Thr Glu Phe Leu Cys Lys Glu Cys
240                 245                 250                 255 cca aaa att cat att cac att gat cgt atc gac aaa aaa gat gtc cca       1118
Pro Lys Ile His Ile His Ile Asp Arg Ile Asp Lys Lys Asp Val Pro
                 260                 265                 270 gaa gaa caa gaa cat atg aga aga tgg ctg cat gaa cgt ttc gaa atc       1166
Glu Glu Gln Glu His Met Arg Arg Trp Leu His Glu Arg Phe Glu Ile
             275                 280                 285
```

```
aaa gat aag atg ctt ata gaa ttt tat gag tca cca gat cca gaa aga     1214
Lys Asp Lys Met Leu Ile Glu Phe Tyr Glu Ser Pro Asp Pro Glu Arg
            290                 295                 300 aga aaa aga ttt cct ggg aaa agt gtt aat tcc aaa tta agt atc aag     1262
Arg Lys Arg Phe Pro Gly Lys Ser Val Asn Ser Lys Leu Ser Ile Lys
305                 310                 315 aag act tta cca tca atg ttg atc tta agt ggt ttg act gca ggc atg     1310
Lys Thr Leu Pro Ser Met Leu Ile Leu Ser Gly Leu Thr Ala Gly Met
320                 325                 330                 335 ctt atg acc gat gct gga agg aag ctg tat gtg aac acc tgg ata tat     1358
Leu Met Thr Asp Ala Gly Arg Lys Leu Tyr Val Asn Thr Trp Ile Tyr
                340                 345                 350 gga acc cta ctt ggc tgc ctg tgg gtt act att aaa gca tagacaagta      1407
Gly Thr Leu Leu Gly Cys Leu Trp Val Thr Ile Lys Ala
            355                 360 gctgtctcca gacagtggga tgtgctacat tgtctatttt tggcggctgc acatgacatc   1467
aaattgtttc ctgaatttat taaggagtgt aaataaagcc ttgttgattg aagattggat   1527
aatagaattt gtgacgaaag ctgatatgca atggtcttgg gcaaacatac ctggttgtac   1587
aactttagca tcgggctgc tggaagggta aaagctaaat ggagtttctc ctgctctgtc    1647
catttcctat gaactaatga caacttgaga aggctgggag gattgtgtat tttgcaagtc   1707
agatggctgc atttttgagc attaatttgc agcgtatttc acttttttctg ttattttcaa  1767 tttattacaa cttgacagct ccaagctctt attactaaag tatttagtat cttgcagcta   1827
gttaatattt catctttttgc ttatttctac aagtcagtga ataaattgt atttaggaag   1887 tgtcaggatg ttcaaaggaa agggtaaaaa gtgttcatgg ggaaaaagct ctgtttagca   1947
catgatttta ttgtattgcg ttattagctg attttactca ttttatattt gcaaaataaa   2007
tttctaatat ttattgaaat tgcttaattt gcacaccctg tacacacaga aaatggtata   2067
aaatatgaga acgaagttta aaattgtgac tctgattcat tatagcagaa ctttaaattt   2127
cccagctttt tgaagattta agctacgcta ttagtacttc cctttgtctg tgccataagt   2187
gcttgaaaac gttaaggttt tctgtttttgt tttgttttttt taatatcaaa agagtcggtg  2247
tgaaccttgg ttggaccca agttcacaag attttttaagg tgatgagagc ctgcagacat   2307
tctgcctaga ttactagcgt gtgccttttg cctgcttctc tttgatttca cagaatattc   2367
attcagaagt cgcgtttctg tagtgtggtg gattcccact gggctctggt ccttcccttg   2427
gatcccgtca gtggtgctgc tcagcggctt gcacgtagac ttgctaggaa gaaatgcaga   2487
gccagcctgt gctgcccact ttcagagttg aactctttaa gcccttgtga gtgggcttca   2547
ccagctactg cagaggcatt ttgcatttgt ctgtgtcaag aagttcacct tctcaagcca   2607
gtgaaataca gacttaattc gtcatgactg aacgaatttg tttatttccc attaggttta   2667
gtggagctac acattaatat gtatcgcctt agagcaagag ctgtgttcca ggaaccagat   2727
cacgattttt agccatggaa caatatatcc catgggnaga agacctttca gtgtgaactg   2787
ttctattttt gtgttataat ttaaacttcc gatttcctca tagtccttta agttgacatt   2847
tctgcnttac tgctactgga tttttgctgc agaaatatat ncagtggccc acattaaaca   2907
taccagttgg atcatgataa gcaaatgaa agaaataatg attaagggaa aattaagtga    2967
ctgtgttaca ctgcttctcc catgccagag aataaactct ttcaagcatc atctttgaag   3027
agtcgtgtgg tgtgaattgg tttngtgtac attagaatgt atgcacacat ccatggacac   3087
tcaggatata ngttggccta ataatcgggg catgggtaaa acttatgaaa atttcctcat   3147
```

-continued

```
gctgaanttg taattttctc ttacctgtaa agtaaaattt agatcaattc catgtctttg    3207
ttaagtnaca gggatttaat atattttgaa tataatgggt atgttctaaa tttgaacttt    3267
gnagaggcaa tactgttgga attatgtgga ttctaactca ttttaacaag gtagcctgac    3327
ctgcataaga tcacttgaat gtntaggttt catagaacta tactaatctt ctcacaaaag    3387
gtctataaaa tacagtcgtt gaaaaaaatt ttgtatcaaa atgtttggaa aattagaang    3447
cttctcctta acctgtattg atactgactt gaattatttt ctaaaattaa gagccgtata    3507
cctacctgta agtctttca catatcattt aaacttttgt ttgtattatt actgatttac    3567
agcttagtta ttaattttc tttataagaa tgccgtcgat gtgcatgctt ttatgttttt    3627
cagaaaaggg tgtgtttgga tgaaagtaaa aaaaaaata aaatctttnc actgtctcta    3687
aaaaaaaaaa aaaaaaaadr mrrmmrmwaa agtcgagc                           3725
```

<210> SEQ ID NO 63
<211> LENGTH: 364
<212> TYPE: PRT
<213> ORGANISM: Homo sapiens

<400> SEQUENCE: 63

```
Met Leu Leu Ser Leu Val Leu His Thr Tyr Ser Met Arg Tyr Leu Leu
 1               5                  10                  15

Pro Ser Val Val Leu Leu Gly Thr Ala Pro Thr Tyr Val Leu Ala Trp
                20                  25                  30

Gly Val Trp Arg Leu Leu Ser Ala Phe Leu Pro Ala Arg Phe Tyr Gln
            35                  40                  45

Ala Leu Asp Asp Arg Leu Tyr Cys Val Tyr Gln Ser Met Val Leu Phe
        50                  55                  60

Phe Phe Glu Asn Tyr Thr Gly Val Gln Ile Leu Leu Tyr Gly Asp Leu
 65                  70                  75                  80

Pro Lys Asn Lys Glu Asn Ile Ile Tyr Leu Ala Asn His Gln Ser Thr
                85                  90                  95

Val Asp Trp Ile Val Ala Asp Ile Leu Ala Ile Arg Gln Asn Ala Leu
            100                 105                 110

Gly His Val Arg Tyr Val Leu Lys Glu Gly Leu Lys Trp Leu Pro Leu
        115                 120                 125

Tyr Gly Cys Tyr Phe Ala Gln His Gly Gly Ile Tyr Val Lys Arg Ser
    130                 135                 140

Ala Lys Phe Asn Glu Lys Glu Met Arg Asn Lys Leu Gln Ser Tyr Val
145                 150                 155                 160

Asp Ala Gly Thr Pro Met Tyr Leu Val Ile Phe Pro Glu Gly Thr Arg
                165                 170                 175

Tyr Asn Pro Glu Gln Thr Lys Val Leu Ser Ala Ser Gln Ala Phe Ala
            180                 185                 190

Ala Gln Arg Gly Leu Ala Val Leu Lys His Val Leu Thr Pro Arg Ile
        195                 200                 205

Lys Ala Thr His Val Ala Phe Asp Cys Met Lys Asn Tyr Leu Asp Ala
    210                 215                 220

Ile Tyr Asp Val Thr Val Tyr Glu Gly Lys Asp Gly Gly Gln
225                 230                 235                 240

Arg Arg Glu Ser Pro Thr Met Thr Glu Phe Leu Cys Lys Glu Cys Pro
                245                 250                 255

Lys Ile His Ile His Ile Asp Arg Ile Asp Lys Lys Asp Val Pro Glu
            260                 265                 270
```

```
Glu Gln Glu His Met Arg Arg Trp Leu His Glu Arg Phe Glu Ile Lys
            275                 280                 285

Asp Lys Met Leu Ile Glu Phe Tyr Glu Ser Pro Asp Pro Glu Arg Arg
        290                 295                 300

Lys Arg Phe Pro Gly Lys Ser Val Asn Ser Lys Leu Ser Ile Lys Lys
305                 310                 315                 320

Thr Leu Pro Ser Met Leu Ile Leu Ser Gly Leu Thr Ala Gly Met Leu
                325                 330                 335

Met Thr Asp Ala Gly Arg Lys Leu Tyr Val Asn Thr Trp Ile Tyr Gly
            340                 345                 350

Thr Leu Leu Gly Cys Leu Trp Val Thr Ile Lys Ala
        355                 360

<210> SEQ ID NO 64
<211> LENGTH: 1095
<212> TYPE: DNA
<213> ORGANISM: Homo sapiens

<400> SEQUENCE: 64
atgctgctgt ccctggtgct ccacacgtac tccatgcgct acctgctgcc cagcgtcgtg      60
ctcctgggca cggcgcccac ctacgtgttg gcctgggggg tctggcggct gctctccgcc     120
ttcctgcccg cccgcttcta ccaagcgctg acgaccggc tctactgcgt ctaccagagc      180
atggtgctct tcttcttcga gaattacacc ggggtccaga tattgctata tggagatttg     240
ccaaaaaata agaaaaatat aatatattta gcaaatcatc aaagcacagt tgactggatt     300
gttgctgaca tcttggccat caggcagaat gcgctaggac atgtgcgcta cgtgctgaaa     360
gaagggttaa aatggctgcc attgtatggg tgttactttg ctcagcatgg aggaatctat     420
gtaaagcgca gtgccaaatt taacgagaaa gagatgcgaa acaagttgca gagctacgtg     480
gacgcaggaa ctccaatgta tcttgtgatt tttccagaag gtacaaggta taatccagag     540
caaacaaaag tcctttcagc tagtcaggca tttgctgccc aacgtggcct tgcagtatta     600
aaacatgtgc taacaccacg aataaaggca actcacgttg cttttgattg catgaagaat     660
tatttagatg caatttatga tgttacggtg gtttatgaag ggaaagacga tggagggcag     720
cgaagagagt caccgaccat gacggaattt ctctgcaaag aatgtccaaa aattcatatt     780
cacattgatc gtatcgacaa aaaagatgtc ccagaagaac aagaacatat gagaagatgg     840
ctgcatgaac gtttcgaaat caagataag atgcttatag aatttttatga gtcaccagat     900 ccagaaagaa gaaaaagatt tcctgggaaa agtgttaatt ccaaattaag tatcaagaag     960
actttaccat caatgttgat cttaagtggt tgactgcag gcatgcttat gaccgatgct    1020
ggaaggaagc tgtatgtgaa cacctggata tatggaaccc tacttggctg cctgtgggtt    1080
actattaaag catag                                                    1095

<210> SEQ ID NO 65
<211> LENGTH: 166
<212> TYPE: PRT
<213> ORGANISM: Artificial Sequence
<220> FEATURE:
<223> OTHER INFORMATION: consensus sequence

<400> SEQUENCE: 65

Gly Val Lys Val Tyr Met Tyr Gly Asp Asp Ile Glu Thr Tyr Asn Lys
1               5                   10                  15

Thr Gly Lys Asp Glu Asn Ala Ile Leu Ile Cys Asn His Gln Ser Tyr
            20                  25                  30
```

Leu Asp Trp Ile Phe Leu Trp Trp Leu Ala Tyr Arg Ser Gly Leu Gly
                35                  40                  45

Ala Asn Thr Tyr Trp Lys Ile Ile Leu Lys Lys Ser Leu Lys Tyr Ile
 50                  55                  60

Pro Val Leu Gly Trp Gly Met Arg Asn His Gly Tyr Ile Phe Leu Glu
 65                  70                  75                  80

Arg Asn Trp Glu Lys Asp Lys Asp Thr Leu Leu Asn Ser Leu Asp Asn
                 85                  90                  95

Cys Gly Pro Asn Tyr Lys Lys His Tyr Lys Arg Leu Asn Glu Ser Glu
                100                 105                 110

Asp Pro Tyr Trp Leu Ile Leu Phe Pro Glu Gly Thr Asn Leu Ser Ala
                115                 120                 125

Lys Lys Arg Glu Lys Ser Gln Glu Tyr Ala Glu Lys Asn Gly Leu Pro
                130                 135                 140

Pro Leu Gln Asn Val Leu Leu Pro Arg Thr Gly Gly Leu Lys Tyr Ala
145                 150                 155                 160

Leu Glu Lys Met Arg Asp
                165

<210> SEQ ID NO 66
<211> LENGTH: 157
<212> TYPE: PRT
<213> ORGANISM: Artificial Sequence
<220> FEATURE:
<223> OTHER INFORMATION: consensus sequence

<400> SEQUENCE: 66

Leu Ser Thr Leu Asp Ala Ile Tyr Asp Val Thr Val Met Tyr Gly Gln
 1               5                  10                  15

Met Arg Phe Asp Leu Gly Leu Asn Leu Thr Ile His Tyr Asn Leu Ile
                20                  25                  30

Ile Ile Tyr Arg Met Ala Glu Arg Gly Leu Ala Pro Gly Met Phe
                35                  40                  45

Asp Phe Cys Cys Gly Ser Gln Gln Phe Lys Gln Leu His Ile His Leu
 50                  55                  60

Asp Arg Ile Pro Ile Asp Glu Val Pro Lys Ala Lys Leu Glu Leu Arg
65                  70                  75                  80

Thr Trp Thr Ile Glu Arg Phe Thr Lys Lys Glu Arg Ile Ile Asp Glu
                 85                  90                  95

Phe Tyr Ser Glu Lys Pro Ser Thr Gly Ser Ala Leu Pro Cys Val Pro
                100                 105                 110

Ile Ser Gln Thr Leu Pro Ser Thr Leu Phe Phe Ser Ala Ala Leu Leu
                115                 120                 125

Ala Pro Phe Phe Ser Arg Thr Ile Gly Arg Ile Tyr Leu Leu Thr Ile
                130                 135                 140

Ala Ser Ser Pro Leu Leu Ile Ala Trp Leu His Ile Arg
145                 150                 155

<210> SEQ ID NO 67
<211> LENGTH: 195
<212> TYPE: PRT
<213> ORGANISM: Artificial Sequence
<220> FEATURE:
<223> OTHER INFORMATION: consensus sequence

<400> SEQUENCE: 67

Leu Glu Asn Leu Pro Lys Lys Gly Pro Ala Ile Val Val Ser Asn His

```
                1               5                   10                  15
           Arg Ser Tyr Leu Asp Ile Leu Val Leu Ser Ala Ala Leu Pro Arg Arg
                           20                  25                  30

Gly Pro Trp Leu Val Arg Arg Leu Val Phe Ile Ala Lys Lys Glu Leu
                       35                  40                  45

Leu Lys Val Pro Leu Leu Phe Gly Trp Leu Met Arg Leu Ala Gly Ala
                   50                  55                  60

Ile Phe Ile Asp Arg Asn Asn Arg Ala Lys Asp Ala Leu Ala Ala Ala
           65                  70                  75                  80

Asp Glu Leu Val Arg Val Leu Glu Leu Leu Arg Lys Gly Arg Ser Val
                           85                  90                  95

Leu Ile Phe Pro Glu Gly Thr Arg Ser Arg Ser Gly Glu Leu Leu Pro
                           100                 105                 110

Pro Phe Lys Lys Gly Ile Ala Ala Phe Arg Leu Ala Leu Lys Ala Gly
                       115                 120                 125

Val Pro Ile Val Pro Val Ile Val Ser Gly Thr Glu Glu Leu Glu
                   130                 135                 140

Pro Lys Asn Glu Ala Gly Lys Leu Leu Arg Leu Ala Arg Lys Lys Gly
           145                 150                 155                 160

Pro Val Thr Val Arg Val Leu Pro Pro Ile Pro Leu Asp Pro Glu Asp
                           165                 170                 175

Ile Lys Glu Leu Ala Glu Arg Leu Arg Asp Ile Leu Val Gln Ala Leu
                           180                 185                 190

Glu Glu Leu
                   195
```

<210> SEQ ID NO 68
<211> LENGTH: 7
<212> TYPE: PRT
<213> ORGANISM: Artificial Sequence
<220> FEATURE:
<223> OTHER INFORMATION: peptide motif
<220> FEATURE:
<221> NAME/KEY: VARIANT
<222> LOCATION: 1
<223> OTHER INFORMATION: Xaa = Asn or any amino acid
<220> FEATURE:
<221> NAME/KEY: VARIANT
<222> LOCATION: 3
<223> OTHER INFORMATION: Xaa = Arg or Gln
<220> FEATURE:
<221> NAME/KEY: VARIANT
<222> LOCATION: 5
<223> OTHER INFORMATION: Xaa = any amino acid
<220> FEATURE:
<221> NAME/KEY: VARIANT
<222> LOCATION: 6
<223> OTHER INFORMATION: Xaa = Leu, Tyr, Ile, or Met

<400> SEQUENCE: 68

```
           Xaa His Xaa Ser Xaa Xaa Asp
           1               5
```

<210> SEQ ID NO 69
<211> LENGTH: 7
<212> TYPE: PRT
<213> ORGANISM: Artificial Sequence
<220> FEATURE:
<223> OTHER INFORMATION: peptide motif
<220> FEATURE:
<221> NAME/KEY: VARIANT
<222> LOCATION: 2
<223> OTHER INFORMATION: Xaa = any amino acid
<220> FEATURE:

```
<221> NAME/KEY: VARIANT
<222> LOCATION: 3
<223> OTHER INFORMATION: Xaa = Ile or Phe
<220> FEATURE:
<221> NAME/KEY: VARIANT
<222> LOCATION: 6
<223> OTHER INFORMATION: Xaa = Arg or Asp

<400> SEQUENCE: 69

Gly Xaa Xaa Phe Ile Xaa Arg
 1               5

<210> SEQ ID NO 70
<211> LENGTH: 8
<212> TYPE: PRT
<213> ORGANISM: Artificial Sequence
<220> FEATURE:
<223> OTHER INFORMATION: peptide motif
<220> FEATURE:
<221> NAME/KEY: VARIANT
<222> LOCATION: 2
<223> OTHER INFORMATION: Xaa = Pro, Leu, or Ile
<220> FEATURE:
<221> NAME/KEY: VARIANT
<222> LOCATION: 5
<223> OTHER INFORMATION: Xaa = Thr or Gly
<220> FEATURE:
<221> NAME/KEY: VARIANT
<222> LOCATION: 7
<223> OTHER INFORMATION: Xaa = Ser or any amino acid
<220> FEATURE:
<221> NAME/KEY: VARIANT
<222> LOCATION: 8
<223> OTHER INFORMATION: Xaa = Arg or any amino acid

<400> SEQUENCE: 70

Phe Xaa Glu Gly Xaa Arg Xaa Xaa
 1               5

<210> SEQ ID NO 71
<211> LENGTH: 6
<212> TYPE: PRT
<213> ORGANISM: Artificial Sequence
<220> FEATURE:
<223> OTHER INFORMATION: peptide motif
<220> FEATURE:
<221> NAME/KEY: VARIANT
<222> LOCATION: 1, 4, 6
<223> OTHER INFORMATION: Xaa = Ile or Val
<220> FEATURE:
<221> NAME/KEY: VARIANT
<222> LOCATION: 2
<223> OTHER INFORMATION: Xaa = Pro or any amino acid
<220> FEATURE:
<221> NAME/KEY: VARIANT
<222> LOCATION: 3
<223> OTHER INFORMATION: Xaa = Ile, Val, or Leu

<400> SEQUENCE: 71

Xaa Xaa Xaa Xaa Pro Xaa
 1               5

<210> SEQ ID NO 72
<211> LENGTH: 859
<212> TYPE: DNA
<213> ORGANISM: Homo sapiens
<220> FEATURE:
<221> NAME/KEY: CDS
<222> LOCATION: (41)...(493)
<220> FEATURE:
<221> NAME/KEY: misc_feature
<222> LOCATION: (1)...(859)
<223> OTHER INFORMATION: n = A,T,C or G
```

<400> SEQUENCE: 72

```
cactatagggg agtcgaccca cgcgtccgga tggttccatc atg gcg tca atg cag      55
                                             Met Ala Ser Met Gln
                                             1               5 aaa cga cta cag aaa gaa ctg ttg gct ttg caa aat gac cca cct cct       103
Lys Arg Leu Gln Lys Glu Leu Leu Ala Leu Gln Asn Asp Pro Pro Pro
             10                  15                  20 gga atg acc tta aat gag aag agt gtt caa aat tca att aca cag tgg       151
Gly Met Thr Leu Asn Glu Lys Ser Val Gln Asn Ser Ile Thr Gln Trp
         25                  30                  35 att gta gac atg gaa ggt gca cca ggt acc tta tat gaa ggg gaa aaa       199
Ile Val Asp Met Glu Gly Ala Pro Gly Thr Leu Tyr Glu Gly Glu Lys
     40                  45                  50 ttt caa ctt cta ttt aaa ttt agt agt cga tat cct ttt gac tct cct       247
Phe Gln Leu Leu Phe Lys Phe Ser Ser Arg Tyr Pro Phe Asp Ser Pro
 55                  60                  65 cag gtc atg ttt act ggt gaa aat att cct gtt cat cct cat gtt tat       295
Gln Val Met Phe Thr Gly Glu Asn Ile Pro Val His Pro His Val Tyr
 70                  75                  80                  85 agc aat ggt cat atc tgt tta tcc att cta aca gaa gac tgg tcc cca       343
Ser Asn Gly His Ile Cys Leu Ser Ile Leu Thr Glu Asp Trp Ser Pro
                 90                  95                 100 gcg ctc tca gtc caa tca gtt tgt ctt agc att att agc atg ctt tcc       391
Ala Leu Ser Val Gln Ser Val Cys Leu Ser Ile Ile Ser Met Leu Ser
             105                 110                 115 agc tgc aag gaa aag aga cga cca ccg gat aat tct ttt tat gtg cga       439
Ser Cys Lys Glu Lys Arg Arg Pro Pro Asp Asn Ser Phe Tyr Val Arg
         120                 125                 130 aca tgt aac aag aat cca aag aaa aca aaa tgg tgg tat cat gat gat       487
Thr Cys Asn Lys Asn Pro Lys Lys Thr Lys Trp Trp Tyr His Asp Asp
     135                 140                 145 act tgt tgatgccact gttatcatcc tcctagcaga agatagtcct actgagaaaa        543
Thr Cys
150 tgagcacttt gatcattcag tctttgaact ttaacctttg actggaagtg acctataggc     603 aatgaagact acttccttt actgcatttt tactcgtgtg cattctgggc gcatgttgat      663 cgctggttca gtccaggcaa ctgacatgct tttattagtc atacagtatt aatgcaggtg     723 tcaggaaatg tcaaatataa ttccatttt tattttatt tttaagct tttggaaaag         783 ctccaggtcc tcatgtattg tgcaataaca atgacttcct tggcggtttt ggtacctgcc     843 cgggcggccg ctcnaa                                                     859
```

<210> SEQ ID NO 73
<211> LENGTH: 151
<212> TYPE: PRT
<213> ORGANISM: Homo sapiens

<400> SEQUENCE: 73

```
Met Ala Ser Met Gln Lys Arg Leu Gln Lys Glu Leu Leu Ala Leu Gln
1               5                  10                  15

Asn Asp Pro Pro Pro Gly Met Thr Leu Asn Glu Lys Ser Val Gln Asn
             20                  25                  30

Ser Ile Thr Gln Trp Ile Val Asp Met Glu Gly Ala Pro Gly Thr Leu
         35                  40                  45

Tyr Glu Gly Glu Lys Phe Gln Leu Leu Phe Lys Phe Ser Ser Arg Tyr
     50                  55                  60
```

-continued

```
Pro Phe Asp Ser Pro Gln Val Met Phe Thr Gly Glu Asn Ile Pro Val
 65                  70                  75                  80

His Pro His Val Tyr Ser Asn Gly His Ile Cys Leu Ser Ile Leu Thr
             85                  90                  95

Glu Asp Trp Ser Pro Ala Leu Ser Val Gln Ser Val Cys Leu Ser Ile
            100                 105                 110

Ile Ser Met Leu Ser Ser Cys Lys Glu Lys Arg Arg Pro Pro Asp Asn
        115                 120                 125

Ser Phe Tyr Val Arg Thr Cys Asn Lys Asn Pro Lys Lys Thr Lys Trp
    130                 135                 140

Trp Tyr His Asp Asp Thr Cys
145                 150
```

<210> SEQ ID NO 74
<211> LENGTH: 456
<212> TYPE: DNA
<213> ORGANISM: Homo sapiens

<400> SEQUENCE: 74

```
atggcgtcaa tgcagaaacg actacagaaa gaactgttgg ctttgcaaaa tgacccacct      60
cctggaatga ccttaaatga aagagtgtt caaaattcaa ttacacagtg gattgtagac     120
atggaaggtg caccaggtac cttatatgaa ggggaaaaat ttcaacttct atttaaattt     180
agtagtcgat atccttttga ctctcctcag gtcatgttta ctggtgaaaa tattcctgtt     240
catcctcatg tttatagcaa tggtcatatc tgtttatcca ttctaacaga agactggtcc     300
ccagcgctct cagtccaatc agtttgtctt agcattatta gcatgctttc cagctgcaag     360
gaaaagagac gaccaccgga taattctttt tatgtgcgaa catgtaacaa gaatccaaag     420
aaaacaaaat ggtggtatca tgatgatact tgttga                               456
```

<210> SEQ ID NO 75
<211> LENGTH: 165
<212> TYPE: PRT
<213> ORGANISM: Artificial Sequence
<220> FEATURE:
<223> OTHER INFORMATION: consensus sequence

<400> SEQUENCE: 75

```
Met Ser Ser Ser Ser Ala Ser Lys Arg Leu Gln Lys Glu Leu Lys Lys
  1               5                  10                  15

Leu Gln Glu Asp Pro Pro Pro Gly Phe Ser Ala Gly Pro Val Asp Asp
             20                  25                  30

Asn Asn Ile Phe Glu Trp Asn Val Ile Met Gly Pro Pro Asp Thr
         35                  40                  45

Pro Tyr Glu Gly Gly Val Phe Lys Leu Glu Ile Glu Phe Pro Glu Asp
     50                  55                  60

Tyr Pro Phe Lys Pro Lys Val Arg Phe Thr Ser Lys Ile Phe His
 65                  70                  75                  80

Pro Asn Ile Tyr Ser Asn Thr Gly Arg Ile Cys Leu Asp Ile Leu Lys
             85                  90                  95

Asp Pro Gly Asp Asp Pro Asn Gly Tyr Glu Leu Ala Glu Glu Arg Trp
            100                 105                 110

Ser Pro Ala Tyr Thr Val Glu Ser Ile Leu Leu Ser Ile Gln Ser Leu
        115                 120                 125

Leu Ser Asp Pro Asn Pro Asp Ser Pro Ala Asn Val Glu Ala Ala Lys
    130                 135                 140
```

-continued

Leu Tyr Arg Lys Lys Glu Asp Arg Glu Glu Tyr Lys Arg Val Lys
145                 150                 155                 160

Glu Trp Val Glu Lys
            165

<210> SEQ ID NO 76
<211> LENGTH: 144
<212> TYPE: PRT
<213> ORGANISM: Artificial Sequence
<220> FEATURE:
<223> OTHER INFORMATION: consensus sequence

<400> SEQUENCE: 76

Lys Arg Leu Gln Lys Glu Leu Lys Glu Leu Gln Lys Asp Pro Pro Pro
1               5                   10                  15

Gly Ile Ser Ala Ile Pro Val Asp Asn Leu Leu Glu Trp Thr Val Thr
            20                  25                  30

Ile Val Gly Pro Pro Asp Thr Pro Tyr Glu Gly Gly Val Phe Lys Leu
        35                  40                  45

Thr Ile Glu Phe Pro Glu Asp Tyr Pro Phe Lys Pro Pro Lys Val Lys
50                  55                  60

Phe Ile Thr Lys Ile Tyr His Pro Asn Val Asp Ser Ser Ser Gly Glu
65                  70                  75                  80

Ile Cys Leu Asp Ile Leu Lys Glu Lys Trp Ser Pro Ala Leu Thr Leu
                85                  90                  95

Glu Thr Val Leu Leu Ser Ile Gln Ser Leu Leu Asn Glu Pro Asn Pro
            100                 105                 110

Asp Ser Pro Leu Asn Val Asp Ala Ala Glu Leu Tyr Arg Lys Asp Arg
        115                 120                 125

Glu Glu Phe Lys Lys Lys Val Arg Glu Trp Thr Lys Lys Tyr Ala Glu
    130                 135                 140

<210> SEQ ID NO 77
<211> LENGTH: 2625
<212> TYPE: DNA
<213> ORGANISM: Homo sapiens
<220> FEATURE:
<221> NAME/KEY: CDS
<222> LOCATION: (136)...(2151)

<400> SEQUENCE: 77
gccgccgccg tcgctgaccc agcccgccag gcgctcctga ccgtcgcttc ctccggtccc        60
aggtccccgg ccctcgcctc agcccggcc cctggtcccc agccctcgtc gcagcccgg        120 ccgcccgccg ccgcc atg tcc aag gag gag cgc ccc ggt cgg gag gag atc        171
                Met Ser Lys Glu Glu Arg Pro Gly Arg Glu Glu Ile
                1               5                   10 ctg gag tgc cag gtg atg tgg gag cct gac agt aag aag aac acg cag        219
Leu Glu Cys Gln Val Met Trp Glu Pro Asp Ser Lys Lys Asn Thr Gln
        15                  20                  25 atg gac cgc ttc cgg gcg gct gtg ggc gcc gcc tgc ggc ctg gcg ctg        267
Met Asp Arg Phe Arg Ala Ala Val Gly Ala Ala Cys Gly Leu Ala Leu
    30                  35                  40 gag agt tat gat gac ttg tac cat tgg tcc gtt gag tca tat tca gac        315
Glu Ser Tyr Asp Asp Leu Tyr His Trp Ser Val Glu Ser Tyr Ser Asp
45                  50                  55                  60 ttc tgg gca gag ttc tgg aaa ttc agt gga att gtc ttc tca cgt gtg        363
Phe Trp Ala Glu Phe Trp Lys Phe Ser Gly Ile Val Phe Ser Arg Val
                65                  70                  75 tat gat gag gtt gtg gac aca tcg aaa gga atc gca gat gtc ccc gag        411

```
                                                                -continued

Tyr Asp Glu Val Val Asp Thr Ser Lys Gly Ile Ala Asp Val Pro Glu
             80                  85                  90 tgg ttc aaa ggc agt cgg ctc aac tat gca gaa aac ctc ctg cgg cac       459
Trp Phe Lys Gly Ser Arg Leu Asn Tyr Ala Glu Asn Leu Leu Arg His
         95                 100                 105 aaa gag aat gac aga gtt gcc ctt tac att gca agg gaa ggc aaa gag       507
Lys Glu Asn Asp Arg Val Ala Leu Tyr Ile Ala Arg Glu Gly Lys Glu
    110                 115                 120 gaa att gtg aag gtg act ttt gaa gag ctg agg caa gaa gtg gct ttg       555
Glu Ile Val Lys Val Thr Phe Glu Glu Leu Arg Gln Glu Val Ala Leu
125                 130                 135                 140 ttt gca gca gca atg agg aaa atg ggt gtg aag aaa gga gat cgg gtt       603
Phe Ala Ala Ala Met Arg Lys Met Gly Val Lys Lys Gly Asp Arg Val
                145                 150                 155 gtt ggt tat tta ccc aac agt gag cac gct gtc gag gcg atg ctg gct       651
Val Gly Tyr Leu Pro Asn Ser Glu His Ala Val Glu Ala Met Leu Ala
                160                 165                 170 gcg gca agc att ggt gcc atc tgg agc tcc acg tcc ccg gac ttc ggt       699
Ala Ala Ser Ile Gly Ala Ile Trp Ser Ser Thr Ser Pro Asp Phe Gly
            175                 180                 185 gtg aat ggt gtg ctg gac cgg ttt tct caa att cag cca aag ctc atc       747
Val Asn Gly Val Leu Asp Arg Phe Ser Gln Ile Gln Pro Lys Leu Ile
        190                 195                 200 ttc tct gtg gag gct gtt gtc tat aat ggc aaa gag cac aac cac atg       795
Phe Ser Val Glu Ala Val Val Tyr Asn Gly Lys Glu His Asn His Met
205                 210                 215                 220 gaa aag ctg cag cag gtg gtt aaa ggc cta cca gac ttg aag aaa gtg       843
Glu Lys Leu Gln Gln Val Val Lys Gly Leu Pro Asp Leu Lys Lys Val
                225                 230                 235 gtg gtg att cct tat gtg tcc tcc aga gag aac ata gac ctt tca aag       891
Val Val Ile Pro Tyr Val Ser Ser Arg Glu Asn Ile Asp Leu Ser Lys
                240                 245                 250 att cca aac agt gtg ttt ctg gat gac ttt ctt gcc acc ggc acc agt       939
Ile Pro Asn Ser Val Phe Leu Asp Asp Phe Leu Ala Thr Gly Thr Ser
            255                 260                 265 gag cag gcc ccg cag ctg gag ttc gag cag ctg ccc ttc agc cac cca       987
Glu Gln Ala Pro Gln Leu Glu Phe Glu Gln Leu Pro Phe Ser His Pro
        270                 275                 280 ctg ttc atc atg ttc tca tcg ggc acc acg ggc gca ccc aag tgc atg      1035
Leu Phe Ile Met Phe Ser Ser Gly Thr Thr Gly Ala Pro Lys Cys Met
285                 290                 295                 300 gtg cat tcc gct ggg ggc acc ctc atc cag cat ctg aag gag cac ctg      1083
Val His Ser Ala Gly Gly Thr Leu Ile Gln His Leu Lys Glu His Leu
                305                 310                 315 ctg cac ggc aac atg acc agc agt gac atc ctc ctg tgc tac acc acg      1131
Leu His Gly Asn Met Thr Ser Ser Asp Ile Leu Leu Cys Tyr Thr Thr
                320                 325                 330 gtc ggc tgg atg atg tgg aac tgg atg gtg tcc ctt ctg gcc aca gga      1179
Val Gly Trp Met Met Trp Asn Trp Met Val Ser Leu Leu Ala Thr Gly
            335                 340                 345 gcg gcc atg gtc ttg tac gat ggc tcc ccc ctg gtg ccc acg ccc aat      1227
Ala Ala Met Val Leu Tyr Asp Gly Ser Pro Leu Val Pro Thr Pro Asn
        350                 355                 360 gtg ctc tgg gac ctg gtt gac agg ata ggc atc act gtc ctg gta act      1275
Val Leu Trp Asp Leu Val Asp Arg Ile Gly Ile Thr Val Leu Val Thr
365                 370                 375                 380 ggg gcc aag tgg ctg tca gtg ctg gaa gag aag gcc atg aag ccg gtg      1323
Gly Ala Lys Trp Leu Ser Val Leu Glu Glu Lys Ala Met Lys Pro Val
                385                 390                 395
```

-continued

```
gaa acc cac agt ctc cag atg ctc cac acg atc ctg tcc act ggc tcc      1371
Glu Thr His Ser Leu Gln Met Leu His Thr Ile Leu Ser Thr Gly Ser
            400                 405                 410 cca ctg aaa gcc cag agc tac gag tat gtc tac agg tgc atc aag agc      1419
Pro Leu Lys Ala Gln Ser Tyr Glu Tyr Val Tyr Arg Cys Ile Lys Ser
        415                 420                 425 agc atc ctc ctg ggc tcc atc tca gga ggc acc gac atc atc tcc tgc      1467
Ser Ile Leu Leu Gly Ser Ile Ser Gly Gly Thr Asp Ile Ile Ser Cys
    430                 435                 440 ttc atg ggc cac aat ttt tct ctt cct gtg tat aaa ggg gag att cag      1515
Phe Met Gly His Asn Phe Ser Leu Pro Val Tyr Lys Gly Glu Ile Gln
445                 450                 455                 460 gcc cgg aac ctg ggc atg gcc gtg gaa gcg tgg aac gag gaa gga aag      1563
Ala Arg Asn Leu Gly Met Ala Val Glu Ala Trp Asn Glu Glu Gly Lys
                465                 470                 475 gcg gtc tgg gga gag agc ggc gag ctg gtg tgt act aag ccg atc cct      1611
Ala Val Trp Gly Glu Ser Gly Glu Leu Val Cys Thr Lys Pro Ile Pro
            480                 485                 490 tgc cag ccc aca cac ttc tgg aac gat gag aac ggc aac aag tac agg      1659
Cys Gln Pro Thr His Phe Trp Asn Asp Glu Asn Gly Asn Lys Tyr Arg
        495                 500                 505 aag gcg tat ttc tcc aaa ttc cca ggt atc tgg gct cat ggc gac tac      1707
Lys Ala Tyr Phe Ser Lys Phe Pro Gly Ile Trp Ala His Gly Asp Tyr
    510                 515                 520 tgc aga atc aac ccc aag acc ggg ggc atc gtc atg ctt ggc cgg agt      1755
Cys Arg Ile Asn Pro Lys Thr Gly Gly Ile Val Met Leu Gly Arg Ser
525                 530                 535                 540 gac ggc acc ctc aac ccc aac ggg gtg cgg ttc ggc agc tcg gaa atc      1803
Asp Gly Thr Leu Asn Pro Asn Gly Val Arg Phe Gly Ser Ser Glu Ile
                545                 550                 555 tat aac att gtg gaa tcc ttc gag gag gtg gag gac agc ctg tgt gtc      1851
Tyr Asn Ile Val Glu Ser Phe Glu Glu Val Glu Asp Ser Leu Cys Val
            560                 565                 570 ccc cag tat aac aag tac agg gag gag agg gtg atc ctc ttc ctg aag      1899
Pro Gln Tyr Asn Lys Tyr Arg Glu Glu Arg Val Ile Leu Phe Leu Lys
        575                 580                 585 atg gcc tcc ggg cac gcc ttc cag cct gac ttg gtt aag agg atc cgt      1947
Met Ala Ser Gly His Ala Phe Gln Pro Asp Leu Val Lys Arg Ile Arg
    590                 595                 600 gac gcc atc cgc atg ggc ttg tct gcg cga cac gtg ccc agc ctc atc      1995
Asp Ala Ile Arg Met Gly Leu Ser Ala Arg His Val Pro Ser Leu Ile
605                 610                 615                 620 ctg gaa acc aag ggc atc ccg tat acg ctc aac ggc aag aaa gtg gaa      2043
Leu Glu Thr Lys Gly Ile Pro Tyr Thr Leu Asn Gly Lys Lys Val Glu
                625                 630                 635 gtt gcc gtc aaa cag atc atc gct gga aaa gcc gtg gag caa gga ggt      2091
Val Ala Val Lys Gln Ile Ile Ala Gly Lys Ala Val Glu Gln Gly Gly
            640                 645                 650 gct ttc tcg aac ccc gag acc ctg gat ctg tac cgg gac atc cct gag      2139
Ala Phe Ser Asn Pro Glu Thr Leu Asp Leu Tyr Arg Asp Ile Pro Glu
        655                 660                 665 ctg cag ggc ttc tgagtcagac tggctggcgt gtcactcagc cgcacccgtg          2191
Leu Gln Gly Phe
    670 tgcactgtaa cttttgtgtg ctcaagaaat tatacagaaa cctacagctg ttgtaaaagg    2251 atgctcgcac caagtgttct gtaggcttgg ggagggatcg tttctctgtt tgttaaatc     2311 tggtgggtac ctggatcttc cacacgagtg ggattctggc cttcagagac caggagggag    2371 tgtctgggcc gcaggtgtgg cactgtggtg agagtgtgtg tctttgcaca cacagtgcag    2431
```

-continued

```
cgggaacggt ggggctggct ggtgctgaag acagacacac tcctgagcca aggtcttgtc    2491
ttcaacctcc ccgtcccgtt gtcccatttt gctctgtgaa ggtgcaaatc cctttcttcc    2551
cttcccatct caggctctcc tgttttccct cagggtccag tatgccctt gagctttagc     2611
```

```
cttcccatct caggctctcc tgttttccct cagggtccag tatgccctt  gagctttagc    2611 tgttagaaag gaac                                                      2625
```

<210> SEQ ID NO 78
<211> LENGTH: 672
<212> TYPE: PRT
<213> ORGANISM: Homo sapiens

<400> SEQUENCE: 78

| | | | | | | | | | | | | | | |
|---|---|---|---|---|---|---|---|---|---|---|---|---|---|---|
Met Ser Lys Glu Glu Arg Pro Gly Arg Glu Ile Leu Glu Cys Gln
1               5                   10                  15

Val Met Trp Glu Pro Asp Ser Lys Lys Asn Thr Gln Met Asp Arg Phe
            20                  25                  30

Arg Ala Ala Val Gly Ala Ala Cys Gly Leu Ala Leu Glu Ser Tyr Asp
        35                  40                  45

Asp Leu Tyr His Trp Ser Val Glu Ser Tyr Ser Asp Phe Trp Ala Glu
    50                  55                  60

Phe Trp Lys Phe Ser Gly Ile Val Phe Ser Arg Val Tyr Asp Glu Val
65                  70                  75                  80

Val Asp Thr Ser Lys Gly Ile Ala Asp Val Pro Glu Trp Phe Lys Gly
                85                  90                  95

Ser Arg Leu Asn Tyr Ala Glu Asn Leu Leu Arg His Lys Glu Asn Asp
            100                 105                 110

Arg Val Ala Leu Tyr Ile Ala Arg Glu Gly Lys Glu Glu Ile Val Lys
        115                 120                 125

Val Thr Phe Glu Glu Leu Arg Gln Glu Val Ala Leu Phe Ala Ala Ala
    130                 135                 140

Met Arg Lys Met Gly Val Lys Lys Gly Asp Arg Val Val Gly Tyr Leu
145                 150                 155                 160

Pro Asn Ser Glu His Ala Val Glu Ala Met Leu Ala Ala Ser Ile
                165                 170                 175

Gly Ala Ile Trp Ser Ser Thr Ser Pro Asp Phe Gly Val Asn Gly Val
            180                 185                 190

Leu Asp Arg Phe Ser Gln Ile Gln Pro Lys Leu Ile Phe Ser Val Glu
        195                 200                 205

Ala Val Val Tyr Asn Gly Lys Glu His Asn His Met Glu Lys Leu Gln
    210                 215                 220

Gln Val Val Lys Gly Leu Pro Asp Leu Lys Lys Val Val Ile Pro
225                 230                 235                 240

Tyr Val Ser Ser Arg Glu Asn Ile Asp Leu Ser Lys Ile Pro Asn Ser
                245                 250                 255

Val Phe Leu Asp Asp Phe Leu Ala Thr Gly Thr Ser Glu Gln Ala Pro
            260                 265                 270

Gln Leu Glu Phe Glu Gln Leu Pro Phe Ser His Pro Leu Phe Ile Met
        275                 280                 285

Phe Ser Ser Gly Thr Thr Gly Ala Pro Lys Cys Met Val His Ser Ala
    290                 295                 300

Gly Gly Thr Leu Ile Gln His Leu Lys Glu His Leu Leu His Gly Asn
305                 310                 315                 320

Met Thr Ser Ser Asp Ile Leu Leu Cys Tyr Thr Thr Val Gly Trp Met
                325                 330                 335

```
Met Trp Asn Trp Met Val Ser Leu Leu Ala Thr Gly Ala Ala Met Val
            340                 345                 350
Leu Tyr Asp Gly Ser Pro Leu Val Pro Thr Pro Asn Val Leu Trp Asp
            355                 360                 365
Leu Val Asp Arg Ile Gly Ile Thr Val Leu Val Thr Gly Ala Lys Trp
            370                 375                 380
Leu Ser Val Leu Glu Glu Lys Ala Met Lys Pro Val Glu Thr His Ser
385                 390                 395                 400
Leu Gln Met Leu His Thr Ile Leu Ser Thr Gly Ser Pro Leu Lys Ala
                405                 410                 415
Gln Ser Tyr Glu Tyr Val Tyr Arg Cys Ile Lys Ser Ser Ile Leu Leu
            420                 425                 430
Gly Ser Ile Ser Gly Gly Thr Asp Ile Ile Ser Cys Phe Met Gly His
            435                 440                 445
Asn Phe Ser Leu Pro Val Tyr Lys Gly Glu Ile Gln Ala Arg Asn Leu
        450                 455                 460
Gly Met Ala Val Glu Ala Trp Asn Glu Glu Gly Lys Ala Val Trp Gly
465                 470                 475                 480
Glu Ser Gly Glu Leu Val Cys Thr Lys Pro Ile Pro Cys Gln Pro Thr
                485                 490                 495
His Phe Trp Asn Asp Glu Asn Gly Asn Lys Tyr Arg Lys Ala Tyr Phe
            500                 505                 510
Ser Lys Phe Pro Gly Ile Trp Ala His Gly Asp Tyr Cys Arg Ile Asn
            515                 520                 525
Pro Lys Thr Gly Gly Ile Val Met Leu Gly Arg Ser Asp Gly Thr Leu
        530                 535                 540
Asn Pro Asn Gly Val Arg Phe Gly Ser Ser Glu Ile Tyr Asn Ile Val
545                 550                 555                 560
Glu Ser Phe Glu Glu Val Glu Asp Ser Leu Cys Val Pro Gln Tyr Asn
                565                 570                 575
Lys Tyr Arg Glu Glu Arg Val Ile Leu Phe Leu Lys Met Ala Ser Gly
            580                 585                 590
His Ala Phe Gln Pro Asp Leu Val Lys Arg Ile Arg Asp Ala Ile Arg
            595                 600                 605
Met Gly Leu Ser Ala Arg His Val Pro Ser Leu Ile Leu Glu Thr Lys
        610                 615                 620
Gly Ile Pro Tyr Thr Leu Asn Gly Lys Lys Val Glu Val Ala Val Lys
625                 630                 635                 640
Gln Ile Ile Ala Gly Lys Ala Val Glu Gln Gly Gly Ala Phe Ser Asn
                645                 650                 655
Pro Glu Thr Leu Asp Leu Tyr Arg Asp Ile Pro Glu Leu Gln Gly Phe
            660                 665                 670

<210> SEQ ID NO 79
<211> LENGTH: 2019
<212> TYPE: DNA
<213> ORGANISM: Homo sapiens

<400> SEQUENCE: 79
atgtccaagg aggagcgccc cggtcgggag gagatcctgg agtgccaggt gatgtgggag    60
cctgacagta agaagaacac gcagatggac cgcttccggg cggctgtggg cgccgcctgc   120
ggcctggcgc tggagagtta tgatgacttg taccattggt ccgttgagtc atattcagac   180
ttctgggcag agttctggaa attcagtgga attgtcttct cacgtgtgta tgatgaggtt   240
```

-continued

| | |
|---|---|
| gtggacacat cgaaaggaat cgcagatgtc cccgagtggt tcaaaggcag tcggctcaac | 300 |
| tatgcagaaa acctcctgcg gcacaaagag aatgacagag ttgcccttta cattgcaagg | 360 |
| gaaggcaaag aggaaattgt gaaggtgact tttgagagc tgaggcaaga agtggctttg | 420 |
| tttgcagcag caatgaggaa atgggtgtg aagaaggag atcggttgt tggttattta | 480 |
| cccaacagtg agcacgctgt cgaggcgatg ctggctgcgg caagcattgg tgccatctgg | 540 |
| agctccacgt ccccggactt cggtgtgaat ggtgtgctgg accggttttc tcaaattcag | 600 |
| ccaaagctca tcttctctgt ggaggctgtt gtctataatg caaagagca caaccacatg | 660 |
| gaaaagctgc agcaggtggt taaaggccta ccagacttga gaaagtggt ggtgattcct | 720 |
| tatgtgtcct ccagagagaa catagacctt tcaaagattc caaacagtgt gtttctggat | 780 |
| gactttcttg ccaccggcac cagtgagcag gccccgcagc tggagttcga gcagctgccc | 840 |
| ttcagccacc cactgttcat catgttctca tcgggcacca cgggcgcacc caagtgcatg | 900 |
| gtgcattccg ctgggggcac cctcatccag catctgaagg agcacctgct gcacggcaac | 960 |
| atgaccagca gtgacatcct cctgtgctac accacggtcg gctggatgat gtggaactgg | 1020 |
| atggtgtccc ttctggccac aggagcggcc atggtcttgt acgatggctc ccccctggtg | 1080 |
| cccacgccca atgtgctctg ggacctggtt gacaggatag gcatcactgt cctggtaact | 1140 |
| ggggccaagt ggctgtcagt gctggaagag aaggccatga agccggtgga acccacagt | 1200 |
| ctccagatgc tccacacgat cctgtccact ggctccccac tgaaagccca gagctacgag | 1260 |
| tatgtctaca ggtgcatcaa gagcagcatc ctcctgggct ccatctcagg aggcaccgac | 1320 |
| atcatctcct gcttcatggg ccacaatttt tctcttcctg tgtataaagg ggagattcag | 1380 |
| gcccggaacc tgggcatggc cgtggaagcg tggaacgagg aaggaaaggc ggtctgggga | 1440 |
| gagagcggcg agctggtgtg tactaagccg atcccttgcc agcccacaca cttctggaac | 1500 |
| gatgagaacg caacaagta caggaaggcg tatttctcca aattcccagg tatctgggct | 1560 |
| catggcgact actgcagaat caaccccaag accgggggca tcgtcatgct tggccggagt | 1620 |
| gacggcaccc tcaaccccaa cggggtgcgg ttcggcagct cggaaatcta taacattgtg | 1680 |
| gaatccttcg aggaggtgga ggacagcctg tgtgtccccc agtataacaa gtacagggag | 1740 |
| gagagggtga tcctcttcct gaagatggcc tccgggcacg ccttccagcc tgacttggtt | 1800 |
| aagaggatcc gtgacgccat ccgcatgggc ttgtctgcgc gacacgtgcc cagcctcatc | 1860 |
| ctggaaacca aggcatccc gtatacgctc aacggcaaga agtggaagt tgccgtcaaa | 1920 |
| cagatcatcg ctggaaaagc cgtggagcaa ggaggtgctt tctcgaaccc cgagaccctg | 1980 |
| gatctgtacc gggacatccc tgagctgcag ggcttctga | 2019 |

<210> SEQ ID NO 80
<211> LENGTH: 672
<212> TYPE: PRT
<213> ORGANISM: Rattus norvegicus

<400> SEQUENCE: 80

Met Ser Lys Leu Ala Arg Leu Glu Arg Glu Glu Ile Met Glu Cys Gln
1               5                   10                  15

Val Met Trp Glu Pro Asp Ser Lys Lys Asp Thr Gln Met Asp Arg Phe
            20                  25                  30

Arg Ala Ala Val Gly Thr Ala Cys Gly Leu Ala Leu Gly Asn Tyr Asp
        35                  40                  45

Asp Leu Tyr His Trp Ser Val Arg Ser Tyr Ser Asp Phe Trp Ala Glu

```
                   50                  55                  60
Phe Trp Lys Phe Ser Gly Ile Val Cys Ser Arg Met Tyr Asp Glu Val
 65                  70                  75                  80

Val Asp Thr Ser Lys Gly Ile Ala Asp Val Pro Glu Trp Phe Arg Gly
                 85                  90                  95

Ser Arg Leu Asn Tyr Ala Glu Asn Leu Leu Arg His Lys Glu Asn Asp
                100                 105                 110

Arg Val Ala Leu Tyr Val Ala Arg Glu Gly Arg Glu Ile Ala Lys
                115                 120                 125

Val Thr Phe Glu Glu Leu Arg Gln Gln Val Ala Leu Phe Ala Ala Ala
130                 135                 140

Met Arg Lys Met Gly Val Lys Lys Gly Asp Arg Val Val Gly Tyr Leu
145                 150                 155                 160

Pro Asn Ser Ala His Ala Val Glu Ala Met Leu Ala Ala Ser Ile
                165                 170                 175

Gly Ala Ile Trp Ser Ser Thr Ser Pro Asp Phe Gly Val Asn Gly Val
                180                 185                 190

Leu Asp Arg Phe Ser Gln Ile Gln Pro Lys Leu Ile Phe Ser Val Glu
                195                 200                 205

Ala Val Val Tyr Asn Gly Lys Glu His Gly His Leu Glu Lys Leu Gln
                210                 215                 220

Arg Val Val Lys Gly Leu Pro Asp Leu Gln Arg Val Val Leu Ile Pro
225                 230                 235                 240

Tyr Val Leu Pro Arg Glu Lys Ile Asp Ile Ser Lys Ile Pro Asn Ser
                245                 250                 255

Met Phe Leu Asp Asp Phe Leu Ala Ser Gly Thr Gly Ala Gln Ala Pro
                260                 265                 270

Gln Leu Glu Phe Glu Gln Leu Pro Phe Ser His Pro Leu Phe Ile Met
                275                 280                 285

Phe Ser Ser Gly Thr Thr Gly Ala Pro Lys Cys Met Val His Ser Ala
                290                 295                 300

Gly Gly Thr Leu Ile Gln His Leu Lys Glu His Val Leu His Gly Asn
305                 310                 315                 320

Met Thr Ser Ser Asp Ile Leu Leu Tyr Tyr Thr Thr Val Gly Trp Met
                325                 330                 335

Met Trp Asn Trp Met Val Ser Ala Leu Ala Thr Gly Ala Ser Leu Val
                340                 345                 350

Leu Tyr Asp Gly Ser Pro Leu Val Pro Thr Pro Asn Val Leu Trp Asp
                355                 360                 365

Leu Val Asp Arg Ile Gly Ile Thr Ile Leu Gly Thr Gly Ala Lys Trp
                370                 375                 380

Leu Ser Val Leu Glu Glu Lys Asp Met Lys Pro Met Glu Thr His Asn
385                 390                 395                 400

Leu His Thr Leu His Thr Ile Leu Ser Thr Gly Ser Pro Leu Lys Ala
                405                 410                 415

Gln Ser Tyr Glu Tyr Val Tyr Arg Cys Ile Lys Ser Thr Val Leu Leu
                420                 425                 430

Gly Ser Ile Ser Gly Gly Thr Asp Ile Ile Ser Cys Phe Met Gly Gln
                435                 440                 445

Asn Ser Ser Ile Pro Val Tyr Lys Gly Glu Ile Gln Ala Arg Asn Leu
                450                 455                 460

Gly Met Ala Val Glu Ala Trp Asp Glu Glu Gly Lys Thr Val Trp Gly
465                 470                 475                 480
```

```
Ala Ser Gly Glu Leu Val Cys Thr Lys Pro Ile Pro Cys Gln Pro Thr
            485                 490                 495

His Phe Trp Asn Asp Glu Asn Gly Ser Lys Tyr Arg Lys Ala Tyr Phe
            500                 505                 510

Ser Lys Tyr Pro Gly Val Trp Ala His Gly Asp Tyr Cys Arg Ile Asn
            515                 520                 525

Pro Lys Thr Gly Gly Ile Val Met Leu Gly Arg Ser Asp Gly Thr Leu
            530                 535                 540

Asn Pro Asn Gly Val Arg Phe Gly Ser Ser Glu Ile Tyr Asn Ile Val
545                 550                 555                 560

Glu Ala Phe Asp Glu Val Asp Ser Leu Cys Val Pro Gln Tyr Asn
                565                 570                 575

Arg Asp Gly Glu Glu Arg Val Val Leu Phe Leu Lys Met Ala Ser Gly
                580                 585                 590

His Thr Phe Gln Pro Asp Leu Val Lys His Ile Arg Asp Ala Ile Arg
            595                 600                 605

Leu Gly Leu Ser Ala Arg His Val Pro Ser Leu Ile Leu Glu Thr Gln
            610                 615                 620

Gly Ile Pro Tyr Thr Ile Asn Gly Lys Lys Val Glu Val Ala Val Lys
625                 630                 635                 640

Gln Val Ile Ala Gly Lys Thr Val Glu His Arg Gly Ala Phe Ser Asn
                645                 650                 655

Pro Glu Ser Leu Asp Leu Tyr Arg Asp Ile Pro Glu Leu Gln Asp Phe
            660                 665                 670
```

<210> SEQ ID NO 81
<211> LENGTH: 600
<212> TYPE: PRT
<213> ORGANISM: Artificial Sequence
<220> FEATURE:
<223> OTHER INFORMATION: consensus sequence

<400> SEQUENCE: 81

```
Met Ser Lys Arg Arg Glu Glu Ile Glu Cys Gln Val Met Trp Glu Pro
1               5                   10                  15

Asp Ser Lys Lys Thr Gln Met Asp Arg Phe Arg Ala Val Gly Ala
            20                  25                  30

Cys Gly Leu Ala Leu Tyr Asp Asp Leu Tyr His Trp Ser Val Ser Tyr
            35                  40                  45

Ser Asp Phe Trp Ala Glu Phe Trp Lys Phe Ser Gly Ile Val Ser Arg
        50                  55                  60

Tyr Asp Glu Val Val Asp Thr Ser Lys Gly Ile Ala Asp Val Pro Glu
65                  70                  75                  80

Trp Phe Gly Ser Arg Leu Asn Tyr Ala Glu Asn Leu Leu Arg His Lys
                85                  90                  95

Glu Asn Asp Arg Val Ala Leu Tyr Ala Arg Glu Gly Glu Ile Lys
            100                 105                 110

Val Thr Phe Glu Glu Leu Arg Gln Val Ala Leu Phe Ala Ala Met
            115                 120                 125

Arg Lys Met Gly Val Lys Lys Gly Asp Arg Val Gly Tyr Leu Pro
130                 135                 140

Asn Ser His Ala Val Glu Ala Met Leu Ala Ala Ala Ser Ile Gly Ala
145                 150                 155                 160

Ile Trp Ser Ser Thr Ser Pro Asp Phe Gly Val Asn Gly Val Leu Asp
                165                 170                 175
```

-continued

```
Arg Phe Ser Gln Ile Gln Pro Lys Leu Ile Phe Ser Val Glu Ala Val
            180                 185                 190
Val Tyr Asn Gly Lys Glu His His Glu Lys Leu Gln Val Val Lys Gly
        195                 200                 205
Leu Pro Asp Leu Val Val Ile Pro Tyr Val Arg Glu Ile Asp Ser Lys
    210                 215                 220
Ile Pro Asn Ser Phe Leu Asp Asp Phe Leu Ala Gly Thr Gln Ala Pro
225                 230                 235                 240
Gln Leu Glu Phe Glu Gln Leu Pro Phe Ser His Pro Leu Phe Ile Met
            245                 250                 255
Phe Ser Ser Gly Thr Thr Gly Ala Pro Lys Cys Met Val His Ser Ala
            260                 265                 270
Gly Gly Thr Leu Ile Gln His Leu Lys Glu His Leu His Gly Asn Met
            275                 280                 285
Thr Ser Ser Asp Ile Leu Leu Tyr Thr Thr Val Gly Trp Met Met Trp
        290                 295                 300
Asn Trp Met Val Ser Leu Ala Thr Gly Ala Val Leu Tyr Asp Gly Ser
305                 310                 315                 320
Pro Leu Val Pro Thr Pro Asn Val Leu Trp Asp Leu Val Asp Arg Ile
            325                 330                 335
Gly Ile Thr Leu Thr Gly Ala Lys Trp Leu Ser Val Leu Glu Glu Lys
            340                 345                 350
Met Lys Pro Glu Thr His Leu Leu His Thr Ile Leu Ser Thr Gly Ser
            355                 360                 365
Pro Leu Lys Ala Gln Ser Tyr Glu Tyr Val Tyr Arg Cys Ile Lys Ser
    370                 375                 380
Leu Leu Gly Ser Ile Ser Gly Gly Thr Asp Ile Ile Ser Cys Phe Met
385                 390                 395                 400
Gly Asn Ser Pro Val Tyr Lys Gly Glu Ile Gln Ala Arg Asn Leu Gly
            405                 410                 415
Met Ala Val Glu Ala Trp Glu Glu Gly Lys Val Trp Gly Ser Gly Glu
            420                 425                 430
Leu Val Cys Thr Lys Pro Ile Pro Cys Gln Pro Thr His Phe Trp Asn
        435                 440                 445
Asp Glu Asn Gly Lys Tyr Arg Lys Ala Tyr Phe Ser Lys Pro Gly Trp
    450                 455                 460
Ala His Gly Asp Tyr Cys Arg Ile Asn Pro Lys Thr Gly Gly Ile Val
465                 470                 475                 480
Met Leu Gly Arg Ser Asp Gly Thr Leu Asn Pro Asn Gly Val Arg Phe
            485                 490                 495
Gly Ser Ser Glu Ile Tyr Asn Ile Val Glu Phe Glu Val Glu Asp Ser
            500                 505                 510
Leu Cys Val Pro Gln Tyr Asn Glu Glu Arg Val Leu Phe Leu Lys Met
        515                 520                 525
Ala Ser Gly His Phe Gln Pro Asp Leu Val Lys Ile Arg Asp Ala Ile
    530                 535                 540
Arg Gly Leu Ser Ala Arg His Val Pro Ser Leu Ile Leu Glu Thr Gly
545                 550                 555                 560
Ile Pro Tyr Thr Asn Gly Lys Lys Val Glu Val Ala Val Lys Gln Ile
            565                 570                 575
Ala Gly Lys Val Glu Gly Ala Phe Ser Asn Pro Glu Leu Asp Leu Tyr
            580                 585                 590
```

Arg Asp Ile Pro Glu Leu Gln Phe
    595                 600

<210> SEQ ID NO 82
<211> LENGTH: 2093
<212> TYPE: DNA
<213> ORGANISM: Rattus norvegicus

<400> SEQUENCE: 82

| | | | | | |
|---|---|---|---|---|---|
| ccacgccttg | cgctctccgc | tgtctccgca | gctaaagccc | gggcagcccc | ggccacgcag | 60 |
| ctccgcaacc | atgtccaagc | tggcacggct | cgagcgcgag | gagatcatgg | agtgccaggt | 120 |
| gatgtgggag | cctgacagca | agaaggacac | gcagatggac | cgcttccggg | cggccgtggg | 180 |
| tactgcctgc | ggcctggcgc | ttgggaatta | cgatgactta | taccactggt | ctgtccggtc | 240 |
| gtattcagac | ttctgggctg | agttctggaa | gttcagtgga | attgtctgct | ctcgcatgta | 300 |
| tgatgaggtt | gtggacacat | ccaaaggaat | tgcagatgtc | cctgagtggt | tcagaggcag | 360 |
| ccgcctcaac | tatgcagaga | accttctgcg | gcacaaggag | aacgacagag | tcgcccttta | 420 |
| cgtggcccgg | gaaggcagag | aggagattgc | gaaggtgact | ttcgaagagc | ttcggcagca | 480 |
| ggtggctctg | tttgcagccg | ccatgaggaa | gatgggcgtg | aagaaagggg | accgtgtggt | 540 |
| cggttatctc | cccaacagtg | cccatgccgt | ggaggccatg | ctggctgctg | ccagtattgg | 600 |
| agccatttgg | agttctacct | caccagactt | tggtgtgaat | ggtgtcctgg | accgcttttc | 660 |
| tcaaattcag | ccgaaactta | tcttctcggt | ggaagctgtg | gtctacaacg | gcaaggaaca | 720 |
| cggccacctg | gagaagctgc | agcgagtcgt | gaaaggactt | cctgaccttc | agcgagtggt | 780 |
| gctgatcccc | tatgtcctcc | aagggagaa | gatagacatt | ccaagatccc | caacagcat | 840 |
| gtttctggat | gacttcctgg | caagcggac | aggtgcgcag | gcaccacagc | tcgagtttga | 900 |
| acagctgccc | ttcagccatc | ccctgttcat | catgttctcc | tcgggcacga | caggagcgcc | 960 |
| caagtgcatg | gtgcactctg | ctgggggcac | cctcatccag | cacctgaagg | agcacgtgct | 1020 |
| acatggcaac | atgacaagca | gtgacatcct | gctctactac | accacggtcg | gctggatgat | 1080 |
| gtggaactgg | atggtgtcag | cgctggccac | aggagcatcc | ttggttctgt | acgatggctc | 1140 |
| cccgctggtt | ccaacaccca | atgtgttgtg | ggaccttgtg | gacaggatag | gaatcaccat | 1200 |
| cctgggaacg | ggagccaagt | ggctgtcagt | gctggaggag | aaggacatga | agccgatgga | 1260 |
| aactcacaac | ctccacacgc | tccacacgat | cctgtccacc | ggctcgccac | tgaaagccca | 1320 |
| gagctatgag | tatgtgtaca | gatgcatcaa | gagcaccgtg | ctcctcggct | ccatctcagg | 1380 |
| tggcactgac | atcatctcct | gtttcatggg | ccagaactca | tctattcctg | tgtacaaggg | 1440 |
| tgagatccaa | gcccggaacc | tcggcatggc | cgtggaagcc | tgggacgagg | aagggaaaac | 1500 |
| cgtctgggga | gcgagtggcg | agctggtttg | caccaagccc | atccctgcc | agcccacgca | 1560 |
| cttctggaac | gacgagaacg | gcagcaagta | caggaaggct | tacttctcca | aatacccagg | 1620 |
| tgtctgggca | cacggcgact | actgcaggat | caaccccaag | acaggaggta | tcgtcatgtt | 1680 |
| gggccggagt | gatggcaccc | tcaaccccaa | tggcgtacgc | tttggcagct | cggagatcta | 1740 |
| caacattgtg | gaagccttcg | atgaggtgga | ggacagcctt | tgtgtgcccc | agtacaacag | 1800 |
| ggatggtgag | gagcgggtag | tcctgttct | gaagatggcc | tctgggcaca | ctttccagcc | 1860 |
| cgacctcgtg | aagcacatcc | gtgatgccat | ccgccttggc | ctgtctgctc | gccacgtgcc | 1920 |
| cagcctcatc | ctggagaccc | aaggcattcc | atacacaatc | aacggcaaga | aagtggaggt | 1980 |
| ggccgtgaag | caggtgatag | ctgggaagac | tgtggagcac | cggggggcct | tctccaaccc | 2040 |

-continued

```
tgagtccctg gacctgtatc gggacatccc tgagctgcag gacttctgaa cca              2093
```

<210> SEQ ID NO 83
<211> LENGTH: 1475
<212> TYPE: DNA
<213> ORGANISM: Homo sapiens
<220> FEATURE:
<221> NAME/KEY: CDS
<222> LOCATION: (81)...(1208)
<220> FEATURE:
<221> NAME/KEY: misc_feature
<222> LOCATION: (1)...(1475)
<223> OTHER INFORMATION: n = A,T,C or G

<400> SEQUENCE: 83

```
ccagcttgcc cacgcacccc actcggcgtc gcgcggcgtg ccctgcttgt cacaggtggg        60
aggctggaac tatcagaatc atg gtg tca tgg aaa ggg att tac ttt ata ctg       113
                     Met Val Ser Trp Lys Gly Ile Tyr Phe Ile Leu
                      1               5                  10 act ctg ttt tgg gga agc ttc ttt gga agc att ttc atg ctg agt ccc         161
Thr Leu Phe Trp Gly Ser Phe Phe Gly Ser Ile Phe Met Leu Ser Pro
             15                  20                  25 ttt tta cct ttg atg ttt gta aac cca tct tgg tat cgc tgg atc aac         209
Phe Leu Pro Leu Met Phe Val Asn Pro Ser Trp Tyr Arg Trp Ile Asn
         30                  35                  40 aac cgc ctt gtg gca aca tgg ctc acc cta cct gtg gca tta ctg gag         257
Asn Arg Leu Val Ala Thr Trp Leu Thr Leu Pro Val Ala Leu Leu Glu
     45                  50                  55 acc atg ttt ggt gta aaa gtg att ata act ggg gat gca ttt gtt cct         305
Thr Met Phe Gly Val Lys Val Ile Ile Thr Gly Asp Ala Phe Val Pro
 60                  65                  70                  75 gga gaa aga ggt gtc att atc atg aac cat cgg aca aga atg gac tgg         353
Gly Glu Arg Gly Val Ile Ile Met Asn His Arg Thr Arg Met Asp Trp
                 80                  85                  90 acg ttc ctg tgg aat tgc ctg atg cga tat agc tac ctc aga ttg gag         401
Thr Phe Leu Trp Asn Cys Leu Met Arg Tyr Ser Tyr Leu Arg Leu Glu
             95                 100                 105 aaa att tgc ctc aaa gcg agt ctc aaa ggt gtt cct gga ttt ggt tgg         449
Lys Ile Cys Leu Lys Ala Ser Leu Lys Gly Val Pro Gly Phe Gly Trp
        110                 115                 120 gcc atg cag gct gct gcc tat atc ttc att cat agg aaa tgg aag gat         497
Ala Met Gln Ala Ala Ala Tyr Ile Phe Ile His Arg Lys Trp Lys Asp
    125                 130                 135 gac aag agc cat ttc gaa gac atg att gat tac ttt tgt gat att cac         545
Asp Lys Ser His Phe Glu Asp Met Ile Asp Tyr Phe Cys Asp Ile His
140                 145                 150                 155 gaa cca ctt caa ctc ctc ata ttc cca gaa ggg act gat ctc aca gaa         593
Glu Pro Leu Gln Leu Leu Ile Phe Pro Glu Gly Thr Asp Leu Thr Glu
                160                 165                 170 aac agc aag tct cga agt aat gca ttt gct gaa aaa aat gga ctt cag         641
Asn Ser Lys Ser Arg Ser Asn Ala Phe Ala Glu Lys Asn Gly Leu Gln
            175                 180                 185 aaa tat gaa tat gtt tta cat cca aga act aca ggc ttt act ttt gtg         689
Lys Tyr Glu Tyr Val Leu His Pro Arg Thr Thr Gly Phe Thr Phe Val
        190                 195                 200 gta gac cgt cta aga gaa ggt aag aac ctt gat gct gtc cat gat atc         737
Val Asp Arg Leu Arg Glu Gly Lys Asn Leu Asp Ala Val His Asp Ile
    205                 210                 215 act gtg gcg tat cct cac aac att cct caa tca gag aag cac ctc ctc         785
Thr Val Ala Tyr Pro His Asn Ile Pro Gln Ser Glu Lys His Leu Leu
220                 225                 230                 235
```

```
caa gga gac ttt ccc agg gaa atc cac ttt cat gtc cac cgg tat cca     833
Gln Gly Asp Phe Pro Arg Glu Ile His Phe His Val His Arg Tyr Pro
            240                 245                 250 gta gac acc ctc ccc aca tcc aag gag gac ctt caa ctc tgg tgc cac     881
Val Asp Thr Leu Pro Thr Ser Lys Glu Asp Leu Gln Leu Trp Cys His
        255                 260                 265 aaa cgg tgg gaa gag aaa gaa gag agg ctg cgt tcc ttc tat caa ggg     929
Lys Arg Trp Glu Glu Lys Glu Glu Arg Leu Arg Ser Phe Tyr Gln Gly
    270                 275                 280 gag aag aat ttt tat ttt acc gga cag agt gtc att cca cct tgc aag     977
Glu Lys Asn Phe Tyr Phe Thr Gly Gln Ser Val Ile Pro Pro Cys Lys
285                 290                 295 tct gaa ctc agg gtc ctt gtg gtc aaa ttg ctc tct ata ctg tat tgg    1025
Ser Glu Leu Arg Val Leu Val Val Lys Leu Leu Ser Ile Leu Tyr Trp
300                 305                 310                 315 acc ctg ttc agc cct gca atg tgc cta ctc ata tat ttg tac agt ctt    1073
Thr Leu Phe Ser Pro Ala Met Cys Leu Leu Ile Tyr Leu Tyr Ser Leu
                320                 325                 330 gtt aag tgg tat ttt ata atc acc att gta atc ttt gtg ctg caa gag    1121
Val Lys Trp Tyr Phe Ile Ile Thr Ile Val Ile Phe Val Leu Gln Glu
            335                 340                 345 aga ata ttt ggt gga ctg gag atc ata gaa ctt gca tgt tac cga ctt    1169
Arg Ile Phe Gly Gly Leu Glu Ile Ile Glu Leu Ala Cys Tyr Arg Leu
        350                 355                 360 tta cac aaa cag cca cat tta aat tca aag aaa aat gag taagattata     1218
Leu His Lys Gln Pro His Leu Asn Ser Lys Lys Asn Glu
    365                 370                 375 aggtttgcca tgtgaaaacc tagagcatat tttggaaatg ttctaaacct ttctaagctc   1278
agatgcattt ttgcatgact atgtcgaata tttcttactg ccatcattat ttgttaaara   1338
tattttgcac ttaattttgt gggaaaaawa nttgctacaa ttttttttaa tctctkrwrt   1398
rwwwtykmka ywstgtryay akmrsrgrgw gwkmkmsgrk gwarwaayww skkssrgmmw   1458
rwwwwtwawy aawcaat                                                  1475

<210> SEQ ID NO 84
<211> LENGTH: 376
<212> TYPE: PRT
<213> ORGANISM: Homo sapiens

<400> SEQUENCE: 84

Met Val Ser Trp Lys Gly Ile Tyr Phe Ile Leu Thr Leu Phe Trp Gly
1               5                   10                  15

Ser Phe Phe Gly Ser Ile Phe Met Leu Ser Pro Phe Leu Pro Leu Met
            20                  25                  30

Phe Val Asn Pro Ser Trp Tyr Arg Trp Ile Asn Asn Arg Leu Val Ala
        35                  40                  45

Thr Trp Leu Thr Leu Pro Val Ala Leu Leu Glu Thr Met Phe Gly Val
    50                  55                  60

Lys Val Ile Ile Thr Gly Asp Ala Phe Val Pro Gly Glu Arg Gly Val
65                  70                  75                  80

Ile Ile Met Asn His Arg Thr Arg Met Asp Trp Thr Phe Leu Trp Asn
                85                  90                  95

Cys Leu Met Arg Tyr Ser Tyr Leu Arg Leu Glu Lys Ile Cys Leu Lys
            100                 105                 110

Ala Ser Leu Lys Gly Val Pro Gly Phe Gly Trp Ala Met Gln Ala Ala
        115                 120                 125

Ala Tyr Ile Phe Ile His Arg Lys Trp Lys Asp Asp Lys Ser His Phe
```

```
                130                 135                 140
Glu Asp Met Ile Asp Tyr Phe Cys Asp Ile His Glu Pro Leu Gln Leu
145                 150                 155                 160

Leu Ile Phe Pro Glu Gly Thr Asp Leu Thr Glu Asn Ser Lys Ser Arg
                165                 170                 175

Ser Asn Ala Phe Ala Glu Lys Asn Gly Leu Gln Lys Tyr Glu Tyr Val
            180                 185                 190

Leu His Pro Arg Thr Thr Gly Phe Thr Phe Val Val Asp Arg Leu Arg
        195                 200                 205

Glu Gly Lys Asn Leu Asp Ala Val His Asp Ile Thr Val Ala Tyr Pro
210                 215                 220

His Asn Ile Pro Gln Ser Glu Lys His Leu Leu Gln Gly Asp Phe Pro
225                 230                 235                 240

Arg Glu Ile His Phe His Val His Arg Tyr Pro Val Asp Thr Leu Pro
                245                 250                 255

Thr Ser Lys Glu Asp Leu Gln Leu Trp Cys His Lys Arg Trp Glu Glu
            260                 265                 270

Lys Glu Glu Arg Leu Arg Ser Phe Tyr Gln Gly Glu Lys Asn Phe Tyr
        275                 280                 285

Phe Thr Gly Gln Ser Val Ile Pro Pro Cys Lys Ser Glu Leu Arg Val
290                 295                 300

Leu Val Val Lys Leu Leu Ser Ile Leu Tyr Trp Thr Leu Phe Ser Pro
305                 310                 315                 320

Ala Met Cys Leu Leu Ile Tyr Leu Tyr Ser Leu Val Lys Trp Tyr Phe
                325                 330                 335

Ile Ile Thr Ile Val Ile Phe Val Leu Gln Glu Arg Ile Phe Gly Gly
            340                 345                 350

Leu Glu Ile Ile Glu Leu Ala Cys Tyr Arg Leu Leu His Lys Gln Pro
        355                 360                 365

His Leu Asn Ser Lys Lys Asn Glu
    370                 375

<210> SEQ ID NO 85
<211> LENGTH: 1131
<212> TYPE: DNA
<213> ORGANISM: Homo sapiens

<400> SEQUENCE: 85
atggtgtcat ggaaagggat ttactttata ctgactctgt tttggggaag cttctttgga    60
agcattttca tgctgagtcc cttttttacct ttgatgtttg taaacccatc ttggtatcgc   120
tggatcaaca accgccttgt ggcaacatgg ctcacccctac ctgtggcatt actggagacc   180
atgtttggtg taaaagtgat tataactggg gatgcatttg ttcctggaga agaggtgtc    240 attatcatga accatcggac aagaatggac tggacgttcc tgtggaattg cctgatgcga    300
tatagctacc tcagattgga gaaaatttgc ctcaaagcga gtctcaaagg tgttcctgga    360
tttggttggg ccatgcaggc tgctgcctat atcttcattc ataggaaatg gaaggatgac    420
aagagccatt cgaagacat gattgattac ttttgtgata ttcacgaacc acttcaactc    480
ctcatattcc cagaagggac tgatctcaca gaaacagca agtctcgaag taatgcattt    540
gctgaaaaaa atggacttca gaaatatgaa tatgttttac atccaagaac tacaggcttt    600
acttttgtgg tagaccgtct aagagaaggt aagaaccttg atgctgtcca tgatatcact    660
gtggcgtatc ctcacaacat tcctcaatca gagaagcacc tcctccaagg agactttccc    720
```

```
agggaaatcc actttcatgt ccaccggtat ccagtagaca ccctcccac atccaaggag    780 gaccttcaac tctggtgcca caaacggtgg gaagagaaag aagagaggct gcgttccttc    840
tatcaagggg agaagaattt ttatttacc ggacagagtg tcattccacc ttgcaagtct    900
gaactcaggg tccttgtggt caaattgctc tctatactgt attggaccct gttcagccct    960
gcaatgtgcc tactcatata tttgtacagt cttgttaagt ggtattttat aatcaccatt   1020
gtaatctttg tgctgcaaga gagaatattt ggtggactgg agatcataga acttgcatgt   1080
taccgacttt tacacaaaca gccacattta aattcaaaga aaatgagta a             1131
```

<210> SEQ ID NO 86
<211> LENGTH: 195
<212> TYPE: PRT
<213> ORGANISM: Artificial Sequence
<220> FEATURE:
<223> OTHER INFORMATION: consensus sequence

<400> SEQUENCE: 86

```
Leu Glu Asn Leu Pro Lys Lys Gly Pro Ala Ile Val Val Ser Asn His
 1               5                  10                  15

Arg Ser Tyr Leu Asp Ile Leu Val Leu Ser Ala Ala Leu Pro Arg Arg
            20                  25                  30

Gly Pro Trp Leu Val Arg Arg Leu Val Phe Ile Ala Lys Lys Glu Leu
        35                  40                  45

Leu Lys Val Pro Leu Leu Phe Gly Trp Leu Met Arg Leu Ala Gly Ala
    50                  55                  60

Ile Phe Ile Asp Arg Asn Asn Arg Ala Lys Asp Ala Leu Ala Ala Ala
65                  70                  75                  80

Asp Glu Leu Val Arg Val Leu Glu Leu Leu Arg Lys Gly Arg Ser Val
                85                  90                  95

Leu Ile Phe Pro Glu Gly Thr Arg Ser Arg Ser Gly Glu Leu Leu Pro
            100                 105                 110

Pro Phe Lys Lys Gly Ile Ala Ala Phe Arg Leu Ala Leu Lys Ala Gly
        115                 120                 125

Val Pro Ile Val Pro Val Ile Val Ser Gly Thr Glu Glu Leu Glu
    130                 135                 140

Pro Lys Asn Glu Ala Gly Lys Leu Leu Arg Leu Ala Arg Lys Lys Gly
145                 150                 155                 160

Pro Val Thr Val Arg Val Leu Pro Pro Ile Pro Leu Asp Pro Glu Asp
                165                 170                 175

Ile Lys Glu Leu Ala Glu Arg Leu Arg Asp Ile Leu Val Gln Ala Leu
            180                 185                 190

Glu Glu Leu
        195
```

<210> SEQ ID NO 87
<211> LENGTH: 7
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 1
<223> OTHER INFORMATION: Xaa = Asn, or any amino acid
<220> FEATURE:
<221> NAME/KEY: VARIANT
<222> LOCATION: 3
<223> OTHER INFORMATION: Xaa = Arg, or Gln
<220> FEATURE:

-continued

```
<221> NAME/KEY: VARIANT
<222> LOCATION: 5
<223> OTHER INFORMATION: Xaa = any amino acid
<220> FEATURE:
<221> NAME/KEY: VARIANT
<222> LOCATION: 6
<223> OTHER INFORMATION: Xaa = Leu, Tyr, Ile, or Met,

<400> SEQUENCE: 87

Xaa His Xaa Ser Xaa Xaa Asp
 1               5

<210> SEQ ID NO 88
<211> LENGTH: 7
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 2
<223> OTHER INFORMATION: Xaa = any amino acid
<220> FEATURE:
<221> NAME/KEY: VARIANT
<222> LOCATION: 3
<223> OTHER INFORMATION: Xaa = Ile, or Phe
<220> FEATURE:
<221> NAME/KEY: VARIANT
<222> LOCATION: 6
<223> OTHER INFORMATION: Xaa = Arg, or Asp

<400> SEQUENCE: 88

Gly Xaa Xaa Phe Ile Xaa Arg
 1               5

<210> SEQ ID NO 89
<211> LENGTH: 8
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 2
<223> OTHER INFORMATION: Xaa = Pro, Leu, or Ile
<220> FEATURE:
<221> NAME/KEY: VARIANT
<222> LOCATION: 5
<223> OTHER INFORMATION: Xaa = Thr, or Gly
<220> FEATURE:
<221> NAME/KEY: VARIANT
<222> LOCATION: 7
<223> OTHER INFORMATION: Xaa = Ser, or any amino acid
<220> FEATURE:
<221> NAME/KEY: VARIANT
<222> LOCATION: 8
<223> OTHER INFORMATION: Xaa = Arg, or any amino acid

<400> SEQUENCE: 89

Phe Xaa Glu Gly Xaa Arg Xaa Xaa
 1               5

<210> SEQ ID NO 90
<211> LENGTH: 6
<212> TYPE: PRT
<213> ORGANISM: Artificial Sequence
<220> FEATURE:
<223> OTHER INFORMATION: exemplary motif
<220> FEATURE:
<221> NAME/KEY: VARIANT
<222> LOCATION: 1,4,6
<223> OTHER INFORMATION: Xaa = Val, or Ile
<220> FEATURE:
```

```
-continued
<221> NAME/KEY: VARIANT
<222> LOCATION: 2
<223> OTHER INFORMATION: Xaa = Pro, or any amino acid
<220> FEATURE:
<221> NAME/KEY: VARIANT
<222> LOCATION: 3
<223> OTHER INFORMATION: Xaa = Ile, Val, or Leu

<400> SEQUENCE: 90

Xaa Xaa Xaa Xaa Pro Xaa
 1               5
```